(12) United States Patent
Franchi et al.

(10) Patent No.: US 12,084,424 B2
(45) Date of Patent: Sep. 10, 2024

(54) COMPOUNDS AND COMPOSITIONS FOR TREATING CONDITIONS ASSOCIATED WITH NLRP ACTIVITY

(71) Applicant: NOVARTIS AG, Basel (CH)

(72) Inventors: Luigi Franchi, Ann Arbor, MI (US);
Shomir Ghosh, Brookline, MA (US);
Gary Glick, Ann Arbor, MI (US);
Jason Katz, Newton, MA (US);
Anthony William Opipari, Jr., Dexter, MI (US); William Roush, Boston, MA (US); Hans Martin Seidel, Concord, MA (US); Dong-Ming Shen, Edison, NJ (US); Shankar Venkatraman, Lansdale, PA (US); David Guenther Winkler, Arlington, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 18/319,630

(22) Filed: May 18, 2023

(65) Prior Publication Data

US 2023/0416211 A1 Dec. 28, 2023

Related U.S. Application Data

(63) Continuation of application No. 17/496,375, filed on Oct. 7, 2021, now Pat. No. 11,724,992, which is a continuation of application No. 16/632,849, filed as application No. PCT/US2018/043338 on Jul. 23, 2018, now Pat. No. 11,203,579.

(60) Provisional application No. 62/573,894, filed on Oct. 18, 2017, provisional application No. 62/536,271, filed on Jul. 24, 2017.

(51) Int. Cl.
| | |
|---|---|
| C07D 277/36 | (2006.01) |
| C07C 307/06 | (2006.01) |
| C07D 215/36 | (2006.01) |
| C07D 231/18 | (2006.01) |
| C07D 239/26 | (2006.01) |
| C07D 263/46 | (2006.01) |
| C07D 307/64 | (2006.01) |
| C07D 307/79 | (2006.01) |
| C07D 317/62 | (2006.01) |
| C07D 333/34 | (2006.01) |
| C07D 487/04 | (2006.01) |
| C07C 335/42 | (2006.01) |
| C07D 213/71 | (2006.01) |
| C07D 231/12 | (2006.01) |
| C07D 405/12 | (2006.01) |
| C07D 409/12 | (2006.01) |
| C07D 417/12 | (2006.01) |
| C07D 471/04 | (2006.01) |

(52) U.S. Cl.
CPC .......... *C07D 277/36* (2013.01); *C07C 307/06* (2013.01); *C07D 215/36* (2013.01); *C07D 231/18* (2013.01); *C07D 239/26* (2013.01); *C07D 263/46* (2013.01); *C07D 307/64* (2013.01); *C07D 307/79* (2013.01); *C07D 317/62* (2013.01); *C07D 333/34* (2013.01); *C07D 487/04* (2013.01); *C07C 335/42* (2013.01); *C07D 213/71* (2013.01); *C07D 231/12* (2013.01); *C07D 405/12* (2013.01); *C07D 409/12* (2013.01); *C07D 417/12* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,666,506 | A | 5/1987 | Hillemann |
| 5,169,860 | A | 12/1992 | Mohamadi et al. |
| 5,258,406 | A | 11/1993 | Toth et al. |
| 10,654,816 | B2 | 5/2020 | Franchi et al. |
| 2002/0077486 | A1 | 6/2002 | Scarborough et al. |
| 2020/0216389 | A1 | 7/2020 | Miller et al. |
| 2021/0171477 | A1 | 6/2021 | Franchi et al. |

FOREIGN PATENT DOCUMENTS

| | | |
|---|---|---|
| EP | 0173498 A1 | 3/1986 |
| EP | 0552553 A1 | 7/1993 |
| EP | 1236468 A1 | 4/2002 |
| EP | 2314593 A1 | 4/2011 |
| EP | 2927214 A1 | 10/2015 |
| WO | 9832733 A1 | 7/1998 |
| WO | 10119390 A1 | 3/2001 |
| WO | 2016131098 A1 | 8/2016 |

(Continued)

OTHER PUBLICATIONS

Izzo, et al., Exploration of Novel Chemical Space: Synthesis and in vitro Evaluation of N-Functionalized Tertiary Sulfonimidamides, Chemistry—A European Journal, 2018, 9295-9304, 24.

(Continued)

*Primary Examiner* — Samantha L Shterengarts
(74) *Attorney, Agent, or Firm* — Timothy P. O'Dea

(57) ABSTRACT

In one aspect, compounds of Formula AA, or a pharmaceutically acceptable salt thereof, are featured:

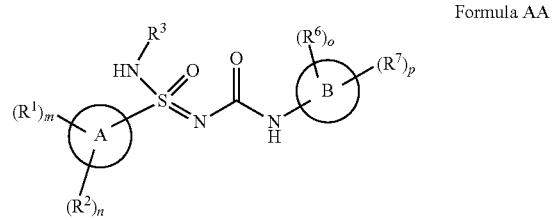

Formula AA or a pharmaceutically acceptable salt thereof, wherein the variables shown in Formula A can be as defined anywhere herein.

3 Claims, 3 Drawing Sheets

Specification includes a Sequence Listing.

(56) References Cited

FOREIGN PATENT DOCUMENTS

| WO | 2017184604 A1 | 10/2017 |
| --- | --- | --- |
| WO | 2017184623 A1 | 10/2017 |
| WO | 2017184624 A1 | 10/2017 |
| WO | 2017184746 A1 | 10/2017 |
| WO | 2018136890 A1 | 7/2018 |
| WO | 2018152396 A1 | 8/2018 |
| WO | 2018225018 A1 | 12/2018 |
| WO | 2019008025 A1 | 1/2019 |
| WO | 2019023145 A1 | 1/2019 |
| WO | 2019023147 A1 | 1/2019 |
| WO | 2019068772 A1 | 4/2019 |
| WO | 2020018975 A1 | 1/2020 |
| WO | 2020035466 A1 | 2/2020 |
| WO | 2020053282 A1 | 3/2020 |
| WO | 2020150674 A1 | 7/2020 |

OTHER PUBLICATIONS

Nandi, et al., Direct Synthesis of N-Acyl Sulfonimidamides and N-Sulfonimidoyl Amidines from Sulfonimidoyl Azides, Adv. Synth. Catal., May 15, 2018, 2465-2469, 360.

Wakchaure, et al., Synthesis of Vinyl- and Aryl-Acyl Sulfonimidamides Through Pd-Catalyzed Carbonylation Using Mo(CO)6 as ex situ CO Source, European Journal of Organic Chemistry, 2015, 213-219.

Coll, Rebecca C. et al.: "A small-molecule inhibitor of the NLRP3 inflammasome for the treatment of inflammatory diseases", Nature Medicine, vol. 21, No. 3, Mar. 2015, pp. 248-257.

Saxena, A. et al.: "Estimation of Antitumor Activity of Sulphonimidamide Analogs of Oncolytic Sulphonylureas", Oxidation Communications, vol. 26, No. 1, (2003), pp. 9-13.

Scozzafava, A. et al.: "Arylsulfonyl-N,N-diethyl-dithiocarbamates: A Novel Class of Antitumor Agents", Bioorganic & Medicinal Chemistry Letters, vol. 10, (2000), pp. 1887-1891.

Supuran, C. et al.: "Carbonic anhydrase inhibitors—Part 94. 1,3,4-Thiadiazole-2-sulfonamide derivatives as antitumor agents?", Eur. J. Med. Chem., vol. 35, (2000), pp. 867-874.

Toth, J. E. et al.: "Synthesis and Resolution of Sulfonimidamide Analogs of Sulfonylureas", J. Org. Chem., vol. 58, (1993), pp. 3469-3472.

Toth, J. E. et al.: "Sulfonimidamide Analogs of Oncolytic Sulfonylureas", J. Med. Chem., vol. 40, (1997), pp. 1018-1025.

Sehgelmeble, Fernando et al. Sulfonimidamides as Sulfonamides Bioisosteres: Rational Evaluation through Synthetic, in Vitro, and in Vivo Studies with y-Secretase Inhibitors, Chem. Med. Chem 2012, 7, 396-399.

FIG. 3

COMPOUNDS AND COMPOSITIONS FOR TREATING CONDITIONS ASSOCIATED WITH NLRP ACTIVITY

PRIORITY CLAIM

This application is a Continuation of U.S. patent application Ser. No. 17/496,375 filed Oct. 7, 2021, which is a Continuation of U.S. patent application Ser. No. 16/632,849 filed Mar. 31, 2020, which is a 371 of PCT/US2018/043338 filed Jul. 23, 2018, which claims the benefit of U.S. Provisional Application No. 62/536,271, filed on Jul. 24, 2017; and U.S. Provisional Application No. 62/573,894, filed on Oct. 18, 2017; which are both incorporated herein by reference in their entirety.

TECHNICAL FIELD

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling) contributes to the pathology and/or symptoms and/or progression of the condition, disease or disorder in a subject (e.g., a human). This disclosure also features compositions as well as other methods of using and making the same.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

NLRP3 can form a complex and has been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NLRP3.

SUMMARY

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling).

In some embodiments, provided herein is a compound of Formula AA

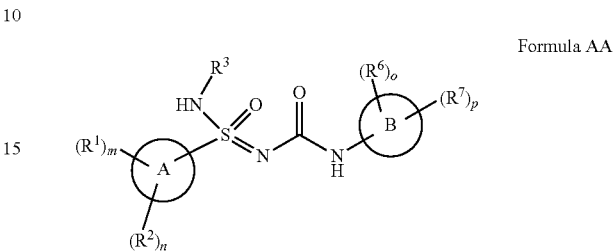

Formula AA or a pharmaceutically acceptable salt thereof, wherein the variables in Formula AA can be as defined anywhere herein.

This disclosure also features compositions as well as other methods of using and making the same.

An "antagonist" of NLRP3 includes compounds that inhibit the ability of NLRP3 to induce the production of IL-1β and/or IL-18 by directly binding to NLRP3, or by inactivating, destabilizing, altering distribution, of NLRP3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP3, as well as in vivo methods.

In a further aspect, methods of treatment of a disease in which NLRP3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP3, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, PA, 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, FL, 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, saturated or unsaturated, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclic rings include five-membered, six-membered, and seven-membered heterocyclic rings.

The term "cycloalkyl" as used herein includes an non-aromatic cyclic, bicylic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to an nonaromatic 5-8 membered monocyclic, 8-12 membered bicyclic, or 11-14 membered tricyclic ring, fused, or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "aryl" is intended to mean an aromatic ring radical containing 6 to 10 ring carbons. Examples include phenyl and naphthyl.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "hydroxy" refers to an OH group.

The term "amino" refers to an NH$_2$ group.

The term "oxo" refers to O. By way of example, substitution of a CH$_2$ a group with oxo gives a C=O group.

As used herein, the terms "the ring A" or "A" are used interchangeably to denote

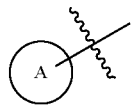

in formula AA, wherein the bond that is shown as being broken by the wavy line connects A to the S(O)(NHR$^3$)=N moiety of Formula AA.

As used herein, the terms "the ring B" or "B" are used interchangeably to denote

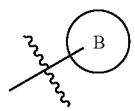

in formula AA wherein the bond that is shown as being broken by the wavy line connects B to the NH(CO) group of Formula AA.

As used herein, the term "the optionally substituted ring A" is used to denote

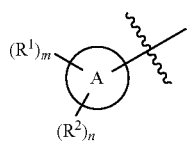

in formula AA, wherein the bond that is shown as being broken by the wavy line connects A to the S(O)(NHR$^3$)=N moiety of Formula AA.

As used herein, the term "the substituted ring B" is used to denote

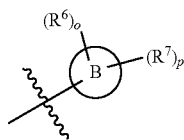

in formula AA, wherein the bond that is shown as being broken by the wavy line connects B to the NH(CO) group of Formula AA.

As used herein, the recitation "S(O₂)", alone or as part of a larger recitation, refers to the group

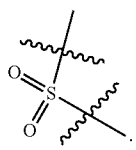 [SMILES: *S(*)(=O)=O]

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The scope of the compounds disclosed herein includes tautomeric form of the compounds. Thus, by way of example, a compound that is represented as containing the moiety

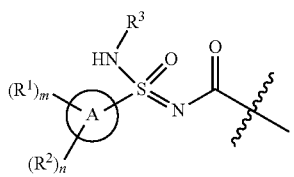

is also intended to include the tautomeric form containing the moiety

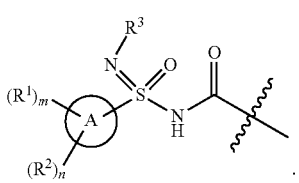

In addition, by way of example, a compound that is represented as containing the moiety

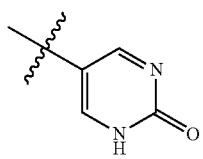 [SMILES: *c1cnc(=O)[nH]c1]

is also intended to include the tautomeric form containing the moiety

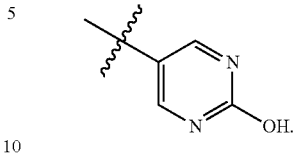

Non-limiting exemplified compounds of the formulae described herein include a stereogenic sulfur atom and optionally one or more stereogenic carbon atoms. This disclosure provides examples of stereoisomer mixtures (e.g., racemic mixture of enantiomers; mixture of diastereomers). This disclosure also describes and exemplifies methods for separating individual components of said stereoisomer mixtures (e.g., resolving the enantiomers of a racemic mixture). In cases of compounds containing only a stereogenic sulfur atom, resolved enantiomers are graphically depicted using one of the two following formats: formulas A/B (hashed and solid wedge three-dimensional representation); and formula C ("flat structures with *-labelled stereogenic sulfur).

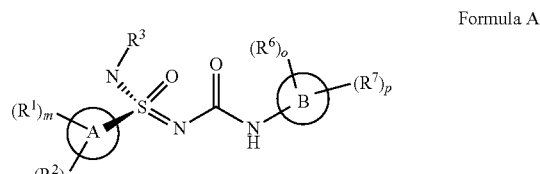

Formula A

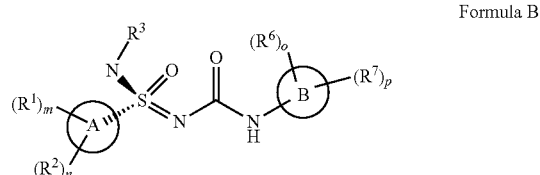

Formula B

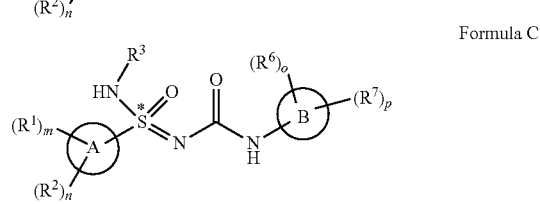

Formula C

In reaction schemes showing resolution of a racemic mixture, Formulas A/B and C are intended only to convey that the constituent enantiomers were resolved in enantiopure pure form (about 98% ee or greater). The schemes that show resolution products using the formula A/B format are not intended to disclose or imply any correlation between absolute configuration and order of elution. Some of the compounds shown in the tables below are graphically represented using the formula A/B format. However, with the exception of compounds 181a and 181b, the depicted stereochemistry shown for each of the tabulated compounds drawn in the formula A/B format is a tentative assignment and based, by analogy, on the absolute stereochemistry assigned to compounds 181b (see, e.g., FIGS. 1 and 2).

The details of one or more embodiments of the invention are set forth in the accompanying drawings and the description below. Other features and advantages of the invention will be apparent from the description and drawings, and from the claims.

DESCRIPTION OF DRAWINGS

FIG. 3 depicts the layout of the microplate used in an hTHP-1 assay.

DETAILED DESCRIPTION

Figure 1:
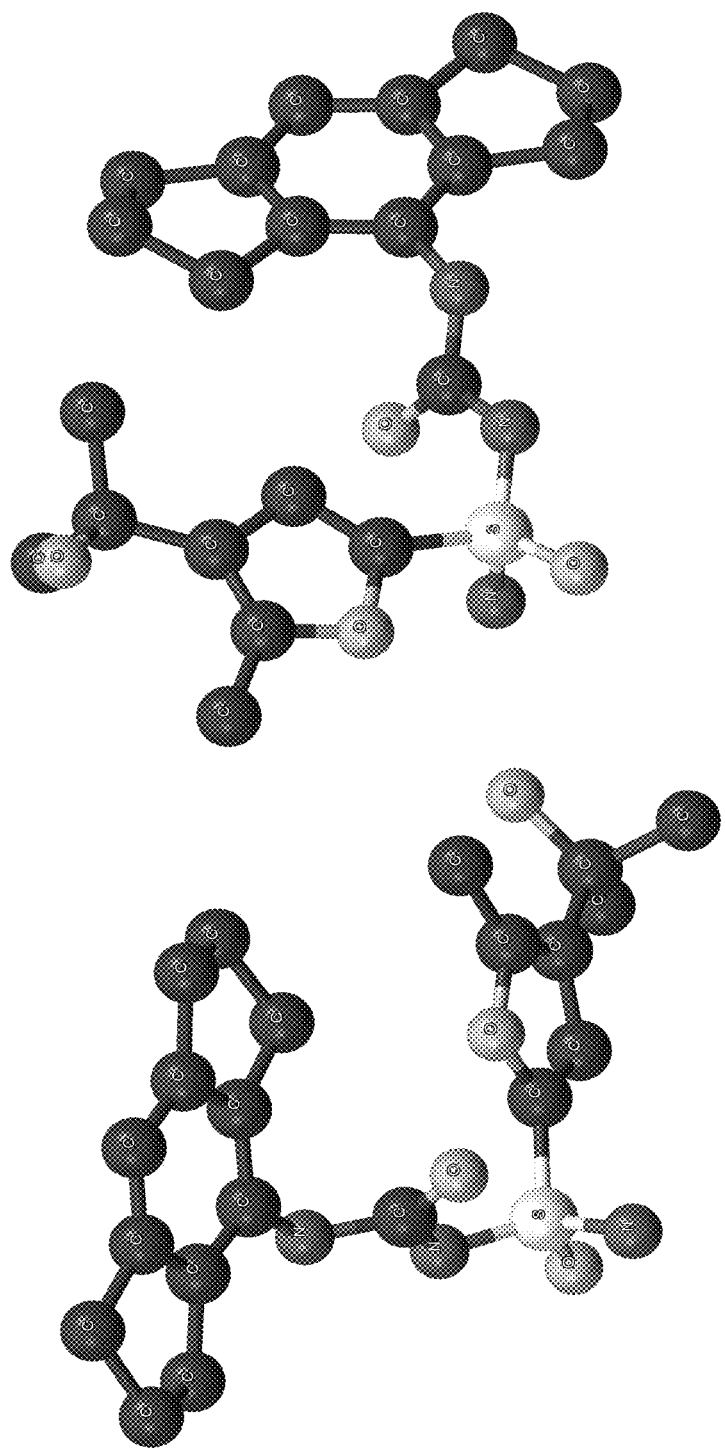
FIG. 1 depicts ball-and-stick representations of two crystallographically independent molecules of compound 181a in the asymmetrical unit.

In some embodiments, provided herein is a compound of Formula AA

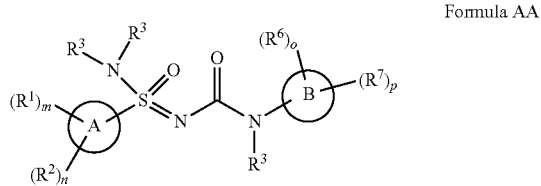

Formula AA wherein
A is a 5-10-membered heteroaryl or a $C_6$-$C_{10}$ aryl;
B is a 5-10-membered heteroaryl or a $C_6$-$C_{10}$ aryl;
wherein
at least one $R^6$ is ortho to the bond connecting the B ring to the $NR^3$(CO) group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl, and 3- to 7-membered heterocycloalkyl,
wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $COOC_1$-$C_6$ alkyl, $NR^8R^9$, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;
wherein the 3- to 7-membered heterocycloalkyl, $C_6$-$C_{10}$ aryl, or 5- to 10-membered heteroaryl, of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, oxo, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $COOC_1$-$C_6$ alkyl, $C_6$-$C_{10}$ aryl, and $CONR^8R^9$;
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl, 3- to 10-membered heterocycloalkyl, and $C_2$-$C_6$ alkenyl,
wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^1R^9$, or wherein $R^6$ or $R^7$ is optionally fused to a five-to-seven-membered carbocyclic ring or heterocyclic ring containing one or two heteroatoms independently selected from oxygen, sulfur and nitrogen;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^6$ and $R^7$ on adjacent atoms, taken together with the atoms connecting them, independently form at least one $C_4$-$C_8$ carbocyclic ring or at least one 4- to 8-membered heterocyclic ring containing 1 or 2 heteroatoms independently selected from O, N, $NR^{20}$, and S,
wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;
each of $R^4$ and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, $C_2$-$C_6$ alkenyl, $C_2$-$C_6$ alkynyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl, $C_2$-$C_6$ alkenyl, or $C_2$-$C_6$ alkynyl is optionally substituted with one or more hydroxy, halo, oxo, $C_1$-$C_6$ alkoxy, $C_2$-$C_6$ alkynyl, $CO_2R^{13}$, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

each $R^3$ is independently selected from hydrogen, cyano, hydroxy, $C_1$-$C_6$ alkoxy, $C_1$-$C_6$ alkyl, $CO_2C_1$-$C_6$ alkyl, and

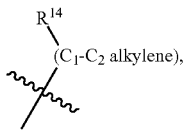

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

In some embodiments, provided herein is a compound of Formula AA

Formula AA

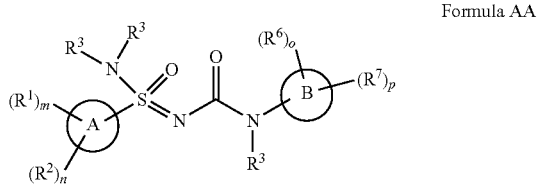

wherein
m=0, 1, or 2;
n=0, 1, or 2;
o=1 or 2;
p=0, 1, 2, or 3;
wherein
A is a 5-10-membered heteroaryl or a $C_6$-$C_{10}$ aryl;
B is a 5-10-membered heteroaryl or a $C_6$-$C_{10}$ aryl;
wherein
at least one $R^6$ is ortho to the bond connecting the B ring to the $NR^3$(CO) group of Formula AA;
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO-(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $COOC_1$-$C_6$ alkyl, $NR^8R^9$, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;

wherein the 3- to 7-membered heterocycloalkyl, $C_6$-$C_{10}$ aryl, or 5- to 10-membered heteroaryl, of the $R^1$ or $R^2$ $C_1$-$C_6$ alkyl, the $R^1$ or $R^2$ $C_1$-$C_6$ haloalkyl, the $R^1$ or $R^2$ $C_3$-$C_7$ cycloalkyl, or the $R^1$ or $R^2$ 3- to 7-membered heterocycloalkyl are optionally substituted with one or more substituents independently selected from halo, $C_1$-$C_6$ alkyl, oxo, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $SC_1$-$C_6$ alkyl, $S(O_2)C_1$-$C_6$ alkyl, $C_3$-$C_{10}$ cycloalkyl, 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^1R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, NHCO$C_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and O$C_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, COO$C_1$-$C_6$ alkyl, $C_6$-$C_{10}$ aryl, and $CONR^8R^9$;

$R^{10}$ is $C_1$-$C_6$ alkyl;

each of $R^8$ and $R^9$ at each occurrence is independently selected from hydrogen, $C_1$-$C_6$ alkyl, $C_2$-$C_6$ alkenyl, $C_2$-$C_6$ alkynyl, (C=$NR^{13}$)$NR^{11}R^{12}$, S(O$_2$)$C_1$-$C_6$ alkyl, S(O$_2$)$NR^{11}R^{12}$, $COR^{13}$, $CO_2R^{13}$ and $CONR^{11}R^{12}$; wherein the $C_1$-$C_6$ alkyl, $C_2$-$C_6$ alkenyl, or $C_2$-$C_6$ alkynyl is optionally substituted with one or more hydroxy, halo, oxo, $C_1$-$C_6$ alkoxy, $C_2$-$C_6$ alkynyl, $CO_2R^{13}$, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl;

each $R^3$ is independently selected from hydrogen, cyano, hydroxy, $C_1$-$C_6$ alkoxy, $C_1$-$C_6$ alkyl, $CO_2C_1$-$C_6$ alkyl, and

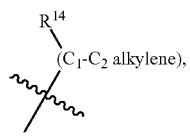

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

In some embodiments, provided herein is a compound of Formula AA

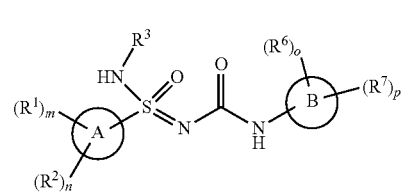

Formula AA wherein
m=0, 1, or 2;
n=0, 1, or 2;
o=1 or 2;
p=0, 1, 2, or 3;
wherein
A is a 5-10-membered heteroaryl or a $C_6$-$C_{10}$ aryl;
B is a 5-10-membered heteroaryl or a $C_6$-$C_{10}$ aryl;
wherein
at least one $R^6$ is ortho to the bond connecting the B ring to the $NR^3$(CO) group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, COC$_1$-$C_6$ alkyl, CO—$C_6$-$C_{10}$ aryl, CO-(5- to 10-membered heteroaryl), $CO_2C_1$-$C_6$ alkyl, $CO_2C_3$-$C_8$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, NH$C_1$-$C_6$ alkyl, N($C_1$-$C_6$ alkyl)$_2$, NHCO$C_1$-$C_6$ alkyl, NHCO$C_6$-$C_{10}$ aryl, NHCO(5- to 10-membered heteroaryl), NHCO(3- to 7-membered heterocycloalkyl), NHCO$C_2$-$C_6$ alkynyl, NHCOO$C_1$-$C_6$ alkyl, NH—(C=$NR^{13}$)$NR^{11}R^{12}$, $CONR^8R^9$, $SF_5$, S$C_1$-$C_6$ alkyl, S(O$_2$)$C_1$-$C_6$ alkyl, S(O$_2$)$NR^{11}R^{12}$, S(O)$C_1$-$C_6$ alkyl, $C_3$-$C_7$ cycloalkyl, and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, COO$C_1$-$C_6$ alkyl, $CONR^8R^9$, 3- to 7-membered heterocycloalkyl, $C_6$-$C_{10}$ aryl, 5- to 10-membered heteroaryl, OCO$C_1$-$C_6$ alkyl, OCO$C_6$-$C_{10}$ aryl, OCO(5- to 10-membered heteroaryl), and OCO(3- to 7-membered heterocycloalkyl), NHCO$C_1$-$C_6$ alkyl, NHCO$C_6$-$C_{10}$ aryl, NHCO(5- to 10-membered heteroaryl), NHCO(3- to 7-membered heterocycloalkyl), and NHCO$C_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, NHCO$C_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and O$C_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)$ $C_1$-$C_6$ alkyl, $C_3$-$C_{10}$ cycloalkyl, 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, halo, $C_6$-$C_{10}$ aryl or $NR^1R^9$, or wherein $R^6$ or $R^7$ is optionally fused to a five-to-seven-membered carbocyclic ring or heterocyclic ring containing one or two heteroatoms independently selected from oxygen, sulfur and nitrogen and optionally substituted with halo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

$R^{10}$ is $C_1$-$C_6$ alkyl;

each of $R^8$ and $R^9$ at each occurrence is independently selected from hydrogen, $C_1$-$C_6$ alkyl, $(C=NR^{13})$ $NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, $CO_2C_1$-$C_6$ alkyl, and

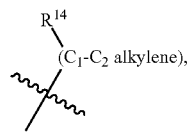

wherein the $C_1$-$C_2$ alkylene group is optionally substituted with oxo; and $R^{14}$ is hydrogen, $C_1$-$C_6$ alkyl, 5-10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1, 2, or 3 $R^6$;

or a pharmaceutically acceptable salt thereof.

In some embodiments, provided herein is a compound of Formula AA

Formula AA

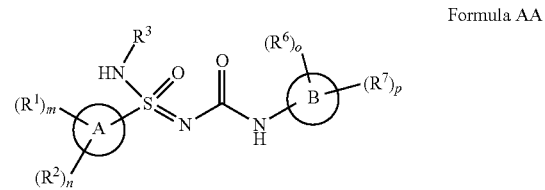

wherein
m=0, 1, or 2;
n=0, 1, or 2;
o=1 or 2;
p=0, 1, 2, or 3;
wherein
A is a 5- to 10-membered monocyclic or bicyclic heteroaryl or a $C_6$-$C_{10}$ monocyclic or bicyclic aryl;
B is a 5- to 10-membered monocyclic or bicyclic heteroaryl or a $C_6$-$C_{10}$ monocyclic or bicyclic aryl;
wherein
at least one $R^6$ is ortho to the bond connecting the B ring to the $NR^3(CO)$ group of Formula AA; $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—$(C=NR^{13})NR^{11}R^{12}$, $CONR^8R^9$, $SF_5$, $SC_1$-$C_6$ alkyl, $S(O_2)C_1$-$C_6$ alkyl, $S(O_2)$ $NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-

$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$, wherein the $C_1$-$C_6$ alkyl and $C_1$-$C_6$ alkoxy are optionally substituted with hydroxy, halo, oxo, $NR^8R^9$, $=NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_{10}$ cycloalkyl and 3- to 10-membered heterocycloalkyl, and $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

$R^{10}$ is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to; $R^{13}$ is $C_1$-$C_6$ alkyl, $C_6$-$C_{10}$ aryl, or 5- to 10-membered heteroaryl; each of $R^{11}$ and $R^{12}$ at each occurrence is independently selected from hydrogen and $C_1$-$C_6$ alkyl; and $R^3$ is selected from hydrogen, cyano, hydroxy, $C_1$-$C_6$ alkoxy, $C_1$-$C_6$ alkyl, and

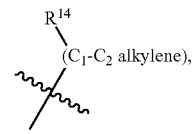

wherein the $C_1$-$C_2$ alkylene group is optionally substituted with oxo;

$R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

or a pharmaceutically acceptable salt thereof.

In some embodiments, provided herein is a compound of Formula AA

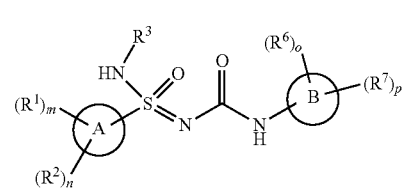

Formula AA wherein m=0, 1, or 2;

n=0, 1, or 2;

o=1 or 2;

p=0, 1, 2, or 3, wherein

A is a 5- to 10-membered monocyclic or bicyclic heteroaryl or a $C_6$-$C_{10}$ monocyclic or bicyclic aryl;

B is a 5- to 10-membered monocyclic or bicyclic heteroaryl or a $C_6$-$C_{10}$ monocyclic or bicyclic aryl;

wherein at least one $R^6$ is ortho to the bond connecting the B ring to the NH(CO) group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$ wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$;

each of $R^1$ and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and

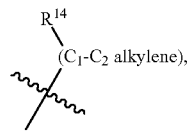

wherein the $C_1$-$C_2$ alkylene group is optionally substituted by oxo;

$R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

with the proviso that the compound of Formula AA is not a compound selected from the group consisting of:

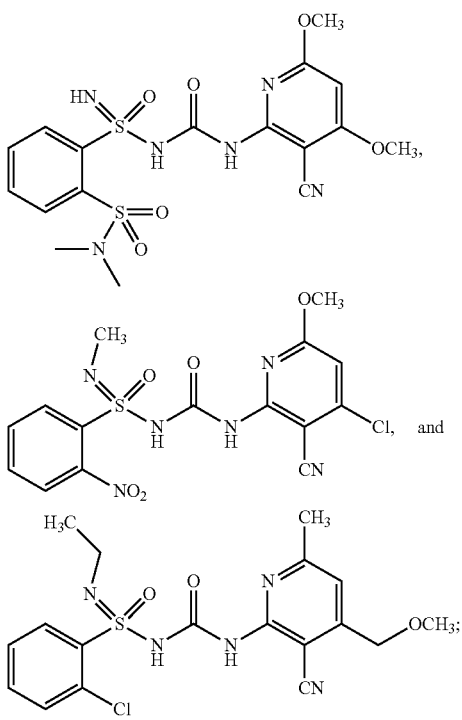

or a pharmaceutically acceptable salt thereof.

In some embodiments, provided herein is a compound of Formula AA

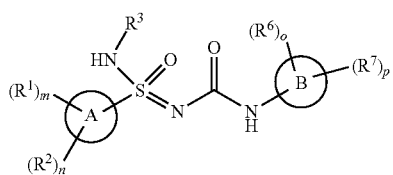

Formula AA wherein
m=0, 1, or 2;
n=0, 1, or 2;
o=1 or 2;
p=0, 1, 2, or 3,
wherein
A is a 5- to 10-membered monocyclic or bicyclic heteroaryl or a $C_6$-$C_{10}$ monocyclic or bicyclic aryl;
B is a 5-membered heteroaryl, a 7-10 membered monocyclic or bicyclic heteroaryl, or a $C_6$-$C_{10}$ monocyclic or bicyclic aryl;
wherein
at least one $R^6$ is ortho to the bond connecting the B ring to the NH(CO) group of Formula AA;

$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOCC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$ wherein the $C_1$-$C_6$ alkyl and $C_1$-$C_6$ alkoxy are optionally substituted with hydroxy, halo, oxo, $NR^8R^9$, =$NR^{10}$, $COOC_1$-$C_6$ alkyl, $C_6$-$C_{10}$ aryl, and $CONR^8R^9$;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

each of W and $R^5$ is independently selected from hydrogen and $C_1$-$C_6$ alkyl;

$R^{10}$ is $C_1$-$C_6$ alkyl;

each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and

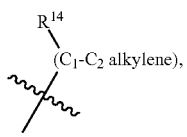

wherein the $C_1$-$C_2$ alkylene group is optionally substituted by oxo; and $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$;

or a pharmaceutically acceptable salt thereof.

In some embodiments the variables shown in the formulae herein are as follows:

The Variables m and n

In some embodiments m=0, 1, or 2.
In some embodiments m=0 or 1.
In some embodiments m=1 or 2.
In some embodiments m=0 or 2.
In some embodiments m=0.
In some embodiments m=1.
In some embodiments m=2.
In some embodiments n=0, 1, or 2.
In some embodiments n=0 or 1.
In some embodiments n=1 or 2.
In some embodiments n=0 or 2.
In some embodiments n=0.
In some embodiments n=1.
In some embodiments n=2.
In some embodiments, m=0 and n=0.
In some embodiments, m=1 and n=0.
In some embodiments, m=1 and n=1.

The Ring A and Substitutions on the Ring A

In some embodiments, A is a 5- to 10-membered (e.g., 5- to 6-membered) monocyclic or bicyclic heteroaryl or a $C_6$-$C_{10}$ (e.g., $C_6$) monocyclic or bicyclic aryl, such as phenyl.

In some embodiments, A is a 5- to 10-membered (e.g., 5- to 6-membered) monocyclic or bicyclic heteroaryl.

In some embodiments, A is a 5-membered heteroaryl containing a sulfur and optionally one or more nitrogens.

In some embodiments, A is a $C_6$-$C_{10}$ monocyclic or bicyclic aryl.

In some embodiments, A is phenyl optionally substituted with 1 or 2 $R^1$ and optionally substituted with 1 or 2 $R^2$.

In some embodiments, A is naphthyl optionally substituted with 1 or 2 $R^1$ and optionally substituted with 1 or 2 $R^2$.

In some embodiments, A is furanyl optionally substituted with 1 or 2 $R^1$ and optionally substituted with 1 $R^2$.

In some embodiments, A is furanyl optionally substituted with 1 $R^1$ and optionally substituted with 1 or 2 $R^2$.

In some embodiments, A is thiophenyl optionally substituted with 1 or 2 $R^1$ and optionally substituted with 1 or 2 $R^2$.

In some embodiments, A is oxazolyl optionally substituted with 1 or 2 $R^1$ and optionally substituted with 1 or 2 $R^2$.

In some embodiments, A is thiazolyl optionally substituted with 1 or 2 $R^1$ and optionally substituted with 1 or 2 $R^2$.

In some embodiments, A is oxazolyl optionally substituted with 2 $R^1$ or optionally substituted with 2 $R^2$.

In some embodiments, A is thiazolyl optionally substituted with 2 $R^1$ or optionally substituted with 2 $R^2$.

In some embodiments, A is pyrazolyl optionally substituted with 1 or 2 $R^1$ and optionally substituted with 1 or 2 $R^2$.

In some embodiments, A is pyrazolyl optionally substituted with 1 $R^1$ and optionally substituted with 1 or 2 $R^2$.

In some embodiments, A is pyrazolyl optionally substituted with 1 or 2 $R^1$ and optionally substituted with 1 $R^2$.

In some embodiments, A is pyridyl optionally substituted with 1 or 2 $R^1$ and optionally substituted with 1 or 2 $R^2$.

In some embodiments, A is indazolyl optionally substituted with 1 or 2 $R^1$ and optionally substituted with 1 or 2 $R^2$.

In some embodiments, A is phenyl substituted with 1 R¹ and optionally substituted with 1 R².

In some embodiments, A is naphthyl substituted with 1 R¹ and optionally substituted with 1 R².

In some embodiments, A is furanyl substituted with 1 R¹ and optionally substituted with 1 R².

In some embodiments, A is thiophenyl substituted with 1 R¹ and optionally substituted with 1 R².

In some embodiments, A is oxazolyl substituted with 1 R¹ and optionally substituted with 1 R².

In some embodiments, A is thiazolyl substituted with 1 R¹ and optionally substituted with 1 R².

In some embodiments, A is pyrazolyl substituted with 1 R¹ and optionally substituted with 1 R².

In some embodiments, A is pyridyl substituted with 1 R¹ and optionally substituted with 1 R².

In some embodiments, A is indazolyl optionally substituted with 1 R¹ and optionally substituted with 1 R².

In some embodiments, A is phenyl substituted with 1 R¹ and substituted with 1 R².

In some embodiments, A is furanyl substituted with 1 R¹ and substituted with 1 R².

In some embodiments, A is thiophenyl substituted with 1 R¹ and substituted with 1 R².

In some embodiments, A is oxazolyl substituted with 1 R¹ and substituted with 1 R².

In some embodiments, A is thiazolyl substituted with 1 R¹ and substituted with 1 R².

In some embodiments, A is pyrazolyl substituted with 1 R¹ and substituted with 1 R².

In some embodiments, A is pyridyl substituted with 1 R¹ and substituted with 1 R².

In some embodiments, A is phenyl, m is 0 or 1, and n is 0, 1, or 2.

In some embodiments, A is furanyl, m is 0 or 1, and n is 0, 1, or 2.

In some embodiments, A is thiophenyl, m is 0 or 1, and n is 0, 1, or 2.

In some embodiments, A is oxazolyl, m is 0 or 1, and n is 0, 1, or 2.

In some embodiments, A is thiazolyl, m is 0 or 1, and n is 0, 1, or 2.

In some embodiments, A is pyrazolyl, m is 0 or 1, and n is 0, 1, or 2.

In some embodiments, A is pyridyl, m is 0 or 1, and n is 0, 1, or 2.

In some embodiments, A is indazolyl, m is 0 or 1, and n is 0, 1, or 2.

In some embodiments, A is phenyl, m is 0, and n is 0 or 1.

In some embodiments, A is furanyl, m is 0, and n is 0 or 1.

In some embodiments, A is thiophenyl, m is 0, and n is 0 or 1.

In some embodiments, A is oxazolyl, m is 0, and n is 0 or 1.

In some embodiments, A is thiazolyl, m is 0, and n is 0 or 1.

In some embodiments, A is pyrazolyl, m is 0, and n is 0 or 1.

In some embodiments, A is pyridyl, m is 0, and n is 0 or 1.

In some embodiments, A is one of the rings disclosed hereinbelow optionally substituted as disclosed hereinbelow wherein in each case the bond that is shown as being broken by the wavy line connects A to the $S(O)(NR^3R^3)=N$ moiety of Formula AA.

In some embodiments, the optionally substituted ring A is

is

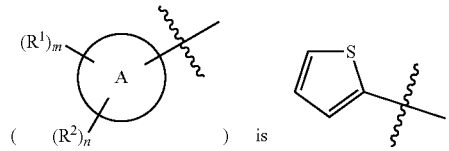

In some embodiments, the optionally substituted ring A is

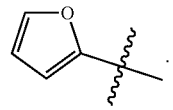 [SMILES: *c1ccco1]

In some embodiments, the optionally substituted ring A is

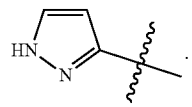

In some embodiments, the optionally substituted ring A is

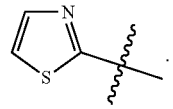 [SMILES: *c1nccs1]

In some embodiments, the optionally substituted ring A is

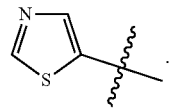 [SMILES: *c1cncs1]

In some embodiments, the optionally substituted ring A is

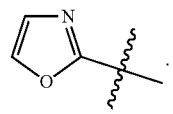 [SMILES: *c1ncco1]

In some embodiments, the optionally substituted ring A is

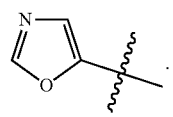 [SMILES: *c1cnco1]

In some embodiments, the optionally substituted ring A is

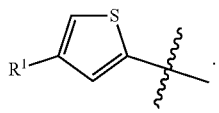

In some embodiments, the optionally substituted ring A is

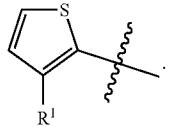

In some embodiments, the optionally substituted ring A is

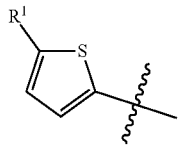

In some embodiments, the optionally substituted ring A is

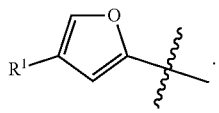

In some embodiments, the optionally substituted ring A is

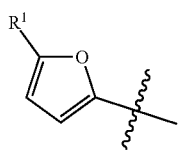

In some embodiments, the optionally substituted ring A is

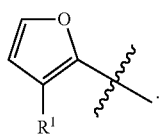

In some embodiments, the optionally substituted ring A is

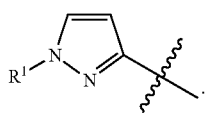

In some embodiments, the optionally substituted ring A is

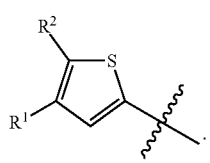

In some embodiments, the optionally substituted ring A is

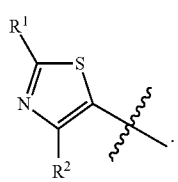

In some embodiments, the optionally substituted ring A is

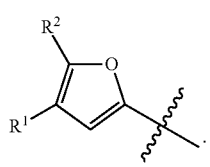

In some embodiments, the optionally substituted ring A is

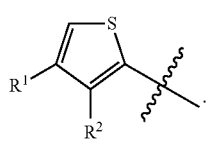

In some embodiments, the optionally substituted ring A is

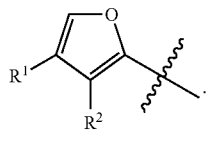

In some embodiments, the optionally substituted ring A is

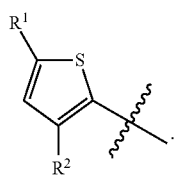

In some embodiments, the optionally substituted ring A is

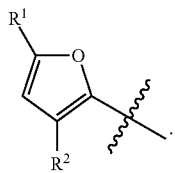

In some embodiments, the optionally substituted ring A is

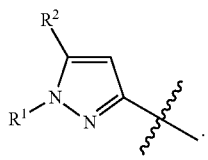

In some embodiments, the optionally substituted ring A is

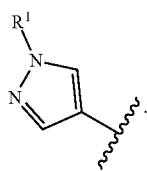

In some embodiments, the optionally substituted ring A is

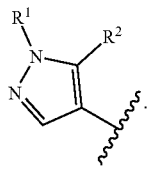

In some embodiments, the optionally substituted ring A is

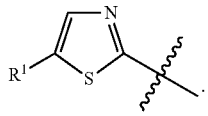

In some embodiments, the optionally substituted ring A is

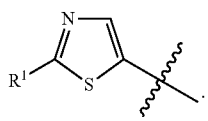

In some embodiments, the optionally substituted ring A is

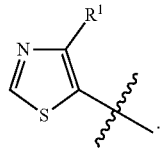

In some embodiments, the optionally substituted ring A is

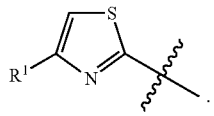

In some embodiments, the optionally substituted ring A is

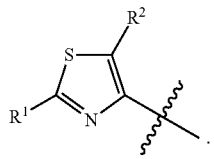

In some embodiments, the optionally substituted ring A is

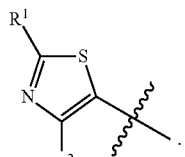

In some embodiments, the optionally substituted ring A is

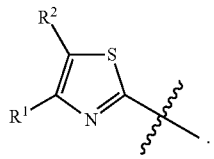

In some embodiments, the optionally substituted ring A is

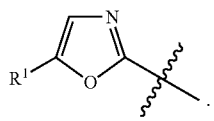

In some embodiments, the optionally substituted ring A is

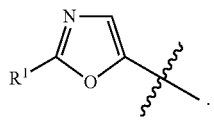

In some embodiments, the optionally substituted ring A is

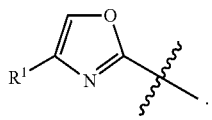

In some embodiments, the optionally substituted ring A is

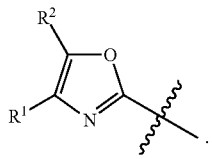

In some embodiments, the optionally substituted ring A is

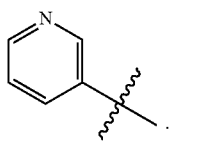 [SMILES: *c1cccnc1]

In some embodiments, the optionally substituted ring A is

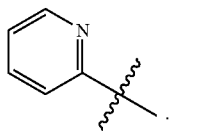 [SMILES: *c1ccccn1]

In some embodiments, the optionally substituted ring A is

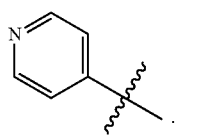

In some embodiments, the optionally substituted ring A is

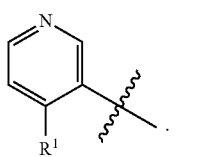

In some embodiments, the optionally substituted ring A is

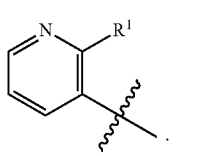

In some embodiments, the optionally substituted ring A is

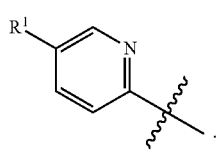

In some embodiments, the optionally substituted ring A is

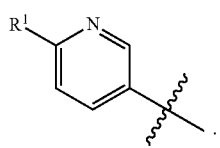

In some embodiments, the optionally substituted ring A is

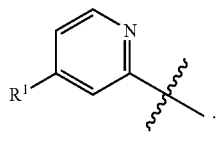

In some embodiments, the optionally substituted ring A is

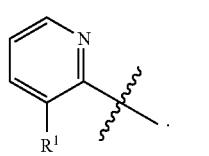

In some embodiments, the optionally substituted ring A is

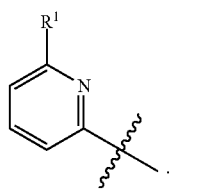

In some embodiments, the optionally substituted ring A is

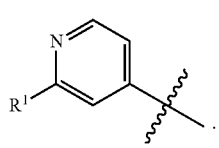

In some embodiments, the optionally substituted ring A is

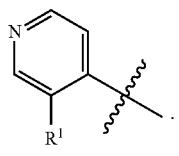

In some embodiments, the optionally substituted ring A is

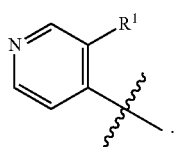

In some embodiments, the optionally substituted ring A is

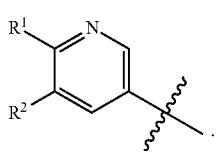

In some embodiments, the optionally substituted ring A is

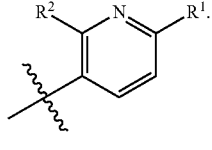

In some embodiments, the optionally substituted ring A is

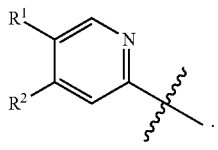

In some embodiments, the optionally substituted ring A is

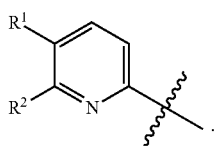

In some embodiments, the optionally substituted ring A is

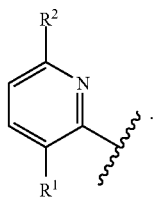

In some embodiments, the optionally substituted ring A is

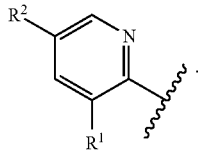

In some embodiments, the optionally substituted ring A is

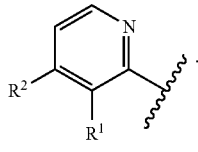

In some embodiments, the optionally substituted ring A is

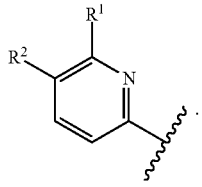

In some embodiments, the optionally substituted ring A is

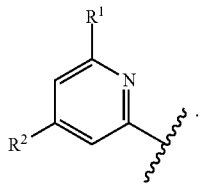

In some embodiments, the optionally substituted ring A is

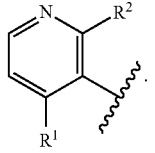

In some embodiments, the optionally substituted ring A is

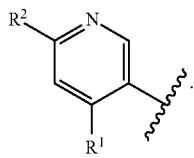

In some embodiments, the optionally substituted ring A is

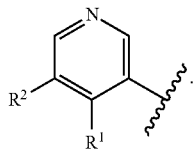

In some embodiments, the optionally substituted ring A is

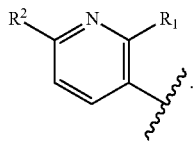

In some embodiments, the optionally substituted ring A is

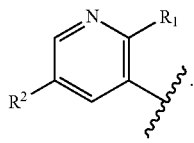

In some embodiments, the optionally substituted ring A is

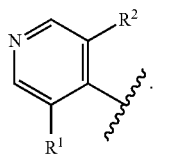

In some embodiments, the optionally substituted ring A is

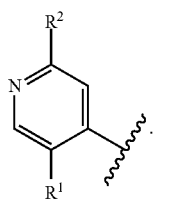

In some embodiments, the optionally substituted ring A is

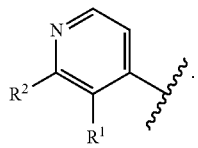

In some embodiments, the optionally substituted ring A is

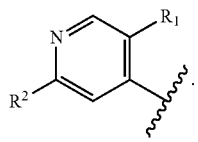

In some embodiments, the optionally substituted ring A is

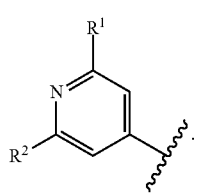

In some embodiments, the optionally substituted ring A is

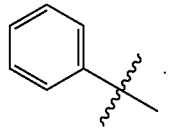

In some embodiments, the optionally substituted ring A is

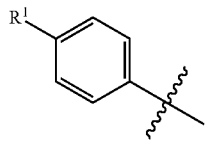

In some embodiments, the optionally substituted ring A is

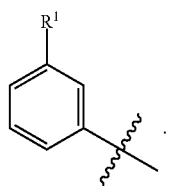

In some embodiments, the optionally substituted ring A is

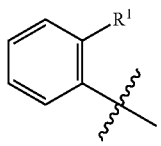

In some embodiments, the optionally substituted ring A is

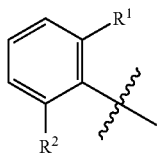

In some embodiments, the optionally substituted ring A is

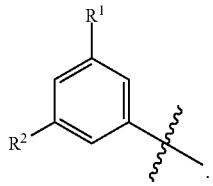

In some embodiments, the optionally substituted ring A is

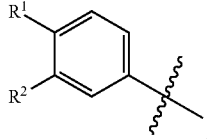

In some embodiments, the optionally substituted ring A is

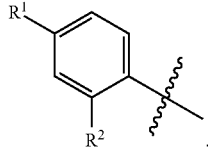

In some embodiments, the optionally substituted ring A is

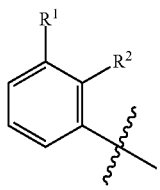

In some embodiments, the optionally substituted ring A is

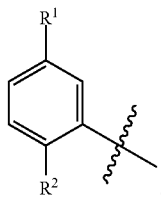

In some embodiments, the optionally substituted ring A is

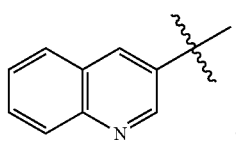

In some embodiments, the optionally substituted ring A is

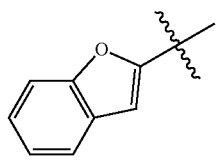

In some embodiments, the optionally substituted ring A is

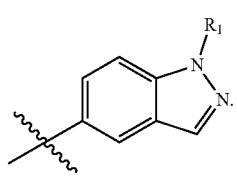

In some embodiments, the optionally substituted ring A is

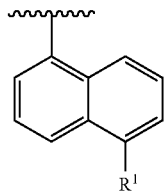

The Groups $R^1$ and $R^2$

In some embodiments, $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), and OCO(3- to 7-membered heterocycloalkyl);
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, and 5- to 10-membered heteroaryl are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;
In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl; CO(5- to 10-membered heteroaryl); $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;
In some embodiments,
$R^1$ and $R^2$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.
In some embodiments,
$R^1$ and $R^2$ are each independently selected from $C_1$-$C_6$ alkyl, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, $NR^8R^9$, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^1R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO$—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
  wherein each $C_1$-$C_6$ alkyl substituent and each $C_1$-$C_6$ alkoxy substituent of the $R^1$ or $R^2$ $C_3$-$C_7$ cycloalkyl or of the $R^1$ or $R^2$ 3- to 7-membered heterocycloalkyl is further optionally independently substituted with one to three hydroxy, halo, or oxo;
  wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments,
$R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO$—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl are each unsubstituted;
or at least one pair of $R^1$ and $R^2$ on adjacent atoms, taken together with the atoms connecting them, independently form at least one $C_4$-$C_8$ carbocyclic ring or at least one 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;

In some embodiments, $R^1$ and $R^2$ are each independently selected from $C_1$-$C_6$ alkyl, halo, CN, $COC_1$-$C_6$ alkyl, $CO_2C_1$-$C_6$ alkyl, $C_6$-$C_{10}$ aryl, $S(O)C_1$-$C_6$ alkyl, 5- to 10-membered heteroaryl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=0; and $R^1$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, m=1; n=0; and, $R^1$ is selected from $C_1$-$C_6$ alkyl, halo, CN, $COC_1$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and $R^1$ and $R^2$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $S(O_2)NR^{11}R^{12}$, $S(O)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

In some embodiments, m=1; n=1; and, $R^1$ and $R^2$ are each independently selected from $C_1$-$C_6$ alkyl, halo, CN, $COG$-$C_6$ alkyl, $CO_2C_1$-$C_6$ alkyl, $C_6$-$C_{10}$ aryl, 5- to 10-membered heteroaryl, $S(O)C_1$-$C_6$ alkyl, and 3- to 7-membered heterocycloalkyl, wherein the $C_1$-$C_6$ alkyl and 3- to 7-membered heterocycloalkyl is optionally substituted with one or more substituents each independently selected from hydroxy and oxo.

In some embodiments, m=1; n=1; and $R^1$ and $R^2$ are on adjacent atoms, and taken together with the atoms connecting them, form a $C_4$-$C_8$ carbocyclic ring or a 5-to-8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_5$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $COOC_1$-$C_6$ alkyl, $C_6$-$C_{10}$ aryl, and $CONR^8R^9$.

In some embodiments, m=1; n=1; and $R^1$ and $R^2$ are on adjacent atoms, and taken together with the atoms connecting them, form a $C_1$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

Particular embodiments wherein m=1 and n=0:

In some embodiments, $R^1$ is $C_1$-$C_6$ alkyl optionally substituted with one or more hydroxy.

In some embodiments, $R^1$ is 1-hydroxy-2-methylpropan-2-yl.

In some embodiments, $R^1$ is 2-hydroxyethyl.

In some embodiments, $R^1$ is $C_1$-$C_6$ alkyl.

In some embodiments, $R^1$ is methyl.

In some embodiments, $R^1$ is isopropyl.

In some embodiments, $R^1$ is isopropyl.

In some embodiments, $R^1$ is $C_1$-$C_6$ alkyl substituted with hydroxy at the carbon directly connected to ring A.

In some embodiments, $R^1$ is 2-hydroxy-2-propyl.

In some embodiments, $R^1$ is hydroxymethyl.

In some embodiments, $R^1$ is 1-hydroxyethyl.

In some embodiments, $R^1$ is 1-hydroxy-2-propyl.

In some embodiments, $R^1$ is $C_1$-$C_6$ alkyl substituted with two or more hydroxy groups.

In some embodiments, $R^1$ is $C_1$-$C_6$ alkyl substituted with two or more hydroxy groups, wherein one of the two or more hydroxy groups is bonded to the carbon directly connected to ring A.

In some embodiments, $R^1$ is 1,2-dihydroxy-prop-2-yl.

In some embodiments, $R^1$ is $C_3$-$C_7$ cycloalkyl optionally substituted with one or more hydroxy.

In some embodiments, $R^1$ is $C_3$-$C_7$ cycloalkyl.

In some embodiments, $R^1$ is $C_3$-$C_7$ cycloalkyl substituted with hydroxy at the carbon directly connected to ring A.

In some embodiments, $R^1$ is 1-hydroxy-1-cyclopropyl.

In some embodiments, $R^1$ is 1-hydroxy-1-cyclobutyl.

In some embodiments, $R^1$ is 1-hydroxy-1-cyclopentyl.

In some embodiments, $R^1$ is 1-hydroxy-1-cyclohexyl.

In some embodiments, $R^1$ is 3- to 7-membered heterocycloalkyl optionally substituted with one or more hydroxy.

In some embodiments, $R^1$ is 3- to 7-membered heterocycloalkyl.

In some embodiments, $R^1$ is morpholinyl (e.g., 1-morpholinyl).

In some embodiments, $R^1$ is 1,3-dioxolan-2-yl.

In some embodiments, $R^1$ is 3- to 7-membered heterocycloalkyl optionally substituted with one or more $C_1$-$C_6$ alkyl.

In some embodiments, $R^1$ is 1-methylpyrrolidin-2-yl.

In some embodiments, $R^1$ is 3- to 7-membered heterocycloalkyl substituted with hydroxy at the carbon directly connected to ring A.

In some embodiments, $R^1$ is $C_1$-$C_6$ alkyl optionally substituted with one or more oxo.

In some embodiments, $R^1$ is $COCH_3$.

In some embodiments, $R^1$ is $COCH_2CH_3$.

In some embodiments, $R^1$ is $C_3$-$C_7$ cycloalkyl optionally substituted with one or more oxo.

In some embodiments, $R^1$ is 3- to 7-membered heterocycloalkyl optionally substituted with one or more oxo.

In some embodiments, $R^1$ is $C_1$-$C_6$ alkyl optionally substituted with one or more $C_1$-$C_6$ alkoxy.

In some embodiments, $R^1$ is 2-methoxy-2-propyl.

In some embodiments, $R^1$ is methoxymethyl.

In some embodiments, $R^1$ is $C_3$-$C_7$ cycloalkyl optionally substituted with one or more $C_1$-$C_6$ alkoxy.

In some embodiments, $R^1$ is 3- to 7-membered heterocycloalkyl optionally substituted with one or more $C_1$-$C_6$ alkoxy.

In some embodiments, $R^1$ is $C_1$-$C_6$ alkyl optionally substituted with one or more $NR^8R^9$.

In some embodiments, $R^1$ is $C_1$-$C_6$ alkyl substituted with $NR^8R^9$ at the carbon directly connected to ring A.

In some embodiments, $R^1$ is (methylamino)methyl.

In some embodiments, $R^1$ is (dimethylamino)methyl.

In some embodiments, $R^1$ is aminomethyl.

In some embodiments, $R^1$ is N-methylacetamidomethyl.

In some embodiments, $R^1$ is 1-(dimethylamino)eth-1-yl.

In some embodiments, $R^1$ is 2-(dimethylamino)prop-2-yl.

In some embodiments, $R^1$ is (2-methoxy-eth-1-yl)(methyl)aminomethyl.

In some embodiments, $R^1$ is (methyl)(acetyl)aminomethyl.

In some embodiments, $R^1$ is (methyl)(cyclopropylmethyl)aminomethyl.

In some embodiments, $R^1$ is (methyl)(2,2-difluoroeth-1-yl)aminomethyl.

In some embodiments, $R^1$ is $C_3$-$C_7$ cycloalkyl optionally substituted with one or more $NR^8R^9$.

In some embodiments, $R^1$ is 3- to 7-membered heterocycloalkyl optionally substituted with one or more $NR^8R^9$.

In some embodiments, $R^1$ is $C_1$-$C_6$ haloalkyl optionally substituted with one or more hydroxy.

In some embodiments, $R^1$ is $C_1$-$C_6$ alkoxy.

In some embodiments, $R^1$ is $C_1$-$C_6$ haloalkoxy.

In some embodiments, $R^1$ is $C_1$-$C_6$ alkyl optionally substituted with 3- to 7-membered heterocycloalkyl, wherein the 3- to 7-membered heterocycloalkyl is further optionally substituted as defined elsewhere herein.

In some embodiments, $R^1$ is pyrrolidinylmethyl (e.g., pyrrolidin-1-ylmethyl).

In some embodiments, $R^1$ is optionally substituted pyrrolidinylmethyl (e.g., 3,3-difluoropyrrolidin-1-ylmethyl).

In some embodiments, $R^1$ is azetidinylmethyl (e.g., azetidin-1-ylmethyl).

In some embodiments, $R^1$ is optionally substituted azetidinylmethyl (e.g., 3-methoxyazetidin-1-ylmethyl).

In some embodiments, $R^1$ is morpholinylmethyl (e.g., morpholin-4-ylmethyl).

In some embodiments, $R^1$ is halo.

In some embodiments, $R^1$ is fluoro.

In some embodiments, $R^1$ is chloro.

In some embodiments, $R^1$ is CN.

In some embodiments, $R^1$ is $NO_2$.

In some embodiments, $R^1$ is $COC_1$-$C_6$ alkyl.

In some embodiments, $R^1$ is CO—$C_6$-$C_{10}$ aryl.

In some embodiments, $R^1$ is CO(5- to 10-membered heteroaryl).

In some embodiments, $R^1$ is $CO_2C_1$-$C_6$ alkyl.

In some embodiments, $R^1$ is $CO_2C_3$-$C_8$ cycloalkyl.

In some embodiments, $R^1$ is $OCOC_1$-$C_6$ alkyl.

In some embodiments, $R^1$ is $OCOC_6$-$C_{10}$ aryl.

In some embodiments, $R^1$ is OCO(5- to 10-membered heteroaryl).

In some embodiments, $R^1$ is OCO(3- to 7-membered heterocycloalkyl).

In some embodiments, $R^1$ is $C_6$-$C_{10}$ aryl.

In some embodiments, $R^1$ is phenyl.

In some embodiments, $R^1$ is 5- to 10-membered heteroaryl.

In some embodiments, $R^1$ is pyridyl (e.g., 4-pyridyl).

In some embodiments, $R^1$ is pyrazolyl (e.g., 1-pyrazolyl).

In some embodiments, $R^1$ is $NH_2$.

In some embodiments, $R^1$ is $NHC_1$-$C_6$ alkyl.

In some embodiments, $R^1$ is $N(C_1$-$C_6$ alkyl$)_2$.

In some embodiments, $R^1$ is $CONR^8R^9$.

In some embodiments, $R^1$ is $SF_5$.

In some embodiments, $R^1$ is $SC_1$-$C_6$ alkyl,

In some embodiments, $R^1$ is $S(O_2)C_1$-$C_6$ alkyl.

In some embodiments, $R^1$ is $S(O_2)CH_3$.

In some embodiments, $R^1$ is $S(O_2)NR^{11}R^{12}$

In some embodiments, $R^1$ is $S(O_2)N(CH_3)_2$.
In some embodiments, $R^1$ is $S(O)C_1$-$C_6$ alkyl.
In some embodiments, $R^1$ is $S(O)CH_3$.
In some embodiments, $R^1$ is attached to a carbon of an aryl ring A.
In some embodiments, $R^1$ is attached to a carbon of a heteroaryl ring A.
In some embodiments, $R^1$ is attached to a nitrogen of a heteroaryl ring A.

Particular embodiments wherein m=1 and n=1:
In some embodiments, $R^1$ is $C_1$-$C_6$ alkyl optionally substituted with one or more hydroxy, and $R^2$ is $C_1$-$C_6$ alkyl optionally substituted with one or more hydroxy.
In some embodiments, $R^1$ is 1-hydroxy-2-methylpropan-2-yl, and $R^2$ is methyl.
In some embodiments, $R^1$ is 2-hydroxy-2-propyl and $R^2$ is methyl.
In some embodiments, $R^1$ is 2-hydroxy-2-propyl and $R^2$ is isopropyl.
In some embodiments, $R^1$ is 2-hydroxy-2-propyl and $R^2$ is 2-hydroxy-2-propyl.
In some embodiments, $R^1$ is 2-hydroxy-2-propyl and $R^2$ is 1-hydroxyethyl.
In some embodiments, $R^1$ is hydroxymethyl and $R^2$ is methyl.
In some embodiments, $R^1$ is 1-hydroxyethyl and $R^2$ is methyl.
In some embodiments, $R^1$ is 2-hydroxyethyl and $R^2$ is methyl.
In some embodiments, $R^1$ is 1-hydroxy-2-propyl and $R^2$ is methyl.
In some embodiments, $R^1$ is $C_1$-$C_6$ alkyl optionally substituted with one or more hydroxy, and $R^2$ is $C_6$-$C_{10}$ aryl.
In some embodiments, $R^1$ is 2-hydroxy-2-propyl and $R^2$ is phenyl.
In some embodiments, $R^1$ is $C_1$-$C_6$ alkyl optionally substituted with one or more hydroxy, and $R^2$ is 5- to 10-membered heteroaryl.
In some embodiments, $R^1$ is 2-hydroxy-2-propyl and $R^2$ is pyridyl.
In some embodiments, $R^1$ is 2-hydroxy-2-propyl and $R^2$ is pyrazolyl.
In some embodiments, $R^1$ is $C_1$-$C_6$ alkyl optionally substituted with one or more hydroxy, and $R^2$ is $SF_5$.
In some embodiments, $R^1$ is $C_1$-$C_6$ alkyl optionally substituted with one or more hydroxy, and $R^2$ is $SC_1$-$C_6$ alkyl.
In some embodiments, $R^1$ is $C_1$-$C_6$ alkyl optionally substituted with one or more hydroxy, and $R^2$ is $S(O_2)C_1$-$C_6$ alkyl.
In some embodiments, $R^1$ is $C_1$-$C_6$ alkyl optionally substituted with one or more hydroxy, and $R^2$ is $S(O_2)CH_3$.
In some embodiments, $R^1$ is $C_1$-$C_6$ alkyl optionally substituted with one or more hydroxy, and $R^2$ is halo.
In some embodiments, $R^1$ is 2-hydroxy-2-propyl and $R^2$ is chloro.
In some embodiments, $R^1$ is 2-hydroxy-2-propyl and $R^2$ is fluoro.
In some embodiments, $R^1$ is $C_3$-$C_7$ cycloalkyl optionally substituted with one or more hydroxy, and $R^2$ is $C_1$-$C_6$ alkyl.
In some embodiments, $R^1$ is 1-hydroxy-1-cyclopropyl, and $R^2$ is methyl.
In some embodiments, $R^1$ is 1-hydroxy-1-cyclobutyl, and $R^2$ is methyl.
In some embodiments, $R^1$ is 1-hydroxy-1-cyclopentyl, and $R^2$ is methyl.
In some embodiments, $R^1$ is 1-hydroxy-1-cyclohexyl, and $R^2$ is methyl.

In some embodiments, $R^1$ is 3- to 7-membered heterocycloalkyl optionally substituted with one or more hydroxy, and $R^2$ is $C_1$-$C_6$ alkyl.
In some embodiments, $R^1$ is morpholinyl, and $R^2$ is methyl.
In some embodiments, $R^1$ is 1,3-dioxolan-2-yl, and $R^2$ is methyl.
In some embodiments, $R^1$ is 3- to 7-membered heterocycloalkyl optionally substituted with one or more hydroxy, and $R^2$ is halo.
In some embodiments, $R^1$ is 1,3-dioxolan-2-yl, and $R^2$ is fluoro.
In some embodiments, $R^1$ is 1,3-dioxolan-2-yl, and $R^2$ is chloro.
In some embodiments, $R^1$ is $C_1$-$C_6$ alkyl optionally substituted with one or more oxo, and $R^2$ is methyl.
In some embodiments, $R^1$ is $COCH_3$, and $R^2$ is methyl.
In some embodiments, $R^1$ is $C_1$-$C_6$ alkyl optionally substituted with one or more $C_1$-$C_6$ alkoxy, and $R^2$ is $C_1$-$C_6$ alkyl.
In some embodiments, $R^1$ is 2-methoxy-2-propyl, and $R^2$ is methyl.
In some embodiments, $R^1$ is $C_1$-$C_6$ alkyl optionally substituted with one or more $NR^8R^9$, and $R^2$ is $C_1$-$C_6$ alkyl.
In some embodiments, $R^1$ is (dimethylamino)methyl, and $R^2$ is methyl.
In some embodiments, $R^1$ is $C_1$-$C_6$ alkyl optionally substituted with one or more $NR^8R^9$, and $R^2$ is halo.
In some embodiments, $R^1$ is (dimethylamino)methyl, and $R^2$ is fluoro.
In some embodiments, $R^1$ is (dimethylamino)methyl, and $R^2$ is fluoro.
In some embodiments, $R^1$ is (methylamino)methyl, and $R^2$ is fluoro.
In some embodiments, $R^1$ is aminomethyl, and $R^2$ is fluoro.
In some embodiments, $R^1$ is $C_1$-$C_6$ alkyl, and $R^2$ is $C_1$-$C_6$ alkyl.
In some embodiments, $R^1$ is methyl, and $R^2$ is methyl.
In some embodiments, $R^2$ is 1-hydroxy-2-methylpropan-2-yl, and $R^1$ is methyl.
In some embodiments, $R^2$ is 2-hydroxy-2-propyl and $R^1$ is methyl.
In some embodiments, $R^2$ is 2-hydroxy-2-propyl and $R^1$ is isopropyl.
In some embodiments, $R^2$ is 2-hydroxy-2-propyl and $R^1$ is 1-hydroxyethyl.
In some embodiments, $R^2$ is hydroxymethyl and $R^1$ is methyl.
In some embodiments, $R^2$ is 1-hydroxyethyl and $R^1$ is methyl.
In some embodiments, $R^2$ is 2-hydroxyethyl and $R^1$ is methyl.
In some embodiments, $R^2$ is 1-hydroxy-2-propyl and $R^1$ is methyl.
In some embodiments, $R^2$ is $C_1$-$C_6$ alkyl optionally substituted with one or more hydroxy, and $R^1$ is $C_6$-$C_{10}$ aryl.
In some embodiments, $R^2$ is 2-hydroxy-2-propyl and $R^1$ is phenyl.
In some embodiments, $R^2$ is $C_1$-$C_6$ alkyl optionally substituted with one or more hydroxy, and $R^1$ is 5- to 10-membered heteroaryl.
In some embodiments, $R^2$ is 2-hydroxy-2-propyl and $R^1$ is pyridyl.
In some embodiments, $R^2$ is 2-hydroxy-2-propyl and $R^1$ is pyrazolyl.

In some embodiments, $R^2$ is $C_1$-$C_6$ alkyl optionally substituted with one or more hydroxy, and $R^1$ is $SF_5$.

In some embodiments, $R^2$ is $C_1$-$C_6$ alkyl optionally substituted with one or more hydroxy, and $R^1$ is $SC_1$-$C_6$ alkyl.

In some embodiments, $R^2$ is $C_1$-$C_6$ alkyl optionally substituted with one or more hydroxy, and $R^1$ is $S(O_2)C_1$-$C_6$ alkyl.

In some embodiments, $R^2$ is $C_1$-$C_6$ alkyl optionally substituted with one or more hydroxy, and $R^1$ is $S(O_2)CH_3$.

In some embodiments, $R^2$ is $C_1$-$C_6$ alkyl optionally substituted with one or more hydroxy, and $R^1$ is halo.

In some embodiments, $R^2$ is 2-hydroxy-2-propyl and $R^1$ is chloro.

In some embodiments, $R^2$ is 2-hydroxy-2-propyl and $R^1$ is fluoro.

In some embodiments, $R^2$ is $C_3$-$C_7$ cycloalkyl optionally substituted with one or more hydroxy, and $R^1$ is $C_1$-$C_6$ alkyl.

In some embodiments, $R^2$ is 1-hydroxy-1-cyclopropyl, and $R^1$ is methyl.

In some embodiments, $R^2$ is 1-hydroxy-1-cyclobutyl, and $R^1$ is methyl.

In some embodiments, $R^2$ is 1-hydroxy-1-cyclopentyl, and $R^1$ is methyl.

In some embodiments, $R^2$ is 1-hydroxy-1-cyclohexyl, and $R^1$ is methyl.

In some embodiments, $R^2$ is 3- to 7-membered heterocycloalkyl optionally substituted with one or more hydroxy, and $R^1$ is $C_1$-$C_6$ alkyl.

In some embodiments, $R^2$ is morpholinyl, and $R^1$ is methyl.

In some embodiments, $R^2$ is 1,3-dioxolan-2-yl, and $R^1$ is methyl.

In some embodiments, $R^2$ is 3- to 7-membered heterocycloalkyl optionally substituted with one or more hydroxy, and $R^1$ is halo.

In some embodiments, $R^2$ is 1,3-dioxolan-2-yl, and $R^1$ is fluoro.

In some embodiments, $R^2$ is 1,3-dioxolan-2-yl, and $R^1$ is chloro.

In some embodiments, $R^2$ is $C_1$-$C_6$ alkyl optionally substituted with one or more oxo, and $R^1$ is methyl.

In some embodiments, $R^2$ is $COCH_3$, and $R^1$ is methyl.

In some embodiments, $R^2$ is $C_1$-$C_6$ alkyl optionally substituted with one or more $C_1$-$C_6$ alkoxy, and $R^1$ is $C_1$-$C_6$ alkyl.

In some embodiments, $R^2$ is 2-methoxy-2-propyl, and $R^1$ is methyl.

In some embodiments, $R^2$ is $C_1$-$C_6$ alkyl optionally substituted with one or more $NR^8R^9$, and $R^1$ is $C_1$-$C_6$ alkyl.

In some embodiments, $R^2$ is (dimethylamino)methyl, and $R^1$ is methyl.

In some embodiments, $R^2$ is $C_1$-$C_6$ alkyl optionally substituted with one or more $NR^8R^9$, and $R^1$ is halo.

In some embodiments, $R^2$ is (dimethylamino)methyl, and $R^1$ is fluoro.

In some embodiments, $R^2$ is (methylamino)methyl, and $R^1$ is fluoro.

In some embodiments, $R^2$ is aminomethyl, and $R^1$ is fluoro.

In some embodiments, $R^2$ is $C_1$-$C_6$ alkoxy, and $R^1$ is $C_1$-$C_6$ alkyl optionally substituted with one or more $NR^8R^9$.

In some embodiments, $R^2$ is methoxy, and $R^1$ is (dimethylamino)methyl.

In some embodiments, $R^1$ and $R^2$ are each attached to a carbon of an aryl ring A.

In some embodiments, $R^1$ and $R^2$ are each attached to a carbon of a heteroaryl ring A.

In some embodiments, $R^1$ is attached to a carbon and $R^2$ is attached to a nitrogen of a heteroaryl ring A.

In some embodiments, $R^2$ is attached to a carbon and $R^1$ is attached to a nitrogen of a heteroaryl ring A.

In some embodiments, $R^1$ and $R^2$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_5$ aliphatic carbocyclic ring.

In some embodiments, $R^1$ and $R^2$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a $C_6$ aliphatic carbocyclic ring.

In some embodiments, $R^1$ and $R^2$ are on adjacent atoms, and taken together with the atoms connecting them, form a $C_6$ aromatic carbocyclic ring.

In some embodiments, $R^1$ and $R^2$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 5-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 5-membered heteroaromatic ring containing 1 or 2 heteroatoms independently selected from O, N, and S.

In some embodiments, $R^1$ and $R^2$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^1$ and $R^2$ are on adjacent atoms, and taken together with the atoms connecting them, form a 6-membered aliphatic heterocyclic ring containing 1 or 2 heteroatoms independently selected from O, N, and S.

In some embodiments, $R^1$ and $R^2$ are on adjacent atoms, and taken together with the atoms connecting them, form a 6-membered heteroaromatic ring containing 1 or 2 heteroatoms independently selected from O, N, and S.

In some embodiments, $R^1$ and $R^2$ are different.

In some embodiments, $R^1$ and $R^2$ are different, and $R^2$ comprises a carbonyl group.

In some embodiments, $R^1$ and $R^2$ are different, and $R^2$ comprises 1 or 2 (e.g., 1) nitrogen atoms.

In some embodiments, $R^1$ and $R^2$ are different, and $R^2$ comprises 1 or 2 (e.g., 1) oxygen atoms.

In some embodiments, $R^1$ and $R^2$ are different, and $R^2$ comprises a sulfur atom.

In some embodiments, $R^2$ and $R^1$ are different, and $R^2$ comprises a carbonyl group.

In some embodiments, $R^2$ and $R^1$ are different, and $R^2$ comprises 1 or 2 (e.g., 1) nitrogen atoms.

In some embodiments, $R^2$ and $R^1$ are different, and $R^2$ comprises 1 or 2 (e.g., 1) oxygen atoms.

In some embodiments, $R^2$ and $R^1$ are different, and $R^2$ comprises a sulfur atom.

In some embodiments, $R^1$ and $R^2$ are the same.

In some embodiments, $R^1$ is para or meta to $R^2$.

In some embodiments, $R^1$ is para or ortho to $R^2$.

In some embodiments, $R^1$ is ortho or meta to $R^2$. In some embodiments, $R^1$ is para to $R^2$.

In some embodiments, $R^1$ is meta to $R^2$.

In some embodiments, $R^1$ is ortho to $R^2$.

The Variables o and p

In some embodiments, o=1 or 2.

In some embodiments, o=1.

In some embodiments, o=2.

In some embodiments, p=0, 1, 2, or 3.

In some embodiments, p=0.

In some embodiments, p=1.

In some embodiments, p=2.

In some embodiments, o=1 and p=0.

In some embodiments, o=2 and p=0.

In some embodiments, o=1 and p=1.

In some embodiments, o=1 and p=2.

In some embodiments, o=2 and p=1.

In some embodiments, o=2 and p=2.

In some embodiments, o=2 and p=3.

The Ring B and Substitutions on the Ring B

In some embodiments, B is a 5- to 10-membered monocyclic or bicyclic heteroaryl or a $C_6$-$C_{10}$ monocyclic or bicyclic aryl, such as phenyl.

In some embodiments, B is a 5- to 6-membered monocyclic heteroaryl or a $C_6$ monocyclic aryl.

In some embodiments, B is a 5- to 10-membered monocyclic or bicyclic heteroaryl.

In some embodiments, B is a $C_6$-$C_{10}$ monocyclic or bicyclic aryl.

In some embodiments, B is a 5-membered heteroaryl.

In some embodiments, B is a 7-10 membered monocyclic or bicyclic heteroaryl.

In some embodiments, B is phenyl substituted with 1 or 2 $R^6$ and optionally substituted with 1, 2, or 3 $R^7$.

In some embodiments, B is pyridyl substituted with 1 or 2 $R^6$ and optionally substituted with 1, 2, or 3 $R^7$.

In some embodiments, B is indazolyl substituted with 1 or 2 $R^6$ and optionally substituted with 1, 2, or 3 $R^7$.

In some embodiments, B is pyrazolyl substituted with 1 or 2$R^6$ and optionally substituted with 1 or 2 $R^7$.

In some embodiments, B is phenyl, o is 1 or 2, and p is 0, 1, 2, or 3.

In some embodiments, B is phenyl, o is 1, and p is 0, 1, 2, or 3.

In some embodiments, B is phenyl, o is 2, and p is 0, 1, 2, or 3.

In some embodiments, B is one of the rings disclosed hereinbelow, substituted as disclosed hereinbelow, wherein in each case the bond that is shown as being broken by the wavy line  connects B to the NH(CO) group of Formula AA.

In some embodiments, the substituted ring B

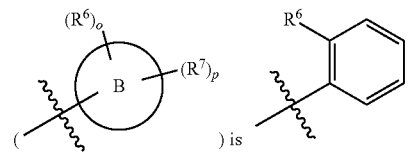

In some embodiments, the substituted ring B

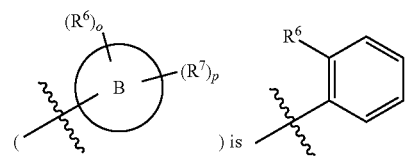

In some embodiments, the substituted ring B is

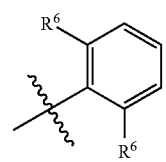

In some embodiments, the substituted ring B is

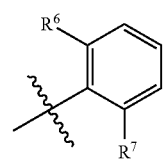

In some embodiments, the substituted ring B is

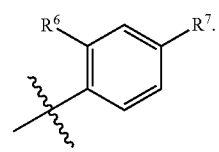

In some embodiments, the substituted ring B is

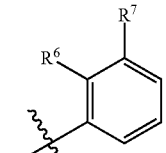

In some embodiments, the substituted ring B is

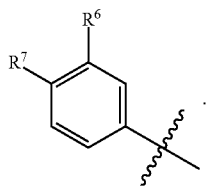

In some embodiments, the substituted ring B is

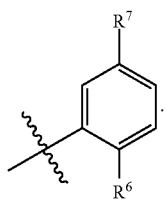

In some embodiments, the substituted ring B is

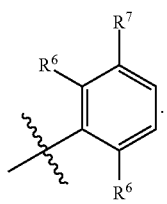

In some embodiments, the substituted ring B is


In some embodiments, the substituted ring B is

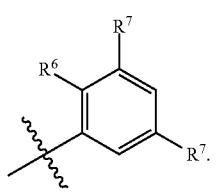

In some embodiments, the substituted ring B is

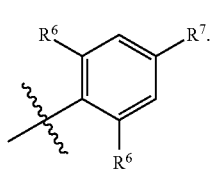

In some embodiments, the substituted ring B is

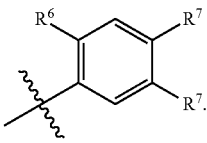

In some embodiments, the substituted ring B is

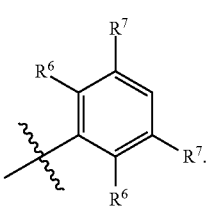

In some embodiments, the substituted ring B is


In some embodiments, the substituted ring B is

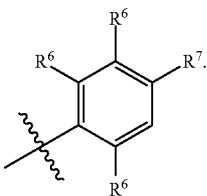

In some embodiments, the substituted ring B is

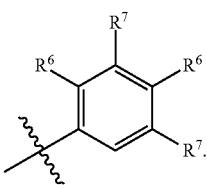

In some embodiments, the substituted ring B is

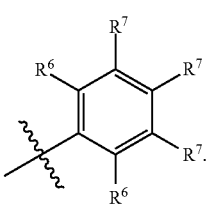

In some embodiments, the substituted ring B is

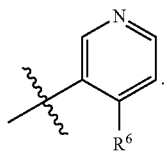

In some embodiments, the substituted ring B is

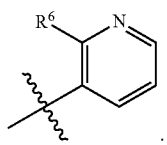

In some embodiments, the substituted ring B is

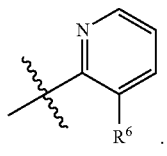

In some embodiments, the substituted ring B is

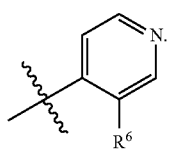

In some embodiments, the substituted ring B is

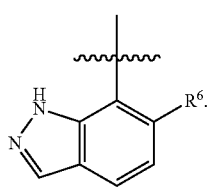

In some embodiments, the substituted ring B is

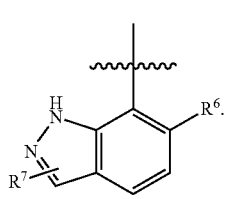

In some embodiments, the substituted ring B is

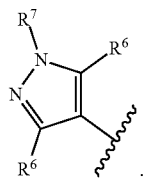

In some embodiments, the substituted ring B is

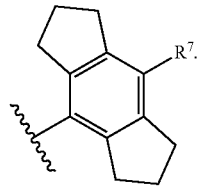

In some embodiments, the substituted ring B is

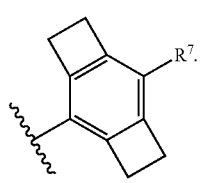

In some embodiments, the substituted ring B is

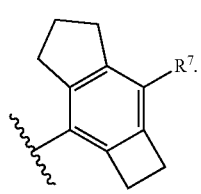

In some embodiments, the substituted ring B is

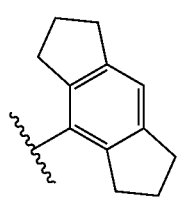

In some embodiments, the substituted ring B is

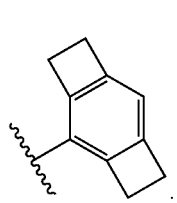 [SMILES: *c1c2c(cc3c1CC3)CC2]

In some embodiments, the substituted ring B is

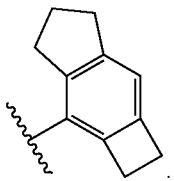 [SMILES: *c1c2c(cc3c1CC3)CCC2]

In some embodiments, the substituted ring B is

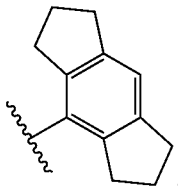

In some embodiments, the substituted ring B is

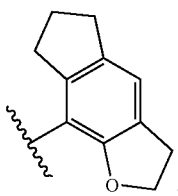

In some embodiments, the substituted ring B is

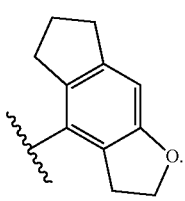 [SMILES: *c1c2c(cc3c1CCO3)CCC2]

In some embodiments, the substituted ring B is

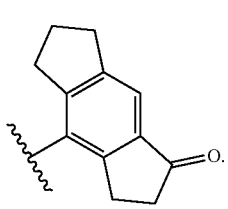 [SMILES: *c1c2c(cc3c1CCC3=O)CCC2]

In some embodiments, the substituted ring B is

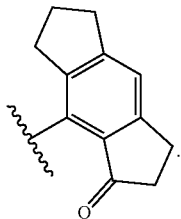 [SMILES: *c1c2c(cc3c1C(=O)CC3)CCC2]

In some embodiments, the substituted ring B is

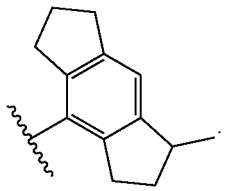 [SMILES: *c1c2c(cc3c1CCC3C)CCC2]

In some embodiments, the substituted ring B is

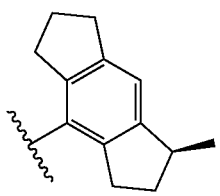

In some embodiments, the substituted ring B is

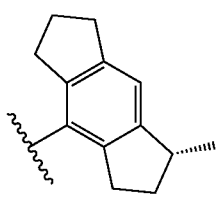

In some embodiments, the substituted ring B is

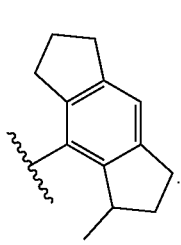 [SMILES: *c1c2c(cc3c1C(C)CC3)CCC2]

In some embodiments, the substituted ring B is

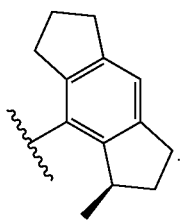 [SMILES: *c1c2c(cc3c1[C@H](C)CC3)CCC2]

In some embodiments, the substituted ring B is

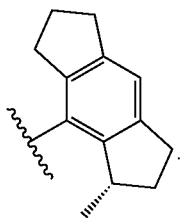 [SMILES: *c1c2c(cc3c1[C@@H](C)CC3)CCC2]

In some embodiments, the substituted ring B is

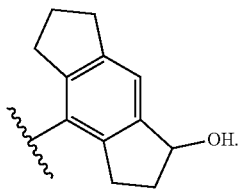

In some embodiments, the substituted ring B is

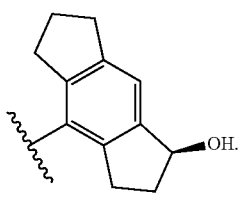 [SMILES: *c1c2c(cc3c1CC[C@@H]3O)CCC2]

In some embodiments, the substituted ring B is

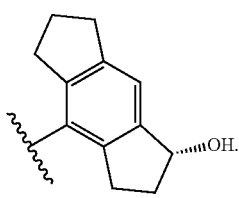 [SMILES: *c1c2c(cc3c1CC[C@H]3O)CCC2]

In some embodiments, the substituted ring B is

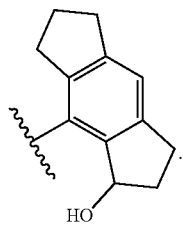 [SMILES: *c1c2c(cc3c1C(O)CC3)CCC2]

In some embodiments, the substituted ring B is

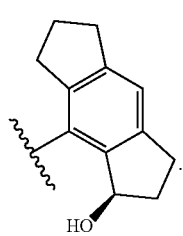 [SMILES: *c1c2c(cc3c1[C@H](O)CC3)CCC2]

In some embodiments, the substituted ring B is HOG

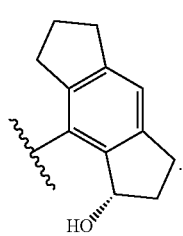 [SMILES: *c1c2c(cc3c1[C@@H](O)CC3)CCC2]

In some embodiments, the substituted ring B is

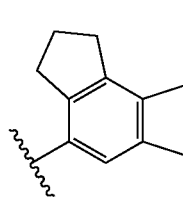

In some embodiments, the substituted ring B is

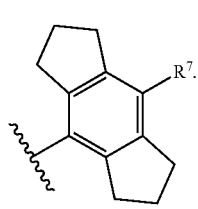

The Groups $R^6$ and $R^7$

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_6$ aliphatic carbocyclic ring or at least one 5- to 6-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl; or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are unsubstituted;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, COG-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one 5- to 8-membered heterocyclic ring containing 1 or 2 heteroatoms independently selected from O, N, and S, wherein the heterocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more hydroxy or oxo.

In some embodiments, at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more $C_1$-$C_6$ alkyl.

In some embodiments, o=1; p=0; and
$R^6$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl.

In some embodiments, o=1; p=1; and
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, o=1 or 2; p=1, 2, or 3; and
$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, NHCOC$_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and OC$_1$-$C_6$ alkyl.

In some embodiments, o=2; p=1; and each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^1$R$^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR$^8$R$^9$, SF$_5$, S(O$_2$)C$_1$-$C_6$alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR$^8$R$^9$, =NR$^{10}$, COOC$_1$-$C_6$ alkyl, $C_6$-$C_{10}$ aryl, and CONR$^8$R$^9$.

In some embodiments, o=2; p=2 or 3; and each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR$^8$R$^9$, SF$_5$, S(O$_2$)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ (e.g., $C_4$-$C_6$) carbocyclic ring (e.g., aliphatic carbocyclic ring) or at least one 5-to-7-membered (e.g., 5-to-6-membered) heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, NR$^8$R$^9$, CH$_2$NR$^8$R$^9$, =NR$^{10}$, COOC$_1$-$C_6$ alkyl, $C_6$-$C_{10}$ aryl, and CONR$^8$R$^9$.

In some embodiments, o=1 or 2; p=1, 2, or 3; and $R^6$ and $R^7$ are each independently selected from $C_1$-$C_6$ alkyl, $C_1$-$C_6$ alkoxy, halo, CN, NO$_2$, COC$_1$-$C_6$ alkyl, CO$_2$C$_1$-$C_6$ alkyl, $C_6$-$C_{10}$ aryl, 5- to 10-membered heteroaryl, CONR$^8$R$^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_8$ carbocyclic ring, wherein the carbocyclic ring is optionally independently substituted with one or more hydroxy or oxo.

In some embodiments, o=1 or 2; p=1, 2, or 3; and $R^6$ and $R^7$ are each independently selected from $C_1$-$C_6$ alkyl, $C_1$-$C_6$ alkoxy, halo, CN, NO$_2$, COG-$C_6$ alkyl, CO$_2$C$_1$-$C_6$ alkyl, $C_6$-$C_{10}$ aryl, 5- to 10-membered heteroaryl, CONR$^8$R$^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo.

In some embodiments, o=1 or 2; p=1, 2, or 3; and one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR$^8$R$^9$, =NR$^{10}$, COOC$_1$-$C_6$ alkyl, $C_6$-$C_{10}$ aryl, and CONR$^8$R$^9$.

In some embodiments, o=1 or 2; p=1, 2, or 3; and one $R^6$ and one $R^7$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR$^8$R$^9$, =NR$^{10}$, COOC$_1$-$C_6$ alkyl, $C_6$-$C_{10}$ aryl, and CONR$^8$R$^9$.

In some embodiments, o=1 or 2; p=1, 2, or 3; and one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$ $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$ $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, one pair of one $R^6$ and one $R^7$ taken together with the atoms connecting them independently form a $C_4$ carbocyclic ring, and the other pair of one $R^6$ and one $R^7$ taken together with the atoms connecting them independently form a $C_5$ carbocyclic ring, wherein each of $C_4$ and $C_5$ carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, one pair of one $R^6$ and one $R^7$ taken together with the atoms connecting them independently form a $C_5$ carbocyclic ring, and the other pair of one $R^6$ and one $R^7$ taken together with the atoms connecting them independently form a 5- to 8-membered heterocyclic ring containing 1 or 2 heteroatoms independently selected from O, N, and S (e.g., a 5-membered heterocyclic ring, e.g., 5-membered heterocyclic ring containing 1 heteroatom), wherein each of carbocyclic and heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms, and each pair of one $R^6$ and one $R^7$ taken together with the atoms connecting them independently form a $C_4$-$C_8$ carbocyclic ring or a 5- to 8-membered heterocyclic ring containing 1 or 2 heteroatoms independently selected from O, N, and S, wherein the carbocyclic ring or heterocyclic ring is unsubstituted.

Particular embodiments wherein o=1; p=0:

In some embodiments, $R^6$ is $C_1$-$C_6$ alkyl.

In some embodiments, $R^6$ is isopropyl.

In some embodiments, $R^6$ is ethyl.

In some embodiments, $R^6$ is methyl.

In some embodiments, $R^6$ is $C_1$-$C_6$ alkyl substituted with one or more halo.

In some embodiments, $R^6$ is trifluoromethyl.

In some embodiments, $R^6$ is trifluoromethoxy.

In some embodiments, $R^6$ is $C_3$-$C_7$ cycloalkyl.

In some embodiments, $R^6$ is cyclopropyl.

In some embodiments, $R^6$ is halo.

In some embodiments, $R^6$ is chloro.

In some embodiments, $R^6$ is fluoro.

In some embodiments, $R^6$ is cyano.

In some embodiments, $R^6$ is attached to a carbon of an aryl ring B.

In some embodiments, $R^6$ is attached to a carbon of a heteroaryl ring B.

In some embodiments, $R^6$ is attached to a nitrogen of a heteroaryl ring B.

Particular embodiments wherein o=1 or 2; p=1, 2, or 3:

In some embodiments, at least one $R^6$ is $C_1$-$C_6$ alkyl, and at least one $R^7$ is $C_1$-$C_6$ alkyl optionally substituted with one or more halo.

In some embodiments, at least one $R^6$ is $C_1$-$C_6$ alkyl and at least one $R^7$ is $C_1$-$C_6$ alkyl.

In some embodiments, at least one $R^6$ is isopropyl and at least one $R^7$ is methyl.

In some embodiments, at least one $R^6$ is isopropyl and at least one $R^7$ is isopropyl.

In some embodiments, o=1; p=1; $R^6$ is isopropyl; and $R^7$ is isopropyl.

In some embodiments, at least one $R^6$ is $C_1$-$C_6$ alkyl, and at least one $R^7$ is $C_1$-$C_6$ alkyl substituted with one or more halo.

In some embodiments, at least one $R^6$ is isopropyl and at least one $R^7$ is trifluoromethyl.

In some embodiments, at least one $R^6$ is $C_1$-$C_6$ alkyl, and at least one $R^7$ is $C_3$-$C_7$ cycloalkyl.

In some embodiments, at least one $R^6$ is isopropyl and at least one $R^7$ is cyclopropyl.

In some embodiments, o=1; p=1; $R^6$ is isopropyl; and $R^7$ is cyclopropyl.

In some embodiments, at least one $R^6$ is $C_1$-$C_6$ alkyl, and at least one $R^7$ is halo.

In some embodiments, at least one $R^6$ is isopropyl and at least one $R^7$ is halo.

In some embodiments, at least one $R^6$ is isopropyl and at least one $R^7$ is chloro.

In some embodiments, at least one $R^6$ is isopropyl and at least one $R^7$ is fluoro.

In some embodiments, o=1; p=1; $R^6$ is isopropyl; and $R^7$ is chloro.

In some embodiments, o=2; p=1; at least one $R^6$ is isopropyl; and $R^7$ is chloro.

In some embodiments, o=1; p=1; $R^6$ is isopropyl; and $R^7$ is fluoro.

In some embodiments, o=2; p=1; at least one $R^6$ is isopropyl; and $R^7$ is fluoro.

In some embodiments, o=2; p=2; at least one $R^6$ is isopropyl; and at least one $R^7$ is fluoro.

In some embodiments, o=2; p=2; at least one $R^6$ is isopropyl; one $R^7$ is fluoro; and the other $R^7$ is cyano.

In some embodiments, o=2; p=3; at least one $R^6$ is isopropyl; two $R^1$ are fluoro; and one $R^7$ is chloro.

In some embodiments, o=2; p=1; at least one $R^6$ is ethyl; and $R^7$ is fluoro.

In some embodiments, o=2; p=1; one $R^6$ is isopropyl; the other $R^6$ is trifluoromethyl; and $R^7$ is chloro.

In some embodiments, at least one $R^6$ is $C_1$-$C_6$ alkyl, and at least one $R^7$ is cyano.

In some embodiments, at least one $R^6$ is isopropyl and at least one $R^7$ is cyano.

In some embodiments, o=1; p=1; $R^6$ is isopropyl; and $R^7$ is cyano.

In some embodiments, o=2; p=1; at least one $R^6$ is isopropyl; and $R^7$ is cyano.

In some embodiments, at least one $R^6$ is $C_3$-$C_7$ cycloalkyl, and at least one $R^7$ is $C_3$-$C_7$ cycloalkyl.

In some embodiments, at least one $R^6$ is cyclopropyl, and at least one $R^7$ is cyclopropyl.

In some embodiments, at least one $R^6$ is $C_3$-$C_7$ cycloalkyl, and at least one $R^7$ is halo.

In some embodiments, at least one $R^6$ is cyclopropyl and at least one $R^7$ is halo.

In some embodiments, at least one $R^6$ is cyclopropyl and at least one $R^7$ is chloro.

In some embodiments, at least one $R^6$ is cyclopropyl and at least one $R^7$ is fluoro.

In some embodiments, o=1; p=1; $R^6$ is cyclopropyl; and $R^7$ is chloro.

In some embodiments, o=1; p=1; $R^6$ is cyclopropyl; and $R^7$ is fluoro.

In some embodiments, at least one $R^6$ is $C_1$-$C_6$ alkyl, and at least one $R^7$ is $C_1$-$C_6$ alkoxy optionally substituted with one or more halo.

In some embodiments, at least one $R^6$ is isopropyl, and at least one $R^7$ is $C_1$-$C_6$ alkoxy.

In some embodiments, at least one $R^6$ is isopropyl, and at least one $R^7$ is methoxy.

In some embodiments, o=1; p=1; $R^6$ is isopropyl, and $R^7$ is methoxy.

In some embodiments, o=2; p=1; at least one $R^6$ is isopropyl, and $R^7$ is methoxy.

In some embodiments, at least one $R^6$ is $C_1$-$C_6$ alkyl, and at least one $R^7$ is $C_1$-$C_6$ alkoxy substituted with one or more halo.

In some embodiments, at least one $R^6$ is isopropyl, and at least one $R^7$ is trifluoromethoxy.

In some embodiments, at least one $R^6$ is isopropyl, and at least one $R^7$ is difluoromethoxy.

In some embodiments, at least one $R^6$ is halo, and at least one $R^7$ is $C_1$-$C_6$ haloalkyl optionally substituted with hydroxy.

In some embodiments, o=1; p=1; $R^6$ is chloro, and $R^7$ is trifluoromethyl.

In some embodiments, at least one $R^6$ is halo, and at least one $R^7$ is $C_1$-$C_6$ haloalkoxy.

In some embodiments, at least one $R^6$ is chloro, and at least one $R^7$ is trifluoromethoxy.

In some embodiments, o=1; p=1; $R^6$ is chloro, and $R^7$ is trifluoromethoxy.

In some embodiments, at least one $R^6$ is $C_1$-$C_6$ alkoxy; and at least one $R^7$ is halo.

In some embodiments, o=1; p=2; $R^6$ is $C_1$-$C_6$ alkoxy; and at least one $R^7$ is chloro.

In some embodiments, at least one $R^7$ is $C_1$-$C_6$ alkyl, and at least one $R^6$ is $C_1$-$C_6$ alkyl optionally substituted with one or more halo.

In some embodiments, at least one $R^7$ is isopropyl and at least one $R^6$ is methyl.

In some embodiments, at least one $R^7$ is $C_1$-$C_6$ alkyl, and at least one $R^6$ is $C_1$-$C_6$ alkyl substituted with one or more halo.

In some embodiments, at least one $R^7$ is isopropyl and at least one $R^6$ is trifluoromethyl.

In some embodiments, at least one $R^7$ is $C_1$-$C_6$ alkyl, and at least one $R^6$ is $C_3$-$C_7$ cycloalkyl.

In some embodiments, at least one $R^7$ is isopropyl and at least one $R^6$ is cyclopropyl.

In some embodiments, o=1; p=1; $R^7$ is isopropyl; and $R^6$ is cyclopropyl.

In some embodiments, at least one $R^7$ is $C_1$-$C_6$ alkyl, and at least one $R^6$ is halo.

In some embodiments, at least one $R^7$ is isopropyl and at least one $R^6$ is halo.

In some embodiments, at least one $R^7$ is isopropyl and least one $R^6$ is chloro.

In some embodiments, at least one $R^7$ is isopropyl and least one $R^6$ is fluoro.

In some embodiments, o=1; p=1; $R^7$ is isopropyl; and $R^6$ is chloro.

In some embodiments, o=2; p=1; $R^7$ is isopropyl; and at least one $R^6$ is chloro.

In some embodiments, o=1; p=1; $R^7$ is isopropyl; and $R^6$ is fluoro.

In some embodiments, o=2; p=1; $R^7$ is isopropyl; and at least one $R^6$ is fluoro.

In some embodiments, o=2; p=2; $R^7$ is isopropyl; and at least one $R^6$ is fluoro.

In some embodiments, o=2; p=2; at least one $R^7$ is isopropyl; one $R^6$ is fluoro; and the other $R^6$ is cyano.

In some embodiments, o=2; p=1; $R^7$ is ethyl; and at least one $R^6$ is fluoro.

In some embodiments, o=1; p=2; one $R^7$ is isopropyl; the other $R^7$ is trifluoromethyl; and $R^6$ is chloro.

In some embodiments, at least one $R^7$ is $C_1$-$C_6$ alkyl, and at least one $R^6$ is cyano.

In some embodiments, at least one $R^7$ is isopropyl and at least one $R^6$ is cyano.

In some embodiments, o=1; p=1; $R^7$ is isopropyl; and $R^6$ is cyano.

In some embodiments, o=2; p=1; $R^7$ is isopropyl; and at least one $R^6$ is cyano.

In some embodiments, at least one $R^7$ is $C_3$-$C_7$ cycloalkyl, and at least one $R^6$ is $C_3$-$C_7$ cycloalkyl.

In some embodiments, at least one $R^7$ is cyclopropyl, and at least one $R^6$ is cyclopropyl.

In some embodiments, at least one $R^7$ is $C_3$-$C_7$ cycloalkyl, and at least one $R^6$ is halo.

In some embodiments, at least one $R^7$ is cyclopropyl and at least one $R^6$ is halo.

In some embodiments, at least one $R^7$ is cyclopropyl and at least one $R^6$ is chloro.

In some embodiments, at least one $R^7$ is cyclopropyl and at least one $R^6$ is fluoro.

In some embodiments, o=1; p=1; $R^7$ is cyclopropyl; and $R^6$ is chloro.

In some embodiments, o=1; p=1; $R^7$ is cyclopropyl; and $R^6$ is fluoro.

In some embodiments, at least one $R^7$ is $C_1$-$C_6$ alkyl, and at least one $R^6$ is $C_1$-$C_6$ alkoxy optionally substituted with one or more halo.

In some embodiments, at least one $R^7$ is isopropyl, and at least one $R^6$ is $C_1$-$C_6$ alkoxy.

In some embodiments, at least one $R^7$ is isopropyl, and at least one $R^6$ is methoxy.

In some embodiments, o=1; p=1; $R^7$ is isopropyl, and $R^6$ is methoxy.

In some embodiments, o=2; p=1; $R^7$ is isopropyl, and at least one $R^6$ is methoxy.

In some embodiments, at least one $R^7$ is $C_1$-$C_6$ alkyl, and at least one $R^6$ is $C_1$-$C_6$ alkoxy substituted with one or more halo.

In some embodiments, at least one $R^7$ is isopropyl, and at least one $R^6$ is trifluoromethoxy.

In some embodiments, at least one $R^7$ is halo, and at least one $R^6$ is $C_1$-$C_6$ haloalkyl optionally substituted with one or more hydroxy.

In some embodiments, o=1; p=1; $R^7$ is chloro, and $R^6$ is trifluoromethyl.

In some embodiments, at least one $R^7$ is halo, and at least one $R^6$ is $C_1$-$C_6$ haloalkoxy.

In some embodiments, at least one $R^7$ is chloro, and at least one $R^6$ is trifluoromethoxy.

In some embodiments, o=1; p=1; $R^7$ is chloro, and $R^6$ is trifluoromethoxy.

In some embodiments, at least one $R^7$ is $C_1$-$C_6$ alkoxy; and at least one $R^6$ is halo.

In some embodiments, o=1; p=2; at least one $R^7$ is $C_1$-$C_6$ alkoxy; and $R^6$ is chloro.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

In some embodiments, one $R^6$ and one $R^7$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_5$ aliphatic carbocyclic ring.

In some embodiments, $R^6$ and $R^7$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a $C_6$ aliphatic carbocyclic ring.

In some embodiments, $R^6$ and $R^7$ are on adjacent atoms, and taken together with the atoms connecting them, form a $C_6$ aromatic carbocyclic ring.

In some embodiments, $R^6$ and $R^7$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 5-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 5-membered heteroaromatic ring containing 1 or 2 heteroatoms independently selected from O, N, and S.

In some embodiments, $R^6$ and $R^7$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, $R^6$ and $R^7$ are on adjacent atoms, and taken together with the atoms connecting them, form a 6-membered aliphatic heterocyclic ring containing 1 or 2 heteroatoms independently selected from O, N, and S.

In some embodiments, $R^6$ and $R^7$ are on adjacent atoms, and taken together with the atoms connecting them, form a 6-membered heteroaromatic ring containing 1 or 2 heteroatoms independently selected from O, N, and S.

In some embodiments, one $R^6$ and one $R^7$ are on adjacent atoms, and taken together with the atoms connecting them, form a $C_4$-$C_8$ carbocyclic ring or a 5- to 8-membered heterocyclic ring containing 1 or 2 heteroatoms independently selected from O, N, and S, wherein the ring is fused to the B ring at the 2- and 3-positions relative to the bond connecting the B ring to the NH(CO) group.

In some embodiments, o=1; p=2; and
one pair of one $R^6$ and one $R^7$, are on adjacent atoms; and said pair of one $R^6$ and one $R^7$ taken together with the atoms connecting them form form a $C_4$-$C_8$ carbocyclic ring or a 5- to 8-membered heterocyclic ring containing 1 or 2 heteroatoms independently selected from O, N, and S, wherein the ring is fused to the B ring at the 2- and 3-positions relative to the bond connecting the B ring to the $NR^3$(CO) group.

In some embodiments, o=1; p=2; and
one pair of one $R^6$ and one $R^7$, are on adjacent atoms; and said pair of one $R^6$ and one $R^7$ taken together with the atoms connecting them form form a $C_4$-$C_8$ carbocyclic ring optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2; and
one pair of one $R^6$ and one $R^7$, are on adjacent atoms; and said pair of one $R^6$ and one $R^7$ taken together with the atoms connecting them form form a $C_4$-$C_8$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2; and
one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_4$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_4$ aliphatic carbocyclic ring and the other pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^1$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^1$ taken together with the atoms connecting them form a $C_6$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aromatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^1$ taken together with the atoms connecting them form a 6-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms independently selected from O, N, and S.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_{4-8}$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$;

and the other pair of one $R^6$ and one $R^7$ taken together with the atoms connecting them form a 5- to 8-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.

In some embodiments, o=2; p=2 or 3; and two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and two pairs, each of one $R^6$ and one $R^7$, are on adjacent atoms, and each pair of one $R^6$ and one $R^1$ taken together with the atoms connecting them independently form a $C_4$-$C_8$ carbocyclic ring or a 5- to 8-membered heterocyclic ring containing 1 or 2 heteroatoms independently selected from O, N, and S, wherein one of the two rings is fused to the B ring at the 2- and 3-positions relative to the bond connecting the B ring to the $NR^3$(CO) group, and the other of the two rings is fused to the B ring at the 5- and 6-positions relative to the bond connecting the B ring to the NH(CO) group.

In some embodiments, o=2; p=2 or 3; and two pairs, each of one $R^6$ and one $R^7$, are on adjacent atoms, and each pair of one $R^6$ and one $R^1$ taken together with the atoms connecting them independently form a $C_4$-$C_8$ carbocyclic ring or a 5- to 8-membered heterocyclic ring containing 1 or 2 heteroatoms independently selected from O, N, and S, wherein one of the two rings is fused to the B ring at the 2- and 3-positions relative to the bond connecting the B ring to the $NR^3$(CO) group, and the other of the two rings is fused to the B ring at the 4- and 5-positions relative to the bond connecting the B ring to the NH(CO) group.

In some embodiments, o=2; p=2; and two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2; and two pairs, each of one $R^6$ and one $R^7$, are on adjacent atoms, one pair of one $R^6$ and one $R^7$ taken together with the atoms connecting them form a $C_4$ aliphatic carbocyclic ring, and the other pair of one $R^6$ and one $R^7$ taken together with the atoms connecting them form a $C_5$ aliphatic carbocyclic ring.

In some embodiments, o=2; p=2; and two pairs, each of one $R^6$ and one $R^7$, are on adjacent atoms, and each pair of one $R^6$ and one $R^7$ taken together with the atoms connecting them form a $C_4$ aliphatic carbocyclic ring.

In some embodiments, o=2; p=2; and two pairs, each of one $R^6$ and one $R^7$, are on adjacent atoms, one pair of one $R^6$ and one $R^7$ taken together with the atoms connecting them form a $C_5$ aliphatic carbocyclic ring, and the other pair of one $R^6$ and one $R^7$ taken together with the atoms connecting them form a 5-membered heterocyclic ring containing 1 or 2 heteroatoms independently selected from O, N, and S.

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is halo (e.g., Cl or F).

In some embodiments, o=2; p=3; and two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is CN.

In some embodiments, one $R^7$ is pyrazolyl and is para to the bond connecting the B ring to the NH(CO) group of Formula AA.

In some embodiments, one $R^7$ is 3-pyrazolyl and is para to the bond connecting the B ring to the NH(CO) group of Formula AA.

In some embodiments, one $R^7$ is 4-pyrazolyl and is para to the bond connecting the B ring to the NH(CO) group of Formula AA.

In some embodiments, one $R^7$ is 5-pyrazolyl and is para to the bond connecting the B ring to the NH(CO) group of Formula AA.

In some embodiments, one $R^7$ is thiazolyl and is para to the bond connecting the B ring to the NH(CO) group of Formula AA.

In some embodiments, one $R^7$ is 4-thiazolyl and is para to the bond connecting the B ring to the NH(CO) group of Formula AA.

In some embodiments, one $R^7$ is 5-thiazolyl and is para to the bond connecting the B ring to the NH(CO) group of Formula AA.

In some embodiments, one $R^7$ is furyl and is para to the bond connecting the B ring to the NH(CO) group of Formula AA.

In some embodiments, one $R^7$ is 2-furyl and is para to the bond connecting the B ring to the NH(CO) group of Formula AA.

In some embodiments, one $R^7$ is thiophenyl and is para to the bond connecting the B ring to the NH(CO) group of Formula AA.

In some embodiments, one $R^7$ is 2-thiophenyl and is para to the bond connecting the B ring to the NH(CO) group of Formula AA.

In some embodiments, one $R^7$ is phenyl and is para to the bond connecting the B ring to the NH(CO) group of Formula AA.

In some embodiments, one $R^7$ is cycloalkenyl (e.g., cyclopentenyl, e.g., 1-cyclopentenyl) and is para to the bond connecting the B ring to the $NR^3$(CO) group of Formula AA.

In some embodiments, one $R^7$ is phenyl optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the NH(CO) group of Formula AA.

In some embodiments, one $R^7$ is phenyl optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl, or methylenedioxyphenyl and is para to the bond connecting the B ring to the NH(CO) group of Formula AA.

In some embodiments, one $R^7$ is phenyl optionally substituted with one or more $C_6$-$C_{10}$ aryloxy (e.g., phenoxy) and is para to the bond connecting the B ring to the NH(CO) group of Formula AA.

In some embodiments, one $R^7$ is phenyl optionally substituted with one or more CN and is para to the bond connecting the B ring to the NH(CO) group of Formula AA.

In some embodiments, one $R^7$ is phenyl optionally substituted with one or more halo (e.g., F, Cl) and is para to the bond connecting the B ring to the NH(CO) group of Formula AA and is para to the bond connecting the B ring to the NH(CO) group of Formula AA.

In some embodiments, one $R^7$ is phenyl optionally substituted with one or more $COOC_1$-$C_6$ alkyl (e.g., $CO_2$t-Bu) and is para to the bond connecting the B ring to the NH(CO) group of Formula AA.

In some embodiments, one $R^7$ is phenyl optionally substituted with one or more $S(O_2)C_1$-$C_6$ alkyl (e.g., $S(O_2)$ methyl) and is para to the bond connecting the B ring to the NH(CO) group of Formula AA.

In some embodiments, one $R^7$ is phenyl optionally substituted with one or more 3- to 7-membered heterocycloalkyl (e.g., morpholinyl) and is para to the bond connecting the B ring to the NH(CO) group of Formula AA.

In some embodiments, one $R^7$ is phenyl optionally substituted with one or more $CONR^8R^9$ (e.g., unsubstituted amido) and is para to the bond connecting the B ring to the NH(CO) group of Formula AA.

In some embodiments, one $R^7$ is phenyl optionally substituted with one or more $C_1$-$C_6$ alkyl (e.g., methyl or propyl, e.g., 2-propyl) and with one or more halo (e.g., F, Cl) and is para to the bond connecting the B ring to the NH(CO) group of Formula AA and is para to the bond connecting the B ring to the NH(CO) group of Formula AA.

In some embodiments, $R^6$ and $R^7$ are each attached to a carbon of an aryl ring B.

In some embodiments, $R^6$ and $R^7$ are each attached to a carbon of a heteroaryl ring B.

In some embodiments, $R^6$ is attached to a carbon and $R^7$ is attached to a nitrogen of a heteroaryl ring B.

In some embodiments, $R^7$ is attached to a carbon and $R^6$ is attached to a nitrogen of a heteroaryl ring B.

In some embodiments of any of the formulae herein, each of $R^1$ and $R^2$ is independently selected from the group consisting of $C_1$-$C_6$ alkyl optionally substituted with one or more hydroxy, halo, oxo, or $C_1$-$C_6$ alkoxy; $C_3$-$C_7$ cycloalkyl optionally substituted with one or more hydroxy, halo, oxo, $C_1$-$C_6$ alkoxy, or $C_1$-$C_6$ alkyl; wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, or $C_1$-$C_6$ alkyl wherein the $C_1$-$C_6$ alkoxy or $C_1$-$C_6$ alkyl is further optionally substituted with one to three hydroxy, halo, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments of any of the formulae herein, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; fluoro; chloro; phenyl; pyridyl; pyrazolyl; $S(O_2)CH_3$, and $S(O_2)NR^{11}R^{12}$.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; $COCH_3$; COPh; 2-methoxy-2-propyl; $S(O_2)CH_3$; and $S(O_2)NR^{11}R^{12}$.

In some embodiments, the substituted ring B is

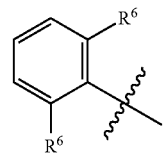

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO (5- to 10-membered heteroaryl), NHCO(4- to 6-membered heterocycloalkyl), and $NHCOC_2$-$C_6$ alkynyl.

In some embodiments, the substituted ring B is

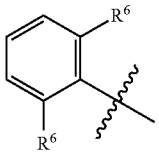

and each R⁶ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments, the substituted ring B is

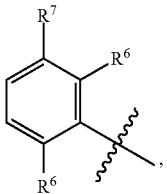

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
  wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC$_1$-C$_6$ alkyl, CONR⁸R⁹, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;
  wherein R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
  or R⁶ and R⁷, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC$_1$-$C_6$ alkyl, $C_6$-$C_{10}$ aryl, and CONR⁸R⁹.

In some embodiments, the substituted ring B is

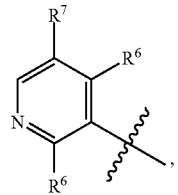

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
  wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, or R⁶ and R⁷, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC$_1$-$C_6$ alkyl, $C_6$-$C_{10}$ aryl, and CONR⁸R⁹.

In some embodiments, the substituted ring B is

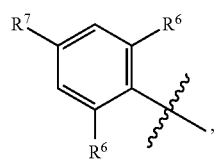

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl,
  wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, COO$C_1$-$C_6$ alkyl, CON$R^8R^9$, 4- to 6-membered heterocycloalkyl, $C_6$-$C_{10}$ aryl, 5- to 10-membered heteroaryl, OCO$C_1$-$C_6$ alkyl, OCO$C_6$-$C_{10}$ aryl, OCO(5- to 10-membered heteroaryl), OCO(4- to 6-membered heterocycloalkyl), NHCO$C_1$-$C_6$ alkyl, NHCO$C_6$-$C_{10}$ aryl, NHCO(5- to 10-membered heteroaryl), NHCO(4- to 6-membered heterocycloalkyl), and NHCO$C_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, COG-$C_6$ alkyl, $CO_2C_1$-$C_6$ alkyl, $CO_2C_3$-$C_6$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CON$R^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

In some embodiments, the substituted ring B is

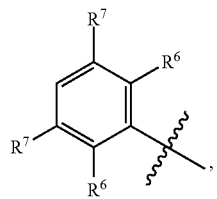

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CON$R^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, COO$C_1$-$C_6$ alkyl, CON$R^8R^9$, 4- to 6-membered heterocycloalkyl, $C_6$-$C_{10}$ aryl, 5- to 10-membered heteroaryl, OCO$C_1$-$C_6$ alkyl, OCO$C_6$-$C_{10}$ aryl, OCO(5- to 10-membered heteroaryl), OCO(4- to 6-membered heterocycloalkyl), NHCO$C_1$-$C_6$ alkyl, NHCO$C_6$-$C_{10}$ aryl, NHCO(5- to 10-membered heteroaryl), NHCO(4- to 6-membered heterocycloalkyl), and NHCO$C_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, CO$C_1$-$C_6$ alkyl, $CO_2C_1$-$C_6$ alkyl, $CO_2C_3$-$C_6$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CON$R^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, COO$C_1$-$C_6$ alkyl, $C_6$-$C_{10}$ aryl, and CON$R^8R^9$.

In some embodiments, the substituted ring B is

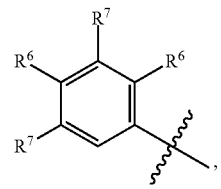

wherein each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CON$R^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, COO$C_1$-$C_6$ alkyl, CON$R^8R^9$, 4- to 6-membered heterocycloalkyl, $C_6$-$C_{10}$ aryl, 5- to 10-membered heteroaryl, OCO$C_1$-$C_6$ alkyl, OCO$C_6$-$C_{10}$ aryl, OCO(5- to 10-membered heteroaryl), OCO(4- to 6-membered heterocycloalkyl), NHCO$C_1$-$C_6$ alkyl, NHCO$C_6$-$C_{10}$ aryl, NHCO(5- to 10-membered heteroaryl), NHCO(4- to 6-membered heterocycloalkyl), and NHCO$C_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, CO$C_1$-$C_6$ alkyl, $CO_2C_1$-$C_6$ alkyl, $CO_2C_3$-$C_6$ cycloalkyl, OCO$C_1$-$C_6$ alkyl, OCO$C_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CON$R^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, =$NR^{10}$, COO$C_1$-$C_6$ alkyl, $C_6$-$C_{10}$ aryl, and CON$R^8R^9$.

In some embodiments, the substituted ring B is

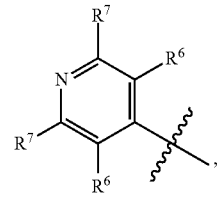

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC$_1$-$C_6$ alkyl, CONR⁸R⁹, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;

wherein each R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of R⁶ and R⁷ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR⁸R⁹, =NR¹⁰, COOC$_1$-$C_6$ alkyl, $C_6$-$C_{10}$ aryl, and CONR⁸R⁹.

In some embodiments, the substituted ring B is

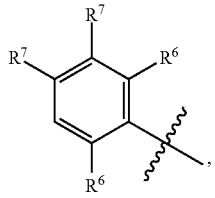

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR⁸R⁹, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR⁸R⁹, =NR¹⁰, COOC$_1$-$C_6$ alkyl, CONR⁸R⁹, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;

wherein each R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, COG-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR⁸R⁹, SF₅, S(O₂)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of R⁶ and R⁷ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$;

The Group $R^3$

In some embodiments, $R^3$ is selected from hydrogen, $C_1$-$C_6$ alkyl, and

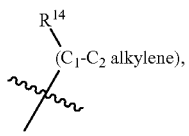

wherein the $C_1$-$C_2$ alkylene group is optionally substituted with oxo.

In some embodiments, $R^3$ is hydrogen.
In some embodiments, $R^3$ is cyano.
In some embodiments, $R^3$ is hydroxy.
In some embodiments, $R^3$ is $C_1$-$C_6$ alkoxy. In some embodiments, $R^3$ is $C_1$-$C_6$ alkyl.
In some embodiments, $R^3$ is methyl.
In some embodiments, $R^3$ is

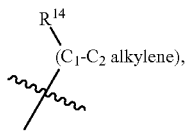

wherein the $C_1$-$C_2$ alkylene group is optionally substituted with oxo.

In some embodiments, $R^3$ is —$CH_2R^{14}$.
In some embodiments, $R^3$ is —$C(O)R^{14}$.
In some embodiments, $R^3$ is —$CH_2CH_2R^{14}$.
In some embodiments, $R^3$ is —$CHR^{14}CH_3$.
In some embodiments, $R^3$ is —$CH_2C(O)R^{14}$.
In some embodiments, $R^3$ is —$C(O)CH_2R^{14}$.
In some embodiments, $R^3$ is $CO_2C_1$-$C_6$ alkyl.

The Group $R^{14}$

In some embodiments, $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.

In some embodiments, $R^{14}$ is hydrogen or $C_1$-$C_6$ alkyl.
In some embodiments, $R^{14}$ is hydrogen, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2R.

In some embodiments, $R^{14}$ is hydrogen.
In some embodiments, $R^{14}$ is $C_1$-$C_6$ alkyl.
In some embodiments, $R^{14}$ is methyl.
In some embodiments, $R^{14}$ is 5- to 10-membered monocyclic or bicyclic heteroaryl optionally independently substituted with 1 or 2R.

In some embodiments, $R^{14}$ is $C_6$-$C_{10}$ monocyclic or bicyclic aryl optionally independently substituted with 1 or 2 $R^6$.

The Moiety $S(=O)(NR^3)=N$—

In some embodiments, the sulfur in the moiety $S(=O)(NHR_3)=N$— has (S) stereochemistry.
In some embodiments, the sulfur in the moiety $S(=O)(NHR^3)=N$— has (R) stereochemistry.

The Group $R^{10}$

In some embodiments, $R^{10}$ is $C_1$-$C_6$ alkyl.
In some embodiments, $R^{10}$ is methyl.
In some embodiments, $R^{10}$ is ethyl.

The Groups $R^8$ and $R^9$

In some embodiments, each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.

In some embodiments, each of $R^8$ and $R^9$ at each occurrence is hydrogen,
In some embodiments, each $R^8$ at each occurrence is hydrogen and each $R^9$ at each occurrence is $C_1$-$C_6$ alkyl.
In some embodiments, each $R^8$ at each occurrence is hydrogen and each $R^9$ at each occurrence is methyl.
In some embodiments, each $R^8$ at each occurrence is hydrogen and each $R^9$ at each occurrence is ethyl.
In some embodiments, each of $R^8$ and $R^9$ at each occurrence is methyl.
In some embodiments, each of $R^8$ and $R^9$ at each occurrence is ethyl.
In some embodiments, $R^8$ and $R^9$ taken together with the nitrogen they are attached to form a 3-membered ring.
In some embodiments, $R^8$ and $R^9$ taken together with the nitrogen they are attached to form a 4-membered ring.
In some embodiments, $R^8$ and $R^9$ taken together with the nitrogen they are attached to form a 5-membered ring.
In some embodiments, $R^8$ and $R^9$ taken together with the nitrogen they are attached to form a 6-membered ring optionally containing one or more oxygen atoms in addition to the nitrogen they are attached to.
In some embodiments, $R^8$ and $R^9$ taken together with the nitrogen they are attached to form a 6-membered ring optionally containing one or more nitrogen atoms in addition to the nitrogen they are attached to.
In some embodiments, $R^8$ and $R^9$ taken together with the nitrogen they are attached to form a 7-membered ring.

The Group $R^3$

In some embodiments, $R^{13}$ is $C_1$-$C_6$ alkyl.
In some embodiments, $R^{13}$ is methyl.
In some embodiments, $R^{13}$ is ethyl.
In some embodiments, $R^{13}$ is $C_6$-$C_{10}$ aryl.

In some embodiments, $R^{13}$ is phenyl.

In some embodiments, $R^{13}$ is 5- to 10-membered heteroaryl.

The Groups $R^{11}$ and $R^{12}$

In some embodiments, each of $R^{11}$ and $R^{12}$ at each occurrence is independently selected from hydrogen and $C_1$-$C_6$ alkyl.

In some embodiments, each of $R^{11}$ and $R^{12}$ at each occurrence is hydrogen, In some embodiments, each $R^{11}$ at each occurrence is hydrogen and each $R^{12}$ at each occurrence is $C_1$-$C_6$ alkyl.

In some embodiments, each $R^{11}$ at each occurrence is hydrogen and each $R^{12}$ at each occurrence is methyl.

In some embodiments, each $R^{11}$ at each occurrence is hydrogen and each $R^{12}$ at each occurrence is ethyl.

In some embodiments, each of $R^{11}$ and $R^{12}$ at each occurrence is methyl.

In some embodiments, each of $R^{11}$ and $R^{12}$ at each occurrence is ethyl.

In some embodiments of the compound of formula AA, the substituted ring A is

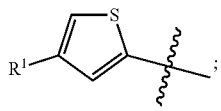

and $R^1$ is selected from:
  $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

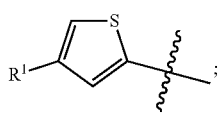

and $R^1$ is selected from:
  1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

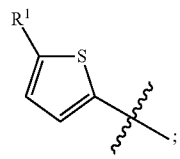

and $R^1$ is selected from:
  $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

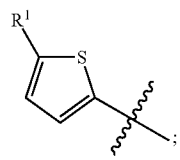

and $R^1$ is selected from:
  1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

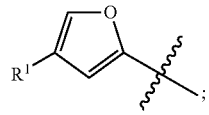

and $R^1$ is selected from:
  $C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

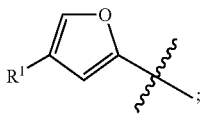

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

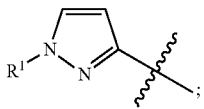

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

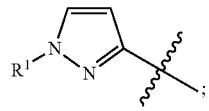

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

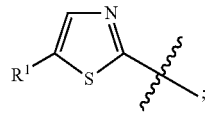

and $R^1$ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO^2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl$)_2$; $CONR^8R^9$; $SF_5$; and $S(O_2)C_1$-$C_6$ alkyl.

In some embodiments of the compound of formula AA, the substituted ring A is

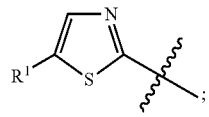

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)

methyl; 1-(dimethylamino)ethyl; fluoro; chloro; phenyl; pyridyl; pyrazolyl; and S(O₂)CH₃.

In some embodiments of the compound of formula AA, the substituted ring A is

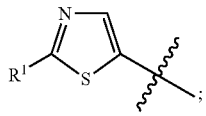

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO (3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

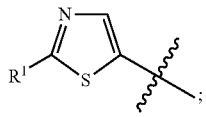

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

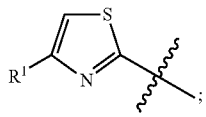

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO (3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

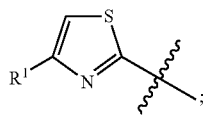

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

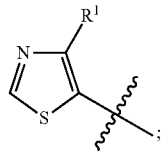

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO (3- to 7-membered heterocycloalkyl); C₆-C₁₀ aryl; 5- to 10-membered heteroaryl; NH₂; NHC₁-C₆ alkyl;

N(C$_1$-C$_6$ alkyl)$_2$; CONR$^8$R$^9$; SF$_5$; and S(O$_2$)C$_1$-C$_6$ alkyl. In some embodiments of the compound of formula AA, the substituted ring A is

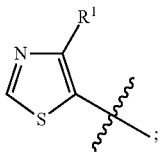

and R$^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

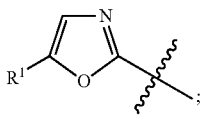

and R$^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COG-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

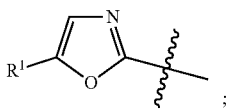

and R$^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

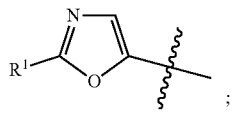

and R$^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

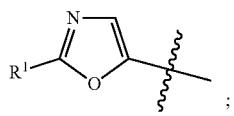

and R$^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

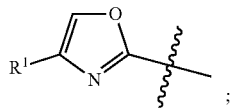

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

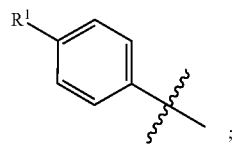

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

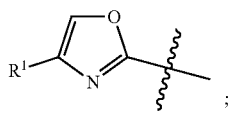

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH₃; COCH₂CH₃; 2-methoxy-2-propyl; (dimethylamino)methyl; 1-(dimethylamino)ethyl; fluoro; chloro; phenyl; pyridyl; pyrazolyl; and S(O₂)CH₃.

In some embodiments of the compound of formula AA, the substituted ring A is

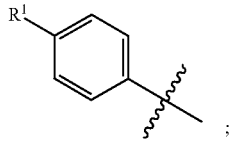

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

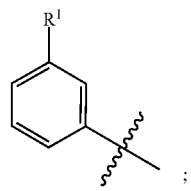

and R¹ is selected from:
C₁-C₆ alkyl optionally substituted with one or more hydroxy; C₃-C₇ cycloalkyl optionally substituted with one or more hydroxy; 3- to 7-membered heterocycloalkyl optionally substituted with one or more hydroxy; C₁-C₆ alkyl substituted with one or more oxo; C₃-C₇ cycloalkyl substituted with one or more oxo; C₁-C₆ alkyl substituted with one or more C₁-C₆ alkoxy; C₃-C₇ cycloalkyl substituted with one or more C₁-C₆ alkoxy; C₁-C₆ alkyl substituted with one or more NR⁸R⁹; 3- to 7-membered heterocycloalkyl substituted with one or more NR⁸R⁹; C₁-C₆ haloalkyl; C₁-C₆ alkoxy; C₁-C₆ haloalkoxy; halo; CN; NO₂; COC₁-C₆ alkyl; CO—C₆-C₁₀ aryl; CO(5- to 10-membered heteroaryl); CO₂C₁-C₆ alkyl; CO₂C₃-C₈ cycloalkyl; OCOC₁-C₆ alkyl; OCOC₆-C₁₀ aryl; OCO(5- to 10-membered heteroaryl); OCO(3- to 7-membered heterocycloalkyl); C₆-C₁₀ aryl; 5- to 10-membered heteroaryl; NH₂; NHC₁-C₆ alkyl; N(C₁-C₆ alkyl)₂; CONR⁸R⁹; SF₅; and S(O₂)C₁-C₆ alkyl.

In some embodiments of the compound of formula AA, the substituted ring A is

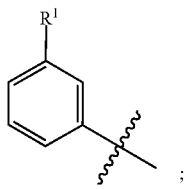
;

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is;

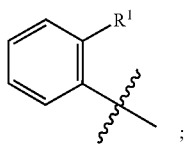
;

and R¹ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COG$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; and $S(O_2)C_1$-$C_6$ alkyl.

In some embodiments of the compound of formula AA, the substituted ring A is

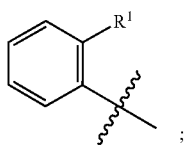
;

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; (dimethylamino)methyl; 1-(dimethylamino)ethyl; fluoro; chloro; phenyl; pyridyl; pyrazolyl; and $S(O_2)CH_3$.

In some embodiments of the compound of formula AA, the substituted ring A is

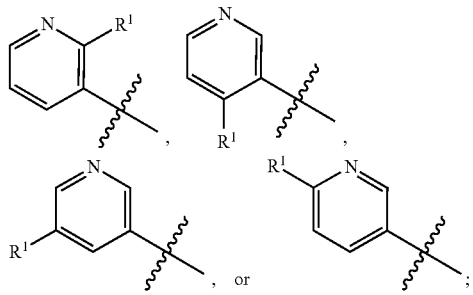
, or ;

and R¹ is selected from:
$C_1$-$C_6$ alkyl optionally substituted with one or more hydroxy; $C_3$-$C_7$ cycloalkyl optionally substituted with one or more hydroxy; 3- to 7-membered heterocycloalkyl optionally substituted with one or more hydroxy; $C_1$-$C_6$ alkyl substituted with one or more oxo; $C_3$-$C_7$ cycloalkyl substituted with one or more oxo; $C_1$-$C_6$ alkyl substituted with one or more $C_1$-$C_6$ alkoxy; $C_3$-$C_7$ cycloalkyl substituted with one or more $C_1$-$C_6$ alkoxy; $C_1$-$C_6$ alkyl substituted with one or more $NR^8R^9$; 3- to 7-membered heterocycloalkyl substituted with one or more $NR^8R^9$; $C_1$-$C_6$ haloalkyl; $C_1$-$C_6$ alkoxy; $C_1$-$C_6$ haloalkoxy; halo; CN; $NO_2$; $COC_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO (3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; and $S(O_2)C_1$-$C_6$ alkyl.

In some embodiments of the compound of formula AA, the substituted ring A is

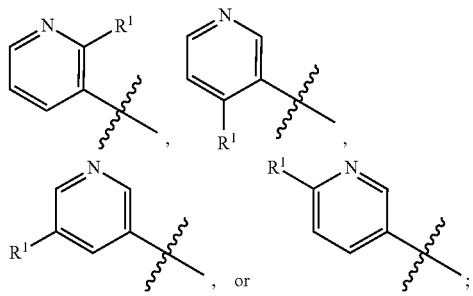
, or ;

and R¹ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

the substituted ring A is

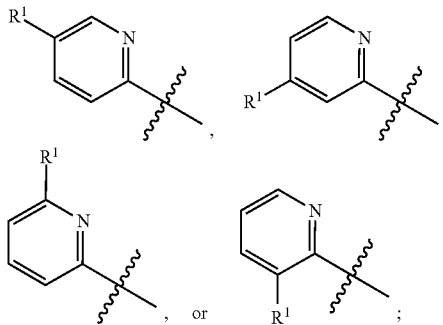

and R$^1$ is selected from:

C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

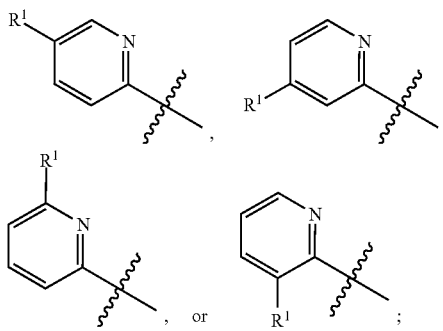

and R$^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

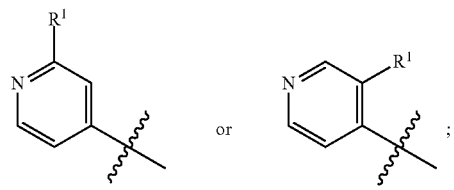

and R$^1$ is selected from:

C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO-5- to 10-membered heteroaryl; CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

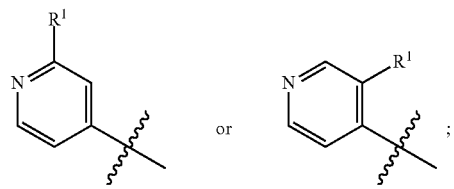

and R$^1$ is selected from:

1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A is

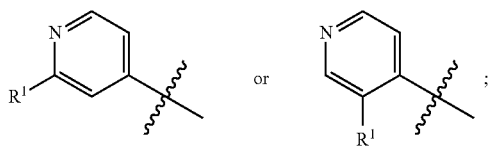

and $R^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ alkyl substituted with one or more NR$^8$R$^9$; 3- to 7-membered heterocycloalkyl substituted with one or more NR$^8$R$^9$; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; and S(O$_2$)C$_1$-C$_6$ alkyl.

In some embodiments of the compound of formula AA, the substituted ring A is

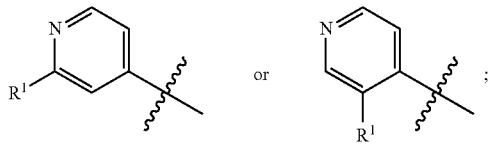

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; COCH$_3$; COCH$_2$CH$_3$; 2-methoxy-2-propyl; (dimethylamino)methyl; 1-(dimethylamino)ethyl; fluoro; chloro; phenyl; pyridyl; pyrazolyl; and S(O$_2$)CH$_3$.

In some embodiments of the compound of formula AA, the substituted ring A

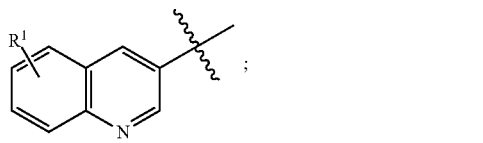

and $R^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; C$_1$-C$_6$ alkyl substituted with one or more NR$^8$R$^9$; and S(O$_2$)C$_1$-C$_6$ alkyl.

the substituted ring A

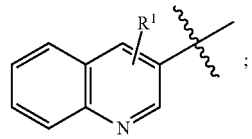

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; (dimethylamino)methyl; 1,3-dioxolan-2-yl; COCH$_3$; COCH$_2$CH$_3$; 2-methoxy-2-propyl; fluoro; chloro; phenyl; pyridyl; pyrazolyl; and S(O$_2$)CH$_3$.

the substituted ring A is

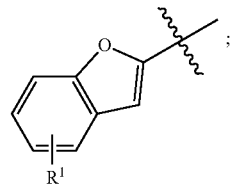

and $R^1$ is selected from:
C$_1$-C$_6$ alkyl optionally substituted with one or more hydroxy; C$_3$-C$_7$ cycloalkyl optionally substituted with one or more hydroxy; 3- to 7-membered heterocycloalkyl optionally substituted with one or more hydroxy; C$_1$-C$_6$ alkyl substituted with one or more oxo; C$_3$-C$_7$ cycloalkyl substituted with one or more oxo; C$_1$-C$_6$ alkyl substituted with one or more C$_1$-C$_6$ alkoxy; C$_3$-C$_7$ cycloalkyl substituted with one or more C$_1$-C$_6$ alkoxy; C$_1$-C$_6$ haloalkyl; C$_1$-C$_6$ alkoxy; C$_1$-C$_6$ haloalkoxy; halo; CN; NO$_2$; COC$_1$-C$_6$ alkyl; CO—C$_6$-C$_{10}$ aryl; CO(5- to 10-membered heteroaryl); CO$_2$C$_1$-C$_6$ alkyl; CO$_2$C$_3$-C$_8$ cycloalkyl; OCOC$_1$-C$_6$ alkyl; OCOC$_6$-C$_{10}$ aryl; OCO(5- to 10-membered heteroaryl); OCO(3- to 7-membered heterocycloalkyl); C$_6$-C$_{10}$ aryl; 5- to 10-membered heteroaryl; NH$_2$; NHC$_1$-C$_6$ alkyl; N(C$_1$-C$_6$ alkyl)$_2$; CONR$^8$R$^9$; SF$_5$; C$_1$-C$_6$ alkyl substituted with one or more NR$^8$R$^9$; and S(O$_2$)C$_1$-C$_6$ alkyl.

the substituted ring A is

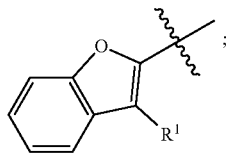

and $R^1$ is selected from:
1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; fluoro; chloro; phenyl; pyridyl; pyrazolyl; (dimethylamino)methyl; and $S(O_2)CH_3$.

In some embodiments of the compound of formula AA, the substituted ring A is

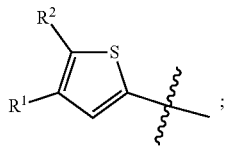

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more oxo, and $R^1$ is methyl;
$R^2$ is $C_1$-$C_6$ alkyl optionally substituted with one or more $C_1$-$C_6$ alkoxy, and $R^1$ is $C_1$-$C_6$ alkyl;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo. In some embodiments of the compound of formula AA, the substituted ring A is

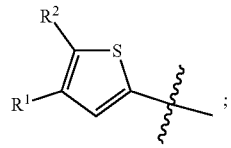

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^2$ is (dimethylamino)methyl, and $R^1$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;

R² is 1-hydroxy-2-propyl and R¹ is methyl;
R² is 2-hydroxy-2-propyl and R¹ is phenyl;
R² is C₁-C₆ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is C₁-C₆ alkyl optionally substituted with one or more hydroxy, and R¹ is S(O₂)CH₃;
R² is 2-hydroxy-2-propyl and R¹ is chloro;
R² is 2-hydroxy-2-propyl and R¹ is fluoro;
R² is C₃-C₇ cycloalkyl optionally substituted with one or more hydroxy, and R¹ is C₁-C₆ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is C₁-C₆ alkyl optionally substituted with one or more oxo, and R¹ is methyl;
R² is COCH₃, and R¹ is methyl; or
R² is 2-methoxy-2-propyl, and R¹ is methyl.

In some embodiments, of the compound of formula AA, the substituted ring A is

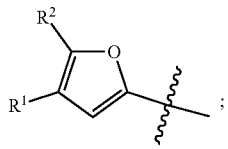

and R¹ and R² are one of the following combinations:
R¹ is C₁-C₆ alkyl optionally substituted with one or more hydroxy, and R² is C₁-C₆ alkyl optionally substituted with one or more hydroxy;
R¹ is C₁-C₆ alkyl optionally substituted with one or more hydroxy, and R² is C₆-C₁₀ aryl;
R¹ is C₁-C₆ alkyl optionally substituted with one or more hydroxy, and R² is 5- to 10-membered heteroaryl;
R¹ is C₁-C₆ alkyl optionally substituted with one or more hydroxy, and R² is SF₅;
R¹ is C₁-C₆ alkyl optionally substituted with one or more hydroxy, and R² is S(O₂)C₁-C₆ alkyl;
R¹ is C₁-C₆ alkyl optionally substituted with one or more hydroxy, and R² is halo;
R¹ is C₃-C₇ cycloalkyl optionally substituted with one or more hydroxy, and R² is C₁-C₆ alkyl;
R¹ is 3- to 7-membered heterocycloalkyl optionally substituted with one or more hydroxy, and R² is C₁-C₆ alkyl;
R¹ is 3- to 7-membered heterocycloalkyl optionally substituted with one or more hydroxy, and R² is halo;
R¹ is C₁-C₆ alkyl optionally substituted with one or more oxo, and R² is methyl;
R¹ is C₁-C₆ alkyl optionally substituted with one or more C₁-C₆ alkoxy, and R² is C₁-C₆ alkyl;
R¹ is C₁-C₆ alkyl optionally substituted with one or more NR⁸R⁹, and R² is C₁-C₆ alkyl;
R¹ is C₁-C₆ alkyl optionally substituted with one or more NR⁸R⁹, and R² is halo;
R² is C₁-C₆ alkyl optionally substituted with one or more hydroxy, and R¹ is C₆-C₁₀ aryl;
R² is C₁-C₆ alkyl optionally substituted with one or more hydroxy, and R¹ is 5- to 10-membered heteroaryl;
R² is C₁-C₆ alkyl optionally substituted with one or more hydroxy, and R¹ is SF₅.
R² is C₁-C₆ alkyl optionally substituted with one or more hydroxy, and R¹ is S(O₂)C₁-C₆ alkyl;
R² is C₁-C₆ alkyl optionally substituted with one or more hydroxy, and R¹ is halo;
R² is C₃-C₇ cycloalkyl optionally substituted with one or more hydroxy, and R¹ is C₁-C₆ alkyl;
R² is 3- to 7-membered heterocycloalkyl optionally substituted with one or more hydroxy, and R¹ is C₁-C₆ alkyl;
R² is 3- to 7-membered heterocycloalkyl optionally substituted with one or more hydroxy, and R¹ is halo;
R² is C₁-C₆ alkyl optionally substituted with one or more oxo, and R¹ is methyl;
or
R² is C₁-C₆ alkyl optionally substituted with one or more C₁-C₆ alkoxy, and R¹ is C₁-C₆ alkyl.
R² is C₁-C₆ alkyl optionally substituted with one or more NR⁸R⁹, and R¹ is C₁-C₆ alkyl;
or
R² is C₁-C₆ alkyl optionally substituted with one or more NR⁸R⁹, and R¹ is halo.

In some embodiments, of the compound of formula AA, the substituted ring A is

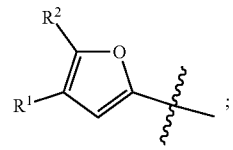

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;
R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is S(O₂)CH₃;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;

R$^1$ is (dimethylamino)methyl, and R$^2$ is methyl.
R$^2$ is 1-hydroxy-2-methylpropan-2-yl, and R$^1$ is methyl;
R$^2$ is 2-hydroxy-2-propyl and R$^1$ is methyl;
R$^2$ is 2-hydroxy-2-propyl and R$^1$ is isopropyl;
R$^2$ is 2-hydroxy-2-propyl and R$^1$ is 1-hydroxyethyl;
R$^2$ is hydroxymethyl and R$^1$ is methyl;
R$^2$ is 1-hydroxyethyl and R$^1$ is methyl;
R$^2$ is 2-hydroxyethyl and R$^1$ is methyl;
R$^2$ is 1-hydroxy-2-propyl and R$^1$ is methyl;
R$^2$ is 2-hydroxy-2-propyl and R$^1$ is phenyl;
R$^2$ is C$_1$-C$_6$ alkyl optionally substituted with one or more hydroxy, and R$^1$ is 5- to 10-membered heteroaryl;
R$^2$ is 2-hydroxy-2-propyl and R$^1$ is pyridyl;
R$^2$ is 2-hydroxy-2-propyl and R$^1$ is pyrazolyl;
R$^2$ is C$_1$-C$_6$ alkyl optionally substituted with one or more hydroxy, and R$^1$ is S(O$_2$)CH$_3$;
R$^2$ is 2-hydroxy-2-propyl and R$^1$ is chloro;
R$^2$ is 2-hydroxy-2-propyl and R$^1$ is fluoro;
R$^2$ is C$_3$-C$_7$ cycloalkyl optionally substituted with one or more hydroxy, and R$^1$ is C$_1$-C$_6$ alkyl;
R$^2$ is 1-hydroxy-1-cyclopropyl, and R$^1$ is methyl;
R$^2$ is 1-hydroxy-1-cyclobutyl, and R$^1$ is methyl;
R$^2$ is 1-hydroxy-1-cyclopentyl, and R$^1$ is methyl;
R$^2$ is 1-hydroxy-1-cyclohexyl, and R$^1$ is methyl;
R$^2$ is morpholinyl, and R$^1$ is methyl;
R$^2$ is 1,3-dioxolan-2-yl, and R$^1$ is methyl;
R$^2$ is 1,3-dioxolan-2-yl, and R$^1$ is fluoro;
R$^2$ is 1,3-dioxolan-2-yl, and R$^1$ is chloro;
R$^2$ is C$_1$-C$_6$ alkyl optionally substituted with one or more oxo, and R$^1$ is methyl;
R$^2$ is (dimethylamino)methyl, and R$^1$ is methyl;
R$^2$ is COCH$_3$, and R$^1$ is methyl; or
R$^2$ is 2-methoxy-2-propyl, and R$^1$ is methyl.

In some embodiments, of the compound of formula AA, the substituted ring A is

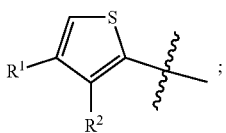

and R$^1$ and R$^2$ are one of the following combinations:
R$^1$ is C$_1$-C$_6$ alkyl optionally substituted with one or more hydroxy, and R$^2$ is C$_1$-C$_6$ alkyl optionally substituted with one or more hydroxy;
R$^1$ is C$_1$-C$_6$ alkyl optionally substituted with one or more hydroxy, and R$^2$ is C$_6$-C$_{10}$ aryl;
R$^1$ is C$_1$-C$_6$ alkyl optionally substituted with one or more hydroxy, and R$^2$ is 5- to 10-membered heteroaryl;
R$^1$ is C$_1$-C$_6$ alkyl optionally substituted with one or more hydroxy, and R$^2$ is SF$_5$;
R$^1$ is C$_1$-C$_6$ alkyl optionally substituted with one or more hydroxy, and R$^2$ is S(O$_2$)C$_1$-C$_6$ alkyl;
R$^1$ is C$_1$-C$_6$ alkyl optionally substituted with one or more hydroxy, and R$^2$ is halo;
R$^1$ is C$_3$-C$_7$ cycloalkyl optionally substituted with one or more hydroxy, and R$^2$ is C$_1$-C$_6$ alkyl;
R$^1$ is 3- to 7-membered heterocycloalkyl optionally substituted with one or more hydroxy, and R$^2$ is C$_1$-C$_6$ alkyl;
R$^1$ is 3- to 7-membered heterocycloalkyl optionally substituted with one or more hydroxy, and R$^2$ is halo;
R$^1$ is C$_1$-C$_6$ alkyl optionally substituted with one or more oxo, and R$^2$ is methyl;
R$^1$ is C$_1$-C$_6$ alkyl optionally substituted with one or more C$_1$-C$_6$ alkoxy, and R$^2$ is C$_1$-C$_6$ alkyl;
R$^1$ is C$_1$-C$_6$ alkyl optionally substituted with one or more NR$^8$R$^9$, and R$^2$ is C$_1$-C$_6$ alkyl;
R$^1$ is C$_1$-C$_6$ alkyl optionally substituted with one or more NR$^8$R$^9$, and R$^2$ is halo;
R$^2$ is C$_1$-C$_6$ alkyl optionally substituted with one or more hydroxy, and R$^1$ is C$_6$-C$_{10}$ aryl;
R$^2$ is C$_1$-C$_6$ alkyl optionally substituted with one or more hydroxy, and R$^1$ is 5- to 10-membered heteroaryl;
R$^2$ is C$_1$-C$_6$ alkyl optionally substituted with one or more hydroxy, and R$^1$ is SF$_5$.
R$^2$ is C$_1$-C$_6$ alkyl optionally substituted with one or more hydroxy, and R$^1$ is S(O$_2$)C$_1$-C$_6$ alkyl;
R$^2$ is C$_1$-C$_6$ alkyl optionally substituted with one or more hydroxy, and R$^1$ is halo;
R$^2$ is C$_3$-C$_7$ cycloalkyl optionally substituted with one or more hydroxy, and R$^1$ is C$_1$-C$_6$ alkyl;
R$^2$ is 3- to 7-membered heterocycloalkyl optionally substituted with one or more hydroxy, and R$^1$ is C$_1$-C$_6$ alkyl;
R$^2$ is 3- to 7-membered heterocycloalkyl optionally substituted with one or more hydroxy, and R$^1$ is halo;
R$^2$ is C$_1$-C$_6$ alkyl optionally substituted with one or more NR$^8$R$^9$, and R$^1$ is C$_1$-C$_6$ alkyl;
R$^2$ is C$_1$-C$_6$ alkyl optionally substituted with one or more NR$^8$R$^9$, and R$^1$ is halo;
R$^2$ is C$_1$-C$_6$ alkyl optionally substituted with one or more oxo, and R$^1$ is methyl; or
R$^2$ is C$_1$-C$_6$ alkyl optionally substituted with one or more C$_1$-C$_6$ alkoxy, and R$^1$ is C$_1$-C$_6$ alkyl.

In some embodiments, of the compound of formula AA, the substituted ring A is

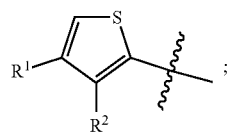

and R$^1$ and R$^2$ are one of the following combinations:
R$^1$ is 1-hydroxy-2-methylpropan-2-yl, and R$^2$ is methyl;
R$^1$ is 2-hydroxy-2-propyl and R$^2$ is methyl;
R$^1$ is 2-hydroxy-2-propyl and R$^2$ is isopropyl;
R$^1$ is 2-hydroxy-2-propyl and R$^2$ is 2-hydroxy-2-propyl;
R$^1$ is 2-hydroxy-2-propyl and R$^2$ is 1-hydroxyethyl;
R$^1$ is hydroxymethyl and R$^2$ is methyl;
R$^1$ is 1-hydroxyethyl and R$^2$ is methyl;
R$^1$ is 2-hydroxyethyl and R$^2$ is methyl;
R$^1$ is 1-hydroxy-2-propyl and R$^2$ is methyl;
R$^1$ is 2-hydroxy-2-propyl and R$^2$ is phenyl;
R$^1$ is 2-hydroxy-2-propyl and R$^2$ is pyridyl;
R$^1$ is 2-hydroxy-2-propyl and R$^2$ is pyrazolyl;
R$^1$ is 2-hydroxy-2-propyl, and R$^2$ is S(O$_2$)CH$_3$;
R$^1$ is 2-hydroxy-2-propyl and R$^2$ is chloro;
R$^1$ is 2-hydroxy-2-propyl and R$^2$ is fluoro;
R$^1$ is 1-hydroxy-1-cyclopropyl, and R$^2$ is methyl;
R$^1$ is 1-hydroxy-1-cyclobutyl, and R$^2$ is methyl;

$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl;
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$; $R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

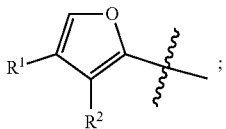

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

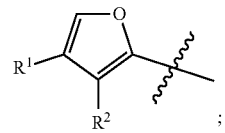

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;

R$^1$ is 1-hydroxy-2-propyl and R$^2$ is methyl;
R$^1$ is 2-hydroxy-2-propyl and R$^2$ is phenyl;
R$^1$ is 2-hydroxy-2-propyl and R$^2$ is pyridyl;
R$^1$ is 2-hydroxy-2-propyl and R$^2$ is pyrazolyl;
R$^1$ is 2-hydroxy-2-propyl, and R$^2$ is S(O$_2$)CH$_3$;
R$^1$ is 2-hydroxy-2-propyl and R$^2$ is chloro;
R$^1$ is 2-hydroxy-2-propyl and R$^2$ is fluoro;
R$^1$ is 1-hydroxy-1-cyclopropyl, and R$^2$ is methyl;
R$^1$ is 1-hydroxy-1-cyclobutyl, and R$^2$ is methyl;
R$^1$ is 1-hydroxy-1-cyclopentyl, and R$^2$ is methyl;
R$^1$ is 1-hydroxy-1-cyclohexyl, and R$^2$ is methyl;
R$^1$ is morpholinyl, and R$^2$ is methyl;
R$^1$ is 1,3-dioxolan-2-yl, and R$^2$ is methyl;
R$^1$ is 1,3-dioxolan-2-yl, and R$^2$ is fluoro;
R$^1$ is 1,3-dioxolan-2-yl, and R$^2$ is chloro;
R$^1$ is COCH$_3$, and R$^2$ is methyl;
R$^1$ is 2-methoxy-2-propyl, and R$^2$ is methyl;
R$^1$ is (dimethylamino)methyl, and R$^2$ is methyl.
R$^2$ is 1-hydroxy-2-methylpropan-2-yl, and R$^1$ is methyl;
R$^2$ is 2-hydroxy-2-propyl and R$^1$ is methyl;
R$^2$ is 2-hydroxy-2-propyl and R$^1$ is isopropyl;
R$^2$ is 2-hydroxy-2-propyl and R$^1$ is 1-hydroxyethyl;
R$^2$ is hydroxymethyl and R$^1$ is methyl;
R$^2$ is 1-hydroxyethyl and R$^1$ is methyl;
R$^2$ is 2-hydroxyethyl and R$^1$ is methyl;
R$^2$ is 1-hydroxy-2-propyl and R$^1$ is methyl;
R$^2$ is 2-hydroxy-2-propyl and R$^1$ is phenyl;
R$^2$ is C$_1$-C$_6$ alkyl optionally substituted with one or more hydroxy, and R$^1$ is 5- to 10-membered heteroaryl;
R$^2$ is 2-hydroxy-2-propyl and R$^1$ is pyridyl;
R$^2$ is 2-hydroxy-2-propyl and R$^1$ is pyrazolyl;
R$^2$ is C$_1$-C$_6$ alkyl optionally substituted with one or more hydroxy, and R$^1$ is S(O$_2$)CH$_3$;
R$^2$ is 2-hydroxy-2-propyl and R$^1$ is chloro;
R$^2$ is 2-hydroxy-2-propyl and R$^1$ is fluoro;
R$^2$ is C$_3$-C$_7$ cycloalkyl optionally substituted with one or more hydroxy, and R$^1$ is C$_1$-C$_6$ alkyl;
R$^2$ is 1-hydroxy-1-cyclopropyl, and R$^1$ is methyl;
R$^2$ is 1-hydroxy-1-cyclobutyl, and R$^1$ is methyl;
R$^2$ is 1-hydroxy-1-cyclopentyl, and R$^1$ is methyl;
R$^2$ is 1-hydroxy-1-cyclohexyl, and R$^1$ is methyl;
R$^2$ is morpholinyl, and R$^1$ is methyl;
R$^2$ is 1,3-dioxolan-2-yl, and R$^1$ is methyl;
R$^2$ is 1,3-dioxolan-2-yl, and R$^1$ is fluoro;
R$^2$ is 1,3-dioxolan-2-yl, and R$^1$ is chloro;
R$^2$ is C$_1$-C$_6$ alkyl optionally substituted with one or more oxo, and R$^1$ is methyl;
R$^2$ is (dimethylamino)methyl, and R$^1$ is methyl;
R$^2$ is COCH$_3$, and R$^1$ is methyl; or
R$^2$ is 2-methoxy-2-propyl, and R$^1$ is methyl.
In some embodiments, of the compound of formula AA, the substituted ring A is

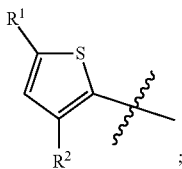
;

and R$^1$ and R$^2$ are one of the following combinations:
R$^1$ is C$_1$-C$_6$ alkyl optionally substituted with one or more hydroxy, and R$^2$ is C$_1$-C$_6$ alkyl optionally substituted with one or more hydroxy;
R$^1$ is C$_1$-C$_6$ alkyl optionally substituted with one or more hydroxy, and R$^2$ is C$_6$-C$_{10}$ aryl;
R$^1$ is C$_1$-C$_6$ alkyl optionally substituted with one or more hydroxy, and R$^2$ is 5- to 10-membered heteroaryl;
R$^1$ is C$_1$-C$_6$ alkyl optionally substituted with one or more hydroxy, and R$^2$ is SF$_5$;
R$^1$ is C$_1$-C$_6$ alkyl optionally substituted with one or more hydroxy, and R$^2$ is S(O$_2$)C$_1$-C$_6$ alkyl;
R$^1$ is C$_1$-C$_6$ alkyl optionally substituted with one or more hydroxy, and R$^2$ is halo;
R$^1$ is C$_3$-C$_7$ cycloalkyl optionally substituted with one or more hydroxy, and R$^2$ is C$_1$-C$_6$ alkyl;
R$^1$ is 3- to 7-membered heterocycloalkyl optionally substituted with one or more hydroxy, and R$^2$ is C$_1$-C$_6$ alkyl;
R$^1$ is 3- to 7-membered heterocycloalkyl optionally substituted with one or more hydroxy, and R$^2$ is halo;
R$^1$ is C$_1$-C$_6$ alkyl optionally substituted with one or more oxo, and R$^2$ is methyl;
R$^1$ is C$_1$-C$_6$ alkyl optionally substituted with one or more C$_1$-C$_6$ alkoxy, and R$^2$ is C$_1$-C$_6$ alkyl;
R$^1$ is C$_1$-C$_6$ alkyl optionally substituted with one or more NR$^8$R$^9$, and R$^2$ is C$_1$-C$_6$ alkyl;
R$^1$ is C$_1$-C$_6$ alkyl optionally substituted with one or more NR$^8$R$^9$, and R$^2$ is halo;
R$^2$ is C$_1$-C$_6$ alkyl optionally substituted with one or more hydroxy, and R$^1$ is C$_6$-C$_{10}$ aryl;
R$^2$ is C$_1$-C$_6$ alkyl optionally substituted with one or more hydroxy, and R$^1$ is 5- to 10-membered heteroaryl;
R$^2$ is C$_1$-C$_6$ alkyl optionally substituted with one or more hydroxy, and R$^1$ is SF$_5$.
R$^2$ is C$_1$-C$_6$ alkyl optionally substituted with one or more hydroxy, and R$^1$ is S(O$_2$)C$_1$-C$_6$ alkyl;
R$^2$ is C$_1$-C$_6$ alkyl optionally substituted with one or more hydroxy, and R$^1$ is halo;
R$^2$ is C$_3$-C$_7$ cycloalkyl optionally substituted with one or more hydroxy, and R$^1$ is C$_1$-C$_6$ alkyl;
R$^2$ is 3- to 7-membered heterocycloalkyl optionally substituted with one or more hydroxy, and R$^1$ is C$_1$-C$_6$ alkyl;
R$^2$ is 3- to 7-membered heterocycloalkyl optionally substituted with one or more hydroxy, and R$^1$ is halo;
R$^2$ is C$_1$-C$_6$ alkyl optionally substituted with one or more NR$^8$R$^9$, and R$^1$ is C$_1$-C$_6$ alkyl;
R$^2$ is C$_1$-C$_6$ alkyl optionally substituted with one or more NR$^8$R$^9$, and R$^1$ is halo;
R$^2$ is C$_1$-C$_6$ alkyl optionally substituted with one or more oxo, and R$^1$ is methyl; or
R$^2$ is C$_1$-C$_6$ alkyl optionally substituted with one or more C$_1$-C$_6$ alkoxy, and R$^1$ is C$_1$-C$_6$ alkyl.
In some embodiments, of the compound of formula AA, the substituted ring A is

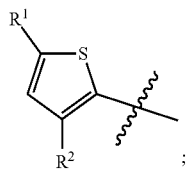
;

and $R^1$ and $R^2$ are one of the following combinations:
- $R^1$ is 1-hydroxy-2-methylpropan-2-yl, and $R^2$ is methyl;
- $R^1$ is 2-hydroxy-2-propyl and $R^2$ is methyl;
- $R^1$ is 2-hydroxy-2-propyl and $R^2$ is isopropyl;
- $R^1$ is 2-hydroxy-2-propyl and $R^2$ is 2-hydroxy-2-propyl;
- $R^1$ is 2-hydroxy-2-propyl and $R^2$ is 1-hydroxyethyl;
- $R^1$ is hydroxymethyl and $R^2$ is methyl;
- $R^1$ is 1-hydroxyethyl and $R^2$ is methyl;
- $R^1$ is 2-hydroxyethyl and $R^2$ is methyl;
- $R^1$ is 1-hydroxy-2-propyl and $R^2$ is methyl;
- $R^1$ is 2-hydroxy-2-propyl and $R^2$ is phenyl;
- $R^1$ is 2-hydroxy-2-propyl and $R^2$ is pyridyl;
- $R^1$ is 2-hydroxy-2-propyl and $R^2$ is pyrazolyl;
- $R^1$ is 2-hydroxy-2-propyl, and $R^2$ is $S(O_2)CH_3$;
- $R^1$ is 2-hydroxy-2-propyl and $R^2$ is chloro;
- $R^1$ is 2-hydroxy-2-propyl and $R^2$ is fluoro;
- $R^1$ is 1-hydroxy-1-cyclopropyl, and $R^2$ is methyl;
- $R^1$ is 1-hydroxy-1-cyclobutyl, and $R^2$ is methyl;
- $R^1$ is 1-hydroxy-1-cyclopentyl, and $R^2$ is methyl;
- $R^1$ is 1-hydroxy-1-cyclohexyl, and $R^2$ is methyl;
- $R^1$ is morpholinyl, and $R^2$ is methyl;
- $R^1$ is 1,3-dioxolan-2-yl, and $R^2$ is methyl;
- $R^1$ is 1,3-dioxolan-2-yl, and $R^2$ is fluoro;
- $R^1$ is 1,3-dioxolan-2-yl, and $R^2$ is chloro;
- $R^1$ is $COCH_3$, and $R^2$ is methyl;
- $R^1$ is 2-methoxy-2-propyl, and $R^2$ is methyl;
- $R^1$ is (dimethylamino)methyl, and $R^2$ is methyl.
- $R^2$ is 1-hydroxy-2-methylpropan-2-yl, and $R^1$ is methyl;
- $R^2$ is 2-hydroxy-2-propyl and $R^1$ is methyl;
- $R^2$ is 2-hydroxy-2-propyl and $R^1$ is isopropyl;
- $R^2$ is 2-hydroxy-2-propyl and $R^1$ is 1-hydroxyethyl;
- $R^2$ is hydroxymethyl and $R^1$ is methyl;
- $R^2$ is 1-hydroxyethyl and $R^1$ is methyl;
- $R^2$ is 2-hydroxyethyl and $R^1$ is methyl;
- $R^2$ is 1-hydroxy-2-propyl and $R^1$ is methyl;
- $R^2$ is 2-hydroxy-2-propyl and $R^1$ is phenyl;
- $R^2$ is $C_1$-$C_6$ alkyl optionally substituted with one or more hydroxy, and $R^1$ is 5- to 10-membered heteroaryl;
- $R^2$ is 2-hydroxy-2-propyl and $R^1$ is pyridyl;
- $R^2$ is 2-hydroxy-2-propyl and $R^1$ is pyrazolyl;
- $R^2$ is $C_1$-$C_6$ alkyl optionally substituted with one or more hydroxy, and $R^1$ is $S(O_2)CH_3$;
- $R^2$ is 2-hydroxy-2-propyl and $R^1$ is chloro;
- $R^2$ is 2-hydroxy-2-propyl and $R^1$ is fluoro;
- $R^2$ is $C_3$-$C_7$ cycloalkyl optionally substituted with one or more hydroxy, and $R^1$ is $C_1$-$C_6$ alkyl;
- $R^2$ is 1-hydroxy-1-cyclopropyl, and $R^1$ is methyl;
- $R^2$ is 1-hydroxy-1-cyclobutyl, and $R^1$ is methyl;
- $R^2$ is 1-hydroxy-1-cyclopentyl, and $R^1$ is methyl;
- $R^2$ is 1-hydroxy-1-cyclohexyl, and $R^1$ is methyl;
- $R^2$ is morpholinyl, and $R^1$ is methyl;
- $R^2$ is 1,3-dioxolan-2-yl, and $R^1$ is methyl;
- $R^2$ is 1,3-dioxolan-2-yl, and $R^1$ is fluoro;
- $R^2$ is 1,3-dioxolan-2-yl, and $R^1$ is chloro;
- $R^2$ is $C_1$-$C_6$ alkyl optionally substituted with one or more oxo, and $R^1$ is methyl;
- $R^2$ is (dimethylamino)methyl, and $R^1$ is methyl;
- $R^2$ is $COCH_3$, and $R^1$ is methyl; or
- $R^2$ is 2-methoxy-2-propyl, and $R^1$ is methyl.

In some embodiments, of the compound of formula AA, the substituted ring A is

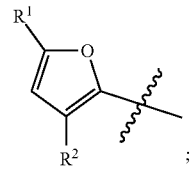

and $R^1$ and $R^2$ are one of the following combinations:
- $R^1$ is $C_1$-$C_6$ alkyl optionally substituted with one or more hydroxy, and $R^2$ is $C_1$-$C_6$ alkyl optionally substituted with one or more hydroxy;
- $R^1$ is $C_1$-$C_6$ alkyl optionally substituted with one or more hydroxy, and $R^2$ is $C_6$-$C_{10}$ aryl;
- $R^1$ is $C_1$-$C_6$ alkyl optionally substituted with one or more hydroxy, and $R^2$ is 5- to 10-membered heteroaryl;
- $R^1$ is $C_1$-$C_6$ alkyl optionally substituted with one or more hydroxy, and $R^2$ is $SF_5$;
- $R^1$ is $C_1$-$C_6$ alkyl optionally substituted with one or more hydroxy, and $R^2$ is $S(O_2)C_1$-$C_6$ alkyl;
- $R^1$ is $C_1$-$C_6$ alkyl optionally substituted with one or more hydroxy, and $R^2$ is halo;
- $R^1$ is $C_3$-$C_7$ cycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is halo;
- $R^1$ is $C_1$-$C_6$ alkyl optionally substituted with one or more oxo, and $R^2$ is methyl;
- $R^1$ is $C_1$-$C_6$ alkyl optionally substituted with one or more $C_1$-$C_6$ alkoxy, and $R^2$ is $C_1$-$C_6$ alkyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is $C_1$-$C_6$ alkyl optionally substituted with one or more hydroxy, and $R^1$ is $C_6$-$C_{10}$ aryl;
- $R^2$ is $C_1$-$C_6$ alkyl optionally substituted with one or more hydroxy, and $R^1$ is 5- to 10-membered heteroaryl;
- $R^2$ is $C_1$-$C_6$ alkyl optionally substituted with one or more hydroxy, and $R^1$ is $SF_5$.
- $R^2$ is $C_1$-$C_6$ alkyl optionally substituted with one or more hydroxy, and $R^1$ is $S(O_2)C_1$-$C_6$ alkyl;
- $R^2$ is $C_1$-$C_6$ alkyl optionally substituted with one or more hydroxy, and $R^1$ is halo;
- $R^2$ is $C_3$-$C_7$ cycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is halo;
- $R^2$ is $C_1$-$C_6$ alkyl optionally substituted with one or more $NR^8R^9$, and $R^1$ is $C_1$-$C_6$ alkyl;
- $R^2$ is $C_1$-$C_6$ alkyl optionally substituted with one or more $NR^8R^9$, and $R^1$ is halo;
- $R^2$ is $C_1$-$C_6$ alkyl optionally substituted with one or more oxo, and $R^1$ is methyl; or
- $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

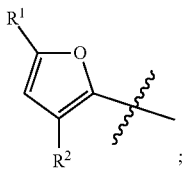

and $R^1$ and $R^2$ are one of the following combinations:
- $R^1$ is 1-hydroxy-2-methylpropan-2-yl, and $R^2$ is methyl;
- $R^1$ is 2-hydroxy-2-propyl and $R^2$ is methyl;
- $R^1$ is 2-hydroxy-2-propyl and $R^2$ is isopropyl;
- $R^1$ is 2-hydroxy-2-propyl and $R^2$ is 2-hydroxy-2-propyl;
- $R^1$ is 2-hydroxy-2-propyl and $R^2$ is 1-hydroxyethyl;
- $R^1$ is hydroxymethyl and $R^2$ is methyl;
- $R^1$ is 1-hydroxyethyl and $R^2$ is methyl;
- $R^1$ is 2-hydroxyethyl and $R^2$ is methyl;
- $R^1$ is 1-hydroxy-2-propyl and $R^2$ is methyl;
- $R^1$ is 2-hydroxy-2-propyl and $R^2$ is phenyl;
- $R^1$ is 2-hydroxy-2-propyl and $R^2$ is pyridyl;
- $R^1$ is 2-hydroxy-2-propyl and $R^2$ is pyrazolyl;
- $R^1$ is 2-hydroxy-2-propyl, and $R^2$ is $S(O_2)CH_3$;
- $R^1$ is 2-hydroxy-2-propyl and $R^2$ is chloro;
- $R^1$ is 2-hydroxy-2-propyl and $R^2$ is fluoro;
- $R^1$ is 1-hydroxy-1-cyclopropyl, and $R^2$ is methyl;
- $R^1$ is 1-hydroxy-1-cyclobutyl, and $R^2$ is methyl;
- $R^1$ is 1-hydroxy-1-cyclopentyl, and $R^2$ is methyl;
- $R^1$ is 1-hydroxy-1-cyclohexyl, and $R^2$ is methyl;
- $R^1$ is morpholinyl, and $R^2$ is methyl;
- $R^1$ is 1,3-dioxolan-2-yl, and $R^2$ is methyl;
- $R^1$ is 1,3-dioxolan-2-yl, and $R^2$ is fluoro;
- $R^1$ is 1,3-dioxolan-2-yl, and $R^2$ is chloro;
- $R^1$ is $COCH_3$, and $R^2$ is methyl;
- $R^1$ is 2-methoxy-2-propyl, and $R^2$ is methyl;
- $R^1$ is (dimethylamino)methyl, and $R^2$ is methyl.
- $R^2$ is 1-hydroxy-2-methylpropan-2-yl, and $R^1$ is methyl;
- $R^2$ is 2-hydroxy-2-propyl and $R^1$ is methyl;
- $R^2$ is 2-hydroxy-2-propyl and $R^1$ is isopropyl;
- $R^2$ is 2-hydroxy-2-propyl and $R^1$ is 1-hydroxyethyl;
- $R^2$ is hydroxymethyl and $R^1$ is methyl;
- $R^2$ is 1-hydroxyethyl and $R^1$ is methyl;
- $R^2$ is 2-hydroxyethyl and $R^1$ is methyl;
- $R^2$ is 1-hydroxy-2-propyl and $R^1$ is methyl;
- $R^2$ is 2-hydroxy-2-propyl and $R^1$ is phenyl;
- $R^2$ is $C_1$-$C_6$ alkyl optionally substituted with one or more hydroxy, and $R^1$ is 5- to 10-membered heteroaryl;
- $R^2$ is 2-hydroxy-2-propyl and $R^1$ is pyridyl;
- $R^2$ is 2-hydroxy-2-propyl and $R^1$ is pyrazolyl;
- $R^2$ is $C_1$-$C_6$ alkyl optionally substituted with one or more hydroxy, and $R^1$ is $S(O_2)CH_3$;
- $R^2$ is 2-hydroxy-2-propyl and $R^1$ is chloro;
- $R^2$ is 2-hydroxy-2-propyl and $R^1$ is fluoro;
- $R^2$ is $C_3$-$C_7$ cycloalkyl optionally substituted with one or more hydroxy, and $R^1$ is $C_1$-$C_6$ alkyl;
- $R^2$ is 1-hydroxy-1-cyclopropyl, and $R^1$ is methyl;
- $R^2$ is 1-hydroxy-1-cyclobutyl, and $R^1$ is methyl;
- $R^2$ is 1-hydroxy-1-cyclopentyl, and $R^1$ is methyl;
- $R^2$ is 1-hydroxy-1-cyclohexyl, and $R^1$ is methyl;
- $R^2$ is morpholinyl, and $R^1$ is methyl;
- $R^2$ is 1,3-dioxolan-2-yl, and $R^1$ is methyl;
- $R^2$ is 1,3-dioxolan-2-yl, and $R^1$ is fluoro;
- $R^2$ is 1,3-dioxolan-2-yl, and $R^1$ is chloro;
- $R^2$ is $C_1$-$C_6$ alkyl optionally substituted with one or more oxo, and $R^1$ is methyl;
- $R^2$ is (dimethylamino)methyl, and $R^1$ is methyl;
- $R^2$ is $COCH_3$, and $R^1$ is methyl; or
- $R^2$ is 2-methoxy-2-propyl, and $R^1$ is methyl.

In some embodiments, of the compound of formula AA, the substituted ring A is

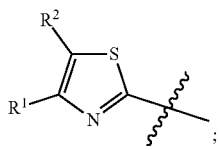

and $R^1$ and $R^2$ are one of the following combinations:
- $R^1$ is $C_1$-$C_6$ alkyl optionally substituted with one or more hydroxy, and $R^2$ is $C_1$-$C_6$ alkyl optionally substituted with one or more hydroxy;
- $R^1$ is $C_1$-$C_6$ alkyl optionally substituted with one or more hydroxy, and $R^2$ is $C_6$-$C_{10}$ aryl;
- $R^1$ is $C_1$-$C_6$ alkyl optionally substituted with one or more hydroxy, and $R^2$ is 5- to 10-membered heteroaryl;
- $R^1$ is $C_1$-$C_6$ alkyl optionally substituted with one or more hydroxy, and $R^2$ is $SF_5$;
- $R^1$ is $C_1$-$C_6$ alkyl optionally substituted with one or more hydroxy, and $R^2$ is $S(O_2)C_1$-$C_6$ alkyl;
- $R^1$ is $C_1$-$C_6$ alkyl optionally substituted with one or more hydroxy, and $R^2$ is halo;
- $R^1$ is $C_3$-$C_7$ cycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is halo;
- $R^1$ is $C_1$-$C_6$ alkyl optionally substituted with one or more oxo, and $R^2$ is methyl;
- $R^1$ is $C_1$-$C_6$ alkyl optionally substituted with one or more $C_1$-$C_6$ alkoxy, and $R^2$ is $C_1$-$C_6$ alkyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is $C_1$-$C_6$ alkyl optionally substituted with one or more hydroxy, and $R^1$ is $C_6$-$C_{10}$ aryl;
- $R^2$ is $C_1$-$C_6$ alkyl optionally substituted with one or more hydroxy, and $R^1$ is 5- to 10-membered heteroaryl;
- $R^2$ is $C_1$-$C_6$ alkyl optionally substituted with one or more hydroxy, and $R^1$ is $SF_5$.
- $R^2$ is $C_1$-$C_6$ alkyl optionally substituted with one or more hydroxy, and $R^1$ is $S(O_2)C_1$-$C_6$ alkyl;
- $R^2$ is $C_1$-$C_6$ alkyl optionally substituted with one or more hydroxy, and $R^1$ is halo;
- $R^2$ is $C_3$-$C_7$ cycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is halo;
- $R^2$ is $C_1$-$C_6$ alkyl optionally substituted with one or more $NR^8R^9$, and $R^1$ is $C_1$-$C_6$ alkyl;

$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

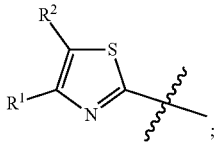

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

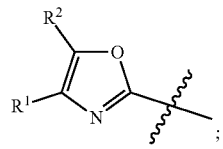

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;

$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

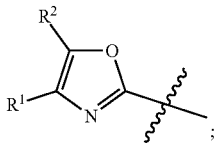

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

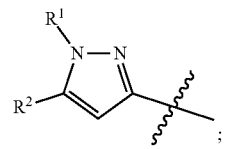

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;

$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments, of the compound of formula AA, the substituted ring A is

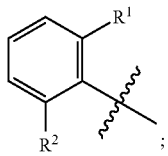

and $R^1$ and $R^2$ are one of the following combinations:
$R^1$ is $C_1$-$C_6$ alkyl optionally substituted with one or more hydroxy, and $R^2$ is $C_1$-$C_6$ alkyl optionally substituted with one or more hydroxy;
$R^1$ is $C_1$-$C_6$ alkyl optionally substituted with one or more hydroxy, and $R^2$ is $C_6$-$C_{10}$ aryl;
$R^1$ is $C_1$-$C_6$ alkyl optionally substituted with one or more hydroxy, and $R^2$ is 5- to 10-membered heteroaryl;
$R^1$ is $C_1$-$C_6$ alkyl optionally substituted with one or more hydroxy, and $R^2$ is $SF_5$;
$R^1$ is $C_1$-$C_6$ alkyl optionally substituted with one or more hydroxy, and $R^2$ is $S(O_2)C_1$-$C_6$ alkyl;
$R^1$ is $C_1$-$C_6$ alkyl optionally substituted with one or more hydroxy, and $R^2$ is halo;
$R^1$ is $C_3$-$C_7$ cycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is $C_1$-$C_6$ alkyl;
$R^1$ is 3- to 7-membered heterocycloalkyl optionally substituted with one or more hydroxy, and $R^2$ is halo;
$R^1$ is $C_1$-$C_6$ alkyl optionally substituted with one or more oxo, and $R^2$ is methyl;
$R^1$ is $C_1$-$C_6$ alkyl optionally substituted with one or more $C_1$-$C_6$ alkoxy, and $R^2$ is $C_1$-$C_6$ alkyl;
$R^1$ is $C_1$-$C_6$ alkyl optionally substituted with one or more $NR^8R^9$, and $R^2$ is $C_1$-$C_6$ alkyl;
$R^1$ is $C_1$-$C_6$ alkyl optionally substituted with one or more $NR^8R^9$, and $R^2$ is halo;
$R^2$ is $C_1$-$C_6$ alkyl optionally substituted with one or more hydroxy, and $R^1$ is $C_6$-$C_{10}$ aryl;
$R^2$ is $C_1$-$C_6$ alkyl optionally substituted with one or more hydroxy, and $R^1$ is 5- to 10-membered heteroaryl;
$R^2$ is $C_1$-$C_6$ alkyl optionally substituted with one or more hydroxy, and $R^1$ is $SF_5$.
$R^2$ is $C_1$-$C_6$ alkyl optionally substituted with one or more hydroxy, and $R^1$ is $S(O_2)C_1$-$C_6$ alkyl;
$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

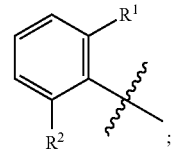

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;

R$^1$ is 2-methoxy-2-propyl, and R$^2$ is methyl;
R$^1$ is (dimethylamino)methyl, and R$^2$ is methyl.
R$^2$ is 1-hydroxy-2-methylpropan-2-yl, and R$^1$ is methyl;
R$^2$ is 2-hydroxy-2-propyl and R$^1$ is methyl;
R$^2$ is 2-hydroxy-2-propyl and R$^1$ is isopropyl;
R$^2$ is 2-hydroxy-2-propyl and R$^1$ is 1-hydroxyethyl;
R$^2$ is hydroxymethyl and R$^1$ is methyl;
R$^2$ is 1-hydroxyethyl and R$^1$ is methyl;
R$^2$ is 2-hydroxyethyl and R$^1$ is methyl;
R$^2$ is 1-hydroxy-2-propyl and R$^1$ is methyl;
R$^2$ is 2-hydroxy-2-propyl and R$^1$ is phenyl;
R$^2$ is C$_1$-C$_6$ alkyl optionally substituted with one or more hydroxy, and R$^1$ is 5- to 10-membered heteroaryl;
R$^2$ is 2-hydroxy-2-propyl and R$^1$ is pyridyl;
R$^2$ is 2-hydroxy-2-propyl and R$^1$ is pyrazolyl;
R$^2$ is C$_1$-C$_6$ alkyl optionally substituted with one or more hydroxy, and R$^1$ is S(O$_2$)CH$_3$;
R$^2$ is 2-hydroxy-2-propyl and R$^1$ is chloro;
R$^2$ is 2-hydroxy-2-propyl and R$^1$ is fluoro;
R$^2$ is C$_3$-C$_7$ cycloalkyl optionally substituted with one or more hydroxy, and R$^1$ is C$_1$-C$_6$ alkyl;
R$^2$ is 1-hydroxy-1-cyclopropyl, and R$^1$ is methyl;
R$^2$ is 1-hydroxy-1-cyclobutyl, and R$^1$ is methyl;
R$^2$ is 1-hydroxy-1-cyclopentyl, and R$^1$ is methyl;
R$^2$ is 1-hydroxy-1-cyclohexyl, and R$^1$ is methyl;
R$^2$ is morpholinyl, and R$^1$ is methyl;
R$^2$ is 1,3-dioxolan-2-yl, and R$^1$ is methyl;
R$^2$ is 1,3-dioxolan-2-yl, and R$^1$ is fluoro;
R$^2$ is 1,3-dioxolan-2-yl, and R$^1$ is chloro;
R$^2$ is C$_1$-C$_6$ alkyl optionally substituted with one or more oxo, and R$^1$ is methyl;
R$^2$ is (dimethylamino)methyl, and R$^1$ is methyl;
R$^2$ is COCH$_3$, and R$^1$ is methyl; or
R$^2$ is 2-methoxy-2-propyl, and R$^1$ is methyl.

In some embodiments, of the compound of formula AA, the substituted ring A is

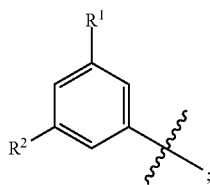

and R$^1$ and R$^2$ are one of the following combinations:
R$^1$ is C$_1$-C$_6$ alkyl optionally substituted with one or more hydroxy, and R$^2$ is C$_1$-C$_6$ alkyl optionally substituted with one or more hydroxy;
R$^1$ is C$_1$-C$_6$ alkyl optionally substituted with one or more hydroxy, and R$^2$ is C$_6$-C$_{10}$ aryl;
R$^1$ is C$_1$-C$_6$ alkyl optionally substituted with one or more hydroxy, and R$^2$ is 5- to 10-membered heteroaryl;
R$^1$ is C$_1$-C$_6$ alkyl optionally substituted with one or more hydroxy, and R$^2$ is SF$_5$;
R$^1$ is C$_1$-C$_6$ alkyl optionally substituted with one or more hydroxy, and R$^2$ is S(O$_2$)C$_1$-C$_6$ alkyl;
R$^1$ is C$_1$-C$_6$ alkyl optionally substituted with one or more hydroxy, and R$^2$ is halo;
R$^1$ is C$_3$-C$_7$ cycloalkyl optionally substituted with one or more hydroxy, and R$^2$ is C$_1$-C$_6$ alkyl;
R$^1$ is 3- to 7-membered heterocycloalkyl optionally substituted with one or more hydroxy, and R$^2$ is C$_1$-C$_6$ alkyl;
R$^1$ is 3- to 7-membered heterocycloalkyl optionally substituted with one or more hydroxy, and R$^2$ is halo;
R$^1$ is C$_1$-C$_6$ alkyl optionally substituted with one or more oxo, and R$^2$ is methyl;
R$^1$ is C$_1$-C$_6$ alkyl optionally substituted with one or more C$_1$-C$_6$ alkoxy, and R$^2$ is C$_1$-C$_6$ alkyl;
R$^1$ is C$_1$-C$_6$ alkyl optionally substituted with one or more NR$^8$R$^9$, and R$^2$ is C$_1$-C$_6$ alkyl;
R$^1$ is C$_1$-C$_6$ alkyl optionally substituted with one or more NR$^8$R$^9$, and R$^2$ is halo;
R$^2$ is C$_1$-C$_6$ alkyl optionally substituted with one or more hydroxy, and R$^1$ is C$_6$-C$_{10}$ aryl;
R$^2$ is C$_1$-C$_6$ alkyl optionally substituted with one or more hydroxy, and R$^1$ is 5- to 10-membered heteroaryl;
R$^2$ is C$_1$-C$_6$ alkyl optionally substituted with one or more hydroxy, and R$^1$ is SF$_5$;
R$^2$ is C$_1$-C$_6$ alkyl optionally substituted with one or more hydroxy, and R$^1$ is S(O$_2$)C$_1$-C$_6$ alkyl;
R$^2$ is C$_1$-C$_6$ alkyl optionally substituted with one or more hydroxy, and R$^1$ is halo;
R$^2$ is C$_3$-C$_7$ cycloalkyl optionally substituted with one or more hydroxy, and R$^1$ is C$_1$-C$_6$ alkyl;
R$^2$ is 3- to 7-membered heterocycloalkyl optionally substituted with one or more hydroxy, and R$^1$ is C$_1$-C$_6$ alkyl;
R$^2$ is 3- to 7-membered heterocycloalkyl optionally substituted with one or more hydroxy, and R$^1$ is halo;
R$^2$ is C$_1$-C$_6$ alkyl optionally substituted with one or more NR$^8$R$^9$, and R$^1$ is C$_1$-C$_6$ alkyl;
R$^2$ is C$_1$-C$_6$ alkyl optionally substituted with one or more NR$^8$R$^9$, and R$^1$ is halo;
R$^2$ is C$_1$-C$_6$ alkyl optionally substituted with one or more oxo, and R$^1$ is methyl; or
R$^2$ is C$_1$-C$_6$ alkyl optionally substituted with one or more C$_1$-C$_6$ alkoxy, and R$^1$ is C$_1$-C$_6$ alkyl.

In some embodiments, of the compound of formula AA, the substituted ring A is

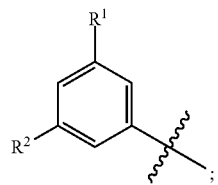

and R$^1$ and R$^2$ are one of the following combinations:
R$^1$ is 1-hydroxy-2-methylpropan-2-yl, and R$^2$ is methyl;
R$^1$ is 2-hydroxy-2-propyl and R$^2$ is methyl;
R$^1$ is 2-hydroxy-2-propyl and R$^2$ is isopropyl;
R$^1$ is 2-hydroxy-2-propyl and R$^2$ is 2-hydroxy-2-propyl;
R$^1$ is 2-hydroxy-2-propyl and R$^2$ is 1-hydroxyethyl;
R$^1$ is hydroxymethyl and R$^2$ is methyl;
R$^1$ is 1-hydroxyethyl and R$^2$ is methyl;
R$^1$ is 2-hydroxyethyl and R$^2$ is methyl;
R$^1$ is 1-hydroxy-2-propyl and R$^2$ is methyl;
R$^1$ is 2-hydroxy-2-propyl and R$^2$ is phenyl;
R$^1$ is 2-hydroxy-2-propyl and R$^2$ is pyridyl;
R$^1$ is 2-hydroxy-2-propyl and R$^2$ is pyrazolyl;

R¹ is 2-hydroxy-2-propyl, and R² is S(O₂)CH₃;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;
R¹ is (dimethylamino)methyl, and R² is methyl.
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is $C_1$-$C_6$ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is $C_1$-$C_6$ alkyl optionally substituted with one or more hydroxy, and R¹ is S(O₂)CH₃;
R² is 2-hydroxy-2-propyl and R¹ is chloro;
R² is 2-hydroxy-2-propyl and R¹ is fluoro;
R² is $C_3$-$C_7$ cycloalkyl optionally substituted with one or more hydroxy, and R¹ is $C_1$-$C_6$ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is $C_1$-$C_6$ alkyl optionally substituted with one or more oxo, and R¹ is methyl;
R² is (dimethylamino)methyl, and R¹ is methyl;
R² is COCH₃, and R¹ is methyl; or
R² is 2-methoxy-2-propyl, and R¹ is methyl.

In some embodiments, of the compound of formula AA, the substituted ring A is

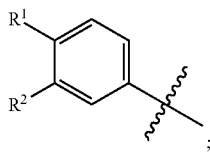

and R¹ and R² are one of the following combinations:
R¹ is $C_1$-$C_6$ alkyl optionally substituted with one or more hydroxy, and R² is $C_1$-$C_6$ alkyl optionally substituted with one or more hydroxy;
R¹ is $C_1$-$C_6$ alkyl optionally substituted with one or more hydroxy, and R² is $C_6$-$C_{10}$ aryl;
R¹ is $C_1$-$C_6$ alkyl optionally substituted with one or more hydroxy, and R² is 5- to 10-membered heteroaryl;
R¹ is $C_1$-$C_6$ alkyl optionally substituted with one or more hydroxy, and R² is SF₅;
R¹ is $C_1$-$C_6$ alkyl optionally substituted with one or more hydroxy, and R² is S(O₂)$C_1$-$C_6$ alkyl;
R¹ is $C_1$-$C_6$ alkyl optionally substituted with one or more hydroxy, and R² is halo;
R¹ is $C_3$-$C_7$ cycloalkyl optionally substituted with one or more hydroxy, and R² is $C_1$-$C_6$ alkyl;
R¹ is 3- to 7-membered heterocycloalkyl optionally substituted with one or more hydroxy, and R² is $C_1$-$C_6$ alkyl;
R¹ is 3- to 7-membered heterocycloalkyl optionally substituted with one or more hydroxy, and R² is halo;
R¹ is $C_1$-$C_6$ alkyl optionally substituted with one or more oxo, and R² is methyl;
R¹ is $C_1$-$C_6$ alkyl optionally substituted with one or more $C_1$-$C_6$ alkoxy, and R² is $C_1$-$C_6$ alkyl;
R¹ is $C_1$-$C_6$ alkyl optionally substituted with one or more NR⁸R⁹, and R² is $C_1$-$C_6$ alkyl;
R¹ is $C_1$-$C_6$ alkyl optionally substituted with one or more NR⁸R⁹, and R² is halo;
R² is $C_1$-$C_6$ alkyl optionally substituted with one or more hydroxy, and R¹ is $C_6$-$C_{10}$ aryl;
R² is $C_1$-$C_6$ alkyl optionally substituted with one or more hydroxy, and R¹ is 5- to 10-membered heteroaryl;
R² is $C_1$-$C_6$ alkyl optionally substituted with one or more hydroxy, and R¹ is SF₅.
R² is $C_1$-$C_6$ alkyl optionally substituted with one or more hydroxy, and R¹ is S(O₂)$C_1$-$C_6$ alkyl;
R² is $C_1$-$C_6$ alkyl optionally substituted with one or more hydroxy, and R¹ is halo;
R² is $C_3$-$C_7$ cycloalkyl optionally substituted with one or more hydroxy, and R¹ is $C_1$-$C_6$ alkyl;
R² is 3- to 7-membered heterocycloalkyl optionally substituted with one or more hydroxy, and R¹ is $C_1$-$C_6$ alkyl;
R² is 3- to 7-membered heterocycloalkyl optionally substituted with one or more hydroxy, and R¹ is halo;
R² is $C_1$-$C_6$ alkyl optionally substituted with one or more NR⁸R⁹, and R¹ is $C_1$-$C_6$ alkyl;
R² is $C_1$-$C_6$ alkyl optionally substituted with one or more NR⁸R⁹, and R¹ is halo;
R² is $C_1$-$C_6$ alkyl optionally substituted with one or more oxo, and R¹ is methyl; or
R² is $C_1$-$C_6$ alkyl optionally substituted with one or more $C_1$-$C_6$ alkoxy, and R¹ is $C_1$-$C_6$ alkyl.

In some embodiments, of the compound of formula AA, the substituted ring A is

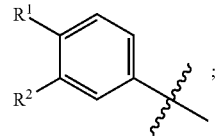

and R¹ and R² are one of the following combinations:
R¹ is 1-hydroxy-2-methylpropan-2-yl, and R² is methyl;
R¹ is 2-hydroxy-2-propyl and R² is methyl;
R¹ is 2-hydroxy-2-propyl and R² is isopropyl;

R¹ is 2-hydroxy-2-propyl and R² is 2-hydroxy-2-propyl;
R¹ is 2-hydroxy-2-propyl and R² is 1-hydroxyethyl;
R¹ is hydroxymethyl and R² is methyl;
R¹ is 1-hydroxyethyl and R² is methyl;
R¹ is 2-hydroxyethyl and R² is methyl;
R¹ is 1-hydroxy-2-propyl and R² is methyl;
R¹ is 2-hydroxy-2-propyl and R² is phenyl;
R¹ is 2-hydroxy-2-propyl and R² is pyridyl;
R¹ is 2-hydroxy-2-propyl and R² is pyrazolyl;
R¹ is 2-hydroxy-2-propyl, and R² is S(O₂)CH₃;
R¹ is 2-hydroxy-2-propyl and R² is chloro;
R¹ is 2-hydroxy-2-propyl and R² is fluoro;
R¹ is 1-hydroxy-1-cyclopropyl, and R² is methyl;
R¹ is 1-hydroxy-1-cyclobutyl, and R² is methyl;
R¹ is 1-hydroxy-1-cyclopentyl, and R² is methyl;
R¹ is 1-hydroxy-1-cyclohexyl, and R² is methyl;
R¹ is morpholinyl, and R² is methyl;
R¹ is 1,3-dioxolan-2-yl, and R² is methyl;
R¹ is 1,3-dioxolan-2-yl, and R² is fluoro;
R¹ is 1,3-dioxolan-2-yl, and R² is chloro;
R¹ is COCH₃, and R² is methyl;
R¹ is 2-methoxy-2-propyl, and R² is methyl;
R¹ is (dimethylamino)methyl, and R² is methyl.
R² is 1-hydroxy-2-methylpropan-2-yl, and R¹ is methyl;
R² is 2-hydroxy-2-propyl and R¹ is methyl;
R² is 2-hydroxy-2-propyl and R¹ is isopropyl;
R² is 2-hydroxy-2-propyl and R¹ is 1-hydroxyethyl;
R² is hydroxymethyl and R¹ is methyl;
R² is 1-hydroxyethyl and R¹ is methyl;
R² is 2-hydroxyethyl and R¹ is methyl;
R² is 1-hydroxy-2-propyl and R¹ is methyl;
R² is 2-hydroxy-2-propyl and R¹ is phenyl;
R² is C₁-C₆ alkyl optionally substituted with one or more hydroxy, and R¹ is 5- to 10-membered heteroaryl;
R² is 2-hydroxy-2-propyl and R¹ is pyridyl;
R² is 2-hydroxy-2-propyl and R¹ is pyrazolyl;
R² is C₁-C₆ alkyl optionally substituted with one or more hydroxy, and R¹ is S(O₂)CH₃;
R² is 2-hydroxy-2-propyl and R¹ is chloro;
R² is 2-hydroxy-2-propyl and R¹ is fluoro;
R² is C₃-C₇ cycloalkyl optionally substituted with one or more hydroxy, and R¹ is C₁-C₆ alkyl;
R² is 1-hydroxy-1-cyclopropyl, and R¹ is methyl;
R² is 1-hydroxy-1-cyclobutyl, and R¹ is methyl;
R² is 1-hydroxy-1-cyclopentyl, and R¹ is methyl;
R² is 1-hydroxy-1-cyclohexyl, and R¹ is methyl;
R² is morpholinyl, and R¹ is methyl;
R² is 1,3-dioxolan-2-yl, and R¹ is methyl;
R² is 1,3-dioxolan-2-yl, and R¹ is fluoro;
R² is 1,3-dioxolan-2-yl, and R¹ is chloro;
R² is C₁-C₆ alkyl optionally substituted with one or more oxo, and R¹ is methyl;
R² is (dimethylamino)methyl, and R¹ is methyl;
R² is COCH₃, and R¹ is methyl; or
R² is 2-methoxy-2-propyl, and R¹ is methyl.

In some embodiments, of the compound of formula AA, the substituted ring A is

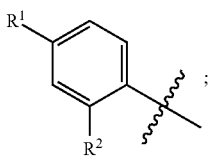

and R¹ and R² are one of the following combinations:
R¹ is C₁-C₆ alkyl optionally substituted with one or more hydroxy, and R² is C₁-C₆ alkyl optionally substituted with one or more hydroxy;
R¹ is C₁-C₆ alkyl optionally substituted with one or more hydroxy, and R² is C₆-C₁₀ aryl;
R¹ is C₁-C₆ alkyl optionally substituted with one or more hydroxy, and R² is 5- to 10-membered heteroaryl;
R¹ is C₁-C₆ alkyl optionally substituted with one or more hydroxy, and R² is SF₅;
R¹ is C₁-C₆ alkyl optionally substituted with one or more hydroxy, and R² is S(O₂)C₁-C₆ alkyl;
R¹ is C₁-C₆ alkyl optionally substituted with one or more hydroxy, and R² is halo;
R¹ is C₃-C₇ cycloalkyl optionally substituted with one or more hydroxy, and R² is C₁-C₆ alkyl;
R¹ is 3- to 7-membered heterocycloalkyl optionally substituted with one or more hydroxy, and R² is C₁-C₆ alkyl;
R¹ is 3- to 7-membered heterocycloalkyl optionally substituted with one or more hydroxy, and R² is halo;
R¹ is C₁-C₆ alkyl optionally substituted with one or more oxo, and R² is methyl;
R¹ is C₁-C₆ alkyl optionally substituted with one or more C₁-C₆ alkoxy, and R² is C₁-C₆ alkyl;
R¹ is C₁-C₆ alkyl optionally substituted with one or more NR⁸R⁹, and R² is C₁-C₆ alkyl;
R¹ is C₁-C₆ alkyl optionally substituted with one or more NR⁸R⁹, and R² is halo;
R² is C₁-C₆ alkyl optionally substituted with one or more hydroxy, and R¹ is C₆-C₁₀ aryl;
R² is C₁-C₆ alkyl optionally substituted with one or more hydroxy, and R¹ is 5- to 10-membered heteroaryl;
R² is C₁-C₆ alkyl optionally substituted with one or more hydroxy, and R¹ is SF₅.
R² is C₁-C₆ alkyl optionally substituted with one or more hydroxy, and R¹ is S(O₂)C₁-C₆ alkyl;
R² is C₁-C₆ alkyl optionally substituted with one or more hydroxy, and R¹ is halo;
R² is C₃-C₇ cycloalkyl optionally substituted with one or more hydroxy, and R¹ is C₁-C₆ alkyl;
R² is 3- to 7-membered heterocycloalkyl optionally substituted with one or more hydroxy, and R¹ is C₁-C₆ alkyl;
R² is 3- to 7-membered heterocycloalkyl optionally substituted with one or more hydroxy, and R¹ is halo;
R² is C₁-C₆ alkyl optionally substituted with one or more NR⁸R⁹, and R¹ is C₁-C₆ alkyl;
R² is C₁-C₆ alkyl optionally substituted with one or more NR⁸R⁹, and R¹ is halo;
R² is C₁-C₆ alkyl optionally substituted with one or more oxo, and R¹ is methyl; or
R² is C₁-C₆ alkyl optionally substituted with one or more C₁-C₆ alkoxy, and R¹ is C₁-C₆ alkyl.

In some embodiments, of the compound of formula AA, the substituted ring A is

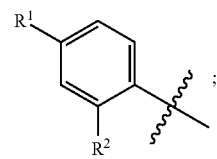

and $R^1$ and $R^2$ are one of the following combinations:
- $R^1$ is 1-hydroxy-2-methylpropan-2-yl, and $R^2$ is methyl;
- $R^1$ is 2-hydroxy-2-propyl and $R^2$ is methyl;
- $R^1$ is 2-hydroxy-2-propyl and $R^2$ is isopropyl;
- $R^1$ is 2-hydroxy-2-propyl and $R^2$ is 2-hydroxy-2-propyl;
- $R^1$ is 2-hydroxy-2-propyl and $R^2$ is 1-hydroxyethyl;
- $R^1$ is hydroxymethyl and $R^2$ is methyl;
- $R^1$ is 1-hydroxyethyl and $R^2$ is methyl;
- $R^1$ is 2-hydroxyethyl and $R^2$ is methyl;
- $R^1$ is 1-hydroxy-2-propyl and $R^2$ is methyl;
- $R^1$ is 2-hydroxy-2-propyl and $R^2$ is phenyl;
- $R^1$ is 2-hydroxy-2-propyl and $R^2$ is pyridyl;
- $R^1$ is 2-hydroxy-2-propyl and $R^2$ is pyrazolyl;
- $R^1$ is 2-hydroxy-2-propyl, and $R^2$ is $S(O_2)CH_3$;
- $R^1$ is 2-hydroxy-2-propyl and $R^2$ is chloro;
- $R^1$ is 2-hydroxy-2-propyl and $R^2$ is fluoro;
- $R^1$ is 1-hydroxy-1-cyclopropyl, and $R^2$ is methyl;
- $R^1$ is 1-hydroxy-1-cyclobutyl, and $R^2$ is methyl;
- $R^1$ is 1-hydroxy-1-cyclopentyl, and $R^2$ is methyl;
- $R^1$ is 1-hydroxy-1-cyclohexyl, and $R^2$ is methyl;
- $R^1$ is morpholinyl, and $R^2$ is methyl;
- $R^1$ is 1,3-dioxolan-2-yl, and $R^2$ is methyl;
- $R^1$ is 1,3-dioxolan-2-yl, and $R^2$ is fluoro;
- $R^1$ is 1,3-dioxolan-2-yl, and $R^2$ is chloro;
- $R^1$ is $COCH_3$, and $R^2$ is methyl;
- $R^1$ is 2-methoxy-2-propyl, and $R^2$ is methyl;
- $R^1$ is (dimethylamino)methyl, and $R^2$ is methyl.
- $R^2$ is 1-hydroxy-2-methylpropan-2-yl, and $R^1$ is methyl;
- $R^2$ is 2-hydroxy-2-propyl and $R^1$ is methyl;
- $R^2$ is 2-hydroxy-2-propyl and $R^1$ is isopropyl;
- $R^2$ is 2-hydroxy-2-propyl and $R^1$ is 1-hydroxyethyl;
- $R^2$ is hydroxymethyl and $R^1$ is methyl;
- $R^2$ is 1-hydroxyethyl and $R^1$ is methyl;
- $R^2$ is 2-hydroxyethyl and $R^1$ is methyl;
- $R^2$ is 1-hydroxy-2-propyl and $R^1$ is methyl;
- $R^2$ is 2-hydroxy-2-propyl and $R^1$ is phenyl;
- $R^2$ is $C_1$-$C_6$ alkyl optionally substituted with one or more hydroxy, and $R^1$ is 5- to 10-membered heteroaryl;
- $R^2$ is 2-hydroxy-2-propyl and $R^1$ is pyridyl;
- $R^2$ is 2-hydroxy-2-propyl and $R^1$ is pyrazolyl;
- $R^2$ is $C_1$-$C_6$ alkyl optionally substituted with one or more hydroxy, and $R^1$ is $S(O_2)CH_3$;
- $R^2$ is 2-hydroxy-2-propyl and $R^1$ is chloro;
- $R^2$ is 2-hydroxy-2-propyl and $R^1$ is fluoro;
- $R^2$ is $C_3$-$C_7$ cycloalkyl optionally substituted with one or more hydroxy, and $R^1$ is $C_1$-$C_6$ alkyl;
- $R^2$ is 1-hydroxy-1-cyclopropyl, and $R^1$ is methyl;
- $R^2$ is 1-hydroxy-1-cyclobutyl, and $R^1$ is methyl;
- $R^2$ is 1-hydroxy-1-cyclopentyl, and $R^1$ is methyl;
- $R^2$ is 1-hydroxy-1-cyclohexyl, and $R^1$ is methyl;
- $R^2$ is morpholinyl, and $R^1$ is methyl;
- $R^2$ is 1,3-dioxolan-2-yl, and $R^1$ is methyl;
- $R^2$ is 1,3-dioxolan-2-yl, and $R^1$ is fluoro;
- $R^2$ is 1,3-dioxolan-2-yl, and $R^1$ is chloro;
- $R^2$ is (dimethylamino)methyl, and $R^1$ is methyl;
- $R^2$ is $C_1$-$C_6$ alkyl optionally substituted with one or more oxo, and $R^1$ is methyl; or
- $R^2$ is $COCH_3$, and $R^1$ is methyl.

In some embodiments, of the compound of formula AA, the substituted ring A is

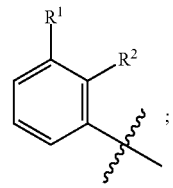

and $R^1$ and $R^2$ are one of the following combinations:
- $R^1$ is $C_1$-$C_6$ alkyl optionally substituted with one or more hydroxy, and $R^2$ is $C_1$-$C_6$ alkyl optionally substituted with one or more hydroxy;
- $R^1$ is $C_1$-$C_6$ alkyl optionally substituted with one or more hydroxy, and $R^2$ is $C_6$-$C_{10}$ aryl;
- $R^1$ is $C_1$-$C_6$ alkyl optionally substituted with one or more hydroxy, and $R^2$ is 5- to 10-membered heteroaryl;
- $R^1$ is $C_1$-$C_6$ alkyl optionally substituted with one or more hydroxy, and $R^2$ is $SF_5$;
- $R^1$ is $C_1$-$C_6$ alkyl optionally substituted with one or more hydroxy, and $R^2$ is $S(O_2)C_1$-$C_6$ alkyl;
- $R^1$ is $C_1$-$C_6$ alkyl optionally substituted with one or more hydroxy, and $R^2$ is halo;
- $R^1$ is $C_3$-$C_7$ cycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is halo;
- $R^1$ is $C_1$-$C_6$ alkyl optionally substituted with one or more oxo, and $R^2$ is methyl;
- $R^1$ is $C_1$-$C_6$ alkyl optionally substituted with one or more $C_1$-$C_6$ alkoxy, and $R^2$ is $C_1$-$C_6$ alkyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is $C_1$-$C_6$ alkyl optionally substituted with one or more hydroxy, and $R^1$ is $C_6$-$C_{10}$ aryl;
- $R^2$ is $C_1$-$C_6$ alkyl optionally substituted with one or more hydroxy, and $R^1$ is 5- to 10-membered heteroaryl;
- $R^2$ is $C_1$-$C_6$ alkyl optionally substituted with one or more hydroxy, and $R^1$ is $SF_5$.
- $R^2$ is $C_1$-$C_6$ alkyl optionally substituted with one or more hydroxy, and $R^1$ is $S(O_2)C_1$-$C_6$ alkyl;
- $R^2$ is $C_1$-$C_6$ alkyl optionally substituted with one or more hydroxy, and $R^1$ is halo;
- $R^2$ is $C_3$-$C_7$ cycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is $C_1$-$C_6$ alkyl;
- $R^2$ is 3- to 7-membered heterocycloalkyl optionally substituted with one or more hydroxy, and $R^1$ is halo;
- $R^2$ is $C_1$-$C_6$ alkyl optionally substituted with one or more $NR^8R^9$, and $R^1$ is $C_1$-$C_6$ alkyl;
- $R^2$ is $C_1$-$C_6$ alkyl optionally substituted with one or more $NR^8R^9$, and $R^1$ is halo;
- $R^2$ is $C_1$-$C_6$ alkyl optionally substituted with one or more oxo, and $R^1$ is methyl; or
- $R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

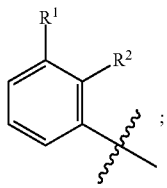

and $R^1$ and $R^2$ are one of the following combinations:
- $R^1$ is 1-hydroxy-2-methylpropan-2-yl, and $R^2$ is methyl;
- $R^1$ is 2-hydroxy-2-propyl and $R^2$ is methyl;
- $R^1$ is 2-hydroxy-2-propyl and $R^2$ is isopropyl;
- $R^1$ is 2-hydroxy-2-propyl and $R^2$ is 2-hydroxy-2-propyl;
- $R^1$ is 2-hydroxy-2-propyl and $R^2$ is 1-hydroxyethyl;
- $R^1$ is hydroxymethyl and $R^2$ is methyl;
- $R^1$ is 1-hydroxyethyl and $R^2$ is methyl;
- $R^1$ is 2-hydroxyethyl and $R^2$ is methyl;
- $R^1$ is 1-hydroxy-2-propyl and $R^2$ is methyl;
- $R^1$ is 2-hydroxy-2-propyl and $R^2$ is phenyl;
- $R^1$ is 2-hydroxy-2-propyl and $R^2$ is pyridyl;
- $R^1$ is 2-hydroxy-2-propyl and $R^2$ is pyrazolyl;
- $R^1$ is 2-hydroxy-2-propyl, and $R^2$ is $S(O_2)CH_3$;
- $R^1$ is 2-hydroxy-2-propyl and $R^2$ is chloro;
- $R^1$ is 2-hydroxy-2-propyl and $R^2$ is fluoro;
- $R^1$ is 1-hydroxy-1-cyclopropyl, and $R^2$ is methyl;
- $R^1$ is 1-hydroxy-1-cyclobutyl, and $R^2$ is methyl;
- $R^1$ is 1-hydroxy-1-cyclopentyl, and $R^2$ is methyl;
- $R^1$ is 1-hydroxy-1-cyclohexyl, and $R^2$ is methyl;
- $R^1$ is morpholinyl, and $R^2$ is methyl;
- $R^1$ is 1,3-dioxolan-2-yl, and $R^2$ is methyl;
- $R^1$ is 1,3-dioxolan-2-yl, and $R^2$ is fluoro;
- $R^1$ is 1,3-dioxolan-2-yl, and $R^2$ is chloro;
- $R^1$ is $COCH_3$, and $R^2$ is methyl;
- $R^1$ is 2-methoxy-2-propyl, and $R^2$ is methyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is 1-hydroxy-2-methylpropan-2-yl, and $R^1$ is methyl;
- $R^2$ is 2-hydroxy-2-propyl and $R^1$ is methyl;
- $R^2$ is 2-hydroxy-2-propyl and $R^1$ is isopropyl;
- $R^2$ is 2-hydroxy-2-propyl and $R^1$ is 1-hydroxyethyl;
- $R^2$ is hydroxymethyl and $R^1$ is methyl;
- $R^2$ is 1-hydroxyethyl and $R^1$ is methyl;
- $R^2$ is 2-hydroxyethyl and $R^1$ is methyl;
- $R^2$ is 1-hydroxy-2-propyl and $R^1$ is methyl;
- $R^2$ is 2-hydroxy-2-propyl and $R^1$ is phenyl;
- $R^2$ is $C_1$-$C_6$ alkyl optionally substituted with one or more hydroxy, and $R^1$ is 5- to 10-membered heteroaryl;
- $R^2$ is 2-hydroxy-2-propyl and $R^1$ is pyridyl;
- $R^2$ is 2-hydroxy-2-propyl and $R^1$ is pyrazolyl;
- $R^2$ is $C_1$-$C_6$ alkyl optionally substituted with one or more hydroxy, and $R^1$ is $S(O_2)CH_3$;
- $R^2$ is 2-hydroxy-2-propyl and $R^1$ is chloro;
- $R^2$ is 2-hydroxy-2-propyl and $R^1$ is fluoro;
- $R^2$ is $C_3$-$C_7$ cycloalkyl optionally substituted with one or more hydroxy, and $R^1$ is $C_1$-$C_6$ alkyl;
- $R^2$ is 1-hydroxy-1-cyclopropyl, and $R^1$ is methyl;
- $R^2$ is 1-hydroxy-1-cyclobutyl, and $R^1$ is methyl;
- $R^2$ is 1-hydroxy-1-cyclopentyl, and $R^1$ is methyl;
- $R^2$ is 1-hydroxy-1-cyclohexyl, and $R^1$ is methyl;
- $R^2$ is morpholinyl, and $R^1$ is methyl;
- $R^2$ is 1,3-dioxolan-2-yl, and $R^1$ is methyl;
- $R^2$ is 1,3-dioxolan-2-yl, and $R^1$ is fluoro;
- $R^2$ is 1,3-dioxolan-2-yl, and $R^1$ is chloro;
- $R^2$ is $C_1$-$C_6$ alkyl optionally substituted with one or more oxo, and $R^1$ is methyl;
- $R^2$ is $C_1$-$C_6$ alkyl optionally substituted with one or more $NR^8R^9$, and $R^1$ is $C_1$-$C_6$ alkyl;
- $R^2$ is $C_1$-$C_6$ alkyl optionally substituted with one or more $NR^8R^9$, and $R^1$ is halo;
- $R^2$ is $COCH_3$, and $R^1$ is methyl; or
- $R^2$ is 2-methoxy-2-propyl, and $R^1$ is methyl.

In some embodiments, of the compound of formula AA, the substituted ring A is

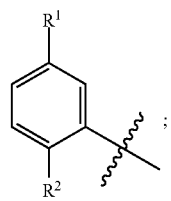

and $R^1$ and $R^2$ are one of the following combinations:
- $R^1$ is $C_1$-$C_6$ alkyl optionally substituted with one or more hydroxy, and $R^2$ is $C_1$-$C_6$ alkyl optionally substituted with one or more hydroxy;
- $R^1$ is $C_1$-$C_6$ alkyl optionally substituted with one or more hydroxy, and $R^2$ is $C_6$-$C_{10}$ aryl;
- $R^1$ is $C_1$-$C_6$ alkyl optionally substituted with one or more hydroxy, and $R^2$ is 5- to 10-membered heteroaryl;
- $R^1$ is $C_1$-$C_6$ alkyl optionally substituted with one or more hydroxy, and $R^2$ is $SF_5$;
- $R^1$ is $C_1$-$C_6$ alkyl optionally substituted with one or more hydroxy, and $R^2$ is $S(O_2)C_1$-$C_6$ alkyl;
- $R^1$ is $C_1$-$C_6$ alkyl optionally substituted with one or more hydroxy, and $R^2$ is halo;
- $R^1$ is $C_3$-$C_7$ cycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is $C_1$-$C_6$ alkyl;
- $R^1$ is 3- to 7-membered heterocycloalkyl optionally substituted with one or more hydroxy, and $R^2$ is halo;
- $R^1$ is $C_1$-$C_6$ alkyl optionally substituted with one or more oxo, and $R^2$ is methyl;
- $R^1$ is $C_1$-$C_6$ alkyl optionally substituted with one or more $C_1$-$C_6$ alkoxy, and $R^2$ is $C_1$-$C_6$ alkyl;
- $R^1$ is $C_1$-$C_6$ alkyl optionally substituted with one or more $NR^8R^9$, and $R^2$ is $C_1$-$C_6$ alkyl;
- $R^1$ is $C_1$-$C_6$ alkyl optionally substituted with one or more $NR^8R^9$, and $R^2$ is halo;
- $R^2$ is $C_1$-$C_6$ alkyl optionally substituted with one or more hydroxy, and $R^1$ is $C_6$-$C_{10}$ aryl;
- $R^2$ is $C_1$-$C_6$ alkyl optionally substituted with one or more hydroxy, and $R^1$ is 5- to 10-membered heteroaryl;
- $R^2$ is $C_1$-$C_6$ alkyl optionally substituted with one or more hydroxy, and $R^1$ is $SF_5$.
- $R^2$ is $C_1$-$C_6$ alkyl optionally substituted with one or more hydroxy, and $R^1$ is $S(O_2)C_1$-$C_6$ alkyl;

$R^2$ is $C_1$-$C_6$ alkyl optionally substituted with one or more hydroxy, and $R^1$ is halo;
$R^2$ is $C_3$-$C_7$ cycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is $C_1$-$C_6$ alkyl;
$R^2$ is 3- to 7-membered heterocycloalkyl optionally substituted with one or more hydroxy, and $R^1$ is halo;
$R^2$ is $C_1$-$C_6$ alkyl optionally substituted with one or more $NR^8R^9$, and $R^1$ is $C_1$-$C_6$ alkyl;
$R^2$ is $C_1$-$C_6$ alkyl optionally substituted with one or more $NR^8R^9$, and $R^1$ is halo;
$R^2$ is $C_1$-$C_6$ alkyl optionally substituted with one or more oxo, and $R^1$ is methyl; or
$R^2$ is $C_1$-$C_6$ alkyl optionally substituted with one or more $C_1$-$C_6$ alkoxy, and $R^1$ is $C_1$-$C_6$ alkyl.

In some embodiments, of the compound of formula AA, the substituted ring A is

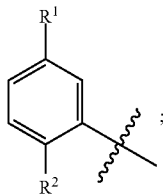

and $R^1$ and $R^2$ are one of the following combinations:
$R^1$ is 1-hydroxy-2-methylpropan-2-yl, and $R^2$ is methyl;
$R^1$ is 2-hydroxy-2-propyl and $R^2$ is methyl;
$R^1$ is 2-hydroxy-2-propyl and $R^2$ is isopropyl;
$R^1$ is 2-hydroxy-2-propyl and $R^2$ is 2-hydroxy-2-propyl;
$R^1$ is 2-hydroxy-2-propyl and $R^2$ is 1-hydroxyethyl;
$R^1$ is hydroxymethyl and $R^2$ is methyl;
$R^1$ is 1-hydroxyethyl and $R^2$ is methyl;
$R^1$ is 2-hydroxyethyl and $R^2$ is methyl;
$R^1$ is 1-hydroxy-2-propyl and $R^2$ is methyl;
$R^1$ is 2-hydroxy-2-propyl and $R^2$ is phenyl;
$R^1$ is 2-hydroxy-2-propyl and $R^2$ is pyridyl;
$R^1$ is 2-hydroxy-2-propyl and $R^2$ is pyrazolyl;
$R^1$ is 2-hydroxy-2-propyl, and $R^2$ is $S(O_2)CH_3$;
$R^1$ is 2-hydroxy-2-propyl and $R^2$ is chloro;
$R^1$ is 2-hydroxy-2-propyl and $R^2$ is fluoro;
$R^1$ is 1-hydroxy-1-cyclopropyl, and $R^2$ is methyl;
$R^1$ is 1-hydroxy-1-cyclobutyl, and $R^2$ is methyl;
$R^1$ is 1-hydroxy-1-cyclopentyl, and $R^2$ is methyl;
$R^1$ is 1-hydroxy-1-cyclohexyl, and $R^2$ is methyl;
$R^1$ is morpholinyl, and $R^2$ is methyl;
$R^1$ is 1,3-dioxolan-2-yl, and $R^2$ is methyl;
$R^1$ is 1,3-dioxolan-2-yl, and $R^2$ is fluoro;
$R^1$ is 1,3-dioxolan-2-yl, and $R^2$ is chloro;
$R^1$ is $COCH_3$, and $R^2$ is methyl;
$R^1$ is 2-methoxy-2-propyl, and $R^2$ is methyl;
$R^1$ is (dimethylamino)methyl, and $R^2$ is methyl.
$R^2$ is 1-hydroxy-2-methylpropan-2-yl, and $R^1$ is methyl;
$R^2$ is 2-hydroxy-2-propyl and $R^1$ is methyl;
$R^2$ is 2-hydroxy-2-propyl and $R^1$ is isopropyl;
$R^2$ is 2-hydroxy-2-propyl and $R^1$ is 1-hydroxyethyl;
$R^2$ is hydroxymethyl and $R^1$ is methyl;
$R^2$ is 1-hydroxyethyl and $R^1$ is methyl;
$R^2$ is 2-hydroxyethyl and $R^1$ is methyl;
$R^2$ is 1-hydroxy-2-propyl and $R^1$ is methyl;
$R^2$ is 2-hydroxy-2-propyl and $R^1$ is phenyl;
$R^2$ is $C_1$-$C_6$ alkyl optionally substituted with one or more hydroxy, and $R^1$ is 5- to 10-membered heteroaryl;
$R^2$ is 2-hydroxy-2-propyl and $R^1$ is pyridyl;
$R^2$ is 2-hydroxy-2-propyl and $R^1$ is pyrazolyl;
$R^2$ is $C_1$-$C_6$ alkyl optionally substituted with one or more hydroxy, and $R^1$ is $S(O_2)CH_3$;
$R^2$ is 2-hydroxy-2-propyl and $R^1$ is chloro;
$R^2$ is 2-hydroxy-2-propyl and $R^1$ is fluoro;
$R^2$ is $C_3$-$C_7$ cycloalkyl optionally substituted with one or more hydroxy, and $R^1$ is $C_1$-$C_6$ alkyl;
$R^2$ is 1-hydroxy-1-cyclopropyl, and $R^1$ is methyl;
$R^2$ is 1-hydroxy-1-cyclobutyl, and $R^1$ is methyl;
$R^2$ is 1-hydroxy-1-cyclopentyl, and $R^1$ is methyl;
$R^2$ is 1-hydroxy-1-cyclohexyl, and $R^1$ is methyl;
$R^2$ is morpholinyl, and $R^1$ is methyl;
$R^2$ is 1,3-dioxolan-2-yl, and $R^1$ is methyl;
$R^2$ is 1,3-dioxolan-2-yl, and $R^1$ is fluoro;
$R^2$ is 1,3-dioxolan-2-yl, and $R^1$ is chloro;
$R^2$ is $C_1$-$C_6$ alkyl optionally substituted with one or more oxo, and $R^1$ is methyl;
$R^2$ is (dimethylamino)methyl, and $R^1$ is methyl;
$R^2$ is $COCH_3$, and $R^1$ is methyl; or
$R^2$ is 2-methoxy-2-propyl, and $R^1$ is methyl.

In some embodiments of the compound of formula AA, the substituted ring B is

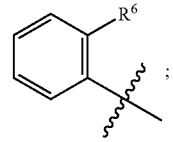

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

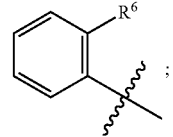

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

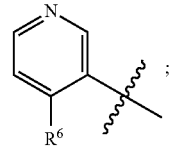

and R⁶ is selected from:
  C₁-C₆ alkyl, C₁-C₆ alkyl substituted with one or more halo, C₁-C₆ alkoxy, C₁-C₆ alkoxy substituted with one or more halo, C₃-C₇ cycloalkyl, halo, and cyano.

In some embodiments of the compound of formula AA, the substituted ring B is

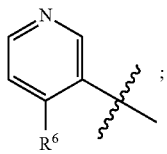;

and R⁶ is selected from:
  isopropyl, ethyl, methyl, trifluoromethyl, trifluoromethoxy, cyclopropyl, halo, chloro, and fluoro.

In some embodiments of the compound of formula AA, the substituted ring B is

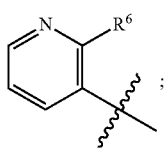;

and R⁶ is selected from:
  C₁-C₆ alkyl, C₁-C₆ alkyl substituted with one or more halo, C₁-C₆ alkoxy, C₁-C₆ alkoxy substituted with one or more halo, C₃-C₇ cycloalkyl, halo, and cyano.

In some embodiments of the compound of formula AA, the substituted ring B is

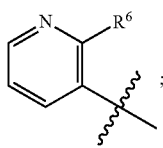;

and R⁶ is selected from:
  isopropyl, ethyl, methyl, trifluoromethyl, trifluoromethoxy, cyclopropyl, halo, chloro, and fluoro.

In some embodiments of the compound of formula AA, the substituted ring B is

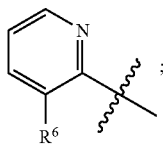;

and R⁶ is selected from:
  C₁-C₆ alkyl, C₁-C₆ alkyl substituted with one or more halo, C₁-C₆ alkoxy, C₁-C₆ alkoxy substituted with one or more halo, C₃-C₇ cycloalkyl, halo, and cyano.

In some embodiments of the compound of formula AA, the substituted ring B is

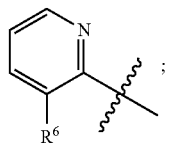;

and R⁶ is selected from:
  isopropyl, ethyl, methyl, trifluoromethyl, trifluoromethoxy, cyclopropyl, halo, chloro, and fluoro.

In some embodiments of the compound of formula AA, the substituted ring B is

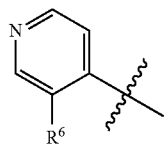;

and R⁶ is selected from:
  C₁-C₆ alkyl, C₁-C₆ alkyl substituted with one or more halo, C₁-C₆ alkoxy, C₁-C₆ alkoxy substituted with one or more halo, C₃-C₇ cycloalkyl, halo, and cyano.

In some embodiments of the compound of formula AA, the substituted ring B is

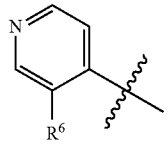;

and R⁶ is selected from:
  isopropyl, ethyl, methyl, trifluoromethyl, trifluoromethoxy, cyclopropyl, halo, chloro, and fluoro.

In some embodiments, of the compound of formula AA, the substituted ring B is

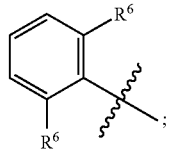;

and the two R⁶ are one of the following combinations:
  (i) One R⁶ is C₁-C₆ alkyl, and the other R⁶ is C₁-C₆ alkyl optionally substituted with one or more halo;
  (ii) One R⁶ is C₁-C₆ alkyl and the other R⁶ is C₁-C₆ alkyl;
  (iii) One R⁶ is C₁-C₆ alkyl, and the other R⁶ is C₁-C₆ alkyl substituted with one or more halo;
  (iv) One R⁶ is C₁-C₆ alkyl, and the other R⁶ is C₃-C₇ cycloalkyl;
  (v) One R⁶ is C₁-C₆ alkyl, and the other R⁶ is halo;
  (vi) One R⁶ is C₁-C₆ alkyl, and the other R⁶ is cyano;
  (vii) One R⁶ is C₃-C₇ cycloalkyl, and the other R⁶ is C₃-C₇ cycloalkyl;
  (viii) One R⁶ is C₃-C₇ cycloalkyl, and the other R⁶ is halo;
  (ix) One R⁶ is cyclopropyl and the other R⁶ is halo;

(x) One $R^6$ is $C_1$-$C_6$ alkyl, and the other $R^6$ is $C_1$-$C_6$ alkoxy optionally substituted with one or more halo;
(xi) One $R^6$ is $C_1$-$C_6$ alkyl, and the other $R^6$ is $C_1$-$C_6$ alkoxy;
(xii) One $R^6$ is $C_1$-$C_6$ alkyl, and the other $R^6$ is $C_1$-$C_6$ alkoxy substituted with one or more halo;
(xiii) One $R^6$ is halo, and the other $R^6$ is $C_1$-$C_6$ haloalkyl;
(xiv) One $R^6$ is halo, and the other $R^6$ is $C_1$-$C_6$ haloalkoxy;
(xv) One $R^6$ is $C_1$-$C_6$ alkoxy; and the other $R^6$ is halo;
(xvi) One $R^6$ is $C_1$-$C_6$ alkoxy; and the other $R^6$ is chloro.

In some embodiments, of the compound of formula AA, the substituted ring B is

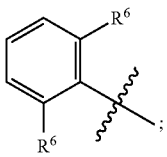

and the two $R^6$ are one of the following combinations:
(i) One $R^6$ is isopropyl; and the other $R^6$ is methyl;
(ii) One $R^6$ is isopropyl; and the other $R^6$ is n-propyl;
(iii) One $R^6$ is isopropyl; and the other $R^6$ is isopropyl;
(iv) One $R^6$ is isopropyl; and the other $R^6$ is trifluoromethyl;
(v) One $R^6$ is isopropyl; and the other $R^6$ is cyclopropyl;
(vi) One $R^6$ is isopropyl; and the other $R^6$ is chloro;
(vii) One $R^6$ is isopropyl; and the other $R^6$ is fluoro;
(viii) One $R^6$ is ethyl; and the other $R^6$ is fluoro;
(ix) One $R^6$ is isopropyl; and the other $R^6$ is cyano;
(x) One $R^6$ is cyclopropyl; and the other $R^6$ is cyclopropyl;
(xi) One $R^6$ is cyclopropyl; and the other $R^6$ is chloro;
(xii) One $R^6$ is cyclopropyl; and the other $R^6$ is fluoro;
(xiii) One $R^6$ is isopropyl; and the other $R^6$ is methoxy;
(xiv) One $R^6$ is isopropyl; and the other $R^6$ is methoxy; or
(xv) One $R^6$ is isopropyl; and the other $R^6$ is trifluoromethoxy.

In some embodiments, of the compound of formula AA, the substituted ring B is

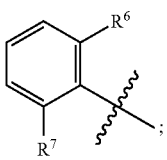

and $R^6$ and $R^7$ are one of the following combinations:
(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;
(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;
(xviii) $R^7$ is $C_1$-$C_6$ alkyl, and $R^6$ is $C_1$-$C_6$ alkyl substituted with one or more halo;
(xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;
(xxiv) $R^7$ is $C_3$-$C_7$ cycloalkyl, and $R^6$ is halo;
(xxv) $R^7$ is $C_3$-$C_7$ cycloalkyl and $R^6$ is halo;
(xxvi) $R^7$ is $C_1$-$C_6$ alkyl, and $R^6$ is $C_1$-$C_6$ alkoxy optionally substituted with one or more halo;
(xxvii) $R^7$ is $C_1$-$C_6$ alkyl, and $R^6$ is $C_1$-$C_6$ alkoxy;
(xxviii) $R^7$ is $C_1$-$C_6$ alkyl, and $R^6$ is $C_1$-$C_6$ alkoxy substituted with one or more halo;
(xxix) $R^7$ is halo, and $R^6$ is $C_1$-$C_6$ haloalkyl;
(xxx) $R^7$ is halo, and $R^6$ is $C_1$-$C_6$ haloalkoxy;
(xxxi) $R^7$ is $C_1$-$C_6$ alkoxy; and $R^6$ is halo; or
(xxxii) $R^7$ is $C_1$-$C_6$ alkoxy; and $R^6$ is chloro.

In some embodiments, of the compound of formula AA, the substituted ring B is

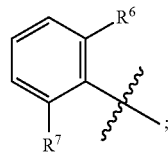

and $R^6$ and $R^7$ are one of the following combinations:
(i) $R^6$ is isopropyl; and $R^7$ is methyl;
(ii) $R^6$ is isopropyl; and $R^7$ is isopropyl;
(iii) $R^6$ is isopropyl; and $R^7$ is trifluoromethyl;
(iv) $R^6$ is isopropyl; and $R^7$ is cyclopropyl;
(v) $R^6$ is isopropyl; and $R^7$ is chloro;
(vi) $R^6$ is isopropyl; and $R^7$ is fluoro;
(vii) $R^6$ is ethyl; and $R^7$ is fluoro;
(viii) $R^6$ is isopropyl; and $R^7$ is cyano;
(ix) $R^6$ is cyclopropyl; and $R^7$ is cyclopropyl;
(x) $R^6$ is cyclopropyl; and $R^7$ is chloro;
(xi) $R^6$ is cyclopropyl; and $R^7$ is fluoro; $R^6$ is isopropyl; and $R^7$ is methoxy;
(xii) $R^6$ is isopropyl; and $R^7$ is trifluoromethoxy;
(xiii) $R^6$ is chloro; and $R^7$ is trifluoromethyl;
(xiv) $R^6$ is chloro; and $R^7$ is trifluoromethoxy;
(xv) $R^7$ is isopropyl; and $R^6$ is methyl;
(xvi) $R^7$ is isopropyl; and $R^6$ is trifluoromethyl;
(xvii) $R^7$ is isopropyl; and $R^6$ is cyclopropyl;
(xviii) $R^7$ is isopropyl; and $R^6$ is chloro;
(xix) $R^7$ is ethyl; and $R^6$ is fluoro;
(xx) $R^7$ is isopropyl; and $R^6$ is cyano;
(xxi) $R^7$ is cyclopropyl; and $R^6$ is cyclopropyl;

(xxii) $R^7$ is cyclopropyl; and $R^6$ is chloro;
(xxiii) $R^7$ is cyclopropyl; and $R^6$ is fluoro;
(xxiv) $R^7$ is isopropyl; and $R^6$ is methoxy;
(xxv) $R^7$ is isopropyl; and $R^6$ is trifluoromethoxy;
(xxvi) $R^7$ is chloro; and $R^6$ is trifluoromethyl; or
(xxvii) $R^7$ is chloro; and $R^6$ is trifluoromethoxy.

In some embodiments, of the compound of formula AA, the substituted ring B is

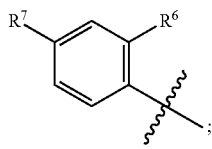

and $R^6$ and $R^7$ are one of the following combinations:
(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;
(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;
(xviii) $R^7$ is $C_1$-$C_6$ alkyl, and $R^6$ is $C_1$-$C_6$ alkyl substituted with one or more halo;
(xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;
(xxiv) $R^7$ is $C_3$-$C_7$ cycloalkyl, and $R^6$ is halo;
(xxv) $R^7$ is $C_3$-$C_7$ cycloalkyl and $R^6$ is halo;
(xxvi) $R^7$ is $C_1$-$C_6$ alkyl, and $R^6$ is $C_1$-$C_6$ alkoxy optionally substituted with one or more halo;
(xxvii) $R^7$ is $C_1$-$C_6$ alkyl, and $R^6$ is $C_1$-$C_6$ alkoxy;
(xxviii) $R^7$ is $C_1$-$C_6$ alkyl, and $R^6$ is $C_1$-$C_6$ alkoxy substituted with one or more halo;
(xxix) $R^7$ is halo, and $R^6$ is $C_1$-$C_6$ haloalkyl;
(xxx) $R^7$ is halo, and $R^6$ is $C_1$-$C_6$ haloalkoxy;
(xxxi) $R^7$ is $C_1$-$C_6$ alkoxy; and $R^6$ is halo; or
(xxxii) $R^7$ is $C_1$-$C_6$ alkoxy; and $R^6$ is chloro.

In some embodiments, of the compound of formula AA, the substituted ring B is

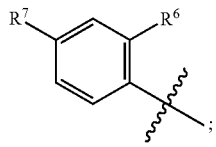

and $R^6$ and $R^7$ are one of the following combinations:
(i) $R^6$ is isopropyl; and $R^7$ is methyl;
(ii) $R^6$ is isopropyl; and $R^7$ is isopropyl;
(iii) $R^6$ is isopropyl; and $R^7$ is trifluoromethyl;
(iv) $R^6$ is isopropyl; and $R^7$ is cyclopropyl;
(v) $R^6$ is isopropyl; and $R^7$ is chloro;
(vi) $R^6$ is isopropyl; and $R^7$ is fluoro;
(vii) $R^6$ is ethyl; and $R^7$ is fluoro;
(viii) $R^6$ is isopropyl; and $R^7$ is cyano;
(ix) $R^6$ is cyclopropyl; and $R^7$ is cyclopropyl;
(x) $R^6$ is cyclopropyl; and $R^7$ is chloro;
(xi) $R^6$ is cyclopropyl; and $R^7$ is fluoro;
(xii) $R^6$ is isopropyl; and $R^7$ is methoxy;
(xiii) $R^6$ is isopropyl; and $R^7$ is trifluoromethoxy;
(xiv) $R^6$ is chloro; and $R^7$ is trifluoromethyl;
(xv) $R^6$ is chloro; and $R^7$ is trifluoromethoxy;
(xvi) $R^7$ is isopropyl; and $R^6$ is methyl;
(xvii) $R^7$ is isopropyl; and $R^6$ is trifluoromethyl;
(xviii) $R^7$ is isopropyl; and $R^6$ is cyclopropyl;
(xix) $R^7$ is isopropyl; and $R^6$ is chloro;
(xx) $R^7$ is ethyl; and $R^6$ is fluoro;
(xxi) $R^7$ is isopropyl; and $R^6$ is cyano;
(xxii) $R^7$ is cyclopropyl; and $R^6$ is cyclopropyl;
(xxiii) $R^7$ is cyclopropyl; and $R^6$ is chloro;
(xxiv) $R^7$ is cyclopropyl; and $R^6$ is fluoro;
(xxv) $R^7$ is isopropyl; and $R^6$ is methoxy;
(xxvi) $R^7$ is isopropyl; and $R^6$ is trifluoromethoxy;
(xxvii) $R^7$ is chloro; and $R^6$ is trifluoromethyl; or
(xxviii) $R^7$ is chloro; and $R^6$ is trifluoromethoxy.

In some embodiments, of the compound of formula AA, the substituted ring B is

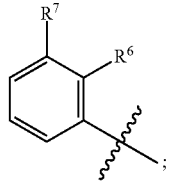

and $R^6$ and $R^7$ are one of the following combinations:
(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;

(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;
(xviii) $R^7$ is $C_1$-$C_6$ alkyl, and $R^6$ is $C_1$-$C_6$ alkyl substituted with one or more halo;
(xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;
(xxiv) $R^7$ is $C_3$-$C_7$ cycloalkyl, and $R^6$ is halo;
(xxv) $R^7$ is $C_3$-$C_7$ cycloalkyl and $R^6$ is halo;
(xxvi) $R^7$ is $C_1$-$C_6$ alkyl, and $R^6$ is $C_1$-$C_6$ alkoxy optionally substituted with one or more halo;
(xxvii) $R^7$ is $C_1$-$C_6$ alkyl, and $R^6$ is $C_1$-$C_6$ alkoxy;
(xxviii) $R^7$ is $C_1$-$C_6$ alkyl, and $R^6$ is $C_1$-$C_6$ alkoxy substituted with one or more halo;
(xxix) $R^7$ is halo, and $R^6$ is $C_1$-$C_6$ haloalkyl;
(xxx) $R^7$ is halo, and $R^6$ is $C_1$-$C_6$ haloalkoxy;
(xxxi) $R^7$ is $C_1$-$C_6$ alkoxy; and $R^6$ is halo; or
(xxxii) $R^7$ is $C_1$-$C_6$ alkoxy; and $R^6$ is chloro;
(xxxiii) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
(xxxiv) $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

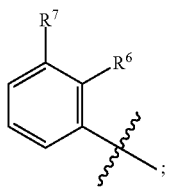

and $R^6$ and $R^7$ are one of the following combinations:
(i) $R^6$ is isopropyl; and $R^7$ is methyl;
(ii) $R^6$ is isopropyl; and $R^7$ is isopropyl;
(iii) $R^6$ is isopropyl; and $R^7$ is trifluoromethyl;
(iv) $R^6$ is isopropyl; and $R^7$ is cyclopropyl;
(v) $R^6$ is isopropyl; and $R^7$ is chloro;
(vi) $R^6$ is isopropyl; and $R^7$ is fluoro;
(vii) $R^6$ is ethyl; and $R^7$ is fluoro;
(viii) $R^6$ is isopropyl; and $R^7$ is cyano;
(ix) $R^6$ is cyclopropyl; and $R^7$ is cyclopropyl;
(x) $R^6$ is cyclopropyl; and $R^7$ is chloro;
(xi) $R^6$ is cyclopropyl; and $R^7$ is fluoro;
(xii) $R^6$ is isopropyl; and $R^7$ is methoxy;
(xiii) $R^6$ is isopropyl; and $R^7$ is trifluoromethoxy;
(xiv) $R^6$ is chloro; and $R^7$ is trifluoromethyl;
(xv) $R^6$ is chloro; and $R^7$ is trifluoromethoxy;
(xvi) $R^7$ is isopropyl; and $R^6$ is methyl;
(xvii) $R^7$ is isopropyl; and $R^6$ is trifluoromethyl;
(xviii) $R^7$ is isopropyl; and $R^6$ is cyclopropyl;
(xix) $R^7$ is isopropyl; and $R^6$ is chloro;
(xx) $R^7$ is ethyl; and $R^6$ is fluoro;
(xxi) $R^7$ is isopropyl; and $R^6$ is cyano;
(xxii) $R^7$ is cyclopropyl; and $R^6$ is cyclopropyl;
(xxiii) $R^7$ is cyclopropyl; and $R^6$ is chloro;
(xxiv) $R^7$ is cyclopropyl; and $R^6$ is fluoro;
(xxv) $R^7$ is isopropyl; and $R^6$ is methoxy;
(xxvi) $R^7$ is isopropyl; and $R^6$ is trifluoromethoxy;
(xxvii) $R^7$ is chloro; and $R^6$ is trifluoromethyl;
(xxviii) $R^7$ is chloro; and $R^6$ is trifluoromethoxy;
(xxix) $R^6$ and $R^7$ on adjacent atoms taken together with the atoms connecting them form a $C_4$ aliphatic carbocyclic ring;
(xxx) $R^6$ and $R^7$ on adjacent atoms taken together with the atoms connecting them form a $C_5$ aliphatic carbocyclic ring;
(xxxi) $R^6$ and $R^7$ on adjacent atoms taken together with the atoms connecting them form a $C_6$ aliphatic carbocyclic ring;
(xxxii) $R^6$ and $R^7$ on adjacent atoms taken together with the atoms connecting them form a 5-membered heterocyclic ring containing 1 heteroatoms independently selected from O, N, and S;
(xxxiii) $R^6$ and $R^7$ on adjacent atoms taken together with the atoms connecting them form a 6-membered heterocyclic ring containing 1 heteroatoms independently selected from O, N, and S; or
(xxxiv) $R^6$ and $R^7$ on adjacent atoms taken together with the atoms connecting them form a $C_5$ aliphatic carbocyclic ring.

In some embodiments, of the compound of formula AA, the substituted ring B is

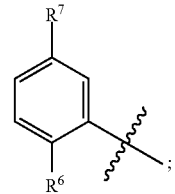

and $R^6$ and $R^7$ are one of the following combinations:
(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;
(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;

(xviii) $R^7$ is $C_1$-$C_6$ alkyl, and $R^6$ is $C_1$-$C_6$ alkyl substituted with one or more halo; (xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;
(xxiv) $R^7$ is $C_3$-$C_7$ cycloalkyl, and $R^6$ is halo;
(xxv) $R^7$ is $C_3$-$C_7$ cycloalkyl and $R^6$ is halo;
(xxvi) $R^7$ is $C_1$-$C_6$ alkyl, and $R^6$ is $C_1$-$C_6$ alkoxy optionally substituted with one or more halo;
(xxvii) $R^7$ is $C_1$-$C_6$ alkyl, and $R^6$ is $C_1$-$C_6$ alkoxy;
(xxviii) $R^7$ is $C_1$-$C_6$ alkyl, and $R^6$ is $C_1$-$C_6$ alkoxy substituted with one or more halo;
(xxix) $R^7$ is halo, and $R^6$ is $C_1$-$C_6$ haloalkyl;
(xxx) $R^7$ is halo, and $R^6$ is $C_1$-$C_6$ haloalkoxy;
(xxxi) $R^7$ is $C_1$-$C_6$ alkoxy; and $R^6$ is halo; or
(xxxii) $R^7$ is $C_1$-$C_6$ alkoxy; and $R^6$ is chloro.

In some embodiments, of the compound of formula AA, the substituted ring B is

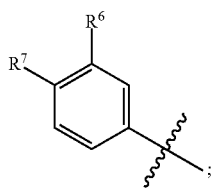

and $R^6$ and $R^7$ are one of the following combinations:
(i) $R^6$ is $C_1$-$C_6$ alkyl, and $R^7$ is $C_1$-$C_6$ alkyl optionally substituted with one or more halo;
(ii) $R^6$ is $C_1$-$C_6$ alkyl and $R^7$ is $C_1$-$C_6$ alkyl;
(iii) $R^6$ is $C_1$-$C_6$ alkyl, and $R^7$ is $C_1$-$C_6$ alkyl substituted with one or more halo;
(iv) $R^6$ is $C_1$-$C_6$ alkyl, and $R^7$ is $C_3$-$C_7$ cycloalkyl;
(v) $R^6$ is $C_1$-$C_6$ alkyl, and $R^7$ is halo;
(vi) $R^6$ is $C_1$-$C_6$ alkyl, and $R^7$ is cyano;
(vii) $R^6$ is $C_3$-$C_7$ cycloalkyl, and $R^7$ is $C_3$-$C_7$ cycloalkyl;
(viii) $R^6$ is $C_3$-$C_7$ cycloalkyl, and $R^7$ is halo;
(ix) $R^6$ is cyclopropyl and $R^7$ is halo;
(x) $R^6$ is $C_1$-$C_6$ alkyl, and $R^7$ is $C_1$-$C_6$ alkoxy optionally substituted with one or more halo;
(xi) $R^6$ is $C_1$-$C_6$ alkyl, and $R^7$ is $C_1$-$C_6$ alkoxy;
(xii) $R^6$ is $C_1$-$C_6$ alkyl, and $R^7$ is $C_1$-$C_6$ alkoxy substituted with one or more halo;
(xiii) $R^6$ is halo, and $R^7$ is $C_1$-$C_6$ haloalkyl;
(xiv) $R^6$ is halo, and $R^7$ is $C_1$-$C_6$ haloalkoxy;
(xv) $R^6$ is $C_1$-$C_6$ alkoxy; and $R^7$ is halo;
(xvi) $R^6$ is $C_1$-$C_6$ alkoxy; and $R^7$ is chloro;
(xvii) $R^7$ is $C_1$-$C_6$ alkyl, and $R^6$ is $C_1$-$C_6$ alkyl optionally substituted with one or more halo;
(xviii) $R^7$ is $C_1$-$C_6$ alkyl, and $R^6$ is $C_1$-$C_6$ alkyl substituted with one or more halo;
(xix) $R^7$ is $C_1$-$C_6$ alkyl, and $R^6$ is $C_3$-$C_7$ cycloalkyl;
(xx) $R^7$ is $C_1$-$C_6$ alkyl, and $R^6$ is halo;
(xxi) $R^7$ is $C_1$-$C_6$ alkyl and $R^6$ is halo;
(xxii) $R^7$ is $C_1$-$C_6$ alkyl, and $R^6$ is cyano;
(xxiii) $R^7$ is $C_3$-$C_7$ cycloalkyl, and $R^6$ is $C_3$-$C_7$ cycloalkyl;
(xxiv) $R^7$ is $C_3$-$C_7$ cycloalkyl, and $R^6$ is halo;
(xxv) $R^7$ is $C_3$-$C_7$ cycloalkyl and $R^6$ is halo;
(xxvi) $R^7$ is $C_1$-$C_6$ alkyl, and $R^6$ is $C_1$-$C_6$ alkoxy optionally substituted with one or more halo;
(xxvii) $R^7$ is $C_1$-$C_6$ alkyl, and $R^6$ is $C_1$-$C_6$ alkoxy;
(xxviii) $R^7$ is $C_1$-$C_6$ alkyl, and $R^6$ is $C_1$-$C_6$ alkoxy substituted with one or more halo;
(xxix) $R^7$ is halo, and $R^6$ is $C_1$-$C_6$ haloalkyl;
(xxx) $R^7$ is halo, and $R^6$ is $C_1$-$C_6$ haloalkoxy;
(xxxi) $R^7$ is $C_1$-$C_6$ alkoxy; and $R^6$ is halo;
(xxxii) $R^7$ is $C_1$-$C_6$ alkoxy; and $R^6$ is chloro;
(xxxiii) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
(xxxiv) $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

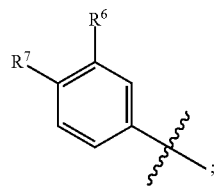

and $R^6$ and $R^7$ are one of the following combinations:
(i) $R^6$ is isopropyl; and $R^7$ is methyl;
(ii) $R^6$ is isopropyl; and $R^7$ is isopropyl;
(iii) $R^6$ is isopropyl; and $R^7$ is trifluoromethyl;
(iv) $R^6$ is isopropyl; and $R^7$ is cyclopropyl;
(v) $R^6$ is isopropyl; and $R^7$ is chloro;
(vi) $R^6$ is isopropyl; and $R^7$ is fluoro;
(vii) $R^6$ is ethyl; and $R^7$ is fluoro;
(viii) $R^6$ is isopropyl; and $R^7$ is cyano;
(ix) $R^6$ is cyclopropyl; and $R^7$ is cyclopropyl;
(x) $R^6$ is cyclopropyl; and $R^7$ is chloro;
(xi) $R^6$ is cyclopropyl; and $R^7$ is fluoro;
(xii) $R^6$ is isopropyl; and $R^7$ is methoxy;
(xiii) $R^6$ is isopropyl; and $R^7$ is trifluoromethoxy;
(xiv) $R^6$ is chloro; and $R^7$ is trifluoromethyl;
(xv) $R^6$ is chloro; and $R^7$ is trifluoromethoxy;
(xvi) $R^7$ is isopropyl; and $R^6$ is methyl;
(xvii) $R^7$ is isopropyl; and $R^6$ is trifluoromethyl;
(xviii) $R^7$ is isopropyl; and $R^6$ is cyclopropyl;
(xix) $R^7$ is isopropyl; and $R^6$ is chloro;
(xx) $R^7$ is ethyl; and $R^6$ is fluoro;
(xxi) $R^7$ is isopropyl; and $R^6$ is cyano;
(xxii) $R^7$ is cyclopropyl; and $R^6$ is cyclopropyl;
(xxiii) $R^7$ is cyclopropyl; and $R^6$ is chloro;
(xxiv) $R^7$ is cyclopropyl; and $R^6$ is fluoro;
(xxv) $R^7$ is isopropyl; and $R^6$ is methoxy;
(xxvi) $R^7$ is isopropyl; and $R^6$ is trifluoromethoxy;
(xxvii) $R^7$ is chloro; and $R^6$ is trifluoromethyl;
(xxviii) $R^7$ is chloro; and $R^6$ is trifluoromethoxy;
(xxix) $R^6$ and $R^7$ on adjacent atoms taken together with the atoms connecting them form a $C_4$ aliphatic carbocyclic ring;
(xxx) $R^6$ and $R^7$ on adjacent atoms taken together with the atoms connecting them form a $C_5$ aliphatic carbocyclic ring;
(xxxi) $R^6$ and $R^7$ on adjacent atoms taken together with the atoms connecting them form a $C_6$ aliphatic carbocyclic ring;

(xxxii) $R^6$ and $R^7$ on adjacent atoms taken together with the atoms connecting them form a 5-membered heterocyclic ring containing 1 heteroatoms independently selected from O, N, and S;
(xxxiii) $R^6$ and $R^7$ on adjacent atoms taken together with the atoms connecting them form a 6-membered heterocyclic ring containing 1 heteroatoms independently selected from O, N, and S; or
(xxxiv) $R^6$ and $R^7$ on adjacent atoms taken together with the atoms connecting them form a $C_5$ aliphatic carbocyclic ring.

In some embodiments, of the compound of formula AA, the substituted ring B is

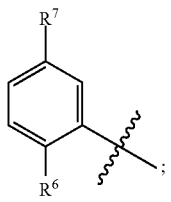

and $R^6$ and $R^7$ are one of the following combinations:
(i) $R^6$ is isopropyl; and $R^7$ is methyl;
(ii) $R^6$ is isopropyl; and $R^7$ is isopropyl;
(iii) $R^6$ is isopropyl; and $R^7$ is trifluoromethyl;
(iv) $R^6$ is isopropyl; and $R^7$ is cyclopropyl;
(v) $R^6$ is isopropyl; and $R^7$ is chloro;
(vi) $R^6$ is isopropyl; and $R^7$ is fluoro;
(vii) $R^6$ is ethyl; and $R^7$ is fluoro;
(viii) $R^6$ is isopropyl; and $R^7$ is cyano;
(ix) $R^6$ is cyclopropyl; and $R^7$ is cyclopropyl;
(x) $R^6$ is cyclopropyl; and $R^7$ is chloro;
(xi) $R^6$ is cyclopropyl; and $R^7$ is fluoro;
(xii) $R^6$ is isopropyl; and $R^7$ is methoxy;
(xiii) $R^6$ is isopropyl; and $R^7$ is trifluoromethoxy;
(xiv) $R^6$ is chloro; and $R^7$ is trifluoromethyl;
(xv) $R^6$ is chloro; and $R^7$ is trifluoromethoxy;
(xvi) $R^7$ is isopropyl; and $R^6$ is methyl;
(xvii) $R^7$ is isopropyl; and $R^6$ is trifluoromethyl;
(xviii) $R^7$ is isopropyl; and $R^6$ is cyclopropyl;
(xix) $R^7$ is isopropyl; and $R^6$ is chloro;
(xx) $R^7$ is ethyl; and $R^6$ is fluoro;
(xxi) $R^7$ is isopropyl; and $R^6$ is cyano;
(xxii) $R^7$ is cyclopropyl; and $R^6$ is cyclopropyl;
(xxiii) $R^7$ is cyclopropyl; and $R^6$ is chloro;
(xxiv) $R^7$ is cyclopropyl; and $R^6$ is fluoro;
(xxv) $R^7$ is isopropyl; and $R^6$ is methoxy;
(xxvi) $R^7$ is isopropyl; and $R^6$ is trifluoromethoxy;
(xxvii) $R^7$ is chloro; and $R^6$ is trifluoromethyl; or
(xxviii) $R^7$ is chloro; and $R^6$ is trifluoromethoxy.

In some embodiments, of the compound of formula AA, the substituted ring B is

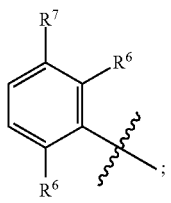

and $R^6$ and $R^7$ are one of the following combinations:
(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;
(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;
(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo;
(xxxii) $R^7$ is $C_1$-$C_6$ alkoxy; and $R^6$ is chloro;

(xxxiii) $R^6$ and $R^7$ on adjacent atoms taken together with the atoms connecting them form a $C_5$ aliphatic carbocyclic ring;

(xxxiv) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or (xxxv) $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

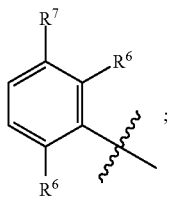

and $R^6$ and $R^7$ are one of the following combinations:
(i) each $R^6$ is isopropyl; and $R^7$ is methyl;
(ii) each $R^6$ is isopropyl; and $R^7$ is isopropyl;
(iii) each $R^6$ is isopropyl; and $R^7$ is trifluoromethyl;
(iv) each $R^6$ is isopropyl; and $R^7$ is cyclopropyl;
(v) each $R^6$ is isopropyl; and $R^7$ is chloro;
(vi) each $R^6$ is isopropyl; and $R^7$ is fluoro;
(vii) each $R^6$ is ethyl; and $R^7$ is fluoro;
(viii) each $R^6$ is isopropyl; and $R^7$ is cyano;
(ix) each $R^6$ is cyclopropyl; and $R^7$ is cyclopropyl;
(x) each $R^6$ is cyclopropyl; and $R^7$ is chloro;
(xi) each $R^6$ is cyclopropyl; and $R^7$ is fluoro;
(xii) each $R^6$ is isopropyl; and $R^7$ is methoxy;
(xiii) each $R^6$ is isopropyl; and $R^7$ is trifluoromethoxy;
(xiv) each $R^6$ is chloro; and $R^7$ is trifluoromethyl;
(xv) each $R^6$ is chloro; and $R^7$ is trifluoromethoxy;
(xvi) $R^7$ is isopropyl; and each $R^6$ is methyl;
(xvii) $R^7$ is isopropyl; and each $R^6$ is trifluoromethyl;
(xviii) $R^7$ is isopropyl; and each $R^6$ is cyclopropyl;
(xix) $R^7$ is isopropyl; and each $R^6$ is chloro;
(xx) $R^7$ is ethyl; and each $R^6$ is fluoro;
(xxi) $R^7$ is isopropyl; and each $R^6$ is cyano;
(xxii) $R^7$ is cyclopropyl; and each $R^6$ is cyclopropyl;
(xxiii) $R^7$ is cyclopropyl; and each $R^6$ is chloro;
(xxiv) $R^7$ is cyclopropyl; and each $R^6$ is fluoro;
(xxv) $R^7$ is isopropyl; and each $R^6$ is methoxy;
(xxvi) $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy;
(xxix) one $R^6$ is isopropyl; the other $R^6$ is trifluoromethyl; and $R^7$ is chloro;
(xxx) $R^6$ and $R^7$ on adjacent atoms taken together with the atoms connecting them form a $C_4$ aliphatic carbocyclic ring; and one $R^6$ is fluoro, chloro, or cyano;
(xxxi) $R^6$ and $R^7$ on adjacent atoms taken together with the atoms connecting them form a $C_5$ aliphatic carbocyclic ring; and one $R^6$ is fluoro, chloro, or cyano;

(xxxii) $R^6$ and $R^7$ on adjacent atoms taken together with the atoms connecting them form a $C_6$ aliphatic carbocyclic ring; and one $R^6$ is fluoro, chloro, or cyano;

(xxxiii) $R^6$ and $R^7$ on adjacent atoms taken together with the atoms connecting them form a 5-membered heterocyclic ring containing 1 heteroatoms independently selected from O, N, and S; and one $R^6$ is fluoro, chloro, or cyano; or (xxxiv) $R^6$ and $R^7$ on adjacent atoms taken together with the atoms connecting them form a 6-membered heterocyclic ring containing 1 heteroatoms independently selected from O, N, and S; and one $R^6$ is fluoro, chloro, or cyano.

In some embodiments, of the compound of formula AA, the substituted ring B is

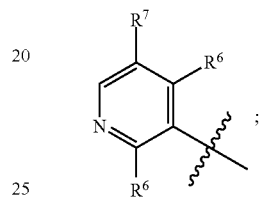

and $R^6$ and $R^7$ are one of the following combinations:
(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;

(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;
(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo; or
(xxxii) $R^7$ is $C_1$-$C_6$ alkoxy; and $R^6$ is chloro.

In some embodiments, of the compound of formula AA, the substituted ring B is

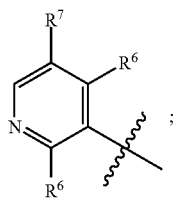

and $R^6$ and $R^7$ are one of the following combinations:
(i) each $R^6$ is isopropyl; and $R^7$ is methyl;
(ii) each $R^6$ is isopropyl; and $R^7$ is isopropyl;
(iii) each $R^6$ is isopropyl; and $R^7$ is trifluoromethyl;
(iv) each $R^6$ is isopropyl; and $R^7$ is cyclopropyl;
(v) each $R^6$ is isopropyl; and $R^7$ is chloro;
(vi) each $R^6$ is isopropyl; and $R^7$ is fluoro;
(vii) each $R^6$ is ethyl; and $R^7$ is fluoro;
(viii) each $R^6$ is isopropyl; and $R^7$ is cyano;
(ix) each $R^6$ is cyclopropyl; and $R^7$ is cyclopropyl;
(x) each $R^6$ is cyclopropyl; and $R^7$ is chloro;
(xi) each $R^6$ is cyclopropyl; and $R^7$ is fluoro;
(xii) each $R^6$ is isopropyl; and $R^7$ is methoxy;
(xiii) each $R^6$ is isopropyl; and $R^7$ is trifluoromethoxy;
(xiv) each $R^6$ is chloro; and $R^7$ is trifluoromethyl;
(xv) each $R^6$ is chloro; and $R^7$ is trifluoromethoxy;
(xvi) $R^7$ is isopropyl; and each $R^6$ is methyl;
(xvii) $R^7$ is isopropyl; and each $R^6$ is trifluoromethyl;
(xviii) $R^7$ is isopropyl; and each $R^6$ is cyclopropyl;
(xix) $R^7$ is isopropyl; and each $R^6$ is chloro;
(xx) $R^7$ is ethyl; and each $R^6$ is fluoro;
(xxi) $R^7$ is isopropyl; and each $R^6$ is cyano;
(xxii) $R^7$ is cyclopropyl; and each $R^6$ is cyclopropyl;
(xxiii) $R^7$ is cyclopropyl; and each $R^6$ is chloro;
(xxiv) $R^7$ is cyclopropyl; and each $R^6$ is fluoro;
(xxv) $R^7$ is isopropyl; and each $R^6$ is methoxy;
(xxvi) $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy; or
(xxix) one $R^6$ is isopropyl; the other $R^6$ is trifluoromethyl; and $R^7$ is chloro.

In some embodiments, of the compound of formula AA, the substituted ring B is

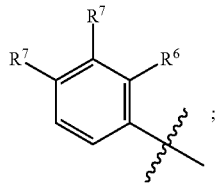

and $R^6$ and $R^7$ are one of the following combinations:
(i) $R^6$ is $C_1$-$C_6$ alkyl, and each $R^7$ is independently $C_1$-$C_6$ alkyl optionally substituted with one or more halo;
(ii) $R^6$ is $C_1$-$C_6$ alkyl and each $R^7$ is independently $C_1$-$C_6$ alkyl;
(iii) $R^6$ is $C_1$-$C_6$ alkyl, and each $R^7$ is independently $C_1$-$C_6$ alkyl substituted with one or more halo;
(iv) $R^6$ is $C_1$-$C_6$ alkyl, and each $R^7$ is independently $C_3$-$C_7$ cycloalkyl;
(v) $R^6$ is $C_1$-$C_6$ alkyl, and each $R^7$ is independently halo;
(vi) $R^6$ is $C_1$-$C_6$ alkyl, and $R^7$ is cyano;
(vii) $R^6$ is $C_3$-$C_7$ cycloalkyl, and each $R^7$ is independently $C_3$-$C_7$ cycloalkyl;
(viii) $R^6$ is $C_3$-$C_7$ cycloalkyl, and each $R^7$ is independently halo;
(ix) $R^6$ is cyclopropyl and each $R^7$ is independently halo;
(x) $R^6$ is $C_1$-$C_6$ alkyl, and each $R^7$ is independently $C_1$-$C_6$ alkoxy optionally substituted with one or more halo;
(xi) $R^6$ is $C_1$-$C_6$ alkyl, and each $R^7$ is independently $C_1$-$C_6$ alkoxy;
(xii) $R^6$ is $C_1$-$C_6$ alkyl, and each $R^7$ is independently $C_1$-$C_6$ alkoxy substituted with one or more halo;
(xiii) $R^6$ is halo, and each $R^7$ is independently $C_1$-$C_6$ haloalkyl;
(xiv) $R^6$ is halo, and each $R^7$ is independently $C_1$-$C_6$ haloalkoxy;
(xv) $R^6$ is $C_1$-$C_6$ alkoxy; and each $R^7$ is independently halo;
(xvi) $R^6$ is $C_1$-$C_6$ alkoxy; and $R^7$ is chloro;
(xvii) each $R^7$ is independently $C_1$-$C_6$ alkyl, and $R^6$ is $C_1$-$C_6$ alkyl optionally substituted with one or more halo;
(xviii) each $R^7$ is independently $C_1$-$C_6$ alkyl, and $R^6$ is $C_1$-$C_6$ alkyl substituted with one or more halo;
(xix) each $R^7$ is independently $C_1$-$C_6$ alkyl, and $R^6$ is $C_3$-$C_7$ cycloalkyl;
(xx) each $R^7$ is independently $C_1$-$C_6$ alkyl, and $R^6$ is halo;
(xxi) each $R^7$ is independently $C_1$-$C_6$ alkyl and $R^6$ is halo;
(xxii) each $R^7$ is independently $C_1$-$C_6$ alkyl, and $R^6$ is cyano;
(xxiii) each $R^7$ is independently $C_3$-$C_7$ cycloalkyl, and $R^6$ is $C_3$-$C_7$ cycloalkyl.

(xxiv) each $R^7$ is independently $C_3$-$C_7$ cycloalkyl, and $R^6$ is halo;
(xxv) each $R^7$ is independently $C_3$-$C_7$ cycloalkyl and $R^6$ is halo;
(xxvi) each $R^7$ is independently $C_1$-$C_6$ alkyl, and $R^6$ is $C_1$-$C_6$ alkoxy optionally substituted with one or more halo;
(xxvii) each $R^7$ is independently $C_1$-$C_6$ alkyl, and $R^6$ is $C_1$-$C_6$ alkoxy;
(xxviii) each $R^7$ is independently $C_1$-$C_6$ alkyl, and $R^6$ is $C_1$-$C_6$ alkoxy substituted with one or more halo;
(xxix) each $R^7$ is independently halo, and $R^6$ is $C_1$-$C_6$ haloalkyl;
(xxx) each $R^7$ is independently halo, and $R^6$ is $C_1$-$C_6$ haloalkoxy;
(xxxi) each $R^7$ is independently $C_1$-$C_6$ alkoxy; and $R^6$ is halo;
(xxxii) each $R^7$ is independently $C_1$-$C_6$ alkoxy; and $R^6$ is chloro;
(xxxiii) $R^6$ and $R^7$ on adjacent atoms taken together with the atoms connecting them form a $C_5$ aliphatic carbocyclic ring;
(xxxiv) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
(xxxv) $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

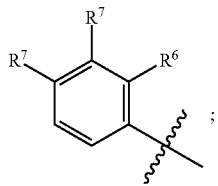

and $R^6$ and $R^7$ are one of the following combinations:
(i) $R^6$ is isopropyl; and each $R^7$ is methyl;
(ii) $R^6$ is isopropyl; and each $R^7$ is isopropyl;
(iii) $R^6$ is isopropyl; and each $R^7$ is trifluoromethyl;
(iv) $R^6$ is isopropyl; and each $R^7$ is cyclopropyl;
(v) $R^6$ is isopropyl; and each $R^7$ is chloro;
(vi) $R^6$ is isopropyl; and each $R^7$ is fluoro;
(vii) $R^6$ is ethyl; and each $R^7$ is fluoro;
(viii) $R^6$ is isopropyl; and each $R^7$ is cyano;
(ix) $R^6$ is cyclopropyl; and each $R^7$ is cyclopropyl;
(x) $R^6$ is cyclopropyl; and each $R^7$ is chloro;
(xi) $R^6$ is cyclopropyl; and each $R^7$ is fluoro;
(xii) $R^6$ is isopropyl; and $R^7$ is methoxy;
(xiii) $R^6$ is isopropyl; and each $R^7$ is trifluoromethoxy;
(xiv) $R^6$ is chloro; and each $R^7$ is trifluoromethyl;
(xv) $R^6$ is chloro; and each $R^7$ is trifluoromethoxy;
(xvi) each $R^7$ is isopropyl; and $R^6$ is methyl;
(xvii) each $R^7$ is isopropyl; and $R^6$ is trifluoromethyl;
(xviii) each $R^7$ is isopropyl; and $R^6$ is cyclopropyl;
(xix) each $R^7$ is isopropyl; and $R^6$ is chloro;
(xx) each $R^7$ is ethyl; and $R^6$ is fluoro;
(xxi) each $R^7$ is isopropyl; and $R^6$ is cyano;
(xxii) each $R^7$ is cyclopropyl; and $R^6$ is cyclopropyl;
(xxiii) each $R^7$ is cyclopropyl; and $R^6$ is chloro;
(xxiv) each $R^7$ is cyclopropyl; and $R^6$ is fluoro;
(xxv) each $R^7$ is isopropyl; and $R^6$ is methoxy;
(xxvi) each $R^7$ is isopropyl; and $R^6$ is trifluoromethoxy;
(xxvii) each $R^7$ is chloro; and $R^6$ is trifluoromethyl;
(xxviii) each $R^7$ is chloro; and $R^6$ is trifluoromethoxy;
(xxix) $R^6$ and $R^7$ on adjacent atoms taken together with the atoms connecting them form a $C_5$ aliphatic carbocyclic ring; and one $R^7$ is fluoro, chloro, or cyano;
(xxx) $R^6$ and $R^7$ on adjacent atoms taken together with the atoms connecting them form a $C_4$ aliphatic carbocyclic ring; and one $R^7$ is fluoro, chloro, or cyano;
(xxxi) $R^6$ and $R^7$ on adjacent atoms taken together with the atoms connecting them form a $C_6$ aliphatic carbocyclic ring; and one $R^7$ is fluoro, chloro, or cyano;
(xxxii) $R^6$ and $R^7$ on adjacent atoms taken together with the atoms connecting them form a 5-membered heterocyclic ring containing 1 heteroatom independently selected from O, N, and S; and one $R^7$ is fluoro, chloro, or cyano; or
(xxxiii) $R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

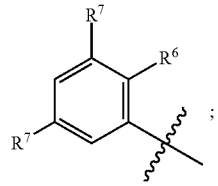

and $R^6$ and $R^7$ are one of the following combinations:
(i) $R^6$ is $C_1$-$C_6$ alkyl, and each $R^7$ is independently $C_1$-$C_6$ alkyl optionally substituted with one or more halo;
(ii) $R^6$ is $C_1$-$C_6$ alkyl and each $R^7$ is independently $C_1$-$C_6$ alkyl;
(iii) $R^6$ is $C_1$-$C_6$ alkyl, and each $R^7$ is independently $C_1$-$C_6$ alkyl substituted with one or more halo;
(iv) $R^6$ is $C_1$-$C_6$ alkyl, and each $R^7$ is independently $C_3$-$C_7$ cycloalkyl;
(v) $R^6$ is $C_1$-$C_6$ alkyl, and each $R^7$ is independently halo;
(vi) $R^6$ is $C_1$-$C_6$ alkyl, and $R^7$ is cyano;
(vii) $R^6$ is $C_3$-$C_7$ cycloalkyl, and each $R^7$ is independently $C_3$-$C_7$ cycloalkyl;
(viii) $R^6$ is $C_3$-$C_7$ cycloalkyl, and each $R^7$ is independently halo;
(ix) $R^6$ is cyclopropyl and each $R^7$ is independently halo;
(x) $R^6$ is $C_1$-$C_6$ alkyl, and each $R^7$ is independently $C_1$-$C_6$ alkoxy optionally substituted with one or more halo;
(xi) $R^6$ is $C_1$-$C_6$ alkyl, and each $R^7$ is independently $C_1$-$C_6$ alkoxy;
(xii) $R^6$ is $C_1$-$C_6$ alkyl, and each $R^7$ is independently $C_1$-$C_6$ alkoxy substituted with one or more halo;
(xiii) $R^6$ is halo, and each $R^7$ is independently $C_1$-$C_6$ haloalkyl;

(xiv) $R^6$ is halo, and each $R^7$ is independently $C_1$-$C_6$ haloalkoxy;
(xv) $R^6$ is $C_1$-$C_6$ alkoxy; and each $R^7$ is independently halo;
(xvi) $R^6$ is $C_1$-$C_6$ alkoxy; and $R^7$ is chloro;
(xvii) each $R^7$ is independently $C_1$-$C_6$ alkyl, and $R^6$ is $C_1$-$C_6$ alkyl optionally substituted with one or more halo;
(xviii) each $R^7$ is independently $C_1$-$C_6$ alkyl, and $R^6$ is $C_1$-$C_6$ alkyl substituted with one or more halo;
(xix) each $R^7$ is independently $C_1$-$C_6$ alkyl, and $R^6$ is $C_3$-$C_7$ cycloalkyl;
(xx) each $R^7$ is independently $C_1$-$C_6$ alkyl, and $R^6$ is halo;
(xxi) each $R^7$ is independently $C_1$-$C_6$ alkyl and $R^6$ is halo;
(xxii) each $R^7$ is independently $C_1$-$C_6$ alkyl, and $R^6$ is cyano;
(xxiii) each $R^7$ is independently $C_3$-$C_7$ cycloalkyl, and $R^6$ is $C_3$-$C_7$ cycloalkyl;
(xxiv) each $R^7$ is independently $C_3$-$C_7$ cycloalkyl, and $R^6$ is halo;
(xxv) each $R^7$ is independently $C_3$-$C_7$ cycloalkyl and $R^6$ is halo;
(xxvi) each $R^7$ is independently $C_1$-$C_6$ alkyl, and $R^6$ is $C_1$-$C_6$ alkoxy optionally substituted with one or more halo;
(xxvii) each $R^7$ is independently $C_1$-$C_6$ alkyl, and $R^6$ is $C_1$-$C_6$ alkoxy;
(xxviii) each $R^7$ is independently $C_1$-$C_6$ alkyl, and $R^6$ is $C_1$-$C_6$ alkoxy substituted with one or more halo;
(xxix) each $R^7$ is independently halo, and $R^6$ is $C_1$-$C_6$ haloalkyl;
(xxx) each $R^7$ is independently halo, and $R^6$ is $C_1$-$C_6$ haloalkoxy;
(xxxi) each $R^7$ is independently $C_1$-$C_6$ alkoxy; and $R^6$ is halo;
(xxxii) each $R^6$ is independently $C_1$-$C_6$ alkoxy; and $R^6$ is chloro;
(xxxiii) $R^6$ and $R^7$ on adjacent atoms taken together with the atoms connecting them form a $C_5$ aliphatic carbocyclic ring;
(xxxiv) $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
(xxxiv) $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

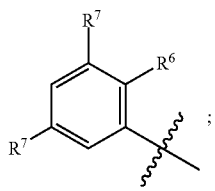

and $R^6$ and $R^7$ are one of the following combinations:
(i) $R^6$ is isopropyl; and each $R^7$ is methyl;
(ii) $R^6$ is isopropyl; and each $R^7$ is isopropyl;
(iii) $R^6$ is isopropyl; and each $R^7$ is trifluoromethyl;
(iv) $R^6$ is isopropyl; and each $R^7$ is cyclopropyl;
(v) $R^6$ is isopropyl; and each $R^7$ is chloro;
(vi) $R^6$ is isopropyl; and each $R^7$ is fluoro;
(vii) $R^6$ is ethyl; and each $R^7$ is fluoro;
(viii) $R^6$ is isopropyl; and each $R^7$ is cyano;
(ix) $R^6$ is cyclopropyl; and each $R^7$ is cyclopropyl;
(x) $R^6$ is cyclopropyl; and each $R^7$ is chloro;
(xi) $R^6$ is cyclopropyl; and each $R^7$ is fluoro;
(xii) $R^6$ is isopropyl; and each $R^7$ is methoxy;
(xiii) $R^6$ is isopropyl; and each $R^7$ is trifluoromethoxy;
(xiv) $R^6$ is chloro; and each $R^7$ is trifluoromethyl;
(xv) $R^6$ is chloro; and each $R^7$ is trifluoromethoxy;
(xvi) each $R^7$ is isopropyl; and $R^6$ is methyl;
(xvii) each $R^7$ is isopropyl; and $R^6$ is trifluoromethyl;
(xviii) each $R^7$ is isopropyl; and $R^6$ is cyclopropyl;
(xix) each $R^7$ is isopropyl; and $R^6$ is chloro;
(xx) each $R^7$ is ethyl; and $R^6$ is fluoro;
(xxi) each $R^7$ is isopropyl; and $R^6$ is cyano;
(xxii) each $R^7$ is cyclopropyl; and $R^6$ is cyclopropyl;
(xxiii) each $R^7$ is cyclopropyl; and $R^6$ is chloro;
(xxiv) each $R^7$ is cyclopropyl; and $R^6$ is fluoro;
(xxv) each $R^7$ is isopropyl; and $R^6$ is methoxy;
(xxvi) each $R^7$ is isopropyl; and $R^6$ is trifluoromethoxy;
(xxvii) each $R^7$ is chloro; and $R^6$ is trifluoromethyl;
(xxviii) each $R^7$ is chloro; and $R^6$ is trifluoromethoxy;
(xxix) $R^6$ and $R^7$ on adjacent atoms taken together with the atoms connecting them form a $C_5$ aliphatic carbocyclic ring; and one $R^7$ is fluoro, chloro, or cyano;
(xxx) $R^6$ and $R^7$ on adjacent atoms taken together with the atoms connecting them form a $C_4$ aliphatic carbocyclic ring; and one $R^7$ is fluoro, chloro, or cyano;
(xxxi) $R^6$ and $R^7$ on adjacent atoms taken together with the atoms connecting them form a $C_6$ aliphatic carbocyclic ring; and one $R^7$ is fluoro, chloro, or cyano;
(xxxii) $R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or
(xxxiii) $R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

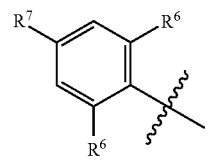

and $R^6$ and $R^7$ are one of the following combinations:
(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;

(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;
(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;
(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo; or
(xxxii) $R^7$ is $C_1$-$C_6$ alkoxy; and $R^6$ is chloro.

In some embodiments, of the compound of formula AA, the substituted ring B is

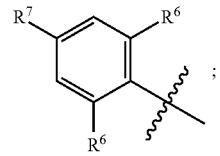

and $R^6$ and $R^7$ are one of the following combinations:
(i) each $R^6$ is isopropyl; and $R^7$ is methyl;
(ii) each $R^6$ is isopropyl; and $R^7$ is isopropyl;
(iii) each $R^6$ is isopropyl; and $R^7$ is trifluoromethyl;
(iv) each $R^6$ is isopropyl; and $R^7$ is cyclopropyl;
(v) each $R^6$ is isopropyl; and $R^7$ is chloro;
(vi) each $R^6$ is isopropyl; and $R^7$ is fluoro;
(vii) each $R^6$ is ethyl; and $R^7$ is fluoro;
(viii) each $R^6$ is isopropyl; and $R^7$ is cyano;
(ix) each $R^6$ is cyclopropyl; and $R^7$ is cyclopropyl;
(x) each $R^6$ is cyclopropyl; and $R^7$ is chloro;
(xi) each $R^6$ is cyclopropyl; and $R^7$ is fluoro;
(xii) each $R^6$ is isopropyl; and $R^7$ is methoxy;
(xiii) each $R^6$ is isopropyl; and $R^7$ is trifluoromethoxy;
(xiv) each $R^6$ is chloro; and $R^7$ is trifluoromethyl;
(xv) each $R^6$ is chloro; and $R^7$ is trifluoromethoxy;
(xvi) $R^7$ is isopropyl; and each $R^6$ is methyl;
(xvii) $R^7$ is isopropyl; and each $R^6$ is trifluoromethyl;
(xviii) $R^7$ is isopropyl; and each $R^6$ is cyclopropyl;
(xix) $R^7$ is isopropyl; and each $R^6$ is chloro;
(xx) $R^7$ is ethyl; and each $R^6$ is fluoro;
(xxi) $R^7$ is isopropyl; and each $R^6$ is cyano;
(xxii) $R^7$ is cyclopropyl; and each $R^6$ is cyclopropyl;
(xxiii) $R^7$ is cyclopropyl; and each $R^6$ is chloro;
(xxiv) $R^7$ is cyclopropyl; and each $R^6$ is fluoro;
(xxv) $R^7$ is isopropyl; and each $R^6$ is methoxy;
(xxvi) $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy; or
(xxix) one $R^6$ is isopropyl; the other $R^6$ is trifluoromethyl; and $R^7$ is chloro.

In some embodiments, of the compound of formula AA, the substituted ring B is

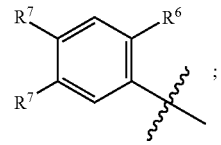

and $R^6$ and $R^7$ are one of the following combinations:
(i) $R^6$ is $C_1$-$C_6$ alkyl, and each $R^7$ is independently $C_1$-$C_6$ alkyl optionally substituted with one or more halo;
(ii) $R^6$ is $C_1$-$C_6$ alkyl and each $R^7$ is independently $C_1$-$C_6$ alkyl;
(iii) $R^6$ is $C_1$-$C_6$ alkyl, and each $R^7$ is independently $C_1$-$C_6$ alkyl substituted with one or more halo;
(iv) $R^6$ is $C_1$-$C_6$ alkyl, and each $R^7$ is independently $C_3$-$C_7$ cycloalkyl;
(v) $R^6$ is $C_1$-$C_6$ alkyl, and each $R^7$ is independently halo;
(vi) $R^6$ is $C_1$-$C_6$ alkyl, and $R^7$ is cyano;
(vii) $R^6$ is $C_3$-$C_7$ cycloalkyl, and each $R^7$ is independently $C_3$-$C_7$ cycloalkyl;

(viii) $R^6$ is $C_3$-$C_7$ cycloalkyl, and each $R^7$ is independently halo;
(ix) $R^6$ is cyclopropyl and each $R^7$ is independently halo;
(x) $R^6$ is $C_1$-$C_6$ alkyl, and each $R^7$ is independently $C_1$-$C_6$ alkoxy optionally substituted with one or more halo;
(xi) $R^6$ is $C_1$-$C_6$ alkyl, and each $R^7$ is independently $C_1$-$C_6$ alkoxy;
(xii) $R^6$ is $C_1$-$C_6$ alkyl, and each $R^7$ is independently $C_1$-$C_6$ alkoxy substituted with one or more halo;
(xiii) $R^6$ is halo, and each $R^7$ is independently $C_1$-$C_6$ haloalkyl;
(xiv) $R^6$ is halo, and each $R^7$ is independently $C_1$-$C_6$ haloalkoxy;
(xv) $R^6$ is $C_1$-$C_6$ alkoxy; and each $R^7$ is independently halo;
(xvi) $R^6$ is $C_1$-$C_6$ alkoxy; and $R^7$ is chloro;
(xvii) each $R^7$ is independently $C_1$-$C_6$ alkyl, and $R^6$ is $C_1$-$C_6$ alkyl optionally substituted with one or more halo;
(xviii) each $R^7$ is independently $C_1$-$C_6$ alkyl, and $R^6$ is $C_1$-$C_6$ alkyl substituted with one or more halo;
(xix) each $R^7$ is independently $C_1$-$C_6$ alkyl, and $R^6$ is $C_3$-$C_7$ cycloalkyl;
(xx) each $R^7$ is independently $C_1$-$C_6$ alkyl, and $R^6$ is halo;
(xxi) each $R^7$ is independently $C_1$-$C_6$ alkyl and $R^6$ is halo;
(xxii) each $R^7$ is independently $C_1$-$C_6$ alkyl, and $R^6$ is cyano;
(xxiii) each $R^7$ is independently $C_3$-$C_7$ cycloalkyl, and $R^6$ is $C_3$-$C_7$ cycloalkyl;
(xxiv) each $R^7$ is independently $C_3$-$C_7$ cycloalkyl, and $R^6$ is halo;
(xxv) each $R^7$ is independently $C_3$-$C_7$ cycloalkyl and $R^6$ is halo;
(xxvi) each $R^7$ is independently $C_1$-$C_6$ alkyl, and $R^6$ is $C_1$-$C_6$ alkoxy optionally substituted with one or more halo;
(xxvii) each $R^7$ is independently $C_1$-$C_6$ alkyl, and $R^6$ is $C_1$-$C_6$ alkoxy;
(xxviii) each $R^7$ is independently $C_1$-$C_6$ alkyl, and $R^6$ is $C_1$-$C_6$ alkoxy substituted with one or more halo;
(xxix) each $R^7$ is independently halo, and $R^6$ is $C_1$-$C_6$ haloalkyl;
(xxx) each $R^7$ is independently halo, and $R^6$ is $C_1$-$C_6$ haloalkoxy;
(xxxi) each $R^7$ is independently $C_1$-$C_6$ alkoxy; and $R^6$ is halo; or
(xxxii) each $R^7$ is independently $C_1$-$C_6$ alkoxy; and $R^6$ is chloro.

In some embodiments, of the compound of formula AA, the substituted ring B is

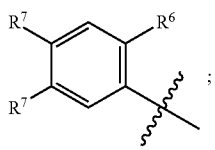

and $R^6$ and $R^7$ are one of the following combinations:
(i) $R^6$ is isopropyl; and each $R^7$ is methyl;
(ii) $R^6$ is isopropyl; and each $R^7$ is isopropyl;
(iii) $R^6$ is isopropyl; and each $R^7$ is trifluoromethyl;
(iv) $R^6$ is isopropyl; and each $R^7$ is cyclopropyl;
(v) $R^6$ is isopropyl; and each $R^7$ is chloro;
(vi) $R^6$ is isopropyl; and each $R^7$ is fluoro;
(vii) $R^6$ is ethyl; and each $R^7$ is fluoro;
(viii) $R^6$ is isopropyl; and each $R^7$ is cyano;
(ix) $R^6$ is cyclopropyl; and each $R^7$ is cyclopropyl;
(x) $R^6$ is cyclopropyl; and each $R^7$ is chloro;
(xi) $R^6$ is cyclopropyl; and each $R^7$ is fluoro;
(xii) $R^6$ is isopropyl; and each $R^7$ is methoxy;
(xiii) $R^6$ is isopropyl; and each $R^7$ is trifluoromethoxy;
(xiv) $R^6$ is chloro; and each $R^7$ is trifluoromethyl;
(xv) $R^6$ is chloro; and each $R^7$ is trifluoromethoxy;
(xvi) each $R^7$ is isopropyl; and $R^6$ is methyl;
(xvii) each $R^7$ is isopropyl; and $R^6$ is trifluoromethyl;
(xviii) each $R^7$ is isopropyl; and $R^6$ is cyclopropyl;
(xix) each $R^7$ is isopropyl; and $R^6$ is chloro;
(xx) each $R^7$ is ethyl; and $R^6$ is fluoro;
(xxi) each $R^7$ is isopropyl; and $R^6$ is cyano;
(xxii) each $R^7$ is cyclopropyl; and $R^6$ is cyclopropyl;
(xxiii) each $R^7$ is cyclopropyl; and $R^6$ is chloro;
(xxiv) each $R^7$ is cyclopropyl; and $R^6$ is fluoro;
(xxv) each $R^7$ is isopropyl; and $R^6$ is methoxy;
(xxvi) each $R^7$ is isopropyl; and $R^6$ is trifluoromethoxy;
(xxvii) each $R^7$ is chloro; and $R^6$ is trifluoromethyl; or
(xxviii) each $R^7$ is chloro; and $R^6$ is trifluoromethoxy.

In some embodiments, of the compound of formula AA, the substituted ring B is

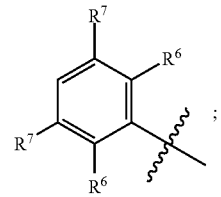

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl;
(v) each $R^6$ is independently $C_1$-$C_6$ alkyl, and each $R^7$ is independently halo;
(vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy;
(xii) each $R^6$ is independently $C_1$-$C_6$ alkyl, and each $R^7$ is independently $C_1$-$C_6$ alkoxy substituted with one or more halo;

(xiii) each $R^6$ is independently halo, and each $R^7$ is independently $C_1$-$C_6$ haloalkyl;
(xiv) each $R^6$ is independently halo, and each $R^7$ is independently $C_1$-$C_6$ haloalkoxy;
(xv) each $R^6$ is independently $C_1$-$C_6$ alkoxy; and each $R^7$ is independently halo;
(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;
(xxiii) each $R^7$ is independently $C_3$-$C_7$ cycloalkyl, and each $R^6$ is independently $C_3$-$C_7$ cycloalkyl
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo;
(xxxii) each $R^7$ is independently $C_1$-$C_6$ alkoxy; and $R^6$ is chloro;
(xxxiii) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;
(xxxiv) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl;
(xxxv) two pairs, each of one $R^6$ and one $R^7$, are on adjacent atoms, and one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring is optionally substituted with one or more hydroxy, oxo, or $C_1$-$C_6$ alkyl; or
(xxxvi) two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

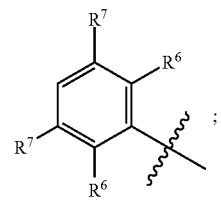

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) one $R^6$ is isopropyl; the other $R^6$ is trifluoromethyl; and each $R^7$ is chloro;
(xxx) each $R^6$ is isopropyl; one $R^7$ is fluoro; and the other $R^7$ is cyano;
(xxxi) two pairs, each of one $R^6$ and one $R^7$, are on adjacent atoms, and each pair of one $R^6$ and one $R^7$ taken together with the atoms connecting them form a $C_5$ aliphatic carbocyclic ring;
(xxxii) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;

(xxxiii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
(xxxiv) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
(xxxv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl;
(xxxvi) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvii) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

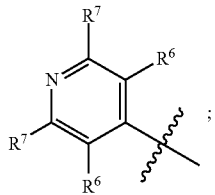

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl;
(v) each $R^6$ is independently $C_1$-$C_6$ alkyl, and each $R^7$ is independently halo;
(vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy;
(xii) each $R^6$ is independently $C_1$-$C_6$ alkyl, and each $R^7$ is independently $C_1$-$C_6$ alkoxy substituted with one or more halo;
(xiii) each $R^6$ is independently halo, and each $R^7$ is independently $C_1$-$C_6$ haloalkyl;
(xiv) each $R^6$ is independently halo, and each $R^7$ is independently $C_1$-$C_6$ haloalkoxy;
(xv) each $R^6$ is independently $C_1$-$C_6$ alkoxy; and each $R^7$ is independently halo;
(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;
(xxiii) each $R^7$ is independently $C_3$-$C_7$ cycloalkyl, and each $R^6$ is independently $C_3$-$C_7$ cycloalkyl;
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo;
(xxxii) each $R^7$ is independently $C_1$-$C_6$ alkoxy; and $R^6$ is chloro;
(xxxiii) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring;
(xxxiv) two pairs, each of one $R^6$ and one $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
(xxxv) two pairs, each of one $R^6$ and one $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

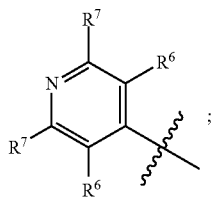

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) one $R^6$ is isopropyl; the other $R^6$ is trifluoromethyl; and each $R^7$ is chloro;
(xxx) each $R^6$ is isopropyl; one $R^7$ is fluoro; and the other $R^7$ is cyano; or
(xxxi) two pairs, each of one $R^6$ and one $R^7$ on adjacent atoms taken together with the atoms connecting them form a $C_4$ aliphatic carbocyclic ring optionally substituted with one or more hydroxy, oxo, or methyl;
(xxxii) two pairs, each of one $R^6$ and one $R^7$ on adjacent atoms taken together with the atoms connecting them form a $C_5$ aliphatic carbocyclic ring optionally substituted with one or more hydroxy, oxo, or methyl;
(xxxiii) two pairs, each of one $R^6$ and one $R^7$ on adjacent atoms taken together with the atoms connecting them form a $C_6$ aliphatic carbocyclic ring optionally substituted with one or more hydroxy, oxo, or methyl;
(xxxiv) two pairs, each of one $R^6$ and one $R^7$ on adjacent atoms taken together with the atoms connecting them form a 5-membered heterocyclic ring containing 1 heteroatom independently selected from O, N, and S, wherein the heterocyclic ring is optionally substituted with one or more hydroxy, oxo, or methyl;
(xxxv) two pairs, each of one $R^6$ and one $R^7$ on adjacent atoms taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvi) two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, of the compound of formula AA, the substituted ring B is

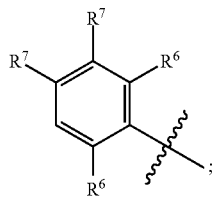

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl; (v) each $R^6$ is independently $C_1$-$C_6$ alkyl, and each $R^7$ is independently halo; (vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy;
(xii) each $R^6$ is independently $C_1$-$C_6$ alkyl, and each $R^7$ is independently $C_1$-$C_6$ alkoxy substituted with one or more halo;
(xiii) each $R^6$ is independently halo, and each $R^7$ is independently $C_1$-$C_6$ haloalkyl;
(xiv) each $R^6$ is independently halo, and each $R^7$ is independently $C_1$-$C_6$ haloalkoxy;
(xv) each $R^6$ is independently $C_1$-$C_6$ alkoxy; and each $R^7$ is independently halo;

(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;
(xxiii) each $R^7$ is independently $C_3$-$C_7$ cycloalkyl, and each $R^6$ is independently $C_3$-$C_7$ cycloalkyl;
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo; or
(xxxii) each $R^7$ is independently $C_1$-$C_6$ alkoxy; and $R^6$ is chloro.

In some embodiments of the compound of formula AA, the substituted ring B is

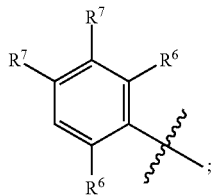

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) one $R^6$ is isopropyl; the other $R^6$ is trifluoromethyl; and $R^7$ is chloro; or
(xxx) $R^6$ is isopropyl; one $R^7$ is fluoro; and the other $R^7$ is cyano.

In some embodiments, of the compound of formula AA, the substituted ring B is

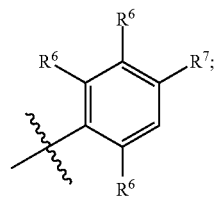

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and each $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;

each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and each $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and each $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and each $R^6$ is chloro;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

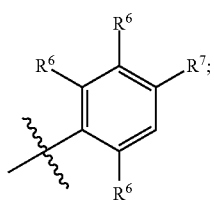

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano;
$R^6$ and $R^7$ on adjacent atoms taken together with the atoms connecting them form a $C_4$ aliphatic carbocyclic ring; and one $R^6$ is chloro, fluoro, or cyano;
$R^6$ and $R^7$ on adjacent atoms taken together with the atoms connecting them form a $C_5$ aliphatic carbocyclic ring; and one $R^6$ is chloro, fluoro, or cyano;
$R^6$ and $R^7$ on adjacent atoms taken together with the atoms connecting them form a $C_6$ aliphatic carbocyclic ring; and one $R^6$ is chloro, fluoro, or cyano;
$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;
$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or
$R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

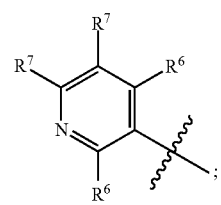

and $R^6$ and $R^7$ are one of the following combinations:
- (i) each $R^6$ is independently $C_1$-$C_6$ alkyl, and each $R^7$ is independently $C_1$-$C_6$ alkyl optionally substituted with one or more halo;
- (ii) each $R^6$ is independently $C_1$-$C_6$ alkyl and each $R^7$ is independently $C_1$-$C_6$ alkyl;
- (iii) each $R^6$ is independently $C_1$-$C_6$ alkyl, and each $R^7$ is independently $C_1$-$C_6$ alkyl substituted with one or more halo;
- (iv) each $R^6$ is independently $C_1$-$C_6$ alkyl, and each $R^7$ is independently $C_3$-$C_7$ cycloalkyl;
- (v) each $R^6$ is independently $C_1$-$C_6$ alkyl, and each $R^7$ is independently halo;
- (vi) each $R^6$ is independently $C_1$-$C_6$ alkyl, and $R^7$ is cyano;
- (vii) each $R^6$ is independently $C_3$-$C_7$ cycloalkyl, and each $R^7$ is independently $C_3$-$C_7$ cycloalkyl;
- (viii) each $R^6$ is independently $C_3$-$C_7$ cycloalkyl, and each $R^7$ is independently halo;
- (ix) each $R^6$ is independently cyclopropyl and each $R^7$ is independently halo;
- (x) each $R^6$ is independently $C_1$-$C_6$ alkyl, and each $R^7$ is independently $C_1$-$C_6$ alkoxy optionally substituted with one or more halo;
- (xi) each $R^6$ is independently $C_1$-$C_6$ alkyl, and each $R^7$ is independently $C_1$-$C_6$ alkoxy;
- (xii) each $R^6$ is independently $C_1$-$C_6$ alkyl, and each $R^7$ is independently $C_1$-$C_6$ alkoxy substituted with one or more halo;
- (xiii) each $R^6$ is independently halo, and each $R^7$ is independently $C_1$-$C_6$ haloalkyl;
- (xiv) each $R^6$ is independently halo, and each $R^7$ is independently $C_1$-$C_6$ haloalkoxy;
- (xv) each $R^6$ is independently $C_1$-$C_6$ alkoxy; and each $R^7$ is independently halo;
- (xvi) each $R^6$ is independently $C_1$-$C_6$ alkoxy; and $R^7$ is chloro;
- (xvii) each $R^7$ is independently $C_1$-$C_6$ alkyl, and each $R^6$ is independently $C_1$-$C_6$ alkyl optionally substituted with one or more halo;
- (xviii) each $R^7$ is independently $C_1$-$C_6$ alkyl, and each $R^6$ is independently $C_1$-$C_6$ alkyl substituted with one or more halo;
- (xix) each $R^7$ is independently $C_1$-$C_6$ alkyl, and each $R^6$ is independently $C_3$-$C_7$ cycloalkyl;
- (xx) each $R^7$ is independently $C_1$-$C_6$ alkyl, and each $R^6$ is independently halo;
- (xxi) each $R^7$ is independently $C_1$-$C_6$ alkyl and each $R^6$ is independently halo;
- (xxii) each $R^7$ is independently $C_1$-$C_6$ alkyl, and $R^6$ is cyano;
- (xxiii) each $R^7$ is independently $C_3$-$C_7$ cycloalkyl, and each $R^6$ is independently $C_3$-$C_7$ cycloalkyl;
- (xxiv) each $R^7$ is independently $C_3$-$C_7$ cycloalkyl, and each $R^6$ is independently halo;
- (xxv) each $R^7$ is independently $C_3$-$C_7$ cycloalkyl and each $R^6$ is independently halo;
- (xxvi) each $R^7$ is independently $C_1$-$C_6$ alkyl, and each $R^6$ is independently $C_1$-$C_6$ alkoxy optionally substituted with one or more halo;
- (xxvii) each $R^7$ is independently $C_1$-$C_6$ alkyl, and each $R^6$ is independently $C_1$-$C_6$ alkoxy;
- (xxviii) each $R^7$ is independently $C_1$-$C_6$ alkyl, and each $R^6$ is independently $C_1$-$C_6$ alkoxy substituted with one or more halo;
- (xxix) each $R^7$ is independently halo, and each $R^6$ is independently $C_1$-$C_6$ haloalkyl;
- (xxx) each $R^7$ is independently halo, and each $R^6$ is independently $C_1$-$C_6$ haloalkoxy;
- (xxxi) each $R^7$ is independently $C_1$-$C_6$ alkoxy; and each $R^6$ is independently halo; or
- (xxxii) each $R^7$ is independently $C_1$-$C_6$ alkoxy; and $R^6$ is chloro.

In some embodiments, of the compound of formula AA, the substituted ring B is

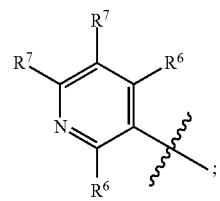

and $R^6$ and $R^7$ are one of the following combinations:
- (i) each $R^6$ is isopropyl; and each $R^7$ is methyl;
- (ii) each $R^6$ is isopropyl; and each $R^7$ is isopropyl;
- (iii) each $R^6$ is isopropyl; and each $R^7$ is trifluoromethyl;
- (iv) each $R^6$ is isopropyl; and each $R^7$ is cyclopropyl;
- (v) each $R^6$ is isopropyl; and each $R^7$ is chloro;
- (vi) each $R^6$ is isopropyl; and each $R^7$ is fluoro;
- (vii) each $R^6$ is ethyl; and each $R^7$ is fluoro;
- (viii) each $R^6$ is isopropyl; and each $R^7$ is cyano;
- (ix) each $R^6$ is cyclopropyl; and each $R^7$ is cyclopropyl;
- (x) each $R^6$ is cyclopropyl; and each $R^7$ is chloro;
- (xi) each $R^6$ is cyclopropyl; and each $R^7$ is fluoro;
- (xii) each $R^6$ is isopropyl; and each $R^7$ is methoxy;
- (xiii) each $R^6$ is isopropyl; and each $R^7$ is trifluoromethoxy;
- (xiv) each $R^6$ is chloro; and each $R^7$ is trifluoromethyl;
- (xv) each $R^6$ is chloro; and each $R^7$ is trifluoromethoxy;
- (xvi) each $R^7$ is isopropyl; and each $R^6$ is methyl;
- (xvii) each $R^7$ is isopropyl; and each $R^6$ is trifluoromethyl;
- (xviii) each $R^7$ is isopropyl; and each $R^6$ is cyclopropyl;
- (xix) each $R^7$ is isopropyl; and each $R^6$ is chloro;
- (xx) each $R^7$ is ethyl; and each $R^6$ is fluoro;
- (xxi) each $R^7$ is isopropyl; and each $R^6$ is cyano;
- (xxii) each $R^7$ is cyclopropyl; and each $R^6$ is cyclopropyl;
- (xxiii) each $R^7$ is cyclopropyl; and each $R^6$ is chloro;
- (xxiv) each $R^7$ is cyclopropyl; and each $R^6$ is fluoro;
- (xxv) each $R^7$ is isopropyl; and each $R^6$ is methoxy;
- (xxvi) each $R^7$ is isopropyl; and each $R^6$ is trifluoromethoxy;
- (xxvii) each $R^7$ is chloro; and each $R^6$ is trifluoromethyl;
- (xxviii) each $R^7$ is chloro; and each $R^6$ is trifluoromethoxy;
- (xxix) one $R^6$ is isopropyl; the other $R^6$ is trifluoromethyl; and each $R^7$ is chloro; or
- (xxx) each $R^6$ is isopropyl; one $R^7$ is fluoro; and the other $R^7$ is cyano.

In some embodiments, of the compound of formula AA, the substituted ring B is

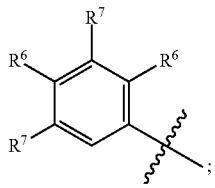

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl;
(v) each $R^6$ is independently $C_1$-$C_6$ alkyl, and each $R^7$ is independently halo;
(vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy;
(xii) each $R^6$ is independently $C_1$-$C_6$ alkyl, and each $R^7$ is independently $C_1$-$C_6$ alkoxy substituted with one or more halo;
(xiii) each $R^6$ is independently halo, and each $R^7$ is independently $C_1$-$C_6$ haloalkyl;
(xiv) each $R^6$ is independently halo, and each $R^7$ is independently $C_1$-$C_6$ haloalkoxy;
(xv) each $R^6$ is independently $C_1$-$C_6$ alkoxy; and each $R^7$ is independently halo;
(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;
(xxiii) each $R^7$ is independently $C_3$-$C_7$ cycloalkyl, and each $R^6$ is independently $C_3$-$C_7$ cycloalkyl;
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo;
(xxxvi) each $R^7$ is independently $C_1$-$C_6$ alkoxy; and $R^6$ is chloro;
(xxxvii) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl;
(xxxii) two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; or
(xxxiii) two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

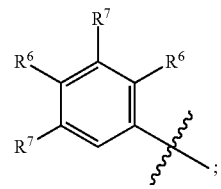

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;

(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy;
(xxix) one $R^6$ is isopropyl; the other $R^6$ is trifluoromethyl; and $R^7$ is chloro;
(xxx) $R^6$ is isopropyl; one $R^7$ is fluoro; and the other $R^7$ is cyano; two pairs, each of one $R^6$ and one $R^7$, are on adjacent atoms, and each pair of one $R^6$ and one $R^7$ taken together with the atoms connecting them form a $C_5$ aliphatic carbocyclic ring;
(xxxi) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
(xxxii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
(xxxiii) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
(xxxiv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl
(xxxv) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvi) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

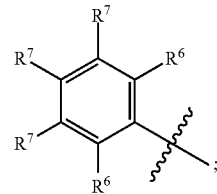

and $R^6$ and $R^7$ are one of the following combinations:
(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;
(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;
(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;

(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo;
(xxxii) $R^7$ is $C_1$-$C_6$ alkoxy; and $R^6$ is chloro;
(xxxiii) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; and one $R^7$ is halo;
(xxxiv) two pairs, each of one $R^6$ and one $R^7$, are on adjacent atoms, and each pair of one $R^6$ and one $R^7$ taken together with the atoms connecting them form a $C_4$-$C_8$ aliphatic carbocyclic ring; and one $R^7$ is cyano;
(xxxv) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; and one $R^7$ is halo or cyano;
(xxxvi) two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano; or
(xxxvii) two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano.

In some embodiments, of the compound of formula AA, the substituted ring B is

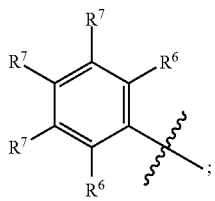

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) each $R^6$ is isopropyl; two $R^7$ are fluoro; and one $R^7$ is chloro;
(xxx) two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is chloro;
(xxxi) two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is fluoro;
(xxxii) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl; and one $R^7$ is fluoro or chloro;
(xxxiii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro;
(xxxiv) two pairs, each of one $R^6$ and one $R^7$, are on adjacent atoms, and each pair of one $R^6$ and one $R^7$ taken together with the atoms connecting them form a CO aliphatic carbocyclic ring optionally substituted with one or more hydroxy, oxo, or methyl; and one $R^7$ is fluoro or chloro;
(xxxv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; and one R⁷ is fluoro or chloro;

(xxxvi) two pairs, each of one R⁶ and one R⁷, are on adjacent atoms, and each pair of one R⁶ and one R⁷ taken together with the atoms connecting them form a 6-membered heterocyclic ring containing 1 heteroatom independently selected from O, N, and S, wherein the heterocyclic ring is optionally substituted with one or more hydroxy, oxo, or methyl; and one R⁷ is fluoro or chloro; or (xxxvii) two pairs, each of one R⁶ and one R⁷, are on adjacent atoms, one pair of one R⁶ and one R⁷ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one R⁶ and one R⁷ taken together with the atoms connecting them form a C₅ aliphatic carbocyclic ring optionally substituted with one or more hydroxy, oxo, or methyl; and one R⁷ is fluoro or chloro.

Additional Features of the Embodiments Herein

In some embodiments of the compound of Formula AA (e.g., Formula AA-1, Formula AA-2, Formula AA-3, Formula AA-4, or Formula AA-5), R⁶ is not CN.

In some embodiments, the compound of Formula AA is not a compound selected from the group consisting of:

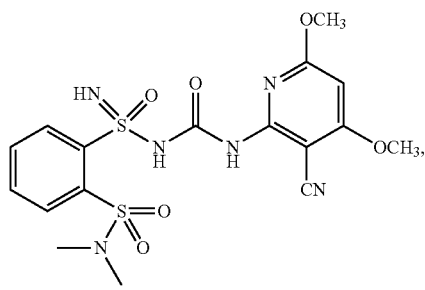

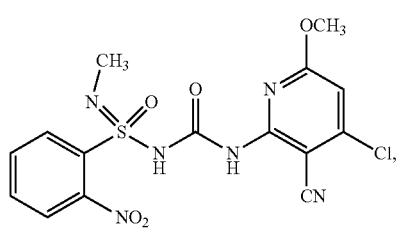

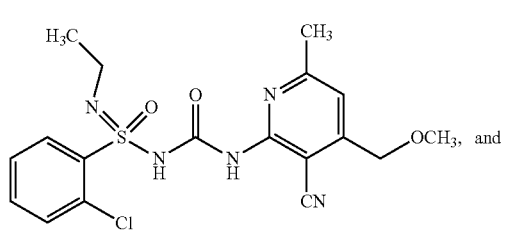

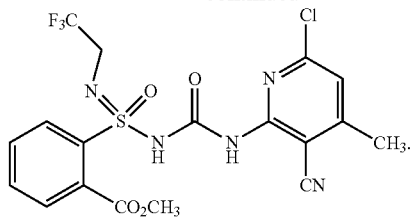

In some embodiments, the compound of Formula AA is not a compound selected from the group consisting of:

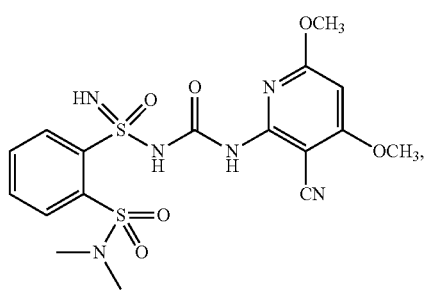

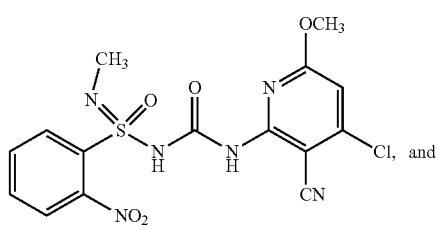

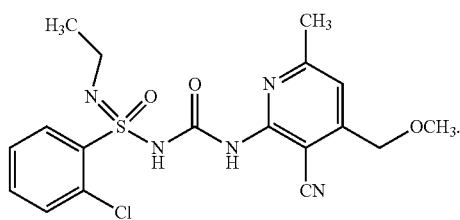

In some embodiments the compound of any of the formulae herein is not a compound disclosed in EP 0173498, which is incorporated herein by reference in its entirety.

In some embodiments the compound of any of the formulae herein is not a compound disclosed in U.S. Pat. No. 4,666,506, which is incorporated herein by reference in its entirety.

It is understood that the combination of variables in the formulae herein is such that the compounds are stable.

In some embodiments, provided herein is a compound that is selected from the group consisting of the compounds in Table 1:

TABLE 1

| Compound | Structure |
|---|---|
| 101' | 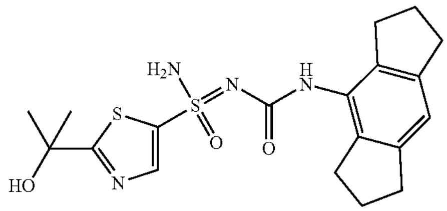 [SMILES: CC(C)(O)c1ncc(S(N)(=O)=NC(=O)Nc2c3c(cc4c2CCC4)CCC3)s1] |
| 101 | 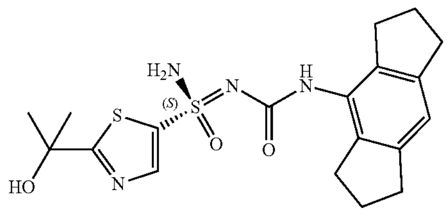 |
| 102 | 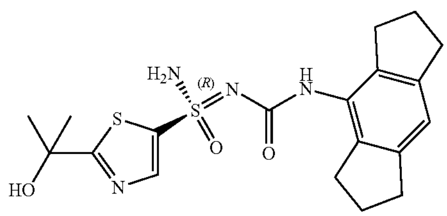 |
| 103' | 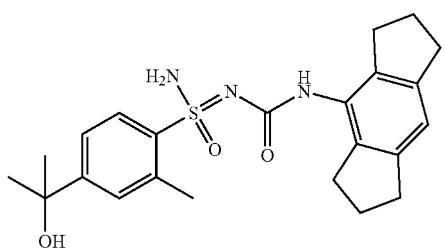 [SMILES: Cc1cc(C(C)(C)O)ccc1S(N)(=O)=NC(=O)Nc1c2c(cc3c1CCC3)CCC2] |
| 103 | 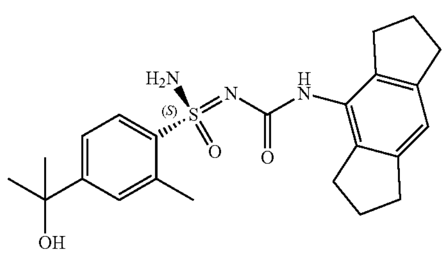 |
| 104 | 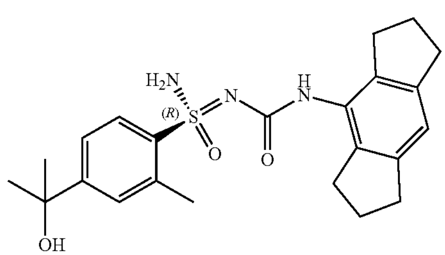 |

TABLE 1-continued

| Compound | Structure |
|---|---|
| 105 | 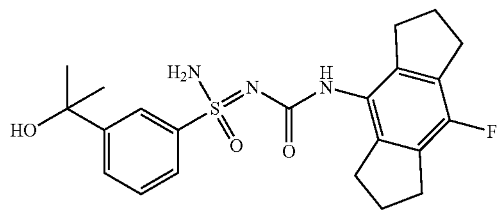 [SMILES: CC(C)(O)c1cccc(S(N)(=O)=NC(=O)Nc2c3c(c(F)c4c2CCC4)CCC3)c1] |
| 105a | 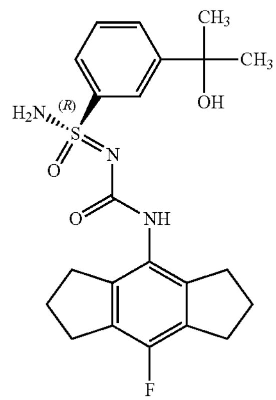 |
| 105b | 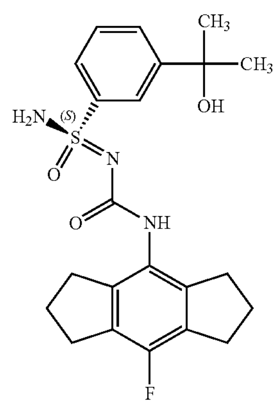 |
| 106 | 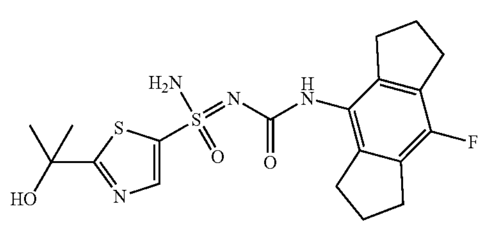 |

TABLE 1-continued

| Compound | Structure |
|---|---|
| 106a | 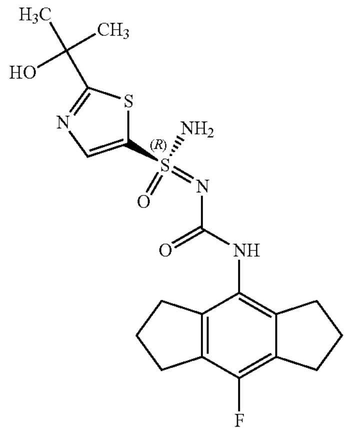 |
| 106b | 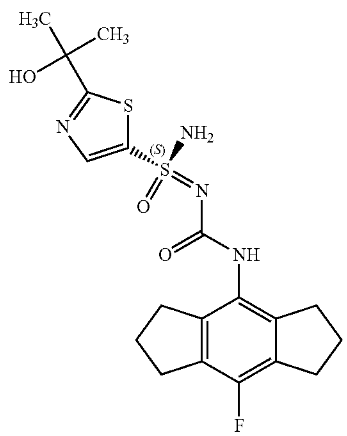 |
| 107 | 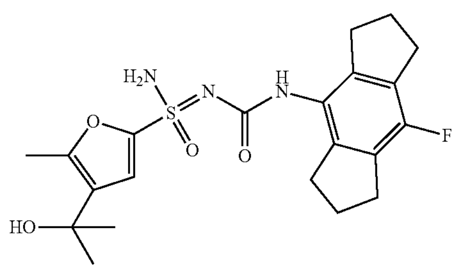 [SMILES: Cc1oc(S(N)(=O)=NC(=O)Nc2c3c(c(F)c4c2CCC4)CCC3)cc1C(C)(C)O] |
| 107a | 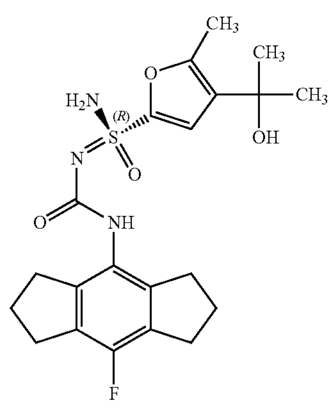 |

TABLE 1-continued
| Compound | Structure |
|---|---|
| 107b | 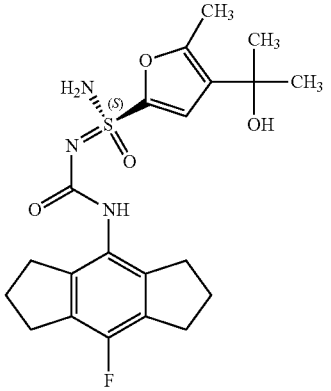 |
| 108 | 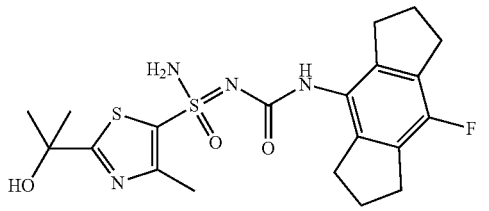 [SMILES: Cc1nc(C(C)(C)O)sc1S(N)(=O)=NC(=O)Nc1c2c(c(F)c3c1CCC3)CCC2] |
| 108a | 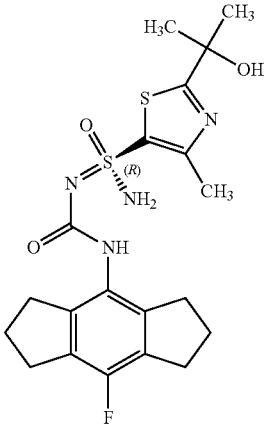 |
| 108b | 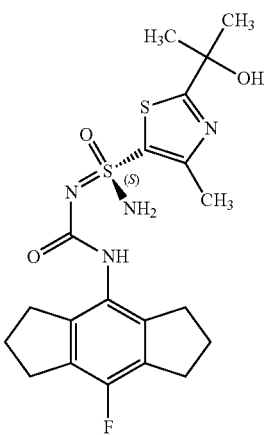 |

TABLE 1-continued

| Compound | Structure |
|---|---|
| 109 | 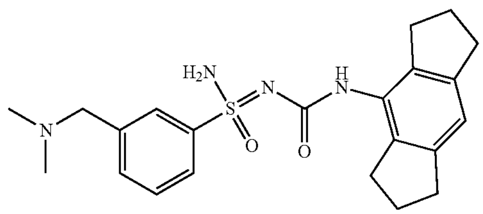 [SMILES: CN(C)Cc1cccc(S(N)(=O)=NC(=O)Nc2c3c(cc4c2CCC4)CCC3)c1] |
| 109a | 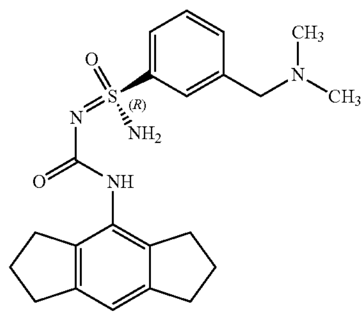 |
| 109b | 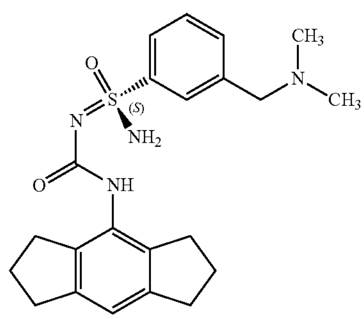 |
| 110 | 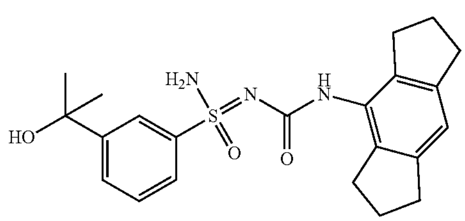 [SMILES: CC(C)(O)c1cccc(S(N)(=O)=NC(=O)Nc2c3c(cc4c2CCC4)CCC3)c1] |
| 110a | 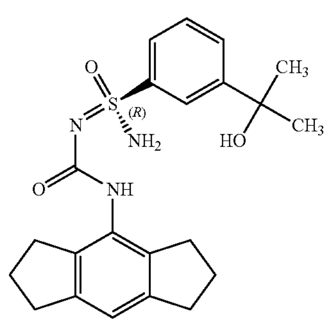 |

TABLE 1-continued

| Compound | Structure |
|---|---|
| 110b | 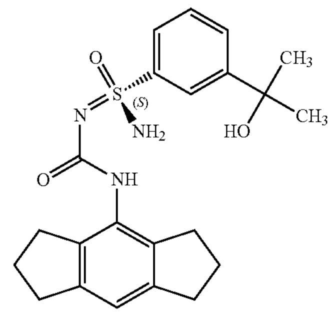 |
| 111 | 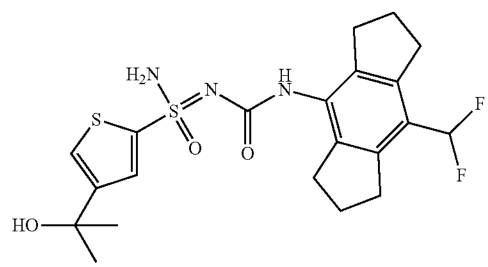 [SMILES: CC(C)(O)c1csc(S(N)(=O)=NC(=O)Nc2c3c(c(C(F)F)c4c2CCC4)CCC3)c1] |
| 112 | 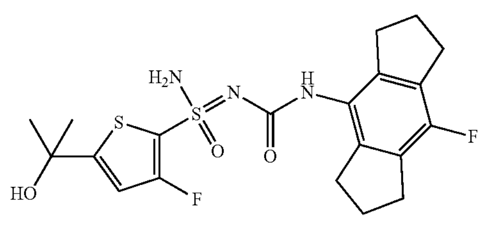 [SMILES: CC(C)(O)c1cc(F)c(S(N)(=O)=NC(=O)Nc2c3c(c(F)c4c2CCC4)CCC3)s1] |
| 112a | 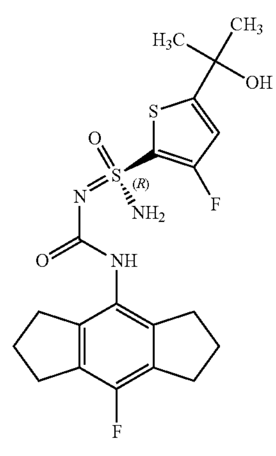 |

TABLE 1-continued

| Compound | Structure |
|---|---|
| 112b | 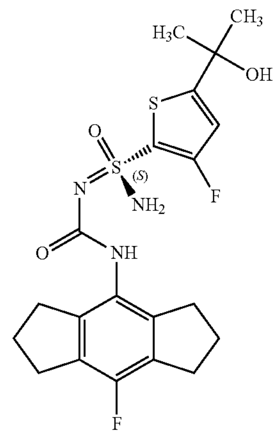 |
| 113 | 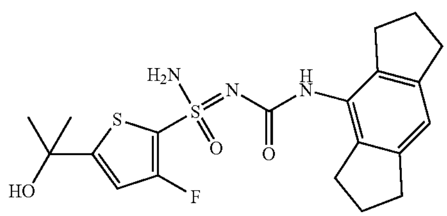 [SMILES: CC(C)(O)c1cc(F)c(S(N)(=O)=NC(=O)Nc2c3c(cc4c2CCC4)CCC3)s1] |
| 113a | 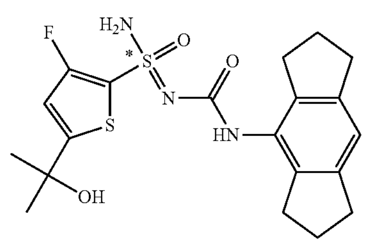 [SMILES: CC(C)(O)c1cc(F)c(S(N)(=O)=NC(=O)Nc2c3c(cc4c2CCC4)CCC3)s1] |
| 113b | 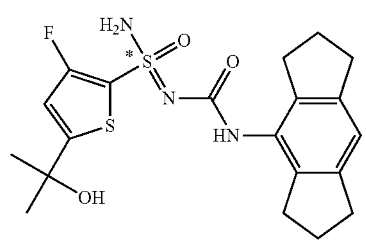 [SMILES: CC(C)(O)c1cc(F)c(S(N)(=O)=NC(=O)Nc2c3c(cc4c2CCC4)CCC3)s1] |
| 114 | 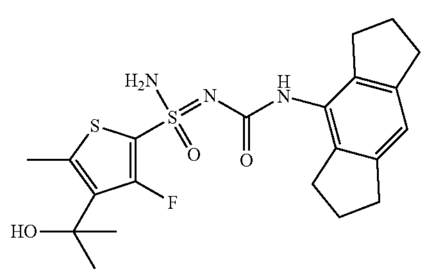 [SMILES: Cc1sc(S(N)(=O)=NC(=O)Nc2c3c(cc4c2CCC4)CCC3)c(F)c1C(C)(C)O] |

TABLE 1-continued

| Compound | Structure |
|---|---|
| 115 | 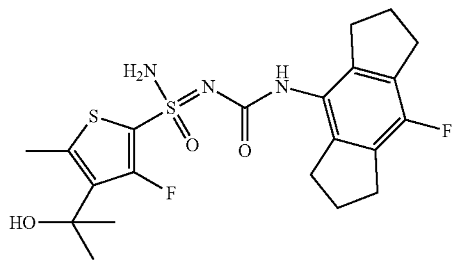 [SMILES: Cc1sc(S(N)(=O)=NC(=O)Nc2c3c(c(F)c4c2CCC4)CCC3)c(F)c1C(C)(C)O] |
| 116 | 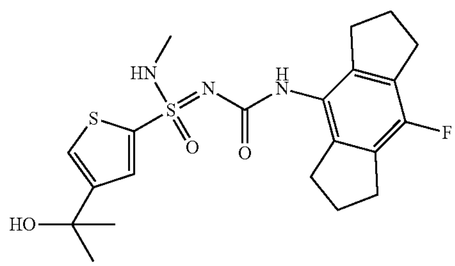 [SMILES: CNS(=O)(=NC(=O)Nc1c2c(c(F)c3c1CCC3)CCC2)c1cc(C(C)(C)O)cs1] |
| 116a | 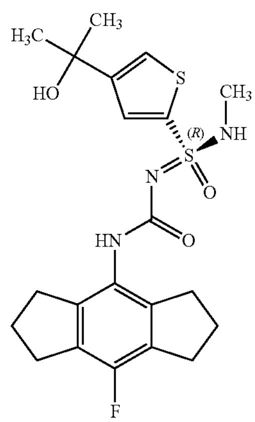 |
| 116b | 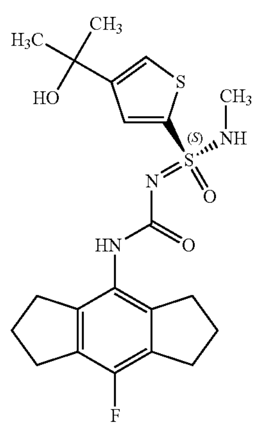 |
| 117 | 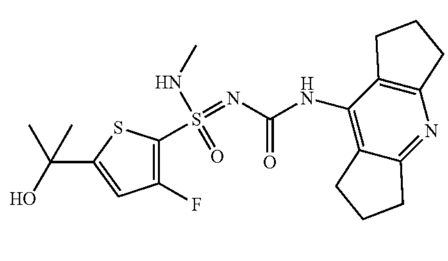 [SMILES: CNS(=O)(=NC(=O)Nc1c2c(nc3c1CCC3)CCC2)c1sc(C(C)(C)O)cc1F] |

TABLE 1-continued

| Compound | Structure |
|---|---|
| 118 | 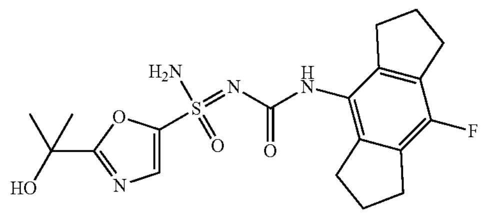 [SMILES: CC(C)(O)c1ncc(S(N)(=O)=NC(=O)Nc2c3c(c(F)c4c2CCC4)CCC3)o1] |
| 119 | 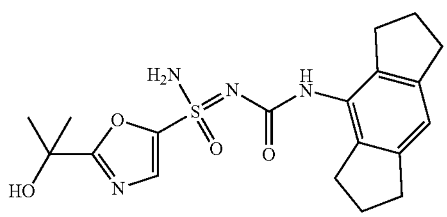 [SMILES: CC(C)(O)c1ncc(S(N)(=O)=NC(=O)Nc2c3c(cc4c2CCC4)CCC3)o1] |
| 120 | 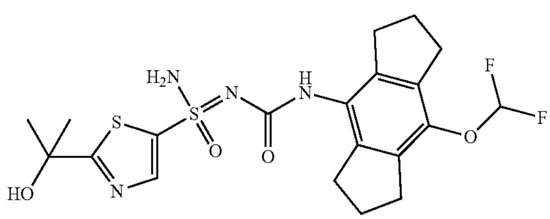 [SMILES: CC(C)(O)c1ncc(S(N)(=O)=NC(=O)Nc2c3c(c(OC(F)F)c4c2CCC4)CCC3)s1] |
| 120a | 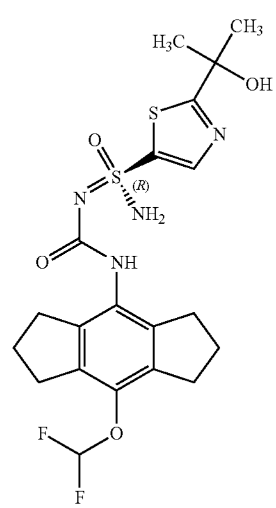 |

TABLE 1-continued
| Compound | Structure |
|---|---|
| 120b | 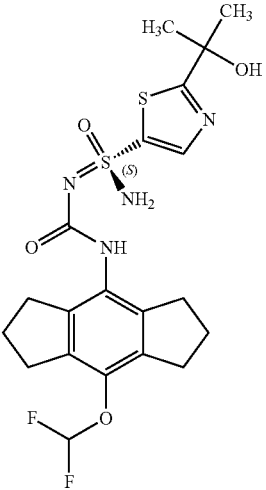 |
| 121 | 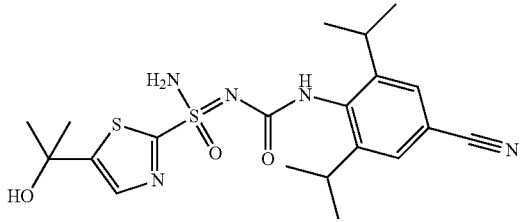 [SMILES: CC(C)c1cc(C#N)cc(C(C)C)c1NC(=O)N=S(N)(=O)c1ncc(C(C)(C)O)s1] |
| 121a | 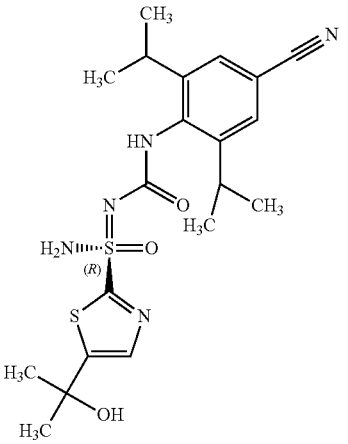 |
| 121b | 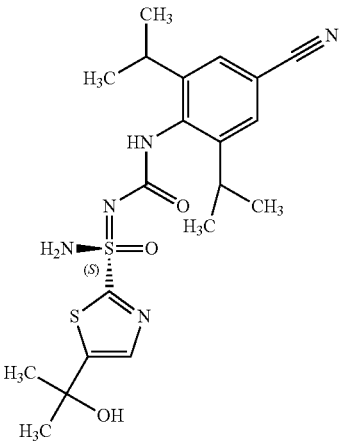 |

TABLE 1-continued

| Compound | Structure |
|---|---|
| 122 | 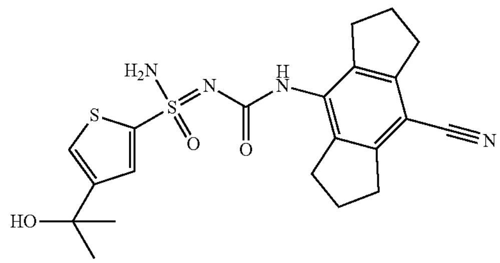 [SMILES: CC(C)(O)c1csc(S(N)(=O)=NC(=O)Nc2c3c(c(C#N)c4c2CCC4)CCC3)c1] |
| 122a | 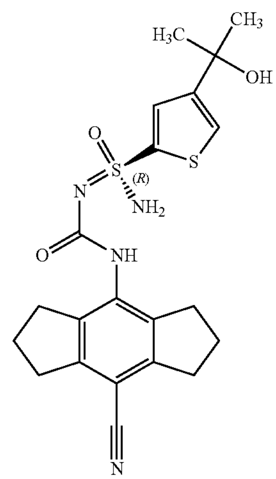 |
| 122b | 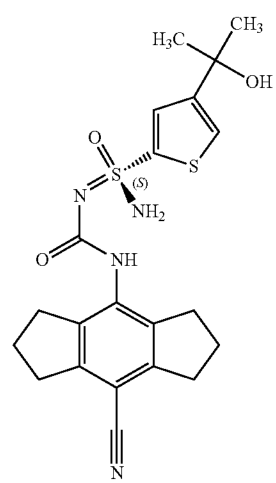 |
| 123 | 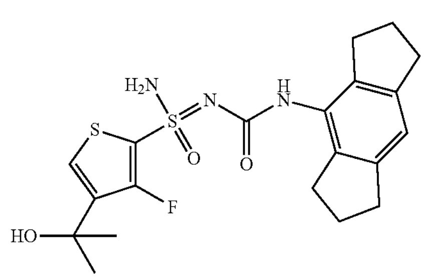 [SMILES: CC(C)(O)c1csc(S(N)(=O)=NC(=O)Nc2c3c(cc4c2CCC4)CCC3)c1F] |

TABLE 1-continued

| Compound | Structure |
| --- | --- |
| 124 | 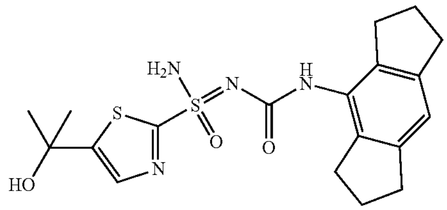 [SMILES: CC(C)(O)c1cnc(S(N)(=O)=NC(=O)Nc2c3c(cc4c2CCC4)CCC3)s1] |
| 125 | 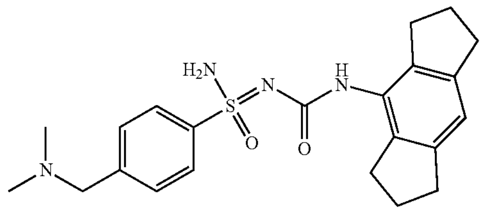 [SMILES: CN(C)Cc1ccc(S(N)(=O)=NC(=O)Nc2c3c(cc4c2CCC4)CCC3)cc1] |
| 125a | 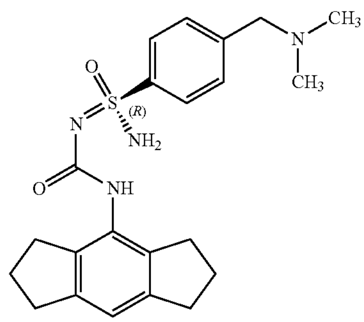 |
| 125b | 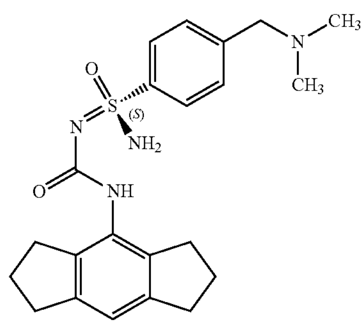 |
| 126 | 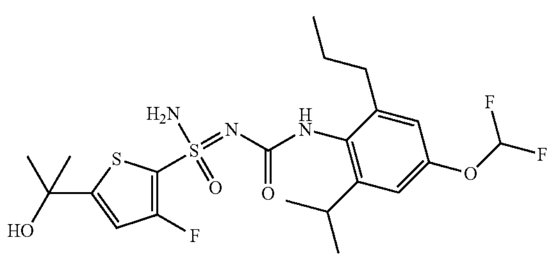 [SMILES: CCCc1cc(OC(F)F)cc(C(C)C)c1NC(=O)N=S(N)(=O)c1sc(C(C)(C)O)cc1F] |
| 127 | 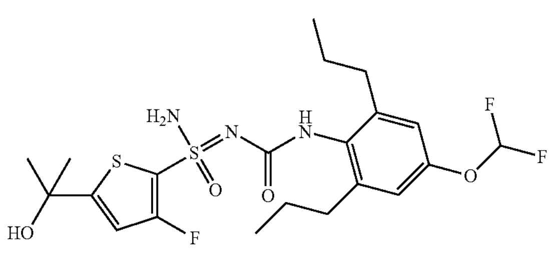 [SMILES: CCCc1cc(OC(F)F)cc(CCC)c1NC(=O)N=S(N)(=O)c1sc(C(C)(C)O)cc1F] |

TABLE 1-continued

| Compound | Structure |
|---|---|
| 128 | 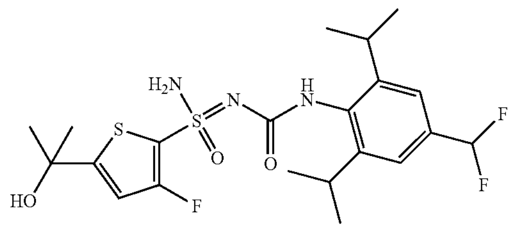 [SMILES: CC(C)c1cc(C(F)F)cc(C(C)C)c1NC(=O)N=S(N)(=O)c1sc(C(C)(C)O)cc1F] |
| 129 | 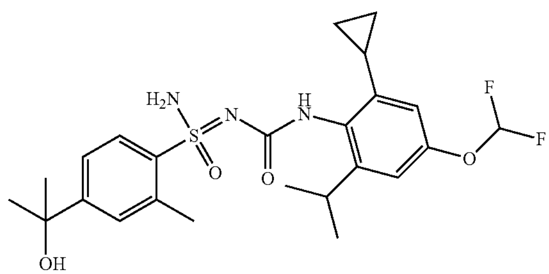 [SMILES: Cc1cc(C(C)(C)O)ccc1S(N)(=O)=NC(=O)Nc1c(C(C)C)cc(OC(F)F)cc1C1CC1] |
| 129a | 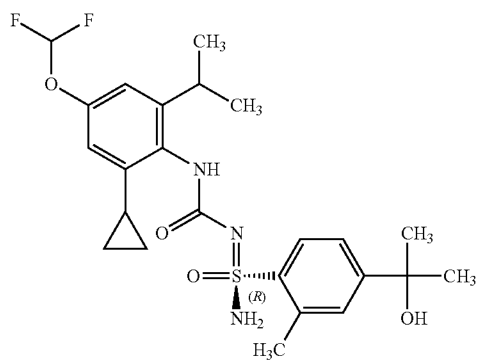 |
| 129b | 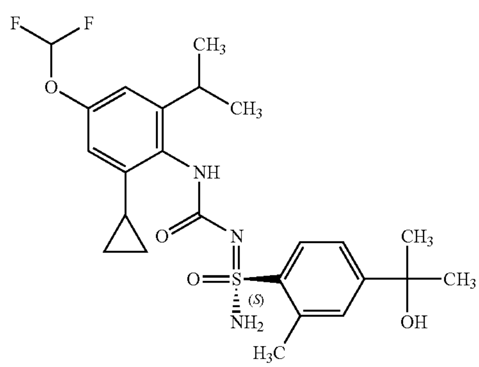 |
| 130 | 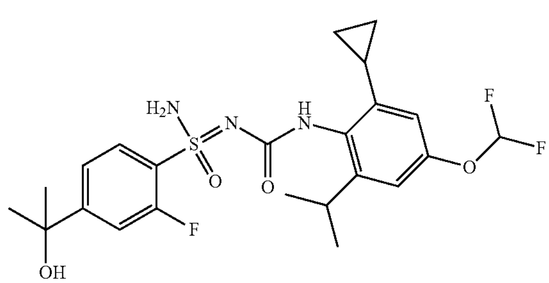 |

TABLE 1-continued

| Compound | Structure |
| --- | --- |
| 130a | (structure of compound 130a) |
| 130b | (structure of compound 130b) |
| 131 | (structure of compound 131) |
| 131a | (structure of compound 131a) |

TABLE 1-continued

| Compound | Structure |
|---|---|
| 131b | (structure) |
| 132 | (structure) |
| 133 | (structure) |
| 134 | (structure) |
| 134a | (structure) |

TABLE 1-continued

| Compound | Structure |
| --- | --- |
| 134b | 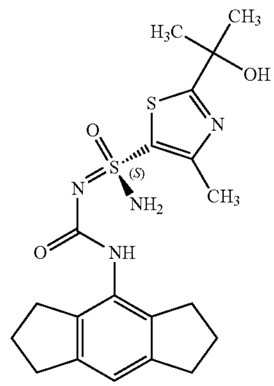 |
| 135 | 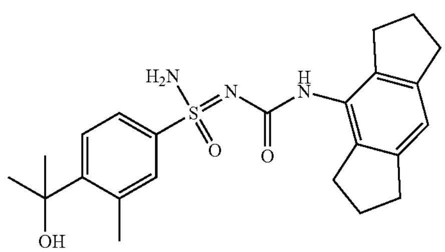 [SMILES: Cc1cc(S(N)(=O)=NC(=O)Nc2c3c(cc4c2CCC4)CCC3)ccc1C(C)(C)O] |
| 135a | 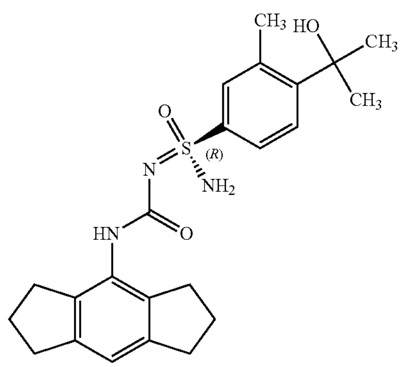 |
| 135b | 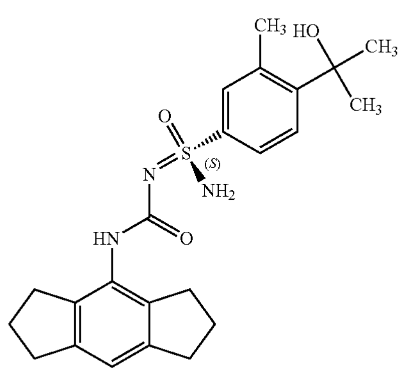 |

TABLE 1-continued

| Compound | Structure |
|---|---|
| 136 | 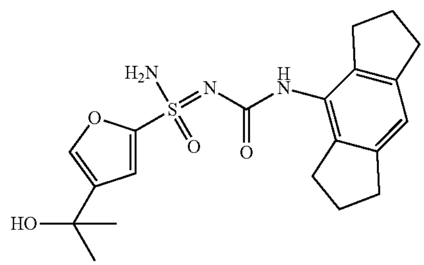 [SMILES: CC(C)(O)c1coc(S(N)(=O)=NC(=O)Nc2c3c(cc4c2CCC4)CCC3)c1] |
| 136a | 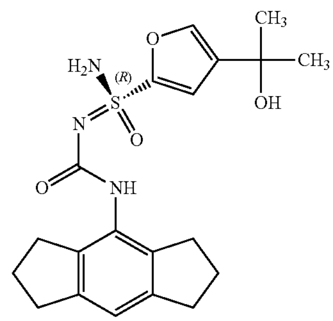 |
| 136b | 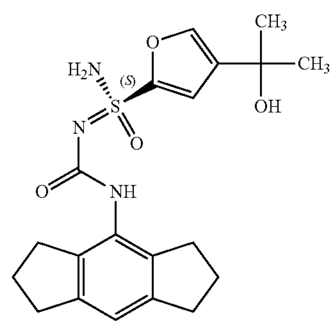 |
| 137 | 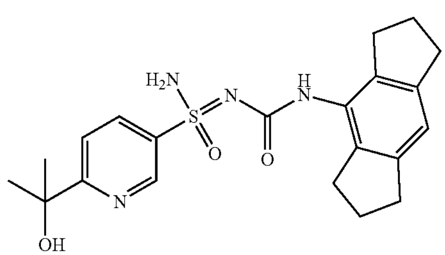 [SMILES: CC(C)(O)c1ccc(S(N)(=O)=NC(=O)Nc2c3c(cc4c2CCC4)CCC3)cn1] |
| 137a | 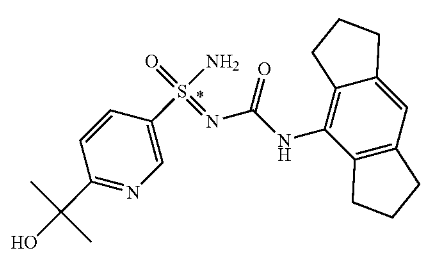 [SMILES: CC(C)(O)c1ccc(S(N)(=O)=NC(=O)Nc2c3c(cc4c2CCC4)CCC3)cn1] |

TABLE 1-continued

| Compound | Structure |
|---|---|
| 137b | 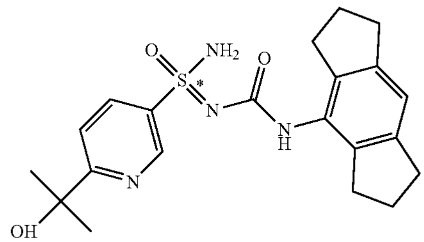 [SMILES: CC(C)(O)c1ccc(S(N)(=O)=NC(=O)Nc2c3c(cc4c2CCC4)CCC3)cn1] |
| 138 | 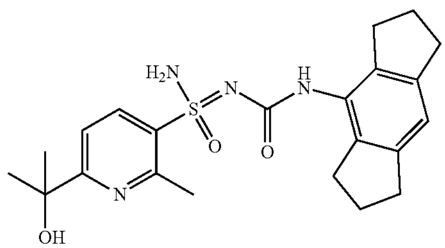 [SMILES: Cc1nc(C(C)(C)O)ccc1S(N)(=O)=NC(=O)Nc1c2c(cc3c1CCC3)CCC2] |
| 138a | 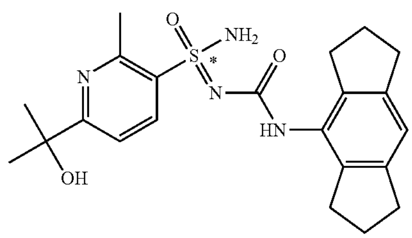 [SMILES: Cc1nc(C(C)(C)O)ccc1S(N)(=O)=NC(=O)Nc1c2c(cc3c1CCC3)CCC2] |
| 138b | 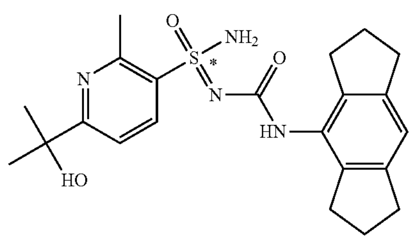 [SMILES: Cc1nc(C(C)(C)O)ccc1S(N)(=O)=NC(=O)Nc1c2c(cc3c1CCC3)CCC2] |
| 139 | 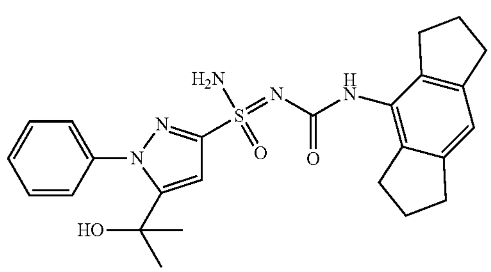 [SMILES: CC(C)(O)c1cc(S(N)(=O)=NC(=O)Nc2c3c(cc4c2CCC4)CCC3)nn1-c1ccccc1] |
| 139a | 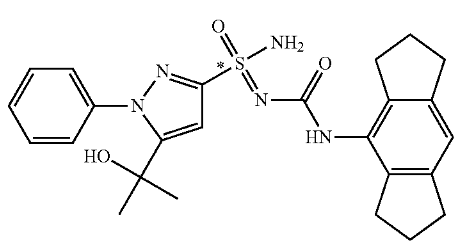 [SMILES: CC(C)(O)c1cc(S(N)(=O)=NC(=O)Nc2c3c(cc4c2CCC4)CCC3)nn1-c1ccccc1] |

TABLE 1-continued

| Compound | Structure |
|---|---|
| 139b | 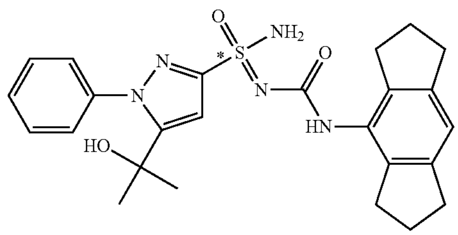 [SMILES: CC(C)(O)c1cc(S(N)(=O)=NC(=O)Nc2c3c(cc4c2CCC4)CCC3)nn1-c1ccccc1] |
| 140 | 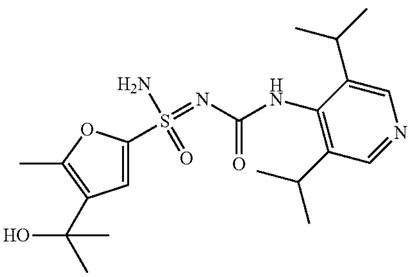 [SMILES: Cc1oc(S(N)(=O)=NC(=O)Nc2c(C(C)C)cncc2C(C)C)cc1C(C)(C)O] |
| 141 | 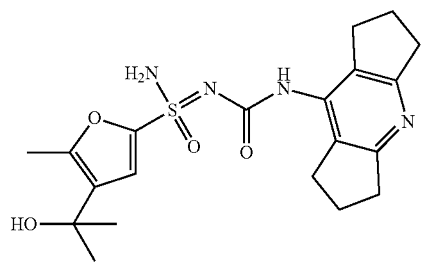 [SMILES: Cc1oc(S(N)(=O)=NC(=O)Nc2c3c(nc4c2CCC4)CCC3)cc1C(C)(C)O] |
| 142 | 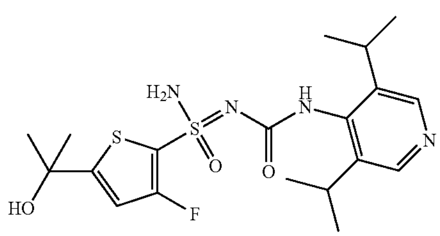 [SMILES: CC(C)c1cncc(C(C)C)c1NC(=O)N=S(N)(=O)c1sc(C(C)(C)O)cc1F] |
| 143 | 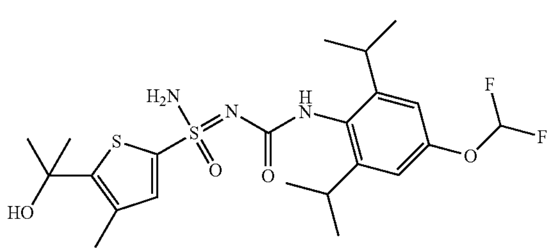 [SMILES: Cc1cc(S(N)(=O)=NC(=O)Nc2c(C(C)C)cc(OC(F)F)cc2C(C)C)sc1C(C)(C)O] |

TABLE 1-continued

| Compound | Structure |
|---|---|
| 143a | 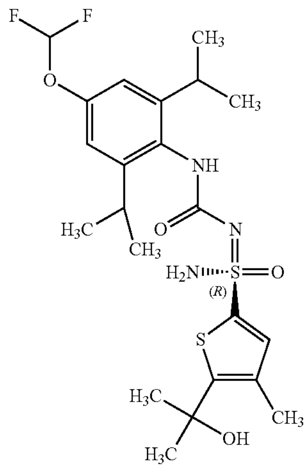 |
| 143b | 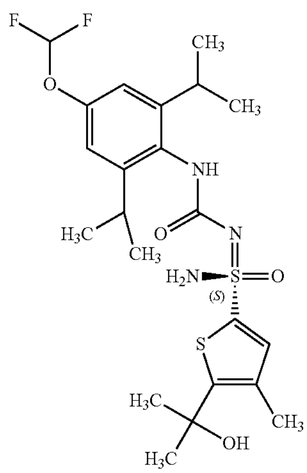 |
| 144 | 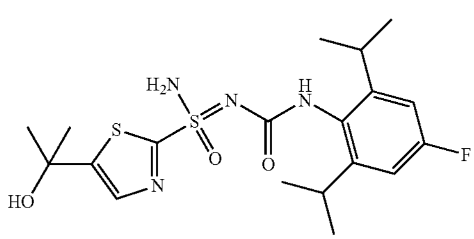 [SMILES: CC(C)c1cc(F)cc(C(C)C)c1NC(=O)N=S(N)(=O)c1ncc(C(C)(C)O)s1] |
| 144a | 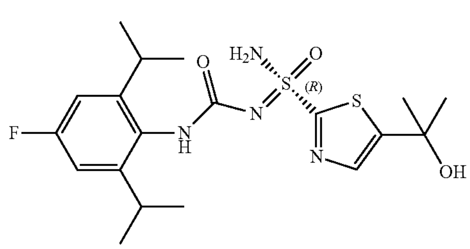 |

TABLE 1-continued

| Compound | Structure |
|---|---|
| 144b | 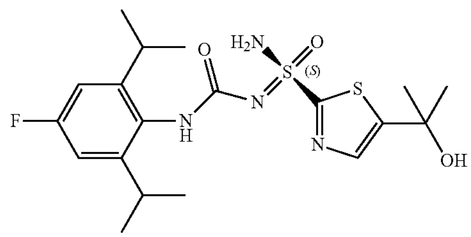 |
| 145 | 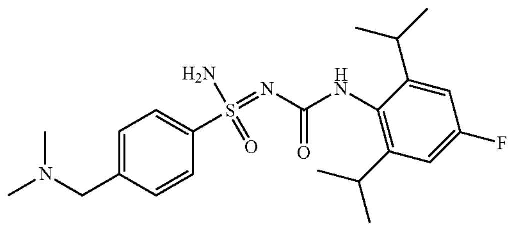 [SMILES: CC(C)c1cc(F)cc(C(C)C)c1NC(=O)N=S(N)(=O)c1ccc(CN(C)C)cc1] |
| 145a | 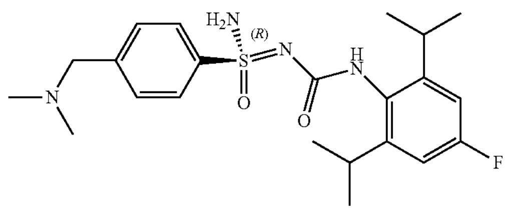 |
| 145b | 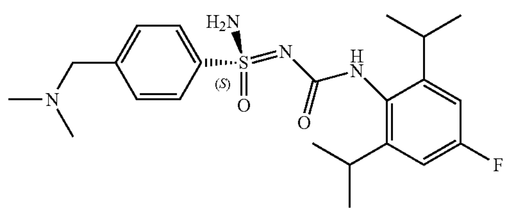 |
| 146 | 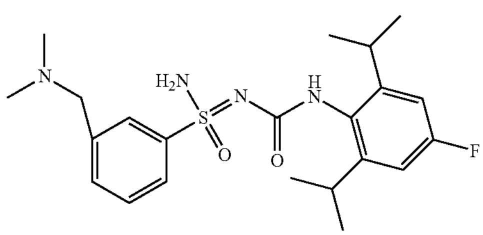 [SMILES: CC(C)c1cc(F)cc(C(C)C)c1NC(=O)N=S(N)(=O)c1cccc(CN(C)C)c1] |
| 147 | 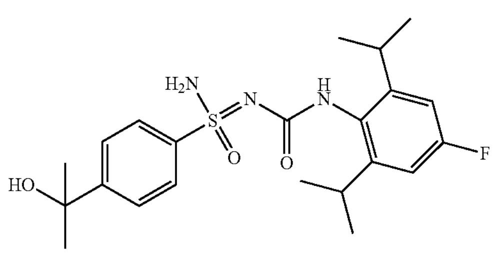 [SMILES: CC(C)c1cc(F)cc(C(C)C)c1NC(=O)N=S(N)(=O)c1ccc(C(C)(C)O)cc1] |

TABLE 1-continued

| Compound | Structure |
|---|---|
| 148 | 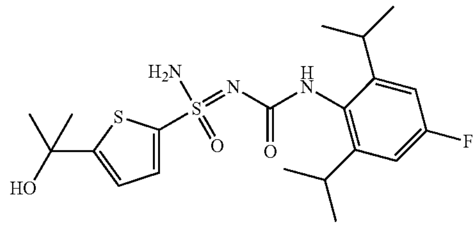 [SMILES: CC(C)c1cc(F)cc(C(C)C)c1NC(=O)N=S(N)(=O)c1ccc(C(C)(C)O)s1] |
| 148a | 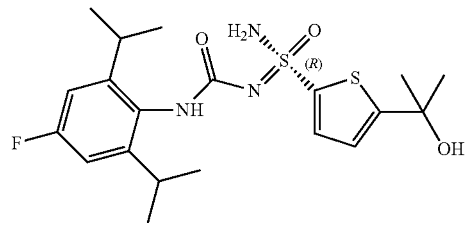 |
| 148b | 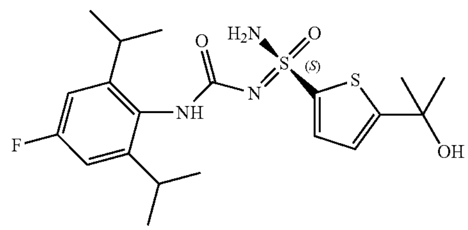 |
| 149 | 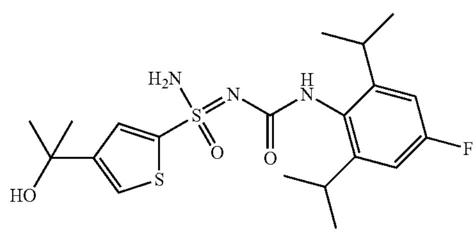 [SMILES: CC(C)c1cc(F)cc(C(C)C)c1NC(=O)N=S(N)(=O)c1cc(C(C)(C)O)cs1] |
| 149a | 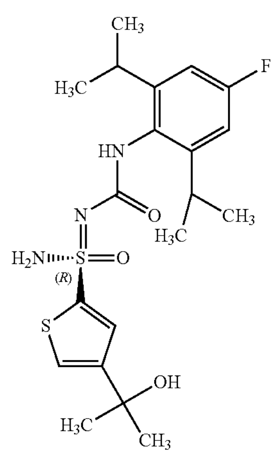 |

TABLE 1-continued

| Compound | Structure |
|---|---|
| 149b | 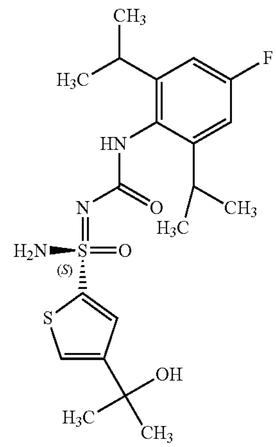 |
| 150 | 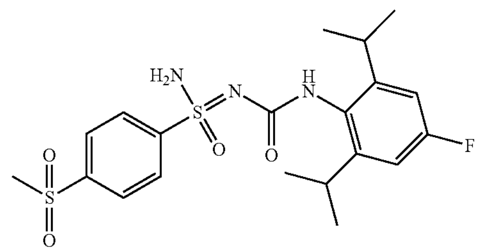 [SMILES: CC(C)c1cc(F)cc(C(C)C)c1NC(=O)N=S(N)(=O)c1ccc(S(C)(=O)=O)cc1] |
| 151a' | 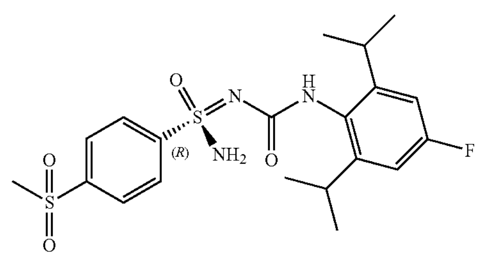 |
| 151b' | 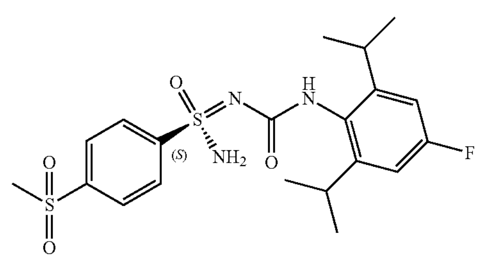 |
| 151 | 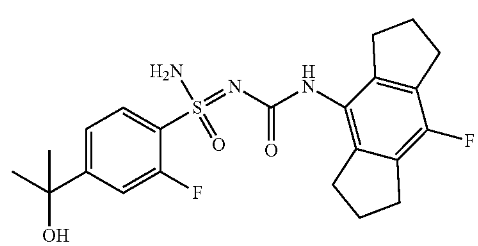 [SMILES: CC(C)(O)c1ccc(S(N)(=O)=NC(=O)Nc2c3c(c(F)c4c2CCC4)CCC3)c(F)c1] |

TABLE 1-continued

| Compound | Structure |
|---|---|
| 151a | 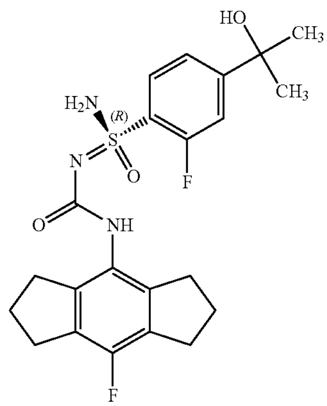 |
| 151b | 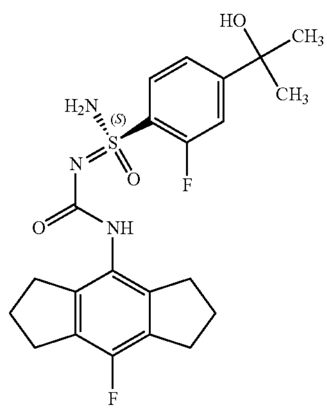 |
| 152 | 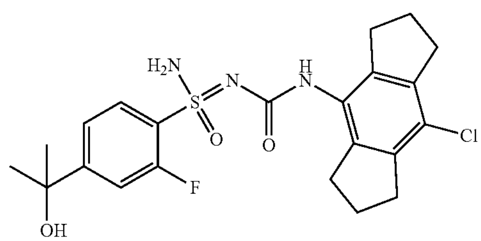 [SMILES: CC(C)(O)c1ccc(S(N)(=O)=NC(=O)Nc2c3c(c(Cl)c4c2CCC4)CCC3)c(F)c1] |
| 152a | 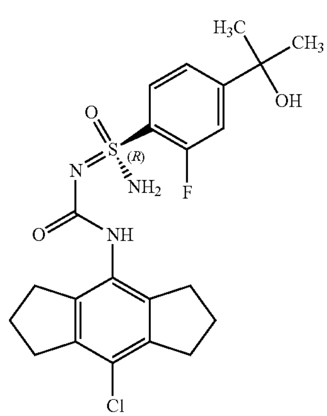 |

TABLE 1-continued
| Compound | Structure |
|---|---|
| 152b | 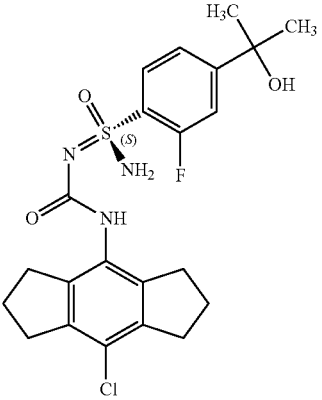 |
| 153 | 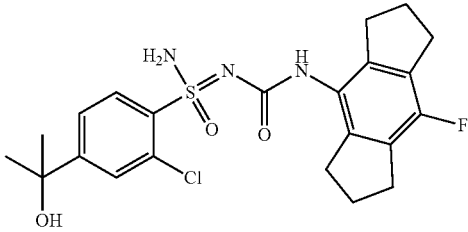 [SMILES: CC(C)(O)c1ccc(S(N)(=O)=NC(=O)Nc2c3c(c(F)c4c2CCC4)CCC3)c(Cl)c1] |
| 153a | 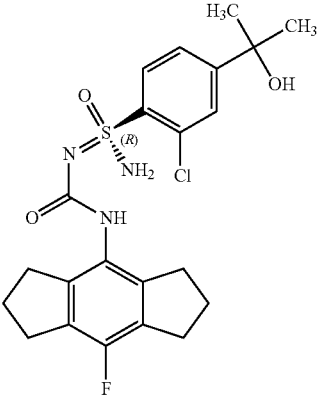 |
| 153b | 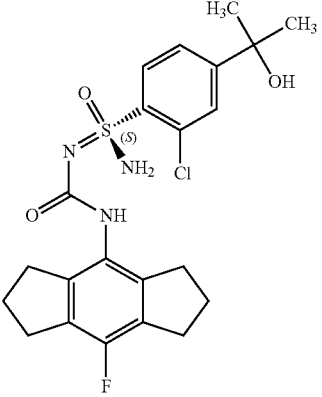 |

TABLE 1-continued

| Compound | Structure |
|---|---|
| 154 | 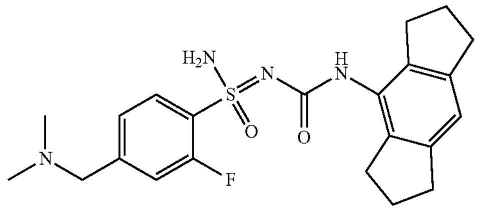 [SMILES: CN(C)Cc1ccc(S(N)(=O)=NC(=O)Nc2c3c(cc4c2CCC4)CCC3)c(F)c1] |
| 154a | 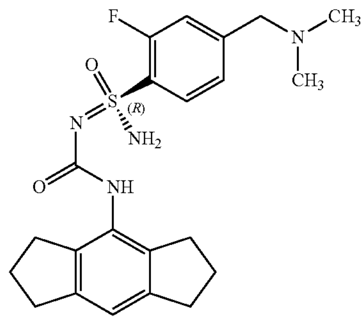 |
| 154b | 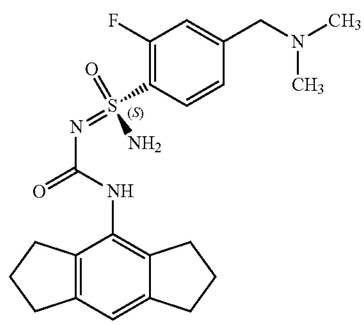 |
| 155 | 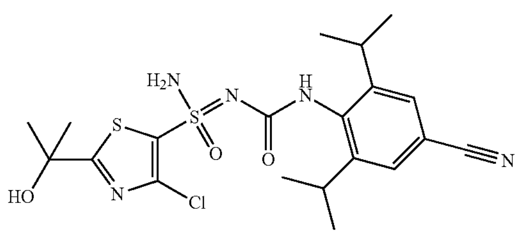 [SMILES: CC(C)c1cc(C#N)cc(C(C)C)c1NC(=O)N=S(N)(=O)c1sc(C(C)(C)O)nc1Cl] |
| 156 | 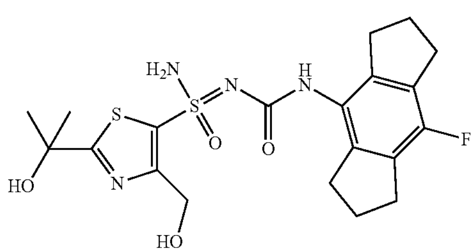 [SMILES: CC(C)(O)c1nc(CO)c(S(N)(=O)=NC(=O)Nc2c3c(c(F)c4c2CCC4)CCC3)s1] |
| 157 | 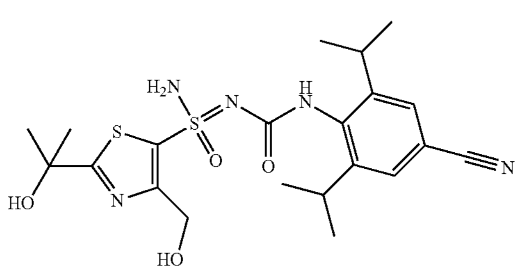 [SMILES: CC(C)c1cc(C#N)cc(C(C)C)c1NC(=O)N=S(N)(=O)c1sc(C(C)(C)O)nc1CO] |

TABLE 1-continued
| Compound | Structure |
|---|---|
| 157a | 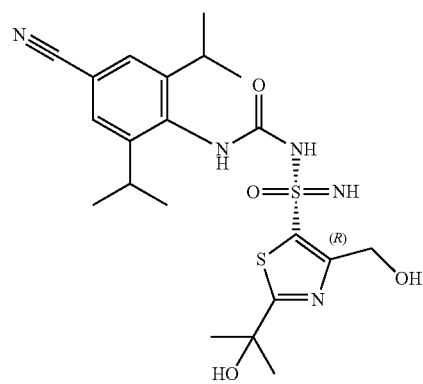 |
| 157b | 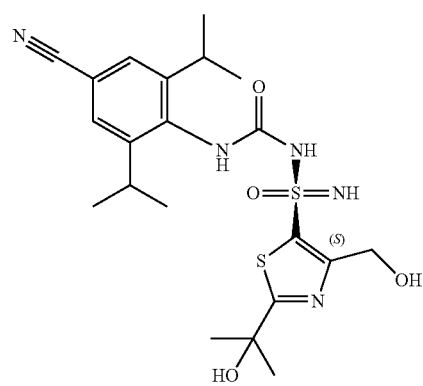 |
| 158 | 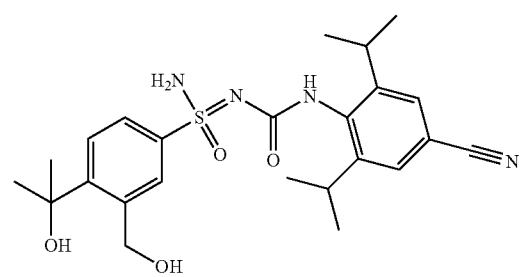 [SMILES: CC(C)c1cc(C#N)cc(C(C)C)c1NC(=O)N=S(N)(=O)c1ccc(C(C)(C)O)c(CO)c1] |
| 158a | 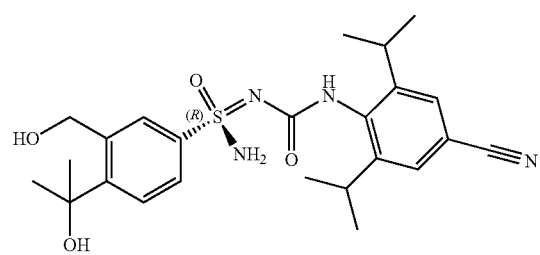 |
| 158b | 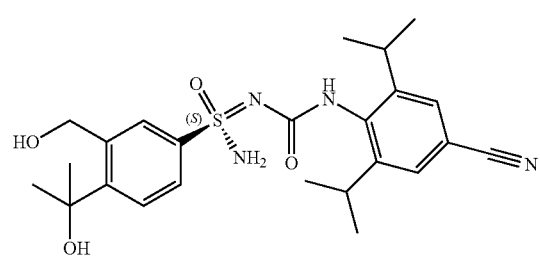 |

TABLE 1-continued

| Compound | Structure |
|---|---|
| 159 | 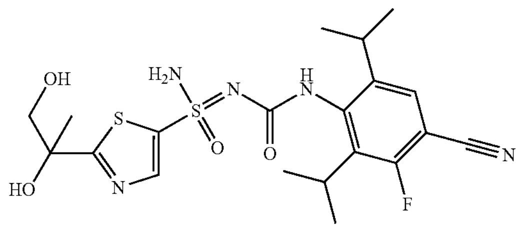 [SMILES: CC(C)c1cc(C#N)c(F)c(C(C)C)c1NC(=O)N=S(N)(=O)c1cnc(C(C)(O)CO)s1] |
| 159a | 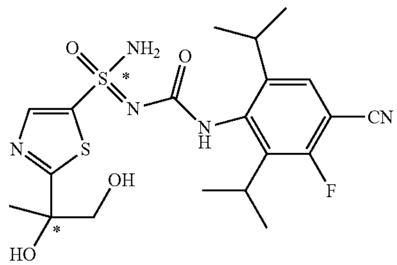 [SMILES: CC(C)c1cc(C#N)c(F)c(C(C)C)c1NC(=O)N=S(N)(=O)c1cnc(C(C)(O)CO)s1] |
| 159ba | 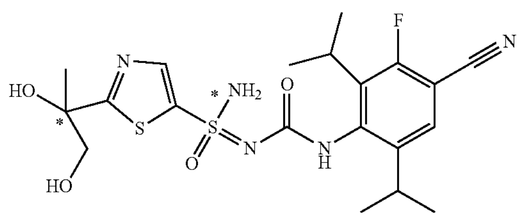 [SMILES: CC(C)c1cc(C#N)c(F)c(C(C)C)c1NC(=O)N=S(N)(=O)c1cnc(C(C)(O)CO)s1] |
| 159ab | 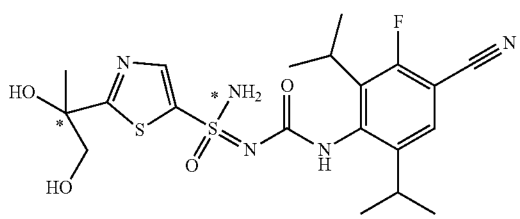 [SMILES: CC(C)c1cc(C#N)c(F)c(C(C)C)c1NC(=O)N=S(N)(=O)c1cnc(C(C)(O)CO)s1] |
| 160 | 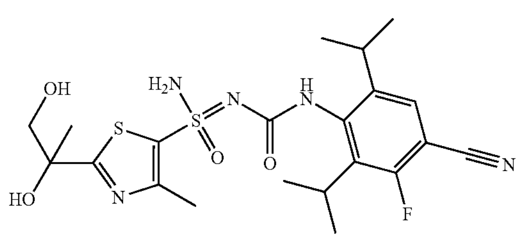 [SMILES: Cc1nc(C(C)(O)CO)sc1S(N)(=O)=NC(=O)Nc1c(C(C)C)cc(C#N)c(F)c1C(C)C] |
| 161 | 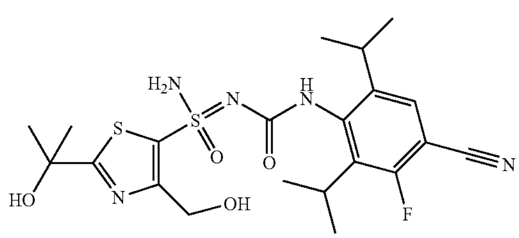 [SMILES: CC(C)c1cc(C#N)c(F)c(C(C)C)c1NC(=O)N=S(N)(=O)c1sc(C(C)(C)O)nc1CO] |

TABLE 1-continued

| Compound | Structure |
|---|---|
| 161a | 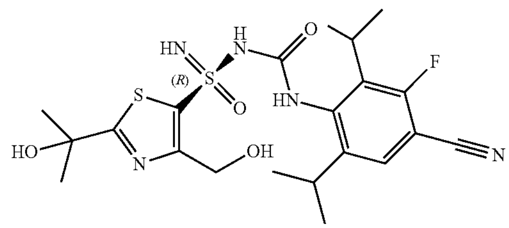 |
| 161b | 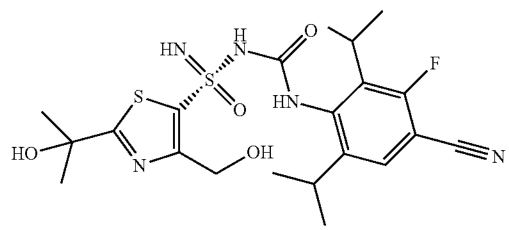 [SMILES: CC(C)c1cc(C#N)c(F)c(C(C)C)c1NC(=O)N[S@](=N)(=O)c1sc(C(C)(C)O)nc1CO] |
| 162 | 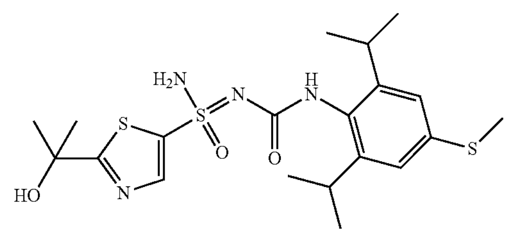 [SMILES: CSc1cc(C(C)C)c(NC(=O)N=S(N)(=O)c2cnc(C(C)(C)O)s2)c(C(C)C)c1] |
| 163 | 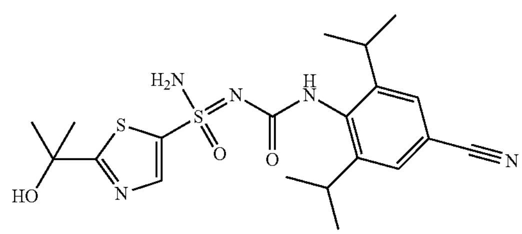 [SMILES: CC(C)c1cc(C#N)cc(C(C)C)c1NC(=O)N=S(N)(=O)c1cnc(C(C)(C)O)s1] |
| 164 | 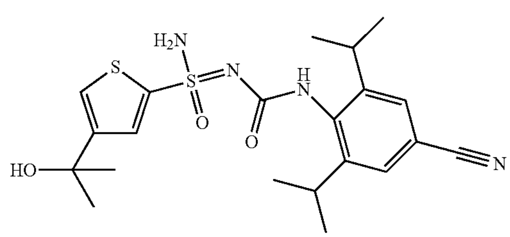 [SMILES: CC(C)c1cc(C#N)cc(C(C)C)c1NC(=O)N=S(N)(=O)c1cc(C(C)(C)O)cs1] |
| 165 | 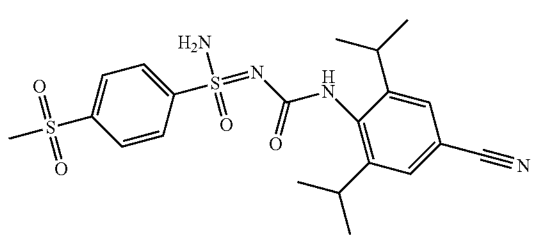 [SMILES: CC(C)c1cc(C#N)cc(C(C)C)c1NC(=O)N=S(N)(=O)c1ccc(S(C)(=O)=O)cc1] |

TABLE 1-continued
| Compound | Structure |
|---|---|
| 165a | 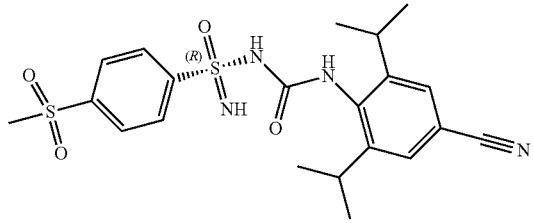 |
| 165b | 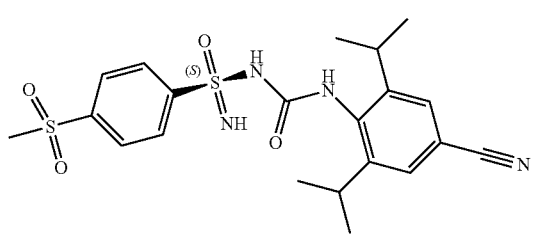 |
| 166 | 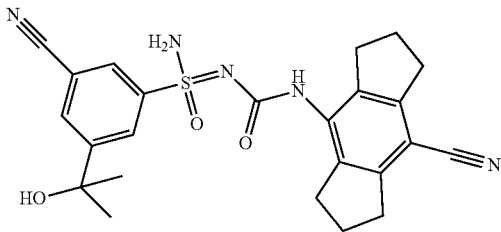 [SMILES: CC(C)(O)c1cc(C#N)cc(S(N)(=O)=NC(=O)Nc2c3c(c(C#N)c4c2CCC4)CCC3)c1] |
| 167 | 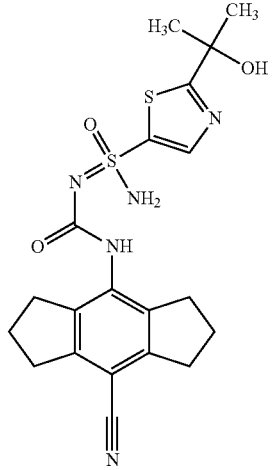 [SMILES: CC(C)(O)c1ncc(S(N)(=O)=NC(=O)Nc2c3c(c(C#N)c4c2CCC4)CCC3)s1] |

TABLE 1-continued

| Compound | Structure |
|---|---|
| 167a | 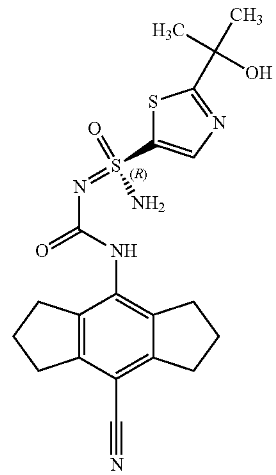 |
| 167b | 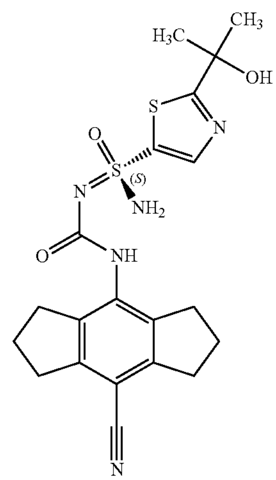 |
| 168 | 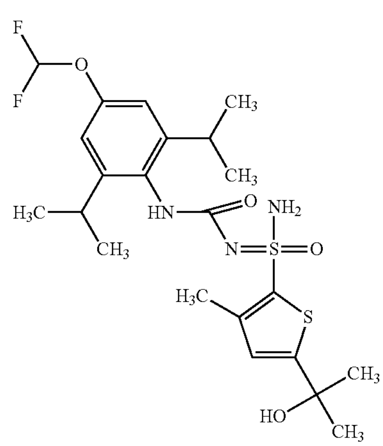 [SMILES: Cc1cc(C(C)(C)O)sc1S(N)(=O)=NC(=O)Nc1c(C(C)C)cc(OC(F)F)cc1C(C)C] |

TABLE 1-continued
| Compound | Structure |
| --- | --- |
| 168a | 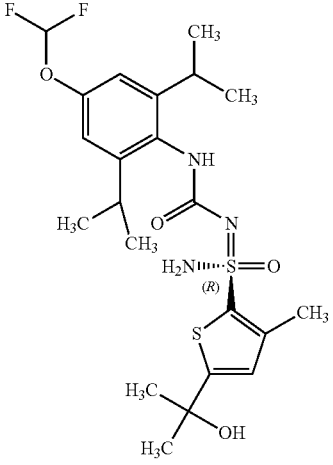 |
| 168b | 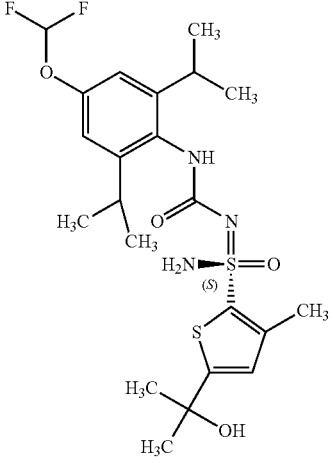 |
| 170 | 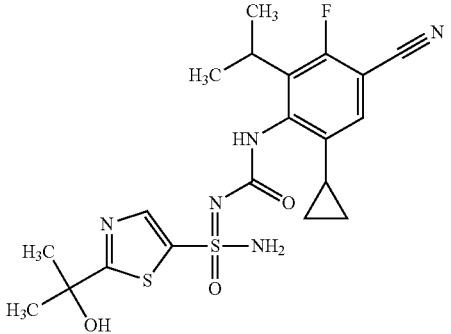 [SMILES: CC(C)c1c(F)c(C#N)cc(C2CC2)c1NC(=O)N=S(N)(=O)c1cnc(C(C)(C)O)s1] |

TABLE 1-continued
| Compound | Structure |
|---|---|
| 170a | 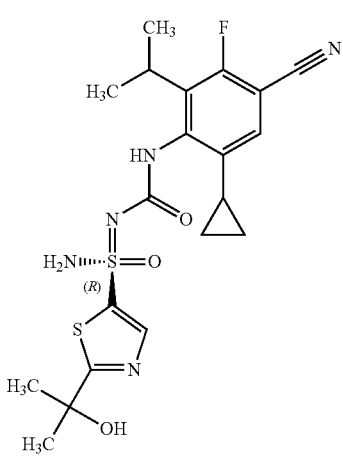 |
| 170b | 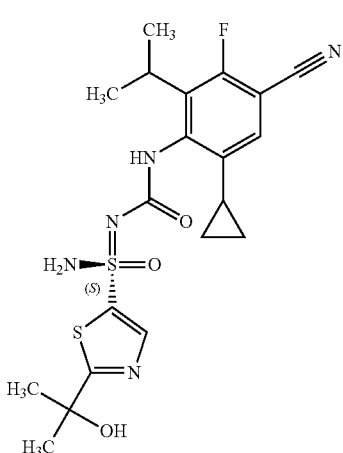 |
| 171 | 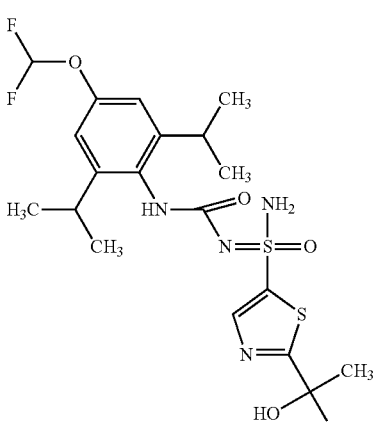 |

TABLE 1-continued
| Compound | Structure |
|---|---|
| 171a | 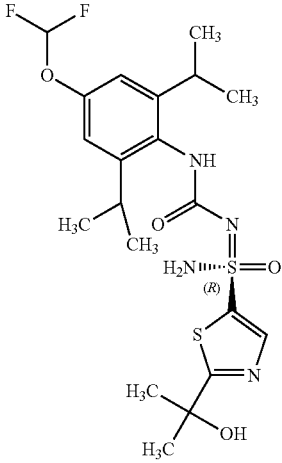 |
| 171b | 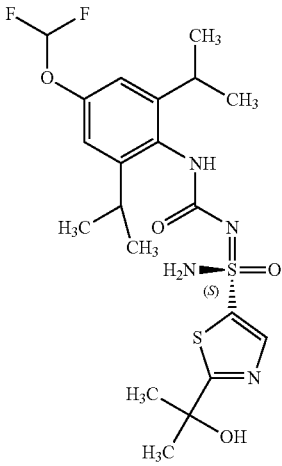 |
| 172 | 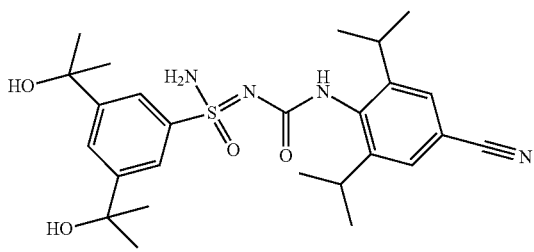 [SMILES: CC(C)c1cc(C#N)cc(C(C)C)c1NC(=O)N=S(N)(=O)c1cc(C(C)(C)O)cc(C(C)(C)O)c1] |
| 172a | 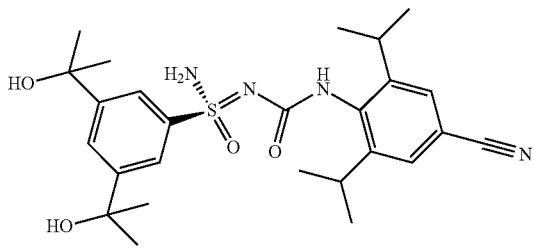 [SMILES: CC(C)c1cc(C#N)cc(C(C)C)c1NC(=O)N=[S@@](N)(=O)c1cc(C(C)(C)O)cc(C(C)(C)O)c1] |

TABLE 1-continued

| Compound | Structure |
|---|---|
| 172b | 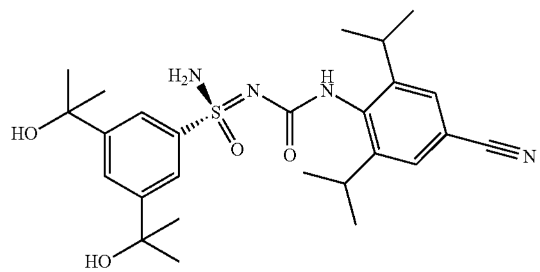 [SMILES: CC(C)c1cc(C#N)cc(C(C)C)c1NC(=O)N=[S@](N)(=O)c1cc(C(C)(C)O)cc(C(C)(C)O)c1] |
| 173 | 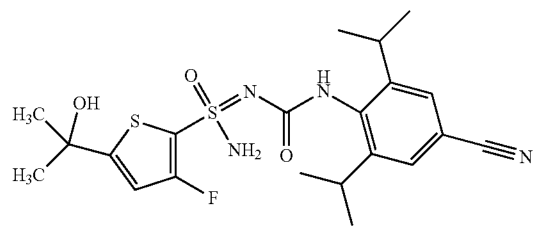 [SMILES: CC(C)c1cc(C#N)cc(C(C)C)c1NC(=O)N=S(N)(=O)c1sc(C(C)(C)O)cc1F] |
| 173a | 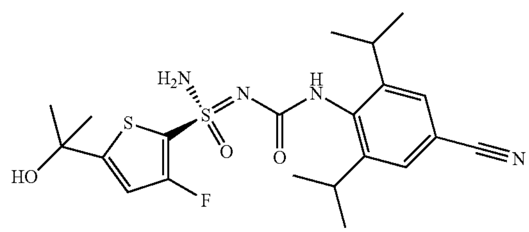 [SMILES: CC(C)c1cc(C#N)cc(C(C)C)c1NC(=O)N=[S@@](N)(=O)c1sc(C(C)(C)O)cc1F] |
| 173b | 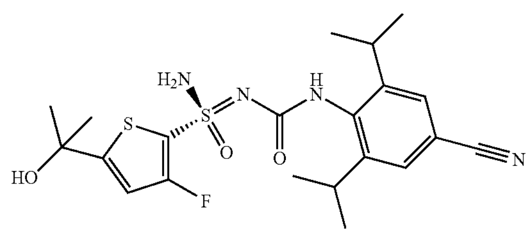 [SMILES: CC(C)c1cc(C#N)cc(C(C)C)c1NC(=O)N=[S@](N)(=O)c1sc(C(C)(C)O)cc1F] |
| 174 | 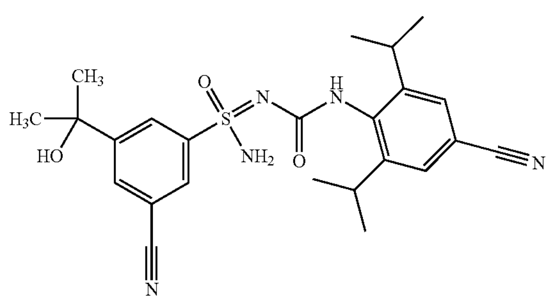 [SMILES: CC(C)c1cc(C#N)cc(C(C)C)c1NC(=O)N=S(N)(=O)c1cc(C#N)cc(C(C)(C)O)c1] |
| 174a | 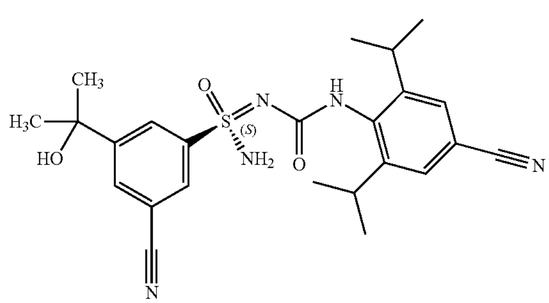 |

TABLE 1-continued

| Compound | Structure |
|---|---|
| 174b | 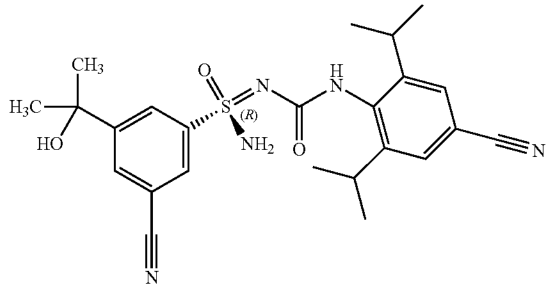 |
| 176 | 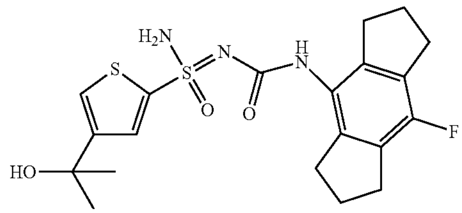 [SMILES: CC(C)(O)c1csc(S(N)(=O)=NC(=O)Nc2c3c(c(F)c4c2CCC4)CCC3)c1] |
| 176a | 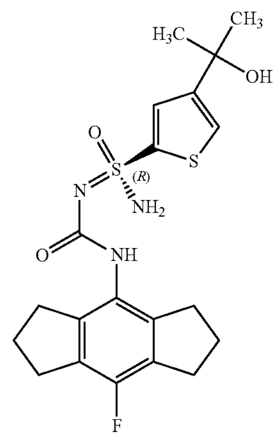 |
| 176b | 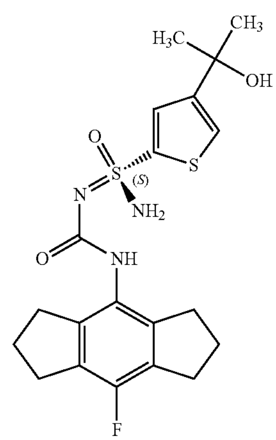 |
| 177 | 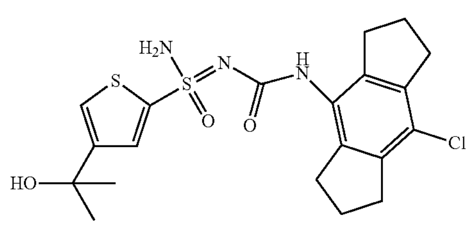 [SMILES: CC(C)(O)c1csc(S(N)(=O)=NC(=O)Nc2c3c(c(Cl)c4c2CCC4)CCC3)c1] |

TABLE 1-continued

| Compound | Structure |
|---|---|
| 177a | (structure) |
| 177b | (structure) |
| 178 | (structure) |
| 178a | (structure) |
| 178b | (structure) |

TABLE 1-continued

| Compound | Structure |
|---|---|
| 179 | 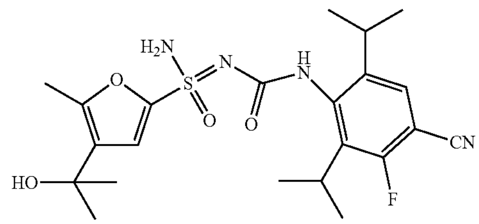 [SMILES: Cc1oc(S(N)(=O)=NC(=O)Nc2c(C(C)C)cc(C#N)c(F)c2C(C)C)cc1C(C)(C)O] |
| 179a | 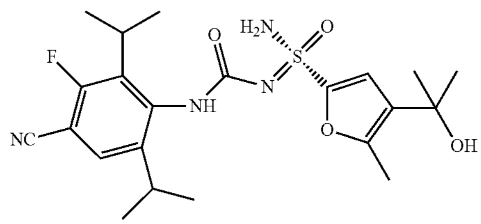 [SMILES: Cc1oc([S@](N)(=O)=NC(=O)Nc2c(C(C)C)cc(C#N)c(F)c2C(C)C)cc1C(C)(C)O] |
| 179b | 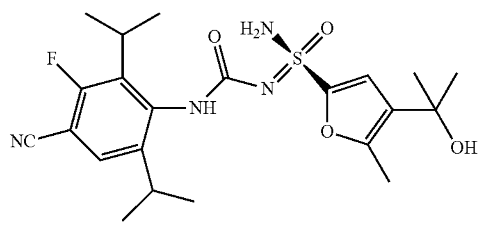 [SMILES: Cc1oc([S@@](N)(=O)=NC(=O)Nc2c(C(C)C)cc(C#N)c(F)c2C(C)C)cc1C(C)(C)O] |
| 180 | 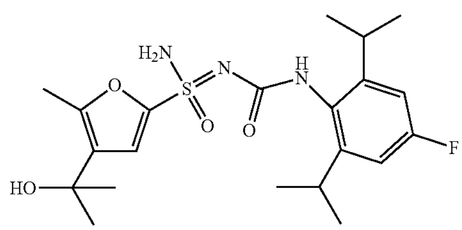 [SMILES: Cc1oc(S(N)(=O)=NC(=O)Nc2c(C(C)C)cc(F)cc2C(C)C)cc1C(C)(C)O] |
| 180a | 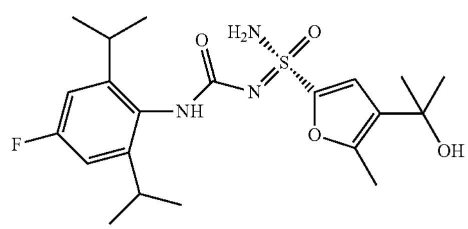 [SMILES: Cc1oc([S@](N)(=O)=NC(=O)Nc2c(C(C)C)cc(F)cc2C(C)C)cc1C(C)(C)O] |
| 180b | 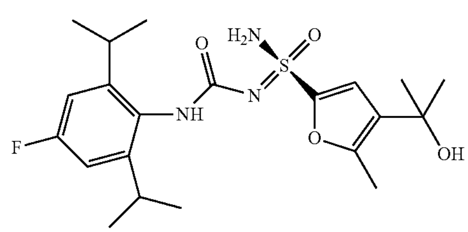 [SMILES: Cc1oc([S@@](N)(=O)=NC(=O)Nc2c(C(C)C)cc(F)cc2C(C)C)cc1C(C)(C)O] |
| 181 | 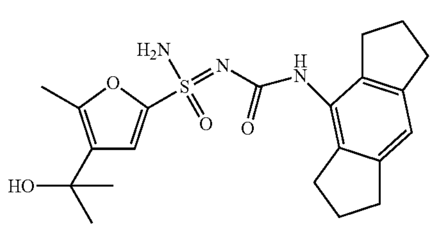 [SMILES: Cc1oc(S(N)(=O)=NC(=O)Nc2c3c(cc4c2CCC4)CCC3)cc1C(C)(C)O] |

TABLE 1-continued

| Compound | Structure |
|---|---|
| 181a | 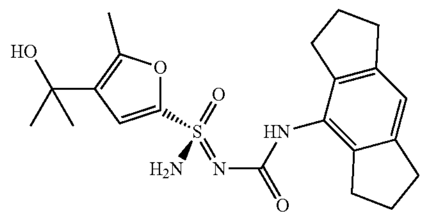 [SMILES: Cc1oc([S@](N)(=O)=NC(=O)Nc2c3c(cc4c2CCC4)CCC3)cc1C(C)(C)O] |
| 181b | 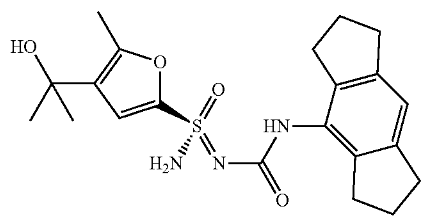 [SMILES: Cc1oc([S@@](N)(=O)=NC(=O)Nc2c3c(cc4c2CCC4)CCC3)cc1C(C)(C)O] |
| 182 | 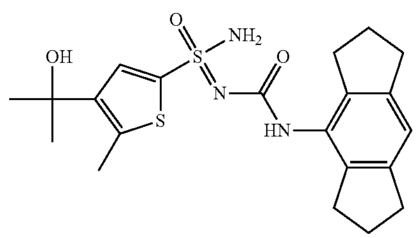 [SMILES: Cc1sc(S(N)(=O)=NC(=O)Nc2c3c(cc4c2CCC4)CCC3)cc1C(C)(C)O] |
| 182a | 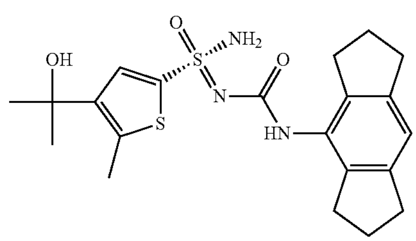 [SMILES: Cc1sc([S@@](N)(=O)=NC(=O)Nc2c3c(cc4c2CCC4)CCC3)cc1C(C)(C)O] |
| 182b | 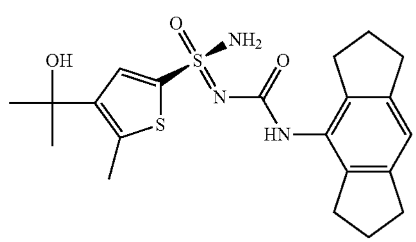 [SMILES: Cc1sc([S@](N)(=O)=NC(=O)Nc2c3c(cc4c2CCC4)CCC3)cc1C(C)(C)O] |
| 183 | 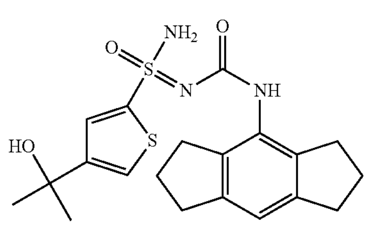 [SMILES: CC(C)(O)c1csc(S(N)(=O)=NC(=O)Nc2c3c(cc4c2CCC4)CCC3)c1] |

TABLE 1-continued
| Compound | Structure |
|---|---|
| 183a | 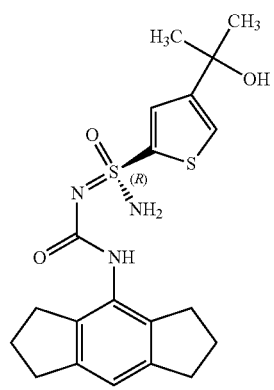 |
| 183b | 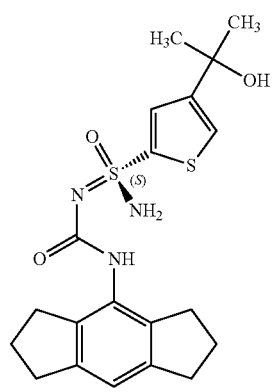 |
| 184 | 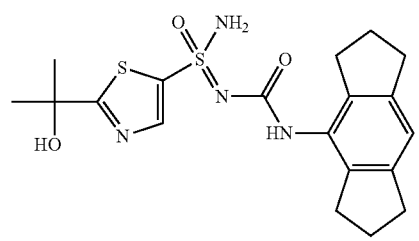 [SMILES: CC(C)(O)c1ncc(S(N)(=O)=NC(=O)Nc2c3c(cc4c2CCC4)CCC3)s1] |
| 185 | 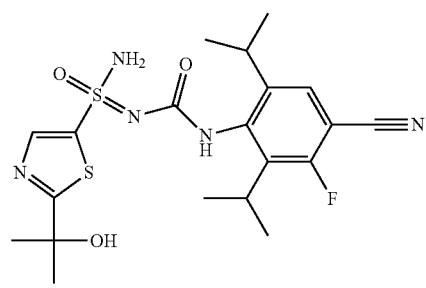 [SMILES: CC(C)c1cc(C#N)c(F)c(C(C)C)c1NC(=O)N=S(N)(=O)c1cnc(C(C)(C)O)s1] |
| 185a | 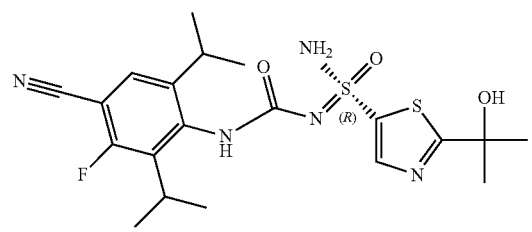 |

TABLE 1-continued

| Compound | Structure |
|---|---|
| 185b | 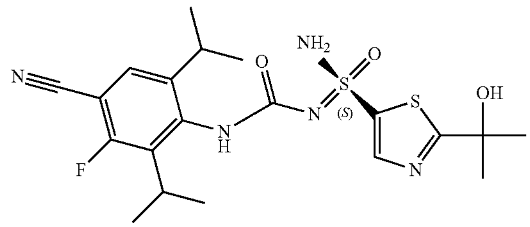 |
| 186 | 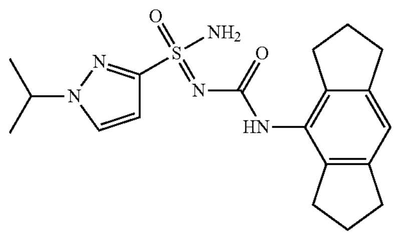 [SMILES: CC(C)n1ccc(S(N)(=O)=NC(=O)Nc2c3c(cc4c2CCC4)CCC3)n1] |
| 186a | 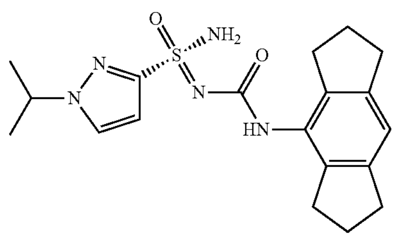 [SMILES: CC(C)n1ccc([S@@](N)(=O)=NC(=O)Nc2c3c(cc4c2CCC4)CCC3)n1] |
| 186b | 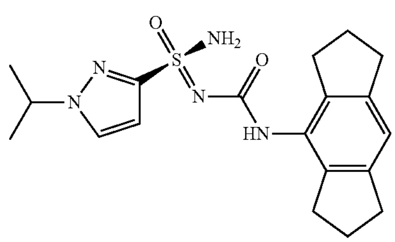 [SMILES: CC(C)n1ccc([S@](N)(=O)=NC(=O)Nc2c3c(cc4c2CCC4)CCC3)n1] |
| 187 | 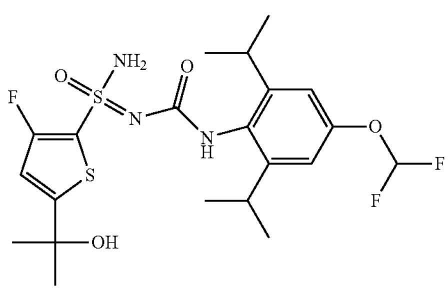 [SMILES: CC(C)c1cc(OC(F)F)cc(C(C)C)c1NC(=O)N=S(N)(=O)c1sc(C(C)(C)O)cc1F] |
| 187a | 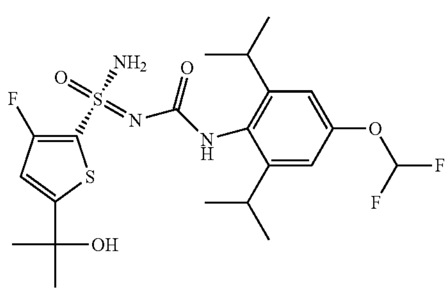 [SMILES: CC(C)c1cc(OC(F)F)cc(C(C)C)c1NC(=O)N=[S@](N)(=O)c1sc(C(C)(C)O)cc1F] |

| Compound | Structure |
|---|---|
| 187b | 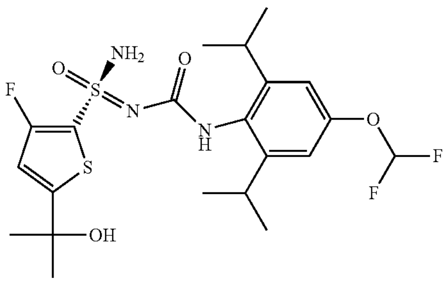 |
| 188 | 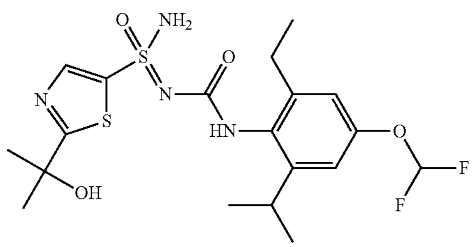 [SMILES: CCc1cc(OC(F)F)cc(C(C)C)c1NC(=O)N=S(N)(=O)c1cnc(C(C)(C)O)s1] |
| 188a | 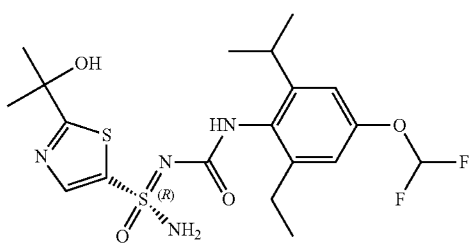 |
| 188b | 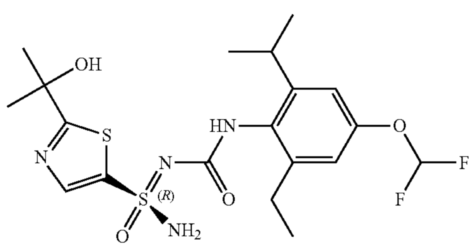 |
| 189 | 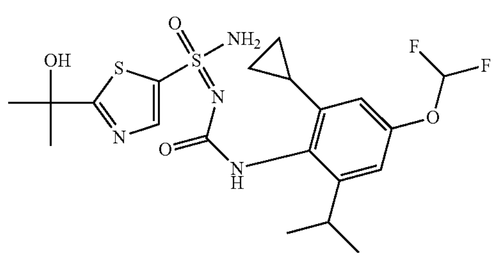 [SMILES: CC(C)c1cc(OC(F)F)cc(C2CC2)c1NC(=O)N=S(N)(=O)c1cnc(C(C)(C)O)s1] |
| 189a | 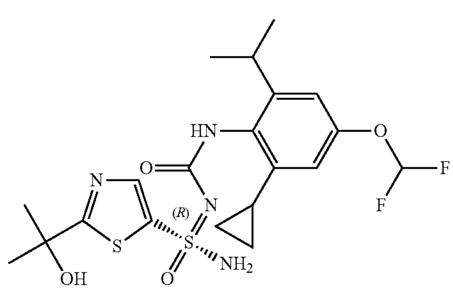 |

TABLE 1-continued

| Compound | Structure |
|---|---|
| 189b | 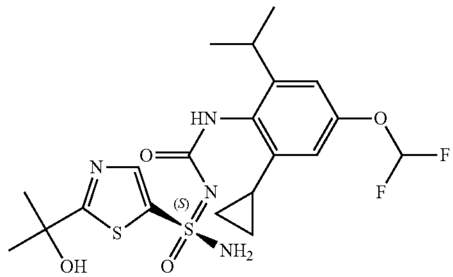 |
| 190 | 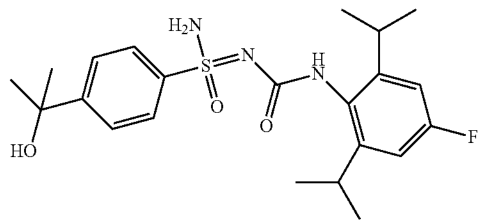 [SMILES: CC(C)c1cc(F)cc(C(C)C)c1NC(=O)N=S(N)(=O)c1ccc(C(C)(C)O)cc1] |
| 190a | 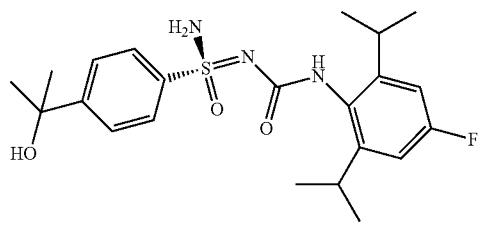 [SMILES: CC(C)c1cc(F)cc(C(C)C)c1NC(=O)N=[S@](N)(=O)c1ccc(C(C)(C)O)cc1] |
| 190b | 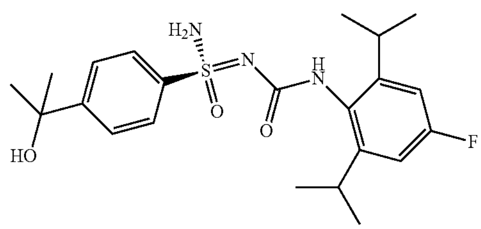 [SMILES: CC(C)c1cc(F)cc(C(C)C)c1NC(=O)N=[S@@](N)(=O)c1ccc(C(C)(C)O)cc1] |
| 191 | 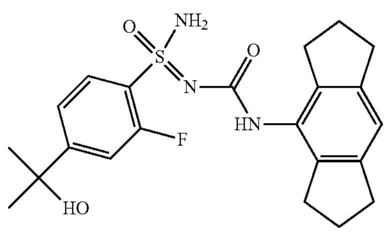 [SMILES: CC(C)(O)c1ccc(S(N)(=O)=NC(=O)Nc2c3c(cc4c2CCC4)CCC3)c(F)c1] |
| 191a | 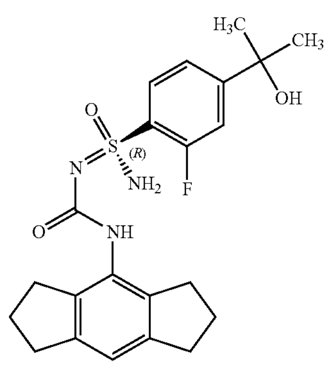 |

TABLE 1-continued

| Compound | Structure |
|---|---|
| 191b | 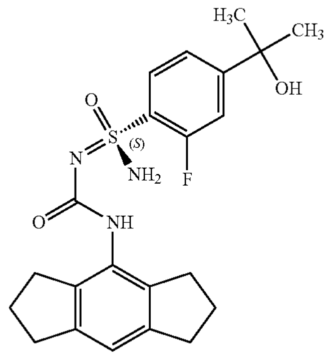 |
| 192 | 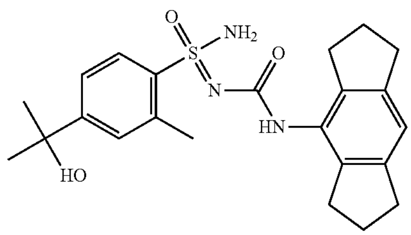 [SMILES: Cc1cc(C(C)(C)O)ccc1S(N)(=O)=NC(=O)Nc1c2c(cc3c1CCC3)CCC2] |
| 192a | 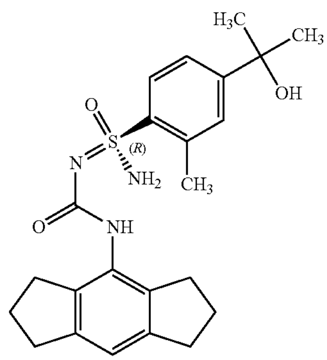 |
| 192b | 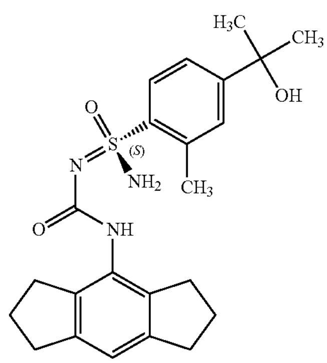 |
| 193 | 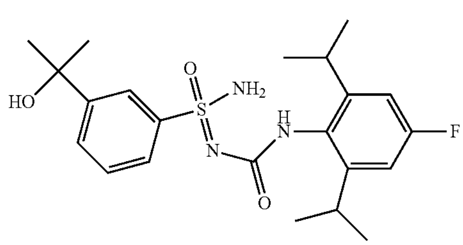 [SMILES: CC(C)c1cc(F)cc(C(C)C)c1NC(=O)N=S(N)(=O)c1cccc(C(C)(C)O)c1] |

TABLE 1-continued

| Compound | Structure |
|---|---|
| 193a | 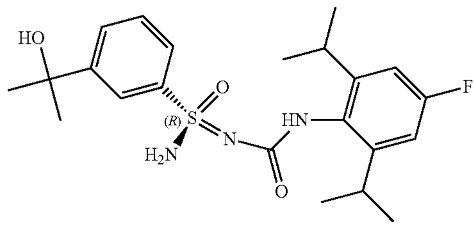 |
| 193b | 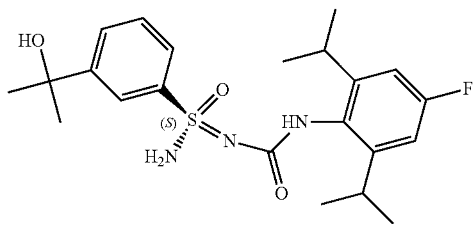 |
| 194 | 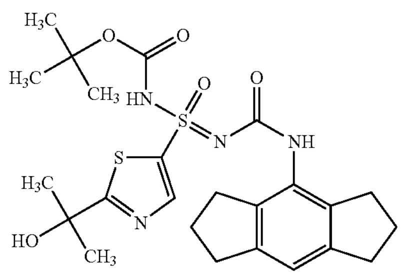 [SMILES: CC(C)(C)OC(=O)NS(=O)(=NC(=O)Nc1c2c(cc3c1CCC3)CCC2)c1cnc(C(C)(C)O)s1] |
| 195 | 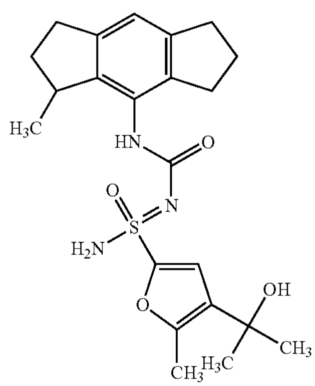 [SMILES: Cc1oc(S(N)(=O)=NC(=O)Nc2c3c(cc4c2C(C)CC4)CCC3)cc1C(C)(C)O] |
| 195a | 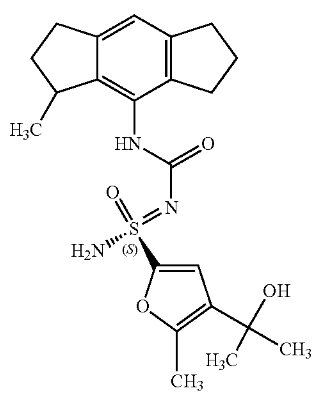 |

| Compound | Structure |
|----------|-----------|
| 195ba | 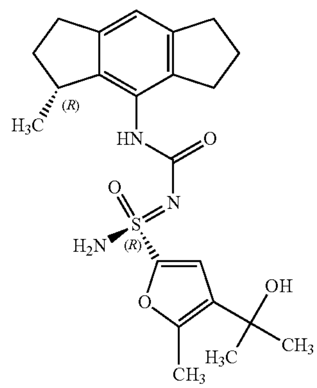 |
| 195bb | 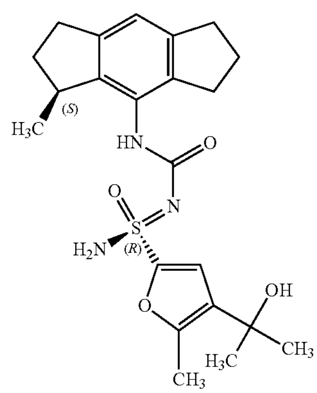 |
| 195e | 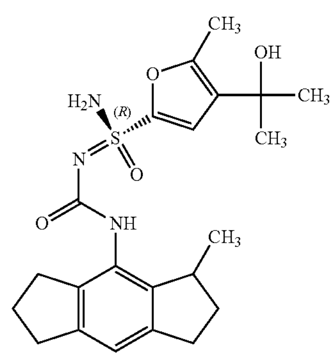 |
| 196 | 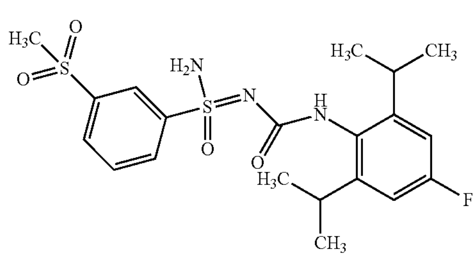 [SMILES: CC(C)c1cc(F)cc(C(C)C)c1NC(=O)N=S(N)(=O)c1cccc(S(C)(=O)=O)c1] |

TABLE 1-continued

| Compound | Structure |
|---|---|
| 197 | 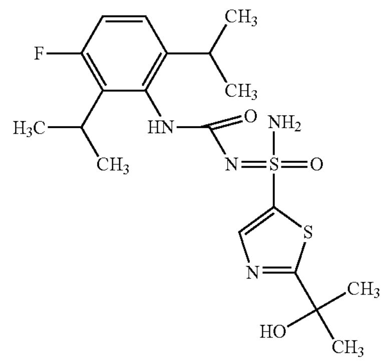 [SMILES: CC(C)c1ccc(F)c(C(C)C)c1NC(=O)N=S(N)(=O)c1cnc(C(C)(C)O)s1] |
| 198 | 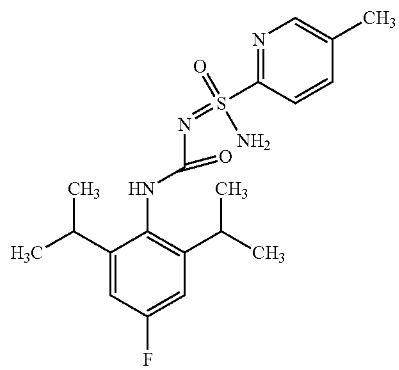 [SMILES: Cc1ccc(S(N)(=O)=NC(=O)Nc2c(C(C)C)cc(F)cc2C(C)C)nc1] |
| 199 | 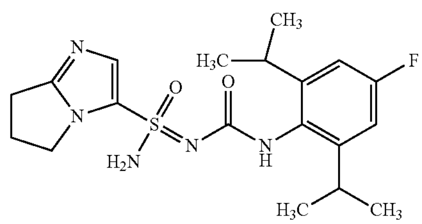 [SMILES: CC(C)c1cc(F)cc(C(C)C)c1NC(=O)N=S(N)(=O)c1cnc2n1CCC2] |
| 200 | 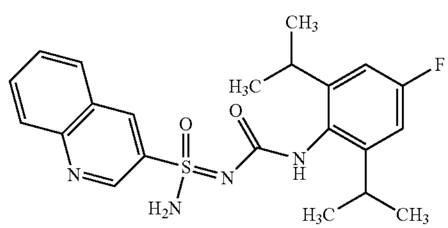 [SMILES: CC(C)c1cc(F)cc(C(C)C)c1NC(=O)N=S(N)(=O)c1cnc2ccccc2c1] |
| 201 | 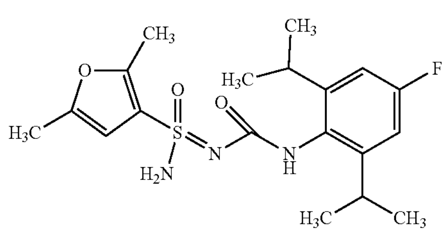 [SMILES: Cc1cc(S(N)(=O)=NC(=O)Nc2c(C(C)C)cc(F)cc2C(C)C)c(C)o1] |

TABLE 1-continued

| Compound | Structure |
|---|---|
| 202 | 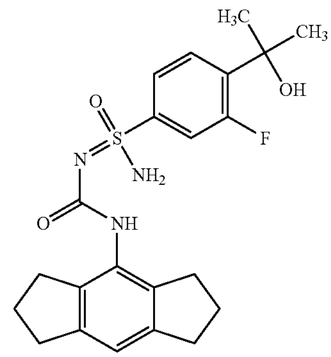 [SMILES: CC(C)(O)c1ccc(S(N)(=O)=NC(=O)Nc2c3c(cc4c2CCC4)CCC3)cc1F] |
| 202a | 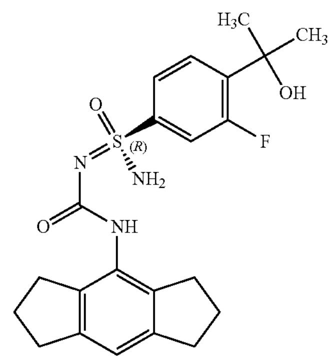 |
| 202b | 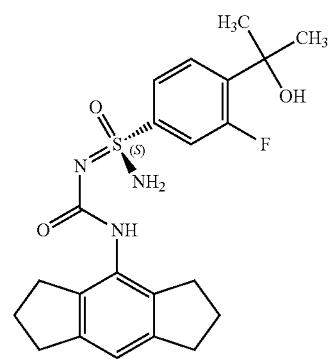 |
| 203 | 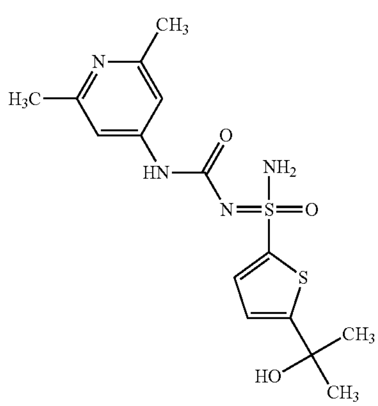 [SMILES: Cc1cc(NC(=O)N=S(N)(=O)c2ccc(C(C)(C)O)s2)cc(C)n1] |

| Compound | Structure |
|---|---|
| 204 | 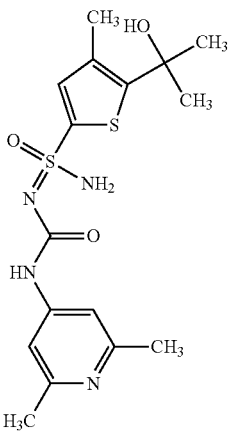 [SMILES: Cc1cc(NC(=O)N=S(N)(=O)c2cc(C)c(C(C)(C)O)s2)cc(C)n1] |
| 205 | 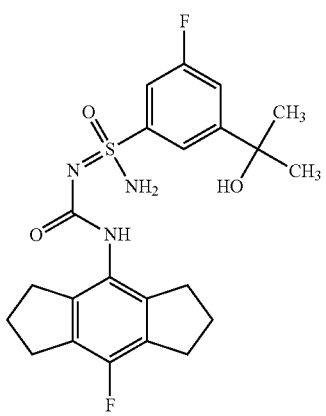 [SMILES: CC(C)(O)c1cc(F)cc(S(N)(=O)=NC(=O)Nc2c3c(c(F)c4c2CCC4)CCC3)c1] |
| 205a | 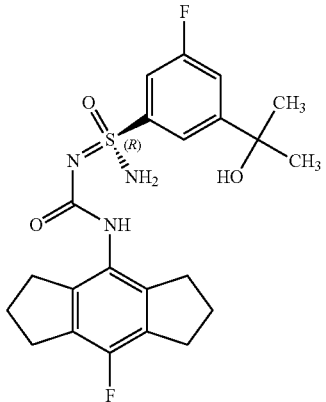 |

TABLE 1-continued

| Compound | Structure |
|---|---|
| 205b | 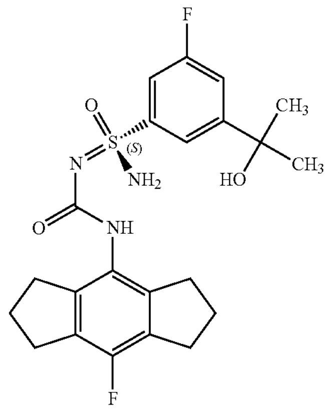 |
| 206 | 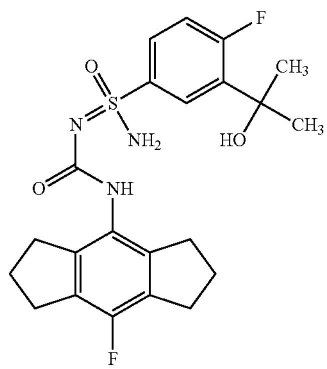 [SMILES: CC(C)(O)c1cc(S(N)(=O)=NC(=O)Nc2c3c(c(F)c4c2CCC4)CCC3)ccc1F] |
| 206a | 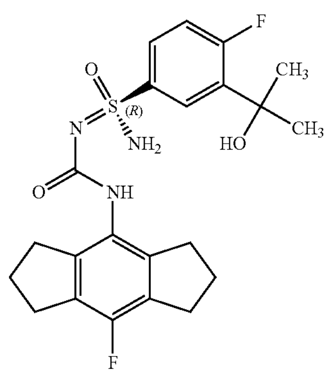 |
| 206b | 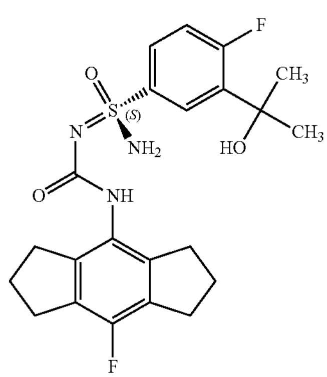 |

TABLE 1-continued

| Compound | Structure |
|---|---|
| 207 | 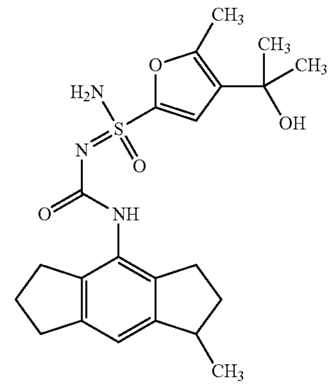 [SMILES: Cc1oc(S(N)(=O)=NC(=O)Nc2c3c(cc4c2CCC4C)CCC3)cc1C(C)(C)O] |
| 207a | 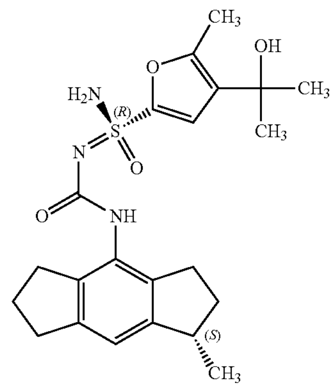 |
| 207b | 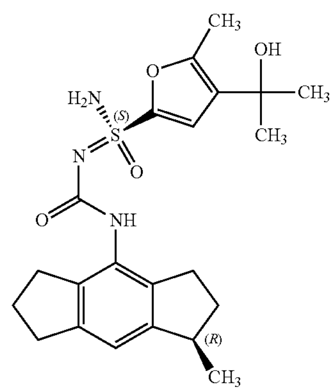 |
| 207bb | 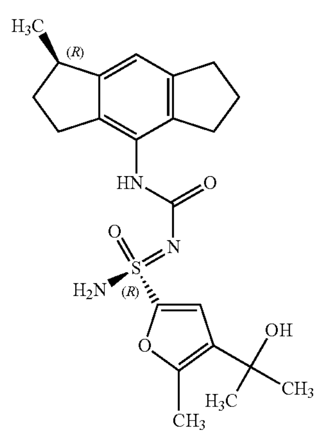 |

TABLE 1-continued
| Compound | Structure |
|---|---|
| 207aa | 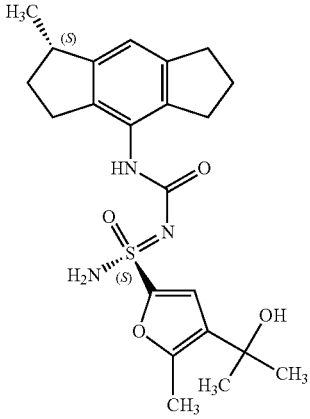 |
| 207c | 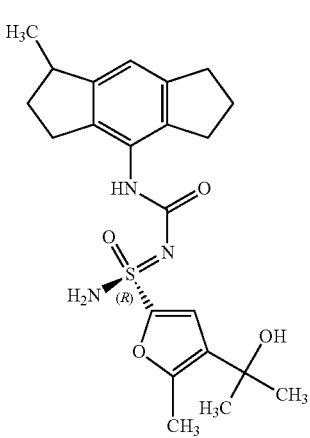 |
| 208 | 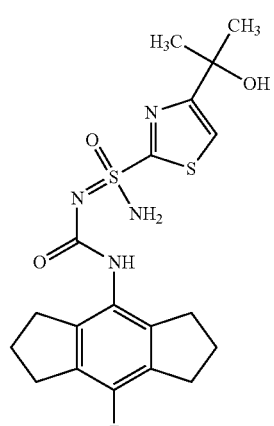 |

TABLE 1-continued
| Compound | Structure |
|---|---|
| 209 | 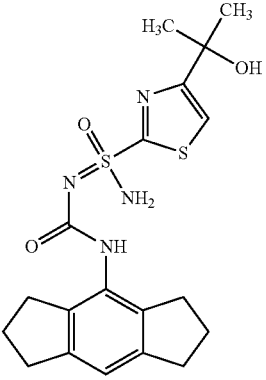 [SMILES: CC(C)(O)c1csc(S(N)(=O)=NC(=O)Nc2c3c(cc4c2CCC4)CCC3)n1] |
| 210 | 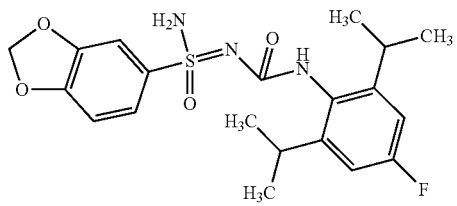 [SMILES: CC(C)c1cc(F)cc(C(C)C)c1NC(=O)N=S(N)(=O)c1ccc2c(c1)OCO2] |
| 211 | 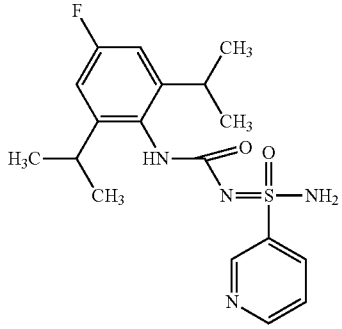 [SMILES: CC(C)c1cc(F)cc(C(C)C)c1NC(=O)N=S(N)(=O)c1cccnc1] |
| 212 | 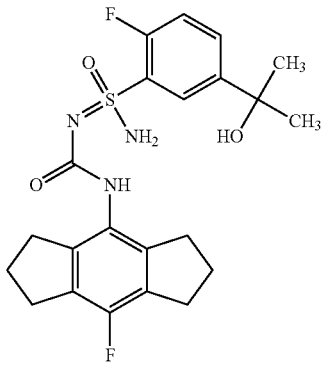 [SMILES: CC(C)(O)c1ccc(F)c(S(N)(=O)=NC(=O)Nc2c3c(c(F)c4c2CCC4)CCC3)c1] |

TABLE 1-continued

| Compound | Structure |
| --- | --- |
| 212a | 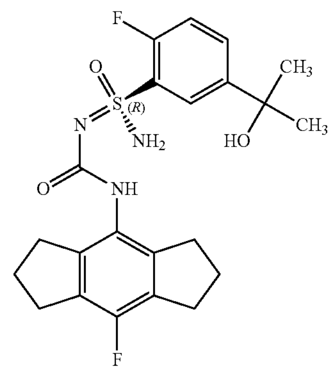 |
| 212b | 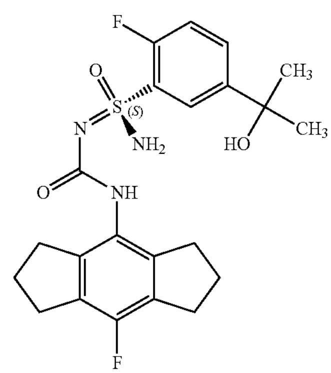 |
| 213 | 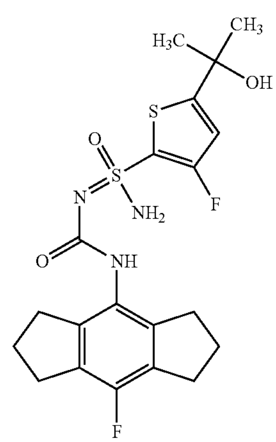 [SMILES: CC(C)(O)c1cc(F)c(S(N)(=O)=NC(=O)Nc2c3c(c(F)c4c2CCC4)CCC3)s1] |
| 214 | 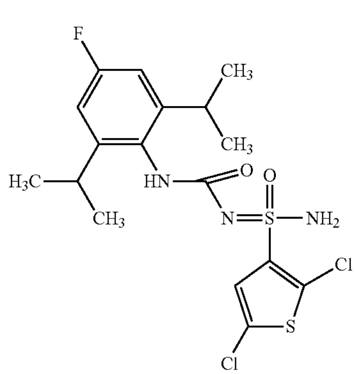 [SMILES: CC(C)c1cc(F)cc(C(C)C)c1NC(=O)N=S(N)(=O)c1cc(Cl)sc1Cl] |

TABLE 1-continued
| Compound | Structure |
|---|---|
| 215 | 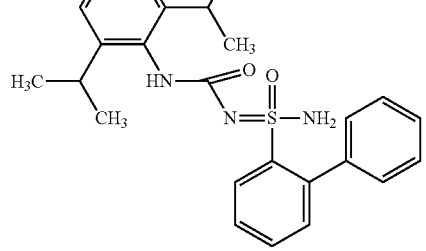 |
| 216 | 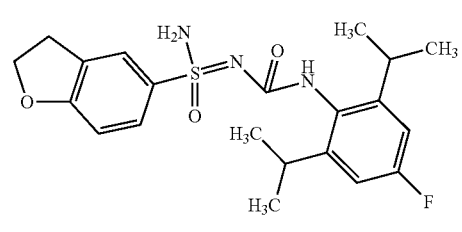 [SMILES: CC(C)c1cc(F)cc(C(C)C)c1NC(=O)N=S(N)(=O)c1ccc2c(c1)CCO2] |
| 217 | 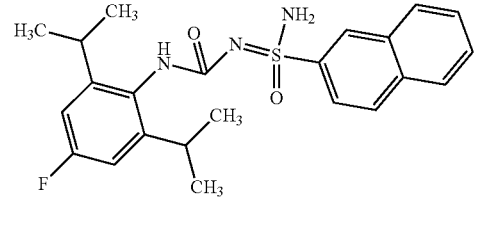 [SMILES: CC(C)c1cc(F)cc(C(C)C)c1NC(=O)N=S(N)(=O)c1ccc2ccccc2c1] |
| 218 | 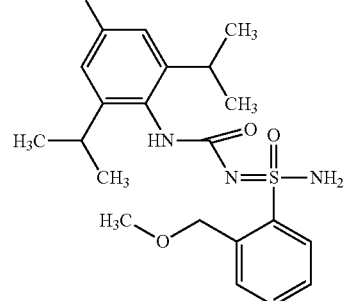 |
| 219 | 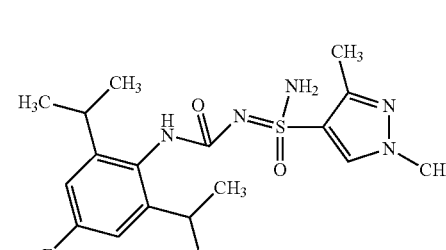 |

TABLE 1-continued

| Compound | Structure |
|---|---|
| 220 | 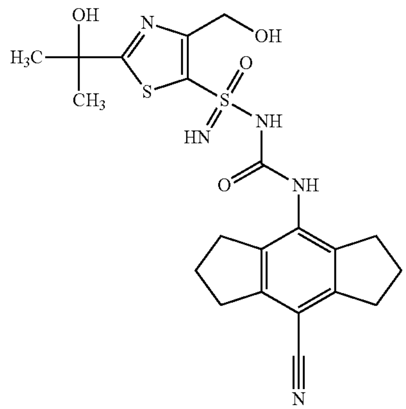 [SMILES: CC(C)(O)c1nc(CO)c(S(=N)(=O)NC(=O)Nc2c3c(c(C#N)c4c2CCC4)CCC3)s1] |
| 220a | 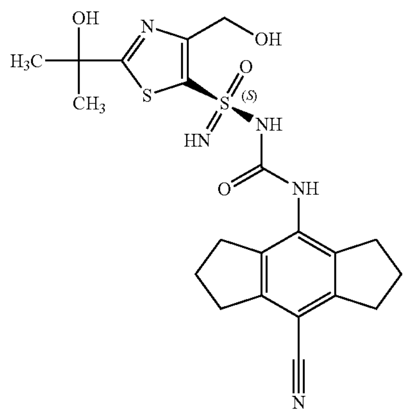 |
| 220b | 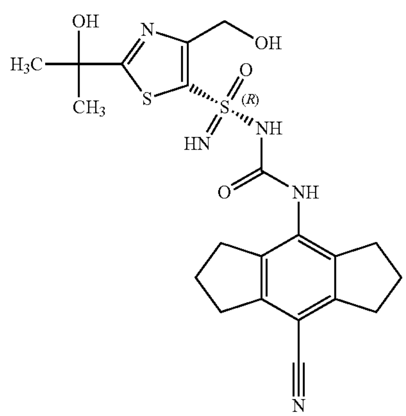 |
| 221 | 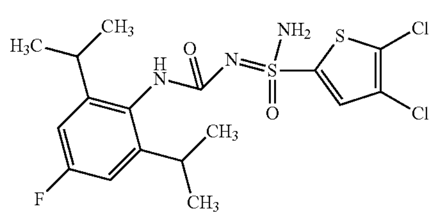 [SMILES: CC(C)c1cc(F)cc(C(C)C)c1NC(=O)N=S(N)(=O)c1cc(Cl)c(Cl)s1] |

TABLE 1-continued

| Compound | Structure |
|---|---|
| 223 | (structure) |
| 223a | (structure) |
| 223b | (structure) |
| 225 | (structure) |
| 225a | (structure) |
| 225b | (structure) |

TABLE 1-continued
| Compound | Structure |
|---|---|
| 226 | 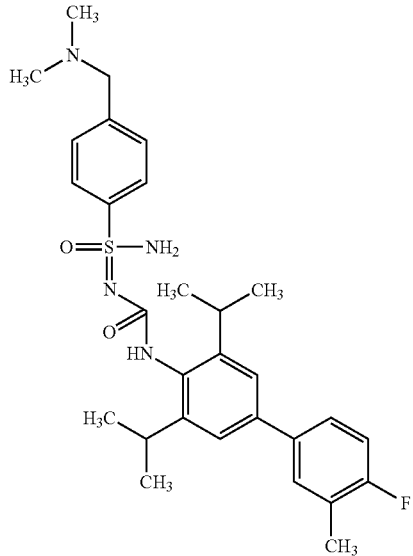 [SMILES: Cc1cc(-c2cc(C(C)C)c(NC(=O)N=S(N)(=O)c3ccc(CN(C)C)cc3)c(C(C)C)c2)ccc1F] |
| 227 | 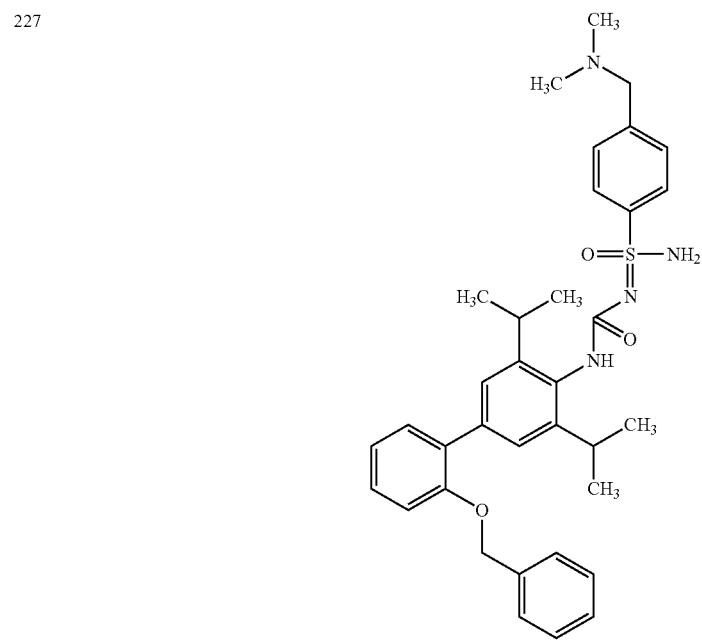 |

TABLE 1-continued
| Compound | Structure |
|---|---|
| 228 | 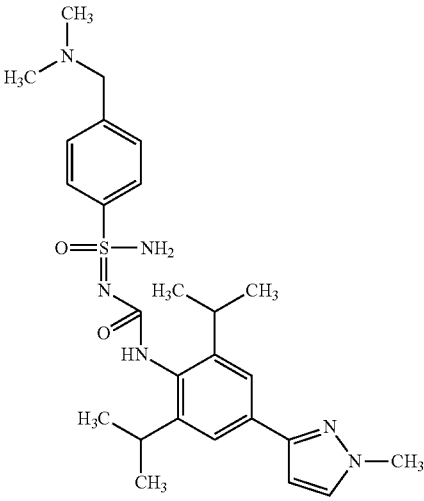 |
| 229 | 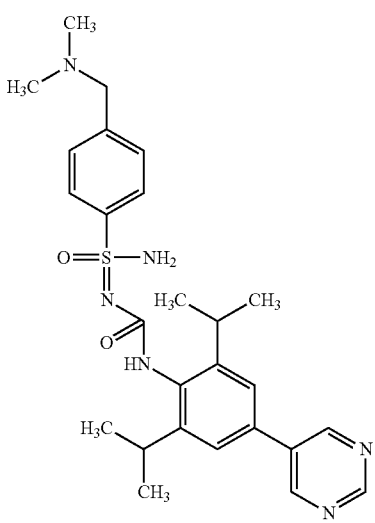 [SMILES: CC(C)c1cc(-c2cncnc2)cc(C(C)C)c1NC(=O)N=S(N)(=O)c1ccc(CN(C)C)cc1] |
| 230 | 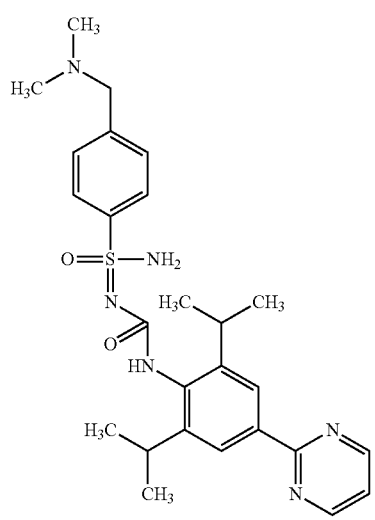 [SMILES: CC(C)c1cc(-c2ncccn2)cc(C(C)C)c1NC(=O)N=S(N)(=O)c1ccc(CN(C)C)cc1] |

TABLE 1-continued

| Compound | Structure |
|---|---|
| 231 | 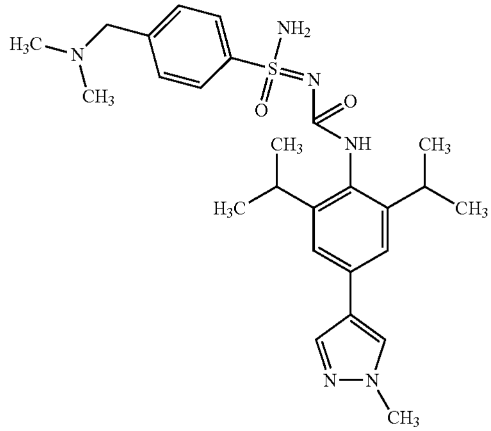 [SMILES: CC(C)c1cc(-c2cnn(C)c2)cc(C(C)C)c1NC(=O)N=S(N)(=O)c1ccc(CN(C)C)cc1] |
| 232 | 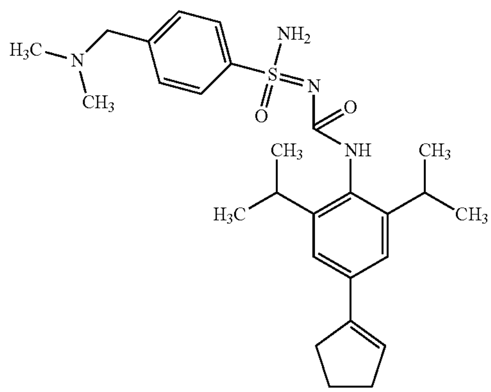 [SMILES: CC(C)c1cc(C2=CCCC2)cc(C(C)C)c1NC(=O)N=S(N)(=O)c1ccc(CN(C)C)cc1] |
| 233 | 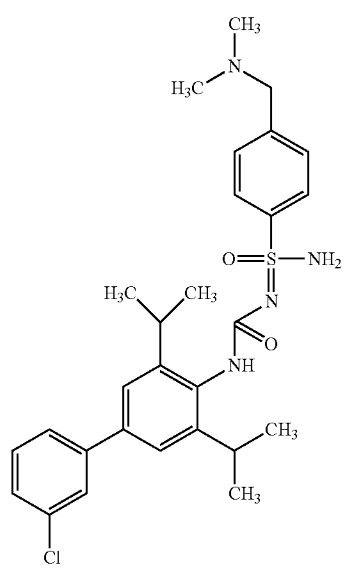 [SMILES: CC(C)c1cc(-c2cccc(Cl)c2)cc(C(C)C)c1NC(=O)N=S(N)(=O)c1ccc(CN(C)C)cc1] |

TABLE 1-continued
| Compound | Structure |
|---|---|
| 234 | 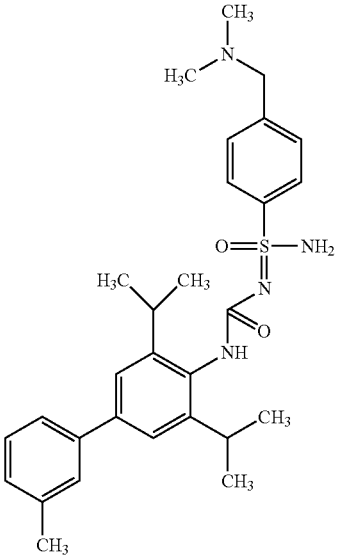 [SMILES: Cc1cccc(-c2cc(C(C)C)c(NC(=O)N=S(N)(=O)c3ccc(CN(C)C)cc3)c(C(C)C)c2)c1] |
| 235 | 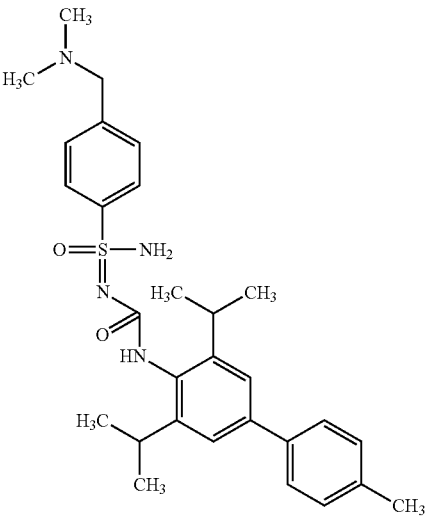 |

TABLE 1-continued
| Compound | Structure |
|---|---|
| 236 | 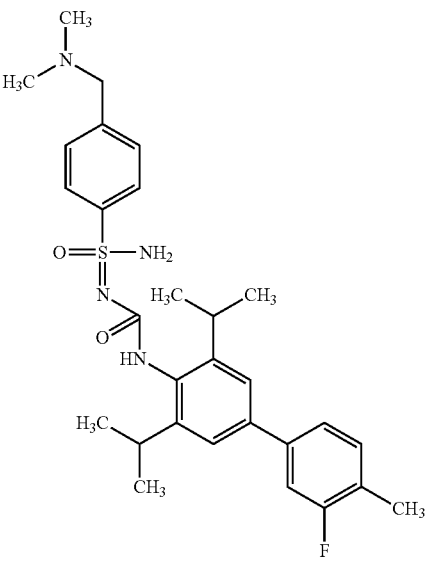 |
| 237 | 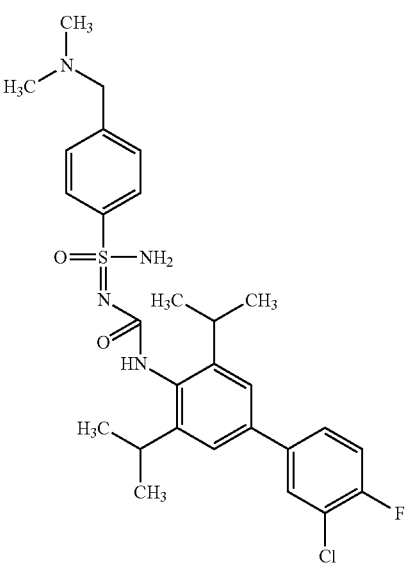 [SMILES: CC(C)c1cc(-c2ccc(F)c(Cl)c2)cc(C(C)C)c1NC(=O)N=S(N)(=O)c1ccc(CN(C)C)cc1] |
| 238 | 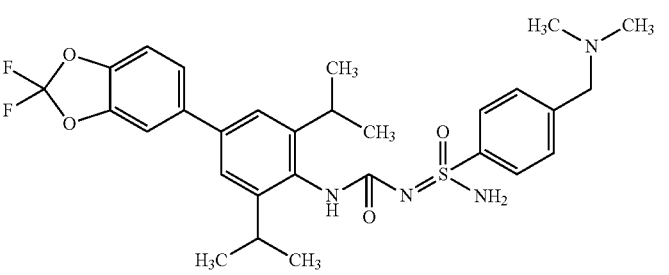 [SMILES: CC(C)c1cc(-c2ccc3c(c2)OC(F)(F)O3)cc(C(C)C)c1NC(=O)N=S(N)(=O)c1ccc(CN(C)C)cc1] |

TABLE 1-continued

| Compound | Structure |
|---|---|
| 239 | 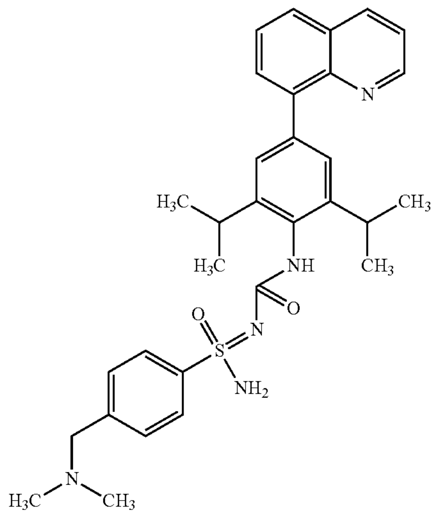 [SMILES: CC(C)c1cc(-c2cccc3cccnc23)cc(C(C)C)c1NC(=O)N=S(N)(=O)c1ccc(CN(C)C)cc1] |
| 240 | 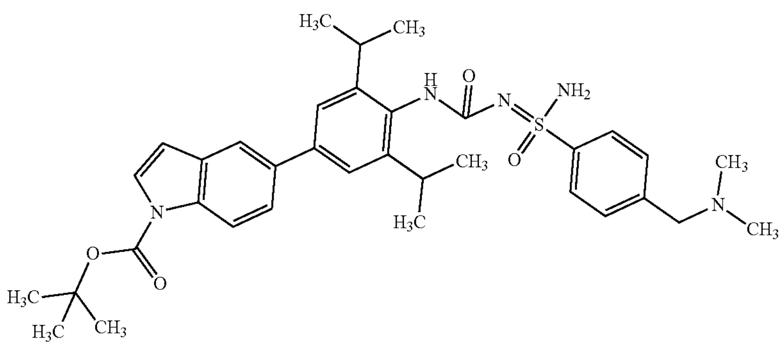 [SMILES: CC(C)c1cc(-c2ccc3c(ccn3C(=O)OC(C)(C)C)c2)cc(C(C)C)c1NC(=O)N=S(N)(=O)c1ccc(CN(C)C)cc1] |
| 241 | 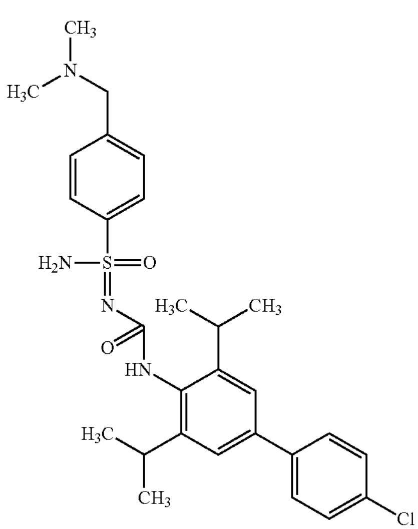 [SMILES: CC(C)c1cc(-c2ccc(Cl)cc2)cc(C(C)C)c1NC(=O)N=S(N)(=O)c1ccc(CN(C)C)cc1] |

TABLE 1-continued
| Compound | Structure |
|---|---|
| 242 | 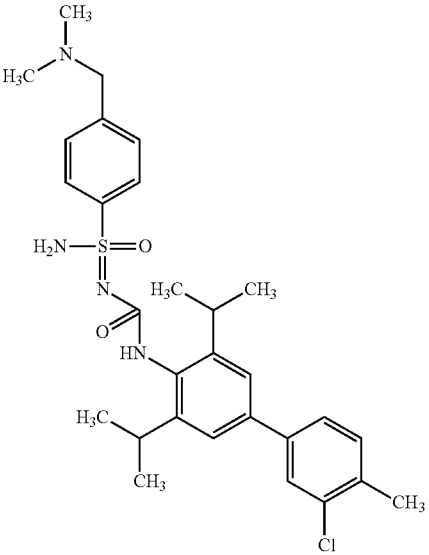 |
| 243 | 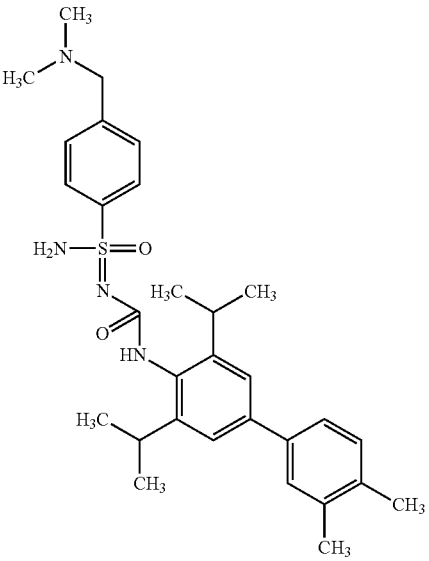 |

TABLE 1-continued
| Compound | Structure |
|---|---|
| 244 | 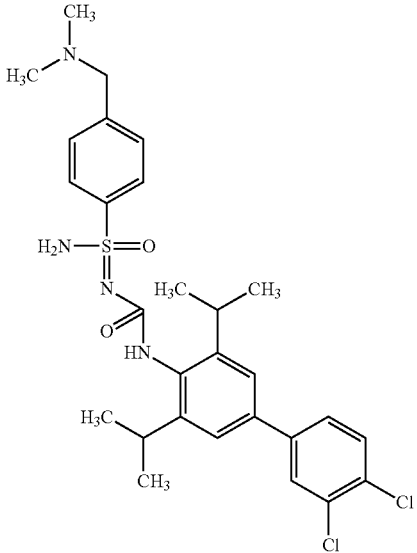 [SMILES: CC(C)c1cc(-c2ccc(Cl)c(Cl)c2)cc(C(C)C)c1NC(=O)N=S(N)(=O)c1ccc(CN(C)C)cc1] |
| 245 | 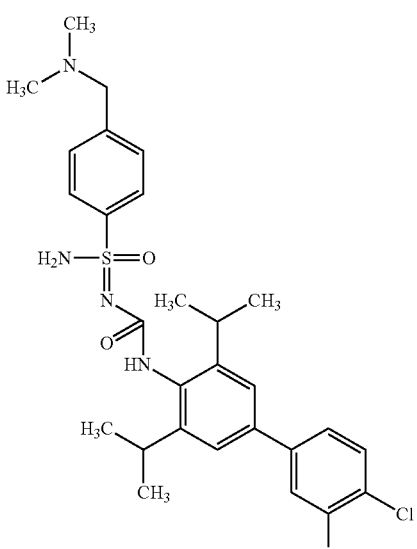 |

TABLE 1-continued

| Compound | Structure |
|---|---|
| 246 | 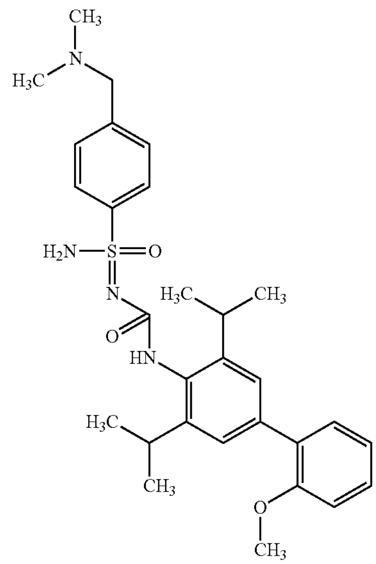 [SMILES: COc1ccccc1-c1cc(C(C)C)c(NC(=O)N=S(N)(=O)c2ccc(CN(C)C)cc2)c(C(C)C)c1] |
| 247 | 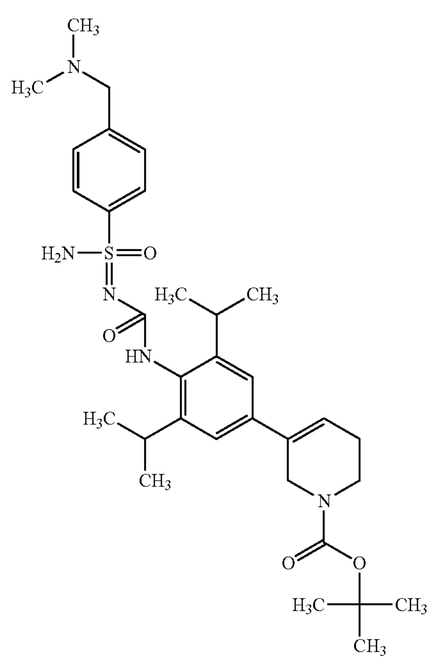 [SMILES: CC(C)c1cc(C2=CCCN(C(=O)OC(C)(C)C)C2)cc(C(C)C)c1NC(=O)N=S(N)(=O)c1ccc(CN(C)C)cc1] |

TABLE 1-continued

| Compound | Structure |
|---|---|
| 248 | *(structure: 4-[(dimethylamino)methyl]-N-{[(2,6-diisopropyl-4-(2-oxo-1,2-dihydropyrimidin-5-yl)phenyl)carbamoyl]}benzenesulfonimidamide)* |
| 249 | *(structure: 4-[(dimethylamino)methyl]-N-{[(2,6-diisopropyl-4-(2'-(hydroxymethyl)biphenyl-4-yl)phenyl)carbamoyl]}benzenesulfonimidamide)* |
| 250 | *(structure: 4-[(dimethylamino)methyl]-N-{[(2,6-diisopropyl-4-(3-(methylsulfonyl)pyridin-2-yl)phenyl)carbamoyl]}benzenesulfonimidamide)* |

TABLE 1-continued

| Compound | Structure |
|---|---|
| 251 | 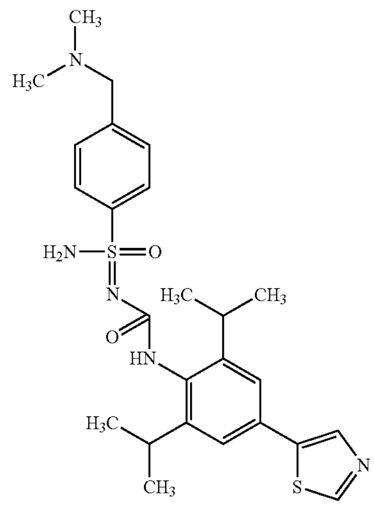 [SMILES: CC(C)c1cc(-c2cncs2)cc(C(C)C)c1NC(=O)N=S(N)(=O)c1ccc(CN(C)C)cc1] |
| 252 | 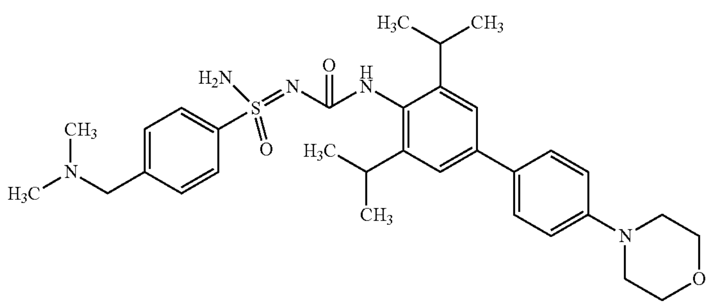 [SMILES: CC(C)c1cc(-c2ccc(N3CCOCC3)cc2)cc(C(C)C)c1NC(=O)N=S(N)(=O)c1ccc(CN(C)C)cc1] |
| 253 | 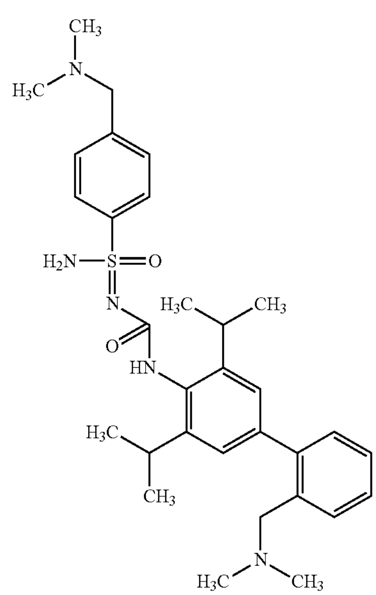 [SMILES: CC(C)c1cc(-c2ccccc2CN(C)C)cc(C(C)C)c1NC(=O)N=S(N)(=O)c1ccc(CN(C)C)cc1] |

TABLE 1-continued
| Compound | Structure |
|---|---|
| 254 | 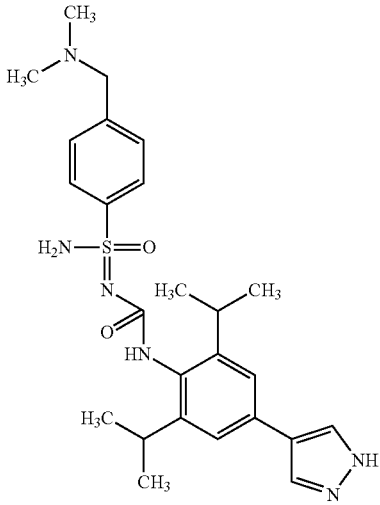 [SMILES: CC(C)c1cc(-c2cn[nH]c2)cc(C(C)C)c1NC(=O)N=S(N)(=O)c1ccc(CN(C)C)cc1] |
| 255 | 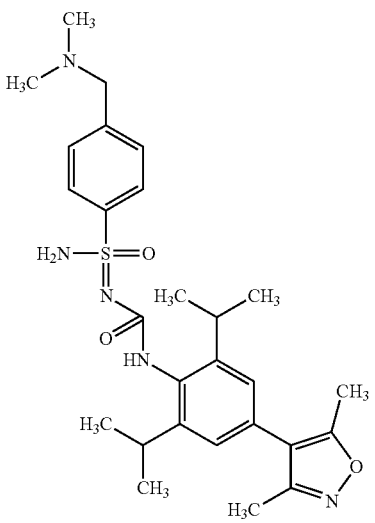 [SMILES: Cc1noc(C)c1-c1cc(C(C)C)c(NC(=O)N=S(N)(=O)c2ccc(CN(C)C)cc2)c(C(C)C)c1] |

TABLE 1-continued
| Compound | Structure |
|---|---|
| 256 | 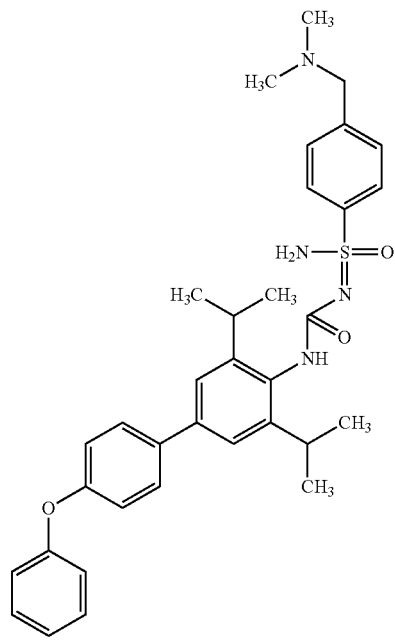 [SMILES: CC(C)c1cc(-c2ccc(Oc3ccccc3)cc2)cc(C(C)C)c1NC(=O)N=S(N)(=O)c1ccc(CN(C)C)cc1] |
| 257 | 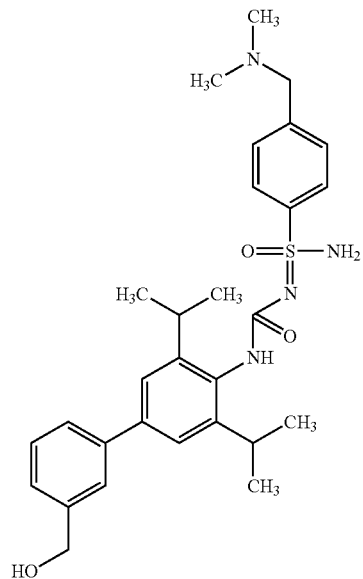 [SMILES: CC(C)c1cc(-c2cccc(CO)c2)cc(C(C)C)c1NC(=O)N=S(N)(=O)c1ccc(CN(C)C)cc1] |

TABLE 1-continued
| Compound | Structure |
|---|---|
| 258 | 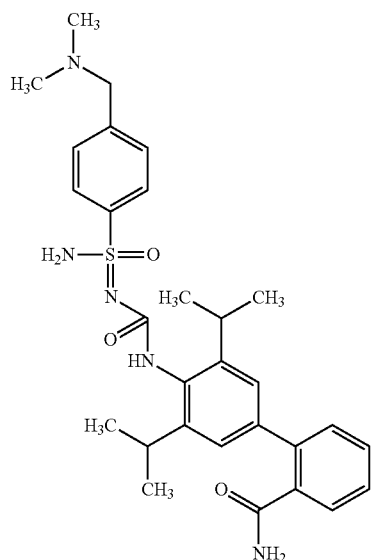 |
| 259 | 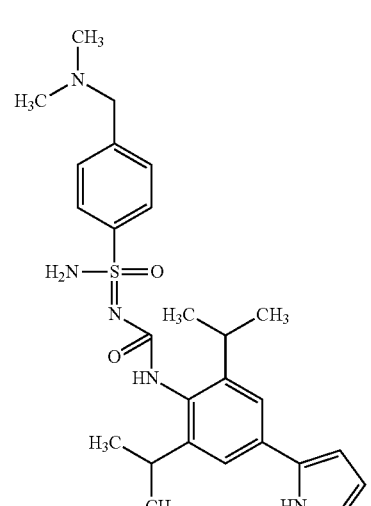 |
| 260 | 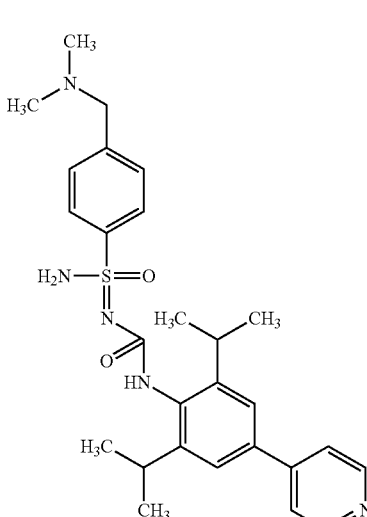 |

TABLE 1-continued
| Compound | Structure |
|---|---|
| 261 | 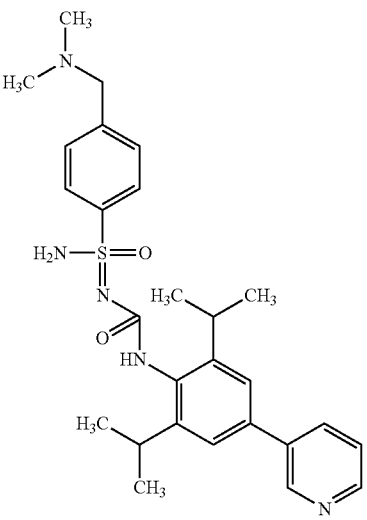 [SMILES: CC(C)c1cc(-c2cccnc2)cc(C(C)C)c1NC(=O)N=S(N)(=O)c1ccc(CN(C)C)cc1] |
| 262 | 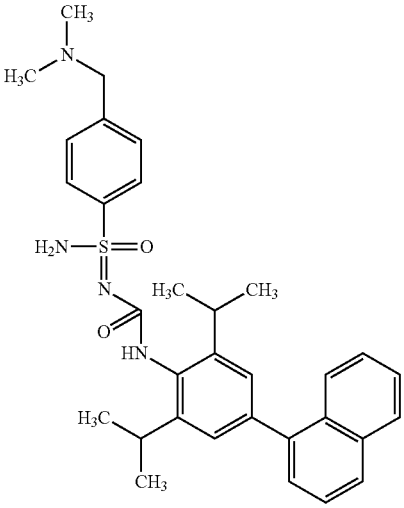 [SMILES: CC(C)c1cc(-c2cccc3ccccc23)cc(C(C)C)c1NC(=O)N=S(N)(=O)c1ccc(CN(C)C)cc1] |
| 263 | 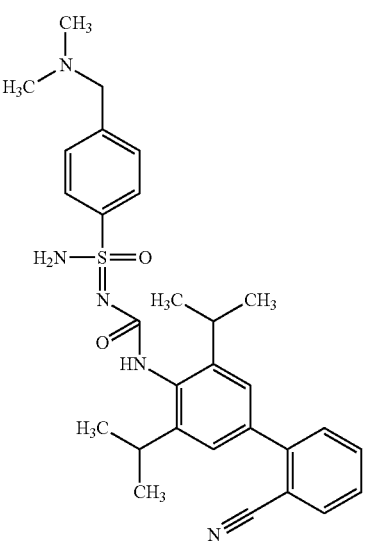 [SMILES: CC(C)c1cc(-c2ccccc2C#N)cc(C(C)C)c1NC(=O)N=S(N)(=O)c1ccc(CN(C)C)cc1] |

| Compound | Structure |
|---|---|
| 264 | 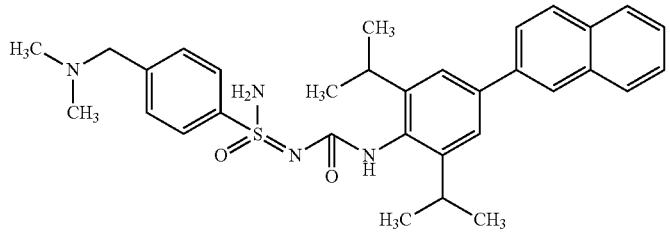 [SMILES: CC(C)c1cc(-c2ccc3ccccc3c2)cc(C(C)C)c1NC(=O)N=S(N)(=O)c1ccc(CN(C)C)cc1] |
| 265 | 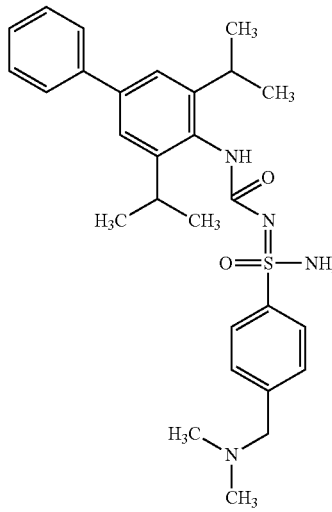 |
| 266 | 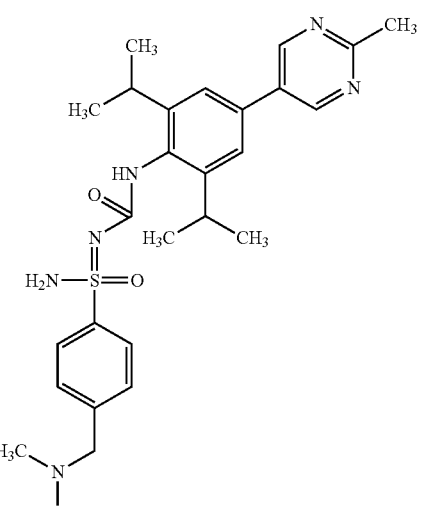 |

TABLE 1-continued
| Compound | Structure |
|---|---|
| 267 | 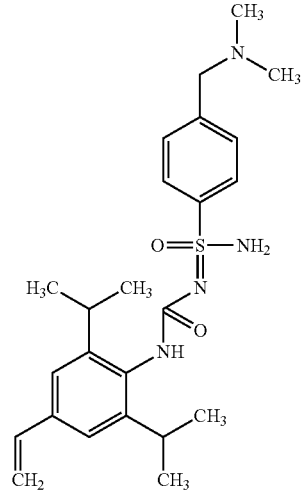 [SMILES: C=Cc1cc(C(C)C)c(NC(=O)N=S(N)(=O)c2ccc(CN(C)C)cc2)c(C(C)C)c1] |
| 268 | 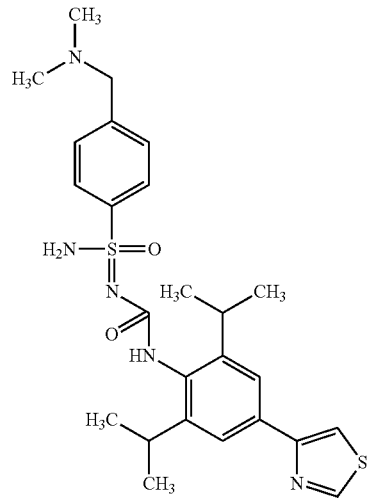 [SMILES: CC(C)c1cc(-c2cscn2)cc(C(C)C)c1NC(=O)N=S(N)(=O)c1ccc(CN(C)C)cc1] |
| 269 | 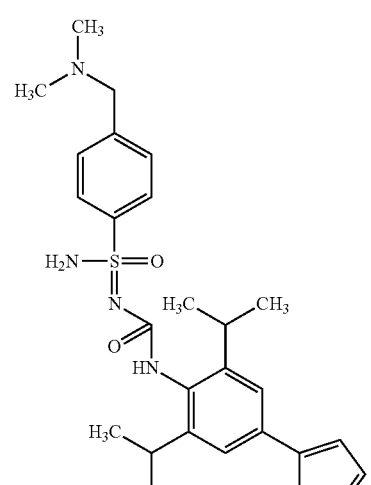 |

TABLE 1-continued

| Compound | Structure |
|---|---|
| 270 | (structure) | and pharmaceutically acceptable salts thereof.

In some embodiments, provided herein is a compound that is selected from the group consisting of the compounds in the following table:

303

303a

303b

306

-continued
| | |
|---|---|
| 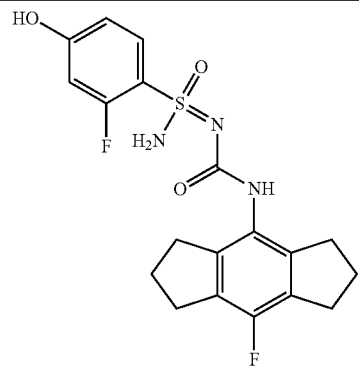 | 307 |
| 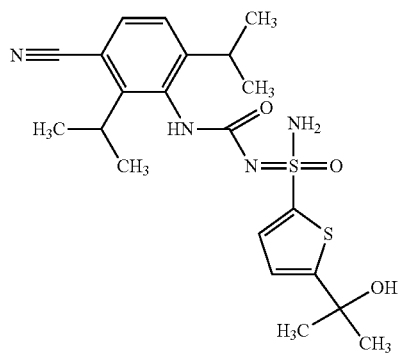 [SMILES: CC(C)c1ccc(C#N)c(C(C)C)c1NC(=O)N=S(N)(=O)c1ccc(C(C)(C)O)s1] | 308 |
| 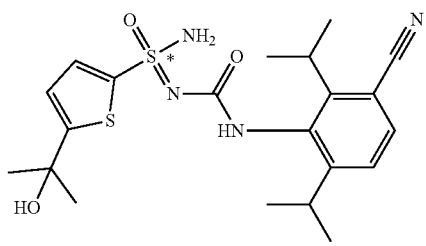 [SMILES: CC(C)c1ccc(C#N)c(C(C)C)c1NC(=O)N=S(N)(=O)c1ccc(C(C)(C)O)s1] | 308a |
| 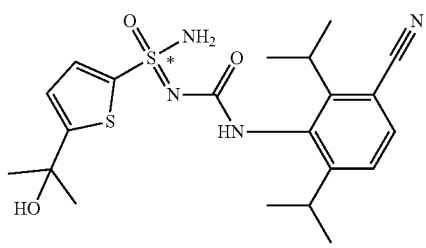 [SMILES: CC(C)c1ccc(C#N)c(C(C)C)c1NC(=O)N=S(N)(=O)c1ccc(C(C)(C)O)s1] | 308b |
| 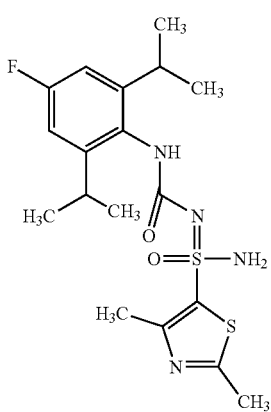 [SMILES: Cc1nc(C)c(S(N)(=O)=NC(=O)Nc2c(C(C)C)cc(F)cc2C(C)C)s1] | 309 |

| | |
|---|---|
| 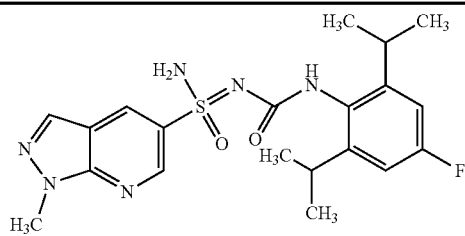 | 310 |
| 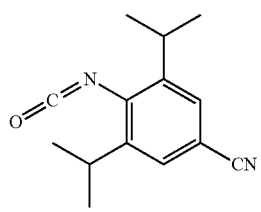 [SMILES: CC(C)c1cc(C#N)cc(C(C)C)c1N=C=O] | 311 |
| 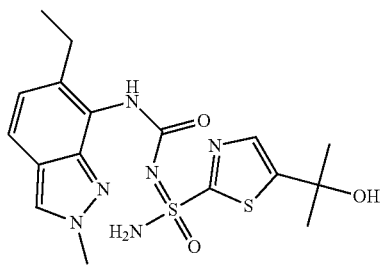 [SMILES: CCc1ccc2cn(C)nc2c1NC(=O)N=S(N)(=O)c1ncc(C(C)(C)O)s1] | 312 |
| 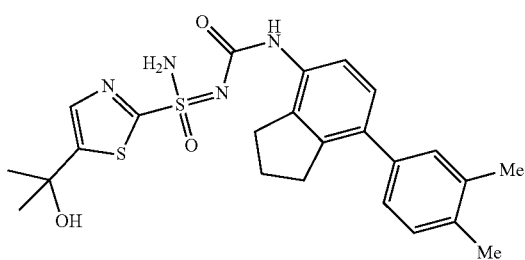 [SMILES: Cc1ccc(-c2ccc(NC(=O)N=S(N)(=O)c3ncc(C(C)(C)O)s3)c3c2CCC3)cc1C] | 313 |
| 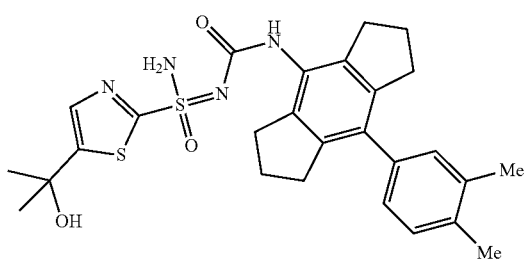 [SMILES: Cc1ccc(-c2c3c(c(NC(=O)N=S(N)(=O)c4ncc(C(C)(C)O)s4)c4c2CCC4)CCC3)cc1C] | 314 |
| 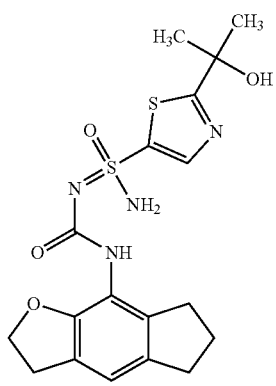 [SMILES: CC(C)(O)c1ncc(S(N)(=O)=NC(=O)Nc2c3c(cc4c2OCC4)CCC3)s1] | 315 |

-continued
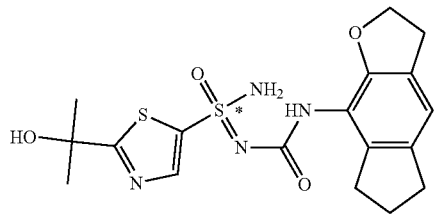 [SMILES: CC(C)(O)c1ncc(S(N)(=O)=NC(=O)Nc2c3c(cc4c2OCC4)CCC3)s1]
315b
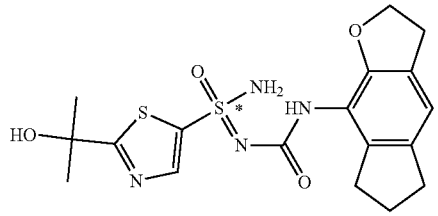 [SMILES: CC(C)(O)c1ncc(S(N)(=O)=NC(=O)Nc2c3c(cc4c2OCC4)CCC3)s1]
315a
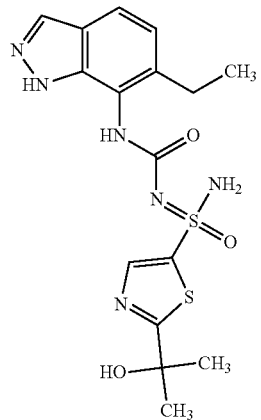 [SMILES: CCc1ccc2cn[nH]c2c1NC(=O)N=S(N)(=O)c1cnc(C(C)(C)O)s1]
316
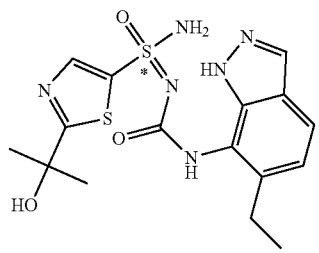 [SMILES: CCc1ccc2cn[nH]c2c1NC(=O)N=S(N)(=O)c1cnc(C(C)(C)O)s1]
316a
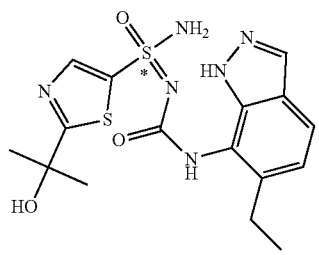 [SMILES: CCc1ccc2cn[nH]c2c1NC(=O)N=S(N)(=O)c1cnc(C(C)(C)O)s1]
316b
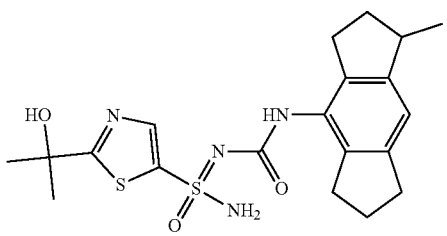 [SMILES: CC1CCc2c1cc1c(c2NC(=O)N=S(N)(=O)c2cnc(C(C)(C)O)s2)CCC1]
317

-continued
| | |
|---|---|
| 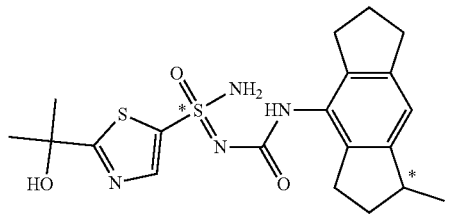 [SMILES: CC1CCc2c1cc1c(c2NC(=O)N=S(N)(=O)c2cnc(C(C)(C)O)s2)CCC1] | 317ab |
| 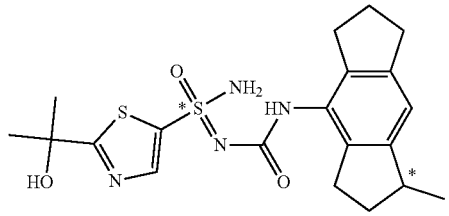 [SMILES: CC1CCc2c1cc1c(c2NC(=O)N=S(N)(=O)c2cnc(C(C)(C)O)s2)CCC1] | 317aa |
| 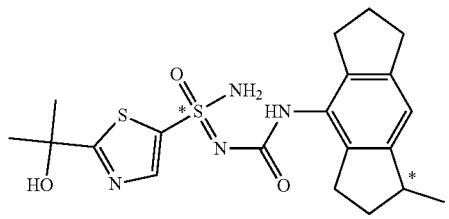 [SMILES: CC1CCc2c1cc1c(c2NC(=O)N=S(N)(=O)c2cnc(C(C)(C)O)s2)CCC1] | 317bb |
| 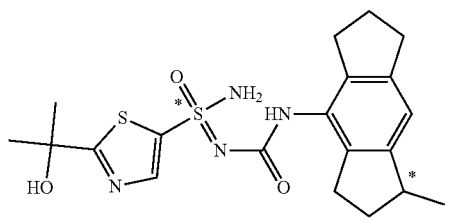 [SMILES: CC1CCc2c1cc1c(c2NC(=O)N=S(N)(=O)c2cnc(C(C)(C)O)s2)CCC1] | 317ba |
| 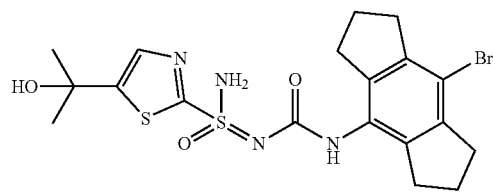 [SMILES: CC(C)(O)c1cnc(S(N)(=O)=NC(=O)Nc2c3c(c(Br)c4c2CCC4)CCC3)s1] | 318 |
| 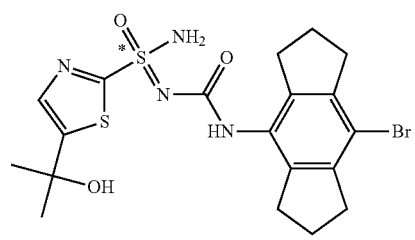 [SMILES: CC(C)(O)c1cnc(S(N)(=O)=NC(=O)Nc2c3c(c(Br)c4c2CCC4)CCC3)s1] | 318a |
| 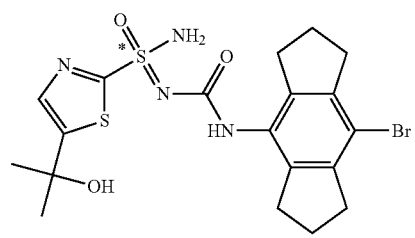 [SMILES: CC(C)(O)c1cnc(S(N)(=O)=NC(=O)Nc2c3c(c(Br)c4c2CCC4)CCC3)s1] | 318b |

-continued
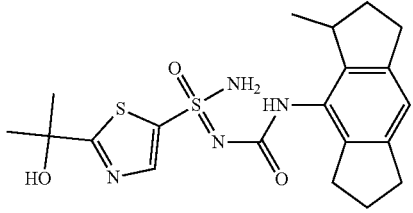 [SMILES: CC1CCc2cc3c(c(NC(=O)N=S(N)(=O)c4cnc(C(C)(C)O)s4)c21)CCC3]
319
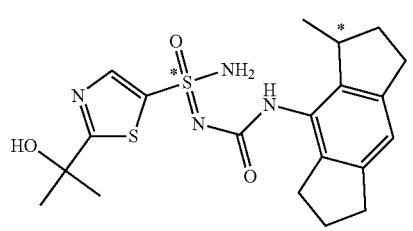 [SMILES: CC1CCc2cc3c(c(NC(=O)N=S(N)(=O)c4cnc(C(C)(C)O)s4)c21)CCC3]
319ab
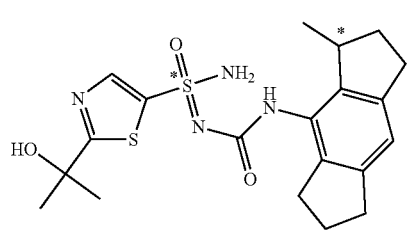 [SMILES: CC1CCc2cc3c(c(NC(=O)N=S(N)(=O)c4cnc(C(C)(C)O)s4)c21)CCC3]
319ba
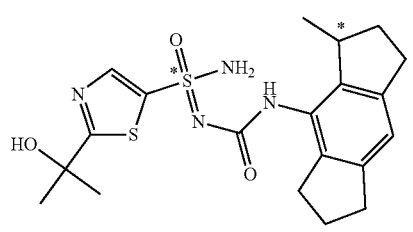
319aa
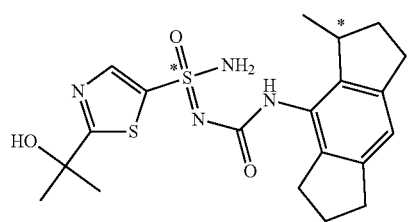 [SMILES: CC1CCc2cc3c(c(NC(=O)N=S(N)(=O)c4cnc(C(C)(C)O)s4)c21)CCC3]
319bb
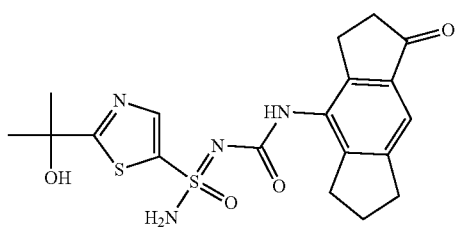 [SMILES: CC(C)(O)c1ncc(S(N)(=O)=NC(=O)Nc2c3c(cc4c2CCC4=O)CCC3)s1]
320
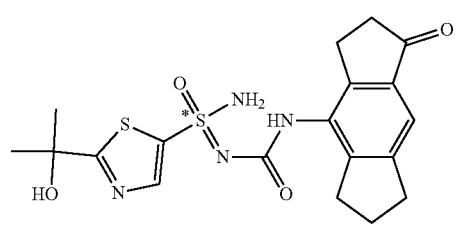 [SMILES: CC(C)(O)c1ncc(S(N)(=O)=NC(=O)Nc2c3c(cc4c2CCC4=O)CCC3)s1]
320a -continued
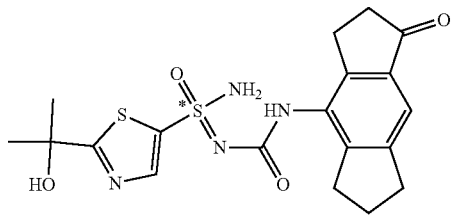 [SMILES: CC(C)(O)c1ncc(S(N)(=O)=NC(=O)Nc2c3c(cc4c2CCC4=O)CCC3)s1]
320b
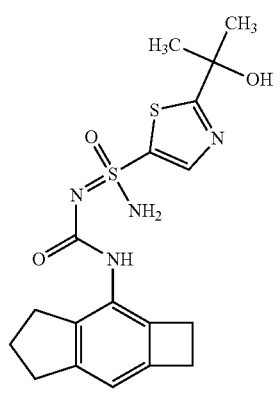 [SMILES: CC(C)(O)c1ncc(S(N)(=O)=NC(=O)Nc2c3c(cc4c2CC4)CCC3)s1]
321
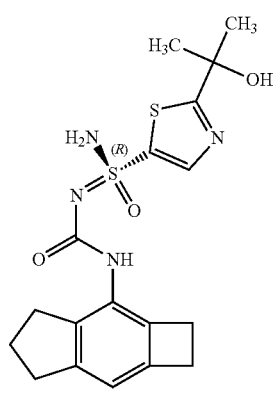
321b
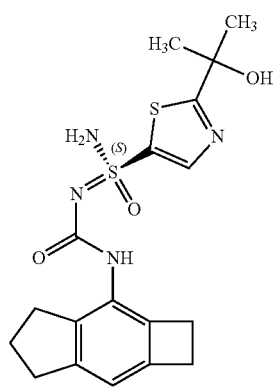
321a
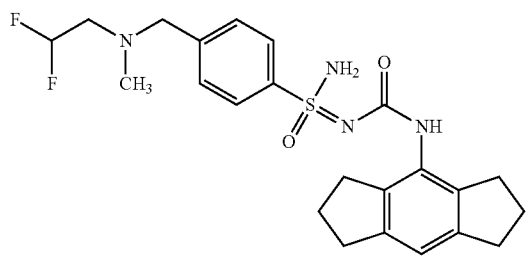 [SMILES: CN(Cc1ccc(S(N)(=O)=NC(=O)Nc2c3c(cc4c2CCC4)CCC3)cc1)CC(F)F]
322

-continued
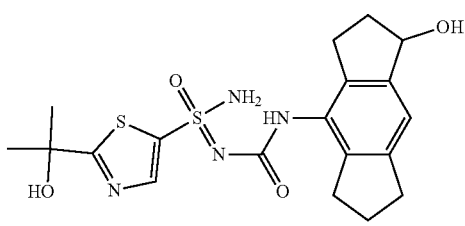 [SMILES: CC(C)(O)c1ncc(S(N)(=O)=NC(=O)Nc2c3c(cc4c2CCC4O)CCC3)s1]
323
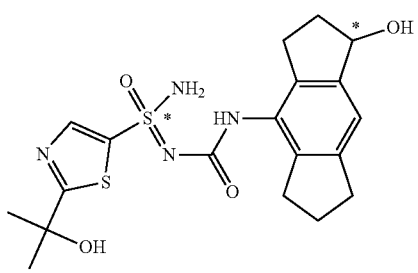 [SMILES: CC(C)(O)c1ncc(S(N)(=O)=NC(=O)Nc2c3c(cc4c2CCC4O)CCC3)s1]
323ab
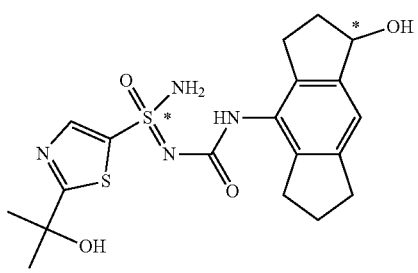 [SMILES: CC(C)(O)c1ncc(S(N)(=O)=NC(=O)Nc2c3c(cc4c2CCC4O)CCC3)s1]
323aa
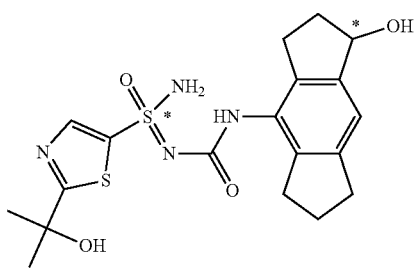 [SMILES: CC(C)(O)c1ncc(S(N)(=O)=NC(=O)Nc2c3c(cc4c2CCC4O)CCC3)s1]
323bb
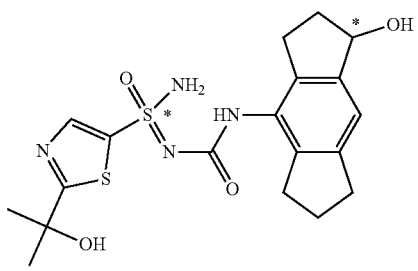 [SMILES: CC(C)(O)c1ncc(S(N)(=O)=NC(=O)Nc2c3c(cc4c2CCC4O)CCC3)s1]
323ba -continued
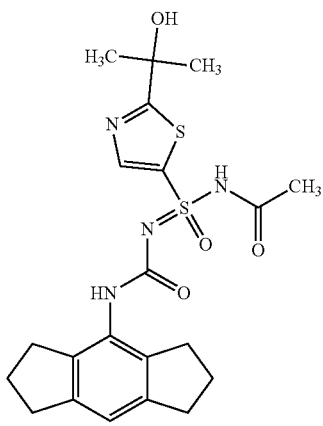 [SMILES: CC(=O)NS(=O)(=NC(=O)Nc1c2c(cc3c1CCC3)CCC2)c1cnc(C(C)(C)O)s1]
324
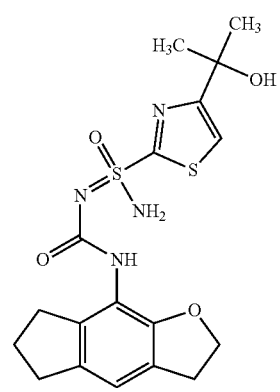 [SMILES: CC(C)(O)c1csc(S(N)(=O)=NC(=O)Nc2c3c(cc4c2OCC4)CCC3)n1]
325
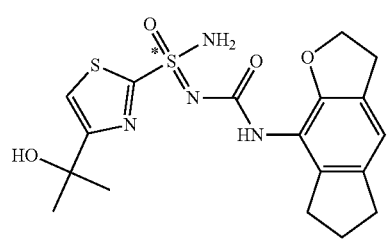 [SMILES: CC(C)(O)c1csc(S(N)(=O)=NC(=O)Nc2c3c(cc4c2OCC4)CCC3)n1]
325a
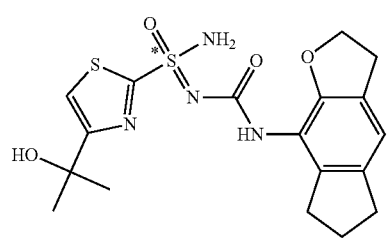 [SMILES: CC(C)(O)c1csc(S(N)(=O)=NC(=O)Nc2c3c(cc4c2OCC4)CCC3)n1]
325b -continued
| | |
|---|---|
| 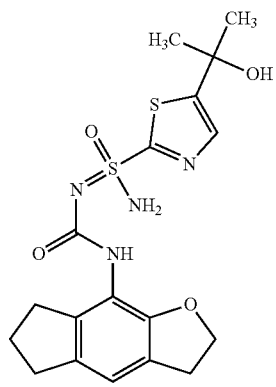 [SMILES: CC(C)(O)c1cnc(S(N)(=O)=NC(=O)Nc2c3c(cc4c2OCC4)CCC3)s1] | 326 |
| 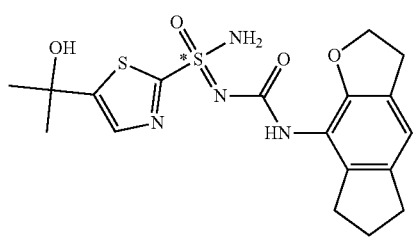 [SMILES: CC(C)(O)c1cnc(S(N)(=O)=NC(=O)Nc2c3c(cc4c2OCC4)CCC3)s1] | 326b |
| 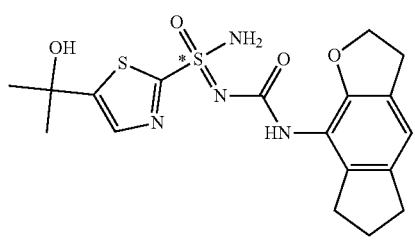 [SMILES: CC(C)(O)c1cnc(S(N)(=O)=NC(=O)Nc2c3c(cc4c2OCC4)CCC3)s1] | 326a |
| 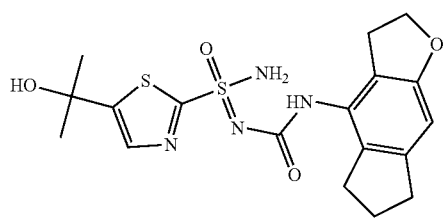 [SMILES: CC(C)(O)c1cnc(S(N)(=O)=NC(=O)Nc2c3c(cc4c2CCO4)CCC3)s1] | 327 |
| 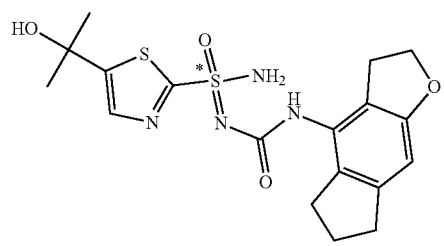 [SMILES: CC(C)(O)c1cnc(S(N)(=O)=NC(=O)Nc2c3c(cc4c2CCO4)CCC3)s1] | 328b |
| 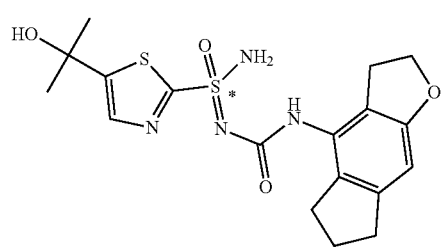 [SMILES: CC(C)(O)c1cnc(S(N)(=O)=NC(=O)Nc2c3c(cc4c2CCO4)CCC3)s1] | 328a |

-continued
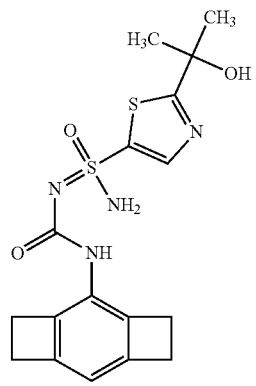 [SMILES: CC(C)(O)c1ncc(S(N)(=O)=NC(=O)Nc2c3c(cc4c2CC4)CC3)s1]
329
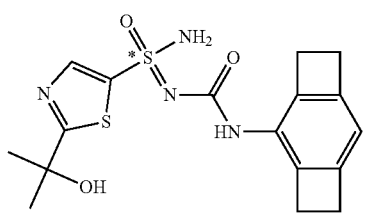 [SMILES: CC(C)(O)c1ncc(S(N)(=O)=NC(=O)Nc2c3c(cc4c2CC4)CC3)s1]
329a
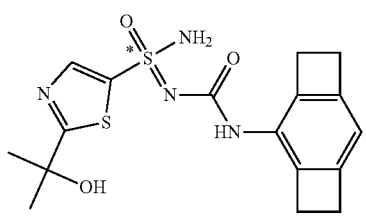 [SMILES: CC(C)(O)c1ncc(S(N)(=O)=NC(=O)Nc2c3c(cc4c2CC4)CC3)s1]
329b
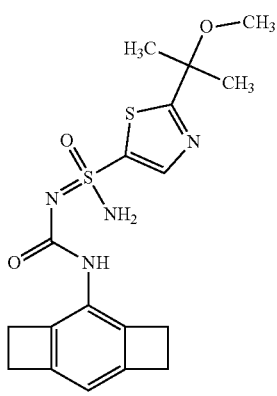 [SMILES: COC(C)(C)c1ncc(S(N)(=O)=NC(=O)Nc2c3c(cc4c2CC4)CC3)s1]
330
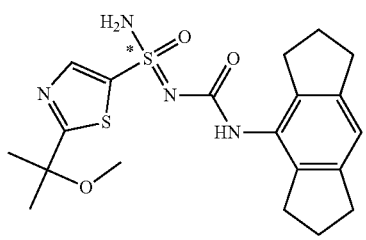 [SMILES: COC(C)(C)c1ncc(S(N)(=O)=NC(=O)Nc2c3c(cc4c2CCC4)CCC3)s1]
330a -continued
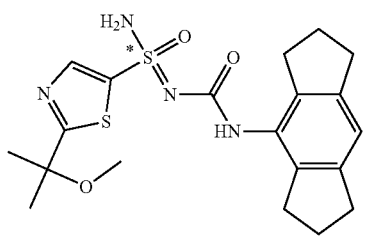 [SMILES: COC(C)(C)c1ncc(S(N)(=O)=NC(=O)Nc2c3c(cc4c2CCC4)CCC3)s1]
330b
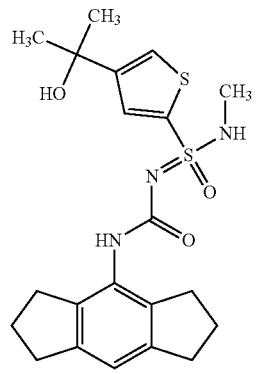 [SMILES: CNS(=O)(=NC(=O)Nc1c2c(cc3c1CCC3)CCC2)c1cc(C(C)(C)O)cs1]
331
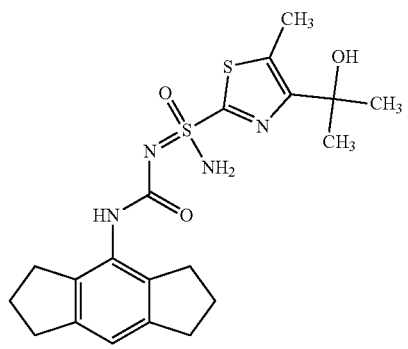 [SMILES: Cc1sc(S(N)(=O)=NC(=O)Nc2c3c(cc4c2CCC4)CCC3)nc1C(C)(C)O]
332
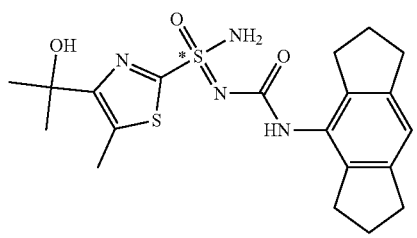 [SMILES: Cc1sc(S(N)(=O)=NC(=O)Nc2c3c(cc4c2CCC4)CCC3)nc1C(C)(C)O]
332a
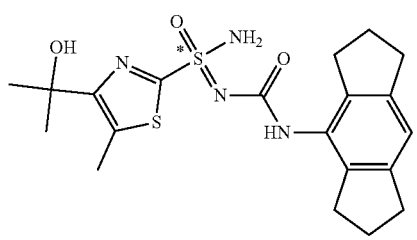 [SMILES: Cc1sc(S(N)(=O)=NC(=O)Nc2c3c(cc4c2CCC4)CCC3)nc1C(C)(C)O]
332b -continued
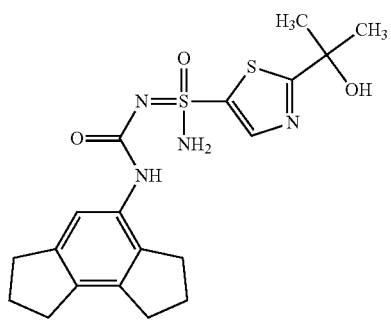 [SMILES: CC(C)(O)c1ncc(S(N)(=O)=NC(=O)Nc2cc3c(c4c2CCC4)CCC3)s1]
333
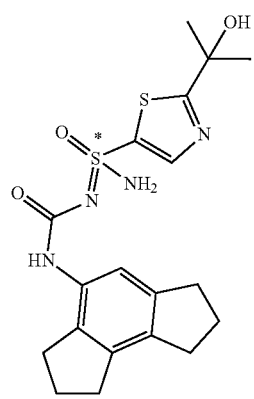 [SMILES: CC(C)(O)c1ncc(S(N)(=O)=NC(=O)Nc2cc3c(c4c2CCC4)CCC3)s1]
333a
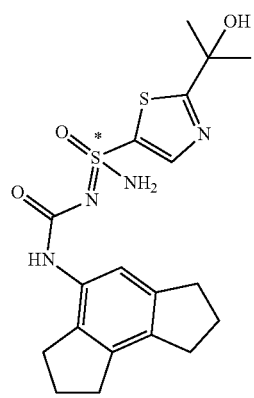 [SMILES: CC(C)(O)c1ncc(S(N)(=O)=NC(=O)Nc2cc3c(c4c2CCC4)CCC3)s1]
333b
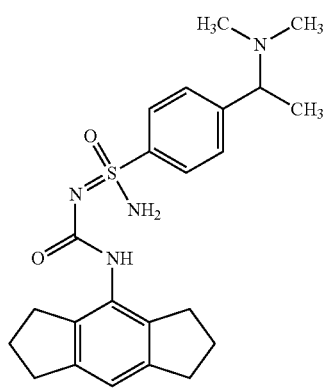 [SMILES: CC(c1ccc(S(N)(=O)=NC(=O)Nc2c3c(cc4c2CCC4)CCC3)cc1)N(C)C]
334

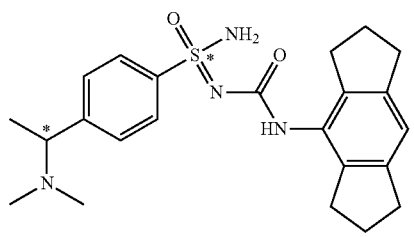 334ba
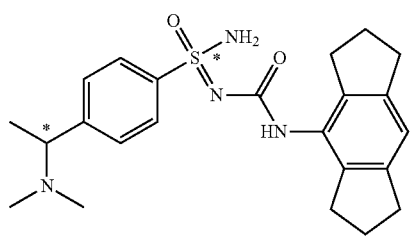 [SMILES: CC(c1ccc(S(N)(=O)=NC(=O)Nc2c3c(cc4c2CCC4)CCC3)cc1)N(C)C] 334bb
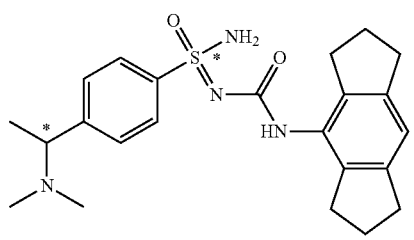 [SMILES: CC(c1ccc(S(N)(=O)=NC(=O)Nc2c3c(cc4c2CCC4)CCC3)cc1)N(C)C] 334aa
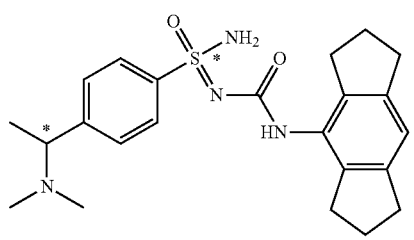 [SMILES: CC(c1ccc(S(N)(=O)=NC(=O)Nc2c3c(cc4c2CCC4)CCC3)cc1)N(C)C] 334ab
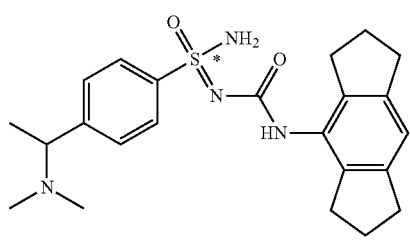 [SMILES: CC(c1ccc(S(N)(=O)=NC(=O)Nc2c3c(cc4c2CCC4)CCC3)cc1)N(C)C] 334b
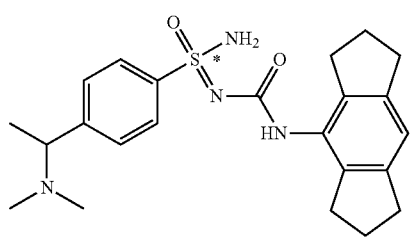 [SMILES: CC(c1ccc(S(N)(=O)=NC(=O)Nc2c3c(cc4c2CCC4)CCC3)cc1)N(C)C] 334a -continued
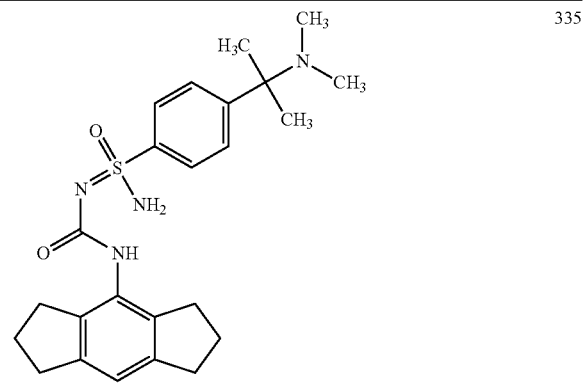
335
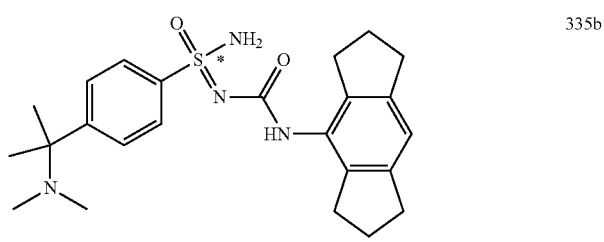
335b
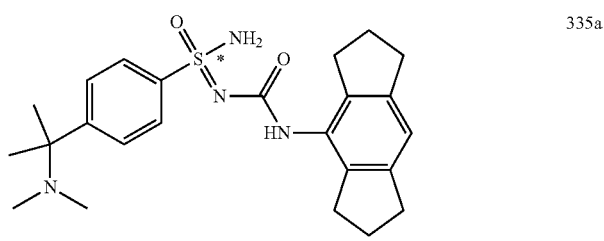
335a
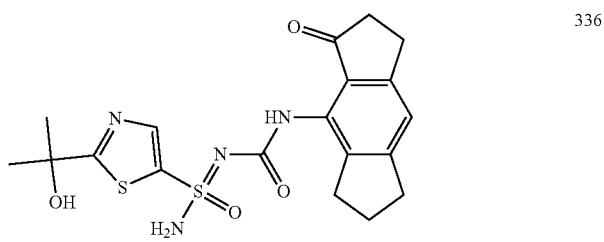
336
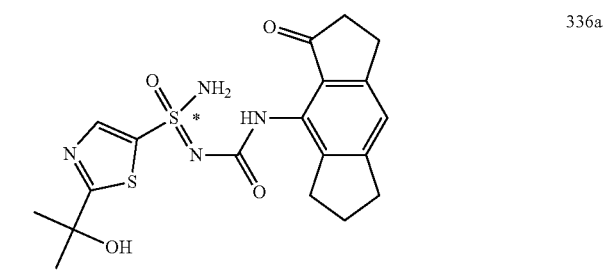
336a
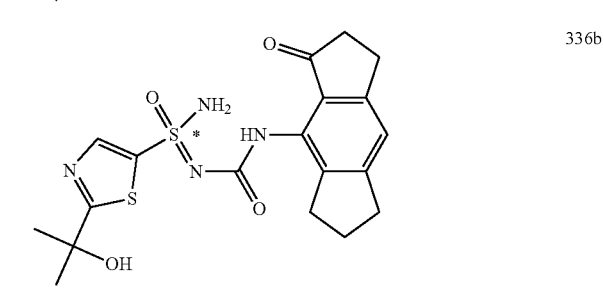
336b -continued
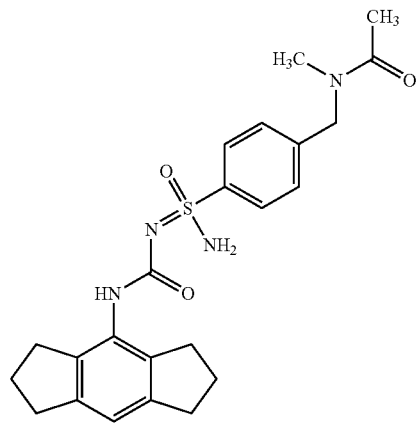 [SMILES: CC(=O)N(C)Cc1ccc(S(N)(=O)=NC(=O)Nc2c3c(cc4c2CCC4)CCC3)cc1]
337
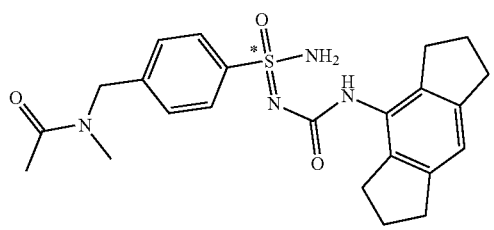 [SMILES: CC(=O)N(C)Cc1ccc(S(N)(=O)=NC(=O)Nc2c3c(cc4c2CCC4)CCC3)cc1]
337a
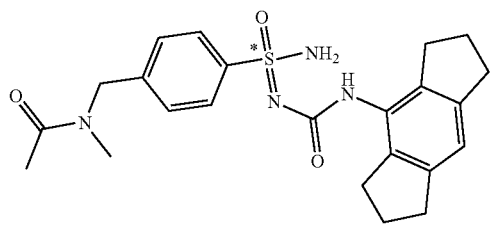 [SMILES: CC(=O)N(C)Cc1ccc(S(N)(=O)=NC(=O)Nc2c3c(cc4c2CCC4)CCC3)cc1]
337b
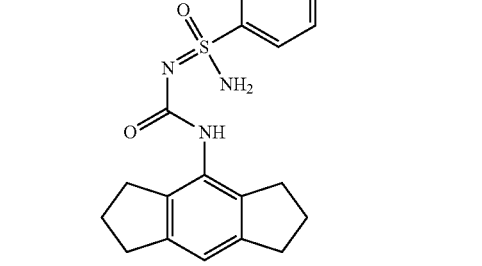
338
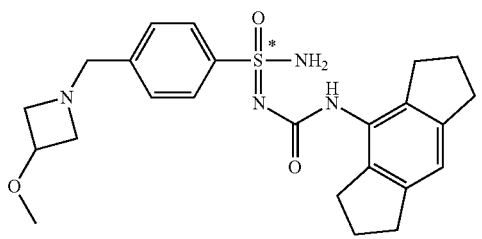
338a -continued
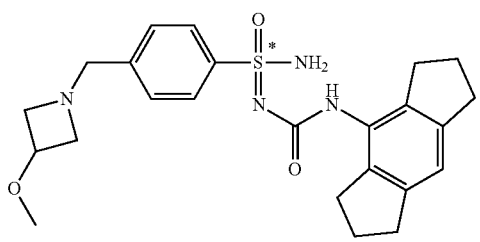
338b
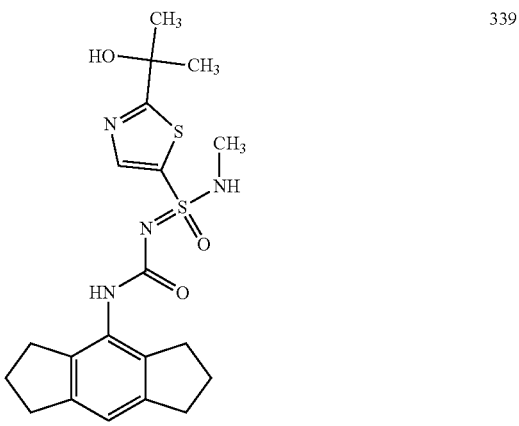
339
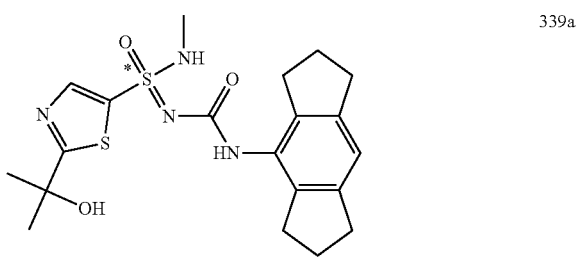
339a
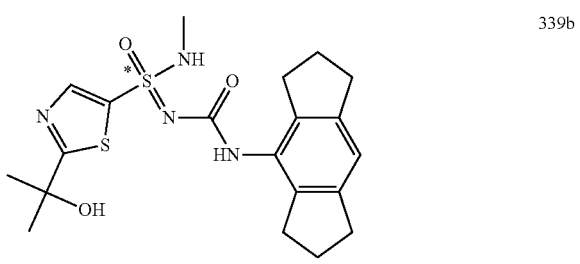
339b
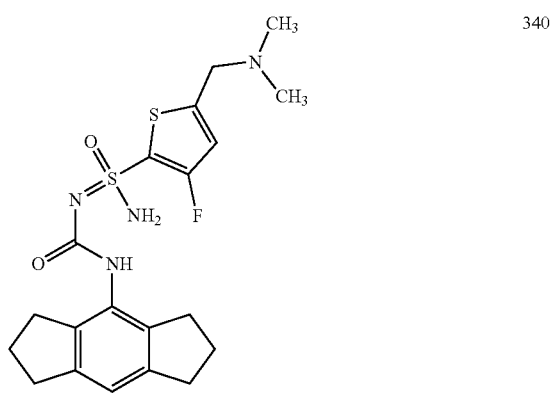
340

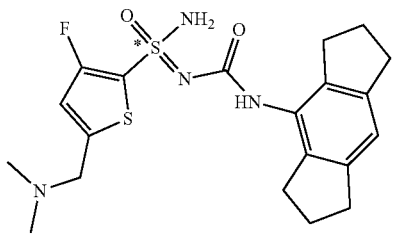 [SMILES: CN(C)Cc1cc(F)c(S(N)(=O)=NC(=O)Nc2c3c(cc4c2CCC4)CCC3)s1]
340a
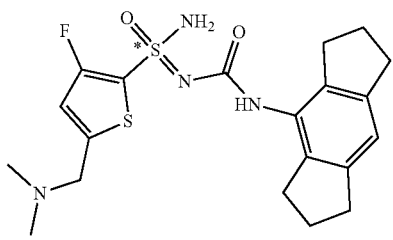 [SMILES: CN(C)Cc1cc(F)c(S(N)(=O)=NC(=O)Nc2c3c(cc4c2CCC4)CCC3)s1]
340b
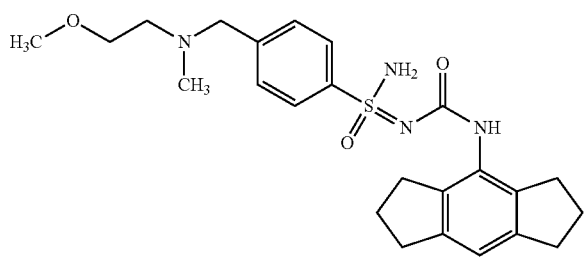 [SMILES: COCCN(C)Cc1ccc(S(N)(=O)=NC(=O)Nc2c3c(cc4c2CCC4)CCC3)cc1]
341
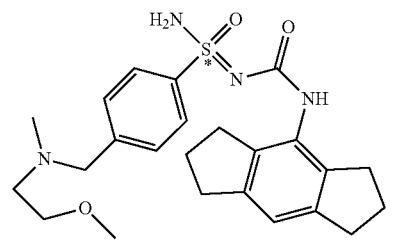 [SMILES: COCCN(C)Cc1ccc(S(N)(=O)=NC(=O)Nc2c3c(cc4c2CCC4)CCC3)cc1]
341b
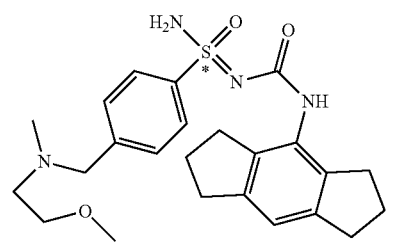 [SMILES: COCCN(C)Cc1ccc(S(N)(=O)=NC(=O)Nc2c3c(cc4c2CCC4)CCC3)cc1]
341a
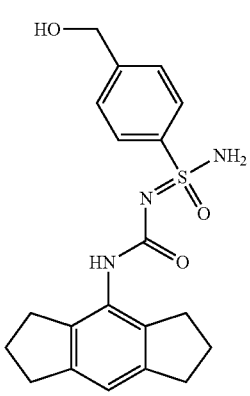 [SMILES: NS(=O)(=NC(=O)Nc1c2c(cc3c1CCC3)CCC2)c1ccc(CO)cc1]
342

-continued
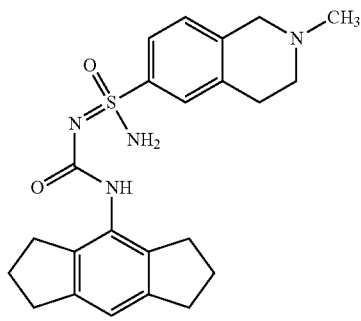 [SMILES: CN1CCc2cc(S(N)(=O)=NC(=O)Nc3c4c(cc5c3CCC5)CCC4)ccc2C1]
343
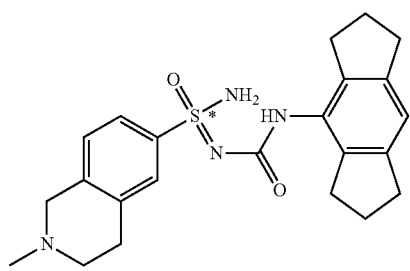 [SMILES: CN1CCc2cc(S(N)(=O)=NC(=O)Nc3c4c(cc5c3CCC5)CCC4)ccc2C1]
343a
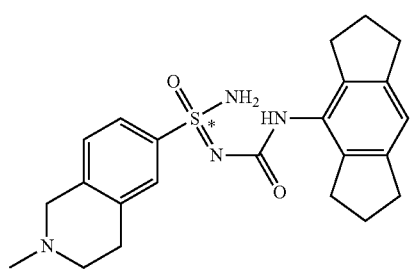 [SMILES: CN1CCc2cc(S(N)(=O)=NC(=O)Nc3c4c(cc5c3CCC5)CCC4)ccc2C1]
343b
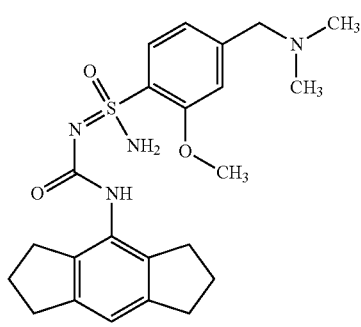 [SMILES: COc1cc(CN(C)C)ccc1S(N)(=O)=NC(=O)Nc1c2c(cc3c1CCC3)CCC2]
344

345
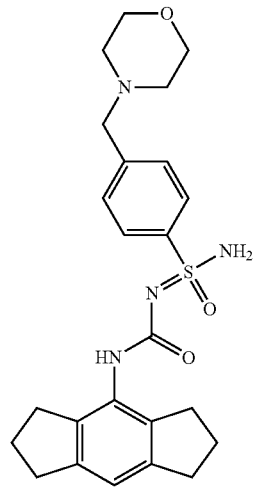 [SMILES: NS(=O)(=NC(=O)Nc1c2c(cc3c1CCC3)CCC2)c1ccc(CN2CCOCC2)cc1]
346
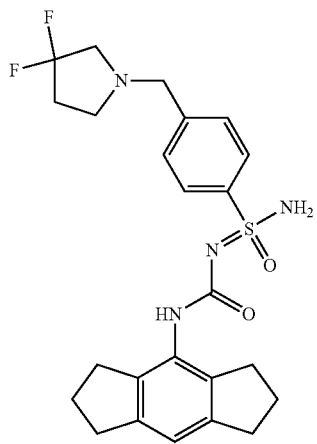 [SMILES: NS(=O)(=NC(=O)Nc1c2c(cc3c1CCC3)CCC2)c1ccc(CN2CCC(F)(F)C2)cc1]
347
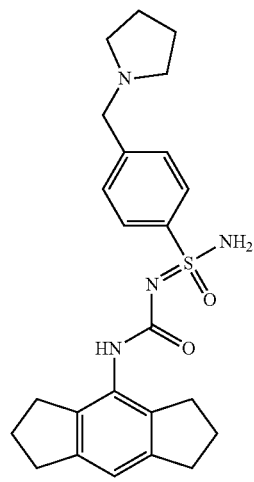 [SMILES: NS(=O)(=NC(=O)Nc1c2c(cc3c1CCC3)CCC2)c1ccc(CN2CCCC2)cc1]

348
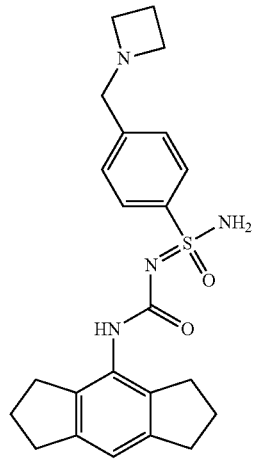 [SMILES: NS(=O)(=NC(=O)Nc1c2c(cc3c1CCC3)CCC2)c1ccc(CN2CCC2)cc1]
349
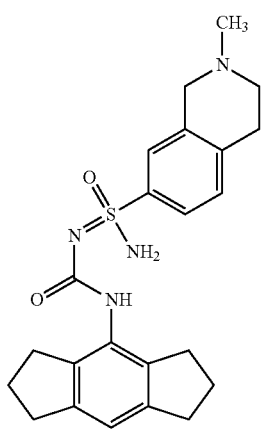 [SMILES: CN1CCc2ccc(S(N)(=O)=NC(=O)Nc3c4c(cc5c3CCC5)CCC4)cc2C1]
350
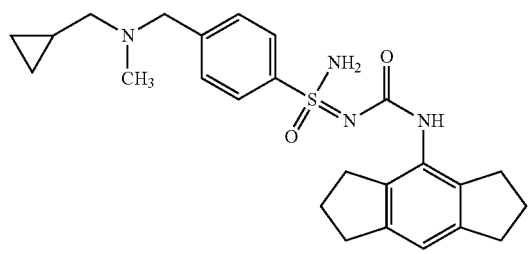 [SMILES: CN(Cc1ccc(S(N)(=O)=NC(=O)Nc2c3c(cc4c2CCC4)CCC3)cc1)CC1CC1]
351
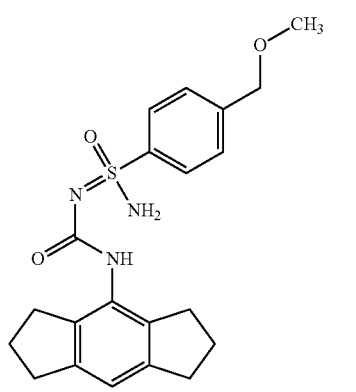 [SMILES: COCc1ccc(S(N)(=O)=NC(=O)Nc2c3c(cc4c2CCC4)CCC3)cc1]

-continued
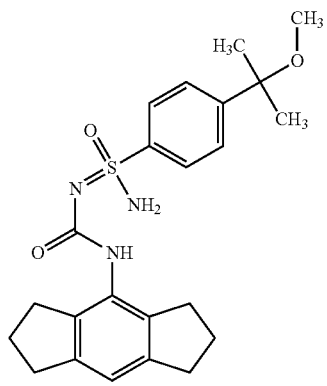 [SMILES: COC(C)(C)c1ccc(S(N)(=O)=NC(=O)Nc2c3c(cc4c2CCC4)CCC3)cc1]
352
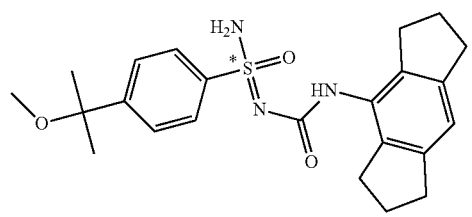 [SMILES: COC(C)(C)c1ccc(S(N)(=O)=NC(=O)Nc2c3c(cc4c2CCC4)CCC3)cc1]
352b
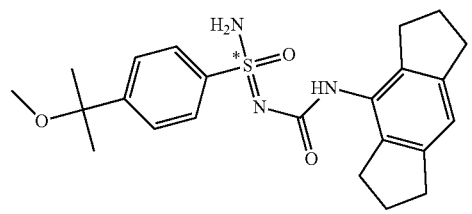 [SMILES: COC(C)(C)c1ccc(S(N)(=O)=NC(=O)Nc2c3c(cc4c2CCC4)CCC3)cc1]
352a
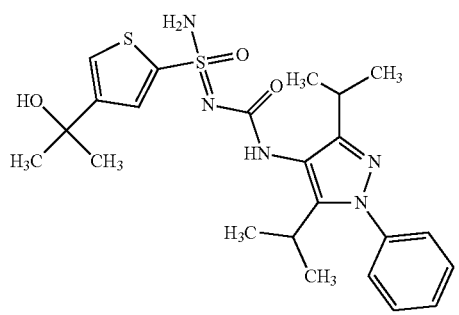 [SMILES: CC(C)c1nn(-c2ccccc2)c(C(C)C)c1NC(=O)N=S(N)(=O)c1cc(C(C)(C)O)cs1]
353
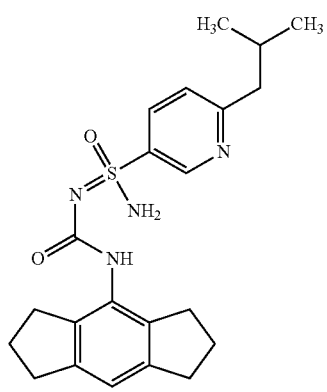 [SMILES: CC(C)Cc1ccc(S(N)(=O)=NC(=O)Nc2c3c(cc4c2CCC4)CCC3)cn1]
354

-continued
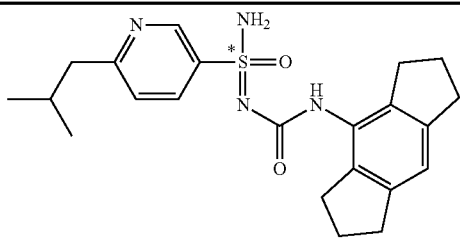
354a
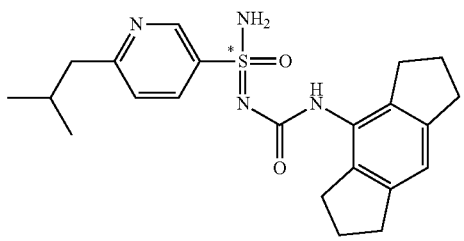
354b
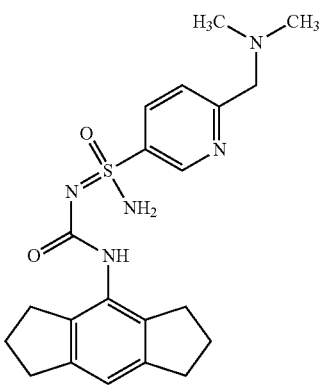 [SMILES: CN(C)Cc1ccc(S(N)(=O)=NC(=O)Nc2c3c(cc4c2CCC4)CCC3)cn1]
355
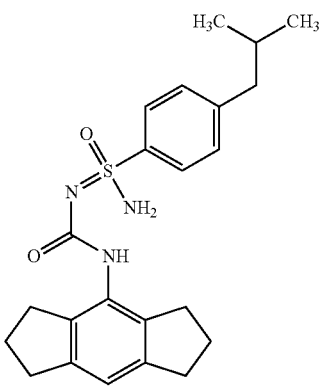 [SMILES: CC(C)Cc1ccc(S(N)(=O)=NC(=O)Nc2c3c(cc4c2CCC4)CCC3)cc1]
356
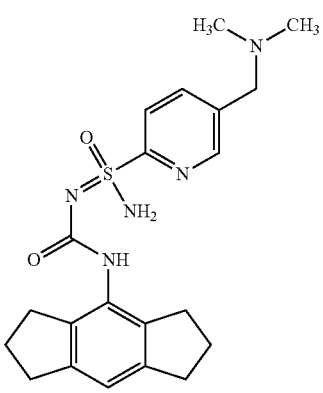 [SMILES: CN(C)Cc1ccc(S(N)(=O)=NC(=O)Nc2c3c(cc4c2CCC4)CCC3)nc1]
357

-continued
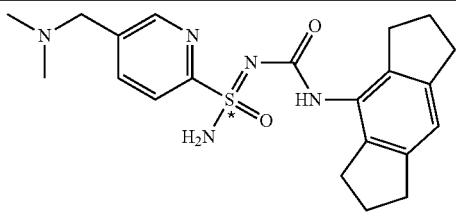
357a
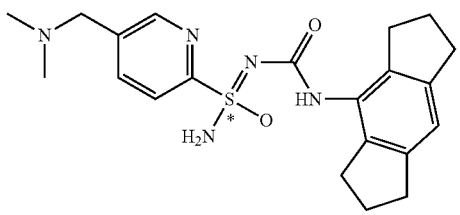
357b
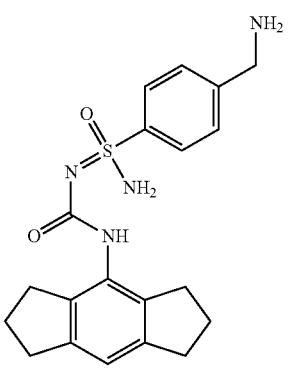 [SMILES: NCc1ccc(S(N)(=O)=NC(=O)Nc2c3c(cc4c2CCC4)CCC3)cc1]
358
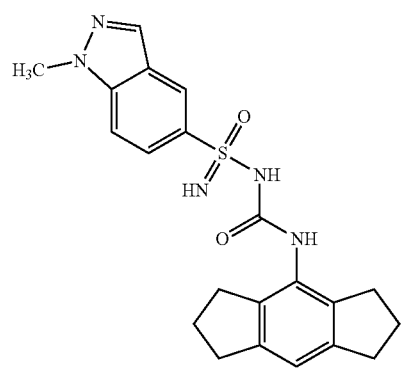 [SMILES: Cn1ncc2cc(S(=N)(=O)NC(=O)Nc3c4c(cc5c3CCC5)CCC4)ccc21]
359
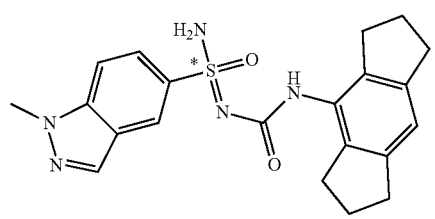 [SMILES: Cn1ncc2cc(S(N)(=O)=NC(=O)Nc3c4c(cc5c3CCC5)CCC4)ccc21]
359a
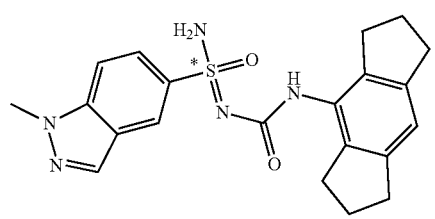 [SMILES: Cn1ncc2cc(S(N)(=O)=NC(=O)Nc3c4c(cc5c3CCC5)CCC4)ccc21]
359b

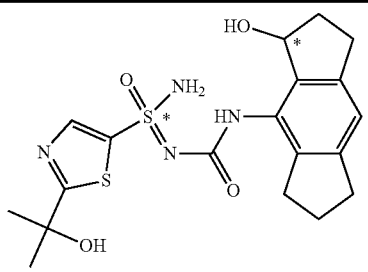
360ba
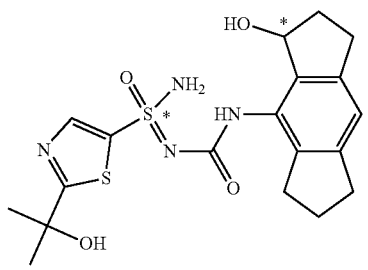 [SMILES: CC(C)(O)c1ncc(S(N)(=O)=NC(=O)Nc2c3c(cc4c2C(O)CC4)CCC3)s1]
360bb
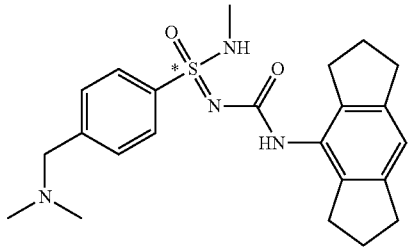 [SMILES: CNS(=O)(=NC(=O)Nc1c2c(cc3c1CCC3)CCC2)c1ccc(CN(C)C)cc1]
361b
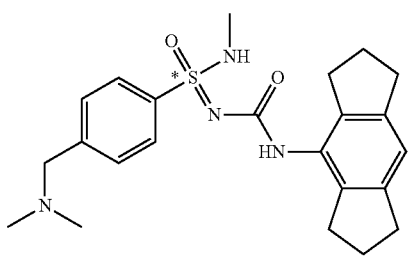
361a
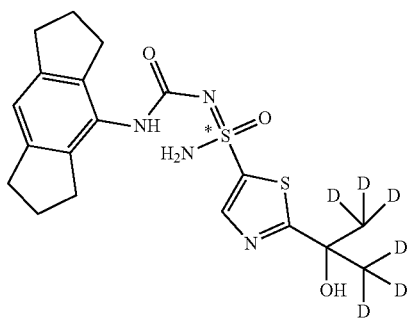 [SMILES: [2H]C([2H])([2H])C(O)(c1ncc(S(N)(=O)=NC(=O)Nc2c3c(cc4c2CCC4)CCC3)s1)C([2H])([2H])[2H]]
363b
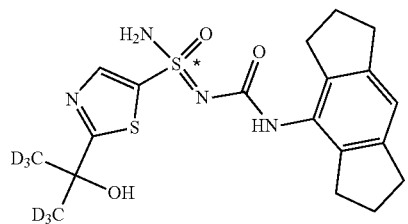 [SMILES: [2H]C([2H])([2H])C(O)(c1ncc(S(N)(=O)=NC(=O)Nc2c3c(cc4c2CCC4)CCC3)s1)C([2H])([2H])[2H]]
363a -continued
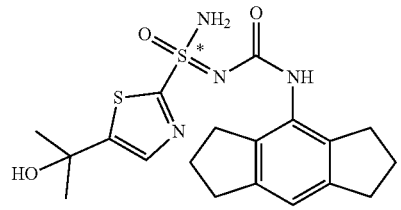 [SMILES: CC(C)(O)c1cnc(S(N)(=O)=NC(=O)Nc2c3c(cc4c2CCC4)CCC3)s1]
364a
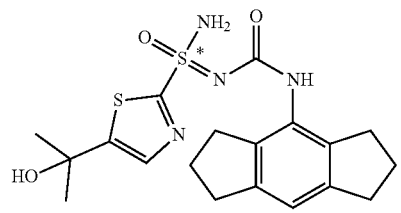 [SMILES: CC(C)(O)c1cnc(S(N)(=O)=NC(=O)Nc2c3c(cc4c2CCC4)CCC3)s1]
364b
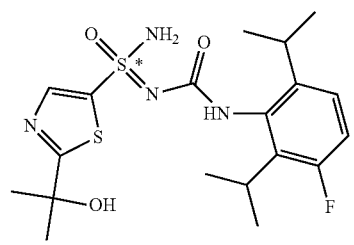 [SMILES: CC(C)c1ccc(F)c(C(C)C)c1NC(=O)N=S(N)(=O)c1cnc(C(C)(C)O)s1]
365a
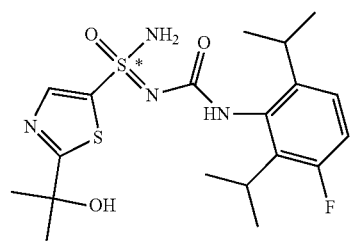 [SMILES: CC(C)c1ccc(F)c(C(C)C)c1NC(=O)N=S(N)(=O)c1cnc(C(C)(C)O)s1]
365b
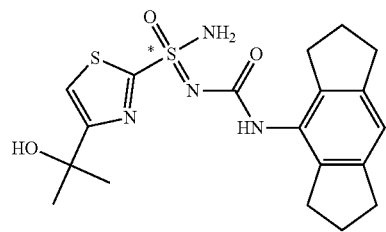 [SMILES: CC(C)(O)c1csc(S(N)(=O)=NC(=O)Nc2c3c(cc4c2CCC4)CCC3)n1]
366a
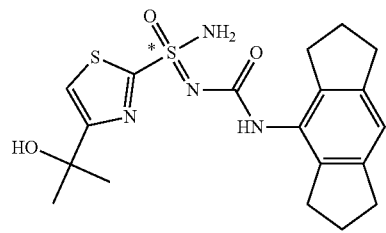
366b
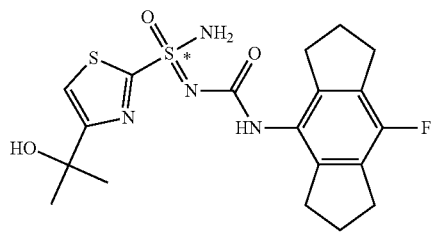
367a -continued
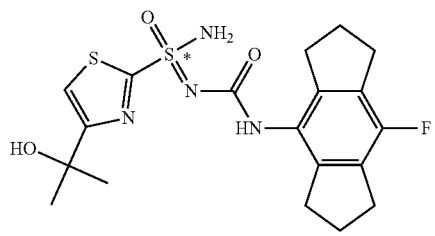 [SMILES: CC(C)(O)c1csc(S(N)(=O)=NC(=O)Nc2c3c(c(F)c4c2CCC4)CCC3)n1]
367b
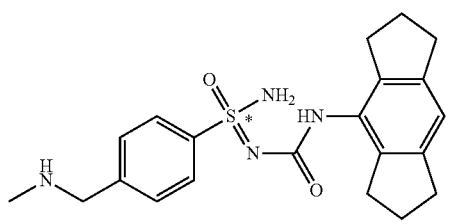
369a
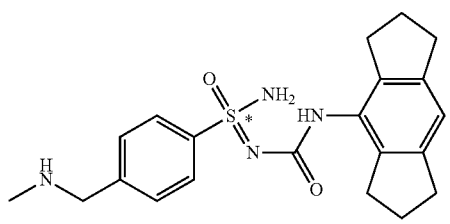 [SMILES: CNCc1ccc(S(N)(=O)=NC(=O)Nc2c3c(cc4c2CCC4)CCC3)cc1]
369b
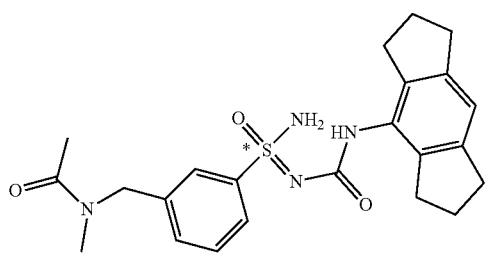 [SMILES: CC(=O)N(C)Cc1cccc(S(N)(=O)=NC(=O)Nc2c3c(cc4c2CCC4)CCC3)c1]
371a
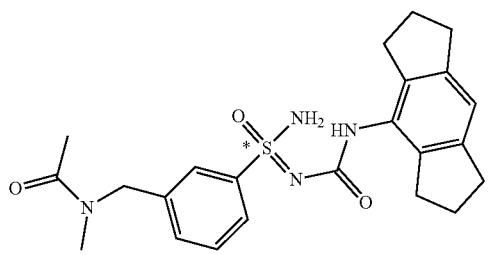 [SMILES: CC(=O)N(C)Cc1cccc(S(N)(=O)=NC(=O)Nc2c3c(cc4c2CCC4)CCC3)c1]
371b
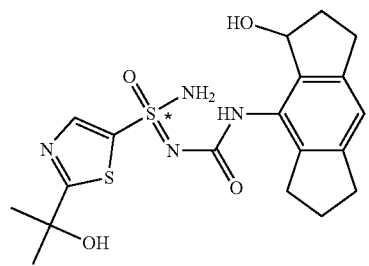 [SMILES: CC(C)(O)c1ncc(S(N)(=O)=NC(=O)Nc2c3c(cc4c2C(O)CC4)CCC3)s1]
372a -continued
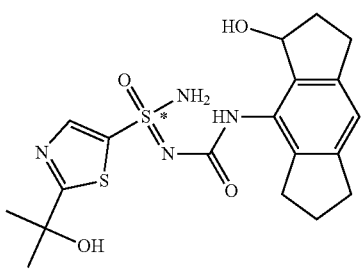 [SMILES: CC(C)(O)c1ncc(S(N)(=O)=NC(=O)Nc2c3c(cc4c2C(O)CC4)CCC3)s1]
372b
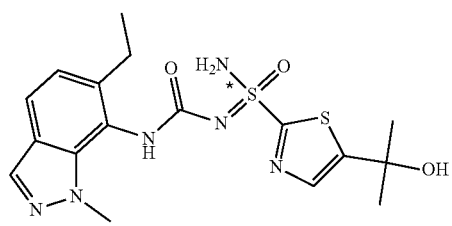 [SMILES: CCc1ccc2cnn(C)c2c1NC(=O)N=S(N)(=O)c1ncc(C(C)(C)O)s1]
373a
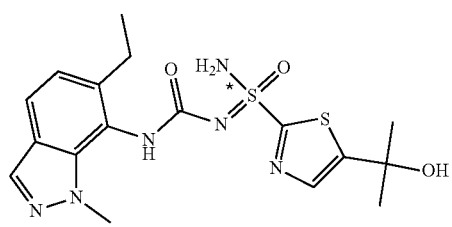 [SMILES: CCc1ccc2cnn(C)c2c1NC(=O)N=S(N)(=O)c1ncc(C(C)(C)O)s1]
373b
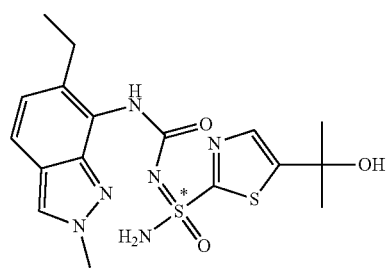 [SMILES: CCc1ccc2cn(C)nc2c1NC(=O)N=S(N)(=O)c1ncc(C(C)(C)O)s1]
374a
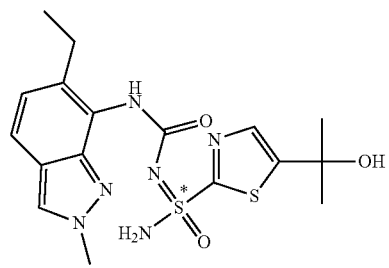 [SMILES: CCc1ccc2cn(C)nc2c1NC(=O)N=S(N)(=O)c1ncc(C(C)(C)O)s1]
374b
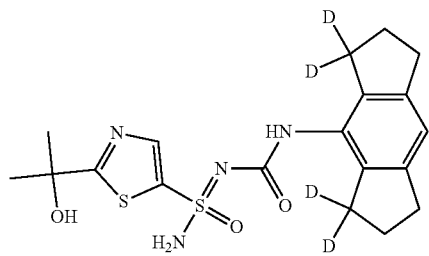 [SMILES: [2H]C1([2H])CCc2cc3c(c(NC(=O)N=S(N)(=O)c4cnc(C(C)(C)O)s4)c21)C([2H])([2H])CC3]
375

-continued
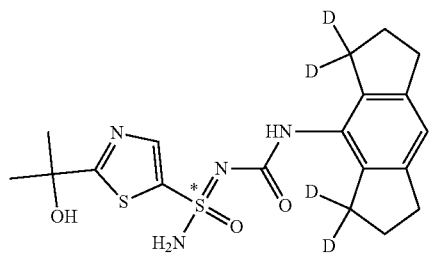 [SMILES: [2H]C1([2H])CCc2cc3c(c(NC(=O)N=S(N)(=O)c4cnc(C(C)(C)O)s4)c21)C([2H])([2H])CC3]
375a
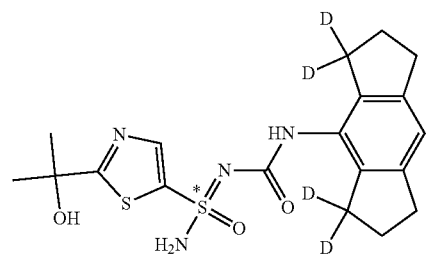 [SMILES: [2H]C1([2H])CCc2cc3c(c(NC(=O)N=S(N)(=O)c4cnc(C(C)(C)O)s4)c21)C([2H])([2H])CC3]
375b
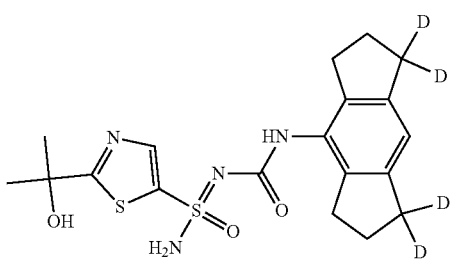 [SMILES: [2H]C1([2H])CCc2c1cc1c(c2NC(=O)N=S(N)(=O)c2cnc(C(C)(C)O)s2)CCC1([2H])[2H]]
376
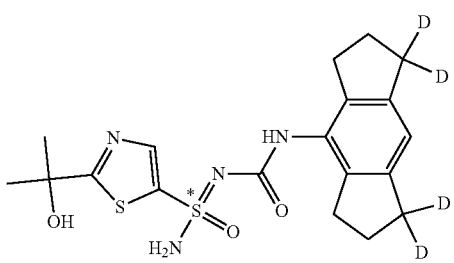 [SMILES: [2H]C1([2H])CCc2c1cc1c(c2NC(=O)N=S(N)(=O)c2cnc(C(C)(C)O)s2)CCC1([2H])[2H]]
376a
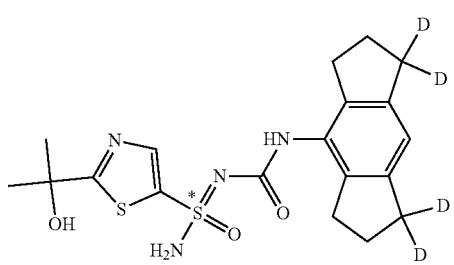 [SMILES: [2H]C1([2H])CCc2c1cc1c(c2NC(=O)N=S(N)(=O)c2cnc(C(C)(C)O)s2)CCC1([2H])[2H]]
376b
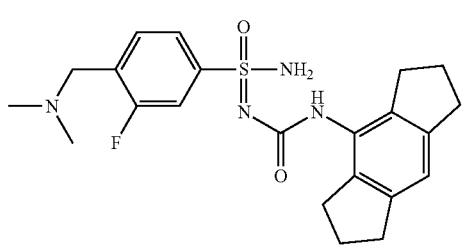 [SMILES: CN(C)Cc1ccc(S(N)(=O)=NC(=O)Nc2c3c(cc4c2CCC4)CCC3)cc1F]
377

| | |
|---|---|
| 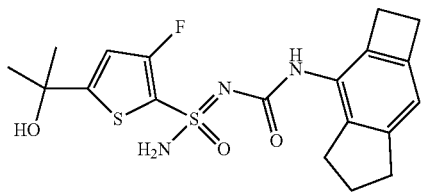 [SMILES: CC(C)(O)c1cc(F)c(S(N)(=O)=NC(=O)Nc2c3c(cc4c2CC4)CCC3)s1] | 378 |
| 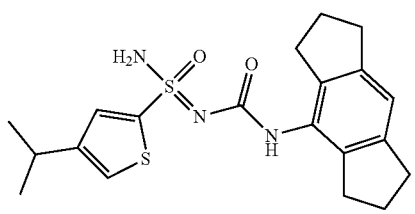 [SMILES: CC(C)c1csc(S(N)(=O)=NC(=O)Nc2c3c(cc4c2CCC4)CCC3)c1] | 379 |
| 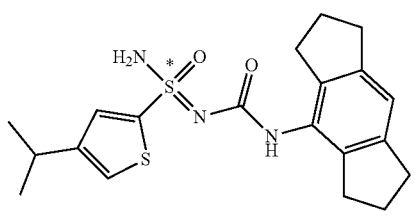 [SMILES: CC(C)c1csc(S(N)(=O)=NC(=O)Nc2c3c(cc4c2CCC4)CCC3)c1] | 379a |
| 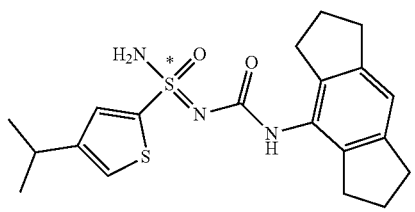 [SMILES: CC(C)c1csc(S(N)(=O)=NC(=O)Nc2c3c(cc4c2CCC4)CCC3)c1] | 379b |
| 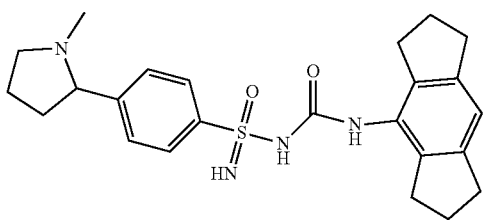 [SMILES: CN1CCCC1c1ccc(S(=N)(=O)NC(=O)Nc2c3c(cc4c2CCC4)CCC3)cc1] | 380 |
| 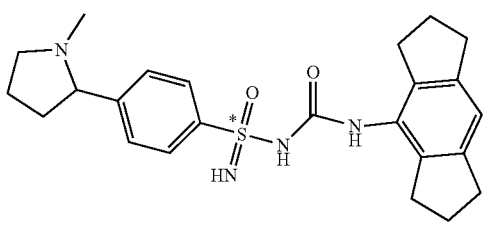 [SMILES: CN1CCCC1c1ccc(S(=N)(=O)NC(=O)Nc2c3c(cc4c2CCC4)CCC3)cc1] | 380a |
| 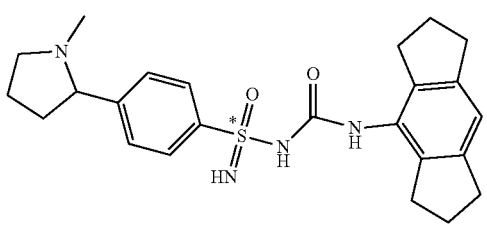 [SMILES: CN1CCCC1c1ccc(S(=N)(=O)NC(=O)Nc2c3c(cc4c2CCC4)CCC3)cc1] | 380b |

-continued
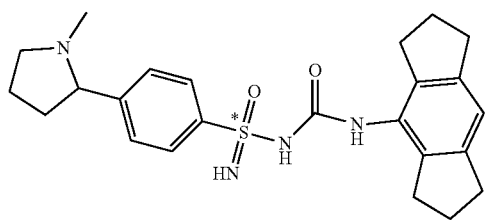 [SMILES: CN1CCCC1c1ccc(S(=N)(=O)NC(=O)Nc2c3c(cc4c2CCC4)CCC3)cc1]
380c
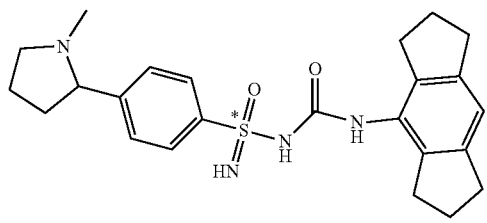 [SMILES: CN1CCCC1c1ccc(S(=N)(=O)NC(=O)Nc2c3c(cc4c2CCC4)CCC3)cc1]
380d
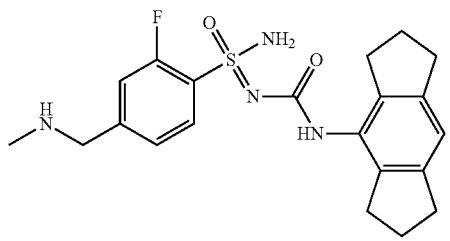
382
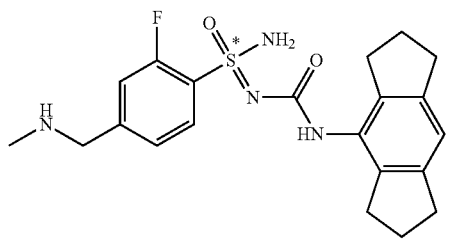 [SMILES: CNCc1ccc(S(N)(=O)=NC(=O)Nc2c3c(cc4c2CCC4)CCC3)c(F)c1]
382a
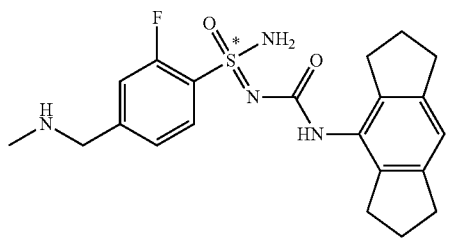 [SMILES: CNCc1ccc(S(N)(=O)=NC(=O)Nc2c3c(cc4c2CCC4)CCC3)c(F)c1]
382b
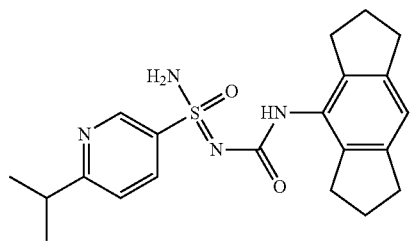
383

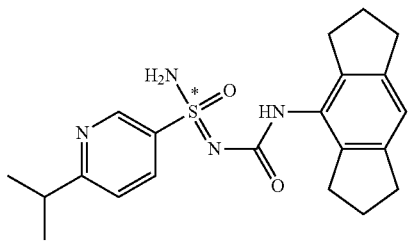
383a
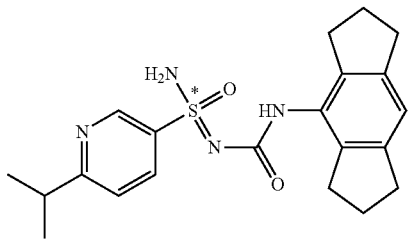
383b
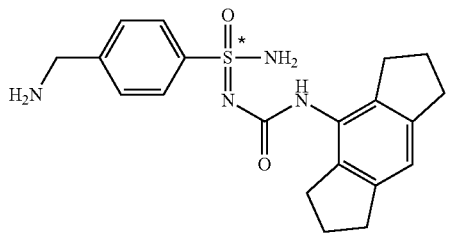 [SMILES: NCc1ccc(S(N)(=O)=NC(=O)Nc2c3c(cc4c2CCC4)CCC3)cc1]
384a
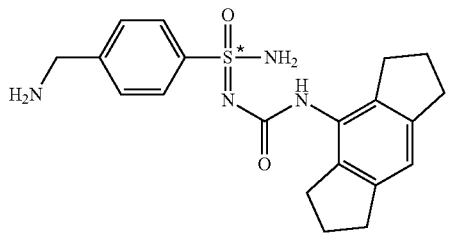 [SMILES: NCc1ccc(S(N)(=O)=NC(=O)Nc2c3c(cc4c2CCC4)CCC3)cc1]
384b
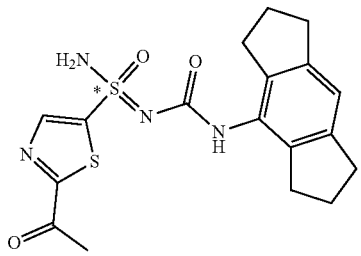 [SMILES: CC(=O)c1ncc(S(N)(=O)=NC(=O)Nc2c3c(cc4c2CCC4)CCC3)s1]
387a
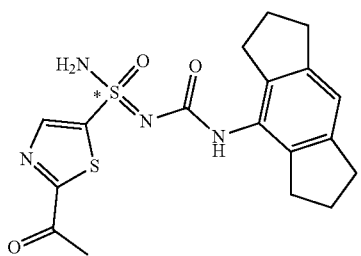 [SMILES: CC(=O)c1ncc(S(N)(=O)=NC(=O)Nc2c3c(cc4c2CCC4)CCC3)s1]
387b
and pharmaceutically acceptable salts thereof.
In some embodiments, provided herein is a compound that is selected from the group consisting of the compounds in the following table:

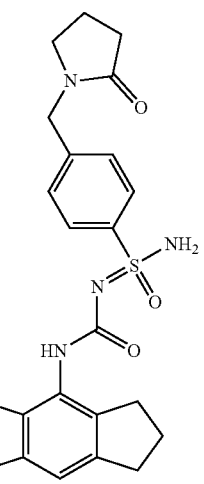
401
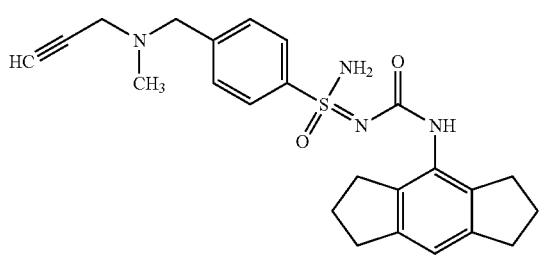 [SMILES: C#CCN(C)Cc1ccc(S(N)(=O)=NC(=O)Nc2c3c(cc4c2CCC4)CCC3)cc1]
402
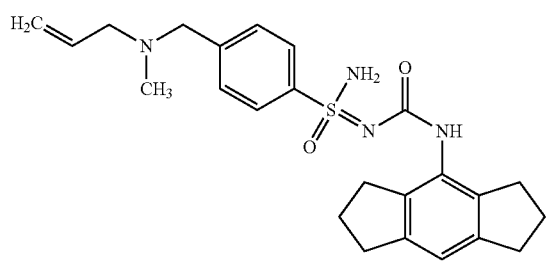 [SMILES: C=CCN(C)Cc1ccc(S(N)(=O)=NC(=O)Nc2c3c(cc4c2CCC4)CCC3)cc1]
403
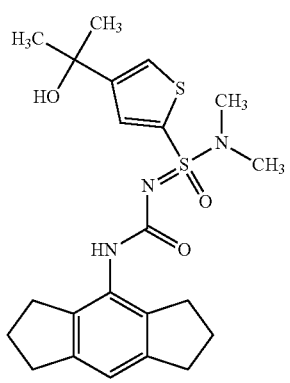 [SMILES: CN(C)S(=O)(=NC(=O)Nc1c2c(cc3c1CCC3)CCC2)c1cc(C(C)(C)O)cs1]
404
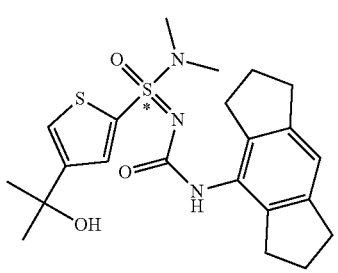 [SMILES: CN(C)S(=O)(=NC(=O)Nc1c2c(cc3c1CCC3)CCC2)c1cc(C(C)(C)O)cs1]
404a -continued
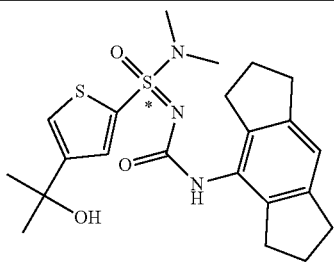
404b
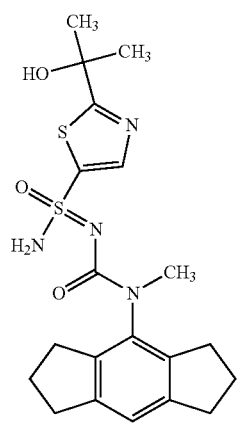
405
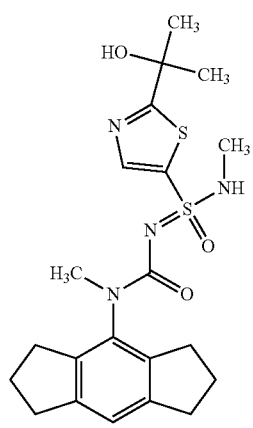 [SMILES: CNS(=O)(=NC(=O)N(C)c1c2c(cc3c1CCC3)CCC2)c1cnc(C(C)(C)O)s1]
406
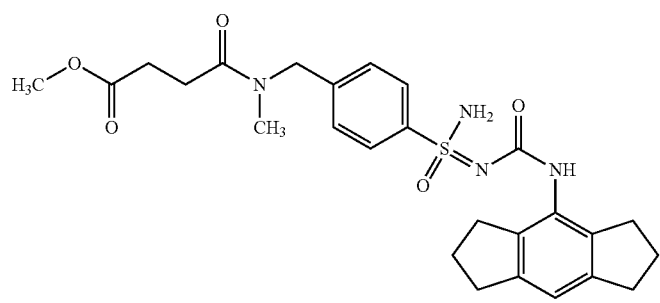 [SMILES: COC(=O)CCC(=O)N(C)Cc1ccc(S(N)(=O)=NC(=O)Nc2c3c(cc4c2CCC4)CCC3)cc1]
407
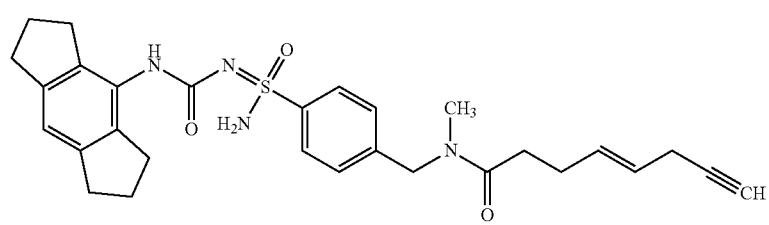 [SMILES: C#CC/C=C/CCC(=O)N(C)Cc1ccc(S(N)(=O)=NC(=O)Nc2c3c(cc4c2CCC4)CCC3)cc1]
408

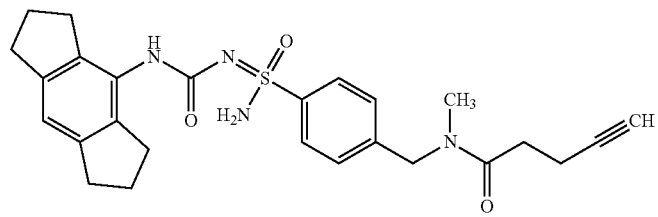 [SMILES: C#CCCC(=O)N(C)Cc1ccc(S(N)(=O)=NC(=O)Nc2c3c(cc4c2CCC4)CCC3)cc1]

409

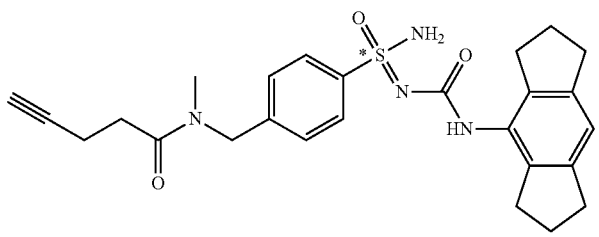 [SMILES: C#CCCC(=O)N(C)Cc1ccc(S(N)(=O)=NC(=O)Nc2c3c(cc4c2CCC4)CCC3)cc1]

409a

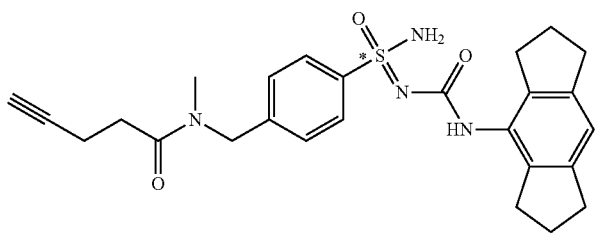 [SMILES: C#CCCC(=O)N(C)Cc1ccc(S(N)(=O)=NC(=O)Nc2c3c(cc4c2CCC4)CCC3)cc1]

409b

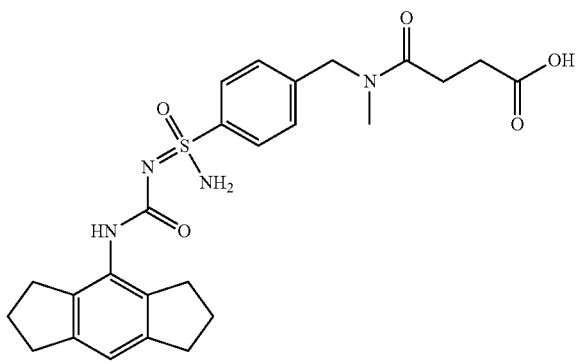 [SMILES: CN(Cc1ccc(S(N)(=O)=NC(=O)Nc2c3c(cc4c2CCC4)CCC3)cc1)C(=O)CCC(=O)O]

410

Pharmaceutical Compositions and Administration

General

In some embodiments, a chemical entity (e.g., a compound that modulates (e.g., antagonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, $22^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" *Neoplasia*. 2006, 10, 788-795.

In certain embodiments, the chemical entities described herein or a pharmaceutical composition thereof are suitable for local, topical administration to the digestive or GI tract, e.g., rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-coglycolic acid) [PLGA]-based or poly anhydride-based nanoparticles or microparticles, and nanoporous particle-supported lipid bilayers.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (i) and (ii) are combined to form the desired enema formulation, e.g., as a suspension. In other embodiments, each of component (i) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selected from thickeners, viscosity enhancing agents, bulking agents, mucoadhesive agents, penetration enhanceers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selected from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selected from thickeners, viscosity enhancing agents, bulking agents, mucoadhesive agents, buffers, preservatives, and fillers.

In certain embodiments, each of the one or more pharmaceutically acceptable excipients can be independently selected from diluents, binders, lubricants, glidants, and disintegrants.

Examples of thickeners, viscosity enhancing agents, and mucoadhesive agents include without limitation: gums, e.g. xanthan gum, guar gum, locust bean gum, tragacanth gums, karaya gum, ghatti gum, cholla gum, psyllium seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof; clays such as montmorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof Examples of buffers include without limitation: phosphate buffer system (sodium dihydrogen phospahate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, polysorbate 80 (polyoxyethylenesorbitan oleate), starch, sodium starch glycolate, hydroxypropyl cellulose pregelatinized starch, clays, cellulose, alginine, gums or cross linked polymers, such as cross-linked PVP (Polyplasdone XL from GAF Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: dicalcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dxtrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone (povidone).

In some embodiments, enema formulations containing the chemical entities described herein include water and one or more (e.g., all) of the following excipients:

One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof;

One or more (e.g., one or two; e.g., two) buffers, such as phosphate buffer system (e.g., sodium dihydrogen phospahate dehydrate, disodium phosphate dodecahydrate);

One or more (e.g., one or two, e.g., two) glidants and/or lubricants, such as magnesium stearate and/or talc;

One or more (e.g., one or two; e.g., one) disintegrants, such as crospovidone; and One or more (e.g., one or two; e.g., one) diluents, such as lactose (e.g., lactose monohydrate).

In certain of these embodiments, the chemical entity is a compound of Formula AA, or a pharmaceutically acceptable salt and/or hydrate and/or cocrystal thereof.

In certain embodiments, enema formulations containing the chemical entities described herein include water, methyl cellulose, povidone, methylparaben, propylparaben, sodium dihydrogen phospahate dehydrate, disodium phosphate dodecahydrate, crospovidone, lactose monohydrate, magnesium stearate, and talc. In certain of these embodiments, the chemical entity is a compound of Formula AA, or a pharmaceutically acceptable salt and/or hydrate and/or cocrystal thereof.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more one or more other pharmaceutically acceptable excipients together forming a liquid carrier. In other embodiments, each of component (i) and (ii) is provided in its own separate kit or pack.

In certain of these embodiments, component (i) includes the chemical entity (e.g., a compound of Formula AA, or a pharmaceutically acceptable salt and/or hydrate and/or cocrystal thereof; e.g., a compound of Formula AA) and one or more (e.g., all) of the following excipients:

(a) One or more (e.g., one) binders (e.g., a polyvinyl polymer, such as polyvinylpyrrolidone (povidone);

(b) One or more (e.g., one or two, e.g., two) glidants and/or lubricants, such as magnesium stearate and/or talc;

(c) One or more (e.g., one or two; e.g., one) disintegrants, such as crospovidone; and (d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) of the chemical entity (e.g., a compound of Formula AA, or a pharmaceutically acceptable salt and/or hydrate and/or cocrystal thereof).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table A.

TABLE A

| Ingredient | Weight Percent |
| --- | --- |
| A compound of Formula AA | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |

TABLE A-continued

| Ingredient | Weight Percent |
|---|---|
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (i) includes the ingredients and amounts as shown in Table B.

TABLE B

| Ingredient | Weight Percent |
|---|---|
| A compound of Formula AA | About 62.1 weight percent) |
| Crospovidone (Kollidon CL) | About 1.93 weight percent |
| lactose monohydrate (Pharmatose 200M) | About 31.03 weight percent |
| Povidone (Kollidon K30) | About 2.76 weight percent |
| talc | About 1.93 weight percent |
| Magnesium stearate | About 0.27 weight percent |

In certain embodiments, component (i) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. It is believed that lubrication of the granulation is important to the flowability of the granulation, in particular for packaging.

In certain of the foregoing embodiments, component (ii) includes water and one or more (e.g., all) of the following excipients:
(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);
(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof; and
(c') One or more (e.g., one or two; e.g., two) buffers, such as phosphate buffer system (e.g., sodium dihydrogen phospahate dihydrate, disodium phosphate dodecahydrate);

In certain of the foregoing embodiments, component (ii) includes water and one or more (e.g., all) of the following excipients:
(a") a first thickener, viscosity enhancing agent, binder, and/or mucoadhesive agent (e.g., a cellulose or cellulose ester or ether or derivative or salt thereof (e.g., methyl cellulose));
(a''') a second thickener, viscosity enhancing agent, binder, and/or mucoadhesive agent (e.g., a polyvinyl polymer, such as polyvinylpyrrolidone (povidone));
(b") a first preservative, such as a paraben, e.g., propyl 4-hydroxybenzoate (propylparaben), or a pharmaceutically acceptable salt or ester thereof;
(b''') a second preservative, such as a paraben, e.g., methyl 4-hydroxybenzoate (methylparaben), or a pharmaceutically acceptable salt or ester thereof,
(c") a first buffer, such as phosphate buffer system (e.g., disodium phosphate dodecahydrate);
(c''') a second buffer, such as phosphate buffer system (e.g., sodium dihydrogen phospahate dehydrate), In certain embodiments, component (ii) includes from about 0.05 weight percent to about weight percent (e.g., from about 0.05 weight percent to about 3 weight percent, from about 0.1 weight percent to about 3 weight percent; e.g., about 1.4 weight percent) of (a").

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a''').

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b''').

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c''').

In certain of these embodiments, each of (a")-(c''') is present.

In certain embodiments, component (ii) includes water (up to 100%) and the ingredients and amounts as shown in Table C.

TABLE C

| Ingredient | Weight Percent |
|---|---|
| methyl cellulose (Methocel A15C premium) | 0.05 weight percent to about 5 weight percent (e.g., from about 0.05 weight percent to about 3 weight percent, from about 0.1 weight percent to about 3 weight percent; e.g., about 1.4 weight percent |

TABLE C-continued

| Ingredient | Weight Percent |
| --- | --- |
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 100%) and the ingredients and amounts as shown in Table D.

TABLE D

| Ingredient | Weight Percent |
| --- | --- |
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum. In some embodiments, the enema formulation can be delivered in the device shown in FIGS. 3A-3C, which includes a plastic bottle, a breakable capsule, and a rectal cannula and single flow pack.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

In some embodiments, enema formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the chemical entity in from about 1 mL to about 3000 mL (e.g., from about 1 mL to about 2000 mL, from about 1 mL to about 1000 mL, from about 1 mL to about 500 mL, from about 1 mL to about 250 mL, from about 1 mL to about 100 mL, from about 10 mL to about 1000 mL, from about 10 mL to about 500 mL, from about 10 mL to about 250 mL, from about 10 mL to about 100 mL, from about 30 mL to about 90 mL, from about 40 mL to about 80 mL; from about 50 mL to about 70 mL; e.g., about 1 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 100 mL, about 250 mL, or about 500 mL, or about 1000 mL, or about 2000 mL, or about 3000 mL; e.g., 60 mL) of liquid carrier.

In certain embodiments, enema formulations include from about 50 mg to about 250 mg (e.g., from about 100 mg to about 200; e.g., about 150 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 150 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 150 mg of a compound of Formula AA in about 60 mL of the liquid carrier.

In certain embodiments, enema formulations include from about 350 mg to about 550 mg (e.g., from about 400 mg to about 500; e.g., about 450 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 450 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 450 mg of a compound of Formula AA in about 60 mL of the liquid carrier.

In some embodiments, enema formulations include from about from about 0.01 mg/mL to about 50 mg/mL (e.g., from about 0.01 mg/mL to about 25 mg/mL; from about 0.01 mg/mL to about 10 mg/mL; from about 0.01 mg/mL to about 5 mg/mL; from about 0.1 mg/mL to about 50 mg/mL; from about 0.01 mg/mL to about 25 mg/mL; from about 0.1 mg/mL to about 10 mg/mL; from about 0.1 mg/mL to about 5 mg/mL; from about 1 mg/mL to about 10 mg/mL; from about 1 mg/mL to about 5 mg/mL; from about 5 mg/mL to about 10 mg/mL; e.g., about 2.5 mg/mL or about 7.5 mg/mL) of the chemical entity in liquid carrier. In certain of these embodiments, the chemical entity is a compound of Formula AA, or a pharmaceutically acceptable salt and/or hydrate and/or cocrystal thereof. For example, enema formulations can include about 2.5 mg/mL or about 7.5 mg/mL of a compound of Formula AA in liquid carrier.

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP3 activity (e.g., an increase, e.g., NLRP3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from major adverse cardiovascular events such as carbiovascular death, non-fatal myocardial infarction and non-fatal stroke in patients with a prior hear attack and inflammatory atherosclerosis (see for example, NCT01327846).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CML); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS.

In some embodiments, the indication is non-small lung cancer in patients carrying mutation or overexpression of NLRP3.

In some embodiments, the indication is ALL in patients resistant to glucocorticoids treatment.

In some embodiments, the indication is LCH.

In some embodiments, the indication is multiple myeloma.

In some embodiments, the indication is promyelocytic leukemia.

In some embodiments, the indication is gastric cancer.

In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR_014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http://www.uniprot.org/uniprot/Q96P20.

In some embodiments, the methods described herein further include the step of identifying a subject (e.g., a patient) in need of treatment for an indication related to NLRP3 activity, such as an indication related to point mutation of NLRP3 signaling.

Anti-TNFα Agents

The term "anti-TNFα agent" refers to an agent which directly or indirectly blocks, down-regulates, impairs, inhibits, impairs, or reduces TNFα activity and/or expression. In some embodiments, an anti-TNFα agent is an antibody or an antigen-binding fragment thereof, a fusion protein, a soluble TNFα receptor (a soluble tumor necrosis factor receptor superfamily member 1A (TNFR1) or a soluble tumor necrosis factor receptor superfamily 1B (TNFR2)), an inhibitory nucleic acid, or a small molecule TNFα antagonist. In some embodiments, the inhibitory nucleic acid is a ribozyme, small hairpin RNA, a small interfering RNA, an antisense nucleic acid, or an aptamer.

Exemplary anti-TNFα agents that directly block, down-regulate, impair, inhibit, or reduce TNFα activity and/or expression can, e.g., inhibit or decrease the expression level of TNFα or a receptor of TNFα (TNFR1 or TNFR2) in a cell (e.g., a cell obtained from a subject, a mammalian cell), or inhibit or reduce binding of TNFα to its receptor (TNFR1 and/or TNFR2) and/or. Non-limiting examples of anti-TNFα agents that directly block, down-regulate, impair, inhibit, or reduce TNFα activity and/or expression include an antibody or fragment thereof, a fusion protein, a soluble TNFα receptor (e.g., a soluble TNFR1 or soluble TNFR2), inhibitory nucleic acids (e.g., any of the examples of inhibitory nucleic acids described herein), and a small molecule TNFα antagonist.

Exemplary anti-TNFα agents that can indirectly block, down-regulate, impair, inhibitreduce TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: AP-1, mitogen-activated protein kinase kinase kinase 5 (ASK1), inhibitor of nuclear factor kappa B (IKK), mitogen-activated protein kinase 8 (JNK), mitogen-activated protein kinase (MAPK), MEKK 1/4, MEKK 4/7, MEKK 3/6, nuclear factor kappa B (NF-κB), mitogen-activated protein kinase kinase kinase 14 (NIK), receptor interacting serine/threonine kinase 1 (RIP), TNFRSF1A associated via death domain (TRADD), and TNF receptor associated factor 2 (TRAF2), in a cell), and/or decrease the level of TNFα-induced gene expression in a mammalian cell (e.g., decrease the transcription of genes regulated by, e.g., one or more transcription factors selected from the group of activating transcription factor 2 (ATF2), c-Jun, and NF-κB). A description of downstream signaling of a TNFα receptor is provided in Wajant et al., *Cell Death Differentiation* 10:45-65, 2003 (incorporated herein by reference). For example, such indirect anti-TNFα agents can be an inhibitory nucleic acid that targets (decreases the expression) a signaling component downstream of a TNFα-induced gene (e.g., any TNFα-induced gene known in the art), a TNFα receptor (e.g., any one or more of the signaling components downstream of a TNFα receptor described herein or known in the art), or a transcription factor selected from the group of NF-κB, c-Jun, and ATF2.

In other examples, such indirect anti-TNFα agents can be a small molecule inhibitor of a protein encoded by a TNFα-induced gene (e.g., any protein encoded by a TNFα-induced gene known in the art), a small molecule inhibitor of a signaling component downstream of a TNFα receptor (e.g., any of the signaling components downstream of a TNFα receptor described herein or known in the art), and a small molecule inhibitor of a transcription factor selected from the group of ATF2, c-Jun, and NF-κB.

In other embodiments, anti-TNFα agents that can indirectly block, down-regulate, impair, or reduce one or more components in a cell (e.g., acell obtained from a subject, a mammalian cell) that are involved in the signaling pathway that results in TNFα mRNA transcription, TNFα mRNA stabilization, and TNFα mRNA translation (e.g., one or more components selected from the group of CD14, c-Jun, ERK1/2, IKK, IκB, interleukin 1 receptor associated kinase 1 (IRAK), JNK, lipopolysaccharide binding protein (LBP), MEK1/2, MEK3/6, MEK4/7, MK2, MyD88, NF-κB, NIK, PKR, p38, AKT serine/threonine kinase 1 (rac), raf kinase (raf), ras, TRAF6, TTP). For example, such indirect anti-TNFα agents can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, LBP, MEK1/2, MEK3/6, MEK4/7, MK2, MyD88, NF-κB, NIK, IRAK, lipopolysaccharide binding protein (LBP), PKR, p38, rac, raf, ras, TRAF6, TTP). In other examples, an indirect anti-TNFα agents is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, lipopolysaccharide binding protein (LBP), MEK1/2, MEK3/6, MEK4/7, MK2, MyD88, NF-κB, NIK, IRAK, lipopolysaccharide binding protein (LBP), PKR, p38, rac, raf, ras, TRAF6, TTP).

Antibodies

In some embodiments, the anti-TNFα agent is an antibody or an antigen-binding fragment thereof (e.g., a Fab or a scFv). In some embodiments, an antibody or antigen-binding fragment of an antibody described herein can bind specifically to TNFα. In some embodiments, an antibody or antigen-binding fragment described herein binds specifically to any one of TNFα, TNFR1, or TNFR2. In some embodiments, an antibody or antigen-binding fragment of an antibody described herein can bind specifically to a TNFα receptor (TNFR1 or TNFR2).

In some embodiments, the antibody can be a humanized antibody, a chimeric antibody, a multivalent antibody, or a fragment thereof. In some embodiments, an antibody can be a scFv-Fc, a VHH domain, a VNAR domain, a (scFv)$_2$, a minibody, or a BiTE.

In some embodiments, an antibody can be a crossmab, a diabody, a scDiabody, a scDiabody-CH$_3$, a Diabody-CH$_3$, a DutaMab, a DT-IgG, a diabody-Fc, a scDiabody-HAS, a charge pair antibody, a Fab-arm exchange antibody, a SEEDbody, a Triomab, a LUZ-Y, a Fcab, a k-body, an orthogonal Fab, a DVD-IgG, an IgG(H)-scFv, a scFv-(H)IgG, an IgG(L)-scFv, a scFv-(L)-IgG, an IgG (L,H)-Fc, an IgG(H)-V, a V(H)-IgG, an IgG(L)-V, a V(L)-IgG, an KIH IgG-scFab, a 2scFv-IgG, an IgG-2scFv, a scFv4-Ig, a Zybody, a DVI-IgG, a nanobody, a nanobody-HSA, a DVD-Ig, a dual-affinity re-targeting antibody (DART), a triomab, a kih IgG with a common LC, an ortho-Fab IgG, a 2-in-1-IgG, IgG-ScFv, scFv2-Fc, a bi-nanobody, tanden antibody, a DART-Fc, a scFv-HAS-scFv, a DAF (two-in-one or four-in-one), a DNL-Fab3, knobs-in-holes common LC, knobs-in-holes assembly, a TandAb, a Triple Body, a miniantibody, a minibody, a TriBi minibody, a scFv-CH3 KIH, a Fab-scFv, a scFv-CH-CL-scFv, a F(ab')2-scFV2, a scFv-KIH, a Fab-scFv-Fc, a tetravalent HCAb, a scDiabody-Fc, a tandem scFv-Fc, an intrabody, a dock and lock bispecific antibody, an ImmTAC, a HSAbody, a tandem scFv, an IgG-IgG, a Cov-X-Body, and a scFv1-PEG-scFv2.

Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); or an antigen-binding fragment of an IgM (e.g., an antigen-binding fragment of a human or humanized IgM).

Non-limiting examples of anti-TNFα agents that are antibodies that specifically bind to TNFα are described in Ben-Horin et al., *Autoimmunity Rev.* 13(1):24-30, 2014; Bongartz et al., *JAMA* 295(19):2275-2285, 2006; Butler et al., *Eur. Cytokine Network* 6(4):225-230, 1994; Cohen et al., *Canadian J. Gastroenterol. Hepatol.* 15(6):376-384, 2001; Elliott et al., *Lancet* 1994; 344: 1125-1127, 1994; Feldmann et al., *Ann. Rev. Immunol.* 19(1):163-196, 2001; Rankin et al., *Br. J. Rheumatol.* 2:334-342, 1995; Knight et al., *Molecular Immunol.* 30(16):1443-1453, 1993; Lorenz et al., *J. Immunol.* 156(4):1646-1653, 1996; Hinshaw et al., *Circulatory Shock* 30(3):279-292, 1990; Ordas et al., *Clin. Pharmacol. Therapeutics* 91(4):635-646, 2012; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Wanner et al., *Shock* 11(6):391-395, 1999; and U.S. Pat. Nos. 6,090,382; 6,258,562; and 6,509,015).

In certain embodiments, the anti-TNFα agent can include or is golimumab (Golimumab™), adalimumab (Humira™), infliximab (Remicade™), CDP571, CDP 870, or certolizumab pegol (Cimzia™). In certain embodiments, the anti-TNFα agent can be a TNFα inhibitor biosimilar. Examples of approved and late-phase TNFα inhibitor biosimilars include, but are not limited to, infliximab biosimilars such as Flixabi™ (SB2) from Samsung Bioepis, Inflectra® (CT-P13) from Celltrion/Pfizer, GS071 from Aprogen, Remsima™, PF-06438179 from Pfizer/Sandoz, NI-071 from Nichi-Iko Pharmaceutical Co., and ABP 710 from Amgen; adalimumab biosimilars such as Amgevita® (ABP 501) from Amgen and Exemptia™ from Zydus Cadila, BMO-2 or MYL-1401-A from Biocon/Mylan, CHS-1420 from Coherus, FKB327 from Kyowa Kirin, and BI 695501 from Boehringer Ingelheim; Solymbic®, SB5 from Samsung Bioepis, GP-2017 from Sandoz, ONS-3010 from Oncobiologics, M923 from Momenta, PF-06410293 from Pfizer, and etanercept biosimilars such as Erelzi™ from Sandoz/Novartis, Brenzys™ (SB4) from Samsung Bioepis, GP2015 from Sandoz, TuNEX® from Mycenax, LBECO101 from LG Life, and CHS-0214 from Coherus.

In some embodiments of any of the methods described herein, the anti-TNFα agent is selected from the group consisting of: adalimumab, certolizumab, etanercept, golimumab, infliximabm, CDP571, and CDP 870.

In some embodiments, any of the antibodies or antigen-binding fragments described herein has a dissociation constant ($K_D$) of less than $1 \times 10^{-5}$ M (e.g., less than $0.5 \times 10^{-5}$ M, less than $1 \times 10^{-6}$ M, less than $0.5 \times 10^{-6}$ M, less than $1 \times 10^{-7}$ M, less than $0.5 \times 10^{-7}$ M, less than $1 \times 10^{-8}$ M, less than $0.5 \times 10^{-8}$ M, less than $1 \times 10^{-9}$ M, less than $0.5 \times 10^{-9}$ M, less than $1 \times 10^{-10}$ M, less than $0.5 \times 10^{-10}$ M, less than $1 \times 10^{-11}$ M, less than $0.5 \times 10^{-11}$ M, or less than $1 \times 10^{-2}$ M), e.g., as measured in phosphate buffered saline using surface plasmon resonance (SPR).

In some embodiments, any of the antibodies or antigen-binding fragments described herein has a $K_D$ of about $1 \times 10^{-12}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, about $1 \times 10^{-11}$ M, or about $0.5 \times 10^{-11}$ M (inclusive); about $0.5 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, about $0.5 \times 10^{-10}$ M, or about $1 \times 10^{-11}$ M (inclusive); about $1 \times 10^{-11}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, about $1 \times 10^{-10}$ M, or about $0.5 \times 10^{-10}$ M (inclusive); about $0.5 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, about $0.5 \times 10^{-9}$ M, or about $1 \times 10^{-10}$ M (inclusive); about $1 \times 10^{-10}$ M to about $1 \times 10^{-7}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$ M, or about $0.5 \times 10^{-9}$ M (inclusive); about $0.5 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, or about $1 \times 10^{-9}$ M (inclusive); about $1 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, or about $0.5 \times 10^{-8}$ M (inclusive); about $0.5 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, or about $1 \times 10^{-7}$ M (inclusive); about $1 \times 10^{-7}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, or about $0.5 \times 10^{-7}$ M (inclusive); about $0.5 \times 10^{-7}$ M to about $1 \times 10^{-5}$ M, about $0.5 \times 10^{-5}$ M, about $1 \times 10^{-6}$ M, about $0.5 \times 10^{-6}$ M, or about $1 \times 10^{-7}$ M (inclusive); about $1 \times 10^{-7}$ M to about $1 \times 10^{-5}$ M, about $0.5 \times 10^{-5}$ M, about $1 \times 10^{-6}$ M, or about $0.5 \times 10^{-6}$ M (inclusive); about $0.5 \times 10^{-6}$ M to about $1 \times 10^{-5}$ M, about $0.5 \times 10^{-5}$ M, or about $1 \times 10^{-6}$ M (inclusive); about $1 \times 10^{-6}$ M to about $1 \times 10^{-5}$ M or about $0.5 \times 10^{-5}$ M (inclusive); or about $0.5 \times 10^{-5}$ M to about $1 \times 10^{-5}$ M (inclusive), e.g., as measured in phosphate buffered saline using surface plasmon resonance (SPR).

In some embodiments, any of the antibodies or antigen-binding fragments described herein has a $K_{off}$ of about $1 \times 10^{-6}$ s$^{-1}$ to about $1 \times 10^{3}$ s$^{-1}$, about $0.5 \times 10^{3}$ s$^{-1}$, about $1 \times 10^{-4}$ s$^{-1}$, about $0.5 \times 10^{-4}$ s$^{-1}$, about $1 \times 10^{-5}$ s$^{-1}$, or about $0.5 \times 10^{-5}$ s$^{-1}$ (inclusive); about $0.5 \times 10^{-5}$ s$^{-1}$ to about $1 \times 10^{3}$ s$^{-1}$, about $0.5 \times 10^{3}$ s$^{-1}$, about $1 \times 10^{-4}$ s$^{-1}$, about $0.5 \times 10^{-4}$ s$^{-1}$, or about $1 \times 10^{-5}$ s$^{-1}$ (inclusive); about $1 \times 10^{-5}$ s$^{-1}$ to about $1 \times 10^{3}$ s$^{-1}$, about $0.5 \times 10^{3}$ s$^{-1}$, about $1 \times 10^{-4}$ s$^{-1}$, or about $0.5 \times 10^{-4}$ s$^{-1}$ (inclusive); about $0.5 \times 10^{-4}$ s$^{-1}$ to about $1 \times 10^{3}$ s$^{-1}$, about $0.5 \times 10^{3}$ s$^{-1}$, or about $1 \times 10^{-4}$ s$^{-1}$ (inclusive); about $1 \times 10^{-4}$ s$^{-1}$ to about $1 \times 10^{-3}$ s$^{-1}$, or about $0.5 \times 10^{-3}$ s$^{-1}$ (inclusive); or about $0.5 \times 10^{-5}$ s$^{-1}$ to about $1 \times 10^{-3}$ s$^{-1}$ (inclusive), e.g., as measured in phosphate buffered saline using surface plasmon resonance (SPR).

In some embodiments, any of the antibodies or antigen-binding fragments described herein has a $K_{on}$ of about $1 \times 10^{2}$ M$^{-1}$s$^{-1}$ to about $1 \times 10^{6}$ M$^{-1}$s$^{-1}$, about $0.5 \times 10^{6}$ M$^{-1}$s$^{-1}$, about $1 \times 10^{5}$ M$^{-1}$s$^{-1}$, about $0.5 \times 10^{5}$ M$^{-1}$s$^{-1}$, about $1 \times 10^{4}$ M$^{-1}$s$^{-1}$, about $0.5 \times 10^{4}$ M$^{-1}$s$^{-1}$, about $1 \times 10^{3}$ M$^{-1}$s$^{-1}$, or about $0.5 \times 10^{3}$ M$^{-1}$s$^{1}$ (inclusive); about $0.5 \times 10^{3}$ M$^{-1}$s$^{-1}$ to about $1 \times 10^{6}$M$^{-1}$s$^{-1}$, about $0.5 \times 10^{6}$ M$^{-1}$s$^{-1}$, about $1 \times 10^{-5}$ M$^{-1}$s$^{-1}$, about $0.5 \times 10^{5}$ M$^{-1}$s$^{-1}$, about $1 \times 10^{4}$ M$^{-1}$s$^{-1}$, about $0.5 \times 10^{4}$ M$^{-1}$s$^{-1}$, or about $1 \times 10^{3}$ M$^{-1}$s$^{-1}$ (inclusive); about $1 \times 10^{3}$ M-s- to about $1 \times 10^{6}$ M$^{-1}$s$^{-1}$, about $0.5 \times 10^{6}$ M$^{-1}$s$^{-1}$, about $1 \times 10^{-5}$ M$^{-1}$s$^{-1}$, about $0.5 \times 10^{5}$ M$^{-1}$s$^{-1}$, about $1 \times 10^{4}$ M$^{-1}$s$^{-1}$, or about $0.5 \times 10^{4}$ M$^{-1}$s$^{-1}$ (inclusive); about $0.5 \times 10^{4}$ M$^{-1}$s$^{-1}$ to about $1 \times 10^{6}$M$^{-1}$s$^{-1}$, about $0.5 \times 10^{6}$ M$^{-1}$s$^{-1}$, about $1 \times 10^{5}$ M$^{-1}$s$^{-1}$, about $0.5 \times 10^{5}$ M$^{-1}$s$^{-1}$, or about $1 \times 10^{4}$ M-1s$^{1}$ (inclusive); about $1 \times 10^{4}$ M$^{-1}$s$^{-1}$ to about $1 \times 10^{6}$M$^{-1}$s$^{-1}$, about $0.5 \times 10^{6}$ M$^{-1}$s$^{-1}$, about $1 \times 10^{5}$ M$^{-1}$s$^{-1}$, or about $0.5 \times 10^{5}$ M$^{-1}$s$^{-1}$ (inclusive); about $0.5 \times 10^{5}$ M$^{-1}$s$^{-1}$ to about $1 \times 10^{6}$M$^{-1}$s$^{-1}$, about $0.5 \times 10^{6}$ M$^{-1}$s$^{-1}$, or about $1 \times 10^{5}$ M$^{-1}$s$^{1}$ (inclusive); about $1 \times 10^{5}$ M$^{-1}$s$^{-1}$ to about $1 \times 10^{6}$M$^{-1}$s$^{-1}$, or about $0.5 \times 10^{6}$ M$^{-1}$s$^{-1}$ (inclusive); or about $0.5 \times 10^{6}$ M$^{-1}$s$^{-1}$ to about $1 \times 10^{6}$M$^{-1}$s$^{-1}$ (inclusive), e.g., as measured in phosphate buffered saline using surface plasmon resonance (SPR).

Fusion Proteins

In some embodiments, the anti-TNFα agent is a fusion protein (e.g., an extracellular domain of a TNFR fused to a partner peptide, e.g., an Fc region of an immunoglobulin, e.g., human IgG) (see, e.g., Deeg et al., *Leukemia* 16(2):162, 2002; Peppel et al., *J. Exp. Med.* 174(6):1483-1489, 1991) or a soluble TNFR (e.g., TNFR1 or TNFR2) that binds specifically to TNFα. In some embodiments, the anti-TNFα agent includes or is a soluble TNFα receptor (e.g., Bjornberg et al., *Lymphokine Cytokine Res.* 13(3):203-211, 1994; Kozak et al., *Am. J. Physiol. Reg. Integrative Comparative Physiol.* 269(1):R23-R29, 1995; Tsao et al., *Eur Respir J.* 14(3):490-495, 1999; Watt et al., *J Leukoc Biol.* 66(6):1005-1013, 1999; Mohler et al., J. *Immunol.* 151(3):1548-1561, 1993; Nophar et al., *EMBO J.* 9(10):3269, 1990; Piguet et al., *Eur. Respiratory J.* 7(3):515-518, 1994; and Gray et al., *Proc. Natl. Acad. Sci. U.S.A.* 87(19):7380-7384, 1990). In some embodiments, the anti-TNFα agent includes or is etanercept (Enbrel™) (see, e.g., WO 91/03553 and WO 09/406,476, incorporated by reference herein). In some embodiments, the anti-TNFα agent inhibitor includes or is r-TBP-I (e.g., Gradstein et al., *J. Acquir. Immune Defic. Syndr.* 26(2): 111-117, 2001).

Inhibitory Nucleic Acids

Inhibitory nucleic acids that can decrease the expression of AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA expression in a mammalian cell include antisense nucleic acid molecules, i.e., nucleic acid molecules whose nucleotide sequence is complementary to all or part of a AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (e.g., complementary to all or a part of any one of SEQ ID NOs: 1-37).

```
Human TNFα CDS
                                          (SEQ ID NO: 1)
ATGAGCACTGAAAGCATGATCCGGGACGTGGAGCTGGCCGAGGAGGCGC

TCCCCAAGAAGACAGGGGGGCCCCAGGGCTCCAGGCGGTGCTTGTTCCT

CAGCCTCTTCTCCTTCCTGATCGTGGCAGGCGCCACCACGCTCTTCTGC

CTGCTGCACTTTGGAGTGATCGGCCCCAGAGGGAAGAGTTCCCCAGGG

ACCTCTCTCTAATCAGCCCTCTGGCCCAGGCAGTCAGATCATCTTCTCG

AACCCCGAGTGACAAGCCTGTAGCCCATGTTGTAGCAAACCCTCAAGCT

GAGGGGCAGCTCCAGTGGCTGAACCGCCGGGCCAATGCCCTCCTGGCCA

ATGGCGTGGAGCTGAGAGATAACCAGCTGGTGGTGCCATCAGAGGGCCT

GTACCTCATCTACTCCCAGGTCCTCTTCAAGGGCCAAGGCTGCCCCTCC

ACCCATGTGCTCCTCACCCACACCATCAGCCGCATCGCCGTCTCCTACC

AGACCAAGGTCAACCTCCTCTCTGCCATCAAGAGCCCCTGCCAGAGGGA

GACCCCAGAGGGGGCTGAGGCCAAGCCCTGGTATGAGCCCATCTATCTG

GGAGGGGTCTTCCAGCTGGAGAAGGGGTGACCGACTCAGCGCTGAGATCA

ATCGGCCCGACTATCTCGACTTTGCCGAGTCTGGGCAGGTCTACTTTGG

GATCATTGCCCTGTGA
```

Human TNFR1 CDS (SEQ ID NO: 2)
ATGGGCCTCTCCACCGTGCCTGACCTGCTGCTGCCACTGGTGCTCCTGG
AGCTGTTGGTGGGAATATACCCCTCAGGGGTTATTGGACTGGTCCCTCA
CCTAGGGGACAGGGAGAAGAGAGATAGTGTGTGTCCCCAAGGAAAATAT
ATCCACCCTCAAATAATTCGATTTGCTGTACCAAGTGCCACAAAGGAA
CCTACTTGTACAATGACTGTCCAGGCCCGGGGCAGGATACGGACTGCAG
GGAGTGTGAGAGCGGCTCCTTCACCGCTTCAGAAAACCACCTCAGACAC
TGCCTCAGCTGCTCCAAATGCCGAAAGGAAATGGGTCAGGTGGAGATCT
CTTCTTGCACAGTGGACCGGGACACCGTGTGTGGCTGCAGGAAGAACCA
GTACCGGCATTATTGGAGTGAAAACCTTTTCCAGTGCTTCAATTGCAGC
CTCTGCCTCAATGGGACCGTGCACCTCTCCTGCCAGGAGAAACAGAACA
CCGTGTGCACCTGCCATGCAGGTTTCTTTCTAAGAGAAAACGAGTGTGT
CTCCTGTAGTAACTGTAAGAAAAGCCTGGAGTGCACGAAGTTGTGCCTA
CCCCAGATTGAGAATGTTAAGGGCACTGAGGACTCAGGCACCACAGTGC
TGTTGCCCCTGGTCATTTTCTTTGGTCTTTGCCTTTTATCCCTCCTCTT
CATTGGTTTAATGTATCGCTACCAACGGTGGAAGTCCAAGCTCTACTCC
ATTGTTTGTGGGAAATCGACACCTGAAAAGAGGGGGAGCTTGAAGGAA
CTACTACTAAGCCCCTGGCCCCAAACCCAAGCTTCAGTCCCACTCCAGG
CTTCACCCCACCCTGGGCTTCAGTCCCGTGCCCAGTTCCACCTTCACC
TCCAGCTCCACCTATACCCCCGGTGACTGTCCCAACTTTGCGGCTCCCC
GCAGAGAGGTGGCACCACCCTATCAGGGGCTGACCCCATCCTTGCGAC
AGCCCTCGCCTCCGACCCCATCCCCAACCCCCTTCAGAAGTGGGAGGAC
AGCGCCCACAAGCCACAGAGCCTAGACACTGATGACCCCGCGACGCTGT
ACGCCGTGGTGGAGAACGTGCCCCCGTTGCGCTGGAAGGAATTCGTGCG
GCGCCTAGGGCTGAGCGACCACGAGATCGATCGGCTGGAGCTGCAGAAC
GGGCGCTGCCTGCGCGAGGCGCAATACAGCATGCTGGCGACCTGGAGGC
GGCGCACGCCGCGGCGCGAGGCCACGCTGGAGCTGCTGGGACGCGTGCT
CCGCGACATGGACCTGCTGGGCTGCCTGGAGGACATCGAGGAGGCGCTT
TGCGGCCCCGCCGCCCTCCCGCCCGCGCCCAGTCTTCTCAGATGA Human TNFR2 CDS (SEQ ID NO: 3)
ATTCTTCCCCTGGTGGCCATGGGACCCAGGTCAATGTCACCTGCATCGT
GAACGTCTGTAGCAGCTCTGACCACAGCTCACAGTGCTCCTCCCAAGCC
AGCTCCACAATGGGAGACACAGATTCCAGCCCCTCGGAGTCCCCGAAGG
ACGAGCAGGTCCCCTTCTCCAAGGAGGAATGTGCCTTTCGGTCACAGCT
GGAGACGCCAGAGACCCTGCTGGGGAGCACCGAAGAGAAGCCCCTGCCC
CTTGGAGTGCCTGATGCTGGGATGAAGCCCAGTTAA Human TRADD CDS (SEQ ID NO: 4)
ATGGCAGCTGGGCAAAATGGGCACGAAGAGTGGGTGGGCAGCGCATACC
TGTTTGTGGAGTCCTCGCTGGACAAGGTGGTCCTGTCGGATGCCTACGC
GCACCCCCAGCAGAAGGTGGCAGTGTACAGGGCTCTGCAGGCTGCCTTG
GCAGAGAGCGGCGGGAGCCCGGACGTGCTGCAGATGCTGAAGATCCACC GCAGCGACCCGCAGCTGATCGTGCAGCTGCGATTCTGCGGGCGGCAGCC
CTGTGGCCGCTTCCTCCGCGCCTACCGCGAGGGGCGCTGCGCGCCGCG
CTGCAGAGGAGCCTGGCGGCCGCGCTCGCCCAGCACTCGGTGCCGCTGC
AACTGGAGCTGCGCGCCGGCGCCGAGCGGCTGGACGCTTTGCTGGCGGA
CGAGGAGCGCTGTTTGAGTTGCATCCTAGCCCAGCAGCCCGACCGGCTC
CGGGATGAAGAACTGGCTGAGCTGGAGGATGCGCTGCGAAATCTGAAGT
GCGGCTCGGGGGCCCGGGTGGCGACGGGGAGGTCGCTTCGGCCCCCTT
GCAGCCCCCGGTGCCCTCTCTGTCGGAGGTGAAGCCGCCGCCGCCGCCG
CCACCTGCCCAGACTTTTCTGTTCCAGGGTCAGCCTGTAGTGAATCGGC
CGCTGAGCCTGAAGGACCAACAGACGTTCGCGCGCTCTGTGGGTCTCAA
ATGGCGCAAGGTGGGCGCTCACTGCAGCGAGGCTGCCGGGCGCTGCGG
GACCCGGCGCTGGACTCGCTGGCCTACGAGTACGAGCGCGAGGGACTGT
ACGAGCAGGCCTTCCAGCTGCTGCGGCGCTTCGTGCAGGCCGAGGGCCG
CCGCGCCACGCTGCAGCGCCTGGTGGAGGCACTCGAGGAGAACGAGCTC
ACCAGCCTGGCAGAGGACTTGCTGGGCCTGACCGATCCCAATGGCGGCC
TGGCCTAG Human TRAF2 CDS (SEQ ID NO: 5)
ATGGCTGCAGCTAGCGTGACCCCCCTGGCTCCCTGGAGTTGCTACAGC
CCGGCTTCTCCAAGACCCTCCTGGGGACCAAGCTGGAAGCCAAGTACCT
GTGCTCCGCCTGCAGAAACGTCCTCCGCAGGCCCTTCCAGGCGCAGTGT
GGCCACCGGTACTGCTCCTTCTGCCTGGCCAGCATCCTCAGCTCTGGGC
CTCAGAACTGTGCTGCCTGTGTTCACGAGGGCATATATGAAGGCAT
TTCTATTTTAGAAAGCAGTTCGGCCTTCCCAGATAATGCTGCCCGCAGG
GAGGTGGAGAGCCTGCCGGCCGTCTGTCCCAGTGATGGATGCACCTGGA
AGGGGACCCTGAAAGAATACGAGAGCTGCCACGAAGGCCGCTGCCCGCT
CATGCTGACCGAATGTCCCGCGTGCAAAGGCCTGGTCCGCCTTGGTGAA
AAGGAGCGCCACCTGGAGCACGAGTGCCCGGAGAGAAGCCTGAGCTGCC
GGCATTGCCGGGCACCCTGCTGCGGAGCAGACGTGAAGGCGCACCACGA
GGTCTGCCCCAAGTTCCCCTTAACTTGTGACGGCTGCGGCAAGAAGAAG
ATCCCCCGGGAGAAGTTTCAGGACCACGTCAAGACTTGTGGCAAGTGTC
GAGTCCCTTGCAGATTCCACGCCATCGGCTGCCTCGAGACGGTAGAGGG
TGAGAAACAGCAGGAGCACGAGGTGCAGTGGCTGCGGGAGCACCTGGCC
ATGCTACTGAGCTCGGTGCTGGAGGCAAAGCCCCTCTTGGGAGACCAGA
GCCACGCGGGTCAGAGCTCCTGCAGAGGTGCGAGAGCCTGGAGAAGAA
GACGGCCACTTTTGAGAACATTGTCTGCGTCCTGAACCGGGAGGTGGAG
AGGGTGGCCATGACTGCCGAGGCCTGCAGCCGGCAGCACCGGCTGGACC
AAGACAAGATTGAAGCCCTGAGTAGCAAGGTGCAGCAGCTGGAGAGGAG
CATTGGCCTCAAGGACCTGGCGATGGCTGACTTGGAGCAGAAGGTCTTG
GAGATGGAGGCATCCACCTACGATGGGGTCTTCATCTGGAAGATCTCAG
ACTTCGCCAGGAAGCGCCAGGAAGCTGTGGCTGGCCGCATACCCGCCAT -continued
CTTCTCCCCAGCCTTCTACACCAGCAGGTACGGCTACAAGATGTGTCTG
CGTATCTACCTGAACGGCGACGGCACCGGGCGAGGAACACACCTGTCCC
TCTTCTTTGTGGTGATGAAGGGCCCGAATGACGCCCTGCTGCGGTGGCC
CTTCAACCAGAAGGTGACCTTAATGCTGCTCGACCAGAATAACCGGGAG
CACGTGATTGACGCCTTCAGGCCCGACGTGACTTCATCCTCTTTTCAGA
GGCCAGTCAACGACATGAACATCGCAAGCGGCTGCCCCCTCTTCTGCCC
CGTCTCCAAGATGGAGGCAAAGAATTCCTACGTGCGGGACGATGCCATC
TTCATCAAGGCCATTGTGGACCTGACAGGGCTCTAA Human AP-1 CDS
(SEQ ID NO: 6)
ATGGAAACACCCTTCTACGGCGATGAGGCGCTGAGCGGCCTGGGCGGCG
GCGCCAGTGGCAGCGGCGGCAGCTTCGCGTCCCCGGGCCGCTTGTTCCC
CGGGGCGCCCCCGACGGCCGCGGCCGGCAGCATGATGAAGAAGGACGCG
CTGACGCTGAGCCTGAGTGAGCAGGTGGCGGCAGCGCTCAAGCCTGCGG
CCGCGCCGCCTCCTACCCCCCTGCGCGCCGACGGCGCCCCCAGCGCGGC
ACCCCCCGACGGCCTGCTCGCCTCTCCCGACCTGGGGCTGCTGAAGCTG
GCCTCCCCCGAGCTCGAGCGCCTCATCATCCAGTCCAACGGGCTGGTCA
CCACCACGCCGACGAGCTCACAGTTCCTCTACCCCAAGGTGGCGGCCAG
CGAGGAGCAGGAGTTCGCCGAGGGCTTCGTCAAGGCCCTGGAGGATTTA
CACAAGCAGAACCAGCTCGGCGCGGGCGCGGCCGCTGCCGCCGCCGCCG
CCGCCGCCGGGGGCCCTCGGGCACGGCCACGGGCTCCGCGCCCCCCGG
CGAGCTGGCCCCGGCGGCGGCCGCGCCCGAAGCGCCTGTCTACGCGAAC
CTGAGCAGCTACGCGGGCGGCGCCGGGGGCGCGGGGGCGCCGCGACGG
TCGCCTTCGCTGCCGAACCTGTGCCCTTCCCGCCGCCGCCACCCCCAGG
CGCGTTGGGGCCGCCGCGCCTGGCTGCGCTCAAGGACGAGCCACAGACG
GTGCCCGACGTGCCGAGCTTCGGCGAGAGCCCGCCGTTGTCGCCCATCG
ACATGGACACGCAGGAGCGCATCAAGGCGGAGCGCAAGCGGCTGCGCAA
CCGCATCGCCGCCTCCAAGTGCCGCAAGCGCAAGCTGGAGCGCATCTCG
CGCCTGGAAGAGAAAGTGAAGACCCTCAAGAGTCAGAACACGGAGCTGG
CGTCCACGGCGAGCCTGCTGCGCGAGCAGGTGGCGCAGCTCAAGCAGAA
AGTCCTCAGCCACGTCAACAGCGGCTGCCAGCTGCTGCCCCAGCACCAG
GTGCCCGCGTACTGA Human ASK1 CDS
(SEQ ID NO: 7)
ATGAGCACGGAGGCGGACGAGGGCATCACTTTCTCTGTGCCACCCTTCG
CCCCCTCGGGCTTCTGCACCATCCCCGAGGGCGGCATCTGCAGGAGGGG
AGGAGCGGCGGCGGTGGGCGAGGGCGAGGAGCACCAGCTGCCACCGCCG
CCGCCGGGCAGTTTCTGGAACGTGGAGAGCGCCGCTGCCCCTGGCATCG
GTTGTCCGGCGGCCACCTCCTCGAGCAGTGCCACCCGAGGCCGGGGCAG
CTCTGTTGGCGGGGCAGCCGACGGACCACGGTGGCATATGTGATCAAC
GAAGCGAGCCAAGGGCAACTGGTGGTGGCCGAGAGCGAGGCCCTGCAGA
GCTTGCGGGAGGCGTGCGAGACAGTGGGCGCCACCCTGGAACCCTGCAT
TTTGGGAAACTCGACTTTGGAGAAACCACCGTGCTGGACCGCTTTTACA -continued
ATGCAGATATTGCGGTGGTGGAGATGAGCGATGCCTTCCGGCAGCCGTC
CTTGTTTTACCACCTTGGGGTGAGAGAAAGTTTCAGCATGGCCAACAAC
ATCATCCTCTACTGCGATACTAACTCGGACTCTCTGCAGTCACTGAAGG
AAATCATTTGCCAGAAGAATACTATGTGCACTGGGAACTACACCTTTGT
TCCTTACATGATAACTCCACATAACAAAGTCTACTGCTGTGACAGCAGC
TTCATGAAGGGGTTGACAGAGCTCATGCAACCGAACTTCGAGCTGCTTC
TTGGACCCATCTGCTTACCTCTTGTGGATCGTTTTATTCAACTTTTGAA
GGTGGCACAAGCAAGTTCTAGCCAGTACTTCCGGGAATCTATACTCAAT
GACATCAGGAAAGCTCGTAATTTATACACTGGTAAAGAATTGGCAGCTG
AGTTGGCAAGAATTCGGCAGCGAGTAGATAATATCGAAGTCTTGACAGC
AGATATTGTCATAAATCTGTTACTTTCCTACAGAGATATCCAGGACTAT
GATTCTATTGTGAAGCTGGTAGAGACTTTAGAAAAACTGCCAACCTTTG
ATTTGGCCTCCCATCACCATGTGAAGTTTCATTATGCATTTGCACTGAA
TAGGAGAAATCTCCCTGGTGACAGAGCAAAAGCTCTTGATATTATGATT
CCCATGGTGCAAAGCGAAGGACAAGTTGCTTCAGATATGTATTGCCTAG
TTGGTCGAATCTACAAAGATATGTTTTTGGACTCTAATTTCACGGACAC
TGAAAGCAGAGACCATGGAGCTTCTTGGTTCAAAAAGGCATTTGAATCT
GAGCCAACACTACAGTCAGGAATTAATTATGCGGTCCTCCTCCTGGCAG
CTGGACACCAGTTTGAATCTTCCTTTGAGCTCCGGAAAGTTGGGGTGAA
GCTAAGTAGTCTTCTTGGTAAAAAGGGAAACTTGGAAAAACTCCAGAGC
TACTGGGAAGTTGGATTTTTTCTGGGGGCCAGCGTCCTAGCCAATGACC
ACATGAGAGTCATTCAAGCATCTGAAAAGCTTTTTAAACTGAAGACACC
AGCATGGTACCTCAAGTCTATTGTAGAGACAATTTTGATATATAAGCAT
TTTGTGAAACTGACCACAGAACAGCCTGTGGCCAAGCAAGAACTTGTGG
ACTTTTGGATGGATTTCCTGGTCGAGGCCACAAAGACAGATGTTACTGT
GGTTAGGTTTCCAGTATTAATATTAGAACCAACCAAAATCTATCAACCT
TCTTATTTGTCTATCAACAATGAAGTTGAGGAAAAGACAATCTCTATTT
GGCACGTGCTTCCTGATGACAAGAAAGGTATACATGAGTGGAATTTTAG
TGCCTCTTCTGTCAGGGGAGTGAGTATTTCTAAATTTGAAGAAAGATGC
TGCTTTCTTTATGTGCTTCACAATTCTGATGATTTCCAAATCTATTTCT
GTACAGAACTTCATTGTAAAAGTTTTTTGAGATGGTGAACACCATTAC
CGAAGAGAAGGGGAGAAGCACAGAGGAAGGAGACTGTGAAAGTGACTTG
CTGGAGTATGACTATGAATATGATGAAAATGGTGACAGAGTCGTTTTAG
GAAAAGGCACTTATGGGATAGTCTACGCAGGTCGGGACTTGAGCAACCA
AGTCAGAATTGCTATTAAGGAAATCCAGAGAGAGACAGCAGATACTCT
CAGCCCCTGCATGAAGAAATAGCATTGCATAAACACCTGAAGCACAAAA
ATATTGTCCAGTATCTGGGCTCTTTCAGTGAGAATGGTTTCATTAAAAT
CTTCATGGAGCAGGTCCCTGGAGGAAGTCTTTCTGCTCTCCTTCGTTCC
AAATGGGGTCCATTAAAAGACAATGAGCAAACAATTGGCTTTTATACAA
AGCAAATACTGGAAGGATTAAAATATCTCCATGACAATCAGATAGTTCA -continued
```
CCGGGACATAAAGGGTGACAATGTGTTGATTAATACCTACAGTGGTGTT
CTCAAGATCTCTGACTTCGGAACATCAAAGAGGCTTGCTGGCATAAACC
CCTGTACTGAAACTTTTACTGGTACCCTCCAGTATATGGCACCAGAAAT
AATAGATAAAGGACCAAGAGGCTACGAAAAGCAGCAGACATCTGGTCT
CTGGGCTGTACAATCATTGAAATGGCCACAGGAAAACCCCCATTTTATG
AACTGGGAGAACCACAAGCAGCTATGTTCAAGGTGGGAATGTTTAAAGT
CCACCCTGAGATCCCAGAGTCCATGTCTGCAGAGGCCAAGGCATTCATA
CTGAAATGTTTTGAACCAGATCCTGACAAGAGAGCCTGTGCTAACGACT
TGCTTGTTGATGAGTTTTTAAAAGTTTCAAGCAAAAAGAAAAAGACACA
ACCTAAGCTTTCAGCTCTTTCAGCTGGATCAAATGAATATCTCAGGAGT
ATATCCTTGCCGGTACCTGTGCTGGTGGAGGACACCAGCAGCAGCAGTG
AGTACGGCTCAGTTTCACCCGACACGGAGTTGAAAGTGGACCCCTTCTC
TTTCAAAACAAGAGCCAAGTCCTGCGGAGAAAGAGATGTCAAGGGAATT
CGGACACTCTTTTTGGGCATTCCAGATGAGAATTTTGAAGATCACAGTG
CTCCTCCTTCCCCTGAAGAAAAAGATTCTGGATTCTTCATGCTGAGGAA
GGACAGTGAGAGGCGAGCTACCCCTTCACAGGATCCTGACGGAAGACCAA
GACAAAATTGTGAGAAACCTAATGAATCTTTAGCTCAGGGGCTGAAG
AACCGAAACTAAAATGGGAACACATCACAACCCTCATTGCAAGCCTCAG
AGAATTTGTGAGATCCACTGACCGAAAAATCATAGCCACCACACTGTCA
AAGCTGAAACTGGAGCTGGACTTCGACAGCCATGGCATTAGCCAAGTCC
AGGTGGTACTCTTTGGTTTTCAAGATGCTGTCAATAAAGTTCTTCGGAA
TCATAACATCAAGCCGCACTGGATGTTTGCCTTAGACAGTATCATTCGG
AAGGCGGTACAGACAGCCATTACCATCCTGGTTCCAGAACTAAGGCCAC
ATTTCAGCCTTGCATCTGAGAGTGATACTGCTGATCAAGAAGACTTGGA
TGTAGAAGATGACCATGAGGAACAGCCTTCAAATCAAACTGTCCGAAGA
CCTCAGGCTGTCATTGAAGATGCTGTGGCTACCTCAGGCGTGAGCACGC
TCAGTTCTACTGTGTCTCATGATTCCCAGAGTGCTCACCGGTCACTGAA
TGTACAGCTTGGAAGGATGAAAATAGAAACCAATAGATTACTGGAAGAA
TTGGTTCGGAAAGAGAAAGAATTACAAGCACTCCTTCATCGAGCTATTG
AAGAAAAAGACCAAGAAATTAAACACCTGAAGCTTAAGTCCCAACCCAT
AGAAATTCCTGAATTGCCTGTATTTCATCTAAATTCTTCTGGCACAAAT
ACTGAAGATTCTGAACTTACCGACTGGCTGAGAGTGAATGGAGCTGATG
AAGACACTATAAGCCGGTTTTTGGCTGAAGATTATACACTATTGGATGT
TCTCTACTATGTTACACGTGATGACTTAAAATGCTTGAGACTAAGGGA
GGGATGCTGTGCACACTGTGGAAGG CTATCATTGACTTTCGAAACAAA
CAGACTTGA
```
Human CD14 CDS
(SEQ ID NO: 8)
```
ATGGAGCGCGCGTCCTGCTTGTTGCTGCTGCTGCTGCCGCTGGTGCACG
TCTCTGCGACCACGCCAGAACCTTGTGAGCTGGACGATGAAGATTTCCG
CTGCGTCTGCAACTTCTCCGAACCTCAGCCCGACTGGTCCGAAGCCTTC
CAGTGTGTGTCTGCAGTAGAGGTGGAGATCCATGCCGGCGGTCTCAACC
TAGAGCCGTTTCTAAAGCGCGTCGATGCGGACGCCGACCCGCGGCAGTA
TGCTGACACGGTCAAGGCTCTCCGCGTGCGGCGGCTCACAGTGGGAGCC
GCACAGGTTCCTGCTCAGCTACTGGTAGGCGCCCTGCGTGTGCTAGCGT
ACTCCCGCCTCAAGGAACTGACGCTCGAGGACCTAAAGATAACCGGCAC
CATGCCTCCGCTGCCTCTGGAAGCCACAGGACTTGCACTTTCCAGCTTG
CGCCTACGCAACGTGTCGTGGGCGACAGGGCGTTCTTGGCTCGCCGAGC
TGCAGCAGTGGCTCAAGCCAGGCCTCAAGGTACTGAGCATTGCCCAAGC
ACACTCGCCTGCCTTTTCCTGCGAACAGGTTCGCGCCTTCCCGGCCCTT
ACCAGCCTAGACCTGTCTGACAATCCTGGACTGGGCGAACGCGGACTGA
TGGCGGCTCTCTGTCCCCACAAGTTCCCGGCCATCCAGAATCTAGCGCT
GCGCAACACAGGAATGGAGACGCCCACAGGCGTGTGCGCCGCACTGGCG
GCGGCAGGTGTGCAGCCCCACAGCCTAGACCTCAGCCACAACTCGCTGC
GCGCCACCGTAAACCCTAGCGCTCCGAGATGCATGTGGTCCAGCGCCCT
GAACTCCCTCAATCTGTCGTTCGCTGGGCTGGAACAGGTGCCTAAAGGA
CTGCCAGCCAAGCTCAGAGTGCTCGATCTCAGCTGCAACAGACTGAACA
GGGCGCCGCAGCCTGACGAGCTGCCCGAGGTGGATAACCTGACACTGGA
CGGGAATCCCTTCCTGGTCCCTGGAACTGCCCTCCCCCACGAGGGCTCA
ATGAACTCCGCGTGGTCCCAGCCTGTGCACGTTCGACCCTGTCGGTGG
GGGTGTCGGGAACCCTGGTGCTGCTCCAAGGGGCCCGGGGCTTTGCCTA
A
```
Human ERK1 CDS
(SEQ ID NO: 9)
```
ATGGCGGCGGCGGCGCTCAGGGGGGCGGGGGCGGGGAGCCCCGTAGAA
CCGAGGGGGTCGGCCCGGGGGTCCCGGGGGAGGTGGAGATGGTGAAGGG
GCAGCCGTTCGACGTGGGCCCGCGCTACACGCAGTTGCAGTACATCGGC
GAGGGCGCGTACGGCATGGTCAGCTCGGCCTATGACCACGTGCGCAAGA
CTCGCGTGGCCATCAAGAAGATCAGCCCCTTCGAACATCAGACCTACTG
CCAGCGCACGCTCCGGGAGATCCAGATCCTGCTGCGCTTCCGCCATGAG
AATGTCATCGGCATCCGAGACATTCTGCGGGCGTCCACCCTGGAAGCCA
TGAGAGATGTCTACATTGTGCAGGACCTGATGGAGACTGACCTGTACAA
GTTGCTGAAAAGCCAGCAGCTGAGCAATGACCATATCTGCTACTTCCTC
TACCAGATCCTGCGGGGCCTCAAGTACATCCACTCCGCCAACGTGCTCC
ACCGAGATCTAAAGCCCTCCAACCTGCTCATCAACACCACCTGCGACCT
TAAGATTTGTGATTTCGGCCTGGCCCGGATTGCCGATCCTGAGCATGAC
CACACCGGCTTCCTGACGGAGTATGTGGCTACGCGCTGGTACCGGGCCC
CAGAGATCATGCTGAACTCCAAGGGCTATACCAAGTCCATCGACATCTG
GTCTGTGGGCTGCATTCTGGCTGAGATGCTCTCTAACCGGCCCATCTTC
CCTGGCAAGCACTACCTGGATCAGCTCAACCACATTCTGGGCATCCTGG
GCTCCCCATCCCAGGAGGACCTGAATTGTATCATCAACATGAAGGCCCG
AAACTACCTACAGTCTCTGCCCTCCAAGACCAAGGTGGCTTGGGCCAAG
CTTTTTCCCCAAGTCAGACTCCAAAGCCCTTGACCTGCTGGACCGGATGT
```

-continued
TAACCTTTAACCCCAATAAACGGATCACAGTGGAGGAAGCGCTGGCTCA
CCCCTACCTGGAGCAGTACTATGACCCGACGGATGAGCCAGTGGCCGAG
GAGCCCTTCACCTTCGCCATGGAGCTGGATGACCTACCTAAGGAGCGGC
TGAAGGAGCTCATCTTCCAGGAGACAGCACGCTTCCAGCCCGGAGTGCT
GGAGGCCCCCTAG Human ERK2 CDS
(SEQ ID NO: 10)
ATGGCGGCGGCGGCGGCGGGCGCGGGCCCGGAGATGGTCCGCGGGC
AGGTGTTCGACGTGGGGCCGCGCTACACCAACCTCTCGTACATCGGCGA
GGGCGCCTACGGCATGGTGTGCTCTGCTTATGATAATGTCAACAAAGTT
CGAGTAGCTATCAAGAAAATCAGCCCCTTTGAGCACCAGACCTACTGCC
AGAGAACCCTGAGGGAGATAAAAATCTTACTGCGCTTCAGACATGAGAA
CATCATTGGAATCAATGACATTATTCGAGCACCAACCATCGAGCAAATG
AAAGATGTATATATAGTACAGGACCTCATGGAAACAGATCTTTACAAGC
TCTTGAAGACACAACACCTCAGCAATGACCATATCTGCTATTTTCTCTA
CCAGATCCTCAGAGGGTTAAAATATATCCATTCAGCTAACGTTCTGCAC
CGTGACCTCAAGCCTTCCAACCTGCTGCTCAACACCACCTGTGATCTCA
AGATCTGTGACTTTGGCCTGGCCCGTGTTGCAGATCCAGACCATGATCA
CACAGGGTTCCTGACAGAATATGTGGCCACACGTTGGTACAGGGCTCCA
GAAATTATGTTGAATTCCAAGGGCTACACCAAGTCCATTGATATTTGGT
CTGTAGGCTGCATTCTGGCAGAAATGCTTTCTAACAGGCCCATCTTTCC
AGGGAAGCATTATCTTGACCAGCTGAACCACATTTTGGGTATTCTTGGA
TCCCCATCACAAGAAGACCTGAATTGTATAATAAATTTAAAAGCTAGGA
ACTATTTGCTTTCTCTTCCACACAAAAATAAGGTGCCATGGAACAGGCT
GTTCCCAAATGCTGACTCCAAAGCTCTGGACTTATTGGACAAAATGTTG
ACATTCAACCCACACAAGAGGATTGAAGTAGAACAGGCTCTGGCCCACC
CATATCTGGAGCAGTATTACGACCCGAGTGACGAGCCCATCGCCGAAGC
ACCATTCAAGTTCGACATGGAATTGGATGACTTGCCTAAGGAAAAGCTC
AAAGAACTAATTTTTGAAGAGACTGCTAGATTCCAGCCAGGATACAGAT
CTTAA Human IKK CDS
(SEQ ID NO: 11)
ATGTTTTCAGGGGGTGTCATAGCCCCGGGTTTGGCCGCCCCAGCCCG
CCTTCCCCGCCCCGGGGAGCCCGCCCCCTGCCCCGCGTCCCTGCCGACA
GGAAACAGGTGAGCAGATTGCCATCAAGCAGTGCCGGCAGGAGCTCAGC
CCCCGGAACCGAGAGCGGTGGTGCCTGGAGATCCAGATCATGAGAAGGC
TGACCCACCCCAATGTGGTGGCTGCCCGAGATGTCCCTGAGGGGATGCA
GAACTTGGCGCCCAATGACCTGCCCCTGCTGGCCATGGAGTACTGCCAA
GGAGGAGATCTCCGGAAGTACCTGAACCAGTTTGAGAACTGCTGTGGTC
TGCGGGAAGGTGCCATCCTCACCTTGCTGAGTGACATTGCCTCTGCGCT
TAGATACCTTCATGAAAACAGAATCATCCATCGGGATCTAAAGCCAGAA
AACATCGTCCTGCAGCAAGGAGAACAGAGGTTAATACACAAATTATTG
ACCTAGGATATGCCAAGGAGCTGGATCAGGGCAGTCTTTGCACATCATT -continued
CGTGGGGACCCTGCAGTACCTGGCCCCAGAGCTACTGGAGCAGCAGAAG
TACACAGTGACCGTCGACTACTGGAGCTTCGGCACCCTGGCCTTTGAGT
GCATCACGGGCTTCCGGCCCTTCCTCCCCAACTGGCAGCCCGTGCAGTG
GCATTCAAAAGTGCGGCAGAAGAGTGAGGTGGACATTGTTGTTAGCGAA
GACTTGAATGGAACGGTGAAGTTTTCAAGCTCTTTACCCTACCCCAATA
ATCTTAACAGTGTCCTGGCTGAGCGACTGGAGAAGTGGCTGCAACTGAT
GCTGATGTGGCACCCCCGACAGAGGGGCACGGATCCCACGTATGGGCCC
AATGGCTGCTTCAAGGCCCTGGATGACATCTTAAACTTAAAGCTGGTTC
ATATCTTGAACATGGTCACGGGCACCATCCACACCTACCCTGTGACAGA
GGATGAGAGTCTGCAGAGCTTGAAGGCCAGAATCCAACAGGACACGGGC
ATCCCAGAGGAGGACCAGGAGCTGCTGCAGGAAGCGGGCCTGGCGTTGA
TCCCCGATAAGCCTGCCACTCAGTGTATTTCAGACGGCAAGTTAAATGA
GGGCCACACATTGGACATGGATCTTGTTTTTCTCTTTGACAACAGTAAA
ATCACCTATGAGACTCAGATCTCCCCACGGCCCCAACCTGAAAGTGTCA
GCTGTATCCTTCAAGAGCCCAAGAGGAATCTCGCCTTCTTCCAGCTGAG
GAAGGTGTGGGGCCAGGTCTGGCACAGCATCCAGACCCTGAAGGAAGAT
TGCAACCGGCTGCAGCAGGGACAGCGAGCCGCCATGATGAATCTCCTCC
GAAACAACAGCTGCCTCTCCAAAATGAAGAATTCCATGGCTTCCATGTC
TCAGCAGCTCAAGGCCAAGTTGGATTTCTTCAAAACCAGCATCCAGATT
GACCTGGAGAAGTACAGCGAGCAAACCGAGTTTGGGATCACATCAGATA
AACTGCTGCTGGCCTGGAGGGAAATGGAGCAGGCTGTGGAGCTCTGTGG
GCGGGAGAACGAAGTGAAACTCCTGGTAGAACGGATGATGGCTCTGCAG
ACCGACATTGTGGACTTACAGAGGAGCCCCATGGGCCGGAAGCAGGGGG
GAACGCTGGACGACCTAGAGGAGCAAGCAAGGGAGCTGTACAGGAGACT
AAGGGAAAAACCTCGAGACCAGCGAACTGAGGGTGACAGTCAGGAAATG
GTACGGCTGCTGCTTCAGGCAATTCAGAGCTTCGAGAAGAAAGTGCGAG
TGATCTATACGCAGCTCAGTAAAACTGTGGTTTGCAAGCAGAAGGCGCT
GGAACTGTTGCCCAAGGTGGAAGAGGTGGTGAGCTTAATGAATGAGGAT
GAGAAGACTGTTGTCCGGCTGCAGGAGAAGCGGCAGAAGGAGCTCTGGA
ATCTCCTGAAGATTGCTTGTAGCAAGGTCCGTGGTCCTGTCAGTGGAAG
CCCGGATAGCATGAATGCCTCTCGACTTAGCCAGCCTGGGCAGCTGATG
TCTCAGCCCTCCACGGCCTCCAACAGCTTACCTGAGCCAGCCAAGAAGA
GTGAAGAACTGGTGGCTGAAGCACATAACCTCTGCACCCTGCTAGAAAA
TGCCATACAGGACACTGTGAGGGAACAAGACCAGAGTTTCACGGCCCTA
GACTGGAGCTGGTTACAGACGGAAGAAGAAGAGCACAGCTGCCTGGAGC
AGGCCTCATGA Human IκB CDS
(SEQ ID NO: 12)
ATGTTCCAGGCGGCCGAGCGCCCCCAGGAGTGGGCCATGGAGGGCCCCC
GCGACGGGCTGAAGAAGGAGCGGCTACTGGACGACCGCCACGACAGCGG
CCTGGACTCCATGAAAGACGAGGAGTACGAGCAGATGGTCAAGGAGCTG CAGGAGATCCGCCTCGAGCCGCAGGAGGTGCCGCGCGGCTCGGAGCCCT
GGAAGCAGCAGCTCACCGAGGACGGGGACTCGTTCCTGCACTTGGCCAT
CATCCATGAAGAAAAGGCACTGACCATGGAAGTGATCCGCCAGGTGAAG
GGAGACCTGGCCTTCCTCAACTTCCAGAACAACCTGCAGCAGACTCCAC
TCCACTTGGCTGTGATCACCAACCAGCCAGAAATTGCTGAGGCACTTCT
GGGAGCTGGCTGTGATCCTGAGCTCCGAGACTTTCGAGGAAATACCCCC
CTACACCTTGCCTGTGAGCAGGGCTGCCTGGCCAGCGTGGGAGTCCTGA
CTCAGTCCTGCACCACCCCGCACCTCCACTCCATCCTGAAGGCTACCAA
CTACAATGGCCACACGTGTCTACACTTAGCCTCTATCCATGGCTACCTG
GGCATCGTGGAGCTTTTGGTGTCCTTGGGTGCTGATGTCAATGCTCAGG
AGCCCTGTAATGGCCGGACTGCCCTTCACCTCGCAGTGGACCTGCAAAA
TCCTGACCTGGTGTCACTCCTGTTGAAGTGTGGGGCTGATGTCAACAGA
GTTACCTACCAGGGCTATTCTCCCTACCAGCTCACCTGGGGCCGCCCAA
GCACCCGGATACAGCAGCAGCTGGGCCAGCTGACACTAGAAAACCTTCA
GATGCTGCCAGAGAGTGAGGATGAGGAGAGCTATGACACAGAGTCAGAG
TTCACGGAGTTCACAGAGGACGAGCTGCCCTATGATGACTGTGTGTTTG
GAGGCCAGCGTCTGACGTTATGA Human IRAK CDS (SEQ ID NO: 13)
ATGGCCGGGGGCCGGGCCCGGGGGAGCCCGCAGCCCCCGGCGCCCAGC
ACTTCTTGTACGAGGTGCCGCCCTGGGTCATGTGCCGCTTCTACAAAGT
GATGGACGCCCTGGAGCCCGCCGACTGGTGCCAGTTCGCCGCCCTGATC
GTGCGCGACCAGACCGAGCTGCGGCTGTGCGAGCGCTCCGGGCAGCGCA
CGGCCAGCGTCCTGTGGCCCTGGATCAACCGCAACGCCCGTGTGGCCGA
CCTCGTGCACATCCTCACGCACCTGCAGCTGCTCCGTGCGCGGGACATC
ATCACAGCCTGGCACCCTCCCGCCCCGCTTCCGTCCCCAGGCACCACTG
CCCCGAGGCCCAGCAGCATCCCTGCACCCGCCGAGGCCGAGGCCTGGAG
CCCCCGGAAGTTGCCATCCTCAGCCTCCACCTTCCTCTCCCCAGCTTTT
CCAGGCTCCCAGACCCATTCAGGGCCTGAGCTCGGCCTGGTCCCAAGCC
CTGCTTCCCTGTGGCCTCCACCGCCATCTCCAGCCCCTTCTTCTACCAA
GCCAGGCCCAGAGAGCTCAGTGTCCCTCCTGCAGGGAGCCCGCCCCTTT
CCGTTTTGCTGGCCCCTCTGTGAGATTTCCCGGGGCACCCACAACTTCT
CGGAGGAGCTCAAGATCGGGGAGGGTGGCTTTGGGTGCGTGTACCGGGC
GGTGATGAGGAACACGGTGTATGCTGTGAAGAGGCTGAAGGAGAACGCT
GACCTGGAGTGGACTGCAGTGAAGCAGAGCTTCCTGACCGAGGTGGAGC
AGCTGTCCAGGTTTCGTCACCCAAACATTGTGGACTTTGCTGGCTACTG
TGCTCAGAACGGCTTCTACTGCCTGGTGTACGGCTTCCTGCCCAACGGC
TCCCTGGAGGACCGTCTCCACTGCCAGACCCAGGCCTGCCCACCTCTCT
CCTGGCCTCAGCGACTGGACATCCTTCTGGGTACAGCCCGGGCAATTCA
GTTTCTACATCAGGACAGCCCCAGCCTCATCCATGGAGACATCAAGAGT
TCCAACGTCCTTCTGGATGAGAGGCTGACACCCAAGCTGGGAGACTTTG
GCCTGGCCCGGTTCAGCCGCTTTGCCGGGTCCAGCCCCAGCCAGAGCAG CATGGTGGCCCGGACACAGACAGTGCGGGGCACCCTGGCCTACCTGCCC
GAGGAGTACATCAAGACGGGAAGGCTGGCTGTGGACACGGACACCTTCA
GCTTTGGGGTGGTAGTGCTAGAGACCTTGGCTGGTCAGAGGGCTGTGAA
GACGCACGGTGCCAGGACCAAGTATCTGAAAGACCTGGTGGAAGAGGAG
GCTGAGGAGGCTGGAGTGGCTTTGAGAAGCACCCAGAGCACACTGCAAG
CAGGTCTGGCTGCAGATGCCTGGGCTGCTCCCATCGCCATGCAGATCTA
CAAGAAGCACCTGGACCCCAGGCCCGGGCCCTGCCCACCTGAGCTGGGC
CTGGGCCTGGGCCAGCTGGCCTGCTGCTGCCTGCACCGCCGGGCCAAAA
GGAGGCCTCCTATGACCCAGGTGTACGAGAGGCTAGAGAAGCTGCAGGC
AGTGGTGGCGGGGGTGCCCGGGCATTCGGAGGCCGCCAGCTGCATCCCC
CCTTCCCCGCAGGAGAACTCCTACGTGTCCAGCACTGGCAGAGCCCACA
GTGGGGCTGCTCCATGGCAGCCCCTGGCAGCGCCATCAGGAGCCAGTGC
CCAGGCAGCAGAGCAGCTGCAGAGAGGCCCCAACCAGCCCGTGGAGAGT
GACGAGAGCCTAGGCGGCCTCTCTGCTGCCCTGCGCTCCTGGCACTTGA
CTCCAAGCTGCCCTCTGGACCCAGCACCCCTCAGGGAGGCCGGCTGTCC
TCAGGGGACACGGCAGGAGAATCGAGCTGGGGGAGTGGCCCAGGATCC
CGGCCCACAGCCGTGGAAGGACTGGCCCTTGGCAGCTCTGCATCATCGT
CGTCAGAGCCACCGCAGATTATCATCAACCCTGCCCGACAGAAGATGGT
CCAGAAGCTGGCCCTGTACGAGGATGGGCCCTGGACAGCCTGCAGCTG
CTGTCGTCCAGCTCCCTCCCAGGCTTGGGCCTGGAACAGGACAGGCAGG
GGCCCGAAGAAAGTGATGAATTTCAGAGCTGA Human JNK CDS (SEQ ID NO: 14)
ATGAGCAGAAGCAAGCGTGACAACAATTTTTATAGTGTAGAGATTGGAG
ATTCTACATTCACAGTCCTGAAACGATATCAGAATTTAAAACCTATAGG
CTCAGGAGCTCAAGGAATAGTATGCGCAGCTTATGATGCCATTCTTGAA
AGAAATGTTGCAATCAAGAAGCTAAGCCGACCATTTCAGAATCAGACTC
ATGCCAAGCGGGCCTACAGAGAGCTAGTTCTTATGAAATGTGTTAATCA
CAAAAATATAATTGGCCTTTTGAATGTTTTCACACCACAGAAATCCCTA
GAAGAATTTCAAGATGTTTACATAGTCATGGAGCTCATGGATGCAAATC
TTTGCCAAGTGATTCAGATGGAGCTAGATCATGAAAGAATGTCCTACCT
TCTCTATCAGATGCTGTGTGGAATCAAGCACCTTCATTCTGCTGGAATT
ATTCATCGGGACTTAAAGCCCAGTAATATAGTAGTAAAATCTGATTGCA
CTTTGAAGATTCTTGACTTCGGTCTGGCCAGGACTGCAGGAACGAGTTT
TATGATGACGCCTTATGTAGTGACTCGCTACTACAGAGCACCCGAGGTC
ATCCTTGGCATGGGCTACAAGGAAAACGTTGACATTTGGTCAGTTGGGT
GCATCATGGGAGAAATGATCAAAGGTGGTGTTTTGTTCCAGGTACAGA
TCATATTGATCAGTGGAATAAAGTTATTGAACAGTTGGAACACCATGT
CCTGAATTCATGAAGAAACTGCAACCAACAGTAAGGACTTACGTTGAAA
ACAGACCTAAATATGCTGGATATAGCTTTGAGAAACTCTTCCCTGATGT
CCTTTTTCCCAGCTGACTCAGAACACAACAAACTTAAAGCCAGTCAGGCA

AGGGATTTGTTATCCAAAATGCTGGTAATAGATGCATCTAAAAGGATCT
CTGTAGATGAAGCTCTCCAACACCCGTACATCAATGTCTGGTATGATCCT
TCTGAAGCAGAAGCTCCACCACCAAAGATCCCTGACAAGCAGTTAGATG
AAAGGGAACACACAATAGAAGAGTGGAAAGAATTGATATATAAGGAAGT

TATGGACTTGGAGGAGAGAACCAAGAATGGAGTTATACGGGGGCAGCCC

TCTCCTTTAGGTGCAGCAGTGATCAATGGCTCTCAGCATCCATCATCAT
CGTCGTCTGTCAATGATGTGTCTTCAATGTCAACAGATCCGACTTTGGC
CTCTGATACAGACAGCAGTCTAGAAGCAGCAGCTGGGCCTCTGGGCTGC
TGTAGATGA

Human LBP CDS (SEQ ID NO: 15)

ATGGGGGCCTTGGCCAGAGCCCTGCCGTCCATACTGCTGGCATTGCTGC

TTACGTCCACCCCAGAGGCTCTGGGTGCCAACCCCGGCTTGGTCGCCAG

GATCACCGACAAGGGACTGCAGTATGCGGCCCAGGAGGGGCTATTAGCT

CTGCAGAGTGAGCTGCTCAGGATCACGCTGCCTGACTTCACCGGGGACT

TGAGGATCCCCCACGTCGGCCGTGGGCGCTATGAGTTCCACAGCCTGAA

CATCCACAGCTGTGAGCTGCTTCACTCTGCGCTGAGGCCTGTCCCTGGC

CAGGGCCTGAGTCTCAGCATCTCCGACTCCTCCATCCGGGTCCAGGGCA

GGTGGAAGGTGCGCAAGTCATTCTTCAAACTACAGGGCTCCTTTGATGT

CAGTGTCAAGGGCATCAGCATTTCGGTCAACCTCCTGTTGGGCAGCGAG

TCCTCCGGGAGGCCCACAGTTACTGCCTCCAGCTGCAGCAGTGACATCG

CTGACGTGGAGGTGGACATGTCGGGAGACTTGGGGTGGCTGTTGAACCT

CTTCCACAACCAGATTGAGTCCAAGTTCCAGAAAGTACTGGAGAGCAGG

ATTTGCGAAATGATCCAGAAATCGGTGTCCTCCGATCTACAGCCTTATC

TCCAAACTCTGCCAGTTACAACAGAGATTGACAGTTTCGCCGACATTGA

TTATAGCTTAGTGGAAGCCCCTCGGGCAACAGCCCAGATGCTGGAGGTG

ATGTTTAAGGGTGAAATCTTTCATCGTAACCACCGTTCTCCAGTTACCC

TCCTTGCTGCAGTCATGAGCCTTCCTGAGGAACACAACAAAATGGTCTA

CTTTGCCATCTCGGATTATGTCTTCAACACGGCCAGCCTGGTTTATCAT

GAGGAAGGATATCTGAACTTCTCCATCACAGATGACATGATACCGCCTG

ACTCTAATATCCGACTGACCACCAAGTCCTTCCGACCCTTCGTCCCACG

GTTAGCCAGGCTCTACCCCAACATGAACCTGGAACTCCAGGGATCAGTG

CCCTCTGCTCCGCTCCTGAACTTCAGCCCTGGGAATCTGTCTGTGGACC

CCTATATGGAGATAGATGCCTTTGTGCTCCTGCCCAGCTCCAGCAAGGA

GCCTGTCTTCCGGCTCAGTGTGGCCACTAATGTGTCCGCCACCTTGACC

TTCAATACCAGCAAGATCACTGGGTTCCTGAAGCCAGGAAAGGTAAAAG

TGGAACTGAAAGAATCCAAAGTTGGACTATTCAATGCAGAGCTGTTGGA

AGCGCTCCTCAACTATTACATCCTTAACACCCTCTACCCCAAGTTCAAT

GATAAGTTGGCCGAAGGCTTCCCCCTTCCTCTGCTGAAGCGTGTTCAGC

TCTACGACCTTGGGCTGCAGATCCATAAGGACTTCCTGTTCTTGGGTGC

CAATGTCCAATACATGAGAGTTTGA

Human MEK1 CDS (SEQ ID NO: 16)

ATGCCCAAGAAGAAGCCGACGCCCATCCAGCTGAACCCGGCCCCCGACG

GCTCTGCAGTTAACGGGACCAGCTCTGCGGAGACCAACTTGGAGGCCTT

GCAGAAGAAGCTGGAGGAGCTAGAGCTTGATGAGCAGCAGCGAAAGCGC

CTTGAGGCCTTTCTTACCCAGAAGCAGAAGGTGGGAGAACTGAAGGATG

ACGACTTTGAGAAGATCAGTGAGCTGGGGGCTGGCAATGGCGGTGTGGT

GTTCAAGGTCTCCCACAAGCCTTCTGGCCTGGTCATGGCCAGAAAGCTA

ATTCATCTGGAGATCAAACCCGCAATCCGGAACCAGATCATAAGGGAGC

TGCAGGTTCTGCATGAGTGCAACTCTCCGTACATCGTGGGCTTCTATGG

TGCGTTCTACAGCGATGGCGAGATCAGTATCTGCATGGAGCACATGGAT

GGAGGTTCTCTGGATCAAGTCCTGAAGAAAGCTGGAAGAATTCCTGAAC

AAATTTTAGGAAAAGTTAGCATTGCTGTAATAAAAGGCCTGACATATCT

GAGGGAGAAGCACAAGATCATGCACAGAGATGTCAAGCCCTCCAACATC

CTAGTCAACTCCCGTGGGGAGATCAAGCTCTGTGACTTTGGGGTCAGCG

GGCAGCTCATCGACTCCATGGCCAACTCCTTCGTGGGCACAAGGTCCTA

CATGTCGCCAGAAAGACTCCAGGGGACTCATTACTCTGTGCAGTCAGAC

ATCTGGAGCATGGGACTGTCTCTGGTAGAGATGGCGGTTGGGAGGTATC

CCATCCCTCCTCCAGATGCCAAGGAGCTGGAGCTGATGTTTGGGTGCCAG

GTGGAAGGAGATGCGGCTGAGACCCCACCCAGGCCAAGGACCCCCGGGA

GGCCCCTTAGCTCATACGGAATGGACAGCCGACCTCCCATGGCAATTTT

TGAGTTGTTGGATTACATAGTCAACGAGCCTCCTCCAAAACTGCCCAGT

GGAGTGTTCAGTCTGGAATTTCAAGATTTTGTGAATAAATGCTTAATAA

AAAACCCCGCAGAGAGAGCAGATTTGAAGCAACTCATGGTTCATGCTTT

TATCAAGAGATCTGATGCTGAGGAAGTGGATTTTGCAGGTTGGCTCTGC

TCCACCATCGGCCTTAACCAGCCCAGC ACACCAACCCATGCTGCTGGC

GTCTAA

Human MEK2 CDS (SEQ ID NO: 17)

ATGCTGGCCCGGAGGAAGCCGGTGCTGCCGGCGCTCACCATCAACCCTA

CCATCGCCGAGGGCCCATCCCCTACCAGCGAGGGCGCCTCCGAGGCAAA

CCTGGTGGACCTGCAGAAGAAGCTGGAGGAGCTGGAACTTGACGAGCAG

CAGAAGAAGCGGCTGGAAGCCTTTCTCACCCAGAAAGCCAAGGTCGGCG

AACTCAAAGACGATGACTTCGAAAGGATCTCAGAGCTGGGCGCGGGCAA

CGGCGGGGTGGTCACCAAAGTCCAGCACAGACCCTCGGGCCTCATCATG

GCCAGGAAGCTGATCCACCTTGAGATCAAGCCGGCCATCCGGAACCAGA

TCATCCGCGAGCTGCAGGTCCTGCACGAATGCAACTCGCCGTACATCGT

GGGCTTCTACGGGGCCTTCTACAGTGACGGGGAGATCAGCATTTGCATG

GAACACATGGACGGCGGCTCCCTGGACCAGGTGCTGAAAGAGGCCAAGA

GGATTCCCGAGGAGATCCTGGGGAAAGTCAGCATCGCGGTTCTCCGGGG

CTTGGCGTACCTCCGAGAGAAGCACCAGATCATGCACCGAGATGTGAAG

CCCTCCAACATCCTCGTGAACTCTAGAGGGGAGATCAAGCTGTGTGACT

TCGGGGTGAGCGGCCAGCTCATCGACTCCATGGCCAACTCCTTCGTGGG

```
CACGCGCTCCTACATGGCTCCGGAGCGGTTGCAGGGCACACATTACTCG
GTGCAGTCGGACATCTGGAGCATGGGCCTGTCCCTGGTGGAGCTGGCCG
TCGGAAGGTACCCCATCCCCCCGCCCGACGCCAAAGAGCTGGAGGCCAT
CTTTGGCCGGCCCGTGGTCGACGGGGAAGAAGGAGAGCCTCACAGCATC
TCGCCTCGGCCGAGGCCCCCGGGCGCCCCGTCAGCGGTCACGGGATGG
ATAGCCGGCCTGCCATGGCCATCTTTGAACTCCTGGACTATATTGTGAA
CGAGCCACCTCCTAAGCTGCCCAACGGTGTGTTCACCCCCGACTTCCAG
GAGTTTGTCAATAAATGCCTCATCAAGAACCCAGCGGAGCGGGCGGACC
TGAAGATGCTCACAAACCACACCTTCATCAAGCGGTCCGAGGTGGAAGA
AGTGGATTTTGCCGGCTGGTTGTGTAAAACCCTGCGGCTGAACCAGCCC
GGCACACCCACGCGCACCGCCGTGTGA
```

Human MEK3 CDS (SEQ ID NO: 18)
```
ATGTCCAAGCCACCCGCACCCAACCCCACACCCCCCGGAACCTGGACT
CCCGGACCTTCATCACCATTGGAGACAGAAACTTTGAGGTGGAGGCTGA
TGACTTGGTGACCATCTCAGAACTGGGCCGTGGAGCCTATGGGGTGGTA
GAGAAGGTGCGGCACGCCCAGAGCGGCACCATCATGGCCGTGAAGCGGA
TCCGGGCCACCGTGAACTCACAGGAGCAGAAGCGGCTGCTCATGGACCT
GGACATCAACATGCGCACGGTCGACTGTTTCTACACTGTCACCTTCTAC
GGGGCACTATTCAGAGAGGGAGACGTGTGGATCTGCATGGAGCTCATGG
ACACATCCTTGGACAAGTTCTACCGGAAGGTGCTGGATAAAAACATGAC
AATTCCAGAGGACATCCTTGGGAGATTGCTGTGTCTATCGTGCGGCC
CTGGAGCATCTGCACAGCAAGCTGTCGGTGATCCACAGAGATGTGAAGC
CCTCCAATGTCCTTATCAACAAGGAGGGCCATGTGAAGATGTGTGACTT
TGGCATCAGTGGCTACTTGGTGGACTCTGTGGCCAAGACGATGGATGCC
GGCTGCAAGCCCTACATGGCCCCTGAGAGGATCAACCCAGAGCTGAACC
AGAAGGGCTACAATGTCAAGTCCGACGTCTGGAGCCTGGGCATCACCAT
GATTGAGATGGCCATCCTGCGCGTTCCCTTACGAGTCCTGGGGGACCCCG
TTCCAGCAGCTGAAGCAGGTGGTGGAGGAGCCGTCCCCCAGCTCCAG
CCGACCGTTTCTCCCCGAGTTTGTGGACTTCACTGCTCAGTGCCTGAG
GAAGAACCCCGCAGAGCGTATGAGCTACCTGGAGCTGATGGAGCACCCC
TTCTTCACCTTGCACAAAACCAAGAAGACGGACATTGCTGCCTTCGTGA
AGGAGATCCTGGGAGAAGACTCATAG
```

Human MEK6 CDS (SEQ ID NO: 19)
```
ATGTCTCAGTCGAAAGGCAAGAAGCGAAACCCTGGCCTTAAAATTCCAA
AAGAAGCATTTGAACAACCTCAGACCAGTTCCACACCACCTCGAGATTT
AGACTCCAAGGCTTGCATTTCTATTGGAAATCAGAACTTTGAGGTGAAG
GCAGATGACCTGGAGCCTATAATGGAACTGGGACGAGGTGCGTACGGGG
TGGTGGAGAAGATGCGGCACGTGCCCAGCGGGCAGATCATGGCAGTGAA
GCGGATCCGAGCCACAGTAAATAGCCAGGAACAGAAACGGCTACTGATG
GATTTGGATATTTCCATGAGGACGGTGGACTGTCCATTCACTGTCACCT
TTTATGGCGCACTGTTTCGGGAGGGTGATGTGTGGATCTGCATGGAGCT
```

CATGGATACATCACTAGATAAATTCTACAAACAAGTTATTGATAAAGGC
CAGACAATTCCAGAGGACATCTTAGGGAAAATAGCAGTTTCTATTGTAA
AAGCATTAGAACATTTACATAGTAAGCTGTCTGTCATTCACAGAGACGT
CAAGCCTTCTAATGTACTCATCAATGCTCTCGGTCAAGTGAAGATGTGC
GATTTTGGAATCAGTGGCTACTTGGTGGACTCTGTTGCTAAAACAATTG
ATGCAGGTTGCAAACCATACATGGCCCCTGAAAGAATAAACCCAGAGCT
CAACCAGAAGGGATACAGTGTGAAGTCTGACATTTGGAGTCTGGGCATC
ACGATGATTGAGTTGGCCATCCTTCGATTTCCCTATGATTCATGGGGAA
CTCCATTTCAGCAGCTCAAACAGGTGGTAGAGGAGCCATCGCCACAACT
CCCAGCAGACAAGTTCTCTGCAGAGTTTGTTGACTTTACCTCACAGTGC
TTAAAGAAGAATTCCAAAGAACGGCCTACATACCCAGAGCTAATGCAAC
ATCCATTTTTCACCCTACATGAATCCAAAGGAACAGATGTGGCATCTTT
TGTAAAACTGATTCTTGGAGACTAA

Human MEKK1 CDS (SEQ ID NO: 20)
```
ATGGCGGCGGCGGCGGGGAATCGCGCCTCGTCGTCGGGATTCCCGGGCG
CCAGGGCTACGAGCCCTGAGGCAGGCGGCGGCGGAGGAGCCCTCAAGGC
GAGCAGCGCGCCCGCGGCTGCCGCGGGACTGCTGCGGGAGGCGGGCAGC
GGGGGCCGCGAGCGGGCGGACTGGCGGCGGCGGCAGCTGCGCAAAGTGC
GGAGTGTGGAGCTGGACCAGCTGCCTGAGCAGCCGCTCTTCCTTGCCGC
CTCACCGCCGGCCTCCTCGACTTCCCCGTCGCCGGAGCCCGCGGACGCA
GCGGGGAGTGGGACCGGCTTCCAGCCTGTGGCGGTGCCGCCGCCCCACG
GAGCCGCGAGCCGCGGCGGCGCCCACCTTACCGAGTCGGTGGCGGCGCC
GGACAGCGGCGCCTCGAGTCCCGCAGCGGCCGAGCCCGGGGAGAAGCGG
GCGCCCGCCGCCAGCCGTCTCCTGCAGCGGCCCCCGCCGGTCGTGAGA
TGGAGAATAAAGAAACTCTCAAAGGGTTGCACAAGATGGATGATCGTCC
AGAGGAACGAATGATCAGGGAGAAACTGAAGGCAACCTGTATGCCAGCC
TGGAAGCACGAATGGTTGGAAAGGAGAAATAGGCGAGGGCCTGTGGTGG
TAAAACCAATCCCAGTTAAAGGAGATGGATCTGAAATGAATCACTTAGC
AGCTGAGTCTCCAGGAGAGGTCCAGGCAAGTGCGGCTTCACCAGCTTCC
AAAGGCCGACGCAGTCCTTCTCCTGGCAACTCCCCATCAGGTCGCACAG
TGAAATCAGAATCTCCAGGAGTAAGGAGAAAAAGAGTTTCCCCAGTGCC
TTTTCAGAGTGGCAGAATCACACCACCCCGAAGAGCCCCTTCACCAGAT
GGCTTCTCACCATATAGCCCTGAGGAAACAAACCGCCGTGTTAACAAAG
TGATGCGGGCCAGACTGTACTTACTGCAGCAGATAGGGCCTAACTCTTT
CCTGATTGAGGAGACAGCCCAGACAATAAATACCGGGTGTTTATTGGG
CCTCAGAACTGCAGCTGTGCACGTGGAACATTCTGTATTCATCTGCTAT
TTGTGATGCTCCGGGTGTTTCAACTAGAACCTTCAGACCCAATGTTATG
GAGAAAAACTTTAAAGAATTTTGAGGTTGAGAGTTTGTTCCAGAAATAT
CACAGTAGGCGTAGCTCAAGGATCAAAGCTCCATCTCGTAACACCATCC
AGAAGTTTGTTTCACGCATGTCAAATTCTCATACATTGTCATCATCTAG
```

```
TACTTCTACGTCTAGTTCAGAAAACAGCATAAAGGATGAAGAGGAACAG
ATGTGTCCTATTTGCTTGTTGGGCATGCTTGATGAAGAAAGTCTTACAG
TGTGTGAAGACGGCTGCAGGAACAAGCTGCACCACCACTGCATGTCAAT
TTGGGCAGAAGAGTGTAGAAGAAATAGAGAACCTTTAATATGTCCCCTT
TGTAGATCTAAGTGGAGATCTCATGATTTCTACAGCCACGAGTTGTCAA
GTCCTGTGGATTCCCCTTCTTCCCTCAGAGCTGCACAGCAGCAAACCGT
ACAGCAGCAGCCTTTGGCTGGATCACGAAGGAATCAAGAGAGCAATTTT
AACCTTACTCATTATGGAACTCAGCAAATCCCTCCTGCTTACAAAGATT
TAGCTGAGCCATGGATTCAGGTGTTTGGAATGGAACTCGTTGGCTGCTT
ATTTTCTAGAAACTGGAATGTGAGAGAGATGGCCCTCAGGCGTCTTTCC
CATGATGTCAGTGGGGCCCTGCTGTTGGCAAATGGGGAGAGCACTGGAA
ATTCTGGGGGCAGCAGTGGAAGCAGCCCGAGTGGGGGAGCCACCAGTGG
GTCTTCCCAGACCAGTATCTCAGGAGATGTGGTGGAGGCATGCTGCAGC
GTTCTGTCAATGGTCTGTGCTGACCCTGTCTACAAAGTGTACGTTGCTG
CTTTAAAAACATTGAGAGCCATGCTGGTATATACTCCTTGCCACAGTTT
AGCGGAAAGAATCAAACTTCAGAGACTTCTCCAGCCAGTTGTAGACACC
ATCCTAGTCAAATGTGCAGATGCCAATAGCCGCACAAGTCAGCTGTCCA
TATCAACACTGTTGGAACTGTGCAAAGGCCAAGCAGGAGAGTTGGCAGT
TGGCAGAGAAATACTAAAAGCTGGATCCATTGGTATTGGTGGTGTTGAT
TATGTCTTAAATTGTATTCTTGGAAACCAAACTGAATCAAACAATTGGC
AAGAACTTCTTGGCCGCCTTTGTCTTATAGATAGACTGTTGTTGGAATT
TCCTGCTGAATTTTATCCTCATATTGTCAGTACTGATGTTTCACAAGCT
GAGCCTGTTGAAATCAGGTATAAGAAGCTGCTGTCCCTCTTAACCTTTG
CTTTGCAGTCCATTGATAATTCCCACTCAATGGTTGGCAAACTTTCCAG
AAGGATCTACTTGAGTTCTGCAAGAATGGTTACTACAGTACCCCATGTG
TTTTCAAAACTGTTAGAAATGCTGAGTGTTTCCAGTTCCACTCACTTCA
CCAGGATGCGTCGCCGTTTGATGGCTATTGCAGATGAGGTGGAAATTGC
CGAAGCCATCCAGTTGGGCGTAGAAGACACTTTGGATGGTCAACAGGAC
AGCTTCTTGCAGGCATCTGTTCCCAACAACTATCTGGAAACCACAGAGA
ACAGTTCCCTGAGTGCACAGTCCATTTAGAGAAAACTGGAAAAGGATT
ATGTGCTACAAAATTGAGTGCCAGTTCAGAGGACATTTCTGAGAGACTG
GCCAGCATTTCAGTAGGACCTTCTAGTTCAACAACAACAACAACAACAA
CAACAGAGCAACCAAAGCCAATGGTTCAAACAAAAGGCAGACCCCACAG
TCAGTGTTTGAACTCCTCTCCTTTATCTCATCATTCCCAATTAATGTTT
CCAGCCTTGTCAACCCCTTCTTCTTCTACCCCATCTGTACCAGCTGGCA
CTGCAACAGATGTCTCTAAGCATAGACTTCAGGGATTCATTCCCTGCAG
AATACCTTCTGCATCTCCTCAAACACAGCGCAAGTTTTCTCTACAATTC
CACAGAAACTGTCCTGAAAACAAAGACTCAGATAAACTTTCCCCAGTCT
TTACTCAGTCAAGACCCTTGCCCTCCAGTAACATACACAGGCCAAAGCC
ATCTAGACCTACCCCAGGTAATACAAGTAAACAGGGAGATCCCTCAAAA
AATAGCATGACACTTGATCTGAACAGTAGTTCCAAATGTGATGACAGCT
TGGCTGTAGCAGCAATAGTAGTAATGCTGTTATACCCAGTGACGAGAC
AGTGTTCACCCCAGTAGAGGAGAAATGCAGATTAGATGTCAATACAGAG
CTCAACTCCAGTATTGAGGACCTTCTTGAAGCATCTATGCCTTCAAGTG
ATACAACAGTAACTTTTAAGTCAGAAGTTGCTGTCCTGTCTCCTGAAAA
GGCTGAAAATGATGATACCTACAAAGATGATGTGAATCATAATCAAAAG
TGCAAAGAGAAGATGGAAGCTGAAGAAGAAGAAGCTTTAGCAATTGCCA
TGGCAATGTCAGCGTCTCAGGATGCCCTCCCCATAGTTCCTCAGCTGCA
GGTTGAAAATGGAGAAGATATCATCATTATTCAACAGGATACACCAGAG
ACTCTACCAGGACATACCAAAGCAAAACAACCGTATAGAGAAGACACTG
AATGGCTGAAAGGTCAACAGATAGGCCTTGGAGCATTTTCTTCTTGTTA
TCAGGCTCAAGATGTGGGAACTGGAACTTTAATGGCTGTTAAACAGGTG
ACTTATGTCAGAAACACATCTTCTGAGCAAGAAGAAGTAGTAGAAGCAC
TAAGAGAAGAGATAAGAATGATGAGCCATCTGAATCATCCAAACATCAT
TAGGATGTTGGGAGCCACGTGTGAGAAGAGCAATTACAATCTCTTCATT
GAATGGATGGCAGGGGATCGGTGGCTCATTTGCTGAGTAAATATGGAG
CCTTCAAAGAATCAGTAGTTATTAACTACACTGAACAGTTACTCCGTGG
CCTTTCGTATCTCCATGAAAACCAAATCATTCACAGAGATGTCAAGGT
GCCAATTTGCTAATTGACAGCACTGGTCAGAGACTAAGAATTGCAGATT
TTGGAGCTGCAGCCAGGTTGGCATCAAAAGGAACTGGTGCAGGAGAGTT
TCAGGGACAATTACTGGGACAATTGCATTTATGGCACCTGAGGTACTA
AGAGGTCAACAGTATGGAAGGAGCTGTGATGTATGGAGTGTTGGCTGTG
CTATTATAGAAATGGCTTGTGCAAAACCACCATGGAATGCAGAAAAACA
CTCCAATCATCTTGCTTTGATATTTAAGATTGCTAGTGCAACTACTGCT
CCATCGATCCCTTCACATTTGTCTCCTGGTTTACGAGATGTGGCTCTTC
GTTGTTTAGAACTTCAACCTCAGGACAGACCTCCATCAAGAGAGCTACT
GAAGCATCCAGTCTTTCGTACTACATGGTAG
Human MEKK 3 CDS
                                    (SEQ ID NO: 21)
ATGGACGAACAGGAGGCATTGAACTCAATCATGAACGATCTGGTGGCCCT
CCAGATGAACCGACGTCACCGGATGCCTGGATATGAGACCATGAAGAACA
AAGACACAGGTCACTCAAATAGGCAGAAAAAACACAACAGCAGCAGCTCA
GCCCTTCTGAACAGCCCCACAGTAACAACAAGCTCATGTGCAGGGGCCAG
TGAGAAAAGAAATTTTTGAGTGACGTCAGAATCAAGTTCGAGCACAACG
GGGAGAGGCGAATTATAGCGTTCAGCCGGCCTGTGAAATATGAAGATGTG
GAGCACAAGGTGACAACAGTATTTGGACAACCTCTTGATCTACATTACAT
GAACAATGAGCTCTCCATCCTGCTGAAAAACCAAGATGATCTTGATAAAG
CAATTGACATTTTAGATAGAAGCTCAAGCATGAAAAGCCTTAGGATATTG
CTGTTGTCCCAGGACAGAAACCATAACAGTTCCTCTCCCCACTCTGGGGT
GTCCAGACAGGTGCGGATCAAGGCTTCCCAGTCCGCAGGGGATATAAATA
CTATCTACCAGCCCCCGAGCCCAGAAGCAGGCACCTCTCTGTCAGCTCC
CAGAACCCTGGCCGAAGCTCACCTCCCCCTGGCTATGTTCCTGAGCGGCA
```

-continued

GCAGCACATTGCCCGGCAGGGGTCCTACACCAGCATCAACAGTGAGGGGG

AGTTCATCCCAGAGACCAGCGAGCAGTGCATGCTGGATCCCCTGAGCAGT

GCAGAAAATTCCTTGTCTGGAAGCTGCCAATCCTTGGACAGGTCAGCAGA

CAGCCCATCCTTCCGGAAATCACGAATGTCCCGTGCCCAGAGCTTCCCTG

ACAACAGACAGGAATACTCAGATCGGGAAACTCAGCTTTATGACAAAGGG

GTCAAAGGTGGAACCTACCCCCGGCGCTACCACGTGTCTGTGCACCACAA

GGACTACAGTGATGGCAGAAGAACATTTCCCCGAATACGGCGTCATCAAG

GCAACTTGTTCACCCTGGTGCCCTCCAGCCGCTCCCTGAGCACAAATGGC

GAGAACATGGGTCTGGCTGTGCAATACCTGGACCCCCGTGGGCGCCTGCG

GAGTGCGGACAGCGAGAATGCCCTCTCTGTGCAGGAGAGGAATGTGCCAA

CCAAGTCTCCCAGTGCCCCCATCAACTGGCGCCGGGGAAAGCTCCTGGGC

CAGGGTGCCTTCGGCAGGGTCTATTTGTGCTATGACGTGGACACGGGACG

TGAACTTGCTTCCAAGCAGGTCCAATTTGATCCAGACAGTCCTGAGACAA

GCAAGGAGGTGAGTGCTCTGGAGTGCGAGATCCAGTTGCTAAAGAACTTG

CAGCATGAGCGCATCGTGCAGTACTATGGCGTGTCTGCGGGACCGCGCTGA

GAAGACCCTGACCATCTTCATGGAGTACATGCCAGGGGCTCGGTGAAAG

ACCAGTTGAAGGCTTACGGTGCTCTGACAGAGAGCGTGACCCGAAAGTAC

ACGCGGCAGATCCTGGAGGGCATGTCCTACCTGCACAGCAACATGATTGT

TCACCGGGACATTAAGGGAGCCAACATCCTCCGAGACTCTGCTGGGAATG

TAAAGCTGGGGACTTTGGGGCCAGCAAACGCCTGCAGACGATCTGTATG

TCGGGGACGGGCATGCGCTCCGTCACTGGCACACCCTACTGGATGAGCCC

TGAGGTGATCAGCGGCGAGGGCTATGGAAGGAAAGCAGACGTGTGGAGCC

TGGGCTGCACTGTGGTGGAGATGCTGACAGAGAAACCACCGTGGGCAGAG

TATGAAGCTATGGCCGCCATCTTCAAGATTGCCACCCAGCCCACCAATCC

TCAGCTGCCCTCCCACATCTCTGAACATGGCCGGGACTTCCTGAGGCGCA

TTTTTGTGGAGGCTCGCCAGAGACCTTCAGCTGAGGAGCTGCTCACACAC

CACTTTGCACAGCTCATGTACTGA

Human MEKK4 CDS (SEQ ID NO: 22)
ATGAGAGAAGCCGCTGCCGCGCTGGTCCCTCCTCCCGCCTTTGCCGTCAC

GCCTGCCGCCGCCATGGAGGAGCCGCCGCCACCGCCGCCGCCGCCACCAC

CGCCACCGGAACCCGAGACCGAGTCAGAACCCGAGTGCTGCTTGGCGGCG

AGGCAAGAGGGCACATTGGGAGATTCAGCTTGCAAGAGTCCTGAATCTGA

TCTAGAAGACTTCTCCGATGAAACAAATACAGAGAATCTTTATGGTACCT

CTCCCCCCAGCACACCTCGACAGATGAAACGCATGTCAACCAAACATCAG

AGGAATAATGTGGGGAGGCCAGCCAGTCGGTCTAATTTGAAAGAAAAAAT

GAATGCACCAAATCAGCCTCCACATAAAGACACTGGAAAAACAGTGGAGA

ATGTGGAAGAATACAGCTATAAGCAGGAGAAAAAGATCCGAGCAGCTCTT

AGAACAACAGAGCGTGATCATAAAAAAAATGTACAGTGCTCATTCATGTT

AGACTCAGTGGGTGGATCTTTGCCAAAAAAATCAATTCCAGATGTGGATC

TCAATAAGCCTTACCTCAGCCTTGGCTGTAGCAATGCTAAGCTTCCAGTA

TCTGTGCCCATGCCTATAGCCAGACCTGCACGCCAGACTTCTAGGACTGA

-continued

CTGTCCAGCAGATCGTTTAAAGTTTTTTGAAACTTTACGACTTTTGCTAA

AGCTTACCTCAGTCTCAAAGAAAAAAGACAGGGAGCAAAGAGGACAAGAA

AATACGTCTGGTTTCTGGCTTAACCGATCTAACGAACTGATCTGGTTAGA

GCTACAAGCCTGGCATGCAGGACGGACAATTAACGACCAGGACTTCTTTT

TATATACAGCCCGTCAAGCCATCCCAGATATTATTAATGAAATCCTTACT

TTCAAAGTCGACTATGGGAGCTTCGCCTTTGTTAGAGATAGAGCTGGTTT

TAATGGTACTTCAGTAGAAGGGCAGTGCAAAGCCACTCCTGGAACAAAGA

TTGTAGGTTACTCAACACATCATGAGCATCTCCAACGCCAGAGGGTCTCA

TTTGAGCAGGTAAAACGGATAATGGAGCTGCTAGAGTACATAGAAGCACT

TTATCCATCATTGCAGGCTCTTCAGAAGGACTATGAAAAATATGCTGCAA

AGACTTCCAGGACAGGGTGCAGGCACTCTGTTTGTGGTTAAACATCACA

AAAGACTTAAATCAGAAATTAAGGATTATGGGCACTGTTTTGGGCATCAA

GAATTTATCAGACATTGGCTGGCCAGTGTTTGAAATCCCTTCCCCTCGAC

CATCCAAAGGTAATGAGCCGGAGTATGAGGGTGATGACACAGAAGGAGAA

TTAAAGGAGTTGGAAAGTAGTACGGATGAGAGTGAAGAAGAACAAATCTC

TGATCCTAGGGTACCGGAAATCAGACAGCCCATAGATAACAGCTTCGACA

TCCAGTCGCGGGACTGCATATCCAAGAAGCTTGAGAGGCTCGAATCTGAG

GATGATTCTCTTGGCTGGGGAGCACCAGACTGGAGCACAGAAGCAGGCTT

TAGTAGACATTGTCTGACTTCTATTTATAGACCATTTGTAGACAAAGCAC

TGAAGCAGATGGGGTTAAGAAAGTTAATTTTAAGACTTCACAAGCTAATG

GATGGTTCCTTGCAAAGGGCACGTATAGCATTGGTAAAGAACGATCGTCC

AGTGGAGTTTTCTGAATTTCCAGATCCCATGTGGGGTTCAGATTATGTGC

AGTTGTCAAGGACACCACCTTCATCTGAGGAGAAATGCAGTGCTGTGTCG

TGGGAGGAGCTGAAGGCCATGGATTTACCTTCATTCGAACCTGCCTTCCT

AGTTCTCTGCCGAGTCCTTCTGAATGTCATACATGAGTGTCTGAAGTTAA

GATTGGAGCAGAGACCTGCTGGAGAACCATCTCTCTTGAGTATTAAGCAG

CTGGTGAGAGTGTAAGGAGGTCCTGAAGGGCGGCCTGCTGATGAAGCA

GTACTACCAGTTCATGCTGCAGGAGGTTCTGGAGGACTTGGAGAAGCCCG

ACTGCAACATTGACGCTTTTGAAGAGGATCTACATAAAATGCTTATGGTG

TATTTTGATTACATGAGAAGCTGGATCCAAATGCTACAGCAATTACCTCA

AGCATCGCATAGTTTAAAAAATCTGTTAGAAGAAGAATGGAATTTCACCA

AAGAAATAACTCATTACATACGGGAGGAGAAGCACAGGCCGGGAAGCTT

TTCTGTGACATTGCAGGAATGCTGCTGAAATCTACAGGAAGTTTTTTAGA

ATTTGGCTTACAGGAGAGCTGTGCTGAATTTTGGACTAGTGCGGATGACA

GCAGTGCTTCCGACGAAATCAGGAGGTCTGTTATAGAGATCAGTCGAGCC

CTGAAGGAGCTCTTCCATGAAGCCAGAGAAAGGGCTTCCAAAGCACTTGG

ATTTGCTAAAATGTTGAGAAAGGACCTGGAAATAGCAGCAGAATTCAGGC

TTTCAGCCCCAGTTAGAGACCTCCTGGATGTTCTGAAATCAAAACAGTAT

GTCAAGGTGCAAATTCCTGGGTTAGAAAACTTGCAAATGTTTGTTCCAGA

CACTCTTGCTGAGGAGAAGAGTATTATTTTGCAGTTACTCAATGCAGCTG

```
CAGGAAAGGACTGTTCAAAAGATTCAGATGACGTACTCATCGATGCCTAT
CTGCTTCTGACCAAGCACGGTGATCGAGCCCGTGATTCAGAGGACAGCTG
GGGCACCTGGGAGGCACAGCCTGTCAAAGTCGTGCCTCAGGTGGAGACTG
TTGACACCCTGAGAAGCATGCAGGTGGATAATCTTTTACTAGTTGTCATG
CAGTCTGCGCATCTCACAATTCAGAGAAAAGCTTTCCAGCAGTCCATTGA
GGGACTTATGACTCTGTGCCAGGAGCAGACATCCAGTCAGCCGGTCATCG
CCAAAGCTTTGCAGCAGCTGAAGAATGATGCATTGGAGCTATGCAACAGG
ATAAGCAATGCCATTGACCGCGTGGACCACATGTTCACATCAGAATTTGA
TGCTGAGGTTGATGAATCTGAATCTGTCACCTTGCAACAGTACTACCGAG
AAGCAATGATTCAGGGGTACAATTTTGGATTTGAGTATCATAAAGAAGTT
GTTCGTTTGATGTCTGGGGAGTTTAGACAGAAGATAGGAGACAAATATAT
AAGCTTTGCCCGGAAGTGGATGAATTATGTCCTGACTAAATGTGAGAGTG
GTAGAGGTACAAGACCCAGGTGGGCGACTCAAGGATTTGATTTTCTACAA
GCAATTGAACCTGCCTTTATTTCAGCTTTACCAGAAGATGACTTCTTGAG
TTTACAAGCCTTGATGAATGAATGCATTGGCCATGTCATAGGAAAACCAC
ACAGTCCTGTTACAGGTTTGTACCTTGCCATTCATCGGAACAGCCCCCGT
CCTATGAAGGTACCTCGATGCCATAGTGACCCTCCTAACCCACACCTCAT
TATCCCCACTCCAGAGGGATTCAGCACTCGGAGCATGCCTTCCGACGCGC
GGAGCCATGGCAGCCCTGCTGCTGCTGCTGCTGCTGCTGCTGCTGCTGTT
GCTGCCAGTCGGCCCAGCCCCTCTGGTGGTGACTCTGTGCTGCCCAAATC
CATCAGCAGTGCCCATGATACCAGGGGTTCCAGCGTTCCTGAAAATGATC
GATTGGCTTCCATAGCTGCTGAATTGCAGTTTAGGTCCCTGAGTCGTCAC
TCAAGCCCCACGGAGGAGCGAGATGAACCAGCATATCCAAGAGGAGATTC
AAGTGGGTCCACAAGAAGAAGTTGGGAACTTCGGACACTAATCAGCCAGA
GTAAAGATACTGCTTCTAAACTAGGACCCATAGAAGCTATCCAGAAGTCA
GTCCGATTGTTTGAAGAAAAGAGGTACCGAGAAATGAGGAGAAAGAATAT
CATTGGTCAAGTTTGTGATACGCCTAAGTCCTATGATAATGTTATGCACG
TTGGCTTGAGGAAGGTGACCTTCAAATGGCAAAGAGGAAACAAAATTGGA
GAAGGCCAGTATGGGAAGGTGTACACCTGCATCAGCGTCGACACCGGGGA
GCTGATGGCCATGAAAGAGATTCGATTTCAACCTAATGACCATAAGACTA
TCAAGGAAACTGCAGACGAATTGAAAATATTCGAAGGCATCAAACACCCC
AATCTGGTTCGGTATTTTGGTGTGGAGCTCCATAGAGAAGAAATGTACAT
CTTCATGGAGTACTGCGATGAGGGGACTTTAGAAGAGGTGTCAAGGCTGG
GACTTCAGGAACATGTGATTAGGCTGTATTCAAAGCAGATCACCATTGCG
ATCAACGTCCTCCATGAGCATGGCATAGTCCACCGTGACATTAAAGGTGC
CAATATCTTCCTTACCTCATCTGGATTAATCAAACTGGGAGATTTTGGAT
GTTCAGTAAAGCTCAAAAACAATGCCCAGACCATGCCTGGTGAAGTGAAC
AGCACCCTGGGGACAGCAGCATACATGGCACCTGAAGTCATCACTCGTGC
CAAAGGAGAGGGCCATGGGCGTGCGGCCGACATCTGGAGTCTGGGGTGTG
TTGTCATAGAGATGGTGACTGGCAAGAGGCCTTGGCATGAGTATGAGCAC
AACTTTCAAATTATGTATAAAGTGGGGATGGGACATAAGCCACCAATCCC
TGAAAGATTAAGCCCTGAAGGAAAGGACTTCCTTTCTCACTGCCTTGAGA
GTGACCCAAAGATGAGATGGACCGCCAGCCAGCTCCTCGACCATTCGTTT
GTCAAGGTTTGCACAGATGAAGAATG
```

Human MEKK 6 CDS (SEQ ID NO: 23)

```
ATGGCGGGGCCGTGTCCCCGGTCCGGGGCGGAGCGCGCCGGCAGCTGCTG
GCAGGACCCGCTGGCCGTGGCGCTGAGCCGGGGCCGGCAGCTCGCGGCGC
CCCCGGGCCGGGGCTGCGCGCGGAGCCGGCCGCTCAGCGTGGTCTACGTG
CTGACCCGGGAGCCGCAGCCCGGGCTCGAGCCTCGGGAGGGAACCGAGGC
GGAGCCGCTGCCCCTGCGCTGCCTGCGCGAGGCTTGCGCGCAGGTCCCCC
GGCCGCGGCCGCCCCCGCAGCTGCGCAGCCTGCCCTTCGGGACGCTGGAG
CTAGGCGACACCGCGGCTCTGGATGCCTTCTACAACGCGGATGTGGTGGT
GCTGGAGGTGAGCAGCTCGCTGGTACAGCCCTCCCTGTTCTACCACCTTG
GTGTGCGTGAGAGCTTCAGCATGACCAACAATGTGCTCCTCTGCTCCCAG
GCCGACCTCCCTGACCTGCAGGCCCTGCGGGAGGATGTTTTCCAGAAGAA
CTCGGATTGCGTTGGCAGCTACACACTGATCCCCTATGTGGTGACGGCCA
CTGGTCGGGTGCTGTGTGGTGATGCAGGCCTTCTGCGGGGCCTGGCTGAT
GGGCTGGTACAGGCTGGAGTGGGGACCGAGGCCCTGCTCACTCCCCTGGT
GGGCCGGCTTGCCCGCCTGCTGGAGGCCACACCCACAGACTCTTGTGGCT
ATTTCCGGGAGACCATTCGGCGGGACATCCGGCAGGCGCGGGAGCGGTTC
AGTGGGCCACAGCTGCGGCAGGAGCTGGCTCGCCTGCAGCGGAGACTGGA
CAGCGTGGAGCTGCTGAGCCCCGACATCATCATGAACTTGCTGCTCTCCT
ACCGCGATGTGCAGGACTACTCGGCCATCATTGAGCTGGTGGAGACGCTG
CAGGCCTTGCCCACCTGTGATGTGGCCGAGCAGCATAATGTCTGCTTCCA
CTACACTTTTGCCCTCAACCGGAGGAACAGGCCTGGGGACCGGGCGAAGG
CCCTGTCTGTGCTGCTGCCGCTGGTACAGCTTGAGGGCTCTGTGGCGCCC
GATCTGTACTGCATGTGTGGCCGTATCTACAAGGACATGTTCTTCAGCTC
GGGGTTTCCAGGATGCTGGGCACCGGGAGCAGGCCTATCACTGGTATCGCA
AGGCTTTTGACGTAGAGCCCAGCCTTCACTCAGGCATCAATGCAGCTGTG
CTCCTCATTGCTGCCGGGCAGCACTTTGAGGATTCCAAAGAGCTCCGGCT
AATAGGCATGAAGCTGGGCTGCCTGCTGGCCCGCAAAGGCTGCGTGGAGA
AGATGCAGTATTACTGGGATGTGGGTTTCTACCTGGGAGCCCAGATCCTC
GCCAATGACCCCACCCAGGTGGTGCTGGCTGCAGAGCAGCTGTATAAGCT
CAATGCCCCCATATGGTACCTGGTGTCCGTGATGGAGACCTTCCTGCTCT
ACCAGCACTTCAGGCCCACGCCAGAGCCCCCTGGAGGGCCACCACGCCGT
GCCCACTTCTGGCTCCACTTCTTGCTACAGTCCTGCCAACCATTCAAGAC
AGCCTGTGCCCAGGGCGACCAGTGCTTGGTGCTGGTCCTGGAGATGAACA
AGGTGCTGCTGCCTGCAAAGCTCGAGGTTCGGGGTACTGACCCAGTAAGC
ACAGTGACCCTGAGCCTGCTGGAGCCTGAGACCCAGGACATTCCCTCCAG
CTGGACCTTCCCAGTCGCCTCCATATGCGGAGTCAGCGCCTCAAAGCGCG
ACGAGCGCTGCTGCTTCCTCTATGCACTCCCCCCGGCTCAGGACGTCCAG
```

-continued

CTGTGCTTCCCCAGCGTAGGGCACTGCCAGTGGTTCTGCGGCCTGATCCA
GGCCTGGGTGACGAACCCGGATTCCACGGCGCCCGCGGAGGAGGCGGAGG
GCGCGGGGGAGATGTTGGAGTTTGATTATGAGTACACGGAGACGGGCGAG
CGGCTGGTGCTGGGCAAGGGCACGTATGGGGTGGTGTACGCGGGCCGCGA
TCGCCACACGAGGGTGCGCATCGCCATCAAGGAGATCCCGGAGCGGGACA
GCAGGTTCTCTCAGCCCCTGCATGAAGAGATCGCTCTTCACAGACGCCTG
CGCCACAAGAACATAGTGCGCTATCTGGGCTCAGCTAGCCAGGGCGGCTA
CCTTAAGATCTTCATGGAGGAAGTGCCTGGAGGCAGCCTGTCCTCCTTGC
TGCGGTCGGTGTGGGGACCCCTGAAGGACAACGAGAGCACCATCAGTTTC
TACACCCGCCAGATCCTGCAGGGACTTGGCTACTTGCACGACAACCACAT
CGTGCACAGGGACATAAAAGGGGACAATGTGCTGATCAACACCTTCAGTG
GGCTGCTCAAGATTTCTGACTTCGGCACCTCCAAGCGGCTGGCAGGCATC
ACACCTTGCACTGAGACCTTCACAGGAACTCTGCAGTATATGGCCCCAGA
AATCATTGACCAGGGCCCACGCGGGTATGGGAAAGCAGCTGACATCTGGT
CACTGGGCTGCACTGTCATTGAGATGGCCACAGGTCGCCCCCCCCTTCCAC
GAGCTCGGGAGCCCACAGGCTGCCATGTTTCAGGTGGGTATGTACAAGGT
CCATCCGCCAATGCCCAGCTCTCTGTCGGCCGAGGCCCAAGCCTTTCTCC
TCCGAACTTTTGAGCCAGACCCCCGCCTCCGAGCCAGCGCCCAGACACTG
CTGGGGGACCCCTTCCTGCAGCCTGGGAAAAGGAGCCGCAGCCCCAGCTC
CCCACGACATGCTCACGCCCTCAGATGCCCCTTCTGCCAGTCCCACTC
CTTCAGCCAACTCAACCACCCAGTCTCAGACATTCCCGTGCCCTCAGGCA
CCCTCTCAGCACCCACCCAGCCCCCCGAAGCGCTGCCTCAGTTATGGGGG
CACCAGCCAGCTCCGGGTGCCCGAGGAGCCTGCGGCCGAGGAGCCTGCGT
CTCCGGAGGAGAGTTCGGGGCTGAGCCTGCTGCACCAGGAGAGCAAGCGT
CGGGCCATGCTGGCCGCAGTATTGGAGCAGGAGCTGCCAGCGCTGGCGGA
GAATCTGCACCAGGAGCAGAAGCAAGAGCAGGGGCCCGTCTGGGCAGAA
ACCATGTGGAAGAGCTGCTGCGCTGCCTCGGGGCACACATCCACACTCCC
AACCGCCGGCAGCTCGCCCAGGAGCTGCGGGCGCTGCAAGGACGGCTGAG
GGCCCAGGGCCTTGGGCCTGCGCTTCTGCACAGACCGCTGTTTGCCTTCC
CGGATGCGGTGAAGCAGATCCTCCGCAAGCGCCAGATCCGTCCACACTGG
ATGTTCGTTCTGGACTCACTGCTCAGCCGTGCTGTGCGGGCAGCCCTGGG
TGTGCTAGGACCGGAGGTGGAGAAGGAGGCGGTCTCACCGAGGTCAGAGG
AGCTGAGTAATGAAGGGGACTCCCAGCAGAGCCCAGGCCAGCAGAGCCCG
CTTCCGGTGGAGCCCGAGCAGGGCCCCGCTCCTCTGATGGTGCAGCTGAG
CCTCTTGAGGGCAGAGACTGATCGGCTGCGCGAAATCCTGGCGGGGAAGG
AACGGGAGTACCAGGCCCTGGTGCAGCGGGCTCTACAGCGGCTGAATGAG
GAAGCCCGGACCTATGTCCTGGCCCCAGAGCCTCCAACTGCTCTTTCAAC
GGACCAGGGCCTGGTGCAGTGGCTACAGGAACTGAATGTGGATTCAGGCA
CCATCCAAATGCTGTTGAACCATAGCTTCACCCTCCACACTCTGCTCACC

-continued

TATGCCACTCGAGATGACCTCATCTACACCCGCATCAGGGGAGGGATGGT
ATGCCGCATCTGGAGGGCCATCTTGGCACAGCGAGCAGGATCCACACCAG
TCACCTCTGGACCCTGA

Human MEKK7 CDS (SEQ ID NO: 24)
ATGTCTACAGCCTCTGCCGCCTCCTCCTCCTCGTCTTCGGCCGGTGA
GATGATCGAAGCCCCTTCCCAGGTCCTCAACTTTGAAGAGATCGACTACA
AGGAGATCGAGGTGGAAGAGGTTGTTGGAAGAGGAGCCTTTGGAGTTGTT
TGCAAAGCTAAGTGGAGAGCAAAAGATGTTGCTATTAAACAAATAGAAAG
TGAATCTGAGAGGAAAGCGTTTATTGTAGAGCTTCGGCAGTTATCCCGTG
TGAACCATCCTAATATTGTAAAGCTTTATGGAGCCTGCTTGAATCCAGTG
TGTCTTGTGATGGAATATGCTGAAGGGGGCTCTTTATATAATGTGCTGCA
TGGTGCTGAACCATTGCCATATTATACTGCTGCCCACGCAATGAGTTGGT
GTTTACAGTGTTCCCAAGGAGTGGCTTATCTTCACAGCATGCAACCCAAA
GCGCTAATTCACAGGGACCTGAAACCACCAAACTTACTGCTGGTTGCAGG
GGGGACAGTTCTAAAAATTTGTGATTTTGGTACAGCCTGTGACATTCAGA
CACACATGACCAATAACAAGGGGAGTGCTGCTTGGATGGCACCTGAAGTT
TTTGAAGGTAGTAATTACAGTGAAAAATGTGACGTCTTCAGCTGGGGTAT
TATTCTTTGGGAAGTGATAACGCGTCGGAAACCCTTTGATGAGATTGGTG
GCCCAGCTTTCCGAATCATGTGGGCTGTTCATAATGGTACTCGACCACCA
CTGATAAAAAATTTACCTAAGCCCATTGAGAGCCTGATGACTCGTTGTTG
GTCTAAAGATCCTTCCCAGCGCCCTTCAATGGAGGAAATTGTGAAAATAA
TGACTCACTTGATGCGGTACTTTCCAGGAGCAGATGAGCCATTACAGTAT
CCTTGTCAGTATTCAGATGAAGGACAGAGCAACTCTGCCACCAGTACAGG
CTCATTCATGGACATTGCTTCTACAAATACGAGTAACAAAGTGACACTA
ATATGGAGCAAGTTCCTGCCACAAATGATACTATTAAGCGCTTAGAATCA
AAATTGTTGAAAAATCAGGCAAAGCAACAGAGTGAATCTGGACGTTTAAG
CTTGGGAGCCTCCCGTGGGAGCAGTGTGGAGAGCTTGCCCCCAACCTCTG
AGGGCAAGAGGATGAGTGCTGACATGTCTGAAATAGAAGCTAGGATCGCC
GCAACCACAGGCAACGGACAGCCAAGACGTAGATCCATCCAAGACTTGAC
TGTAACTGGAACAGAACCTGGTCAGGTGAGCAGTAGGTCATCCAGTCCCA
GTGTCAGAATGATTACTACCTCAGGACCAACCTCAGAAAAGCCAACTCGA
AGTCATCCATGGACCCCTGATGATTCCACAGATACCAATGGATCAGATAA
CTCCATCCAATGGCTTATCTTACACTGGATCACCAACTACAGCCTCTAG
CACCGTGCCCAAACTCCAAAGAATCTATGGCAGTGTTTGAACAGCATTGT
AAAATGGCACAAGAATATATGAAAGTTCAAACAGAAATTGCATTGTTATT
ACAGAGAAAGCAAGAACTAGTTGCAGAACTGGACCAGGATGAAAAGGACC
AGCAAAATACATCTCGCCTGGTACAGGAACATAAAAAGCTTTTAGATGAA
AACAAAAGCCTTTCTACTTACTACCAGCAATGCAAAAAACAACTAGAGGT
CATCAGAAGTCAGCAGCAGAAACGACAAGGCACTTCATGA Human MK2 CDS (SEQ ID NO: 25)
ATGCTGTCCAACTCCCAGGGCCAGAGCCCGCCGGTGCCGTTCCCCGCCCC
GGCCCCGCCGCCGCAGCCCCCCACCCCTGCCCTGCCGCACCCCCCGGCGC
AGCCGCCGCCGCCCCCCGCAGCAGTTCCCGCAGTTCCACGTCAAGTCC
GGCCTGCAGATCAAGAAGAACGCCATCATCGATGACTACAAGGTCACCAG
CCAGGTCCTGGGGCTGGGCATCAACGGCAAAGTTTTGCAGATCTTCAACA
GAGGACCCAGGAGAAATTCGCCCTCAAAATGCTTCAGGACTGCCCCAAG
GCCCGCAGGGAGGTGGAGCTGCACTGGCGGGCCTCCCAGTGCCCGCACAT
CGTACGGATCGTGGATGTGTACGAGAATCTGTACGCAGGGAGGAAGTGCC
TGCTGATTGTCATGGAATGTTTGGACGGTGGAGAACTCTTTAGCCGAATC
CAGGATCGAGGAGACCAGGCATTCACAGAAAGAGAAGCATCCGAAATCAT
GAAGAGCATCGGTGAGGCCATCCAGTATCTGCATTCAATCAACATTGCCC
ATCGGGATGTCAAGCCTGAGAATCTCTTATACACCTCCAAAAGGCCCAAC
GCCATCCTGAAACTCACTGACTTTGGCTTTGCCAAGGAAACCACCAGCCA
CAACTCTTTGACCACTCCTTGTTATACACCGTACTATGTGGCTCCAGAAG
TGCTGGGTCCAGAGAAGTATGACAAGTCCTGTGACATGTGGTCCCTGGGT
GTCATCATGTACATCCTGCTGTGTGGGTATCCCCCCTTCTACTCCAACCA
CGGCCTTGCCATCTCTCCGGGCATGAAGACTCGCATCCGAATGGGCCAGT
ATGAATTTCCCAACCCAGAATGGTCAGAAGTATCAGAGGAAGTGAAGATG
CTCATTCGGAATCTGCTGAAAACAGAGCCCACCCAGAGAATGACCATCAC
CGAGTTTATGAACCACCCTTGGATCATGCAATCAACAAAGGTCCCTCAAA
CCCCACTGCACACCAGCCGGGTCCTGAAGGAGGACAAGGAGCGGTGGGAG
GATGTCAAGGGGTGTCTTCATGACAAGAACAGCGACCAGGCCACTTGGCT
GACCAGGTTGTGA Human MyD88 CDS (SEQ ID NO: 26)
ATGCGACCCGACCGCGCTGAGGCTCCAGGACCGCCCGCCATGGCTGCAGG
AGGTCCCGGCGCGGGGTCTGCGGCCCCGGTCTCCTCCACATCCTCCCTTC
CCCTGGCTGCTCTCAACATGCGAGTGCGGCGCGCCGCCTGTCTCTGTTCTTG
AACGTGCGGACACAGGTGGCGGCCGACTGGACGCGCTGGCGGAGGAGAT
GGACTTTGAGTACTTGGAGATCCGGCAACTGGAGACACAAGCGGACCCCA
CTGGCAGGCTGCTGGACGCCTGGCAGGACGCCCTGGCGCCTCTGTAGGC
CGACTGCTCGAGCTGCTTACCAAGCTGGGCCGCGACGACGTGCTGCTGGA
GCTGGGACCCAGCATTGAGGAGGATTGCCAAAAGTATATCTTGAAGCAGC
AGCAGGAGGAGGCTGAGAAGCCTTTACAGGTGGCCGCTGTAGACAGCAGT
GTCCCACGGACAGCAGAGCTGGCGGGCATCACCACACTTGATGACCCCCT
GGGGCATATGCCTGAGCGTTTCGATGCCTTCATCTGCTATTGCCCCAGCG
ACATCCAGTTTGTGCAGGAGATGATCCGGCAACTGGAACAGACAAACTAT
CGACTGAAGTTGTGTGTGTCTGACCGCGATGTCCTGCCTGGCACCTGTGT
CTGGTCTATTGCTAGTGAGCTCATCGAAAAGAGGTTGGCTAGAAGGCCAC
GGGGTGGGTGCCGCCGGATGGTGGTGGTTGTCTCTGATGATTACCTGCAG
AGCAAGGAATGTGACTTCCAGACCAAATTTGCACTCAGCCTCTCTCCAGG
TGCCCATCAGAAGCGACTGATCCCCATCAAGTACAAGGCAATGAAGAAAG
AGTTCCCCAGCATCCTGAGGTTCATCACTGTCTGCGACTACACCAACCCC
TGCACCAAATCTTGGTTCTGGACTCGCCTTGCCAAGGCCTTGTCCCTGCC
CTGA Human NF-κB CDS (SEQ ID NO: 27)
ATGGCAGAAGATGATCCATATTTGGGAAGGCCTGAACAAATGTTTCATTT
GGATCCTTCTTTGACTCATACAATATTTAATCCAGAAGTATTTCAACCAC
AGATGGCACTGCCAACAGATGGCCCATACCTTCAAATATTAGAGCAACCT
AAACAGAGAGGATTTCGTTTCCGTTATGTATGTGAAGGCCCATCCCATGG
TGGACTACCTGGTGCCTCTAGTGAAAAGAACAAGAAGTCTTACCCTCAGG
TCAAAATCTGCAACTATGTGGGACCAGCAAAGGTTATTGTTCAGTTGGTC
ACAAATGGAAAAAATATCCACCTGCATGCCCACAGCCTGGTGGGAAAACA
CTGTGAGGATGGGATCTGCACTGTAACTGCTGGACCCAAGGACATGGTGG
TCGGCTTCGCAAACCTGGGTATACTTCATGTGACAAAGAAAAAGTATTT
GAAACACTGGAAGCACGAATGACAGAGGCGTGTATAAGGGCTATAATCC
TGGACTCTTGGTGCACCCTGACCTTGCCTATTTGCAAGCAGAAGGTGGAG
GGGACCGGCAGCTGGGAGATCGGGAAAAAGAGCTAATCCGCCAAGCAGCT
CTGCAGCAGACCAAGGAGATGGACCTCAGCGTGGTGCGGCTCATGTTTAC
AGCTTTTCTTCCGGATAGCACTGGCAGCTTCACAAGGCGCCTGGAACCCG
TGGTATCAGACGCCATCTATGACAGTAAAGCCCCCAATGCATCCAACTTG
AAAATTGTAAGAATGGACAGGACAGCTGGATGTGTGACTGGAGGGGAGGA
AATTTATCTTCTTTGTGACAAAGTTCAGAAAGATGACATCCAGATTCGAT
TTTATGAAGAGGAAGAAATGGTGGAGTCTGGGAAGGATTTGGAGATTTT
TCCCCCACAGATGTTCATAGACAATTTGCCATTGTCTTCAAAACTCCAAA
GTATAAAGATATTAATATTACAAAACCAGCCTCTGTGTTTGTCCAGCTTC
GGAGGAAATCTGACTTGGAAACTAGTGAACCAAAACCTTTCCTCTACTAT
CCTGAAATCAAAGATAAAGAAGAAGTGCAGAGGAAACGTCAGAAGCTCAT
GCCCAATTTTTCGGATAGTTTCGGCGGTGGTAGTGGTGCTGGAGCTGGAG
GCGGAGGCATGTTTGGTAGTGGCGGTGGAGGAGGGGCACTGGAAGTACA
GGTCCAGGGTATAGCTTCCCACACTATGGATTTCCTACTTATGGTGGGAT
TACTTTCCATCCTGGAACTACTAAATCTAATGCTGGGATGAAGCATGGAA
CCATGGACACTGAATCTAAAAAGGACCCTGAAGGTTGTGACAAAAGTGAT
GACAAAAACACTGTAAACCTCTTTGGAAAGTTATTGAAACCACAGAGCA
AGATCAGGAGCCCAGCGAGGCCACCGTTGGGAATGGTGAGGTCACTCTAA
CGTATGCAACAGGAACAAAAGAAGAGAGTGCTGGAGTTCAGGATAACCTC
TTTCTAGAGAAGGCTATGCAGCTTGCAAAGAGGCATGCCAATGCCCTTTT
CGACTACGCGGTGACAGGAGACGTGAAGATGCTGCTGGCCGTCCAGCGCC
ATCTCACTGCTGTGCAGGATGAGAATGGGACAGTGTCTTACACTTAGCA
ATCATCCACCTTCATTCTCAACTTGTGAGGGATCTACTAGAAGTCACATC
TGGTTTGATTTCTGATGACATTATCAACATGAGAAATGATCTGTACCAGA -continued

```
CGCCCTTGCACTTGGCAGTGATCACTAAGCAGGAAGATGTGGTGGAGGAT
TTGCTGAGGGCTGGGGCCGACCTGAGCCTTCTGGACCGCTTGGGTAACTC
TGTTTTGCACCTAGCTGCCAAAGAAGGACATGATAAAGTTCTCAGTATCT
TACTCAAGCACAAAAGGCAGCACTACTTCTTGACCACCCCAACGGGGAC
GGTCTGAATGCCATTCATCTAGCCATGATGAGCAATAGCCTGCCATGTTT
GCTGCTGCTGGTGGCCGCTGGGGCTGACGTCAATGCTCAGGAGCAGAAGT
CCGGGCGCACAGCACTGCACCTGGCTGTGGAGCACGACAACATCTCATTG
GCAGGCTGCCTGCTCCTGGAGGGTGATGCCCATGTGGACAGTACTACCTA
CGATGGAACCACACCCCTGCATATAGCAGCTGGGAGAGGGTCCACCAGGC
TGGCAGCTCTTCTCAAAGCAGCAGGAGCAGATCCCCTGGTGGAGAACTTT
GAGCCTCTCTATGACCTGGATGACTCTTGGGAAAATGCAGGAGAGGATGA
AGGAGTTGTGCCTGGAACCACGCCTCTAGATATGGCCACCAGCTGGCAGG
TATTTGACATATTAAATGGGAAACCATATGAGCCAGAGTTTACATCTGAT
GATTTACTAGCACAAGGAGACATGAAACAGCTGGCTGAAGATGTGAAGCT
GCAGCTGTATAAGTTACTAGAAATTCCTGATCCAGACAAAAACTGGGCTA
CTCTGGCGCAGAAATTAGGTCTGGGGATACTTAATAATGCCTTCCGGCTG
AGTCCTGCTCCTTCCAAAACACTTATGGACAACTATGAGGTCTCTGGGGG
TACAGTCAGAGAGCTGGTGGAGGCCCTGAGACAAATGGGCTACACCGAAG
CAATTGAAGTGATCCAGGCAGCCTCCAGCCCAGTGAAGACCACCTCTCAG
GCCCACTCGCTGCCTCTCTCGCCTGCCTCCACAAGGCAGCAAATAGACGA
GCTCCGAGACAGTGACAGTGTCTGCGACAGCGGCGTGGAGACATCCTTCC
GCAAACTCAGCTTTACCGAGTCTCTGACCAGTGGTGCCTCACTGCTAACT
CTCAACAAAATGCCCCATGATTATGGGCAGGAAGGACCTCTAGAAGGCAA
AATTTAG
```

Human NIK CDS   (SEQ ID NO: 28)

```
ATGGCAGTGATGGAAATGGCCTGCCCAGGTGCCCCTGGCTCAGCAGTGGG
GCAGCAGAAGGAACTCCCCAAAGCCAAGGAGAAGACGCCGCCACTGGGAA
AGAAACAGAGCTCCGTCTACAAGCTTGAGGCCGTGGAGAAGAGCCCTGTG
TTCTGCGGAAAGTGGGAGATCCTGAATGACGTGATTACCAAGGGCACAGC
CAAGGAAGGCTCCGAGGCAGGGCCAGCTGCCATCTCTATCATCGCCCAGG
CTGAGTGTGAGAATAGCCAAGAGTTCAGCCCCACCTTTTCAGAACGCATT
TTCATCGCTGGGTCCAAACAGTACAGCCAGTCCGAGAGTCTTGATCAGAT
CCCCAACAATGTGGCCCATGCTACAGAGGGCAAAATGGCCCGTGTGTGTT
GGAAGGGAAAGCGTCGCAGCAAAGCCCGGAAGAAACGGAAGAAGAAGAGC
TCAAAGTCCCTGGCTCATGCAGGAGTGGCCTTGGCCAAACCCCTCCCCAG
GACCCCTGAGCAGGAGAGCTGCACCATCCCAGTGCAGGAGGATGAGTCTC
CACTCGGCGCCCCATATGTTAGAAACACCCCGCAGTTCACCAAGCCTCTG
AAGGAACCAGGCCTTGGGCAACTCTGTTTTAAGCAGCTTGGCGAGGGCCT
ACGGCCGGCTCTGCCTCGATCAGAACTCCACAAACTGATCAGCCCCTTGC
AATGTCTGAACCACGTGTGGAAACTGCACCACCCCCAGGACGGAGGCCCC
CTGCCCCTGCCCACGCACCCCTTCCCCTATAGCAGACTGCCTCATCCCTT
```

-continued

```
CCCATTCCACCCTCTCCAGCCCTGGAAACCTCACCCTCTGGAGTCCTTCC
TGGGCAAACTGGCCTGTGTAGACAGCCAGAAACCCTTGCCTGACCCACAC
CTGAGCAAACTGGCCTGTGTAGACAGTCCAAAGCCCCTGCCTGGCCCACA
CCTGGAGCCCAGCTGCCTGTCTCGTGGTGCCCATGAGAAGTTTTCTGTGG
AGGAATACCTAGTGCATGCTCTGCAAGGCAGCGTGAGCTCAGGCCAGGCC
CACAGCCTGACCAGCCTGGCCAAGACCTGGGCAGCAAGGGGCTCCAGATC
CCGGGAGCCCAGCCCCAAAACTGAGGACAACGAGGGTGTCCTGCTCACTG
AGAAACTCAAGCCAGTGGATTATGAGTACCGAGAAGAAGTCCACTGGGCC
ACGCACCAGCTCCGCCTGGGCAGAGGCTCCTTCGGAGAGGTGCACAGGAT
GGAGGACAAGCAGACTGGCTTCCAGTGCGCTGTCAAAAAGGTGCGGCTGG
AAGTATTTCGGGCAGAGGAGCTGATGGCATGTGCAGGATTGACCTCACCC
AGAATTGTCCCTTTGTATGGAGCTGTGAGAGAAGGGCCTTGGGTCAACAT
CTTCATGGAGCTGCTGGAAGGTGGCTCCCTGGGCCAGCTGGTCAAGGAGC
AGGGCTGTCTCCCAGAGGACCGGGCCCTGTACTACCTGGGCCAGGCCCTG
GAGGGTCTGGAATACCTCCACTCACGAAGGATTCTGCATGGGGACGTCAA
AGCTGACAACGTGCTCCTGTCCAGCGATGGGAGCCACGCAGCCCTCTGTG
ACTTTGGCCATGCTGTGTGTCTTCAACCTGATGGCCTGGGAAAGTCCTTG
CTCACAGGGGACTACATCCCTGGCACAGAGACCCACATGGCTCCGGAGGT
GGTGCTGGGCAGGAGCTGCGACGCCAAGGTGGATGTCTGGAGCAGCTGCT
GTATGATGCTGCACATGCTCAACGGCTGCCACCCCTGGACTCAGTTCTTC
CGAGGGCCGCTCTGCCTCAAGATTGCCAGCGAGCCTCCGCCTGTGAGGGA
GATCCCACCCTCCTGCGCCCCTCTCACAGCCCAGGCCATCCAAGAGGGGC
TGAGGAAGAGCCCATCCACCGCGTGTCTGCAGCGGAGCTGGGAGGGAAG
GTGAACCGGGCACTACAGCAAGTGGGAGGTCTGAAGAGCCCTTGGAGGGG
AGAATATAAAGAACCAAGACATCCACCGCCAAATCAAGCCAATTACCACC
AGACCCTCCATGCCCAGCCGAGAGAGCTTTCGCCAAGGGCCCCAGGGCCC
CGGCCAGCTGAGGAGACAACAGGCAGAGCCCCTAAGCTCCAGCCTCCTCT
CCCACCAGAGCCCCCAGAGCCAAACAAGTCTCCTCCCTTGACTTTGAGCA
AGGAGGAGTCTGGGATGTGGGAACCCTTACCTCTGTCCTCCCTGGAGCCA
GCCCCTGCCAGAAACCCCAGCTCACCAGAGCGGAAAGCAACCGTCCCGGA
GCAGGAACTGCAGCAGCTGGAAATAGAATTATTCCTCAACAGCCTGTCCC
AGCCATTTTCTCTGGAGGAGCAGGAGCAAATTCTCTCGTGCCTCAGCATC
GACAGCCTCTCCCTGTCGGATGACAGTGAGAAGAACCCATCAAAGGCCTC
TCAAAGCTCGCGGGACACCCTGAGCTCAGGCGTACACTCCTGGAGCAGCC
AGGCCGAGGCTCGAAGCTCCAGCTGGAACATGGTGCTGGCCCGGGGCGG
CCCACCGACACCCCAAGCTATTTCAATGGTGTGAAAGTCCAAATACAGTC
TCTTAATGGTGAACACCTGCACATCCGGGAGTTCCACCGGGTCAAAGTGG
GAGACATCGCCACTGGCATCAGCAGCCAGATCCCAGCTGCAGCCTTCAGC
TTGGTCACCAAAGACGGGCAGCCTGTTCGCTACGACATGGAGGTGCCAGA
CTCGGGCATCGACCTGCAGTGCACACTGGCCCCTGATGGCAGCTTCGCCT
```

GGAGCTGGAGGGTCAAGCATGGCCAGCTGGAGAACAGGCCCTAA

Human p38 CDS (SEQ ID NO: 29)
ATGTCTCAGGAGAGGCCCACGTTCTACCGGCAGGAGCTGAACAAGACAAT
CTGGGAGGTGCCCGAGCGTTACCAGAACCTGTCTCCAGTGGGCTCTGGCG
CCTATGGCTCTGTGTGTGCTGCTTTTGACACAAAAACGGGGTTACGTGTG
GCAGTGAAGAAGCTCTCCAGACCATTTCAGTCCATCATTCATGCGAAAAG
AACCTACAGAGAACTGCGGTTACTTAAACATATGAAACATGAAAATGTGA
TTGGTCTGTTGGACGTTTTTACACCTGCAAGGTCTCTGGAGGAATTCAAT
GATGTGTATCTGGTGACCCATCTCATGGGGGCAGATCTGAACAACATTGT
GAAATGTCAGAAGCTTACAGATGACCATGTTCAGTTCCTTATCTACCAAA
TTCTCCGAGGTCTAAAGTATATACATTCAGCTGACATAATTCACAGGGAC
CTAAAACCTAGTAATCTAGCTGTGAATGAAGACTGTGAGCTGAAGATTCT
GGATTTTGGACTGGCTCGGCACACAGATGATGAAATGACAGGCTACGTGG
CCACTAGGTGGTACAGGGCTCCTGAGATCATGCTGAACTGGATGCATTAC
AACCAGACAGTTGATATTTGGTCAGTGGGATGCATAATGGCCGAGCTGTT
GACTGGAAGAACATTGTTTCCTGGTACAGACCATATTAACCAGCTTCAGC
AGATTATGCGTCTGACAGGAACACCCCCCGCTTATCTCATTAACAGGATG
CCAAGCCATGAGGCAAGAAACTATATTCAGTCTTTGACTCAGATGCCGAA
GATGAACTTTGCGAATGTATTTATTGGTGCCAATCCCCTGGCTGTCGACT
TGCTGGAGAAGATGCTTGTATTGGACTCAGATAAGAGAATTACAGCGGCC
CAAGCCCTTGCACATGCCTACTTTGCTCAGTACCACGATCCTGATGATGA
ACCAGTGGCCGATCCTTATGATCAGTCCTTTGAAAGCAGGGACCTCCTTA
TAGATGAGTGGAAAAGCCTGACCTATGATGAAGTCATCAGCTTTGTGCCA
CCACCCCTTGACCAAGAAGAGATGGAGTCCTGA Human PKR CDS (SEQ ID NO: 30)
ATGGCTGGTGATCTTTCAGCAGGTTTCTTCATGGAGGAACTTAATACATA
CCGTCAGAAGCAGGGAGTAGTACTTAAATATCAAGAACTGCCTAATTCAG
GACCTCCACATGATAGGAGGTTTACATTTCAAGTTATAATAGATGGAAGA
GAATTTCCAGAAGGTGAAGGTAGATCAAAGAAGGAAGCAAAAAATGCCGC
AGCCAAATTAGCTGTTGAGATACTTAATAAGGAAAAGAAGGCAGTTAGTC
CTTTATTATTGACAACAACGAATTCTTCAGAAGGATTATCCATGGGGAAT
TACATAGGCCTTATCAATAGAATTGCCCAGAAGAAAAGACTAACTGTAAA
TTATGAACAGTGTGCATCGGGGGTGCATGGGCCAGAAGGATTTCATTATA
AATGCAAAATGGGACAGAAAGAATATAGTATTGGTACAGGTTCTACTAAA
CAGGAAGCAAAACAATTGGCCGCTAAACTTGCATATCTTCAGATATTATC
AGAAGAAACCTCAGTGAAATCTGACTACCTGTCCTCTGGTTCTTTTGCTA
CTACGTGTGAGTCCCAAAGCAACTCTTTAGTGACCAGCACACTCGCTTCT
GAATCATCATCTGAAGGTGACTTCTCAGCAGATACATCAGAGATAAATTC
TAACAGTGACAGTTTAAACAGTTCTTCGTTGCTTATGAATGGTCTCAGAA
ATAATCAAAGGAAGGCAAAAAGATCTTTGGCACCCAGATTTGACCTTCCT
GACATGAAAGAAACAAAGTATACTGTGGACAAGAGGTTTGGCATGGATTT TAAAGAAATAGAATTAATTGGCTCAGGTGGATTTGGCCAAGTTTTCAAAG
CAAAACACAGAATTGACGGAAAGACTTACGTTATTAAACGTGTTAAATAT
AATAACGAGAAGGCGGAGCGTGAAGTAAAAGCATTGGCAAAACTTGATCA
TGTAAATATTGTTCACTACAATGGCTGTTGGGATGGATTTGATTATGATC
CTGAGACCAGTGATGATTCTCTTGAGAGCAGTGATTATGATCCTGAGAAC
AGCAAAAATAGTTCAAGGTCAAAGACTAAGTGCCTTTTCATCCAAATGGA
ATTCTGTGATAAAGGGACCTTGGAACAATGGATTGAAAAAGAAGAGGCG
AGAAACTAGACAAAGTTTTGGCTTTGGAACTCTTTGAACAAATAACAAAA
GGGGTGGATTATATACATTCAAAAAAATTAATTCATAGAGATCTTAAGCC
AAGTAATATATTCTTAGTAGATACAAAACAAGTAAAGATTGGAGACTTTG
GACTTGTAACATCTCTGAAAAATGATGGAAAGCGAACAAGGAGTAAGGGA
ACTTTGCGATACATGAGCCCAGAACAGATTTCTTCGCAAGACTATGGAAA
GGAAGTGGACCTCTACGCTTTGGGCTAATTCTTGCTGAACTTCTTCATG
TATGTGACACTGCTTTTGAAACATCAAAGTTTTTCACAGACCTACGGGAT
GGCATCATCTCAGATATATTTGATAAAAAGAAAAAACTCTTCTACAGAA
ATTACTCTCAAAGAAACCTGAGGATCGACCTAACACATCTGAAATACTAA
GGACCTTGACTGTGTGGAAGAAAAGCCCAGAGAAAAATGAACGACACACA
TGTTAG Human Rac CDS (SEQ ID NO: 31)
ATGAGCGACGTGGCTATTGTGAAGGAGGGTTGGCTGCACAAACGAGGGGA
GTACATCAAGACCTGGCGGCCACGCTACTTCCTCCTCAAGAATGATGGCA
CCTTCATTGGCTACAAGGAGCGGCCGCAGGATGTGGACCAACGTGAGGCT
CCCCTCAACAACTTCTCTGTGGCGCAGTGCCAGCTGATGAAGACGGAGCG
GCCCCGGCCCAACACCTTCATCATCCGCTGCCTGCAGTGGACCACTGTCA
TCGAACGCACCTTCCATGTGGAGACTCCTGAGGAGCGGGAGGAGTGGACA
ACCGCCATCCAGACTGTGGCTGACGGCCTCAAGAAGCAGGAGGAGGAGA
GATGGACTTCCGGTCGGGCTCACCCAGTGACAACTCAGGGGCTGAAGAGA
TGGAGGTGTCCCTGGCCAAGCCCAAGCACCGCGTGACCATGAACGAGTTT
GAGTACCTGAAGCTGCTGGGCAAGGGCACTTCGGCAAGGTGATCCTGGT
GAAGGAGAAGGCCACAGGCCGCTACTACGCCATGAAGATCCTCAAGAAGG
AAGTCATCGTGGCCAAGGACGAGGTGGCCCACACACTCACCGAGAACCGC
GTCCTGCAGAACTCCAGGCACCCCTTCCTCACAGCCCTGAAGTACTCTTT
CCAGACCCACGACCGCCTCTGCTTTGTCATGGAGTACGCCAACGGGGGCG
AGCTGTTCTTCCACCTGTCCCGGGAGCGTGTGTTCTCCGAGGACCGGGCC
CGCTTCTATGCGCTGAGATTGTGTCAGCCCTGGACTACCTGCACTCGGA
GAAGAACGTGGTGTACCGGGACCTCAAGCTGGAGAACCTCATGCTGGACA
AGGACGGGCACATTAAGATCACAGACTTCGGGCTGTGCAAGGAGGGGATC
AAGGACGGTGCCACCATGAAGACCTTTTGCGGCACACCTGAGTACCTGGC
CCCCGAGGTGCTGGAGGACAATGACTACGGCCGTGCAGTGGACTGGTGGG
GGCTGGGCGTGGTCATGTACGAGATGATGTGCGGTCGCCTGCCCTTCTAC -continued

AACCAGGACCATGAGAAGCTTTTTGAGCTCATCCTCATGGAGGAGATCCG

CTTCCCGCGCACGCTTGGTCCCGAGGCCAAGTCCTTGCTTTCAGGGCTGC

TCAAGAAGGACCCCAAGCAGAGGCTTGGCGGGGGCTCCGAGGACGCCAAG

GAGATCATGCAGCATCGCTTCTTTGCCGGTATCGTGTGGCAGCACGTGTA

CGAGAAGAAGCTCAGCCCACCCTTCAAGCCCCAGGTCACGTCGGAGACTG

ACACCAGGTATTTTGATGAGGAGTTCACGGCCCAGATGATCACCATCACA

CCACCTGACCAAGATGACAGCATGGAGTGTGTGGACAGCGAGCGCAGGCC

CCACTTCCCCCAGTTCTCCTACTCGGCCAGCGGCACGGCCTGA

Human Raf CDS (SEQ ID NO: 32)

ATGGCTAGCAAACGAAAATCTACAACTCCATGCATGGTTCGGACATCACA

AGTAGTAGAACAAGATGTGCCCGAGGAAGTAGACAGGGCCAAAGAGAAAG

GAATCGGCACACCACAGCCTGACGTGGCCAAGGACAGTTGGGCAGCAGAA

CTTGAAAACTCTTCCAAAGAAAACGAAGTGATAGAGGTGAAATCTATGGG

GGAAAGCCAGTCCAAAAAACTCCAAGGTGGTTATGAGTGCAAATACTGCC

CCTACTCCACGCAAAACCTGAACGAGTTCACGGAGCATGTCGACATGCAG

CATCCCAACGTGATTCTCAACCCCCTCTACGTGTGTGCAGAATGTAACTT

CACAACCAAAAAGTACGACTCCCTATCCGACCACAACTCCAAGTTCCATC

CCGGGGAGGCCAACTTCAAGCTGAAGTTAATTAAACGCAATAATCAAACT

GTCTTGGAACAGTCCATCGAAACCACCAACCATGTCGTGTCCATCACCAC

CAGTGGCCCTGGAACTGGTGACAGTGATTCTGGGATCTCGGTGAGTAAAA

CCCCCATCATGAAGCCTGGAAAACCAAAAGCGGATGCCAAGAAGGTGCCC

AAGAAGCCCGAGGAGATCACCCCCGAGAACCACGTGGAAGGGACCGCCCG

CCTGGTGACAGACACAGCTGAGATCCTCTCGAGACTCGGCGGGGTGGAGC

TCCTCCAAGACACATTAGGACACGTCATGCCTTCTGTACAGCTGCCACCA

AATATCAACCTTGTGCCCAAGGTCCCTGTCCCACTAAATACTACCAAATA

CAACTCTGCCCTGGATACAAATGCCACGATGATCAACTCTTTCAACAAGT

TTCCTTACCCGACCCAGGCTGAGTTGTCCTGGCTGACAGCTGCCTCCAAA

CACCCAGAGGAGCACATCAGAATCTGGTTTGCCACCCAGCGCTTAAAGCA

TGGCATCAGCTGGTCCCCAGAAGAGGTGGAGGAGGCCCGGAAGAAGATGT

TCAACGGCACCATCCAGTCAGTACCCCCGACCATCACTGTGCTGCCCGCC

CAGTTGGCCCCCACAAAGGTGACGCAGCCCATCCTCCAGACGGCTCTACC

GTGCCAGATCCTCGGCCAGACTAGCCTGGTGCTGACTCAGGTGACCAGCG

GGTCAACAACCGTCTCTTGCTCCCCATCACACTTGCCGTGGCAGGAGTC

ACCAACCATGGCCAGAAGAGACCCTTGGTGACTCCCCAAGCTGCCCCCGA

ACCCAAGCGTCCACACATCGCTCAGGTGCCAGAGCCCCCACCCAAGGTGG

CCAACCCCCCGCTCACACCAGCCAGTGACCGCAAGAAGACAAAGGAGCAG

ATAGCACATCTCAAGGCCAGCTTTCTCCAGAGCCAGTTCCCTGACGATGC

CGAGGTTTACCGGCTCATCGAGGTGACTGGCCTTGCCAGGAGCGAGATCA

AGAAGTGGTTCAGTGACCACCGATATCGGTGTCAAAGGGGCATCGTCCAC

ATCACCAGCGAATCCCTTGCCAAAGACCAGTTGGCCATCGCGGCCTCCCG

ACACGGTCGCACGTATCATGCGTACCCAGACTTTGCCCCCCAGAAGTTCA

-continued

AAGAGAAAACACAGGGTCAGGTTAAAATCTTGGAAGACAGCTTTTTGAAA

AGTTCTTTTCCTACCCAAGCAGAACTGGATCGGCTAAGGGTGGAGACCAA

GCTGAGCAGGAGAGAGATCGACTCCTGGTTCTCGGAGAGGCGGAAGCTTC

GAGACAGCATGGAACAAGCTGTCTTGGATTCCATGGGGTCTGGCAAAAAA

GGCCAAGATGTGGGAGCCCCCAATGGTGCTCTGTCTCGACTCGACCAGCT

CTCCGGTGCCCAGTTAACAAGTTCTCTGCCCAGCCCTTCGCCAGCAATTG

CAAAAAGTCAAGAACAGGTTCATCTCCTGAGGAGCACGTTTGCAAGAACC

CAGTGGCCTACTCCCCAGGAGTACGACCAGTTAGCGGCCAAGACTGGCCT

GGTCCGAACTGAGATTGTGCGTTGGTTCAAGGAGAACAGATGCTTGCTGA

AAACGGGAACCGTGAAGTGGATGGAGCAGTACCAGCACCAGCCCATGGCA

GATGATCACGGCTACGATGCCGTAGCAAGGAAAGCAACAAAACCCATGGC

CGAGAGCCCAAAGAACGGGGGTGATGTGGTTCCACAATATTACAAGGACC

CCAAAAAGCTCTGCGAAGAGGACTTGGAGAAGTTGGTGACCAGGGTAAAA

GTAGGCAGCGAGCCAGCAAAAGACTGTTTGCCAGCAAAGCCCTCAGAGGC

CACCTCAGACCGGTCAGAGGGCAGCAGCCGGGACGGCCAGGGTAGCGACG

AGAACGAGGAGTCGAGCGTTGTGGATTACGTGGAGGTGACGGTCGGGGAG

GAGGATGCGATCTCAGATAGATCAGATAGCTGGAGTCAGGCTGCGGCAGA

AGGTGTGTCGGAACTGGCTGAATCAGACTCCGACTGCGTCCCTGCAGAGG

CTGGCCAGGCCTAG

Human K-Ras CDS (SEQ ID NO: 33)

ATGACTGAATATAAACTTGTGGTAGTTGGAGCTGGTGGCGTAGGCAAGAG

TGCCTTGACGATACAGCTAATTCAGAATCATTTTGTGGACGAATATGATC

CAACAATAGAGGATTCCTACAGGAAGCAAGTAGTAATTGATGGAGAAACC

TGTCTCTTGGATATTCTCGACACAGCAGGTCAAGAGGAGTACAGTGCAAT

GAGGGACCAGTACATGAGGACTGGGGAGGGCTTTCTTTGTGTATTTGCCA

TAAATAATACTAAATCATTTGAAGATATTCACCATTATAGAGAACAAATT

AAAAGAGTTAAGGACTCTGAAGATGTACCTATGGTCCTAGTAGGAAATAA

ATGTGATTTGCCTTCTAGAACAGTAGACACAAAACAGGCTCAGGACTTAG

CAAGAAGTTATGGAATTCCTTTTATTGAAACATCAGCAAAGACAAGACAG

GGTGTTGATGATGCCTTCTATACATTAGTTCGAGAAATTCGAAAACATAA

AGAAAAGATGAGCAAAGATGGTAAAAAGAAGAAAAAGAAGTCAAAGACAA

AGTGTGTAATTATGTAA

Human N-Ras CDS (SEQ ID NO: 34)

ATGACTGAGTACAAACTGGTGGTGGTTGGAGCAGGTGGTGTTGGGAAAAG

CGCACTGACAATCCAGCTAATCCAGAACCACTTTGTAGATGAATATGATC

CCACCATAGAGGATTCTTACAGAAAACAAGTGGTTATAGATGGTGAAACC

TGTTTGTTGGACATACTGGATACAGCTGGACAAGAAGAGTACAGTGCCAT

GAGAGACCAATACATGAGGACAGGCGAAGGCTTCCTCTGTGTATTTGCCA

TCAATAATAGCAAGTCATTTGCGGATATTAACCTCTACAGGGAGCAGATT

AAGCGAGTAAAAGACTCGGATGATGTACCTATGGTGCTAGTGGGAAACAA

```
                                  -continued
GTGTGATTTGCCAACAAGGACAGTTGATACAAAACAAGCCCACGAACTGG

CCAAGAGTTACGGGATTCCATTCATTGAAACCTCAGCCAAGACCAGACAG

GGTGTTGAAGATGCTTTTTACACACTGGTAAGAGAAATACGCCAGTACCG

AATGAAAAAACTCAACAGCAGTGATGATGGGACTCAGGGTTGTATGGGAT

TGCCATGTGTGGTGATGTAA

Human RIP CDS
                                               (SEQ ID NO: 35)
ATGCAACCAGACATGTCCTTGAATGTCATTAAGATGAAATCCAGTGACTT

CCTGGAGAGTGCAGAACTGGACAGCGGAGGCTTTGGGAAGGTGTCTCTGT

GTTTCCACAGAACCCAGGGACTCATGATCATGAAAACAGTGTACAAGGGG

CCCAACTGCATTGAGCACAACGAGGCCCTCTTGGAGGAGGCGAAGATGAT

GAACAGACTGAGACACAGCCGGGTGGTGAAGCTCCTGGGCGTCATCATAG

AGGAAGGGAAGTACTCCCTGGTGATGGAGTACATGGAGAAGGGCAACCTG

ATGCACGTGCTGAAAGCCGAGATGAGTACTCCGCTTTCTGTAAAGGAAG

GATAATTTTGGAAATCATTGAAGGAATGTGCTACTTACATGGAAAAGGCG

TGATACACAAGGACCTGAAGCCTGAAAATATCCTTGTTGATAATGACTTC

CACATTAAGATCGCAGACCTCGGCCTTGCCTCCTTTAAGATGTGGAGCAA

ACTGAATAATGAAGAGCACAATGAGCTGAGGGAAGTGGACGGCACCGCTA

AGAAGAATGGCGGCACCCTCTACTACATGGCGCCCGAGCACCTGAATGAC

GTCAACGCAAAGCCCACAGAGAAGTCGGATGTGTACAGCTTTGCTGTAGT

ACTCTGGGCGATATTTGCAAATAAGGAGCCATATGAAAATGCTATCTGTG

AGCAGCAGTTGATAATGTGCATAAAATCTGGGAACAGGCCAGATGTGGAT

GACATCACTGAGTACTGCCCAAGAGAAATTATCAGTCTCATGAAGCTCTG

CTGGGAAGCGAATCCGGAAGCTCGGCCGACATTTCCTGGCATTGAAGAAA

AATTTAGGCCTTTTTATTTAAGTCAATTAGAAGAAAGTGTAGAAGAGGAC

GTGAAGAGTTTAAAGAAAGAGTATTCAAACGAAAATGCAGTTGTGAAGAG

AATGCAGTCTCTTCAACTTGATTGTGTGGCAGTACCTTCAAGCCGGTCAA

ATTCAGCCACAGAACAGCCTGGTTCACTGCACAGTTCCCAGGGACTTGGG

ATGGGTCCTGTGGAGGAGTCCTGGTTTGCTCCTTCCCTGGAGCACCCACA

AGAAGAGAATGAGCCCAGCCTGCAGAGTAAACTCCAAGACGAAGCCAACT

ACCATCTTTATGGCAGCCGCATGGACAGGCAGACGAAACAGCAGCCCAGA

CAGAATGTGGCTTACAACAGAGGAGGAAAGGAGACGCAGGGTCTCCCA

TGACCCTTTTGCACAGCAAAGACCTTACGAGAATTTTCAGAATACAGAGG

GAAAAGGCACTGCTTATTCCAGTGCAGCCAGTCATGGTAATGCAGTGCAC

CAGCCCTCAGGGCTCACCAGCCAACCTCAAGTACTGTATCAGAACAATGG

ATTATATAGCTCACATGGCTTTGGAACAAGACCACTGGATCCAGGAACAG

CAGGTCCCAGAGTTTGGTACAGGCCAATTCCAAGTCATATGCCTAGTCTG

CATAATATCCCAGTGCCTGAGACCAACTATCTAGGAAATACACCCACCAT

GCCATTCAGCTCCTTGCCACCAACAGATGAATCTATAAAATATACCATAT

ACAATAGTACTGGCATTCAGATTGGAGCCTACAATTATATGGAGATTGGT

GGGACGAGTTCATCACTACTAGACAGCACAAATACGAACTTCAAAGAAGA

GCCAGCTGCTAAGTACCAAGCTATCTTTGATAATACCACTAGTCTGACGG
```
```
                                  -continued
ATAAACACCTGGACCCAATCAGGGAAAATCTGGGAAAGCACTGGAAAAAC

TGTGCCCGTAAACTGGGCTTCACACAGTCTCAGATTGATGAAATTGACCA

TGACTATGAGCGAGATGGACTGAAAGAAAAGGTTTACCAGATGCTCCAAA

AGTGGGTGATGAGGGAAGGCATAAAGGGAGCCACGGTGGGGAAGCTGGCC

CAGGCGCTCCACCAGTGTTCCAGGATCGACCTTCTGAGCAGCTTGATTTA

CGTCAGCCAGAACTAA

Human TRAF6 CDS
                                               (SEQ ID NO: 36)
ATGAGTCTGCTAAACTGTGAAAACAGCTGTGGATCCAGCCAGTCTGAAAG

TGACTGCTGTGTGGCCATGGCCAGCTCCTGTAGCGCTGTAACAAAAGATG

ATAGTGTGGGTGGAACTGCCAGCACGGGGAACCTCTCCAGCTCATTTATG

GAGGAGATCCAGGGATATGATGTAGAGTTTGACCCACCCCTGGAAAGCAA

GTATGAATGCCCCATCTGCTTGATGGCATTACGAGAAGCAGTGCAAACGC

CATGCGGCCATAGGTTCTGCAAAGCCTGCATCATAAAATCAATAAGGGAT

GCAGGTCACAAATGTCCAGTTGACAATGAAATACTGCTGGAAAATCAACT

ATTTCCAGACAATTTTGCAAAACGTGAGATTCTTTCTCTGATGGTGAAAT

GTCCAAATGAAGGTTGTTTGCACAAGATGGAACTGAGACATCTTGAGGAT

CATCAAGCACATTGTGAGTTTGCTCTTATGGATTGTCCCCAATGCCAGCG

TCCCTTCCAAAAATTCCATATTAATATTCACATTCTGAAGGATTGTCCAA

GGAGACAGGTTTCTTGTGACAACTGTGCTGCATCAATGGCATTTGAAGAT

AAAGAGATCCATGACCAGAACTGTCCTTTGGCAAATGTCATCTGTGAATA

CTGCAATACTATACTCATCAGAGAACAGATGCCTAATCATTATGATCTAG

ACTGCCCTACAGCCCCAATTCCATGCACATTCAGTACTTTTGGTTGCCAT

GAAAAGATGCAGAGGAATCACTTGGCACGCCACCTACAAGAGAACACCCA

GTCACACATGAGAATGTTGGCCCAGGCTGTTCATAGTTTGAGCGTTATAC

CCGACTCTGGGTATATCTCAGAGGTCCGGAATTTCCAGGAAACTATTCAC

CAGTTAGAGGGTCGCCTTGTAAGACAAGACCATCAAATCCGGGAGCTGAC

TGCTAAAATGGAAACTCAGAGTATGTATGTAAGTGAGCTCAAACGAACCA

TTCGAACCCTTGAGGACAAAGTTGCTGAAATCGAAGCACAGCAGTGCAAT

GGAATTTATATTTGGAAGATTGGCAACTTTGGAATGCATTTGAAATGTCA

AGAAGAGGAGAAACCTGTTGTGATTCATAGCCCTGGATTCTACACTGGCA

AACCCGGGTACAAACTGTGCATGCGCTTGCACCTTCAGTTACCGACTGCT

CAGCGCTGTGCAAACTATATATCCCTTTTTGTCCACACAATGCAAGGAGA

ATATGACAGCCACCTCCCTTGGCCCTTCCAGGGTACAATACGCCTTACAA

TTCTTGATCAGTCTGAAGCACCTGTAAGGCAAAACCACGAAGAGATAATG

GATGCCAAACCAGAGCTGCTTGCTTTCCAGCGACCCACAATCCCACGGAA

CCCAAAAGGTTTTGGCTATGTAACTTTTATGCATCTGGAAGCCCTAAGAC
```

```
-continued
AAAGAACTTTCATTAAGGATGACACATTATTAGTGCGCTGTGAGGTCTCC

ACCCGCTTTGACATGGGTAGCCTTCGGAGGGAGGGTTTTCAGCCACGAAG

TACTGATGCAGGGGTATAG

Human TTP CDS
                                         (SEQ ID NO: 37)
ATGGCCAACCGTTACACCATGGATCTGACTGCCATCTACGAGAGCCTCCT

GTCGCTGAGCCCTGACGTGCCCGTGCCATCCGACCATGGAGGGACTGAGT

CCAGCCCAGGCTGGGGCTCCTCGGGACCCTGGAGCCTGAGCCCCTCCGAC

TCCAGCCCGTCTGGGGTCACCTCCCGCCTGCCTGGCCGCTCCACCAGCCT

AGTGGAGGGCCGCAGCTGTGGCTGGGTGCCCCCACCCCCTGGCTTCGCAC

CGCTGGCTCCCCGCCTGGGCCCTGAGCTGTCACCCTCACCCACTTCGCCC

ACTGCAACCTCCACCACCCCTCGCGCTACAAGACTGAGCTATGTCGGAC

CTTCTCAGAGAGTGGGCGCTGCCGCTACGGGCCAAGTGCCAGTTTGCCC

ATGGCCTGGGCGAGCTGCGCCAGGCCAATCGCCACCCCAAATACAAGACG

GAACTCTGTCACAAGTTCTACCTCCAGGGCCGCTGCCCCTACGGCTCTCG

CTGCCACTTCATCCACAACCCTAGCGAAGACCTGGCGGCCCCGGGCCACC

CTCCTGTGCTTCGCCAGAGCATCAGCTTCTCCGGCCTGCCCTCTGGCCGC

CGGACCTCACCACCACCACCAGGCCTGGCCGGCCCTTCCCTGTCCTCCAG

CTCCTTCTCGCCCTCCAGCTCCCACCACCACCTGGGGACCTTCCACTGT

CACCCTCTGCCTTCTCTGCTGCCCCTGGCACCCCCCTGGCTCGAAGAGAC

CCCACCCCAGTCTGTTGCCCCTCCTGCCGAAGGGCCACTCCTATCAGCGT

CTGGGGGCCCTTGGGTGGCCTGGTTCGGACCCCCTCTGTACAGTCCCTGG

GATCCGACCCTGATGAATATGCCAGCAGCGGCAGCAGCCTGGGGGGCTCT

GACTCTCCCGTCTTCGAGGCGGGAGTTTTTGCACCACCCCAGCCCGTGGC

AGCCCCCGGCGACTCCCCATCTTCAATCGCATCTCTGTTTCTGAGTGA
```

An antisense nucleic acid molecule can be complementary to all or part of a non-coding region of the coding strand of a nucleotide sequence encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTPMEKK1protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TIP protein described herein. Antisense nucleic acids targeting a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTPMEKK1protein can be designed using the software available at the Integrated DNA Technologies website.

An antisense nucleic acid can be, for example, about 5, 10, 15, 18, 20, 22, 24, 25, 26, 28, 30, 32, 35, 36, 38, 40, 42, 44, 45, 46, 48, or 50 nucleotides or more in length. An antisense oligonucleotide can be constructed using enzymatic ligation reactions and chemical synthesis using procedures known in the art. For example, an antisense nucleic acid can be chemically synthesized using variously modified nucleotides or naturally occurring nucleotides designed to increase the physical stability of the duplex formed between the antisense and sense nucleic acids, e.g., phosphorothioate derivatives and acridine substituted nucleotides or to increase the biological stability of the molecules.

Examples of modified nucleotides which can be used to generate an antisense nucleic acid include 1-methylguanine, 1-methylinosine, 2,2-dimethylguanine, 2-methyladenine, 2-methylguanine, 3-methylcytosine, 2-methylthio-N6-isopentenyladenine, uracil-5-oxyacetic acid (v), wybutoxosine, pseudouracil, queosine, 2-thiocytosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a subject, e.g., a human subject. Alternatively, they can be generated in situ such that they hybridize with or bind to cellular mRNA and/or genomic DNA encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., an adenovirus vector, a lentivirus, or a retrovirus).

An antisense nucleic acid can be an α-anomeric nucleic acid molecule. An α-anomeric nucleic acid molecule forms specific double-stranded hybrids with complementary RNA in which, contrary to the usual, β-units, the strands run parallel to each other (Gaultier et al., *Nucleic Acids Res.* 15:6625-6641, 1987). The antisense nucleic acid can also comprise a chimeric RNA-DNA analog (Inoue et al., *FEBS Lett.* 215:327-330, 1987) or a 2'-O-methylribonucleotide (Inoue et al., *Nucleic Acids Res.* 15:6131-6148, 1987).

Another example of an inhibitory nucleic acid is a ribozyme that has specificity for a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA, e.g., specificity for any one of SEQ ID NOs: 1-37). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, *Nature* 334:585-591, 1988)) can be used to catalytically cleave mRNA transcripts to thereby inhibit translation of the protein encoded by the mRNA. An AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be used to select a catalytic RNA having a specific ribonuclease activity from a pool of RNA molecules. See, e.g., Bartel et al., *Science* 261:1411-1418, 1993.

Alternatively, a ribozyme having specificity for an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be designed based upon the nucleotide sequence of any of the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA sequences disclosed herein. For example, a derivative of a Tetrahymena L-19 IVS RNA can be constructed in which the nucleotide sequence of the active site is complementary to the nucleotide sequence to be cleaved in an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (see, e.g., U.S. Pat. Nos. 4,987,071 and 5,116,742).

An inhibitory nucleic acid can also be a nucleic acid molecule that forms triple helical structures. For example, expression of an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide can be inhibited by targeting nucleotide sequences complementary to the regulatory region of the gene encoding the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Maher, Bioassays 14(12):807-15, 1992; Helene, *Anticancer Drug Des.* 6(6):569-84, 1991; and Helene, *Ann. N.Y. Acad. Sci.* 660:27-36, 1992.

In various embodiments, inhibitory nucleic acids can be modified at the sugar moiety, the base moiety, or phosphate backbone to improve, e.g., the solubility, stability, or hybridization, of the molecule. For example, the deoxyribose phosphate backbone of the nucleic acids can be modified to generate peptide nucleic acids (see, e.g., Hyrup et al., *Bioorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to RNA and DNA under conditions of low ionic strength. PNA oligomers can be synthesized using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

Small Molecules

In some embodiments, the anti-TNFα agent is a small molecule. In some embodiments, the small molecule is a tumor necrosis factor-converting enzyme (TACE) inhibitor (e.g., Moss et al., *Nature Clinical Practice Rheumatology* 4: 300-309, 2008). In some embodiments, the anti-TNFα agent is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the TACE inhibitor is TMI-005 and BMS-561392. Additional examples of small molecule inhibitors are described in, e.g., He et al., *Science* 310(5750):1022-1025, 2005.

In some examples, the anti-TNFα agent is a small molecule that inhibits the activity of one of AP-1, ASK1, IKK, JNK, MAPK, MEKK 1/4, MEKK4/7, MEKK 3/6, NIK, TRADD, RIP, NF-κB, and TRADD in a cell (e.g., in a cell obtained from a subject, a mammalian cell).

In some examples, the anti-TNFα agent is a small molecule that inhibits the activity of one of CD14, MyD88 (see, e.g., Olson et al., *Scientific Reports* 5:14246, 2015), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, RO5126766 (CH5126766), PLX7904, and MLN2480).

In some examples, the anti-TNFα agent TNFα inhibitor is a small molecule that inhibits the activity of one of MK2 (PF 3644022 and PHA 767491), JNK (e.g., AEG 3482, BI 78D3, CEP 1347, c-JUN peptide, IQ 1S, JIP-1 (153-163), SP600125, SU 3327, and TCS JNK6o), c-jun (e.g., AEG 3482, BI 78D3, CEP 1347, c-JUN peptide, IQ 1S, JIP-1 (153-163), SP600125, SU 3327, and TCS JNK6o), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), MEK1/2 (e.g., Facciorusso et al., *Expert Review Gastroenterol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, IRAK (Chaudhary et al., *J. Med. Chem.* 58(1):96-110, 2015), LBP (see, e.g., U.S. Pat. No. 5,705,398), and TRAF6 (e.g., 3-[(2,5-Dimethylphenyl) amino]-1-phenyl-2-propen-1-one).

In some embodiments of any of the methods described herein, the inhibitory nucleic acid can be about 10 nucleotides to about 50 nucleotides (e.g., about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 28 nucleotides, about 10 nucleotides to about 26 nucleotides, about 10 nucleotides to about 25 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 50 nucleotides, about 12 nucleotides to about 45 nucleotides, about 12 nucleotides to about 40 nucleotides, about 12 nucleotides to about 35 nucleotides, about 12 nucleotides to about 30 nucleotides, about 12 nucleotides to about 28 nucleotides, about 12 nucleotides to about 26 nucleotides, about 12 nucleotides to about 25 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 28 nucleotides, about 15 nucleotides to about 26 nucleotides, about 15 nucleotides to about 25 nucleotides, about 15 nucleotides to about 24 nucleotides, about 15 nucleotides to about 22 nucleotides, about 15 nucleotides to about 20 nucleotides, about 15 nucleotides to about 18 nucleotides, about 15 nucleotides to about 16 nucleotides, about 16 nucleotides to about 50 nucleotides, about 16 nucleotides to about 45 nucleotides, about 16 nucleotides to about 40 nucleotides, about 16 nucleotides to about 35 nucleotides, about 16 nucleotides to about 30 nucleotides, about 16 nucleotides to about 28 nucleotides, about 16 nucleotides to about 26 nucleotides, about 16 nucleotides to about 25 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 28 nucleotides, about 20 nucleotides to about 26 nucleotides, about 20 nucleotides to about 25 nucleotides, about 20 nucleotides to about 24 nucleotides, about 20 nucleotides to about 22 nucleotides, about 24 nucleotides to about 50 nucleotides, about 24 nucleotides to about 45 nucleotides, about 24 nucleotides to about 40 nucleotides, about 24 nucleotides to about 35 nucleotides, about 24 nucleotides to about 30 nucleotides, about 24 nucleotides to about 28 nucleotides, about 24 nucleotides to about 26 nucleotides, about 24 nucleotides to about 25 nucleotides, about 26 nucleotides to about 50 nucleotides, about 26 nucleotides to about 45 nucleotides, about 26 nucleotides to about 40 nucleotides, about 26 nucleotides to about 35 nucleotides, about 26 nucleotides to about 30 nucleotides, about 26 nucleotides to about 28 nucleotides, about 28 nucleotides to about 50 nucleotides, about 28 nucleotides to about 45 nucleotides, about 28 nucleotides to about 40 nucleotides, about 28 nucleotides to about 35 nucleotides, about 28 nucleotides to about 30 nucleotides, about 30 nucleotides to about 50 nucleotides, about 30 nucleotides to about 45 nucleotides, about 30 nucleotides to about 40 nucleotides, about 30 nucleotides to about 38 nucleotides, about 30 nucleotides to about 36 nucleotides, about 30 nucleotides to about 34 nucleotides, about 30 nucleotides to about 32 nucleotides, about 32 nucleotides to about 50 nucleotides, about 32 nucleotides to about 45 nucleotides, about 32 nucleotides to about 40 nucleotides, about 32 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, about 42 nucleotides to about 50 nucleotides, about 42 nucleotides to about 45 nucleotides, or about 45 nucleotides to about 50 nucleotides) in length. One skilled in the art will appreciate that inhibitory nucleic acids may comprises at least one modified nucleic acid at either the 5' or 3' end of DNA or RNA.

In some embodiments, the inhibitory nucleic acid can be formulated in a liposome, a micelle (e.g., a mixed micelle), a nanoemulsion, or a microemulsion, a solid nanoparticle, or a nanoparticle (e.g., a nanoparticle including one or more synthetic polymers). Additional exemplary structural features of inhibitory nucleic acids and formulations of inhibitory nucleic acids are described in US 2016/0090598.

In some embodiments, the inhibitory nucleic acid (e.g., any of the inhibitory nucleic acid described herein) can include a sterile saline solution (e.g., phosphate-buffered saline (PBS)). In some embodiments, the inhibitory nucleic acid (e.g., any of the inhibitory nucleic acid described herein) can include a tissue-specific delivery molecule (e.g., a tissue-specific antibody).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

PREPARATIVE EXAMPLES

The following abbreviations have the indicated meanings:
ACN=acetonitrile
BTC=trichloromethyl chloroformate
Boc=t-butyloxy carbonyl
Davephos=2-Dicyclohexylphosphino-2'-(N,N-dimethylamino)biphenyl
DCM=dichloromethane
DEA=diethylamine
DMF=N,N-dimethylformamide
DMSO=dimethyl sulfoxide
DIEA=N,N-diisopropylethylamine
DPPA=diphenylphosphoryl azide
dppf 1,1'-Bis(diphenylphosphino)ferrocene
EtOH=ethanol
HATU=1-[Bis(dimethylamino)methylene]-1H-1,2,3-triazolo[4,5-b]pyridinium 3-oxid hexafluorophosphate
Hex=hexane
HPLC=high performance liquid chromatography LC-MS=liquid chromatography-mass spectrometry
LiHMDS=lithium bis(trimethylsilyl)amide
LDA=lithium diisopropylamide
M=mol/L
Me=methyl
MeOH=methanol
MSA=methanesulfonic acid
NBS=N-bromosuccinimide
NCS=N-chlorosuccinimide
NMR=nuclear magnetic resonance
Pd(dppf)Cl$_2$=dichloro[1,1'-bis(diphenylphosphino)ferrocene]palladium
Ph=phenyl
PPh$_3$Cl$_2$=dichlorotriphenylphosphorane
Py=pyridine
RT=room temperature
Rt=Retention time
R$_f$=Retardation factor
Sat.=saturated
TBAF=tetrabutylammonium fluoride
TBS=tert-butyldimethylsilyl
TBSCl=tert-butyldimethylsilyl chloride
TBDPSCl=tert-butyldiphenylsilyl chloride
TEA=triethylamine
TFA=trifluoroacetic acid
THF=tetrahydrofuran
TLC=thin layer chromatography
TsOH=4-methylbenzenesulfonic acid
UV=ultraviolet General The progress of reactions was often monitored by TLC or LC-MS. The identity of the products was often confirmed by LC-MS. The LC-MS was recorded using one of the following methods.

Method A: Shim-pack XR-ODS, C18, 3×50 mm, 2.5 um column, 1.0 uL injection, 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 um column, 1.0 uL injection, 1.5 mL/min flow rate, 90-900 amu scan range, 190-400 nm UV range, 10-95% (1.1 min), 95% (0.6 min) gradient with ACN and water (0.5% NH$_4$HCO$_3$), 2 minute total run time.

Method C: Shim-pack XR-ODS, C18, 3×50 mm, 2.5 um column, 1.0 uL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 um column, 1.0 uL injection, 1.5 mL/min flow rate, 90-900 amu scan range, 190-400 nm UV range, 10-95% (2.1 min), 95% (0.6 min) gradient with ACN and water (0.5% NH$_4$HCO$_3$), 3 minute total run time.

Method F: Phenomenex, CHO-7644, Onyx Monolithic C18, 50×4.6 mm, 10.0 uL injection, 1.5 mL/min flow rate, 100-1500 amu scan range, 220 and 254 nm UV detection, 5% with ACN (0.1% TFA) to 100% water (0.1% TFA) over 9.5 min, with a stay at 100% (ACN, 0.1% TFA) for 1 min, then equilibration to 5% (ACN, 0.1% TFA) over 1.5 min.

The final targets were purified by Prep-HPLC. The Prep-HPLC was carried out using the following method.

Method E: Prep-HPLC: Column, XBridge Shield RP18 OBD (19×250 mm, 10 um); mobile phase, Water (10 mmol/L NH$_4$HCO$_3$) and ACN, UV detection 254/210 nm.

Method G: Prep-HPLC: Higgins Analytical Proto 200, C18 Column, 250×20 mm, 10 um; mobile phase, Water (0.1% TFA) and ACN (0.1% TFA), UV detection 254/210 nm.

NMR was recorded on BRUKER NMR 300.03 MHz, DUL-C-H, ULTRASHIELD™300, AVANCE II 300 B-ACS™120 or BRUKER NMR 400.13 MHz, BBFO, ULTRASHIELD™400, AVANCE III 400, B-ACS™120 or BRUKER AC 250 NMR instrument with TMS as reference measured in ppm (part per million).

Racemic compounds of this invention can be resolved to give individual enantiomers using a variety of known methods. For example, chiral stationary phases can used and the elution conditions can include normal phase or super-critical fluid with or without acidic or basic additives. Enantiomerically pure acids or bases can be used to form diatereomeric salts with the racemic compounds whereby pure enantiomers can be obtained by fractional crystallization. The racemates can also be derivatized with enantiomerically pure auxiliary reagents to form diastereomeric mixtures that can be separated. The auxiliary is then removed to give pure enantiomers.

Schemes for the Preparation of Final Targets:

Schemes 1-3 below illustrate several conditions used for coupling of sulfonimidamide 1 or 5 and isocyanate 2 to afford aminocarbonyl sulfonimidamide 4 via 3 or 6 after deprotection. As used in the schemes, rings "A" and "B" may be substituted as disclosed herein.

Scheme 1

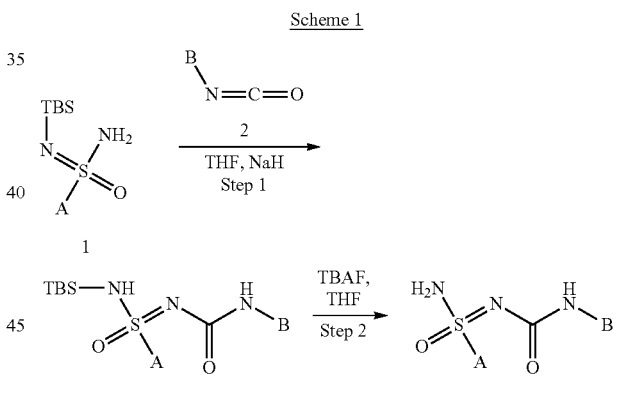

Scheme 2

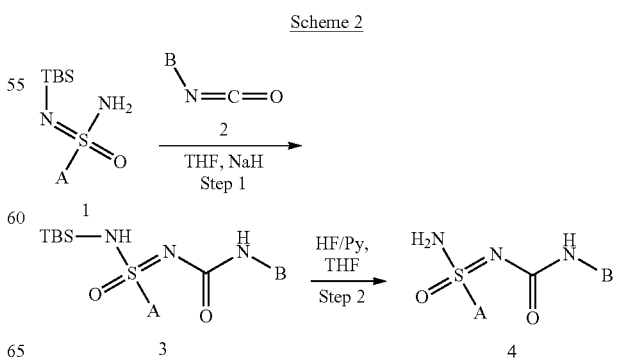

Scheme 3

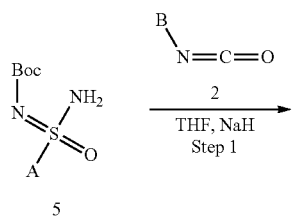

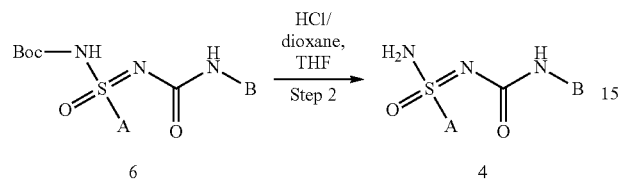

Scheme 3A

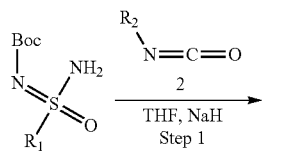

Scheme 3B

Scheme 4 below illustrates the coupling between sulfonimidamide 7 and isocyanate 2 to provide sulfonimidamide 8.

Scheme 4

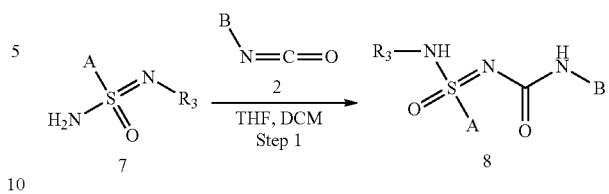

Scheme 4A

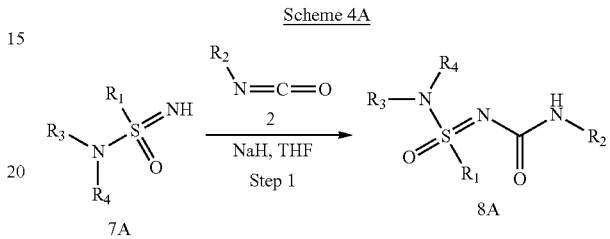

Scheme 5 below illustrates the conversion of carboxylic acid 9 through Curtius rearrangement to isocyanate 2 via acyl azide 10, whereupon coupling between 2 and sulfonimidamide 5 affords aminocarbonyl sulfonimidamide 4.

Scheme 5

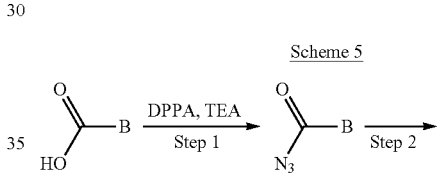

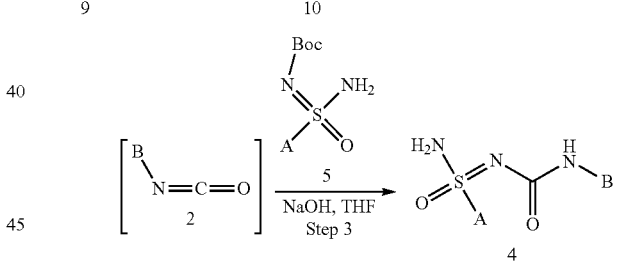

Schemes for the Preparation of Sulfonimidamide Intermediates 1-29

Schemes below illustrate the preparation of sulfonamide intermediates.

Scheme 6

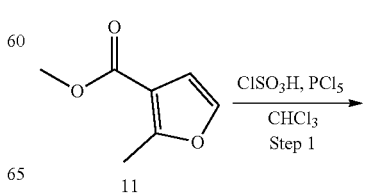

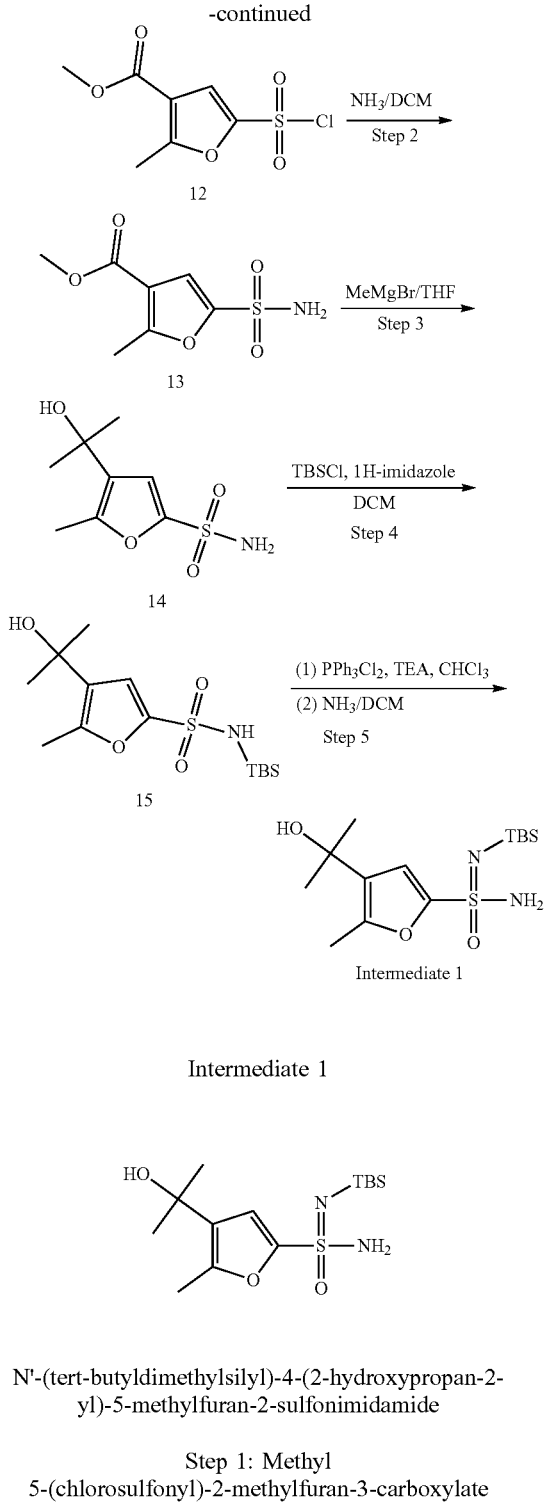

Intermediate 1

N'-(tert-butyldimethylsilyl)-4-(2-hydroxypropan-2-yl)-5-methylfuran-2-sulfonimidamide Step 1: Methyl 5-(chlorosulfonyl)-2-methylfuran-3-carboxylate Into a 500-mL 3-necked round-bottom flask was placed methyl 2-methylfuran-3-carboxylate (7 g, 50 mmol) in CHCl₃ (200 mL). This was followed by the addition of chlorosulfonic acid (11.6 g, 100 mmol) dropwise with stirring at −10° C. The reaction mixture was stirred for 48 h at RT, after which the system was cooled to −10° C. Then to the above was added phosphorus pentachloride (22.9 g, 110 mmol). The resulting solution was stirred for 0.5 h at 50° C. and then was quenched by pouring onto 200 mL of water/ice. The resulting mixture was extracted with 3×200 mL of DCM. The organic layers were combined and dried over anhydrous Na₂SO₄, and then concentrated under vacuum. This resulted in 7.5 g (crude, 63%) of the title compound as light brown oil. The crude product was used in the next step.

Step 2: Methyl 2-methyl-5-sulfamoylfuran-3-carboxylate

Into a 250-mL round-bottom flask was placed a solution of methyl 5-(chlorosulfonyl)-2-methylfuran-3-carboxylate (7.5 g, crude) in DCM (75 mL). To the above was added a saturated solution of ammonia in DCM (50 mL). The resulting solution was stirred for 3 h at RT and then was concentrated under vacuum. The residue was applied onto a silica gel column and eluted with a gradient of ethyl acetate/petroleum ether (1:4 to 1:2). This resulted in 5.0 g (46% over two steps) of the title compound as a light yellow solid. MS-ESI: 218.0 (M−1).

Step 3: 4-(2-Hydroxypropan-2-yl)-5-methylfuran-2-sulfonamide

Into a 250-mL 3-necked round-bottom flask purged with and maintained under nitrogen was placed a solution of methyl 2-methyl-5-sulfamoylfuran-3-carboxylate (3.7 g, 16.9 mmol) in THF (100 mL). This was followed by the addition of MeMgBr (3 M in THF, 25 mL) dropwise with stirring at −10° C. The resulting mixture was stirred for 10 h at RT and then was quenched by the addition of 50 mL of NH₄Cl (sat.). The resulting solution was extracted with 3×50 mL of ethyl acetate. The organic layers were combined and dried over anhydrous Na₂SO₄, then concentrated under vacuum. The residue was applied onto a silica gel column and eluted with a gradient of ethyl acetate/petroleum ether (1:3 to 1:1). This resulted in 2.6 g (75%) of the title compound as a light yellow solid. MS-ESI: 218.0 (M−1).

Step 4: N-(tert-butyldimethylsilyl)-4-(2-hydroxypropan-2-yl)-5-methylfuran-2-sulfonamide Into a 250-mL round-bottom flask purged with and maintained under nitrogen was placed 4-(2-hydroxypropan-2-yl)-5-methylfuran-2-sulfonamide (1.0 g, 4.56 mmol), DCM (100 mL), 1H-imidazole (612 mg, 9.12 mmol), and TBSCl (3.4 g, 22.6 mmol). The resulting solution was stirred for 14 h at RT and then was diluted with 100 mL of water. The resulting mixture was extracted with 3×50 mL of DCM and the organic layers were combined and concentrated under vacuum. The residue was applied onto a silica gel column and eluted with a gradient of ethyl acetate/petroleum ether (1:10 to 1:3). This resulted in 1.4 g (92%) of the title compound as a white solid. MS-ESI: 332.0 (M−1).

Step 5: N'-(tert-butyldimethylsilyl)-4-(2-hydroxypropan-2-yl)-5-methylfuran-2-sulfonimidamide Into a 250-mL 3-necked round-bottom flask purged with and maintained under nitrogen was placed PPh₃Cl₂ (3.0 g, 10.2 mmol) in CHCl₃ (100 mL). This was followed by the addition of TEA (2.06 g, 20.4 mmol) dropwise with stirring at RT. After stirred at 0° C. for 10 min, to the above was added a solution of N-(tert-butyldimethylsilyl)-4-(2-hydroxypropan-2-yl)-5-methylfuran-2-sulfonamide (2.3 g, 6.8 mmol) in CHCl₃ (10 mL) dropwise with stirring at 0° C. The resulting solution was allowed to react for 30 min at 0° C. To the mixture was added a saturated solution of ammonia in DCM (10 mL) at 0° C. The resulting solution was stirred for 2 h at RT. The reaction was then quenched by the addition of 100 mL of water. The resulting solution was extracted with 3×50 mL of DCM and the organic layers combined and concentrated under vacuum. The residue was applied onto a silica gel column and eluted with a gradient of ethyl acetate/petroleum ether (1:10 to 1:3). This resulted in 0.80 g (52.8%) of the title compound as a light yellow solid. MS-ESI: 333.0 (M+1).

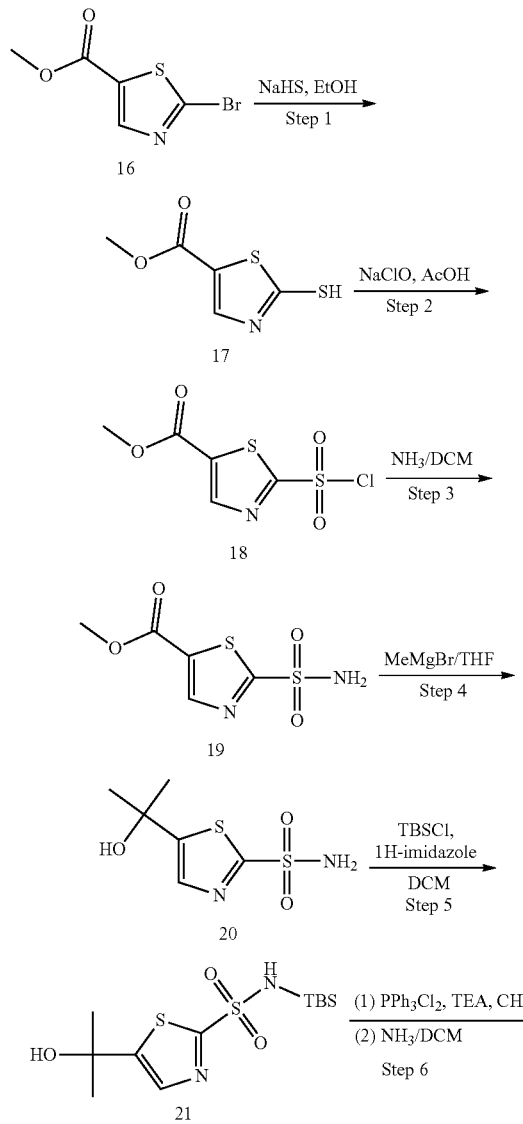

Scheme 7A

Intermediate 2

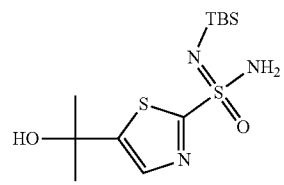

N'-(tert-butyldimethylsilyl)-5-(2-hydroxypropan-2-yl)thiazole-2-sulfonimidamide

Step 1: Methyl 2-mercaptotriazole-5-carboxylate

Into a 250-mL round-bottom flask was placed methyl 2-bromothiazole-5-carboxylate (10 g, 45 mmol), EtOH (100 mL), and sodium hydrogensulfide (5 g, 89 mmol). The resulting solution was stirred for 2 h at 80° C. and then was cooled to 0° C. with a water/ice bath. The pH value of the solution was adjusted to 3 with aq. HCl (1 N). The solids were collected by filtration. This resulted in 6 g (76%) of the title compound as a light yellow solid. MS-ESI: 176.0 (M+1).

Step 2: Methyl 2-(chlorosulfonyl)thiazole-5-carboxylate

Into a 250-mL round-bottom flask was placed methyl 2-mercaptotriazole-5-carboxylate (6 g, 34 mmol) and acetic acid (60 mL). This was followed by the addition of sodium hypochlorite (60 mL, 8%-10% wt.) in portions at 0° C. The resulting solution was stirred for 1 h at RT and then was diluted with 100 mL of water. The solution was extracted with 3×50 mL of DCM. The organic layers were combined and dried over anhydrous Na₂SO₄, then concentrated under vacuum. This resulted in 5 g (crude, 60%) of the title compound as yellow oil. The crude product was used in the next step.

Step 3-6 used similar procedure for converting compound 12 to Intermediate 1 shown in Scheme 6 to afford Intermediate 2. MS-ESI: 336.1 (M+1).

Scheme 7B

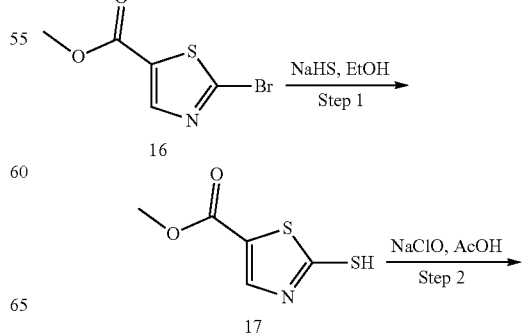

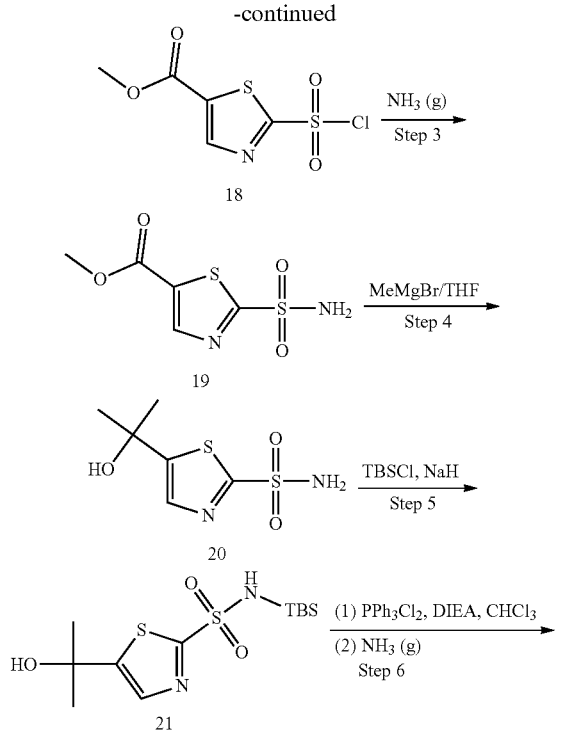

Intermediate 2

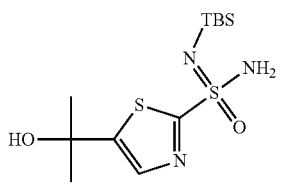

N'-(tert-butyldimethylsilyl)-5-(2-hydroxypropan-2-yl)thiazole-2-sulfonimidamide

Step 1: Methyl 2-mercaptothiazole-5-carboxylate

Into a 2-L round-bottom flask was placed methyl 2-bromothiazole-5-carboxylate (100 g, 450 mmol), EtOH (1000 mL), sodium hydrogensulfide (50 g, 890 mmol). The resulting solution was stirred for 2 h at 80° C. and then was cooled to 0° C. with a water/ice bath. The pH value of the solution was adjusted to 3 with hydrogen chloride (1 N). The solids were collected by filtration. This resulted in 63.2 g (80%) of the title compound as a light yellow solid. MS-ESI: 176.0 (M+1).

Step 2: Methyl 2-(chlorosulfonyl)thiazole-5-carboxylate

Into a 1-L round-bottom flask was placed methyl 2-mercaptothiazole-5-carboxylate (30 g, 170 mmol) and acetic acid (300 mL). This was followed by the addition of sodium hypochlorite (300 mL, 8%-10% wt.) in portions at 0° C. The resulting solution was stirred for 2 h at RT and then was diluted with 500 mL of water. The solution was extracted with 3×300 mL of DCM and the combined organic layers were washed with 2×300 mL of brine and dried over anhydrous $Na_2SO_4$. The crude product as a yellow solution in DCM was used in the next step.

Step 3: Methyl 2-sulfamoylthiazole-5-carboxylate

Into a 2-L round-bottom flask was placed methyl 2-(chlorosulfonyl)thiazole-5-carboxylate as a crude solution in DCM (900 mL). To the solution was introduced $NH_3$ (g) below 0° C. for 20 minutes. The resulting solution was stirred for 1 h at RT and then concentrated under vacuum. The residue was applied onto a silica gel column and eluted with ethyl acetate/petroleum ether (1:5 to 1:3). This resulted in 23 g (75%, 2 steps) of the title compound as a white solid. MS-ESI: 223.0 (M+1).

Step 4: 5-(2-Hydroxypropan-2-yl)thiazole-2-sulfonamide

Into a 500-mL round-bottom flask purged with and maintained under nitrogen was placed a solution of methyl 2-sulfamoylthiazole-5-carboxylate (15 g, 67.5 mmol) in THF (150 mL). This was followed by the addition of MeMgBr/THF (3 M, 90 mL) dropwise with stirring at 0° C. The resulting solution was stirred for 14 h at RT and then was quenched by the addition of 100 mL of $NH_4Cl$ (sat.). The resulting solution was extracted with 3×150 mL of DCM. The organic layers were combined and dried over anhydrous $Na_2SO_4$, then concentrated under vacuum. The residue was applied onto a silica gel column and eluted with ethyl acetate/petroleum ether (1:5 to 1:3). This resulted in 11.5 g (78%) of the title compound as a white solid. MS-ESI: 223.0 (M+1), 221.0 (M−1) in positive and negative ion mode, respectively.

Step 5: N-(tert-butyldimethylsilyl)-5-(2-hydroxypropan-2-yl)thiazole-2-sulfonamide Into a 250-mL 3-necked round-bottom flask purged with and maintained under nitrogen was placed a solution of 5-(2-hydroxypropan-2-yl)thiazole-2-sulfonamide (5 g, 22.5 mmol) in THF (100 mL). Then to the above was added NaH (60% wt, 1.8 g, 45.0 mmol) in portions in an ice/water bath. After stirring for 20 minutes in a water/ice bath, this was followed by the addition of a solution of TBSCl (4.1 g, 27.2 mmol) in THF (10 mL) dropwise with stirring at 0° C. The resulting solution was stirred for 4 h at RT. The reaction was quenched with sat. $NH_4Cl$ (100 mL). The resulting solution was extracted with 3×100 mL of ethyl acetate and the combined organic layers were dried over $Na_2SO_4$ and concentrated under vacuum. The crude solid was washed with ethyl acetate/hexane (1:5) (2×100 mL). This resulted in 6.81 g (90%) of the title compound as a yellow solid. MS-ESI: 337.1 (M+1), 335.1 (M−1) in positive and negative ion mode, respectively.

Step 6: N'-(tert-butyldimethylsilyl)-5-(2-hydroxy-propan-2-yl)thiazole-2-sulfonimidamide Into a 100-mL 3-necked round-bottom flask purged with and maintained under nitrogen was placed a solution of PPh₃Cl₂ (3 g, 9.0 mmol) in CHCl₃ (100 mL). This was followed by the addition of DIEA (1.54 g, 11.9 mmol) dropwise with stirring at RT. The resulting solution was stirred for 10 min at RT. This was followed by the addition of a solution of N-(tert-butyldimethylsilyl)-5-(2-hydroxy-propan-2-yl)thiazole-2-sulfonamide (2.0 g, 5.9 mmol) in CHCl₃ (30 mL) dropwise with stirring in an ice/water bath. The resulting solution was stirred for 30 min in an ice/water bath. To the above was introduced NH₃ (g) below 0° C. for 15 minutes. The resulting solution was stirred for 20 minutes at RT. The solids were filtered out and the filtrate was concentrated and the residue was dissolved in 300 mL of ethyl acetate. The solution was washed with brine (2×100 mL), dried over Na₂SO₄ and concentrated under vacuum. The crude solid was washed with CHCl₃ (100 mL). Then the filtrate was concentrated under vacuum and the residue was further purified by a silica gel column with ethyl acetate/petroleum ether (1:10 to 1:3). The original washed solid and solid from silica gel purification were combined. This resulted in 1.2 g (60%) of the title compound as a white solid. MS-ESI: 336.1 (M+1). ¹H-NMR (300 MHz, DMSO-d₆) δ 7.66 (s, 1H), 7.12 (s, 2H), 5.78 (s, 1H), 1.51 (s, 6H), 0.86 (s, 9H), 0.02 (s, 3H), 0.01 (s, 3H).

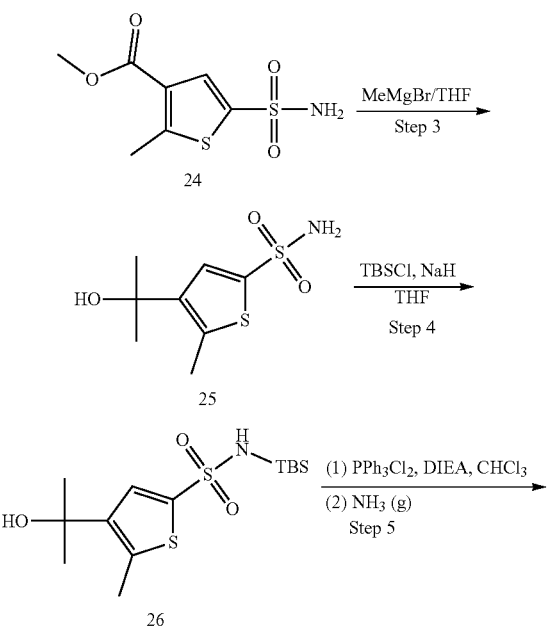

TABLE 2

The Intermediate in the following Table was prepared using the similar procedures for converting compound 16 to Intermediate 2 shown in Scheme 7B starting from ethyl 5-bromo-4-methylthiazole-2-carboxylate.

| Intermediate # | Structure | IUPAC Name | Exact Mass[M + H]⁺ |
|---|---|---|---|
| Intermediate 3 | 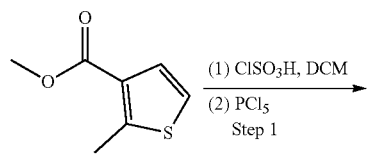 | N'-(tert-butyldimethylsilyl)-2-(2-hydroxypropan-2-yl)-4-methylthiazole-5-sulfonimidamide | 350.2 |

Scheme 8

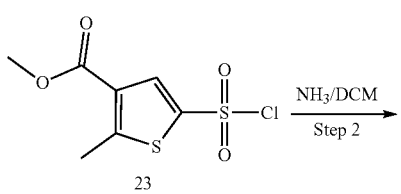

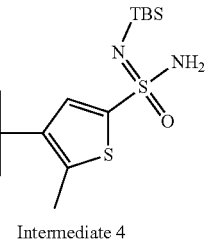

Intermediate 4

Intermediate 4

N'-(tert-butyldimethylsilyl)-4-(2-hydroxypropan-2-yl)-5-methylthiophene-2-sulfonimidamide

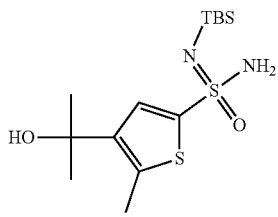

Steps 1-3 used similar procedures for converting compound 11 to compound 14 shown in Scheme 6 to afford compound 25 from compound 22. MS-ESI: 234.0 (M−1).

Steps 4-5 used similar procedure for converting compound 20 to Intermediate 2 shown in Scheme 7B to afford Intermediate 4 from compound 25. MS-ESI: 349.1 (M+1).

TABLE 3

The Intermediate in the following Table was prepared using similar procedure as shown in Scheme 8 above for converting compound 22 to Intermediate 4 starting from the appropriate materials.

| Intermediate # | Structure | IUPAC Name | Exact Mass[M + H]$^+$ |
| --- | --- | --- | --- |
| Intermediate 5 | 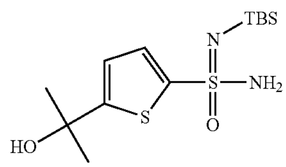 | N'-(tert-butyldimethylsilyl)-5-(2-hydroxypropan-2-yl)thiophene-2-sulfonimidamide | 335.1 |
| Intermediate 6 | 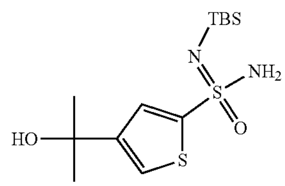 | N'-(tert-butyldimethylsilyl)-4-(2-hydroxypropan-2-yl)thiophene-2-sulfonimidamide | 335.1 |
| Intermediate 7 | 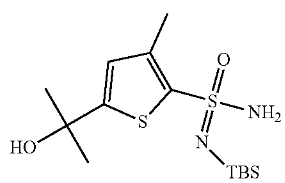 | N'-(tert-butyldimethylsilyl)-5-(2-hydroxypropan-2-yl)-3-methylthiophene-2-sulfonimidamide | 349.1 |
| Intermediate 8 | 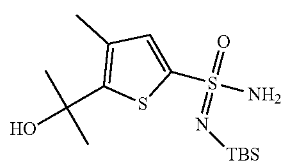 | N'-(tert-butyldimethylsilyl)-5-(2-hydroxypropan-2-yl)-4-methylthiophene-2-sulfonimidamide | 349.1 |
| Intermediate 9 | 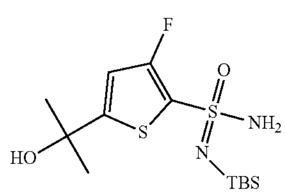 | N'-(tert-butyldimethylsilyl)-3-fluoro-5-(2-hydroxypropan-2-yl)thiophene-2-sulfonimidamide | 353.1 |
| Intermediate 10 | 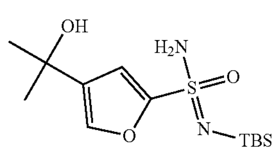 | N'-(tert-butyldimethylsilyl)-4-(2-hydroxypropan-2-yl)furan-2-sulfonimidamide | 319.1 |

Scheme 9

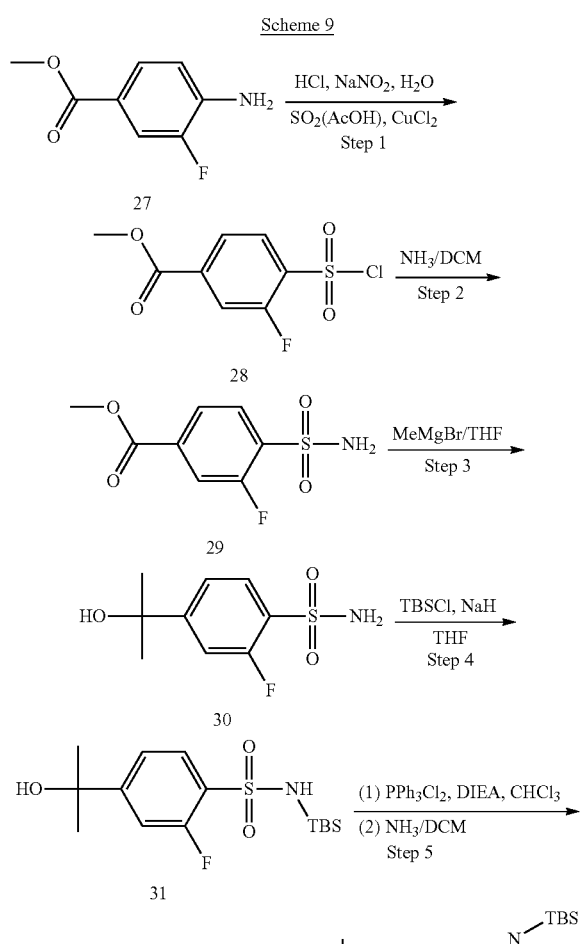

Intermediate 11

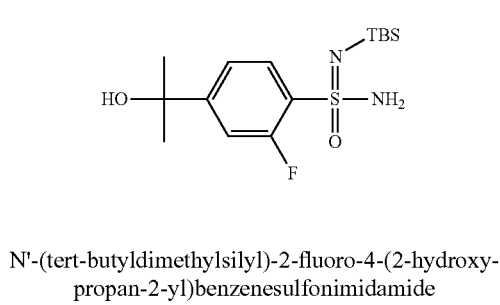

N'-(tert-butyldimethylsilyl)-2-fluoro-4-(2-hydroxypropan-2-yl)benzenesulfonimidamide

Step 1: Methyl 4-(chlorosulfonyl)-3-fluorobenzoate

Into a 1 L round-bottom flask was placed a solution of methyl 4-amino-3-fluorobenzoate (10 g, 59.1 mmol) in aq. HCl (6 N, 200 mL). This was followed by the addition of a solution of $NaNO_2$ (6.1 g, 88.8 mmol) in water (20 mL) dropwise with stirring at 0° C. The resulting solution was stirred for 30 min at 0° C. The above mixture was added to a saturated solution of $SO_2$ in AcOH (200 mL) dropwise with stirring at 0° C. Then to the above was added $CuCl_2$ (8.0 g, 59.6 mmol). The resulting solution was stirred for 1 h at RT and was then quenched by the addition of 200 mL of water. The resulting solution was extracted with 3×200 mL of DCM. The organic layers were combined, dried over anhydrous $Na_2SO_4$ and concentrated under vacuum. This resulted in 10 g (67%) of the title compound as yellow oil. The product was used in the next step without further purification.

Step 2: Methyl 3-fluoro-4-sulfamoylbenzoate

Into a 1000 mL round bottom flask was placed a solution of methyl 4-(chlorosulfonyl)-3-fluorobenzoate solution (10 g, 39.5 mmol) in DCM (50 mL). This was followed by the addition of a saturated solution of ammonia in DCM (500 mL) in portions with stirring at 0° C. The resulting solution was stirred for 1 h at 0° C. The resulting solution was concentrated and the residue was purified with $SiO_2$-gel column and diluted with ethyl acetate/petroleum ether (1:2 to 1:1). This resulted in 8.28 g (90%) of the title compound as yellow solid. MS-ESI: 232.1 (M−1).

Step 3: 2-Fluoro-4-(2-hydroxypropan-2-yl)benzenesulfonamide

Into a 1 L 3-necked round-bottom flask was placed a solution of methyl 3-fluoro-4-sulfamoylbenzoate (8.28 g 35.5 mmol) in THF (500 mL). This was followed by the addition of MeMgBr/THF (3 M, 60 mL) dropwise with stirring at 0° C. The resulting solution was stirred overnight at RT and then was quenched by the addition of 100 mL of sat. $NH_4Cl$. The resulting solution was extracted with 3×200 mL of ethyl acetate and the combined organic layers were concentrated under vacuum. The residue was applied onto a silica gel column and eluted with ethyl acetate/petroleum ether (1:2 to 1:1). This resulted 7.45 g (89.9%) of the title compound as a white solid. MS-ESI: 233.1 (M+1).

Step 4: N-(tert-butyldimethylsilyl)-2-fluoro-4-(2-hydroxypropan-2-yl)benzenesulfonamide Into a 500 mL round bottom flask was placed a solution of 2-fluoro-4-(2-hydroxypropan-2-yl)benzenesulfonamide (7.45 g 31.9 mmol) in THF (200 mL). This was followed by the addition of NaH (60% wt, 1.91 g, 79.6 mmol). The mixture was stirred at 0° C. for 0.5 h. This was followed by the addition of the solution of TBSCl (7.19 g, 47.9 mmol) in THF (50 mL) dropwise. The resulting solution was stirred at RT overnight. The reaction was quenched with ice-water (100 mL); the resulting solution was extracted with EtOAc (3×200 mL). The combined organic layers were dried over anhydrous $Na_2SO_4$ and concentrated under vacuum. The residue was purified with $SiO_2$-gel column and eluted with ethyl acetate/petroleum ether (1:5 to 1:2). This resulted 10 g (90%) of the title compound as a white solid. MS-ESI: 348.1 (M+1).

Step 5: N'-(tert-butyldimethylsilyl)-2-fluoro-4-(2-hydroxypropan-2-yl)benzenesulfonimidamide Into a 1 L 3-necked round-bottom flask purged with and maintained under nitrogen was placed a solution of $PPh_3Cl_2$ (19.2 g, 57.6 mmol) in $CHCl_3$ (100 mL). This was followed by the addition of DIEA (7.4 g, 57.6 mmol) dropwise with stirring at 0° C. After stirred at 0° C. for 10 min, to the above was added a solution of N'-(tert-butyldimethylsilyl)-2-fluoro-4-(2-hydroxypropan-2-yl)benzenesulfonimidamide (10 g, 28.8 mmol) in CHCl₃ (100 mL) dropwise with stirring at 0° C. The resulting solution was allowed to react for 30 min at 0° C. To the mixture was added a saturated solution of ammonia in DCM (500 mL) at 0° C. The resulting solution was stirred for 2 h at RT. The solids were filtered out, and the filtrate was dilute with 100 mL of water. The resulting solution was extracted with 3×200 mL of DCM and the combined organic layers were dried over anhydrous Na₂SO₄ concentrated under vacuum. The residue was applied onto a silica gel column and eluted with a gradient of ethyl acetate/petroleum ether (1:10 to 1:3). This resulted in 5 g (50%) of the title compound as a light yellow solid. MS-ESI: 347.2 (M+1).

TABLE 4

The Intermediates in the following Table were prepared using similar procedure as shown in Scheme 9 above for converting compound 27 to Intermediate 11 starting from the appropriate materials.

| Intermediate # | Structure | IUPAC Name | Exact Mass[M + H]⁺ |
|---|---|---|---|
| Intermediate 12 | 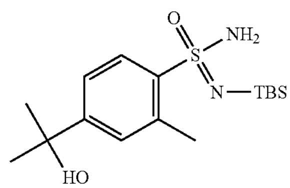 | N'-(tert-butyldimethylsilyl)-4-(2-hydroxypropan-2-yl)-2-methylbenzenesulfonimidamide | 343.2 |
| Intermediate 13 | 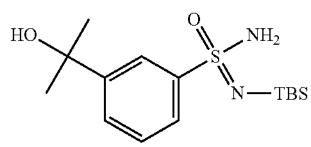 | N'-(tert-butyldimethylsilyl)-3-(2-hydroxypropan-2-yl)benzenesulfonimidamide | 329.1 |
| Intermediate 14 | 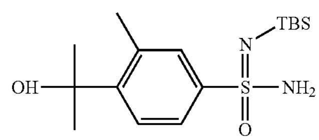 | N'-(tert-butyldimethylsilyl)-4-(2-hydroxypropan-2-yl)-3-methylbenzenesulfonimidamide | 343.2 |
| Intermediate 15 | 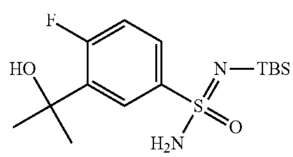 | N'-(tert-butyldimethylsilyl)-4-fluoro-3-(2-hydroxypropan-2-yl)benzenesulfonimidamide | 347.2 |
| Intermediate 16 | 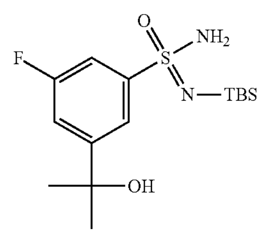 | N'-(tert-butyldimethylsilyl)-3-fluoro-5-(2-hydroxypropan-2-yl)benzenesulfonimidamide | 347.2 |
| Intermediate 17 | 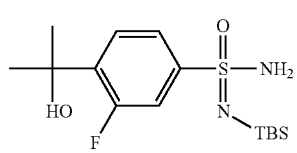 | N'-(tert-butyldimethylsilyl)-3-fluoro-4-(2-hydroxypropan-2-yl)benzenesulfonimidamide | 347.2 |
| Intermediate 18 | 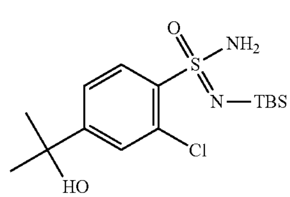 | N'-(tert-butyldimethylsilyl)-2-chloro-4-(2-hydroxypropan-2-yl)benzenesulfonimidamide | 363.1 |

TABLE 5

The Intermediate in the following Table was prepared using similar procedure as shown in Scheme 9 above for converting compound 28 to Intermediate 11 starting from methyl 4-(chlorosulfonyl)benzoate.

| Intermediate # | Structure | IUPAC Name | Exact Mass[M + H]+ |
|---|---|---|---|
| Intermediate 19 | 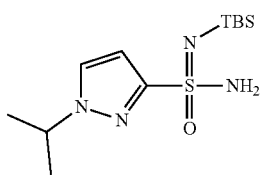 | N'-(tert-butyldimethylsilyl)-4-(2-hydroxypropan-2-yl)benzenesulfonimidamide | 329.2 |

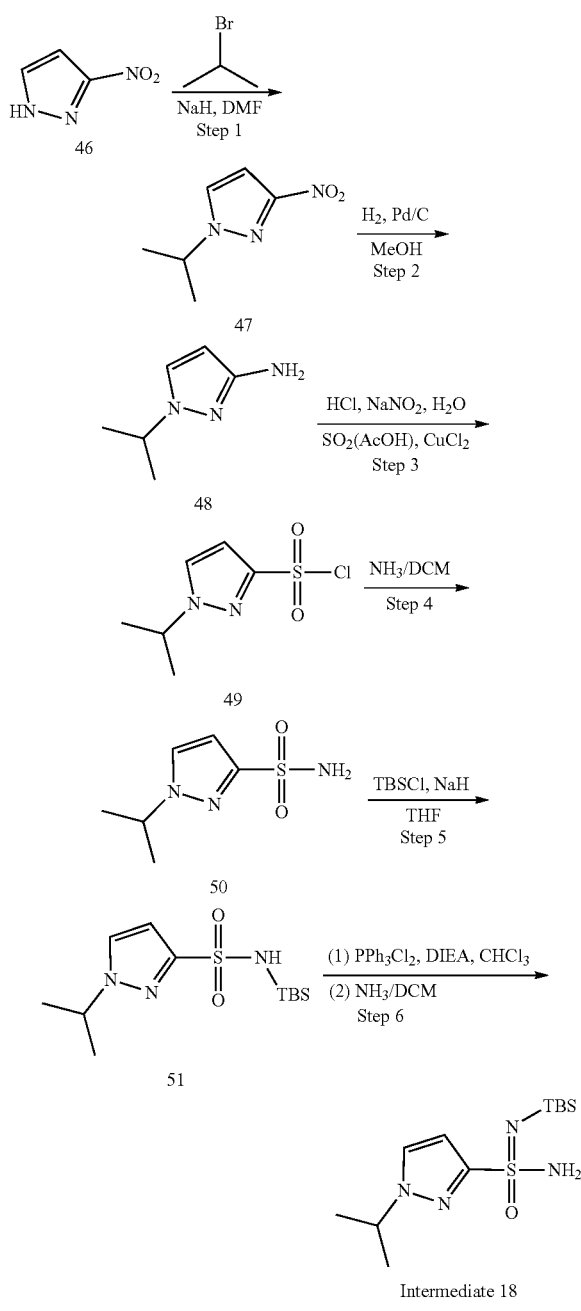

Intermediate 18

N'-(tert-butyldimethylsilyl)-1-isopropyl-1H-pyrazole-3-sulfonimidamide

Step 1: 1-Isopropyl-3-nitro-1H-pyrazole

Into a 250-mL round-bottom flask was placed a solution of 3-nitro-1H-pyrazole (10 g, 88.4 mmol) in DMF (100 mL). This was followed by the addition of NaH (60% wt., 3.9 g, 97.5 mmol) in portions at 0° C. The resulting solution was stirred for 0.5 h at 0° C. This was followed by the addition of 2-bromopropane (14.1 g, 114.6 mmol) dropwise with stirring at 0° C. in 10 min. The resulting solution was stirred for 16 h at RT and then was quenched by the addition of 100 mL of water. The resulting solution was extracted with 3×100 mL of ethyl acetate. The organic layers were combined and dried over anhydrous $Na_2SO_4$, then concentrated under vacuum. The residue was applied onto a silica gel column and eluted with a gradient of ethyl acetate/petroleum ether (1:5 to 1:3). This resulted in 11.8 g (86%) of the title compound as yellow oil. MS-ESI: 156.1 (M+1).

Step 2: 3-Amino-1-(propan-2-yl)-1H-pyrazole

Into a 250-mL round-bottom flask was placed a solution of 1-isopropyl-3-nitro-1H-pyrazole (10.8 g, 69.6 mmol) in MeOH (100 mL). Then Pd/C (10% wt., 1.5 g) was added. The flask was evacuated and flushed three times with hydrogen. The mixture was stirred for 24 h at RT under an atmosphere of hydrogen. The solids were filtered out. The resulting filtrate was concentrated under vacuum. This resulted in 7.27 g (83%) of the title compound as yellow oil. MS-ESI: 126.1 (M+1).

Steps 3-4 used similar procedures for converting compound 27 to compound 29 shown in Scheme 9 to afford compound 50 from compound 48. MS-ESI: 188.0 (M−1).

Steps 5-6 were using the similar procedures for converting compound 30 to Intermediate 11 shown in Scheme 9 to afford Intermediate 18 from compound 50. MS-ESI: 303.2 (M+1).

TABLE 6

The Intermediate in the following Table was prepared using similar procedure as shown in Scheme 10 above for converting compound 48 to Intermediate 18 starting from the appropriate materials.

| Intermediate # | Structure | IUPAC Name | Exact Mass[M + H]+ |
| --- | --- | --- | --- |
| Intermediate 21 | 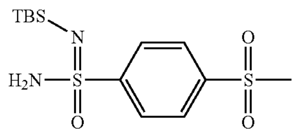 | N'-(tert-butyldimethylsilyl)-4-(methylsulfonyl)benzenesulfonimidamide | 349.1 |
| Intermediate 22 | 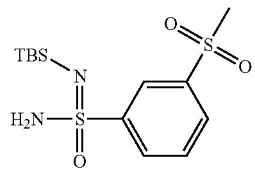 | N'-(tert-butyldimethylsilyl)-3-(methylsulfonyl)benzenesulfonimidamide | 349.1 |

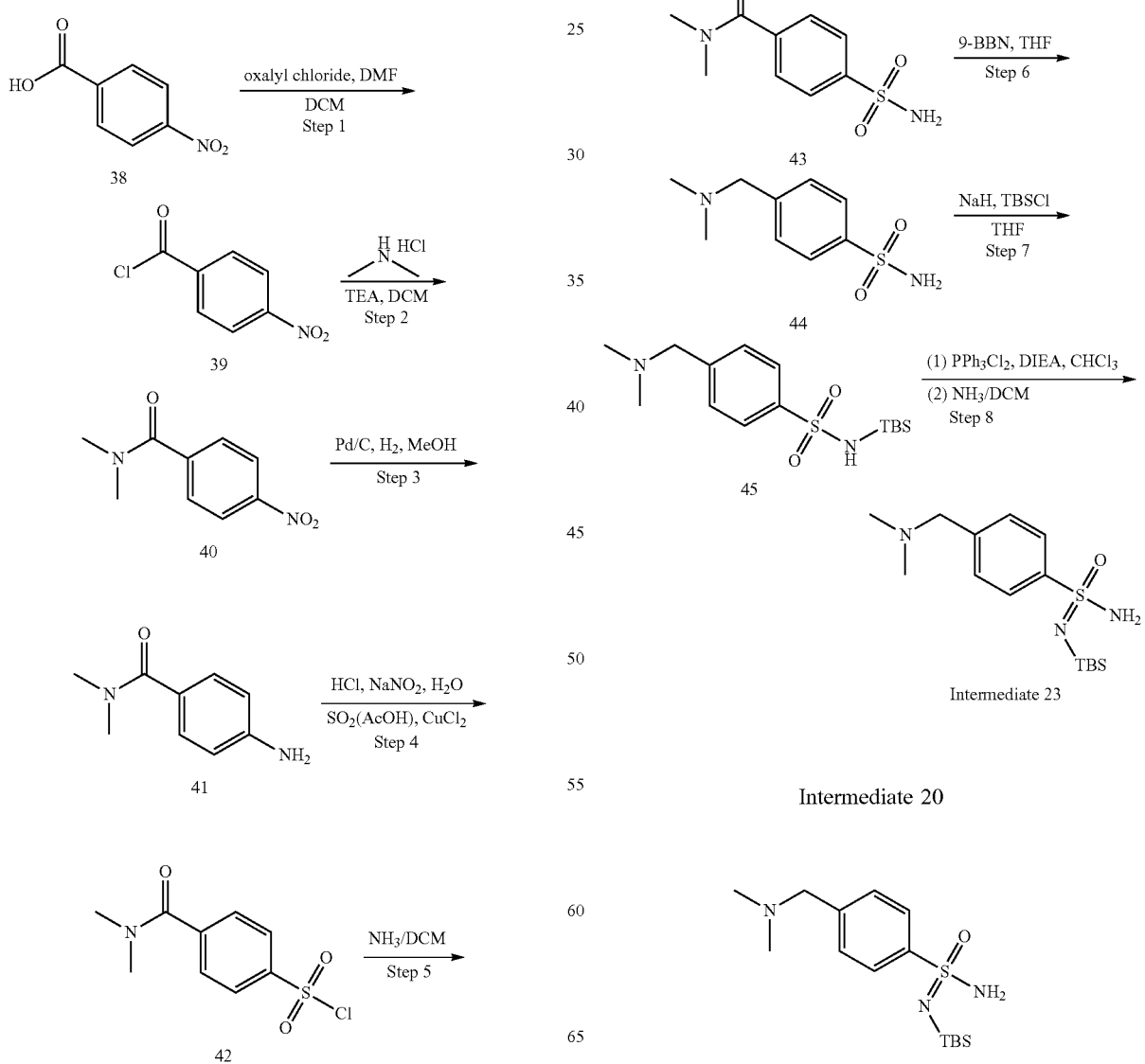

N'-(tert-butyldimethylsilyl)-4-((dimethylamino)methyl)benzenesulfonimidamide

Step 1: 4-Nitrobenzoyl Chloride

Into a 500-mL round-bottom flask was placed 4-nitrobenzoic acid (20 g, 120 mmol), DCM (200 mL), and DMF (0.2 mL). This was followed by the addition of oxalyl chloride (15 mL, 177.1 mmol) dropwise with stirring at 0° C. The resulting solution was stirred for 4 h at RT and then was concentrated under vacuum. This resulted in 22 g (crude) of the title compound as yellow oil. The crude product was used in the next step.

Step 2: N,N-dimethyl-4-nitrobenzamide

Into a 500-mL round-bottom flask was placed dimethylamine hydrochloride (6.5 g, 79.7 mmol), DCM (200 mL), and TEA (50 mL). This was followed by the addition of 4-nitrobenzoyl chloride (22 g, 119 mmol) dropwise with stirring at 0° C. The resulting solution was stirred for 6 h at RT and then was concentrated under vacuum. The resulting mixture was washed with 2×50 mL of water. The solids were collected by filtration. This resulted in 16 g (69% over two steps) of the title compound as a white solid. MS-ESI: 195.1 (M+1).

Step 3: 4-Amino-N,N-dimethylbenzamide

Into a 250-mL round-bottom flask was placed N,N-dimethyl-4-nitrobenzamide (16 g, 82.4 mmol), MeOH (100 mL). Then Pd/C (10% wt., 1 g) was added. The flask was evacuated and flushed three times with hydrogen. The resulting solution was stirred for 12 h at RT under an atmosphere of hydrogen. The solids were filtered out. The resulting filtrate was concentrated under vacuum. This resulted in 13 g (96%) of the title compound as a white solid. MS-ESI: 165.1 (M+1).

Steps 4-5 used similar procedures for converting compound 27 to compound 29 shown in Scheme 9 to afford compound 43 from compound 41. MS-ESI: 229.1 (M+1).

Step 6: 4-((Dimethylamino)methyl)benzenesulfonamide

Into a 100-mL round-bottom flask purged with and maintained under nitrogen was placed a solution of N,N-dimethyl-4-sulfamoylbenzamide (1.8 g, 7.9 mmol) in THF (50 mL). This was followed by the addition of 9-BBN (5.8 g) in portions at 0° C. The resulting solution was stirred for 12 h at 70° C. and then was quenched by the addition of 20 mL of water/ice. The resulting solution was extracted with 3×100 mL of ethyl acetate and the organic layers were combined. The resulting mixture was washed with 200 ml of water and then the organic layer was concentrated under vacuum. The residue was applied onto a silica gel column and eluted with a gradient of DCM/MeOH (20:1 to 15:1). This resulted in 1 g (59%) of the title compound as a white solid. MS-ESI: 215.1 (M+1).

Steps 7-8 were using the similar procedures for converting compound 30 to Intermediate 11 shown in Scheme 9 to afford Intermediate 23 from compound 44. MS-ESI: 328.2 (M+1).

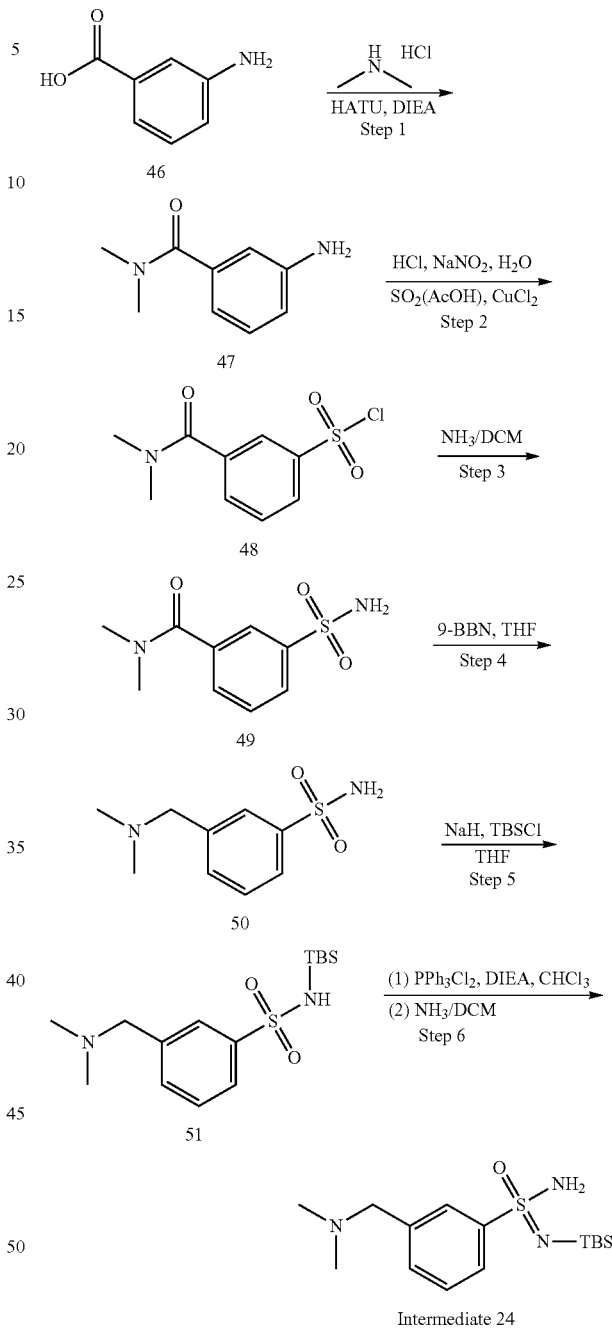

Scheme 12

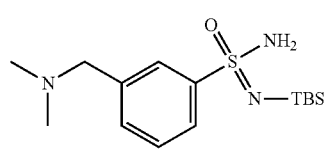

Intermediate 24

N'-(tert-butyldimethylsilyl)-3-((dimethylamino)methyl)benzenesulfonimidamide

Step 1: 3-amino-N,N-dimethylbenzamide

Into a 1000-mL round-bottom flask was placed dimethylamine as a hydrochloride salt (16.3 g, 200 mmol) in DCM (500 mL), DIEA (25.83 mg, 200 mmol). To the above was added 3-aminobenzoic acid (13.7 g, 100 mmol), HATU (57 g, 150 mmol). The resulting solution was stirred for 1 h at RT. The reaction was then quenched by the addition of 500 mL of NH$_4$Cl (aq.). The resulting solution was extracted with 3×500 ml of ethyl acetate and the organic layers combined and dried over anhydrous sodium sulfate and concentrated. The residue was applied onto a silica gel column and eluted with a gradient of DCM/methanol (50:1 to 20:1). This resulted in 13.14 g (80%) of the title compound as a yellow solid. MS-ESI: 165.1 (M+1).

Steps 2-6 used the similar procedures for converting compound 41 to Intermediate 23 shown in Scheme 11 to afford Intermediate 24 from compound 47. MS-ESI: 328.2 (M+1).

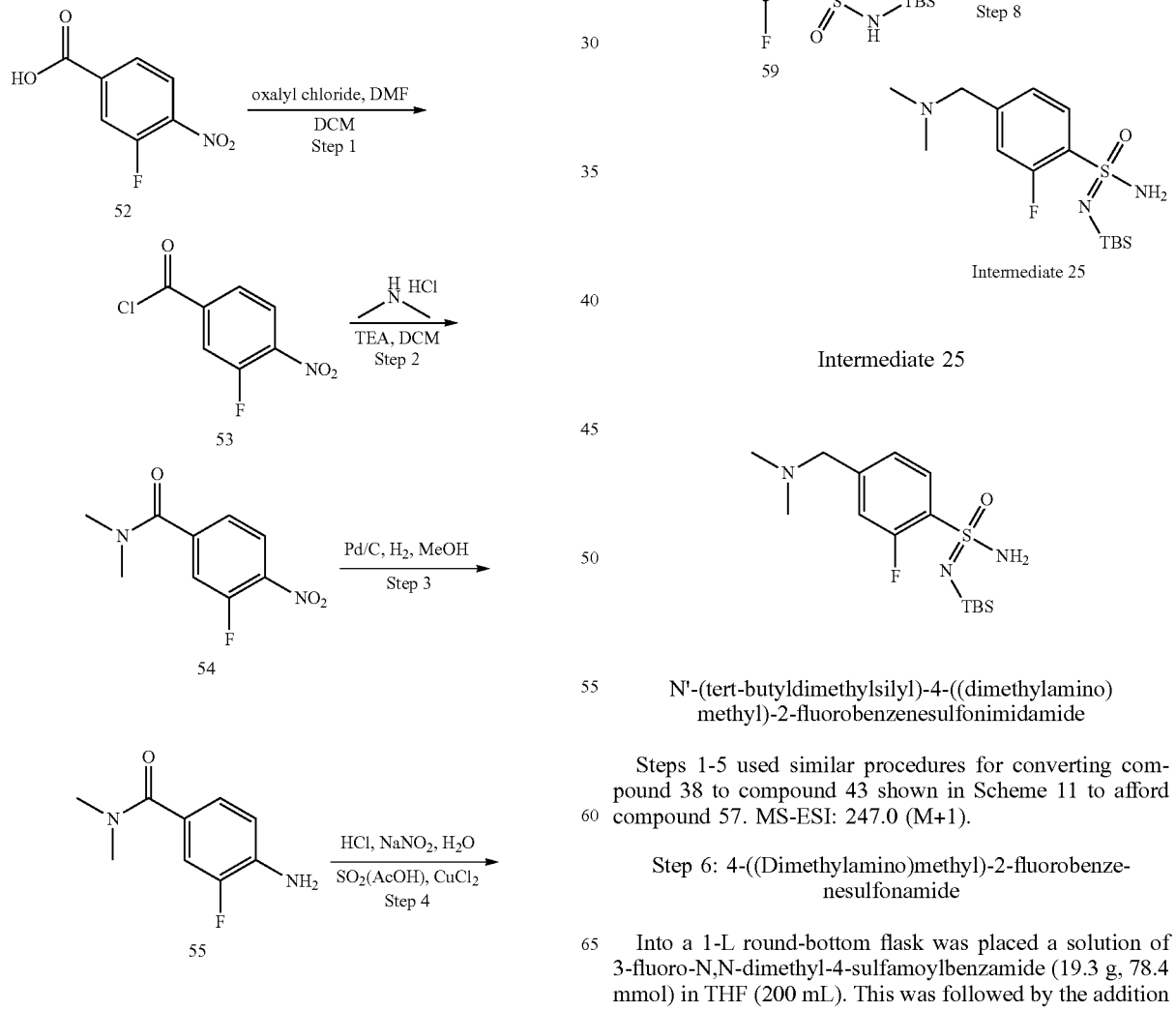

Intermediate 25

N'-(tert-butyldimethylsilyl)-4-((dimethylamino)methyl)-2-fluorobenzenesulfonimidamide Steps 1-5 used similar procedures for converting compound 38 to compound 43 shown in Scheme 11 to afford compound 57. MS-ESI: 247.0 (M+1).

Step 6: 4-((Dimethylamino)methyl)-2-fluorobenzenesulfonamide

Into a 1-L round-bottom flask was placed a solution of 3-fluoro-N,N-dimethyl-4-sulfamoylbenzamide (19.3 g, 78.4 mmol) in THF (200 mL). This was followed by the addition of LiAlH₄ (8.8 g, 231.9 mmol) in portions at 0° C. The resulting solution was stirred for 12 h at RT and then was quenched by the addition of 10 mL of water. The resulting mixture was concentrated under vacuum. The residue was applied onto a silica gel column and eluted with a gradient of ethyl acetate/petroleum ether (6:1 to 8:1). This resulted in 7.0 g (38%) of the title compound as a white solid. MS-ESI: 233.1 (M+1).

Steps 7-8 used similar procedures for converting compound 44 to Intermediate 23 shown in Scheme 11 to afford Intermediate 25. MS-ESI: 346.2 (M+1).

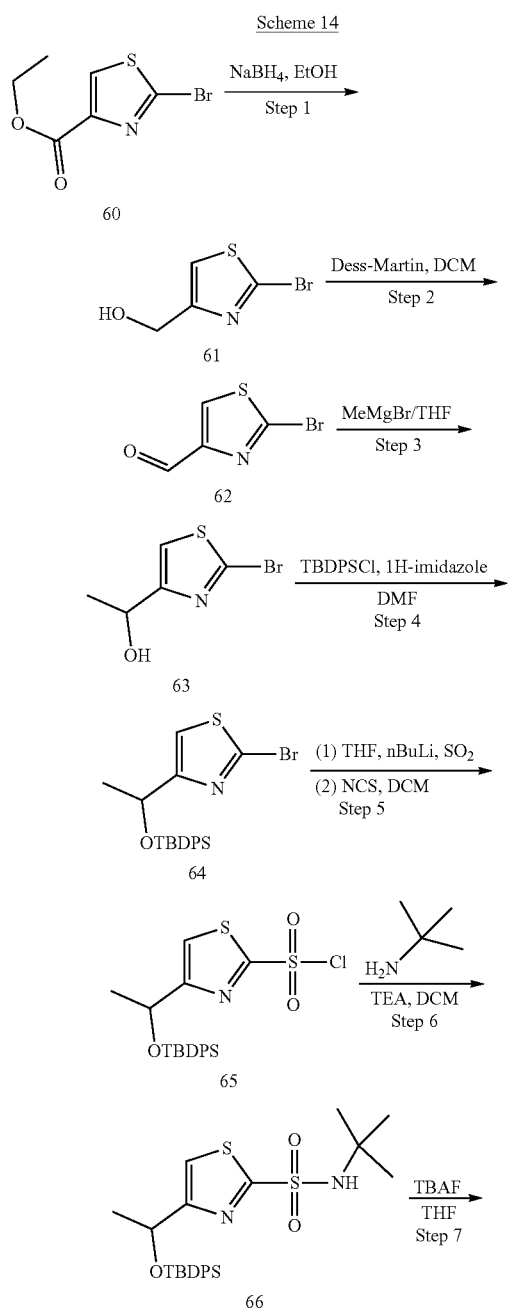

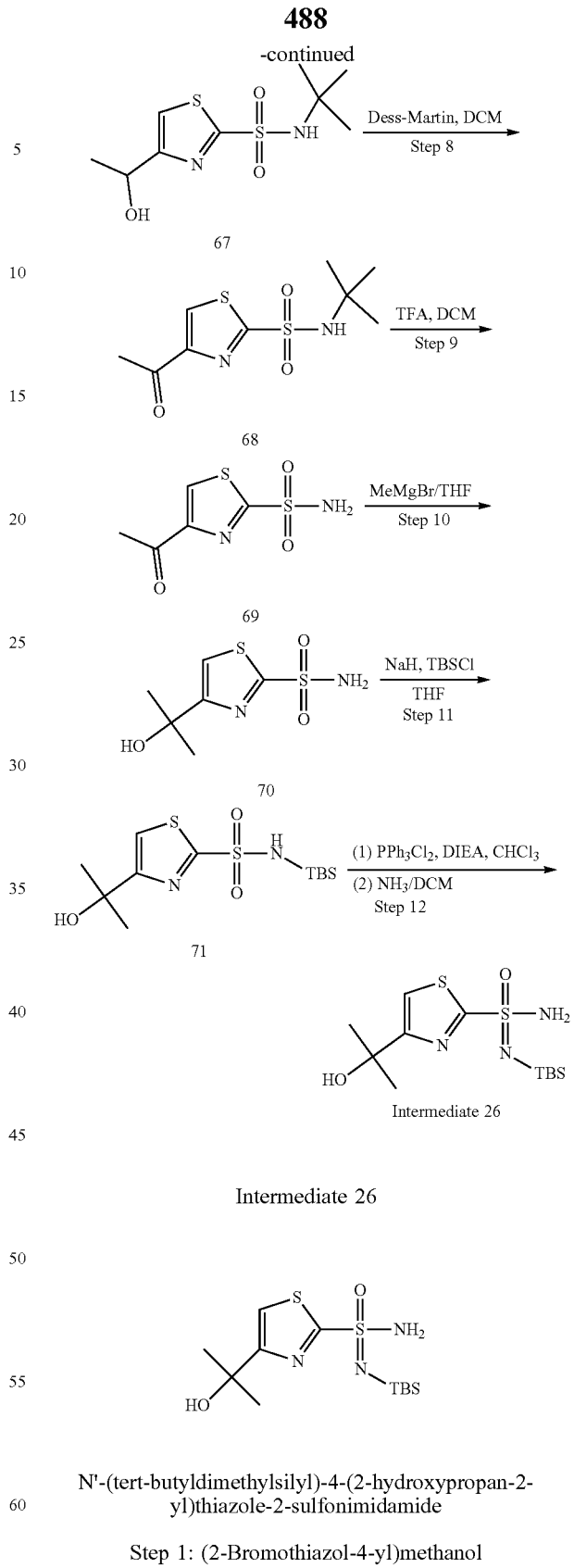

N'-(tert-butyldimethylsilyl)-4-(2-hydroxypropan-2-yl)thiazole-2-sulfonimidamide

Step 1: (2-Bromothiazol-4-yl)methanol

Into a 500-mL round-bottom flask was placed a solution of ethyl 2-bromothiazole-4-carboxylate (14 g, 59.3 mmol), EtOH (200 mL). This was followed by the addition of NaBH₄ (2.3 g, 60.5 mmol) in portions at 0° C. The resulting solution was stirred for 3 h at RT and then was quenched by the addition of 100 mL of water. The resulting solution was extracted with 2×200 mL of DCM. The organic layers were combined, dried over anhydrous $Na_2SO_4$ and then concentrated under vacuum. This resulted in 10.0 g (87%) of the title compound as colorless oil. MS-ESI: 195.9, 193.9 (M+1).

Step 2: 2-Bromothiazole-4-carbaldehyde

Into a 250-mL round-bottom flask was placed a solution of (2-bromothiazol-4-yl)methanol (10.0 g, 51.5 mmol) in DCM (100 mL). To the solution was added Dess-Martin reagent (24.0 g, 56.6 mmol). The resulting solution was stirred for 2 h at RT and then was concentrated under vacuum.
The residue was applied onto a silica gel column and eluted with a gradient of ethyl acetate/petroleum ether (1:50 to 1:20). This resulted in 8.0 g (81%) of the title compound as yellow oil. MS-ESI: 193.9, 191.9 (M+1).

Step 3: 1-(2-Bromothiazol-4-yl)ethanol

Into a 250-mL 3-necked round-bottom flask purged with and maintained under nitrogen was placed a solution of 2-bromothiazole-4-carbaldehyde (8 g, 41.7 mmol) in THF (100 mL). This was followed by the addition of MeMgBr (3 M in THF, 15 mL) dropwise with stirring at 0° C. The resulting solution was stirred for 2 h at RT and then was quenched by the addition of 100 mL of $NH_4Cl$ (sat.). The resulting solution was extracted with 3×100 mL of DCM and the combined organic layers were concentrated under vacuum. The residue was applied onto a silica gel column and eluted with a gradient of ethyl acetate/petroleum ether (1:10 to 1:5). This resulted in 6.0 g (69%) of the title compound as brown oil. MS-ESI: 209.9, 207.9 (M+1).

Step 4: 2-Bromo-4-(1-(tert-butyldiphenylsilyloxy) ethyl)thiazole

Into a 250-mL round-bottom flask was placed a solution of 1-(2-bromothiazol-4-yl)ethanol (6.0 g, 28.8 mmol) and 1H-imidazole (4.0 g, 58.8 mmol) in DMF (50 mL). To the solution was added TBDPSCl (8.7 g, 31.6 mmol). The resulting solution was stirred for 12 h at RT and then was diluted with 100 mL of water. The resulting solution was extracted with 3×100 mL of DCM and the combined organic layers were concentrated under vacuum. The residue was applied onto a silica gel column and eluted with a gradient of ethyl acetate/petroleum ether (1:100 to 1:50). This resulted in 10.0 g (78%) of the title compound as light yellow oil. MS-ESI: 448.1, 446.1 (M+1).

Step 5: 4-(1-(Tert-butyldiphenylsilyloxy)ethyl)thiazole-2-sulfonyl chloride

Into a 250-mL 3-necked round-bottom flask purged with and maintained under nitrogen was placed a solution of 2-bromo-4-(1-(tert-butyldiphenylsilyloxy)ethyl)thiazole (10.0 g, 22.4 mmol) in THF (100 mL). This was followed by the addition of n-BuLi (2.5 M in THF, 11 mL) dropwise with stirring at −78° C. The resulting solution was stirred for 30 min at −78° C. To the above $SO_2$ gas was introduced. The reaction was warmed to RT and stirred for 30 min and then was concentrated under vacuum. The residue was dissolved in DCM (100 mL) and then NCS (3.6 g, 26.9 mmol) was added. The resulting solution was stirred for 30 min at RT and then was concentrated under vacuum. This resulted in 8.0 g (crude, 77%) of the title compound as a white solid. The crude product was used in the next step.

Step 6: N-tert-butyl-4-(1-(tert-butyldiphenylsilyloxy)ethyl)thiazole-2-sulfonamide Into a 100-mL round-bottom flask purged with and maintained under nitrogen was placed a solution of 4-(1-(tert-butyldiphenylsilyloxy)ethyl)thiazole-2-sulfonyl chloride (8.0 g, 17.2 mmol) in DCM (50 mL). To the solution were added TEA (3.5 g, 34.6 mmol) and 2-methylpropan-2-amine (1.9 g, 26.0 mmol). The resulting solution was stirred for 2 h at RT and then was concentrated under vacuum. The residue was applied onto a silica gel column and eluted with a gradient of ethyl acetate/petroleum ether (1:15 to 1:5). This resulted in 8.0 g (71%, 2 steps) of the title compound as brown oil. MS-ESI: 503.2 (M+1).

Step 7: N-tert-butyl-4-(1-hydroxyethyl)thiazole-2-sulfonamide

Into a 250-mL round-bottom flask was placed a solution of N-tert-butyl-4-(1-(tert-butyldiphenylsilyloxy)ethyl)thiazole-2-sulfonamide (8.0 g, 15.9 mmol) in THF (100 mL). To the solution was added TBAF (9.6 g, 292.5 mmol). The resulting solution was stirred for 2 h at RT and then was diluted with 100 mL of water. The resulting solution was extracted with 3×100 mL of DCM and the combined organic layers were concentrated under vacuum. The residue was applied onto a silica gel column and eluted with a gradient of ethyl acetate/petroleum ether (1:10 to 1:3). This resulted in 4.0 g (95%) of the title compound as light yellow oil. MS-ESI: 265.1 (M+1).

Step 8: 4-Acetyl-N-tert-butylthiazole-2-sulfonamide

Into a 100-mL round-bottom flask was placed a solution of N-tert-butyl-4-(1-hydroxyethyl)thiazole-2-sulfonamide (4.0 g, 15.1 mmol) in DCM (50 mL). To the solution was added Dess-Martin reagent (7.1 g, 16.6 mmol). The resulting solution was stirred for 2 h at RT and then was concentrated under vacuum. The residue was applied onto a silica gel column and eluted with a gradient of ethyl acetate/petroleum ether (1:10 to 1:3). This resulted in 3.5 g (88%) of the title compound as light yellow oil. MS-ESI: 363.0 (M+1).

Step 9: 4-Acetylthiazole-2-sulfonamide

Into a 100-mL round-bottom flask was placed a solution of 4-acetyl-N-tert-butylthiazole-2-sulfonamide (3.5 g, 13.3 mmol) in DCM (5 mL). To the solution was added TFA (20 mL). The resulting solution was stirred for 14 h at 40° C. and then was concentrated under vacuum. The residue was applied onto a silica gel column and eluted with a gradient of ethyl acetate/petroleum ether (1:10 to 1:3). This resulted in 2.5 g (91%) of the title compound as a gray solid. MS-ESI: 207.0 (M+1).

Steps 10-12 used similar procedures for converting compound 29 to Intermediate 11 shown in Scheme 9 to afford Intermediate 26 from compound 69. MS-ESI: 336.1 (M+1).

Scheme 15A

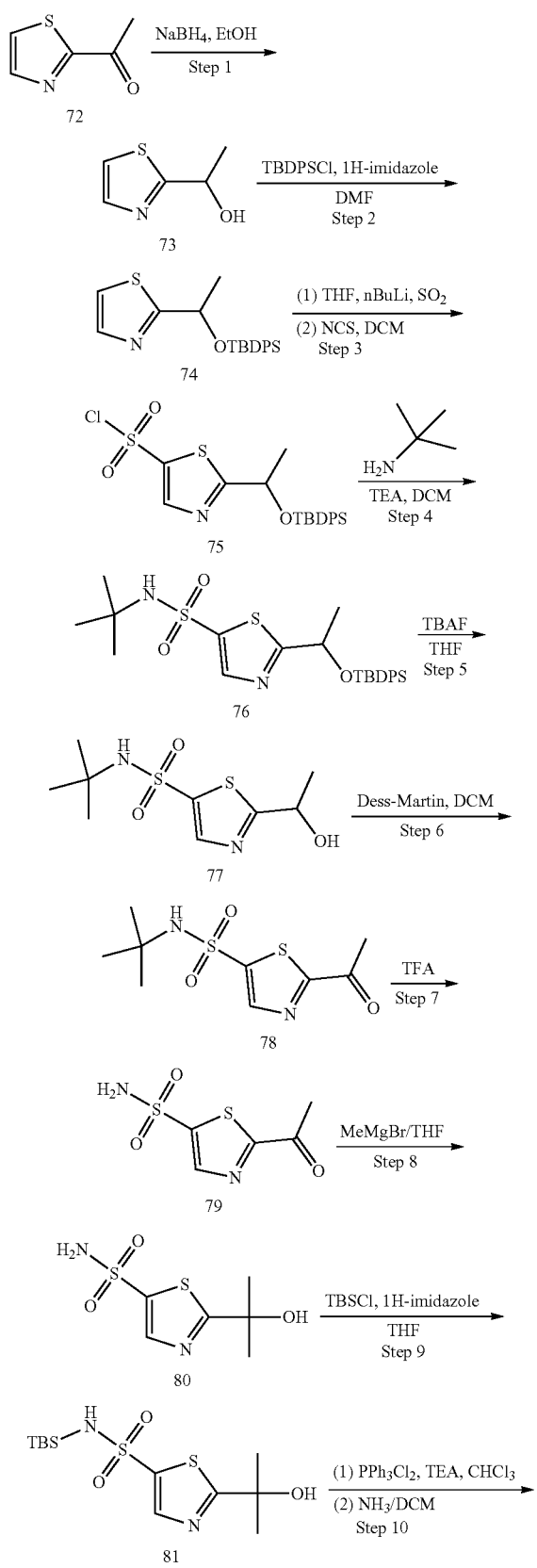

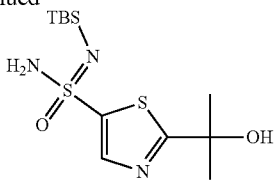

Intermediate 27

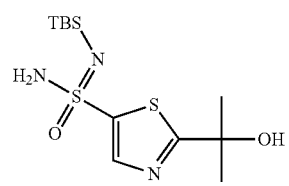

N'-(tert-butyldimethylsilyl)-2-(2-hydroxypropan-2-yl)thiazole-5-sulfonimidamide

Step 1: 1-(Thiazol-2-yl)ethanol

Into a 500-mL round-bottom flask was placed 1-(thiazol-2-yl)ethanone (20 g, 157 mmol), EtOH (200 mL). This was followed by the addition of NaBH$_4$ (3 g, 81.3 mmol) in portions at 0° C. The resulting solution was stirred for 2 h at RT and then was quenched by the addition of 10 mL of NH$_4$Cl (sat.). The resulting solution was diluted with 200 mL of water and extracted with 2×200 mL of DCM. The organic layers were combined and dried over anhydrous Na$_2$SO$_4$, then concentrated under vacuum. This resulted in 20 g (98%) of the title compound as light yellow oil. MS-ESI: 130.0 (M+1).

Step 2: 2-(1-(Tert-butyldiphenylsilyloxy)ethyl)thiazole

Into a 500-mL round-bottom flask was placed 1-(thiazol-2-yl)ethanol (20 g, 154.8 mmol), DMF (150 mL), 1H-imidazole (20.5 g, 301 mmol). This was followed by the addition of TBDPSCl (46 g, 167 mmol) dropwise with stirring at 0° C. The resulting solution was stirred for 2 h at RT and then was diluted with 300 mL of water. The resulting solution was extracted with 3×200 mL of DCM. The organic layers were combined and concentrated under vacuum. The residue was applied onto a silica gel column and eluted with a gradient of ethyl acetate/petroleum ether (1:100 to 1:80). This resulted in 55 g (97%) of the title compound as colorless oil. MS-ESI: 368.1 (M+1).

Step 3: 2-(1-(Tert-butyldiphenylsilyloxy)ethyl)thiazole-5-sulfonyl chloride

Into a 500-mL 3-necked round-bottom flask purged with and maintained under nitrogen was placed a solution of 2-(1-(tert-butyldiphenylsilyloxy)ethyl)thiazole (30 g, 81.6 mmol) in THF (200 mL). This was followed by the addition of n-BuLi (2.5 M in THF, 35.2 mL) dropwise with stirring at −78° C. The resulting solution was stirred for 0.5 h at −78° C. and then SO$_2$ was introduced into the above reaction mixture. The reaction was slowly warmed to RT and then NCS (12.8 g, 95.86 mmol) was added. The resulting solution was stirred for 1 h at RT. The solids were filtered out. The resulting filtrate was concentrated under vacuum. This resulted in 30 g (crude, 79%) of the title compound as brown oil. The crude product was used in the next step.

Step 4: N-tert-butyl-2-(1-(tert-butyldiphenylsilyloxy)ethyl)thiazole-5-sulfonamide Into a 500-mL round-bottom flask was placed 2-(1-(tert-butyldiphenylsilyloxy)ethyl)thiazole-5-sulfonyl chloride (crude, 30 g, 64.37 mmol), DCM (200 mL), TEA (13 g, 128.47 mmol). This was followed by the addition of 2-methylpropan-2-amine (5.6 g, 76.6 mmol) dropwise with stirring at 0° C. The resulting solution was stirred for 2 h at RT and then was concentrated under vacuum. The residue was applied onto a silica gel column and eluted with a gradient of ethyl acetate/petroleum ether (1:30 to 1:20). This resulted in 25 g (61% over two steps) of the title compound as brown oil. MS-ESI: 503.2 (M+1).

Step 5: N-tert-butyl-2-(1-hydroxyethyl)thiazole-5-sulfonamide

Into a 500-mL round-bottom flask was placed N-tert-butyl-2-(1-(tert-butyldiphenylsilyloxy)ethyl)thiazole-5-sulfonamide (25 g, 49.7 mmol), THF (200 mL), TBAF (30 g, 99.67 mmol). The resulting solution was stirred for 2 h at RT and then was diluted with 200 mL of water. The resulting solution was extracted with 3×200 mL of DCM. The organic layers were combined and concentrated under vacuum. The residue was applied onto a silica gel column and eluted with a gradient of ethyl acetate/petroleum ether (1:20 to 1:10). This resulted in 12 g (91%) of the title compound as light yellow oil. MS-ESI: 265.1 (M+1).

Step 6: 2-Acetyl-N-tert-butylthiazole-5-sulfonamide

Into a 500-mL round-bottom flask was placed N-tert-butyl-2-(1-hydroxyethyl)thiazole-5-sulfonamide (12 g, 45.4 mmol), DCM (200 mL). To this solution was added Dess-Martin reagent (20 g, 47.2 mmol) in portions at RT. The resulting solution was stirred for 2 h at RT and then was concentrated under vacuum. The residue was applied onto a silica gel column and eluted with a gradient of ethyl acetate/petroleum ether (1:20 to 1:10). This resulted in 9 g (76%) of the title compound as a light yellow solid. MS-ESI: 263.0 (M+1).

Step 7: 2-Acetylthiazole-5-sulfonamide

Into a 100-mL round-bottom flask was placed 2-acetyl-N-tert-butylthiazole-5-sulfonamide (7 g, 26.7 mmol), TFA (20 mL). The resulting solution was stirred for 14 h at 70° C. and then was concentrated under vacuum. The residue was applied onto a silica gel column and eluted with a gradient of ethyl acetate/petroleum ether (1:5 to 1:3). This resulted in 5 g (91%) of the title compound as a yellow solid. MS-ESI: 207.0 (M+1).

Step 8:
2-(2-Hydroxypropan-2-yl)thiazole-5-sulfonamide

Into a 500-mL 3-necked round-bottom flask purged with and maintained under nitrogen was placed 2-acetylthiazole-5-sulfonamide (5 g, 24.3 mmol), THF (100 mL). This was followed by the addition of MeMgBr (3 M in THF, 8.1 mL, 24.3 mmol) dropwise with stirring at 0° C. The resulting solution was stirred for 14 h at RT and then was quenched by the addition of 100 nl of NH₄Cl (sat.). The resulting solution was extracted with 2×150 mL of DCM. The organic layers were combined and concentrated under vacuum. The residue was applied onto a silica gel column and eluted with a gradient of ethyl acetate/petroleum ether (1:5 to 1:3). This resulted in 2.9 g (54%) of the title compound as a light yellow solid. MS-ESI: 223.0 (M+1).

Steps 9-10 used similar procedures for converting compound 14 to Intermediate 1 shown in Scheme 6 to afford Intermediate 27 from compound 80. MS-ESI: 336.1 (M+1).

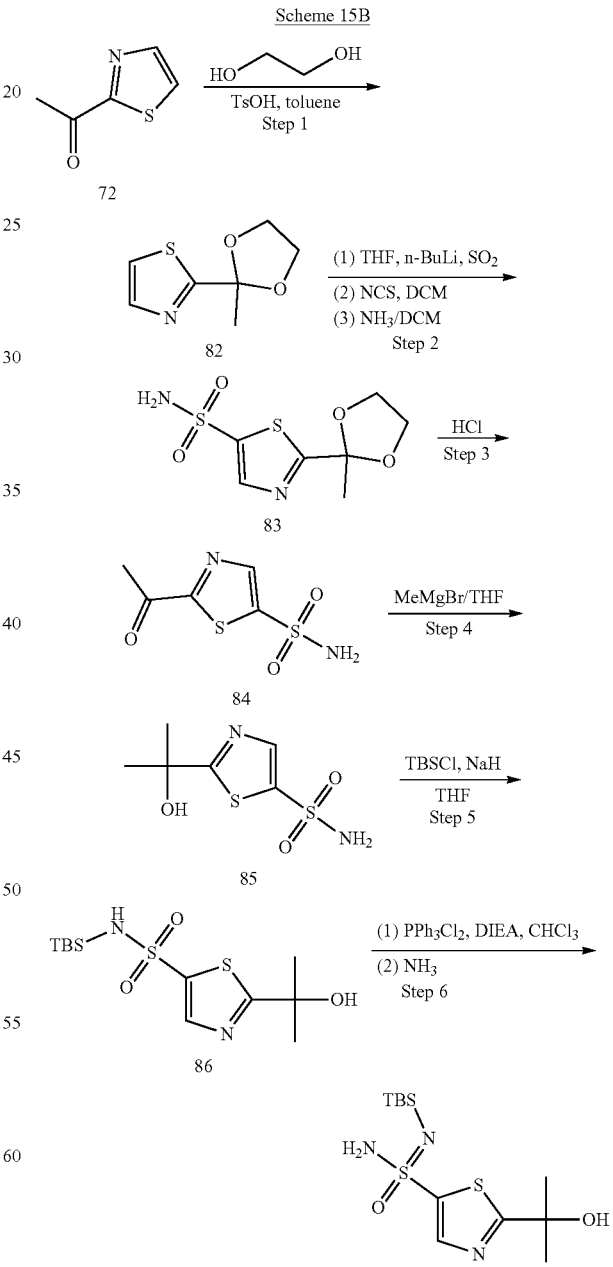

Intermediate 27

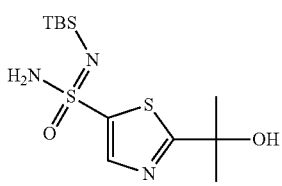

N'-(tert-butyldimethylsilyl)-2-(2-hydroxypropan-2-yl)thiazole-5-sulfonimidamide

Step 1: 2-(2-Methyl-1,3-dioxolan-2-yl)thiazole

Into a 500-mL round-bottom flask was placed a solution of 1-(thiazol-2-yl)ethanone (20 g, 157.0 mmol) in toluene (300 mL) and ethane-1,2-diol (19.5 g, 314 mmol). To the solution was added TsOH (2.7 g, 15.7 mmol). The resulting solution was refluxed overnight and water was separated from the solution during the reflux. The resulting solution was diluted with 200 mL of water and extracted with 2×100 mL of ethyl acetate. The organic layers were combined, dried over anhydrous $Na_2SO_4$, and then concentrated under vacuum. This resulted in 26.6 g (99%) of the title compound as light yellow oil. MS-ESI: 172.0 (M+1).

Step 2: 2-(2-Methyl-1,3-dioxolan-2-yl)thiazole-5-sulfonamide

Into a 500-mL 3-necked round-bottom flask purged with and maintained under nitrogen was placed a solution of 2-(2-methyl-1,3-dioxolan-2-yl)thiazole (14 g, 81.6 mmol) in THF (200 mL). This was followed by the addition of n-BuLi (2.5 M in THF, 35.2 mL, 88.0 mmol) dropwise with stirring at −78° C. The resulting solution was stirred for 0.5 h at −78° C. and then $SO_2$ was introduced into the above reaction mixture. The reaction was slowly warmed to RT and then NCS (12.8 g, 95.86 mmol) was added. The resulting solution was stirred for 1 h at RT. The solids were filtered out. The resulting filtrate was concentrated under vacuum and then was diluted in DCM (160 mL). To the above was added a saturated solution of ammonia in DCM (300 mL). The resulting solution was stirred for 3 h at RT and then was concentrated under vacuum. The residue was applied onto a silica gel column and eluted with a gradient of ethyl acetate/petroleum ether (1:20 to 1:5). This resulted in 12.5 g (61%) of the title compound as a yellow solid. MS-ESI: 251.0 (M+1).

Step 3: 2-Acetylthiazole-5-sulfonamide

Into a 250-mL round-bottom flask was placed a solution of 2-(2-methyl-1,3-dioxolan-2-yl)thiazole-5-sulfonamide (12.5 g, 50.0 mmol) in THF (125 mL). To the above was added aq. HCl (4 N, 50.0 mL). The resulting solution was stirred for 6 h at 70° C. The resulting solution was diluted with 100 mL of water and extracted with 2×200 mL of ethyl acetate. The organic layers were combined, dried over anhydrous $Na_2SO_4$, then concentrated under vacuum. The residue was applied onto a silica gel column and eluted with a gradient of ethyl acetate/petroleum ether (1:2 to 1:1). This resulted in 9.3 g (90%) of the title compound as a yellow solid. MS-ESI: 207.0 (M+1).

Steps 4-6 used the same procedures for converting compound 19 to Intermediate 2 shown in Scheme 7B to afford Intermediate 27 from compound 84. MS-ESI: 336.1 (M+1).

Scheme 16

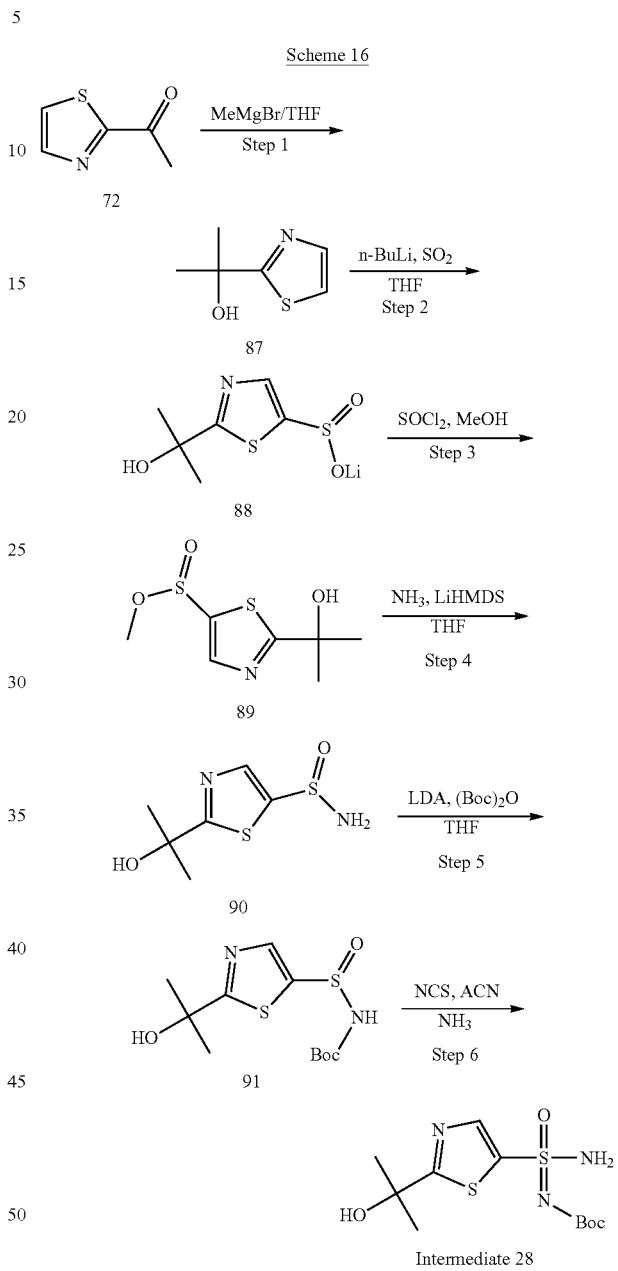

Intermediate 28

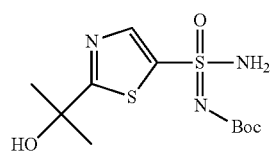 [SMILES: CC(C)(C)OC(=O)N=S(N)(=O)c1cnc(C(C)(C)O)s1]

Intermediate 28

N'-(tert-butoxycarbonyl)-2-(2-hydroxypropan-2-yl)thiazole-5-sulfonimidamide

Step 1: 2-(Thiazol-2-yl)propan-2-ol

Into a 10-L 4-necked round-bottom flask purged with and maintained under nitrogen was placed a solution of 1-(thiazol-2-yl)ethanone (200 g, 1.6 mol) in THF (4 L). This was followed by the addition of MeMgBr (3 M in THF, 942 mL) dropwise with stirring at 0° C. The mixture was stirred at 0° C. for 2 h. After warmed the mixture to RT, the solution was stirred for an additional 16 h. Then the reaction was quenched by the addition of 3 L of NH$_4$Cl (sat.). The resulting solution was extracted with 3×1 L of ethyl acetate. The organic layers were combined, dried over anhydrous Na$_2$SO$_4$, then concentrated under vacuum. The residue was applied onto a silica gel column and eluted with a gradient of ethyl acetate/petroleum ether (1:3 to 1:1). This resulted in 210 g (93%) of the title compound as a brown oil. MS-ESI: 144.0 (M+1).

Step 2: Lithium 2-(2-hydroxypropan-2-yl)thiazole-5-sulfinate

Into a 10-L 4-necked round-bottom flask purged with and maintained under nitrogen was placed a solution of 2-(thiazol-2-yl)propan-2-ol (50 g, 349.0 mmol) in THF (1.5 L). This was followed by the addition of n-BuLi (2.5 M in hexane, 350 mL) dropwise with stirring at −78° C. The mixture was stirred at −78° C. for 1 h. Then SO$_2$ was bubbled into the mixture for 15 min below −30° C. The mixture was stirred for an additional 1 h at RT and then was concentrated under vacuum. This resulted in 87 g (crude) of the title compound as a light yellow solid. The crude product was used directly in the next step.

Step 3: Methyl 2-(2-hydroxypropan-2-yl)thiazole-5-sulfinate

Into a 2-L 3-necked round-bottom flask, lithium 2-(2-hydroxypropan-2-yl)thiazole-5-sulfinate (87 g, crude) was dissolved in anhydrous MeOH (500 mL). Then SOCl$_2$ (43 g, 360 mmol) was added to the mixture dropwise with stirring at 0° C. The mixture was stirred overnight at RT and then was concentrated under vacuum. The residue was diluted with 500 mL of ethyl acetate. The resulting solution was washed with 2×200 mL of water and 2×200 mL of brine. The solution was dried over anhydrous Na$_2$SO$_4$, then concentrated under vacuum. This resulted in 72 g (crude) of the title compound as light yellow oil. The crude product was used directly in the next step.

Step 4: 2-(2-Hydroxypropan-2-yl)thiazole-5-sulfinamide

Into a 10-L 4-necked round-bottom flask purged with and maintained under nitrogen was placed a solution of methyl 2-(2-hydroxypropan-2-yl)thiazole-5-sulfinate (72 g, 326 mmol) in THF (500 mL). Then to the above NH$_3$ (0.5 M in THF, 2.0 L) was added. After cooling to −78° C., LiHMDS (1 M in THF, 2.0 L) was added to the mixture dropwise with stirring. Then the mixture was stirred at −78° C. for 2 h. The reaction was quenched by the addition of 500 mL of NH$_4$Cl (sat.). The resulting solution was extracted with 3×300 mL of ethyl acetate. The organic layers were combined, dried over anhydrous Na$_2$SO$_4$, then concentrated under vacuum. This resulted in 32 g (crude) of the title compound as brown oil. The crude product was used directly in the next step.

Step 5: Tert-butyl 2-(2-hydroxypropan-2-yl)thiazol-5-ylsulfinylcarbamate

Into a 1-L 3-necked round-bottom flask purged with and maintained under nitrogen was placed a solution of 2-(2-hydroxypropan-2-yl)thiazole-5-sulfinamide (32 g, crude) in THF (300 mL). This was followed by the addition of LDA (2 M in THF, 116 mL) dropwise with string at 0° C. The mixture was stirred at 0° C. for 1 h, then (Boc)$_2$O (33.8 g, 155 mmol) was added in portions at 0° C. The mixture was warmed to RT and stirred for an additional 2 h. The reaction was quenched with 200 mL of ice-water (200 mL), and the pH value of the solution was adjusted to 6 with HCOOH. The resulting solution was extracted with 3×200 mL of ethyl acetate. The organic layers were combined, dried over anhydrous Na$_2$SO$_4$, then concentrated under vacuum. The residue was applied onto a silica gel column and eluted with a gradient of ethyl acetate/petroleum ether (1:2 to 1:1). This resulted in 19 g (18%, 4 steps) of the title compound as a white solid.

Step 6: N-(tert-butyldimethylsilyl)-2-(2-hydroxypropan-2-yl)thiazole-5-sulfonimidamide Into a 1-L 3-necked round-bottom flask purged with and maintained under nitrogen, tert-butyl 2-(2-hydroxypropan-2-yl)thiazol-5-ylsulfinylcarbamate (19 g, 62 mmol) was dissolved in fresh distilled ACN (200 mL). Then to the above solution was added NCS (9.8 g, 74 mmol) in portions. The mixture was stirred for 1 h at RT and then NH$_3$ was bubbled in the mixture for 15 min. The mixture was stirred at RT for 2 h and then was concentrated under vacuum. The residue was applied onto a silica gel column and eluted with a gradient of ethyl acetate/petroleum ether (1:2 to 1:1). This resulted in 13 g (65%) of the title compound as a white solid.

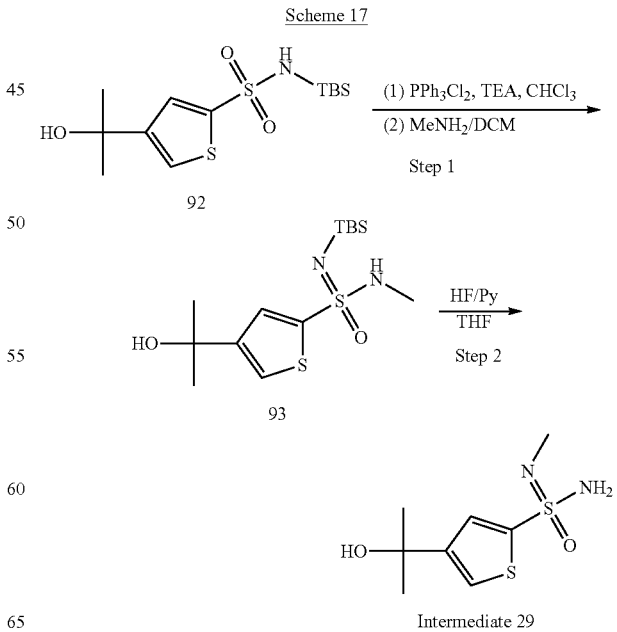

Intermediate 29

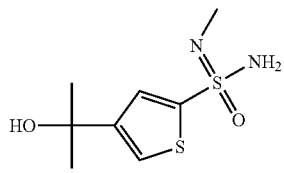

4-(2-Hydroxypropan-2-yl)-N'-methylthiophene-2-sulfonimidamide

Step 1 used the procedures for converting compound 15 to Intermediate 1 shown in Scheme 6 to afford compound 93 by substituting ammonia with methylamine. MS-ESI: 349.1 (M+1).

Step 2: 4-(2-Hydroxypropan-2-yl)-N'-methylthiophene-2-sulfonimidamide

Into a 25-mL round-bottom flask purged with under nitrogen was placed a solution of N'-(tert-butyldimethylsilyl)-4-(2-hydroxypropan-2-yl)-N-methylthiophene-2-sulfonimidamide (500 mg, 1.43 mmol) in DCM (10 mL). To the solution was added HF/Py (70% wt., 200 mg). The resulting solution was stirred for 2 h at RT. The pH value of the solution was adjusted to 8 with aq. $Na_2CO_3$ (5% wt.). The resulting solution was extracted with 3×10 mL of ethyl acetate. The organic layers were combined, dried over anhydrous $Na_2SO_4$, then concentrated under vacuum. This resulted in 300 mg (89%) of the title compound as brown oil. MS-ESI: 235.0 (M+1).

Schemes for the Preparation of Isocyanate Intermediates 30-58

Schemes below illustrate the synthesis of isocyanates.

Scheme 18

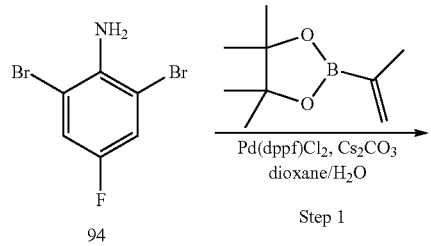

Intermediate 30

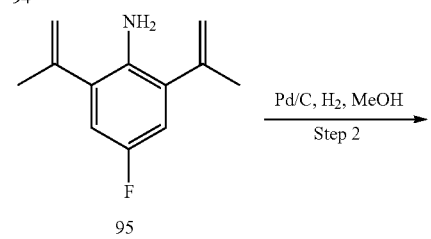

Intermediate 30

4-Fluoro-2,6-diisopropylbenzenamine

Step 1: 4-Fluoro-2,6-bis(prop-1-en-2-yl)aniline

Into a 500-mL round-bottom flask purged with and maintained under nitrogen was placed 2,6-dibromo-4-fluoroaniline (15 g, 55.8 mmol), dioxane (150 mL), water (15 mL), $Cs_2CO_3$ (55 g, 169 mmol), 4,4,5,5-tetramethyl-2-(prop-1-en-2-yl)-1,3,2-dioxaborolane (25 g, 149 mmol), and Pd(dppf)$Cl_2$ (4 g, 5.47 mmol). The resulting solution was stirred for 15 h at 100° C. and then was concentrated under vacuum. The residue was applied onto a silica gel column and eluted with a gradient of ethyl acetate/petroleum ether (1:10 to 1:8). This resulted in 9.2 g (86%) of the title compound as brown oil. MS-ESI: 192.1 (M+1).

Step 2: 4-Fluoro-2,6-bis(propan-2-yl)aniline

Into a 500-mL round-bottom flask was placed 4-fluoro-2,6-bis(prop-1-en-2-yl)aniline (9.2 g, 48.1 mmol), and MeOH (200 mL). Then Pd/C (10% wt., 900 mg) was added. The flask was evacuated and flushed three times with hydrogen. The resulting solution was stirred for 12 h at RT under an atmosphere of hydrogen. The solids were filtered out. The resulting filtrate was concentrated under vacuum. The residue was applied onto a silica gel column and eluted with a gradient of ethyl acetate/petroleum ether (1:10 to 1:8). This resulted in 7.2 g (77%) of the title compound as brown oil. MS-ESI: 196.1 (M+1).

Scheme 19

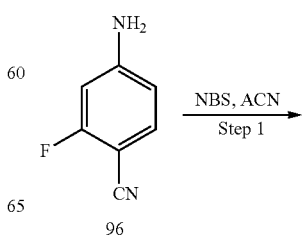

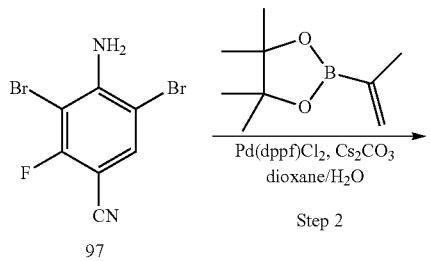

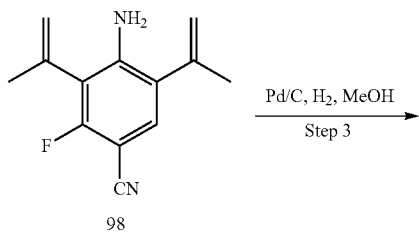

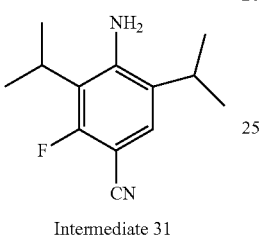

Intermediate 31

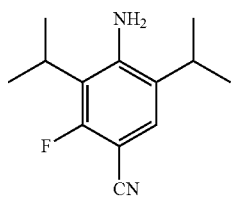 [SMILES: CC(C)c1cc(C#N)c(F)c(C(C)C)c1N]

Intermediate 31

4-Amino-2-fluoro-3,5-diisopropylbenzonitrile

Step 1: 4-Amino-3,5-dibromo-2-fluorobenzonitrile

Into a 1-L round-bottom flask was placed 4-amino-2-fluorobenzonitrile (25 g, 184 mmol), ACN (500 mL), and NBS (81.7 g, 459 mmol). The resulting solution was stirred overnight at 75° C. and then was concentrated under vacuum. The residue was applied onto a silica gel column and eluted with a gradient of ethyl acetate/petroleum ether (1:100 to 1:98). This resulted in 50 g (93%) of the title compound as brown oil. MS-ESI: 294.9/292.9/296.9 (M+1).

Steps 2-3 used similar procedures for converting compound 94 to Intermediate 30 shown in Scheme 18 to afford Intermediate 31 from compound 97. MS-ESI: 221.1 (M+1).

Scheme 20

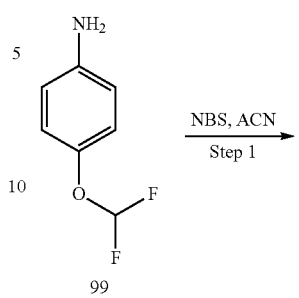

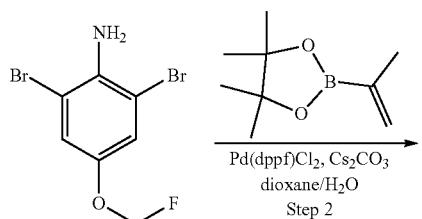

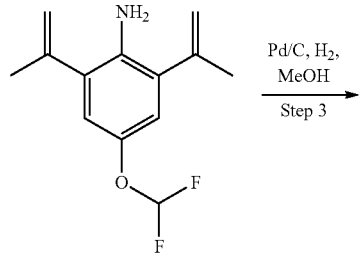

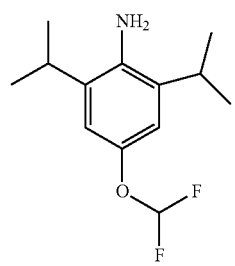

Intermediate 32

Intermediate 32

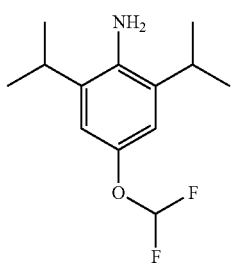 [SMILES: CC(C)c1cc(OC(F)F)cc(C(C)C)c1N]

4-(Difluoromethoxy)-2,6-diisopropylbenzenamine

Step 1: 2,6-Dibromo-4-(difluoromethoxy)benzenamine

Into a 100-mL round-bottom flask was placed 4-(difluoromethoxy)benzenamine (3 g, 18.9 mmol), ACN (30 mL), and NBS (7.7 g, 43.3 mmol). The resulting solution was stirred overnight at RT and then was concentrated under vacuum. The residue was applied onto a silica gel column and eluted with a gradient of ethyl acetate/petroleum ether (1:30 to 1:20). This resulted in 2.9 g (48%) of the title compound as brown oil. MS-ESI: 317.9/315.9/319.9 (M+1).

Steps 2-3 used similar procedures for converting compound 94 to Intermediate 30 shown in Scheme 18 to afford Intermediate 32 from compound 100″. MS-ESI: 244.1 (M+).

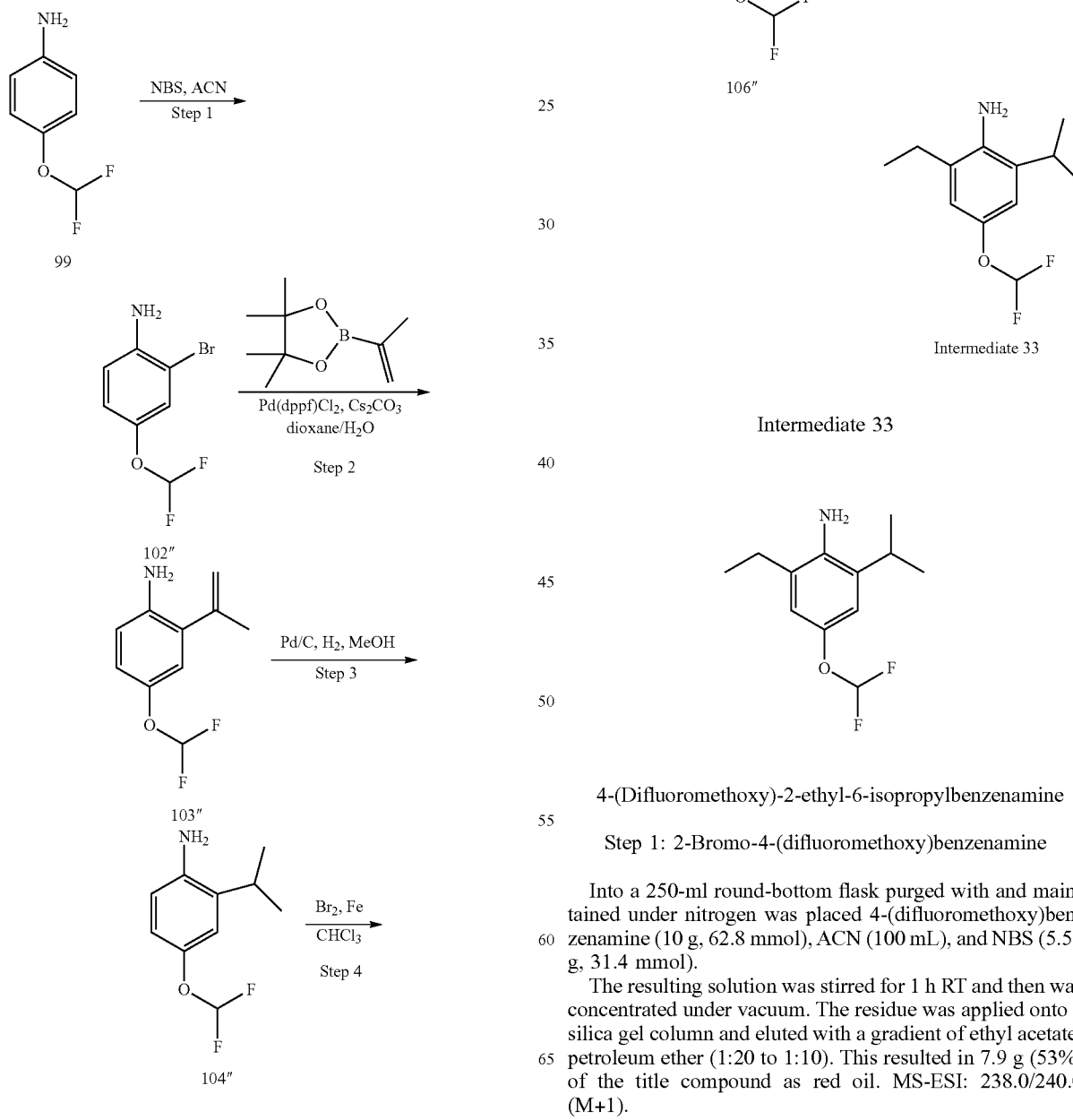

Intermediate 33

4-(Difluoromethoxy)-2-ethyl-6-isopropylbenzenamine

Step 1: 2-Bromo-4-(difluoromethoxy)benzenamine

Into a 250-ml round-bottom flask purged with and maintained under nitrogen was placed 4-(difluoromethoxy)benzenamine (10 g, 62.8 mmol), ACN (100 mL), and NBS (5.59 g, 31.4 mmol).

The resulting solution was stirred for 1 h RT and then was concentrated under vacuum. The residue was applied onto a silica gel column and eluted with a gradient of ethyl acetate/petroleum ether (1:20 to 1:10). This resulted in 7.9 g (53%) of the title compound as red oil. MS-ESI: 238.0/240.0 (M+1).

Step 2: 4-(Difluoromethoxy)-2-(prop-1-en-2-yl) benzenamine

Into a 250-mL round-bottom flask purged with and maintained under nitrogen was placed 2-bromo-4-(difluoromethoxy)benzenamine (7.9 g, 33.2 mmol), dioxane (100 mL), water (10 mL), Cs$_2$CO$_3$ (32.46 g, 99.63 mmol), 4,4,5,5-tetramethyl-2-(prop-1-en-2-yl)-1,3,2-dioxaborolane (8.36 g, 49.8 mmol), and Pd(dppf)Cl$_2$ (1.21 g, 1.65 mmol). The resulting solution was stirred overnight at 90° C. The solids were filtered out. The filtrate was concentrated under vacuum. The residue was applied onto a silica gel column and eluted with a gradient of ethyl acetate/petroleum ether (1:30 to 1:20). This resulted in 5.3 g (80%) of the title compound as a yellow solid. MS-ESI: 200.1 (M+1).

Step 3: 4-(Difluoromethoxy)-2-isopropylbenzenamine

Into a 250-mL round-bottom flask was placed 4-(difluoromethoxy)-2-(prop-1-en-2-yl)benzenamine (5.3 g, 26.6 mmol) in MeOH (100 mL). Then Pd/C (10% wt., 500 mg) was added. The flask was evacuated and filled three times with hydrogen. The resulting solution was stirred for 3 h at RT under hydrogen. The solids were filtered out. The resulting filtrate was concentrated under vacuum. This resulted in 5.15 g (96%) of the title compound as red oil. MS-ESI: 202.1 (M+1).

Step 4: 2-Bromo-4-(difluoromethoxy)-6-isopropylbenzenamine

Into a 500-mL round-bottom flask was placed 4-(difluoromethoxy)-2-isopropylbenzenamine (5.15 g, 25.6 mmol), CHCl$_3$ (200 mL), Fe turnings (500 mg), and Br$_2$ (4.45 g, 27.9 mmol). The resulting mixture was stirred overnight at 70° C. and then was quenched by the addition of 200 mL of water. The resulting solution was extracted with 3×100 mL of DCM and the organic layers combined and concentrated under vacuum. The residue was applied onto a silica gel column and eluted with a gradient of ethyl acetate/petroleum ether (1:30 to 1:20). This resulted in 6.98 g (97%) of the title compound as dark red oil. MS-ESI: 280.0/282.0 (M+1).

Step 5: 4-(Difluoromethoxy)-2-isopropyl-6-vinylbenzenamine

Into a 250-mL round-bottom flask purged with and maintained under nitrogen was placed 2-bromo-4-(difluoromethoxy)-6-isopropylbenzenamine (3 g, 10.7 mmol), dioxane (100 mL), water (10 mL), Cs$_2$CO$_3$ (10.47 g, 32.13 mmol), 4,4,5,5-tetramethyl-2-vinyl-1,3,2-dioxaborolane (2.47 g, 16.0 mmol), and Pd(dppf)Cl$_2$ (784 mg, 1.07 mmol). The resulting solution was stirred overnight at 90° C. and then was concentrated under vacuum. The residue was applied onto a silica gel column and eluted with a gradient of ethyl acetate/petroleum ether (1:30 to 1:20). This resulted in 2.3 g (94%) of the title compound as dark green oil. MS-ESI: 228.1 (M+1).

Step 6: 4-(Difluoromethoxy)-2-ethyl-6-isopropylbenzenamine

Into a 250-mL round-bottom flask was placed 4-(difluoromethoxy)-2-isopropyl-6-vinylbenzenamine (2.3 g, 10.1 mmol), MeOH (100 mL). Then Pd/C (10% wt., 200 mg) was added. The flask was evacuated and filled three times with hydrogen. The resulting solution was stirred overnight at RT under hydrogen. The solids were filtered out. The filtrate was concentrated under vacuum. This resulted in 2.2 g (95%) of the title compound as red oil. MS-ESI: 230.1 (M+1).

TABLE 7

The Intermediate 34 in the following Table was prepared from compound 105" using similar procedure as shown in Scheme 21 above for converting compound 105" to 106".

| Intermediate # | Structure | IUPAC Name | Exact Mass[M + H]$^+$ |
|---|---|---|---|
| Intermediate 34 | 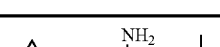 | 2-Cyclopropyl-4-(difluoromethoxy)-6-isopropylbenzenamine | 242.1 |

Scheme 22

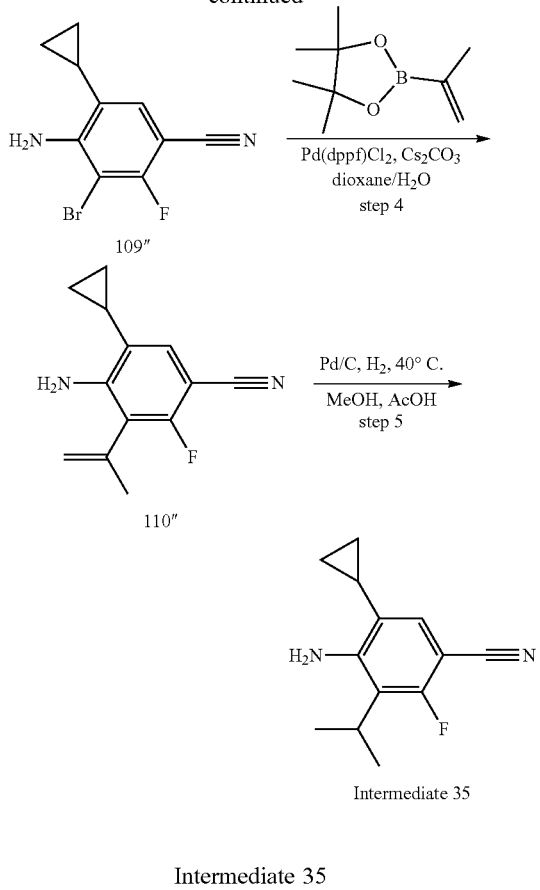

Intermediate 35

4-Amino-5-cyclopropyl-2-fluoro-3-isopropylbenzo-nitrile

Step 1: 4-Amino-5-bromo-2-fluorobenzonitrile

Into a 250-mL round-bottom flask was placed a solution of 4-amino-2-fluorobenzonitrile (9 g, 66.1 mmol) in ACN (120 mL). Then NBS (12.4 g, 69.7 mmol) was added. The resulting solution was stirred overnight at 80° C. and then was concentrated under vacuum. The residue was applied onto a silica gel column and eluted with a gradient of ethyl acetate/petroleum ether (1:20 to 1:10). This resulted in 10.9 g (77%) of the title compound as a yellow solid. MS-ESI: 215.0/217.0 (M+1). ¹H NMR (300 MHz, DMSO-$d_6$) δ 7.89 (d, J=6.0 Hz, 1H), 6.69 (br s, 2H), 6.63 (d, J=12.0 Hz, 1H).

Step 2: 4-Amino-5-cyclopropyl-2-fluorobenzonitrile

Into a 250-mL round-bottom flask purged with and maintained under nitrogen was placed a solution of 4-amino-5-bromo-2-fluorobenzonitrile (6.37 g, 29.6 mmol) in dioxane (70 mL) and water (10 mL). To the solution were added $Cs_2CO_3$ (9.7 g, 29.8 mmol), cyclopropylboronic acid (3.8 g, 44.2 mmol) and Pd(dppf)Cl$_2$ (1.08 g, 1.48 mmol). The resulting solution was stirred overnight at 90° C. and then was concentrated under vacuum. The residue was applied onto a silica gel column and eluted with a gradient of ethyl acetate/petroleum ether (1:10 to 1:5). This resulted in 5.03 g (96%) of the title compound as a yellow solid. MS-ESI: 177.1 (M+1).

Step 3: 4-Amino-3-bromo-5-cyclopropyl-2-fluorobenzonitrile

Into a 250-mL round-bottom flask was placed a solution of 4-amino-5-cyclopropyl-2-fluorobenzonitrile (5.03 g, 28.7 mmol) in ACN (50 mL). To the solution was added NBS (5.6 g, 31.5 mmol). The resulting solution was stirred overnight at 80° C. and then was concentrated under vacuum. The residue was applied onto a silica gel column and eluted with a gradient of ethyl acetate/petroleum ether (1:10 to 1:5). This resulted in 6.972 g (96%) of the title compound as a yellow solid. MS-ESI: 255.0/257.0 (M+1).

Step 4: 4-Amino-5-cyclopropyl-2-fluoro-3-(prop-1-en-2-yl)benzonitrile

Into a 250-mL round-bottom flask purged with and maintained under nitrogen was placed a solution of 4-amino-3-bromo-5-cyclopropyl-2-fluorobenzonitrile (6.972 g, 27.33 mmol) in dioxane (120 mL) and water (20 mL). To the solution were added 4,4,5,5-tetramethyl-2-(prop-1-en-2-yl)-1,3,2-dioxaborolane (6.9 g, 41.00 mmol), $Cs_2CO_3$ (13.4 g, 41.00 mmol) and Pd(dppf)Cl$_2$ (0.4 g, 0.55 mmol). The resulting solution was stirred overnight at 80° C. and then was concentrated under vacuum. The residue was applied onto a silica gel column and eluted with a gradient of ethyl acetate/petroleum ether (1:10 to 1:5). This resulted in 4.73 g (80%) of the title compound as a yellow solid. MS-ESI: 217.1 (M+1).

Step 5: 4-Amino-5-cyclopropyl-2-fluoro-3-isopropylbenzonitrile

Into a 250-mL round-bottom flask was placed a solution of 4-amino-5-cyclopropyl-2-fluoro-3-(prop-1-en-2-yl)benzonitrile (4.73 g, 21.97 mmol), MeOH (100 mL). To the solution was added AcOH (0.5 mL). Then Pd/C (10% wt., 500 mg) was added. The flask was evacuated and filled three times with hydrogen. The resulting solution was stirred for 4 h at 40° C. under an atmosphere of hydrogen. The solids were filtered out. The filtrate was concentrated under vacuum. This resulted in 4.71 g (99%) of the title compound as a light yellow solid. MS-ESI: 219.1 (M+1).

Scheme 23

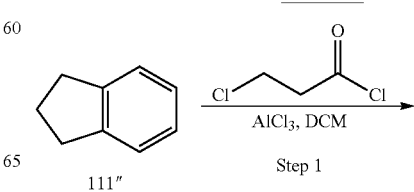

Step 1

509
-continued

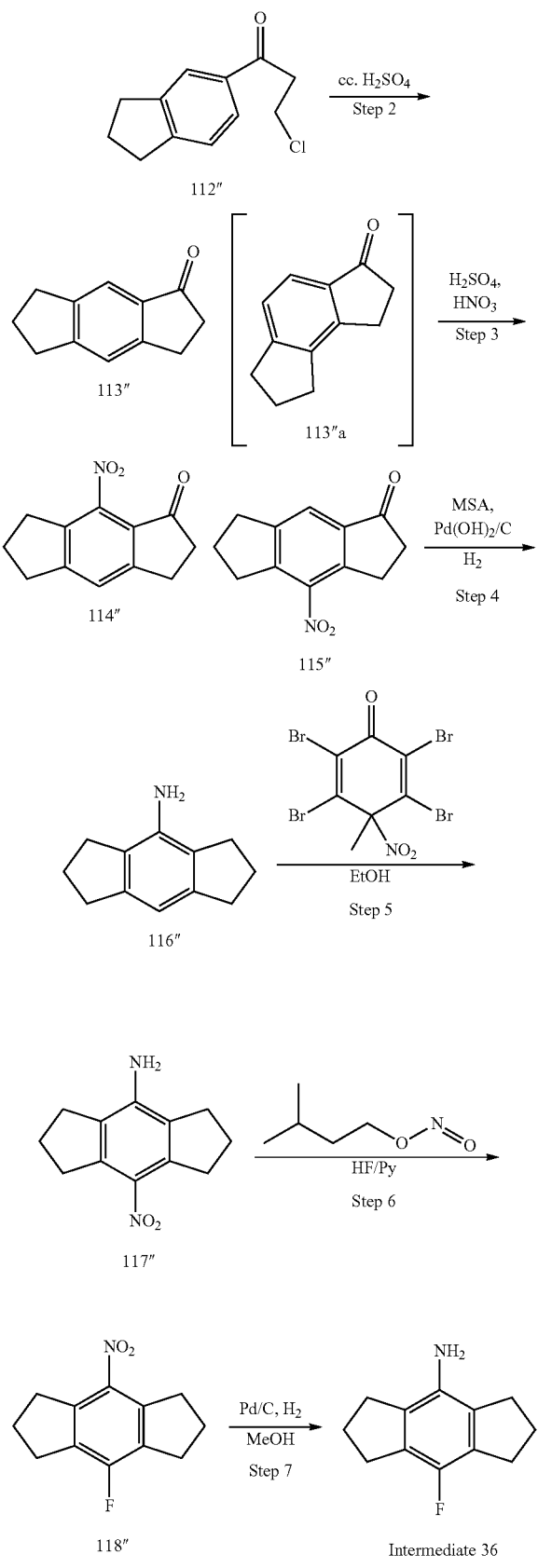

510

Intermediate 36

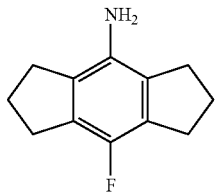 [SMILES: Nc1c2c(c(F)c3c1CCC3)CCC2]

8-Fluoro-1,2,3,5,6,7-hexahydro-s-indacen-4-amine

Step 1: 3-Chloro-1-(2,3-dihydro-1H-inden-5-yl)propan-1-one

Into a 3-L round-bottom flask was placed a solution of AlCl$_3$ (111 g, 834 mmol) in DCM (1200 mL). This was followed by the addition of a solution of 2,3-dihydro-1H-indene (90 g, 762 mmol) and 3-chloropropanoyl chloride (96.3 g, 759 mmol) in DCM (300 mL) dropwise with stirring at −10° C. in 30 min. The resulting solution was stirred for 16 h at RT. Then the reaction mixture was added dropwise to cold HCl (3 N, 1200 mL) over 45 min at −10° C. The resulting solution was extracted with 3×600 mL of DCM and the organic layers were combined, dried over anhydrous Na$_2$SO$_4$, then concentrated under vacuum. This resulted in 160.5 g (crude) of the title compound as a yellow solid. The crude product was used in the next step.

Step 2: 1,2,3,5,6,7-Hexahydro-s-indacen-1-one

Into a 1-L round-bottom flask was placed a solution of 3-chloro-1-(2,3-dihydro-1H-inden-5-yl)propan-1-one (160.5 g, 759 mmol) in conc. H$_2$SO$_4$ (900 mL). The resulting solution was stirred for 16 h at 55° C. and then was quenched by adding the reaction mixture carefully to 4500 mL of water/ice. The solids were collected by filtration and dried over infrared lamp for 24 h. The crude mixture was purified by chromatography and eluted with ethyl acetate/petroleum ether (1:100). This resulted in 10 g (7.6%) of 1,6,7,8-tetrahydro-as-indacen-3(2H)-one (compound 113″a) and 112.2 g (85%) of the title compound (compound 113″) as a yellow solid. $^1$H NMR (400 MHz, DMSO-d$_6$) δ 7.44 (s, 1H), 7.39 (s, 1H), 3.13-2.79 (m, 8H), 2.70-2.55 (m, 2H), 2.20-1.90 (m, 2H). $^1$H NMR (400 MHz, DMSO-d$_6$) δ 7.49 (d, J=7.7 Hz, 1H), 7.31 (d, J=7.7 Hz, 1H), 3.19-2.98 (m, 4H), 2.93-2.80 (m, 3H), 2.68-2.54 (m, 2H), 2.15-1.95 (m, 2H).

Step 3: 4-nitro-2,3,6,7-tetrahydro-s-indacen-1(5H)-one (114) (Major) and 8-nitro-2,3,6,7-tetrahydro-s-indacen-1(5H)-one (115) (Minor)

Into a 1-L round-bottom flask was placed a solution of 1,2,3,5,6,7-hexahydro-s-indacen-1-one (80 g, 464.5 mmol) in H$_2$SO$_4$ (500 mL). Then HNO$_3$ (58.5 g, 929 mmol) was added dropwise over 1 h at 0° C. The resulting solution was stirred for 1 hr at 0° C. The reaction mixture was slowly added to a mixture of water/ice (1000 mL) and DCM (500 mL) with ice bath cooling. The organic layer was collected, dried over Na$_2$SO$_4$ and concentrated under vacuum. This resulted in 90 g (90%) of the mixture of 4-nitro-2,3,6,7-hexahydro-s-indacen-1-one and 8-nitro-2,3,6,7-tetrahydro-s-indacen-1(5H)-one as a yellow solid.

Step 4: 1,2,3,5,6,7-hexahydro-s-indacen-4-amine

Into a 1-L round-bottom flask was placed a solution of the mixture of 4-nitro-1,2,3,5,6,7-hexahydro-s-indacen-1-one and 8-nitro-2,3,6,7-tetrahydro-s-indacen-1(5H)-one (21.7 g, 100 mmol) in MeOH (300 mL). To the solution was added MSA (11.5 g, 120 mmol). Then Pd(OH)$_2$/C (20% wt, 5.5 g) was added. The flask was evacuated and filled three times with hydrogen. The resulting mixture was stirred for 16 h at RT under hydrogen (50 psi). The solids were filtered out and washed with methanol. The methanol filtrate and wash was diluted with water (500 mL) and the pH was adjusted to 10.6 with 2N NaOH. The resulting slurry was filtered and the crude solids were recrystallized from methanol/water (9:1) with heating. This resulted in 13.7 g (79%) of the title compound as an off-white solid.

Step 5: 8-Nitro-1,2,3,5,6,7-hexahydro-s-indacen-4-amine

Into a 500-mL round-bottom flask was placed 1,2,3,5,6,7-hexahydro-s-indacen-4-amine (8 g, 46.2 mmol), EtOH (200 mL), and 2,3,5,6-tetrabromo-4-methyl-4-nitrocyclohexa-2,5-dienone (21.6 g, 46.1 mmol). The resulting solution was stirred for 12 h at RT and then was concentrated under vacuum. The residue was applied onto a silica gel column and eluted with a gradient of ethyl acetate/petroleum ether (1:50 to 1:30). This resulted in 5 g (50%) of the title compound as a yellow solid. MS-ESI: 219.1 (M+1).

Step 6: 4-Fluoro-8-nitro-1,2,3,5,6,7-hexahydro-s-indacene

Into a 100-mL round-bottom flask was placed 8-nitro-1,2,3,5,6,7-hexahydro-s-indacen-4-amine (5 g, 22.9 mmol) and HF/Py (70% wt., 20 mL). This was followed by the addition of 3-methylbutyl nitrite (3 g, 25.6 mmol) dropwise with stirring at 0° C. The resulting solution was stirred for 2 h at RT and then was diluted with 50 mL of water. The resulting solution was extracted with 3×50 mL of DCM. The organic layers were combined and dried over anhydrous Na$_2$SO$_4$, then concentrated under vacuum. This resulted in 4 g (crude, 79%) of the title compound as brown oil.

Step 7: 8-Fluoro-1,2,3,5,6,7-hexahydro-s-indacen-4-amine

Into a 100-mL round-bottom flask was placed 4-fluoro-8-nitro-1,2,3,5,6,7-hexahydro-s-indacene (4 g, 18.1 mmol) in MeOH (50 mL). Then Pd/C (10% wt., 0.5 g) was added. The flask was evacuated and filled three times with hydrogen. The resulting mixture was stirred for 12 h at RT under an atmosphere of hydrogen. The solids were filtered out and the filtrate was concentrated under vacuum. The residue was applied onto a silica gel column and eluted with a gradient of ethyl acetate/petroleum ether (1:10 to 1:5). This resulted in 2 g (46%, 2 steps) of the title compound as a white solid. MS-ESI: 192.1 (M+1).

Scheme 24

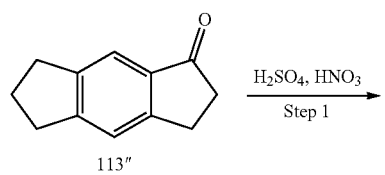

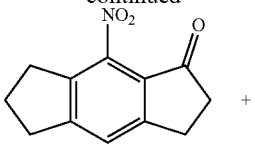

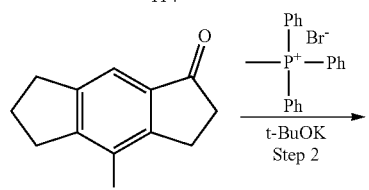

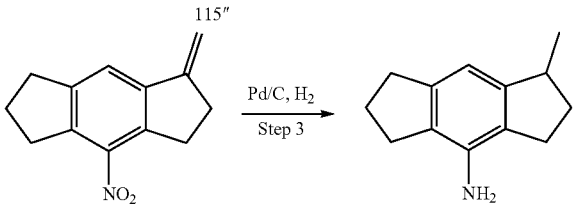

Intermediate 37

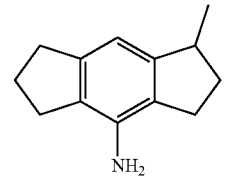

1-methyl-1,2,3,5,6,7-hexahydro-s-indacen-4-amine

Step 1: 4-nitro-2,3,6,7-tetrahydro-s-indacen-1(5H)-one

Into a 1-L round-bottom flask was placed a solution of 1,2,3,5,6,7-hexahydro-s-indacen-1-one (40 g, 232 mmol) in H$_2$SO$_4$ (250 mL). Then HNO$_3$ (29 g, 464 mmol) was added dropwise over 1 h at 0° C. The resulting solution was stirred for 1 hr at 0° C. The reaction mixture was slowly added to a mixture of water/ice (500 mL) and DCM (250 mL) with ice bath cooling. The organic layer was collected, dried over anhydrous Na$_2$SO$_4$ and concentrated under vacuum. The crude product was purified by silica gel column with a gradient of ethyl acetate and petroleum ether (1:50 to 1:1). This resulted in minor product 5 g (10%) of the title compound and major product 30 g (60%) of 8-nitro-2,3,6,7-tetrahydro-s-indacen-1(5H)-one both as a yellow solid.

Step 2: 1-methylene-4-nitro-1,2,3,5,6,7-hexahydro-s-indacene

Into a 250-mL round-bottom flask was placed a solution of methyltriphenylphosphanium bromide (16.4 g, 46.04 mmol) and t-BuOK (5.2 g, 46.0 mmol) in THF (150 mL) at 0° C. The resulting solution was stirred for 30 min at 0° C.

Then the solution of 4-nitro-1,2,3,5,6,7-hexahydro-s-indacen-1-one (5 g, 23.0 mmol) in THF (10 mL) was added dropwise to the reaction mixture at 0° C. The resulting solution was stirred overnight at RT. The resulting mixture was concentrated. The residue was applied onto a silica gel column with ethyl acetate/petroleum ether (1:10). This resulted in 2.6 g (52%) of the title compound as a green solid.

Step 3:
1-methyl-1,2,3,5,6,7-hexahydro-s-indacen-4-amine

Into a 100-mL round-bottom flask was placed a solution of 1-methylidene-4-nitro-1,2,3,5,6,7-hexahydro-s-indacene (2.6 g, 12.1 mmol) in MeOH (20 mL), Pd/C (10% wt, 300 mg) was added. The flask was evacuated and filled three times with hydrogen. then H$_2$ (g) was introduced in with a balloon. The resulting solution was stirred for 2 h at RT. The Pd/C catalyst was filtered out. The filtrate was concentrated. This resulted in 2 g of the title compound as red oil.

8-Chloro-1,2,3,5,6,7-hexahydro-s-indacen-4-amine

Step 1:
8-Chloro-1,2,3,5,6,7-hexahydro-s-indacen-4-amine

Into a 50-mL round-bottom flask was placed a solution of 1,2,3,5,6,7-hexahydro-s-indacen-4-amine (1.73 g, 9.99 mmol) in DMF (10 mL). To the solution was added NCS (1.47 g, 11.0 mmol). The resulting solution was stirred overnight at RT and then was diluted with 30 ml of DCM. The resulting mixture was washed with 3×10 ml of water and the organic layer was concentrated under vacuum. The residue was applied onto a silica gel column and eluted with a gradient of ethyl acetate/petroleum ether (1:20 to 1:10). This resulted in 1.88 g (91%) of the title compound as a yellow solid. MS-ESI: 208.1/210.1 (M+1).

TABLE 8

Intermediate 38 in the following Table was prepared from Compound 114″ using similar procedure as shown in Scheme 24 above for converting compound 115″ to intermediate 37.

| Intermediate # | Structure | IUPAC Name | Exact Mass[M + H]$^+$ |
| --- | --- | --- | --- |
| Intermediate 38 | 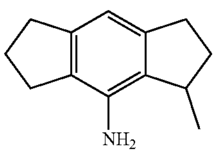 | 3-methyl-1,2,3,5,6,7-hexahydro-s-indacen-4-amine | 188.1 |

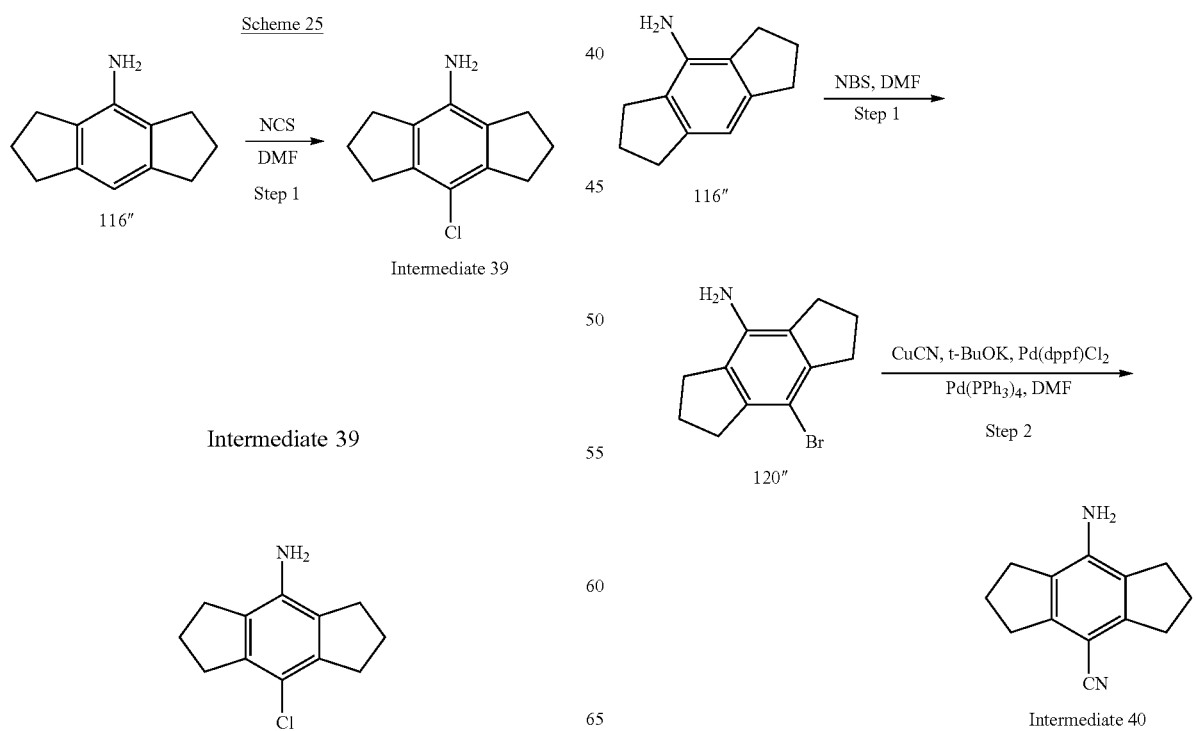

515

Intermediate 40

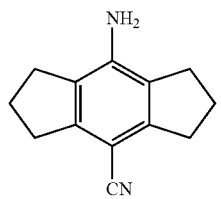 [SMILES: N#Cc1c2c(c(N)c3c1CCC3)CCC2]

8-Amino-1,2,3,5,6,7-hexahydro-s-indacene-4-carbonitrile

Step 1:
8-Bromo-1,2,3,5,6,7-hexahydro-s-indacen-4-amine

Into a 100-mL round-bottom flask was placed a solution of 1,2,3,5,6,7-hexahydro-s-indacen-4-amine (2.6 g, 15.0 mmol) in DMF (30 mL). To the solution was added NBS (2.9 g, 16.3 mmol). The resulting solution was stirred for 12 h at RT and then was diluted with 80 mL of ethyl acetate. The resulting mixture was washed with 3×20 mL of water and concentrated under vacuum. The residue was applied onto a silica gel column and eluted with a gradient of ethyl acetate/petroleum ether (1:30 to 1:20). This resulted in 3.0 g (79%) of the title compound as a brown solid. MS-ESI: 252.0, 254.0 (M+1).

Step 2: 8-Amino-1,2,3,5,6,7-hexahydro-s-indacene-4-carbonitrile

Into a 50-mL round-bottom flask purged with and maintained under nitrogen was placed a solution of 8-bromo-1,2,3,5,6,7-hexahydro-s-indacen-4-amine (725 mg, 2.88 mmol) in DMF (10 mL). To the solution were added t-BuOK (330 mg, 2.90 mmol), CuCN (386 mg, 4.32 mmol), and Pd(dppf)Cl$_2$ (424 mg, 0.58 mmol). The resulting solution was stirred for 12 h at 120° C. and then was diluted with 20 mL of water. The resulting solution was extracted with 3×20 mL ethyl acetate. The organic layers were combined, dried over anhydrous Na$_2$SO$_4$, then concentrated under vacuum. The residue was applied onto a silica gel column and eluted with a gradient of ethyl acetate/petroleum ether (1:60 to 1:40). This resulted in 192 mg (34%) of the title compound as a yellow solid. MS-ESI: 199.1 (M+1).

Scheme 27

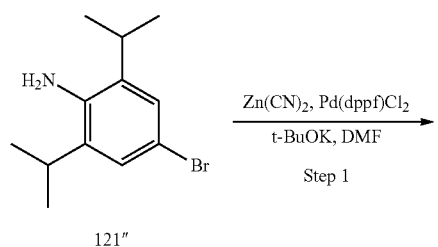

516

-continued

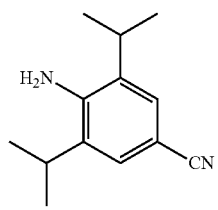

Intermediate 41

Intermediate 41

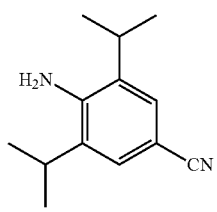

4-Amino-3,5-diisopropylbenzonitrile

Step 1: 4-Amino-3,5-diisopropylbenzonitrile

Into a 100-mL round-bottom flask purged with and maintained under nitrogen was placed a solution of 4-bromo-2,6-diisopropylbenzenamine (5.1 g, 19.9 mmol) in DMF (30 mL). To the solution were added Zn(CN)$_2$ (2.80 g, 23.9 mmol), Pd(dppf)Cl$_2$ (732 mg, 1.00 mmol) and t-BuOK (3.36 g, 29.9 mmol). The resulting mixture was stirred for 16 h at 120° C. and then was diluted with 30 mL of water. The solution was extracted with 3×30 mL of ethyl acetate and the combined organic layers were concentrated under vacuum. The residue was applied onto a silica gel column and eluted with a gradient of ethyl acetate/petroleum ether (1:30 to 1:20). This resulted in 3.2 g (80%) of the title compound as a yellow solid. MS-ESI: 203.1 (M+1).

Scheme 28

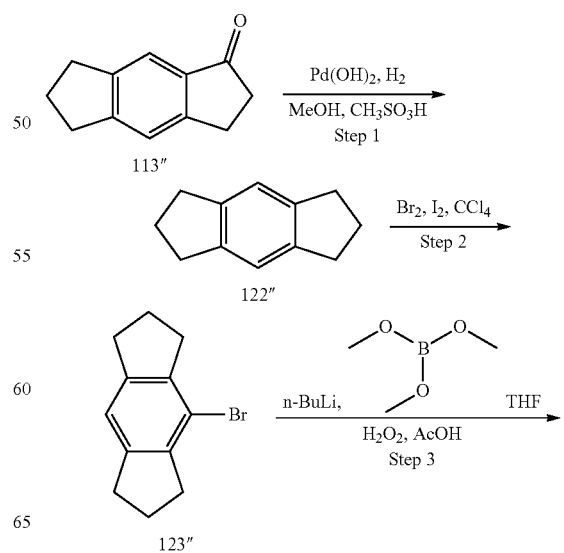

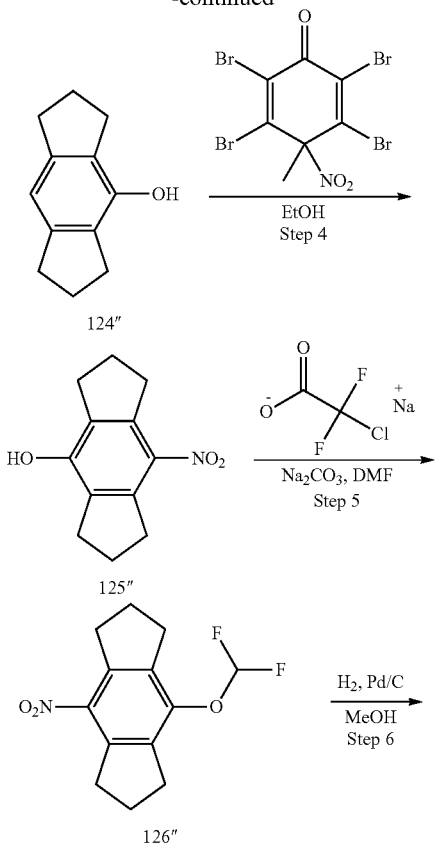

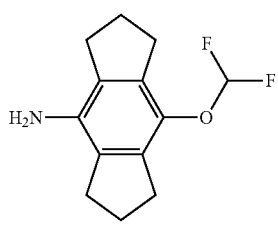 [SMILES: Nc1c2c(c(OC(F)F)c3c1CCC3)CCC2]

8-(Difluoromethoxy)-1,2,3,5,6,7-hexahydro-s-indacen-4-amine

Step 1: 1,2,3,5,6,7-Hexahydro-s-indacene

Into a 1-L round-bottom flask was placed a solution of 1,2,3,5,6,7-hexahydro-s-indacen-1-one (37.2 g, 216 mmol) and MSA (42 g, 437.5 mmol) in MeOH (300 mL). Then Pd(OH)$_2$/C (20% wt, 8 g) was added. The flask was evacuated and filled three times with hydrogen. The resulting solution was stirred for 16 h at RT under an atmosphere of hydrogen. The solids were filtered out. The resulting mixture was concentrated under vacuum. The residue was applied onto a silica gel column and eluted with a gradient of ethyl acetate/petroleum ether (1:150 to 1:100). This resulted in 27.1 g (79%) of the title compound as a white solid.

Step 2: 4-Bromo-1,2,3,5,6,7-hexahydro-s-indacene

Into a 500-mL 3-necked round-bottom flask purged with and maintained under nitrogen was placed a solution of 1,2,3,5,6,7-hexahydro-s-indacene (15 g, 94.8 mmol) in CCl$_4$ (200 mL). Then 12 (1.2 g, 4.72 mmol) was added. This was followed by the addition of a solution of Br$_2$ (16 g, 100 mmol) in CCl$_4$ (50 mL) dropwise with stirring at 0° C. in 10 min. The resulting solution was stirred for 2 h at 0° C. The reaction was then quenched by the addition of 150 mL of NH$_4$Cl (sat.). The resulting solution was extracted with 3×150 mL of DCM and the combined organic layers were dried over anhydrous Na$_2$SO$_4$ and concentrated under vacuum. The crude product was purified by silica gel column with a gradient of ethyl acetate/hexane (1:500 to 1:100). This resulted in 19 g (85%) of the title compound as yellow oil. $^1$H NMR (300 MHz, DMSO-d$_6$) δ 7.02 (s, 1H), 2.95-2.75 (m, 8H), 2.03-2.01 (m, 4H)

Step 3: 1,2,3,5,6,7-Hexahydro-s-indacen-4-ol

Into a 500-mL 3-necked round-bottom flask purged with and maintained under nitrogen was placed a solution of 4-bromo-1,2,3,5,6,7-hexahydro-s-indacene (5 g, 21.08 mmol) in THF (150 mL). This was followed by the addition of n-BuLi (2.5 M in hexane, 10 mL) dropwise with stirring at −78° C. The resulting solution was stirred for 30 min at −78° C. Then to the above was added trimethyl borate (2.6 g, 25.30 mmol) dropwise with stirring at −78° C. The reaction was warmed to RT slowly and then was stirred for 1 h at RT. Then to the mixture was added AcOH (2.0 mL, 33.20 mmol) and H$_2$O$_2$ (1.0 mL, 28.88 mmol) dropwise with stirring at RT. The resulting solution was stirred for 2 h at RT and then was quenched by the addition of 200 mL of NH$_4$Cl (sat.). The resulting solution was extracted with 3×200 mL of DCM. The organic layers were combined and dried over anhydrous Na$_2$SO$_4$, then concentrated under vacuum. The residue was applied onto a silica gel column and eluted with a gradient of ethyl acetate/petroleum ether (1:7 to 1:5). This resulted in 1.9 g (52%) of the title compound as an off-white solid. MS-ESI: 175.1 (M+1).

Step 4:
8-Nitro-1,2,3,5,6,7-hexahydro-s-indacen-4-ol

Into a 250-mL round-bottom flask purged with and maintained under nitrogen was placed a solution of 1,2,3,5,6,7-hexahydro-s-indacen-4-ol (1.9 g, 10.9 mmol) in EtOH (100 mL). To the solution was added 2,3,5,6-tetrabromo-4-methyl-4-nitrocyclohexa-2,5-dienone (6.1 g, 13.1 mmol). The resulting solution was stirred overnight at RT and then was concentrated under vacuum. The residue was applied onto a silica gel column and eluted with a gradient of ethyl acetate/petroleum ether (1:5 to 1:3). This resulted in 1.1 g (46%) of the title compound as a light yellow solid. MS-ESI: 218.1 (M−1).

Step 5: 4-(Difluoromethoxy)-8-nitro-1,2,3,5,6,7-hexahydro-s-indacene

Into a 100-mL round-bottom flask purged with and maintained under nitrogen was placed a solution of 8-nitro-1,2,3,5,6,7-hexahydro-s-indacen-4-ol (1.1 g, 5.0 mmol) in DMF (20 mL) and water (2 mL). To the solution were added $K_2CO_3$ (1.4 g, 10.0 mmol) and sodium 2-chloro-2,2-difluoroacetate (1.5 g, 10.0 mmol). The resulting solution was stirred for 1 h at 120° C. and then was diluted with 20 ml of water. The pH value of the solution was adjusted to 7 with aq. HCl (1 N). The resulting solution was extracted with 3×20 mL of DCM. The organic layers were combined and dried over anhydrous $Na_2SO_4$, then concentrated under vacuum. The residue was applied onto a silica gel column and eluted with a gradient of ethyl acetate/petroleum ether (1:2 to 1:3). This resulted in 0.55 g (41%) of the title compound as a light yellow solid. MS-ESI: 270.1 (M+1).

Step 6: 8-(Difluoromethoxy)-1,2,3,5,6,7-hexahydro-s-indacen-4-amine

Into a 100-mL round-bottom flask was placed a solution of 4-(difluoromethoxy)-8-nitro-1,2,3,5,6,7-hexahydro-s-indacene (550 mg, 2.0 mmol) in MeOH (10 mL). Then Pd/C (10% wt., 100 mg) was added. The flask was evacuated and filled three times with hydrogen. The resulting solution was stirred for 12 h at RT under an atmosphere of hydrogen. The solids were filtered out. The resulting filtrate was concentrated under vacuum. This resulted in 460 mg (94%) of the title compound as a light yellow solid. MS-ESI: 240.1 (M+1).

Scheme 29

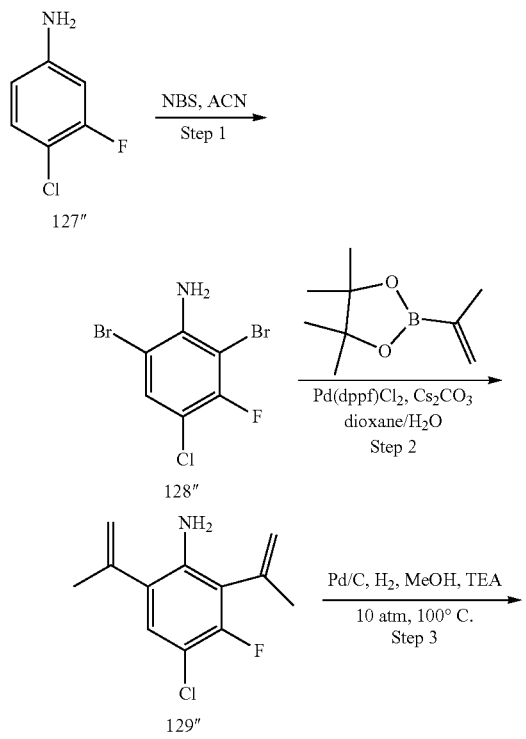

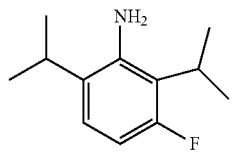

Intermediate 43

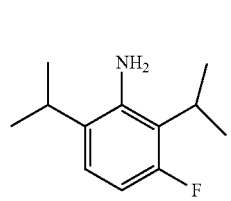

3-Fluoro-2,6-diisopropylbenzenamine

Step 1: 2,6-Dibromo-4-chloro-3-fluoroaniline

Into a 500-mL round-bottom flask was placed 4-chloro-3-fluoroaniline (5.08 g, 34.9 mmol), ACN (200 mL), and NBS (18.69 g, 105.0 mmol). The resulting solution was stirred for 12 h at RT and then was concentrated under vacuum. The residue was applied onto a silica gel column and eluted with a gradient of ethyl acetate/petroleum ether (1:200 to 1:100). This resulted in 9.7 g (92%) of the title compound as a light yellow solid. MS-ESI: 303.8/305.8/301.8 (M+1).

Step 2: 4-Chloro-3-fluoro-2,6-bis(prop-1-en-2-yl)aniline

Into a 500-mL round-bottom flask purged with and maintained under nitrogen was placed a solution of 2,6-dibromo-4-chloro-3-fluoroaniline (9.03 g, 29.8 mmol) in 1,4-dioxane (200 mL) and water (20 mL). To the solution were added 4,4,5,5-tetramethyl-2-(prop-1-en-2-yl)-1,3,2-dioxaborolane (15.12 g, 89.98 mmol), $Cs_2CO_3$ (29.34 g, 90.1 mmol) and Pd(dppf)Cl$_2$ (2.20 g, 3.0 mmol). The resulting solution was stirred for 12 h at 90° C. and then was concentrated under vacuum. The residue was applied onto a silica gel column and eluted with a gradient of ethyl acetate/petroleum ether (1:30 to 1:20). This resulted in 4.3 g (64%) of the title compound as yellow oil. MS-ESI: 226.1, 228.1 (M+1).

Step 3: 3-Fluoro-2,6-bis(propan-2-yl)aniline

Into a 100-mL round-bottom flask was placed a solution of 4-chloro-3-fluoro-2,6-bis(prop-1-en-2-yl)aniline (1 g, 4.4 mmol) in MeOH (15 mL). Then Pd/C (10% wt., 100 mg) was added. The flask was evacuated and filled three times with hydrogen. The resulting solution was stirred for 3 h at RT under an atmosphere of hydrogen. The solids were filtered out. The resulting filtrate was concentrated under vacuum. The residue was applied onto a silica gel column and eluted with a gradient of ethyl acetate/petroleum ether (1:5 to 1:3). This resulted in 700 mg (81%) of the title compound as light yellow oil. MS-ESI: 196.1 (M+1).

Intermediate 44

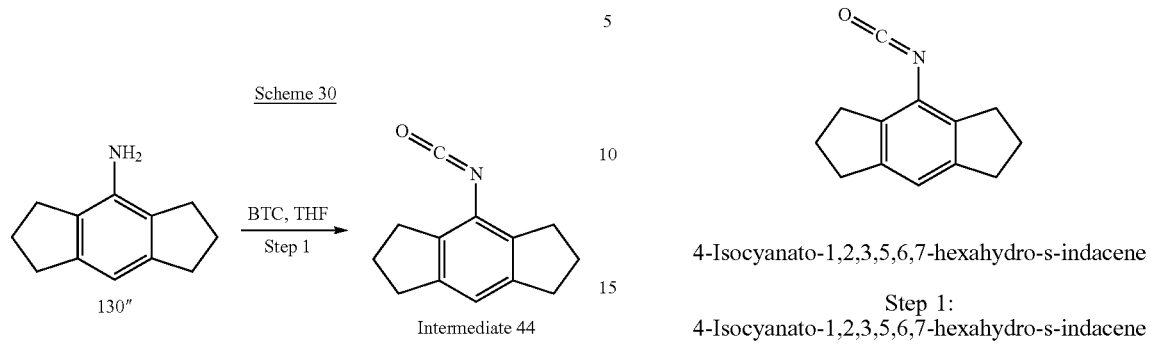

4-Isocyanato-1,2,3,5,6,7-hexahydro-s-indacene

Step 1:
4-Isocyanato-1,2,3,5,6,7-hexahydro-s-indacene

Into a 50-n round-bottom flask purged with and maintained under nitrogen was placed 1,2,3,5,6,7-hexahydro-s-indacen-4-amine (64 mg, 0.4 mmol), THF (5 mL) and BTC (37 mg, 0.1 mmol). The resulting solution was stirred for 2 h at 65° C. and then was concentrated under vacuum. This resulted in 75 mg (crude) of the title compound as light brown oil. The crude product was used directly in the next step.

TABLE 9

The Intermediates in the following Table were prepared using similar procedure as shown in Scheme 30 above for converting compound 130" to Intermediate 44.

| Intermediate # | Structure | IUPAC Name |
| --- | --- | --- |
| Intermediate 45 | 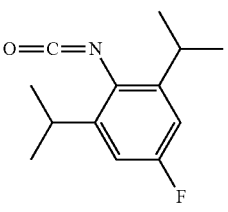 [SMILES: CC(C)c1cc(F)cc(C(C)C)c1N=C=O] | 5-Fluoro-2-isocyanato-1,3-diisopropylbenzene |
| Intermediate 46 | 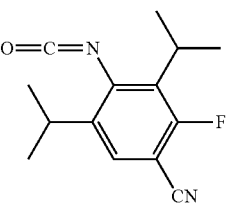 [SMILES: CC(C)c1cc(C#N)c(F)c(C(C)C)c1N=C=O] | 2-Fluoro-4-isocyanato-3,5-diisopropylbenzonitrile |
| Intermediate 47 | 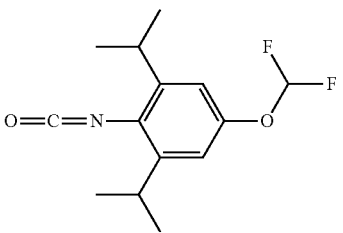 [SMILES: CC(C)c1cc(OC(F)F)cc(C(C)C)c1N=C=O] | 5-(Difluoromethoxy)-2-isocyanato-1,3-diisopropylbenzene |

TABLE 9-continued

The Intermediates in the following Table were prepared using similar procedure as shown in Scheme 30 above for converting compound 130" to Intermediate 44.

| Intermediate # | Structure | IUPAC Name |
| --- | --- | --- |
| Intermediate 48 | 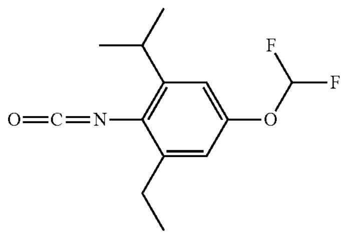 [SMILES: CCc1cc(OC(F)F)cc(C(C)C)c1N=C=O] | 5-(Difluoromethoxy)-1-ethyl-2-isocyanato-3-isopropylbenzene |
| Intermediate 49 | 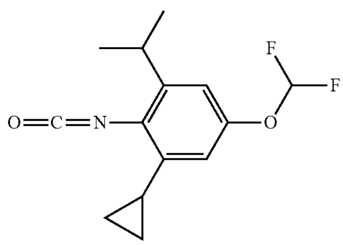 [SMILES: CC(C)c1cc(OC(F)F)cc(C2CC2)c1N=C=O] | 1-Cyclopropyl-5-(difluoromethoxy)-2-isocyanato-3-isopropylbenzene |
| Intermediate 50 | 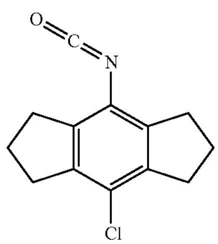 [SMILES: O=C=Nc1c2c(c(Cl)c3c1CCC3)CCC2] | 4-Chloro-8-isocyanato-1,2,3,5,6,7-hexahydro-s-indacene |
| Intermediate 51 | 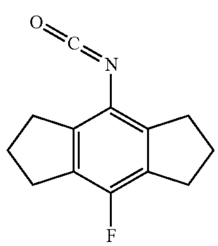 [SMILES: O=C=Nc1c2c(c(F)c3c1CCC3)CCC2] | 4-Fluoro-8-isocyanato-1,2,3,5,6,7-hexahydro-s-indacene |
| Intermediate 52 | 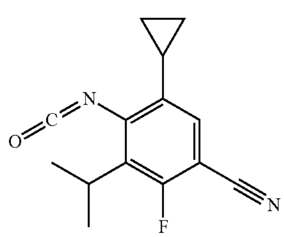 [SMILES: CC(C)c1c(F)c(C#N)cc(C2CC2)c1N=C=O] | 5-Cyclopropyl-2-fluoro-4-isocyanato-3-isopropylbenzonitrile |
| Intermediate 53 | 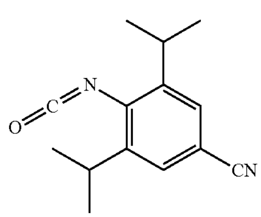 [SMILES: CC(C)c1cc(C#N)cc(C(C)C)c1N=C=O] | 4-Isocyanato-3,5-diisopropylbenzonitrile |

TABLE 9-continued

The Intermediates in the following Table were prepared using similar procedure as shown in Scheme 30 above for converting compound 130″ to Intermediate 44.

| Intermediate # | Structure | IUPAC Name |
| --- | --- | --- |
| Intermediate 54 | 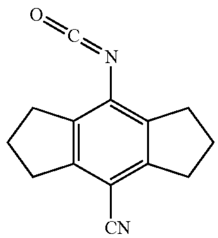 [SMILES: N#Cc1c2c(c(N=C=O)c3c1CCC3)CCC2] | 1,2,3,5,6,7-Hexahydro-8-isocyanato-s-indacene-4-carbonitrile |
| Intermediate 55 | 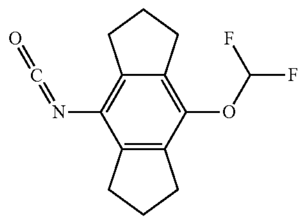 [SMILES: O=C=Nc1c2c(c(OC(F)F)c3c1CCC3)CCC2] | 4-(Difluoromethoxy)-1,2,3,5,6,7-hexahydro-8-isocyanato-s-indacene |
| Intermediate 56 | 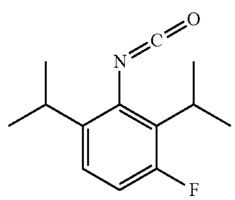 [SMILES: CC(C)c1ccc(F)c(C(C)C)c1N=C=O] | 1-Fluoro-3-isocyanato-2,4-diisopropylbenzene |
| Intermediate 57 | 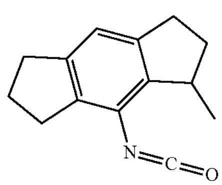 [SMILES: CC1CCc2cc3c(c(N=C=O)c21)CCC3] | 1,2,3,5,6,7-Hexahydro-8-isocyanato-1-methyl-s-indacene |
| Intermediate 58 | 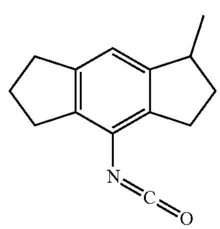 [SMILES: CC1CCc2c1cc1c(c2N=C=O)CCC1] | 1,2,3,5,6,7-Hexahydro-4-isocyanato-1-methyl-s-indacene |

The following schemes illustrate additional general methods for the synthesis of compounds of Formula AA:

Scheme 31

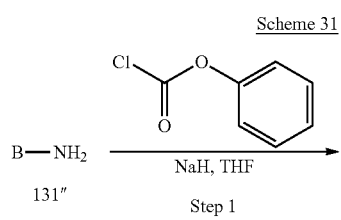

527
-continued
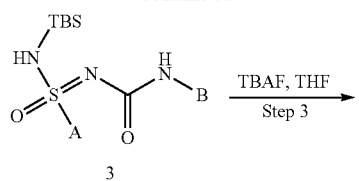
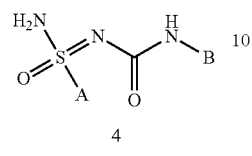
4
Scheme 32
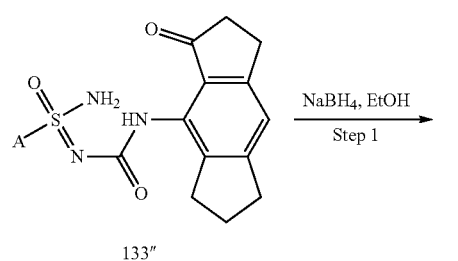
133''
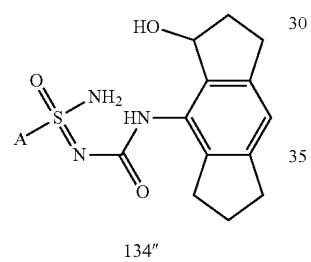
134''
Scheme 33A
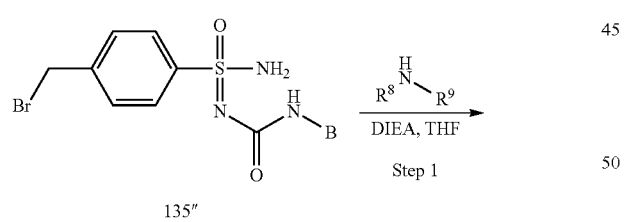
135''
136''
528
Scheme 33B
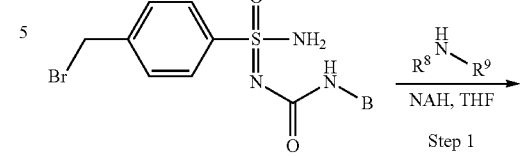
135''
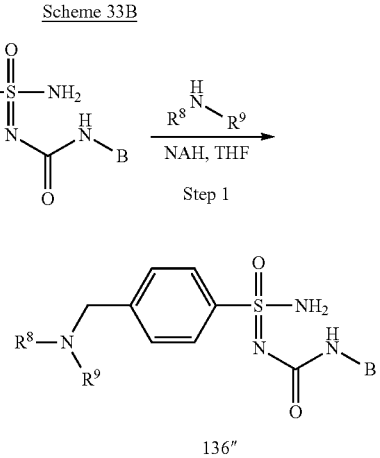
136''
Scheme 34
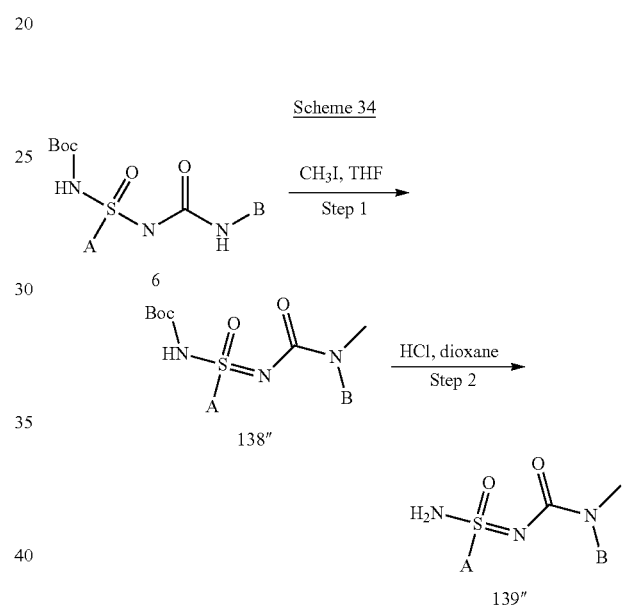
Scheme 35
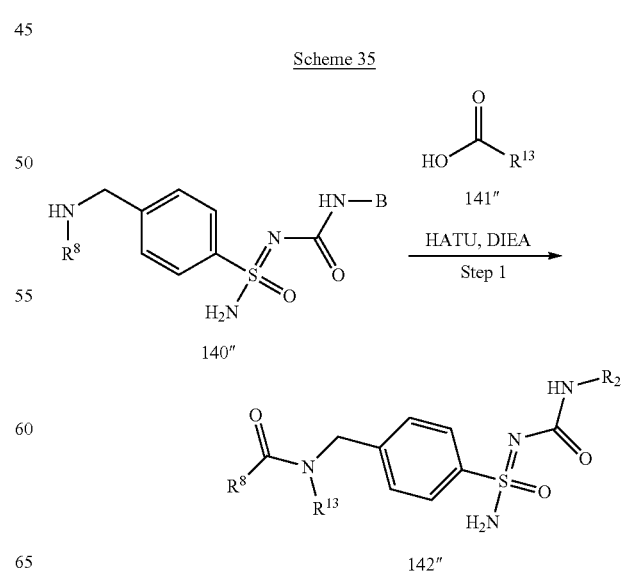
140''
142''

Scheme 35A

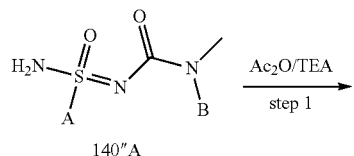

140″A

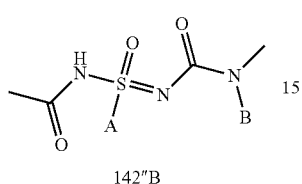

142″B

Scheme for the preparation of Sulfonimidamide Intermediates: Schemes below illustrate the preparation of sulfonimidamide intermediates 59-88 and 112-113.

Scheme 36

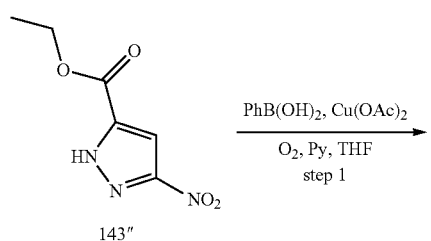

143″

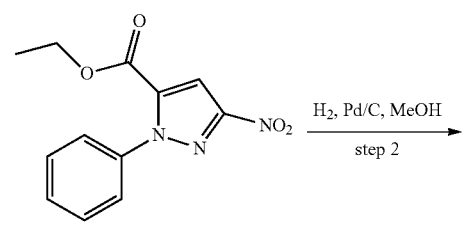

144″

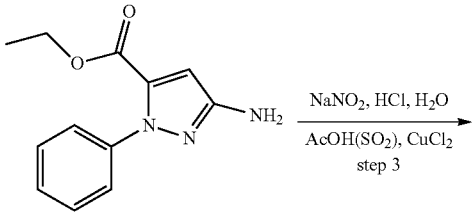

145″

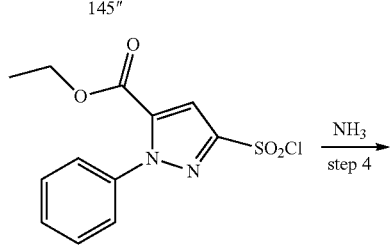

146″

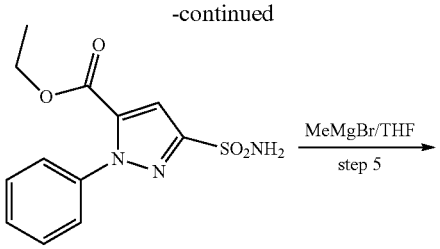

147″

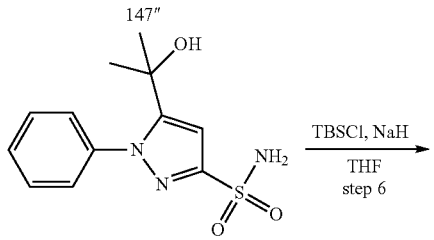

148″

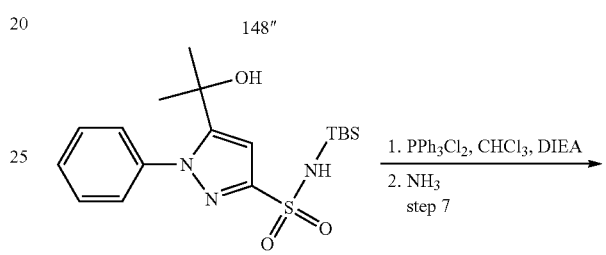

149″

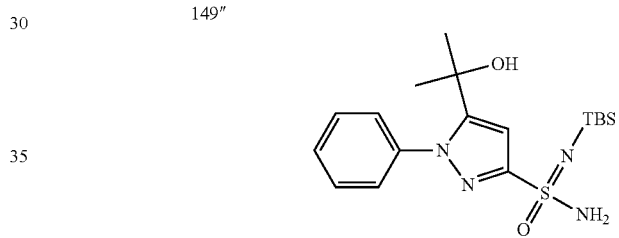

Intermediate 59

Intermediate 59

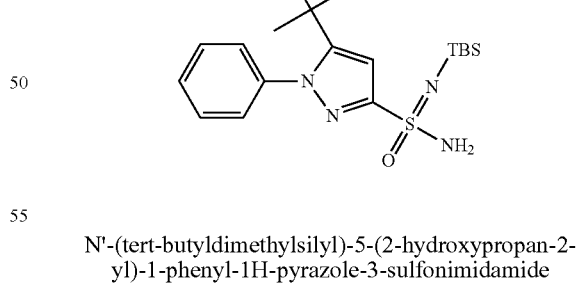

N'-(tert-butyldimethylsilyl)-5-(2-hydroxypropan-2-yl)-1-phenyl-1H-pyrazole-3-sulfonimidamide Step 1: Ethyl 3-nitro-1-phenyl-1H-pyrazole-5-carboxylate Into a 250-mL round-bottom flask purged and maintained with an inert atmosphere of nitrogen, was placed ethyl 3-nitro-1H-pyrazole-5-carboxylate (5.0 g, 27.0 mmol), THF (150 mL), phenylboronic acid (6.6 g, 54.1 mmol), Cu(OAc)₂ (7.38 g, 40.6 mmol), and pyridine (8.54 g, 108 mmol). The resulting solution was stirred overnight at RT. The resulting mixture was concentrated under vacuum. The residue was eluted from a silica gel column with ethyl acetate/petroleum ether (1:1). This resulted in 3.1 g (44%) of the title compound as an off-white solid. MS-ESI: 262 (M+1).

Step 2: Ethyl 3-amino-1-phenyl-1H-pyrazole-5-carboxylate

Into a 100-mL round-bottom flask, was placed ethyl 3-nitro-1-phenyl-1H-pyrazole-5-carboxylate (3.92 g, 15.0 mmol), MeOH (50 mL), and Pd/C (wet 10% wt., 400 mg). The flask was evacuated and filled three times with hydrogen. The resulting solution was stirred overnight at RT. The solids were filtered out. The resulting mixture was concentrated under vacuum. This resulted in 2.8 g (81%) of the title compound as a light yellow solid. MS-ESI: 232 (M+1).

Step 3: Ethyl 3-(chlorosulfonyl)-1-phenyl-1H-pyrazole-5-carboxylate

Into a 100-mL round-bottom flask, was placed ethyl 3-amino-1-phenyl-1H-pyrazole-5-carboxylate (1.8 g, 7.78 mmol), HCl (cc. 6.0 mol/L, 15 mL). This was followed by the addition of a solution of $NaNO_2$ (646 mg, 9.36 mmol) in water (2.0 mL) dropwise with stirring at −10° C. The resulting solution was stirred for 30 min at −10° C. The above mixture was added to a saturated solution of $SO_2$ in AcOH (20 mL) dropwise with stirring at 0° C. Then to the above was added $CuCl_2$ (1.05 g, 7.81 mmol). The resulting solution was stirred for 1 h at RT. The reaction was then quenched by the addition of 30 mL of water. The resulting solution was extracted with 3×30 mL of DCM and the organic layers combined and dried over anhydrous sodium sulfate and concentrated under vacuum. This resulted in 2.2 g (90%) of the title compound as a light yellow solid.

Step 4: Ethyl 1-phenyl-3-sulfamoyl-1H-pyrazole-5-carboxylate

Into a 100-mL round-bottom flask, was placed a solution of ethyl 3-(chlorosulfonyl)-1-phenyl-1H-pyrazole-5-carboxylate (2.2 g, 6.99 mmol) in DCM (10 mL). Then to the above was introduced $NH_3$ gas bubbled at 0° C. for 10 min. The resulting solution was stirred for 2 h at RT. The resulting mixture was concentrated under vacuum. The residue was eluted from a silica gel column with ethyl acetate/petroleum ether (1:1). This resulted in 1.07 g (52%) of the title compound as a light yellow solid. MS-ESI: 296 (M+1).

Step 5: 5-(2-Hydroxypropan-2-yl)-1-phenyl-1H-pyrazole-3-sulfonamide

Into a 100-mL 3-necked round-bottom flask purged and maintained with an inert atmosphere of nitrogen, was placed a solution of ethyl 1-phenyl-3-sulfamoyl-1H-pyrazole-5-carboxylate (1.65 g, 5.59 mmol) in THF (30 mL). This was followed by the addition of MeMgBr/THF (3.0 M, 18.6 mL) dropwise with stirring at 0° C. The resulting solution was stirred overnight at RT. The reaction was then quenched by the addition of 30 mL of $NH_4Cl$ (sat.). The resulting solution was extracted with 3×30 mL of DCM and the organic layers combined and dried over anhydrous sodium sulfate and concentrated under vacuum. The residue was eluted from a silica gel column with ethyl acetate/petroleum ether (2:1). This resulted in 1.35 g (86%) of the title compound as a yellow solid. MS-ESI: 282 (M+1).

Step 6: N-(tert-butyldimethylsilyl)-5-(2-hydroxypropan-2-yl)-1-phenyl-1H-pyrazole-3-sulfonamide Into a 100-mL round-bottom flask, was placed 5-(2-hydroxypropan-2-yl)-1-phenyl-1H-pyrazole-3-sulfonamide (500 mg, 1.78 mmol), THF (10 mL). This was followed by the addition of sodium hydride (60% wt. oil dispersion, 86 mg, 3.58 mmol) in portions at 0° C. Then to the above was added TBSCl (538 mg, 3.57 mmol). The resulting solution was stirred for 2 h at RT. The reaction was then quenched by the addition of 10 mL of water. The resulting solution was extracted with 3×10 mL of DCM. The organic layers were combined, dried over anhydrous sodium sulfate, and concentrated under vacuum. The residue was eluted from a silica gel column with ethyl acetate/petroleum ether (1:2). This resulted in 660 mg (94%) of the title compound as a light yellow solid. MS-ESI: 396 (M+1).

Step 7: N'-(tert-butyldimethylsilyl)-5-(2-hydroxypropan-2-yl)-1-phenyl-1H-pyrazole-3-sulfonimidamide Into a 100-mL 3-necked round-bottom flask purged and maintained with an inert atmosphere of nitrogen, was placed the solution of $PPh_3Cl_2$ (1.67 g, 5.01 mmol) in chloroform (30 mL). This was followed by the addition of DIEA (1.29 g, 9.98 mmol) dropwise with stirring at RT. The resulting solution was stirred for 10 min at RT and the reaction system was cooled to 0° C. To this was added a solution of N-(tert-butyldimethylsilyl)-5-(2-hydroxypropan-2-yl)-1-phenyl-1H-pyrazole-3-sulfonamide (660 mg, 1.67 mmol) in chloroform (3.0 mL) dropwise with stirring at 0° C. The resulting solution was stirred for 30 min at 0° C. To the mixture was added introduced $NH_3$ gas bubble for 15 min at 0° C. The resulting solution was stirred for 2 h at RT. The resulting solution was diluted with 30 mL of water. The resulting solution was extracted with 3×30 mL of DCM and the organic layers combined and dried over anhydrous sodium sulfate and concentrated under vacuum. The residue was eluted from a silica gel column with ethyl acetate/petroleum ether (1:1). This resulted in 530 mg (81%) of the title compound as a light yellow solid. MS-ESI: 395 (M+1).

Scheme 37

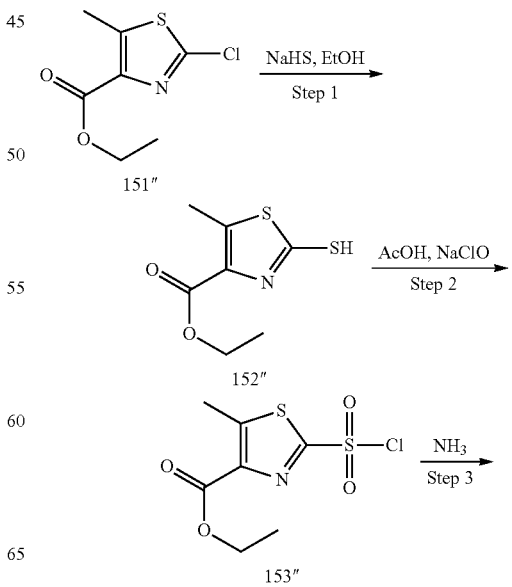

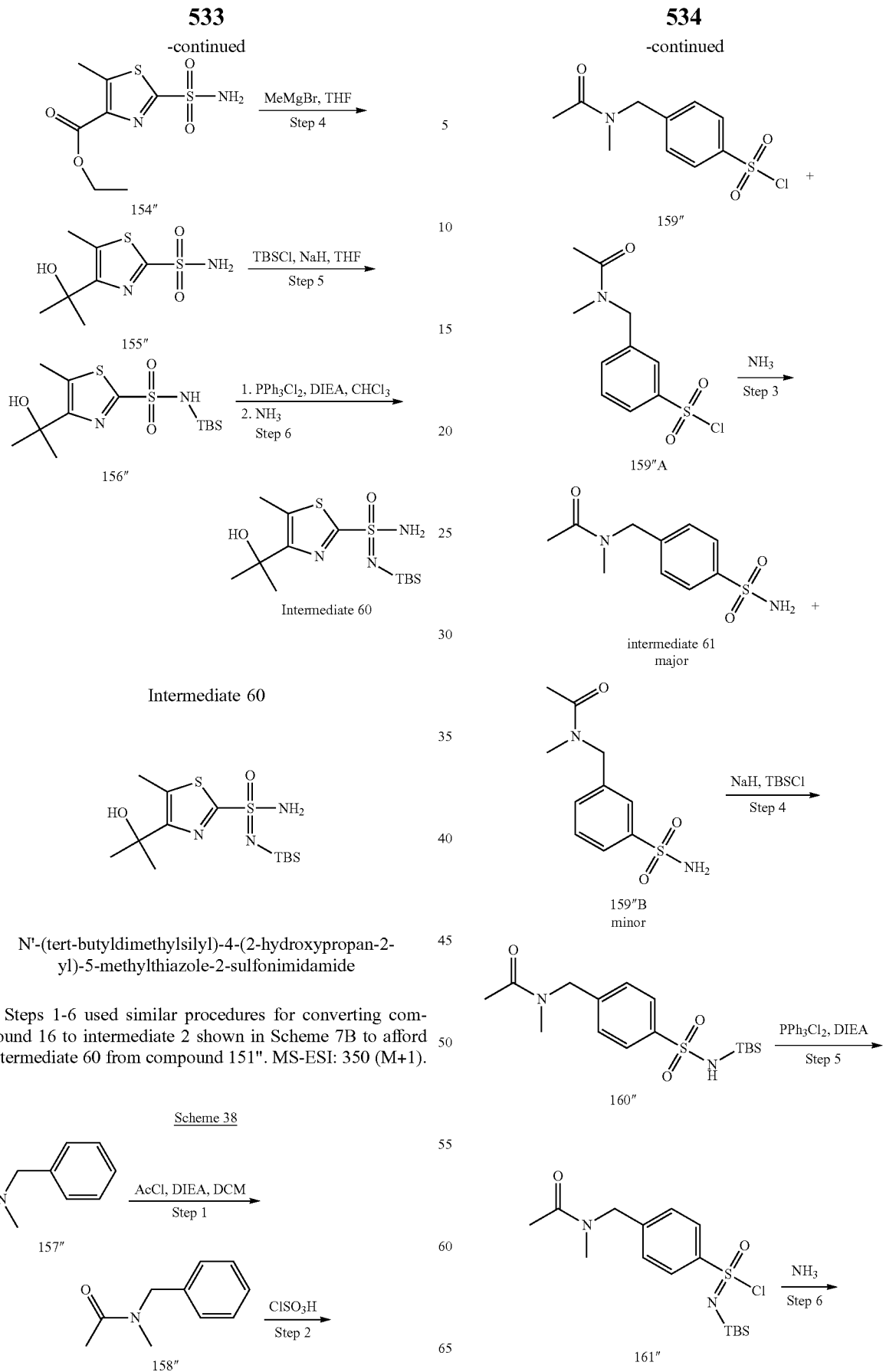
Intermediate 60
N'-(tert-butyldimethylsilyl)-4-(2-hydroxypropan-2-yl)-5-methylthiazole-2-sulfonimidamide
Steps 1-6 used similar procedures for converting compound 16 to intermediate 2 shown in Scheme 7B to afford intermediate 60 from compound 151". MS-ESI: 350 (M+1).
Scheme 38

N-(4-(N'-(tert-butyldimethylsilyl)sulfamidimidoyl)benzyl)-N-methylacetamide

Step 1: N-benzyl-N-methylacetamide

Into a 1.0 L round-bottom flask were added benzyl(methyl)amine (10 g, 82.5 mmol) and DCM (500 mL) at 0° C. To this stirred solution were added DIEA (21.3 g, 165 mmol) and acetyl chloride (9.72 g, 124 mmol) in portions at 0° C. The resulting mixture was stirred for 4 h at RT. The resulting mixture was concentrated under reduced pressure. The residue was eluted from a silica gel column with ethyl acetate/petroleum ether (1:1) to afford the title compound (13 g, 96.5%) as a yellow oil. MS-ESI: 164 (M+1).

Step 2: 4-((N-methylacetamido)methyl)benzenesulfonyl chloride

Into a 250 mL round-bottom flask were added N-benzyl-N-methylacetamide (3.0 g, 18.4 mmol,) and DCM (6.0 mL) at 0° C. To this stirred solution were added $ClSO_2OH$ (6.0 mL) in one portion at 0° C. The resulting mixture was stirred for 3 h at RT. The reaction was quenched by the addition of water/ice (150 mL) at 0° C. The resulting solution was extracted with 3×150 mL of DCM and the organic layers combined and dried over anhydrous sodium sulfate and concentrated under vacuum. The crude product of the title compound (2.2 g, 45.7%)) was used in the next step directly without further purification.

Step 3: N-methyl-N-(4-sulfamoylbenzyl)acetamide

Into a 250 ml round-bottom flask were added 4-[(N-methylacetamido)methyl]benzene-1-sulfonyl chloride (2.2 g, 8.41 mmol) and DCM (3.0 mL) at 0° C. To this stirred solution were added $NH_3(g)$ in DCM (40 mL) dropwise at 0° C. The resulting mixture was stirred overnight at RT. The resulting mixture was concentrated under reduced pressure. The residue was eluted from a silica gel column with ethyl acetate/petroleum ether (1:1) to afford the minor compound 159B (122 mg, 6.1%) and the title compound (1.9 g, 93.3%) both as white solids. MS-ESI: 243 (M+1).

Step 4-6 used similar procedures for converting compound 148″ to intermediate 59 shown in Scheme 36 to afford intermediate 62 from intermediate 61. MS-ESI: 356 (M+1).

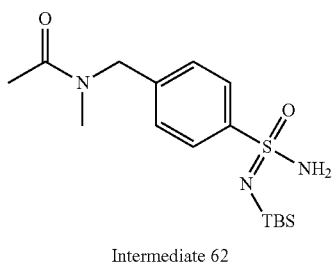

Intermediate 62

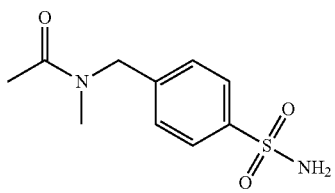 [SMILES: CC(=O)N(C)Cc1ccc(S(N)(=O)=O)cc1]

Intermediate 61

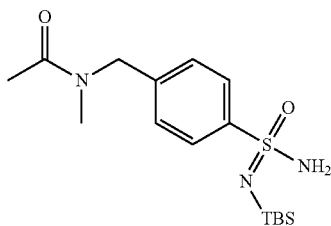

N-methyl-N-(4-sulfamoylbenzyl)acetamide
Intermediate 62

TABLE 10

Intermediate 62B in the following Table was prepared using the similar procedures for converting compound 157″ to Intermediate 62 shown in Scheme 38 from compound 159″B which 5 was separated from step 3 in Scheme 38. The Intermediate 63 was prepared using similar procedures for converting compound 157″ to Intermediate 62 shown in Scheme 38 from appropriate starting materials.

| Intermediate # | Structure | IUPAC Name | Exact Mass[M + H]+ |
|---|---|---|---|
| Intermediate 62B | (structure shown) | N-(3-(N'-(tert-butyldimethylsilyl)sulfamimidoyl)benzyl)-N-methylacetamide | 356 |

TABLE 10-continued

| Intermediate 63 | N'-(tert-butyldimethylsilyl)-2-fluoro-4-methoxybenzenesulfonimidamide | 319 |
|---|---|---|

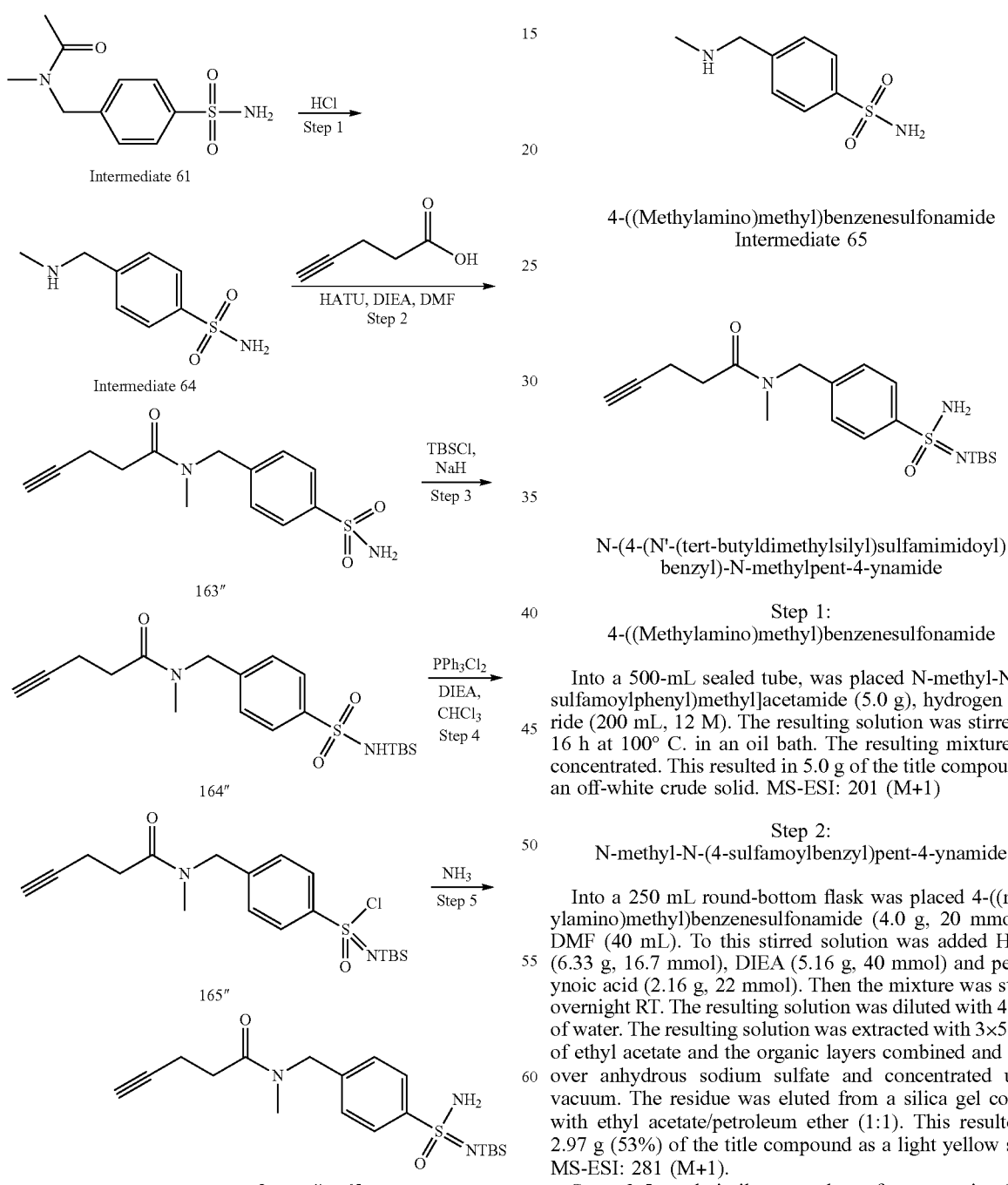

Intermediate 64

4-((Methylamino)methyl)benzenesulfonamide

Intermediate 65

N-(4-(N'-(tert-butyldimethylsilyl)sulfamimidoyl)benzyl)-N-methylpent-4-ynamide

Step 1:
4-((Methylamino)methyl)benzenesulfonamide

Into a 500-mL sealed tube, was placed N-methyl-N-[(4-sulfamoylphenyl)methyl]acetamide (5.0 g), hydrogen chloride (200 mL, 12 M). The resulting solution was stirred for 16 h at 100° C. in an oil bath. The resulting mixture was concentrated. This resulted in 5.0 g of the title compound as an off-white crude solid. MS-ESI: 201 (M+1)

Step 2:
N-methyl-N-(4-sulfamoylbenzyl)pent-4-ynamide

Into a 250 mL round-bottom flask was placed 4-((methylamino)methyl)benzenesulfonamide (4.0 g, 20 mmol) in DMF (40 mL). To this stirred solution was added HATU (6.33 g, 16.7 mmol), DIEA (5.16 g, 40 mmol) and pent-4-ynoic acid (2.16 g, 22 mmol). Then the mixture was stirred overnight RT. The resulting solution was diluted with 40 mL of water. The resulting solution was extracted with 3×50 mL of ethyl acetate and the organic layers combined and dried over anhydrous sodium sulfate and concentrated under vacuum. The residue was eluted from a silica gel column with ethyl acetate/petroleum ether (1:1). This resulted in 2.97 g (53%) of the title compound as a light yellow solid. MS-ESI: 281 (M+1).

Steps 3-5 used similar procedures for converting Intermediate 61 to Intermediate 62 shown in Scheme 38 to afford Intermediate 65 from compound 163". MS-ESI: 394 (M+1).

Scheme 40A

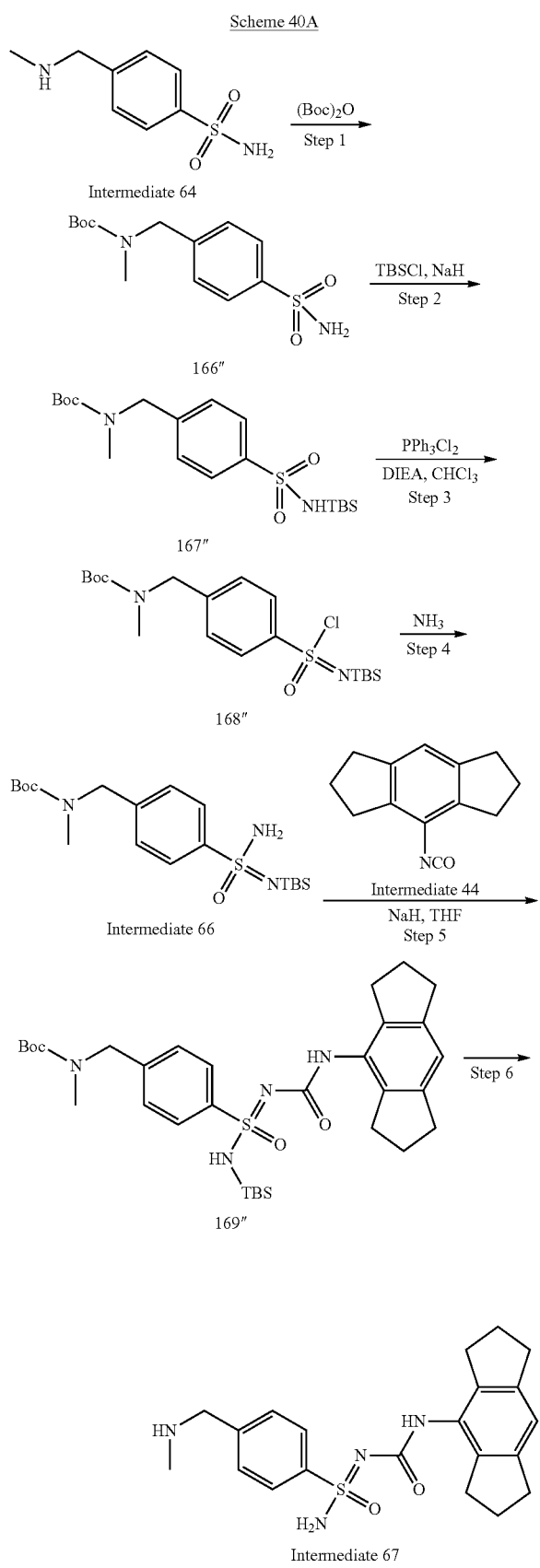

Intermediate 66

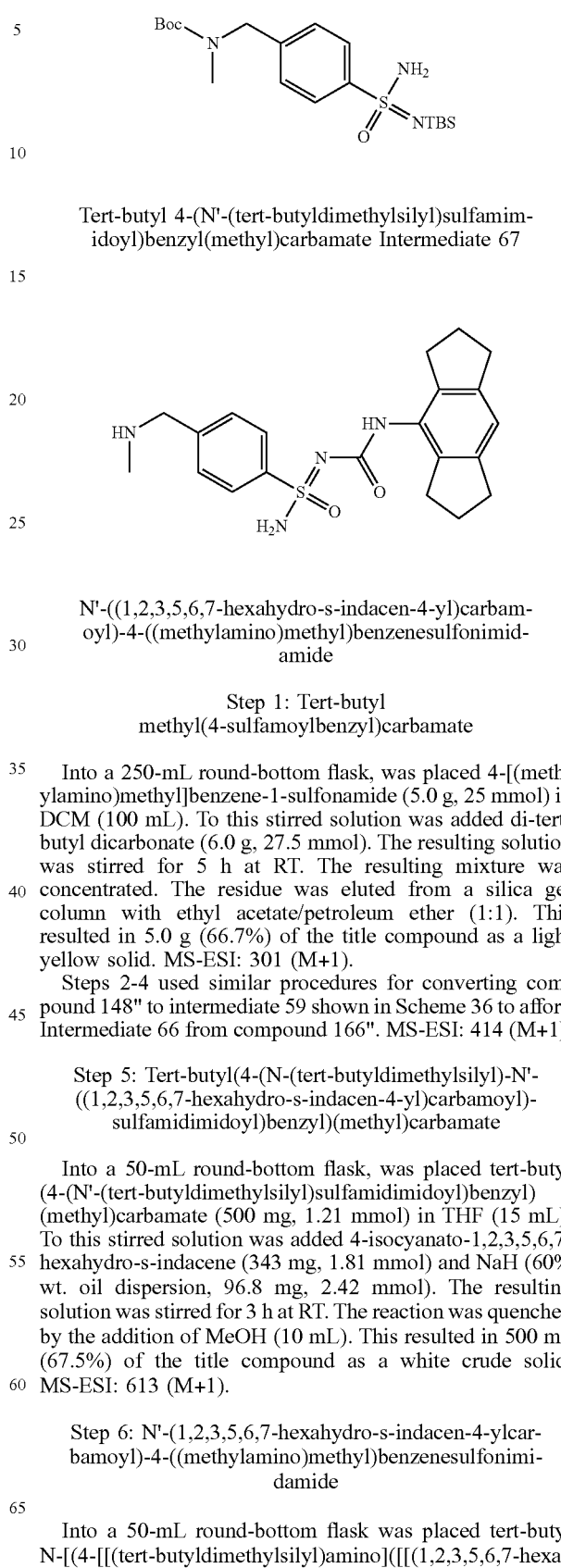

Tert-butyl 4-(N'-(tert-butyldimethylsilyl)sulfamim-idoyl)benzyl(methyl)carbamate Intermediate 67

N'-((1,2,3,5,6,7-hexahydro-s-indacen-4-yl)carbam-oyl)-4-((methylamino)methyl)benzenesulfonimid-amide

Step 1: Tert-butyl methyl(4-sulfamoylbenzyl)carbamate

Into a 250-mL round-bottom flask, was placed 4-[(methylamino)methyl]benzene-1-sulfonamide (5.0 g, 25 mmol) in DCM (100 mL). To this stirred solution was added di-tert-butyl dicarbonate (6.0 g, 27.5 mmol). The resulting solution was stirred for 5 h at RT. The resulting mixture was concentrated. The residue was eluted from a silica gel column with ethyl acetate/petroleum ether (1:1). This resulted in 5.0 g (66.7%) of the title compound as a light yellow solid. MS-ESI: 301 (M+1).

Steps 2-4 used similar procedures for converting compound 148" to intermediate 59 shown in Scheme 36 to afford Intermediate 66 from compound 166". MS-ESI: 414 (M+1).

Step 5: Tert-butyl(4-(N-(tert-butyldimethylsilyl)-N'-((1,2,3,5,6,7-hexahydro-s-indacen-4-yl)carbamoyl)-sulfamidimidoyl)benzyl)(methyl)carbamate Into a 50-mL round-bottom flask, was placed tert-butyl (4-(N'-(tert-butyldimethylsilyl)sulfamidimidoyl)benzyl)(methyl)carbamate (500 mg, 1.21 mmol) in THF (15 mL). To this stirred solution was added 4-isocyanato-1,2,3,5,6,7-hexahydro-s-indacene (343 mg, 1.81 mmol) and NaH (60% wt. oil dispersion, 96.8 mg, 2.42 mmol). The resulting solution was stirred for 3 h at RT. The reaction was quenched by the addition of MeOH (10 mL). This resulted in 500 mg (67.5%) of the title compound as a white crude solid. MS-ESI: 613 (M+1).

Step 6: N'-(1,2,3,5,6,7-hexahydro-s-indacen-4-ylcarbamoyl)-4-((methylamino)methyl)benzenesulfonimi-damide Into a 50-mL round-bottom flask was placed tert-butyl N-[(4-[[(tert-butyldimethylsilyl)amino]([[(1,2,3,5,6,7-hexahydro-s-indacen-4-yl)carbamoyl]imino])oxo-λ⁶-sulfanyl]phenyl)methyl]-N-methylcarbamate (90 mg) and HCl in dioxane (4 M, 5.0 mL). The resulting solution was stirred for 16 h at RT. The resulting mixture was concentrated. The crude product was purified by Prep-HPLC with the following conditions: Column, Sunfire Prep C18 OBD, 10 um, 19*250 mm; mobile phase A: water (0.05% TFA) and B: ACN (20% to 50% gradient of B over 17 min); Detector, UV 220/254 nm. This resulted in 30 mg of the title compound as a white solid. MS-ESI: 399 (M+1).

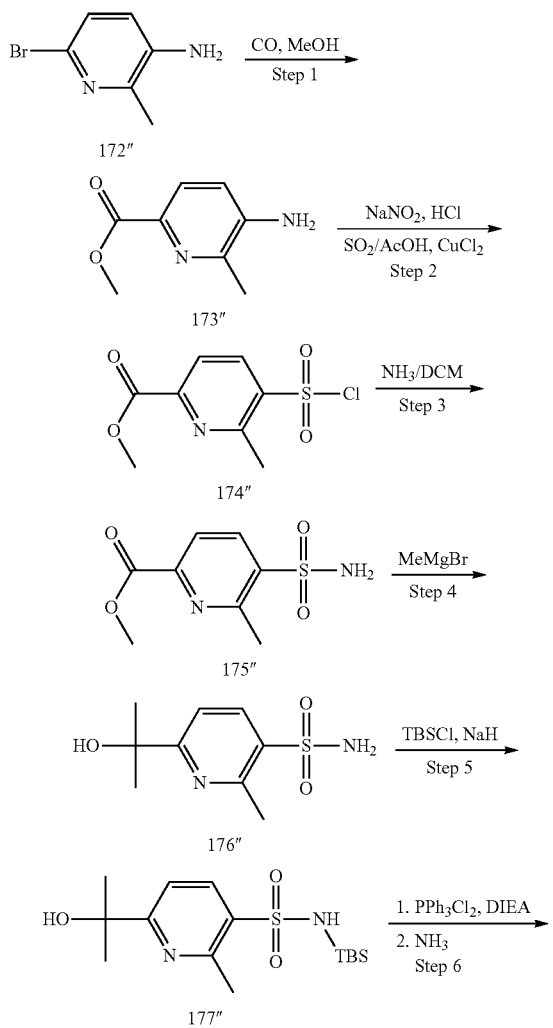

Scheme 42

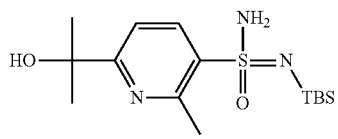

Intermediate 70

Intermediate 70

N'-(tert-butyldimethylsilyl)-6-(2-hydroxypropan-2-yl)-2-methylpyridine-3-sulfonimidamide Step 1: Methyl 5-amino-6-methylpicolinate Into a 50-ml seal tube was placed methyl 6-bromo-2-methylpyridin-3-amine (500 mg, 2.67 mmol) in MeOH (15 mL) and Pd(OAc)₂ (120 mg, 0.53 mmol), dppf (444 mg, 0.80 mmol), TEA (809 mg, 8.01 mmol). The seal tube was evacuated and flushed three times with CO. The resulting solution was stirred for 5 h at 100° C. under 10 atm of CO. Then the solution was concentrated under vacuum. The residue was eluted from a silica gel column with ethyl acetate/petroleum ether (1:1).

This resulted in 351 mg (79.2%) of the title compound as a light yellow solid. MS-ESI: 167 (M+1).

Steps 2-4 used similar procedures for converting compound 27 to Intermediate 30 shown in Scheme 9 to afford compound 176" from compound 173". MS-ESI: 231 (M+1).

Steps 5-6 used similar procedures for converting compound 148" to intermediate 59 shown in Scheme 36 to afford Intermediate 70 from compound 176". MS-ESI: 344 (M+1).

TABLE 11

The Intermediates in the following Table were prepared using the similar procedures for converting compound 172" to Intermediate 70 shown in Scheme 42 from appropriate starting materials.

| Intermediate # | Structure | IUPAC Name | Exact Mass[M + H]⁺ |
| --- | --- | --- | --- |
| Intermediate 71 | 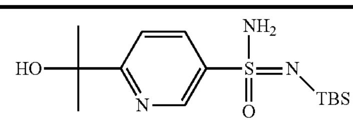 | N'-(tert-butyldimethylsilyl)-6-(2-hydroxypropan-2-yl)pyridine-3-sulfonimidamide | 330 |

Scheme 43

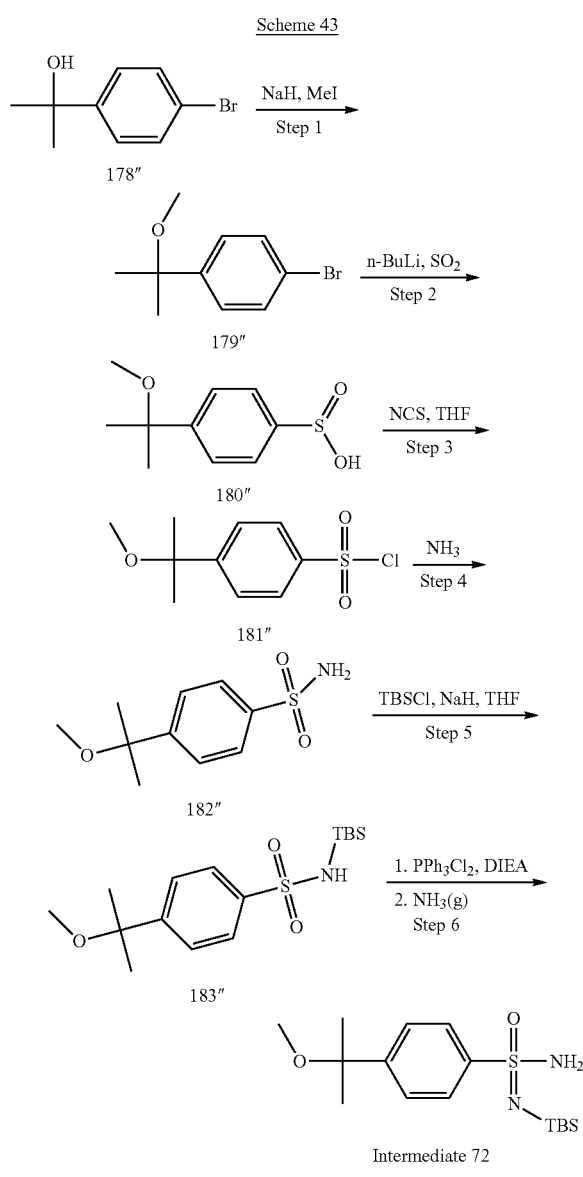

Intermediate 72

N'-(tert-butyldimethylsilyl)-4-(2-methoxypropan-2-yl)benzenesulfonimidamide

Step 1: 1-Bromo-4-(2-methoxypropan-2-yl)benzene

Into a 250-mL round-bottom flask, was placed a solution of 2-(4-bromophenyl)propan-2-ol (10 g, 46.5 mmol) in THF (50 mL). To this stirred solution was added NaH (60% wt. oil dispersion, 5.19 g, 93 mmol) at 0° C. The resulting solution was stirred for 30 min at 0° C. To this stirred solution was added MeI (6.60 g, 46.5 mmol) dropwise with stirring at 0° C. The resulting solution was allowed to react for an additional 15 h at RT. The resulting solution was quenched with 40 mL of water. The resulting solution was extracted with 3×50 mL of ethyl acetate and the organic layers combined and dried over anhydrous sodium sulfate and concentrated under vacuum. The residue was eluted from a silica gel column with ethyl acetate/petroleum ether (15/85). This resulted in 8.5 g (50.3%) of the title compound as a yellow solid.

Step 2: 4-(2-Methoxypropan-2-yl)benzenesulfinic acid

Into a 250-mL 3-necked round-bottom flask purged and maintained with an inert atmosphere of nitrogen, was placed a solution of 1-bromo-4-(2-methoxypropan-2-yl)benzene (5.0 g, 21.8 mmol) in THF (50 mL). To this stirred solution was added n-BuLi (13 mL, 32.7 mmol, 2.5 M) dropwise with stirring at −78° C. The resulting solution was stirred for 30 min at −78° C. $SO_2$(g) was introduced into the stirring solution at −78° C. The resulting solution was allowed to react for an additional 60 min at RT. The resulting mixture was concentrated. This resulted in 6.0 g (crude) of the title compound as a yellow solid. MS-ESI: 213 (M−1)

Step 3: 4-(2-Methoxypropan-2-yl)benzenesulfonyl chloride

Into a 50-mL round-bottom flask, was placed 4-(2-methoxypropan-2-yl)benzene-1-sulfinic acid (4.9 g, 22.9 mmol) in THF (50 mL). To this stirred solution was added NCS (4.58 g, 34.3 mmol). The resulting solution was stirred for 30 min at 0° C. The mixture was allowed to react for an additional 60 min at RT. $NH_3$ (g) was introduced into the reaction solution. The resulting solution was allowed to react for an additional 120 min at RT. The resulting mixture was concentrated. The residue was eluted from a silica gel column with ethyl acetate/petroleum ether (1/4). This resulted in 4.3 g (82%) of the title compound as a yellow solid.

Step 4: 4-(2-Methoxypropan-2-yl)benzenesulfonamide

Into a 250-mL round-bottom flask was placed 4-(2-methoxypropan-2-yl)benzene-1-sulfonyl chloride (4.3 g, 17.3 mmol) in DCM (50 mL). $NH_3$ (g) was introduced into the reaction solution at 0° C. The resulting solution was stirred for 180 min at RT. The resulting mixture was concentrated. The residue was eluted from a silica gel column with ethyl acetate/petroleum ether (1/3). This resulted in 3.9 g (98.5%) of the title compound as a yellow solid. MS-ESI: 230 (M+1).

Step 5: N-(tert-butyldimethylsilyl)-4-(2-methoxypropan-2-yl)benzenesulfonamide Into a 100-mL round-bottom flask, was placed a solution of 4-(2-methoxypropan-2-yl)benzene-1-sulfonamide (4.0 g, 17.5 mmol) in THF (40 mL). To this stirred solution was added NaH (1.4 g, 34.9 mmol, 60% wt. oil dispersion) and TBSCl (3.16 g, 21 mmol) at 0° C. The resulting solution was allowed to react with stirring for 15 h at RT. The resulting solution was quenched with 40 mL of water. The resulting solution was extracted with 3×50 mL of ethyl acetate and the organic layers combined and dried over anhydrous sodium sulfate and concentrated under vacuum. The residue was eluted from a silica gel column with ethyl acetate/petroleum ether (30/70). This resulted in 2.3 g (38.4%) of the title compound as a yellow solid. MS-ESI: 344 (M+1)

Step 6: N'-(tert-butyldimethylsilyl)-4-(2-methoxypropan-2-yl)benzenesulfonimidamide Into a 500-mL 3-necked round-bottom flask purged and maintained with an inert atmosphere of nitrogen, was placed the solution of $PPh_3Cl_2$ (12.4 g, 37.3 mmol) in chloroform (150 mL). This was followed by the addition of DIEA (9.63 g, 74.5 mmol) dropwise with stirring at RT. The resulting solution was stirred for 10 min at RT and the reaction system was cooled to 0° C. To this was added a solution of N-(tert-butyldimethylsilyl)-4-(2-methoxypropan-2-yl)benzene-1-sulfonamide (3.2 g, 9.31 mmol) in chloroform (30 mL) dropwise with stirring at 0° C. The resulting solution was stirred for 30 min at 0° C. To the mixture was introduced $NH_3$ gas bubble for 15 min at 0° C. The resulting solution was stirred for 2 h at RT. The resulting solution was diluted with 100 mL of water. The resulting solution was extracted with 3×200 mL of DCM and the organic layers combined and dried over anhydrous sodium sulfate and concentrated under vacuum. The residue was eluted from a silica gel column with ethyl acetate/petroleum ether (36/64). This resulted in 1.4 g (36.5%) of the title compound as a yellow solid. MS-ESI: 343 (M+1)

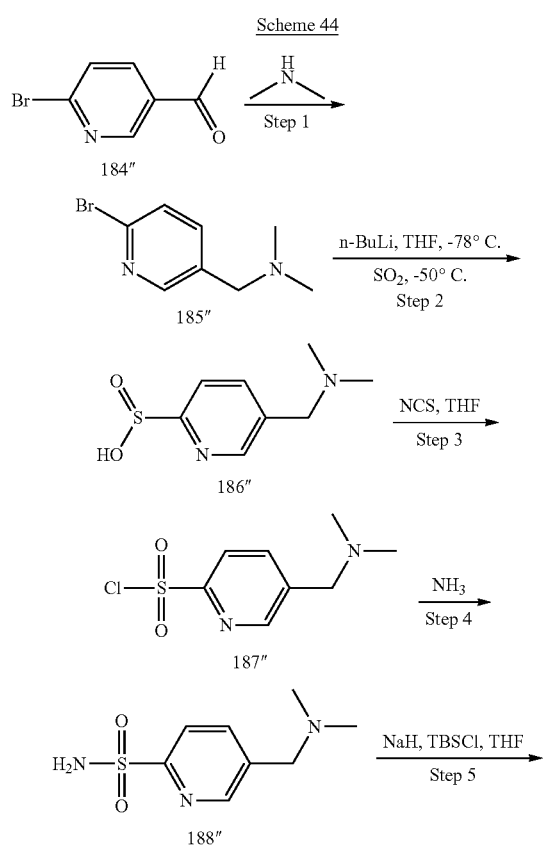

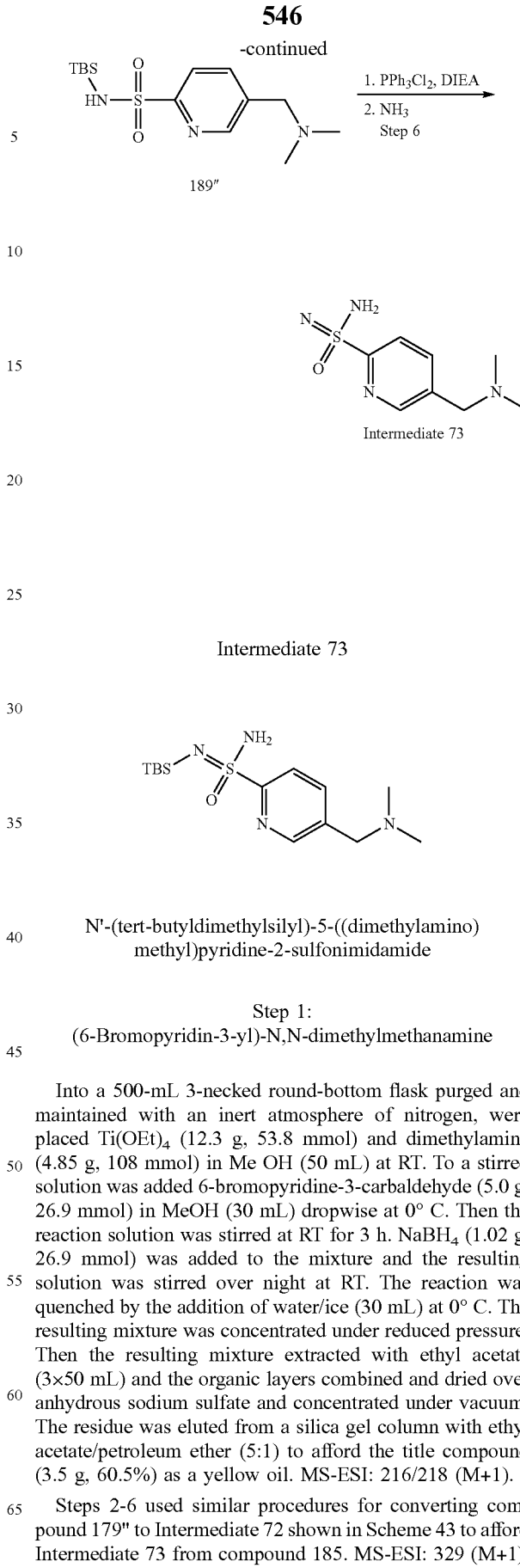

Intermediate 73

N'-(tert-butyldimethylsilyl)-5-((dimethylamino)methyl)pyridine-2-sulfonimidamide

Step 1: (6-Bromopyridin-3-yl)-N,N-dimethylmethanamine

Into a 500-mL 3-necked round-bottom flask purged and maintained with an inert atmosphere of nitrogen, were placed $Ti(OEt)_4$ (12.3 g, 53.8 mmol) and dimethylamine (4.85 g, 108 mmol) in MeOH (50 mL) at RT. To a stirred solution was added 6-bromopyridine-3-carbaldehyde (5.0 g, 26.9 mmol) in MeOH (30 mL) dropwise at 0° C. Then the reaction solution was stirred at RT for 3 h. $NaBH_4$ (1.02 g, 26.9 mmol) was added to the mixture and the resulting solution was stirred over night at RT. The reaction was quenched by the addition of water/ice (30 mL) at 0° C. The resulting mixture was concentrated under reduced pressure. Then the resulting mixture extracted with ethyl acetate (3×50 mL) and the organic layers combined and dried over anhydrous sodium sulfate and concentrated under vacuum. The residue was eluted from a silica gel column with ethyl acetate/petroleum ether (5:1) to afford the title compound (3.5 g, 60.5%) as a yellow oil. MS-ESI: 216/218 (M+1).

Steps 2-6 used similar procedures for converting compound 179" to Intermediate 72 shown in Scheme 43 to afford Intermediate 73 from compound 185. MS-ESI: 329 (M+1).

TABLE 12

The Intermediates in the following Table were prepared using the similar procedures for converting compound 184" to Intermediate 73 shown in Scheme 44 from appropriate starting materials.

| Intermediate # | Structure | IUPAC Name | Exact Mass [M + H]+ |
|---|---|---|---|
| Intermediate 74 | 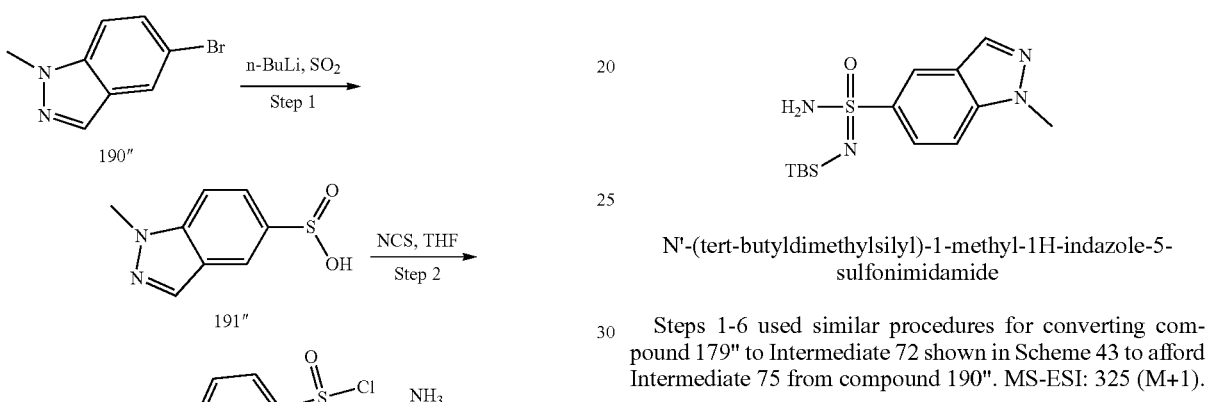 | N'-(tert-butyldimethylsilyl)-6-((dimethylamino)methyl)pyridine-3-sulfonimidamide | 329 |

Scheme 45

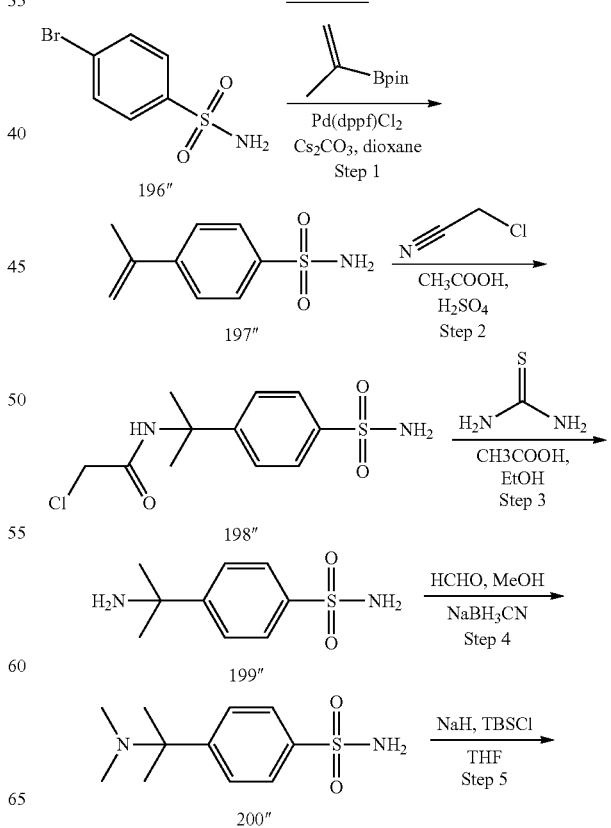

Intermediate 75

N'-(tert-butyldimethylsilyl)-1-methyl-1H-indazole-5-sulfonimidamide

Steps 1-6 used similar procedures for converting compound 179" to Intermediate 72 shown in Scheme 43 to afford Intermediate 75 from compound 190". MS-ESI: 325 (M+1).

Scheme 46

549

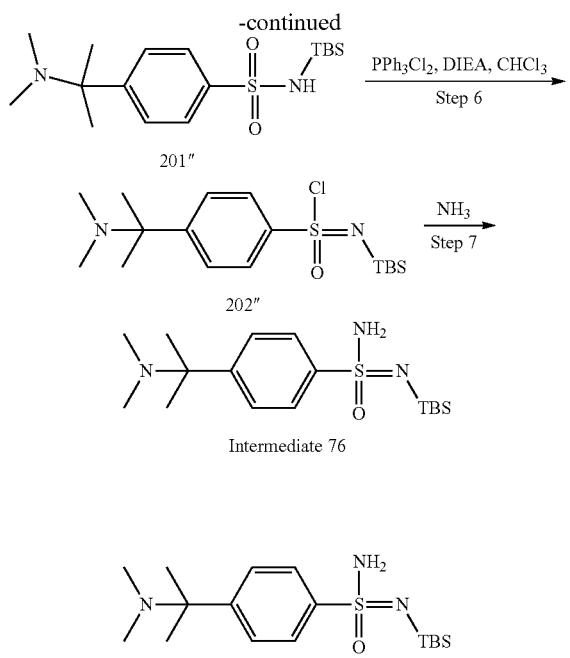

N'-(tert-butyldimethylsilyl)-4-(2-(dimethylamino)propan-2-yl)benzenesulfonimidamide

Step 1: 4-(Prop-1-en-2-yl)benzenesulfonamide

Into a 250-mL round-bottom flask purged and maintained with an inert atmosphere of nitrogen, was placed 4-bromobenzene-1-sulfonamide (5.0 g, 21.2 mmol) in dioxane (100 mL) and H₂O (15 mL). To this stirred solution was added 4,4,5,5-tetramethyl-2-(prop-1-en-2-yl)-1,3,2-dioxaborolane (14.2 g, 84.7 mmol), Pd(dppf)Cl₂ (4.65 g, 6.35 mmol) and Cs₂CO₃ (13.8 g, 42.4 mmol). The resulting solution was stirred for 15 h at 100° C. The resulting mixture was concentrated under reduced pressure. The residue was eluted from a silica gel column with ethyl acetate/petroleum ether (40/60). This resulted in 3.6 g (86.2%) of the title compound as a yellow solid. MS-ESI: 198 (M+1).

Step 2: 2-Chloro-N-(2-(4-sulfamoylphenyl)propan-2-yl)acetamide

Into a 1.0-L round-bottom flask, was placed 4-(prop-1-en-2-yl)benzene-1-sulfonamide (5.0 g, 25.4 mmol) in H₂SO₄ (50 mL) and AcOH (250 mL). To the stirred solution was added 2-chloroacetonitrile (38.3 g, 507 mmol). The resulting solution was stirred for 30 min at 0° C. The resulting solution was allowed to react for an additional 15 h at RT. The pH value of the solution was adjusted to 7 with Na₂CO₃ (5.0 M). Then the resulting mixture was extracted with ethyl acetate (3×200 mL) and the organic layers combined and dried over anhydrous sodium sulfate and concentrated under vacuum. The residue was eluted from a silica gel column with ethyl acetate/petroleum ether (2/3). This resulted in 4.2 g (57%) of the title compound as yellow oil. MS-ESI: 291 (M+1).

Step 3: 4-(2-Aminopropan-2-yl)benzenesulfonamide

Into a 250-mL round-bottom flask, was placed 2-chloro-N-[2-(4-sulfamoylphenyl)propan-2-yl]acetamide (4.2 g,

550

14.5 mmol) in CH₃COOH (15 mL) and ethanol (75 mL). To this stirred solution was added thiourea (1.32 g, 17.3 mmol). The resulting solution was stirred for 16 h at 85° C. The resulting mixture was washed with 100 ml of H₂O and extracted with 3×250 mL of ethyl acetate and the organic layers combined and dried over anhydrous sodium sulfate and concentrated under vacuum. This resulted in 2.3 g (54.3%) of the title compound as a yellow solid. MS-ESI: 215 (M+1).

Step 4: 4-(2-(Dimethylamino)propan-2-yl)benzenesulfonamide

Into a 250-mL round-bottom flask, was placed 4-(2-aminopropan-2-yl)benzene-1-sulfonamide (2.14 g, 9.99 mmol) in MeOH (50 mL). To this stirred solution was added HCHO (37% wt., 599 mg, 20 mmol) and NaBH₃CN (1.86 g, 30 mmol). The resulting solution was stirred for 120 min at RT. The resulting mixture was diluted with 100 mL of water and extracted with 3×250 mL of ethyl acetate and the organic layers combined and dried over anhydrous sodium sulfate and concentrated under vacuum The residue was eluted from a silica gel column with ethyl acetate/petroleum ether (30/70). This resulted in 1.0 g (41.3%) of the title compound as a yellow solid. MS-ESI: 243 (M+1).

Steps 5-7 used similar procedures for converting compound 148″ to intermediate 59 shown in Scheme 36 to afford Intermediate 76 from compound 200. MS-ESI: 356 (M+1).

Scheme 47

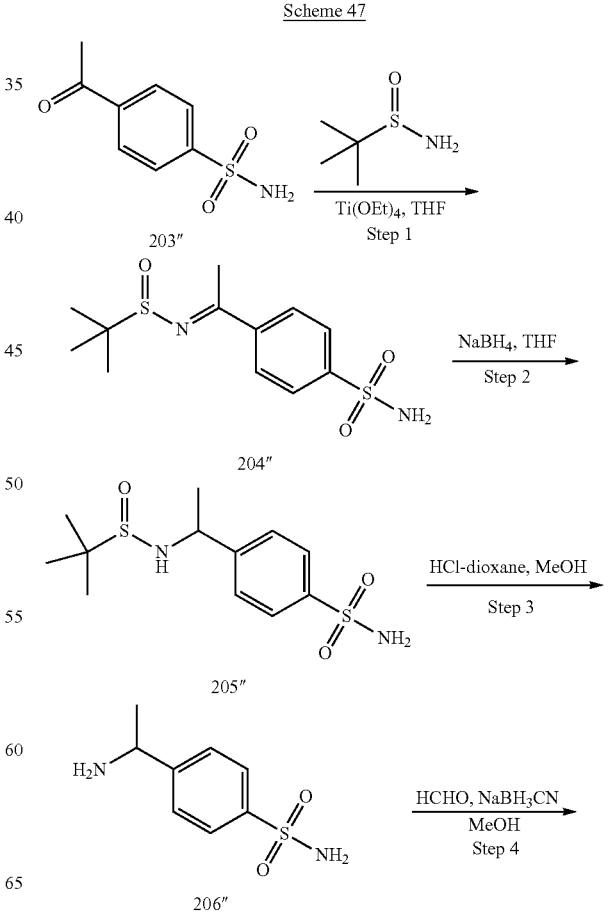

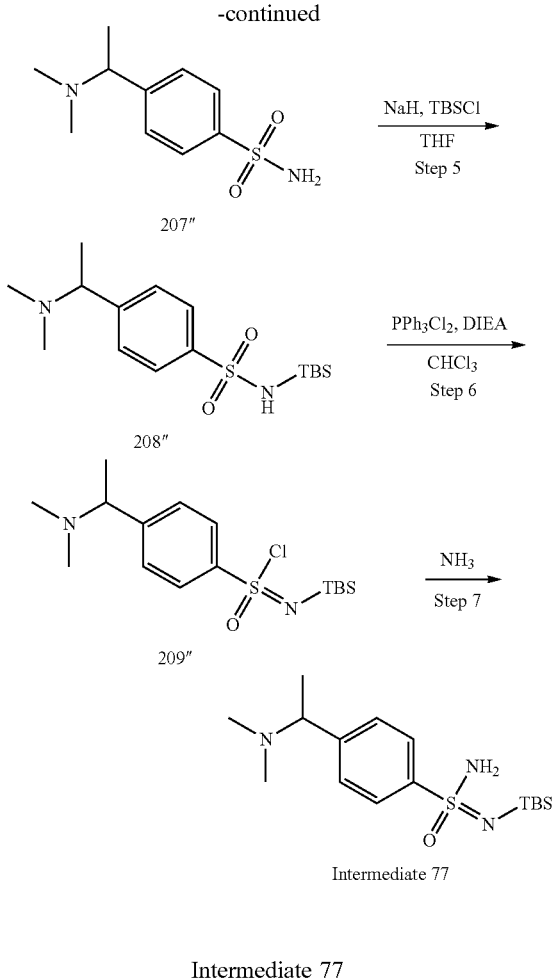

Intermediate 77

N'-(tert-butyldimethylsilyl)-4-(1-(dimethylamino)ethyl)benzenesulfonimidamide

Step 1: (E)-4-(1-((tert-butylsulfinyl)imino)ethyl)benzenesulfonamide

Into a 250-mL 3-necked round-bottom flask purged and maintained with an inert atmosphere of nitrogen was added 2-methylpropane-2-sulfinamide (3.04 g, 25.1 mmol) in THF (50 mL). To this stirred solution was added Ti(OEt)$_4$ (11.5 g, 50.2 mmol) and 4-acetylbenzene-1-sulfonamide (5.0 g, 25.1 mmol) in portions at RT. The resulting mixture was stirred for overnight at 70° C. under nitrogen atmosphere. The reaction was quenched with Water (20 mL) at 0° C. The resulting mixture was extracted with ethyl acetate (3×30 mL). The combined organic layers were dried over anhydrous Na$_2$SO$_4$. After filtration, the filtrate was concentrated under reduced pressure. The residue was purified by silica gel column chromatography, eluted with ethyl acetate/petroleum ether (1:1) to afford the title compound (5.0 g, 75.8%) as a yellow solid. MS-ESI: 303 (M+1).

Step 2: 4-(1-((Tert-butylsulfinyl)amino)ethyl)benzenesulfonamide

Into a 500 mL round-bottom flask were added 4-[(1E)-1-[(2-methylpropane-2-sulfinyl)imino]ethyl]benzene-1-sulfonamide (4.65 g, 15.4 mmol) in THF (200 mL) at RT. To this stirred solution was added NaBH$_4$ (1.16 g, 30.8 mmol) in portions at 0° C. under nitrogen atmosphere. The resulting mixture was stirred for 4 h at RT under nitrogen atmosphere. The reaction was quenched by the addition of HCl (2M, 50 mL) at 0° C. The resulting mixture was extracted with ethyl acetate (3×50 mL). The combined organic layers were dried over anhydrous Na$_2$SO$_4$. After filtration, the filtrate was concentrated under reduced pressure to afford the title compound (4.5 g, 96.1%) as a white solid. MS-ESI: 305 (M+1).

Step 3: 4-(1-Aminoethyl)benzenesulfonamide

Into a 250 mL round-bottom flask were added 4-[1-[(2-methylpropane-2-sulfinyl)amino]ethyl]benzene-1-sulfonamide (4.4 g, 14.5 mmol) and MeOH (50 mL) at room temperature. To this stirred solution was added HCl (gas) in 1,4-dioxane (8.0 mL, 26.3 mmol) in one portions at RT. The resulting mixture was stirred overnight at RT. The resulting mixture was concentrated under reduced pressure. The residue was purified by reverse flash chromatography with the following conditions (column, C18 silica gel; mobile phase, MeCN in water, 10% to 50% gradient in 10 min; detector, UV 254 nm) to afford the title compound (2.6 g, 89.7%) as a white solid. MS-ESI: 201 (M+1).

Step 4: 4-(1-(Dimethylamino)ethyl)benzenesulfonamide

Into a 250 mL round-bottom flask was added 4-(1-aminoethyl)benzene-1-sulfonamide (2.0 g, 9.99 mmol) and MeOH (60 mL) at RT. To this stirred solution was added HCHO (37% wt., 1.61 g, 53.6 mmol) and NaBH$_3$CN (1.25 g, 20 mmol) in portions at RT. The resulting mixture was stirred overnight at RT. The reaction solution was diluted with 100 mL of water and extracted with 3×100 mL of ethyl acetate and the organic layers combined and dried over anhydrous sodium sulfate and concentrated under vacuum. The residue was eluted from a silica gel column with ethyl acetate/petroleum ether. The residue was purified by silica gel column chromatography, eluted with ethyl acetate/petroleum ether (1:2) to afford the title compound (1.5 g, 65.8%) as a white solid. MS-ESI: 229 (M+1).

Steps 5-7 used similar procedures for converting compound 148" to intermediate 59 shown in Scheme 36 to afford Intermediate 77 from compound 207". MS-ESI: 342 (M+1).

Scheme 48

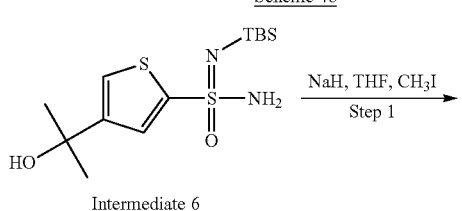

Intermediate 6

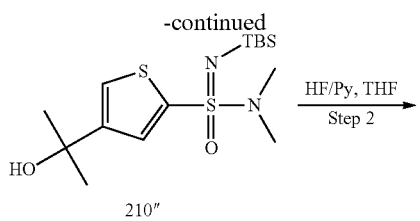

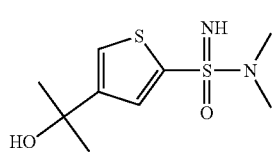

Intermediate 78

4-(2-Hydroxypropan-2-yl)-N,N-dimethylthiophene-2-sulfonimidamide

Step 1: N'-(tert-butyldimethylsilyl)-4-(2-hydroxypropan-2-yl)-N,N-dimethylthiophene-2-sulfonimidamide Into a 50-mL 3-necked round-bottom flask, was placed N-(tert-butyldimethylsilyl)-4-(2-hydroxypropan-2-yl) thiophene-2-sulfonoimidamide (300 mg, 0.90 mmol) in THF (3.0 mL). To the solution were added NaH (60% wt. oil dispersion, 53.8 mg, 1.35 mmol) at −10° C. in ethanol/ice bath. To the solution were added iodomethane (0.50 mL) dropwise with stirring at 0° C. in 30 min. The resulting solution was stirred for 30 min at RT. The reaction was then quenched by the addition of NH$_4$Cl(aq.). The resulting solution was extracted with 3×20 mL of ethyl acetate and the organic layers combined, dried over anhydrous sodium sulfate and concentrated under vacuum. The residue was eluted from a silica gel column with ethyl acetate/petroleum ether (1:5). This resulted in 252 mg (77.5%) of the title compound as a white solid. MS-ESI: 363 (M+1).

Step 2: N'-(tert-butyldimethylsilyl)-4-(2-hydroxypropan-2-yl)-N,N-dimethylthiophene-2-sulfonimidamide Into a 50-mL round-bottom flask, was placed N-(tert-butyldimethylsilyl)-4-(2-hydroxypropan-2-yl)-N,N-dimethylthiophene-2-sulfonoimidamide (200 mg, 0.55 mmol) in THF (10 mL). To the solution was added HF/Py (70% wt., 0.10 mL) dropwise with stirring at RT. The resulting solution was stirred for 60 min at RT. The resulting mixture was concentrated under vacuum. The resulting solution was extracted with ethyl acetate (3×10 mL), the organic layers combined and dried over anhydrous sodium sulfate. The residue was eluted from a silica gel column with ethyl acetate. This resulted in 127 mg (92.7%) of the title compound as a white solid. MS-ESI: 249 (M+1).

Scheme 49

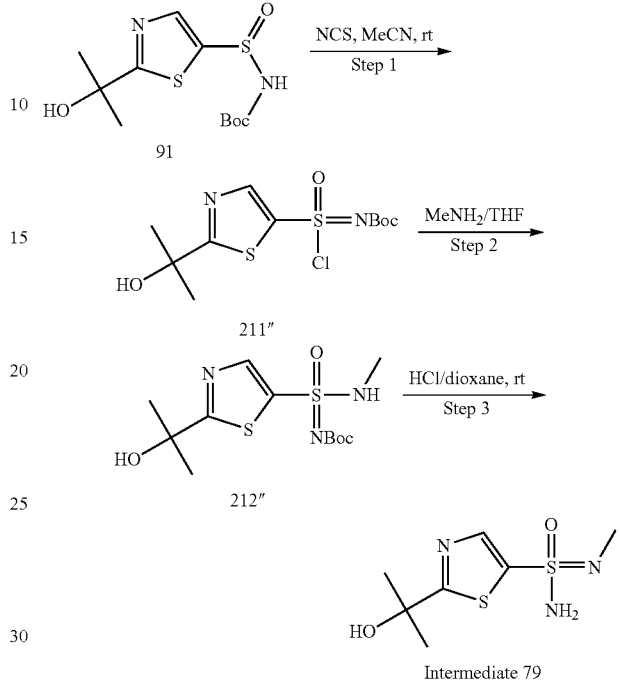

Intermediate 79

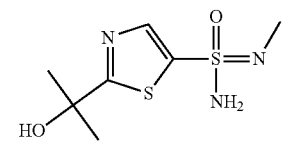

2-(2-Hydroxypropan-2-yl)-N-methylthiazole-5-sulfonimidamide

Step 1: Tert-butyl (chloro(2-(2-hydroxypropan-2-yl)thiazol-5-yl)(oxo)-λ$^6$-sulfaneylidene)carbamate Into a 1.0-L round-bottom flask, was placed tert-butyl N-[[2-(2-hydroxypropan-2-yl)-1,3-thiazol-5-yl] sulfinyl]carbamate (100 g, 326 mmol) in ACN (500 mL). To the stirred solution was added NCS (65.4 g, 490 mmol). The resulting solution was stirred for 2 h at RT. The resulted solution was concentrated. This resulted in 120 g (crude) of the title compound as yellow oil. MS-ESI: 341/343 (M+1).

Step 2: Tert-butyl((2-(2-hydroxypropan-2-yl)thiazol-5-yl)(methylamino)(oxo)-λ$^6$-sulfaneylidene) carbamate Into a 250-mL round-bottom flask, was placed tert-butyl (chloro(2-(2-hydroxypropan-2-yl)thiazol-5-yl)(oxo)-λ$^6$-sulfaneylidene)carbamate (10 g, 29.3 mmol) in THF (100 mL).

To the stirred solution was added CH$_3$NH$_2$ (1.82 g, 58.6 mmol). The resulting solution was stirred for 2 h at RT. The resulted solution was concentrated. The residue was eluted from a silica gel column with ethyl acetate/petroleum ether (1:1). This resulted in 6.1 g (62%) of the title compound as a yellow solid. MS-ESI: 336 (M+1).

Step 3: 2-(2-Hydroxypropan-2-yl)-N'-methylthiazole-5-sulfonimidamide

Into a 100-mL round-bottom flask, was placed tert-butyl ((2-(2-hydroxypropan-2-yl)thiazol-5-yl)(methylamino) (oxo)-λ$^6$-sulfaneylidene) carbamate (3.0 g, 8.94 mmol) in HCl (gas) in 1,4-dioxane (8 mL, 26.3 mmol) in one portion at RT. The resulting solution was stirred for 60 min at RT. The resulting mixture was concentrated under vacuum. This resulted in 2.10 g (crude) of the title compound as a yellow solid. MS-ESI: 236 (M+1).

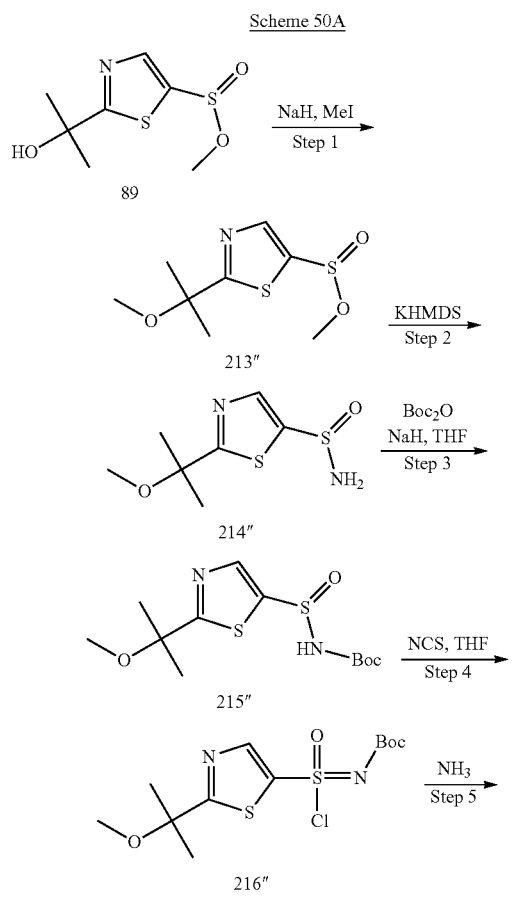

Scheme 50A

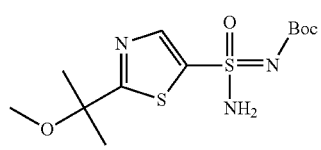

Intermediate 80

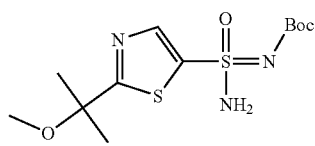 [SMILES: COC(C)(C)c1ncc(S(N)(=O)=NC(=O)OC(C)(C)C)s1]

Tert-butyl (amino(2-(2-methoxypropan-2-yl)thiazol-5-yl)(oxo)-λ$^6$-sulfaneylidene)carbamate

Step 1: Methyl 2-(2-methoxypropan-2-yl)thiazole-5-sulfinate

Into a 1-L round-bottom flask, was placed a solution of methyl 2-(2-hydroxypropan-2-yl)-1,3-thiazole-5-sulfinate (40 g, 181 mmol) in THF (500 mL). To this stirred solution was added NaH (60% wt. oil dispersion, 7.95 g, 199 mmol) in three portions at 0° C. in an ice/ethanol bath. To this reaction solution was added MeI (51.3 g, 362 mmol) dropwise with stirring at 0° C. in an ice/ethanol bath. The resulting solution was stirred for 3 h at RT. The reaction was then quenched by the addition of water (50 mL) at 0° C. The resulting solution was extracted with 3×300 mL of ethyl acetate and the organic layers combined and dried over anhydrous sodium sulfate and concentrated under vacuum. This resulted in 32 g (75.3%) of the title compound as a white solid. MS-ESI: 236 (M+1).

Step 2: 2-(2-Methoxypropan-2-yl)thiazole-5-sulfinamide

Into a 1-L 3-necked round-bottom flask purged and maintained with an inert atmosphere of nitrogen, was placed a solution of methyl 2-(2-methoxypropan-2-yl)-1,3-thiazole-5-sulfinate (20 g, 85 mmol) in THF (500 mL). This was followed by the addition of KHMIDS (500 mL, 1.0 mole, 2 M) dropwise with stirring at −78° C. in a liquid nitrogen/ethanol bath. The resulting solution was stirred for 3 h at −78° C. in a liquid nitrogen/ethanol bath. The reaction quenched by the addition of water (50 mL). The resulting solution was extracted with 3×300 mL of ethyl acetate dried over anhydrous sodium sulfate and concentrated under vacuum. The residue was eluted from a silica gel column with ethyl acetate/petroleum ether (1:3). This resulted in 14 g (74.8%) of the title compound as a white solid. MS-ESI: 221.0 (M+1).

Step 3: Tert-butyl ((2-(2-methoxypropan-2-yl)thiazol-5-yl)sulfinyl)carbamate Into a 500-mL round-bottom flask purged and maintained with an inert atmosphere of nitrogen, was placed a solution of 2-(2-methoxypropan-2-yl)-1,3-thiazole-5-sulfinamide (10 g, 45.4 mmol) in THF (250 mL). To this stirred solution was added NaH (60% wt. oil dispersion, 3.63 g, 90.8 mmol) in three times at 0° C. in an ice/ethanol bath. To this solution was added Boc$_2$O (9.91 g, 45.4 mmol) in portions at 0° C. in an ice/ethanol bath. The resulting solution was stirred for 3 h at RT. The reaction was then quenched by the addition of water (50 mL). The resulting solution was extracted with 3×300 mL of ethyl acetate concentrated under vacuum. This resulted in 12 g (82.5%) of the title compound as a white solid. MS-ESI: 321.1 (M+1).

Step 4: Tert-butyl (chloro(2-(2-methoxypropan-2-yl) thiazol-5-yl)(oxo)-$\lambda^6$-sulfaneylidene)carbamate Into a 500-mL round-bottom flask purged and maintained with an inert atmosphere of nitrogen, was placed a solution of tert-butyl N-[[2-(2-methoxypropan-2-yl)-1,3-thiazol-5-yl]sulfinyl]carbamate (11 g, 34.3 mmol) in THF (200 mL). NCS (13.8 g, 103 mmol) was added to the reaction solution in one portion at RT. The resulting solution was stirred for 3 h at RT. This reaction solution was used to the next step directly without further purification.

Step 5: Tert-butyl (amino(2-(2-methoxypropan-2-yl) thiazol-5-yl)(oxo)-$\lambda^6$-sulfaneylidene)carbamate Into a 500-mL round-bottom flask purged and maintained with an inert atmosphere of nitrogen, was placed a solution of tert-butyl N-[[2-(2-methoxypropan-2-yl)-1,3-thiazol-5-yl]sulfinyl]carbamate (9.0 g, 28.9 mmol) in THF (200 mL). To the mixture was added introduced NH₃ gas bubble for 15 min at 0° C. The resulting solution was stirred for 1 h at RT. The resulting mixture was concentrated. The residue was eluted from a silica gel column with ethyl acetate/petroleum ether (1:1). This resulted in 7 g (72.3%) of the title compound as a white solid. MS-ESI: 336.1 (M+1).

Scheme 51

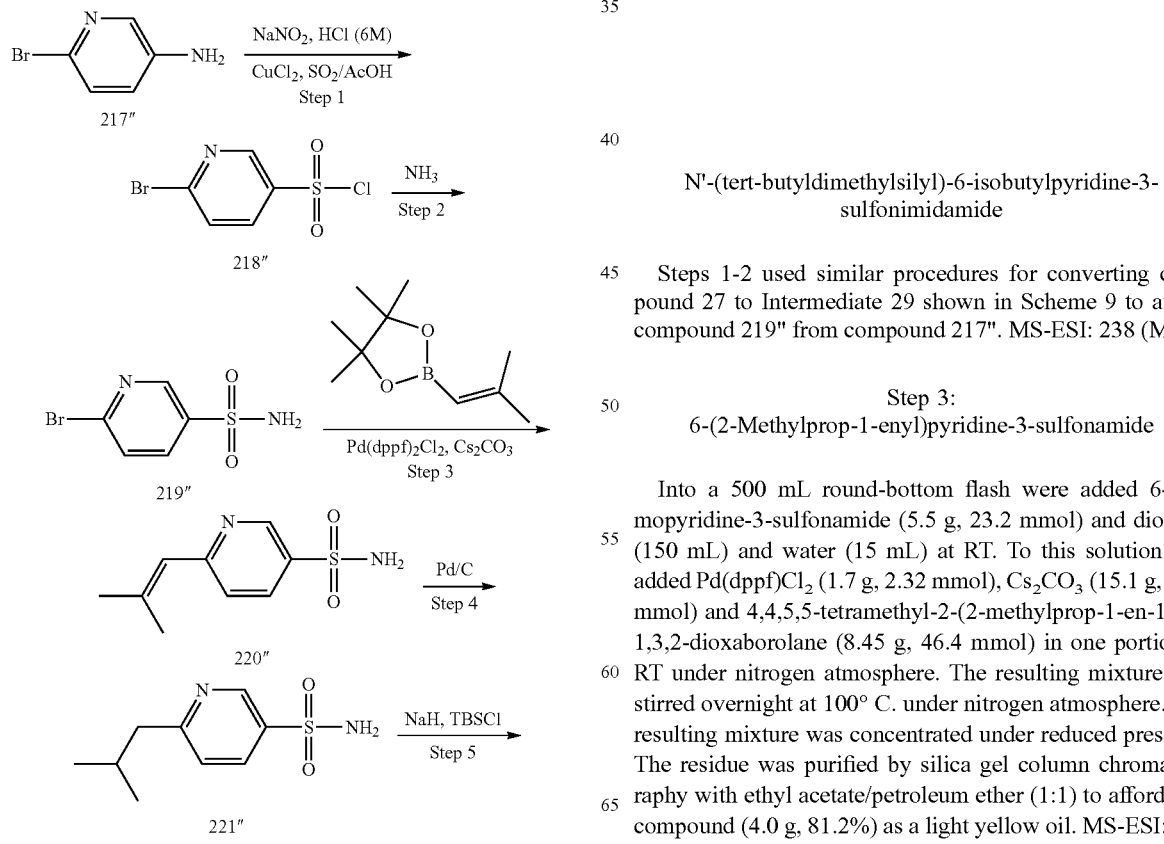

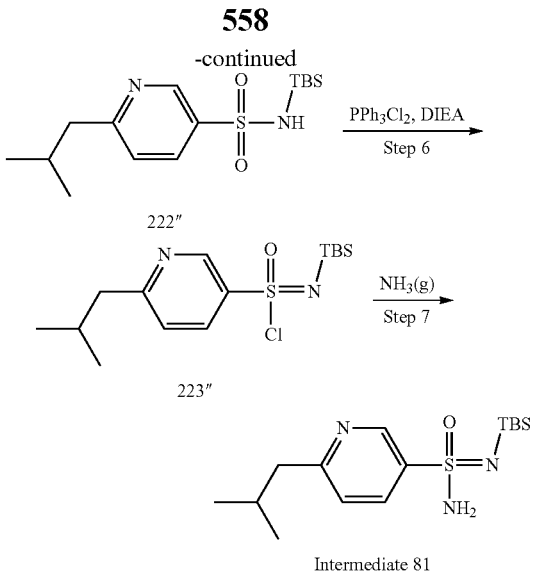

Intermediate 81

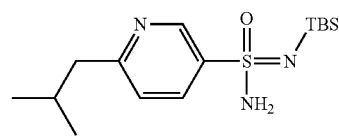

N'-(tert-butyldimethylsilyl)-6-isobutylpyridine-3-sulfonimidamide

Steps 1-2 used similar procedures for converting compound 27 to Intermediate 29 shown in Scheme 9 to afford compound 219″ from compound 217″. MS-ESI: 238 (M+1).

Step 3: 6-(2-Methylprop-1-enyl)pyridine-3-sulfonamide

Into a 500 mL round-bottom flash were added 6-bromopyridine-3-sulfonamide (5.5 g, 23.2 mmol) and dioxane (150 mL) and water (15 mL) at RT. To this solution was added Pd(dppf)Cl₂ (1.7 g, 2.32 mmol), Cs₂CO₃ (15.1 g, 46.4 mmol) and 4,4,5,5-tetramethyl-2-(2-methylprop-1-en-1-yl)-1,3,2-dioxaborolane (8.45 g, 46.4 mmol) in one portion at RT under nitrogen atmosphere. The resulting mixture was stirred overnight at 100° C. under nitrogen atmosphere. The resulting mixture was concentrated under reduced pressure. The residue was purified by silica gel column chromatography with ethyl acetate/petroleum ether (1:1) to afford title compound (4.0 g, 81.2%) as a light yellow oil. MS-ESI: 213 (M+1).

Step 4: 6-Isobutylpyridine-3-sulfonamide

Into a 250 mL 3-necked round-bottom flask was added 6-(2-methylprop-1-en-1-yl)pyridine-3-sulfonamide (4 g, 18.8 mmol) and MeOH (100 mL) at RT under nitrogen atmosphere. To this stirred solution was added Pd/C (wet 10% wt., 900 mg). The flask was evacuated and filled three times with hydrogen. The resulting mixture was stirred overnight at RT under hydrogen atmosphere. The resulting mixture was filtered; the filter cake was washed with MeOH (3×20 mL). The filtrate was concentrated under reduced pressure. The crude product of the title compound (3.8 g) was used to the next step directly without further purification. MS-ESI: 215 (M+1).

Steps 5-7 used similar procedures for converting compound 148" to intermediate 59 shown in Scheme 36 to afford intermediate 81 from compound 221". MS-ESI: 328 (M+1).

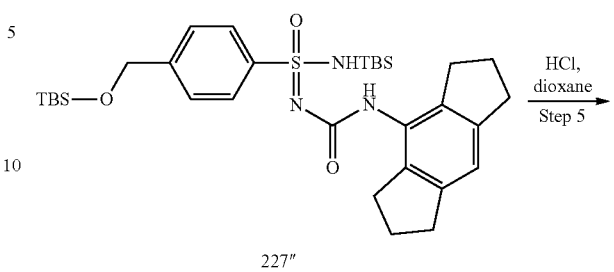

227"

TABLE 13

The Intermediates in the following Table were prepared using the similar procedures for converting compound 217" to Intermediate 81 shown in Scheme 51 from appropriate starting materials.

| Intermediate # | Structure | IUPAC Name | Exact Mass [M + H]+ |
|---|---|---|---|
| Intermediate 82 | 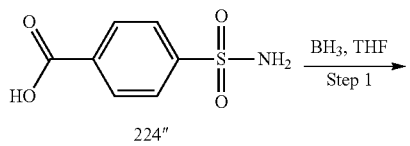 | N'-(tert-butyldimethylsilyl)-4-isobutylbenzenesulfonimidamide | 327 |

Scheme 52

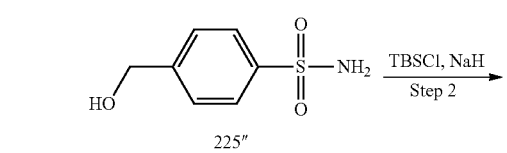

224"

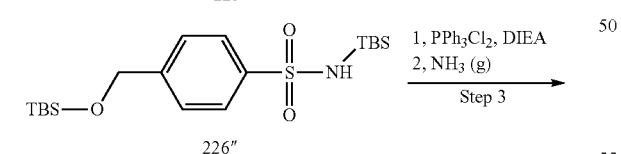

225"

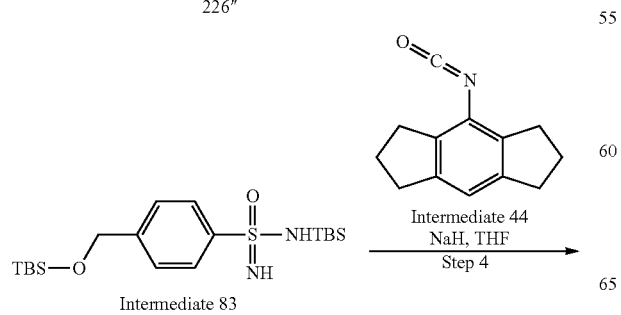

Intermediate 83

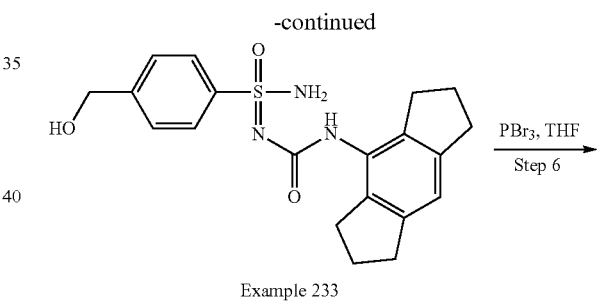

Example 233

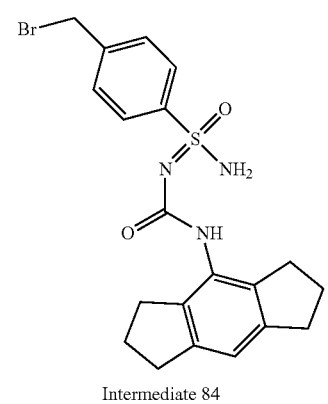 [SMILES: NS(=O)(=NC(=O)Nc1c2c(cc3c1CCC3)CCC2)c1ccc(CBr)cc1]

Intermediate 84

561

Intermediate 83

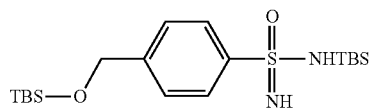

N-(tert-butyldimethylsilyl)-4-((tert-butyldimethylsilyloxy)methyl)benzenesulfonimidamide Example 233 (Compound 3421

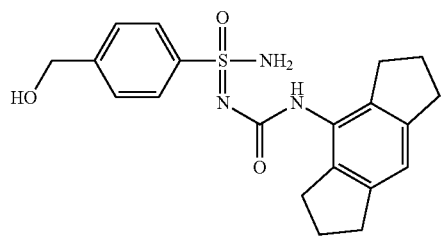

N'-((1,2,3,5,6,7-hexahydro-s-indacen-4-yl)carbamoyl)-4-(hydroxymethyl)benzenesulfonimidamide Step 1: 4-(Hydroxymethyl)benzenesulfonamide Into a 100-mL round-bottom flask, was placed 4-sulfamoylbenzoic acid (1.0 g, 4.97 mmol) in THF (15 mL). This was followed by the addition of $BH_3$-THF (14.3 mL, 149 mmol) dropwise with stirring at 0° C. in an ice/ethanol bath. The resulting solution was stirred for 12 h at RT. The reaction was then quenched by the addition of HCl (50 mL, 2 M) dropwise in an ice bath and stirred for 1 h at RT. The mixture was extracted with 8×50 mL of ethyl acetate. The organic layers were combined and concentrated. This resulted in 800 mg (86%) of the title compound as a yellow solid. MS-ESI: 188 (M+1).

Steps 2-3 used similar procedures for converting compound 148" to Intermediate 59 shown in Scheme 36 to afford Intermediate 83 from compound 225". MS-ESI: 415 (M+1). Steps 4-5 used similar procedures for converting compound 166" to Intermediate 67 shown in Scheme 40A to afford compound Example 233 from Intermediate 83. MS-ESI: 386 (M+1).

Intermediate 84

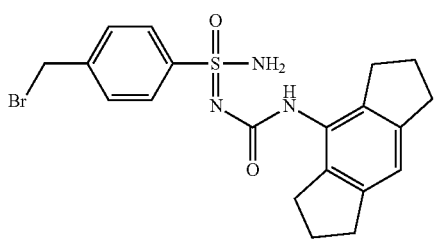 [SMILES: NS(=O)(=NC(=O)Nc1c2c(cc3c1CCC3)CCC2)c1ccc(CBr)cc1]

562

4-(Bromomethyl)-N'-(1,2,3,5,6,7-hexahydro-s-indacen-4-ylcarbamoyl)benzenesulfonimidamide Step 6: 4-(Bromomethyl)-N'-(1,2,3,5,6,7-hexahydro-s-indacen-4-ylcarbamoyl)benzenesulfonimidamide Into a 250-mL round-bottom flask purged and maintained with an inert atmosphere of nitrogen, was placed 1-[amino[4-(hydroxymethyl)phenyl]oxo-$\lambda^6$-sulfanylidene]-3-(1,2,3,5,6,7-hexahydro-s-indacen-4-yl)urea (1.0 g, 2.59 mmol) in THF (50 mL). To the stirred solution was added $PBr_3$ (702 mg, 2.59 mmol) in portions. The resulting solution was stirred for 3 h at RT. The solids were collected by filtration. This resulted in 500 mg (43%) of the title compound as a white solid. MS-ESI: 449/411 (M+1).

Scheme 53

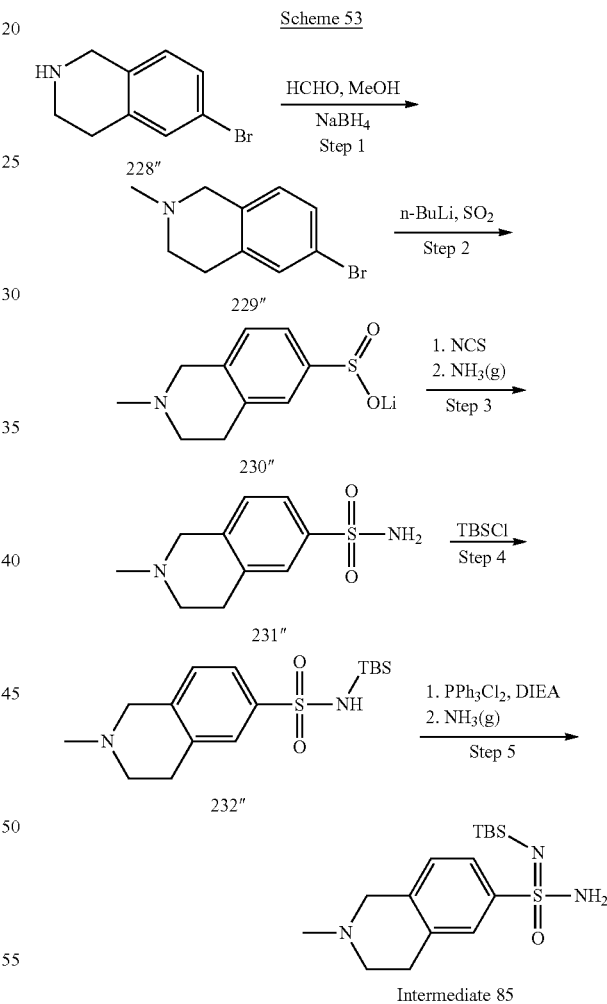

Intermediate 85

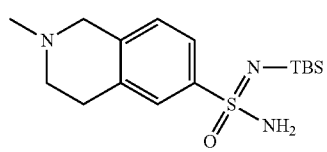

N'-(tert-butyldimethylsilyl)-2-methyl-1,2,3,4-tetra-hydroisoquinoline-6-sulfonimidamide Step 1:
6-Bromo-2-methyl-1,2,3,4-tetrahydroisoquinoline Into a 250-mL round-bottom flask, was placed 6-bromo-1,2,3,4-tetrahydroisoquinoline (6.0 g, 28.3 mmol) in MeOH (100 mL) under $N_2$. To the stirred solution was added HCHO (1.02 g, 34 mmol) in portions at RT. The resulting solution was stirred for 4 h, then $NaBH_3CN$ (3.56 g, 56.6 mmol) was added in portions at RT. The resulting solution was stirred overnight at RT. The reaction was then quenched by the addition of water (100 mL) and extracted with 3×150 mL ethyl acetate. The organic layers were combined and dried over anhydrous sodium sulfate and concentrated under vacuum. The crude product was eluted from a silica gel column with acetate/petroleum ether (1:1). This resulted in 5 g (78.2%) of the title compound as a white solid. MS-ESI: 226/228 (M+1).

Steps 2-5 used similar procedures for converting compound 185" to Intermediate 173" shown in Scheme 44 to afford Intermediate 85 from compound 229. MS-ESI: 238 (M+1).

Scheme 54

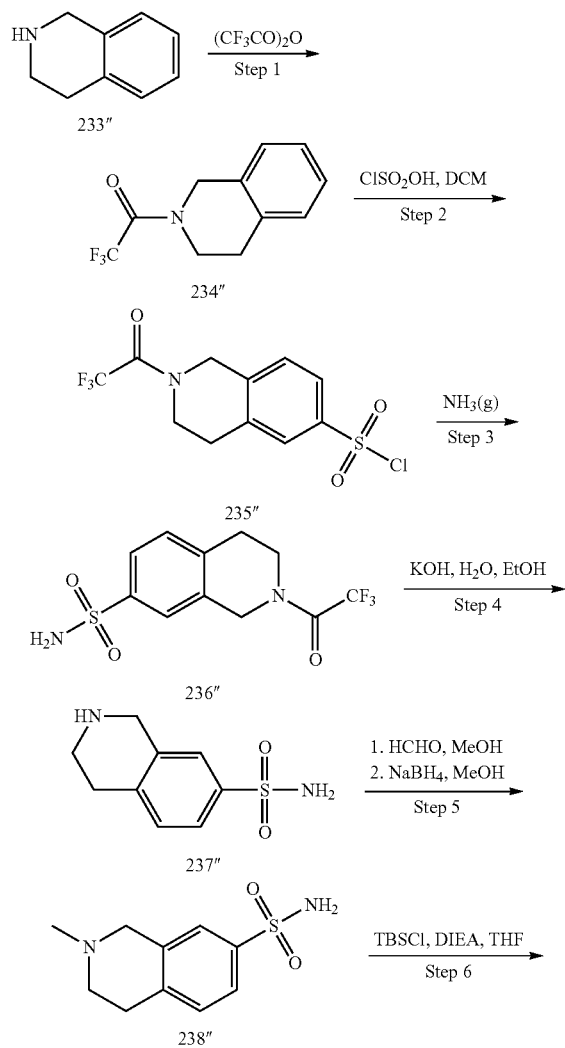

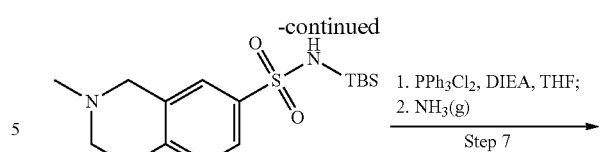

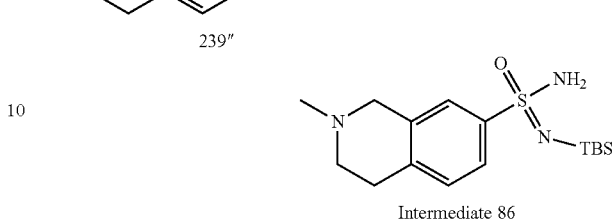

Intermediate 86

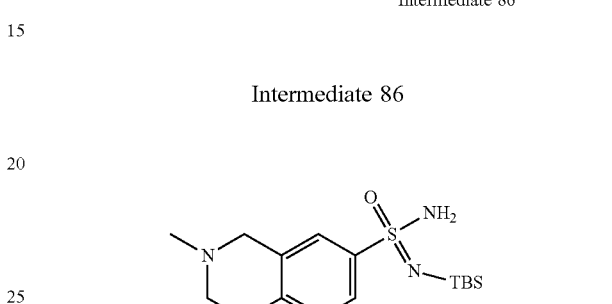

N'-(tert-butyldimethylsilyl)-2-methyl-1,2,3,4-tetra-hydroisoquinoline-7-sulfonimidamide Step 1: 1-(3,4-Dihydroisoquinolin-2(1H)-yl)-2,2,2-trifluoroethanone Into a 250-mL round-bottom flask purged and maintained with an inert atmosphere of nitrogen, was placed 1,2,3,4-tetrahydroisoquinoline (8.0 g, 60.1 mmol) and 2,2,2-trifluoroacetic anhydride (25.2 g, 120 mmol). The resulting solution was stirred for 12 h at RT. The reaction was then quenched by the addition of 100 mL of water/ice. The resulting solution was extracted with 3×100 mL of ethyl acetate and the organic layers were combined and dried over anhydrous sodium sulfate and concentrated under vacuum. This resulted in 10 g (72.6%) of the title compound as a yellow solid. MS-ESI: 230 (M+1).

Steps 2-3 used similar procedures for converting compound 158" to Intermediate 61 shown in Scheme 38 to afford compound 236" from compound 234". MS-ESI: 309 (M+1).

Step 4:
1,2,3,4-Tetrahydroisoquinoline-7-sulfonamide

Into a 100-mL round-bottom flask, was placed 2-(2,2,2-trifluoroacetyl)-1,2,3,4-tetrahydroisoquinoline-7-sulfonamide (8.0 g, 26 mmol) in ethanol (12 mL) and $H_2O$ (60 mL). To the stirred solution was added KOH (7.28 g, 123 mmol) in one portion at RT. The resulting solution was stirred for 12 h at RT. The resulting mixture was concentrated. The crude product was applied onto a silica gel column with DCM/MeOH (10:1). This resulted in 5.0 g (90.8%) of the title compound as a light yellow solid.

Step 5 used similar procedures for converting compound 228" to compound 229" shown in Scheme 53 to afford compound 238" from compound 237". MS-ESI: 227 (M+1).

Steps 6-7 used similar procedures for converting compound 148" to intermediate 59 shown in Scheme 36 to afford intermediate 86 from compound 238". MS-ESI: 340 (M+1).

Scheme 55

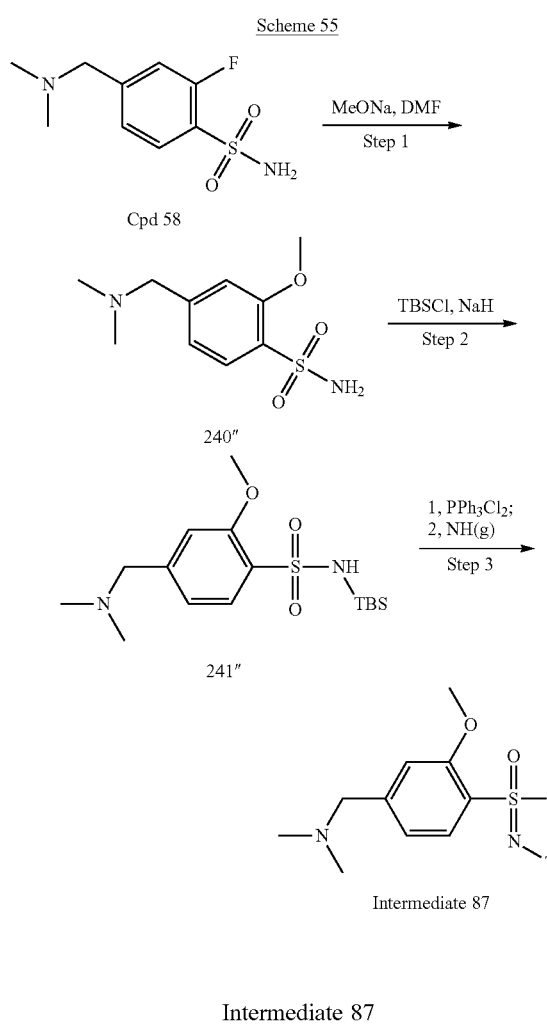

Intermediate 87

N'-(tert-butyldimethylsilyl)-2-methyl-1,2,3,4-tetra-hydroisoquinoline-7-sulfonimidamide Step 1: 4-((Dimethylamino)methyl)-2-methoxybenzene-sulfonamide Into a 50-mL round-bottom flask, was placed 4-[(dimethylamino)methyl]-2-fluorobenzene-1-sulfonamide (1 g, 4.31 mmol) and DMF (10 mL, 0.14 mmol). Then to the above was added sodium methoxide (2.16 g, 40 mmol). The resulting solution was stirred for 12 h at RT. The reaction was then quenched by the addition of 5.0 mL of water. The residue was eluted from a C18 column with ACN:H$_2$O (3:7). This resulted in 800 mg (76.1%) of the title compound as a yellow solid. MS-ESI: 245 (M+1).

Steps 2-3 used similar procedures for converting compound 148″ to intermediate 59 shown in Scheme 36 to afford intermediate 87 from compound 240″. MS-ESI: 358 (M+1).

Scheme 56

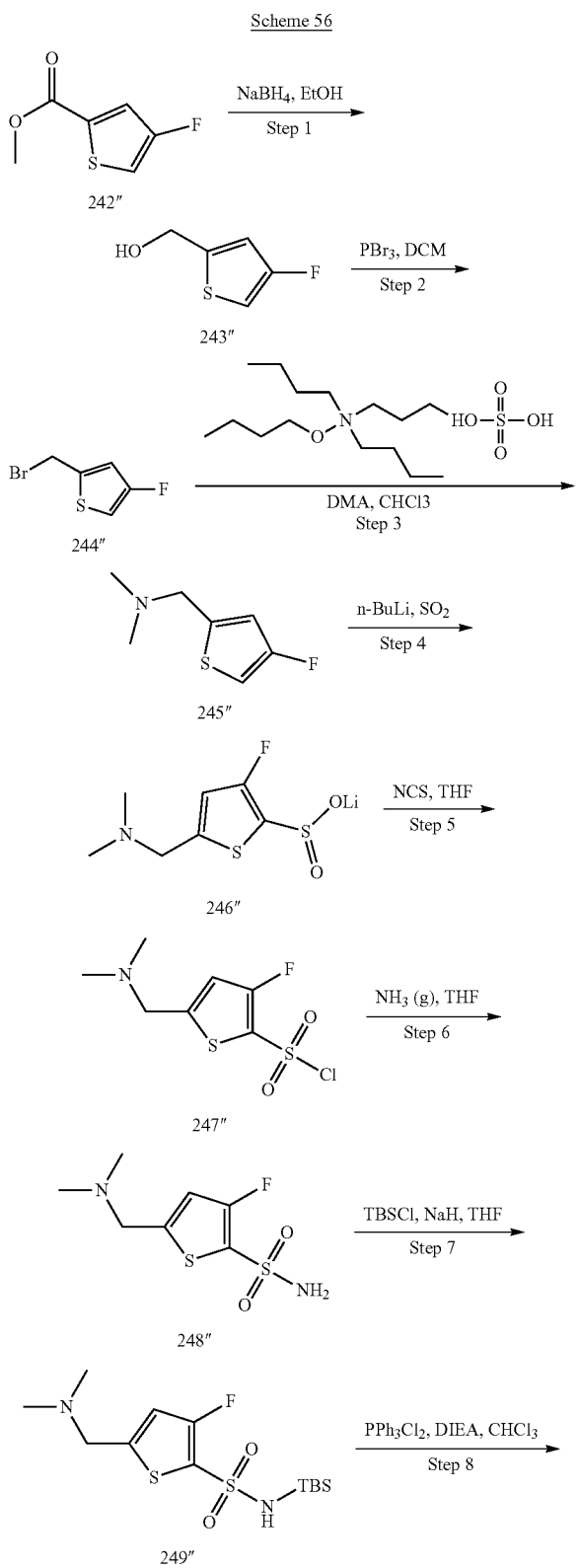

-continued

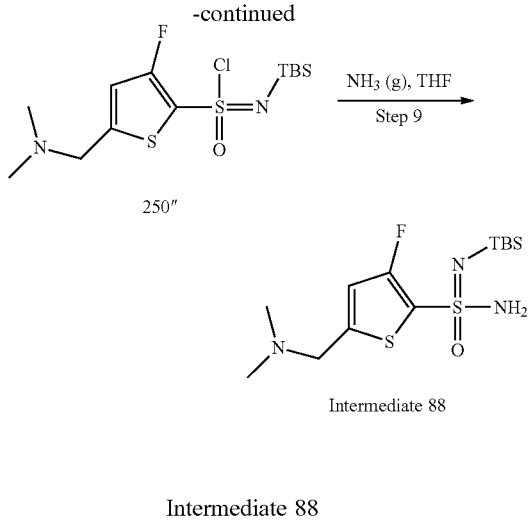

Intermediate 88

N'-(tert-butyldimethylsilyl)-5-((dimethylamino)
methyl)-3-fluorothiophene-2-sulfonimidamide Step 1: (4-Fluorothiophen-2-yl)methanol Into a 1000-mL round-bottom flask, was placed methyl 4-fluorothiophene-2-carboxylate (10 g, 62.4 mmol) in ethanol (300 mL). Then to the above solution was added NaBH₄ (4.62 g, 125 mmol) in portions at 0° C. in an ice/ethanol bath. The resulting solution was stirred for 30 min at 0° C. and then the reaction solution was allowed to react for an additional 16 h at RT. The reaction was then quenched by the addition of 50 mL of water. Then the mixture was concentrated and extracted with 3×100 mL of ethyl acetate and the organic layers were combined and dried over anhydrous sodium sulfate and concentrated under vacuum. This resulted in 6.4 g (77.6%) of the title compound as white oil. MS-ESI: 133 (M+1)

Step 2: 2-(Bromomethyl)-4-fluorothiophene

Into a 250-mL round-bottom flask, was placed (4-fluorothiophen-2-yl)methanol (8.5 g, 64.3 mmol) in DCM (70 mL). To the stirred solution was added PBr₃ (19.2 g, 70.8 mmol) dropwise at 0° C. in an ice/ethanol bath. The resulting solution was stirred for 30 min at 0° C. The resulting solution was allowed to react for an additional 12 h at RT. The reaction was then quenched by the addition of 50 mL of water. Then the mixture was concentrated and extracted with 3×100 mL of ethyl acetate and the organic layers were combined and dried over anhydrous sodium sulfate and concentrated under vacuum. The residue was eluted from a silica gel column with ethyl acetate/petroleum ether (15/85). This resulted in 7.0 g (55.8%) of the title compound as yellow oil. MS-ESI: 194/196 (M+1).

Step 3:
1-(4-Fluorothiophen-2-yl)-N,N-dimethylmethanamine

Into a 250-mL round-bottom flask, was placed 2-(bromomethyl)-4-fluorothiophene (7.4 g, 37.9 mmol) in CHCl₃ (50 mL). To the above solution was added butoxytributyl-14-azane sulfate (6.76 g, 19 mmol) and DMA (37 mL, 425 mmol) with stirring at RT. The resulting solution was stirred for 2 h at 60° C. The reaction was then quenched by the addition of 50 mL of water. Then the mixture was concentrated and extracted with 3×100 mL of ethyl acetate and the organic layers were combined and dried over anhydrous sodium sulfate and concentrated under vacuum. The residue was eluted from a silica gel column with ethyl acetate/petroleum ether (17/83). This resulted in 6.0 g (99.5%) of the title compound as a yellow solid. MS-ESI: 160 (M+1).

Step 4: Lithium 5-((dimethylamino)methyl)-3-fluorothiophene-2-sulfinate

Into a 500-mL 3-necked round-bottom flask purged with and maintained under nitrogen, was placed a solution of [(4-fluorothiophen-2-yl)methyl]dimethylamine (6.2 g, 38.9 mmol) in THF (60 mL). This was followed by the addition of n-BuLi/THF (18.7 mL, 2.5 M) dropwise with stirring at −78° C. in a liquid nitrogen/ethanol bath. The resulting solution was stirred for 30 min at −78° C. To the above SO₂(g) was introduced into the reaction solution at −78° C. The resulting solution was allowed to react for an additional 2 h at RT. The resulting mixture was concentrated. This resulted in 10 g (crude) of the title compound as a yellow solid. MS-ESI: 222 (M−1).

Step 5: 5-((Dimethylamino)methyl)-3-fluorothiophene-2-sulfonyl chloride

Into a 500-mL round-bottom flask, was placed a solution of 5-[(dimethylamino)methyl]-3-fluorothiophene-2-sulfinic acid (10 g, 44.8 mmol) in THF (100 mL). To the above solution was added NCS (7.18 g, 53.8 mmol). The resulting solution was stirred for 30 min at 0° C. and then allowed to react for an additional 2 h at RT. This reaction was used for next step without purification.

Step 6: 5-((Dimethylamino)methyl)-3-fluorothiophene-2-sulfonamide

Into a 500-mL round-bottom flask, was placed a solution of 5-[(dimethylamino)methyl]-3-fluorothiophene-2-sulfonyl chloride (10 g, 38.8 mmol) in THF (100 mL). To the above NH₃ (g) was introduced at RT. The resulting solution was stirred for 30 min at RT. The resulting mixture was concentrated. The residue was eluted from a silica gel column with ethyl acetate/petroleum ether (60/40). This resulted in 2.1 g (22.7%) of the title compound as yellow oil. MS-ESI: 239 (M+1).

Step 7: N-(tert-butyldimethylsilyl)-5-((dimethylamino)methyl)-3-fluorothiophene-2-sulfonamide Into a 100-mL round-bottom flask, was placed a solution of 5-[(dimethylamino)methyl]-3-fluorothiophene-2-sulfonamide (1.8 g, 7.55 mmol) in THF (30 mL) under N₂. To the above solution was added NaH (60% wt. oil dispersion, 640 mg, 15 mmol) with stirring at 0° C. The resulting solution was stirred for 5 min at 0° C. This was followed by the addition of TBSCl (1.37 g, 9.09 mmol) at 0° C. The resulting solution was allowed to react for an additional 15 h at RT. The reaction was then quenched by the addition of 20 mL of water. Then the mixture was concentrated and extracted with 3×100 mL of ethyl acetate and the organic layers were combined and dried over anhydrous sodium sulfate and concentrated under vacuum. The residue was eluted from a silica gel column with ethyl acetate/petroleum ether (1:1). This resulted in 2.0 g (75.2%) of the title compound as yellow oil. MS-ESI: 353 (M+1).

Step 8: N-(tert-butyldimethylsilyl)-5-((dimethyl-amino)methyl)-3-fluorothiophene-2-sulfonimidoyl chloride Into a 500-mL round-bottom flask purged and maintained with an inert atmosphere of nitrogen was placed a solution of PPh₃Cl₂ (29.5 g, 88.7 mmol) in CHCl₃ (50 mL). To the above solution was added DIEA (17.2 g, 133 mmol) dropwise in an ice/water bath. The solution was stirred at RT for 20 minutes. This was followed by the addition of N-(tert-butyldimethylsilyl)-5-[(dimethylamino)methyl]-3-fluorothiophene-2-sulfonamide (15.7 g, 44.4 mmol) in CHCl₃ (30 mL) at 0° C. The resulting solution was allowed to react for an additional 30 min at 0° C. Then the reaction solution was used for next step without purification.

Step 9: N'-(tert-butyldimethylsilyl)-5-((dimethyl-amino)methyl)-3-fluorothiophene-2-sulfonimid-amide Into a 500-mL round-bottom flask purged and maintained with an inert atmosphere of nitrogen, was placed [(tert-butyldimethylsilyl)imino](chloro)[5-[(dimethylamino)methyl]-3-fluorothiophen-2-yl]-λ⁶-sulfanone (16.5 g, 44.4 mmol) in CHCl₃ (80 mL). To the above NH₃(g) was introduced at 0° C. for 15 min. The resulting solution was stirred for 15 min at 0° C. and then allowed to react for an additional 15 h at RT. The resulting mixture was concentrated. The residue was eluted from a silica gel column with ethyl acetate/petroleum ether (60/40). This resulted in 5.8 g (37.2%) of the title compound as a yellow solid. MS-ESI: 352 (M+1).

Intermediate 112

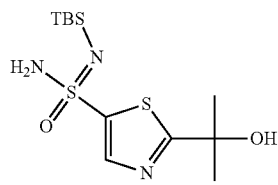

N'-(tert-butyldimethylsilyl)-2-(2-hydroxypropan-2-yl)thiazole-5-sulfonimidamide

Step 1: 2-(2-Hydroxypropan-2-yl)thiazole-5-sulfonimidamide

Into a 250-mL round-bottom flask, was placed a solution of tert-butyl 2-(2-hydroxypropan-2-yl)thiazole-5-sulfonimidoylcarbamate (3.21 g, 10 mmol) in HCl/dioxane (4 M, 50 mL). The resulting solution was stirred for 1 h at RT. The solution was concentrated to give the title compound (3.2 g, crude, yellow oil). MS-ESI: 222 (M+1).

Step 2: N'-(tert-butyldimethylsilyl)-2-(2-hydroxy-propan-2-yl)thiazole-5-sulfonimidamide Into a 250-mL round-bottom flask, was placed 2-(2-hydroxypropan-2-yl)thiazole-5-sulfonimidamide (3.2 g crude, 10 mmol) in THF (100 mL), DIEA (3.87 g, 30 mmol) was added in at RT. Then TBSCl (3.0 g, 20 mmol) was added to the solution in portions. The resulting solution was stirred for 16 h at RT. The solution was concentrated and the crude product was purified by silica gel column with ethyl acetate/petroleum ether (1:1) to give the title compound (2.3 g, yield 70%, yellow solid). MS-ESI: 336 (M+1).

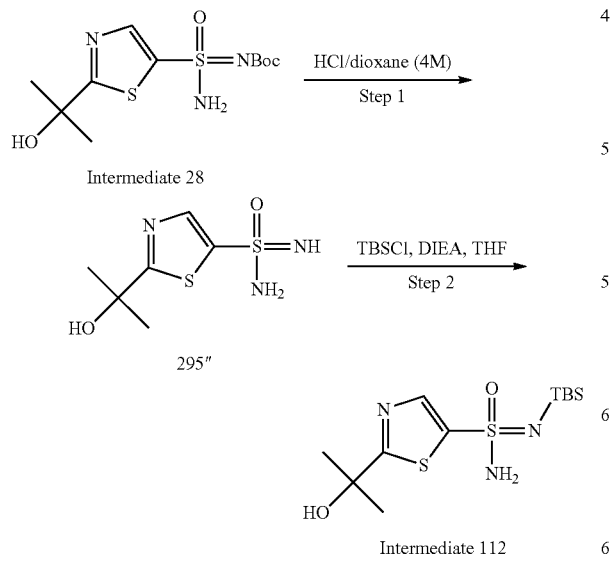

Scheme 68

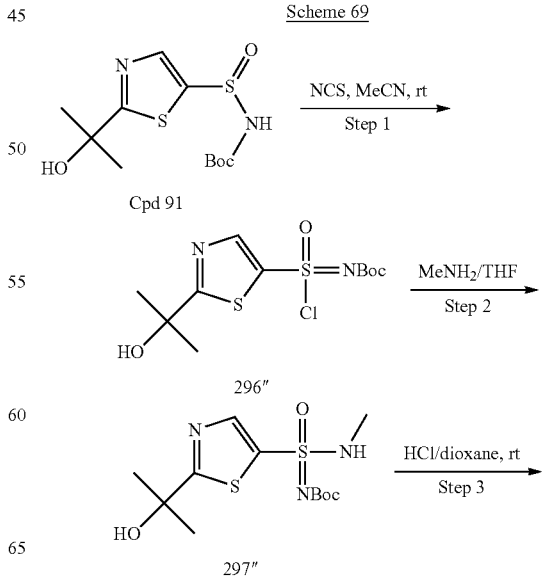

Scheme 69

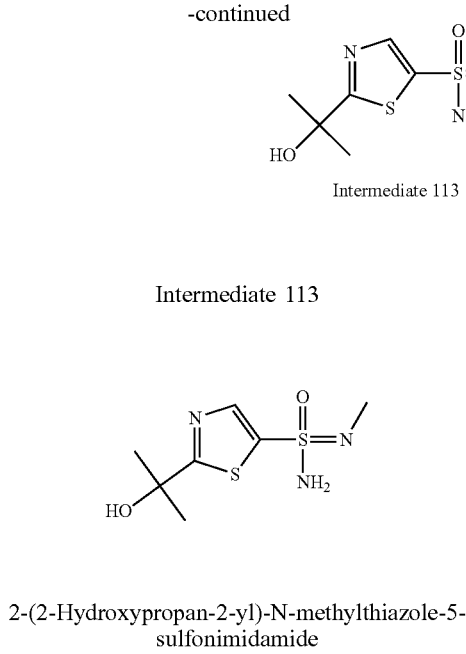

Intermediate 113

Intermediate 113

2-(2-Hydroxypropan-2-yl)-N-methylthiazole-5-sulfonimidamide

Step 1: Tert-butyl (chloro(2-(2-hydroxypropan-2-yl)thiazol-5-yl)(oxo)-λ⁶-sulfaneylidene)carbamate Into a 1-L round-bottom flask, was placed tert-butyl N-[[2-(2-hydroxypropan-2-yl)-1,3-thiazol-5-yl]sulfinyl]carbamate (100 g, 326 mmol) in ACN (500 mL). To the stirred solution was added NCS (65.4 g, 49 mmol). The resulting solution was stirred for 2 h at RT. The resulted solution was concentrated. This resulted in 120 g crude title compound as yellow oil.

Step 2: Tert-((2-(2-hydroxypropan-2-yl)thiazol-5-yl)(methylamino)(oxo)-λ⁶-sulfaneylidene)carbamate Into a 250-mL round-bottom flask, was placed tert-butyl N-[chloro[2-(2-hydroxypropan-2-yl)-1,3-thiazol-5-yl]oxo-λ⁶-sulfanylidene]carbamate (10 g, 29.3 mmol) in THF (100 mL). To the stirred solution was added $CH_3NH_2$ (1.82 g, 58.6 mmol). The resulted solution was stirred for 2 h at RT. The resulted solution was concentrated. The residue was eluted from silica gel with ethyl acetate/petroleum ether (1:1). This resulted in 6.1 g (62%) of the title compound as a yellow solid. MS-ESI: 336 (M+1).

Step 3: 2-(2-Hydroxypropan-2-yl)-N'-methylthiazole-5-sulfonimidamide

Into a 100-mL round-bottom flask, was placed tert-butyl ((2-(2-hydroxypropan-2-yl)thiazol-5-yl)(methylamino)(oxo)-λ⁶-sulfaneylidene)carbamate (3.0 g, 8.94 mmol) in HCl (gas) in 1,4-dioxane (8.0 mL, 26.3 mmol) in one portion at RT. The resulting solution was stirred for 60 min at RT. The resulting mixture was concentrated under vacuum. This resulted in 2.10 g crude title compound as a yellow solid. MS-ESI: 236 (M+1).

The schemes below illustrate the synthesis of Intermediates 89-96, 101-104, 114-117A, and 118"-126", which are isocyanate and precursors thereof as well as other intermediates:

Scheme 57

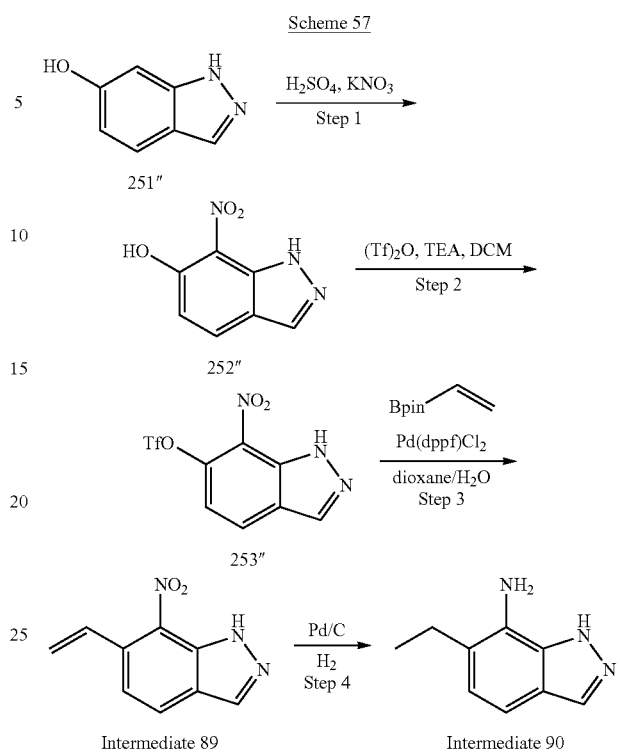

Intermediate 89

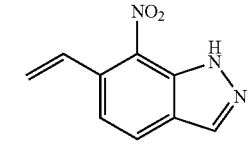

7-Nitro-6-vinyl-1H-indazole

Step 1: 7-Nitro-1H-indazol-6-ol

Into a 25-mL round-bottom flask, was placed 1H-indazol-6-ol (500 mg, 3.73 mmol). This was followed by the addition of $H_2SO_4$ (5.0 mL) in several batches at 0° C. To this was added $KNO_3$ (377 mg, 3.73 mmol) in portions at 0° C. The resulting solution was stirred for 30 min at 0° C. in a water/ice bath. The reaction was then quenched by the addition of 50 mL of water/ice. The solids were collected by filtration. This resulted in 350 mg (52.4%) of the title compound as a brown solid. MS-ESI: 180 (M+1).

Step 2: 7-Nitro-1H-indazol-6-yl trifluoromethanesulfonate

Into a 50-mL round-bottom flask, was placed 7-nitro-1H-indazol-6-ol (350 mg, 1.95 mmol) in DCM (10 mL), TEA (593 mg, 5.86 mmol), $Tf_2O$ (717 mg, 2.54 mmol). The resulting solution was stirred for 16 h at RT. The resulting solution was diluted with 20 mL of $H_2O$. The resulting solution was extracted with 3×20 mL of ethyl acetate dried over anhydrous sodium sulfate and concentrated. The residue was eluted from a silica gel column with ethyl acetate/petroleum ether (1:3). This resulted in 80 mg (13.2%) of the title compound as a yellow solid. MS-ESI: 312 (M+1).

Step 3: 7-Nitro-6-vinyl-1H-indazole

Into a 50-mL round-bottom flask purged and maintained with an inert atmosphere of nitrogen, was placed 7-nitro-1H-indazol-6-yl trifluoromethanesulfonate (100 mg, 0.32 mmol) in dioxane (10 mL) and $H_2O$ (2.0 mL), $Cs_2CO_3$ (209 mg, 0.64 mmol), 2-ethenyl-4,4,5,5-tetramethyl-1,3,2-dioxaborolane (59.4 mg, 0.39 mmol), Pd(dppf)Cl$_2$ (23.5 mg, 0.030 mmol). The resulting solution was stirred for 16 h at 90° C. in an oil bath. Then the mixture was concentrated under vacuum. The residue was eluted from a silica gel column with ethyl acetate/petroleum ether (1:3). This resulted in 50 mg (82.6%) of the title compound as a yellow solid. MS-ESI: 190 (M+1).

Intermediate 90

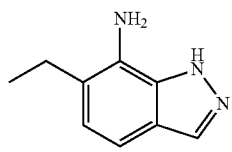

6-Ethyl-1H-indazol-7-amine

Step 4: 6-Ethyl-1H-indazol-7-amine

Into a 50-mL round-bottom flask, was placed 6-ethenyl-7-nitro-1H-indazole (50 mg) in MeOH (10 mL), and Pd/C (10% wt., 5.0 mg). The flask was evacuated and flushed three times with hydrogen. The resulting solution was stirred for 12 h at RT under an atmosphere of hydrogen. The Pd/C catalysts were filtered out, the filtrate was concentrated under vacuum. This resulted in 44 mg of the title compound as a yellow solid. MS-ESI: 162 (M+1).

Scheme 58

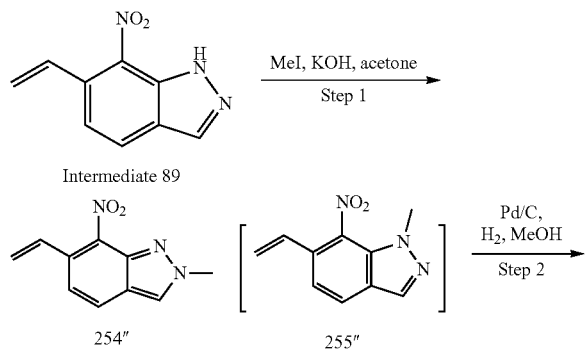

-continued

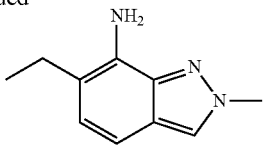

Intermediate 91

Intermediate 91

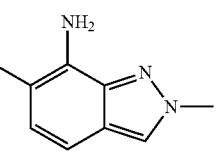

6-Ethyl-2-methyl-2H-indazol-7-amine

Step 1: 2-Methyl-7-nitro-6-vinyl-2H-indazole

Into a 50-mL round-bottom flask, was placed 6-ethenyl-7-nitro-1H-indazole (380 mg, 2.01 mmol) in acetone (20 mL), KOH (225 mg, 4.02 mmol). This was followed by the addition of MeI (342 mg, 2.41 mmol) dropwise with stirring. The resulting solution was stirred for 1 h at 0° C. in a water/ice bath. The resulting solution was diluted with 20 mL of $H_2O$. The resulting solution was extracted with 3×30 ml of ethyl acetate dried over anhydrous sodium sulfate and concentrated. The residue was eluted from a silica gel column with ethyl acetate/petroleum ether (1:1). This resulted in 210 mg (51.5%) of 254" as a yellow solid and 180 mg (44%) of 255" as a yellow solid. MS-ESI: 208 (M+1).

Step 2: 6-Ethyl-2-methyl-2H-indazol-7-amine

Into a 50-mL round-bottom flask purged and maintained with an inert atmosphere of $N_2$, was placed 6-ethenyl-1-methyl-7-nitro-1H-indazole (210 mg, 1.03 mmol) in MeOH (15 mL) and Pd/C (10% wt., 50 mg). The flask was evacuated and flushed three times with hydrogen. The resulting solution was stirred for 12 h at RT under an atmosphere of hydrogen. The Pd/C catalysts were filtered out, and the filtrate was concentrated under vacuum. This resulted in 160 mg (88.4%) of the title compound as a yellow solid. MS-ESI: 176 (M+1).

TABLE 14

The Intermediates in the following Table were prepared using the similar procedures for converting compound 254" to Intermediate 91 shown in Scheme 58 from 255".

| Intermediate # | Structure | IUPAC Name | Exact Mass [M + H]+ |
|---|---|---|---|
| Intermediate 92 | (structure shown) | 6-Ethyl-1-methyl-1H-indazol-7-amine | 176 |

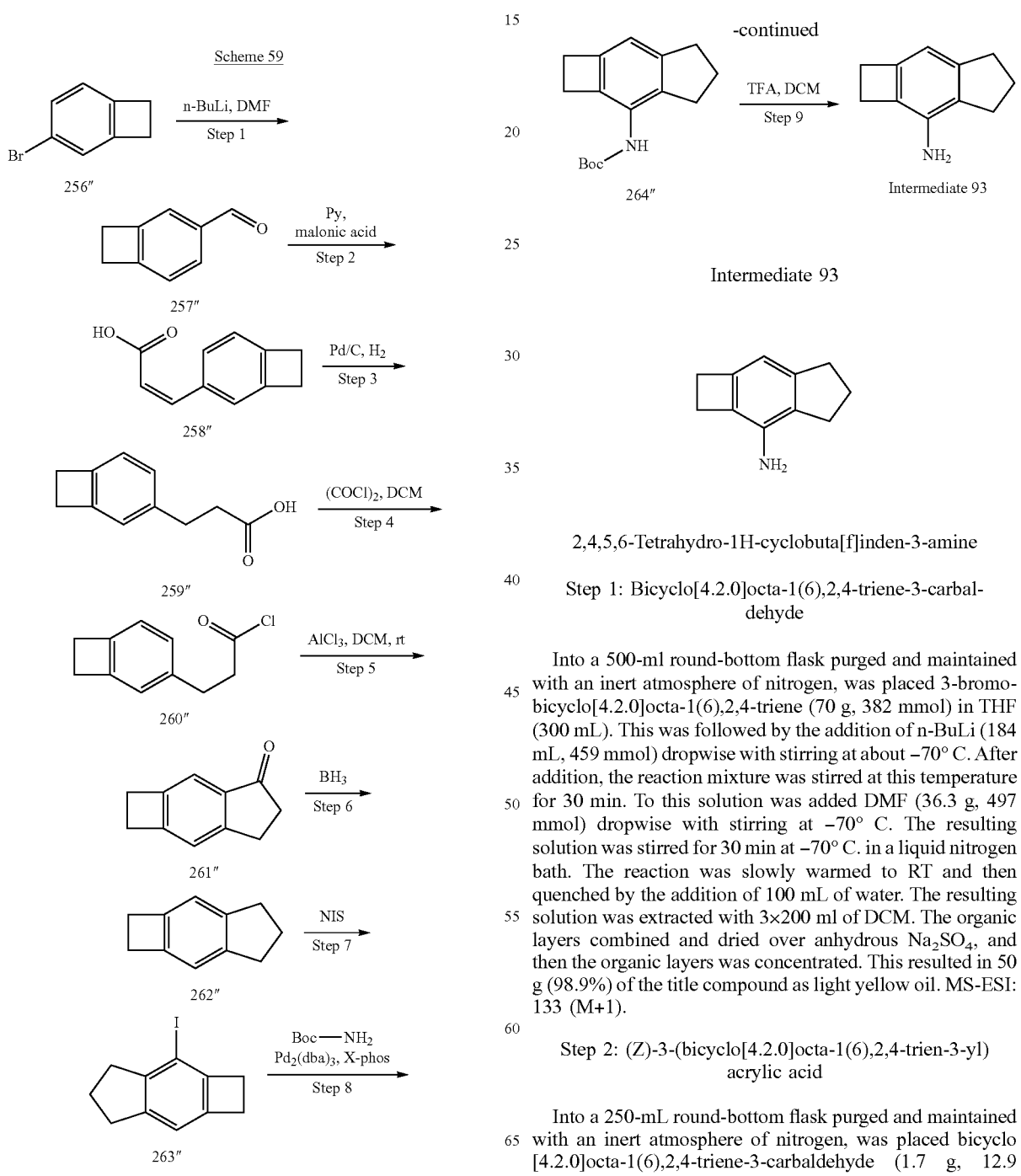

Intermediate 93

2,4,5,6-Tetrahydro-1H-cyclobuta[f]inden-3-amine

Step 1: Bicyclo[4.2.0]octa-1(6),2,4-triene-3-carbaldehyde

Into a 500-ml round-bottom flask purged and maintained with an inert atmosphere of nitrogen, was placed 3-bromobicyclo[4.2.0]octa-1(6),2,4-triene (70 g, 382 mmol) in THF (300 mL). This was followed by the addition of n-BuLi (184 mL, 459 mmol) dropwise with stirring at about −70° C. After addition, the reaction mixture was stirred at this temperature for 30 min. To this solution was added DMF (36.3 g, 497 mmol) dropwise with stirring at −70° C. The resulting solution was stirred for 30 min at −70° C. in a liquid nitrogen bath. The reaction was slowly warmed to RT and then quenched by the addition of 100 mL of water. The resulting solution was extracted with 3×200 ml of DCM. The organic layers combined and dried over anhydrous $Na_2SO_4$, and then the organic layers was concentrated. This resulted in 50 g (98.9%) of the title compound as light yellow oil. MS-ESI: 133 (M+1).

Step 2: (Z)-3-(bicyclo[4.2.0]octa-1(6),2,4-trien-3-yl)acrylic acid

Into a 250-mL round-bottom flask purged and maintained with an inert atmosphere of nitrogen, was placed bicyclo[4.2.0]octa-1(6),2,4-triene-3-carbaldehyde (1.7 g, 12.9 mmol) in pyridine (20 mL), propanedioic acid (1.99 g, 19.2 mmol) and piperidine (110 mg, 1.29 mmol). The resulting solution was stirred for overnight at 90° C. in an oil bath. The resulting mixture was concentrated. This resulted in 2.1 g (93.7%) of the title compound as a solid. MS-ESI: 173 (M−1).

Step 3: 3-(Bicyclo[4.2.0]octa-1(6),2,4-trien-3-yl) propanoic acid

Into a 250-mL round-bottom flask, was placed 2-(Z or E)-3-[bicyclo[4.2.0]octa-1(6),2,4-trien-3-yl]prop-2-enoic acid (2.1 g, 12.1 mmol) and Pd/C (10% wt., 200 mg). The flask was evacuated and flushed three times with hydrogen. The resulting solution was stirred for 12 h at RT under an atmosphere of hydrogen. The Pd/C catalysts were filtered out, the filtrate was concentrated under vacuum. This resulted in 2.1 g (98.9%) of the title compound as a solid. MS-ESI: 175 (M−1).

Step 4: 3-(Bicyclo[4.2.0]octa-1(6),2,4-trien-3-yl) propanoyl chloride

Into a 250-mL round-bottom flask purged and maintained with an inert atmosphere of nitrogen, was placed 3-[bicyclo [4.2.0]octa-1(6),2,4-trien-3-yl]propanoic acid (10 g, 56.8 mmol) in DCM (100 mL). This was followed by the addition of oxalyl chloride (7.2 g, 56.8 mmol) dropwise with stirring at 0° C. The resulting solution was stirred for 2 h at 0° C. in a water/ice bath. The resulting mixture was concentrated. This resulted in 10 g (90.5%) of the title compound as light yellow oil.

Step 5: 1,2,5,6-Tetrahydro-4H-cyclobuta[f]inden-4-one

Into a 100-mL round-bottom flask, was placed 3-[bicyclo [4.2.0]octa-1(6),2,4-trien-3-yl]propanoyl chloride (5.0 g, 25.7 mmol) in DCM (50 mL). This was followed by the addition of AlCl$_3$ (3.4 g, 25.7 mmol) in portions at 0° C. for 10 min. The resulting solution was stirred for 1 h at 0° C. in a water/ice bath. The reaction was then quenched by the addition of 100 mL of water. The resulting solution was extracted with 2×50 mL of DCM. The organic layers combined and dried over anhydrous Na$_2$SO$_4$, then concentrated. The residue was eluted from a silica gel column with ethyl acetate/petroleum ether (1:20 to 1:15). This resulted in 3.5 g (86.1%) of the title compound as a white solid. $^1$H NMR (300 MHz, CDCl$_3$) δ 7.45 (s, 1H), 7.17 (s, 1H), 3.22 (m, 4H), 3.18-3.00 (m, 2H), 2.73-2.63 (m, 2H).

Step 6: 2,4,5,6-Tetrahydro-1H-cyclobuta[f]indene

Into a 500-mL round-bottom flask purged and maintained with an inert atmosphere of nitrogen, was placed 1,2,5,6-tetrahydrocyclobuta[f]inden-4-one (20 g, 126 mmol) in THF (200 mL). This was followed by the addition of BH$_3$-Me$_2$S (25.3 mL, 253 mmol, 10 M) dropwise at 0° C. in an ice bath. The resulting solution was stirred for 14 h at 70° C. in an oil bath. The reaction was then quenched by the addition of 20 mL of MeOH. The resulting mixture was concentrated. The residue was eluted from a silica gel column with ethyl acetate/petroleum ether (1:100 to 1:50). This resulted in 15 g (82.3%) of the title compound as colorless oil. $^1$H NMR (300 MHz, CDCl$_3$) δ 6.95 (s, 2H), 3.10 (s, 4H), 2.88 (t, J=7.4 Hz, 4H), 2.03 (p, J=7.4 Hz, 2H).

Step 7: 3-Iodo-2,4,5,6-tetrahydro-1H-cyclobuta[f] indene

Into a 500-mL round-bottom flask, was placed acetic acid (100 mL), 2,4,5,6-tetrahydro-1H-cyclobuta[f]indene (15 g, 104 mmol) and NIS (35.1 g, 156 mmol). The resulting solution was stirred for 3 h at 50° C. in an oil bath. The resulting solution was diluted with 200 mL of water. The mixture was extracted with 3×100 mL of DCM. The organic layers combined and dried over anhydrous Na$_2$SO$_4$, then concentrated. The residue was eluted from a silica gel column with ethyl acetate/petroleum ether (1:100 to 1:80). This resulted in 5.0 g (17.8%) of the title compound as yellow oil.

Step 8: Tert-butyl (2,4,5,6-tetrahydro-1H-cyclobuta [f]inden-3-yl)carbamate

Into a 250-mL round-bottom flask purged and maintained with an inert atmosphere of nitrogen, was placed 3-iodo-2, 4,5,6-tetrahydro-1H-cyclobuta[f]indene (5.0 g, 18.5 mmol) in toluene (100 mL), tert-butyl carbamate (6.5 g, 55.5 mmol), X-phos (900 mg, 1.85 mmol), Pd$_2$(dba)$_3$ (800 mg, 0.93 mmol), t-BuOK (6.2 g, 55.5 mmol). The resulting solution was stirred for 14 h at 100° C. in an oil bath. The resulting mixture was concentrated. The residue was eluted from a silica gel column with ethyl acetate/petroleum ether (1:50 to 1:20). This resulted in 3.0 g (83.3%) of the title compound as a white solid. MS-ESI: 260 (M+1).
$^1$H NMR (300 MHz, CDCl$_3$) δ 6.72 (s, 1H), 6.13 (br, 1H), 3.26 (d, J=4.5 Hz, 2H), 3.01 (d, J=4.5 Hz, 2H), 2.90 (t, J=7.4 Hz, 2H), 2.75 (t, J=7.4 Hz, 2H), 2.06 (p, J=7.4 Hz, 2H), 1.52 (s, 9H).

Step 9: 2,4,5,6-Tetrahydro-1H-cyclobuta[f]inden-3-amine

Into a 100-mL round-bottom flask, was placed tert-butyl2, 4,5,6-tetrahydro-1H-cyclobuta[f]inden-3-ylcarbamate (3.0 g, 11.6 mmol) in DCM (20 mL), 2,2,2-trifluoroacetic acid (5.0 mL). The resulting solution was stirred for 2 h at RT. The resulting solution was diluted with 50 mL of water. The pH value of the solution was adjusted to 10 with sat. aqueous Na$_2$CO$_3$. The resulting solution was extracted with 3×20 mL of DCM. The organic layers combined and dried over anhydrous Na$_2$SO$_4$, then concentrated. This resulted in 1.5 g (81.4%) of the title compound as a yellow solid. MS-ESI: 160 (M+1).

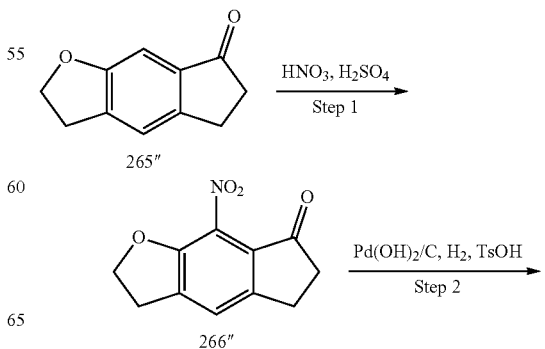

Scheme 60

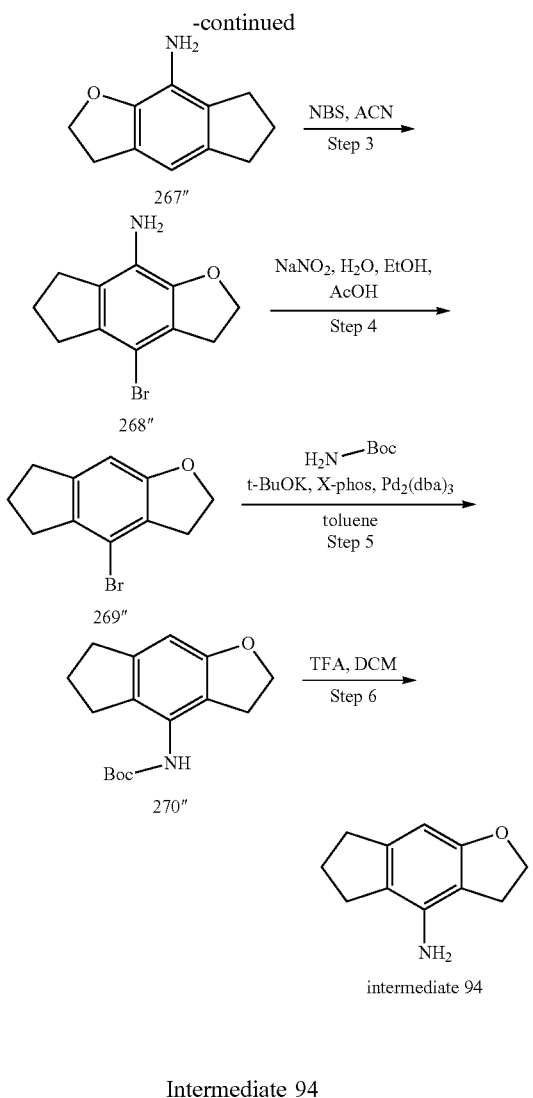

Intermediate 94

3,5,6,7-tetrahydro-2H-indeno[5,6-b]furan-4-amine

Step 1: 8-Nitro-2,3,5,6-tetrahydro-7H-indeno[5,6-b]furan-7-one

Into a 100-mL round-bottom flask, was placed 2H,3H,5H,6H,7H-indeno[5,6-b]furan-7-one (4 g, 23 mmol) in H$_2$SO$_4$ (20 mL). This was followed by the addition of HNO$_3$ (2.13 g, 23 mmol, 68%) dropwise with stirring at 0° C. in an ice/ethanol bath. The resulting solution was stirred for 1 h at 0° C. The reaction was then quenched by the addition of 200 mL of water/ice. The solids were collected by filtration. This resulted in 4.0 g (79.5%) of the title compound as a light brown solid. MS-ESI: 220 (M+1).

Step 2: 3,5,6,7-Tetrahydro-2H-indeno[5,6-b]furan-8-amine

Into a 100-mL round-bottom flask purged and maintained with an inert atmosphere of nitrogen, was placed 8-nitro-2H,3H,5H,6H,7H-indeno[5,6-b]furan-7-one (4.0 g, 18.3 mmol) in MeOH (50 mL), TsOH (1.0 mL), Pd(OH)$_2$/C (20% wt., 1 g). The flask was evacuated and flushed three times with hydrogen. The resulting solution was stirred for 16 h at RT under an atmosphere of hydrogen. The solids were filtered out. The resulting mixture was concentrated. The residue was dissolved in 50 mL of EA. The resulting mixture was washed with 2×50 ml of NaHCO$_3$ and 3×40 ml of H$_2$O. The mixture was dried over anhydrous sodium sulfate. The residue was eluted from a silica gel column with ethyl acetate/petroleum ether (1:9). This resulted in 1.1 g (34.4%) of the title compound as a yellow solid. MS-ESI: 176 (M+1).

Step 3: 4-Bromo-3,5,6,7-tetrahydro-2H-indeno[5,6-b]furan-8-amine

Into a 50-mL round-bottom flask, was placed 2H,3H,5H,6H,7H-indeno[5,6-b]furan-8-amine (1.1 g, 6.28 mmol) in ACN (30 mL) and NBS (1.34 g, 7.53 mmol). The resulting solution was stirred for 2 h at RT. The resulting mixture was concentrated. The residue was eluted from a silica gel column with ethyl acetate/petroleum ether (1:8). This resulted in 83 mg (52%) of the title compound as a yellow solid. MS-ESI: 254 (M+1).

Step 4: 4-Bromo-3,5,6,7-tetrahydro-2H-indeno[5,6-b]furan

Into a 50-mL round-bottom flask, was placed 4-bromo-2H,3H,5H,6H,7H-indeno[5,6-b]furan-8-amine (500 mg, 1.97 mmol) in ethanol (15 mL) and acetic acid (3.0 mL, 0.050 mmol). To the above solution was added NaNO$_2$ (1.36 g, 19.7 mmol) in H$_2$O (3 mL) dropwise at 0° C. The resulting solution was stirred for 2 h at RT. The resulting solution was diluted with 30 mL of H$_2$O. The resulting solution was extracted with 3×30 ml of ethyl acetate dried over anhydrous sodium sulfate and concentrated. The residue was eluted from a silica gel column with ethyl acetate/petroleum ether (1:10). This resulted in 100 mg (21.3%) of the title compound as a yellow solid. MS-ESI: 239 (M+1).

Step 5: Tert-butyl (3,5,6,7-tetrahydro-2H-indeno[5,6-b]furan-4-yl)carbamate

Into a 50-mL round-bottom flask purged and maintained with an inert atmosphere of nitrogen, was placed 4-bromo-2H,3H,5H,6H,7H-indeno[5,6-b]furan (120 mg, 0.50 mmol) in toluene (15 mL), t-BuOK (282 mg, 2.51 mmol), tert-butyl carbamate (588 mg, 5.02 mmol), Xphos (47.8 mg, 0.10 mmol), and Pd$_2$(dba)$_3$CHCl$_3$ (104 mg, 0.10 mmol). The resulting solution was stirred for 16 h at 100° C. in an oil bath. The resulting mixture was concentrated. The residue was eluted from a silica gel column with ethyl acetate/petroleum ether (1:5). This resulted in 80 mg (57.9%) of the title compound as a yellow solid. MS-ESI: 276 (M+1).

Step 6: 3,5,6,7-Tetrahydro-2H-indeno[5,6-b]furan-4-amine

Into a 50-mL round-bottom flask, was placed tert-butyl N-[2H,3H,5H,6H,7H-indeno[5,6-b]furan-4-yl] carbamate (80 mg, 0.29 mmol) in DCM (8 mL) and TFA (3.0 mL, 0.030 mmol). The resulting solution was stirred for 2 h at room temperature. The resulting mixture was concentrated. The residue was dissolved in 15 mL of DCM. The resulting mixture was washed with 2×15 ml of NaOH (aq.). The organic layer was dried with $Na_2SO_4$ and then concentrated. This resulted in 50 mg (98.2%) of the title compound as a yellow solid. MS-ESI: 176 (M+1).

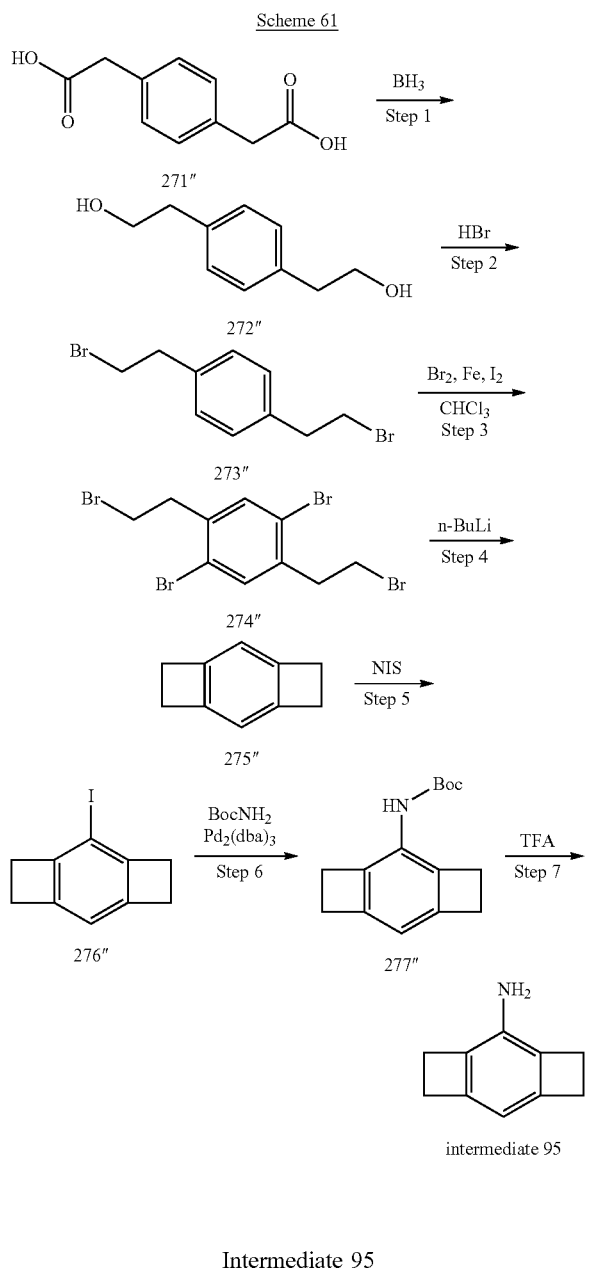

Intermediate 95

Tricyclo[6.2.0.0$^{3,6}$]deca-1,3(6),7-trien-2-amine

Step 1: 2,2'-(1,4-Phenylene)bis(ethan-1-ol)

Into a 1.0-L round-bottom flask purged and maintained with an inert atmosphere of nitrogen, was placed 2-[4-(carboxymethyl)phenyl]acetic acid (40 g, 200 mmol) in THF (500 mL). This was followed by the addition of $BH_3$-$Me_2S$ (60 mL, 600 mmol, 10 M) dropwise with stirring at 0° C. The resulting solution was stirred for 24 h at RT. The reaction was then quenched by the addition of 200 mL of water. The resulting solution was extracted with 2×150 mL of ethyl acetate. The organic layers combined and dried over anhydrous $Na_2SO_4$, then concentrated. The residue was eluted from a silica gel column with ethyl acetate/petroleum ether (1:10 to 1:3). This resulted in 28 g (81.8%) of the title compound as brown oil. MS-ESI: 167 (M+1).

Step 2: 1,4-Bis(2-bromoethyl)benzene

Into a 50-mL round-bottom flask purged and maintained with an inert atmosphere of nitrogen, was placed 2-[4-(2-hydroxyethyl)phenyl]ethan-1-ol (28 g, 168 mmol) in aq. HBr (300 mL, 40% wt.).

The resulting solution was stirred for 5 h at 100° C. in an oil bath. The resulting solution was diluted with 500 mL of water. The resulting solution was extracted with 3×200 mL of DCM. The organic layers combined, then concentrated. This resulted in 40 g (81.4%) of the title compound as a white solid. MS-ESI: 291, 293, 295 (M+1).

Step 3: 1,4-Dibromo-2,5-bis(2-bromoethyl)benzene

Into a 500-mL round-bottom flask, was placed 1,4-bis(2-bromoethyl)benzene (30 g, 103 mmol) in trichloromethane (200 mL). To the above solution was added I2 (0.78 g, 3.08 mmol), iron powder (0.75 g, 13.4 mmol), $Br_2$ (41 g, 257 mmol). The resulting solution was stirred for 24 h at RT. The reaction was then quenched by the addition of aqueous $Na_2SO_3$. The resulting solution was extracted with 3×200 mL DCM and the organic layers was combined and dried over anhydrous $Na_2SO_4$ then concentrated. This resulted in 40 g (86.6%) of the title compound as a white solid. MS-ESI: 449/451/453 (M+1).

Step 4: Tricyclo[6.2.0.0$^{3,6}$]deca-1,3(6),7-triene

Into a 1000-mL round-bottom flask purged and maintained with an inert atmosphere of nitrogen, was placed 1,4-dibromo-2,5-bis(2-bromoethyl)benzene (40 g, 88.9 mmol) in THF (400 mL). This was followed by the addition of n-BuLi (74.7 mL, 187 mmol, 2.5 M) dropwise with stirring at −78° C. in a liquid nitrogen bath. The resulting solution was stirred for 30 min at −78° C. The reaction was then quenched by the addition of aqueous $NH_4Cl$ (300 ml) and extracted with 2×200 mL of DCMDCM and the organic layers was combined and dried over anhydrous $Na_2SO_4$ then concentrated. This resulted in 8.0 g (69.1%) of the title compound as a light yellow solid.

Step 5: 2-Iodotricyclo[6.2.0.0$^{3,6}$]deca-1,3(6),7-triene

Into a 250-mL round-bottom flask purged and maintained with an inert atmosphere of nitrogen, was placed tricyclo[6.2.0.0$^{3,6}$]deca-1,3(6),7-triene (8 g, 61.45 mmol) in acetic acid (50 mL) and NIS (20.7 g, 92.2 mmol). The resulting solution was stirred for 3 h at 50° C. in an oil bath. The resulting solution was diluted with 100 mL of water. The reaction was then quenched by the addition of aqueous Na$_2$SO$_3$. The resulting solution was extracted with 3×50 mL of DCM and the organic layers was combined and dried over anhydrous Na$_2$SO$_4$ then concentrated. The residue was eluted from a silica gel column with ethyl acetate/petroleum ether (1:100). This resulted in 2.5 g (18.2%) of the title compound as a white solid.

Step 6: Tert-butyl tricyclo[6.2.0.0$^{3,6}$]deca-1,3(6),7-trien-2-ylcarbamate

Into a 250-mL round-bottom flask purged and maintained with an inert atmosphere of nitrogen, was placed 2-iodotricyclo[6.2.0.0$^{3,6}$]deca-1,3(6),7-triene (2.5 g, 9.76 mmol) in toluene (50 mL). To the stirred solution was added tert-butyl carbamate (3.43 g, 29.3 mmol), Pd$_2$(dba)$_3$ (447 mg, 0.49 mmol), Xphos (466 mg, 0.98 mmol), and t-BuOK (3.29 g, 29.3 mmol). The resulting solution was stirred for 14 h at 100° C. in an oil bath. The resulting mixture was concentrated. The residue was eluted from a silica gel column with ethyl acetate/petroleum ether (1:50 to 1:30). This resulted in 1.5 g (62.6%) of the title compound as a light yellow solid. MS-ESI: 246 (M+1).

Step 7: Tricyclo[6.2.0.0$^{3,6}$]deca-1,3(6),7-trien-2-amine

Into a 50-mL round-bottom flask purged and maintained with an inert atmosphere of nitrogen, was placed tert-butyl N-[tricyclo[6.2.0.0$^{3,6}$]deca-1,3(6),7-trien-2-yl]carbamate (1.5 g, 6.1 mmol) in DCM (20 mL) and 2,2,2-trifluoroacetic acid (4.0 mL). The resulting solution was stirred for 2 h at RT. The resulting mixture was concentrated. This resulted in 800 mg (90.1%) of the title compound as a brown solid. MS-ESI: 146 (M+1).

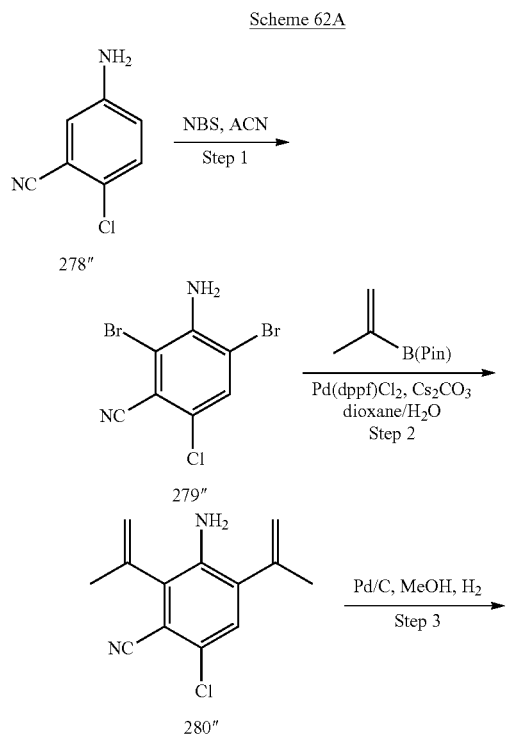

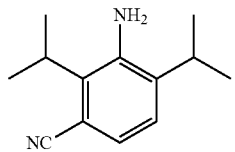

Intermediate 96

Intermediate 96

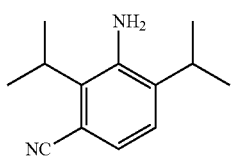

3-Amino-2,4-diisopropylbenzonitrile

Step 1: 3-Amino-2,4-dibromo-6-chlorobenzonitrile

Into a 500-mL round-bottom flask, was placed 5-amino-2-chlorobenzonitrile (10 g, 65.8 mmol), ACN (200 mL) and NBS (17.6 g, 98.7 mmol). The resulting solution was stirred for 14 h at RT. The resulting mixture was concentrated. The residue was eluted from a silica gel column with ethyl acetate/petroleum ether (1:15 to 1:5). This resulted in 18 g of the title compound as a yellow solid. MS-ESI: 310, 312 (M+1).

Step 2: 3-Amino-6-chloro-2,4-di(prop-1-en-2-yl)benzonitrile

Into a 500-mL round-bottom flask purged and maintained with an inert atmosphere of nitrogen, was placed 3-amino-2,4-dibromo-6-chlorobenzonitrile (15 g, 48 mmol) in dioxane (200 mL) and H$_2$O (20 mL), 2-(tetramethyl-1,3,2-dioxaborolan-2-yl)prop-2-en-1-ylium (17.6 g, 106 mmol), Cs$_2$CO$_3$ (47 g, 144 mmol), and Pd(dppf)Cl$_2$ (1.5 g, 4.8 mmol). The resulting solution was stirred for 14 h at 100° C. in an oil bath. The resulting mixture was concentrated. The residue was eluted from a silica gel column with ethyl acetate/petroleum ether (1:0 to 1:25). This resulted in 10 g of the title compound as brown oil. MS-ESI: 233 (M+1).

Step 3: 3-Amino-2,4-diisopropylbenzonitrile

Into a 500-mL round-bottom flask purged and maintained with an inert atmosphere of nitrogen, was placed 3-amino-6-chloro-2,4-bis(prop-1-en-2-yl)benzonitrile (10 g, 43 mmol) in MeOH (50 mL). Then Pd/C (10% wt., 2.0 g) was added. The flask was evacuated and flushed three times with hydrogen. The resulting solution was stirred for 16 h at RT under an atmosphere of hydrogen. The solids were filtered out. The resulting filtrate was concentrated under vacuum. This resulted in 8.0 g of the title compound as brown oil. MS-ESI: 203 (M+1).

Scheme 65

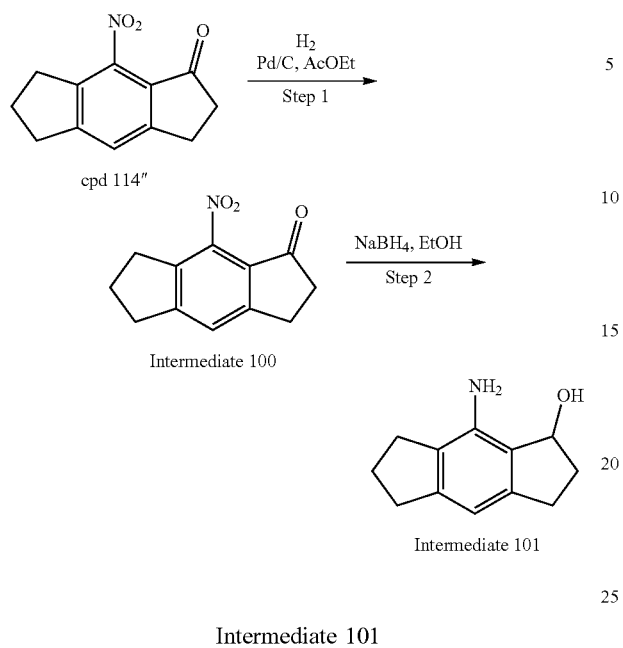

8-Amino-1,2,3,5,6,7-hexahydro-s-indacen-1-ol

Step 1: 8-Amino-3,5,6,7-tetrahydro-s-indacen-1(2H)-one

Into a 250-mL round-bottom flask purged and maintained with an inert atmosphere of hydrogen, was placed a solution of 8-nitro-1,2,3,5,6,7-hexahydro-s-indacen-1-one (700 mg, 3.22 mmol) in MeOH (10 mL), and Pd/C (10% wt., 100 mg). The flask was evacuated and flushed three times with hydrogen. The resulting solution was stirred for 2 h at RT under an atmosphere of hydrogen. The Pd/C catalysts were filtered out, and the filtrate was concentrated under vacuum. This resulted in 550 mg (91.2%) of the title compound as a yellow oil. MS-ESI: 188 (M+1).

Step 2: 8-Amino-1,2,3,5,6,7-hexahydro-s-indacen-1-ol

Into a 100 mL round-bottom flask, was placed a solution of 8-amino-3,5,6,7-tetrahydro-s-indacen-1 (2H)-one (2.0 g, 10.7 mmol) in ethanol. To this solution was added NaBH$_4$ (1.9 g, 50 mmol) with stirring in portions at 0° C. in an ice bath. The resulting solution was stirred for 16 h at RT. The reaction was quenched by water (10 mL). The resulting solution was extracted with 3×50 mL of ethyl acetate and the organic layers combined and dried over anhydrous sodium sulfate, and then concentrated under vacuum. This resulted in 1.5 g of the title compound as a yellow solid. MS-ESI: 189 (M+1).

Scheme 66

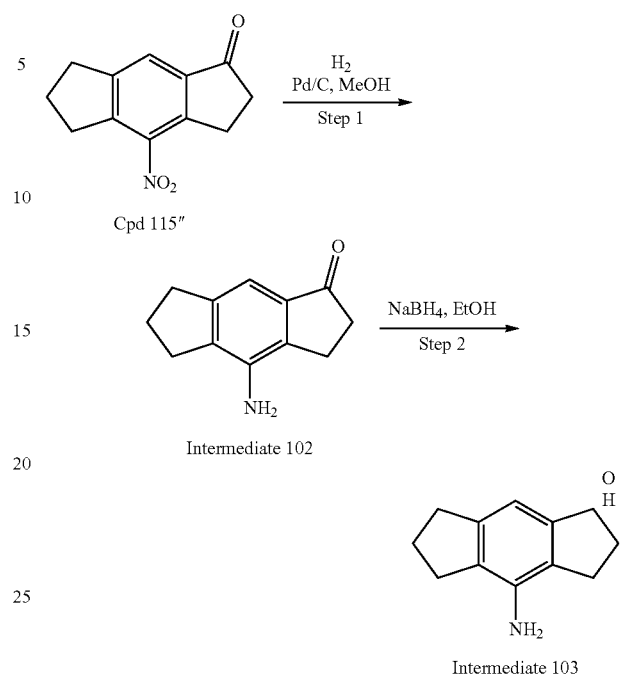

4-Amino-1,2,3,5,6,7-hexahydro-s-indacen-1-ol

Step 1: 4-Amino-3,5,6,7-tetrahydro-s-indacen-1(2H)-one

Into a 250-mL round-bottom flask purged and maintained with an inert atmosphere of hydrogen, was placed a solution of 4-nitro-1,2,3,5,6,7-hexahydro-s-indacen-1-one (3.0 g, 13.8 mmol) in MeOH (30 mL), and Pd/C (10% wt., 500 mg). The flask was evacuated and flushed three times with hydrogen. The resulting solution was stirred for 4 h at RT under an atmosphere of hydrogen. The Pd/C catalysts were filtered out, the filtrate was concentrated under vacuum. The residue was eluted from a silica gel column with DCM/MeOH (10:1). This resulted in 2.2 g (85.1%) of the title compound as a white solid. MS-ESI: 187 (M+1).

Step 2: 4-Amino-1,2,3,5,6,7-hexahydro-s-indacen-1-ol

Into a 100-mL round-bottom flask, was placed a solution of 8-amino-3,5,6,7-tetrahydro-s-indacen-1(2H)-one (2.0 g, 10.7 mmol) in ethanol (20 mL) and NaBH$_4$ (1.9 g, 50 mmol).

The resulting solution was stirred for 16 h at RT. The reaction was quenched with water. The resulting solution was extracted with 3×50 mL of ethyl acetate and the organic layers combined and dried over anhydrous sodium sulfate. The mixture was concentrated under vacuum. This resulted in 1.36 g of the title compound as a yellow solid. MS-ESI: 190 (M+1).

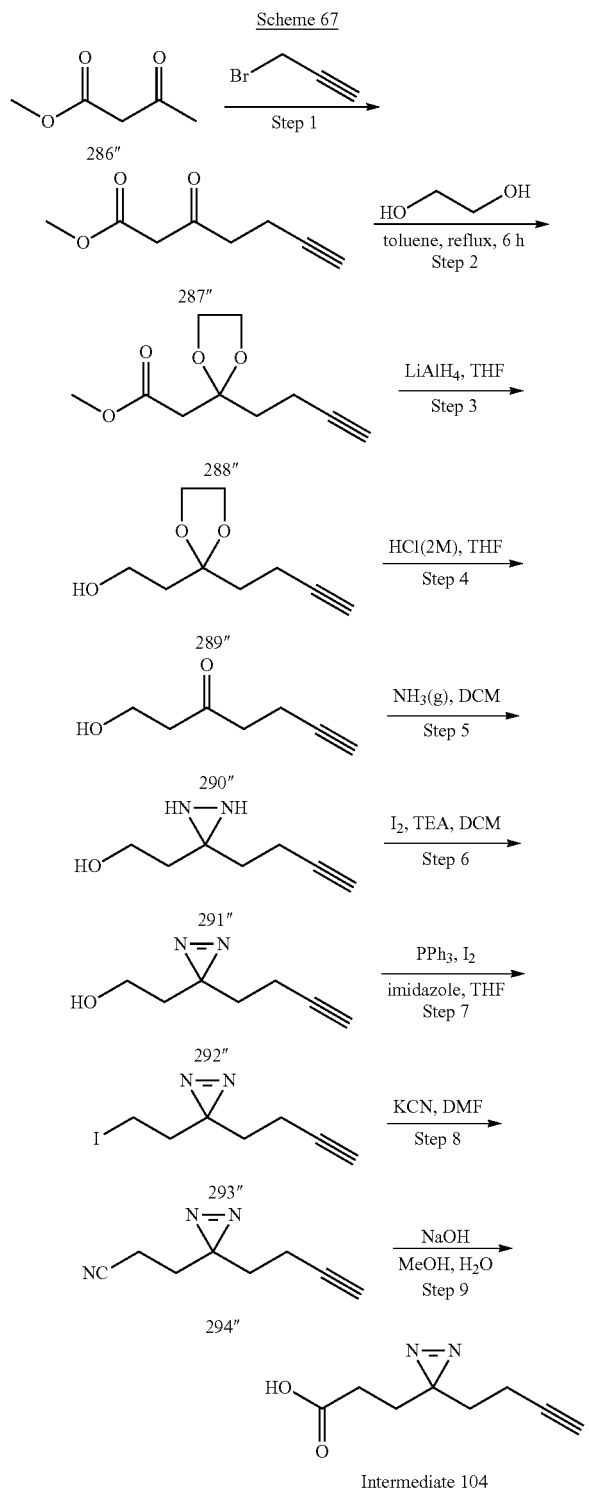

Intermediate 104

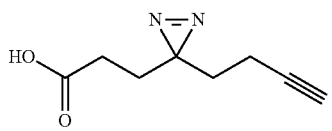

3-(3-(But-3-ynyl)-3H-diazirin-3-yl)propanoic acid

Step 1: Methyl 3-oxohept-6-ynoate

Into a 2000-mL 3-neck round-bottom flask purged with and maintained under nitrogen, was placed methyl 3-oxobutanoate (20 g, 172 mmol) in THF (200 mL). To the above solution was added LDA (200 mL, 400 mmol, 2 M) dropwise at −20° C. in a dry ice bath. Then reaction was allowed to react at −20° C. for 30 min. Then 3-bromoprop-1-yne (20.5 g, 172 mmol) was added to the reaction solution in portions at −20° C. The resulting solution was stirred for 3 h at −20° C. in a dry ice bath. The reaction was then quenched by the addition of 500 mL of NH$_4$Cl solution. The pH value of the solution was adjusted to 3 with HCl (aq). The resulting solution was extracted with 3×200 ml of ethyl acetate and the organic layers was combined and dried over anhydrous Na$_2$SO$_4$, then concentrated. This resulted in the title compound (2.0 g, 7.53%) as white oil.

Step 2: Methyl 2-(2-(but-3-ynyl)-1,3-dioxolan-2-yl)acetate

Into a 500-mL round-bottom flask, was placed methyl 3-oxohept-6-ynoate (20 g, 130 mmol) in toluene (200 mL), ethane-1,2-diol (40.2 g, 649 mmol) and TsOH (2.23 g, 13 mmol). The resulting solution was stirred for 6 h at 120° C. in an oil bath. The resulting solution was diluted with 200 mL of Et$_2$O. The resulting mixture was washed with 3×100 ml of NaHCO$_3$ and 3×100 ml of saturated NaCl solution. The mixture was dried over anhydrous sodium sulfate and concentrated. This resulted in the title compound (20 g, 77.9%) as yellow oil.

Step 3: 2-(2-(But-3-ynyl)-1,3-dioxolan-2-yl)ethanol

Into a 1.0-L 3-necked round-bottom flask purged and maintained with an inert atmosphere of nitrogen, was placed methyl 2-[2-(but-3-yn-1-yl)-1,3-dioxolan-2-yl]acetate (90 g, 454 mmol) in THF (300 mL). To this above solution was added LiAlH$_4$ (17.9 g, 472 mmol) in portions with stirring at 0° C. in an ice/ethanol bath. The resulting solution was stirred for 6 h at RT. The reaction was then quenched by the addition of water/ice. The solids were filtered out. The resulting filtrate was concentrated under vacuum. This resulted in the title compound (80 g crude) and used in the next step directly. MS-ESI: 169 (M−1).

Step 4: 1-Hydroxyhept-6-yn-3-one

Into a 3.0-L 3-necked round-bottom flask purged and maintained with an inert atmosphere of nitrogen, was placed 2-[2-(but-3-yn-1-yl)-1,3-dioxolan-2-yl]ethan-1-ol (80 g, 470 mmol) in THF (1.0 L) and HCl (500 mL). The resulting solution was stirred for 16 h at RT. The resulting solution was diluted with 1.0 L of water. The mixture was extracted with 3×1.0 L of ethyl acetate and the organic layer was combined and dried over anhydrous sodium sulfate. The solids were filtered out. The resulting filtrate was concentrated under vacuum. The residue was eluted from a silica gel column with DCM/petroleum ether (1:1). This resulted in 20 g of the title compound as a white solid. MS-ESI: 125 (M−1).

Step 5: 2-(3-(But-3-ynyl)diaziridin-3-yl)ethanol

Into a 500-mL round-bottom flask purged and maintained with an inert atmosphere of nitrogen, was placed 1-hydroxy-hept-6-yn-3-one (20 g, 159 mmol) in DCM (250 mL). To the above solution was introduced NH$_3$ (g) for 15 min at −40° C. in a liquid nitrogen/ethanol bath. The resulting solution was stirred for 1 h at −40° C. and then allowed to react for 16 h at RT. The resulting mixture was concentrated. This resulted in 18 g (crude) of the title compound as a white solid. MS-ESI: 141 (M+1).

Step 6: 2-(3-(But-3-ynyl)-3H-diazirin-3-yl)ethanol

Into a 500-mL 3-necked round-bottom flask purged and maintained with an inert atmosphere of nitrogen, was placed 2-[3-(but-3-yn-1-yl)diaziridin-3-yl]ethan-1-ol (14.4 g, 114 mmol) in DCM (200 mL), TEA (34.6 g, 342 mmol), I2 (58 g, 228 mmol). The resulting solution was stirred for 4 h at RT. The reaction was then quenched by the addition of Na$_2$S$_2$O$_3$. The resulting mixture was quenched with 100 mL of water. The resulting solution was extracted with 3×300 mL of DCM and the organic layers combined and dried over anhydrous sodium sulfate. The solids were filtered out. The resulting mixture was concentrated. This resulted in 6.0 g (38%) of the title compound as a white solid. MS-ESI: 139 (M+1).

Step 7: 3-(But-3-ynyl)-3-(2-iodoethyl)-3H-diazirine

Into a 250-mL round-bottom flask purged and maintained with an inert atmosphere of nitrogen, was placed 2-[3-(but-3-yn-1-yl)-3H-diazirin-3-yl]ethan-1-ol (5.0 g, 36.2 mmol) in THF (20 mL), imidazole (3.7 g, 54.3 mmol), I2 (9.18 g, 36.2 mmol), PPh$_3$ (14.2 g, 54.3 mmol). The resulting solution was stirred for 16 h at RT. The reaction was then quenched by the addition of 20 mL of saturated Na$_2$S$_2$O$_3$ solution. The resulting solution was extracted with 3×50 mL of DCM dried over anhydrous sodium sulfate. The solids were filtered out. The resulting mixture was concentrated. This resulted in 5.0 g (crude) of the title compound as a yellow solid. MS-ESI: 248 (M+1).

Step 8: 3-(3-(But-3-ynyl)-3H-diazirin-3-yl)propanenitrile

Into a 500-mL round-bottom flask purged and maintained with an inert atmosphere of nitrogen, was placed 3-(but-3-yn-1-yl)-3-(2-iodoethyl)-3H-diazirine (5.0 g, 20.2 mmol) in DMF (250 mL), KCN (2.62 g, 40.3 mmol). The resulting solution was stirred for 16 h at 60° C. in an oil bath. The reaction was then quenched by the addition of 20 mL of FeSO$_4$ solution. The resulting solution was extracted with 3×50 ml of ethyl acetate dried over anhydrous sodium sulfate. The solids were filtered out. The resulting mixture was concentrated. This resulted in 2.0 g (crude) of the title compound as a solid. MS-ESI: 148 (M+1).

Step 9: 3-(3-(But-3-ynyl)-3H-diazirin-3-yl)propanoic acid

Into a 100-mL round-bottom flask purged and maintained with an inert atmosphere of nitrogen, was placed 3-[3-(but-3-yn-1-yl)-3H-diazirin-3-yl]propanenitrile (1.0 g, 3.40 mmol) in MeOH (40 mL), NaOH (272 mg, 6.79 mmol). The resulting solution was stirred for 16 h at 90° C. in an oil bath. The resulting solution was concentrated. The residue was eluted from a silica gel column with ethyl acetate/petroleum ether (1:1). This resulted in 400 mg crude (26.6%) of the title compound as yellow oil. MS-ESI: 167 (M+1).

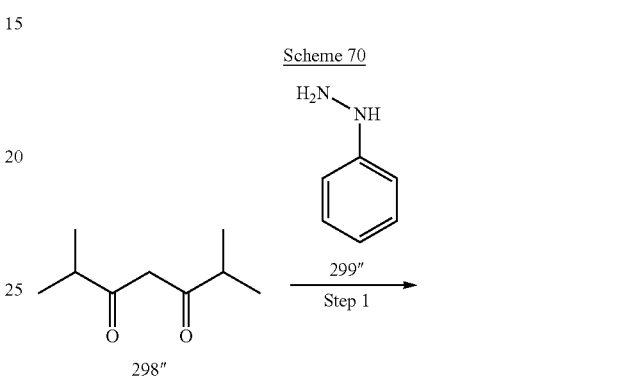

Intermediate 114

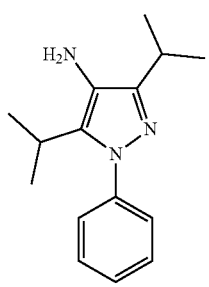 [SMILES: CC(C)c1nn(-c2ccccc2)c(C(C)C)c1N]

3,5-Diisopropyl-1-phenyl-1H-pyrazol-4-amine

Step 1: 3,5-Diisopropyl-1-phenyl-1H-pyrazole

Into a 100-mL round-bottom flask, was placed 2-propanol (50 mL), phenylhydrazine (3.81 g, 35.2 mmol) and 2,6-dimethylheptane-3,5-dione (5.0 g, 32.0 mmol). The resulting solution was stirred overnight at 85° C. in an oil bath. The resulting mixture was concentrated. The residue was dissolved in 100 mL of ethyl acetate. The resulting mixture was washed with 50 mL of H$_2$O. The mixture was dried over anhydrous sodium sulfate and then concentrated. This resulted in 6.9 g (94%) of the title compound as a light yellow oil. MS-ESI: 229 (M+1).

Step 2: 3,5-Diisopropyl-4-nitro-1-phenyl-1H-pyrazole

Into a 100-mL round-bottom flask, was placed 1-phenyl-3,5-bis(propan-2-yl)-1H-pyrazole (6.9 g, 30 mmol) in Ac$_2$O (50 mL). This was followed by the addition of HNO$_3$ (4.07 mL, 91 mmol) dropwise with stirring at 0° C. in 10 min. The resulting solution was stirred for overnight at RT. The residue was dissolved in 150 mL of ethyl acetate. The resulting mixture was washed with 2×100 mL of H$_2$O. The mixture was dried over anhydrous sodium sulfate and then concentrated. This resulted in 3.7 g (44.8%) of the title compound as yellow oil. MS-ESI: 274 (M+1).

Step 3: 3,5-Diisopropyl-1-phenyl-1H-pyrazol-4-amine

Into a 250-mL round-bottom flask, was placed 4-nitro-1-phenyl-3,5-bis(propan-2-yl)-1H-pyrazole (3.7 g, 13.5 mmol) in MeOH (100 mL), to the stirred solution was added Pd/C (10% wt., 400 mg). The flask was evacuated and flushed three times with hydrogen. The resulting solution was stirred overnight at RT under an atmosphere of hydrogen. The Pd/C catalysts were filtered out, the filtrate was concentrated under vacuum. This resulted in 2.7 g (82%) of the title compound as a light yellow oil. MS-ESI: 244 (M+1).

Scheme 72

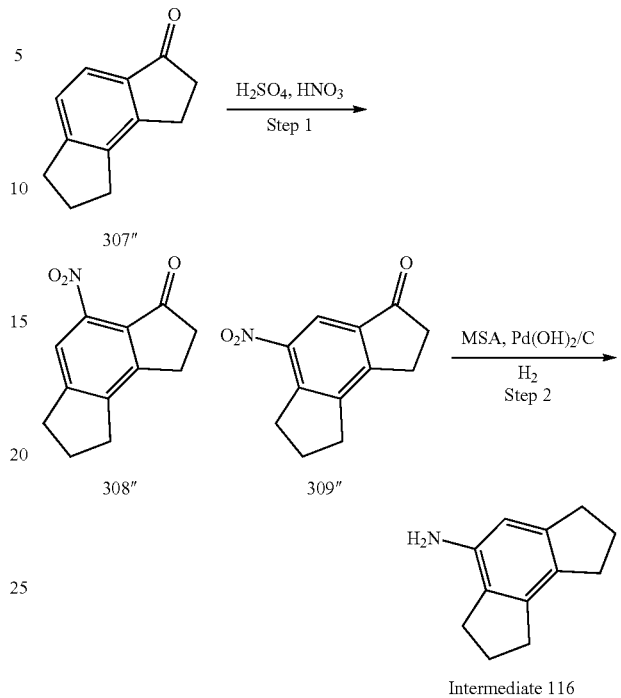

Intermediate 116

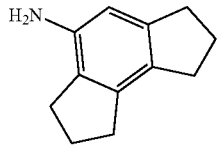 [SMILES: Nc1cc2c(c3c1CCC3)CCC2]

1,2,3,6,7,8-Hexahydro-as-indacen-4-amine

Step 1: 4-Nitro-1,6,7,8-tetrahydro-as-indacen-3(2H)-one (308″) and 5-nitro-1,6,7,8-tetrahydro-as-indacen-3(2H)-one (309″)

Into a 250-mL round-bottom flask was placed a solution of 1,6,7,8-tetrahydro-as-indacen-3(2H)-one (Cpd 307″ was isolated from 113″ in Scheme 23 by chromatography) (9.8 g, 46.5 mmol) in H$_2$SO$_4$ (50 mL). Then HNO$_3$ (5.85 g, 92.9 mmol) was added dropwise over 10 min at 0° C. The resulting solution was stirred for 1 h at 0° C. The reaction mixture was slowly added to a mixture of water/ice (100 mL) and DCM (50 mL) with ice bath cooling. The organic layer was collected, dried over Na$_2$SO$_4$ and concentrated under vacuum. This resulted in 11 g (89%) of a mixture of cpd 308″ and cpd 309″ as a yellow solid. The mixture was monitored by TLC (ethyl acetate/petroleum ether=1/10, R$_f$=0.4),

Step 2: 1,2,3,6,7,8-hexahydro-as-indacen-4-amine (116)

Into a 100-mL round-bottom flask was placed a solution of the mixture of 4-nitro-1,6,7,8-tetrahydro-as-indacen-3

(2H)-one and 5-nitro-1,6,7,8-tetrahydro-as-indacen-3(2H)-one (2.17 g, 10 mmol) in MeOH (30 mL). To the solution was added MSA (1.15 g, 12 mmol). Then Pd(OH)₂/C (20% wt., 550 mg) was added. The flask was evacuated and filled three times with hydrogen. The resulting mixture was stirred for 16 h at RT under hydrogen (50 psi). The solids were filtered out and washed with MeOH. The MeOH filtrate and wash was diluted with water (50 mL) and the pH was adjusted to 10.6 with 2 N NaOH. The resulting mixture was filtered and the crude solids were recrystallized from MeOH/water (9:1) with heating. This resulted in 1.38 g (80%) of the title compound as an off-white solid. MS-ESI: 174 (M+1).

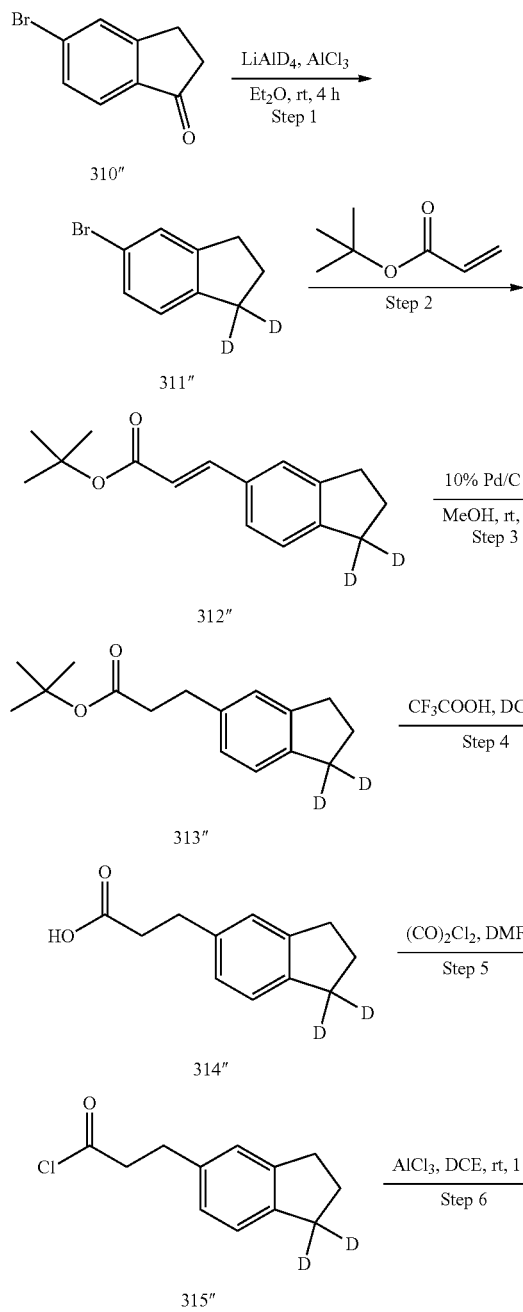

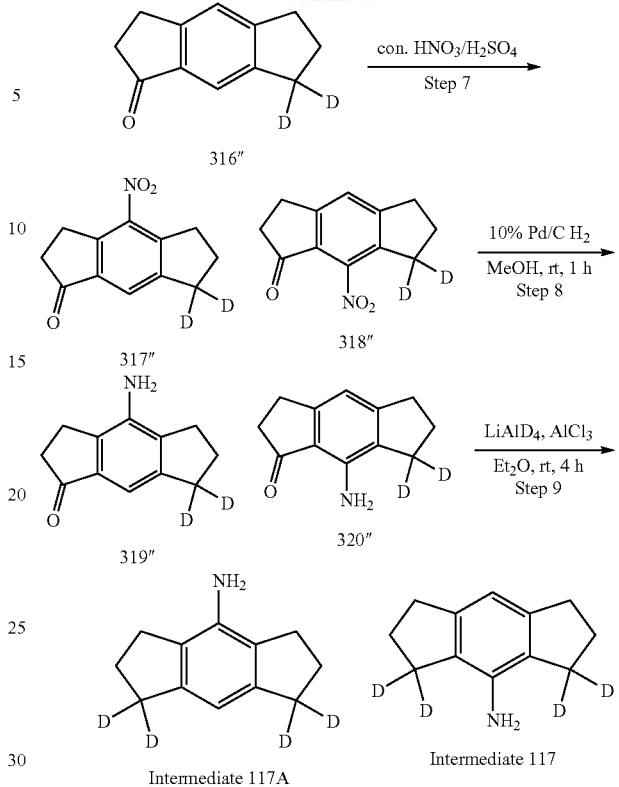

Intermediate 117

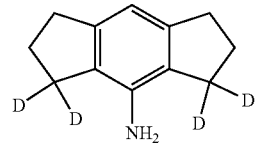 [SMILES: [2H]C1([2H])CCc2cc3c(c(N)c21)C([2H])([2H])CC3]

1,2,3,5,6,7-Hexahydro-s-indacen-3,3,5,5-d₄-4-amine

Step 1: 5-Bromo-2,3-dihydro-1H-indene-1,1-d₂

Into a 250-mL 3-necked round-bottom flask purged and maintained with an inert atmosphere of nitrogen, was placed a solution of LiAlD₄ (1.57 g, 37 mmol) in Et₂O (150 mL). This was followed by the addition of AlCl₃ (10.1 g, 76 mmol) in portions at 0° C. in 5 min. To this was added 5-bromo-2,3-dihydro-1H-inden-1-one (4.0 g, 19 mmol) in portions at 0° C. in 5 min. The resulting solution was stirred for 4 h at RT. The reaction mixture was cooled to 0° C. with a water/ice bath. The reaction was then quenched by careful addition of 10 mL of water. The solids were filtered out. The resulting solution was extracted with 3×100 mL of ethyl acetate and concentrated under vacuum. This resulted in 3.5 g (93%) of the title compound as brown oil. MS-ESI: 199/201 (M+1).

Step 2: Tert-butyl (E)-3-(2,3-dihydro-1H-inden-5-yl-1,1-d₂)acrylate

Into a 250-mL round-bottom flask purged and maintained with an inert atmosphere of nitrogen, was placed a solution of 5-bromo-2,3-dihydro-1H-indene-1,1-d$_2$ (7.0 g, 35 mmol) in DMF (80 mL), to the stirred solution was added tris(4-methylphenyl)phosphane (1.07 g, 3.52 mmol), tert-butyl prop-2-enoate (4.0 mL), triethylamine (5.0 mL) and Pd(OAc)$_2$ (395 mg, 1.76 mmol). The resulting solution was stirred overnight at 100° C. in an oil bath. The resulting mixture was concentrated under vacuum. The resulting solution was extracted with 3×50 mL of ethyl acetate and the organic layers combined and dried over anhydrous sodium sulfate. The residue was eluted from a silica gel column with DCM/petroleum ether (1:1). This resulted in 5.7 g (66%) of the title compound as light yellow oil. MS-ESI: 247 (M+1).

Step 3: Tert-butyl 3-(2,3-dihydro-1H-inden-5-yl-1,1-d$_2$)propanoate

Into a 100-mL round-bottom flask purged and maintained with an inert atmosphere of nitrogen, was placed a solution of tert-butyl (E)-3-(2,3-dihydro-1H-inden-5-yl-1,1-d$_2$)acrylate (5.8 g, 24 mmol) in MeOH (40 mL), to the stirred solution was added Pd/C (580 mg, 10% wt.). The flask was evacuated and flushed three times with hydrogen. The resulting solution was stirred for 1 h at RT under an atmosphere of hydrogen. The Pd/C catalysts were filtered out, the filtrate was concentrated under vacuum. This resulted in 5.7 g (98%) of the title compound as colorless oil. MS-ESI: 249 (M+1).

Step 4: 3-(2,3-Dihydro-1H-inden-5-yl-1,1-d$_2$)propanoic acid

Into a 100-mL round-bottom flask, was placed a solution of tert-butyl 3-(2,3-dihydro-1H-inden-5-yl-1,1-d$_2$)propanoate (4.3 g, 17.3 mmol) in DCM (50 mL), to the stirred solution was added CF$_3$COOH (5.5 mL, 74 mmol). The resulting solution was stirred for overnight at RT. The resulting mixture was concentrated under vacuum. This resulted in 3.1 g (93%) of the title compound as an off-white solid. MS-ESI: 191 (M−1).

Step 5: 3-(2,3-Dihydro-1H-inden-5-yl-1,1-d$_2$)propanoyl chloride

Into a 100-mL round-bottom flask purged and maintained with an inert atmosphere of nitrogen, was placed a solution of 3-(2,3-dihydro-1H-inden-5-yl-1,1-d$_2$)propanoic acid (9.0 g, 41.7 mmol) in DCM (40 mL). This was followed by the addition of oxalic dichloride (8.0 mL) at 0° C. To this was added DMF (0.5 mL) at 0° C. The resulting solution was stirred for 3 h at RT. The resulting mixture was concentrated under vacuum. This resulted in 4.0 g (41%) of the title compound as brown oil.

Step 6: 3,5,6,7-Tetrahydro-s-indacen-1(2H)-one-7,7-d$_2$

Into a 100-mL round-bottom flask purged and maintained with an inert atmosphere of nitrogen, was placed a solution of 3-(2,3-dihydro-1H-inden-5-yl-1,1-d$_2$)propanoyl chloride (3.9 g, 18 mmol) in DCE (40 mL). This was followed by the addition of AlCl$_3$ (3.3 g, 25 mmol) in portions at 0° C. in 2 min. The resulting solution was stirred for 1 h at RT. The reaction was then quenched by the addition of 200 mL of water/ice. The resulting solution was extracted with 3×50 mL of DCM and the organic layers combined and dried over anhydrous sodium sulfate. The residue was eluted from a silica gel column with ethyl acetate/petroleum ether (2:100). This resulted in 1.5 g (46%) of the title compound as an off-white solid. MS-ESI: 175 (M+1).

Step 7: 8-Nitro-3,5,6,7-tetrahydro-s-indacen-1(2H)-one-7,7-d$_2$ (Cpd 318″, major) and 4-Nitro-3,5,6,7-tetrahydro-s-indacen-1(21H)-one-7,7-d$_2$ (Cpd 317″, minor)

Into a 25-mL round-bottom flask, was placed 3,5,6,7-tetrahydro-s-indacen-1(2H)-one-7,7-d$_2$ (120 g). This was followed by the addition of H$_2$SO$_4$ (8.0 mL) at 0° C. To this was added HNO$_3$ (2.0 mL) at 0° C. in 2 min. To the mixture was added H$_2$SO$_4$ (2.0 mL) at 0° C. in 2 min. The resulting solution was stirred for 1 h at 0° C. The reaction was then quenched by the addition of water/ice. The resulting solution was extracted with 3×50 mL of ethyl acetate dried in an oven under reduced pressure. The residue was separated on silica gel eluted with ethyl acetate/petroleum ether (3:100). This resulted in 870 mg of cpd 318″ and 290 mg of cpd 317″, both as yellow solids. Cpd 317″: $^1$H NMR (300 MHz, CDCl$_3$) δ 7.83 (s, 1H), 3.55-3.45 (m, 2H), 3.42 (t, J=7.6 Hz, 2H), 2.84-2.74 (m, 2H), 2.22 (t, J 7.6 Hz, 2H). Cpd 318″: $^1$H NMR (300 MHz, CDCl$_3$) δ 7.46 (s, 1H), 3.20-3.00 (m, 4H), 2.83-2.73 (m, 2H), 2.20 (t, J=7.5 Hz, 2H).

Step 8: 8-Amino-3,5,6,7-tetrahydro-s-indacen-1(2H)-one-7,7-d$_2$

Into a 250-mL round-bottom flask purged and maintained with an inert atmosphere of nitrogen, was placed a solution of 8-nitro-3,5,6,7-tetrahydro-s-indacen-1(2H)-one-7,7-d$_2$ (870 mg) in MeOH (100 mL), to the stirred solution was added Pd/C (87 mg, 10% wt.). The flask was evacuated and flushed three times with hydrogen. The resulting solution was stirred for 1 h at RT under an atmosphere of hydrogen. The Pd/C catalysts were filtered out, the filtrate was concentrated under vacuum. This resulted in 700 mg of the title compound as a yellow solid. MS-ESI: 190 (M+1).

Step 9: 1,2,3,5,6,7-Hexahydro-s-indacen-3,3,5,5-d$_4$-4-amine

Into a 250-mL round-bottom flask purged and maintained with an inert atmosphere of nitrogen, was placed a solution of LiAlD$_4$ (160 mg, 3.8 mmol) in Et$_2$O (40 mL). This was followed by the addition of AlCl$_3$ (634 mg, 4.8 mmol) in portions at 0° C. in 2 min. To this solution was added 8-amino-3,5,6,7-tetrahydro-s-indacen-1(2H)-one-7,7-d$_2$ (600 mg, 3.17 mmol) at 0° C. The resulting solution was stirred for 4 h at RT. The reaction was then quenched by the addition of 10 mL of water. The resulting solution was diluted with 20 ml of EtOAc. The solids were filtered out. The resulting solution was extracted with 3×50 mL of ethyl acetate dried over anhydrous sodium sulfate and concentrated under vacuum. The residue was eluted from a silica gel column with ethyl acetate/petroleum ether (5:1). This resulted in 470 mg (78%) of the Intermediate 117 as a yellow solid. MS-ESI: 178 (M+1).

Intermediate 117A

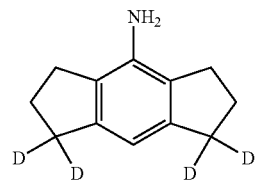 [SMILES: [2H]C1([2H])CCc2c1cc1c(c2N)CCC1([2H])[2H]]

1,2,3,5,6,7-hexahydro-s-indacen-1,1,7,7-d$_4$-4-amine

Intermediate 117A was prepared starting from compound 317" and using the same procedure as shown in scheme 73 above for converting compound 318" to intermediate 117. MS-ESI: 178 (M+1).

TABLE 15

The Intermediates in the following Table were prepared using similar procedure as shown in Scheme 30 above for converting compound 130" to Intermediate 44.

| Intermediate # | Structure | IUPAC Name |
|---|---|---|
| Intermediate 118" | 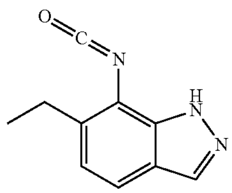 | 6-Ethyl-7-isocyanato-1H-indazole |
| Intermediate 119" | 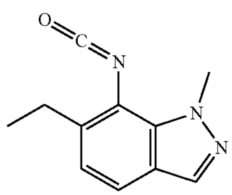 | 6-Ethyl-7-isocyanato-1-methyl-1H-indazole |
| Intermediate 120" | 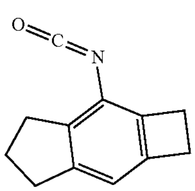 [SMILES: O=C=Nc1c2c(cc3c1CC3)CCC2] | 3-Isocyanato-2,4,5,6-tetrahydro-1H-cyclobuta[f]indene |
| Intermediate 121" | 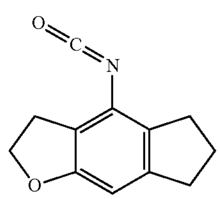 [SMILES: O=C=Nc1c2c(cc3c1CCO3)CCC2] | 4-Isocyanato-3,5,6,7-tetrahydro-2H-indeno[5,6-b]furan |
| Intermediate 122" | 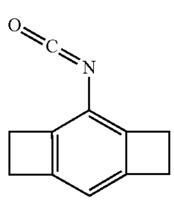 [SMILES: O=C=Nc1c2c(cc3c1CC3)CC2] | 2-Isocyanato-tricyclo[6.2.0.03,6]deca-1,3(6),7-triene |
| Intermediate 123" | 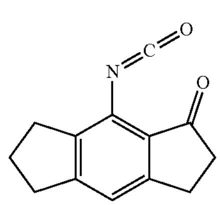 [SMILES: O=C=Nc1c2c(cc3c1C(=O)CC3)CCC2] | 8-Isocyanato-2,3,6,7-tetrahydros-indacen-1(5H)-one |

TABLE 15-continued

The Intermediates in the following Table were prepared using similar procedure as shown in Scheme 30 above for converting compound 130" to Intermediate 44.

| Intermediate # | Structure | IUPAC Name |
|---|---|---|
| Intermediate 124" | 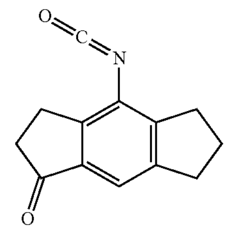 [SMILES: O=C=Nc1c2c(cc3c1CCC3=O)CCC2] | 4-Isocyanato-2,3,6,7-tetrahydros-indacen-1(5H)-one |
| Intermediate 125" | 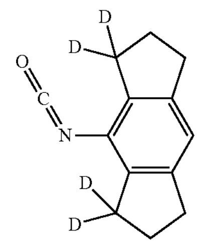 [SMILES: [2H]C1([2H])CCc2cc3c(c(N=C=O)c21)C([2H])([2H])CC3] | 4-isocyanato-1,2,3,5,6,7-hexahydro-s-indacene-3,3,5,5-d$_4$ |
| Intermediate 126" | 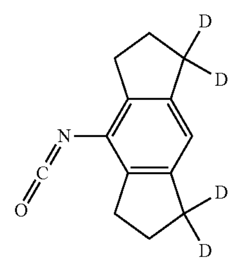 [SMILES: [2H]C1([2H])CCc2c1cc1c(c2N=C=O)CCC1([2H])[2H]] | 4-isocyanato-1,2,3,5,6,7-hexahydro-s-indacene-1,1,7,7-d$_4$ |

Schemes below the synthesis of sulfonimidamide Intermediates 118-123.

Scheme 74

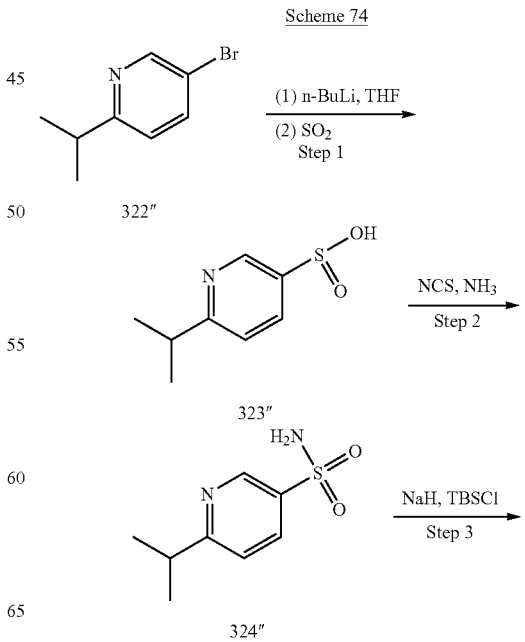

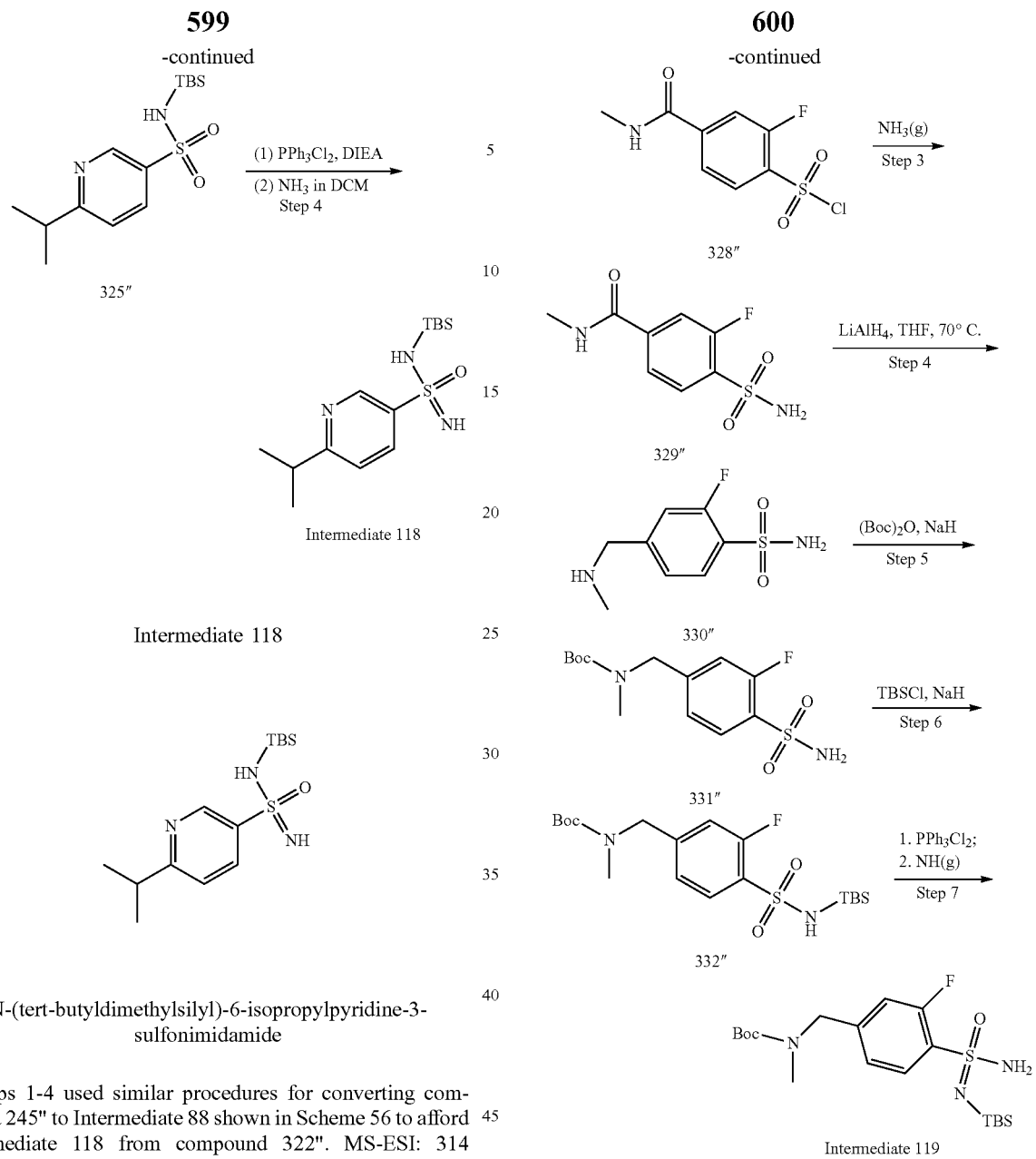

Intermediate 118

N-(tert-butyldimethylsilyl)-6-isopropylpyridine-3-sulfonimidamide

Steps 1-4 used similar procedures for converting compound 245" to Intermediate 88 shown in Scheme 56 to afford Intermediate 118 from compound 322". MS-ESI: 314 (M+1).

Scheme 75

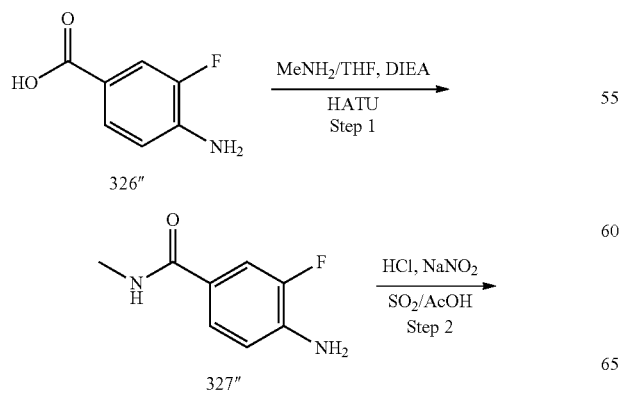

Intermediate 119

Step 1: 4-Amino-3-fluoro-N-methylbenzamide

Into a 500 mL round-bottom flask were added 4-amino-3-fluorobenzoic acid (15 g, 97 mmol) and DMF (100 mL) at RT. To the stirred solution was added HATU (74 mg, 0.19 mmol) and DIEA (25 mg, 0.19 mmol) at 0° C. To the above mixture was added MeNH$_2$/THF (2M, 97 mL, 194 mmol) in one portion at 0° C. The resulting mixture was stirred for additional 2 h at RT. The resulting mixture was extracted with EtOAc (3×100 mL). The combined organic layers were dried over anhydrous Na$_2$SO$_4$. After filtration, the filtrate was concentrated under reduced pressure. The residue was eluted from silica gel column with petroleum ether/EtOAc (1:1) to afford the title compound (16 g, 98%) as yellow oil. MS-ESI: 169 (M+1).

Steps 2-3 used similar procedures for converting compound 27 to Intermediate 29 shown in Scheme 9 to afford compound 329" from compound 327". MS-ESI: 233 (M+1).

Step 4:
2-Fluoro-4-((methylamino)methyl)benzenesulfonamide

Into a 250-mL round-bottom flask were placed 3-fluoro-N-methyl-4-sulfamoylbenzamide (1.2 g) in THF (40 mL) at 0° C. To the stirred solution was added LiAlH$_4$ (543 mg, 14 mmol) in portions at 0° C. under nitrogen atmosphere. The resulting mixture was stirred overnight at 70° C. The reaction was quenched with water (2 mL). The resulting mixture was filtered, the filter cake was washed with EtOAc (3×10 mL). The filtrate was concentrated under reduced pressure. The residue was purified by Prep-TLC (EtOAc/MeOH=25:1) to afford the title compound (800 mg, 77%) as a white solid. MS-ESI: 219 (M+1).

Step 5: Tert-butyl (3-fluoro-4-sulfamoylbenzyl)(methyl)carbamate

Into a 100-mL round-bottom flask were placed 2-fluoro-4-[(methylamino)methyl]benzene-1-sulfonamide (800 mg, 3.7 mmol) in THF (20 mL) at 0° C. To a stirred solution was added (Boc)$_2$O (1.5 g, 6.89 mmol) in portions at 0° C. The resulting mixture was stirred for 2 h at RT and concentrated under reduced pressure. The residue was purified by Prep-TLC (PE/EtOAc 1:1) to afford the title compound (900 mg, 77%) as a white solid. MS-ESI: 319 (M+1).

Steps 6-7 used similar procedures for converting compound 248" to Intermediate 88 shown in Scheme 56 to afford Intermediate 119 from compound 331". MS-ESI: 432 (M+1).

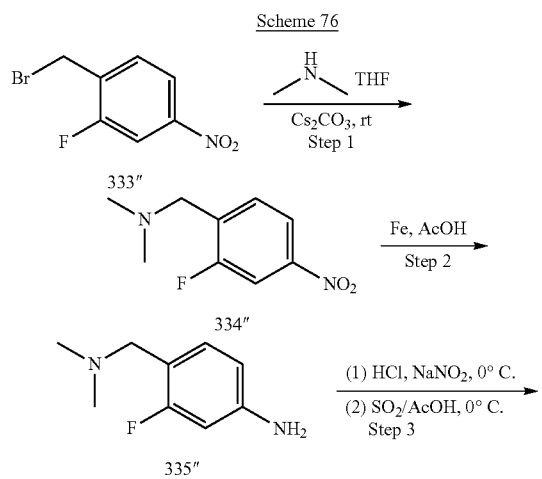

Scheme 76

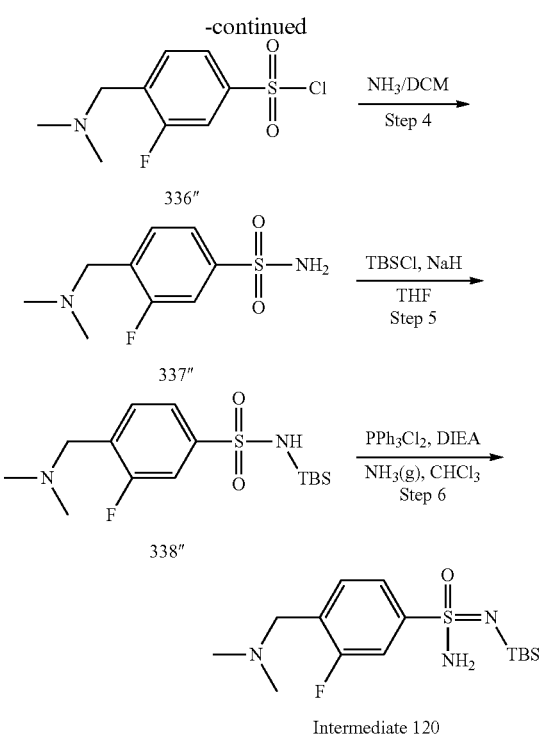

Intermediate 120

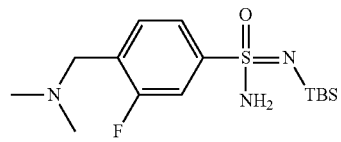

N'-(tert-butyldimethylsilyl)-4-((dimethylamino)methyl)-3-fluorobenzenesulfonimidamide Step 1:
1-(2-Fluoro-4-nitrophenyl)-N,N-dimethylmethanamine Into a 250-mL round-bottom flask, was placed a solution of 1-(bromomethyl)-2-fluoro-4-nitrobenzene (8.0 g, 34 mmol) in MeOH (50 mL). This was followed by the addition of dimethylamine (2 M, 21 mL) dropwise with stirring at 0° C. in 5 min. The resulting solution was stirred for 4 h at RT. The resulting mixture was concentrated under vacuum. This resulted in 7.0 g crude title compound as yellow oil. MS-ESI: 199 (M+1).

Step 2: 4-((Dimethylamino)methyl)-3-fluoroaniline

Into a 100-mL round-bottom flask, was placed the solution of [(2-fluoro-4-nitrophenyl)methyl]dimethylamine (7.0 g, 35 mmol) in AcOH (20 mL), to the stirred solution was added iron powder (10 g, 179 mmol). The resulting solution was stirred for 16 h at RT. The solids were filtered out. The resulting filtrate was concentrated under vacuum. The residue was eluted from a silica gel column with DCM/MeOH (9:1). This resulted in 6.5 g crude title compound as yellow oil. MS-ESI: 169 (M+1).

Steps 3-4 used similar procedures for converting compound 145" to compound 147" shown in Scheme 36 to afford compound 337" from compound 335". MS-ESI: 233 (M+1).

Steps 5-6 used similar procedures for converting compound 148" to Intermediate 59 shown in Scheme 36 to afford Intermediate 120 from compound 337". MS-ESI: 233 (M+1).

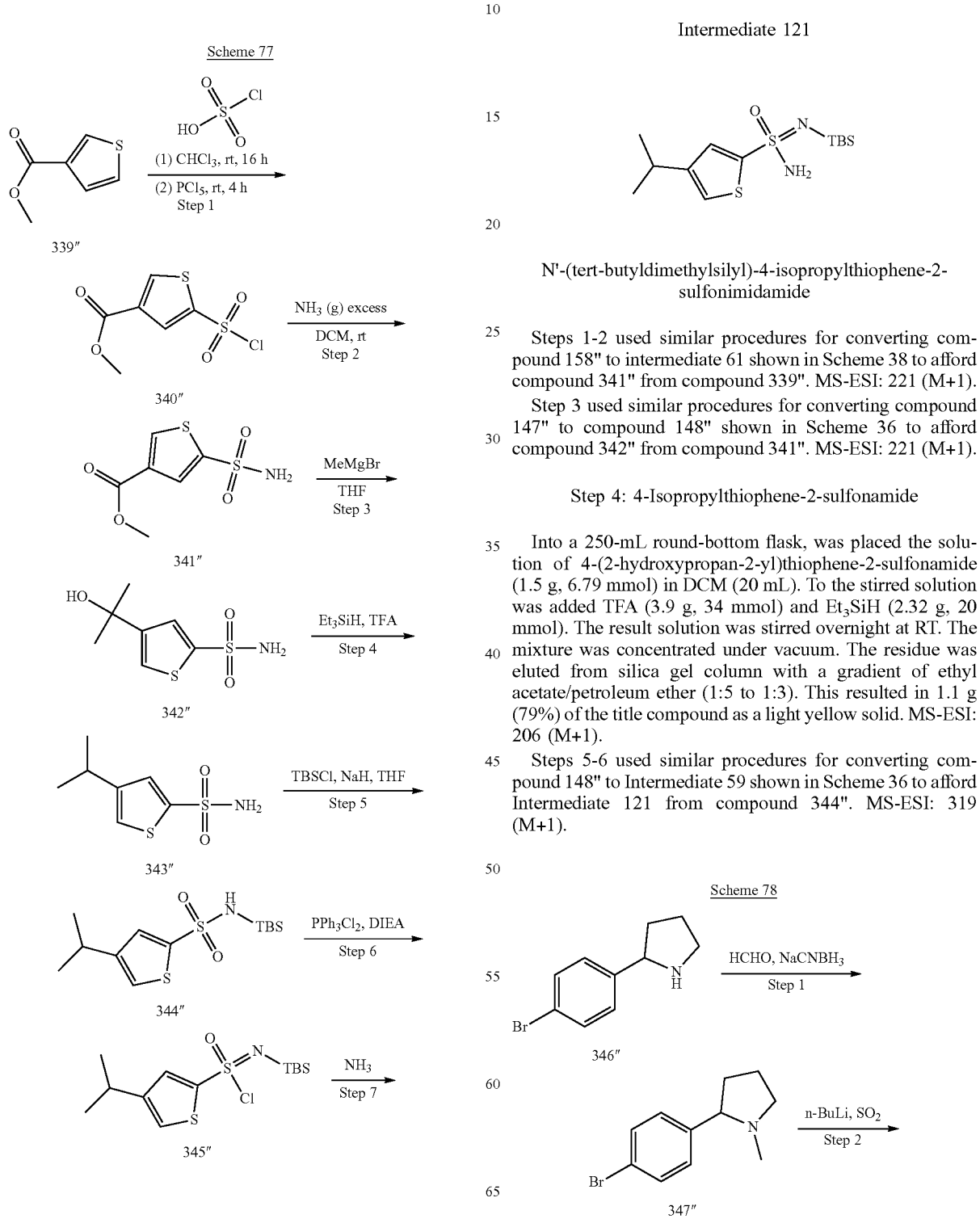

Scheme 77

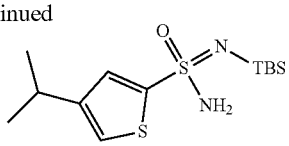

Intermediate 121

Intermediate 121

N'-(tert-butyldimethylsilyl)-4-isopropylthiophene-2-sulfonimidamide

Steps 1-2 used similar procedures for converting compound 158" to intermediate 61 shown in Scheme 38 to afford compound 341" from compound 339". MS-ESI: 221 (M+1).

Step 3 used similar procedures for converting compound 147" to compound 148" shown in Scheme 36 to afford compound 342" from compound 341". MS-ESI: 221 (M+1).

Step 4: 4-Isopropylthiophene-2-sulfonamide

Into a 250-mL round-bottom flask, was placed the solution of 4-(2-hydroxypropan-2-yl)thiophene-2-sulfonamide (1.5 g, 6.79 mmol) in DCM (20 mL). To the stirred solution was added TFA (3.9 g, 34 mmol) and Et₃SiH (2.32 g, 20 mmol). The result solution was stirred overnight at RT. The mixture was concentrated under vacuum. The residue was eluted from silica gel column with a gradient of ethyl acetate/petroleum ether (1:5 to 1:3). This resulted in 1.1 g (79%) of the title compound as a light yellow solid. MS-ESI: 206 (M+1).

Steps 5-6 used similar procedures for converting compound 148" to Intermediate 59 shown in Scheme 36 to afford Intermediate 121 from compound 344". MS-ESI: 319 (M+1).

Scheme 78

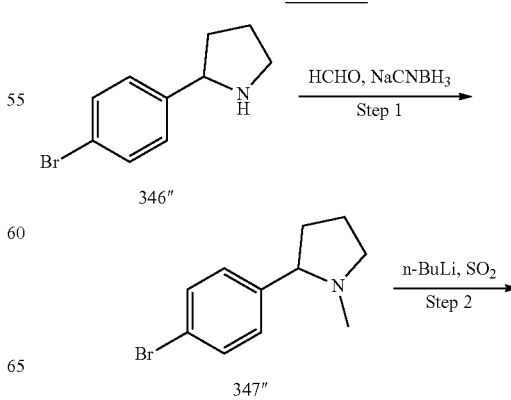

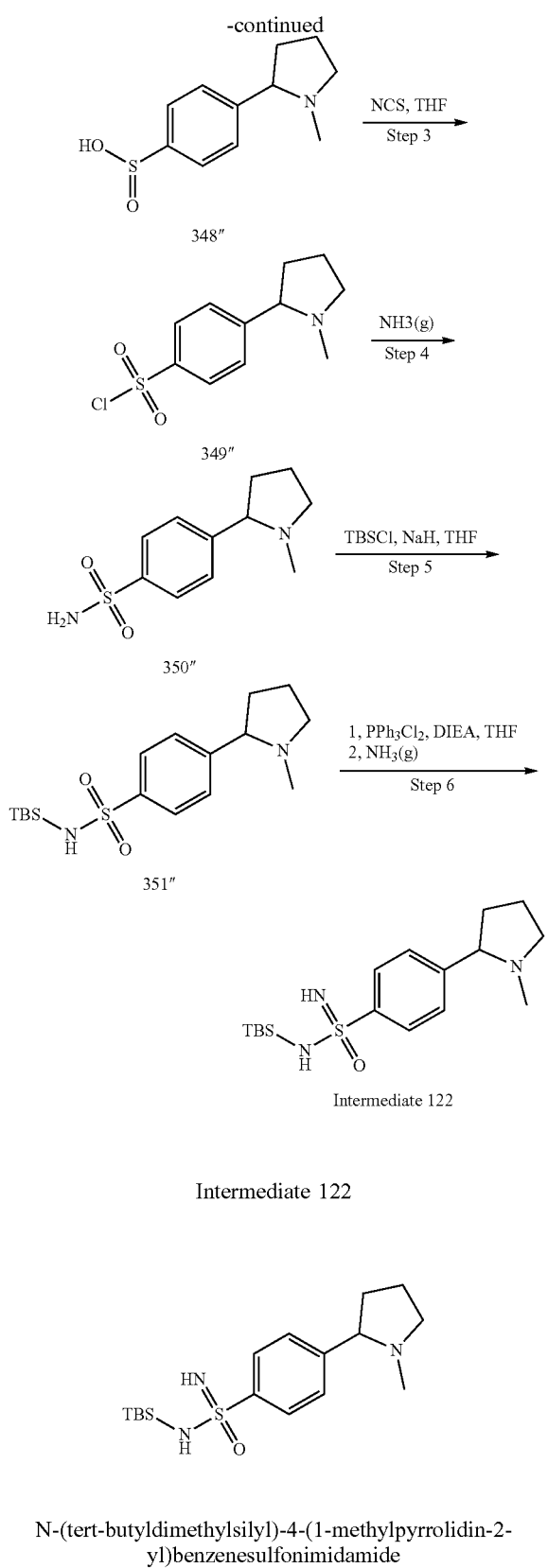

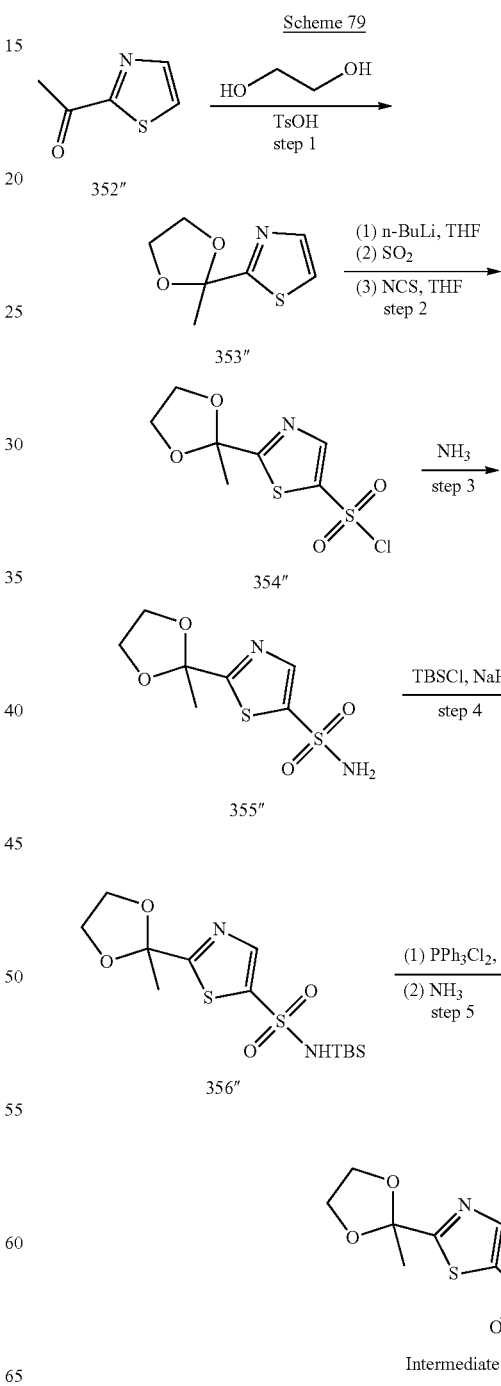

g, 37% wt.), to the stirred solution was added NaBH₃CN (2.5 g, 40 mmol). The resulting solution was stirred for 12 h at RT and concentrated under vacuum. The residue was eluted from a silica gel column with ethyl acetate/petroleum ether (1:1). This resulted in 2.8 g (88%) of the title compound as a light yellow solid. MS-ESI: 240/242 (M+1).

Steps 2-6 used similar procedures for converting compound 245" to Intermediate 88 shown in Scheme 56 to afford Intermediate 122" from compound 347". MS-ESI: 354 (M+1).

Intermediate 122

N-(tert-butyldimethylsilyl)-4-(1-methylpyrrolidin-2-yl)benzenesulfonimidamide

Step 1: 2-(4-Bromophenyl)-1-methylpyrrolidine

Into a 100-mL round-bottom flask, was placed 2-(4-bromophenyl)pyrrolidine (3.0 g, 13.3 mmol) in HCHO (3.23

Intermediate 123

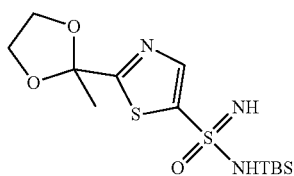

N-(tert-butyldimethylsilyl)-2-(2-methyl-1,3-dioxo-lan-2-yl)thiazole-5-sulfonimidamide

Step 1: 2-(2-Methyl-1,3-dioxolan-2-yl)thiazole

Into a 50-mL round-bottom flask purged and maintained with an inert atmosphere of nitrogen, was placed 1-(1,3-thiazol-2-yl)ethan-1-one (27 g, 212 mmol) in toluene (300 mL), to the stirred solution was added TsOH (2.0 g, 11.6 mmol) and ethane-1,2-diol (40 g, 644 mmol). The resulting solution was stirred for 14 h at 110° C. in an oil bath. The resulting mixture was concentrated under vacuum. The residue was eluted from a silica gel column with ethyl acetate/petroleum ether (1:20 to 1:10). This resulted in 36 g (99%) of the title compound as brown oil. MS-ESI: 172 (M+1).

Steps 2-5 used similar procedures for converting compound 245" to Intermediate 88 shown in Scheme 56 to afford Intermediate 123 from compound 353". MS-ESI: 363 (M+1).

Reagent 1

Dichlorotriphenylphosphorane

This reagent was either purchased or prepared using the following procedure:

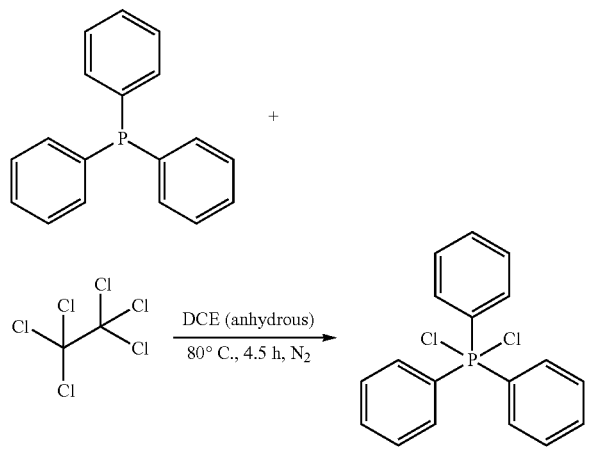

An oven dried 40 mL vial equipped with a stir bar was capped with a rubber septum and flushed with nitrogen. At room temperature, a solution of PPh$_3$ (0.85 g, 3.2 mmol) in anhydrous 1,2-dichloroethane (5 mL) was introduced via syringe. The reaction vessel was immersed in an ice/water bath and cooled for 5 min. A solution of hexachloroethane (0.76 g, 3.2 mmol) in anhydrous 1,2-dichloroethane (5 mL) was introduced dropwise via syringe. After the addition was complete the reaction mixture was stirred at the same temperature for an additional 5 min and then placed into a preheated block set at 80° C. Heating was continued for 4.5 h, at which time the reaction was assumed to be complete. The light golden clear solution was cooled to ambient temperature. The reagent thus prepared was transferred via syringe in subsequent reactions without any work up or purification. The total volume of the reaction mixture was 11 mL for the molar calculations for next steps. This solution containing PPh$_3$Cl$_2$ was stored under nitrogen at room temperature until used.

Reagent 2

Polymer-bound dichlorotriphenylphosphorane

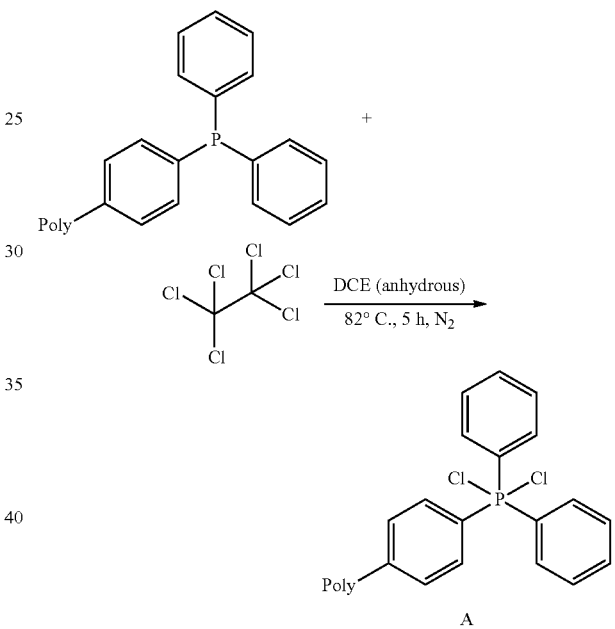

Polystyrene bound PPh$_3$ (0.32 g, 0.32 mmol) was suspended in anhydrous dichloroethane (6 mL) and shaken on a shaker for 5 mins. It was then filtered and the process was repeated again to swell the polymer. Filtered resin was suspended in anhydrous dichloroethane (6 mL) a third time and the whole suspension was transferred into an oven dried 40 mL vial with a stir bar via pipette. The vial was capped with a rubber septum and connected to a steady flow of nitrogen. The reaction vessel was immersed in an ice/water bath and cooled down for 10 min. A solution of hexachloroethane (0.076 g, 0.32 mmol) in anhydrous 1,2-dichloroethane (2 mL) was introduced drop wise via syringe. After the addition was complete the reaction mixture was placed in an already heated block set at 82° C. for 5 h. At this point the reaction is assumed to be completed. It was gradually brought to room temperature and used in the next step as is. This reagent was used at 1.5 equiv. with respect to sulfonamide in the next step.

SYNTHETIC EXAMPLES

Example 1

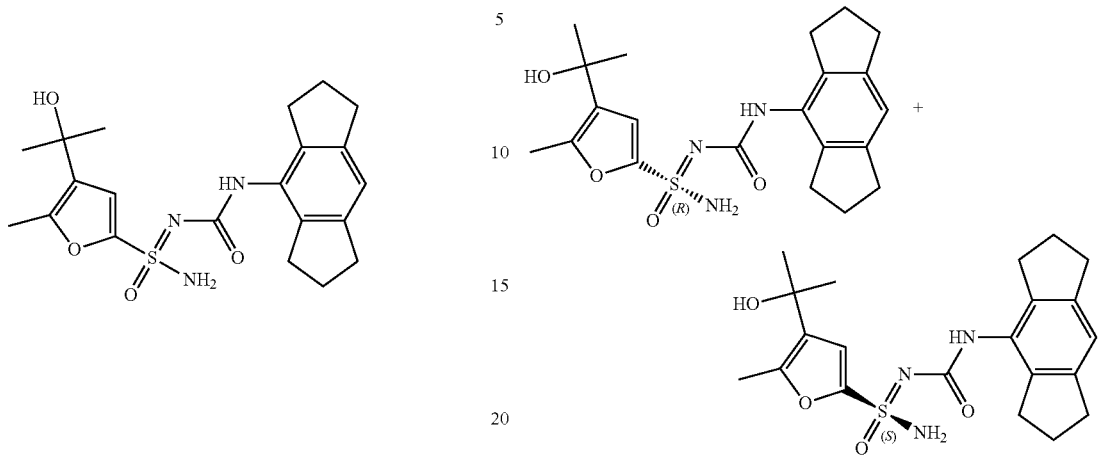

Example 1 (181): N'-(1,2,3,5,6,7-hexahydro-s-indacen-4-ylcarbamoyl)-4-(2-hydroxypropan-2-yl)-5-methylfuran-2-sulfonimidamide Example 1 was synthesized according to the general method shown in Scheme 1, as illustrated below.

Examples 2 and 3

Examples 2 (181a) and 3 (181b): (S)- and (R)-N'-(1,2,3,5,6,7-hexahydro-s-indacen-4-ylcarbamoyl)-4-(2-hydroxypropan-2-yl)-5-methylfuran-2-sulfonimidamide Examples 2 and 3 were prepared through chiral separation of Example 1 as illustrated below.

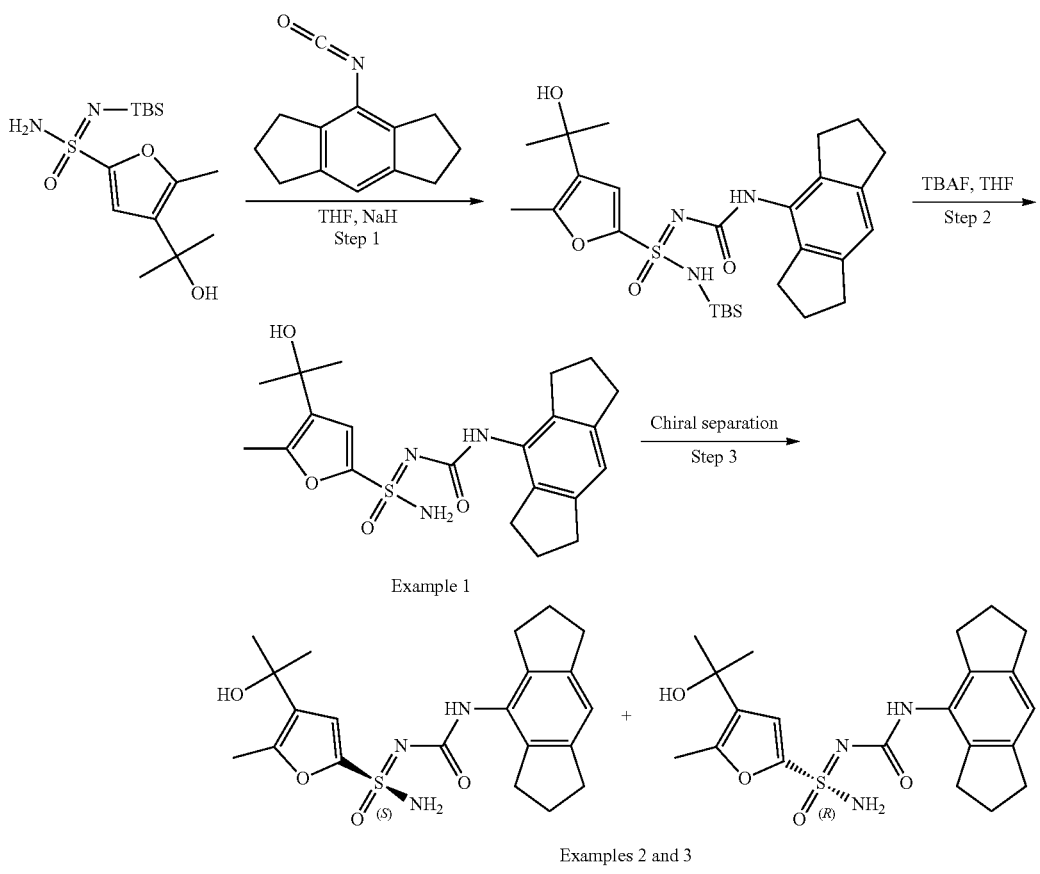

Step 1: N'-(tert-butyldimethylsilyl)-N-(1,2,3,5,6,7-hexahydro-s-indacen-4-ylcarbamoyl)-4-(2-hydroxy-propan-2-yl)-5-methylfuran-2-sulfonimidamide Into a 50-mL round-bottom flask was placed N'-(tert-butyldimethylsilyl)-4-(2-hydroxypropan-2-yl)-5-methyl-furan-2-sulfonimidamide (200 mg, 0.6 mmol), THF (10 mL), NaH (60% wt, 48 mg, 1.2 mmol). This was followed by the addition of a solution of 4-isocyanato-1,2,3,5,6,7-hexahydro-s-indacene (120 mg, 0.6 mmol) in THF (1 mL) dropwise with stirring at RT. The resulting solution was stirred for 12 h at RT. The reaction was then quenched by the addition of 10 mL of NH$_4$Cl (sat.). The resulting solution was extracted with 3×10 ml of DCM and the organic layers combined and concentrated under vacuum. The residue was applied onto a silica gel column and eluted with ethyl acetate/petroleum ether (1:10 to 1:3). This resulted in 140 mg (43.8%) of the title compound as brown oil. MS-ESI: 532.0 (M−1).

Step 2: N'-(1,2,3,5,6,7-hexahydro-s-indacen-4-ylcarbamoyl)-4-(2-hydroxypropan-2-yl)-5-methylfuran-2-sulfonimidamide Into a 50-mL round-bottom flask was placed N'-(tert-butyldimethylsilyl)-N-(1,2,3,5,6,7-hexahydro-s-indacen-4-ylcarbamoyl)-4-(2-hydroxypropan-2-yl)-5-methylfuran-2-sulfonimidamide (130 g, 0.2 mmol), THF (10 mL), and TBAF (300 mg, 0.5 mmol). The resulting solution was stirred for 2 h at RT and then concentrated under vacuum. The crude product was purified by Prep-HPLC using method E eluted with a gradient of 30~60% ACN. This resulted in 82 mg (80.3%) of Example 1 as a white solid.

Example 1: MS-ESI: 418.0 (M+1). $^1$H NMR (400 MHz, DMSO-d$_6$) δ 8.39 (s, 1H), 7.57 (s, 2H), 6.87 (s, 1H), 6.85 (s, 1H), 5.04 (s, 1H), 2.79 (t, J=7.4 Hz, 4H), 2.71-2.63 (m, 4H), 2.42 (s, 3H), 1.94 (tt, J=7.4 and 7.4 Hz, 4H), 1.40 (s, 6H).

Step 3: Chiral Separation

The product obtained as described in the previous step (70 mg) was resolved by Chiral-Prep-HPLC using the following conditions: Column, ChiralPak ID, 2*25 cm, 5 um; mobile phase, Hex and EtOH (hold 20% EtOH over 18 min); Flow rate, 20 mL/min; Detector, UV 254/220 nm. This resulted in 26.8 mg of Example 2 (front peak, 99% ee) as a white solid and 27.7 mg (second peak, 99.3% ee) of Example 3 as a white solid.

Example 2: MS-ESI: 418.0 (M+1). $^1$H NMR (400 MHz, DMSO-d$_6$) δ 8.36 (s, 1H), 7.57 (s, 2H), 6.87 (s, 1H), 6.85 (s, 1H), 5.03 (s, 1H), 2.78 (t, J=7.2 Hz, 4H), 2.73-2.60 (m, 4H), 2.41 (s, 3H), 1.93 (tt, J=7.2 and 7.2 Hz, 4H), 1.39 (s, 6H).

Example 3: MS-ESI: 418.0 (M+1). $^1$H NMR (400 MHz, DMSO-d$_6$) δ 8.39 (s, 1H), 7.58 (s, 2H), 6.87 (s, 1H), 6.85 (s, 1H), 5.03 (s, 1H), 2.78 (t, J=7.2 Hz, 4H), 2.73-2.60 (m, 4H), 2.41 (s, 3H), 1.93 (tt, J=7.2 and 7.2 Hz, 4H), 1.39 (s, 6H).

Single crystal X-ray crystallographic analysis was performed on compound 181a. FIG. 1 shows ball and stick models of the asymmetrical unit containing two crystallographically independent molecules of compound 181a, with hydrogen atoms omitted for clarity. Table M below shows fractional atomic coordinates of compound 181a.

TABLE M

Fractional Atomic Coordinates (×10$^4$) and Equivalent Isotropic Displacement Parameters (Å$^2$ × 10$^3$) for Example 2. U$_{eq}$ is defined as 13 of the trace of the orthogonalised U$_{IJ}$ tensor.

| Atom | x | y | z | U(eq) |
|---|---|---|---|---|
| S1 | 722.5(7) | 5368.3(5) | 6903.3(4) | 14.52(18) |
| S2 | 4304.8(7) | 505.4(5) | 3262.9(4) | 16.15(18) |
| O1 | 2143(2) | 6680.8(16) | 8220.2(13) | 16.1(4) |
| O2 | −195(2) | 4624.4(17) | 6478.0(14) | 21.9(5) |
| O5 | 2874(2) | 1624.4(17) | 1805.2(15) | 22.8(5) |
| O6 | 5238(2) | −141.6(18) | 3795.4(15) | 25.6(5) |
| O3 | 1492(3) | 5769.7(18) | 5397.8(14) | 25.5(5) |
| O7 | 2974(2) | 2151.0(17) | 3638.1(14) | 24.6(5) |
| N1 | 51(2) | 7218.5(19) | 8513.8(16) | 14.6(5) |
| N2 | 59(3) | 5986.0(18) | 7536.5(16) | 15.3(5) |
| O4 | 2422(3) | 8513(2) | 4297.8(17) | 34.3(6) |
| N4 | 4956(2) | 2247(2) | 1576.1(16) | 16.9(5) |
| O8 | 2771(3) | 3430(2) | 6070.3(18) | 36.7(6) |
| N5 | 4980(3) | 1071.7(19) | 2602.6(17) | 16.6(5) |
| N3 | 2120(3) | 4817(2) | 7347.5(17) | 16.3(5) |
| C13 | 854(3) | 6633(2) | 8105.0(18) | 12.9(6) |
| C1 | 605(3) | 7947(2) | 9133.7(19) | 14.4(6) |
| N6 | 2978(3) | −121(2) | 2801.8(19) | 20.2(6) |
| C22 | 4388(3) | 2952(2) | 936.5(19) | 16.2(6) |
| C24 | 5733(3) | 2203(2) | −207(2) | 18.3(6) |
| C34 | 4164(3) | 1656(2) | 1979(2) | 16.6(6) |
| C11 | −695(3) | 7200(2) | 10304.5(19) | 17.2(6) |
| C12 | 267(3) | 7915(2) | 9953.6(19) | 14.2(6) |
| C23 | 4754(3) | 2918(2) | 127(2) | 17.0(6) |
| C27 | 4221(3) | 3614(2) | −494(2) | 18.1(6) |
| C8 | 800(3) | 8626(2) | 10566(2) | 17.0(6) |
| C28 | 3315(3) | 4357(2) | −324(2) | 18.6(6) |
| C4 | 2436(4) | 10034(2) | 8218(2) | 23.3(7) |
| C7 | 1688(3) | 9377(2) | 10382(2) | 16.9(6) |
| C29 | 2969(3) | 4399(2) | 492(2) | 18.0(6) |
| C9 | 237(3) | 8445(2) | 11388(2) | 20.4(6) |
| C38 | 2557(3) | 2633(3) | 4320(2) | 24.9(7) |
| C2 | 1458(3) | 8717(2) | 8931.9(19) | 15.1(6) |
| C6 | 2005(3) | 9409(2) | 9557(2) | 17.2(6) |
| C26 | 4804(3) | 3424(2) | −1310(2) | 21.8(7) |
| C31 | 2476(4) | 5023(2) | 1822(2) | 24.4(7) |
| C5 | 2927(3) | 10137(2) | 9193(2) | 19.6(6) |
| C16 | 2044(3) | 7389(2) | 5427(2) | 22.4(7) |
| C25 | 5416(4) | 2367(2) | −1181(2) | 24.1(7) |
| C15 | 1514(3) | 7144(2) | 6188(2) | 21.6(7) |
| C33 | 3503(3) | 3713(2) | 1124(2) | 16.9(6) |
| C37 | 3005(3) | 2117(3) | 5067(2) | 23.8(7) |
| C30 | 2028(3) | 5128(2) | 844(2) | 20.5(6) |
| C10 | −360(4) | 7379(2) | 11275(2) | 23.9(7) |
| C36 | 3748(3) | 1285(3) | 4821(2) | 24.5(7) |
| C17 | 2020(4) | 6535(3) | 4974(2) | 28.3(7) |
| C14 | 1181(3) | 6178(2) | 6137.8(19) | 19.0(6) |
| C35 | 3710(3) | 1326(2) | 3973(2) | 23.7(7) |
| C19 | 2583(3) | 8401(3) | 5214(2) | 26.0(7) |
| C3 | 1902(3) | 8960(2) | 8090(2) | 19.0(6) |
| C32 | 3002(3) | 3944(2) | 1954(2) | 21.0(6) |
| C40 | 2768(4) | 2390(3) | 5955(2) | 33.7(8) |
| C20 | 1804(4) | 9231(3) | 5566(3) | 34.6(8) |
| C39 | 1810(4) | 3575(3) | 4092(3) | 35.7(8) |
| C42 | 1313(4) | 2062(3) | 6087(3) | 40.3(9) |
| C21 | 4139(4) | 8447(3) | 5541(3) | 40.0(9) |
| C18 | 2406(5) | 6256(3) | 4130(3) | 44.7(10) |
| C41 | 3893(5) | 1934(4) | 6622(3) | 54.3(12) |

Figure 2:
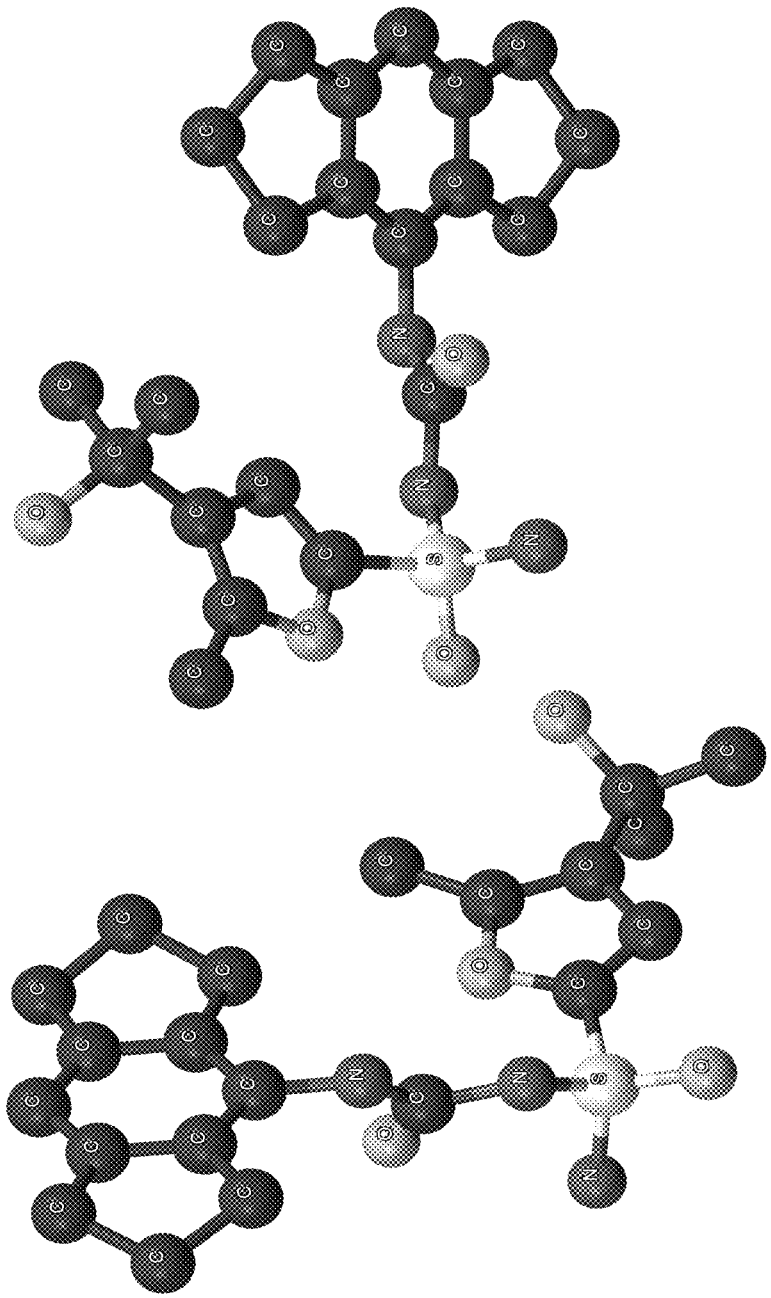
FIG. 2 depicts ball-and-stick representations of two crystallographically independent molecules of compound 181b in the asymmetrical unit.

Single crystal X-ray crystallographic analysis was performed on compound 181b. FIG. 2 shows ball and stick models of the asymmetrical unit containing two crystallographically independent molecules of compound 181b, with hydrogen atoms omitted for clarity. Table N below shows fractional atomic coordinates of compound 181b. PP58T,

TABLE N

Fractional Atomic Coordinates (×10⁴) and Equivalent Isotropic Displacement Parameters (Å² × 10³) for Example 3. $U_{eq}$ is defined as ⅓ of the trace of the orthogonalised $U_{IJ}$ tensor.

| Atom | x | y | z | U(eq) |
|---|---|---|---|---|
| S1 | 9264.0(7) | 4621.3(5) | 3094.0(4) | 16.15(17) |
| S2 | 5705.1(7) | 9485.8(5) | 6733.7(4) | 19.00(17) |
| O1 | 7853(2) | 3305.2(16) | 1778.9(13) | 18.6(4) |
| O7 | 7027(2) | 7842.4(18) | 6357.2(15) | 26.4(5) |
| O2 | 10182(2) | 5364.5(17) | 3520.0(14) | 23.6(5) |
| O5 | 7131(2) | 8368.0(19) | 8192.5(15) | 25.5(5) |
| O3 | 8512(3) | 4220.7(18) | 4605.0(14) | 26.6(5) |
| O6 | 4770(2) | 10133.7(19) | 6200.8(15) | 28.4(5) |
| O8 | 7211(3) | 6563(2) | 3921.7(19) | 38.6(7) |
| O4 | 7597(3) | 1484(2) | 5713.0(18) | 37.3(6) |
| N2 | 9933(3) | 4006.4(19) | 2465.8(16) | 17.8(5) |
| N1 | 9943(2) | 2773(2) | 1482.7(16) | 16.3(5) |
| N4 | 5051(3) | 7745(2) | 8421.8(17) | 20.2(5) |
| N3 | 7870(3) | 5173(2) | 2653.4(17) | 18.4(5) |
| N5 | 5031(3) | 8923(2) | 7390.2(17) | 19.9(5) |
| C14 | 9136(3) | 3353(2) | 1894.3(18) | 15.8(6) |
| C1 | 9391(3) | 2043(2) | 864.7(19) | 17.4(6) |
| N6 | 7031(3) | 10109(2) | 7191.6(19) | 23.0(6) |
| C30 | 5618(3) | 7045(2) | 9058(2) | 19.3(6) |
| C6 | 9205(3) | 1370(2) | −570(2) | 20.1(6) |
| C53 | 7446(4) | 7363(3) | 5675(2) | 26.1(7) |
| C32 | 4273(3) | 7792(2) | 10199(2) | 20.6(6) |
| C2 | 9731(3) | 2078(2) | 44.2(19) | 16.8(6) |
| C43 | 5846(3) | 8333(2) | 8016(2) | 20.2(6) |
| C3 | 10685(3) | 2795(2) | −304(2) | 20.3(6) |
| C37 | 7028(3) | 5597(2) | 9506(2) | 21.2(6) |
| C7 | 8316(3) | 620(2) | −386(2) | 20.2(6) |
| C35 | 5773(3) | 6383(2) | 10493(2) | 20.7(6) |
| C10 | 7573(4) | −36(3) | 1780(2) | 27.4(7) |
| C36 | 6681(3) | 5639(2) | 10322(2) | 21.2(6) |
| C22 | 8481(3) | 2845(3) | 3816(2) | 23.0(6) |
| C8 | 8002(3) | 584(2) | 440(2) | 20.3(6) |
| C39 | 7525(4) | 4977(3) | 8177(2) | 28.0(7) |
| C31 | 5248(3) | 7078(2) | 9867(2) | 19.6(6) |
| C52 | 6981(3) | 7875(3) | 4927(2) | 24.2(7) |
| C12 | 8541(3) | 1280(2) | 1066.4(19) | 18.0(6) |
| C34 | 5191(4) | 6574(3) | 11302(2) | 24.8(7) |
| C51 | 6252(4) | 8707(3) | 5170(2) | 26.7(7) |
| C33 | 4585(4) | 7630(3) | 11175(2) | 27.6(7) |
| C24 | 7990(4) | 3461(3) | 5032(2) | 30.5(8) |
| C23 | 7962(3) | 2603(3) | 4580(2) | 24.0(7) |
| C50 | 6302(4) | 8662(3) | 6020(2) | 25.4(7) |
| C9 | 7077(3) | −142(2) | 804(2) | 23.6(7) |
| C38 | 7972(3) | 4873(2) | 9155(2) | 23.5(7) |
| C5 | 9763(4) | 1551(3) | −1391(2) | 24.9(7) |
| C41 | 6502(3) | 6286(2) | 8872(2) | 20.5(6) |
| C21 | 8811(3) | 3816(2) | 3866.6(19) | 20.4(6) |
| C4 | 10356(4) | 2619(3) | −1277(2) | 28.3(7) |
| C11 | 8099(3) | 1036(2) | 1909(2) | 22.6(6) |
| C40 | 7006(3) | 6055(3) | 8044(2) | 24.5(6) |
| C25 | 7419(4) | 1599(3) | 4793(2) | 26.8(7) |
| C58 | 8189(4) | 6425(3) | 5905(3) | 37.6(9) |
| C54 | 7221(4) | 7601(3) | 4036(2) | 34.1(8) |
| C27 | 8195(4) | 774(3) | 4438(3) | 38.1(9) |
| C29 | 7607(6) | 3737(3) | 5874(3) | 46.7(10) |
| C56 | 8674(4) | 7924(3) | 3907(3) | 42.4(10) |
| C28 | 5872(4) | 1551(3) | 4471(3) | 44.2(10) |
| C57 | 6101(6) | 8060(4) | 3369(3) | 58.9(14) |

Example 4

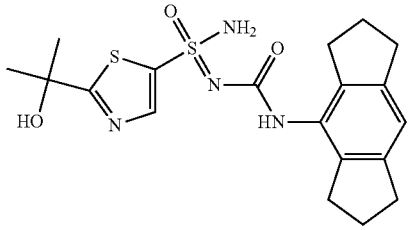 [SMILES: CC(C)(O)c1ncc(S(N)(=O)=NC(=O)Nc2c3c(cc4c2CCC4)CCC3)s1]

Example 4 (101'): N'-(1,2,3,5,6,7-hexahydro-s-indacen-4-ylcarbamoyl)-2-(2-hydroxypropan-2-yl)thiazole-5-sulfonimidamide Example 4 (above) was synthesized according to the general methods in Schemes 2 and 3, as illustrated in Route 1 and Route 2 below.

Examples 5 and 6

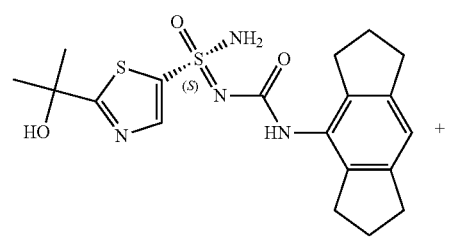

+

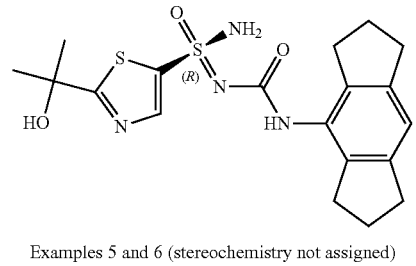

Examples 5 and 6 (stereochemistry not assigned)

Examples 5 (101) and 6 (102): (S)- and (R)-N'-(1,2,3,5,6,7-hexahydro-s-indacen-4-ylcarbamoyl)-2-(2-hydroxypropan-2-yl)thiazole-5-sulfonimidamide Examples 5 and 6 (above) were synthesized according to general methods shown in Schemes 2 and 3, as illustrated in Route 1 and Route 2 below.

Example 7

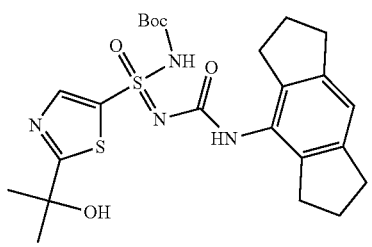 [SMILES: CC(C)(C)OC(=O)NS(=O)(=NC(=O)Nc1c2c(cc3c1CCC3)CCC2)c1cnc(C(C)(C)O)s1]

Example 7 (194): Tert-butyl N-(1,2,3,5,6,7-hexahydro-s-indacen-4-ylcarbamoyl)-2-(2-hydroxypropan-2-yl)thiazole-5-sulfonimidoylcarbamate Example 7 was synthesized according to general method shown in Scheme 3, as illustrated in Route 2 below.
Route 1 minutes, and this was followed by the addition of a solution of 4-isocyanato-1,2,3,5,6,7-hexahydro-s-indacene (209 mg, 1.1 mmol) in THF (5 mL) dropwise with stirring at RT. The resulting solution was stirred for 12 h at RT. The reaction was then quenched by the addition of 10 mL of NH₄Cl (sat.). The resulting solution was extracted with 3×10 mL of DCM and the combined organic layers were concentrated under vacuum. This resulted in 535 mg (crude) of the title compound as a brown oil. MS-ESI: 535.0 (M+1).

Step 2: N'-(1,2,3,5,6,7-hexahydro-s-indacen-4-ylcarbamoyl)-2-(2-hydroxypropan-2-yl)thiazole-5-sulfonimidamide Into a 50-mL round-bottom flask was placed a solution of N-(tert-butyldimethylsilyl)-N'-(1,2,3,5,6,7-hexahydro-s-indacen-4-ylcarbamoyl)-2-(2-hydroxypropan-2-yl)thiazole-5-sulfonimidamide (535 mg, crude, 1.0 mmol) in THF (10 mL). To this solution was added HF/Py (70% wt, 143 mg, 5.0 mmol) dropwise at 0° C. The solution was stirred at RT for 4 h. The reaction was then quenched by the addition of 10 mL of water. The resulting solution was extracted with

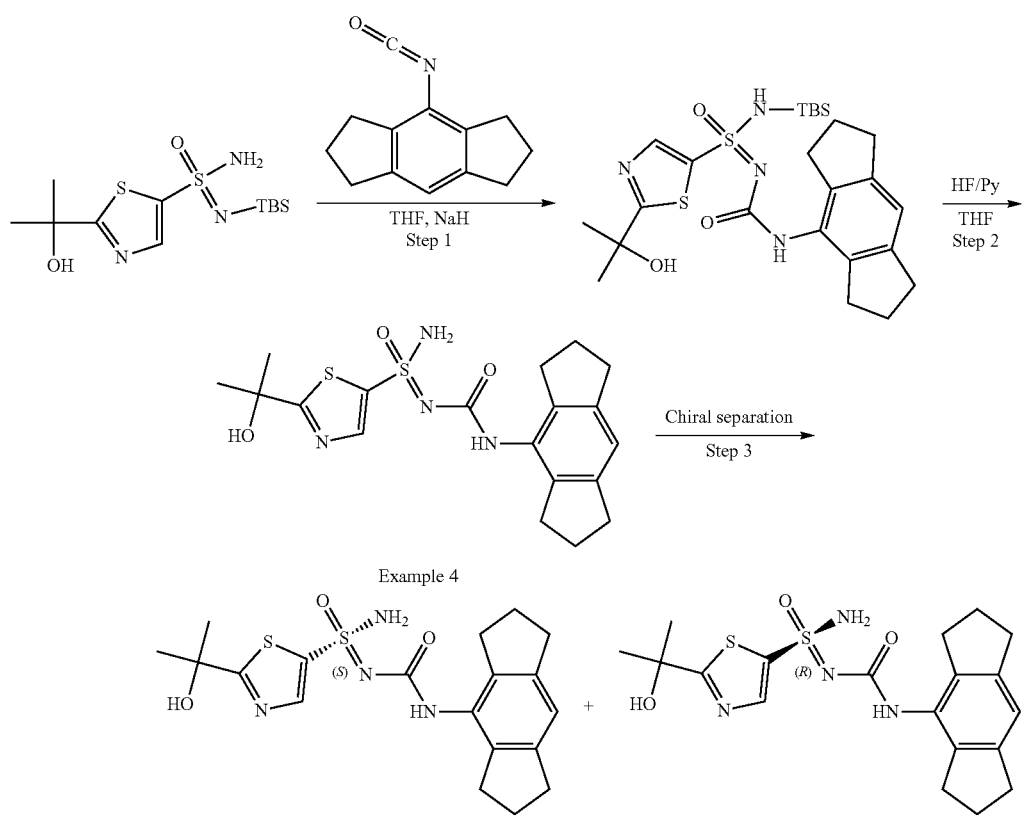

Examples 5 and 6 (stereochemistry not assigned)

Step 1: N-(tert-butyldimethylsilyl)-N'-(1,2,3,5,6,7-hexahydro-s-indacen-4-ylcarbamoyl)-2-(2-hydroxypropan-2-yl)thiazole-5-sulfonimidamide Into a 50-mL round-bottom flask was placed a solution of N'-(tert-butyldimethylsilyl)-2-(2-hydroxypropan-2-yl)thiazole-5-sulfonimidamide (336 mg, 1.0 mmol) in THF (10 mL). To this solution was added NaH (60% wt, 80 mg, 2.0 mmol) in portions at 0° C. The solution was stirred at 0° C. for 15

3×10 mL of ethyl acetate and the combined organic layers were concentrated under vacuum. The crude product was purified by Prep-HPLC using Method E with ACN/water (20% to 60% in 10 minutes). This resulted in 189 mg (45%, 2 steps) of Example 4 as a white solid.

Example 4: MS-ESI: 421.0 (M+1). $^1$H NMR (400 MHz, DMSO-$d_6$) δ 8.46 (br s, 1H), 8.04 (s, 1H), 7.80 (br s, 2H), 6.86 (s, 1H) 6.28 (s, 1H), 2.88-2.71 (m, 4H), 2.71-2.56 (m, 4H), 2.02-1.80 (m, 4H), 1.49 (s, 6H).

Step 2: Chiral Separation

The product obtained as described in the previous step (189 mg) was resolved by Chiral-Prep-HPLC using the following conditions: Column, CHIRAL Cellulose-SB, 2*25 cm, 5 um; mobile phase, Hex (0.1% DEA) and EtOH (hold 20% EtOH over 16 min); Flow rate, 20 mL/min; Detector, UV 254/220 nm. This resulted in 70 mg of Example 5 (front peak, 99% ee 101) as a white solid and 65 mg of Example 6 (second peak, 97.5% ee 102) as a white solid. Absolute stereochemistry of these two isomers has not been assigned.

Example 5: MS-ESI: 421.0 (M+1). $^1$H NMR (400 MHz, DMSO-$d_6$) δ 8.43 (br s, 1H), 8.05 (s, 1H), 7.83 (br s, 2H), 6.87 (s, 1H) 6.29 (s, 1H), 2.82-2.71 (m, 4H), 2.71-2.56 (m, 4H), 2.02-1.80 (m, 4H), 1.50 (s, 6H).

Example 6: MS-ESI: 421.0 (M+1). $^1$H NMR (400 MHz, DMSO-$d_6$) δ 8.41 (br s, 1H), 8.05 (s, 1H), 7.83 (s, 2H), 6.87 (s, 1H) 6.27 (s, 1H), 2.82-2.71 (m, 4H), 2.71-2.56 (m, 4H), 2.02-1.80 (m, 4H), 1.50 (s, 6H).

Route 2:

hexahydro-s-indacene (7.4 g, 37 mmol) was dissolved in dried THF (50 mL) and the solution was added to the front mixture dropwise at 0° C. The mixture was stirred at RT for 1 h. The reaction was quenched with ice-water (100 mL), and the pH value of the resulting solution was adjusted to 6 with HCO$_2$H. The solution was extracted with EtOAc (3×200 mL) and the combined organic layers were dried over anhydrous Na$_2$SO$_4$ and concentrated to give 17.5 g of Example 7 as a crude grey solid.

Example 7: MS-ESI: 521.0 (M+1). $^1$H NMR (300 MHz, MeOD-$d_4$) δ 8.14 (s, 1H), 6.89 (s, 1H), 3.00-2.60 (m, 8H), 2.20-1.90 (m, 4H), 1.51 (s, 6H), 1.37 (s, 9H).

Step 2: N'-(1,2,3,5,6,7-hexahydro-s-indacen-4-ylcarbamoyl)-2-(2-hydroxypropan-2-yl)thiazole-5-sulfonimidamide The crude tert-butyl (N-((1,2,3,5,6,7-hexahydro-s-indacen-4-yl)carbamoyl)-2-(2-hydroxypropan-2-yl)-thiazole-5-sulfonimidoyl)carbamate (crude 17.5 g) was dissolved in THF (200 mL). To the solution was added HCl (200 mL, 4M

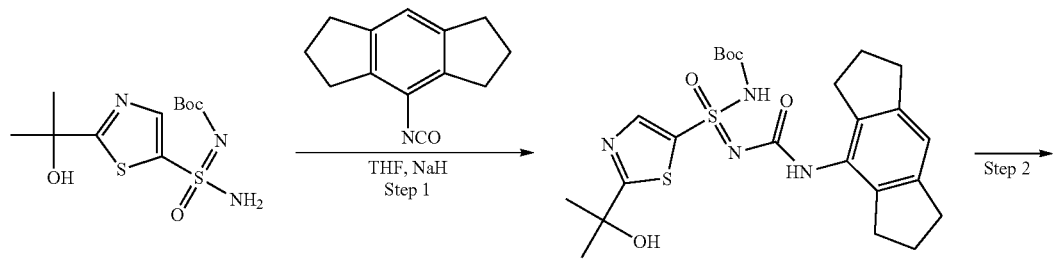

Example 7

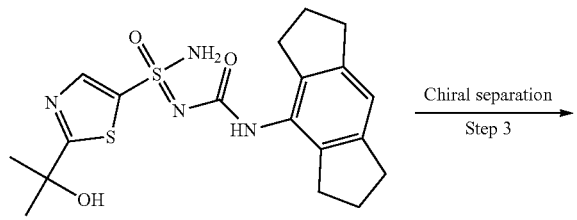

Example 4

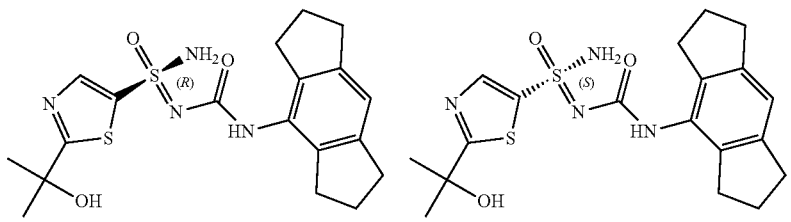

Examples 5 and 6 (stereochemistry not assigned)

Step 1: Tert-butyl N-(1,2,3,5,6,7-hexahydro-s-indacen-4-ylcarbamoyl)-2-(2-hydroxypropan-2-yl)thiazole-5-sulfonimidoylcarbamate Tert-butyl (amino(2-(2-hydroxypropan-2-yl)thiazol-5-yl)(oxo)-$\lambda^6$-sulfaneylidene)carbamate (12 g, 37 mmol) was dissolved in dried THF (200 mL). To the solution was added NaH (17.7 g, 60%, 44 mmol) in portions at 0° C. under nitrogen atmosphere, and then the mixture was stirred at 0° C. for 0.5 h. Freshly prepared 4-isocyanato-1,2,3,5,6,7- in 1,4-dioxane) at RT. The mixture was stirred at RT overnight and concentrated. The residue was purified with SiO$_2$-gel column and eluted with MeOH/DCM (5%) and further purified by reverse column with MeOH/water (50% to 80% in 50 minutes) to give 12 g of Example 4 (51%, 2 steps) as a white solid.

Example 4: MS-ESI: 421.0 (M+1). $^1$H NMR (400 MHz, DMSO-$d_6$) δ 8.46 (br s, 1H), 8.04 (s, 1H), 7.80 (br s, 2H), 6.86 (s, 1H) 6.28 (s, 111), 2.88-2.71 (m, 4H), 2.71-2.56 (m, 4H), 2.02-1.80 (m, 4H), 1.49 (s, 6H).

619
Step 3: Chiral Separation

The product obtained as described in the previous step (12 g) was resolved by Chiral-Prep-SFC using the following conditions: Column, CHIRALPAK IF, 2*25 cm, 5 um; Mobile Phase A: CO₂:60, Mobile Phase B: MeOH (2 mM NH₃-MeOH):40; Flow rate: 40 mL/min; Detector, UV 220 nm. This resulted in 3.8 g of Example 6 (front peak, 99% ee 102) as a white solid and 4.6 g of Example 5 (second peak, 97.5% ee 101) as a white solid. Absolute stereochemistry of these two isomers has not been assigned.

Example 5: MS-ESI: 421.0 (M+1). $^1$H NMR (400 MHz, DMSO-$d_6$) δ 8.43 (br s, 1H), 8.05 (s, 1H), 7.83 (br s, 2H), 6.87 (s, 1H) 6.29 (s, 1H), 2.82-2.71 (m, 4H), 2.71-2.56 (m, 4H), 2.02-1.80 (m, 4H), 1.50 (s, 6H).

Example 6: MS-ESI: 421.0 (M+1). $^1$H NMR (400 MHz, DMSO-$d_6$) δ 8.41 (br s, 1H), 8.05 (s, 1H), 7.83 (s, 2H), 6.87 (s, 1H) 6.27 (s, 1H), 2.82-2.71 (m, 4H), 2.71-2.56 (m, 4H), 2.02-1.80 (m, 4H), 1.50 (s, 6H).

Example 8

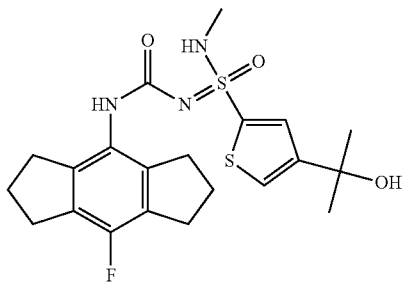 [SMILES: CNS(=O)(=NC(=O)Nc1c2c(c(F)c3c1CCC3)CCC2)c1cc(C(C)(C)O)cs1]

Example 8 (270): N'-(8-fluoro-1,2,3,5,6,7-hexahydro-s-indacen-4-ylcarbamoyl)-4-(2-hydroxypropan-2-yl)-N-methylthiophene-2-sulfonimidamide (Scheme 4)

Example 8 was synthesized according to the general method shown in Scheme 4.

Into a 50-mL round-bottom flask purged with and maintained under nitrogen was placed a solution of 4-fluoro-8-isocyanato-1,2,3,5,6,7-hexahydro-s-indacene (110 mg, 0.51 mmol) in DCM (5 mL). To the solution were added TEA (153 mg, 1.51 mmol) and 4-(2-hydroxypropan-2-yl)-N'-methylthiophene-2-sulfonimidamide (120 mg, 0.51 mmol). The resulting solution was stirred for 14 h at RT and then was concentrated under vacuum. The crude product was purified by Prep-HPLC using method E eluted with a gradient of 30~74% ACN. This resulted in 80 mg (35%) of Example 8 as a white solid.

Example 8: MS-ESI: 450.1 (M−1). $^1$H NMR (400 MHz, DMSO-$d_6$) δ 8.50 (br s, 1H), 7.64 (s, 1H), 7.59-7.50 (m, 2H), 5.23 (s, 1H), 2.84-2.69 (m, 8H), 2.50 (s, 3H), 1.99 (t, J=7.2 Hz, 4H), 1.42 (d, J=2.8 Hz, 6H)

620
Example 9 (204)

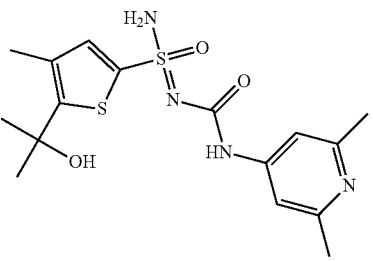 [SMILES: Cc1cc(NC(=O)N=S(N)(=O)c2cc(C)c(C(C)(C)O)s2)cc(C)n1]

N'-((2,6-dimethylpyridin-4-yl)carbamoyl)-4-methyl-5-(2-hydroxypropan-2-yl)thiophene-2-sulfonimidamide (Scheme 5)

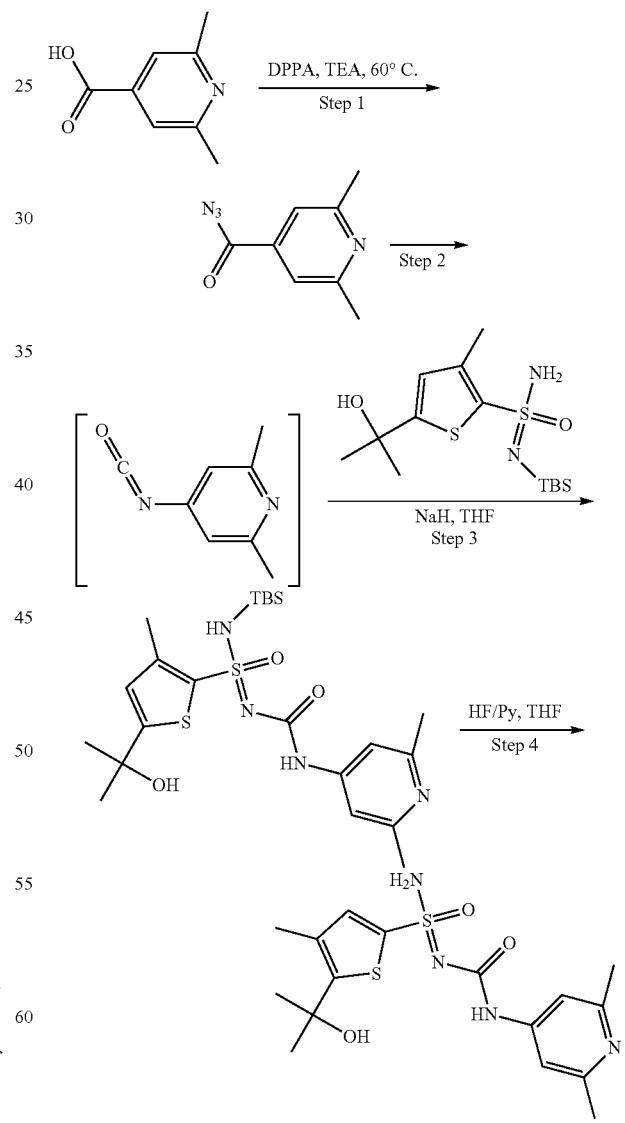

Example 9

Step 1: 4-Azido-2,6-dimethylpyridine

To the solution of 2,6-dimethylpyridine-4-carboxylic acid (151 mg, 1.0 mmol) in dried toluene (15 mL). To the solution was added DPPA (825 mg, 3.0 mmol) and TEA (303 mg, 3.0 mmol). The mixture was stirred at 60° C. for 4 h. The solution was concentrated under vacuum. This gave 900 mg (crude) of the title compound as yellow oil.

Step 2 & 3: N-(tert-butyldimethylsilyl)-N'-((2,6-dimethylpyridin-4-yl)carbamoyl)-5-(2-hydroxypropan-2-yl)-3-methylthiophene-2-sulfonimidamide The 4-azido-2,6-dimethylpyridine (900 mg, crude) was dissolved in THF (20 mL). To the solution was added N'-(tert-butyldimethylsilyl)-5-(2-hydroxypropan-2-yl)-3-methylthiophene-2-sulfonimidamide (349 mg, 1.0 mmol) and NaOH (120 mg, 3.0 mmol). The mixture was stirred at 50° C. for 12 h. The solution was diluted with water 20 mL, then the resulting solution was extracted with 3×20 mL of ethyl acetate. The organic layers were combined, dried over anhydrous $Na_2SO_4$, then concentrated under vacuum. This gave 500 mg (crude) of the title compound as a yellow solid. MS-ESI: 497.0 (M+1).

Step 4: N'-((2,6-dimethylpyridin-4-yl)carbamoyl)-4-methyl-5-(2-hydroxypropan-2-yl)thiophene-2-sulfonimidamide Into a 50-mL round-bottom flask was placed a solution of N-(tert-butyldimethylsilyl)-N'-((2,6-dimethylpyridin-4-yl)carbamoyl)-4-methyl-5-(2-hydroxypropan-2-yl)thiophene-2-sulfonimidamide (500 mg, crude) in THF (10 mL), to this solution was added HF/Py (70% wt, 143 mg, 5.0 mmol) dropwise at 0° C. The solution was stirred at RT for 4 h. The reaction was then quenched by the addition of 10 mL of water. The resulting solution was extracted with 3×10 mL of ethyl acetate and the combined organic layers were concentrated under vacuum. The crude product was purified by Prep-HPLC using method E eluted with a gradient of ACN/water (10% to 30% in 10 minutes). This resulted in 15 mg (4%, 4 steps) of Example 9 as a white solid. MS-ESI: 383.0 (M+1). $^1$H NMR (300 MHz, DMSO-$d_6$) δ 9.31 (s, 1H), 7.53 (br s, 2H), 7.31 (s, 1H), 7.14 (s, 2H), 5.81 (s, 1H), 2.28 (s, 6H), 2.23 (s, 3H), 1.50 (s, 6H).

TABLE 16

Examples in the following table were prepared using similar conditions as described in Example 1 and Scheme 1 from appropriate starting materials.

| Example # | Final Target Number | Structure | IUPAC Name | Exact Mass [M + H]⁺ |
|---|---|---|---|---|
| 10 | 180 | 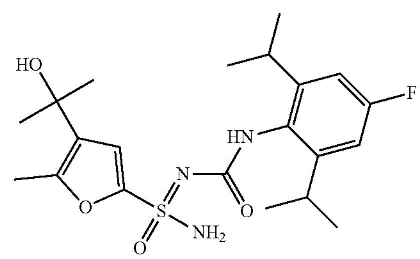 [SMILES: Cc1oc(S(N)(=O)=NC(=O)Nc2c(C(C)C)cc(F)cc2C(C)C)cc1C(C)(C)O] | N'-(4-fluoro-2,6-diisopropylphenylcarbamoyl)-4-(2-hydroxypropan-2-yl)-5-methylfuran-2-sulfonimidamide | 440.2 |
| 11 | 190 | 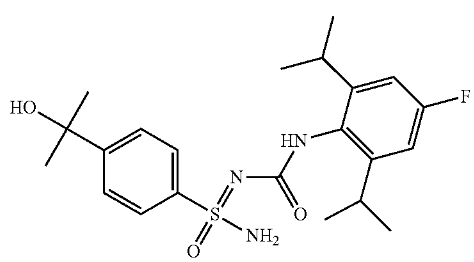 [SMILES: CC(C)c1cc(F)cc(C(C)C)c1NC(=O)N=S(N)(=O)c1ccc(C(C)(C)O)cc1] | N'-(4-fluoro-2,6-diisopropylphenylcarbamoyl)-4-(2-hydroxypropan-2-yl)benzenesulfonimidamide | 436.2 |
| 12 | 182 | 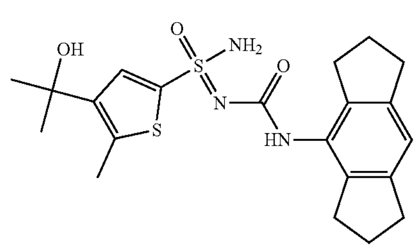 [SMILES: Cc1sc(S(N)(=O)=NC(=O)Nc2c3c(cc4c2CCC4)CCC3)cc1C(C)(C)O] | N'-(1,2,3,5,6,7-hexahydro-s-indacen-4-ylcarbamoyl)-4-(2-hydroxypropan-2-yl)-5-methylthiophene-2-sulfonimidamide | 434.1 |

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]+ |
|---|---|---|---|---|
| 13 | 191 | 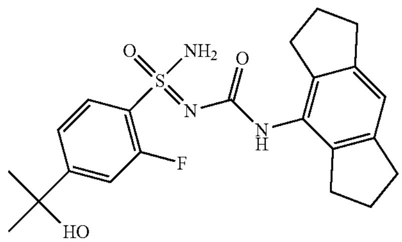 [SMILES: CC(C)(O)c1ccc(S(N)(=O)=NC(=O)Nc2c3c(cc4c2CCC4)CCC3)c(F)c1] | 2-fluoro-N'-(1,2,3,5,6,7-hexahydro-s-indacen-4-ylcarbamoyl)-4-(2-hydroxypropan-2-yl)benzenesulfonimidamide | 432.2 |
| 14 | 177 | 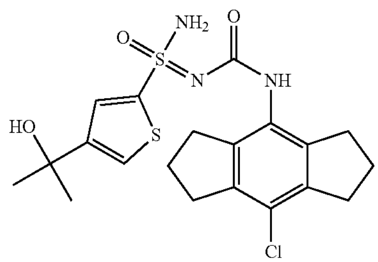 [SMILES: CC(C)(O)c1csc(S(N)(=O)=NC(=O)Nc2c3c(c(Cl)c4c2CCC4)CCC3)c1] | N'-(8-chloro-1,2,3,5,6,7-hexahydro-s-indacen-4-ylcarbamoyl)-4-(2-hydroxypropan-2-yl)thiophene-2-sulfonimidamide | 452.0 (M − 1) |
| 15 | 185 | 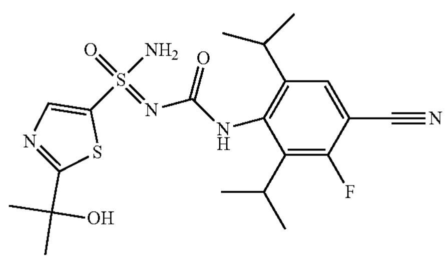 [SMILES: CC(C)c1cc(C#N)c(F)c(C(C)C)c1NC(=O)N=S(N)(=O)c1cnc(C(C)(C)O)s1] | N'-(4-cyano-3-fluoro-2,6-diisopropylphenylcarbamoyl)-2-(2-hydroxypropan-2-yl)thiazole-5-sulfonimidamide | 468.2 |
| 16 | 186 | 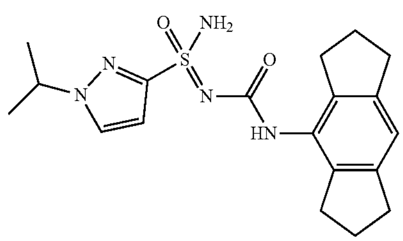 [SMILES: CC(C)n1ccc(S(N)(=O)=NC(=O)Nc2c3c(cc4c2CCC4)CCC3)n1] | N'-(1,2,3,5,6,7-hexahydro-5-indacen-4-ylcarbamoyl)-1-isopropyl-1H-pyrazole-3-sulfonimidamide | 388.1 |
| 17 | 187 | 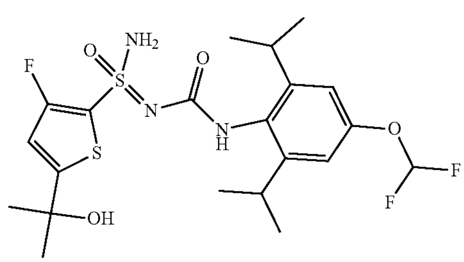 [SMILES: CC(C)c1cc(OC(F)F)cc(C(C)C)c1NC(=O)N=S(N)(=O)c1sc(C(C)(C)O)cc1F] | N'-(4-(difluoromethoxy)-2,6-diisopropylphenylcarbamoyl)-3-fluoro-5-(2-hydroxypropan-2-yl)thiophene-2-sulfonimidamide | 508.2 |
| 18 | 188 | 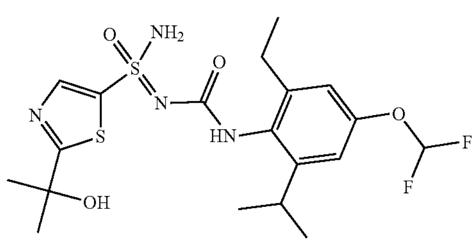 [SMILES: CCc1cc(OC(F)F)cc(C(C)C)c1NC(=O)N=S(N)(=O)c1cnc(C(C)(C)O)s1] | N'-(4-(difluoromethoxy)-2-ethyl-6-isopropylphenylcarbamoyl)-2-(2-hydroxypropan-2-yl)thiazole-5-sulfonimidamide | 477.1 |

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]+ |
|---|---|---|---|---|
| 19 | 192 | 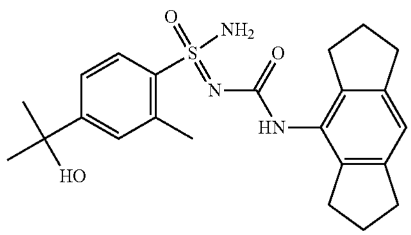 [SMILES: Cc1cc(C(C)(C)O)ccc1S(N)(=O)=NC(=O)Nc1c2c(cc3c1CCC3)CCC2] | N'-(1,2,3,5,6,7-hexahydro-s-indacen-4-ylcarbamoyl)-4-(2-hydroxypropan-2-yl)-2-methylbenzenesulfonimidamide | 426.2 (M − 1) |
| 20 | 189 | 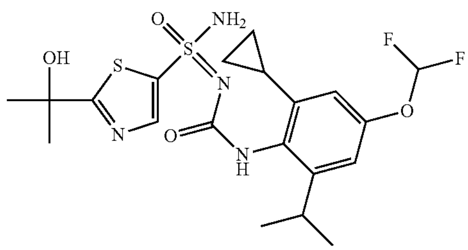 [SMILES: CC(C)c1cc(OC(F)F)cc(C2CC2)c1NC(=O)N=S(N)(=O)c1cnc(C(C)(C)O)s1] | N'-(2-cyclopropyl-4-(difluoromethoxy)-6-isopropylphenylcarbamoyl)-2-(2-hydroxypropan-2-yl)thiazole-5-sulfonimidamide | 487.1 (M − 1) |
| 21 | 178 | 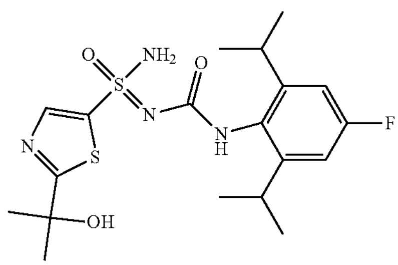 [SMILES: CC(C)c1cc(F)cc(C(C)C)c1NC(=O)N=S(N)(=O)c1cnc(C(C)(C)O)s1] | N'-(4-fluoro-2,6-diisopropylphenylcarbamoyl)-2-(2-hydroxypropan-2-yl)thiazole-5-sulfonimidamide | 441.1 (M − 1) |
| 22 | 193 | 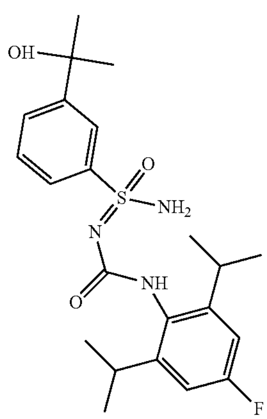 [SMILES: CC(C)c1cc(F)cc(C(C)C)c1NC(=O)N=S(N)(=O)c1cccc(C(C)(C)O)c1] | N'-(4-fluoro-2,6-diisopropylphenylcarbamoyl)-3-(2-hydroxypropan-2-yl)benzenesulfonimidamide | 436.1 |
| 23 | 170 | 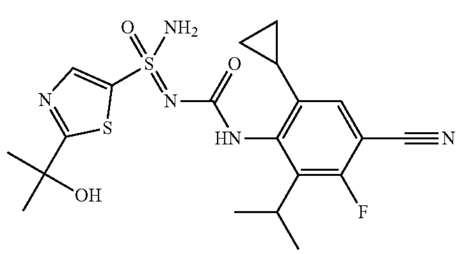 [SMILES: CC(C)c1c(F)c(C#N)cc(C2CC2)c1NC(=O)N=S(N)(=O)c1cnc(C(C)(C)O)s1] | N'-(4-cyano-6-cyclopropyl-3-fluoro-2-isopropylphenylcarbamoyl)-2-(2-hydroxypropan-2-yl)thiazole-5-sulfonimidamide | 466.1 |

US 12,084,424 B2

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]+ |
|---|---|---|---|---|
| 24 | 168 | 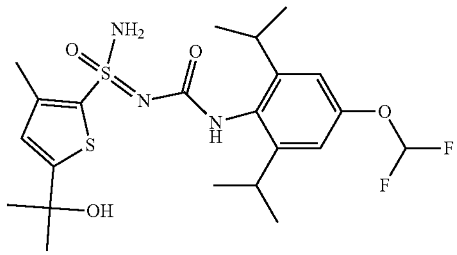 [SMILES: Cc1cc(C(C)(C)O)sc1S(N)(=O)=NC(=O)Nc1c(C(C)C)cc(OC(F)F)cc1C(C)C] | N'-(4-(difluoromethoxy)-2,6-diisopropylphenylcarbamoyl)-5-(2-hydroxypropan-2-yl)-3-methylthiophene-2-sulfonimidamide | 504.3 |
| 25 | 171 | 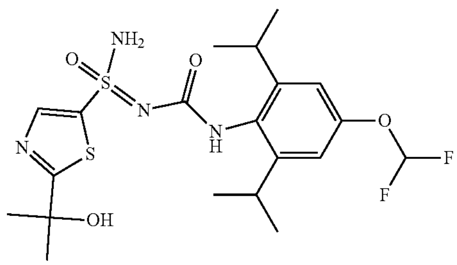 [SMILES: CC(C)c1cc(OC(F)F)cc(C(C)C)c1NC(=O)N=S(N)(=O)c1cnc(C(C)(C)O)s1] | N'-(4-(difluoromethoxy)-2,6-diisopropylphenylcarbamoyl)-2-(2-hydroxypropan-2-yl)thiazole-5-sulfonimidamide | 491.1 |
| 26 | 122 | 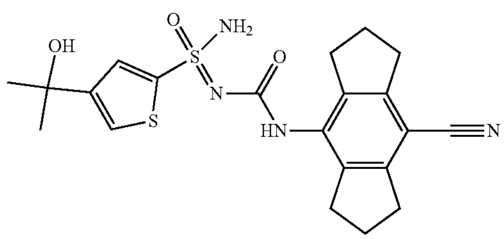 [SMILES: CC(C)(O)c1csc(S(N)(=O)=NC(=O)Nc2c3c(c(C#N)c4c2CCC4)CCC3)c1] | N'-(8-cyano-1,2,3,5,6,7-hexahydro-s-indacen-4-ylcarbamoyl)-4-(2-hydroxypropan-2-yl)thiophene-2-sulfonimidamide | 443.1 (M − 1) |
| 27 | 120 | 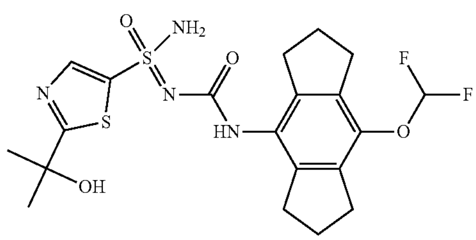 [SMILES: CC(C)(O)c1ncc(S(N)(=O)=NC(=O)Nc2c3c(c(OC(F)F)c4c2CCC4)CCC3)s1] | N'-(8-(difluoromethoxy)-1,2,3,5,6,7-hexahydro-s-indacen-4-ylcarbamoyl)-2-(2-hydroxypropan-2-yl)thiazole-5-sulfonimidamide | 487.1 |
| 28 | 125 | 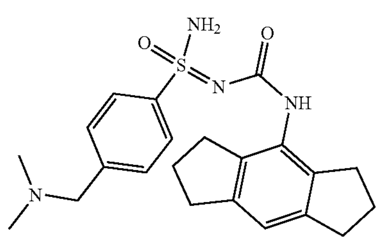 [SMILES: CN(C)Cc1ccc(S(N)(=O)=NC(=O)Nc2c3c(cc4c2CCC4)CCC3)cc1] | 4-((dimethylamino)methyl)-N'-(1,2,3,5,6,7-hexahydro-s-indacen-4-ylcarbamoyl)benzenesulfonimidamide | 413.3 |
| 29 | 129 | 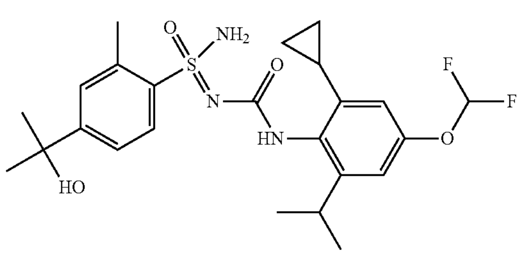 [SMILES: Cc1cc(C(C)(C)O)ccc1S(N)(=O)=NC(=O)Nc1c(C(C)C)cc(OC(F)F)cc1C1CC1] | N'-(2-cyclopropyl-4-(difluoromethoxy)-6-isopropylphenylcarbamoyl)-4-(2-hydroxypropan-2-yl)-2-methylbenzenesulfonimidamide | 496.2 |

TABLE 16-continued

Examples in the following table were prepared using similar conditions as described in Example 1 and Scheme 1 from appropriate starting materials.

| Example # | Final Target Number | Structure | IUPAC Name | Exact Mass [M + H]+ |
|---|---|---|---|---|
| 30 | 213 | 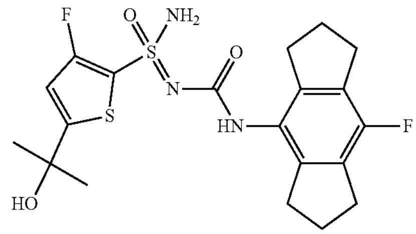 [SMILES: CC(C)(O)c1cc(F)c(S(N)(=O)=NC(=O)Nc2c3c(c(F)c4c2CCC4)CCC3)s1] | 3-fluoro-N'-(8-fluoro-1,2,3,5,6,7-hexahydro-s-indacen-4-ylcarbamoyl)-5-(2-hydroxypropan-2-yl)thiophene-2-sulfonimidamide | 456.1 |
| 31 | 207 | 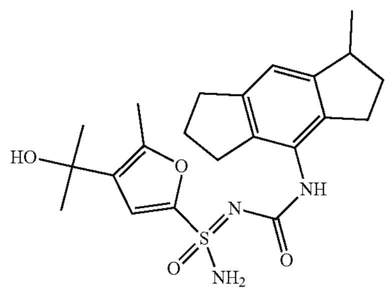 [SMILES: Cc1oc(S(N)(=O)=NC(=O)Nc2c3c(cc4c2CCC4C)CCC3)cc1C(C)(C)O] | 4-(2-hydroxypropan-2-yl)-5-methyl-N'-((3-methyl-1,2,3,5,6,7-hexahydro-s-indacen-4-yl)carbamoyl)furan-2-sulfonimidamide | 432.2 |
| 32 | 195 | 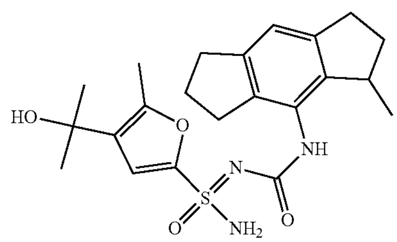 [SMILES: Cc1oc(S(N)(=O)=NC(=O)Nc2c3c(cc4c2C(C)CC4)CCC3)cc1C(C)(C)O] | 4-(2-hydroxypropan-2-yl)-5-methyl-N'-((1-methyl-1,2,3,5,6,7-hexahydro-s-indacen-4-yl)carbamoyl)furan-2-sulfonimidamide | 432.2 |

TABLE 17

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 33 | 179 | 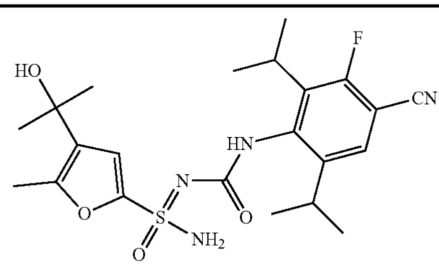 | N'-(4-cyano-3-fluoro-2,6-diisopropylphenylcarbamoyl)-4-(2-hydroxypropan-2-yl)-5-methylfuran-2-sulfonimidamide | 465.2 |
| 34 | 105 | 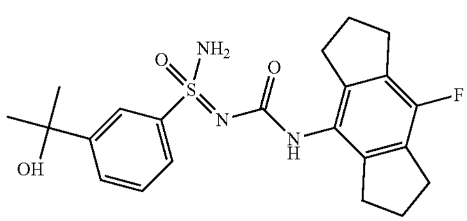 [SMILES: CC(C)(O)c1cccc(S(N)(=O)=NC(=O)Nc2c3c(c(F)c4c2CCC4)CCC3)c1] | N'-(8-fluoro-1,2,3,5,6,7-hexahydro-s-indacen-4-ylcarbamoyl)-3-(2-hydroxypropan-2-yl)benzenesulfonimidamide | 432.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 35 | 121 | 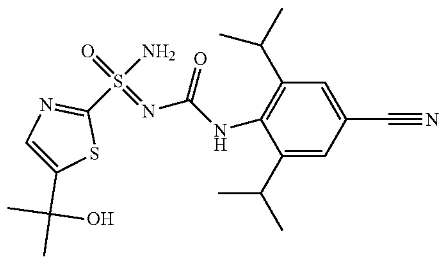 [SMILES: CC(C)c1cc(C#N)cc(C(C)C)c1NC(=O)N=S(N)(=O)c1ncc(C(C)(C)O)s1] | N'-(4-cyano-2,6-diisopropylphenylcarbamoyl)-5-(2-hydroxypropan-2-yl)thiazole-2-sulfonimidamide | 448.1 (M − 1) |
| 36 | 145 | 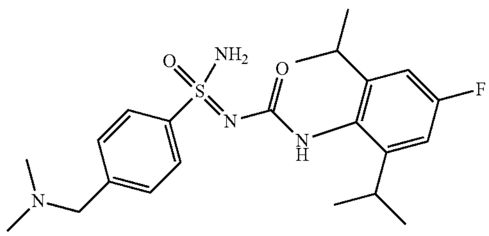 [SMILES: CC(C)c1cc(F)cc(C(C)C)c1NC(=O)N=S(N)(=O)c1ccc(CN(C)C)cc1] | 4-((dimethylamino)methyl)-N'-(4-fluoro-2,6-diisopropylphenylcarbamoyl)benzenesulfonimidamide | 435.2 |
| 37 | 131 | 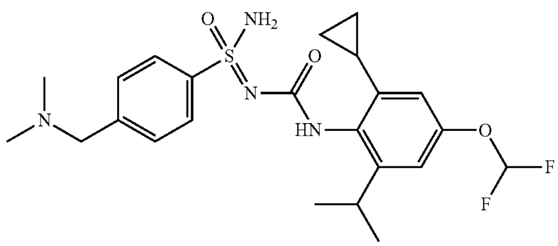 [SMILES: CC(C)c1cc(OC(F)F)cc(C2CC2)c1NC(=O)N=S(N)(=O)c1ccc(CN(C)C)cc1] | N'-(2-cyclopropyl-4-(difluoromethoxy)-6-isopropylphenylcarbamoyl)-4-((dimethylamino)methyl)benzenesulfonimidamide | 481.3 |
| 38 | 132 | 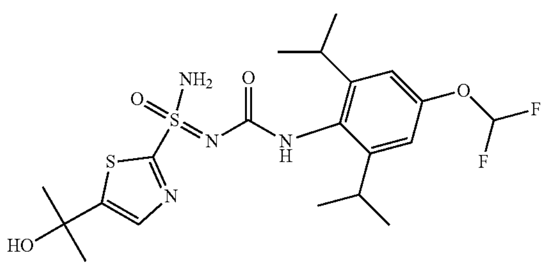 [SMILES: CC(C)c1cc(OC(F)F)cc(C(C)C)c1NC(=O)N=S(N)(=O)c1ncc(C(C)(C)O)s1] | N'-(4-(difluoromethoxy)-2,6-diisopropylphenylcarbamoyl)-5-(2-hydroxypropan-2-yl)thiazole-2-sulfonimidamide | 489.1 (M − 1) |
| 39 | 144 | 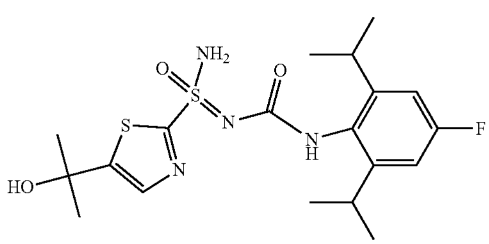 [SMILES: CC(C)c1cc(F)cc(C(C)C)c1NC(=O)N=S(N)(=O)c1ncc(C(C)(C)O)s1] | N'-(4-fluoro-2,6-diisopropylphenylcarbamoyl)-5-(2-hydroxypropan-2-yl)thiazole-2-sulfonimidamide | 441.1 (M − 1) |
| 40 | 149 | 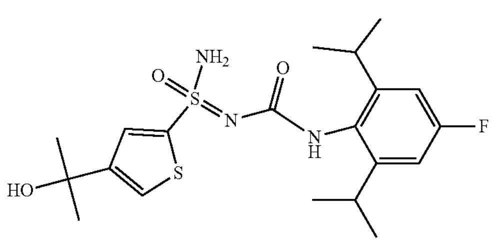 [SMILES: CC(C)c1cc(F)cc(C(C)C)c1NC(=O)N=S(N)(=O)c1cc(C(C)(C)O)cs1] | N'-(4-fluoro-2,6-diisopropylphenylcarbamoyl)-4-(2-hydroxypropan-2-yl)thiophene-2-sulfonimidamide | 440.1 (M − 1) |

TABLE 17-continued

Examples in the following table were prepared using similar conditions as described in
Example 4 - route 1 and Scheme 2 from appropriate starting materials.

| Example # | Final Target Number | Structure | IUPAC Name | Exact Mass [M + H]+ |
|---|---|---|---|---|
| 41 | 152 | 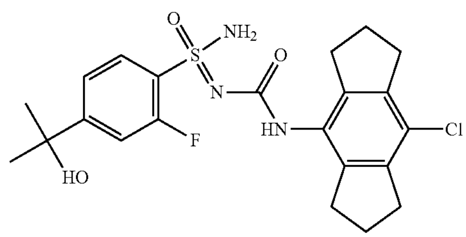 [SMILES: CC(C)(O)c1ccc(S(N)(=O)=NC(=O)Nc2c3c(c(Cl)c4c2CCC4)CCC3)c(F)c1] | N'-(8-chloro-1,2,3,5,6,7-hexahydro-s-indacen-4-ylcarbamoyl)-2-fluoro-4-(2-hydroxypropan-2-yl)benzenesulfonimidamide | 466.2 |
| 42 | 150 | 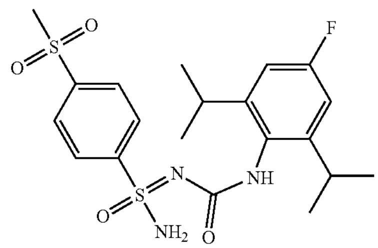 [SMILES: CC(C)c1cc(F)cc(C(C)C)c1NC(=O)N=S(N)(=O)c1ccc(S(C)(=O)=O)cc1] | N'-(4-fluoro-2,6-diisopropylphenylcarbamoyl)-4-(methylsulfonyl)benzene-sulfonimidamide | 454.1 (M − 1) |
| 43 | 167 | 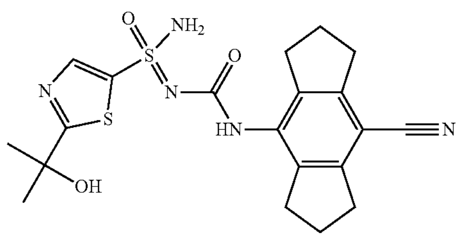 [SMILES: CC(C)(O)c1ncc(S(N)(=O)=NC(=O)Nc2c3c(c(C#N)c4c2CCC4)CCC3)s1] | N'-(8-cyano-1,2,3,5,6,7-hexahydro-s-indacen-4-ylcarbamoyl)-2-(2-hydroxypropan-2-yl)thiazole-5-sulfonimidamide | 444.2 (M − 1) |
| 44 | 106 | 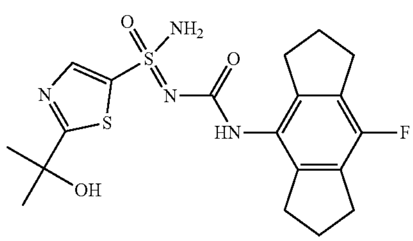 [SMILES: CC(C)(O)c1ncc(S(N)(=O)=NC(=O)Nc2c3c(c(F)c4c2CCC4)CCC3)s1] | N'-(8-fluoro-1,2,3,5,6,7-hexahydro-s-indacen-4-ylcarbamoyl)-2-(2-hydroxypropan-2-yl)thiazole-5-sulfonimidamide | 437.1 (M − 1) |
| 45 | 107 | 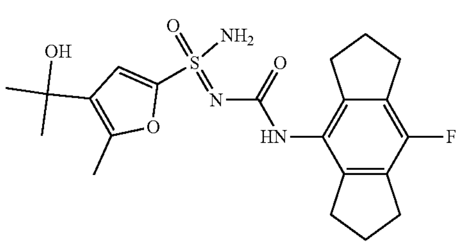 [SMILES: Cc1oc(S(N)(=O)=NC(=O)Nc2c3c(c(F)c4c2CCC4)CCC3)cc1C(C)(C)O] | N'-(8-fluoro-1,2,3,5,6,7-hexahydro-s-indacen-4-ylcarbamoyl)-4-(2-hydroxypropan-2-yl)-5-methylfuran-2-sulfonimidamide | 436.2 |
| 46 | 110 | 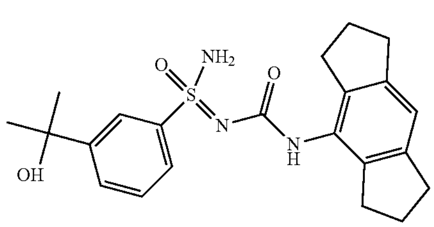 [SMILES: CC(C)(O)c1cccc(S(N)(=O)=NC(=O)Nc2c3c(cc4c2CCC4)CCC3)c1] | N'-(1,2,3,5,6,7-hexahydro-s-indacen-4-ylcarbamoyl)-3-(2-hydroxypropan-2-yl)benzenesulfonimidamide | 414.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 47 | 151 | 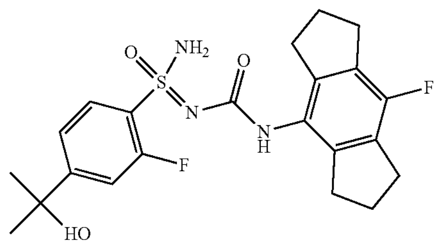 [SMILES: CC(C)(O)c1ccc(S(N)(=O)=NC(=O)Nc2c3c(c(F)c4c2CCC4)CCC3)c(F)c1] | 2-fluoro-N'-(8-fluoro-1,2,3,5,6,7-hexahydro-s-indacen-4-ylcarbamoyl)-4-(2-hydroxypropan-2-yl)benzenesulfonimidamide | 448.1 (M − 1) |
| 48 | 154 | 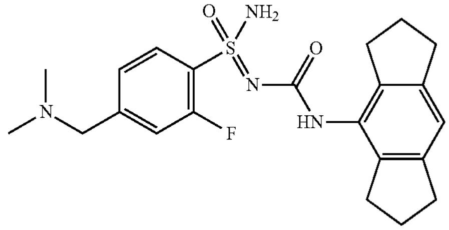 [SMILES: CN(C)Cc1ccc(S(N)(=O)=NC(=O)Nc2c3c(cc4c2CCC4)CCC3)c(F)c1] | 4-((dimethylamino)methyl)-2-fluoro-N'-(1,2,3,5,6,7-hexahydro-s-indacen-4-ylcarbamoyl)benzenesulfonimidamide | 431.2 |
| 49 | 148 | 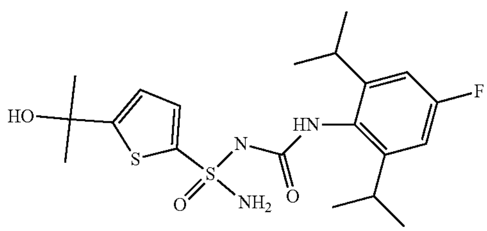 | N'-(4-fluoro-2,6-diisopropylphenylcarbamoyl)-5-(2-hydroxypropan-2-yl)thiophene-2-sulfonimidamide | 442.2 |
| 50 | 153 | 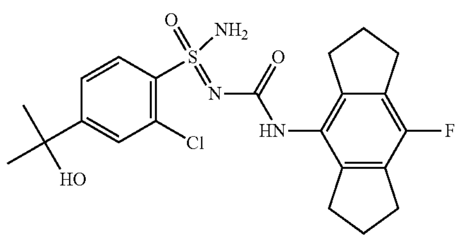 [SMILES: CC(C)(O)c1ccc(S(N)(=O)=NC(=O)Nc2c3c(c(F)c4c2CCC4)CCC3)c(Cl)c1] | 2-chloro-N'-(8-fluoro-1,2,3,5,6,7-hexahydro-s-indacen-4-ylcarbamoyl)-4-(2-hydroxypropan-2-yl)benzenesulfonimidamide | 464.1 (M − 1) |
| 51 | 109 | 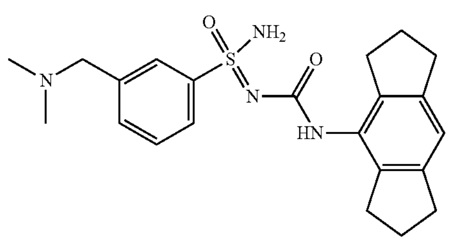 [SMILES: CN(C)Cc1cccc(S(N)(=O)=NC(=O)Nc2c3c(cc4c2CCC4)CCC3)c1] | 3-((dimethylamino)methyl)-N'-(1,2,3,5,6,7-hexahydro-s-indacen-4-ylcarbamoyl)benzenesulfonimidamide | 411.1 (M − 1) |
| 52 | 135 | 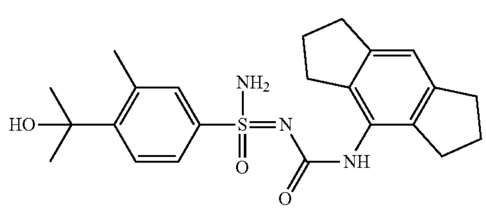 [SMILES: Cc1cc(S(N)(=O)=NC(=O)Nc2c3c(cc4c2CCC4)CCC3)ccc1C(C)(C)O] | N'-((1,2,3,5,6,7-hexahydro-s-indacen-4-yl)carbamoyl)-4-(2-hydroxypropan-2-yl)-3-methylbenzenesulfonimidamide | 428.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 53 | 134 | 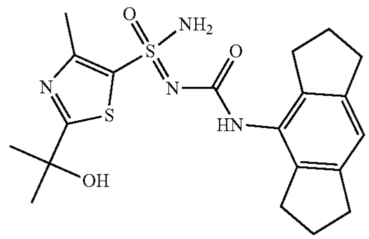 [SMILES: Cc1nc(C(C)(C)O)sc1S(N)(=O)=NC(=O)Nc1c2c(cc3c1CCC3)CCC2] | N'-((1,2,3,5,6,7-hexahydro-s-indacen-4-yl)carbamoyl)-2-(2-hydroxypropan-2-yl)-4-methylthiazole-5-sulfonimidamide | 435.1 |
| 54 | 130 | 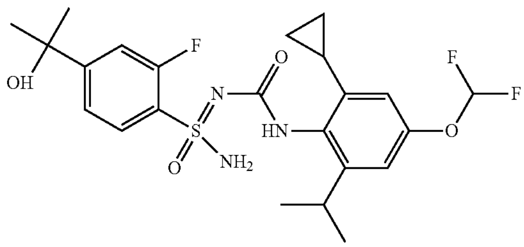 [SMILES: CC(C)c1cc(OC(F)F)cc(C2CC2)c1NC(=O)N=S(N)(=O)c1ccc(C(C)(C)O)cc1F] | N'-((2-cyclopropyl-4-(difluoromethoxy)-6-isopropylphenyl)carbamoyl)-2-fluoro-4-(2-hydroxypropan-2-yl)benzenesulfonimidamide | 500.2 |
| 55 | 212 | 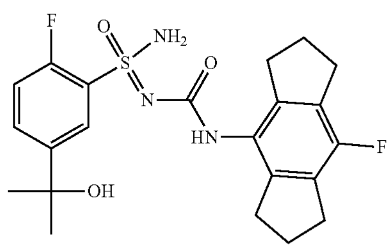 [SMILES: CC(C)(O)c1ccc(F)c(S(N)(=O)=NC(=O)Nc2c3c(c(F)c4c2CCC4)CCC3)c1] | 2-fluoro-N'-((8-fluoro-1,2,3,5,6,7-hexahydro-s-indacen-4-yl)carbamoyl)-5-(2-hydroxypropan-2-yl)benzenesulfonimidamide | 450.2 |
| 56 | 205 | 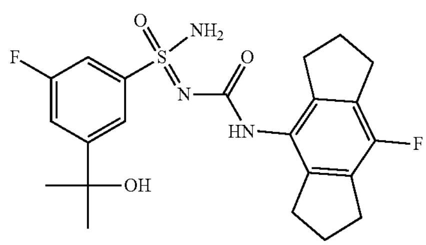 [SMILES: CC(C)(O)c1cc(F)cc(S(N)(=O)=NC(=O)Nc2c3c(c(F)c4c2CCC4)CCC3)c1] | 3-fluoro-N'-((8-fluoro-1,2,3,5,6,7-hexahydro-s-indacen-4-yl)carbamoyl)-5-(2-hydroxypropan-2-yl)benzenesulfonimidamide | 450.2 |
| 57 | 143 | 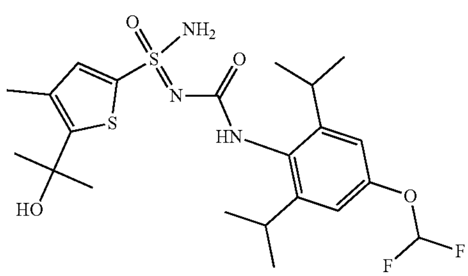 [SMILES: Cc1cc(S(N)(=O)=NC(=O)Nc2c(C(C)C)cc(OC(F)F)cc2C(C)C)sc1C(C)(C)O] | N'-((4-(difluoromethoxy)-2,6-diisopropylphenyl)carbamoyl)-5-(2-hydroxypropan-2-yl)-4-methylthiophene-2-sulfonimidamide | 504.2 |
| 58 | 206 | 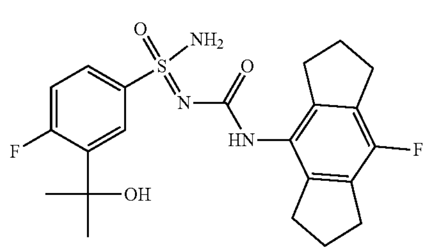 [SMILES: CC(C)(O)c1cc(S(N)(=O)=NC(=O)Nc2c3c(c(F)c4c2CCC4)CCC3)ccc1F] | 4-fluoro-N'-((8-fluoro-1,2,3,5,6,7-hexahydro-s-indacen-4-yl)carbamoyl)-3-(2-hydroxypropan-2-yl)benzenesulfonimidamide | 450.2 |

TABLE 17-continued

Examples in the following table were prepared using similar conditions as described in
Example 4 - route 1 and Scheme 2 from appropriate starting materials.

| Example # | Final Target Number | Structure | IUPAC Name | Exact Mass [M + H]+ |
|---|---|---|---|---|
| 59 | 108 | 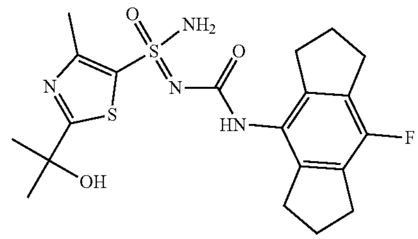 [SMILES: Cc1nc(C(C)(C)O)sc1S(N)(=O)=NC(=O)Nc1c2c(c(F)c3c1CCC3)CCC2] | N'-((8-fluoro-1,2,3,5,6,7-hexahydro-s-indacen-4-yl)carbamoyl)-2-(2-hydroxypropan-2-yl)-4-methylthiazole-5-sulfonimidamide | 453.1 |
| 60 | 202 | 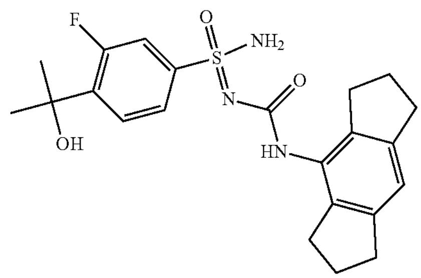 [SMILES: CC(C)(O)c1ccc(S(N)(=O)=NC(=O)Nc2c3c(cc4c2CCC4)CCC3)cc1F] | 3-fluoro-N'-((1,2,3,5,6,7-hexahydro-s-indacen-4-yl)carbamoyl)-4-(2-hydroxypropan-2-yl)benzenesulfonimidamide | 432.2 |
| 61 | 208 | 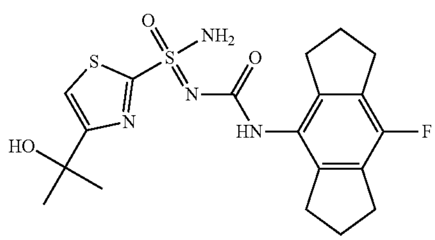 [SMILES: CC(C)(O)c1csc(S(N)(=O)=NC(=O)Nc2c3c(c(F)c4c2CCC4)CCC3)n1] | N'-((8-fluoro-1,2,3,5,6,7-hexahydro-s-indacen-4-yl)carbamoyl)-4-(2-hydroxypropan-2-yl)thiazole-2-sulfonimidamide | 439.1 |
| 62 | 197 | 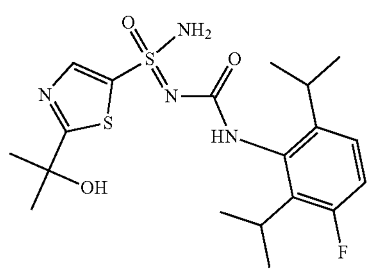 [SMILES: CC(C)c1ccc(F)c(C(C)C)c1NC(=O)N=S(N)(=O)c1cnc(C(C)(C)O)s1] | N'-((3-fluoro-2,6-diisopropylphenyl)carbamoyl)-2-(2-hydroxypropan-2-yl)thiazole-5-sulfonimidamide | 443.2 |
| 63 | 196 | 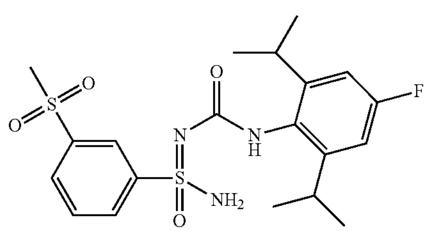 [SMILES: CC(C)c1cc(F)cc(C(C)C)c1NC(=O)N=S(N)(=O)c1cccc(S(C)(=O)=O)c1] | N'-((4-fluoro-2,6-diisopropylphenyl)carbamoyl)-3-(methylsulfonyl)benzene-sulfonimidamide | 456.1 |
| 64 | 124 | 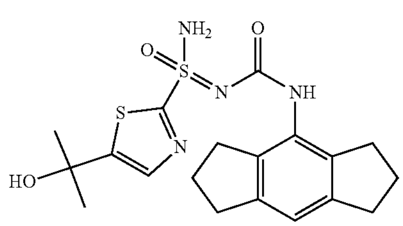 [SMILES: CC(C)(O)c1cnc(S(N)(=O)=NC(=O)Nc2c3c(cc4c2CCC4)CCC3)s1] | N'-((1,2,3,5,6,7-hexahydro-s-indacen-4-yl)carbamoyl)-5-(2-hydroxypropan-2-yl)thiazole-2-sulfonimidamide | 421.1 |

TABLE 17-continued

Examples in the following table were prepared using similar conditions as described in
Example 4 - route 1 and Scheme 2 from appropriate starting materials.

| Example # | Final Target Number | Structure | IUPAC Name | Exact Mass [M + H]+ |
|---|---|---|---|---|
| 65 | 173 | 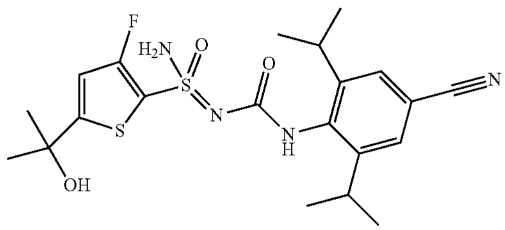 [SMILES: CC(C)c1cc(C#N)cc(C(C)C)c1NC(=O)N=S(N)(=O)c1sc(C(C)(C)O)cc1F] | N'-((4-cyano-2,6-diisopropylphenyl)carbamoyl)-3-fluoro-5-(2-hydroxypropan-2-yl)thiophene-2-sulfonimidamide | 467.2 |
| 66 | 172 | 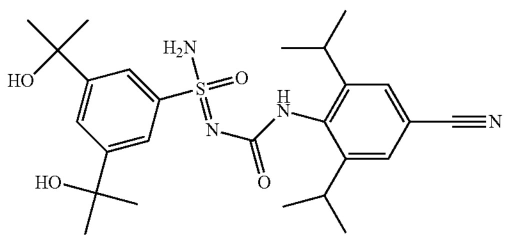 [SMILES: CC(C)c1cc(C#N)cc(C(C)C)c1NC(=O)N=S(N)(=O)c1cc(C(C)(C)O)cc(C(C)(C)O)c1] | N'-((4-cyano-2,6-diisopropylphenyl)carbamoyl)-3,5-bis(2-hydroxypropan-2-yl)benzenesulfonimidamide | 501.2 |
| 67 | 174 | 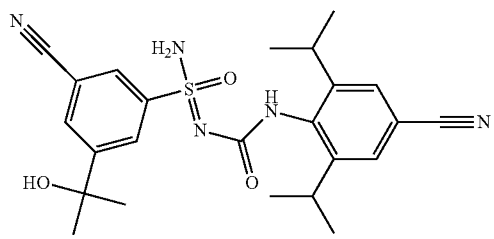 [SMILES: CC(C)c1cc(C#N)cc(C(C)C)c1NC(=O)N=S(N)(=O)c1cc(C#N)cc(C(C)(C)O)c1] | 3-cyano-N'-((4-cyano-2,6-diisopropylphenyl)carbamoyl)-5-(2-hydroxypropan-2-yl)benzenesulfonimidamide | 468.2 |
| 68 | 158 | 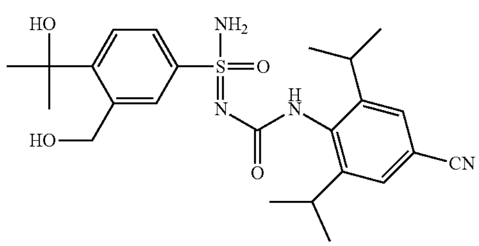 [SMILES: CC(C)c1cc(C#N)cc(C(C)C)c1NC(=O)N=S(N)(=O)c1ccc(C(C)(C)O)c(CO)c1] | N'-((4-cyano-2,6-diisopropylphenyl)carbamoyl)-3-(hydroxymethyl)-4-(2-hydroxypropan-2-yl)benzenesulfonimidamide | 473.2 |
| 69 | 220 | 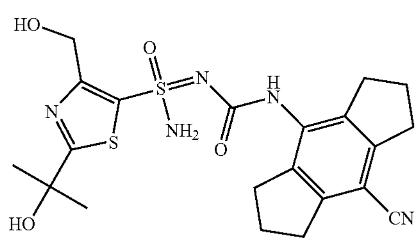 [SMILES: CC(C)(O)c1nc(CO)c(S(N)(=O)=NC(=O)Nc2c3c(c(C#N)c4c2CCC4)CCC3)s1] | N'-((8-cyano-1,2,3,5,6,7-hexahydro-s-indacen-4-yl)carbamoyl)-4-(hydroxymethyl)-2-(2-hydroxypropan-2-yl)thiazole-5-sulfonimidamide | 476.1 |
| 70 | 157 | 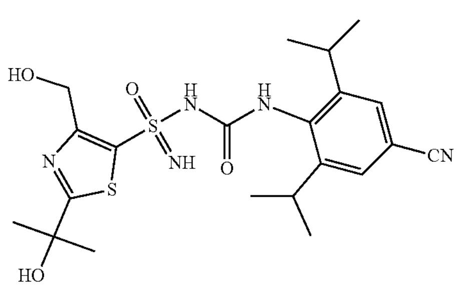 [SMILES: CC(C)c1cc(C#N)cc(C(C)C)c1NC(=O)NS(=N)(=O)c1sc(C(C)(C)O)nc1CO] | N-((4-cyano-2,6-diisopropylphenyl)carbamoyl)-4-(hydroxymethyl)-2-(2-hydroxypropan-2-yl)thiazole-5-sulfonimidamide | 480.2 |

TABLE 17-continued

Examples in the following table were prepared using similar conditions as described in
Example 4 - route 1 and Scheme 2 from appropriate starting materials.

| Example # | Final Target Number | Structure | IUPAC Name | Exact Mass [M + H]+ |
|---|---|---|---|---|
| 71 | 161 | 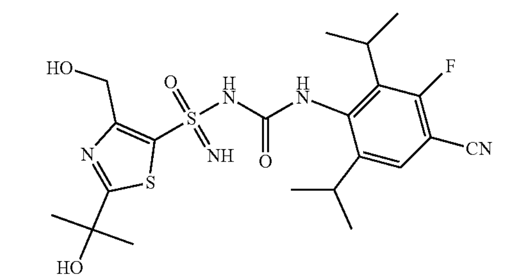 [SMILES: CC(C)c1cc(C#N)c(F)c(C(C)C)c1NC(=O)NS(=N)(=O)c1sc(C(C)(C)O)nc1CO] | N-((4-cyano-3-fluoro-2,6-diisopropylphenyl)carbamoyl)-4-(hydroxymethyl)-2-(2-hydroxypropan-2-yl)thiazole-5-sulfonimidamide | 498.2 |
| 72 | 159 | 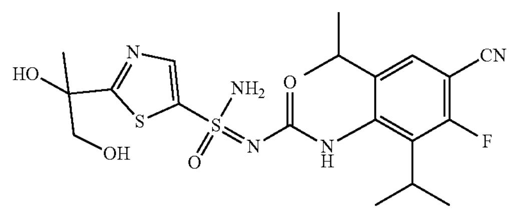 [SMILES: CC(C)c1cc(C#N)c(F)c(C(C)C)c1NC(=O)N=S(N)(=O)c1cnc(C(C)(O)CO)s1] | N'-((4-cyano-3-fluoro-2,6-diisopropylphenyl)carbamoyl)-2-(1,2-dihydroxypropan-2-yl)thiazole-5-sulfonimidamide | 484.1 |
| 73 | 165 | 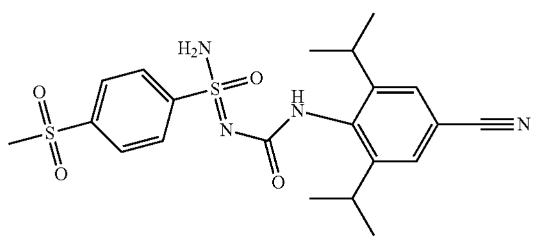 [SMILES: CC(C)c1cc(C#N)cc(C(C)C)c1NC(=O)N=S(N)(=O)c1ccc(S(C)(=O)=O)cc1] | N'-((4-cyano-2,6-diisopropylphenyl)carbamoyl)-4-(methylsulfonyl)benzenesulfonimidamide | 463.1 |
| 74 | 183 | 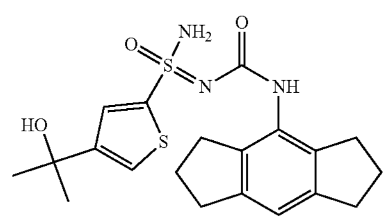 [SMILES: CC(C)(O)c1csc(S(N)(=O)=NC(=O)Nc2c3c(cc4c2CCC4)CCC3)c1] | N'-(1,2,3,5,6,7-hexahydro-s-indacen-4-ylcarbamoyl)-4-(2-hydroxypropan-2-yl)thiophene-2-sulfonimidamide | 418.1 (M − 1) |
| 75 | 176 | 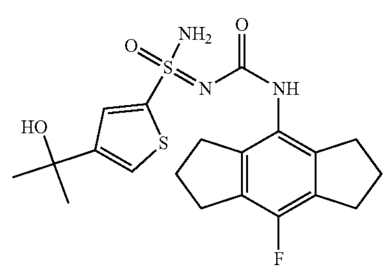 [SMILES: CC(C)(O)c1csc(S(N)(=O)=NC(=O)Nc2c3c(c(F)c4c2CCC4)CCC3)c1] | N'-(8-fluoro-1,2,3,5,6,7-hexahydro-s-indacen-4-ylcarbamoyl)-4-(2-hydroxypropan-2-yl)thiophene-2-sulfonimidamide | 438.0 |
| 76 | 136 | 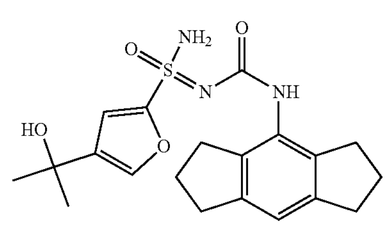 [SMILES: CC(C)(O)c1coc(S(N)(=O)=NC(=O)Nc2c3c(cc4c2CCC4)CCC3)c1] | N'-(1,2,3,5,6,7-hexahydro-s-indacen-4-ylcarbamoyl)-4-(2-hydroxypropan-2-yl)furan-2-sulfonimidamide | 404.2 |

TABLE 17-continued

Examples in the following table were prepared using similar conditions as described in Example 4 - route 1 and Scheme 2 from appropriate starting materials.

| Example # | Final Target Number | Structure | IUPAC Name | Exact Mass [M + H]+ |
|---|---|---|---|---|
| 77 | 209 | 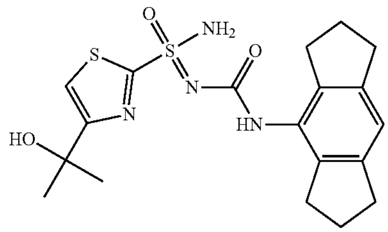 [SMILES: CC(C)(O)c1csc(S(N)(=O)=NC(=O)Nc2c3c(cc4c2CCC4)CCC3)n1] | N'-(1,2,3,5,6,7-hexahydro-s-indacen-4-ylcarbamoyl)-4-(2-hydroxypropan-2-yl)thiazole-2-sulfonimidamide | 421.1 |

TABLE 18

Examples in the following table were prepared using similar conditions as described in Example 9 and Scheme 5 from appropriate materials.

| Example # | Final Target Number | Structure | IUPAC Name | Exact Mass [M + H]+ |
|---|---|---|---|---|
| 78 | 203 | 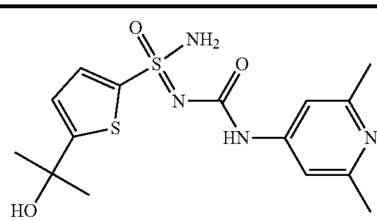 | N-((2,6-dimethylpyridin-4-yl)carbamoyl)-5-(2-hydroxypropan-2-yl)thiophene-2-sulfonimidamide | 369.1 |

TABLE 19

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 79 | 180a or 180b | 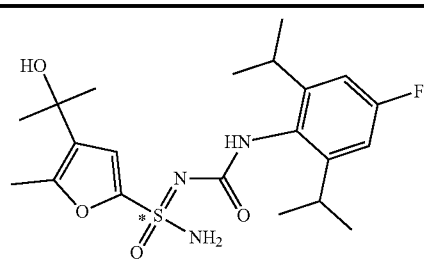 | (S)-or (R)-N'-(4-fluoro-2,6-diisopropylphenylcarbamoyl)-4-(2-hydroxypropan-2-yl)-5-methylfuran-2-sulfonimidamide | ChiralPak ID, 2 * 25 cm, 5 um | 20% EtOH in Hex | 440.3 |
| 80 | 180b or 180a | 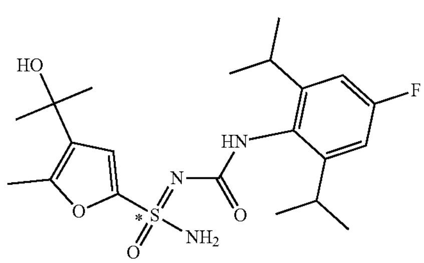 [SMILES: Cc1oc(S(N)(=O)=NC(=O)Nc2c(C(C)C)cc(F)cc2C(C)C)cc1C(C)(C)O] | (R)-or (S)-N'-(4-fluoro-2,6-diisopropylphenylcarbamoyl)-4-(2-hydroxypropan-2-yl)-5-methylfuran-2-sulfonimidamide | ChiralPak ID, 2 * 25 cm, 5 um | 20% EtOH in Hex | 440.3 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 81 | 179a or 179b | 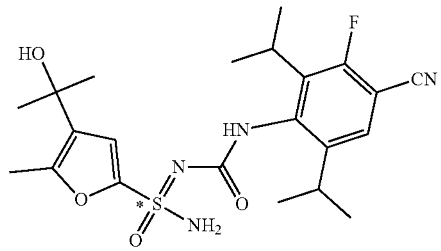 [SMILES: Cc1oc(S(N)(=O)=NC(=O)Nc2c(C(C)C)cc(C#N)c(F)c2C(C)C)cc1C(C)(C)O] | (S)-or (R)-N'-(4-cyano-3-fluoro-2,6-diisopropylphenylcarbamoyl)-4-(2-hydroxypropan-2-yl)-5-methylfuran-2-sulfonimidamide | ChiralPak ID, 2 * 25 cm, 5 um | 23% EtOH in Hex | 465.3 |
| 82 | 179b or 179a | 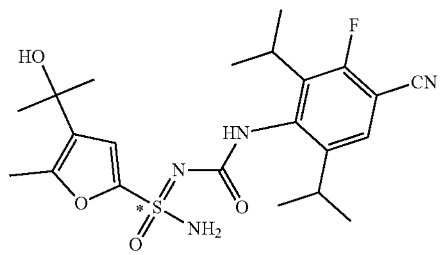 [SMILES: Cc1oc(S(N)(=O)=NC(=O)Nc2c(C(C)C)cc(C#N)c(F)c2C(C)C)cc1C(C)(C)O] | (R)-or (S)-N'-(4-cyano-3-fluoro-2,6-diisopropylphenylcarbamoyl)-4-(2-hydroxypropan-2-yl)-5-methylfuran-2-sulfonimidamide | ChiralPak ID, 2 * 25 cm, 5 um | 23% EtOH in Hex | 465.3 |
| 83 | 190a or 190b | 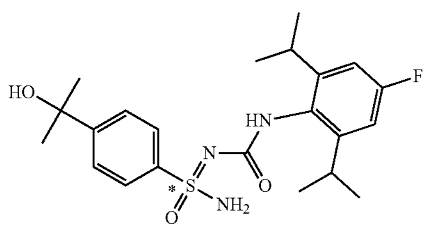 [SMILES: CC(C)c1cc(F)cc(C(C)C)c1NC(=O)N=S(N)(=O)c1ccc(C(C)(C)O)cc1] | (S)-or (R)-N'-(4-fluoro-2,6-diisopropylphenylcarbamoyl)-4-(2-hydroxypropan-2-yl)benzenesulfonimidamide | ChiralPak ID, 2 * 25 cm, 5 um | 20% EtOH in Hex | 436.2 |
| 84 | 190b or 190a | 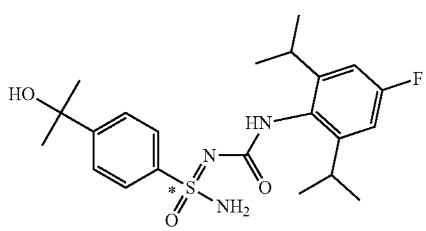 [SMILES: CC(C)c1cc(F)cc(C(C)C)c1NC(=O)N=S(N)(=O)c1ccc(C(C)(C)O)cc1] | (R)-or (S)-N'-(4-fluoro-2,6-diisopropylphenylcarbamoyl)-4-(2-hydroxypropan-2-yl)benzenesulfonimidamide | ChiralPak ID, 2 * 25 cm, 5 um | 20% EtOH in Hex | 436.2 |
| 85 | 182a or 182b | 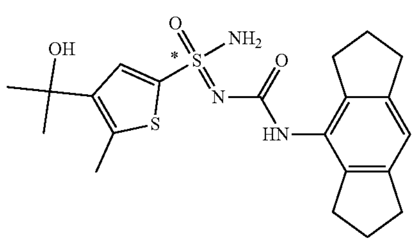 [SMILES: Cc1sc(S(N)(=O)=NC(=O)Nc2c3c(cc4c2CCC4)CCC3)cc1C(C)(C)O] | (S)-or (R)-N'-(1,2,3,5,6,7-hexahydro-s-indacen-4-ylcarbamoyl)-4-(2-hydroxypropan-2-yl)-5-methylthiophene-2-sulfonimidamide | ChiralPak IC, 2 * 25 cm, 5 um | 20% EtOH in Hex | 434.1 |
| 86 | 182b or 182a | 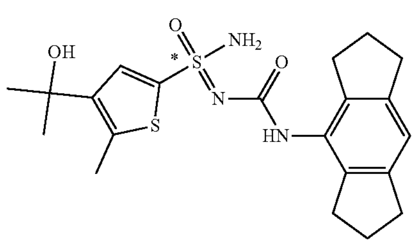 [SMILES: Cc1sc(S(N)(=O)=NC(=O)Nc2c3c(cc4c2CCC4)CCC3)cc1C(C)(C)O] | (R)-or (S)-N'-(1,2,3,5,6,7-hexahydro-s-indacen-4-ylcarbamoyl)-4-(2-hydroxypropan-2-yl)-5-methylthiophene-2-sulfonimidamide | ChiralPak IC, 2 * 25 cm, 5 um | 20% EtOH in Hex | 434.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]$^+$ |
|---|---|---|---|---|---|---|
| 87 | 191a or 191b | 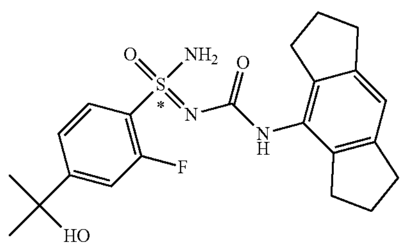 [SMILES: CC(C)(O)c1ccc(S(N)(=O)=NC(=O)Nc2c3c(cc4c2CCC4)CCC3)c(F)c1] | (S)- or (R)-2-fluoro-N'-(1,2,3,5,6,7-hexahydro-s-indacen-4-ylcarbamoyl)-4-(2-hydroxypropan-2-yl)benzenesulfonimidamide | ChiralPak IG, 2 * 25 cm, 5 um | 30% IPA in Hex (0.1% DEA) | 430.1 (M − 1) |
| 88 | 191b or 191a | 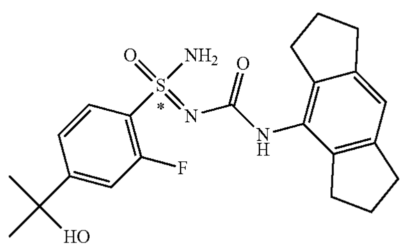 [SMILES: CC(C)(O)c1ccc(S(N)(=O)=NC(=O)Nc2c3c(cc4c2CCC4)CCC3)c(F)c1] | (R)- or (S)-2-fluoro-N'-(1,2,3,5,6,7-hexahydro-s-indacen-4-ylcarbamoyl)-4-(2-hydroxypropan-2-yl)benzenesulfonimidamide | ChiralPak IG, 2 * 25 cm, 5 um | 30% IPA in Hex (0.1% DEA) | 430.1 (M − 1) |
| 89 | 177a or 177b | 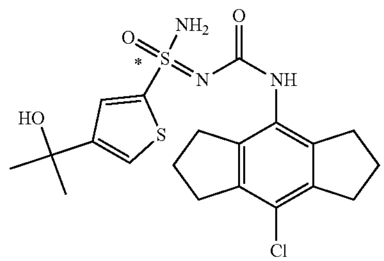 [SMILES: CC(C)(O)c1csc(S(N)(=O)=NC(=O)Nc2c3c(c(Cl)c4c2CCC4)CCC3)c1] | (S)- or (R)-N'-(8-chloro-1,2,3,5,6,7-hexahydro-s-indacen-4-ylcarbamoyl)-4-(2-hydroxypropan-2-yl)thiophene-2-sulfonimidamide | ChiralPak ID, 2 * 25 cm, 5 um | 20% EtOH in Hex (0.1% DEA) | 452.0 (M − 1) |
| 90 | 177b or 177a | 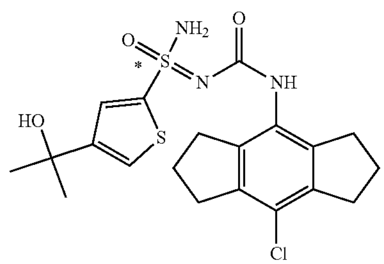 [SMILES: CC(C)(O)c1csc(S(N)(=O)=NC(=O)Nc2c3c(c(Cl)c4c2CCC4)CCC3)c1] | (R)- or (S)-N'-(8-chloro-1,2,3,5,6,7-hexahydro-s-indacen-4-ylcarbamoyl)-4-(2-hydroxypropan-2-yl)thiophene-2-sulfonimidamide | ChiralPak ID, 2 * 25 cm, 5 um | 20% EtOH in Hex (0.1% DEA) | 452.0 (M − 1) |
| 91 | 185a or 185b | 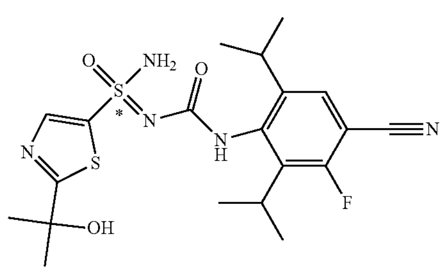 [SMILES: CC(C)c1cc(C#N)c(F)c(C(C)C)c1NC(=O)N=S(N)(=O)c1cnc(C(C)(C)O)s1] | (S)- or (R)-N'-(4-cyano-3-fluoro-2,6-diisopropylphenylcarbamoyl)-2-(2-hydroxypropan-2-yl)thiazole-5-sulfonimidamide | ChiralPak ID, 2 * 25 cm, 5 um | 30% EtOH in Hex (0.1% DEA) | 466.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 92 | 185b or 185a | 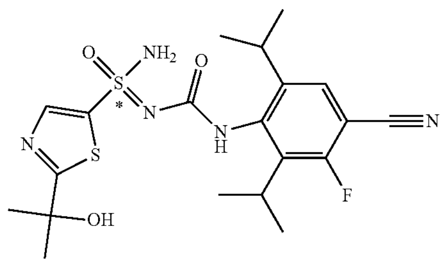 [SMILES: CC(C)c1cc(C#N)c(F)c(C(C)C)c1NC(=O)N=S(N)(=O)c1cnc(C(C)(C)O)s1] | (R)-or (S)-N'-(4-cyano-3-fluoro-2,6-diisopropylphenylcarbamoyl)-2-(2-hydroxypropan-2-yl)thiazole-5-sulfonimidamide | ChiralPak ID, 2 * 25 cm, 5 um | 30% EtOH in Hex (0.1% DEA) | 466.1 (M − 1) |
| 93 | 186a or 186b | 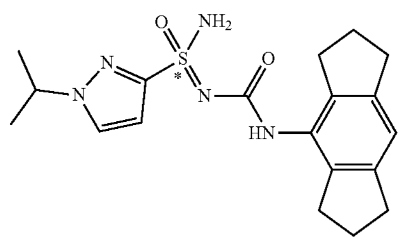 [SMILES: CC(C)n1ccc(S(N)(=O)=NC(=O)Nc2c3c(cc4c2CCC4)CCC3)n1] | (S)-or (R)-N'-(1,2,3,5,6,7-hexahydro-s-indacen-4-ylcarbamoyl)-1-isopropyl-1H-pyrazole-3-sulfonimidamide | ChiralPak IG, 2 * 25 cm, 5 um | 30% EtOH in Hex (0.1% DEA) | 388.1 |
| 94 | 186b or 186a | 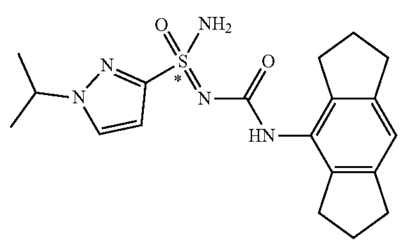 [SMILES: CC(C)n1ccc(S(N)(=O)=NC(=O)Nc2c3c(cc4c2CCC4)CCC3)n1] | (R)-or (S)-N'-(1,2,3,5,6,7-hexahydro-s-indacen-4-ylcarbamoyl)-1-isopropyl-1H-pyrazole-3-sulfonimidamide | ChiralPak IG, 2 * 25 cm, 5 um | 30% EtOH in Hex (0.1% DEA) | 388.1 |
| 95 | 187a or 187b | 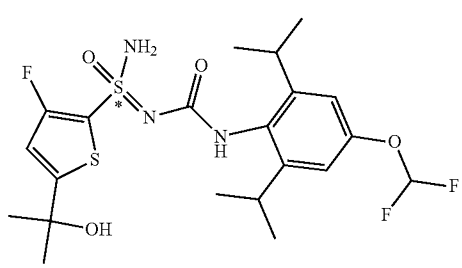 [SMILES: CC(C)c1cc(OC(F)F)cc(C(C)C)c1NC(=O)N=S(N)(=O)c1sc(C(C)(C)O)cc1F] | (S)-or (R)-N'-(4-(difluoromethoxy)-2,6-diisopropylphenylcarbamoyl)-3-fluoro-5-(2-hydroxypropan-2-yl)thiophene-2-sulfonimidamide | ChiralPak ID, 2 * 25 cm, 5 um | 20% EtOH in Hex (0.1% DEA) | 508.2 |
| 96 | 187b or 187a | 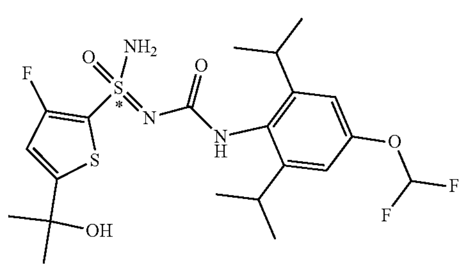 [SMILES: CC(C)c1cc(OC(F)F)cc(C(C)C)c1NC(=O)N=S(N)(=O)c1sc(C(C)(C)O)cc1F] | (R)-or (S)-N'-(4-(difluoromethoxy)-2,6-diisopropylphenylcarbamoyl)-3-fluoro-5-(2-hydroxypropan-2-yl)thiophene-2-sulfonimidamide | ChiralPak ID, 2 * 25 cm, 5 um | 20% EtOH in Hex (0.1% DEA) | 508.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]$^+$ |
|---|---|---|---|---|---|---|
| 97 | 188a or 188b | 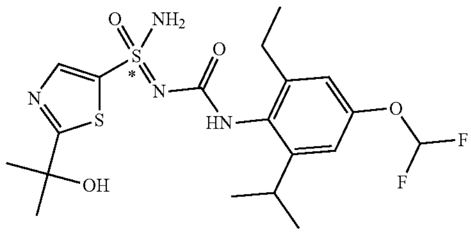 [SMILES: CCc1cc(OC(F)F)cc(C(C)C)c1NC(=O)N=S(N)(=O)c1cnc(C(C)(C)O)s1] | (S)-or (R)-N'-(4-(difluoromethoxy)-2-ethyl-6-isopropylphenylcarbamoyl)-2-(2-hydroxypropan-2-yl)thiazole-5-sulfonimidamide | ChiralPak ID, 2 * 25 cm, 5 um | 30% IPA in Hex (0.1% DEA) | 477.2 |
| 98 | 188b or 188a | 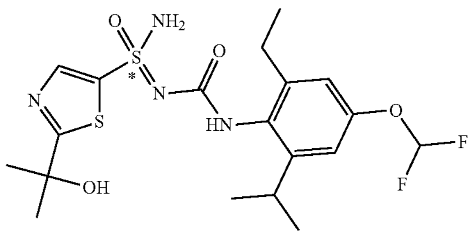 [SMILES: CCc1cc(OC(F)F)cc(C(C)C)c1NC(=O)N=S(N)(=O)c1cnc(C(C)(C)O)s1] | (R)-or (S)-N'-(4-(difluoromethoxy)-2-ethyl-6-isopropylphenylcarbamoyl)-2-(2-hydroxypropan-2-yl)thiazole-5-sulfonimidamide | ChiralPak ID, 2 * 25 cm, 5 um | 30% IPA in Hex (0.1% DEA) | 477.2 |
| 99 | 192a or 192b | 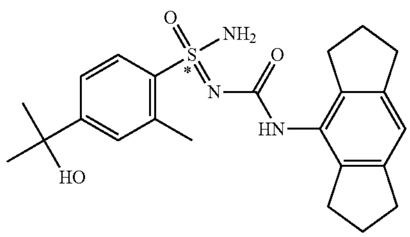 [SMILES: Cc1cc(C(C)(C)O)ccc1S(N)(=O)=NC(=O)Nc1c2c(cc3c1CCC3)CCC2] | (S)-or (R)-N'-(1,2,3,5,6,7-hexahydro-s-indacen-4-ylcarbamoyl)-4-(2-hydroxypropan-2-yl)-2-methyl-benzenesulfonimidamide | ChiralPak ID, 2 * 25 cm, 5 um | 30% EtOH in Hex (0.1% DEA) | 428.2 |
| 100 | 192b or 192a | 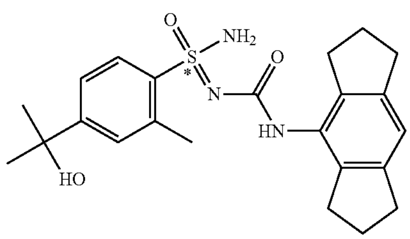 [SMILES: Cc1cc(C(C)(C)O)ccc1S(N)(=O)=NC(=O)Nc1c2c(cc3c1CCC3)CCC2] | (R)-or (S)-N'-(1,2,3,5,6,7-hexahydro-s-indacen-4-ylcarbamoyl)-4-(2-hydroxypropan-2-yl)-2-methyl-benzenesulfonimidamide | ChiralPak ID, 2 * 25 cm, 5 um | 30% EtOH in Hex (0.1% DEA) | 428.2 |
| 101 | 189a or 189b | 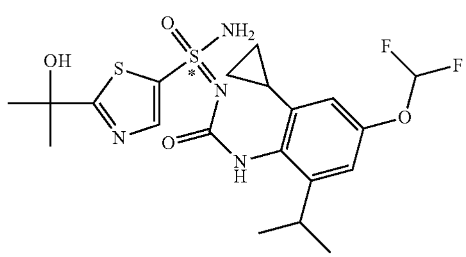 [SMILES: CC(C)c1cc(OC(F)F)cc(C2CC2)c1NC(=O)N=S(N)(=O)c1cnc(C(C)(C)O)s1] | (S)-or (R)-N'-(2-cyclopropyl-4-(difluoromethoxy)-6-isopropylphenylcarbamoyl)-2-(2-hydroxypropan-2-yl)thiazole-5-sulfonimidamide | ChiralPak ID, 2 * 25 cm, 5 um | 50% IPA in Hex (0.1% DEA) | 489.3 |
| 102 | 189b or 189a | 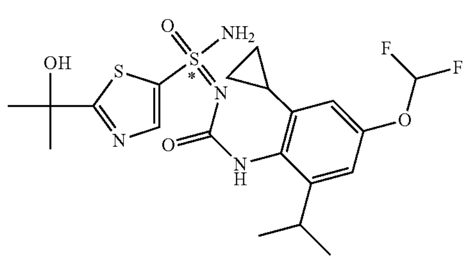 [SMILES: CC(C)c1cc(OC(F)F)cc(C2CC2)c1NC(=O)N=S(N)(=O)c1cnc(C(C)(C)O)s1] | (R)-or (S)-N'-(2-cyclopropyl-4-(difluoromethoxy)-6-isopropylphenylcarbamoyl)-2-(2-hydroxypropan-2-yl)thiazole-5-sulfonimidamide | ChiralPak ID, 2 * 25 cm, 5 um | 50% IPA in Hex (0.1% DEA) | 489.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 103 | 178a or 178b | 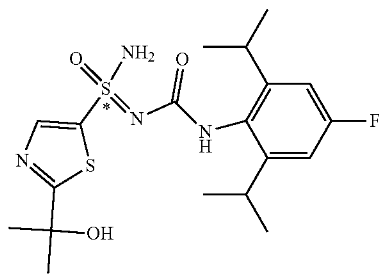 [SMILES: CC(C)c1cc(F)cc(C(C)C)c1NC(=O)N=S(N)(=O)c1cnc(C(C)(C)O)s1] | (S)- or (R)- N'-(4-fluoro-2,6-diisopropylphenylcarbamoyl)-2-(2-hydroxypropan-2-yl)thiazole-5-sulfonimidamide | ChiralPak ID, 2 * 25 cm, 5 um | 30% IPA (0.1% DEA) in Hex:DCM = 3:1 | 443.2 |
| 104 | 178b or 178a | 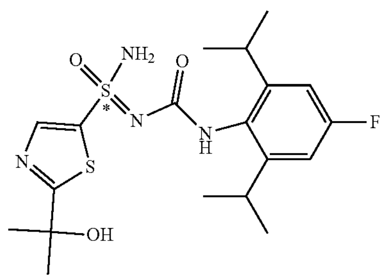 [SMILES: CC(C)c1cc(F)cc(C(C)C)c1NC(=O)N=S(N)(=O)c1cnc(C(C)(C)O)s1] | (R)- or (S)- N'-(4-fluoro-2,6-diisopropylphenylcarbamoyl)-2-(2-hydroxypropan-2-yl)thiazole-5-sulfonimidamide | ChiralPak ID, 2 * 25 cm, 5 um | 30% IPA (0.1% DEA) in Hex:DCM = 3:1 | 443.1 |
| 105 | 193a or 193b | 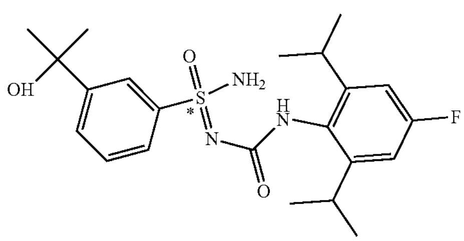 [SMILES: CC(C)c1cc(F)cc(C(C)C)c1NC(=O)N=S(N)(=O)c1cccc(C(C)(C)O)c1] | (S)- or (R)- N'-(4-fluoro-2,6-diisopropylphenylcarbamoyl)-3-(2-hydroxypropan-2-yl)benzenesulfonimidamide | ChiralPak IG, 2 * 25 cm, 5 um | 20% IPA in Hex (0.1% DEA) | 436.2 |
| 106 | 193b or 193a | 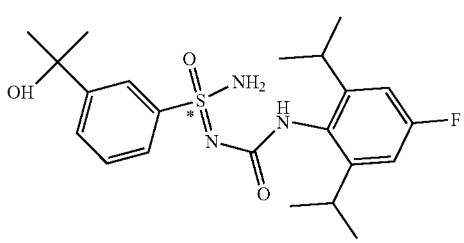 [SMILES: CC(C)c1cc(F)cc(C(C)C)c1NC(=O)N=S(N)(=O)c1cccc(C(C)(C)O)c1] | (R)- or (S)- N'-(4-fluoro-2,6-diisopropylphenylcarbamoyl)-3-(2-hydroxypropan-2-yl)benzenesulfonimidamide | ChiralPak IG, 2 * 25 cm, 5 um | 20% IPA in Hex (0.1% DEA) | 436.2 |
| 107 | 170a or 170b | 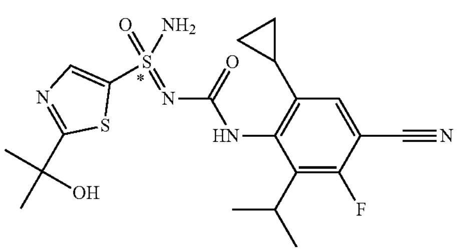 [SMILES: CC(C)c1c(F)c(C#N)cc(C2CC2)c1NC(=O)N=S(N)(=O)c1cnc(C(C)(C)O)s1] | (S)- or (R)- N'-(4-cyano-6-cyclopropyl-3-fluoro-2-isopropylphenylcarbamoyl)-2-(2-hydroxypropan-2-yl)thiazole-5-sulfonimidamide | ChiralPak IG, 2 * 25 cm, 5 um | 15% EtOH in Hex (0.1% DEA) | 466.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 108 | 170b or 170a | 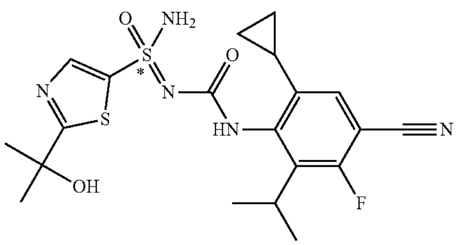 [SMILES: CC(C)c1c(F)c(C#N)cc(C2CC2)c1NC(=O)N=S(N)(=O)c1cnc(C(C)(C)O)s1] | (R)-or (S)-N'-(4-cyano-6-cyclopropyl-3-fluoro-2-isopropylphenylcarbamoyl)-2-(2-hydroxypropan-2-yl)thiazole-5-sulfonimidamide | ChiralPak IG, 2 * 25 cm, 5 um | 15% EtOH in Hex (0.1% DEA) | 466.1 |
| 109 | 168a or 168b | 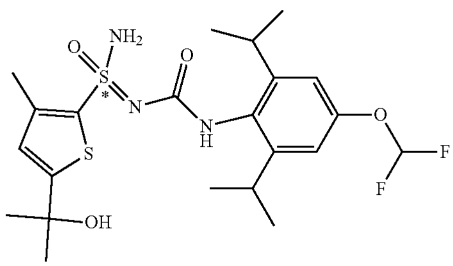 [SMILES: Cc1cc(C(C)(C)O)sc1S(N)(=O)=NC(=O)Nc1c(C(C)C)cc(OC(F)F)cc1C(C)C] | (S)-or (R)-N'-(4-(difluoromethoxy)-2,6-diisopropylphenylcarbamoyl)-5-(2-hydroxypropan-2-yl)-3-methylthiophene-2-sulfonimidamide | ChiralPak ID, 2 * 25 cm, 5 um | 30% IPA in Hex (0.1% DEA) | 504.2 |
| 110 | 168b or 168a | 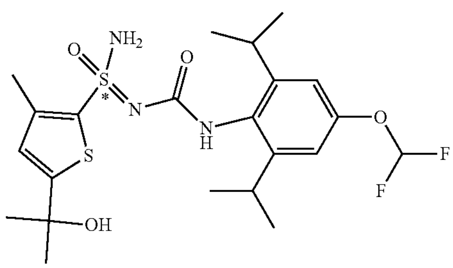 [SMILES: Cc1cc(C(C)(C)O)sc1S(N)(=O)=NC(=O)Nc1c(C(C)C)cc(OC(F)F)cc1C(C)C] | (R)-or (S)-N'-(4-(difluoromethoxy)-2,6-diisopropylphenylcarbamoyl)-5-(2-hydroxypropan-2-yl)-3-methylthiophene-2-sulfonimidamide | ChiralPak ID, 2 * 25 cm, 5 um | 30% IPA in Hex (0.1% DEA) | 504.2 |
| 111 | 171a or 171b | 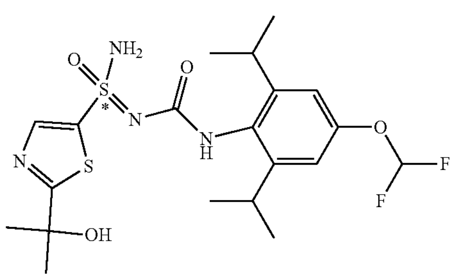 [SMILES: CC(C)c1cc(OC(F)F)cc(C(C)C)c1NC(=O)N=S(N)(=O)c1cnc(C(C)(C)O)s1] | (S)-or (R)-N'-(4-(difluoromethoxy)-2,6-diisopropylphenylcarbamoyl)-2-(2-hydroxypropan-2-yl)thiazole-5-sulfonimidamide | ChiralPak ID, 2 * 25 cm, 5 um | 50% IPA in Hex:DCM = 1:1 | 489.1 (M − 1) |
| 112 | 171b or 171a | 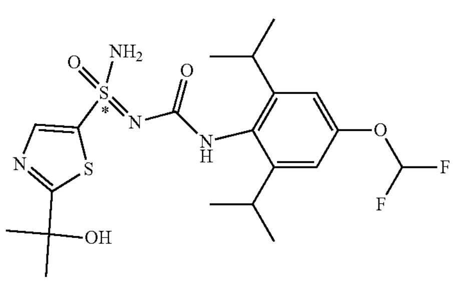 [SMILES: CC(C)c1cc(OC(F)F)cc(C(C)C)c1NC(=O)N=S(N)(=O)c1cnc(C(C)(C)O)s1] | (R)-or (S)-N'-(4-(difluoromethoxy)-2,6-diisopropylphenylcarbamoyl)-2-(2-hydroxypropan-2-yl)thiazole-5-sulfonimidamide | ChiralPak ID, 2 * 25 cm, 5 um | 50% IPA in Hex:DCM = 1:1 | 489.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 113 | 122a or 122b | 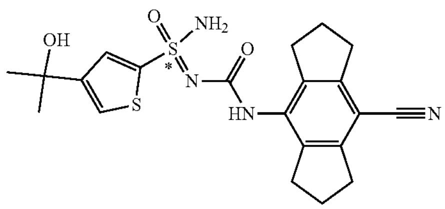 [SMILES: CC(C)(O)c1csc(S(N)(=O)=NC(=O)Nc2c3c(c(C#N)c4c2CCC4)CCC3)c1] | (S)-or (R)-N'-(8-cyano-1,2,3,5,6,7-hexahydro-s-indacen-4-ylcarbamoyl)-4-(2-hydroxypropan-2-yl)thiophene-2-sulfonimidamide | ChiralPak ID, 2 * 25 cm, 5 um | 30% IPA in Hex | 443.1 (M − 1) |
| 114 | 122b or 122a | 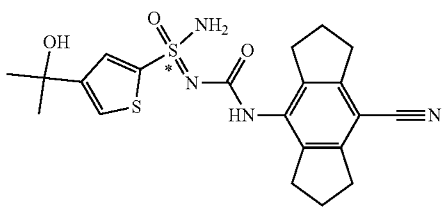 [SMILES: CC(C)(O)c1csc(S(N)(=O)=NC(=O)Nc2c3c(c(C#N)c4c2CCC4)CCC3)c1] | (R)-or (S)-N'-(8-cyano-1,2,3,5,6,7-hexahydro-s-indacen-4-ylcarbamoyl)-4-(2-hydroxypropan-2-yl)thiophene-2-sulfonimidamide | ChiralPak ID, 2 * 25 cm, 5 um | 30% IPA in Hex | 443.1 (M − 1) |
| 115 | 120a or 120b | 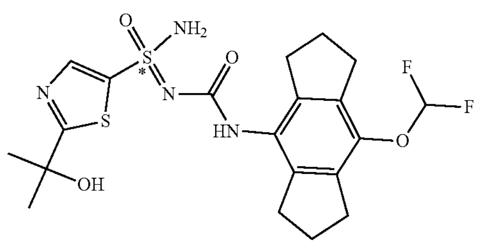 [SMILES: CC(C)(O)c1ncc(S(N)(=O)=NC(=O)Nc2c3c(c(OC(F)F)c4c2CCC4)CCC3)s1] | (S)-or (R)-N'-(8-(difluoromethoxy)-1,2,3,5,6,7-hexahydro-s-indacen-4-ylcarbamoyl)-2-(2-hydroxypropan-2-yl)thiazole-5-sulfonimidamide | Chiral ART Cellulose-SB 2 * 25 cm, 5 um | 20% EtOH in Hex (0.1% DEA) | 485.1 (M − 1) |
| 116 | 120b or 120a | 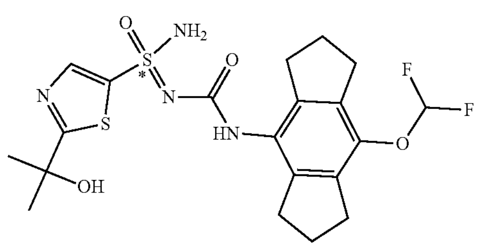 [SMILES: CC(C)(O)c1ncc(S(N)(=O)=NC(=O)Nc2c3c(c(OC(F)F)c4c2CCC4)CCC3)s1] | (R)-or (S)-N'-(8-(difluoromethoxy)-1,2,3,5,6,7-hexahydro-s-indacen-4-ylcarbamoyl)-2-(2-hydroxypropan-2-yl)thiazole-5-sulfonimidamide | Chiral ART Cellulose-SB 2 * 25 cm, 5 um | 20% EtOH in Hex (0.1% DEA) | 485.1 (M − 1) |
| 117 | 125a or 125b | 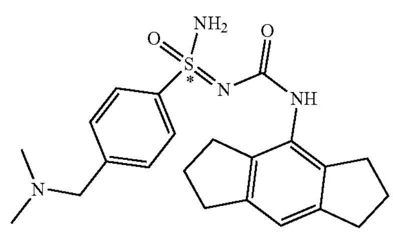 [SMILES: CN(C)Cc1ccc(S(N)(=O)=NC(=O)Nc2c3c(cc4c2CCC4)CCC3)cc1] | (S)-or (R)-4-((dimethylamino)methyl)-N'-(1,2,3,5,6,7-hexahydro-s-indacen-4-ylcarbamoyl)benzenesulfonimidamide | ChiralPak ID, 2 * 25 cm, 5 um | 50% IPA in Hex:DCM = 3:1 | 413.2 |
| 118 | 125b or 125a | 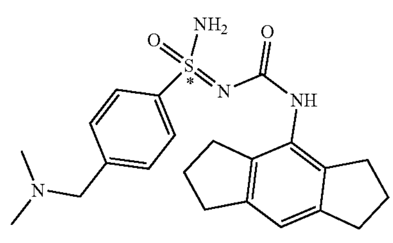 [SMILES: CN(C)Cc1ccc(S(N)(=O)=NC(=O)Nc2c3c(cc4c2CCC4)CCC3)cc1] | (R)-or (S)-4-((dimethylamino)methyl)-N'-(1,2,3,5,6,7-hexahydro-s-indacen-4-ylcarbamoyl)benzenesulfonimidamide | ChiralPak ID, 2 * 25 cm, 5 um | 50% IPA in Hex:DCM = 3:1 | 413.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 119 | 129a or 129b | 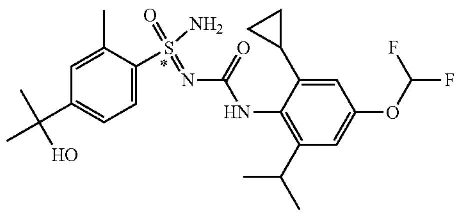 [SMILES: Cc1cc(C(C)(C)O)ccc1S(N)(=O)=NC(=O)Nc1c(C(C)C)cc(OC(F)F)cc1C1CC1] | (S)- or (R)- N'-(2-cyclopropyl-4-(difluoromethoxy)-6-isopropylphenylcarbamoyl)-4-(2-hydroxypropan-2-yl)-2-methyl-benzenesulfonimidamide | ChiralPak ID, 2 * 25 cm, 5 um | 50% IPA in Hex:DCM = 3:1 | 496.2 |
| 120 | 129b or 129a | 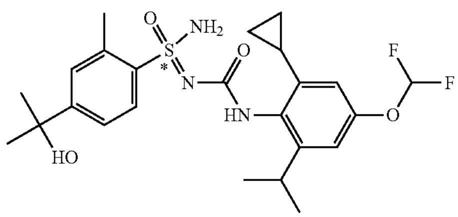 [SMILES: Cc1cc(C(C)(C)O)ccc1S(N)(=O)=NC(=O)Nc1c(C(C)C)cc(OC(F)F)cc1C1CC1] | (R)- or (S)- N'-(2-cyclopropyl-4-(difluoromethoxy)-6-isopropylphenylcarbamoyl)-4-(2-hydroxypropan-2-yl)-2-methyl-benzenesulfonimidamide | ChiralPak ID, 2 * 25 cm, 5 um | 50% IPA in Hex:DCM = 3:1 | 496.2 |
| 121 | 112a or 112b | 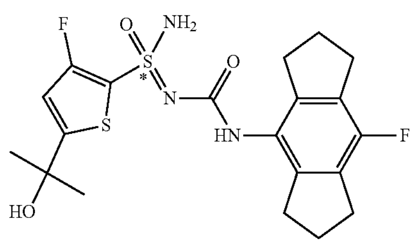 [SMILES: CC(C)(O)c1cc(F)c(S(N)(=O)=NC(=O)Nc2c3c(c(F)c4c2CCC4)CCC3)s1] | (S)- or (R)- 3-fluoro-N'-(8-fluoro-1,2,3,5,6,7-hexahydro-s-indacen-4-ylcarbamoyl)-5-(2-hydroxypropan-2-yl)thiophene-2-sulfonimidamide | ChiralPak IG, 2 * 25 cm, 5 um | 15% EtOH in Hex (0.1% DEA) | 456.1 |
| 122 | 112b or 112a | 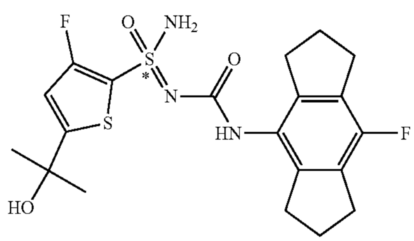 [SMILES: CC(C)(O)c1cc(F)c(S(N)(=O)=NC(=O)Nc2c3c(c(F)c4c2CCC4)CCC3)s1] | (R)- or (S)- 3-fluoro-N'-(8-fluoro-1,2,3,5,6,7-hexahydro-s-indacen-4-ylcarbamoyl)-5-(2-hydroxypropan-2-yl)thiophene-2-sulfonimidamide | ChiralPak IG, 2 * 25 cm, 5 um | 15% EtOH in Hex (0.1% DEA) | 456.1 |
| 128 | 105a or 105b | 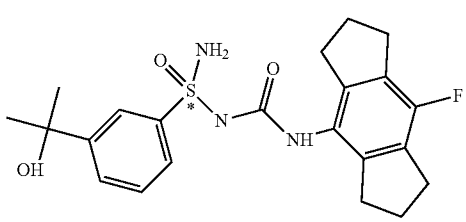 | (S)- or (R)- N'-(8-fluoro-1,2,3,5,6,7-hexa-hydro-s-indacen-4-ylcarbamoyl)-3-(2-hydroxypropan-2-yl)benzenesulfonimidamide | ChiralPak ID, 2 * 25 cm, 5 um | 40% EtOH in Hex | 432.1 |
| 129 | 105b or 105a | 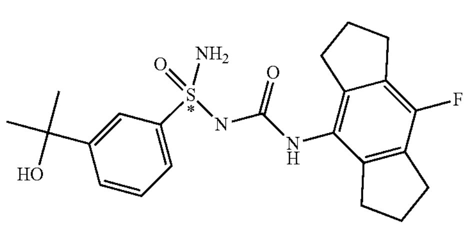 | (R)- or (S)- N'-(8-fluoro-1,2,3,5,6,7-hexa-hydro-s-indacen-4-ylcarbamoyl)-3-(2-hydroxypropan-2-yl)benzenesulfonimidamide | ChiralPak ID, 2 * 25 cm, 5 um | 40% EtOH in Hex | 432.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 130 | 121a or 121b | 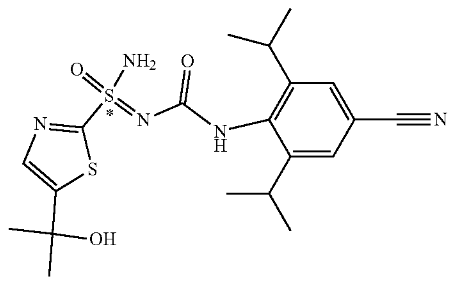 [SMILES: CC(C)c1cc(C#N)cc(C(C)C)c1NC(=O)N=S(N)(=O)c1ncc(C(C)(C)O)s1] | (S)-or (R)-N'-(4-cyano-2,6-diisopropylphenylcarbamoyl)-5-(2-hydroxypropan-2-yl)thiazole-2-sulfonimidamide | ChiralPak ID, 2 * 25 cm, 5 um | 40% EtOH in Hex | 448.1 (M − 1) |
| 131 | 121b or 121a | 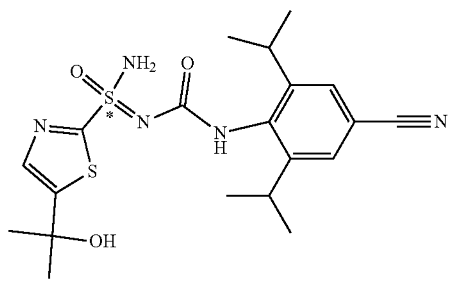 [SMILES: CC(C)c1cc(C#N)cc(C(C)C)c1NC(=O)N=S(N)(=O)c1ncc(C(C)(C)O)s1] | (R)-or (S)-N'-(4-cyano-2,6-diisopropylphenylcarbamoyl)-5-(2-hydroxypropan-2-yl)thiazole-2-sulfonimidamide | ChiralPak ID, 2 * 25 cm, 5 um | 40% EtOH in Hex | 448.1 (M − 1) |
| 132 | 145a or 145b | 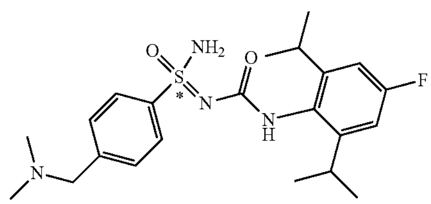 [SMILES: CC(C)c1cc(F)cc(C(C)C)c1NC(=O)N=S(N)(=O)c1ccc(CN(C)C)cc1] | (S)-or (R)-4-((dimethylamino)methyl)-N'-(4-fluoro-2,6-diisopropyl-phenylcarbamoyl)benzene-sulfonimidamide | ChiralPak IG, 2 * 25 cm, 5 um | 30% EtOH in Hex | 435.2 |
| 133 | 145b or 145a | 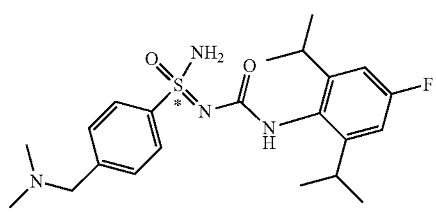 [SMILES: CC(C)c1cc(F)cc(C(C)C)c1NC(=O)N=S(N)(=O)c1ccc(CN(C)C)cc1] | (R)-or (S)-4-((dimethylamino)methyl)-N'-(4-fluoro-2,6-diisopropyl-phenylcarbamoyl)benzene-sulfonimidamide | ChiralPak IG, 2 * 25 cm, 5 um | 30% EtOH in Hex | 435.2 |
| 134 | 131a or 131b | 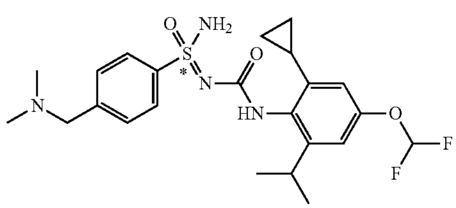 [SMILES: CC(C)c1cc(OC(F)F)cc(C2CC2)c1NC(=O)N=S(N)(=O)c1ccc(CN(C)C)cc1] | (S)-or (R)-N'-(2-cyclopropyl-4-(difluoromethoxy)-6-isopropylphenylcarbamoyl)-4-((dimethylamino)methyl)-benzene-sulfonimidamide | ChiralPak IG, 2 * 25 cm, 5 um | 50% EtOH in Hex | 481.2 |
| 135 | 131b or 131a | 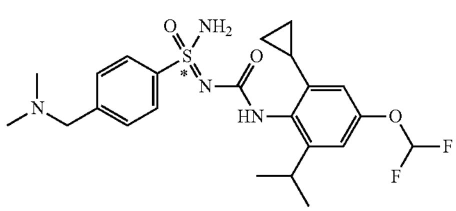 [SMILES: CC(C)c1cc(OC(F)F)cc(C2CC2)c1NC(=O)N=S(N)(=O)c1ccc(CN(C)C)cc1] | (R)-or (S)-N'-(2-cyclopropyl-4-(difluoromethoxy)-6-isopropylphenylcarbamoyl)-4-((dimethylamino)methyl)-benzene-sulfonimidamide | ChiralPak IG, 2 * 25 cm, 5 um | 50% EtOH in Hex | 481.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 136 | 225a or 225b | 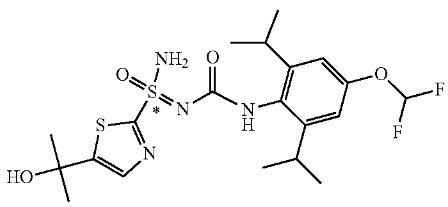 [SMILES: CC(C)c1cc(OC(F)F)cc(C(C)C)c1NC(=O)N=S(N)(=O)c1ncc(C(C)(C)O)s1] | (S)-or (R)-N'-(4-(difluoromethoxy)-2,6-diisopropylphenylcarbamoyl)-5-(2-hydroxypropan-2-yl)thiazole-2-sulfonimidamide | ChiralPak IF, 2 * 25 cm, 5 um | 20% MeOH (0.1% TFA) in $CO_2$ | 489.1 (M − 1) |
| 137 | 225b or 225a | 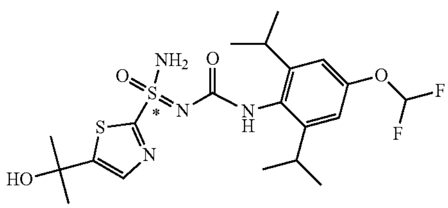 [SMILES: CC(C)c1cc(OC(F)F)cc(C(C)C)c1NC(=O)N=S(N)(=O)c1ncc(C(C)(C)O)s1] | (R)-or (S)-N'-(4-(difluoromethoxy)-2,6-diisopropylphenylcarbamoyl)-5-(2-hydroxypropan-2-yl)thiazole-2-sulfonimidamide | ChiralPak IF, 2 * 25 cm, 5 um | 20% MeOH (0.1% TFA) in $CO_2$ | 489.1 (M − 1) |
| 138 | 144a or 144b | 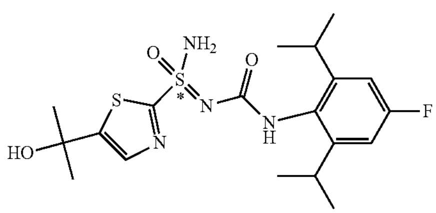 [SMILES: CC(C)c1cc(F)cc(C(C)C)c1NC(=O)N=S(N)(=O)c1ncc(C(C)(C)O)s1] | (S)-or (R)-N'-(4-fluoro-2,6-diisopropylphenylcarbamoyl)-5-(2-hydroxypropan-2-yl)thiazole-2-sulfonimidamide | ChiralPak IF, 2 * 25 cm, 5 um | 20% MeOH (0.1% TFA) in $CO_2$ | 443.2 |
| 139 | 144b or 144a | 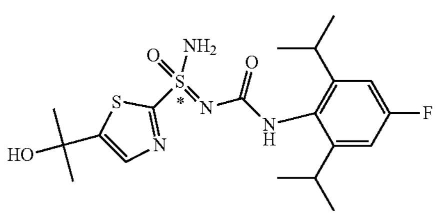 [SMILES: CC(C)c1cc(F)cc(C(C)C)c1NC(=O)N=S(N)(=O)c1ncc(C(C)(C)O)s1] | (R)-or (S)-N'-(4-fluoro-2,6-diisopropylphenylcarbamoyl)-5-(2-hydroxypropan-2-yl)thiazole-2-sulfonimidamide | ChiralPak IF, 2 * 25 cm, 5 um | 20% MeOH (0.1% TFA) in $CO_2$ | 443.1 |
| 140 | 149a or 149b | 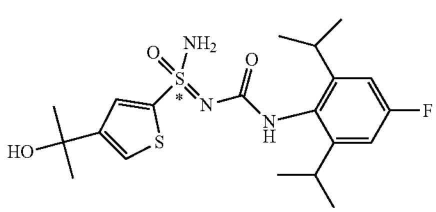 [SMILES: CC(C)c1cc(F)cc(C(C)C)c1NC(=O)N=S(N)(=O)c1cc(C(C)(C)O)cs1] | (S)-or (R)-N'-(4-fluoro-2,6-diisopropylphenylcarbamoyl)-4-(2-hydroxypropan-2-yl)thiophene-2-sulfonimidamide | ChiralPak ID, 2 * 25 cm, 5 um | 30% EtOH in Hex | 440.1 (M − 1) |
| 141 | 149b or 149a | 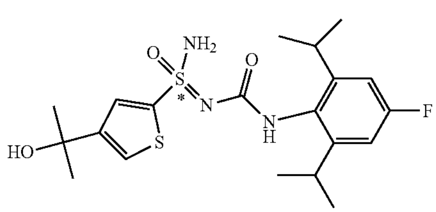 [SMILES: CC(C)c1cc(F)cc(C(C)C)c1NC(=O)N=S(N)(=O)c1cc(C(C)(C)O)cs1] | (R)-or (S)-N'-(4-fluoro-2,6-diisopropylphenylcarbamoyl)-4-(2-hydroxypropan-2-yl)thiophene-2-sulfonimidamide | ChiralPak ID, 2 * 25 cm, 5 um | 30% EtOH in Hex | 440.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 142 | 152a or 152b | 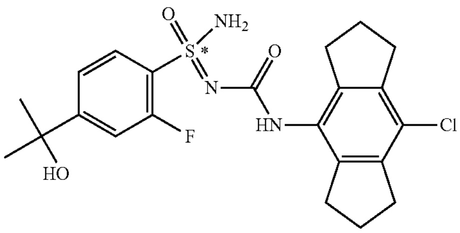 [SMILES: CC(C)(O)c1ccc(S(N)(=O)=NC(=O)Nc2c3c(c(Cl)c4c2CCC4)CCC3)c(F)c1] | (S)-or (R)-N'-(4-fluoro-2,6-diisopropylphenylcarbamoyl)-4-(2-hydroxypropan-2-yl)thiophene-2-sulfonimidamide | ChiralPak IG, 2 * 25 cm, 5 um | 30% IPA in Hex | 466.2 |
| 143 | 152b or 152a | 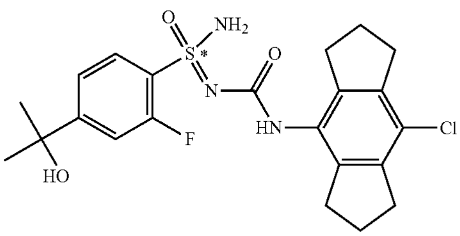 [SMILES: CC(C)(O)c1ccc(S(N)(=O)=NC(=O)Nc2c3c(c(Cl)c4c2CCC4)CCC3)c(F)c1] | (R)-or (S)-N'-(4-fluoro-2,6-diisopropylphenylcarbamoyl)-4-(2-hydroxypropan-2-yl)thiophene-2-sulfonimidamide | ChiralPak IG, 2 * 25 cm, 5 um | 30% IPA in Hex | 466.2 |
| 144 | 151a' or 151b' | 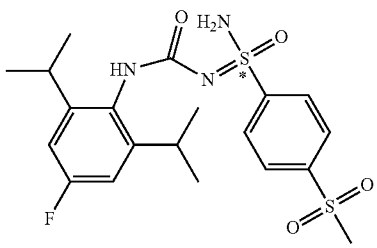 [SMILES: CC(C)c1cc(F)cc(C(C)C)c1NC(=O)N=S(N)(=O)c1ccc(S(C)(=O)=O)cc1] | (S)-or (R)-N'-(4-fluoro-2,6-diisopropylphenylcarbamoyl)-4-(methylsulfonyl)benzene-sulfonimidamide | Lux 5u Cellulose-4, AXIA Packed, 2.12 * 25 cm, 5 um | 35% MeOH (2 mM $NH_3$) in $CO_2$ | 454.1 (M − 1) |
| 145 | 151b' or 151a' | 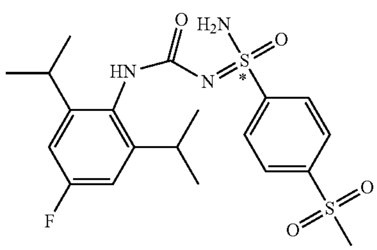 [SMILES: CC(C)c1cc(F)cc(C(C)C)c1NC(=O)N=S(N)(=O)c1ccc(S(C)(=O)=O)cc1] | (R)-or (S)-N'-(4-fluoro-2,6-diisopropylphenylcarbamoyl)-4-(methylsulfonyl)benzene-sulfonimidamide | Lux 5u Cellulose-4, AXIA Packed, 2.12 * 25 cm, 5 um | 35% MeOH (2 mM $NH_3$) in $CO_2$ | 454.1 (M − 1) |
| 146 | 167a or 167b | 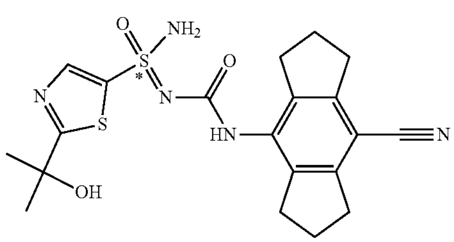 [SMILES: CC(C)(O)c1ncc(S(N)(=O)=NC(=O)Nc2c3c(c(C#N)c4c2CCC4)CCC3)s1] | (S)-or (R)-N'-(8-cyano-1,2,3,5,6,7-hexa-hydro-s-indacen-4-ylcarbamoyl)-2-(2-hydroxypropan-2-yl)thiazole-5-sulfonimidamide | ChiralPak IC, 2 * 25 cm, 5 um | 30% EtOH in Hex (0.1% DEA) | 444.1 (M − 1) |
| 147 | 167b or 167a | 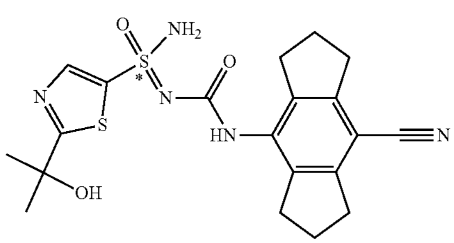 [SMILES: CC(C)(O)c1ncc(S(N)(=O)=NC(=O)Nc2c3c(c(C#N)c4c2CCC4)CCC3)s1] | (R)-or (S)-N'-(8-cyano-1,2,3,5,6,7-hexa-hydro-s-indacen-4-ylcarbamoyl)-2-(2-hydroxypropan-2-yl)thiazole-5-sulfonimidamide | ChiralPak IC, 2 * 25 cm, 5 um | 30% EtOH in Hex (0.1% DEA) | 444.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 148 | 107a or 107b | 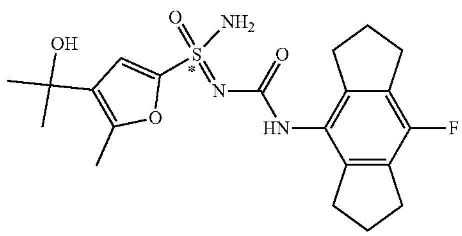 [SMILES: Cc1oc(S(N)(=O)=NC(=O)Nc2c3c(c(F)c4c2CCC4)CCC3)cc1C(C)(C)O] | (S)-or (R)-N'-(8-fluoro-1,2,3,5,6,7-hexa-hydro-s-indacen-4-ylcarbamoyl)-4-(2-hydroxypropan-2-yl)-5-methylfuran-2-sulfonimidamide | ChiralPak ID, 2 * 25 cm, 5 um | 50% IPA in Hex | 434.1 (M − 1) |
| 149 | 107b or 107a | 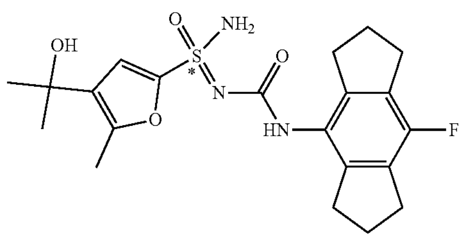 [SMILES: Cc1oc(S(N)(=O)=NC(=O)Nc2c3c(c(F)c4c2CCC4)CCC3)cc1C(C)(C)O] | (R)-or (S)-N'-(8-fluoro-1,2,3,5,6,7-hexa-hydro-s-indacen-4-ylcarbamoyl)-4-(2-hydroxypropan-2-yl)-5-methylfuran-2-sulfonimidamide | ChiralPak ID, 2 * 25 cm, 5 um | 50% IPA in Hex | 434.1 (M − 1) |
| 150 | 110a or 110b | 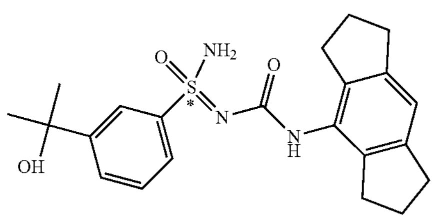 [SMILES: CC(C)(O)c1cccc(S(N)(=O)=NC(=O)Nc2c3c(cc4c2CCC4)CCC3)c1] | (S)-or (R)-N'-(1,2,3,5,6,7-hexahydro-s-indacen-4-ylcarbamoyl)-3-(2-hydroxypropan-2-yl)benzenesulfonimidamide | ChiralPak IF, 2 * 25 cm, 5 um | 30% EtOH in Hex | 412.1 (M − 1) |
| 151 | 110b or 110a | 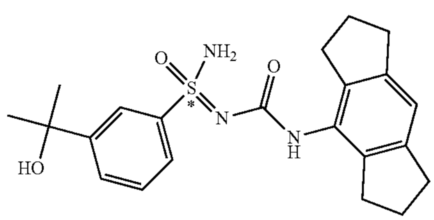 [SMILES: CC(C)(O)c1cccc(S(N)(=O)=NC(=O)Nc2c3c(cc4c2CCC4)CCC3)c1] | (R)-or (S)-N'-(1,2,3,5,6,7-hexahydro-s-indacen-4-ylcarbamoyl)-3-(2-hydroxypropan-2-yl)benzenesulfonimidamide | ChiralPak IF, 2 * 25 cm, 5 um | 30% EtOH in Hex | 412.1 (M − 1) |
| 152 | 151a or 151b | 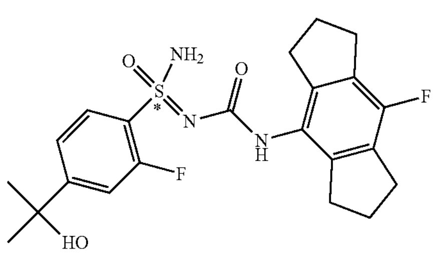 [SMILES: CC(C)(O)c1ccc(S(N)(=O)=NC(=O)Nc2c3c(c(F)c4c2CCC4)CCC3)c(F)c1] | (S)-or (R)-2-fluoro-N'-(8-fluoro-1,2,3,5,6,7-hexahydro-s-indacen-4-ylcarbamoyl)-4-(2-hydroxypropan-2-yl)benzenesulfonimidamide | ChiralPak IG, 2 * 25 cm, 5 um | 30% IPA in Hex | 448.1 (M − 1) |
| 153 | 151b or 151a | 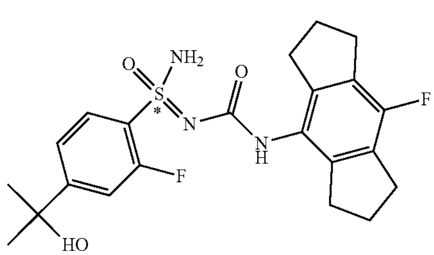 [SMILES: CC(C)(O)c1ccc(S(N)(=O)=NC(=O)Nc2c3c(c(F)c4c2CCC4)CCC3)c(F)c1] | (R)-or (S)-2-fluoro-N'-(8-fluoro-1,2,3,5,6,7-hexahydro-s-indacen-4-ylcarbamoyl)-4-(2-hydroxypropan-2-yl)benzenesulfonimidamide | ChiralPak IG, 2 * 25 cm, 5 um | 30% IPA in Hex | 448.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 154 | 154a or 154b | 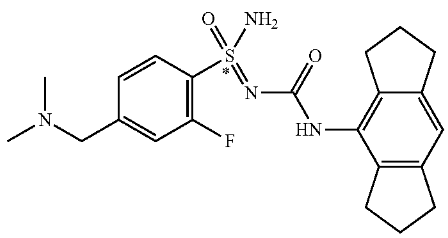 [SMILES: CN(C)Cc1ccc(S(N)(=O)=NC(=O)Nc2c3c(cc4c2CCC4)CCC3)c(F)c1] | (S)-or (R)-4-((dimethylamino)methyl)-2-fluoro-N'-(1,2,3,5,6,7-hexahydro-s-indacen-4-ylcarbamoyl)benzene-sulfonimidamide | ChiralPak IG, 2 * 25 cm, 5 um | 30% EtOH in Hex | 431.2 |
| 155 | 154b or 154a | 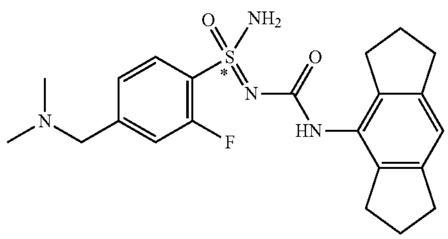 [SMILES: CN(C)Cc1ccc(S(N)(=O)=NC(=O)Nc2c3c(cc4c2CCC4)CCC3)c(F)c1] | (R)-or (S)-4-((dimethylamino)methyl)-2-fluoro-N'-(1,2,3,5,6,7-hexahydro-s-indacen-4-ylcarbamoyl)benzene-sulfonimidamide | ChiralPak IG, 2 * 25 cm, 5 um | 30% EtOH in Hex | 431.2 |
| 156 | 148a or 148b | 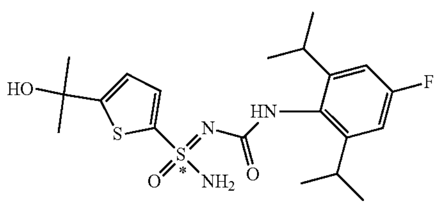 [SMILES: CC(C)c1cc(F)cc(C(C)C)c1NC(=O)N=S(N)(=O)c1ccc(C(C)(C)O)s1] | (S)-or (R)-N'-(4-fluoro-2,6-diisopropylphenylcarbamoyl)-5-(2-hydroxypropan-2-yl)thiophene-2-sulfonimidamide | ChiralPak ID, 2 * 25 cm, 5 um | 30% EtOH in Hex | 442.1 |
| 157 | 148b or 148a | 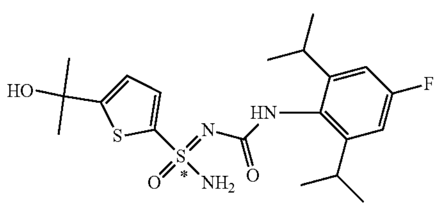 [SMILES: CC(C)c1cc(F)cc(C(C)C)c1NC(=O)N=S(N)(=O)c1ccc(C(C)(C)O)s1] | (R)-or (S)-N'-(4-fluoro-2,6-diisopropylphenylcarbamoyl)-5-(2-hydroxypropan-2-yl)thiophene-2-sulfonimidamide | ChiralPak ID, 2 * 25 cm, 5 um | 30% EtOH in Hex | 442.1 |
| 158 | 153a or 153b | 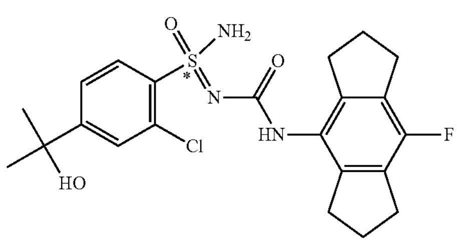 [SMILES: CC(C)(O)c1ccc(S(N)(=O)=NC(=O)Nc2c3c(c(F)c4c2CCC4)CCC3)c(Cl)c1] | (S)-or (R)-2-chloro-N'-(8-fluoro-1,2,3,5,6,7-hexahydro-s-indacen-4-ylcarbamoyl)-4-(2-hydroxypropan-2-yl)benzenesulfonimidamide | ChiralPak IF, 2 * 25 cm, 5 um | 30% EtOH in Hex | 464.1 (M − 1) |
| 159 | 153a or 153b | 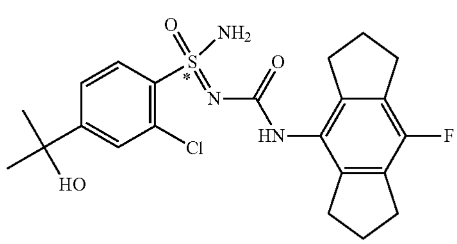 [SMILES: CC(C)(O)c1ccc(S(N)(=O)=NC(=O)Nc2c3c(c(F)c4c2CCC4)CCC3)c(Cl)c1] | (R)-or (S)-2-chloro-N'-(8-fluoro-1,2,3,5,6,7-hexahydro-s-indacen-4-ylcarbamoyl)-4-(2-hydroxypropan-2-yl)benzenesulfonimidamide | ChiralPak IF, 2 * 25 cm, 5 um | 30% EtOH in Hex | 464.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 160 | 109a or 109b | 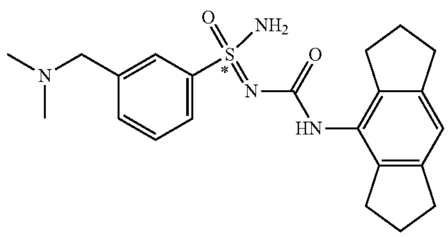 [SMILES: CN(C)Cc1cccc(S(N)(=O)=NC(=O)Nc2c3c(cc4c2CCC4)CCC3)c1] | (S)-or (R)-3-((dimethylamino)methyl)-N'-(1,2,3,5,6,7-hexahydro-s-indacen-4-ylcarbamoyl)benzene-sulfonimidamide | ChiralPak ID, 2 * 25 cm, 5 um | 50% EtOH in Hex (0.1% DEA) | 413.1 |
| 161 | 109b or 109a | 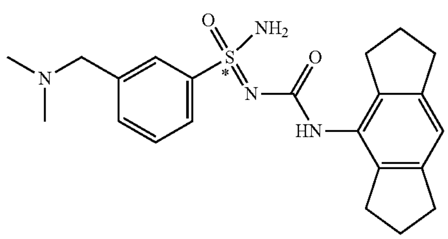 [SMILES: CN(C)Cc1cccc(S(N)(=O)=NC(=O)Nc2c3c(cc4c2CCC4)CCC3)c1] | (R)-or (S)-3-((dimethylamino)methyl)-N'-(1,2,3,5,6,7-hexahydro-s-indacen-4-ylcarbamoyl)benzene-sulfonimidamide | ChiralPak ID, 2 * 25 cm, 5 um | 50% EtOH in Hex (0.1% DEA) | 413.1 |
| 162 | 135a or 135b | 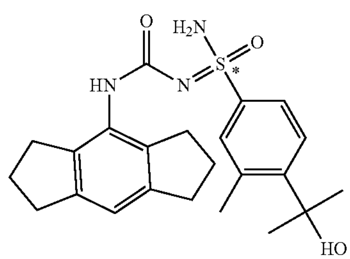 [SMILES: Cc1cc(S(N)(=O)=NC(=O)Nc2c3c(cc4c2CCC4)CCC3)ccc1C(C)(C)O] | (S)-or (R)-N'-((1,2,3,5,6,7-hexahydro-s-indacen-4-yl)carbamoyl)-4-(2-hydroxypropan-2-yl)-3-methyl-benzenesulfonimidamide | ChiralPak ID, 2 * 25 cm, 5 um | 30% IPA in Hex | 428.2 |
| 163 | 135b or 135a | 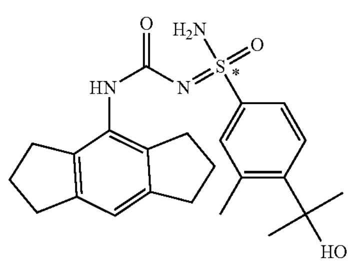 [SMILES: Cc1cc(S(N)(=O)=NC(=O)Nc2c3c(cc4c2CCC4)CCC3)ccc1C(C)(C)O] | (R)-or (S)-N'-((1,2,3,5,6,7-hexahydro-s-indacen-4-yl)carbamoyl)-4-(2-hydroxypropan-2-yl)-3-methyl-benzenesulfonimidamide | ChiralPak ID, 2 * 25 cm, 5 um | 30% IPA in Hex | 428.2 |
| 164 | 134a or 134b | 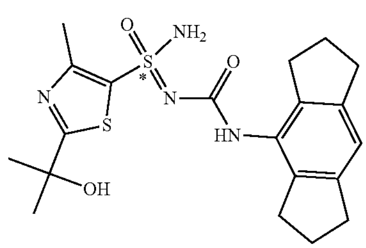 [SMILES: Cc1nc(C(C)(C)O)sc1S(N)(=O)=NC(=O)Nc1c2c(cc3c1CCC3)CCC2] | (S)-or (R)-N'-((1,2,3,5,6,7-hexahydro-s-indacen-4-yl)carbamoyl)-2-(2-hydroxypropan-2-yl)-4-methylthiazole-5-sulfonimidamide | ChiralPak ID, 2 * 25 cm, 5 um | 30% IPA in Hex | 435.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 165 | 134b or 134a | 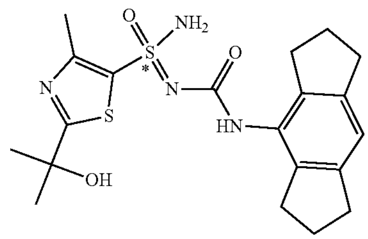 [SMILES: Cc1nc(C(C)(C)O)sc1S(N)(=O)=NC(=O)Nc1c2c(cc3c1CCC3)CCC2] | (R)-or (S)-N'-((1,2,3,5,6,7-hexahydro-s-indacen-4-yl)carbamoyl)-2-(2-hydroxypropan-2-yl)-4-methylthiazole-5-sulfonimidamide | ChiralPak ID, 2 * 25 cm, 5 um | 30% IPA in Hex | 435.1 |
| 166 | 130a or 130b | 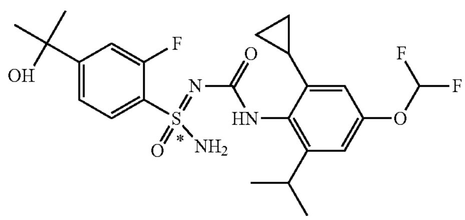 [SMILES: CC(C)c1cc(OC(F)F)cc(C2CC2)c1NC(=O)N=S(N)(=O)c1ccc(C(C)(C)O)cc1F] | (S)-or (R)-N'-((2-cyclopropyl-4-(difluoromethoxy)-6-isopropylphenyl)carbamoyl)-2-fluoro-4-(2-hydroxypropan-2-yl)benzenesulfonimidamide | ChiralPak ID, 2 * 25 cm, 5 um | 40% IPA in Hex | 500.2 |
| 167 | 130b or 130a | 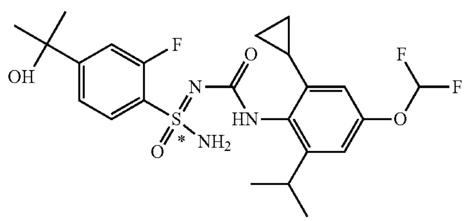 [SMILES: CC(C)c1cc(OC(F)F)cc(C2CC2)c1NC(=O)N=S(N)(=O)c1ccc(C(C)(C)O)cc1F] | (R)-or (S)-N'-((2-cyclopropyl-4-(difluoromethoxy)-6-isopropylphenyl)carbamoyl)-2-fluoro-4-(2-hydroxypropan-2-yl)benzenesulfonimidamide | ChiralPak ID, 2 * 25 cm, 5 um | 40% IPA in Hex | 500.2 |
| 168 | 212a or 212b | 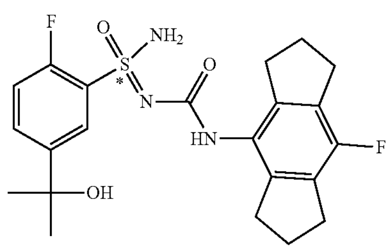 [SMILES: CC(C)(O)c1ccc(F)c(S(N)(=O)=NC(=O)Nc2c3c(c(F)c4c2CCC4)CCC3)c1] | (S)-or (R)-2-fluoro-N'-((8-fluoro-1,2,3,5,6,7-hexahydro-s-indacen-4-yl)carbamoyl)-5-(2-hydroxypropan-2-yl)benzenesulfonimidamide | ChiralPak ID, 2 * 25 cm, 5 um | 40% EtOH in Hex | 450.2 |
| 169 | 212b or 212a | 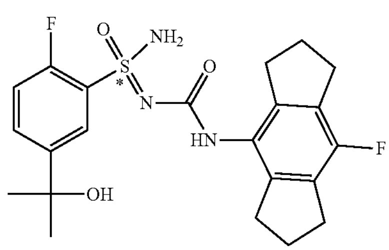 [SMILES: CC(C)(O)c1ccc(F)c(S(N)(=O)=NC(=O)Nc2c3c(c(F)c4c2CCC4)CCC3)c1] | (S)-or (R)-2-fluoro-N'-((8-fluoro-1,2,3,5,6,7-hexahydro-s-indacen-4-yl)carbamoyl)-5-(2-hydroxypropan-2-yl)benzenesulfonimidamide | ChiralPak ID, 2 * 25 cm, 5 um | 40% EtOH in Hex | 450.2 |
| 170 | 205a or 205b | 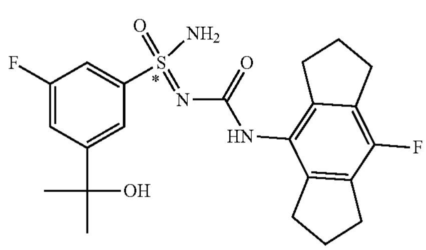 [SMILES: CC(C)(O)c1cc(F)cc(S(N)(=O)=NC(=O)Nc2c3c(c(F)c4c2CCC4)CCC3)c1] | (R)-or (S)-3-fluoro-N'-((8-fluoro-1,2,3,5,6,7-hexahydro-s-indacen-4-yl)carbamoyl)-5-(2-hydroxypropan-2-yl)benzenesulfonimidamide | Chiral ART Cellulose-SB, 2 * 25 cm, 5 um | 30% EtOH in Hex | 450.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 171 | 205a or 205b | 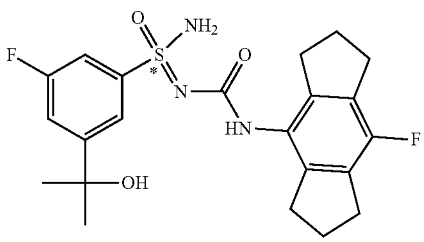 [SMILES: CC(C)(O)c1cc(F)cc(S(N)(=O)=NC(=O)Nc2c3c(c(F)c4c2CCC4)CCC3)c1] | (S)- or (R)-3-fluoro-N'-((8-fluoro-1,2,3,5,6,7-hexahydro-s-indacen-4-yl)carbamoyl)-5-(2-hydroxypropan-2-yl)benzenesulfonimidamide | Chiral ART Cellulose-SB, 2 * 25 cm, 5 um | 40% EtOH in Hex | 450.2 |
| 172 | 143a or 143b | 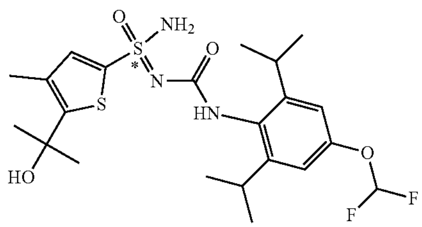 [SMILES: Cc1cc(S(N)(=O)=NC(=O)Nc2c(C(C)C)cc(OC(F)F)cc2C(C)C)sc1C(C)(C)O] | (S)- or (R)-N'-((4-(difluoromethoxy)-2,6-diisopropylphenyl)carbamoyl)-5-(2-hydroxypropan-2-yl)-4-methylthiophene-2-sulfonimidamide | ChiralPak ID, 2 * 25 cm, 5 um | 30% EtOH in Hex | 504.2 |
| 173 | 143b or 143a | 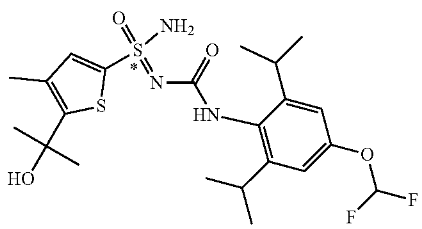 [SMILES: Cc1cc(S(N)(=O)=NC(=O)Nc2c(C(C)C)cc(OC(F)F)cc2C(C)C)sc1C(C)(C)O] | (R)- or (S)-N'-((4-(difluoromethoxy)-2,6-diisopropylphenyl)carbamoyl)-5-(2-hydroxypropan-2-yl)-4-methylthiophene-2-sulfonimidamide | ChiralPak ID, 2 * 25 cm, 5 um | 30% EtOH in Hex | 504.2 |
| 174 | 206a or 206b | 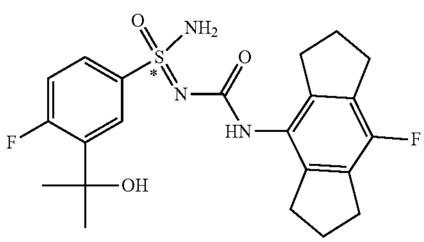 [SMILES: CC(C)(O)c1cc(S(N)(=O)=NC(=O)Nc2c3c(c(F)c4c2CCC4)CCC3)ccc1F] | (S)- or (R)-4-fluoro-N'-((8-fluoro-1,2,3,5,6,7-hexahydro-s-indacen-4-yl)carbamoyl)-3-(2-hydroxypropan-2-yl)benzenesulfonimidamide | ChiralPak ID, 2 * 25 cm, 5 um | 30% EtOH in Hex (8 mM NH3•MeOH) | 450.2 |
| 175 | 206b or 206a | 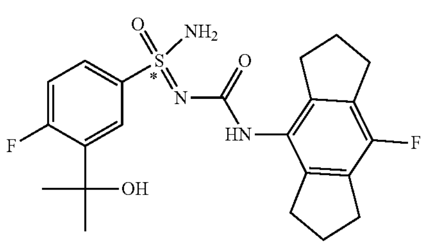 [SMILES: CC(C)(O)c1cc(S(N)(=O)=NC(=O)Nc2c3c(c(F)c4c2CCC4)CCC3)ccc1F] | (R)- or (S)-4-fluoro-N'-((8-fluoro-1,2,3,5,6,7-hexahydro-s-indacen-4-yl)carbamoyl)-3-(2-hydroxypropan-2-yl)benzenesulfonimidamide | ChiralPak ID, 2 * 25 cm, 5 um | 30% EtOH in Hex (8 mM NH3•MeOH) | 450.2 |
| 176 | 108a or 108b | 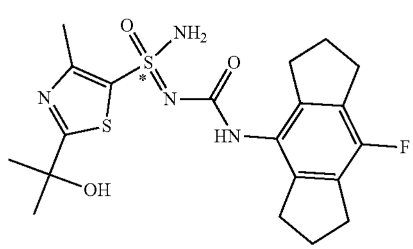 [SMILES: Cc1nc(C(C)(C)O)sc1S(N)(=O)=NC(=O)Nc1c2c(c(F)c3c1CCC3)CCC2] | (S)- or (R)-N'-((8-fluoro-1,2,3,5,6,7-hexahydro-s-indacen-4-yl)carbamoyl)-2-(2-hydroxypropan-2-yl)-4-methylthiazole-5-sulfonimidamide | ChiralPak IG, 2 * 25 cm, 5 um | 30% IPA in Hex | 453.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 177 | 108b or 108a | 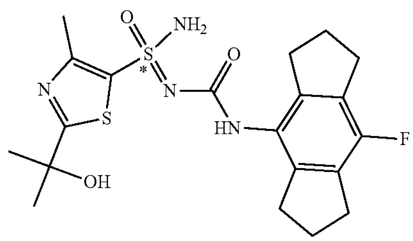 [SMILES: Cc1nc(C(C)(C)O)sc1S(N)(=O)=NC(=O)Nc1c2c(c(F)c3c1CCC3)CCC2] | (R)-or (S)-N'-((8-fluoro-1,2,3,5,6,7-hexahydro-s-indacen-4-yl)carbamoyl)-2-(2-hydroxypropan-2-yl)-4-methylthiazole-5-sulfonimidamide | ChiralPak IG, 2 * 25 cm, 5 um | 40% IPA in Hex | 453.1 |
| 178 | 202a or 202b | 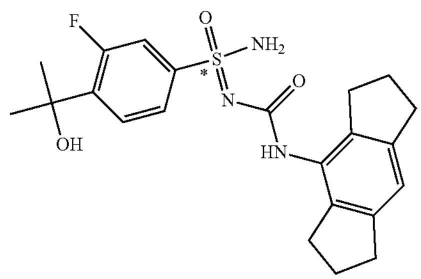 [SMILES: CC(C)(O)c1ccc(S(N)(=O)=NC(=O)Nc2c3c(cc4c2CCC4)CCC3)cc1F] | (S)-or (R)-3-fluoro-N'-((1,2,3,5,6,7-hexahydro-s-indacen-4-yl)carbamoyl)-4-(2-hydroxypropan-2-yl)benzenesulfonimidamide | Chiral ART Cellulose-SB, 2 * 25 cm, 5 um | 50% EtOH in Hex (8 mM NH$_3$•MeOH) | 432.2 |
| 179 | 202b or 202a | 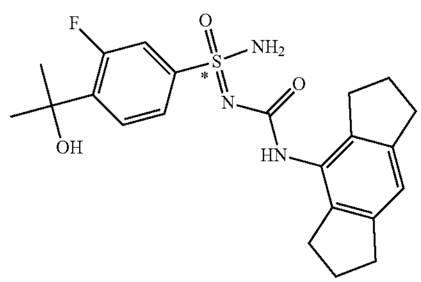 [SMILES: CC(C)(O)c1ccc(S(N)(=O)=NC(=O)Nc2c3c(cc4c2CCC4)CCC3)cc1F] | (R)-or (S)-3-fluoro-N'-((1,2,3,5,6,7-hexahydro-s-indacen-4-yl)carbamoyl)-4-(2-hydroxypropan-2-yl)benzenesulfonimidamide | Chiral ART Cellulose-SB, 2 * 25 cm, 5 um | 50% EtOH in Hex (8 mM NH$_3$•MeOH) | 432.2 |
| 180 | 116a or 116b | 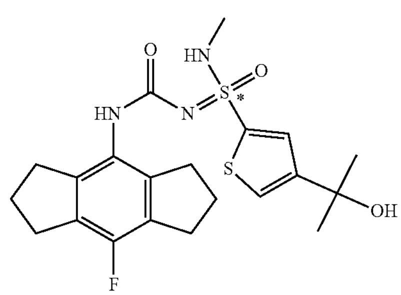 [SMILES: CNS(=O)(=NC(=O)Nc1c2c(c(F)c3c1CCC3)CCC2)c1cc(C(C)(C)O)cs1] | (S)-or (R)-N'-((8-fluoro-1,2,3,5,6,7-hexahydro-s-indacen-4-yl)carbamoyl)-4-(2-hydroxypropan-2-yl)-N-methylthiophene-2-sulfonimidamide | ChiralPak IG, 2 * 25 cm, 5 um | 30% EtOH in Hex | 452.1 |
| 181 | 116b or 116a | 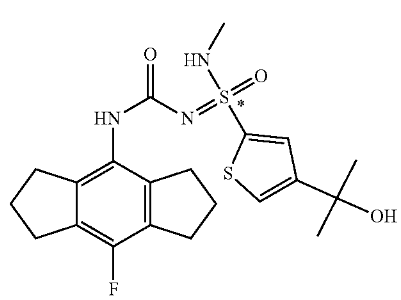 [SMILES: CNS(=O)(=NC(=O)Nc1c2c(c(F)c3c1CCC3)CCC2)c1cc(C(C)(C)O)cs1] | (R)-or (S)-N'-((8-fluoro-1,2,3,5,6,7-hexahydro-s-indacen-4-yl)carbamoyl)-4-(2-hydroxypropan-2-yl)-N-methylthiophene-2-sulfonimidamide | ChiralPak IG, 2 * 25 cm, 5 um | 30% EtOH in Hex | 452.1 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined.

| Ex.# | Final Target Number | Structure | IUPAC Name | Column | Eluents | LC-MS [M + H]+ |
|---|---|---|---|---|---|---|
| 182 | 173a or 173b | 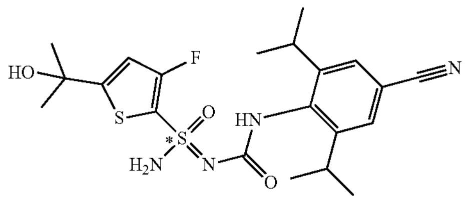 [SMILES: CC(C)c1cc(C#N)cc(C(C)C)c1NC(=O)N=S(N)(=O)c1sc(C(C)(C)O)cc1F] | (S)-or (R)-N'-((4-cyano-2,6-diisopropylphenyl)carbamoyl)-3-fluoro-5-(2-hydroxypropan-2-yl)thiophene-2-sulfonimidamide | ChiralPak ID, 2 * 25 cm, 5 um | 15% EtOH in Hex (0.1% DEA) | 467.2 |
| 183 | 173b or 173a | 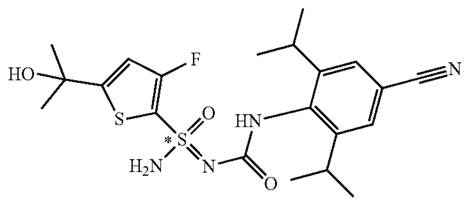 [SMILES: CC(C)c1cc(C#N)cc(C(C)C)c1NC(=O)N=S(N)(=O)c1sc(C(C)(C)O)cc1F] | (R)-or (S)-N'-((4-cyano-2,6-diisopropylphenyl)carbamoyl)-3-fluoro-5-(2-hydroxypropan-2-yl)thiophene-2-sulfonimidamide | ChiralPak ID, 2 * 25 cm, 5 um | 15% EtOH in Hex (0.1% DEA) | 467.2 |
| 184 | 174a or 174b | 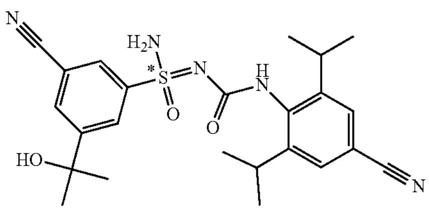 [SMILES: CC(C)c1cc(C#N)cc(C(C)C)c1NC(=O)N=S(N)(=O)c1cc(C#N)cc(C(C)(C)O)c1] | (S)-or (R)-3-cyano-N'-((4-cyano-2,6-diisopropylphenyl)carbamoyl)-5-(2-hydroxypropan-2-yl)benzenesulfonimidamide | ChiralPak IG, 2 * 25 cm, 5 um | 15% EtOH in Hex (0.1% DEA) | 468.2 |
| 185 | 174b or 174a | 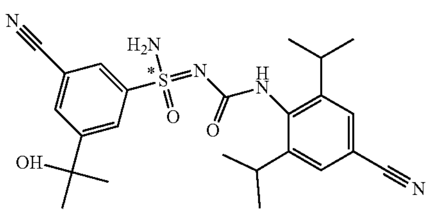 [SMILES: CC(C)c1cc(C#N)cc(C(C)C)c1NC(=O)N=S(N)(=O)c1cc(C#N)cc(C(C)(C)O)c1] | (R)-or (S)-3-cyano-N'-((4-cyano-2,6-diisopropylphenyl)carbamoyl)-5-(2-hydroxypropan-2-yl)benzenesulfonimidamide | ChiralPak IG, 2 * 25 cm, 5 um | 15% EtOH in Hex (0.1% DEA) | 468.2 |
| 186 | 223a or 223b | 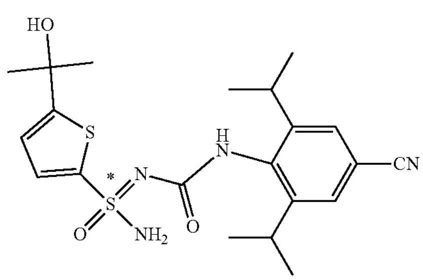 [SMILES: CC(C)c1cc(C#N)cc(C(C)C)c1NC(=O)N=S(N)(=O)c1ccc(C(C)(C)O)s1] | (S)-or (R)-N'-((4-cyano-2,6-diisopropylphenyl)carbamoyl)-5-(2-hydroxypropan-2-yl)thiophene-2-sulfonimidamide | ChiralPak ID, 2 * 25 cm, 5 um | 30% EtOH in Hex (0.1% DEA) | 449.2 |
| 187 | 223b or 223a | 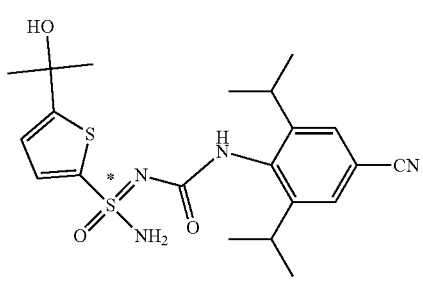 [SMILES: CC(C)c1cc(C#N)cc(C(C)C)c1NC(=O)N=S(N)(=O)c1ccc(C(C)(C)O)s1] | (R)-or (S)-N'-((4-cyano-2,6-diisopropylphenyl)carbamoyl)-5-(2-hydroxypropan-2-yl)thiophene-2-sulfonimidamide | ChiralPak ID, 2 * 25 cm, 5 um | 30% EtOH in Hex (0.1% DEA) | 449.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 188 | 158a or 158b | 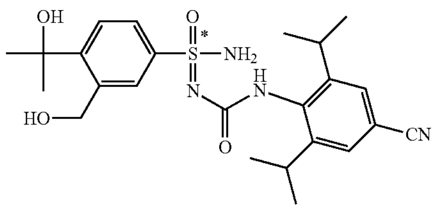 [SMILES: CC(C)c1cc(C#N)cc(C(C)C)c1NC(=O)N=S(N)(=O)c1ccc(C(C)(C)O)c(CO)c1] | (S)-or (R)-N'-((4-cyano-2,6-diisopropylphenyl)carbamoyl)-3-(hydroxymethyl)-4-(2-hydroxypropan-2-yl)benzenesulfonimidamide | ChiralPak ID, 2 * 25 cm, 5 um | 30% EtOH in Hex (0.1% DEA) | 473.2 |
| 189 | 158b or 158a | 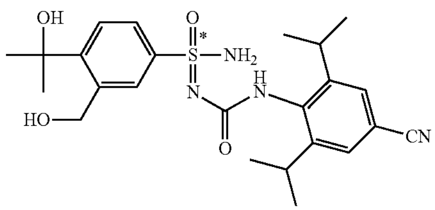 [SMILES: CC(C)c1cc(C#N)cc(C(C)C)c1NC(=O)N=S(N)(=O)c1ccc(C(C)(C)O)c(CO)c1] | (R)-or (S)-N'-((4-cyano-2,6-diisopropylphenyl)carbamoyl)-3-(hydroxymethyl)-4-(2-hydroxypropan-2-yl)benzenesulfonimidamide | ChiralPak ID, 2 * 25 cm, 5 um | 30% EtOH in Hex (0.1% DEA) | 473.2 |
| 190 | 220a or 220b | 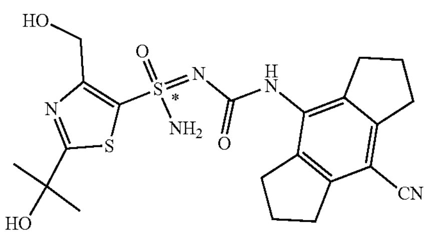 [SMILES: CC(C)(O)c1nc(CO)c(S(N)(=O)=NC(=O)Nc2c3c(c(C#N)c4c2CCC4)CCC3)s1] | (S)-or (R)-N'-((8-cyano-1,2,3,5,6,7-hexahydro-s-indacen-4-yl)carbamoyl)-4-(hydroxymethyl)-2-(2-hydroxypropan-2-yl)thiazole-5-sulfonimidamide | ChiralPak IF, 2 * 25 cm, 5 um | MeOH (0.1% DEA) | 476.1 |
| 191 | 220b or 220a | 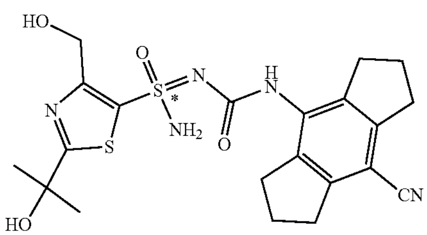 [SMILES: CC(C)(O)c1nc(CO)c(S(N)(=O)=NC(=O)Nc2c3c(c(C#N)c4c2CCC4)CCC3)s1] | (R)-or (S)-N'-((8-cyano-1,2,3,5,6,7-hexahydro-s-indacen-4-yl)carbamoyl)-4-(hydroxymethyl)-2-(2-hydroxypropan-2-yl)thiazole-5-sulfonimidamide | ChiralPak IF, 2 * 25 cm, 5 um | MeOH (0.1% DEA) | 476.1 |
| 192 | 157a or 157b | 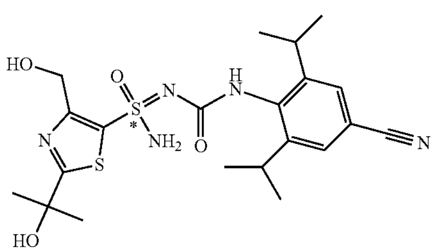 [SMILES: CC(C)c1cc(C#N)cc(C(C)C)c1NC(=O)N=S(N)(=O)c1sc(C(C)(C)O)nc1CO] | (S)-or (R)-N'-((4-cyano-2,6-diisopropylphenyl)carbamoyl)-4-(hydroxymethyl)-2-(2-hydroxypropan-2-yl)thiazole-5-sulfonimidamide | ChiralPak IC, 2 * 25 cm, 5 um | 15% EtOH in Hex | 480.2 |
| 193 | 157b or 157a | 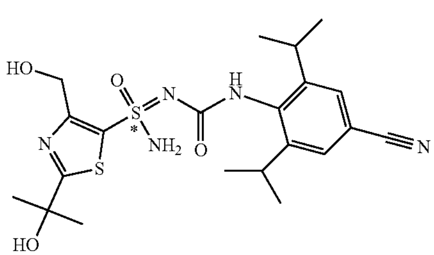 [SMILES: CC(C)c1cc(C#N)cc(C(C)C)c1NC(=O)N=S(N)(=O)c1sc(C(C)(C)O)nc1CO] | (R)-or (S)-N'-((4-cyano-2,6-diisopropylphenyl)carbamoyl)-4-(hydroxymethyl)-2-(2-hydroxypropan-2-yl)thiazole-5-sulfonimidamide | ChiralPak IC, 2 * 25 cm, 5 um | 15% EtOH in Hex | 480.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 194 | 161a or 161b | 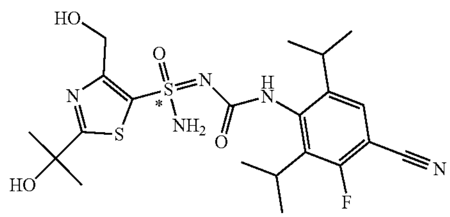 [SMILES: CC(C)c1cc(C#N)c(F)c(C(C)C)c1NC(=O)N=S(N)(=O)c1sc(C(C)(C)O)nc1CO] | (S)-or (R)-N'-((4-cyano-3-fluoro-2,6-diisopropylphenyl)carbamoyl)-4-(hydroxymethyl)-2-(2-hydroxypropan-2-yl)thiazole-5-sulfonimidamide | ChiralPak IC, 2 * 25 cm, 5 um | 15% EtOH in Hex | 498.2 |
| 195 | 161b or 161a | 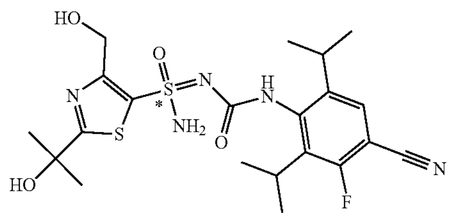 [SMILES: CC(C)c1cc(C#N)c(F)c(C(C)C)c1NC(=O)N=S(N)(=O)c1sc(C(C)(C)O)nc1CO] | (R)-or (S)-N'-((4-cyano-3-fluoro-2,6-diisopropylphenyl)carbamoyl)-4-(hydroxymethyl)-2-(2-hydroxypropan-2-yl)thiazole-5-sulfonimidamide | ChiralPak IC, 2 * 25 cm, 5 um | 15% EtOH in Hex | 498.2 |
| 196 | 165a or 165b | 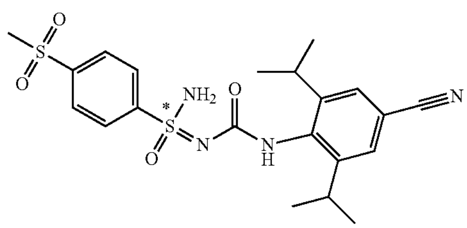 [SMILES: CC(C)c1cc(C#N)cc(C(C)C)c1NC(=O)N=S(N)(=O)c1ccc(S(C)(=O)=O)cc1] | (S)-or (R)-N'-((4-cyano-2,6-diisopropylphenyl)carbamoyl)-4-(methylsulfonyl)benzene-sulfonimidamide | ChiralPak IG, 2 * 25 cm, 5 um | 30% EtOH in Hex (0.1% DEA) | 463.1 |
| 197 | 165b or 165a | 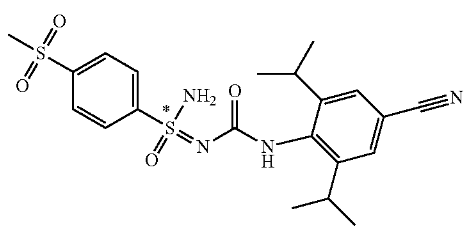 [SMILES: CC(C)c1cc(C#N)cc(C(C)C)c1NC(=O)N=S(N)(=O)c1ccc(S(C)(=O)=O)cc1] | (R)-or (S)-N'-((4-cyano-2,6-diisopropylphenyl)carbamoyl)-4-(methylsulfonyl)benzene-sulfonimidamide | ChiralPak IG, 2 * 25 cm, 5 um | 30% EtOH in Hex (0.1% DEA) | 463.1 |
| 198 | 172a or 172b | 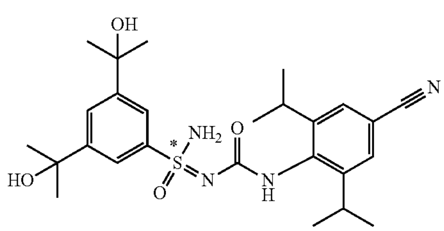 [SMILES: CC(C)c1cc(C#N)cc(C(C)C)c1NC(=O)N=S(N)(=O)c1cc(C(C)(C)O)cc(C(C)(C)O)c1] | N'-((4-cyano-2,6-diisopropylphenyl)carbamoyl)-3,5-bis(2-hydroxypropan-2-yl)benzenesulfonimidamide | ChiralPak IC, 2 * 25 cm, 5 um | 15% EtOH in Hex (0.1% DEA) | 501.2 |
| 199 | 172b or 172a | 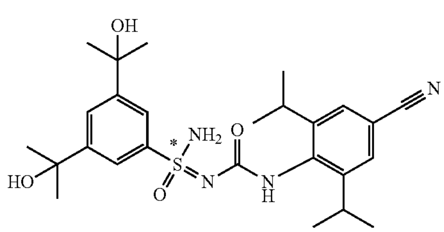 [SMILES: CC(C)c1cc(C#N)cc(C(C)C)c1NC(=O)N=S(N)(=O)c1cc(C(C)(C)O)cc(C(C)(C)O)c1] | N'-((4-cyano-2,6-diisopropylphenyl)carbamoyl)-3,5-bis(2-hydroxypropan-2-yl)benzenesulfonimidamide | ChiralPak IC, 2 * 25 cm, 5 um | 15% EtOH in Hex (0.1% DEA) | 501.2 |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]$^+$ |
|---|---|---|---|---|---|---|
| 200 | 106a or 106b | 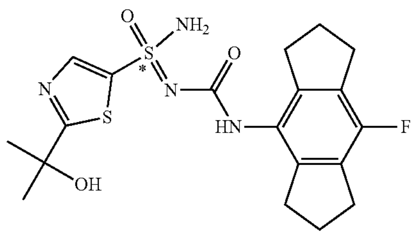 [SMILES: CC(C)(O)c1ncc(S(N)(=O)=NC(=O)Nc2c3c(c(F)c4c2CCC4)CCC3)s1] | (R)-or (S)-N'-(8-fluoro-1,2,3,5,6,7-hexa-hydro-s-indacen-4-ylcarbamoyl)-2-(2-hydroxypropan-2-yl)thiazole-5-sulfonimidamide | ChiralPak AD-H, 2 * 25 cm, 5 um | 25% EtOH in CO2 | 439.2 |
| 201 | 106b or 106a | 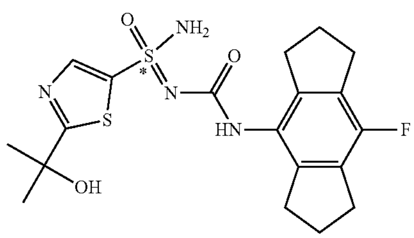 | (S)-or (R)-N'-(8-fluoro-1,2,3,5,6,7-hexa-hydro-s-indacen-4-ylcarbamoyl)-2-(2-hydroxypropan-2-yl)thiazole-5-sulfonimidamide | ChiralPak AD-H, 2 * 25 cm, 5 um | 25% EtOH in CO$_2$ | 439.2 |
| 202 | 136a or 136b | 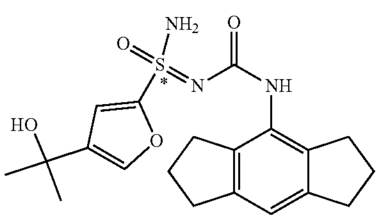 [SMILES: CC(C)(O)c1coc(S(N)(=O)=NC(=O)Nc2c3c(cc4c2CCC4)CCC3)c1] | (S)-or (R)-N'-(1,2,3,5,6,7-hexahydro-s-in-dacen-4-ylcarbamoyl)-4-(2-hydroxypropan-2-yl)furan-2-sulfonimidamide | Chiral ART Cellulose-SB, 2 * 25 cm, 5 um | 20% EtOH in Hex (0.2% DEA) | 404.2 |
| 203 | 136b or 136a | 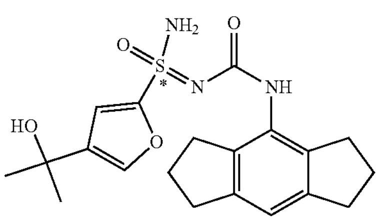 [SMILES: CC(C)(O)c1coc(S(N)(=O)=NC(=O)Nc2c3c(cc4c2CCC4)CCC3)c1] | (R)-or (S)-N'-(1,2,3,5,6,7-hexahydro-s-in-dacen-4-ylcarbamoyl)-4-(2-hydroxypropan-2-yl)furan-2-sulfonimidamide | Chiral ART Cellulose-SB, 2 * 25 cm, 5 um | 20% EtOH in Hex (0.2% DEA) | 404.2 |
| 204 | 183a or 183b | 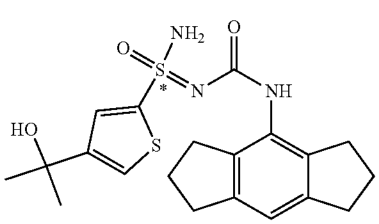 [SMILES: CC(C)(O)c1csc(S(N)(=O)=NC(=O)Nc2c3c(cc4c2CCC4)CCC3)c1] | (R)-or (S)-N'-(1,2,3,5,6,7-hexahydro-s-in-dacen-4-ylcarbamoyl)-4-(2-hydroxypropan-2-yl)thiophene-2-sulfonimidamide | ChiralPak ID, 2 * 25 cm, 5 um | 20% EtOH in Hex (0.1% DEA) | 418.1 (M − 1) |

TABLE 19-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and thea bsolute stereochemistry at that center has not been determined.

| Ex.# | Final Target Number | Structure | IUPAC Name | Column | Eluents | LC-MS [M + H]+ |
|---|---|---|---|---|---|---|
| 205 | 183a or 183b | 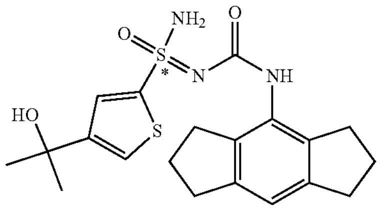 [SMILES: CC(C)(O)c1csc(S(N)(=O)=NC(=O)Nc2c3c(cc4c2CCC4)CCC3)c1] | (S)-or (R)-N'-(1,2,3,5,6,7-hexahydro-s-in-dacen-4-ylcarbamoyl)-4-(2-hydroxypropan-2-yl)thiophene-2-sulfonimidamide | ChiralPak ID, 2 * 25 cm, 5 um | 20% EtOH in Hex (0.1% DEA) | 418.1 (M − 1) |
| 206 | 176a or 176b | 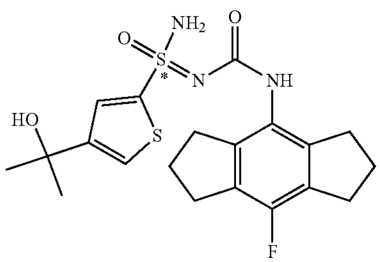 [SMILES: CC(C)(O)c1csc(S(N)(=O)=NC(=O)Nc2c3c(c(F)c4c2CCC4)CCC3)c1] | (S)-or (R)-N'-(8-fluoro-1,2,3,5,6,7-hexa-hydro-s-indacen-4-ylcarbamoyl)-4-(2-hydroxypropan-2-yl)thiophene-2-sulfonimidamide | ChiralPak IG, 2 * 25 cm, 5 um | 30% EtOH in Hex | 438.2 |
| 207 | 176b or 176a | 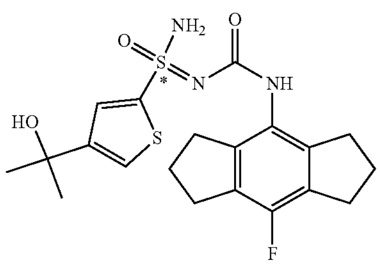 [SMILES: CC(C)(O)c1csc(S(N)(=O)=NC(=O)Nc2c3c(c(F)c4c2CCC4)CCC3)c1] | (R)-or (S)-N'-(8-fluoro-1,2,3,5,6,7-hexa-hydro-s-indacen-4-ylcarbamoyl)-4-(2-hydroxypropan-2-yl)thiophene-2-sulfonimidamide | ChiralPak IG, 2 * 25 cm, 5 um | 30% EtOH in Hex | 438.2 |

Example 77: MS-ESI: 421.1 (M+1). $^1$H NMR (400 MHz, DMSO-d$_6$) δ 8.41 (br s, 1H), 7.74 (br s, 2H), 7.68 (s, 1H), 6.87 (s, 1H), 5.36 (s, 1H), 3.02-2.50 (m, 8H), 2.10-1.80 (m, 4H), 1.48 (s, 6H).

Example 200: MS-ESI: 439.2 (M+1). 1H NMR (400 MHz, DMSO-d$_6$) δ 8.38 (br, 1H), 8.02 (s, 1H), 7.75 (br, 1H), 6.27 (s, 1H), 2.81 (t, J=7.6 Hz, 4H), 2.70 (t, J=6.8 Hz, 4H), 2.02-1.95 (m, 4H), 1.50 (s, 6H).

Example 203: MS-ESI: 404.2 (M+1). $^1$H NMR (300 MHz, DMSO-d$_6$) δ 8.42 (br s, 1H), 7.76 (s, 1H), 7.72 (s, 2H), 7.01 (s, 1H), 6.88 (s, 1H), 5.11 (s, 1H), 2.90-2.72 (m, 4H), 2.72-2.60 (m, 4H), 2.10-1.80 (m, 4H), 1.46 (s, 6H).

Example 205: MS-ESI: 418.1 (M−1). $^1$H NMR (400 MHz, DMSO-d$_6$) δ 8.39 (br s, 1H), 7.68 (s, 2H), 7.63 (s, 1H), 7.59 (s, 1H), 6.88 (s, 1H), 5.23 (s, 1H), 2.95-2.75 (m, 4H), 2.75-2.60 (m, 4H), 2.05-1.80 (m, 4H), 1.43 (s, 6H).

Example 206: MS-ESI: 438.2 (M+1). $^1$H NMR (300 MHz, DMSO-d$_6$) δ 8.41 (br s, 1H), 7.65 (s, 2H), 7.59 (s, 1H), 7.55 (s, 1H), 5.20 (s, 1H), 2.90-2.60 (m, 8H), 2.10-1.80 (m, 4H), 1.39 (s, 6H).

Example 208 (Compound 221)

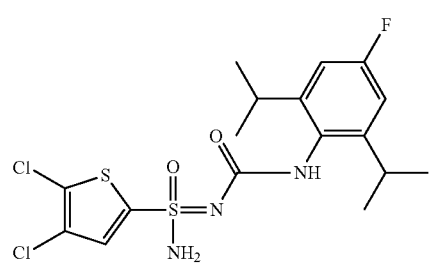 [SMILES: CC(C)c1cc(F)cc(C(C)C)c1NC(=O)N=S(N)(=O)c1cc(Cl)c(Cl)s1]

691

4,5-Dichloro-N'-((4-fluoro-2,6-diisopropylphenyl)carbamoyl)thiophene-2-sulfonimidamide

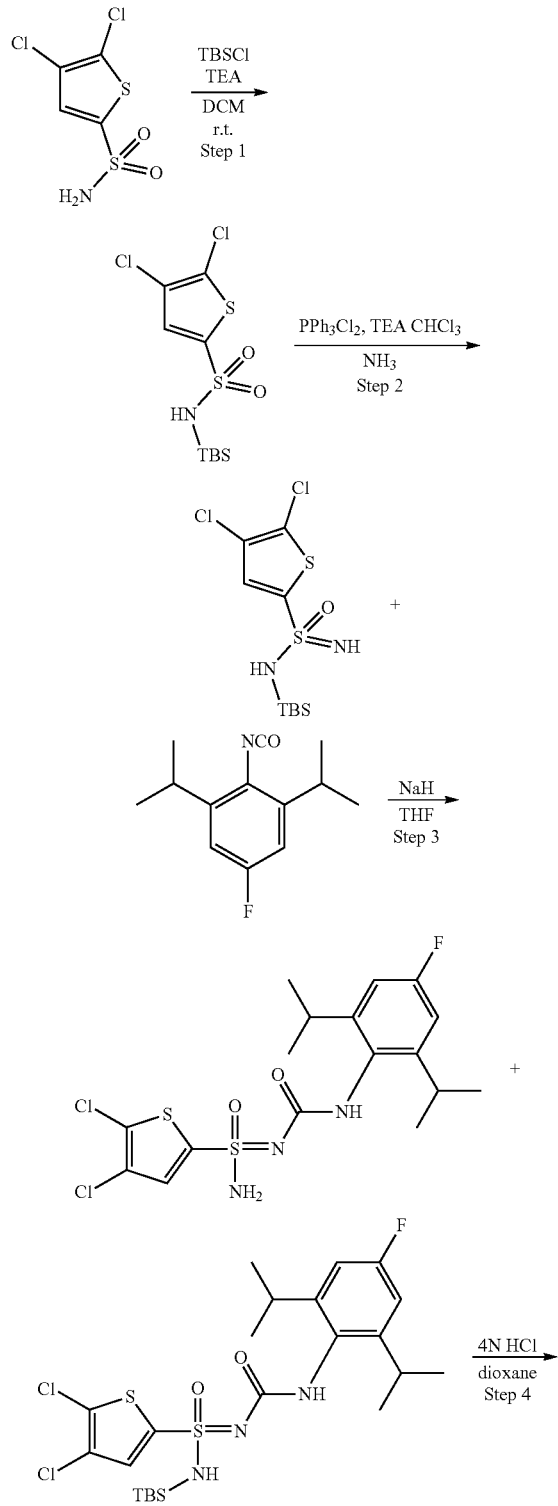

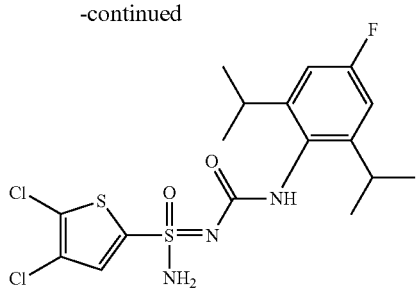

Step 1: N-(tert-butyldimethylsilyl)-4,5-dichlorothiophene-2-sulfonamide 4,5-Dichlorothiophene-2-sulfonamide (50 mg, 0.22 mmol) was dissolved in anhydrous $CH_2Cl_2$ (2 mL). Triethylamine (0.090 mL, 0.65 mmol) and TBSCl (38 mg, 0.25 mmol) were added and the resulting mixture was stirred overnight at room temperature, or until the reaction was complete as indicated by LCMS (Method F: m/Z=424.1 $[M+DMSO+H]^+$, retention time=3.70 min). The reaction mixture was used in the next step as is.

Step 2: N-(tert-butyldimethylsilyl)-4,5-dichlorothiophene-2-sulfonimidamide

In an oven-dried vial under nitrogen, a solution of $PPh_3Cl_2$ (143 mg, 0.44 mmol) was prepared in dichloroethane (1.5 mL). Triethylamine (0.120 mL, 0.86 mmol) was introduced in a steady stream via syringe at 0° C. The reaction mixture was stirred at room temperature for 10 min. The reaction mixture was then cooled in an ice/water bath for 2 min and the reaction mixture of TBS protected sulfonamide (prepared in 2 mL DCM) from step 1 was introduced via syringe rapidly drop by drop (addition time <30 seconds). The resulting mixture was stirred at 0° C. for 30 min, at which time anhydrous ammonia was bubbled into the reaction mixture for 45 seconds. The suspension thus formed was stirred in an ice/water bath for 30 min and then warmed to room temperature and centrifuged to remove solids. The supernatant was concentrated in vacuo and dried under high vacuum for 30 min.

Step 3: 4,5-Dichloro-N'-((4-fluoro-2,6-diisopropylphenyl)carbamoyl)thiophene-2-sulfonimidamide and N-(tert-butyldimethylsilyl)-4,5-dichloro-N'-((4-fluoro-2,6-diisopropyl phenyl)carbamoyl)thiophene-2-sulfonimidamide To the crude reaction mixture from step 2 was added anhydrous THF (1.5 mL) and the resulting solution was stirred in an ice/water bath for 5 min, at which time NaH (17 mg, 0.44 mmol) was added. After 2 min stirring, a solution of 5-fluoro-2-isocyanato-1,3-diisopropylbenzene (36.5 mg, 0.165 mmol) in THF (3 ml) was added dropwise at 0° C. The resulting mixture was brought to room temperature and stirred for 30 min to give a mixture of crude products. LC-MS (Method F): m/Z=451.8 $[M+H]^+$, retention time=6.18 mi; for TBS-protected product, 566.4 [M+H]M, retention time=9.25 min.

Step 4: 4,5-Dichloro-N'-((4-fluoro-2,6-diisopropylphenyl)carbamoyl)thiophene-2-sulfonimidamide To the reaction mixture from step 3 was carefully added 4N HCl in dioxane (0.3 mL) and the resulting mixture was stirred at room temperature for approximately 30 min until the completion of reaction, as determined by LCMS analysis (Method F: 451.8 $[M+H]^+$, retention time=6.18 min). The reaction mixture was then concentrated in vacuo. DM50 (0.5 mL) was added to the residue and the resulting solution was purified on a prep-HPLC to afford the title compound. LC-MS: 451 $[M+H]+$.

TABLE 20

Examples in the following table were prepared using similar procedures as described in Example 208 above starting from appropriate sulfonamides.

| Example # | Final Target Number | Structure | IUPAC Name | Exact Mass [M + H]+ |
|---|---|---|---|---|
| 209 | 219 | 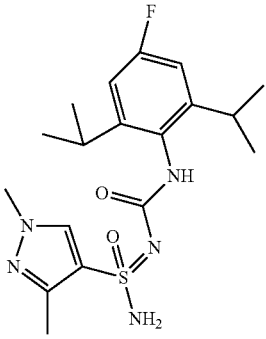 [SMILES: Cc1nn(C)cc1S(N)(=O)=NC(=O)Nc1c(C(C)C)cc(F)cc1C(C)C] | N'-((4-fluoro-2,6-diisopropylphenyl)carbamoyl)-1,3-dimethyl-1H-pyrazole-4-sulfonimidamide | 396.05 |
| 210 | 217 | 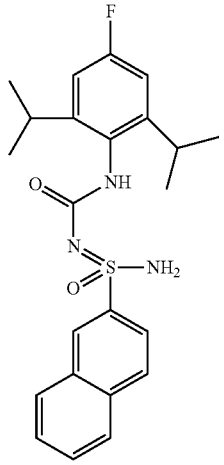 [SMILES: CC(C)c1cc(F)cc(C(C)C)c1NC(=O)N=S(N)(=O)c1ccc2ccccc2c1] | N'-((4-fluoro-2,6-diisopropylphenyl)carbamoyl)naphthalene-2-sulfonimidamide | 428.17 |
| 211 | 216 | 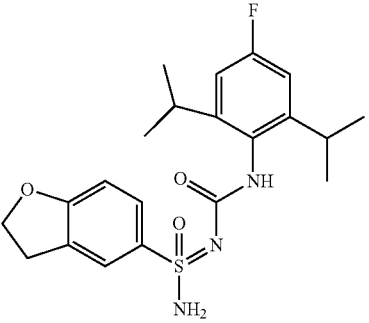 [SMILES: CC(C)c1cc(F)cc(C(C)C)c1NC(=O)N=S(N)(=O)c1ccc2c(c1)CCO2] | N'-((4-fluoro-2,6-diisopropylphenyl)carbamoyl)-2,3-dihydrobenzofuran-5-sulfonimidamide | 420.07 |

TABLE 20-continued

Examples in the following table were prepared using similar procedures as described in Example 208 above starting from appropriate sulfonamides.

| Example # | Final Target Number | Structure | IUPAC Name | Exact Mass [M + H]+ |
|---|---|---|---|---|
| 212 | 215 | 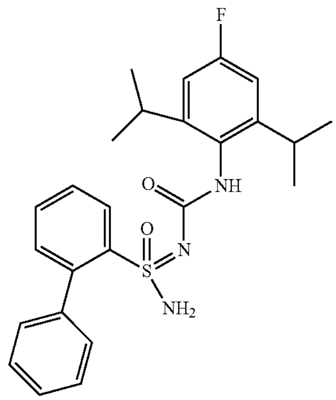 [SMILES: CC(C)c1cc(F)cc(C(C)C)c1NC(=O)N=S(N)(=O)c1ccccc1-c1ccccc1] | N'-((4-fluoro-2,6-diisopropylphenyl)carbamoyl)-[1,1'-biphenyl]-2-sulfonimidamide | 454.28 |
| 213 | 218 | 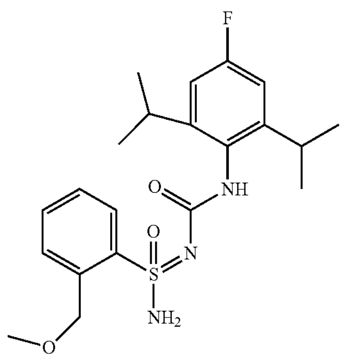 [SMILES: COCc1ccccc1S(N)(=O)=NC(=O)Nc1c(C(C)C)cc(F)cc1C(C)C] | N'-((4-fluoro-2,6-diisopropylphenyl)carbamoyl)-2-(methoxymethyl)benzenesulfonimidamide | 422.17 |
| 214 | 214 | 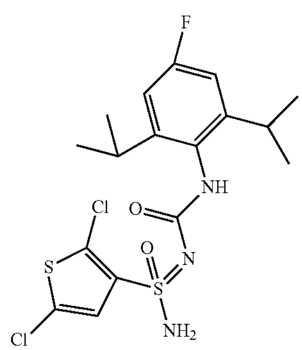 [SMILES: CC(C)c1cc(F)cc(C(C)C)c1NC(=O)N=S(N)(=O)c1cc(Cl)sc1Cl] | 2,5-dichloro-N'-((4-fluoro-2,6-diisopropylphenyl)carbamoyl)thiophene-3-sulfonimidamide | 452.18 |
| 215 | 211 | 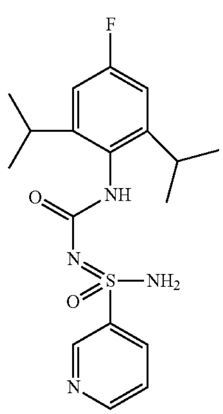 [SMILES: CC(C)c1cc(F)cc(C(C)C)c1NC(=O)N=S(N)(=O)c1cccnc1] | N'-((4-fluoro-2,6-diisopropylphenyl)carbamoyl)pyridine-3-sulfonimidamide | 379.24 |

TABLE 20-continued

Examples in the following table were prepared using similar procedures as described in Example 208 above starting from appropriate sulfonamides.

| Example # | Final Target Number | Structure | IUPAC Name | Exact Mass [M + H]+ |
|---|---|---|---|---|
| 216 | 210 | 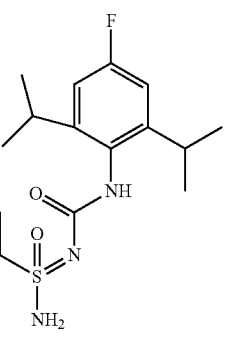 | N'-((4-fluoro-2,6-diisopropylphenyl)carbamoyl)benzo[d][1,3]dioxole-5-sulfonimidamide | 422.17 |
| 217 | 201 | 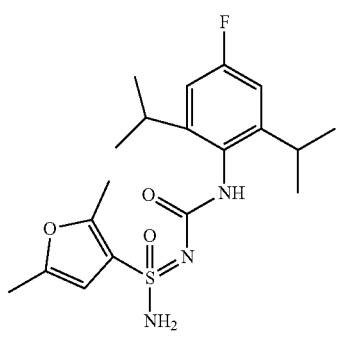 [SMILES: Cc1cc(S(N)(=O)=NC(=O)Nc2c(C(C)C)cc(F)cc2C(C)C)c(C)o1] | N'-((4-fluoro-2,6-diisopropylphenyl)carbamoyl)-2,5-dimethylfuran-3-sulfonimidamide | 396.40 |
| 218 | 200 | 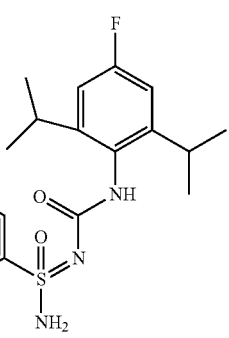 | N'-((4-fluoro-2,6-diisopropylphenyl)carbamoyl)quinoline-3-sulfonimidamide | 429.40 |
| 219 | 199 | 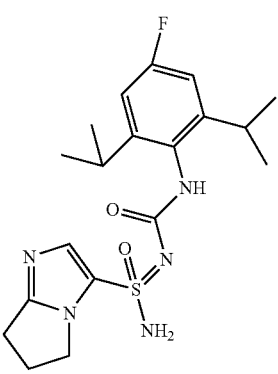 [SMILES: CC(C)c1cc(F)cc(C(C)C)c1NC(=O)N=S(N)(=O)c1cnc2n1CCC2] | N'-((4-fluoro-2,6-diisopropylphenyl)carbamoyl)-6,7-dihydro-5H-pyrrolo[1,2-a]imidazole-3-sulfonimidamide | 408.40 |

TABLE 20-continued

Examples in the following table were prepared using similar procedures as described in Example 208 above starting from appropriate sulfonamides.

| Example # | Final Target Number | Structure | IUPAC Name | Exact Mass [M + H]+ |
|---|---|---|---|---|
| 220 | 198 | 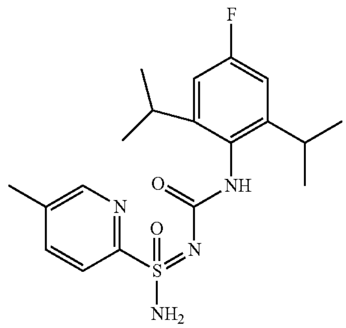 [SMILES: Cc1ccc(S(N)(=O)=NC(=O)Nc2c(C(C)C)cc(F)cc2C(C)C)nc1] | N'-((4-fluoro-2,6-diisopropylphenyl)carbamoyl)-5-methylpyridine-2-sulfonimidamide | 393.40 |

Example 221 (Compound 141)

N'-((1,2,3,5,6,7-hexahydrodicyclopenta[b,e]pyridin-8-yl)carbamoyl)-4-(2-hydroxypropan-2-yl)-5-methylfuran-2-sulfonimidamide (Scheme 31)

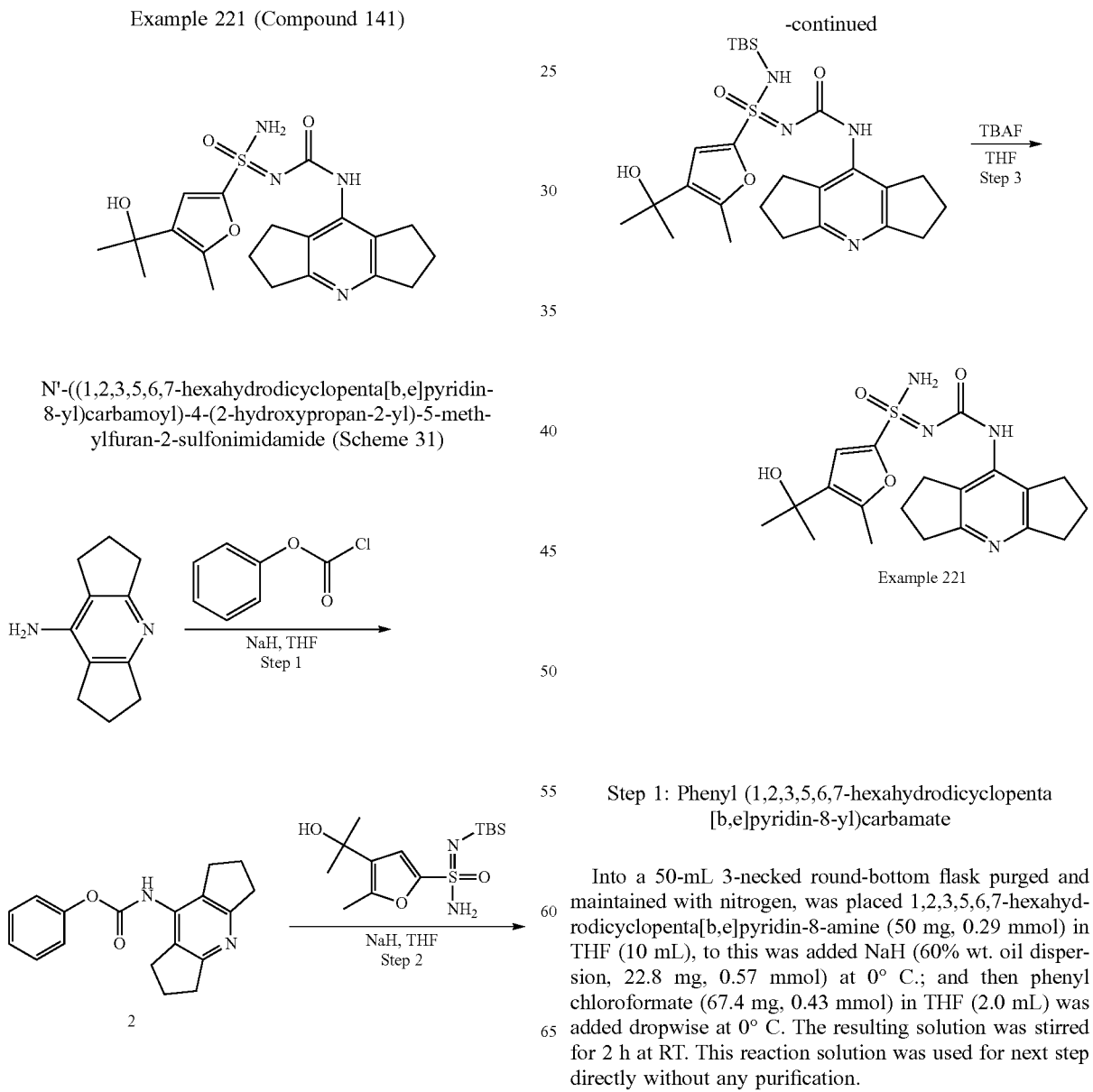

Step 1: Phenyl (1,2,3,5,6,7-hexahydrodicyclopenta[b,e]pyridin-8-yl)carbamate

Into a 50-mL 3-necked round-bottom flask purged and maintained with nitrogen, was placed 1,2,3,5,6,7-hexahydrodicyclopenta[b,e]pyridin-8-amine (50 mg, 0.29 mmol) in THF (10 mL), to this was added NaH (60% wt. oil dispersion, 22.8 mg, 0.57 mmol) at 0° C.; and then phenyl chloroformate (67.4 mg, 0.43 mmol) in THF (2.0 mL) was added dropwise at 0° C. The resulting solution was stirred for 2 h at RT. This reaction solution was used for next step directly without any purification.

Step 2: N-(tert-butyldimethylsilyl)-N'-((1,2,3,5,6,7-hexahydrodicyclopenta[b,e]pyridin-8-yl)carbamoyl)-4-(2-hydroxypropan-2-yl)-5-methylfuran-2-sulfonimidamide Into a 50-mL 3-necked round-bottom flask purged and maintained with nitrogen, was placed N-(tert-butyldimethylsilyl)-4-(2-hydroxypropan-2-yl)-5-methylfuran-2-sulfonoimidamide (96 mg, 0.29 mmol) in THF (10 mL). To this was added NaH (60% wt. oil dispersion, 23.2 mg, 0.58 mmol) at 0° C., followed by phenyl (1,2,3,5,6,7-hexahydrodicyclopenta[b,e]pyridin-8-yl)carbamate (127 mg, 0.43 mmol) crude in THF from via syringe rapidly drop by drop. The resulting mixture was stirred for 16 h at RT. The reaction was then quenched by the addition of 5.0 mL of water. The resulting solution was extracted with 4×10 ml of ethyl acetate. The combined organic layers were dried over anhydrous sodium sulfate and concentrated under vacuum. The residue was eluted from a silica gel column with ethyl acetate/petroleum ether (1;1). This resulted in 50 mg (38.4%) of the title compound as an off-white solid. MS-ESI: 533 (M+1).

Step 3: N'-((1,2,3,5,6,7-hexahydrodicyclopenta[b,e]pyridin-8-yl)carbamoyl)-4-(2-hydroxypropan-2-yl)-5-methylfuran-2-sulfonimidamide Into a 50-mL round-bottom flask, was placed N-(tert-butyldimethylsilyl)-N'-((1,2,3,5,6,7-hexahydrodicyclopenta[b,e]pyridin-8-yl)carbamoyl)-4-(2-hydroxypropan-2-yl)-5-methylfuran-2-sulfonimidamide (58 mg, 0.11 mmol) in THF (10 mL), to this was added TBAF (28.8 mg, 0.11 mmol). The resulting solution was stirred for 1 h at RT. The resulting mixture was concentrated under vacuum. The residue was eluted from a silica gel column with DCM/MeOH (10:1). The crude product was further purified by Prep-HPLC with the following conditions: Column: XBridge Prep OBD C18 Column 19*250 mm, 5 um; Mobile Phase A: water (10 mM $NH_4HCO_3$), Mobile Phase B: ACN; Flow rate: 25 mL/min; Gradient: 11% B to 40% B in 7 min; UV 254/210 nm; Rt: 6 min. This resulted in 25 mg (54.87%) of Example 221 as a white solid. MS-ESI: 419 (M+1). $^1$H NMR (400 MHz, DMSO-$d_6$, ppm) δ: 8.82 (s, 1H), 7.65 (s, 2H), 6.90 (s, 1H), 5.03 (s, 1H), 2.82-2.78 (m, 4H), 2.76-2.67 (m, 4H), 2.41 (s, 3H), 2.00-1.92 (m, 4H), 1.39 (s, 6H).

Example 223 (Compound 321)

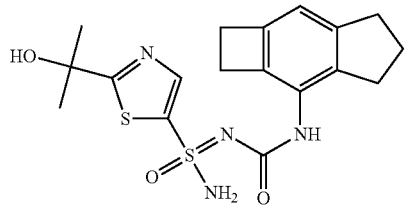 [SMILES: CC(C)(O)c1ncc(S(N)(=O)=NC(=O)Nc2c3c(cc4c2CC4)CCC3)s1]

2-(2-Hydroxypropan-2-yl)-N'-((2,4,5,6-tetrahydro-1H-cyclobuta[f]inden-3-yl)carbamoyl)thiazole-5-sulfonimidamide (Scheme 3A)

Examples 224 and 225 (Compound 321b and 321a)

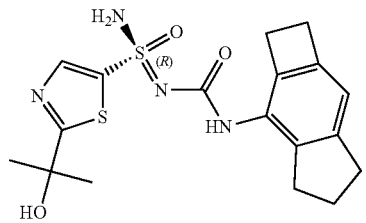

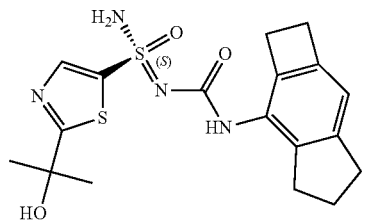

Examples 224 and 225 (stereochemistry tentatively assigned)

TABLE 21

Examples in the following table were prepared using similar conditions as described in Example 221 and Scheme 31 from appropriate starting materials.

| Example # | Final Target Number | Structure | IUPAC Name | Exact Mass [M + H]$^+$ |
|---|---|---|---|---|
| 222 | 140 | 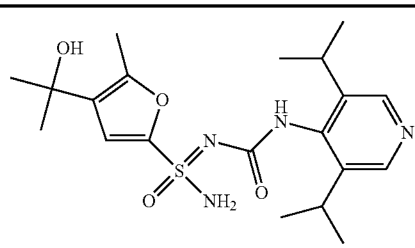 | N'-((3,5-diisopropylpyridin-4-yl)carbamoyl)-4-(2-hydroxypropan-2-yl)-5-methylfuran-2-sulfonimidamide | 423 |

(R)- and (S)-2-(2-hydroxypropan-2-yl)-N'-((2,4,5,6-tetrahydro-1H-cyclobuta[f]inden-3-yl)carbamoyl)thiazole-5-sulfonimidamide Route 1:

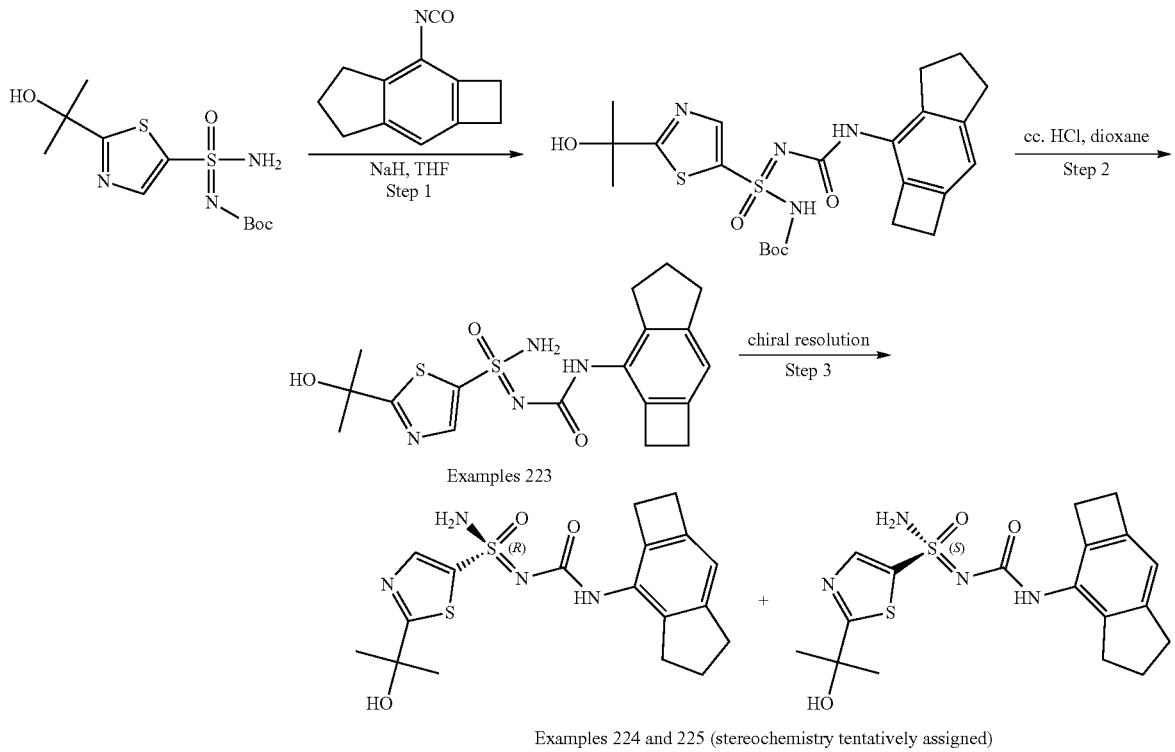

Examples 224 and 225 (stereochemistry tentatively assigned)

Step 1: Tert-butyl(2-(2-hydroxypropan-2-yl)-N-((2,4,5,6-tetrahydro-1H-cyclobuta[f]inden-3-yl)carbamoyl)thiazole-5-sulfonimidoyl)carbamate Into a 100-mL round-bottom flask purged and maintained with an inert atmosphere of nitrogen, was placed tert-butyl N-[amino[2-(2-hydroxypropan-2-yl)-1,3-thiazol-5-yl]oxo-λ⁶-sulfanylidene]carbamate (1.39 g, 4.32 mmol) in THF (50 mL). To this solution was added NaH (60% wt. oil dispersion, 518 mg, 13 mmol) at 0° C., followed by the addition of 3-isocyanato-2,4,5,6-tetrahydro-1H-cyclobuta[f]indene (800 mg, 4.32 mmol) in THF (5.0 mL) dropwise at 0° C. The resulting solution was stirred for 14 h at RT. The reaction was then quenched by the addition of 100 mL of water. The resulting solution was extracted with 3×50 mL of DCM. The organic layers combined and dried over anhydrous $Na_2SO_4$, then concentrated. The residue was eluted from a silica gel column with ethyl acetate/petroleum ether (1:5 to 1:1). This resulted in 2.0 g (91%) of title compound as a light yellow solid. MS-ESI: 507 (M+1).

Step 2: 2-(2-Hydroxypropan-2-yl)-N'-((2,4,5,6-tetrahydro-1H-cyclobuta[f]inden-3-yl)carbamoyl)thiazole-5-sulfonimidamide Into a 100-mL round-bottom flask purged and maintained with an inert atmosphere of nitrogen, was placed tert-butyl (2-(2-hydroxypropan-2-yl)-N-((2,4,5,6-tetrahydro-1H-cyclobuta[f]inden-3-yl)carbamoyl) thiazole-5-sulfonimidoyl) carbamate (2.2 g, 4.34 mmol) in dioxane (40 mL). To this was added conc. HCl (8 mL, 12 M) dropwise at 0° C. The resulting solution was stirred for 14 h at RT. The resulting solution was diluted with 100 mL of water. The resulting solution was extracted with 3×50 mL of DCM. The organic layers combined and dried over anhydrous $Na_2SO_4$, then concentrated. The crude product was purified by HP-Flash with the following conditions: Column, C18 silica gel; mobile phase, $ACN:H_2O$=25:75 increasing to $ACN:H_2O$=55:45 within 25; Detector, UV 254 nm. This resulted in 1.5 g (85%) of Example 223. MS-ESI: 407 (M+1). $^1$H NMR (300 MHz, DMSO-$d_6$) δ 8.35 (s, 1H), 8.05 (s, 1H), 7.74 (s, 2H), 6.66 (s, 1H), 6.25 (s, 1H), 3.06-2.94 (m, 2H), 2.93-2.84 (m, 2H), 2.82-2.60 (m, 4H), 2.03-1.79 (m, 2H), 1.50 (s, 6H).

Step 3: Chiral Resolution

Example 223 (1.5 g) was separated with the followed condition: Column: CHIRALPAK IG, 20*250 mm, 5 um; Mobile Phase A: $CO_2$:60, Mobile Phase B: MeOH—Preparative:40; Flow rate: 50 mL/min; 220 nm. The resulting solution was stirred for 20 min at 10° C. This resulted in 546 mg (99% ee, 36.4%) of Example 224 ($RT_1$: 3.47 min) as a white solid and 595 mg (99% ee, 39.6%) of Example 225 ($RT_2$: 5.35 min) as a white solid. The absolute stereochemistry was tentatively assigned.

Example 224: MS-ESI: 407.1 (M+1). $^1$H NMR (300 MHz, DMSO-$d_6$) δ 8.35 (s, 1H), 8.05 (s, 1H), 7.74 (s, 2H), 6.66 (s, 1H), 6.25 (s, 1H), 3.06-2.94 (m, 2H), 2.93-2.84 (m, 2H), 2.82-2.60 (m, 4H), 2.03-1.79 (m, 2H), 1.50 (s, 6H).

Example 225: MS-ESI: 407.1 (M+1). $^1$H NMR (300 MHz, DMSO-$d_6$) δ 8.35 (s, 1H), 8.05 (s, 1H), 7.74 (s, 2H), 6.66 (s, 1H), 6.25 (s, 1H), 3.06-2.94 (m, 2H), 2.93-2.84 (m, 2H), 2.82-2.60 (m, 4H), 2.03-1.79 (m, 2H), 1.50 (s, 6H).

Route 2:

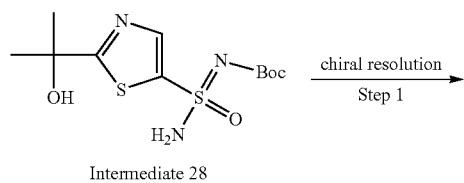

Intermediate 28

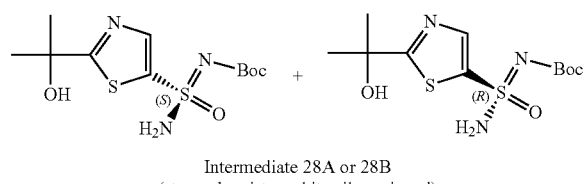

Intermediate 28A or 28B
(stereochemistry arbitrarily assigned)

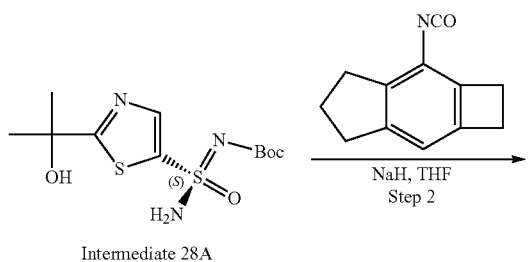

Intermediate 28A

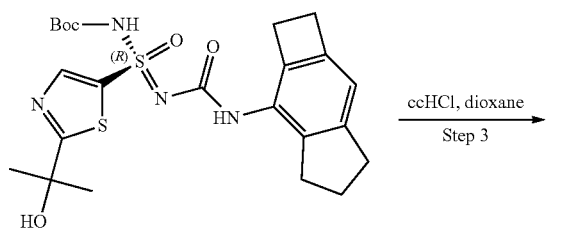

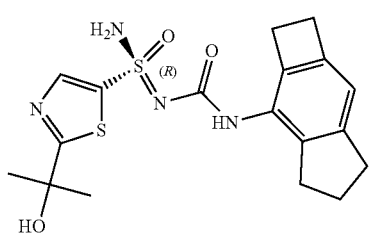

Example 224

Step 1: Chiral Resolution (R) and (S)-tert-butyl (amino(2-(2-hydroxypropan-2-yl)thiazol-5-yl)(oxo)-$\lambda^6$-sulfaneylidene)carbamate The product 10 g of Intermediate 28 was separated with the followed condition: Column: CHIRALPAK IC, 5*25 cm, 5 um; Mobile Phase A: $CO_2$:55, Mobile Phase B: EtOH:HeX=1:1:45; Flow rate: 150 mL/min; UV 220 nm; $Rt_1$: 5.13 (Intermediate 28A); $Rt_2$: 5.65 (Intermediate 28B). This resulted in 3 g (99.5% ee, 60%) of 28A, and 3 g (99.0% ee, 60%) of 28B.

Step 2: Tert-butyl (R)-(2-(2-hydroxypropan-2-yl)-N-((2,4,5,6-tetrahydro-1H-cyclobuta[f]inden-3-yl) carbamoyl)thiazole-5-sulfonimidoyl)carbamate Into a 100-mL round-bottom flask purged and maintained with an inert atmosphere of nitrogen, was placed intermediate 28A (>99% ee, 1.67 g, 5.20 mmol) in THF (50 mL), NaH (60% wt. oil dispersion, 624 mg, 15.6 mmol) was added at 0° C., this was followed by the addition of 3-isocyanato-2,4,5,6-tetrahydro-1H-cyclobuta[f]indene (850 mg, crude) in THF (5 mL) dropwise at 0° C. The resulting solution was stirred for 14 h at RT. The reaction was then quenched by the addition of 100 mL of water. The resulting solution was extracted with 3×100 mL of DCM. The organic layers combined and dried over anhydrous $Na_2SO_4$, then concentrated. This resulted in 2.2 g (83.5%) of title compound as a light yellow solid. MS-ESI: 507 (M+1).

Step 3: (R)-2-(2-hydroxypropan-2-yl)-N'-((2,4,5,6-tetrahydro-1H-cyclobuta[f]inden-3-yl)carbamoyl) thiazole-5-sulfonimidamide Into a 100-mL round-bottom flask purged and maintained with an inert atmosphere of nitrogen, was placed tert-butyl (S)-(2-(2-hydroxypropan-2-yl)-N-((2,4,5,6-tetrahydro-1H-cyclobuta[f]inden-3-yl)carbamoyl) thiazole-5-sulfonimidoyl)carbamate (2.2 g, 4.34 mmol) in dioxane (40 mL), to this was added conc. HCl (8 mL, 12M) dropwise at 0° C. The resulting solution was stirred for 8 h below 10° C. The resulting solution was diluted with 100 mL of water. The resulting solution was extracted with 3×100 mL of DCM. The organic layers combined and dried over anhydrous $Na_2SO_4$, then concentrated. The crude product was purified by HP-Flash with the following conditions: Column, C18 silica gel; mobile phase, MeCN:water=25:75 increasing to MeCN:water=55:45 within 30 min; Detector, UV 210 nm. This resulted in 1.37 g (77.3%) of Example 224 (99.4% ee) as a white solid. MS-ESI: 407 (M+1).

$^1$H NMR (300 MHz, DMSO-$d_6$) δ 8.43 (s, 1H), 8.09 (s, 1H), 7.90 (s, 2H), 6.67 (s, 1H), 6.29 (s, 1H), 2.92 (d, J=3.9 Hz, 2H), 2.89 (d, J=3.9 Hz, 2H), 2.90-2.55 (m, 4H), 2.00-1.75 (m, 6H), 1.50 (s, 6H).

TABLE 22

Examples in the following table were prepared using similar conditions as described in
Example 223-Route 1 and Scheme 3A from appropriate starting materials.

| Example # | Final Target # | Structure | IUPAC Name | Exact Mass [M + H]+ |
|---|---|---|---|---|
| 226 | 329 | 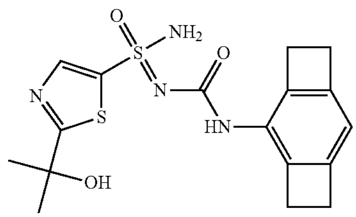 [SMILES: CC(C)(O)c1ncc(S(N)(=O)=NC(=O)Nc2c3c(cc4c2CC4)CC3)s1] | 2-(2-Hydroxypropan-2-yl)-N'-(tricyclo[6.2.0.0³,⁶]deca-1,3(6),7-trien-2-ylcarbamoyl)thiazole-5-sulfonimidamide | 393 |
| 227 | 375 | 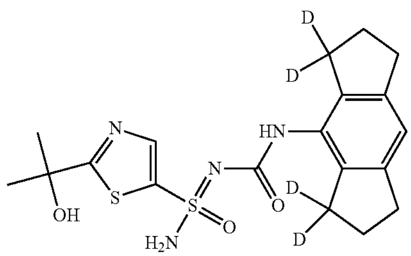 [SMILES: [2H]C1([2H])CCc2cc3c(c(NC(=O)N=S(N)(=O)c4cnc(C(C)(C)O)s4)c21)C([2H])([2H])CC3] | N'-((1,2,3,5,6,7-hexahydro-s-indacen-4-yl-3,3,5,5-d₄)carbamoyl)-2-(2-hydroxypropan-2-yl)thiazole-5-sulfonimidamide | 425 |
| 228 | 376 | 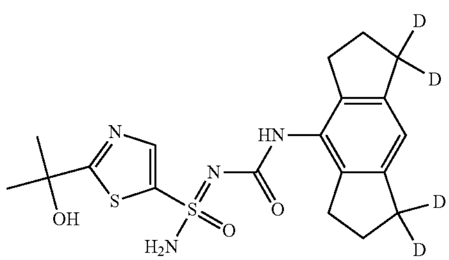 [SMILES: [2H]C1([2H])CCc2c1cc1c(c2NC(=O)N=S(N)(=O)c2cnc(C(C)(C)O)s2)CCC1([2H])[2H]] | N'-((1,2,3,5,6,7-hexahydro-s-indacen-4-yl-1,1,7,7-d₄)carbamoyl)-2-(2-hydroxypropan-2-yl)thiazole-5-sulfonimidamide | 425 |

Example 229 (Compound 307)

2-Fluoro-N'-((8-fluoro-1,2,3,5,6,7-hexahydro-s-indacen-4-yl)carbamoyl)-4-hydroxybenzenesulfonimidamide (Scheme 3B)

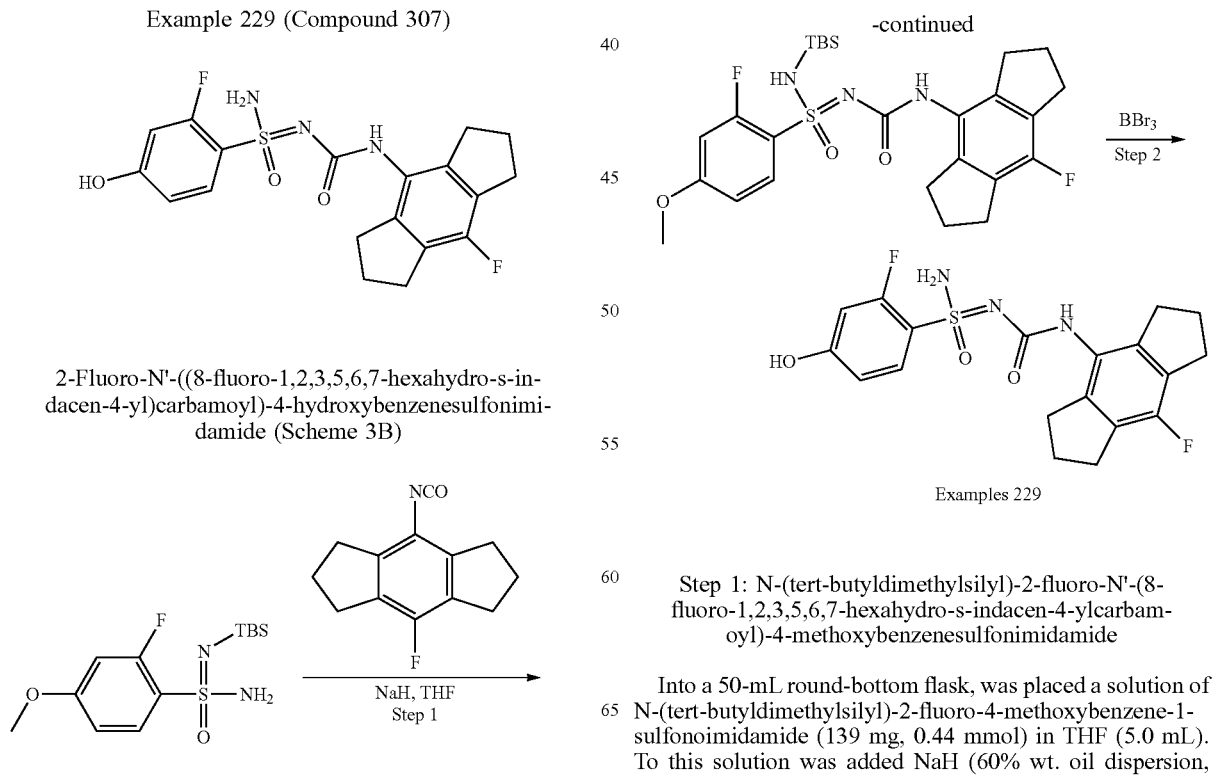

Examples 229

Step 1: N-(tert-butyldimethylsilyl)-2-fluoro-N'-(8-fluoro-1,2,3,5,6,7-hexahydro-s-indacen-4-ylcarbamoyl)-4-methoxybenzenesulfonimidamide Into a 50-mL round-bottom flask, was placed a solution of N-(tert-butyldimethylsilyl)-2-fluoro-4-methoxybenzene-1-sulfonoimidamide (139 mg, 0.44 mmol) in THF (5.0 mL). To this solution was added NaH (60% wt. oil dispersion, 35.2 mg, 0.44 mmol) at 0° C. This was followed by the addition of 4-fluoro-8-isocyanato-1,2,3,5,6,7-hexahydro-s-indacene (95 mg, 0.44 mmol) in THF (5 mL) dropwise at RT. The resulting solution was stirred for 1 h at RT. The reaction was then quenched by the addition of 100 mL of water. The resulting solution was extracted with 3×50 mL of ethyl acetate. The organic layers combined and dried over anhydrous Na₂SO₄, and then concentrated. The residue was eluted from a silica gel column with ethyl acetate/petroleum ether (1:5 to 1:1). This resulted in 120 mg (51.2%) of the title compound as yellow oil. MS-ESI: 536 (M+1).

Step 2: 2-Fluoro-N'-(8-fluoro-1,2,3,5,6,7-hexahydro-s-indacen-4-ylcarbamoyl)-4-hydroxybenzenesulfonimidamide Into a 50-mL round-bottom flask, was placed a solution of 1-[[(tert-butyldimethylsilyl)imino](2-fluoro-4-methoxybenzene)sulfinyl]-3-(8-fluoro-1,2,3,5,6,7-hexahydro-s-indacen-4-yl)urea (120 mg, 0.22 mmol) in ACN (5.0 mL), to this solution was added BBr₃ (561 mg, 2.24 mmol) dropwise at 0° C. The resulting solution was stirred for 2 h at RT. The reaction was then quenched by the addition of 5 mL of MeOH. The resulting mixture was concentrated. The crude product (100 mg) was purified by Prep-HPLC under the following conditions: Column, XBridge Prep OBD C18, 19*250 mm, 5 um; mobile phase: water (10 mM NH₄HCO₃) and ACN (25% to 43% ACN gradient in 7 min); Detector, UV. This resulted in 17.7 mg (19.4%) of Example 229 as a white solid. MS-ESI: 408 (M+1).

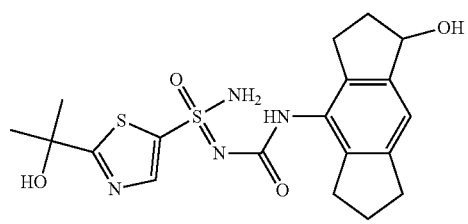

Examples 230

Into a 50-mL round-bottom flask, was placed 2-(2-hydroxypropan-2-yl)-N'-((1-oxo-1,2,3,5,6,7-hexahydro-s-indacen-4-yl)carbamoyl)thiazole-5-sulfonimidamide (100 mg, 0.23 mmol) in ethanol (10 mL). To this solution was added NaBH₄ (17.4 mg, 0.46 mmol) in portions at 0° C. The resulting solution was stirred for 2 h at RT. The crude product (5 mL) was purified by Flash-Prep-HPLC with the following conditions: Column: XBridge Prep OBD C18 Column 30×150 mm 5 um; Mobile Phase A: water (10 mM NH₄HCO₃), Mobile Phase B: ACN; Flow rate: 60 mL/min; Gradient: 10% to 28% B in 7 min; 210/254 nm; Rt: 6.00 min. This resulted in 180 mg of the title compound (Example 230) as a solid. MS-ESI: 437.1 (M+1).

¹H NMR (400 MHz, DMSO-d₆) δ 8.51 (br s, 1H), 8.04 (s, 1H), 7.82 (br s, 2H), 6.97 (s, 1H), 6.28 (s, 1H), 5.07 (d, J=5.6 Hz, 1H), 5.05-4.85 (m, 1H), 2.95-2.75 (m, 2H), 2.75-50 (m, 4H), 2.35-2.15 (m, 1H), 2.00-1.80 (m, 2H), 1.80-1.60 (m, 1H), 1.51 (s, 6H).

Example 230 (Compound 323)

Example 231 (Compound 338)

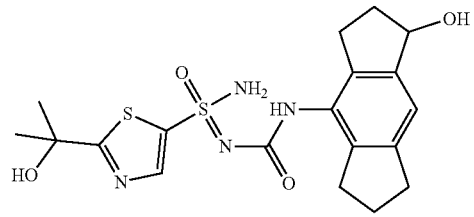 [SMILES: CC(C)(O)c1ncc(S(N)(=O)=NC(=O)Nc2c3c(cc4c2CCC4O)CCC3)s1]

N'-((1-hydroxy-1,2,3,5,6,7-hexahydro-s-indacen-4-yl)carbamoyl)-2-(2-hydroxypropan-2-yl)thiazole-5-sulfonimidamide (Scheme 32)

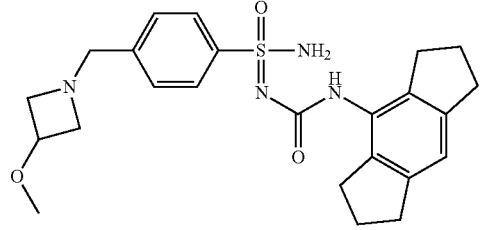 [SMILES: COC1CN(Cc2ccc(S(N)(=O)=NC(=O)Nc3c4c(cc5c3CCC5)CCC4)cc2)C1]

N'-((1,2,3,5,6,7-hexahydro-s-indacen-4-yl)carbamoyl)-4-((3-methoxyazetidin-1-yl)methyl)benzenesulfonimidamide (Scheme 33A)

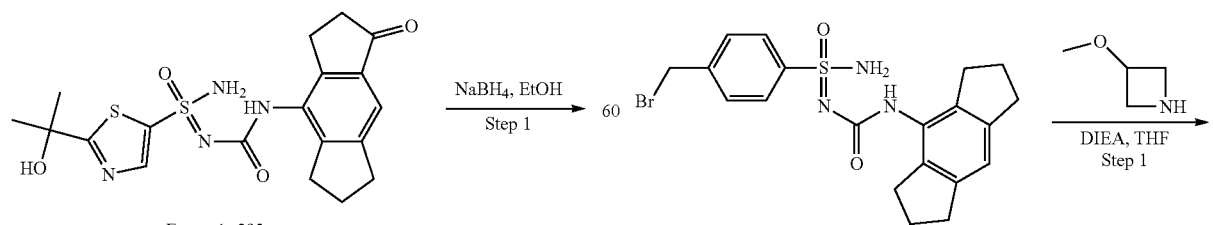

-continued

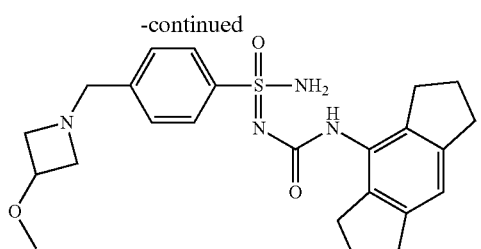

Example 231

Into a 50-mL round-bottom flask purged and maintained with an inert atmosphere of nitrogen, was placed 1-[amino [4-(bromomethyl)phenyl]oxo-λ⁶-sulfanylidene]-3-(1,2,3,5, 6,7-hexahydro-s-indacen-4-yl)urea (50 mg, 0.11 mmol) in THF (5 mL). To this solution was added DIEA (28.4 mg, 0.22 mmol) and 3-methoxyazetidine (10.5 mg, 0.12 mmol) at RT. The resulting solution was stirred for 1 h at 65° C. The resulting mixture was concentrated. The crude product was purified by Prep-HPLC with the following conditions: Column: XBridge Prep C18 OBD Column 19×100 mm 5 um 13 nm; Mobile Phase A: water (10 mM NH₄HCO₃ mM+0.1% NH₃·H₂O), Mobile Phase B: ACN; Flow rate: 25 mL/min; Gradient: 30% to 37% B in 9.5 min; 254/210 nm; Rt: 9.62 min. This resulted in 5 mg of Example 231 as a white solid. MS-ESI 455 (M+1). ¹H NMR (300 MHz DMSO-d₆) δ: 8.27 (br s, 1H), 7.81 (d, J=8.4 Hz, 2H), 7.45 (d, J=8.4 Hz, 2H), 7.34 (s, 2H), 6.85 (s, 1H), 4.02-3.94 (m, 1H), 3.67 (s, 2H), 3.51-3.46 (m, 2H), 3.14 (s, 3H), 2.95-2.80 (m, 2H), 2.78-2.73 (m, 4H), 2.69-2.63 (m, 4H), 1.96-1.88 (in, 4H).

TABLE 23

Examples in the following table were prepared using similar conditions as described in Example 231 and Scheme 33A from appropriate starting materials.

| Example # | Final Target # | Structure | IUPAC Name | Exact Mass [M + H]⁺ |
|---|---|---|---|---|
| 232 | 341 | 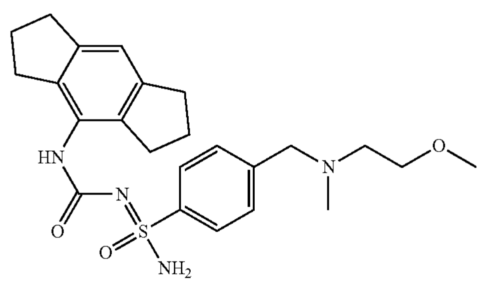 [SMILES: COCCN(C)Cc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-(((2-methoxyethyl)(methyl)amino)methyl)benzenesulfonimidamide | 457 |
| 233 | 342 | 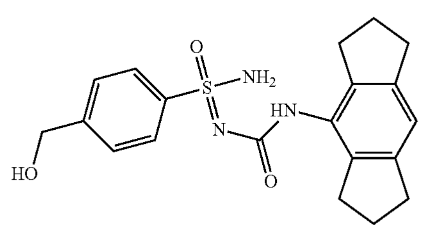 [SMILES: NS(=O)(=NC(=O)Nc1c2c(cc3c1CCC3)CCC2)c1ccc(CO)cc1] | N'-(1,2,3,5,6,7-hexahydro-s-indacen-4-ylcarbamoyl)-4-(hydroxymethyl)benzenesulfonimidamide | 386 |
| 234 | 345 | 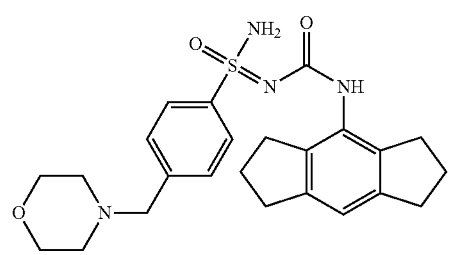 [SMILES: NS(=O)(=NC(=O)Nc1c2c(cc3c1CCC3)CCC2)c1ccc(CN2CCOCC2)cc1] | N'-(1,2,3,5,6,7-hexahydro-s-indacen-4-ylcarbamoyl)-4-(morpholinomethyl)benzenesulfonimidamide | 455 |
| 235 | 346 | 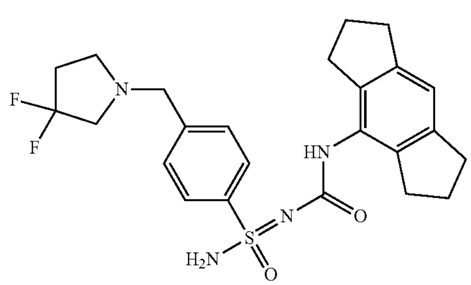 [SMILES: NS(=O)(=NC(=O)Nc1c2c(cc3c1CCC3)CCC2)c1ccc(CN2CCC(F)(F)C2)cc1] | 4-((3,3-Difluoropyrrolidin-1-yl)methyl)-N'-(1,2,3,5,6,7-hexahydro-s-indacen-4-ylcarbamoyl)benzenesulfonimidamide | 475 |

TABLE 23-continued

Examples in the following table were prepared using similar conditions as described in Example 231 and Scheme 33A from appropriate starting materials.

| Example # | Final Target # | Structure | IUPAC Name | Exact Mass [M + H]+ |
|---|---|---|---|---|
| 236 | 347 | 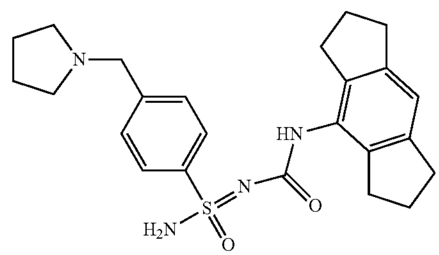 [SMILES: NS(=O)(=NC(=O)Nc1c2c(cc3c1CCC3)CCC2)c1ccc(CN2CCCC2)cc1] | N'-(1,2,3,5,6,7-hexahydro-s-indacen-4-ylcarbamoyl)-4-(pyrrolidin-1-ylmethyl)benzenesulfonimidamide | 439 |
| 237 | 348 | 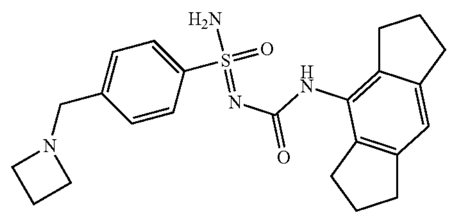 [SMILES: NS(=O)(=NC(=O)Nc1c2c(cc3c1CCC3)CCC2)c1ccc(CN2CCC2)cc1] | 4-(Azetidin-1-ylmethyl)-N'-(1,2,3,5,6,7-hexahydro-s-indacen-4-ylcarbamoyl)benzene-sulfonimidamide | 425 |
| 238 | 403 | 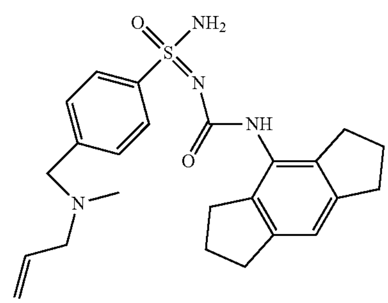 [SMILES: C=CCN(C)Cc1ccc(S(N)(=O)=NC(=O)Nc2c3c(cc4c2CCC4)CCC3)cc1] | 4-((Allyl(methyl)amino)methyl)-N'-(1,2,3,5,6,7-hexahydro-s-indacen-4-ylcarbamoyl)benzene-sulfonimidamide | 439 |
| 239 | 402 | 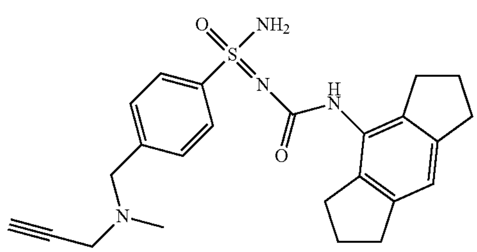 [SMILES: C#CCN(C)Cc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-((methyl(prop-2-ynyl)amino)methyl)benzenesulfonimidamide | 437 |
| 240 | 350 | 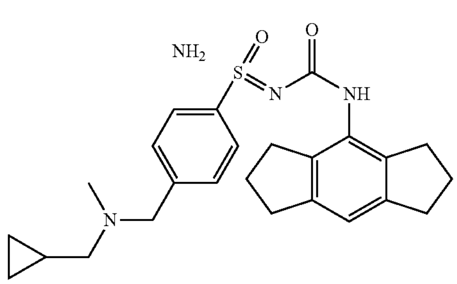 | 4-(((Cyclopropylmethyl)(methyl)amino)methyl)-N'-(1,2,3,5,6,7-hexahydro-s-indacen-4-ylcarbamoyl)benzene-sulfonimidamide | 453 |

TABLE 23-continued

Examples in the following table were prepared using similar conditions as described in Example 231 and Scheme 33A from appropriate starting materials.

| Example # | Final Target # | Structure | IUPAC Name | Exact Mass [M + H]+ |
|---|---|---|---|---|
| 241 | 322 | 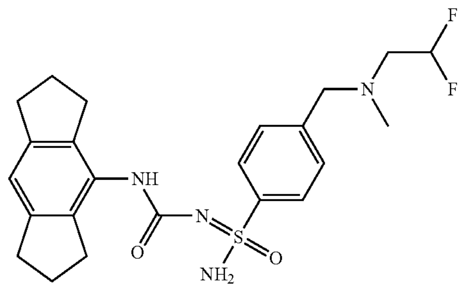 [SMILES: CN(Cc1ccc(S(N)(=O)=NC(=O)Nc2c3c(cc4c2CCC4)CCC3)cc1)CC(F)F] | 4-(((2,2-Difluoroethyl)(methyl)amino)methyl)-N'-(1,2,3,5,6,7-hexahydro-s-indacen-4-ylcarbamoyl)benzenesulfonimidamide | 463 |
| 242 | 351 | 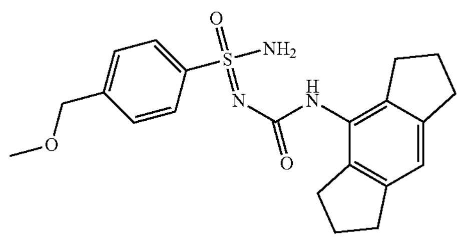 [SMILES: COCc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-(methoxymethyl)benzenesulfonimidamide | 400 |
| 243 | 358 | 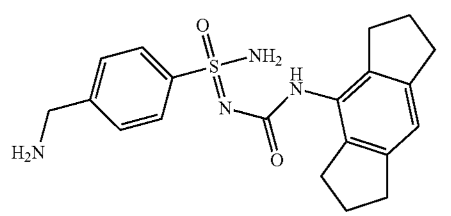 [SMILES: NCc1ccc(S(N)(=O)=NC(=O)Nc2c3c(cc4c2CCC4)CCC3)cc1] | 4-(Aminomethyl)-N'-(1,2,3,5,6,7-hexahydro-s-indacen-4-ylcarbamoyl)benzenesulfonimidamide | 385 |

Example 244 (Compound 401)

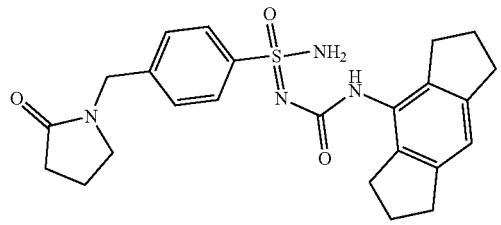 [SMILES: NS(=O)(=NC(=O)Nc1c2c(cc3c1CCC3)CCC2)c1ccc(CN2CCCC2=O)cc1]

N'-((1,2,3,5,6,7-hexahydro-s-indacen-4-yl)carbamoyl)-4-((2-oxopyrrolidin-1-yl)methyl)benzenesulfonimidamide (Scheme 33B)

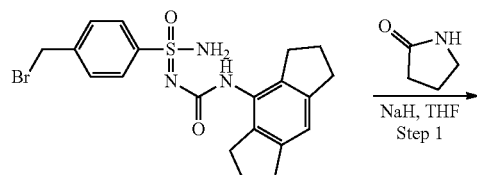

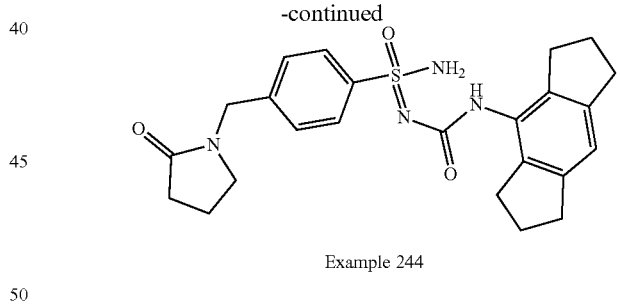

Example 244

Into a 40-mL sealed tube purged and maintained with an inert atmosphere of nitrogen, was placed 1-[amino[4-(bromomethyl)phenyl]oxo-λ⁶-sulfanylidene]-3-(1,2,3,5,6,7-hexahydro-s-indacen-4-yl)urea (200 mg, 0.45 mmol) in THF (10 mL), to this stirred solution was added DIEA (173 mg, 1.34 mmol) and pyrrolidin-2-one (114 mg, 1.34 mmol) at RT. The resulting solution was stirred for 3 h at 60° C. The resulting mixture was concentrated. The crude product was purified by Prep-HPLC with the following conditions: Column, XBridge Prep OBD C18, 30×150 mm 5 um; mobile phase, water (10 mM NH$_4$HCO$_3$) and ACN (25% to 44% ACN gradient in 7 min); Detector, UV. This resulted in 10 mg (4.95%) of Example 244 as a white solid. MS-ESI: 453 (M+1).
$^1$H NMR (400 MHz, DMSO-d$_6$) δ: 8.26 (br s, 1H), 7.83 (d, J=8.0 Hz, 2H), 7.40 (d, J=8.0 Hz, 2H), 7.27 (br s, 2H), 6.85 (s, 1H), 4.43 (s, 2H), 3.26-3.22 (m, 2H), 2.78-2.74 (m, 4H), 2.65-2.61 (m, 4H), 2.30 (t, J=8.20 Hz, 2H), 1.98-1.89 (m, 6H).

Example 245 (Compound 404)

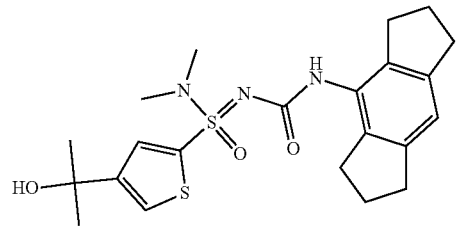 [SMILES: CN(C)S(=O)(=NC(=O)Nc1c2c(cc3c1CCC3)CCC2)c1cc(C(C)(C)O)cs1]

N'-((1,2,3,5,6,7-hexahydro-s-indacen-4-yl)carbamoyl)-4-(2-hydroxypropan-2-yl)-N,N-dimethylthiophene-2-sulfonimidamide (Scheme 4A)

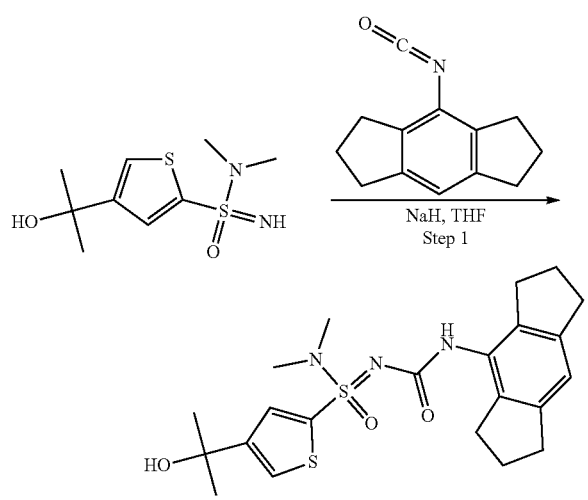

Example 245

Into a 50-mL 3-necked round-bottom flask, was placed a solution of 4-(2-hydroxypropan-2-yl)-N,N-dimethylthiophene-2-sulfonoimidamide (125 mg, 0.50 mmol) in THF (2.0 mL). To this was added NaH (60% wt. oil dispersion, 30.2 mg, 0.75 mmol) in several batches at 0° C. in an ice/water bath. To the mixture was added 4-isocyanato-1,2,3,5,6,7-hexahydro-s-indacene (110 mg, 0.55 mmol) at 0° C. in an ice/water bath. The resulting solution was stirred for 30 min at 0° C. in a water/ice bath. The reaction was then quenched by the addition of $NH_4Cl$ (aq.). The resulting solution was extracted with ethyl acetate and the organic layers combined, the organic layer was dried over anhydrous sodium sulfate and concentrated under vacuum. The crude product was purified by Prep-HPLC with the following conditions: X Bridge Prep Cis OBD, 19*150 mm 5 um; mobile phase, water (10 mM $NH_4HCO_3$) and ACN (10% to 80% in 6 min); Detector, UV 254 nm. This resulted in 90 mg (39.9%) of Example 245 as a white powder. MS-ESI: 448.2 (M+1). $^1H$ NMR (DMSO-$d_6$, 300 MHz): δ 8.60 (br s, 1H), 7.71 (s, 1H), 7.58 (br s, 1H), 6.88 (s, 1H), 5.21 (s, 1H), 2.86-2.70 (m, 8H), 2.70 (s, 6H), 1.98-1.90 (m, 4H), 1.3 (s, 6H).

Example 246 (Compound 331)

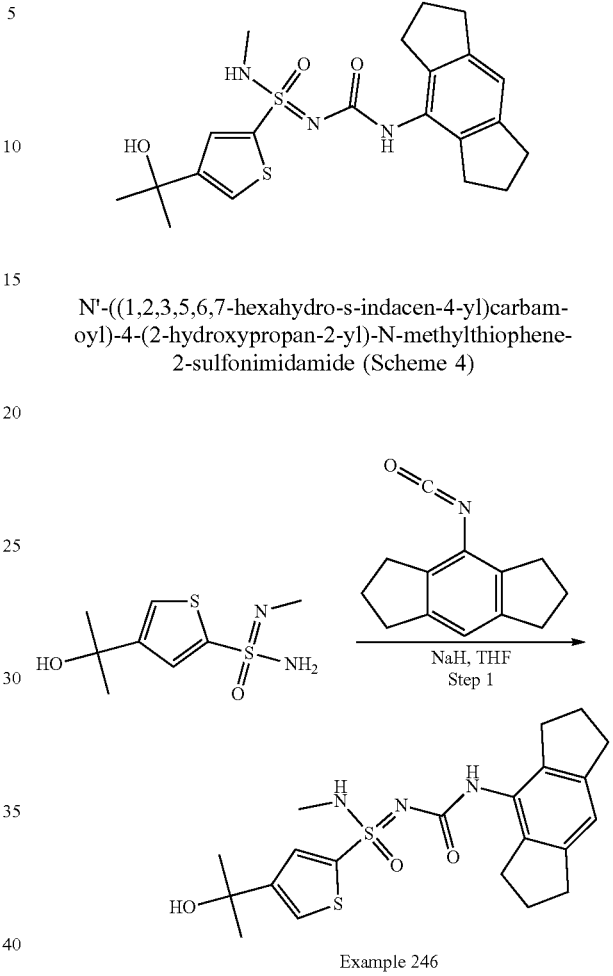

N'-((1,2,3,5,6,7-hexahydro-s-indacen-4-yl)carbamoyl)-4-(2-hydroxypropan-2-yl)-N-methylthiophene-2-sulfonimidamide (Scheme 4)

Example 246

Into a 50-mL 3-necked round-bottom flask purged and maintained with an inert atmosphere of nitrogen, was placed 4-(2-hydroxypropan-2-yl)-N-methylthiophene-2-sulfonoimidamide (106 mg, 0.45 mmol) in THF (4.0 mL). This was followed by the addition of NaH (60% wt. oil dispersion, 23.5 mg, 0.59 mmol) in several batches at 0° C. in a water/ice bath. To this was added a solution of 4-isocyanato-1,2,3,5,6,7-hexahydro-s-indacene (99.1 mg, 0.50 mmol) in THF (2.0 mL) dropwise with stirring at 0° C. The resulting solution was stirred for 30 min at 0° C. in a water/ice bath. The reaction was then quenched by the addition of water/ice. The resulting solution was extracted with ethyl acetate and the organic layers combined, the organic layer was dried over anhydrous sodium sulfate and concentrated under vacuum. The crude product was purified by Prep-HPLC with the following conditions: Column, X Bridge Shield RP18 OBD, 19×250 mm, 10 um; mobile phase, water (10 mM $NH_4HCO_3$+0.1% $NH_3·H_2O$) and ACN (43% to 67% ACN gradient in 6 min); Detector, UV 254 nm. This resulted in 80 mg (40.79%) of Example 246 as a white solid. MS-ESI: 434.15 (M+1). $^1H$ NMR (DMSO-$d_6$, 300 MHz): δ 8.55 (br s, 1H) 7.65 (s, 1H), 7.59 (s, 1H), 7.53 (s, 1H), 6.89 (s, 1H), 5.22 (s, 1H) 2.63-2.85 (m, 8H) 2.49 (s, 3H) 2.00-1.80 (m, 4H) 1.31 (s, 6H).

TABLE 24

Examples in the following table were prepared using similar conditions as described in Example 246 and Scheme 4 from appropriate starting materials.

| Example # | Final Target Number | Structure | IUPAC Name | Exact Mass [M + H]+ |
|---|---|---|---|---|
| 247 | 339 | 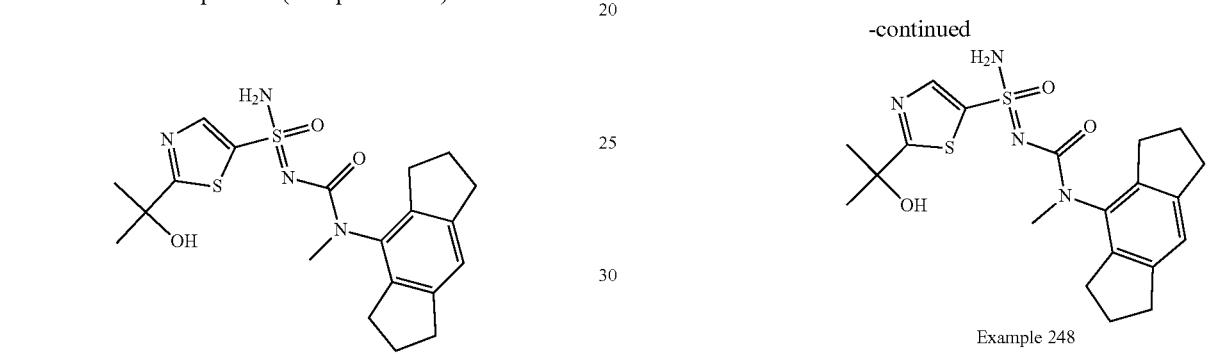 | N'-((1,2,3,5,6,7-hexahydro-s-indacen-4-yl)carbamoyl)-2-(2-hydroxypropan-2-yl)-N-methylthiazole-5-sulfonimidamide | 435 |

Example 248 (Compound 405)

N'-((1,2,3,5,6,7-hexahydro-s-indacen-4-yl)(methyl)carbamoyl)-2-(2-hydroxypropan-2-yl)thiazole-5-sulfonimidamide (Scheme 34)

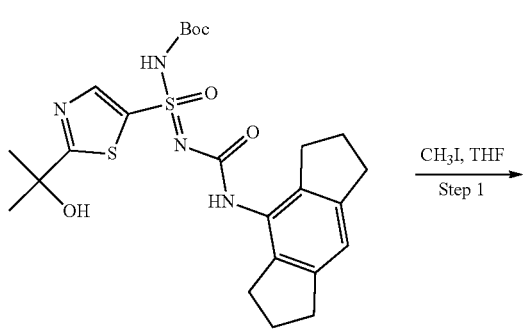

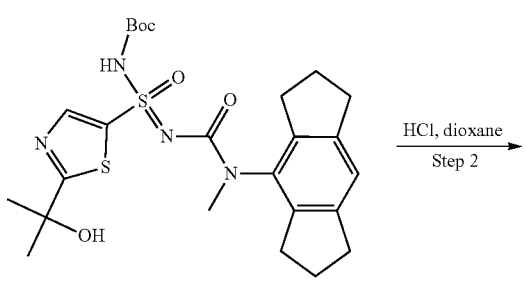

Example 248

Step 1: Tert-butyl(N-((1,2,3,5,6,7-hexahydro-s-indacen-4-yl)(methyl)carbamoyl)-2-(2-hydroxypropan-2-yl)thiazole-5-sulfonimidoyl)carbamate Into a 50-mL round-bottom flask, was placed tert-butyl N-([[(1,2,3,5,6,7-hexahydro-s-indacen-4-yl) carbamoyl]imino][2-(2-hydroxypropan-2-yl)-1,3-thiazol-5-yl]oxo-$\lambda^6$-sulfanyl)carbamate (200 mg, 0.38 mmol) in THF (10 mL), to this stirred solution was added $CH_3I$ (60 mg, 0.42 mmol) dropwise at 0° C. The resulting solution was stirred for 1 d at RT. The resulting mixture was concentrated. This resulted in 100 mg (49%) of the title compound as a solid. MS-ESI: 535 (M+1).

Step 2: N'-((1,2,3,5,6,7-hexahydro-s-indacen-4-yl)(methyl)carbamoyl)-2-(2-hydroxypropan-2-yl) thiazole-5-sulfonimidamide Into a 25-mL round-bottom flask, was placed tert-butyl N-([[(1,2,3,5,6,7-hexahydro-s-indacen-4-yl) (methyl)carbamoyl]imino][2-(2-hydroxypropan-2-yl)-1,3-thiazol-5-yl] oxo-$\lambda^6$-sulfanyl)carbamate (100 mg) in HCl (4M, 10 mL). The resulting solution was stirred for 5 h at RT. The crude product was purified by Prep-HPLC with the following conditions: Column, XBridge Prep $C_{18}$ OBD, 5 um, 19*150 mm; mobile phase, water (10 mM $NH_4HCO_3$ mM) and ACN (22% to 53% ACN gradient in 7 min); Detector, UV. This resulted in 15.7 mg of Example 248 as a solid. MS-ESI: 435 (M+1).

TABLE 25

Example 249 was isolated as a side product from the preparation of Example 248.

| Example # | Final Target Number | Structure | IUPAC Name | Exact Mass [M + H]+ |
|---|---|---|---|---|
| 249 | 406 | 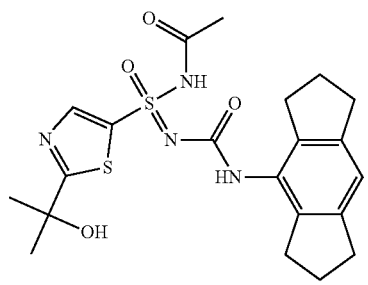 [SMILES: CC(=O)NS(=O)(=NC(=O)Nc1c2c(cc3c1CCC3)CCC2)c1cnc(C(C)(C)O)s1] | N'-((1,2,3,5,6,7-hexahydro-s-indacen-4-yl)(methyl)carbamoyl)-2-(2-hydroxypropan-2-yl)-N-methylthiazole-5-sulfonimidamide | 449 |

Example 250 (Compound 324)

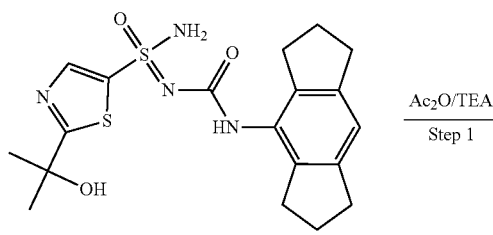

N—(N-((1,2,3,5,6,7-hexahydro-s-indacen-4-yl)carbamoyl)-2-(2-hydroxypropan-2-yl)thiazole-5-sulfonimidoyl)acetamide (Scheme 35A)

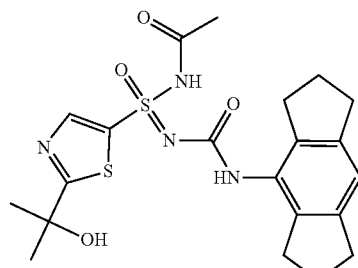

Into a 50-mL round-bottom flask purged and maintained with an inert atmosphere of nitrogen, was placed a mixture of N'-((1,2,3,5,6,7-hexahydro-s-indacen-4-yl)carbamoyl)-2-(2-hydroxypropan-2-yl)thiazole-5-sulfonimidamide (200 mg, 0.48 mmol) and TEA (96 mg, 0.96 mmol) in DCM (20 mL). To the stirred solution, Ac$_2$O (74 mg, 0.72 mmol) was added dropwise at 0° C. The resulting solution was stirred overnight. Then 80 mg of the product was obtained by Prep-HPLC with the following conditions: Column: XBridge Prep C$_{18}$ OBD Column 19×150 mm 5 um; Mobile Phase A: water (10 mM NH$_4$HCO$_3$), Mobile Phase B: ACN; Flow rate: 25 mL/min; Gradient: 18% B to 41% B in 7 min; 254/210 nm; Rt: 5.05 min, this resulted in 100 mg of the Example 250 as a white solid. MS-ESI: 462.14 (M+1). $^1$H NMR (300 MHz, CD$_3$OD-d$_4$) δ: 8.11 (s, 1H), 6.89 (s, 1H), 2.92-2.69 (m, 8H), 2.09-2.01 (m, 4H), 1.99 (s, 3H), 1.60 (d, J=2.3 Hz, 6H).

Example 251 (Compound 407)

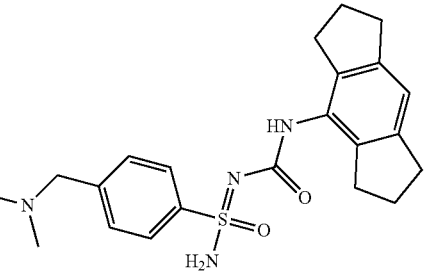

723 methyl 4-((4-(N'-((1,2,3,5,6,7-hexahydro-s-indacen-4-yl)carbamoyl)sulfamidimidoyl)benzyl)(methyl)amino)-4-oxobutanoate (Scheme 35)

724

4-((4-(N'-(1,2,3,5,6,7-hexahydro-s-indacen-4-ylcarbamoyl)sulfamimidoyl)benzyl)(methyl)amino)-4-oxobutanoic acid

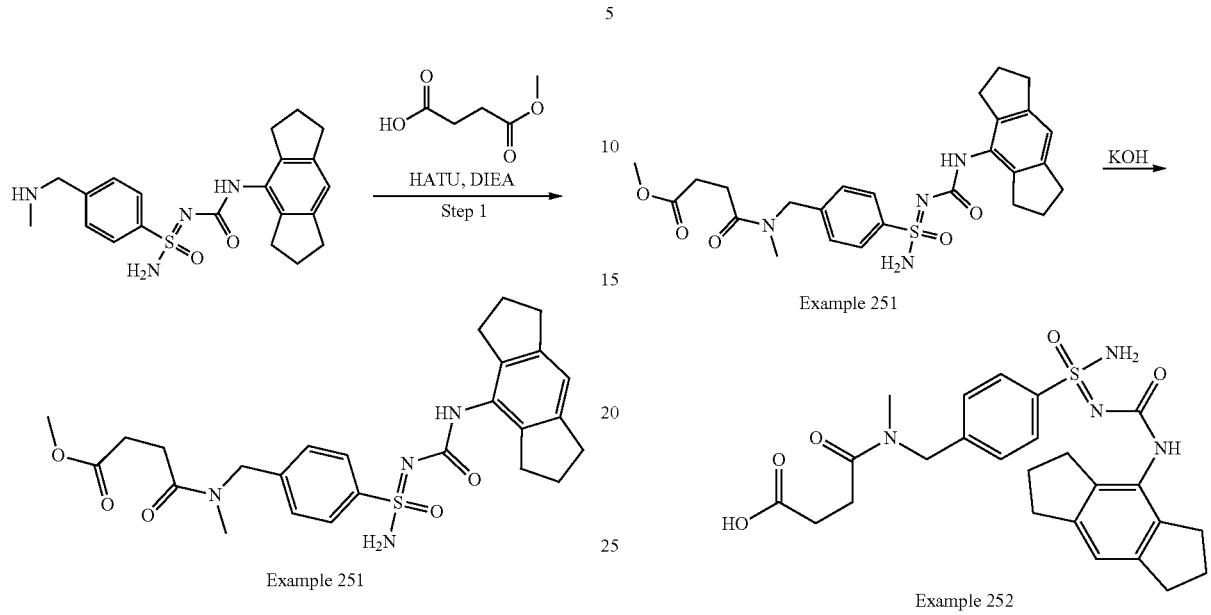

Example 251

Into a 8-mL round-bottom flask, was placed a solution of 1-[amino([4-[(methylamino)methyl]-phenyl])oxo-λ⁶-sulfanylidene]-3-(1,2,3,5,6,7-hexahydro-s-indacen-4-yl)urea (100 mg, 0.25 mmol), methyl 4-chloro-4-oxobutanoate (37.8 mg, 0.25 mmol) in DMF (10 mL), to this stirred solution was added HATU (191 mg, 0.50 mmol) and DIEA (64.9 mg, 0.50 mmol). The resulting solution was stirred for 20 min at RT. The crude product was purified by Prep-HPLC with the following conditions: Column, XBridge Shield RP18 OBD, 19*250 mm, 10 um; mobile phase, water (10 mM $NH_4HCO_3$) and ACN (15% to 75% ACN gradient in 7 min); Detector, UV 250 nm. This resulted in 4.2 mg (3.27%) of Example 251 as a white solid. MS-ESI: 513 (M+1). ¹H NMR (300 MHz, $CD_3OD-d_4$) δ: 8.02-7.94 (m, 2H), 7.49-7.41 (m, 2H), 6.89 (s, 1H), 4.68 (s, 2H), 3.68 (s, 3H), 3.04 (s, 3H), 2.85-2.80 (m, 4H), 2.75-2.60 (m, 8H), 2.03-1.97 (m, 4H).

Example 252 (Compound 410)

Into a 50-mL round-bottom flask, was placed a solution of methyl 3-[([4-[amino([[(1,2,3,5,6,7-hexahydro-s-indacen-4-yl)carbamoyl]imino])oxo-λ⁶-sulfanyl]phenyl]methyl)(methyl)-carbamoyl]propanoate (80 mg, 0.16 mmol) in THF (3.0 mL) and $H_2O$ (3.0 mL), to the stirred solution was added KOH (17.5 mg, 0.31 mmol). The resulting solution was stirred for 120 min at RT. The crude product was purified by Prep-HPLC with the following conditions: Column, XBridge Shield RP18 OBD, 19*250 mm, 10 um; mobile phase, water (10 mM $NH_4HCO_3$) and ACN (15% to 75% gradient in 7 min); Detector, UV250 num. This resulted in 39 mg (50%) of Example 252 as a white solid. MS-ESI: 499 (M+1). ¹H-NMR (300 MHz, $CD_3OD-d_4$) δ: 8.10-7.80 (m, 2H), 7.55-7.30 (m, 2H), 6.89 (s, 1H), 4.68 (s, 2H), 3.04 (s, 3H), 2.90-2.60 (m, 12H), 2.10-1.80 (m, 4H).

Example 253 (Compound 408)

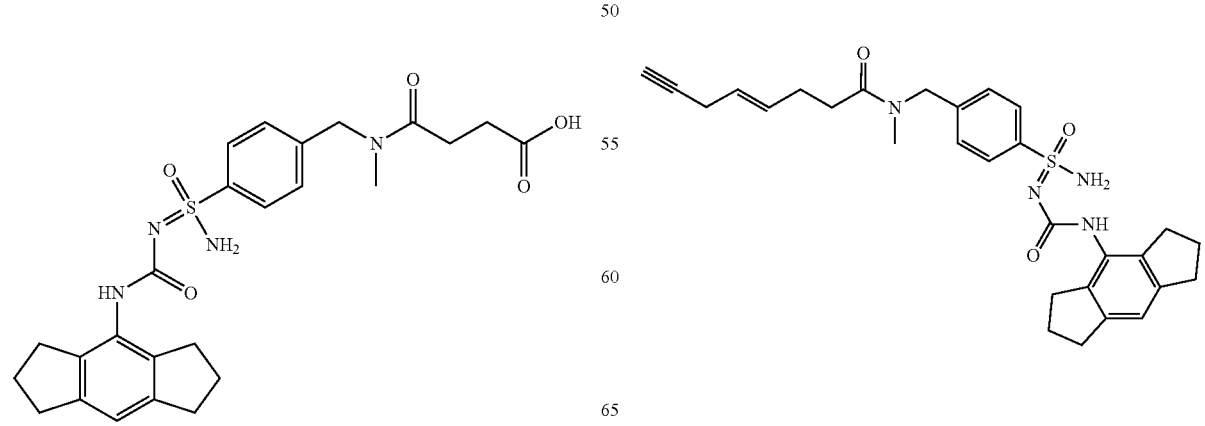

(E)-N-(4-(N'-((1,2,3,5,6,7-hexahydro-s-indacen-4-yl)carbamoyl)sulfamidimidoyl)benzyl)-N-methyloct-4-en-7-ynamide (Scheme 35)

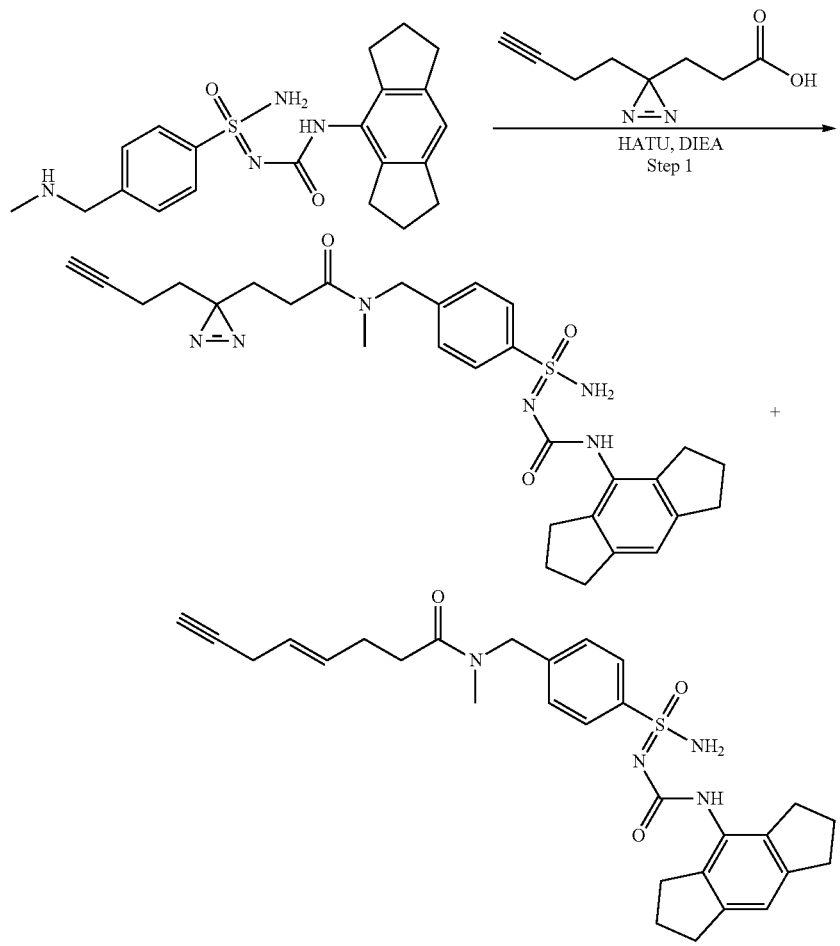

Example 253

Example 253 was prepared using similar conditions as described in Example 251 and Scheme 35 from 3-(3-(but-3-ynyl)-3H-diazirin-3-yl)propanoic acid and Intermediate 67. MS-ESI: 519 (M+1)

TABLE 26

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 254 | 308 | 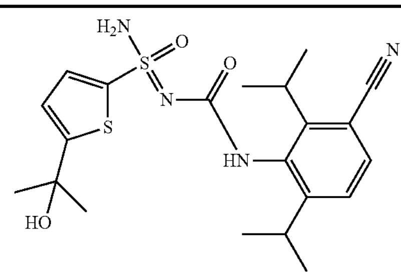 | N'-((3-cyano-2,6-diisopropylphenyl)carbamoyl)-5-(2-hydroxypropan-2-yl)thiophene-2-sulfonimidamide | 449 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 255 | 311 | 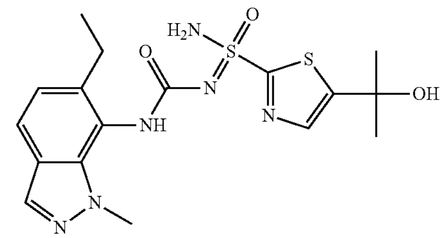 [SMILES: CCc1ccc2cnn(C)c2c1NC(=O)N=S(N)(=O)c1ncc(C(C)(C)O)s1] | N'-((6-ethyl-1-methyl-1H-indazol-7-yl)carbamoyl)-5-(2-hydroxypropan-2-yl)thiazole-2-sulfonimidamide | 423 |
| 256 | 312 | 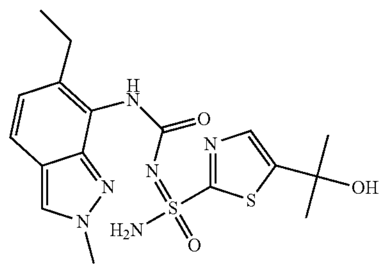 [SMILES: CCc1ccc2cn(C)nc2c1NC(=O)N=S(N)(=O)c1ncc(C(C)(C)O)s1] | N'-((6-ethyl-2-methyl-2H-indazol-7-yl)carbamoyl)-5-(2-hydroxypropan-2-yl)thiazole-2-sulfonimidamide | 423 |
| 257 | 327 | 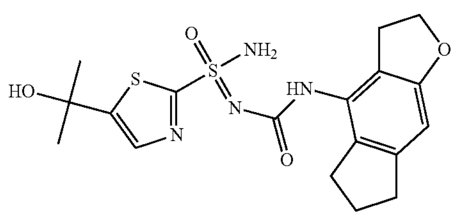 [SMILES: CC(C)(O)c1cnc(S(N)(=O)=NC(=O)Nc2c3c(cc4c2CCO4)CCC3)s1] | 5-(2-hydroxypropan-2-yl)-N'-((3,5,6,7-tetrahydro-2H-indeno[5,6-b]furan-4-yl)carbamoyl)thiazole-2-sulfonimidamide | 423 |
| 258 | 326 | 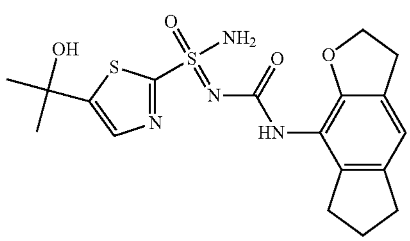 [SMILES: CC(C)(O)c1cnc(S(N)(=O)=NC(=O)Nc2c3c(cc4c2OCC4)CCC3)s1] | 5-(2-Hydroxypropan-2-yl)-N'-((3,5,6,7-tetrahydro-2H-indeno[5,6-b]furan-8-yl)carbamoyl)thiazole-2-sulfonimidamide | 423 |
| 259 | 139 | 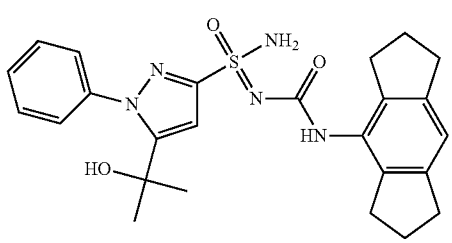 [SMILES: CC(C)(O)c1cc(S(N)(=O)=NC(=O)Nc2c3c(cc4c2CCC4)CCC3)nn1-c1ccccc1] | N'-((1,2,3,5,6,7-hexahydro-s-indacen-4-yl)carbamoyl)-5-(2-hydroxypropan-2-yl)-1-phenyl-1H-pyrazole-3-sulfonimidamide | 480 |
| 260 | 137 | 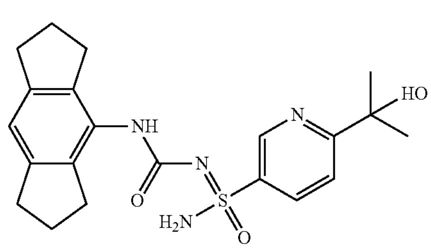 [SMILES: CC(C)(O)c1ccc(S(N)(=O)=NC(=O)Nc2c3c(cc4c2CCC4)CCC3)cn1] | N'-((1,2,3,5,6,7-hexahydro-s-indacen-4-yl)carbamoyl)-6-(2-hydroxypropan-2-yl)pyridine-3-sulfonimidamide | 415 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]⁺ |
|---|---|---|---|---|
| 261 | 409 | 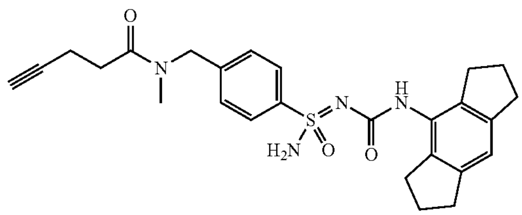 [SMILES: C#CCCC(=O)N(C)Cc1ccc(S(N)(=O)=NC(=O)Nc2c3c(cc4c2CCC4)CCC3)cc1] | N-(4-(N'-((1,2,3,5,6,7-hexahydro-s-indacen-4-yl)carbamoyl)sulfamidimidoyl)benzyl)-N-methylpent-4-ynamide | 479 |
| 262 | 303 | 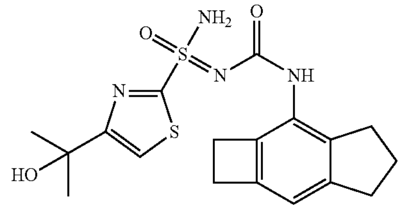 [SMILES: CC(C)(O)c1csc(S(N)(=O)=NC(=O)Nc2c3c(cc4c2CC4)CCC3)n1] | 4-(2-Hydroxypropan-2-yl)-N'-((2,4,5,6-tetrahydro-1H-cyclobuta[f]inden-3-yl)carbamoyl)thiazole-2-sulfonimidamide | 407 |
| 263 | 325 | 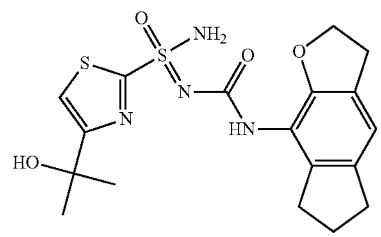 [SMILES: CC(C)(O)c1csc(S(N)(=O)=NC(=O)Nc2c3c(cc4c2OCC4)CCC3)n1] | 4-(2-Hydroxypropan-2-yl)-N'-((3,5,6,7-tetrahydro-2H-indeno[5,6-b]furan-8-yl)carbamoyl)thiazole-2-sulfonimidamide | 423 |
| 264 | 138 | 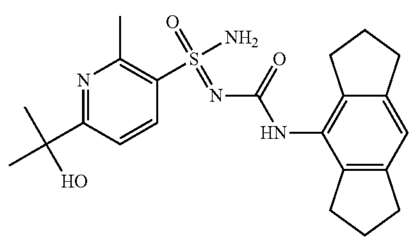 [SMILES: Cc1nc(C(C)(C)O)ccc1S(N)(=O)=NC(=O)Nc1c2c(cc3c1CCC3)CCC2] | N'-((1,2,3,5,6,7-hexahydro-s-indacen-4-yl)carbamoyl)-6-(2-hydroxypropan-2-yl)-2-methylpyridine-3-sulfonimidamide | 429 |
| 265 | 332 | 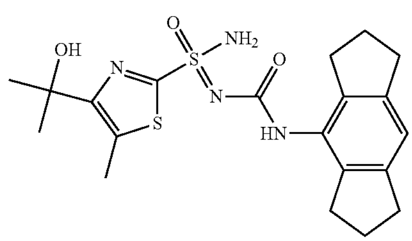 [SMILES: Cc1sc(S(N)(=O)=NC(=O)Nc2c3c(cc4c2CCC4)CCC3)nc1C(C)(C)O] | N'-(1,2,3,5,6,7-hexahydro-s-indacen-4-ylcarbamoyl)-4-(2-hydroxypropan-2-yl)-5-methylthiazole-2-sulfonimidamide | 435 |
| 266 | 334 | 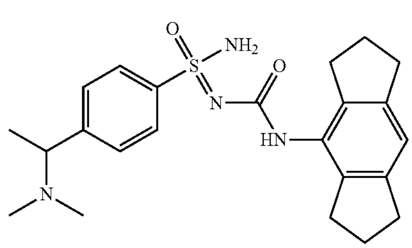 [SMILES: CC(c1ccc(S(N)(=O)=NC(=O)Nc2c3c(cc4c2CCC4)CCC3)cc1)N(C)C] | 4-(1-(Dimethylamino)ethyl)-N'-(1,2,3,5,6,7-hexahydro-s-indacen-4-ylcarbamoyl)benzenesulfonimidamide | 427 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 267 | 335 | 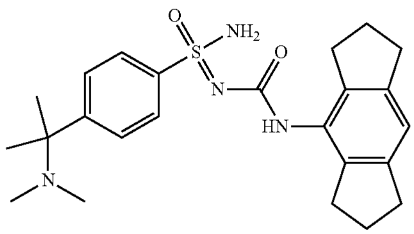 [SMILES: CN(C)C(C)(C)c1ccc(S(N)(=O)=NC(=O)Nc2c3c(cc4c2CCC4)CCC3)cc1] | 4-(2-(Dimethylamino)propan-2-yl)-N'-(1,2,3,5,6,7-hexahydro-s-indacen-4-yl-carbamoyl)benzene-sulfonimidamide | 441 |
| 268 | 337 | 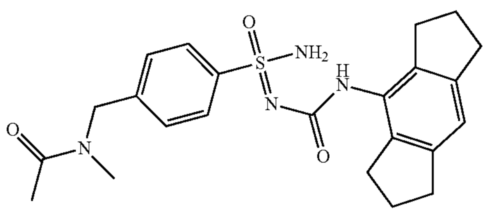 [SMILES: CC(=O)N(C)Cc1ccc(S(N)(=O)=NC(=O)Nc2c3c(cc4c2CCC4)CCC3)cc1] | N-(4-(N'-(1,2,3,5,6,7-hexahydro-s-indacen-4-ylcarbamoyl)sulfamimidoyl)benzyl)-N-methylacetamide | 441 |
| 269 | 113 | 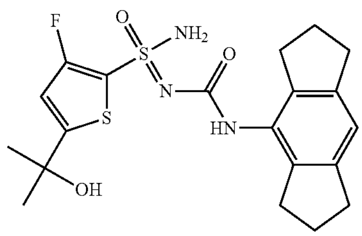 [SMILES: CC(C)(O)c1cc(F)c(S(N)(=O)=NC(=O)Nc2c3c(cc4c2CCC4)CCC3)s1] | 3-Fluoro-N'-(1,2,3,5,6,7-hexahydro-s-indacen-4-ylcarbamoyl)-5-(2-hydroxypropan-2-yl)thiophene-2-sulfonimidamide | 438 |
| 270 | 343 | 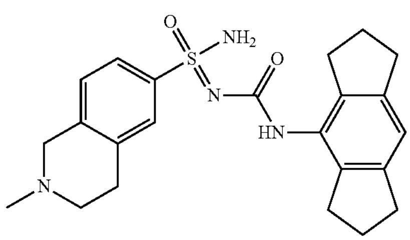 [SMILES: CN1CCc2cc(S(N)(=O)=NC(=O)Nc3c4c(cc5c3CCC5)CCC4)ccc2C1] | N'-((1,2,3,5,6,7-hexahydro-s-indacen-4-yl)carbamoyl)-2-methyl-1,2,3,4-tetrahydroisoquinoline-6-sulfonimidamide | 425 |
| 271 | 349 | 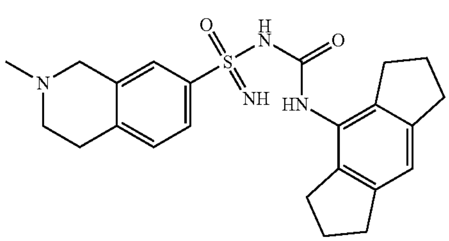 [SMILES: CN1CCc2ccc(S(=N)(=O)NC(=O)Nc3c4c(cc5c3CCC5)CCC4)cc2C1] | N-(1,2,3,5,6,7-hexahydro-s-indacen-4-ylcarbamoyl)-2-methyl-1,2,3,4-tetrahydroisoquinoline-7-sulfonimidamide | 425 |
| 272 | 344 | 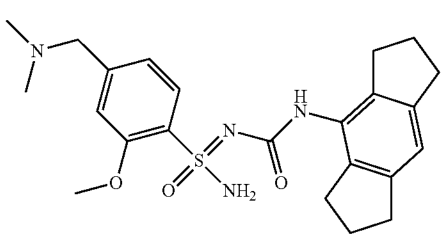 [SMILES: COc1cc(CN(C)C)ccc1S(N)(=O)=NC(=O)Nc1c2c(cc3c1CCC3)CCC2] | 4-((Dimethylamino)methyl)-N'-((1,2,3,5,6,7-hexahydro-s-indacen-4-yl)carbamoyl)-2-methoxybenzene-sulfonimidamide | 443 |

TABLE 26-continued

Examples in the following table were prepared using similar conditions as described in
Example 4-route 1 and Scheme 2 from appropriate starting materials.

| Example # | Final Target Number | Structure | IUPAC Name | Exact Mass [M + H]+ |
|---|---|---|---|---|
| 273 | 359 | 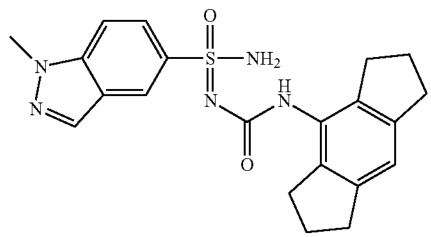 [SMILES: Cn1ncc2cc(S(N)(=O)=NC(=O)Nc3c4c(cc5c3CCC5)CCC4)ccc21] | N'-(1,2,3,5,6,7-hexahydro-s-indacen-4-ylcarbamoyl)-1-methyl-1H-indazole-5-sulfonimidamide | 410 |
| 274 | 352 | 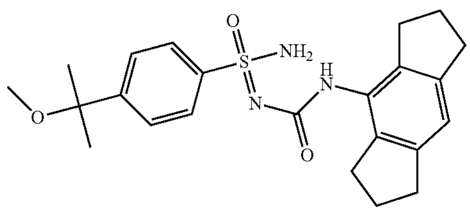 [SMILES: COC(C)(C)c1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-(2-methoxypropan-2-yl)benzenesulfonimidamide | 428 |
| 275 | 354 | 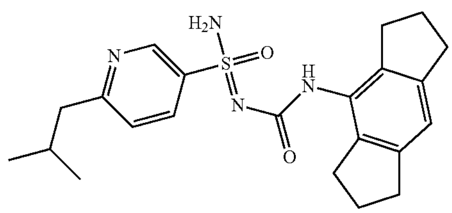 [SMILES: CC(C)Cc1ccc(S(N)(=O)=NC(=O)Nc2c3c(cc4c2CCC4)CCC3)cn1] | N'-(1,2,3,5,6,7-hexahydro-s-indacen-4-ylcarbamoyl)-6-isobutylpyridine-3-sulfonimidamide | 413 |
| 276 | 355 | 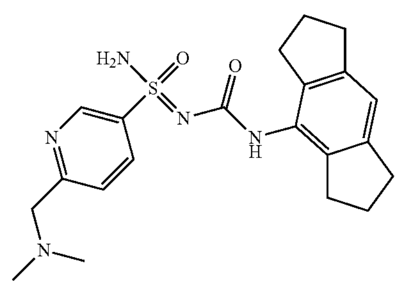 [SMILES: CN(C)Cc1ccc(S(N)(=O)=NC(=O)Nc2c3c(cc4c2CCC4)CCC3)cn1] | 6-((Dimethylamino)methyl)-N'-(1,2,3,5,6,7-hexahydro-s-indacen-4-ylcarbamoyl)pyridine-3-sulfonimidamide | 414 |
| 277 | 356 | 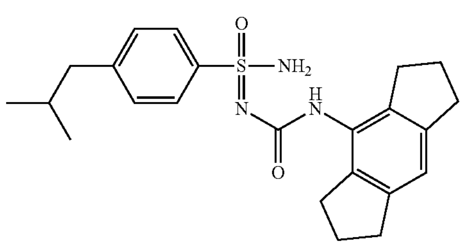 [SMILES: CC(C)Cc1ccc(S(N)(=O)=NC(=O)Nc2c3c(cc4c2CCC4)CCC3)cc1] | N'-(1,2,3,5,6,7-hexahydro-s-indacen-4-ylcarbamoyl)-4-isobutylbenzenesulfonimidamide | 412 |
| 278 | 357 | 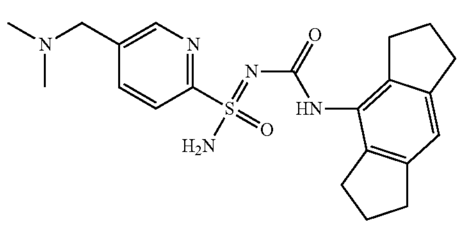 | 5-((Dimethylamino)methyl)-N'-(1,2,3,5,6,7-hexahydro-s-indacen-4-ylcarbamoyl)pyridine-2-sulfonimidamide | 414 |

TABLE 26-continued

Examples in the following table were prepared using similar conditions as described in Example 4-route 1 and Scheme 2 from appropriate starting materials.

| Example # | Final Target Number | Structure | IUPAC Name | Exact Mass [M + H]+ |
|---|---|---|---|---|
| 279 | 340 | 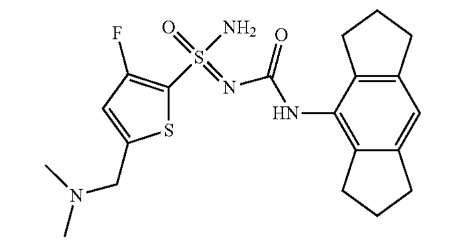 [SMILES: CN(C)Cc1cc(F)c(S(N)(=O)=NC(=O)Nc2c3c(cc4c2CCC4)CCC3)s1] | 5-((Dimethylamino)methyl)-3-fluoro-N'-(1,2,3,5,6,7-hexahydro-s-indacen-4-ylcarbamoyl)thiophene-2-sulfonimidamide | 437 |
| 280 | 377 | 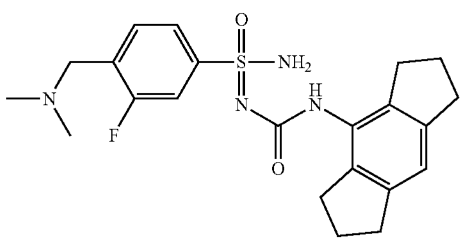 [SMILES: CN(C)Cc1ccc(S(N)(=O)=NC(=O)Nc2c3c(cc4c2CCC4)CCC3)cc1F] | 4-((dimethylmino)methyl)-3-fluoro-N'-((1,2,3,5,6,7-hexahydro-s-indacen-4-yl)carbamoyl)benzenesulfonimidamide | 431 |
| 281 | 378 | 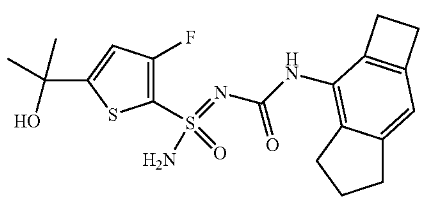 [SMILES: CC(C)(O)c1cc(F)c(S(N)(=O)=NC(=O)Nc2c3c(cc4c2CC4)CCC3)s1] | 3-fluoro-5-(2-hydroxy-propan-2-yl)-N'-((2,4,5,6-tetrahydro-1H-cyclobuta[f]inden-3-yl)carbamoyl)thiophene-2-sulfonimidamide | 424 |
| 282 | 379 | 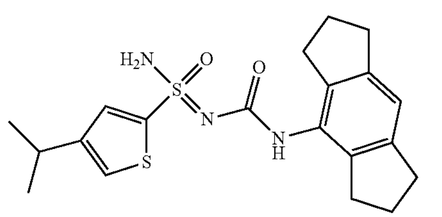 [SMILES: CC(C)c1csc(S(N)(=O)=NC(=O)Nc2c3c(cc4c2CCC4)CCC3)c1] | N'-((1,2,3,5,6,7-hexahydro-s-indacen-4-yl)carbamoyl)-4-isopropylthiophene-2-sulfonimidamide | 404 |
| 283 | 380 | 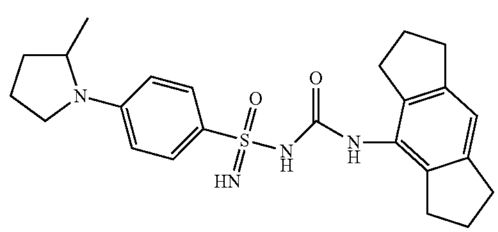 [SMILES: CC1CCCN1c1ccc(S(=N)(=O)NC(=O)Nc2c3c(cc4c2CCC4)CCC3)cc1] | N-((1,2,3,5,6,7-hexahydro-s-indacen-4-yl)carbamoyl)-4-(1-methylpyrrolidin-2-yl)benzenesulfonimidamide | 439 |
| 284 | 353 | 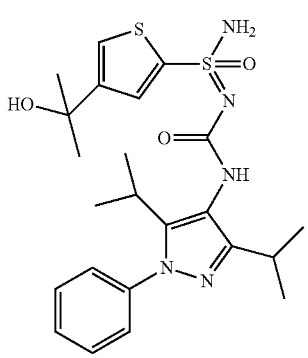 [SMILES: CC(C)c1nn(-c2ccccc2)c(C(C)C)c1NC(=O)N=S(N)(=O)c1cc(C(C)(C)O)cs1] | N'-((3,5-diisopropyl-1-phenyl-1H-pyrazol-4-yl)carbamoyl)-4-(2-hydroxy-propan-2-yl)thiophene-2-sulfonimidamide | 490 |

TABLE 26-continued

Examples in the following table were prepared using similar conditions as described in
Example 4-route 1 and Scheme 2 from appropriate starting materials.

| Example # | Final Target Number | Structure | IUPAC Name | Exact Mass [M + H]+ |
|---|---|---|---|---|
| 285 | 333 | 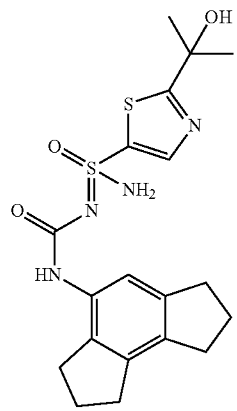 [SMILES: CC(C)(O)c1ncc(S(N)(=O)=NC(=O)Nc2cc3c(c4c2CCC4)CCC3)s1] | N'-((1,2,3,6,7,8-hexahydro-as-indacen-4-yl)carbamoyl)-2-(2-hydroxypropan-2-yl)thiazole-5-sulfonimidamide | 421 |
| 287 | 382 | 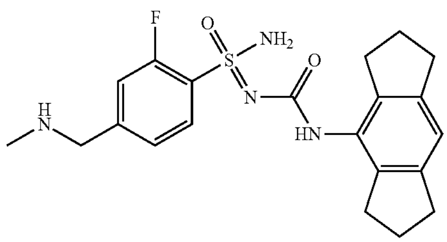 [SMILES: CNCc1ccc(S(N)(=O)=NC(=O)Nc2c3c(cc4c2CCC4)CCC3)c(F)c1] | 2-fluoro-N'-((1,2,3,5,6,7-hexahydro-s-indacen-4-yl)carbamoyl)-4-((methylamino)methyl)benzenesulfonimidamide | 417 |
| 288 | 383 | 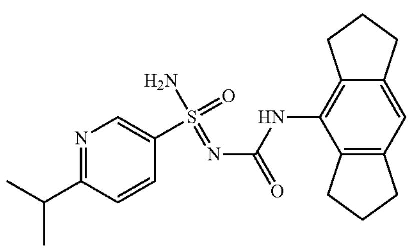 | N'-((1,2,3,5,6,7-hexahydro-s-indacen-4-yl)carbamoyl)-6-isopropylpyridine-3-sulfonimidamide | 399 |

TABLE 27

Examples in the following table were prepared using similar conditions as described in
Example 4-route 2 and Scheme 3 from appropriate starting materials.

| Example # | Final Target Number | Structure | IUPAC Name | Exact Mass [M + H]+ |
|---|---|---|---|---|
| 289 | 315 | 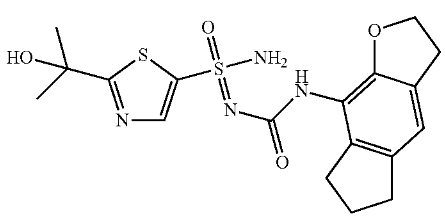 [SMILES: CC(C)(O)c1ncc(S(N)(=O)=NC(=O)Nc2c3c(cc4c2OCC4)CCC3)s1] | 2-(2-Hydroxypropan-2-yl)-N'-((3,5,6,7-tetrahydro-2H-indeno[5,6-b]furan-8-yl)carbamoyl)thiazole-5-sulfonimidamide | 423 |

TABLE 27-continued

Examples in the following table were prepared using similar conditions as described in
Example 4-route 2 and Scheme 3 from appropriate starting materials.

| Example # | Final Target Number | Structure | IUPAC Name | Exact Mass [M + H]+ |
|---|---|---|---|---|
| 290 | 316 | 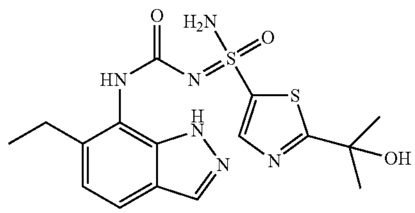 [SMILES: CCc1ccc2cn[nH]c2c1NC(=O)N=S(N)(=O)c1cnc(C(C)(C)O)s1] | N'-((6-ethyl-1H-indazol-7-yl)carbamoyl)-2-(2-hydroxypropan-2-yl)thiazole-5-sulfonimidamide | 409 |
| 291 | 317 | 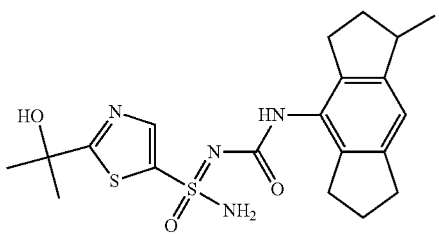 [SMILES: CC1CCc2c1cc1c(c2NC(=O)N=S(N)(=O)c2cnc(C(C)(C)O)s2)CCC1] | 2-(2-Hydroxypropan-2-yl)-N'-((1-methyl-1,2,3,5,6,7-hexahydro-s-indacen-4-yl)carbamoyl)thiazole-5-sulfonimidamide | 435 |
| 292 | 319 | 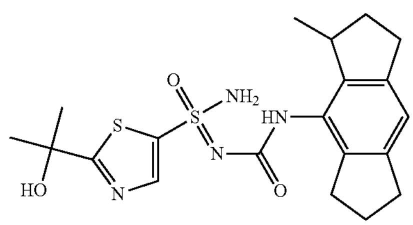 [SMILES: CC1CCc2cc3c(c(NC(=O)N=S(N)(=O)c4cnc(C(C)(C)O)s4)c21)CCC3] | 2-(2-Hydroxypropan-2-yl)-N'-((3-methyl-1,2,3,5,6,7-hexahydro-s-indacen-4-yl)carbamoyl)thiazole-5-sulfonimidamide | 435 |
| 293 | 320 | 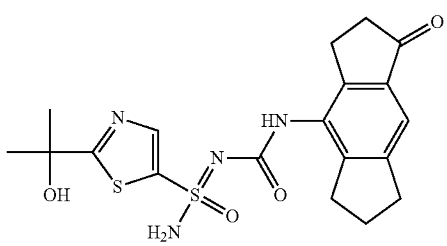 [SMILES: CC(C)(O)c1ncc(S(N)(=O)=NC(=O)Nc2c3c(cc4c2CCC4=O)CCC3)s1] | 2-(2-Hydroxypropan-2-yl)-N'-((1-oxo-1,2,3,5,6,7-hexahydro-s-indacen-4-yl)carbamoyl)thiazole-5-sulfonimidamide | 435 |
| 294 | 336 | 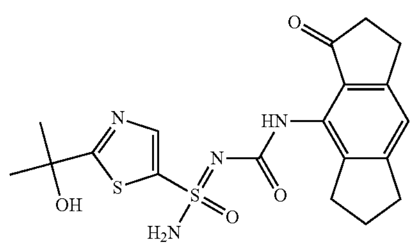 [SMILES: CC(C)(O)c1ncc(S(N)(=O)=NC(=O)Nc2c3c(cc4c2C(=O)CC4)CCC3)s1] | 2-(2-Hydroxypropan-2-yl)-N'-((3-oxo-1,2,3,5,6,7-hexahydro-s-indacen-4-yl)carbamoyl)thiazole-5-sulfonimidamide | 435 |
| 295 | 330 | 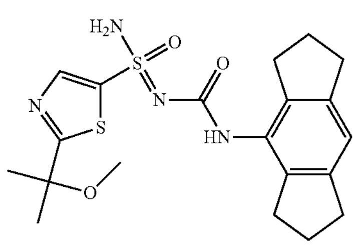 [SMILES: COC(C)(C)c1ncc(S(N)(=O)=NC(=O)Nc2c3c(cc4c2CCC4)CCC3)s1] | N'-((1,2,3,5,6,7-hexahydro-s-indacen-4-yl)carbamoyl)-2-(2-methoxypropan-2-yl)thiazole-5-sulfonimidamide | 435 |

TABLE 28

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]⁺ |
|---|---|---|---|---|---|---|
| 296 | 364a | 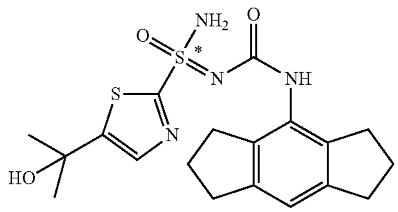 | (R) or (S)-N'-((1,2,3,5,6,7-hexahydro-s-indacen-4-yl)carbamoyl)-5-(2-hydroxypropan-2-yl)thiazole-2-sulfonimidamide | CHIRAL-PAK IG 2*25 cm (5 um) | 50% MeOH (8 mM NH$_3$·MeOH) in CO$_2$# | 421 |
| 297 | 364b | 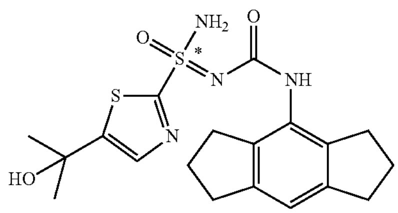 | (S) or (R)-N'-((1,2,3,5,6,7-hexahydro-s-indacen-4-yl)carbamoyl)-5-(2-hydroxypropan-2-yl)thiazole-2-sulfonimidamide | CHIRAL-PAK IG 2*25 cm (5 um) | 50% MeOH (8 mM NH$_3$·MeOH) in CO$_2$ | 421 |
| 298 | 365a | 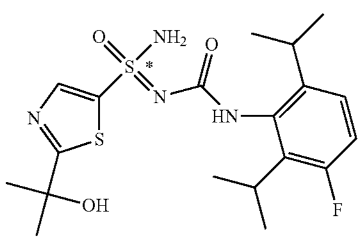 | (R) or (S)-N'-((3-fluoro-2,6-diisopropylphenyl)carbamoyl)-2-(2-hydroxypropan-2-yl)thiazole-5-sulfonimidamide | Chiralpak ID, 2*25 cm, 5 um | IPA in Hex:DCM = 5:1 | 443 |
| 299 | 365b | 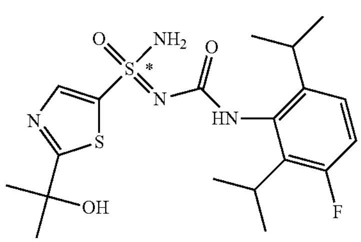 | (S) or (R)-N'-((3-fluoro-2,6-diisopropylphenyl)carbamoyl)-2-(2-hydroxypropan-2-yl)thiazole-5-sulfonimidamide | Chiralpak ID, 2*25 cm, 5 um | IPA in Hex:DCM= 5:1 | 443 |
| 300 | 308a | 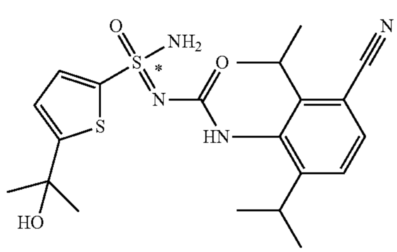 | (R) or (S)-N'-((3-cyano-2,6-diisopropylphenyl)carbamoyl)-5-(2-hydroxypropan-2-yl)thiophene-2-sulfonimidamide | CHIRAL-PAK IG, 20*250 mm, 5 um | 30% EtOH in Hex (0.1% DEA) | 449 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 301 | 308b | 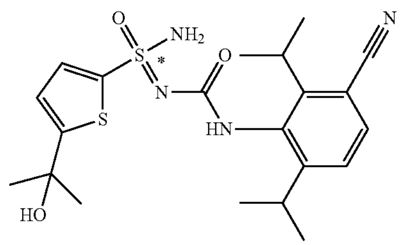 | (S) or (R)-N'-((3-fluoro-2,6-diisopropylphenyl)carbamoyl)-2-(2-hydroxypropan-2-yl)thiazole-5-sulfonimidamide | CHIRAL-PAK IG, 20*250 mm, 5 um | 30% EtOH in Hex (0.1% DEA) | 449 |
| 126 | 195a | 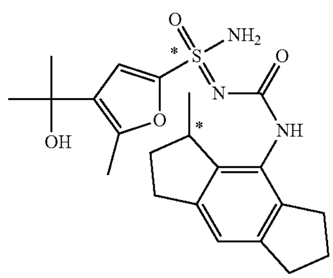 | Two isomers of (S,S)-and (S,R)-or (R,S)-and (R,R) 4-(2-hydroxypropan-2-yl)-5-methyl-N'-((3-methyl-1,2,3,5,6,7-hexahydro-s-indacen-4-yl)carbamoyl)furan-2-sulfonimidamide | CHIRAL-ART Cellulose-SB, 2*25 cm, 5 um | MeOH (0.1% DEA); 1st and 2nd peaks | 432 |
| 127 | 195e | 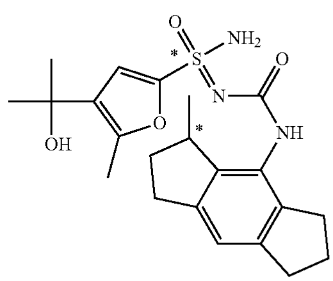 | Two isomers of (R,S)-and (R,R)-or (S,S)-and (S,R) 4-(2-hydroxypropan-2-yl)-5-methyl-N'-((3-methyl-1,2,3,5,6,7-hexahydro-s-indacen-4-yl)carbamoyl)furan-2-sulfonimidamide | | MeOH (0.1% DEA); 3rd peak | 432 |
| 302 | 195ba | 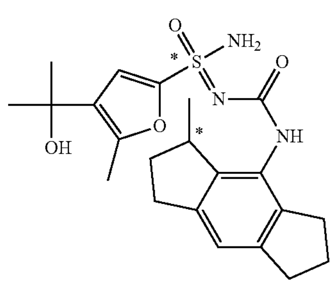 | (R,R) or (R,S) or (S,S) or (S,R)-4-(2-hydroxypropan-2-yl)-5-methyl-N'-((3-methyl-1,2,3,5,6,7-hexahydro-s-indacen-4-yl)carbamoyl)furan-2-sulfonimidamide resolved from example 127 | Phenomenex Lux 5u Cellulose-4, AXIA Packed 2.12*25 cm, 5 um | 40% MeOH in CO2 | 432 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 303 | 195bb | 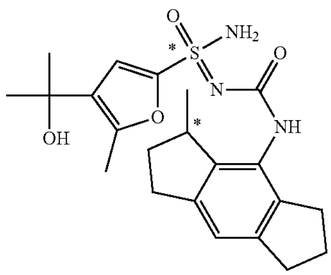 | (R,S) or (R,R) or (S,R) or (S,S)-4-(2-hydroxypropan-2-yl)-5-methyl-N'-((3-methyl-1,2,3,5,6,7-hexahydro-s-indacen-4-yl)carbamoyl)furan-2-sulfonimidamide resolved from example 127 | Phenomenex Lux 5u Cellulose-4, AXIA Packed 2.12*25 cm, 5 um | 40% MeOH in $CO_2$ | 432 |
| 123 | 207c | 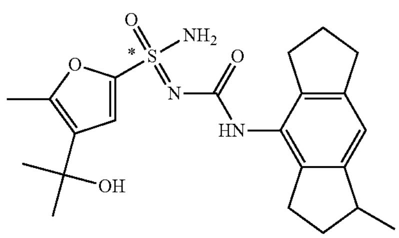 | Two isomers of (R,S)- and (R,R) 4-(2-hydroxypropan-2-yl)-5-methyl-N'-(1-methyl-1,2,3,5,6,7-hexahydros-indacen-4-yl-carbamoyl)furan-2-sulfonimidamide | ChiralPak IC, 2*25 cm, 5 um | 50% EtOH in MTBE; $1^{st}$ and $2^{nd}$ peaks | 432.2 |
| 124 | 207aa | 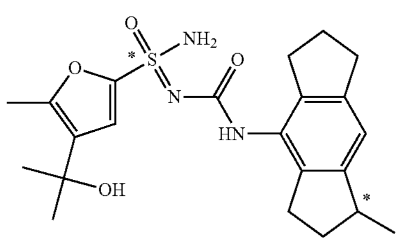 | (S,S)-or (S,R)-4-(2-hydroxypropan-2-yl)-5-methyl-N'-(1-methyl-1,2,3,5,6,7-hexahydros-indacen-4-yl-carbamoyl)furan-2-sulfonimidamide | | 50% EtOH in MTBE; $3^{rd}$ peak | 432.2 |
| 125 | 207b | 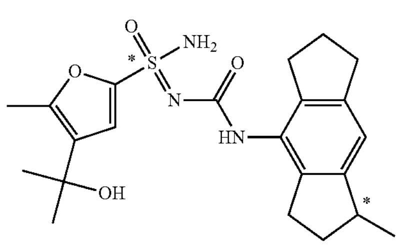 | (S,R)-or (S,S)-4-(2-hydroxypropan-2-yl)-5-methyl-N'-(1-methyl-1,2,3,5,6,7-hexahydros-indacen-4-yl-carbamoyl)furan-2-sulfonimidamide | | 50% EtOH in MTBE; $4^{th}$ peak | 432.2 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 304 | 207a | 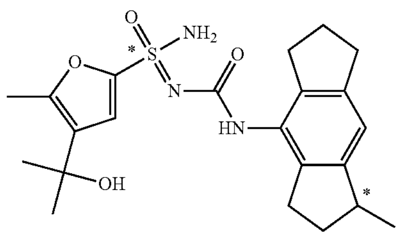 | (R,R) or (R,S)-4-(2-hydroxypropan-2-yl)-5-methyl-N'-((3-methyl-1,2,3,5,6,7-hexahydro-s-indacen-4-yl)carbamoyl)furan-2-sulfonimidamide; resolved from example 123 | CHIRAL-PAK IG, 20*250 mm, 5 um | EtOH in Hex (0.1% FA) | 432 |
| 305 | 207bb | 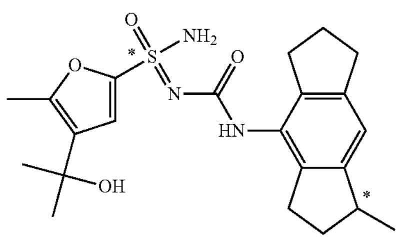 | (R,S) or (R,R)-4-(2-hydroxypropan-2-yl)-5-methyl-N'-((3-methyl-1,2,3,5,6,7-hexahydro-s-indacen-4-yl)carbamoyl)furan-2-sulfonimidamide; resolved from example 123 | CHIRAL-PAK IG, 20*250 mm, 5 um | EtOH in Hex (0.1% FA) | 432 |
| 306 | 366a | 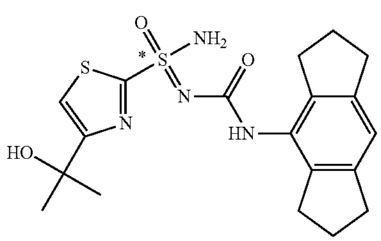 | (R) or (S)-N'-((1,2,3,5,6,7-hexahydro-s-indacen-4-yl)carbamoyl)-4-(2-hydroxypropan-2-yl)thiazole-2-sulfonimidamide | CHIRAL-PAK AS-H, 2*25 cm (5 um) | 35% IPA (2 mM NH3-MeOH) in CO2 | 421 |
| 307 | 366b | 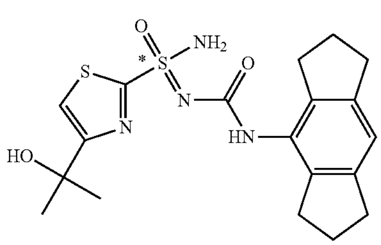 | (S) or (R)-N'-((1,2,3,5,6,7-hexahydro-s-indacen-4-yl)carbamoyl)-4-(2-hydroxypropan-2-yl)thiazole-2-sulfonimidamide | CHIRAL-PAK AS-H, 2*25 cm (5 um) | 35% IPA (2 mM NH3-MeOH) in CO2 | 421 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 308 | 139a | 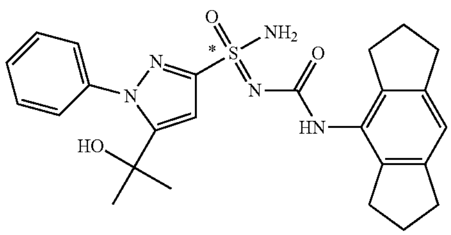 | (S) or (R)-N'-((1,2,3,5,6,7-hexahydro-s-indacen-4-yl)carbamoyl)-5-(2-hydroxypropan-2-yl)-1-phenyl-1H-pyrazole-3-sulfonimidamide | CHIRAL-PAK AS-H, 2*25 cm (5 um) | EtOH in Hex (0.1% DEA) | 480 |
| 309 | 139b | 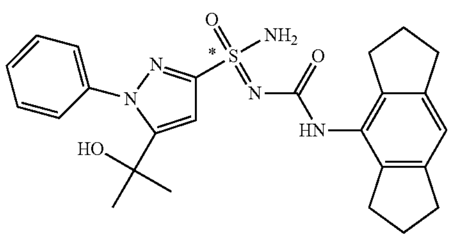 | (R) or (S)-N'-((1,2,3,5,6,7-hexahydro-s-indacen-4-yl)carbamoyl)-5-(2-hydroxypropan-2-yl)-1-phenyl-1H-pyrazole-3-sulfonimidamide | CHIRAL-PAK AS-H, 2*25 cm (5 um) | EtOH in Hex (0.1% DEA) | 480 |
| 310 | 367a | 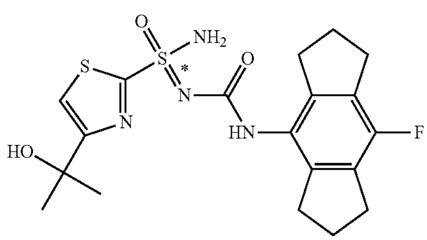 | (R) or (S)-N'-((8-fluoro-1,2,3,5,6,7-hexahydro-s-indacen-4-yl)carbamoyl)-4-(2-hydroxypropan-2-yl)thiazole-2-sulfonimidamide | Chiralpak AS-H 2*25 cm (5 um) | 35% IPA in CO2 | 439 |
| 311 | 367b | 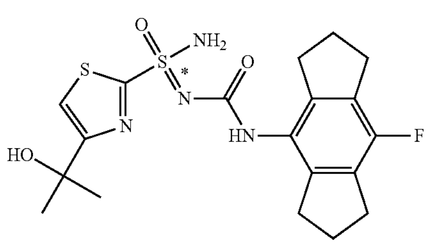 | (S) or (R)-N'-((8-fluoro-1,2,3,5,6,7-hexahydro-s-indacen-4-yl)carbamoyl)-4-(2-hydroxypropan-2-yl)thiazole-2-sulfonimidamide | Chiralpak AS-H 2*25 cm (5 um) | 35% IPA in CO2 | 439 |
| 312 | 409b | 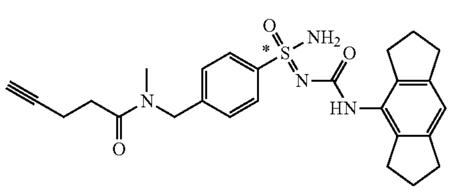 | (S) or (R)-N-(4-(N'-((1,2,3,5,6,7-hexahydro-s-indacen-4-yl)carbamoyl)sulfamidimidoyl)benzyl)-N-methylpent-4-ynamide | CHIRAL ART Cellulose-SB, 2*25 cm, 5 um | EtOH in Hex (8 mM NH3-MeOH) | 479 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 313 | 409a | 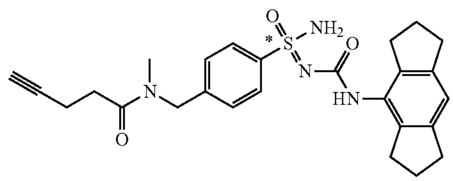 | (R) or (S)-N-(4-(N'-((1,2,3,5,6,7-hexahydro-s-indacen-4-yl)carbamoyl)sulfamidimidoyl)benzyl)-N-methylpent-4-ynamide | CHIRAL ART Cellulose-SB, 2*25 cm, 5 um | EtOH in Hex (8 mM NH₃• MeOH) | 479 |
| 314 | 369a | 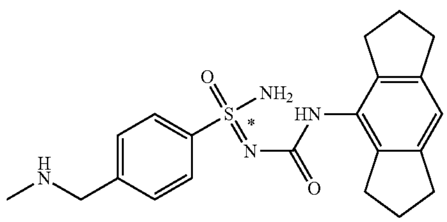 | (S) or (R)-N'-((1,2,3,5,6,7-hexahydro-s-indacen-4-yl)carbamoyl)-4-((methylamino)methyl)benzenesulfonimidamide | Chiralpak ID-2, 2*25 cm, 5 um | EtOH in Hex (8 mM NH₃• MeOH) | 399 |
| 315 | 369b | 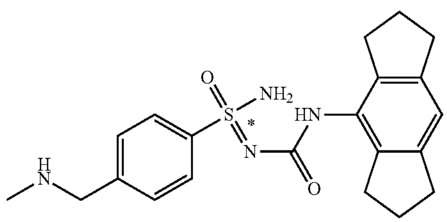 | (R) or (S)-N'-((1,2,3,5,6,7-hexahydro-s-indacen-4-yl)carbamoyl)-4-((methylamino)methyl)benzenesulfonimidamide | Chiralpak ID-2, 2*25 cm, 5 um | EtOH in Hex (8 mM NH₃• MeOH) | 399 |
| 316 | 159a | 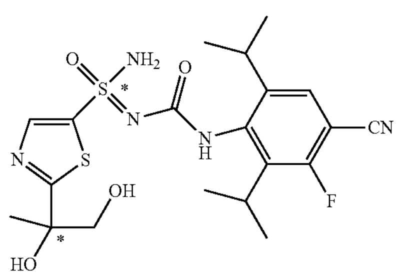 | Two isomers of (R,R) or (R,S) or (S,S) or (S,R)-N'-((4-cyano-3-fluoro-2,6-diisopropylphenyl)carbamoyl)-2-(1,2-dihydroxypropan-2-yl)thiazole-5-sulfonimidamide | CHIRAL ART Cellulose-SB, 2*25 cm, 5 um | EtOH in Hex (0.1% FA) 1ˢᵗ and 2ⁿᵈ peak | 484 |
| 317 | 159ab | 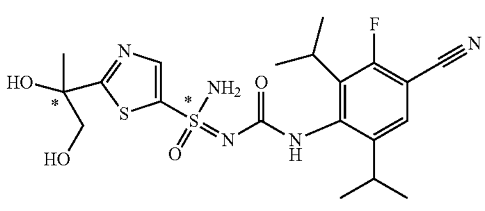 | (R,R) or (R,S) or (S,S) or (S,R)-N-((4-cyano-3-fluoro-2,6-diisopropylphenyl)carbamoyl)-2-(1,2-di- | CHIRAL ART Cellulose-SB, 2*25 cm, 5 um | EtOH in Hex (0.1% FA) 3ʳᵈ peak | 484 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| | | | hydroxy-propan-2-yl)thiazole-5-sulfonimidamide | | | |
| 318 | 159ba | 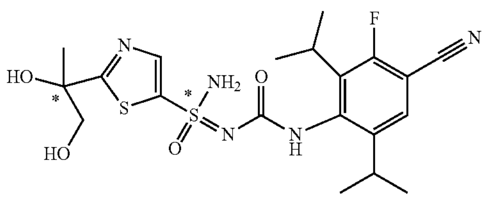 | (S,S) or (S,R) or (R,R) or (R,S)-N-((4-cyano-3-fluoro-2,6-diisopropylphenyl)carbamoyl)-2-(1,2-dihydroxypropan-2-yl)thiazole-5-sulfonimidamide | CHIRAL ART Cellulose-SB, 2*25 cm, 5 um | EtOH in Hex (0.1% FA) 4th peak | 484 |
| 319 | 137a | 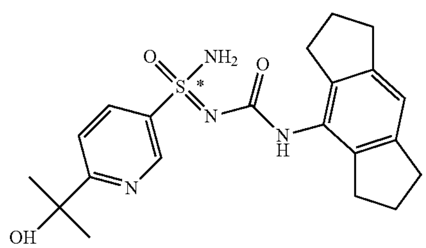 | (S) or (R)-N'-((1,2,3,5,6,7-hexahydro-s-indacen-4-yl)carbamoyl)-6-(2-hydroxypropan-2-yl)pyridine-3-sulfonimidamide | CHIRAL ART Cellulose-SB, 2*25 cm, 5 um | EtOH in Hex (0.1% FA) | 415 |
| 320 | 137b | 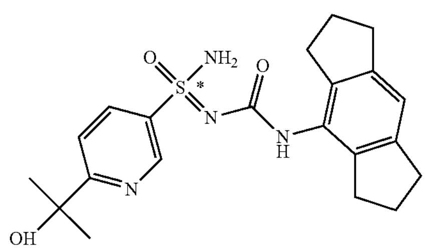 | (R) or (S)-N'-((1,2,3,5,6,7-hexahydro-s-indacen-4-yl)carbamoyl)-6-(2-hydroxypropan-2-yl)pyridine-3-sulfonimidamide | CHIRAL ART Cellulose-SB, 2*25 cm, 5 um | EtOH in Hex (0.1% FA) | 415 |
| 321 | 317ab | 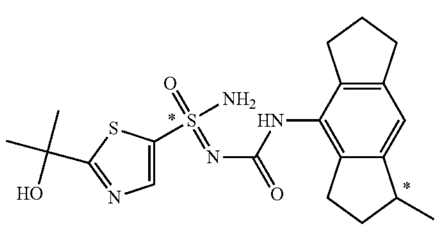 | (S,S) or (S,R)-2-(2-hydroxypropan-2-yl)-N'-((1-methyl-1,2,3,5,6,7-hexahydro-s-indacen-4-yl)carbamoyl)thiazole-5-sulfonimidamide (from Example 291) | 1st and 2nd peak (two isomers) Faster-eluting on column 1: CHIRAL ART Cellulose-SB, 2*25 cm, 5 um, IPA in Hex (0.1% FA). Separated further on column 2: CHIRALPAK IE, EtOH in MTBE (0.1% FA) to obtain single isomers. | | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 322 | 317aa | 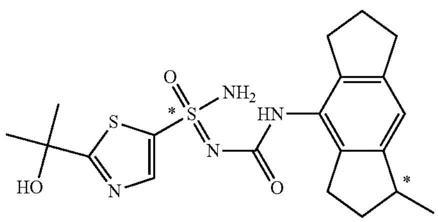 | (S,R) or (S,S)-2-(2-hydroxypropan-2-yl)-N'-((1-methyl-1,2,3,5,6,7-hexahydro-s-indacen-4-yl)carbamoyl)thiazole-5-sulfonimidamide (from Example 291) | | | 435 |
| 323 | 317bb | 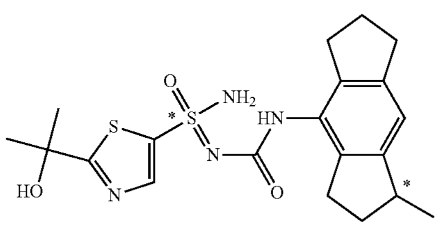 | (R,R) or (R,S)-2-(2-hydroxypropan-2-yl)-N'-((1-methyl-1,2,3,5,6,7-hexahydro-s-indacen-4-yl)carbamoyl)thiazole-5-sulfonimidamide (from Example 291) | CHIRAL ART Cellulose-SB, 2*25 cm, 5 um | IPA in Hex (0.1% FA) 3$^{rd}$ peak | 435 |
| 324 | 317ba | 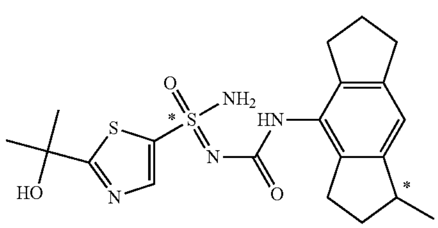 | (R,S) or (R,R)-2-(2-hydroxypropan-2-yl)-N'-((1-methyl-1,2,3,5,6,7-hexahydro-s-indacen-4-yl)carbamoyl)thiazole-5-sulfonimidamide (from Example 291) | | IPA in Hex (0.1% FA) 4$^{th}$ peak | 435 |
| 325 | 316a | 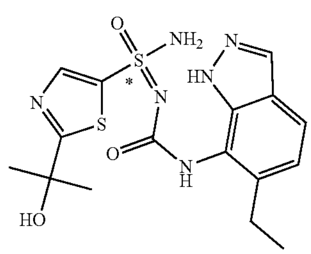 | (S) or (R)-N'-((6-ethyl-1H-indazol-7-yl)carbamoyl)-2-(2-hydroxypropan-2-yl)thiazole-5-sulfonimidamide | Chiralpak ID, 2*25 cm, 5 um | EtOH in Hex (0.1% FA) | 409 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 326 | 316b | 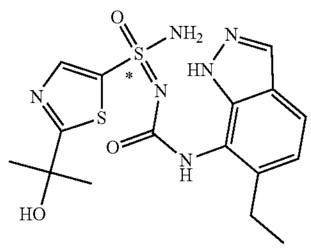 | (R) or (S)-N'-((6-ethyl-1H-indazol-7-yl)carbamoyl)-2-(2-hydroxypropan-2-yl)thiazole-5-sulfonimidamide | Chiralpak ID, 2*25 cm, 5 um | EtOH in Hex (0.1% FA) | 409 |
| 327 | 373a | 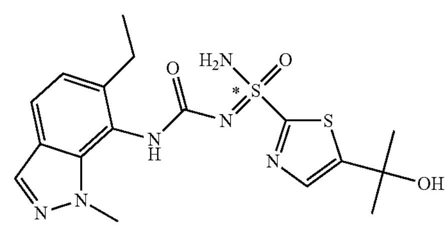 | (S) or (R)-N'-((6-ethyl-1-methyl-1H-indazol-7-yl)carbamoyl)-5-(2-hydroxypropan-2-yl)thiazole-2-sulfonimidamide | CHIRALPAK IG, 20*250 mm, 5 um | EtOH in Hex (0.1% FA) | 423 |
| 328 | 373b | 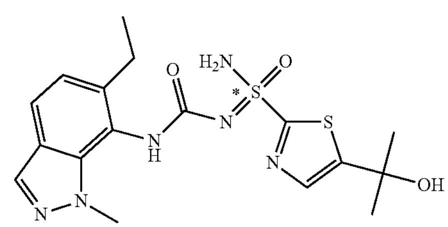 | (R) or (S)-N'-((6-ethyl-1-methyl-1H-indazol-7-yl)carbamoyl)-5-(2-hydroxypropan-2-yl)thiazole-2-sulfonimidamide | CHIRALPAK IG, 20*250 mm, 5 um | EtOH in Hex (0.1% FA) | 423 |
| 329 | 374a | 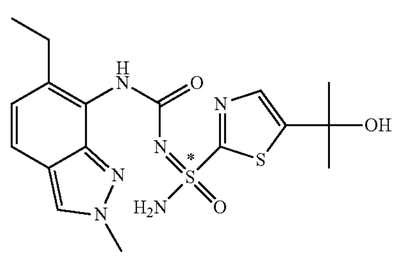 | (S) or (R)-N'-((6-ethyl-2-methyl-2H-indazol-7-yl)carbamoyl)-5-(2-hydroxypropan-2-yl)thiazole-2-sulfonimidamide | CHIRAL ART Cellulose-SB S-5 um, 250*20 mm | EtOH in Hex (0.1% FA) | 423 |
| 330 | 374b | 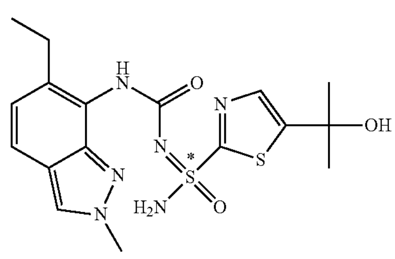 | (R) or (S)-N'-((6-ethyl-2-methyl-2H-indazol-7-yl)carbamoyl)-5-(2-hydroxypropan-2-yl)thiazole-2-sulfonimidamide | CHIRAL ART Cellulose-SB S-5 um, 250*20 mm | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 331 | 319ab | 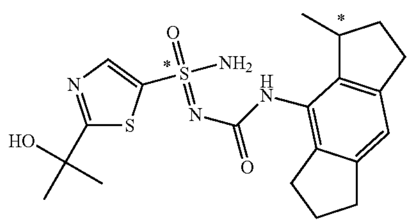 | (S,S) or (S,R)-2-(2-hydroxypropan-2-yl)-N'-((3-methyl-1,2,3,5,6,7-hexahydro-s-indacen-4-yl)carbamoyl)thiazole-5-sulfonimidamide | 1st peak CHIRAL ART Cellulose-SB, 2*25 cm, 5 um | EtOH in Hex (0.1% FA) | 435 |
| 332 | 319aa | 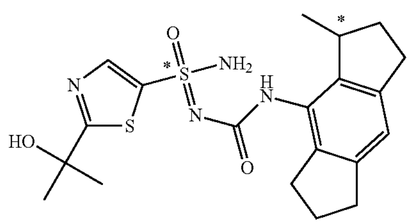 | (R,R) or (R,S)-2-(2-hydroxypropan-2-yl)-N'-((3-methyl-1,2,3,5,6,7-hexahydro-s-indacen-4-yl)carbamoyl)thiazole-5-sulfonimidamide | 2nd peak CHIRAL ART Cellulose-SB, 2*25 cm, 5 um | EtOH in Hex (0.1% FA) | 435 |
| 333 | 319bb | 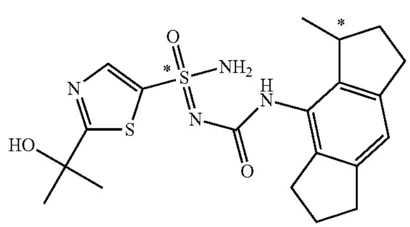 | (S,R) or (S,S)-2-(2-hydroxypropan-2-yl)-N'-((3-methyl-1,2,3,5,6,7-hexahydro-s-indacen-4-yl)carbamoyl)thiazole-5-sulfonimidamide | 3rd peak CHIRAL ART Cellulose-SB, 2*25 cm, 5 um | EtOH in Hex (0.1% FA) | 435 |
| 334 | 319ba | 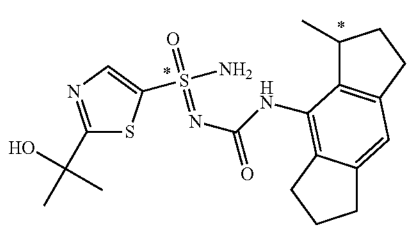 | (R,S) or (R,R)-2-(2-hydroxypropan-2-yl)-N'-((3-methyl-1,2,3,5,6,7-hexahydro-s-indacen-4-yl)carbamoyl)thiazole-5-sulfonimidamide | 4th peak CHIRAL ART Cellulose-SB, 2*25 cm, 5 um | EtOH in Hex (0.1% FA) | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 335 | 320a | 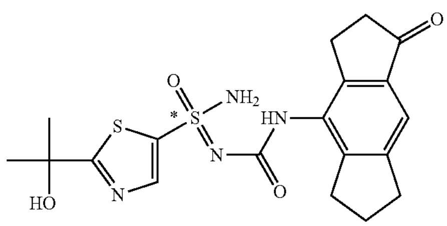 | (S) or (R)-2-(2-Hydroxy-propan-2-yl)-N'-((1-oxo-1,2,3,5,6,7-hexahydro-s-indacen-4-yl)carbamoyl)thiazole-5-sulfonimidamide from Example 293 | Chiralpak IA, 2*25 cm, 5 um | EtOH in Hex (0.1% FA) | 435 |
| 336 | 320b | 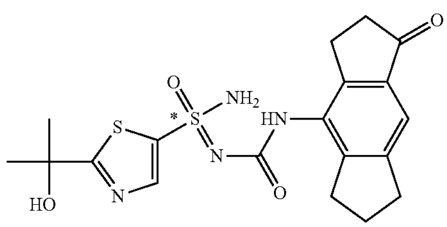 | (R) or (S)-2-(2-Hydroxy-propan-2-yl)-N'-((1-oxo-1,2,3,5,6,7-hexahydro-s-indacen-4-yl)carbamoyl)thiazole-5-sulfonimidamide from Example 293 | Chiralpak IA, 2*25 cm, 5 um | EtOH in Hex (0.1% FA) | 435 |
| 337 | 323ab | 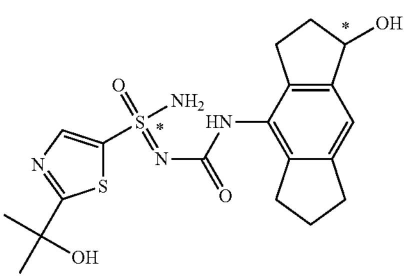 | (R,R) or (R,S)-N'-((1-hydroxy-1,2,3,5,6,7-hexahydro-s-indacen-4-yl)carbamoyl)-2-(2-hydroxy-propan-2-yl)thiazole-5-sulfonimidamide (from example 336) | CHIRAL-PAK AD, 2*25 cm, 5 um | EtOH (0.1% DEA) in CO$_2$, 1$^{st}$ peak | 437 |
| 338 | 323bb | 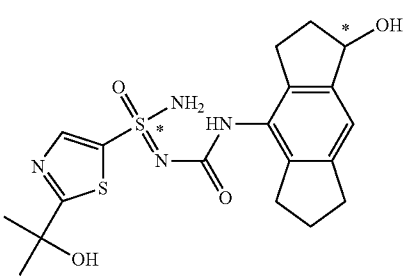 | (R,S) or (R,R)-N'-((1-hydroxy-1,2,3,5,6,7-hexahydro-s-indacen-4-yl)carbamoyl)-2-(2-hydroxy-propan-2-yl)thiazole-5-sulfonimidamide (from example 336) | | EtOH (0.1% DEA) in CO$_2$, 2$^{nd}$ peak | 437 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 339 | 323aa | 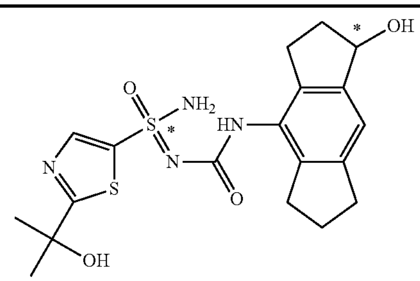 | (S,S) or (S,R)-N'-((1-hydroxy-1,2,3,5,6,7-hexahydro-s-indacen-4-yl)carbamoyl)-2-(2-hydroxypropan-2-yl)thiazole-5-sulfonimidamide (from example 335) | CHIRAL-PAK AD, 2*25 cm, 5 um | EtOH (0.1% DEA) in CO$_2$, 1$^{st}$ peak | 437 |
| 340 | 323ba | 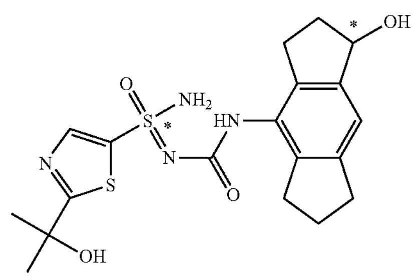 | (S,R) or (S,S)-N'-((1-hydroxy-1,2,3,5,6,7-hexahydro-s-indacen-4-yl)carbamoyl)-2-(2-hydroxypropan-2-yl)thiazole-5-sulfonimidamide (from example 335) | | EtOH (0.1% DEA) in CO$_2$, 2$^{nd}$ peak | 437 |
| 341 | 303a | 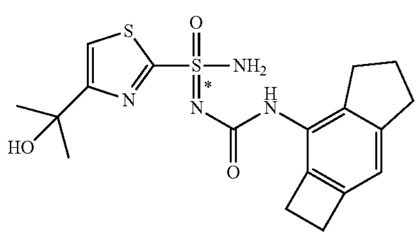 | (R) or (S)-4-(2-hydroxypropan-2-yl)-N'-((2,4,5,6-tetrahydro-1H-cyclobuta[f]inden-3-yl)carbamoyl)thiazole-2-sulfonimidamide | Chiralpak ID, 2*25 cm, 5 um | EtOH in Hex (0.1% FA) | 407 |
| 342 | 303b | 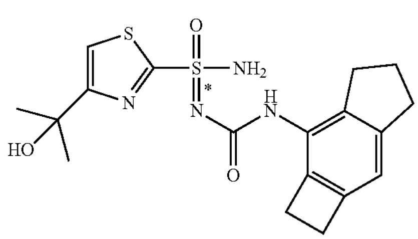 | (R) or (S)-4-(2-hydroxypropan-2-yl)-N'-((2,4,5,6-tetrahydro-1H-cyclobuta[f]inden-3-yl)carbamoyl)thiazole-2-sulfonimidamide | Chiralpak ID, 2*25 cm, 5 um | EtOH in Hex (0.1% FA) | 407 |
| 343 | 315a | 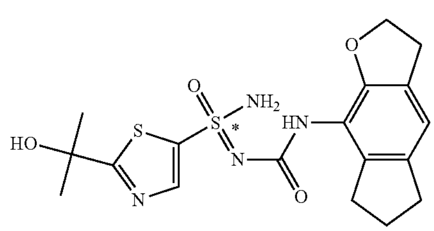 | (R) or (S)-2-(2-hydroxypropan-2-yl)-N'-((3,5,6,7-tetrahydro-2H-indeno[5,6-b]furan-8-yl)carbamoyl)thiazole-5-sulfonimidamide | Chiralpak ID, 2*25 cm, 5 um | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 344 | 315b | 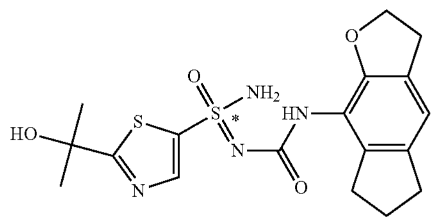 | (R) or (S)-2-(2-hydroxypropan-2-yl)-N'-((3,5,6,7-tetrahydro-2H-indeno[5,6-b]furan-8-yl)carbamoyl)thiazole-5-sulfonimidamide | Chiralpak ID, 2*25 cm, 5 um | EtOH in Hex (0.1% FA) | 423 |
| 345 | 138a | 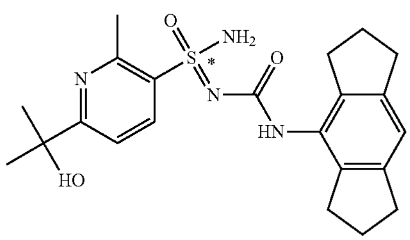 | (R) or (S)-N'-((1,2,3,5,6,7-hexahydro-s-indacen-4-yl)carbamoyl)-6-(2-hydroxypropan-2-yl)-2-methylpyridine-3-sulfonimidamide | CHIRALPAK IF, 2*25 cm, 5 um | EtOH in Hex (8 mM NH₃• MeOH) | 429 |
| 346 | 138b | 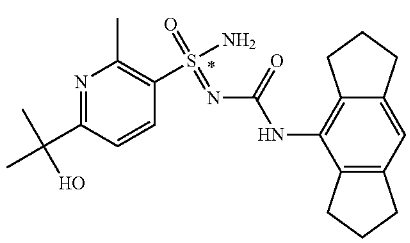 | (R) or (S)-N'-((1,2,3,5,6,7-hexahydro-s-indacen-4-yl)carbamoyl)-6-(2-hydroxypropan-2-yl)-2-methylpyridine-3-sulfonimidamide | CHIRALPAK IF, 2*25 cm, 5 um | EtOH in Hex (8 mM NH₃• MeOH) | 429 |
| 347 | 328a | 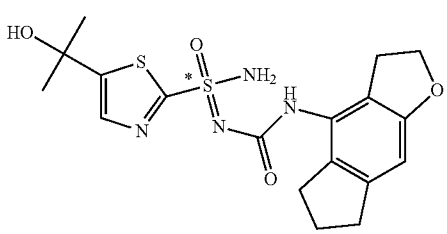 | (R) or (S)-5-(2-hydroxypropan-2-yl)-N'-((3,5,6,7-tetrahydro-2H-indeno[5,6-b]furan-4-yl)carbamoyl)thiazole-2-sulfonimidamide | CHIRALPAK IC, 2*25 cm, 5 um | EtOH in Hex (0.1% FA) | 423 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 348 | 328b | 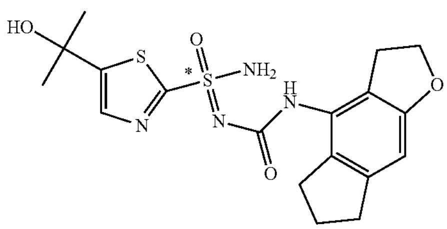 | (S) or (R)-5-(2-hydroxy-propan-2-yl)-N'-((3,5,6,7-tetrahydro-2H-indeno[5,6-b]furan-4-yl)carbamoyl)thiazole-2-sulfonimidamide | CHIRAL-PAK IC, 2*25 cm, 5 um | EtOH in Hex (0.1% FA) | 423 |
| 349 | 326b | 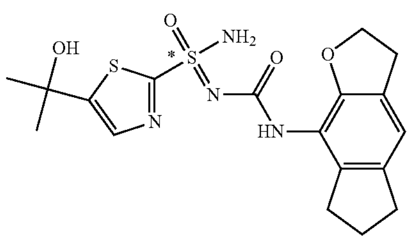 | (S) or (R)-5-(2-hydroxy-propan-2-yl)-N'-((3,5,6,7-tetrahydro-2H-indeno[5,6-b]furan-8-yl)carbamoyl)thiazole-2-sulfonimidamide | CHIRAL-PAK IG, 20*250 mm, 5 um | IPA in Hex: DCM = 5:1 (0.1% FA) | 423 |
| 350 | 326a | 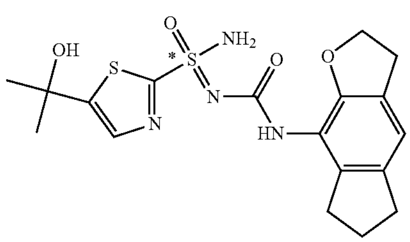 | (R) or (S)-5-(2-hydroxy-propan-2-yl)-N'-((3,5,6,7-tetrahydro-2H-indeno[5,6-b]furan-8-yl)carbamoyl)thiazole-2-sulfonimidamide | CHIRAL-PAK IG, 20*250 mm, 5 um | IPA in Hex: DCM = 5:1 (0.1% FA) | 423 |
| 351 | 318a | 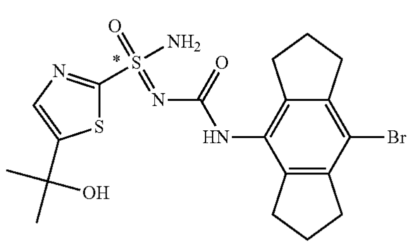 | (S) or (R)-N'-((8-bromo-1,2,3,5,6,7-hexahydro-s-indacen-4-yl)carbamoyl)-5-(2-hydroxy-propan-2-yl)thiazole-2-sulfonimidamide | CHIRAL ART Cellulose-SB S-5 um, 2*25 cm, 5 um | EtOH in Hex (8 mM NH3• MeOH) | 499 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 352 | 318b | 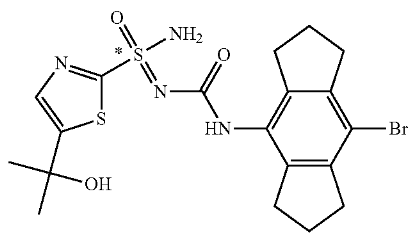 | (R) or (S)-N'-((8-bromo-1,2,3,5,6,7-hexahydro-s-indacen-4-yl)carbamoyl)-5-(2-hydroxypropan-2-yl)thiazole-2-sulfonimidamide | CHIRAL ART Cellulose-SB S-5 um, 2*25 cm, 5 um | EtOH in Hex (8 mM NH3• MeOH) | 499 |
| 353 | 325a | 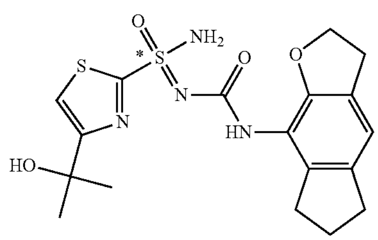 | (S) or (R)-4-(2-hydroxypropan-2-yl)-N'-((3,5,6,7-tetrahydro-2H-indeno[5,6-b]furan-8-yl)carbamoyl)thiazole-2-sulfonimidamide | CHIRAL ART Cellulose-SB, 2*25 cm, 5 um | EtOH in Hex (0.1% FA) | 423 |
| 354 | 325b | 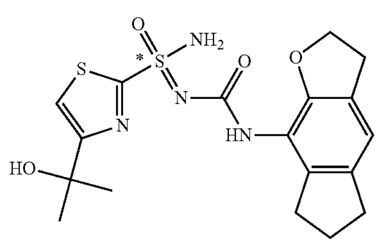 | (R) or (S)-4-(2-hydroxypropan-2-yl)-N'-((3,5,6,7-tetrahydro-2H-indeno[5,6-b]furan-8-yl)carbamoyl)thiazole-2-sulfonimidamide | CHIRAL ART Cellulose-SB, 2*25 cm, 5 um | EtOH in Hex (0.1% FA) | 423 |
| 355 | 329a | 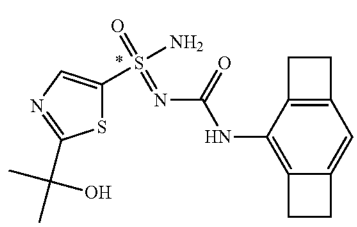 | (R) or (S)-2-(2-hydroxypropan-2-yl)-N'-(tricyclo[6.2.0.0³,⁶]deca-1,3(6),7-trien-2-ylcarbamoyl)thiazole-5-sulfonimidamide | Chiralpak ID, 2*25 cm, 5 um | IPA in Hex (0.1% FA) | 393 |
| 356 | 329b | 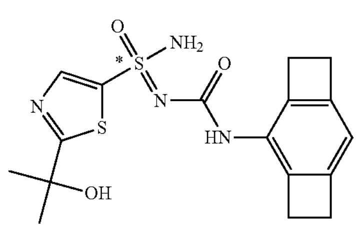 | (S) or (R)-2-(2-hydroxypropan-2-yl)-N'-(tricyclo[6.2.0.0³,⁶]deca-1,3(6),7-trien-2-ylcarbamoyl)thiazole-5-sulfonimidamide | Chiralpak ID, 2*25 cm, 5 um | IPA in Hex (0.1% FA) | 393 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 357 | 404b | 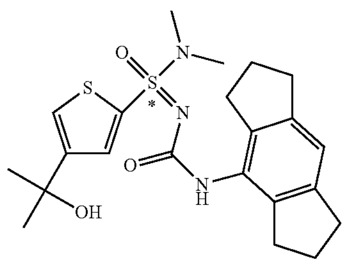 | (R) or (S)-N'-((1,2,3,5,6,7-hexahydro-s-indacen-4-yl)carbamoyl)-4-(2-hydroxypropan-2-yl)-N,N-dimethylthiophene-2-sulfonimidamide | CHIRALPAK IG, 20*250 mm, 5 um | IPA in Hex: DCM = 3:1 (10 mM NH$_3$-MeOH) | 448 |
| 358 | 404a | 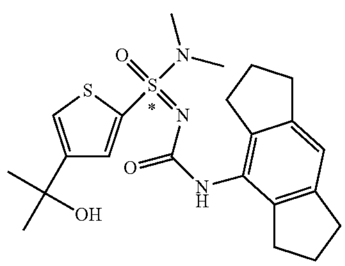 | (S) or (R)-N'-((1,2,3,5,6,7-hexahydro-s-indacen-4-yl)carbamoyl)-4-(2-hydroxypropan-2-yl)-N,N-dimethylthiophene-2-sulfonimidamide | CHIRALPAK IG, 20*250 mm, 5 um | IPA in Hex: DCM = 3:1 (10 mM NH$_3$-MeOH) | 448 |
| 359 | 332a | 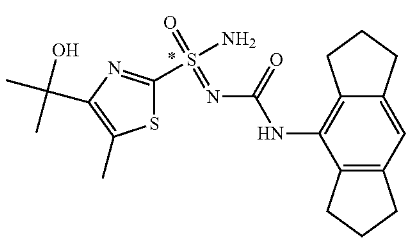 | (R) or (S)-N'-((1,2,3,5,6,7-hexahydro-s-indacen-4-yl)carbamoyl)-4-(2-hydroxypropan-2-yl)-5-methylthiazole-2-sulfonimidamide | Chiralpak ID, 2*25 cm, 5 um | IPA in Hex (0.1% FA) | 435 |
| 360 | 332b | 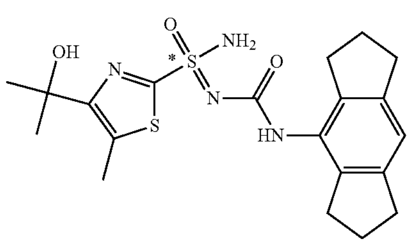 | (S) or (R)-N'-((1,2,3,5,6,7-hexahydro-s-indacen-4-yl)carbamoyl)-4-(2-hydroxypropan-2-yl)-5-methylthiazole-2-sulfonimidamide | Chiralpak ID, 2*25 cm, 5 um | IPA in Hex (0.1% FA) | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 361 | 335a | 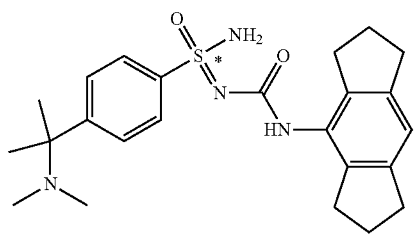 | (R) or (S)-4-(2-(dimethyl-amino)propan-2-yl)-N'-((1,2,3,5,6,7-hexahydro-s-indacen-4-yl)carbamoyl)benzene-sulfonimi-damide | CHIRAL-PAK IG, 2.0*25 cm (5 um) | IPA in Hex (8 mM $NH_3$-MeOH) | 441 |
| 362 | 335b | 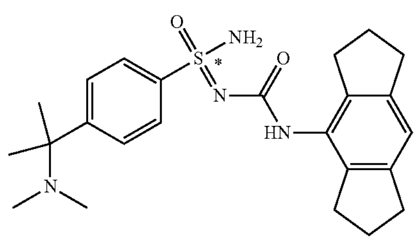 | (S) or (R)-4-(2-(dimethyl-amino)propan-2-yl)-N'-((1,2,3,5,6,7-hexahydro-s-indacen-4-yl)carbamoyl)benzene-sulfonimi-damide | CHIRAL-PAK IG, 2.0*25 cm (5 um) | IPA in Hex (8 mM $NH_3$-MeOH) | 441 |
| 363 | 336a | 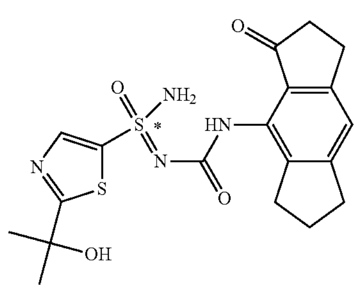 | (S) or (R)-2-(2-Hydroxy-propan-2-yl)-N'-((3-oxo-1,2,3,5,6,7-hexahydro-s-indacen-4-yl)carbamoyl)thiazole-5-sulfonimi-damide | CHIRAL ART Cellu-lose-SB, 2*25 cm, 5 um | EtOH in MTBE (10 mM $NH_3$-MeOH) | 435 |
| 364 | 336b | 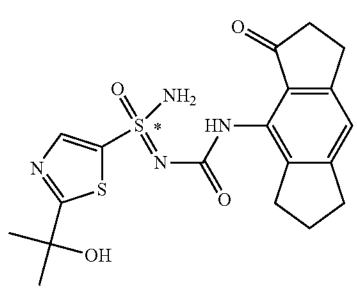 | (R) or (S)-2-(2-Hydroxy-propan-2-yl)-N'-((3-oxo-1,2,3,5,6,7-hexahydro-s-indacen-4-yl)carbamoyl)thiazole-5-sulfonimi-damide | CHIRAL ART Cellu-lose-SB, 2*25 cm, 5 um | EtOH in MTBE (10 mM $NH_3$-MeOH) | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 365 | 337a | 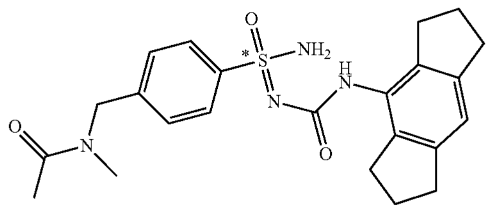 | (S) or (R)-N-(4-(N'-((1,2,3,5,6,7-hexahydro-s-indacen-4-yl)carbamoyl)sulfamidimidoyl)benzyl)-N-methylacetamide | CHIRAL ART Cellulose-SB, 2*25 cm, 5 um | EtOH in Hex (8 mM NH₃-MeOH) | 441 |
| 366 | 337b | 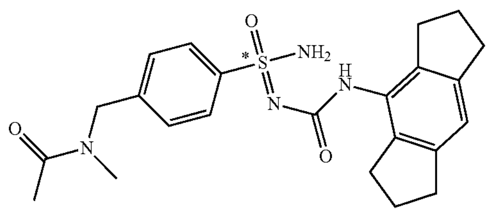 | (R) or (S)-N-(4-(N'-((1,2,3,5,6,7-hexahydro-s-indacen-4-yl)carbamoyl)sulfamidimidoyl)benzyl)-N-methylacetamide | CHIRAL ART Cellulose-SB, 2*25 cm, 5 um | EtOH in Hex (8 mM NH₃-MeOH) | 441 |
| 367 | 371a | 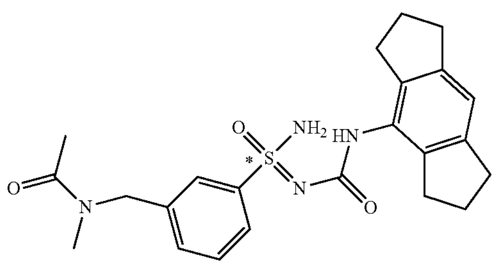 | (S) or (R)-N-(3-(N'-((1,2,3,5,6,7-hexahydro-s-indacen-4-yl)carbamoyl)sulfamidimidoyl)benzyl)-N-methylacetamide | CHIRAL ART Cellulose-SB, 2*25 cm, 5 um | EtOH in Hex (8 mM NH₃-MeOH) | 441 |
| 368 | 371b | 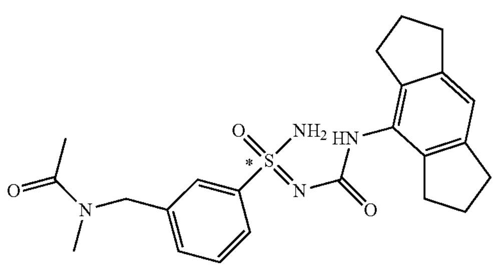 | (R) or (S)-N-(3-(N'-((1,2,3,5,6,7-hexahydro-s-indacen-4-yl)carbamoyl)sulfamidimidoyl)benzyl)-N-methylacetamide | CHIRAL ART Cellulose-SB, 2*25 cm, 5 um | EtOH in Hex (8 mM NH₃-MeOH) | 441 |
| 369 | 372a | 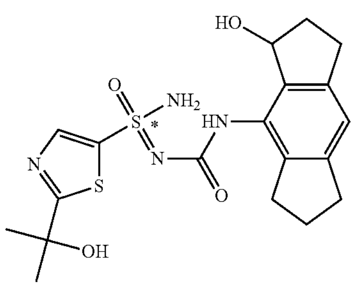 | (S,R/S) or (R,R/S)-N'-((3-hydroxy-1,2,3,5,6,7-hexahydro-s-indacen-4-yl)carbamoyl)-2-(2-hydroxypropan-2-yl)thiazole-5-sulfonimidamide | Obtained from Example 363 | N/A | 435 (M − 1) |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 370 | 372b | 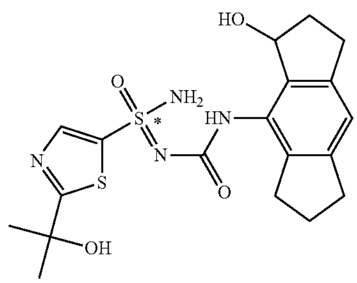 | (R,R/S) or (S,R/S)-N'-((3-hydroxy-1,2,3,5,6,7-hexahydro-s-indacen-4-yl)carbamoyl)-2-(2-hydroxypropan-2-yl)thiazole-5-sulfonimidamide | Obtained from Example 364 | N/A | 435 (M − 1) |
| 371 | 334a | 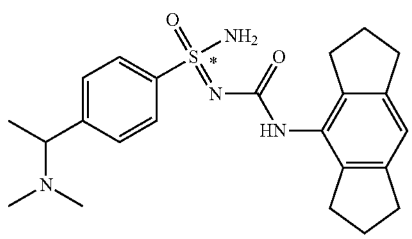 | (S) or (R)-4-(1-(dimethylamino)ethyl)-N'-((1,2,3,5,6,7-hexahydro-s-indacen-4-yl)carbamoyl)benzenesulfonimidamide | CHIRAL ART Cellulose-SB, 2*25 cm, 5 um | IPA in Hex (8 mM NH$_3$-MeOH) | 427 |
| 372 | 334b | 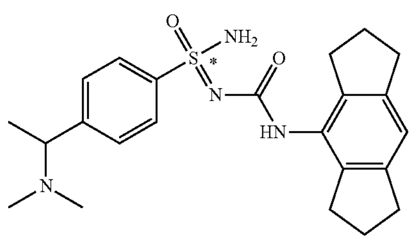 | (R) or (S)-4-(1-(dimethylamino)ethyl)-N'-((1,2,3,5,6,7-hexahydro-s-indacen-4-yl)carbamoyl)benzenesulfonimidamide | CHIRAL ART Cellulose-SB, 2*25 cm, 5 um | IPA in Hex (8 mM NH$_3$-MeOH) | 427 |
| 373 | 339a | 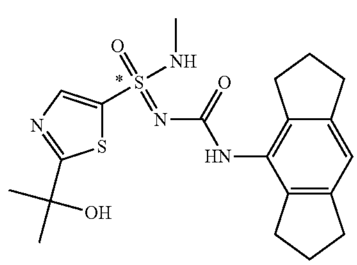 | (R) or (S)-N'-((1,2,3,5,6,7-hexahydro-s-indacen-4-yl)carbamoyl)-2-(2-hydroxypropan-2-yl)-N-methylthiazole-5-sulfonimidamide | CHIRAL-PAK IE, 2*25 cm, 5 um | IPA in Hex (8 mM NH$_3$-MeOH) | 435 |
| 374 | 339b | 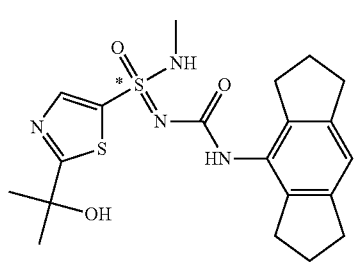 | (S) or (R)-N'-((1,2,3,5,6,7-hexahydro-s-indacen-4-yl)carbamoyl)-2-(2-hydroxypropan-2-yl)-N-methylthiazole-5-sulfonimidamide | CHIRAL-PAK IE, 2*25 cm, 5 um | IPA in Hex (8 mM NH$_3$-MeOH) | 435 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 375 | 334ab | 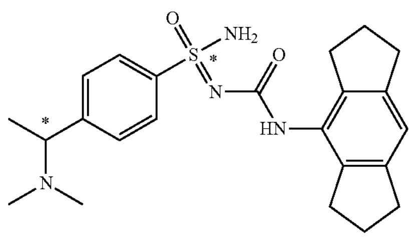 | (S,R) or (S,S) or (R,S) or (R,R)-4-(1-(dimethylamino)ethyl)-N'-((1,2,3,5,6,7-hexahydro-s-indacen-4-yl)carbamoyl)benzenesulfonimidamide | CHIRAL-PAK IG, 20*250 mm, 5 um | EtOH in Hex (8 mM NH$_3$-MeOH) | 427 |
| 376 | 334aa | 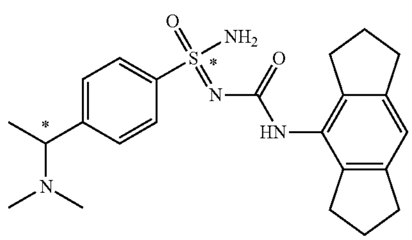 | (S,S) or (S,R) or (R,R) or (R,S)-4-(1-(dimethylamino)ethyl)-N'-((1,2,3,5,6,7-hexahydro-s-indacen-4-yl)carbamoyl)benzenesulfonimidamide | CHIRAL-PAK IG, 20*250 mm, 5 um | EtOH in Hex (8 mM NH$_3$-MeOH) | 427 |
| 377 | 334bb | 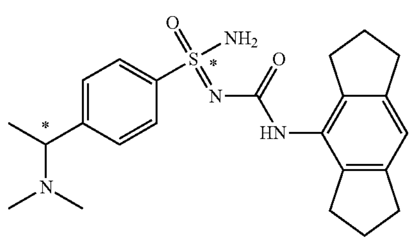 | (R,R) or (R,S) or (S,S) or (S,R)-4-(1-(dimethylamino)ethyl)-N'-((1,2,3,5,6,7-hexahydro-s-indacen-4-yl)carbamoyl)benzenesulfonimidamide | CHIRAL-PAK IG, 20*250 mm, 5 um | EtOH in Hex (8 mM NH$_3$-MeOH) | 427 |
| 378 | 334ba | 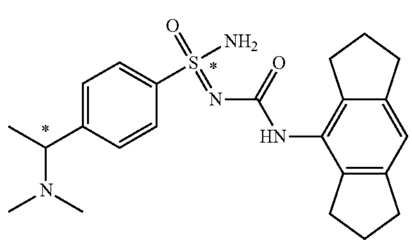 | (R,S) or (R,R) or (S,R) or (S,S)-4-(1-(dimethylamino)ethyl)-N'-((1,2,3,5,6,7-hexahydro-s-indacen-4-yl)carbamoyl)benzenesulfonimidamide | CHIRAL-PAK IG, 20*250 mm, 5 um | EtOH in Hex (8 mM NH$_3$-MeOH) | 427 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 379 | 338a | 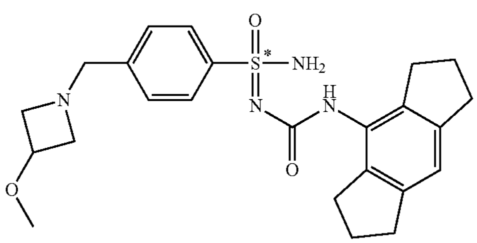 | (R) or (S)-N'-((1,2,3,5,6,7-hexahydro-s-indacen-4-yl)carbamoyl)-4-((3-methoxyazetidin-1-yl)methyl)benzenesulfonimidamide | CHIRAL-PAK IF, 2*25 cm, 5 um | EtOH in Hex (8 mM NH3-MeOH) | 455 |
| 380 | 338b | 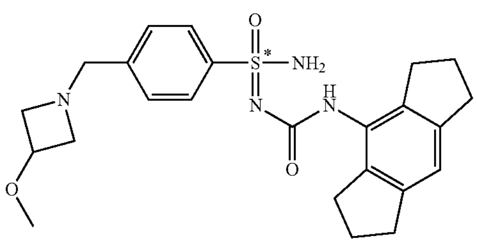 | (S) or (R)-N'-((1,2,3,5,6,7-hexahydro-s-indacen-4-yl)carbamoyl)-4-((3-methoxyazetidin-1-yl)methyl)benzenesulfonimidamide | CHIRAL-PAK IF, 2*25 cm, 5 um | EtOH in Hex (8 mM NH3-MeOH) | 455 |
| 381 | 340a | 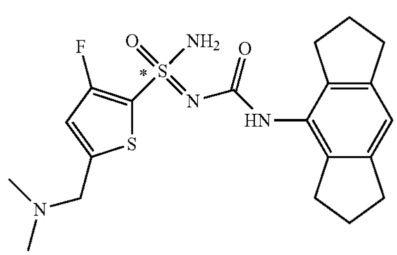 | (R) or (S)-5-((dimethylamino)methyl)-3-fluoro-N'-((1,2,3,5,6,7-hexahydro-s-indacen-4-yl)carbamoyl)thiophene-2-sulfonimidamide | CHIRAL-PAK IG, 20*250 mm, 5 um | Hex (0.1% DEA): EtOH = 50:50 | 437 |
| 382 | 340b | 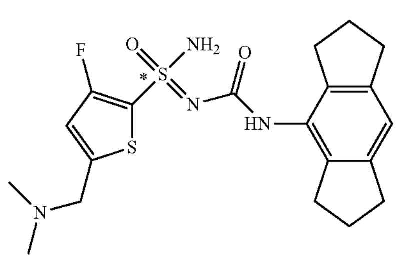 | (S) or (R)-5-((dimethylamino)methyl)-3-fluoro-N'-((1,2,3,5,6,7-hexahydro-s-indacen-4-yl)carbamoyl)thiophene-2-sulfonimidamide | CHIRAL-PAK IG, 20*250 mm, 5 um | Hex (0.1% DEA): EtOH = 50:50 | 437 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]⁺ |
|---|---|---|---|---|---|---|
| 383 | 361b | 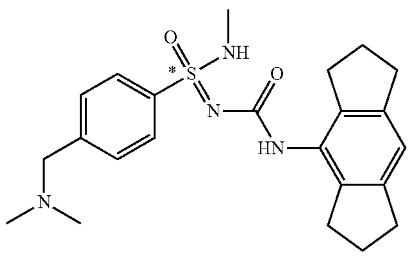 | (R) or (S)-4-((dimethylamino)methyl)-N'-((1,2,3,5,6,7-hexahydro-s-indacen-4-yl)carbamoyl)-N-methylbenzenesulfonimidamide | CHIRALPAK IE, 2*25 cm, 5 um | EtOH in Hex (8 mM NH$_3$-MeOH) | 427 |
| 384 | 361a | 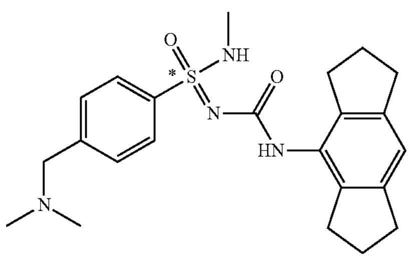 | (S) or (R)-4-((dimethylamino)methyl)-N'-((1,2,3,5,6,7-hexahydro-s-indacen-4-yl)carbamoyl)-N-methylbenzenesulfonimidamide | CHIRALPAK IE, 2*25 cm, 5 um | EtOH in Hex (8 mM NH$_3$-MeOH) | 427 |
| 385 | 113a | 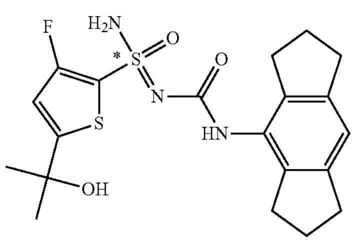 | (R) or (S)-3-fluoro-N'-((1,2,3,5,6,7-hexahydro-s-indacen-4-yl)carbamoyl)-5-(2-hydroxypropan-2-yl)thiophene-2-sulfonimidamide | CHIRALPAK IG, 20*250 mm, 5 um | IPA in Hex (8 mM NH$_3$-MeOH) | 438 |
| 386 | 113b | 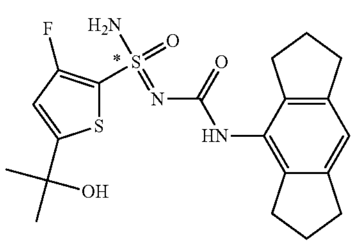 | (S) or (R)-3-fluoro-N'-((1,2,3,5,6,7-hexahydro-s-indacen-4-yl)carbamoyl)-5-(2-hydroxypropan-2-yl)thiophene-2-sulfonimidamide | CHIRALPAK IG, 20*250 mm, 5 um | IPA in Hex (8 mM NH$_3$-MeOH) | 438 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]⁺ |
|---|---|---|---|---|---|---|
| 387 | 330a | 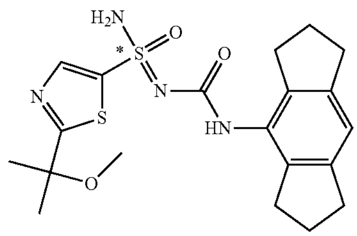 | (S) or (R)-N'-((1,2,3,5,6,7-hexahydro-s-indacen-4-yl)carbamoyl)-2-(2-methoxypropan-2-yl)thiazole-5-sulfonimidamide | CHIRAL ART Cellulose-SB, 2*25 cm, 5 um | EtOH in Hex (8 mM NH₃-MeOH) | 435 |
| 388 | 330b | 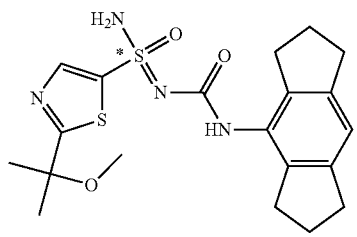 | (R) or (S)-N'-((1,2,3,5,6,7-hexahydro-s-indacen-4-yl)carbamoyl)-2-(2-methoxypropan-2-yl)thiazole-5-sulfonimidamide | CHIRAL ART Cellulose-SB, 2*25 cm, 5 um | EtOH in Hex (8 mM NH₃-MeOH) | 435 |
| 389 | 341a | 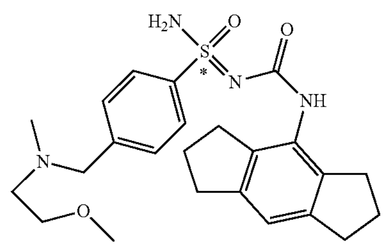 | (S) or (R)-N'-((1,2,3,5,6,7-hexahydro-s-indacen-4-yl)carbamoyl)-4-(((2-methoxyethyl)(methyl)amino)methyl)benzenesulfonimidamide | CHIRAL-Cellulose-SB 4.6*100 mm 3 um | Hex (0.1% DEA): EtOH = 70:30 | 457 |
| 390 | 341b | 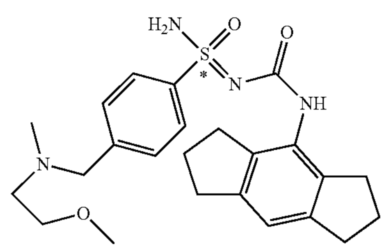 | (R) or (S)-N'-((1,2,3,5,6,7-hexahydro-s-indacen-4-yl)carbamoyl)-4-(((2-methoxyethyl)(methyl)amino)methyl)benzenesulfonimidamide | CHIRAL-Cellulose-SB 4.6*100 mm 3 um | Hex (0.1% DEA): EtOH = 70:30 | 457 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]$^+$ |
|---|---|---|---|---|---|---|
| 391 | 360ba | 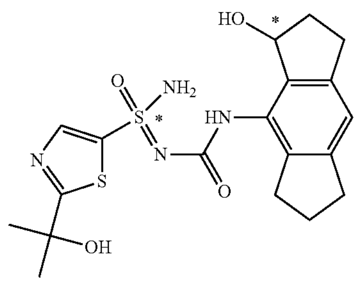 | (R,R) or (R,S) or (S,S) or (S,R)-N'-((3-hydroxy-1,2,3,5,6,7-hexahydro-s-indacen-4-yl)carbamoyl)-2-(2-hydroxypropan-2-yl)thiazole-5-sulfonimidamide (from Example 370) | CHIRAL-PAK IG, 20*250 mm, 5 um | EtOH in MTBE (10 mM NH$_3$-MeOH) | 437 |
| 392 | 360bb | 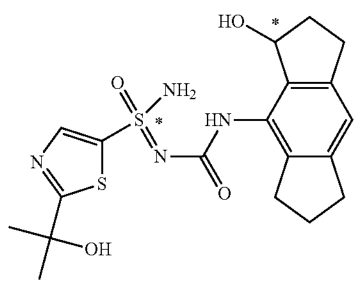 | (R,S) or (R,R) or (S,R) or (S,S)-N'-((3-hydroxy-1,2,3,5,6,7-hexahydro-s-indacen-4-yl)carbamoyl)-2-(2-hydroxypropan-2-yl)thiazole-5-sulfonimidamide (from Example 370) | CHIRAL-PAK IG, 20*250 mm, 5 um | EtOH in MTBE (10 mM NH$_3$-MeOH) | 437 |
| 393 | 363b | 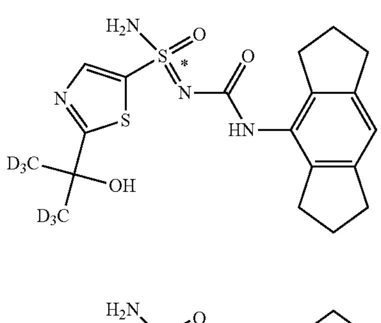 | (R)-N'-((1,2,3,5,6,7-hexahydro-s-indacen-4-yl)carbamoyl)-2-(2-hydroxypropan-2-yl-1,1,1,3,3,3-d$_6$)thiazole-5-sulfonimidamide | CHIRAL-PAK IF, 2*25 cm, 5 um | 40% MeOH in CO$_2$ | 427 |
| 394 | 363a | 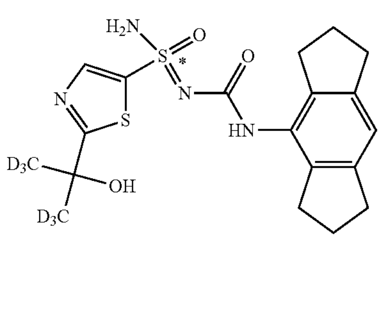 | (S)-N'-((1,2,3,5,6,7-hexahydro-s-indacen-4-yl)carbamoyl)-2-(2-hydroxypropan-2-yl-1,1,1,3,3,3-d$_6$)thiazole-5-sulfonimidamide | CHIRAL-PAK IF, 2*25 cm, 5 um | 40% MeOH in CO$_2$ | 427 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]⁺ |
|---|---|---|---|---|---|---|
| 395 | 343a | 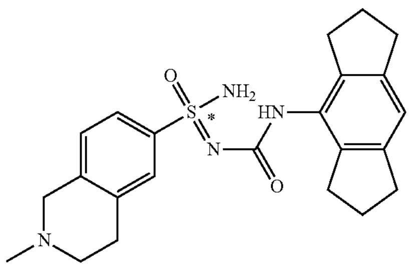 | (R) or (S)-N'-((1,2,3,5,6,7-hexahydro-s-indacen-4-yl)carbamoyl)-2-methyl-1,2,3,4-tetrahydroisoquinoline-6-sulfonimidamide | CHIRAL-PAK IG, 20*250 mm, 5 um | EtOH in Hex (8 mM NH₃-MeOH) | 425 |
| 396 | 343b | 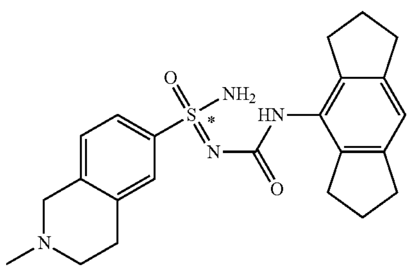 | (S) or (R)-N'-((1,2,3,5,6,7-hexahydro-s-indacen-4-yl)carbamoyl)-2-methyl-1,2,3,4-tetrahydroisoquinoline-6-sulfonimidamide | CHIRAL-PAK IG, 20*250 mm, 5 um | EtOH in Hex (8 mM NH₃-MeOH) | 425 |
| 397 | 359a | 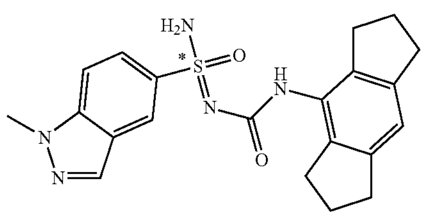 | (R) or (S)-N'-((1,2,3,5,6,7-hexahydro-s-indacen-4-yl)carbamoyl)-1-methyl-1H-indazole-5-sulfonimidamide | ChiralpakID, 2*25 cm, 5 um | IPA in Hex: DCM = 3:1 (10 mM NH₂-MeOH) | 410 |
| 398 | 359b | 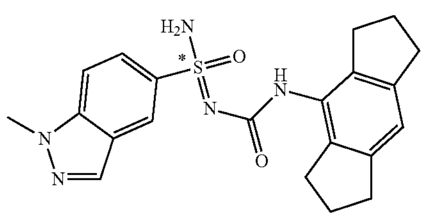 | (S) or (R)-N'-((1,2,3,5,6,7-hexahydro-s-indacen-4-yl)carbamoyl)-1-methyl-1H-indazole-5-sulfonimidamide | ChiralpakID, 2*25 cm, 5 um | IPA in Hex: DCM = 3:1 (10 mM NH₂-MeOH) | 410 |
| 399 | 352a | 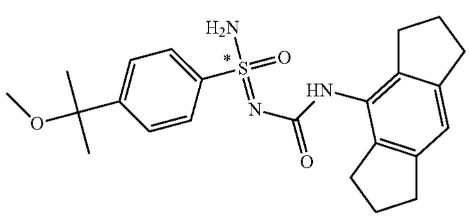 | (R) or (S)-N'-((1,2,3,5,6,7-hexahydro-s-indacen-4-yl)carbamoyl)-4-(2-methoxypropan-2-yl)benzenesulfonimidamide | CHIRAL-PAK IG, 2.0*25 cm (5 um) | Hex (0.1% DEA): IPA = 70:30 | 428 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 400 | 352b | 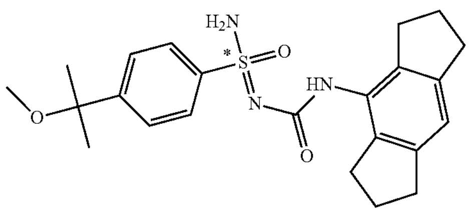 | (S) or (R)-N'-((1,2,3,5,6,7-hexahydro-s-indacen-4-yl)carbamoyl)-4-(2-methoxypropan-2-yl)benzenesulfonimidamide | CHIRALPAK IG, 2.0*25 cm (5 um) | Hex (0.1% DEA): IPA = 70:30 | 428 |
| 401 | 383a | 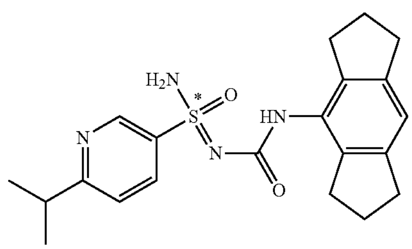 | (R) or (S)-N'-((1,2,3,5,6,7-hexahydro-s-indacen-4-yl)carbamoyl)-6-isopropylpyridine-3-sulfonimidamide | CHIRALPAK IG, 2*25 cm, 5 um | EtOH in Hex (8 mM NH$_3$-MeOH) | 399 |
| 402 | 383b | 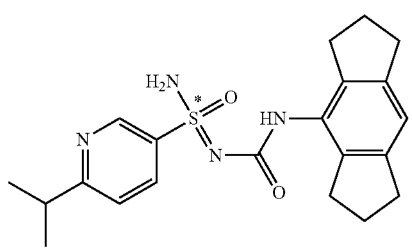 | (S) or (R)-N'-((1,2,3,5,6,7-hexahydro-s-indacen-4-yl)carbamoyl)-6-isopropylpyridine-3-sulfonimidamide | CHIRALPAK IG, 2*25 cm, 5 um | EtOH in Hex (8 mM NH$_3$-MeOH) | 399 |
| 403 | 382a | 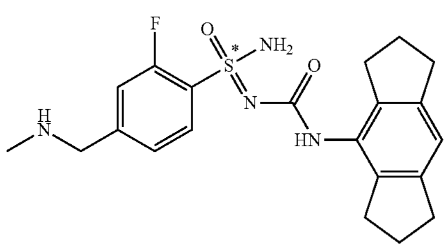 | (R) or (S)-2-fluoro-N'-((1,2,3,5,6,7-hexahydro-s-indacen-4-yl)carbamoyl)-4-((methylamino)methyl)benzenesulfonimidamide | CHIRALPAK IG, 2*25 cm, 5 um | EtOH in Hex (8 mM NH$_3$-MeOH) | 417 |
| 404 | 382b | 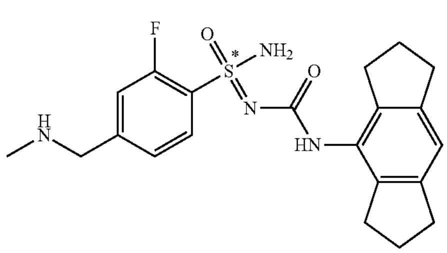 | (S) or (R)-2-fluoro-N'-((1,2,3,5,6,7-hexahydro-s-indacen-4-yl)carbamoyl)-4-((methylamino)methyl)benzenesulfonimidamide | CHIRALPAK IG, 2*25 cm, 5 um | EtOH in Hex (8 mM NH$_3$•MeOH) | 417 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 405 | 379a | 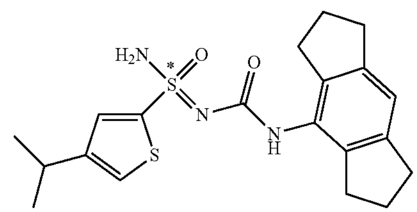 | (R) or (S)-N'-((1,2,3,5,6,7-hexahydro-s-indacen-4-yl)carbamoyl)-4-isopropyl-thiophene-2-sulfonimidamide | CHIRAL-PAK IG, 2.0*25 cm (5 um) | EtOH in Hex (8 mM NH3-MeOH) | 404 |
| 406 | 379b | 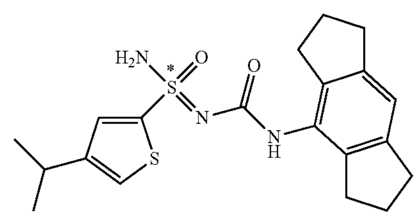 | (S) or (R)-N'-((1,2,3,5,6,7-hexahydro-s-indacen-4-yl)carbamoyl)-4-isopropyl-thiophene-2-sulfonimidamide | CHIRAL-PAK IG, 2.0*25 cm (5 um) | EtOH in Hex (8 mM NH3-MeOH) | 404 |
| 407 | 380a | 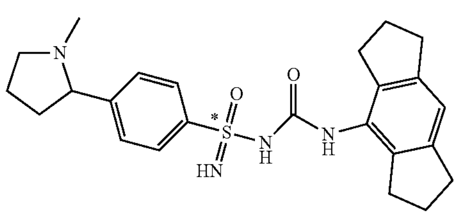 | (R,R) or (R,S) or (S,S) or (S,R)-N-((1,2,3,5,6,7-hexahydro-s-indacen-4-yl)carbamoyl)-4-(1-methyl-pyrrolidin-2-yl)benzene-sulfonimidamide | CHIRAL-PAK IG, 20*250 mm, 5 um | IPA in Hex: DCM = 5:1 (10 mM NH3-MeOH) | 439 |
| 408 | 380b | 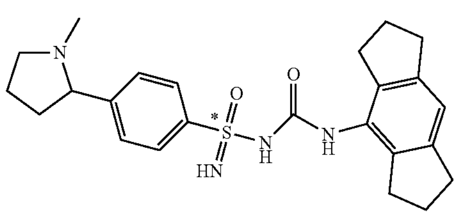 | (S,R) or (S,S) or (R,S) or (R,R)-N-((1,2,3,5,6,7-hexahydro-s-indacen-4-yl)carbamoyl)-4-(1-methyl-pyrrolidin-2-yl)benzene-sulfonimidamide | CHIRAL-PAK IG, 20*250 mm, 5 um | IPA in Hex: DCM = 5:1 (10 mM NH3-MeOH) | 439 |
| 409 | 380c | 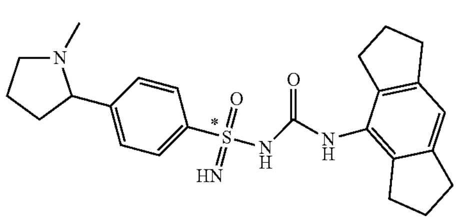 | (R,S) or (S,R) or (S,R) or (R,R)-N-((1,2,3,5,6,7-hexahydro-s-indacen-4-yl)carbamoyl)-4-(1-methyl-pyrrolidin-2-yl)benzene-sulfonimidamide | CHIRAL-PAK IG, 20*250 mm, 5 um | IPA in Hex: DCM = 5:1 (10 mM NH3-MeOH) | 439 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 410 | 380d | 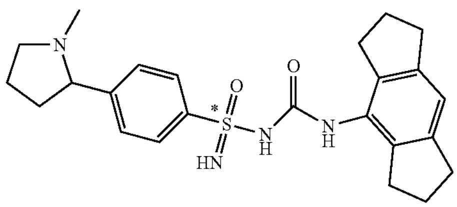 | (R,S) or (S,R) or (R,S or (S,S)-N-((1,2,3,5,6,7-hexahydro-s-indacen-4-yl)carbamoyl)-4-(1-methyl-pyrrolidin-2-yl)benzene-sulfonimi-damide | CHIRAL-PAK IG, 20*250 mm, 5 um | IPA in Hex: DCM = 5:1 (10 mM NH$_3$-MeOH) | 439 |
| 411 | 384a | 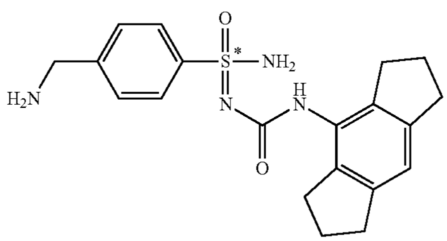 | (R) or (S)-4-(amino-methyl)-N'-((1,2,3,5,6,7-hexahydro-s-indacen-4-yl)carbamoyl)benzene-sulfonimi-damide | CHIRAL-PAK IG, 2*25 cm, 5 um | EtOH in Hex (8 mM NH$_3$-MeOH) | 385 |
| 412 | 384b | 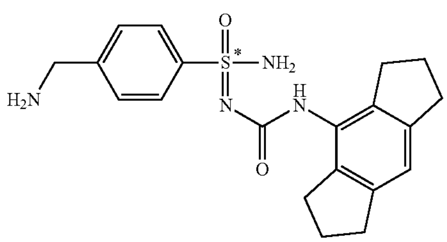 | (S) or (R)-4-(amino-methyl)-N'-((1,2,3,5,6,7-hexahydro-s-indacen-4-yl)carbamoyl)benzene-sulfonimi-damide | CHIRAL-PAK IG, 2*25 cm, 5 um | EtOH in Hex (8 mM NH$_3$-MeOH) | 385 |
| 413 | 357a | 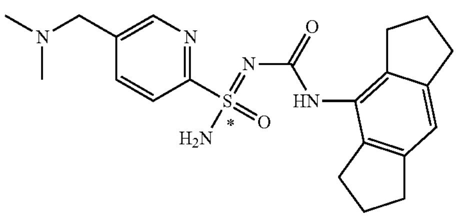 | (R) or (S)-5-((dimethyl-amino)methyl)-N'-((1,2,3,5,6,7-hexahydro-s-indacen-4-yl)carbamoyl)pyridine-2-sulfonimi-damide | CHIRAL-PAK AD-H, 2.0.*25 cm | EtOH in Hex (8 mM NH$_3$-MeOH) | 414 |
| 414 | 357b | 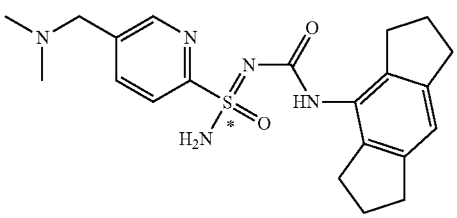 | (S) or (R)-5-((dimethyl-amino)methyl)-N'-((1,2,3,5,6,7-hexahydro-s-indacen-4-yl)carbamoyl)pyridine-2-sulfonimi-damide | CHIRAL-PAK AD-H, 2.0.*25 cm | EtOH in Hex (8 mM NH$_3$-MeOH) | 414 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 415 | 354a | 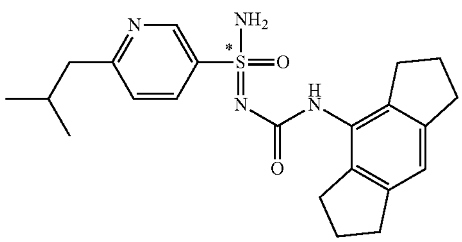 | (R) or (S)-N'-((1,2,3,5,6,7-hexahydro-s-indacen-4-yl)carbamoyl)-6-isobutyl-pyridine-3-sulfonimidamide | CHIRAL ART Cellulose-SB, 2*25 cm, 5 um | EtOH in Hex (0.1% DEA) | 413 |
| 416 | 354b | 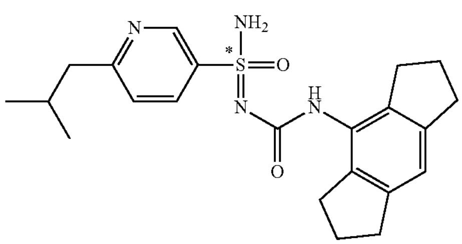 | (S) or (R)-N'-((1,2,3,5,6,7-hexahydro-s-indacen-4-yl)carbamoyl)-6-isobutyl-pyridine-3-sulfonimidamide | CHIRAL ART Cellulose-SB, 2*25 cm, 5 um | EtOH in Hex (0.1% DEA) | 413 |
| 417 | 387a | 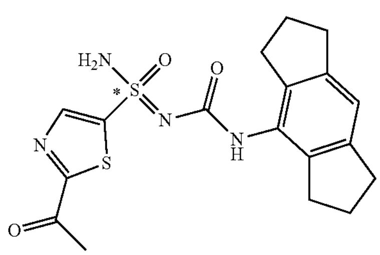 | (R) or (S)-2-acetyl-N'-((1,2,3,5,6,7-hexahydro-s-indacen-4-yl)carbamoyl)thiazole-5-sulfonimidamide | CHIRAL ART Cellulose-SB, 2*25 cm, 5 um | IPA in CO2 | 405 |
| 418 | 387b | 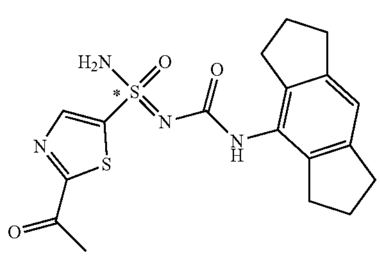 | (S) or (R)-2-acetyl-N'-((1,2,3,5,6,7-hexahydro-s-indacen-4-yl)carbamoyl)thiazole-5-sulfonimidamide | CHIRAL ART Cellulose-SB, 2*25 cm, 5 um | IPA in CO2 | 405 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 419 | 333a | 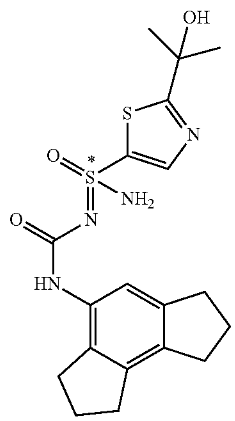 | (R) or (S)-N'-((1,2,3,6,7,8-hexahydro-as-indacen-4-yl)carbamoyl)-2-(2-hydroxypropan-2-yl)thiazole-5-sulfonimidamide | CHIRAL-PAK IF, 5*25 cm, 5 um | EtOH in Hex (8 mM NH₃-MeOH) | 421 |
| 420 | 333b | 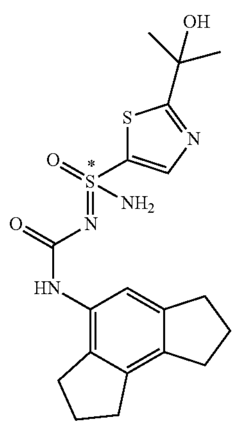 | (S) or (R)-N'-((1,2,3,6,7,8-hexahydro-as-indacen-4-yl)carbamoyl)-2-(2-hydroxypropan-2-yl)thiazole-5-sulfonimidamide | CHIRAL-PAK IF, 5*25 cm, 5 um | EtOH in Hex (8 mM NH₃-MeOH) | 421 |
| 421 | 375a | 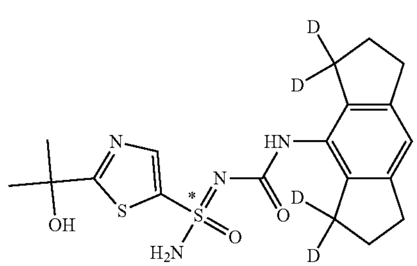 | (R) or (S)-N'-((1,2,3,5,6,7-hexahydro-s-indacen-4-yl-3,3,5,5-d₄)carbamoyl)-2-(2-hydroxypropan-2-yl)thiazole-5-sulfonimidamide | CHIRAL-PAK IF, 2*25 cm, 5 um | MeOH (2 mM NH₃-MeOH) in CO₂ | 425 |

TABLE 28-continued

Examples in the following table were obtained from chiral HPLC resolutions of racemic examples described above. The chiral column and eluents are listed in the table. As a convention, the faster-eluting enantiomer is always listed first in the table followed by the slower-eluting enantiomer of the pair. The symbol * at a chiral center denotes that this chiral center has been resolved and the absolute stereochemistry at that center has not been determined. For mixtures contained two chiral centers and if two columns are used for separating the four diastereomers, the individual isomers are listed in the order of faster column 1/faster column 2; faster column 1/slower column 2; slower column 1/faster column 2; followed by slower column 1/slower column 2.

| Ex. # | Final Target Number | Structure | IUPAC Name | Column | Eluents | LC-MS [M + H]+ |
|---|---|---|---|---|---|---|
| 422 | 375b | 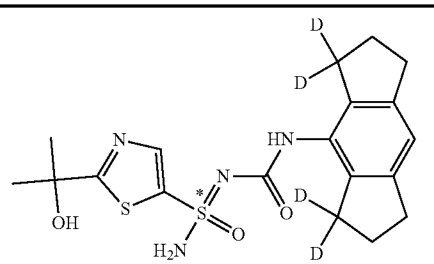 | (S) or (R)-N'-((1,2,3,5,6,7-hexahydro-s-indacen-4-yl-3,3,5,5-$d_4$)carbamoyl)-2-(2-hydroxypropan-2-yl)thiazole-5-sulfonimidamide | CHIRAL-PAK IF, 2*25 cm, 5 um | MeOH (2 mM $NH_3$-MeOH) in $CO_2$ | 425 |
| 423 | 376a | 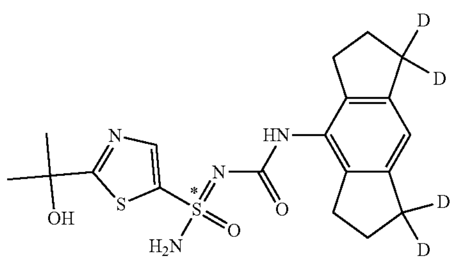 | (R) or (S)-N'-((1,2,3,5,6,7-hexahydro-s-indacen-4-yl-1,1,7,7-$d_4$)carbamoyl)-2-(2-hydroxypropan-2-yl)thiazole-5-sulfonimidamide | CHIRAL-PAK ID, 2*25 cm (5 um) | MeOH (2 mM $NH_3$-MeOH) in $CO_2$ | 425 |
| 424 | 376b | 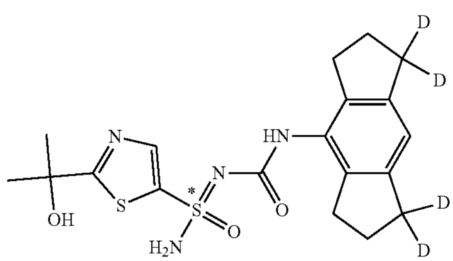 | (S) or (R)-N'-((1,2,3,5,6,7-hexahydro-s-indacen-4-yl-1,1,7,7-$d_4$)carbamoyl)-2-(2-hydroxypropan-2-yl)thiazole-5-sulfonimidamide | CHIRAL-PAK ID, 2*25 cm (5 um) | MeOH (2 mM $NH_3$-MeOH) in $CO_2$ | 425 |

The amount of $NH_3$ in this chiral chromatographic solvent and similar solvents were adjusted by adding 2M $NH_3$ in methanol to the desired $NH_3$ concentration. In this case, the resulting concentration of $NH_3$ in methanol is 8 mM.

Example 425 (Compound 318)

1-{Amino[5-(2-hydroxypropan-2-yl)-1,3-thiazol-2-yl]oxo-$\lambda^6$-sulfanylidene}-3-(8-bromo-1,2,3,5,6,7-hexahydro-s-indacen-4-yl)urea

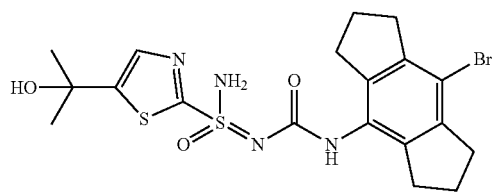

803

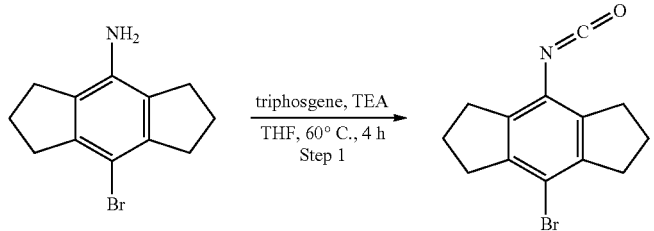

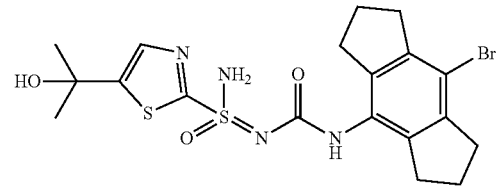

Step 1: 4-Bromo-1,2,3,5,6,7-hexahydro-8-isocyanato-s-indacene

To a solution of 8-bromo-1,2,3,5,6,7-hexahydros-indacen-4-amine (1.5 g, 5.94 mmol) in anhydrous THF (50 mL) was added triethylamine (1.07 mL, 7.73 mmol) and triphosgene (882 mg, 2.97 mmol) at room temperature. The resulting mixture was then stirred at 60° C. for 4 h. Reaction mixture was then brought to room temperature and used directly in the next step.

Step 2: 1-{Amino[5-(2-hydroxypropan-2-yl)-1,3-thiazol-2-yl]oxo-λ⁶-sulfanylidene}-3-(8-bromo-1,2,3,5,6,7-hexahydro-s-indacen-4-yl)urea To a solution of N-(tert-butyldimethylsilyl)-5-(2-hydroxypropan-2-yl)-1,3-thiazole-2-sulfonoimidamide (400 mg, 1.2 mmol) in anhydrous THF (10 mL) was added NaH (60% wt. oil dispersion, 96 mg, 2.4 mmol) at room temperature. After 5 min, a solution of 4-bromo-1,2,3,5,6,7-hexahydro-8-isocyanato-s-indacene (2 mL, 2 mmol, from Step 1) was added drop wise. The resulting mixture was stirred at room temperature for 20 min before quenching carefully with 4 M HCl solution in dioxane (3 mL). Saturated aqueous ammonium chloride was added and the mixture was extracted with dichloromethane (15 mL×3). The combined organic layers were washed with brine, dried over MgSO₄, filtered, and concentrated in vacuo. The crude product was purified by prep-HPLC to obtain the titled compound (280 mg, 47%). LCMS: [M+H]⁺=499.3.

Example 426 (Compound 313)

1-{Amino[5-(2-hydroxypropan-2-yl)-1,3-thiazol-2-yl]oxo-λ⁶-sulfanylidene}-3-[7-(3,4-dimethylphenyl)-2,3-dihydro-1H-inden-4-yl]urea

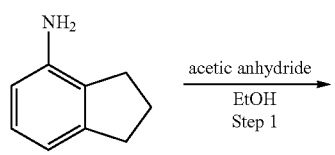

804

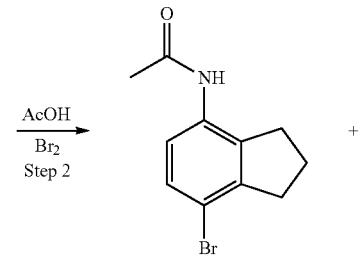

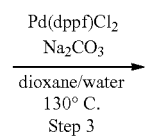

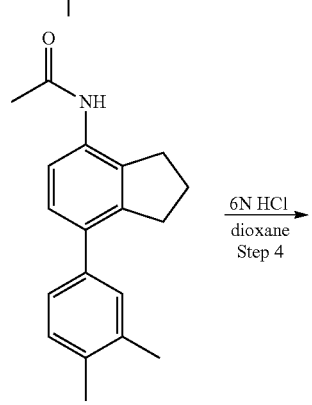

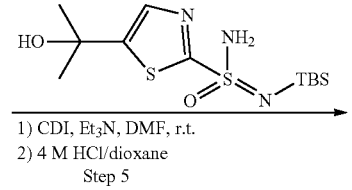

-continued

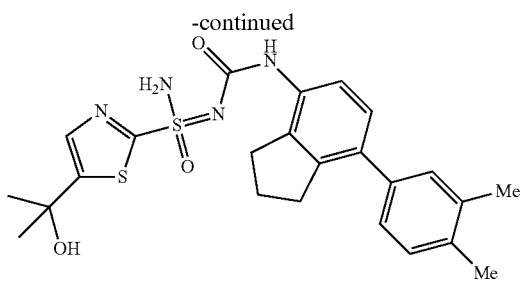

Step 1: N-(2,3-dihydro-1H-inden-4-yl)acetamide

To a solution of 2,3-dihydro-1H-inden-4-amine (3.4 g, 26 mmol) in ethanol (45 mL) was added a solution of acetic anhydride (4.9 mL, 52 mmol) in ethanol (15 mL) dropwise at 0° C. The resulting mixture was gradually warmed up to RT and stirred for 15 h. Solvent was removed under reduced pressure and the residue was triturated with diethyl ether to afford titled compound as off white solid (3 g, 66%). LCMS [M+H]$^+$=176.3.

Step 2: N-(4-bromo-2,3-dihydro-1H-inden-7-yl)acetamide

Into a 250-ml round-bottom flask was added N-(2,3-dihydro-1H-inden-4-yl)acetamide (3 g, 17.1 mmol) and acetic acid (45 mL). The resulting solution was cooled to 0° C. and then a solution of bromine (5.4 g, 34.2 mmol) in acetic acid (12 mL) was added dropwise with stirring over 10 min.

The cooling bath was removed and the reaction mixture was stirred at RT for 1 h. Water was added and the resulting precipitates of product were collected by filtration and dried under vacuum to afford titled compound as off white solid (3.9 g, 90%). LCMS [M+H]$^+$=254.4.

Step 3: N-(2,3-dihydro-4-(3,4-dimethylphenyl)-1H-inden-7-yl)acetamide

A mixture of N-(4-bromo-2,3-dihydro-1H-inden-7-yl)acetamide (1 g, 3.9 mmol), 3,4-dimethylphenylboronic acid (700 mg, 4.68 mmol), Pd(dppf)Cl$_2$·DCM (160 mg, 0.19 mmol), sodium carbonate (900 mg, 8.58 mmol as 2 M aqueous solution) in dioxane (12 mL) was stirred at 100° C. in an oil bath for 72 h. The reaction mixture was brought to RT, water (20 mL) was added and extracted with EtOAc (15 mL×3). The combined organic layers were washed with brine, dried over MgSO$_4$, filtered, and concentrated in vacuo. The crude product was purified by silica gel flash chromatography using 0-30% gradient of EtOAc in hexanes to afford titled compound (880 mg, 81%). LCMS [M+H]$^+$=280.6.

Step 4: 2,3-Dihydro-7-(3,4-dimethylphenyl)-1H-inden-4-amine

A solution of N-(2,3-dihydro-4-(3,4-dimethylphenyl)-1H-inden-7-yl)acetamide (880 mg, 3.15 mmol) in 6 N HCl (20 mL) was stirred at 100° C. for 40 h. After consumption of the starting material, the reaction mixture was cooled to 0° C. and adjusted to pH=8 with 10 M aqueous sodium hydroxide solution. The precipitates formed were collected, washed with water and dried under vacuum to afford the titled compound (81 mg, 67%) as tan colored powder. LCMS [M+H]+=238.3.

Step 5: 1-{Amino[5-(2-hydroxypropan-2-yl)-1,3-thiazol-2-yl]oxo-λ$^6$-sulfanylidene}-3-[7-(3,4-dimethylphenyl)-2,3-dihydro-1H-inden-4-yl]urea To a solution of N-(tert-butyldimethylsilyl)-5-(2-hydroxypropan-2-yl)-1,3-thiazole-2-sulfonoimidamide (42 mg, 0.13 mmol) in DMF (1 mL) was added Et$_3$N (35 uL, 0.25 mmol) and the resulting mixture was stirred at room temperature for 10 min, followed by the addition of CDI (41 mg, 0.25 mmol). The reaction mixture was further stirred at RT for 1 h, and then 2,3-dihydro-7-(3,4-dimethylphenyl)-1H-inden-4-amine (30 mg, 0.13 mmol) was added. The resulting reaction mixture was stirred overnight at room temperature. The presence of desired product was then confirmed by LC-MS. The reaction mixture was quenched with 4 M HCl in dioxane (1 mL) and stirred for 30 min to de-protect the TBS group which indicated the formation of desired product on LCMS. The crude product was purified by preparative HPLC to provide titled compound (16.4 mg, 27%). LCMS [M+H]$^+$=485.49.

Example 427 (Compound 314)

1-{Amino[5-(2-hydroxypropan-2-yl)-1,3-thiazol-2-yl]oxo-λ$^6$-sulfanylidene}-3-[8-(3,4-dimethylphenyl)-1,2,3,5,6,7-hexahydro-s-indacen-4-yl]urea

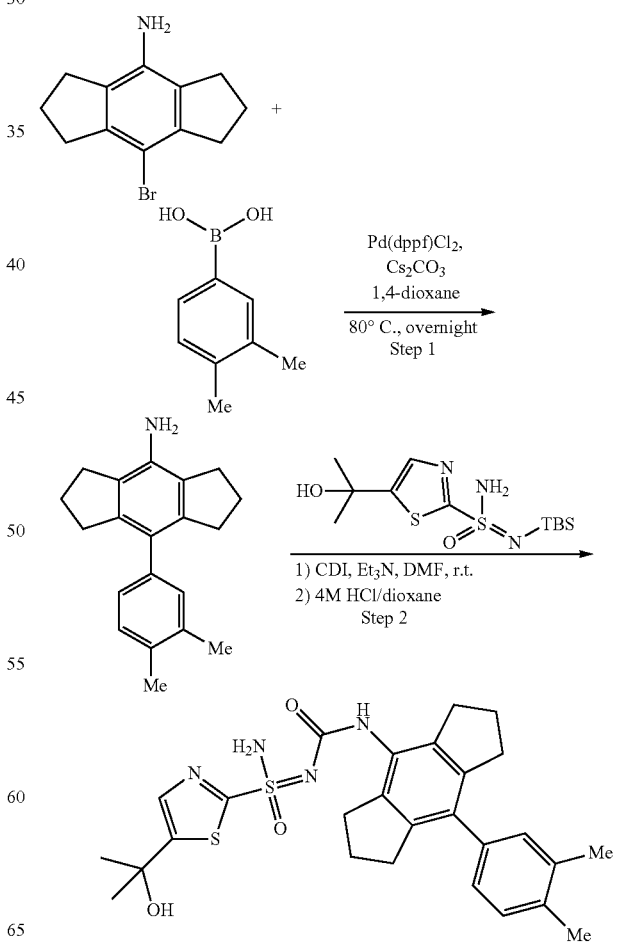

Step 1: 1,2,3,5,6,7-Hexahydro-8-(3,4-dimethylphenyl)-s-indacen-4-amine

8-Bromo-1,2,3,5,6,7-hexahydro-s-indacen-4-amine (105 mg, 0.42 mmol), 3,4-dimethylphenyl-boronic acid (187 mg, 1.25 mmol), Pd(dppf)Cl$_2$ (30.4 mg, 0.04 mmol) and dioxane (1.5 mL) were added to a reaction vial. Cesium carbonate (1.24 mL, 1 M in H$_2$O) was then added and the reaction mixture was stirred at 80° C. for 16 h. Reaction mixture was brought to RT and filtered through a small bed of Celite and rinsed with dioxane (5 mL). Water (5 mL) was added to the filtrates and extracted with diethyl ether (5 mL×3). The combined organic layers were washed with brine, dried over anhydrous MgSO$_4$, filtered, and concentrated in vacuo to provide titled compound which was used in the next step without any purification. LCMS [M+H]$^+$=278.4.

Step 2: 1-{Amino[5-(2-hydroxypropan-2-yl)-1,3-thiazol-2-yl]oxo-λ$^6$-sulfanylidene}-3-[8-(3,4-dimethylphenyl)-1,2,3,5,6,7-hexahydro-s-indacen-4-yl]urea

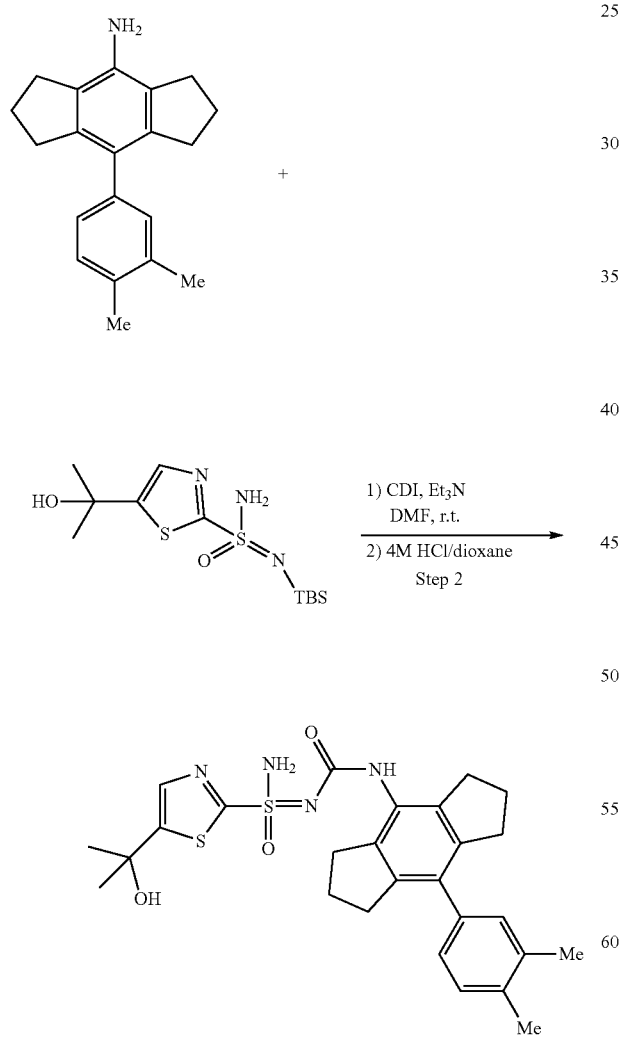

The title product was obtained using similar procedure as in Step 5 Example 426. LCMS: [M+H]+=525.42.

Example 428 (Compound 309)

3-[Amino(dimethyl-1,3-thiazol-5-yl)oxo-λ$^6$-sulfanylidene]-1-[4-fluoro-2,6-bis(propan-2-yl)phenyl]urea

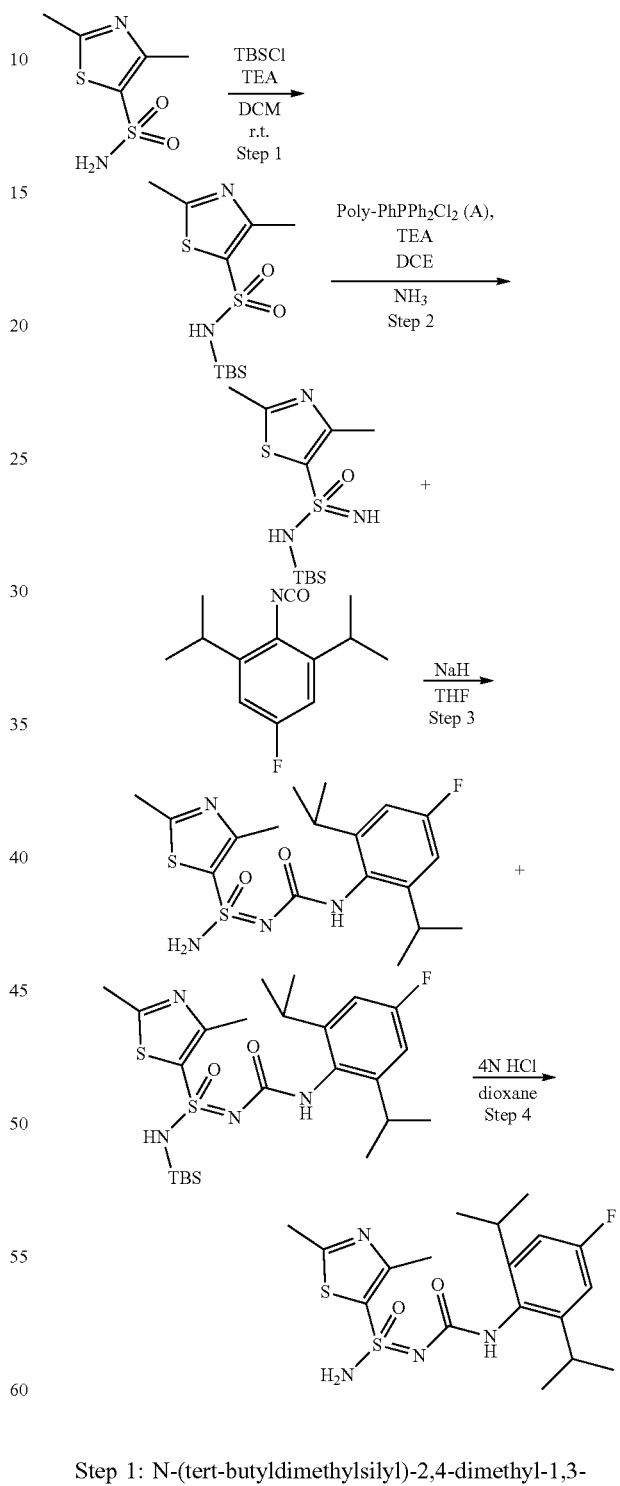

Step 1: N-(tert-butyldimethylsilyl)-2,4-dimethyl-1,3-thiazole-5-sulfonamide

Dimethyl-1,3-thiazole-5-sulfonamide (41.4 mg, 0.22 mmol) was dissolved in anhydrous CH$_2$Cl$_2$ (2 mL). Triethylamine (0.090 mL, 0.65 mmol) and TBSCl (38 mg, 0.25 mol) were added and the resulting mixture was stirred at 50° C. for 18 h. Reaction mixture was brought to RT and used directly in the next step. LCMS: [M+H]$^+$=307.2.

Step 2: N-(tert-butyldimethylsilyl)-2,4-dimethyl-1,3-thiazole-5-sulfonoimidamide Polymer bound dichlorotriphenylphosphorane reaction mixture (described for Reagent 2) was cooled in an ice/water bath under nitrogen. Triethylamine (0.1 mL, 0.72 mmol, 2.25 equiv.) was added slowly via syringe. Resulting mixture was stirred at 0° C. for 10 min and then the reaction mixture from Step 1 above was added dropwise via syringe. This reaction mixture was further stirred at 0° C. for 30 min and then a steady stream of anhydrous ammonia was bubbled into the reaction mixture for 3 min. Reaction vial was screw capped and stirred in ice/water bath for 2 h. Reaction mixture was warmed up to room temperature, carefully opened and filtered to remove resin. The cloudy filtrate was centrifuged to remove any solids. Supernatant was concentrated in vacuo and dried under high vacuum for 1 h and used directly in the next step. LCMS: [M+H]$^+$=306.8.

Step 3: 3-{[(Tert-butyldimethylsilyl)amino](dimethyl-1,3-thiazol-5-yl)oxo-λ$^6$-sulfanylidene}-1-[4-fluoro-2,6-bis(propan-2-yl)phenyl]urea To the crude reaction mixture from Step 2 was added anhydrous THF (1.5 mL) and the resulting mixture was stirred in an ice/water bath for 5 min. NaH (17 mg, 0.44 mmol) was added and after 2 min of stirring a solution of isocyanate (0.165 mmol) in THF (3 ml) was added dropwise at 0° C. The resulting mixture was brought to RT and stirred for 15 min to give a mixture of crude products. LCMS: [M+H]$^+$=527.5; for de-protected product, [M+H]$^+$=413.5.

Step 4: 3-[amino(dimethyl-1,3-thiazol-5-yl)oxo-λ$^6$-sulfanylidene]-1-[4-fluoro-2,6-bis(propan-2-yl)phenyl]urea To the reaction from Step 3 was carefully added 4N HCl in dioxane (0.3 mL) and the resulting mixture was stirred at RT for 30 min or till the completion of reaction as determined by the LCMS analysis ([M+H]$^+$=413.5). Reaction mix was then concentrated in vacuo. DMSO (0.8 mL) was added to the residue and purified by prep-HPLC to afford titled compound (10 mg).

Examples in the following table were prepared using similar procedures described in Example 428.

TABLE 29

| Example # | Final Target # | IUPAC Name | Structure | LCMS: [M + H]$^+$ |
|---|---|---|---|---|
| 428 | 309 | 3-[amino(dimethyl-1,3-thiazol-5-yl)oxo-λ$^6$-sulfanylidene]-1-[4-fluoro-2,6-bis(propan-2-yl)phenyl]urea | 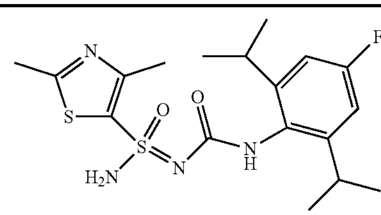 | 413.16 |
| 430 | 310 | 3-[amino({1-methyl-1H-pyrazolo[3,4-b]pyridin-5-yl})oxo-λ$^6$-sulfanylidene]-1-[4-fluoro-2,6-bis(propan-2-yl)phenyl]urea | 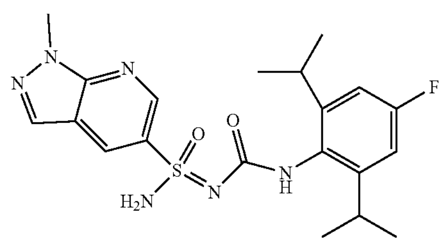 [SMILES: CC(C)c1cc(F)cc(C(C)C)c1NC(=O)N=S(N)(=O)c1cnc2c(cnn2C)c1] | 433.27 |
| 431 | 306 | 1-{amino[5-(dimethylamino)naphthalen-1-yl]oxo-λ$^6$ sulfanylidene}-3-[4-fluoro-2,6-bis(propan-2-yl)phenyl]urea | 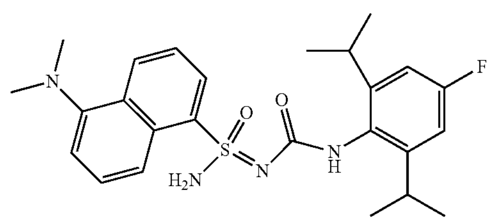 [SMILES: CC(C)c1cc(F)cc(C(C)C)c1NC(=O)N=S(N)(=O)c1cccc2c(N(C)C)cccc12] | 471.70 |

The following protocol is suitable for testing the activity of the compounds disclosed herein.

Procedure 1: IL-1β Production in PMA-Differentiated THP-1 Cells Stimulated with Gramicidin.

THP-1 cells were purchased from the American Type Culture Collection and sub-cultured according to instructions from the supplier. Cells were cultured in complete RPMI 1640 (containing 10% heat inactivated FBS, penicillin (100 units/ml) and streptomycin (100 μg/ml)), and maintained in log phase prior to experimental setup. Prior to the experiment, compounds were dissolved in dimethyl sulfoxide (DMSO) to generate a 30 mM stock. The compound stock was first pre-diluted in DMSO to 3, 0.34, 0.042 and 0.0083 mM intermediate concentrations and subsequently spotted using Echo550 liquid handler into an empty 384-well assay plate to achieve desired final concentration (e.g.

100, 33, 11, 3.7, 1.2, 0.41, 0.14, 0.046, 0.015, 0.0051, 0.0017 µM). DMSO was backfilled in the plate to achieve a final DMSO assay concentration of 0.37%. The plate was then sealed and stored at room temperature until required.

THP-1 cells were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, and resuspended in RPMI 1640 (containing 2% heat inactivated FBS, penicillin (100 units/ml) and streptomycin (100 µg/ml). The cells were plated in the 384-well assay plate containing the spotted compounds at a density of 50,000 cells/well (final assay volume 50 µl). Cells were incubated with compounds for 1 hour and then stimulated with gramicidin (5 µM) (Enzo) for 2 hours. Plates were then centrifuged at 340 g for 5 min. Cell free supernatant (40 L) was collected using a 96-channel PlateMaster (Gilson) and the production of IL-Iβ was evaluated by HTRF (cisbio). The plates were incubated for 18 h at 4° C. and read using the preset HTRF program (donor emission at 620 nm, acceptor emission at 668 nm) of the SpectraMax i3x spectrophotometer (Molecular Devices, software SoftMax 6). A vehicle only control and a dose titration of CRID3 (100-0.0017 µM) were run concurrently with each experiment. Data was normalized to vehicle-treated samples (equivalent to 0% inhibition) and CRID3 at 100 µM (equivalent to 100% inhibition). Compounds exhibited a concentration-dependent inhibition of IL-Iβ production in PMA-differentiated THP-1 cells.

Procedure 2: IL-1β Production in PMA-Differentiated THP-1 Cells Stimulated with Gramicidin.

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 µg/ml)), and maintained in log phase prior to experimental setup. Prior to the experiment THP-1 were treated with PMA (Phorbol 12-myristate 13-acetate) (20 ng/ml) for 16-18 hours. Compounds were dissolved in dimethyl sulfoxide (DMSO) to generate a 30 mM stock. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 µg/ml). The cells were plated in a 384-well plate at a density of 50,000 cells/well (final assay volume 50 µl). Compounds were first dissolved in assay medium to obtain a 5× top concentration of 500 µM. 10 step dilutions (1:3) were then undertaken in assay medium containing 1.67% DMSO. 5× compound solutions were added to the culture medium to achieve desired final concentration (e.g. 100, 33, 11, 3.7, 1.2, 0.41, 0.14, 0.046, 0.015, 0.0051, 0.0017 µM). Final DMSO concentration was at 0.37%. Cells were incubated with compounds for 1 hour and then stimulated with gramicidin (5 µM) (Enzo) for 2 hours. Plates were then centrifuged at 340 g for 5 min. Cell free supernatant (40 µL) was collected using a 96-channel PlateMaster (Gilson) and the production of IL-Iβ was evaluated by HTRF (cisbio). A vehicle only control and a dose titration of CRID3 (100-0.0017 µM) were run concurrently with each experiment. Data was normalized to vehicle-treated samples (equivalent to 0% inhibition) and CRID3 at 100 M (equivalent to 100% inhibition). Compounds exhibited a concentration-dependent inhibition of IL-Iβ production in PMA-differentiated THP-1 cells.

Figure 3:
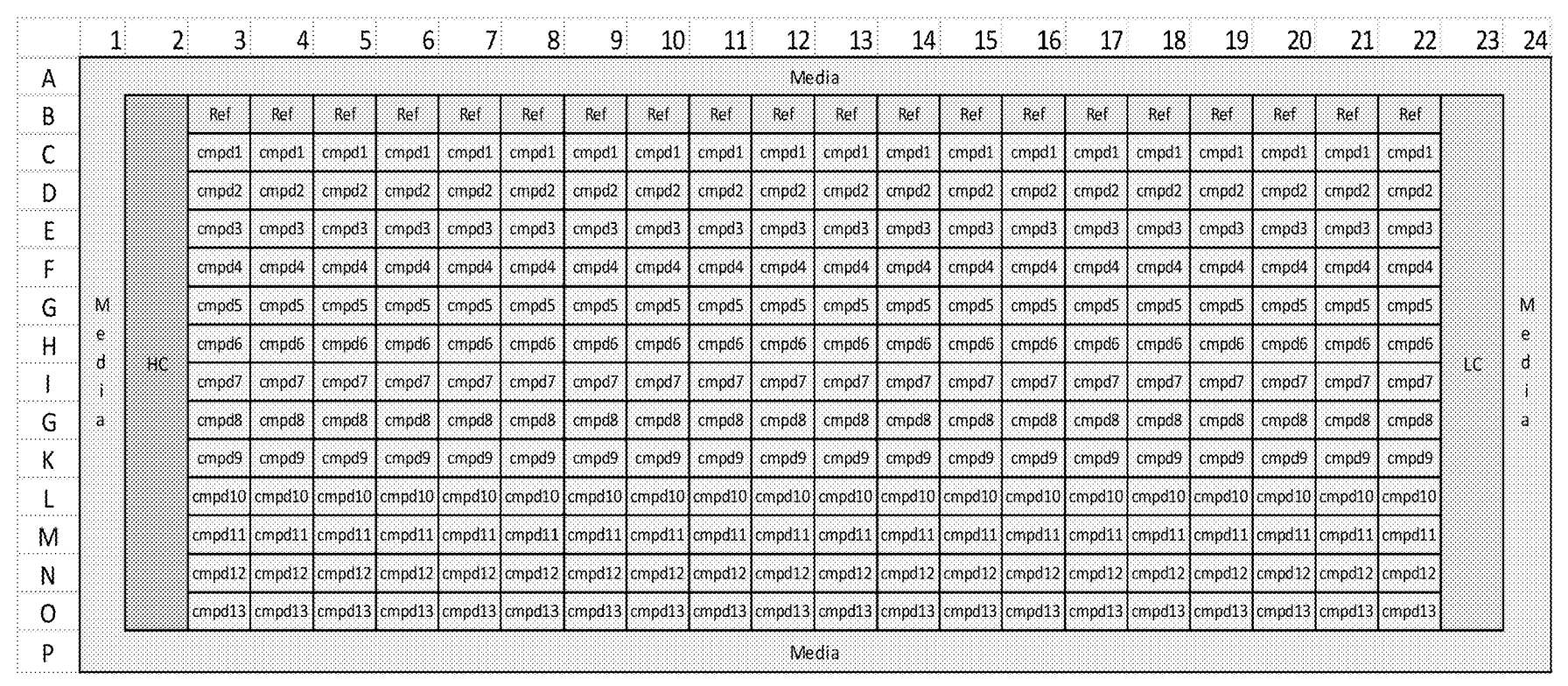

Procedure 3
1. Experimental Procedure
  1.1 Cell Culture
    1) Culture THP-1 cells in the complete RPMI-1640 medium with 10% FBS at 37° C., 5% $CO_2$.
    2) Passage the cells every 3 days by inoculating $3 \times 10^{-5}$ cells per ml.
  1.2 Compound Preparation
  Prepare the 3-fold serial dilution of the compounds with DMSO in a 384-well LDV Microplate using TECAN EVO system to generate the compound source plate with 10 concentrations. Top concentration is 30 mM. FIG. 3 depicts the layout of the microplate.
  1.3 Cell preparation
    1) Centrifuge THP-1 cells at 350 g for 5 min.
    2) Re-suspend cells with complete RMPI-1640 medium, and count cells.
    3) Seed cells in T225 flask, about $2.5 \times 10^7$ per flask, treat cells with 20 ng/ml PMA (final DMSO concentration<1%).
    4) Incubate overnight.
  1.4 THP-1 Stimulation
    1) Wash adherent THP-1 cells with PBS, and detach cells with 4 ml trypsin for T225 flask.
    2) Centrifuge cells at 350 g for 5 min, re-suspend cells with RPMI-1640 containing 2% FBS and count cells with trypan blue.
    3) Transfer 50 nl/well the serial dilution of test compound to 384-well plate by Echo; For the high control and first point of CRID3 (MCC950), transfer 165 nl, then backfill to make the DMSO concentration is consistent in all wells, the plate layout is as below.
    4) Seed 50 k cells in 40 ul RPMI-1640 with 2% FBS per well in 384-well plate.
    5) Incubate for 1 h at 37° C., 5% $CO_2$.
    6) Prepare 5× gramicidin, add 10 µl per well, the final concentration is 5 µM, incubate for 2 hrs at 37° C., 5% $CO_2$.
    7) Centrifuge at 350 g for 1 min.
    8) Pipet 16 µl supernatant by apricot, and transfer into white 384 proxiplate. FIG. 3 depicts the layout of the plates: HC: 100 µM CRID3 (MCC950)+5 µM gramicidin LC: 5 µM Gramicidin.
  1.5 IL-1β detection
    1) Homogenize the 5× diluent #5 with a vortex and add 1 volume of stock solution in 4 volumes of distilled water.
    2) Thaw 20× stock solution of anti-IL1β-Cryptate-antibody and anti-IL1β XL-antibody. Dilute these two antibodies to 1× with detection buffer #3.
    3) Pre-mix the two ready-to-use antibody solutions just prior to use.
    4) Dispense 4 ul of pre-mixed Anti-IL1β antibodies working solution into all wells.
    5) Seal the plate and incubate overnight at 4° C.
    6) Read the cell plate using EnVison and plot Readout vs. the test compound concentration to calculate the $IC_{50}$.
2. Data Analysis:
  1. $IC_{50}$ of compounds can be calculated using the following formulas
  Formula for $IC_{50}$ $$\% \text{ inhibition} = 100 - 100 \times [HC_{ave} - \text{Readout}/(HC_{ave} - LC_{ave})]$$

2. Fit the normalized data in a dose-response manner using XLfit, and calculate the compound concentration.

Table 30 shows the biological activity of compounds in hTHP-1 assay containing 2% fetal bovine serum: <0.008 µM="++++++"; ≥0.008 and <0.04 µM="+++++"; ≥0.04 and <0.2 µM="++++"; ≥0.2 and <1 M="+++"; ≥1 and <5 M="++"; ≥5 and <30 M="+".

TABLE 30

Average IC$_{50}$ of compounds in hTHP-1 assay

| Example # | Compound Number | hTHP-1 IC$_{50}$ |
| --- | --- | --- |
| 1 | 181 | +++++ |
| 2 | 181a | +++++ |
| 3 | 181b | +++ |
| 4 | 101' | ++++ |
| 5 | 101 or 102 | +++ |
| 6 | 102 or 101 | +++++ |
| 7 | 194 | +++ |
| 8 | 270 | + |
| 9 | 204 | >30 µM |
| 10 | 180 | ++++ |
| 11 | 190 | + |
| 12 | 182 | ++++ |
| 13 | 191 | ++++ |
| 14 | 177 | +++++ |
| 15 | 185 | ++++ |
| 16 | 186 | ++++ |
| 17 | 187 | +++++ |
| 18 | 188 | +++ |
| 19 | 192 | ++ |
| 20 | 189 | ++++ |
| 21 | 178 | ++++ |
| 22 | 193 | ++ |
| 23 | 170 | ++++ |
| 24 | 168 | ++ |
| 25 | 171 | ++++ |
| 26 | 122 | ++++ |
| 27 | 120 | +++ |
| 28 | 125 | ++++ |
| 29 | 129 | + |
| 30 | 213 | +++++ |
| 31 | 207 | ++++ |
| 32 | 195 | +++++ |
| 33 | 179 | ++++ |
| 34 | 105 | ++ |
| 35 | 121 | +++ |
| 36 | 145 | ++ |
| 37 | 131 | ++ |
| 38 | 132 | ++++ |
| 39 | 144 | +++ |
| 40 | 149 | ++++ |
| 41 | 152 | ++++ |
| 42 | 150 | + |
| 43 | 167 | ++++ |
| 44 | 106 | +++++ |
| 45 | 107 | ++++++ |
| 46 | 110 | ++ |
| 47 | 151 | +++ |
| 48 | 154 | ++++ |
| 49 | 148 | +++ |
| 50 | 153 | ++ |
| 51 | 109 | ++ |
| 52 | 135 | +++ |
| 53 | 134 | +++++ |
| 54 | 130 | ++ |
| 55 | 212 | +++ |
| 56 | 205 | +++ |
| 57 | 143 | +++ |
| 58 | 206 | ++ |
| 59 | 108 | +++++ |
| 60 | 202 | ++ |
| 61 | 208 | +++++ |
| 62 | 197 | ++++ |
| 63 | 196 | ++ |
| 64 | 124 | ++++ |
| 65 | 173 | ++++ |
| 66 | 172 | + |
| 67 | 174 | +++ |
| 68 | 158 | ++ |
| 69 | 220 | ++ |
| 70 | 157 | ++ |
| 71 | 161 | ++ |
| 72 | 159 | +++ |
| 73 | 165 | ++ |
| 74 | 183 | +++++ |
| 75 | 176 | +++++ |
| 76 | 136 | +++++ |
| 77 | 209 | ++++ |
| 78 | 203 | >30 µM |
| 79 | 180b or 180a | +++++ |
| 80 | 180a or 180b | +++ |
| 81 | 179b | +++++ |
| 82 | 179a | +++ |
| 83 | 190a or 190b | ++ |
| 84 | 190b or 190a | >30 µM |
| 85 | 182a or 182b | +++++ |
| 86 | 182b or 182a | +++ |
| 87 | 191b or 191a | ++++ |
| 88 | 191a or 191b | ++ |
| 89 | 177b or 177a | +++++ |
| 90 | 177a or 177b | +++ |
| 91 | 185b or 185a | ++++ |
| 92 | 185a or 185b | ++ |
| 93 | 186a or 186b | ++++ |
| 94 | 186b or 186a | ++ |
| 95 | 187a or 187b | ++++++ |
| 96 | 187b or 187a | +++ |
| 97 | 188b or 188a | ++++ |
| 98 | 188a or 188b | + |
| 99 | 192b or 192a | +++ |
| 100 | 192a or 192b | + |
| 101 | 189b or 189a | ++++ |
| 102 | 189a or 189b | ++ |
| 103 | 178b or 178a | ++++ |
| 104 | 178a or 178b | ++ |
| 105 | 193b or 193a | +++ |
| 106 | 193a or 193b | + |
| 107 | 170b or 170a | + |
| 108 | 170a or 170b | ++++ |
| 109 | 168b or 168a | +++ |
| 110 | 168a or 168b | >30 µM |
| 111 | 171b or 171a | ++++ |
| 112 | 171a or 171b | + |
| 113 | 122b or 122a | +++++ |
| 114 | 122a or 122b | ++ |
| 115 | 120b or 120a | ++ |
| 116 | 120a or 120b | ++++ |
| 117 | 125b or 125a | ++++ |
| 118 | 125a or 125b | ++ |
| 119 | 129b or 129a | + |
| 120 | 129a or 129b | >30 µM |
| 121 | 112b or 112a | +++++ |
| 122 | 112a or 112b | +++ |
| 123 | 207c | ++++ |
| 124 | 207aa | ++ |
| 125 | 207b | ++++ |
| 126 | 195a or 195e | ++ |
| 127 | 195e or 195a | ++++ |
| 128 | 105b or 105a | +++ |
| 129 | 105a or 105b | + |
| 130 | 121b or 121a | ++++ |
| 131 | 121a or 121b | ++ |
| 132 | 145b or 145a | ++ |
| 133 | 145a or 145b | >30 µM |
| 134 | 131b or 131a | >30 µM |
| 135 | 131a or 131b | ++ |
| 136 | 225b or 225a | ++ |
| 137 | 225a or 225b | ++++ |
| 138 | 144b or 144a | ++ |
| 139 | 144a or 144b | ++++ |
| 140 | 149b or 149a | +++++ |
| 141 | 149a or 149b | ++ |
| 142 | 152b or 152a | ++++ |
| 143 | 152a or 152b | + |
| 144 | 151b' or 151a' | >30 µM |
| 145 | 151a' or 151b' | + |

TABLE 30-continued

Average IC$_{50}$ of compounds in hTHP-1 assay

| Example # | Compound Number | hTHP-1 IC$_{50}$ |
|---|---|---|
| 146 | 167b or 167a | ++ |
| 147 | 167a or 167b | +++ |
| 148 | 107b or 107a | ++++++ |
| 149 | 107a or 107b | +++ |
| 150 | 110b or 110a | + |
| 151 | 110a or 110b | +++ |
| 152 | 151b or 151a | ++++ |
| 153 | 151a or 151b | ++ |
| 154 | 154b or 154a | ++++ |
| 155 | 154a or 154b | ++ |
| 156 | 148b or 148a | +++ |
| 157 | 148a or 148b | + |
| 158 | 153b or 153a | ++ |
| 159 | 153a or 153b | + |
| 160 | 109b or 109a | +++ |
| 161 | 109a or 109b | + |
| 162 | 135b or 135a | +++ |
| 163 | 135a or 135b | + |
| 164 | 134b or 134a | +++++ |
| 165 | 134a or 134b | ++ |
| 166 | 130b or 130a | +++ |
| 167 | 130a or 130b | >11.2150 |
| 168 | 212b or 212a | +++ |
| 169 | 212a or 212b | >5.5915 |
| 170 | 205b or 205a | ++ |
| 171 | 205a or 205b | +++ |
| 172 | 143b or 143a | +++ |
| 173 | 143a or 143b | ++ |
| 174 | 206b or 206a | +++ |
| 175 | 206a or 206b | ++ |
| 176 | 108b or 108a | +++++ |
| 177 | 108a or 108b | ++ |
| 178 | 202b or 202a | + |
| 179 | 202a or 202b | ++ |
| 180 | 116b or 116a | ++ |
| 181 | 116a or 116b | + |
| 182 | 173a or 173b | +++++ |
| 183 | 173b or 173a | +++ |
| 184 | 174b or 174a | +++ |
| 185 | 174a or 174b | + |
| 186 | 223b or 223a | ++++ |
| 187 | 223a or 223b | + |
| 188 | 158b or 158a | ++ |
| 189 | 158a or 158b | >30 μM |
| 190 | 220b or 220a | +++ |
| 191 | 220a or 220b | + |
| 192 | 157a or 157b | +++ |
| 193 | 157b or 157a | >30 μM |
| 194 | 161b or 161a | ++ |
| 195 | 161a or 161b | + |
| 196 | 165b or 165a | + |
| 197 | 165a or 165b | >30 μM |
| 198 | 172b or 172a | + |
| 199 | 172a or 172b | >30 μM |
| 200 | 106a or 106b | +++++ |
| 201 | 106b or 106a | +++ |
| 202 | 136b or 136a | ++ |
| 203 | 136a or 136b | ++++++ |
| 204 | 183a or 183b | +++ |
| 205 | 183b or 183a | +++++ |
| 206 | 176b or 176a | +++++ |
| 207 | 176a or 176b | +++ |
| 208 | 221 | + |
| 209 | 219 | >30 μM |
| 210 | 217 | >30 μM |
| 211 | 216 | + |
| 212 | 215 | >30 μM |
| 213 | 218 | >30 μM |
| 214 | 214 | >30 μM |
| 215 | 211 | + |
| 216 | 210 | >30 μM |
| 217 | 201 | + |
| 218 | 200 | ++ |
| 219 | 199 | >30 μM |
| 220 | 198 | + |
| 221 | 141 | ++++ |
| 222 | 140 | +++ |
| 223 | 321 | +++++ |
| 224 | 321b or 321a | +++++ |
| 225 | 321a or 321b | ++ |
| 226 | 329 | +++++ |
| 227 | 375 | ++++ |
| 228 | 376 | ++++ |
| 229 | 307 | ++ |
| 230 | 323 | ++ |
| 231 | 338 | ++ |
| 232 | 341 | ++ |
| 233 | 342 | ++ |
| 234 | 345 | ++ |
| 235 | 346 | ++ |
| 236 | 347 | ++ |
| 237 | 348 | ++ |
| 238 | 403 | ++ |
| 239 | 402 | ++ |
| 240 | 350 | ++ |
| 241 | 322 | ++ |
| 242 | 351 | ++ |
| 243 | 358 | ++ |
| 244 | 401 | + |
| 245 | 404 | + |
| 246 | 331 | + |
| 247 | 339 | + |
| 248 | 405 | + |
| 249 | 406 | >30 μM |
| 250 | 324 | + |
| 251 | 407 | ++ |
| 252 | 410 | >30 μM |
| 253 | 408 | |
| 254 | 308 | ++ |
| 255 | 311 | + |
| 256 | 312 | >30 μM |
| 257 | 327 | ++++ |
| 258 | 326 | ++++ |
| 259 | 139 | +++ |
| 260 | 137 | +++ |
| 261 | 409 | ++ |
| 262 | 303 | +++++ |
| 263 | 325 | +++++ |
| 264 | 138 | ++ |
| 265 | 332 | ++++ |
| 266 | 334 | ++++ |
| 267 | 335 | ++++ |
| 268 | 337 | ++ |
| 269 | 113 | +++++ |
| 270 | 343 | ++ |
| 271 | 349 | ++ |
| 272 | 344 | +++ |
| 273 | 359 | + |
| 274 | 352 | +++ |
| 275 | 354 | ++ |
| 276 | 355 | +++ |
| 277 | 356 | >30 μM |
| 278 | 357 | +++ |
| 279 | 340 | +++++ |
| 280 | 377 | +++ |
| 281 | 378 | +++++ |
| 282 | 379 | +++ |
| 283 | 380 | +++ |
| 284 | 353 | + |
| 285 | 333 | ++++ |
| 287 | 382 | ++ |
| 288 | 383 | ++ |
| 289 | 315 | ++++ |
| 290 | 316 | ++ |
| 291 | 317 | ++++ |
| 292 | 319 | ++++ |
| 293 | 320 | +++ |
| 294 | 336 | ++++ |
| 295 | 330 | ++++ |
| 296 | 364a | ++++++ |
| 297 | 364b | +++ |
| 298 | 365a | ++++ |

TABLE 30-continued

Average IC$_{50}$ of compounds in hTHP-1 assay

| Example # | Compound Number | hTHP-1 IC$_{50}$ |
|---|---|---|
| 299 | 365b | ++ |
| 300 | 308a | +++ |
| 301 | 308b | + |
| 302 | 195ba or 195bb | +++ |
| 303 | 195bb or 195ba | +++++ |
| 304 | 207a or 207bb | ++++ |
| 305 | 207bb or 207a | +++++ |
| 306 | 366a | ++++++ |
| 307 | 366b | ++++ |
| 308 | 139a | ++ |
| 309 | 139b | ++++ |
| 310 | 367a | +++++ |
| 311 | 367b | +++ |
| 312 | 409b | ++ |
| 313 | 409a | ++ |
| 314 | 369a | +++ |
| 315 | 369b | + |
| 316 | 159a | +++ |
| 317 | 159ab | ++ |
| 318 | 159ba | +++ |
| 319 | 137a | ++ |
| 320 | 137b | ++++ |
| 321 | 317ab | ++ |
| 322 | 317aa | +++ |
| 323 | 317bb | ++++ |
| 324 | 317ba | +++++ |
| 325 | 316a | >28.4352 |
| 326 | 316b | + |
| 327 | 373a | >30 μM |
| 328 | 373b | ++ |
| 329 | 374a | >30 μM |
| 330 | 374b | >30 μM |
| 331 | 319ab | + |
| 332 | 319aa | +++ |
| 333 | 319bb | ++ |
| 334 | 319ba | +++++ |
| 335 | 320a | ++ |
| 336 | 320b | +++ |
| 337 | 323ab | ++ |
| 338 | 323bb | ++ |
| 339 | 323aa | ++ |
| 340 | 323ba | ++ |
| 341 | 303a | ++++++ |
| 342 | 303b | +++ |
| 343 | 315a | ++++ |
| 344 | 315b | ++ |
| 345 | 138a | +++ |
| 346 | 138b | + |
| 347 | 328a | +++++ |
| 348 | 328b | ++ |
| 349 | 326b | ++ |
| 350 | 326a | ++++ |
| 351 | 318a | +++ |
| 352 | 318b | ++++ |
| 353 | 325a | ++ |
| 354 | 325b | +++++ |
| 355 | 329a | ++++++ |
| 356 | 329b | +++ |
| 357 | 404b | + |
| 358 | 404a | >30 μM |
| 359 | 332a | +++++ |
| 360 | 332b | +++ |
| 361 | 335a | ++++ |
| 362 | 335b | ++ |
| 363 | 336a | ++ |
| 364 | 336b | ++++ |
| 365 | 337a | >30 μM |
| 366 | 337b | ++ |
| 367 | 371a | >30 μM |
| 368 | 371b | ++ |
| 369 | 372a | >30 μM |
| 370 | 372b | +++ |
| 371 | 334a | + |
| 372 | 334b | ++++ |
| 373 | 339a | + |
| 374 | 339b | +++++ |
| 375 | 334ab | + |
| 376 | 334aa | + |
| 377 | 334bb | ++++ |
| 378 | 334ba | +++ |
| 379 | 338a | ++ |
| 380 | 338b | >30 μM |
| 381 | 340a | +++++ |
| 382 | 340b | ++ |
| 383 | 361b | >30 μM |
| 384 | 361a | >30 μM |
| 385 | 113a | +++++ |
| 386 | 113b | +++ |
| 387 | 330a | ++ |
| 388 | 330b | ++++ |
| 389 | 341a | >30 μM |
| 390 | 341b | ++ |
| 391 | 360ba | +++ |
| 392 | 360bb | +++ |
| 393 | 363b | +++++ |
| 394 | 363a | +++ |
| 395 | 343a | ++ |
| 396 | 343b | >30 μM |
| 397 | 359a | ++ |
| 398 | 359b | >30 μM |
| 399 | 352a | +++ |
| 400 | 352b | + |
| 401 | 383a | >30 μM |
| 402 | 383b | ++ |
| 403 | 382a | +++ |
| 404 | 382b | + |
| 405 | 379a | |
| 406 | 379b | >30 μM |
| 407 | 380a | + |
| 408 | 380b | ++ |
| 409 | 380c | +++ |
| 410 | 380d | ++++ |
| 411 | 384a | ++ |
| 412 | 384b | >30 μM |
| 413 | 357a | +++ |
| 414 | 357b | + |
| 415 | 354a | >30 μM |
| 416 | 354b | +++ |
| 417 | 387a | ++ |
| 418 | 387b | ++++ |
| 419 | 333a | ++++ |
| 420 | 333b | ++ |
| 421 | 375a | +++++ |
| 422 | 375b | |
| 423 | 376a | +++++ |
| 424 | 376b | |
| 425 | 318 | +++ |
| 426 | 313 | + |
| 427 | 314 | + |
| 428 | 309 | + |
| 430 | 310 | + |
| 431 | 306 | + |

A number of embodiments of the invention have been described. Nevertheless, it will be understood that various modifications may be made without departing from the spirit and scope of the invention. Accordingly, other embodiments are within the scope of the following claims.

We claim:
1. A compound selected from the group consisting of:
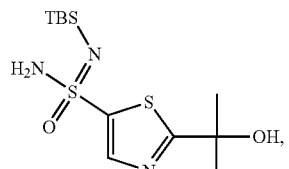
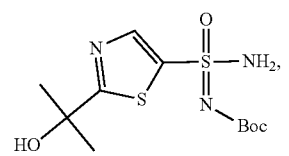
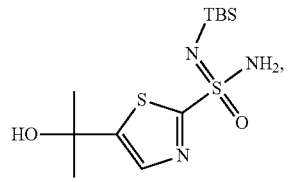
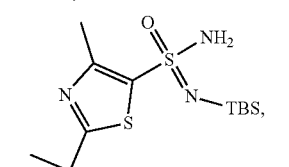
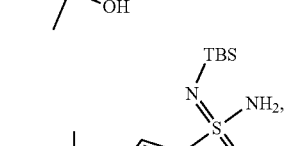
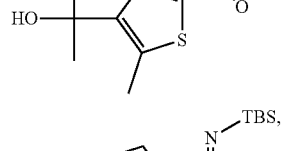
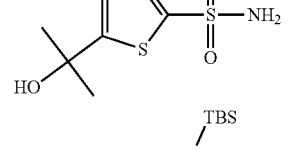
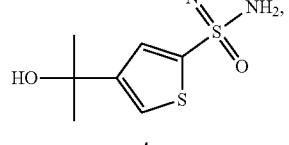
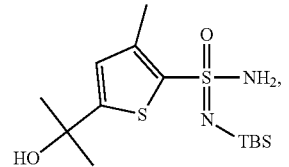
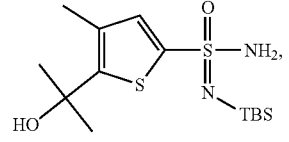
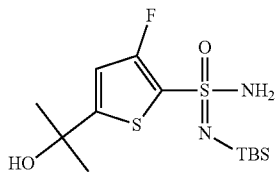
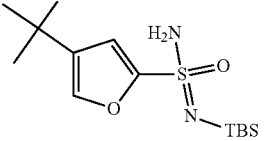
wherein TBS is tert-butyldimethylsilyl and Boc is tert-butyloxy carbonyl, and pharmaceutically acceptable salts thereof.
2. The compound of claim 1, selected from the group consisting of:
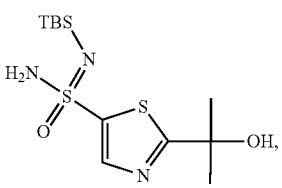
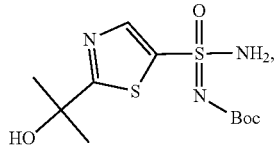
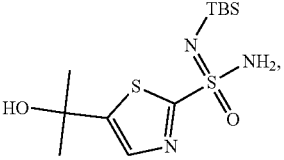
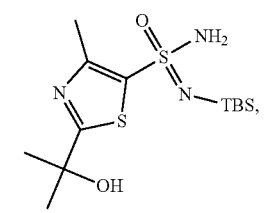
and pharmaceutically acceptable salts thereof.
3. The compound of claim 1, selected from the group consisting of:
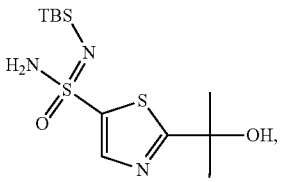

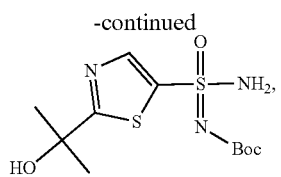
and pharmaceutically acceptable salts thereof.
* * * * *

SEQUENCE LISTING

Sequence total quantity: 37
SEQ ID NO: 1              moltype = DNA   length = 702
FEATURE                   Location/Qualifiers
source                    1..702
                          mol_type = unassigned DNA
                          organism = Homo sapiens
SEQUENCE: 1
atgagcactg aaagcatgat ccgggacgtg gagctggccg aggaggcgct ccccaagaag   60
acaggggggc cccagggctc caggcggtgc ttgttcctca gcctcttctc cttcctgatc  120
gtggcaggcg ccaccacgct cttctgcctg ctgcactttg gagtgatcgg ccccagagg   180
gaagagttcc ccagggacct ctctctaatc agccctctgg cccaggcagt cagatcatct  240
tctcgaaccc cgagtgacaa gcctgtagcc catgttgtag caaaccctca agctgagggg  300
cagctccagt ggctgaaccg ccgggccaat gccttcctgg ccaatggcgt ggagctgaga  360
gataaccagc tggtggtgcc atcagagggc ctgtacctca tctactccca ggtcctcttc  420
aagggccaag gctgcccctc cacccatgtg ctcctcacca acaccatcag ccgcatcgtc  480
gtctcctacc agaccaaggt caacctcctc tctgccatca agagccctg ccagagggag   540
accccagagg gggctgaggc caagccctgg tatgagccca tctatctggg agggtcttc   600
cagctggaga agggtgaccg actcagcgct gagatcaatc ggcccgacta tctcgactt   660
gccgagtctg gcaggtcta ctttgggatc attgccctgt ga                      702

SEQ ID NO: 2              moltype = DNA   length = 1368
FEATURE                   Location/Qualifiers
source                    1..1368
                          mol_type = unassigned DNA
                          organism = Homo sapiens
SEQUENCE: 2
atgggcctct ccaccgtgcc tgacctgctg ctgccactgg tgctcctgga gctgttggtg   60
ggaatatacc cctcaggggt tattggactg gtccctcacc taggggacag ggagaagaga  120
gatagtgtgt gtccccaagg aaaatatatc caccctcaaa ataattcgat ttgctgtacc  180
aagtgccaca aaggaaccta cttgtacaat gactgtccag gccgggggca ggatacggac  240
tgcagggagt gtgagagcgg ctccttcacc gcttcagaaa accacctcag acactgcctc  300
agctgctcca aatgccgaaa ggaaatgggt caggtggaga tctcttcttg cacagtggac  360
cgggacaccg tgtgtggctg caggaagaac cagtaccggc attattggag tgaaaacctt  420
ttccagtgct tcaattgcag cctctgcctc aatgggaccg tgcacctctc ctgccaggag  480
aaacagaaca ccgtgtgcac ctgccatgca ggtttctttc taagagaaaa cgagtgtgtc  540
tcctgtagta actgtaagaa aagcctggag tgcacgaagt tgtgcctacc ccagattgag  600
aatgttaagg gcactgagga ctcaggcacc acagtgctgt tgcccctggt catttttcttt  660
ggtctttgcc ttttatccct cctcttcatt ggtttaatgt atcgctacca acggtggaag  720
tccaagctct actccattgt ttgtgggaaa tcgacacctg aaaaagaggg ggagcttgaa  780
ggaactacta ctaagcccct ggccccaaac ccaagtctca gtccactcc aaggcttcacc  840
cccaccctgg gcttcagtcc cgtgccagt tccaccttca cctccagctc cacctatacc   900
cccggtgact gtcccaactt gcggctcccc gcagagagg tggcaccacc ctatcagggg  960
gctgacccca tccttgcgac agccctcgcc tccgacccca tccccaaccc ccttcagaag 1020
tgggagacga gcgcccacaa gccacagagc ctagacactg atgaccccgc cgagcgtgac 1080
gccgtggtgg agaacgtgcc cccgttcgcc tggaaggaat tcgtgcgcg cctagggctg 1140
agcgaccacg agatcgatcg gctggagctg cagaacgggc gctgcctgcg cgaggcgcaa 1200
tacagcatgc tggcgacctg gaggcggcgc acgccgcggc gcgaggccac gctggagctg 1260
ctgggacgcg tgctccgcga catggacctg ctgggctgcc tggaggacat cgaggaggcg 1320
cttttgcggcc ccgccgccct cccgcccgcg cccagtcttc tcagatga                  1368

SEQ ID NO: 3              moltype = DNA   length = 281
FEATURE                   Location/Qualifiers
source                    1..281
                          mol_type = unassigned DNA
                          organism = Homo sapiens
SEQUENCE: 3
attcttcccc tggtggccat gggacccagg tcaatgtcac ctgcatcgtg aacgtctgta   60
gcagctctga ccacagctca cagtgctcct cccaagccag ctccacaatg ggagacacag  120
attccagccc ctcggagtcc ccgaaggacg agcaggtccc cttctccaag gaggaatgtg  180
cctttcggtc acagctggag acgccagaga ccctgctggg gagcaccgaa gagaagcccc  240
tgccccttgg agtgcctgat gctgggatga agcccagtta a                      281

SEQ ID NO: 4              moltype = DNA   length = 939
FEATURE                   Location/Qualifiers
source                    1..939
                          mol_type = unassigned DNA
                          organism = Homo sapiens
SEQUENCE: 4
atggcagctg ggcaaaatgg gcacgaagag tgggtgggca gcgcatacct gtttgtggag   60
tcctcgctgg acaaggtggt cctgtcggat gcctacgcgc accccagca gaaggtggca  120
gtgtacaggg ctctgcaggc tgccttggca gagagcggcg ggagcccgga cgtgctcag   180
atgctgaaga tccaccgcag cgacccgcag ctgatcgtgc agctgcgatt ctgcgggcgg  240
cagcccgtg gccgcttcct ccgcgcctac cgcgaggggg cgctgccgcc cgcgctgaa   300
aggagcctgc cggccgcgct cgcccagcac tcggtgcccg tgcaactgga gctgcgcgca  360
ggcgccgagc ggctggacgc tttgctggcg gacgaggagc gctgtttgag ttgcatccta  420
gcccagcagc ccgaccggct ccgggatgaa gaactggctg agctggagga tgcgctgcga  480
aatctgaagt gcggctcggg ggcccgggt ggcgacgggg aggtcgcttc ggccccctg    540
cagcccccgg tgccctctct gtcggaggtg aagccgcgc gccgccgcc acctgcccag   600

```
actttctgt tccagggtca gcctgtagtg aatcggccgc tgagcctgaa ggaccaacag    660
acgttcgcgc gctctgtggg tctcaaatgg cgcaaggtgg ggcgctcact gcagcgaggc    720
tgccgggcgc tgcgggaccc ggcgctggac tcgctggcct acgagtacga gcgcgaggga    780
ctgtacgagc aggccttcca gctgctgcgg cgcttcgtgc aggccgaggg ccgccgcgcc    840
acgctgcagc gcctggtgga ggcactcgag gagaacgagc tcaccagcct ggcagaggac    900
ttgctgggcc tgaccgatcc caatggcggc ctggcctag                           939

SEQ ID NO: 5              moltype = DNA   length = 1506
FEATURE                   Location/Qualifiers
source                    1..1506
                          mol_type = unassigned DNA
                          organism = Homo sapiens
SEQUENCE: 5
atggctgcag ctagcgtgac ccccctggc tccctggagt tgctacagcc cggcttctcc      60
aagaccctcc tggggaccaa gctggaagcc aagtacctgt gctccgcctg cagaaacgtc    120
ctccgcaggc ccttccaggc gcagtgtggc accggtact gctccttctg cctggccagc     180
atcctcagct ctgggcctca gaactgtgct gcctgtgttc acgagggcat atatgaagaa    240
ggcatttcta ttttagaaag cagttcggcc ttcccagata atgctgcccg caggaggtg     300
gagagcctgc cggccgtctg tcccagtgat ggatgcacct ggaaggggac cctgaaagaa    360
tacgagagct gccacgaagg ccgctgcccg ctcatgctga ccgaatgtcc cgcgtgcaaa    420
ggcctggtcc gccttggtga aaaggagcgc cacctggagc acgagtgccc ggagagaagc    480
ctgagctgcc ggcattgccg ggcaccccgc tgcggagcag acgtgaaggc gcaccacgag    540
gtctgccccca agttccccctt aacttgtgac ggctgcggca agaagaagat ccccgggag    600
aagtttcagg accacgtcaa gacttgtgc aagtgtcgag tcccttgcag attccacgcc    660
atcggctgcc tcgagacggt agagggtgag aaacagcagg agcacgaggt gcagtggctg    720
cgggagcacc tggccatgct actgagctcg gtgctgaaga caaagccccct cttgggagac    780
cagagccacg cggggtcaga gctcctgcag aggtgcgaga gcctggagaa gaagacggcc    840
actttgaga acattgtctg cgtcctgaac cgggaggtgg agaggtggc catgactgcc       900
gaggcctgca gccggcagca ccggctggac aagacaaga ttgaagccct gagtagcaag      960
gtgcagcagc tggagaggag cattggcctc aaggacctga cgatggctga cttggagcag   1020
aaggtcttgg agatggaggc atccacctac gatgggtct tcatctggaa gatctcagac    1080
ttcgccagga agcgccagga agctgtggct ggccgcatac ccgccatctt ctccccagcc   1140
ttctacacca gcaggtacgg ctacaagatg tgtctgcgta tctacctgaa cggcgacggc    1200
accgggcgag gaacacacct gtcccctctt ttttgtggta tgaagggccc gaatgagcc    1260
ctgctgcggt ggcccttcaa ccagaaggtg accttaatgc tgctcgacca gaataaccgg   1320
gagcacgtga ttgacgcctt caggcccgac gtgacttcat cctctttca gaggccagtc    1380
aacgacatga acatcgcaag cggctgcccc ctcttctgcc ccgtctccaa gatggaggca   1440
aagaattcct acgtgcggga cgatgccatc ttcatcaagg ccattgtgga cctgacaggg    1500
ctctaa                                                              1506

SEQ ID NO: 6              moltype = DNA   length = 1044
FEATURE                   Location/Qualifiers
source                    1..1044
                          mol_type = unassigned DNA
                          organism = Homo sapiens
SEQUENCE: 6
atggaaacac ccttctacgg cgatgaggcg ctgagcggcc tgggcggcgg cgccagtggc      60
agcggcggca gcttcgcgtc cccgggccgg ttgttcccg gggcgccccc gacggccgcg     120
gccggcagca tgatgaagaa ggacgcgctg acgctgagcc tgagtgagca ggtggcggca    180
gcgctcaagc ctgcggccgc gccgcctcct accccctgc gcgccgacgg cgcccccagc    240
gcggcacccc ccgacggcct gctcgcctct cccgacctgg ggctgctgaa gctgctctaa    300
cccgagctcg agcgcctcat catccagtcc aacgggctgg tcaccaccac gccgacgagc    360
tcacagttcc tctaccccaa ggtgcggcc agcgaggagc aggagttcgc cgagggcttc    420
gtcaaggccc tggaggattt acacaagcag aaccagctcg gcgcgggcgc ggccgctgcc    480
gccgcgcgg ccgccgccgg ggcccctccc ggcacggccca cgggctccgc gccccccggc    540
gagctggccc cggcgcgcgg cgcgcccgaa gcgcctgtct acgcgaacct gagcagctac    600
gcgggcggcg ccggggcgc ggggggcgcc gcgacggtcg ccttcgctgc cgaacctgtg    660
cccttccccgc cgccgccacc cccaggcgcg ttgggcccgc cgcgcctggc tgcgctcaag    720
gacgagccac agacggtgcc cgacgtgcgg agcttcggcg agagcccgcg gttgtcgccc    780
atcgacatgg acacgcagga gcgcatcaag gggagcgca agcggctgcg caaccgcatc    840
gccgcctcca gtgccgcaa gcgcaagctg gagcgcatct gcgcgcctgga agagaaagtg    900
aagaccctca agagtcagaa cacggagctg gcgtccacgg cgagcctgct gcgcgagcag    960
gtgccgcagc tcaagcagaa agtcctcagc cacgtcaaca gcggctgcca gctgctgccc   1020
cagcaccagg tgccgcgta ctga                                           1044

SEQ ID NO: 7              moltype = DNA   length = 4124
FEATURE                   Location/Qualifiers
source                    1..4124
                          mol_type = unassigned DNA
                          organism = Homo sapiens
SEQUENCE: 7
atgagcacgg aggcggacga gggcatcact ttctctgtgc cacccttcgc ccctcgggc      60
ttctgcacca tccccgaggg cggcatctgc aggagggga gagcggcggc ggtgggcgag     120
ggcgaggagc accagctgcc accgcgccg ccggcagtt tctggaacgt ggagagcgg       180
gctgccctg gcatcggttg tccggcggcc acctcctcga gcagtgccac ccgaggccgga    240
ggcagctctg ttggcggggg cagccgacgg accacggtgg catatgtgat caacgaagcg    300
agccaagggc aactggtggt ggccgagagc gaggccctgc agagcttgcg ggaggcgtgc    360
gagacagtgg gcgccaccct ggaaccctgc attttggaa actcgacttt ggagaaacca    420
ccgtgctgga ccgcttttac aatgcagata ttgcggtggt ggagatgagc gatgcctccc    480
```

```
ggcagccgtc cttgttttac caccttgggg tgagagaaag tttcagcatg gccaacaaca    540
tcatcctcta ctgcgatact aactcggact ctctgcagtc actgaaggaa atcatttgcc    600
agaagaatac tatgtgcact gggaactaca cctttgttcc ttacatgata actccacata    660
acaaagtcta ctgctgtgac agcagcttca tgaaggggtt gacagagctc atgcaaccga    720
acttcgagct gcttcttgga cccatctgct tacctcttgt ggatcgtttt attcaacttt    780
tgaaggtggc acaagcaagt tctagccagt acttccggga atctatactc aatgacatca    840
ggaaagctcg taatttatac actggtaaag aattggcagc tgagttggca agaattcggc    900
agcgagtaga taatatcgaa gtcttgcacg cagatattgt cataaatctg ttactttcct    960
acagagatat ccaggactat gattctattg tgaagctggt agagactttta gaaaaactgg   1020
caacctttga tttggcctcc catcaccatg tgaagtttca ttatgcattt gcactgaata   1080
ggagaaatct ccctggtgac agagcaaaag ctcttgatat tatgattccc atggtgcaaa   1140
gcgaaggaca agttgcttca gatatgtatt gcctagttgg tcgaatctac aaagatatgt   1200
ttttggactc taatttcacg gacactgaaa gcagagacca tggagcttct tggttcaaaa   1260
aggcatttga atctgagcca acactacagt caggaattaa ttatgcggtc ctcctcctgg   1320
cagctggaca ccagtttgaa tcttcctttg agctccggaa agttggggtg aagctaagta   1380
gtcttcttgg taaaaaggga aacttggaaa actccagag ctactgggaa gttggatttt    1440
ttctgggggc cagcgtccta gccaatgacc acatgagagt cattcaagca tctgaaaagc   1500
tttttaaact gaagacacca gcatggtacc tcaagtctat tgtagagaca attttgatat   1560
ataagcattt tgtgaaactg accacagaac agcctgtggc caagcaagaa cttgtgggact  1620
tttgatgga tttcctggtc gaggccacaa agacagatgt tactgtggtt aggtttccag    1680
tattaatatt agaaccaacc aaaatctatc aaccttctta tttgtctatc aacaatgaag   1740
ttgaggaaaa gacaatctct atttggcacg tgcttcctga tgacaagaaa ggtatacatg   1800
agtggaattt tagtgcctct tctgtcaggg gagtgagtat ttctaaattt gaagaaagat   1860
gctgctttct ttatgtgctt cacaattctg atgatttcca aatctatttc tgtacagaac   1920
ttcattgtaa aaagttttt gagatggtga acaccattac cgaagagaag gggagaagca    1980
cagaggaagg agactgtgaa agtgacttgc tggagtataa ctatgaatat gatgaaaatg   2040
gtgacagagt cgttttagga aaaggcactt atgggatgat ctacgcaggt cgggacttga   2100
gcaaccaagt cagaattgct attaaggaaa tcccagagag agacagcaga tactctcagc   2160
ccctgcatga agaaatagca ttgcataaac acctgaagca caaaaatatt gtccagtatc   2220
tgggctcttt cagtgagaat ggtttcatta aaatcttcat ggagcaggtc cctgaggaa    2280
gtctttctgc tctccttcgt tccaaatggg gtccattaaa agacaatgag caaacaattg   2340
gcttttatac aaagcaaata ctggaaggat taaaatatct ccatgacaat cagatagttc   2400
accgggacat aaagggtgac aatgtgttga ttaataccta cagtggtgtt ctcaagatct   2460
ctgacttcgg aacatcaaag aggcttgctg gcataaaccc ctgtactgaa acttttactg   2520
gtaccctcca gtatatggca ccagaaataa tagataaagg accaagaggc tacggaaaag   2580
cagcagacat ctggtctctg ggctgtacaa tcattgaaat ggccacagga aaaccccat    2640
tttatgaact gggagaacca caagcagcta tgttcaaggt gggaatgttt aaagtccacc   2700
ctgagatccc agagtccatg tctgcagagg ccaaggcatt catactgaaa tgttttgaac   2760
cagatcctga caagagcc tgtgctaacg acttgcttgt tgatgagttt ttaaaagttt     2820
caagcaaaaa gaaaagaca caacctaagc tttcagctct ttcagctgga tcaaatgaat    2880
atctcaggag tatatccttg ccggtacctg tgctggtgga ggacaccagc agcagcagtg   2940
agtacggctc agtttcaccc gacacggagt tgaaagtgga ccccttctct ttcaaaacaa   3000
gagccaagtc ctgcggagaa agatgtca agggaattgc gacactcttt ttgggcattc     3060
cagatgagaa ttttgaagat cacagtgctc ctccttcccc tgaagaaaaa gattctggat   3120
tcttcatgct gaggaaggac agtgagaggc gagctaccct tcacaggatc ctgacggaag   3180
accaagacaa aattgtgaga aacctaatgg aatctttagc tcaggggct gaagaaccga    3240
aactaaaatg ggaacacatc acaaccctca ttgcaagcct cagagaattt gtgagatcca   3300
ctgaccgaaa aatcatagcc accacactgt caaagctgaa actggagctg gacttcgaca   3360
gccatggcat tagccaagtc caggtggtac tctttggttt tcaagatgct gtcaataaag   3420
ttcttcgaa tcataacatc aagccgcact ggatgtttgc cttagacagt atcattcgga    3480
aggcggtaca gacagccatt accatcctgg ttccagaact aaggccacat ttcagccttg   3540
catctgagag tgatactgct gatcaagaag acttggatgt agaagatgac catgaggaac   3600
agccttcaaa tcaaactgtc cgaagacctc aggctgtcat tgaagatgct gtggctacct   3660
caggcgtgag cacgctcagt tctactgtgt ctcatgattc ccagagtgct caccggtcac   3720
tgaatgtaca gcttggaagg atgaaaatag aaaccaatag attactggaa gaattggttc   3780
ggaaagagaa agaattacaa gcactccttc atcgagctat tgaagaaaaa gaccaagaaa   3840
ttaaacacct gaagcttaag tcccaaccca tagaaattcc tgaattgcct gtatttcatc   3900
taaattcttc tggcacaaat actgaagatt ctgaacttac cgactggctg agagtgaatg   3960
gagctgatga agacactata agccggtttt tggctgaaga ttatacacta ttggatgttc   4020
tctactatgt tacacgtgat gacttaaaat gcttgagact aaggggaggg atgctgtgca   4080
cactgctgaa ggctatcatt gactttcgaa acaaacagat ttga                    4124
SEQ ID NO: 8         moltype = DNA   length = 1128
FEATURE              Location/Qualifiers
source               1..1128
                     mol_type = unassigned DNA
                     organism = Homo sapiens
SEQUENCE: 8
atggagcgcg cgtcctgctt gttgctgctg ctgctgccgc tggtgcacgt ctctgcgacc     60
acgccagaac cttgtgagct ggacgatgaa gatttccgct gcgtctgcaa cttctccgaa    120
cctcagcccg actggtccga agccttccag tgtgtgtctg cagtagaggt ggagatccat    180
gccggcggtc tcaacctaga gccgtttcta aagcgcgtcg atgcggacgc cgaccgcgcg    240
cagtatgctg acacggtcaa ggctctccgc gtgcggcggc tcagtgggag ccgcacag     300
gttcctgctc agctactggt aggcccctg cgtgtgctgc cgtactcccg cctcaaggaa     360
ctgacgctcg aggacctaaa gataaccggc accatgcctc cgctgcctct ggaagccaca    420
ggacttgcac tttccagctt gcgcctacgc aacgtgtcgt gggcgacagg gcgttcttgg    480
ctcgccgagc tgcagcagtg gctcaagcca ggcctcaagg tactgagcat tgcccaagca    540
cactcgcctg ccttttcctg cgaacaggtt cgcgccttcc cggcccttac cagcctgac     600
ctgtctgaca atcctggact gggcgaacgc ggactgatgg cggctctctg tccccacaag    660
```

```
ttcccggcca tccagaatct agcgctgcgc aacacaggaa tggagacgcc cacaggcgtg  720
tgcgccgcac tggcggcggc aggtgtgcag ccccacagcc tagacctcag ccacaactcg  780
ctgcgcgcca ccgtaaaccc tagcgctccg agatgcatgt ggtccagcgc cctgaactcc  840
ctcaatctgt cgttcgctgg gctggaacag gtgcctaaag gactgccagc caagctcaga  900
gtgctcgatc tcagctgcaa cagactgaac agggcgccgc agcctgacga gctgcccgag  960
gtggataacc tgacactgga cgggaatccc ttcctggtcc ctggaactgc cctccccac  1020
gagggctcaa tgaactccgg cgtggtccca gcctgtgcac gttcgaccct gtcggtgggg 1080
gtgtcgggaa ccctggtgct gctccaaggg gcccggggct tgcctaa             1128

SEQ ID NO: 9              moltype = DNA length = 1140
FEATURE                   Location/Qualifiers
source                    1..1140
                          mol_type = unassigned DNA
                          organism = Homo sapiens
SEQUENCE: 9
atggcggcgg cggcggctca gggggcgggg ggcggggagc ccgtagaac cgaggggtc    60
ggcccggggg tccggggga ggtggagatg gtgaagggc agccgttcga cgtgggcccg   120
cgctacacgc agttgcagta catcggcgag ggcgcgtac gcatggtcag ctcggccat   180
gaccacgtgc gcaagactcg cgtggccatc aagaagatca gccccttcga acatcagacc  240
tactgccagc gcacgctccg ggagatccag atcctgctgc gcttccgcca tgagaatgtc  300
atcggcatcc gagacattct gcgggcgtcc accctggaag ccatgagaga tgtctacatt  360
gtgcaggacc tgatggagac tgacctgtac aagttgtcga aaagccagca gctgagcaat  420
gaccatatct gctacttcct ctaccagatc ctgcggggcc tcaagtacat ccactccgcc  480
aacgtgctcc accgagatct aaagccctcc aactgctca tcaacaccac ctgcgacctt  540
aagatttgtg atttcggcct ggccggatt gccgatcctg agcatgacca caccggcttc  600
ctgacggagt atgtggctac gcgctggtac cgggcccag agatcatgct gaactccaag  660
ggctatacca agtccatcga catctggtct gtgggctgca ttctggctga gatgctctct  720
aaccggccca tcttccctgg caagcactac ctggatcagc tcaaccacat tctgggcatc  780
ctgggctccc catcccagga ggacctgaat tgtatcatca acatgaaggc ccgaaactac  840
ctacagtctc tgcccctccaa gaccaaggtg gcttgggca agcttttccc caagtcagac  900
tccaaagccc ttgacctgct ggaccaggatg ttaacccttta accccaataa acggatcaca  960
gtggaggaag cgctggctca cccctacctg gagcagtact atgacccgac ggatgagcca 1020
gtggccgagg agcccttcac cttgccatg gagctggatg acctacctaa ggagcggctg 1080
aaggagctca tcttccagga gacagcacgc ttccagcccg gagtgctgga ggcccctag  1140

SEQ ID NO: 10             moltype = DNA length = 1083
FEATURE                   Location/Qualifiers
source                    1..1083
                          mol_type = unassigned DNA
                          organism = Homo sapiens
SEQUENCE: 10
atggcggcgg cggcggcggc gggcgcgggc ccggagatgg tccgcgggca ggtgttcgac   60
gtggggccgc gctacaccaa cctctcgtac atcggcgagg gcgcctacgg catggtgtgc  120
tctgcttatg ataatgtcaa caaagttcga gtagctatca agaaaatcag ccccttgag  180
caccagacct actgccagag aacctgagg gagataaaaa tcttactgcg cttcagacat  240
gagaacatca ttgaatcaa tgacattatt cgagcaccaa ccatcgagca atgaaagat  300
gtatatatag tacaggacct catggaaaca gatctttaca agtcttgaa gacacaacac  360
ctcagcaatg accatatctg ctattttctc taccagatcc tcagagggtt aaaatatatc  420
cattcagcta acgttctgca ccgtgacctc aagccttcca acctgctgct caacaccacc  480
tgtgatctca agatctgtga ctttggcctg gcccgtgttg cagatccaga ccatgatcac  540
acagggttcc tgacagaata tgtggccaca cgttggtaca cgggctccaga aattatgtg  600
aattccaagg gctacaccaa gtccattgat atttggtctg taggctgcat tctggcagaa  660
atgcttctta cagggccccat ctttccaggg aagcattatc ttgaccagct gaaccacatt  720
ttgggttattc ttgatccccc atcacaagaa gacctgaatt gtataataaa tttaaaagct  780
aggaactatt tgctttctct tccacacaaa aataaggtgc catggaacag gctgttccca  840
aatgctgact ccaaagctct ggacttattg gacaaaatgt tgacattcaa cccacacaag  900
aggattgaag tagaacaggc tctggcccac ccatatctgg agcagtatta cgacccgagt  960
gacgagccca tcgccgaagc accattcaag ttcgacatgg aattggatga cttgcctaag 1020
gaaaagctca agaactaatt ttttgaagag actgctagat tccagccagg atacagatct 1080
taa                                                              1083

SEQ ID NO: 11             moltype = DNA length = 2265
FEATURE                   Location/Qualifiers
source                    1..2265
                          mol_type = unassigned DNA
                          organism = Homo sapiens
SEQUENCE: 11
atgttttcag ggggtgtca tagccccggg tttggccgcc ccagccccgc cttcccccgcc   60
ccggggagcc cgccccctgc cccgcgtccc tgccgacagg aaacaggtga gcagattgcc  120
atcaagcagt gccggcagga gctcagcccc cggaaccgag agcggtggtg cctggagatc  180
cagatcatga aaggctgac ccaccccaat gtggtggctg cccgagatgt ccctgagggg  240
atgcagaact ggcgcccaa tgacctgccc tgctggcca tggagtactg ccaaggagga  300
gatctccgga agtacctgaa ccagtttgag aactgctgtg gtctgcggga aggtgccatc  360
ctcacccttgc tgagtgacat tgcctctgcg ttagataccc ttcatgaaaa cagaatcatt  420
catcggggatc taaagccaga aaacatcgtc ctgcagcaag agaacagag gttaatacac  480
aaaaattattg acctaggata tgccaaggag ctggatcagg gcagtctttg cacatcattc  540
gtggggaccc tgcagtacct ggccccagag ctactggagc agcagaagta cacagtgacc  600
gtcgactact ggagcttcgg cacctgcc tttgagtgca tcacgggctt ccggcccttc  660
ctccccaact ggcagcccgt gcagtggcat tcaaaagtgc ggcagaagag tgaggtggac  720
```

-continued

```
attgttgtta gcgaagactt gaatggaacg gtgaagtttt caagctcttt accctacccc    780
aataatctta acagtgtcct ggctgagcga ctgagaagt ggctgcaact gatgctgatg    840
tggcacccc gacagagggg cacggatccc acgtatgggc caatggctg cttcaaggcc    900
ctggatgaca tcttaaactt aaagctggtt catatcttga acatggtcac gggcaccatc    960
cacacctacc ctgtgacaga ggatgagagt ctgcagagct tgaaggccag aatccaacag    1020
gacacgggca tcccagagga ggaccaggag ctgctgcagg aagcgggcct ggcgttgatc    1080
cccgataagc ctgccactca gtgtatttca gacggcaagt taaatgaggg ccacacattg    1140
gacatggatc ttgttttct ctttgacaac agtaaaatca cctatgagac tcagatctcc    1200
ccacggcccc aacctgaaag tgtcagctgt atccttcaag agcccaagg gaatctcgcg    1260
ttcttccagc tgaggaaggt gtgggggcag gtctggcaca gcatccagac cctgaaggaa    1320
gattgcaacc ggctgcagca gggacagcga gccgccatga tgaatctcct ccgaaacaac    1380
agctgcctct ccaaaatgaa gaattccatg gcttccatgt ctcagcagct caaggccaag    1440
ttggatttct tcaaaaccag catccagatt gacctggaga agtacagcga gcaaaccgag    1500
tttgggatca catcagataa actgctgctg gcctggaggg aaatggagca ggctgtggag    1560
ctctgtgggc gggagaacga agtgaaactc ctggtagaac ggatgatggc tctgcagacc    1620
gacattgtgg acttacagag gagcccatg ggccggaagc aggggggaac gctgacgac    1680
ctagaggagc aagcaaggga gctgtacagg agactaaggg aaaaacctcg agaccagcga    1740
actgagggtg acagtcagga aattgtacgg ctgctgcttc aggcaattca gagcttcgag    1800
aagaaagtgc gagtgatcta tacgcagctc agtaaaactg tggtttgcaa gcagaaggcg    1860
ctggaactgt tgcccaaggt ggaagaggtg gtgagcttaa tgaatgagga tgagaagact    1920
gttgtccggc tgcaggagaa gcggcagaag gagctctgga atctcctgaa gattgcttgt    1980
agcaaggtcc gtggtcctgt cagtggaagc ccggatagca tgaatgcctc tcgacttagc    2040
cagcctgggc agctgatgtc tcagccctcc acggcctcca acagcttacc tgagccagcc    2100
aagaagagtg aagaactggt ggctgaagca cataacctct gcaccctgct agaaaatgcc    2160
atacaggaca ctgtgaggga acaagaccag agtttcacgg ccctagactg gagctggtta    2220
cagacgaag aagaagagca cagctgcctg gagcaggcct catga    2265

SEQ ID NO: 12          moltype = DNA   length = 954
FEATURE                Location/Qualifiers
source                 1..954
                       mol_type = unassigned DNA
                       organism = Homo sapiens
SEQUENCE: 12
atgttccagg cggccgagcg ccccaggag tgggccatgg agggcccccg cgacgggctg      60
aagaaggagc ggctactgga cgaccgccac gacagcggcc tggactccat gaaagacgag    120
gagtacgagc agatggtcaa ggagctgcag gagatccgcc tcgagccgca ggaggtgccg    180
cgcggctcgg agccctggaa gcagcagctc accgaggacg gggactcgtt cctgcacttg    240
gccatcatcc atgaagaaaa ggcactgacc atggaagtga tccgccaggt gaaggggac    300
ctggcccttcc tcaacttcca gaacaacctg cagcagactc cactccactt ggctgtgatc    360
accaaccagc cagaaattgc tgaggcactt ctgggagctg gctgtgatcc tgagctccga    420
gactttcgag gaaatacccc cctacacctt gcctgtgagc agggctgcct ggccagcgtg    480
ggagtcctga ctcagtcctg caccacccg cacctccact ccatcctgaa ggctaccaac    540
tacaatggcc acacgtgtct acacttagcc tctatccatg ctacctggg catcgtggag    600
cttttggtgt ccttgggtgc tgatgtcaat gctcaggagc cctgtaatgg ccggactgcc    660
cttcacctcg cagtggacct gcaaaatcct gacctggtgt cactcctgtt gaagtgtggg    720
gctgatgtca acagagttac ctaccagggc tattctcct accagctcac ctggggccgc    780
ccaagcaccc ggatacagca gcagctgggc cagctgacac tagaaaacct tcagatgctg    840
ccagagagtg aggatgagga gagctatgac acagagtcag agttcacgga gttcacagag    900
gacgagctgc cctatgatga ctgtgtgttt ggaggccagc gtctgacgtt atga           954

SEQ ID NO: 13          moltype = DNA   length = 2139
FEATURE                Location/Qualifiers
source                 1..2139
                       mol_type = unassigned DNA
                       organism = Homo sapiens
SEQUENCE: 13
atggccgggg ggccgggccc ggggagccc gcagcccccg cgcccagca cttcttgtac      60
gaggtgccgc cctgggtcat gtgccgcttc tacaaagtga tggacgccct ggagcccgcc    120
gactggtgcc agttcgccgc ctgatcgtg cgcgaccaga ccgacgctgcg gctgtgcgag    180
cgctccgggca agcgcacggc cagcgtcctg tggccctgga tcaaccgcaa cgcccgttg    240
gccgacctcg tgcacatcct cacgcacctg cagctgctcc gtgcgcggga catcatcaca    300
gcctggcacc ctccgcccc gcttccgtcc ccaggcacca ctgccccgag gcccagcagc    360
atccctgcac ccgccgaggc cgaggcctgg agccccgga agtgccatc ctcagcctcc    420
accttcctct ccccagcttt tccaggctcc cagaccatt caggcctga gctcggccctg    480
gtcccaagcc ctgcttccct gtggcctcca ccgccatctc cagcccttc ttctaccaag    540
ccaggcccag agagctcagt gtccctcctg caggagccc gccctttcc gttttgctgg    600
cccctctgtg agatttccg gggcacccac aacttctcgg aggagctcaa gatcgggag    660
ggtggctttg ggtgcgtgta ccgggcggtg atgaggaaca cggtctatgc tgtgaagagg    720
ctgaaggaga acgctgacct ggagtggact gcagtgaagc agagcttcct gaccgaggtg    780
gagcagctgt ccaggtttcg tcacccaaac attgtggact tgctggcta ctgtgctcag    840
aacggcttct actgccttggt gtacggcttc ctgcccaacg gctccctgga ggaccgtctc    900
cactgccaga cccaggcctg cccacctctc tcctggcctc agcgactgga catccttctg    960
ggtacagccc gggcaattca gtttctacat caggacagcc ccagcctcat ccatggagac    1020
atcaagagtt ccaacgtcct tctggatgag aggctgacac ccaagtggg agactttgg    1080
ctggcccggt tcagccgctt tgcccggtcc agccccagcc agagcagcat ggtggccgg    1140
acacagacag tgcggggcac cctggcctac ctgcccgagg agtacatcaa gacgggaagg    1200
ctggctgtga acacggacac cttcagcttt gggtggtag tgctagagac cttggctggt    1260
cagagggctg tgaagacgca cggtgccagg accaagtatc tgaaagacct ggtggaagag    1320
gaggctgagg aggctggagt ggctttgaga agcacccaga gcacactgca agcaggtctg    1380
```

```
gctgcagatg cctgggctgc tcccatcgcc atgcagatct acaagaagca cctggacccc   1440
aggcccgggc cctgcccacc tgagctgggc ctgggcctgg gccagctggc ctgctgctgc   1500
ctgcaccgcc gggccaaaag gaggcctcct atgacccagg tgtacgagag ctagagaag    1560
ctgcaggcag tggtggcggg ggtgcccggg cattcggagg ccgccagctg catccccct    1620
tccccgcagg agaactccta cgtgtccagc actggcaggc cccacagtgg ggctgctcca   1680
tggcagcccc tggcagcgcc atcaggagcc agtgcccagg cagcagagca gctgcagaga   1740
ggccccaacc agcccgtgga gagtgacgag agcctaggcg gcctctctgc tgccctgcgc   1800
tcctggcact tgactccaag ctgccctctg acccagcac ccctcaggga ggccggctgt    1860
cctcaggggg acacggcagg agaatcgagc tgggggagtg gcccaggacc ccggcccaca   1920
gccgtggaag gactggccct tggcagctct gcatcatcgt cgtcagagcc accgcagatt   1980
atcatcaacc ctgccgaca gaagatggtc cagaagctgg ccctgtacga ggatggggcc    2040
ctggacagcc tgcagctgct gtcgtccagc tccctcccag gcttgggcct ggaacaggac   2100
aggcagggcc ccgaagaaag tgatgaattt cagagctga                         2139

SEQ ID NO: 14           moltype = DNA    length = 1284
FEATURE                 Location/Qualifiers
source                  1..1284
                        mol_type = unassigned DNA
                        organism = Homo sapiens
SEQUENCE: 14
atgagcagaa gcaagcgtga caacaatttt tatagtgtag agattggaga ttctacattc   60
acagtcctga aacgatatca gaatttaaaa cctataggct caggagctca aggaatagta   120
tgcgcagctt atgatgccat tcttgaaaga aatgttgcaa tcaagaagct aagccgacca   180
tttcagaatc agactcatgc caagcgggcc tacagagagc tagttcttat gaaatgtgtt   240
aatcacaaaa atataattgg ccttttgaat gttttcacac cacagaaatc cctagaagaa   300
tttcaagatg tttacatagt catggagctc atggatgcaa atctttgcca agtgattcag   360
atggagctag atcatgaaag aatgtcctac cttctctatc agatgctgtg tggaatcaag   420
cacctttcatt ctgctggaat tattcatcgg gacttaaagc ccagtaatat agtagtaaaa   480
tctgattgca ctttgaagat tcttgacttc ggtctggcca ggactgcagg aacgagtttt   540
atgatgacgc cttatgtagt gactcgctac tacagagcca ccgaggtcat ccttggcatg   600
ggctacaagg aaaacgttga catttggtca gttgggtgca tcatgggaga aatgatcaaa   660
ggtggtgtt tgttcccagg tacagatcat attgatcagt ggataaagt tattgaacag    720
cttggaacac catgtcctga attcatgaag aaactgcaac caacagtaag gacttacgtt   780
gaaaacagac ctaaatatgc tggatatagc tttgagaaac tcttccctga tgtcctttc    840
ccagctgact cagaacacaa caaacttaaa gccagtcagg caagggattt gttatccaaa   900
atgctggtaa tagatgcatc taaaaggatc tctgtagatg aagctctcca cacccgtac    960
atcaatgtct ggtatgatcc ttctgaagca gaagctccac caccaaagat ccctgacaag   1020
cagttagatg aaagggaaca cacaatagaa gagtggaaca aattgatata taggaagtt    1080
atggacttgg aggagagaac caagaatgga gttatacggg agcagccctc tcctttaggt   1140
gcagcagtga tcaatggctc tcagcatcca tcatcatcgt cgtctgtcaa tgatgtgtct   1200
tcaatgtcaa cagatccgac tttggcctct gatacagaca gcagtctaga agcagcagct   1260
gggcctctgg gctgctgtag atga                                          1284

SEQ ID NO: 15           moltype = DNA    length = 1446
FEATURE                 Location/Qualifiers
source                  1..1446
                        mol_type = unassigned DNA
                        organism = Homo sapiens
SEQUENCE: 15
atgggggcct tggccagagc cctgccgtcc atactgctgg cattgctgct tacgtccacc   60
ccagagggct ctgggtgccaa ccccggcttg gtcgccagga tcaccgacaa gggactgcag   120
tatgcggccc aggaggggct attagctctg cagagtgagc tgctcaggat cacgctgcct   180
gacttcaccg gggacttgag gatccccac gtcggccgtg ggcgctatga gttccacagc   240
ctgaacatcc acagctgtga gctgcttcac tctgcgctga ggcctgtccc tggccagggc   300
ctgagtctca gcatctccga ctcctccatc cgggtccagg gcaggtggaa ggtgcgcaag   360
tcattcttca aactacaggg ctcctttgat gtcagtgcta agggcatcag catttcggtc   420
aacctcctgt gggcagcga gtcctccggg aggcccacag ttactgcctc cagctgcagc   480
agtgacatcg ctgacgtgga ggtggacatg tcgggagact gggggtggct gttgaacctc   540
ttccacaacc agattgagtc caagttccag aaagtactgg agagcaggat ttgcgaaatg   600
atccagaaat cggtgtcctc cgatctacag ccttatctcc aaactctgcc agttacaaca   660
gagattgaca gtttcgccga cattgattat agcttagtgg aagcccctcg ggcaacagcc   720
cagatgctgg aggtgatgtt taaggggtgaa atctttcatc gtaaccaccg ttctccagtt   780
accctccttg ctgcagtcat gagccttcct gaggaacaca caaaaatggt ctactttgcc   840
atctcggatt atgtcttcaa cacggccagc ctggtttatc atgaggaagg atatctgaag   900
ttctccatca cagatgacat gataccgcct gactctaata tccgactgac caccaagtcc   960
ttccgaccct tcgtccacg gttagccagg ctctaccca acatgaacct ggaactccag    1020
ggatcagtgc cctctgctcc gctcctgaac ttcagccctg gaatctgtc tgtggacccc    1080
tatatggaga tagatgcctt tgtgctgcctg cccagtcagg gcaaggagcc tgtcttccgg   1140
ctcagtgtgg ccactaatgt gtccgccacc ttgaccttca ataccagcaa gatcactgga   1200
ttcctgaagc caggaaaggt aaaagtggaa ctgaaagaat ccaaagttgg actattcaat   1260
gcagagctgt ggaagcgct cctcaactat tacatcctta cacccctcta ccccaagttc   1320
aatgataagt tggccgaagg cttccccctt cctctgctga gcgtgttca gctctacgac   1380
cttgggctgc agatccataa ggacttcctg ttcttgggtg ccaatgtcca atacatgaga   1440
gtttga                                                              1446

SEQ ID NO: 16           moltype = DNA    length = 1182
FEATURE                 Location/Qualifiers
source                  1..1182
                        mol_type = unassigned DNA
```

```
                       organism = Homo sapiens
SEQUENCE: 16
atgcccaaga agaagccgac gcccatccag ctgaacccgg cccccgacgg ctctgcagtt    60
aacgggacca gctctgcgga gaccaacttg gaggccttgc agaagaagct ggaggagcta   120
gagcttgatg agcagcagcg aaagcgcctt gaggcctttc ttacccagaa gcagaaggtg   180
ggagaactga aggatgacga cttgagaag atcagtgagc tggggctgg caatggcggt    240
gtggtgttca aggtctccca caagccttct ggcctggtca tggccagaaa gctaattcat   300
ctggagatca aacccgcaat ccggaaccag atcataaggg agctgcaggt tctgcatgag   360
tgcaactctc cgtacatcgt gggcttctat ggtgcgttct acagcgatgg cgagatcagt   420
atctgcatgg agcacatgga tggaggttct ctggatcaag tcctgaagaa agctggaaga   480
attcctgaac aaattttagg aaaagttagc attgctgtaa taaaaggcct gacatatctg   540
agggagaagc acaagatcat gcacagagat gtcaagccct ccaacatcct agtcaactcc   600
cgtgggagaa tcaagctctg tgactttggg gtcagcgggc agctcatcga ctccatggcc   660
aactccttcg tgggcacaag gtcctacatg tcgccagaaa gactccaggg gactcattac   720
tctgtgcagt cagacatctg gagcatggga ctgtctctgg tagagatggc ggttgggagg   780
tatcccatcc ctcctccaga tgccaaggag ctggagctga tgtttgggtg ccaggtggaa   840
ggagatgcgc tgagacccc acccaggcca aggaccccg ggaggcccct tagctcatac    900
ggaatggaca gccgacctcc catggcaatt tttgagttgt tggattacat agtcaacgag   960
cctcctccaa aactgcccag tggagtgttc agtctggaat ttcaagattt tgtgaataaa  1020
tgcttaataa aaaaccccgc agagagagca gatttgaagc aactcatggt tcatgctttt  1080
atcaagagat ctgatgctga ggaagtggat tttgcaggtt ggctctgctc caccatcggc  1140
cttaaccagc ccagcacacc aacccatgct gctggcgtct aa                     1182

SEQ ID NO: 17          moltype = DNA  length = 1203
FEATURE                Location/Qualifiers
source                 1..1203
                       mol_type = unassigned DNA
                       organism = Homo sapiens
SEQUENCE: 17
atgctggccc ggaggaagcc ggtgctgccg gcgctcacca tcaaccctac catcgccgag    60
ggcccatccc ctaccagcga gggcgcctcc gaggcaaacc tggtggacct gcagaagaag   120
ctggaggagc tggaacttga cgagcagcag aagaagcggc tggaagcctt ctcacccag    180
aaagccaagg tcggcgaact caaagacgat gacttcgaaa ggatctcaga gctgggcgcg   240
ggcaacggcg gggtggtcac caaagtccag cacagacccc cgggcctcat catggccagg   300
aagctgatcc accttgagat caagccggcc atccggaacc agatcatccg cgagctgcag   360
gtcctgcacg aatgcaactc gccgtacatc gtgggcttct acggggcctt ctacagtgac   420
ggggagatca gcatttgcat ggaacacatg gacggcggct ccctgaccca ggtgctgaaa   480
gaggccaaga ggattcccga ggagatcctg ggaaagtca gcatgcgcgt tctccggggc   540
ttggcgtacc tccgagagaa gcaccagatc atgcaccgag atgtgaagcc ctccaacatc   600
ctcgtgaact ctagaggga gatcaagctg tgtgacttcg gggtgagcgg ccagctcatc   660
gactccatgg ccaactcctt cgtgggcacg cgctcctaca tggctccgga gcggttgcag   720
ggcacacatt actcggtgca gtcggacatc tggagcatgg gcctgtccct ggtggagctg   780
gccgtcggaa ggtaccccat cccccccgcc gacgccaagg agtggagc catctttggc   840
cggcccgtgg tcgacgggga agaaggagag cctcacagca tctcgcctcg gccgaggccc   900
cccgggcgcc ccgtcagcgg tcacgggatg gatagccggc tgccatggc catctttgaa   960
ctcctggact atattgtgaa cgagccacct cctaagctgc caacggtgt gttcacccc    1020
gacttccagg agtttgtcaa taaatgcctc atcaagaacc tggaggagcc cgcggacctg  1080
aagatgctca caaaccacac cttcatcaag cggtccgagg tggaagaagt ggattttgcc  1140
ggctggttgt gtaaaaccct gcggctgaac cagcccggca cacccacgcg caccgccgtg  1200
tga                                                                1203

SEQ ID NO: 18          moltype = DNA  length = 957
FEATURE                Location/Qualifiers
source                 1..957
                       mol_type = unassigned DNA
                       organism = Homo sapiens
SEQUENCE: 18
atgtccaagc caccgcacc caaccccaca ccccccgga acctggactc ccggaccttc      60
atcaccattg gagacagaaa ctttgaggtg gaggctgatg acttggtgac catctcagaa   120
ctgggccgtg gagcctatgg ggtggtagag aaggtgcggc acgccagac cggcaccatc   180
atggccgtga gcggatccgg gccaccgtg aactcacagg agcagaagcg gctgctcatg   240
gacctgaca tcaacatgcg cacggtcgac tgtttctaca ctgtcacctt ctacggggca   300
ctattcagag agggagacgt gtggatctgc atggagctca tggacacatc cttggacaag  360
ttctaccgga aggtgctgga taaaaacatg acaattccag aggacatcct tgggagatt    420
gctgtgtcta tcgtgcgggc cctggagcat ctgcacagca agctgtcggt gatccacaga   480
gatgtgaagc cctccaatgt cctatcaac aaggagggcc atgtgaagat gtgtgacttt   540
ggcatcagtg gctacttggt ggactctgtg gccaagacga tggatgccgg ctgcaagccc  600
tacatggccc ctgagaggat caaccagag ctgaaccaga agggctacaa tgtcaagtcc   660
gacgtctgga gcctgggcat caccatgatt gatgtgcggt tcctgcggtt cccttacgag  720
tcctgggga cccgttcca gcagctgaag caggtggtgg aggagccgtc ccccagctc    780
ccagccgacc gtttctcccc cgagtttgtg gacttcactg ctcagtgcct gaggaagaac   840
cccgcagagc gtatgagcta cctggagctg atggagcacc ccttcttcac cttgcacaaa   900
accaagaaga cggacattgc tgccttcgtg aaggagatcc tgggagaaga ctcatag       957

SEQ ID NO: 19          moltype = DNA  length = 1005
FEATURE                Location/Qualifiers
source                 1..1005
                       mol_type = unassigned DNA
                       organism = Homo sapiens
```

```
SEQUENCE: 19
atgtctcagt cgaaaggcaa gaagcgaaac cctggcctta aaattccaaa agaagcattt    60
gaacaacctc agaccagttc cacaccacct cgagatttag actccaaggc ttgcatttct   120
attgaaaatc agaactttga ggtgaaggca gatgacctgg agcctataat ggaactggga   180
cgaggtgcgt acggggtggt ggagaagatg cggcacgtgc ccagcgggca gatcatggca   240
gtgaagcgga tccgagccac agtaaatagc caggaacaga aacggctact gatggatttg   300
gatatttcca tgaggacggt ggactgtcca ttcactgtca cctttatgg cgcactgttt    360
cgggagggtg atgtgtggat ctgcatggag ctcatggata tcactagaa taaattctac    420
aaacaagtta ttgataaagg ccagacaatt ccagagacaa tcttagggaa aatagcagtt   480
tctattgtaa aagcattaga acatttacat agtaagctgt ctgtcattca cagagacgtc   540
aagccttcta atgtactcat caatgctctc ggtcaagtga agatgtgcga ttttggaatc   600
agtggctact tggtggactc tgttgctaaa acaattgatg caggttgcaa accatacatg   660
gcccctgaaa gaataaaccc agagctcaac cagaagggat acagtgtgaa gtctgacatt   720
tggagtctgg gcatcacgat gattgagttg gccatccttc gatttcccta tgattcatgg   780
ggaactccat ttcagcagct caaacaggtg gtagaggagc catcgccaca actcccagca   840
gacaagttct ctgcagagtt tgttgacttt acctcacagt gcttaaagaa gaattccaaa   900
gaacggccta catacccaga gctaatgcaa catccatttt tcaccctaca tgaatccaaa   960
ggaacagatg tggcatcttt tgtaaaactg attcttggag actaa                  1005

SEQ ID NO: 20            moltype = DNA  length = 4539
FEATURE                  Location/Qualifiers
source                   1..4539
                         mol_type = unassigned DNA
                         organism = Homo sapiens
SEQUENCE: 20
atggcggcgg cggcggggaa tcgcgcctcg tcgtcgggat tcccgggcgc cagggctacg    60
agccctgagg caggcggcgg cggaggagcc ctcaaggcga gcagcgcgcc cgcggctgcc   120
gcgggactgc tgcgggaggc gggcagcggg ggccgcgagc gggcggactg gcggcggcgg   180
cagctgcgca aagtgcggag tgtggagctg accagctgc ctgagcagcc gctcttcctt    240
gccgcctcac cgccggcctc ctcgacttcc ccgtcgccgg agcccgcgga cgcagcgggg   300
agtgggaccg gcttccagcc tgtggcggtg ccgccgcccc acgagccgc gagccgcctc   360
ggcgccacc ttaccgagtc ggtggcggcg ccggacagcg gcgcctcgag tcccgcagcg    420
gccgagcccg gggagaagcg ggcgcccgcc gccgagccgt ctcctgcagc ggccccgcc    480
ggtcgtgaga tggagaataa agaaactctc aaagggttgc acaagatgga tgatcgtcga   540
gaggaacgaa tgatcaggga gaaactgaag gcaacctgta tgccagcctg gaagcacgaa   600
tggttggaaa ggagaaatag gcgagggcct gtggtggtaa aaccaatccc agttaaagga   660
gatggatctg aaatgaatca cttagcagct gagtctccag gagaggtcca ggcaagtgcg   720
gcttcaccag cttccaaagg ccgacgcagt ccttctcctg gcaactcccc atcaggtcgc   780
acagtgaaat cagaatctcc aggagtaagg agaaaaagag tttccccagt gccttttcag   840
agtggcagaa tcacaccacc ccgaagagcc ccttccaccag atggcttctc accatatagc   900
cctgaggaaa caaccgccg tgttaacaaa gtgatgcggg ccagactgta cttactgcag   960
cagatagggc ctaactcttt cctgattgga ggagacagcc cagacaataa ataccgggtg  1020
tttattgggc ctcagaactg cagctgtgca cgtggaacat tctgtattca tctgctattt  1080
gtgatgctcc gggtgtttca actagaacct tcagacccaa tgttatggag aaaaacttta  1140
aagaattttg aggttgagag tttgttccag aaatatcaca gtaggcgtag ctcaaggatc  1200
aaaagctcct ctcgtaacac catccagaag tttgtttcac gcatgtcaaa ttctcataca  1260
ttgtcatcat ctagtacttc tacgtctagt tcagaaaaca gcataaagga tgaagaggaa  1320
cagatgtgtc ctatttgctt gttgggcatg cttgatgaag aaagtcttac agtgtgtgaa  1380
gacggctgca ggaacaagct gcaccaccac tgcatgtcaa tttgggcaga agagtgtaga  1440
agaaatagag aacctttaat atgtcccctt tgtagatcta gtggagatc tcatgatttc   1500
tacagccacg agttgtcaag tcctgtggat tccccttctt ccctcagagc tgcacagcag  1560
caaaccgtac agcagcagcc tttggctgga tcacgaagga atcaagagag caattttaac  1620
cttactcatt atggaactca gcaaatccct cctgcttaca aagatttagc tgagccatgg  1680
attcaggtgt ttggaatgga actcgttggc tgcttatttt ctagaaactg gatgtgaga   1740
gagatggccc tcaggcgtct ttcccatgat gtcagtgggg ccctgctgtt ggcaaatggg  1800
gagagcactg gaaattctgg gggcagcagt ggaagcagcc cgagtggggg agccaccagt  1860
gggtcttccc agaccagtat ctcaggagat gtggtggagg catgctgcag cgttctgtca  1920
atggtctgtg ctgaccctgt ctacaaagtg tacgttgctg ctttaaaac attgagagcc  1980
atgctggtat atactccttg ccacagttta gcggaaagaa tcaaacttca gagacttctc  2040
cagccagttg tagacaccat cctagtcaaa tgtgcagatg ccaatagcccg cacaagtcag  2100
ctgtccatat caacactgtt ggaactgtgc aaaggccaag caggagagtt ggcagttggc  2160
agagaaatac taaaagctgg atccattggt attggtggtg ttgattatgt cttaaattgt  2220
attcttggaa ccaaactga tcaaacaat tggcaagaac ttcttggccg cctttgtctt   2280
atagatagac tgttgttgga atttcctgct gaatttttat ctcatattgt cagtactgat  2340
gtttcacaag ctgagcctgt tgaaatcagg tataagaagc tgctgtccct cttaaccttt  2400
gctttgcagt ccattgataa ttcccactca atggttggca aacttccag aaggatctac   2460
ttgagttctg caagaatggt tactacagta ccccatgtgt ttcaaaaact gttagaaatg  2520
ctgagtgttt ccagttccac tcacttcacc aggatcgcgt gccgtttgat ggctattgca  2580
gatgaggtgg aaattgccga agccatccag ttgggcgtag aagacacttt ggatggtcaa  2640
caggacagct tcttgcaggc atctgttccc aacaactatc tggaaccac agagaacagt   2700
tcccctgagt gcacagtcca tttagagaaa actggaaaag gattatgtgc tacaaaattg  2760
agtgccagtt cagaggacat ttctgagaga ctggccagca tttcagtagg accttctagt   2820
tcaacaacaa caacaacaac aacaacagag caaccaaagc caatggttca aacaaaaggc  2880
agacccacca gtcagttttt gaactcctct ccttatctc atcattccca attaatgttt   2940
ccagccttgt caacccttc ttcttctacc ccatctgtac cagctggcac tgcaacagat  3000
gtctctaagc atagacttca gggattcatt ccctgcagaa taccttctgc atctcctcaa  3060
acacagcgca gttttctct acaattccac agaaactgtc ctgaaaacaa agactcagat  3120
aaactttccc cagtctttac tcagtcaaga cccttgccct ccagtaacat acacaggcca  3180
aagccatcta gacctacccc aggtaataca agtaaacagg gagatccctc aaaaaatagc  3240
```

-continued

```
atgacacttg atctgaacag tagttccaaa tgtgatgaca gctttggctg tagcagcaat  3300
agtagtaatg ctgttatacc cagtgacgag acagtgttca ccccagtaga ggagaaatgc  3360
agattagatg tcaatacaga gctcaactcc agtattgagg accttcttga agcatctatg  3420
ccttcaagtg atacaacagt aacttttaag tcagaagttg ctgtcctgtc tcctgaaaag  3480
gctgaaaatg atgatcccta caaagatgat gtgaatcata atcaaaagtg caaagagaag  3540
atggaagctg aagaagaaga agctttagca attgccatgg caatgtcagc gtctcaggat  3600
gccctcccca tagttcctca gctgcaggtt gaaaatggag aagatatcat cattattcaa  3660
caggatacac cagagactct accaggacat accaaagcaa acaaccgta tagagaagac  3720
actgaatggc tgaaaggtca acagataggc cttgagcat tttcttcttg ttatcaggct  3780
caagatgtgg gaactggaac tttaatggct gttaaacagg tgacttatgt cagaaacaca  3840
tcttctgagc aagaagaagt agtagaagca ctaagagaag agataagaat gatgagccat  3900
ctgaatcatc caaacatcat taggatgttg ggagccacgt gtgagaagag caattacaat  3960
ctcttcattg aatggatggc aggggatcg gtggctcatt tgctgagtaa atatggagcc  4020
ttcaaagaat cagtagttat taactacact gaacagttca tccgtggcct ttcgtatctc  4080
catgaaaacc aaatcattca cagagatgtc aaggtgccaa atttgctaat tgacagcact  4140
ggtcagagac taagaattgc agattttgga gctgcagcca ggttggcatc aaaaggaact  4200
ggtgcaggag agtttcaggg acaattactg gggacaattg catttatggc acctgaggta  4260
ctaagaggtc aacagtatgg aaggagctgt gatgtatgga gtgttggctg tgctattata  4320
gaaatggctt gtgcaaaacc accatgcaat gcagaaaaac actccaatca tcttgcttg  4380
atatttaaga ttgctagtgc aactactgct ccatcgatcc cttcacattt gtctcctggt  4440
ttacgagatg tggctcttcg ttgtttagaa cttcaacctc aggacagacc tccatcaaga  4500
gagctactga agcatccagt ctttcgtact acatggtag                        4539
```

SEQ ID NO: 21           moltype = DNA   length = 1974
FEATURE                 Location/Qualifiers
source                  1..1974
                        mol_type = unassigned DNA
                        organism = Homo sapiens
SEQUENCE: 21
```
atggacgaac aggaggcatt gaactcaatc atgaacgatc tggtggccct ccagatgaac  60
cgacgtcacc ggatgcctgg atatgagacc atgaagaaca agacacagg tcactcaaat  120
aggcagaaaa acacaacag cagcagctca gcccttctga cagcccac agtaacaaca  180
agctcatgtg caggggccag tgagaaaaag aaattttga gtgacgtcag aatcaagttc  240
gagcaaacg gggagaggcg aattatagcg ttcagccggc ctgtgaaata tgaagatgtg  300
gagcacaagg tgacaacagt atttggacaa cctcttgatc tacattacat gaacaatgag  360
ctctccatcc tgctgaaaaa ccaagatgat cttgataaag caattgacat tttagataga  420
agctcaagca tgaaaagcct taggatattg ctgttgtccc aggacagaaa ccataacagt  480
tcctctcccc actctggggt gtccagacag gtgcggatca aggcttccca gtccgcaggg  540
gatataaata ctatctacca gcccccccgag cccagaaggga ggcacctctc tgtcagctcg  600
cagaaccctg gccgaagctc acctcccct ggctatgttc ctgagcggca gcagcacatt  660
gcccggcagg ggtcctacac cagcatcaac agtgaggggg agttcatccc agagaccagc  720
gagcagtgca tgctggatcc cctgagcagt gcagaaaatt ccttgtctgg aagctgccaa  780
tccttggaca ggtcagcaga cagcccatcc ttccggaat cacgaatgtc ccgtgcccag  840
agcttccctg acaacagaca ggaatactca gatcgggaaa ctcagcttta tgacaaaggg  900
gtcaaaggtg aacctaccc ccggcgctac cacgtgtctg tgcaccacaa ggactacagt  960
gatggcagaa gaacatttcc ccgaatacgg cgtcatcaag gcaacttgtt cacccctggtg 1020
ccctccagcc gctccctgag cacaaatggc gagaacattg gtctggctgt gcaatacctg 1080
gaccccccgtg ggcgcctgcg gagtgcggac agcgagaatg ccctctcgt gcaggagagg 1140
aatgtgccaa ccagtctcc cagtgccccc atcaactggc gccggggaaa gctcctgggc 1200
cagggtgcct cggcagggt ctatttgtgc tatgacgtgg acacggaacg tgaacttgct 1260
tccaagcagg tccaatttga tccagacagt cctgagacaa gcaaagaggt gagtgctctg 1320
gagtgcgaga tccagttgct aaagaacttg cagcatgagc gcatcgtgca gtactatgcc 1380
tgtctgcggg accgcgctga aagaccctg accatcttca tggagtacat gccagggggc 1440
tcggtgaaaa accagttgaa ggcttacggt gtctctgacag agagcgtgac ccgaaagtac 1500
acgcggcaga tcctggaggg catgtcctac ctgcacacga acatgattgt tcaccgggac 1560
attaagggag ccaacatcct ccgagactct gctgggaatg taaagctggg ggactttggg 1620
gccagcaaac gcctgcagac gatctgtatg tcggggacgg gcatgcgctc cgtcactggc 1680
acacccactact ggatgagccc tgaggtgatc agcggcgagg gctatggaag gaaagcagac 1740
gtgtggagcc tgggctgcac tgtggtggag atgctgacag agaaaccacc gtgggcagg 1800
tatgaagcta tggccgccat cttcaagatt gccacccagc ccaccaatcc tcagctgccc 1860
tcccacatct ctgaacatgg ccgggacttc ctgaggcgca tttttgtgga ggctcgccag 1920
agaccttcag ctgaggagct gctcacacac cactttgcac agctcatgta ctga        1974
```

SEQ ID NO: 22           moltype = DNA   length = 4826
FEATURE                 Location/Qualifiers
source                  1..4826
                        mol_type = unassigned DNA
                        organism = Homo sapiens
SEQUENCE: 22
```
atgagagaag ccgctgccgc gctggtccct cctcccgcct ttgccgtcac gcctgccgcc  60
gccatggagg agccgccgcc accgccgccg ccgccaccac cgccaccgga cccgagacc  120
gagtcagaac ccgagtgctg cttggcggcg aggcaagagg gcacattggg agattcagct  180
tgcaagagtc ctgaatctga tctagaagac ttctccgatg aaacaaatac agagaatctt  240
tatggtacct ctccccccag cacacctcga cagatgcaaca caaacatcag acc        300
aggaataatg tggggaggcc agccagtcgg tctaatttga agaaaaaat gaatgcacca  360
aatcagcctc cacataaaga cactggaaaa acagtggaga atgtggaaga atacagctat  420
aagcaggaga aaagatccg agcagctctt agaacaacag agcgtgatca taaaaaaaat  480
gtacagtgct cattcatgtt agactcagtg gtgatctgc tgccaaaaaa atcaattcca  540
gatgtggatc tcaataagcc ttacctcagc cttggctgta gcaatgctaa gcttccagta  600
```

```
tctgtgccca tgcctatagc cagacctgca cgccagactt ctaggactga ctgtccagca    660
gatcgtttaa agttttttga aactttacga cttttgctaa agcttacctc agtctcaaag    720
aaaaaagaca gggagcaaag aggacaagaa aatacgtctg gtttctggct taaccgatct    780
aacgaactga tctggttaga gctacaagcc tggcatgcag gacggacaat taacgaccag    840
gacttctttt tatatacagc ccgtcaagcc atcccagata ttattaatga aatccttact    900
ttcaaagtcg actatgggag cttcgccttt gttagagata gagctggttt taatggtact    960
tcagtagaag ggcagtgcaa agccactcct ggaacaaaga ttgtaggtta ctcaacacat   1020
catgagcatc tccaacgcca gagggtctca tttgagcagg taaaacggat aatggagctg   1080
ctagagtaca tagaagcact ttatccatca ttgcagctc ttcagaagga ctatgaaaaa    1140
tatgctgcaa aagacttcca ggacagggtg caggcactct gtttgtggtt aaacatcaca   1200
aaagacttaa atcagaaatt aaggattatg ggcactgttt tgggcatcaa gaatttatca   1260
gacattggct ggccagtgtt tgaaatccct tcccctcgac catccaaagg taatgagccg   1320
gagtatgagg gtgatgacac agaaggagaa ttaaaggagt tggaaagtag tacggatgag   1380
agtgaagaag aacaaatctc tgatcctagg gtaccggaaa ctcagacagcc catagataac   1440
agcttcgaca tccagtcgcg ggactgcata tccaagaagc ttgagaggct cgaatctgag   1500
gatgattctc ttggctgggg agcaccagac tggagcacag aagcaggctt tagtagacat   1560
tgtctgactt ctatttatag accatttgta gacaaagcac tgaagcagat gggggttaaga  1620
aagttaattt taagacttca caagctaatg gatggttcct tgcaaagggc acgtatagca   1680
ttggtaaaga acgatcgtcc agtggagttt tctgaatttc cagatcccat gtggggttca   1740
gattatgtgc agttgtcaag gacaccacct tcatctgagg agaaatgcag tgctgtgtcg   1800
tgggaggagc tgaaggccat ggatttacct tcattcgaac ctgccttcct agttctctgc   1860
cgagtccttc tgaatgtcat acatgagtgt ctgaagttaa gattggagca gagacctgct   1920
ggagaaccat ctctcttgag tattaagcag ctggtgagag agtgtaagga ggtcctgaag   1980
ggcggcctgc tgatgaagca gtactaccag ttcatgctgc aggaggttct ggaggacttg   2040
gagaagcccg actgcaacat tgacgctttt gaagaggatc tacataaaat gcttatggtg   2100
tattttgatt acatgagaag ctggatccaa atgctacagc aattacctca agcatcgcat   2160
agtttaaaaa atctgttaga agaagaatgg aatttcacca agaaataac tcattacata   2220
cggggaggag aagcacaggc cgggaagctt ttctgtgaca ttgcaggaat gctgctgaaa   2280
tctacaggaa gttttttaga atttggctta caggagagct gtgctgaatt ttggactagt   2340
gcggatgaca gcagtgcttc cgacgaaatc aggaggtctg ttatagagat cagtcgagcc   2400
ctgaaggagc tcttccatga agccagaaa agggcttcca aagcacttgg atttgctaaa   2460
atgttgagaa aggacctgga aatagcagca gaattcaggc tttcagcccc agttagagac   2520
ctcctgatg ttctgaaatc aaaacagtat gtcaaggtgc aaattcctgg gttagaaaac    2580
ttgcaaatgt ttgttccaga cactcttgct gaggagagag gtattatttt gcagttactc   2640
aatgcagctg caggaaagga ctgttcaaaa gattcagatg acgtactcat cgatgcctat   2700
ctgcttctga ccaagcacgg tgatcgagcc cgtgattcag aggacagctg ggggcacctgg  2760
gaggcacagc ctgtcaaagt cgtgcctcag gtggagactg ttgacaccct gagaagcatg   2820
caggtggata atctttttact agttgtcatg cagtctgcgc atctcacaat tcagagaaaa   2880
gcttttccagc agtccattga gggacttatg actctgtgac aggagcagac atccagtcag  2940
ccggtcatcg ccaaagcttt gcagcagctg aagaatgatg cattggagct atgcaacagg   3000
ataagcaatg ccattgaccg cgtggaccac atgttcacat cagaatttga tgctgaggtt   3060
gatgaatctg aatctgtcac cttgcaacag tactaccgag aagcaatgat tcaggggtac   3120
aattttggat ttgagtatca taaagaagtt gttcgtttga tgtctgggga gtttagacag   3180
aagataggag acaaatatat aagctttgcc cggaagtgga tgaattatgt cctgactaaa   3240
tgtgagagtg gtagaggtac aagacccagg tgggcgactc aagaatttga ttttctacaa   3300
gcaattgaac ctgcctttat ttcagcttta ccagaagatg acttcttgag tttacaagcc   3360
ttgatgaatg aatgcattgg ccatgtcata ggaaaaccac acagtcctgt tacaggtttg   3420
taccttgcca ttcatcggaa cagccccgt cctatgaagg tacctcgatg ccatagtgac    3480
cctcctaacc cacacctcat tatccccact ccagagggat tcagcactcg gagcatgcct   3540
tccgacgcgc ggagccatgg cagccctgct gctgctgctg ctgctgctgc tgctgctgtt   3600
gctgccagtc ggcccagccc ctctggtggt gactctgtgc tgcccaaatc catcagcagt   3660
gcccatgata ccaggggttc cagcgttcct gaaaatgatc gattggcttc catgctgct   3720
gaattgcagt ttaggtccct gagtcgtcac tcaagcccca cggaggagcg agatgaacca   3780
gcatatccaa gaggagattc aagtgggtcc acaagaagaa gttgggaact tcggacacta   3840
atcagccgaa gtaaagatac tgcttctaaa ctaggacca tagaagctat ccagaagtca   3900
gtccgattgt ttgaagaaaa gaggtaccga gaaatgagga gaaagaatat cattggtcaa   3960
gtttgtgata cgcctaagtc ctatgataat gttatgcacg ttgcttgag gaaggtgacc    4020
ttcaaatggc aaagaggaaa caaaattgga gaaggccagt atgggaaggt gtacacctgc   4080
atcagcgtcg acaccgggga gctgatggcc atgaaagaga ttcgattca acctaatgac    4140
cataagacta tcaaggaaac tgcagacgaa ttgaaaatat tcgaaggcat caaacacccc   4200
aatctggttc ggtattttgg tgtggagctc cataagaag aaatgtacat cttcatggag   4260
tactgcgatg aggggacttt agaagaggtg tcaaggctgg gacttcagga acatgtgatt   4320
aggctgtatt caaagcagat caccattgcg atcaacgtcc tccatgagca tggcatagtc   4380
caccgtgaca ttaaaggtgc caatatcttc cttacctcat ctggattaat caactggga    4440
gattttggat gttcagtaaa gctcaaaaac aatgcccaga ccatgcctgg tgaagtgaac   4500
agcaccctgg ggacagcagc atacatggca cctgaagtca tcactcgtgc caaggagag    4560
ggccatgggc gtgcggccga catctggagt ctggggtgtg ttgtcataga gatggtgact   4620
ggcaagaggc cttggcatga gtatgagcac aactttcaaa ttatgtataa agtgggggatg   4680
ggacataagc caccaatccc tgaaagatta gcccctgagga gaaggactt cctttctcac  4740
tgccttgaga gtgacccaaa gatgagatgg accgccagcc agctcctcga ccattcgttt   4800
gtcaaggttt gcacagatga agaatg                                       4826
```

SEQ ID NO: 23  moltype = DNA length = 3867
FEATURE    Location/Qualifiers
source     1..3867
       mol_type = unassigned DNA
       organism = Homo sapiens
SEQUENCE: 23
atggcgggc cgtgtccccg gtccggggcg gagcgcgccg gcagctgctg gcaggacccg    60

```
ctggccgtgg cgctgagccg gggccggcag ctcgcggcgc ccccgggccg gggctgcgcg    120
cggagccggc cgctcagcgt ggtctacgtg ctgacccggg agccgcagcc cgggctcgag    180
cctcgggagg gaaccgaggc ggagccgctg ccctgcgct gcctgcgcga ggcttgcgcg     240
caggtccccc ggccgcggcc gccccgcag ctgcgcagcc tgcccttcgg gacgctggag      300
ctaggcgaca ccgcggctct ggatgccttc tacaacgcag atgtggtggt gctggaggtg    360
agcagctcgc tggtacagcc ctccctgttc taccaccttg gtgtgcgtga gagcttcagc    420
atgaccaaca atgtgctcct ctgctcccag gccgacctcc ctgacctgca ggccctgcgg    480
gaggatgttt tccagaagaa ctcggattgc gttggcagct acacactgat ccctatgtg    540
gtgacggcca ctggtcgggt gctgtgtggt gatgcaggcc ttctgcgggg cctggctgat    600
gggctggtac aggctggagt ggggaccgag gccctgctca ctcccctggt gggccggctt    660
gcccgcctgc tggaggccac acccacagac tcttgtggct atttccggga gaccattcgg    720
cgggacatcc ggcaggcgcg ggagcggttc agtgggccac agctgcggca ggagctggct    780
cgcctgcagc ggagactgga cagcgtggag ctgctgagcc ccgacatcat catgaacttg    840
ctgctctcct accgcgatgt gcaggactac tcggccatca ttgagctggt ggagacgctg    900
caggccttgc ccacctgtga tgtggccgag cagcataatg tctgcttcca ctacactttt    960
gccctcaacc ggaggaacag gcctgggac cgggcgaagg ccctgtctgt gctgctgccg    1020
ctggtacagc ttgagggctc tgtggcgccc gatctgtact gcatgtgtgg ccgtatctac    1080
aaggacatgt tcttcagctc gggttttcca gatgctgggc accgggagca ggcctatcac    1140
tggtatcgca aggcttttga cgtagagccc agccttcact caggcatcaa tgcagctgtg    1200
ctcctcattg ctgccgggca gcactttgag gattccaaag agctccggct aataggcatg    1260
aagctgggct gcctgctggc ccgcaaaggc tgcgtggaga gatgcagta ttactgggat    1320
gtgggtttct acctgggagc ccagatcctc gccaatgacc ccaccaggt ggctggcct    1380
gcagagcagc tgtataagct caatgccccc atatggtacc tggtgtccgt gatggagacc    1440
ttcctgctct accagcactt caggcccacg ccagagcccc tggaggcc accacgccgt    1500
gcccacttct ggctccactt cttgctacag tcctgccaac cattcaagac agcctgtgcc    1560
cagggcgacc agtgcttggt gctggtcctg gagatgaaga aggtgctgct gcctgcaaag    1620
ctcgaggttc ggggtactga cccagtaagc acagtgaccc tgagcctgct ggagcctgag    1680
acccaggaca ttccctccag ctggaccttc ccagtcgcct ccatatgcgg agtcagcgcc    1740
tcaaagcgcg acgagcgctg ctgcttcctc tatgcactcc ccccggctca ggacgtccag    1800
ctgtgcttcc ccagcgtagg gcactgccaa tggttctgcc tgctgatcca ggcctggctg    1860
acgaacccgg attccacggc gcccgcggag gaggcggagg gcgcggggga gatgttggag    1920
tttgattatg agtacacgga gacgggcgag cggctggtgc tgggcaaggg cacgtatggg    1980
gtggtgtacg cgggccgcga tcgccacacg agggtgcgca tcgccatcaa ggagatcccg    2040
gagcgggaca gcaggttctc tcagcccctg catgaagaga tcgctcttca cagacgcgtg    2100
cgccacaaga acatagtgcg ctatctgggc tcagctagcc agggcggcta ccttaagatc    2160
ttcatggagg aagtgcctgg aggcagcctg tcctccttgc tgcggtcggt gtggggaccc    2220
ctgaaggaca acgagagcac catcagtttc tacacccgcc agatcctgca gggacttggc    2280
tacttgcacg acaaccacat cgtgcacagg gacataaaag gggacaatgt gctgatcaac    2340
accttcagtg ggctgctcaa gatttctgac ttcggcaact ccaagcggct ggcaggcatc    2400
acaccttgca ctgagacctt cacaggaact ctgcagtata tggccccaga aatcattgac    2460
cagggcccac gcgggtatgg gaaagcagct gacatctggt cactgggctg cactgtcatt    2520
gagatggcca caggtcgccc ccccttccac gagctcggga gccacaggc tgccatgttt    2580
caggtgggta tgtacaaggt ccatccgcca atgcccagct ctctgtcgg gcaggcccaa    2640
gccttttctcc tccgaacttt tgagccagac ccccgcctcc gagccagcgc ccagacactg    2700
ctgggggacc ccttcctgca gcctgggaaa aggagccgca gccccagctc cccacgacat    2760
gctccacggc cctcagatgc ccccttctgcc agtcccactc cttcagccaa ctcaaccacc    2820
cagtctcaga cattcccgtg ccctcaggca ccctctcagc caccacccag cccccgaag    2880
cgctgcctca gttatggggg caccagccag ctccgggtgc ccgaggagcc tgcggccgag    2940
gagcctgcgt ctccggagga gagttcgggg ctgagcctgc tgcaccagga gcaagcgt     3000
cgggccatgc tggccgcagt attggagcag gagctgccag cgctggcgga gaatctgcac    3060
caggagacaa agcaagaca ggggcccgt ctgggcagaa accatgtgga agactgcctg    3120
cgctgcctcg gggcacacat ccacactccc aaccgccggc agctcgccca ggagctgcgg    3180
gcgctgcaag gacggctgag ggcccagggc cttgggcctg cgcttctgca cagaccgctg    3240
tttgccttcc cggatgcggt gaagcagatc ctccgcaagc gccagatccg tccacactgg    3300
atgttcgttc tggactcact gctcagccgt gctgtgcggg cagccctgg tgtgctagga    3360
ccggaggtgg agaaggaggc ggtctcaccg aggtcagagg agctgagtaa tgaaggggac    3420
tcccagcaga gcccaggcca gcagagcccg cttccggtgg agcccgagca gggccccgct    3480
cctctgatgt tgcagctgag cctcttgagg gcagagactg atcggctgcg cgaaatcctg    3540
gcggggaagg aacgggagta ccaggccctg gtgcagcggg ctctacagcg gctgaatgag    3600
gaagcccgga cctatgtcct ggccccagag cctccaacg ctctttcaac ggaccagggc    3660
ctggtgcagt ggctacagga actgaatgtg gattcaggca ccatccaaat gctgttgaac    3720
catagcttca ccctccacac tctgctcacc tatgccactc gagatgacct catctacacc    3780
cgcatcaggg gagggatggt atgccgcatc tggagggcca tcttggcaca gcgagcagga    3840
tccacaccag tcacctctgg accctga                                        3867
```

SEQ ID NO: 24        moltype = DNA   length = 1740
FEATURE              Location/Qualifiers
source               1..1740
                     mol_type = unassigned DNA
                     organism = Homo sapiens

SEQUENCE: 24

```
atgtctacag cctctgccgc ctcctcctcc tcctcgtctt cggccggtga gatgatcgaa     60
gccccttccc aggtcctcaa ctttgaagag atcgactaca aggagatcga ggtggaagag    120
gttgttggaa ggagagcctt tggagttgtt gcaaagcta agtggaagag aaaagatgtt    180
gctattaaac aaatagaaag tgaatctgag aggaaagcgt ttattgtaga gcttcggcag    240
ttatcccgtg tgaccatcc taatattgta aagcttatg gagcctgctt gaatccagtg    300
tgtcttgtga tggaatatgc tgaagggggc tcttttatata atgtgctgca tggtgctgaa    360
ccattgccat attatactgc tgcccacgca atgagttggt gtttacagtg ttcccaagga    420
gtggcttatc ttcacagcat gcaacccaaa gcgctaattc acagggacct gaaaccacca    480
```

-continued

```
aacttactgc tggttgcagg ggggacagtt ctaaaaattt gtgattttgg tacagcctgt   540
gacattcaga cacacatgac caataacaag gggagtgctg cttggatggc acctgaagtt   600
tttgaaggta gtaattacag tgaaaaatgt gacgtcttca gctggggtat tattctttgg   660
gaagtgataa cgcgtcggaa acctttgat gagattggtg gcccagcttt ccgaatcatg   720
tgggctgttc ataatggtac tcgaccacca ctgataaaaa atttacctaa gcccattgag   780
agcctgatga ctcgttgttg gtctaaagat ccttcccagc gcccttcaat ggaggaaatt   840
gtgaaaataa tgactcactt gatgcggtac tttccaggag cagatgagcc attacagtat   900
ccttgtcagt attcagatga aggacagagc aactctgcca ccagtacagg ctcattcatg   960
gacattgctt ctacaaatac gagtaacaaa agtgacacta tatggagca agttcctgcc  1020
acaaatggat tattaagcg cttagaatca aaattgttga aaaatcaggc aaagcaacag  1080
agtgaatctg gacgtttaag cttgggagcc tcccgtggga gcagtgtgga gagcttgccc  1140
ccaacctctg agggcaagag gatgagtgct gacatgtctg aaatagaagc taggatcgcc  1200
gcaaccacag gcaacggaca gccaagacgt agatccatcc aagcttgac tgtaactgga  1260
acagaacctg gtcaggtgag cagtaggtca tccagtccca gtgtcagaat gattactacc  1320
tcaggaccaa cctcagaaaa gccaactcga agtcatccat ggacccctga tgattccaca  1380
gataccaatg gatcagataa ctccatccca atggcttatc ttacactgga tcaccaacta  1440
cagcctctag caccgtgccc aaactccaaa gaatctatgg cagtgtttga acagcattgt  1500
aaaatggcac aagaatatat gaaagttcaa acagaaattg cattgttatt acagagaaag  1560
caagaactag ttgcagaact ggaccaggat gaaaaggacc agcaaaatac atctcgcctg  1620
gtacaggaac ataaaaagct tttagatgaa acaaaaagcc tttctactta ctaccagcaa  1680
tgcaaaaaac aactagaggt catcagaagt cagcagcaga aacgacaagg cacttcatga  1740

SEQ ID NO: 25        moltype = DNA  length = 1113
FEATURE              Location/Qualifiers
source               1..1113
                     mol_type = unassigned DNA
                     organism = Homo sapiens
SEQUENCE: 25
atgctgtcca actcccaggg ccagagcccg ccggtgccgt tccccgcccc ggcccgccg    60
ccgcagcccc ccaccctgc cctgccgcac ccccgggcg agccgccgcc gccgccccg    120
cagcagttcc cgcagttcca cgtcaagtcc ggcctgcaga tcaagaagaa cgccatcatc   180
gatgactaca aggtcaccag ccaggtcctg gggctgggca tcaacggcaa agttttgcag   240
atcttcaaca gaggaccca ggagaaattc gccctcaaaa tgcttcagga ctgccccaag   300
gcccgcaggg aggtggagct gcactggcgg gcctcccagt gcccgcacat cgtacggatc   360
gtggatgtgt acgagaatct gtacgcaggg aggaagtgcc tgctgattgt catggaatgt   420
ttggacggtg gagaactctt tagccgaatc caggatcgag agaccaggc attcacagaa   480
agagaagcat ccgaaatcat gaagagcatc ggtgaggcca tccagtatct gcattcaatc   540
aacattgccc atcgggatgt caagcctgag aatctcttat acacctccaa aaggcccaac   600
gccatcctga aactcactga ctttggcttt gccaaggaaa ccaccagcca caactcttg   660
accactcctt gttatacacc gtactatgtg gctccagaag tgctgggtcc agagaagtat   720
gacaagtcct gtgacatgtg gtccctgggt gtcatcatgt acatcctgct gtgtgggtat   780
cccccttct actccaacca cggccttgcc atctctccgg gcatgaagac tcgcatccga   840
atgggccagt atgaatttcc caaccccagaa tggtcagaag tatcagagga agtgaagatg   900
ctcattcgga atctgctgaa aacagagccc acccagagaa tgaccatcac cgagtttatg   960
aaccaccctt ggatcatgca atcaacaaag gtccctcaaa ccccactgca caccagccgg  1020
gtcctgaagg aggacaagga gcggtgggag gatgtcaagg ggtgtcttca tgacaagaac  1080
agcgaccagg ccacttggct gaccaggttg tga                                1113

SEQ ID NO: 26        moltype = DNA  length = 954
FEATURE              Location/Qualifiers
source               1..954
                     mol_type = unassigned DNA
                     organism = Homo sapiens
SEQUENCE: 26
atgcgacccg accgcgctga ggctccagga ccgcccgcca tggctgcagg aggtcccggc    60
gcggggtctg cggccccggt ctcctccaca tcctcccttc ccctggctgc tctcaacatg   120
cgagtgcggc gccgcctgtc tctgttcttg aacgtgcgga cacaggtggc ggccgactgg   180
accgcgctgc ggaggagat ggactttgag tacttggaga tccggcaact ggagacacaa   240
gcggaccca ctggcaggct gctggacgcc tggcaggac gcctggcgc tctgtaggc    300
cgactgctcg agctgcttac caagctgggc cgcgacgacg tgctgctgga gctggaaccc   360
agcattgagg aggattgcca aaagtatatc ttgaagcagc agcaggagga ggctgagaag   420
ccttttacagg tggccgctgt agacagcagt gtcccacgga cagcagagct ggcgggcatc   480
accacacttg atgaccccct ggggcatatg cctgagcgtt tcgatgcctt catctgctat   540
tgcccagcg acatccagtt tgtgcaggag atgatccgac aactggaaca gacaaactat   600
cgactgaagt tgtgtgtgtc tgaccgcgat gtcctgcctg gcacctgtgt ctggtctatt   660
gctagtgagc tcatcgaaaa gaggttggct agaaggccac ggggtgggtg ccgccggatg   720
gtggtggttt ctctgatga ttacctgcag agcaaggaat gtgacttcca gaccaaattt   780
gcactcagcc tctctccagg tgcccatcag aagcgactga tccccatcaa gtacaaggca   840
atgaagaaag agttcccccag catcctgagg ttcatcactg tctgcgacta caccaacccc   900
tgcaccaaat cttggttctg gactcgcctt gccaaggcct tgtccctgcc ctga          954

SEQ ID NO: 27        moltype = DNA  length = 2907
FEATURE              Location/Qualifiers
source               1..2907
                     mol_type = unassigned DNA
                     organism = Homo sapiens
SEQUENCE: 27
atggcagaag atgatcccata tttgggaagg cctgaacaaa tgtttcattt ggatccttct    60
ttgactcata caatatttaa tccagaagta tttcaaccac agatgcact gccaacagat   120
```

```
ggcccatacc ttcaaatatt agagcaacct aaacagagag gatttcgttt ccgttatgta   180
tgtgaaggcc catcccatgg tggactacct ggtgcctcta gtgaaaagaa caagaagtct   240
taccctcagg tcaaaatctg caactatgtg ggaccagcaa aggttattgt tcagttggtc   300
acaaatggaa aaaatatcca cctgcatgcc cacagcctgg tgggaaaaca ctgtgaggat   360
gggatctgca ctgtaactgc tggacccaag gacatggcgt tcggcttcgc aaacctgggt   420
atacttcatg tgacaaagaa aaaagtattt gaaacactgg aagcacgaat gacagaggcg   480
tgtataaggg gctataatcc tggactcttg gtgcaccctg accttgccta tttgcaagca   540
gaaggtggag gggaccggca gctgggagat cgggaaaaag agctaatccg ccaagcagct   600
ctgcagcaga ccaaggagat ggacctcagc gtggtgcggc tcatgttttac agcttttctt   660
ccggatagca ctggcagctt cacaaggcgc ctggaacccg tggtatcaga cgccatctat   720
gacagtaaag cccccaatgc atccaacttg aaaattgtaa gaatgacag acagctgga    780
tgtgtgactg gaggggagga aatttatctt ctttgtgaca aagttcagaa agatgacatc   840
cagattcgat tttatgaaga ggaagaaaat ggtgagtct gggaaggatt tggagatttt   900
tccccccacag atgttcatag acaatttgcc attgtcttca aaactccaaa gtataaagat   960
attaatatta caaaaccagc ctctgtgttt gtccagcttc ggaggaaatc tgacttggaa  1020
actagtgaac caaaacccttt cctctactat cctgaaatca aagataaaga agaagtgcag  1080
aggaaacgtc agaagctcat gcccaatttt tcggatagtt tcggcggtgg tagtggtgct  1140
ggagctgggag gcggaggcat gtttggtagt ggcggtgggc caccgttgg gaatggtgag  1200
ggtccagggt atagcttccc acactatgga tttcctactt atggtgggat tacttttccat  1260
cctggaacta ctaaatctaa tgctgggatg aagcatggaa ccatgacac tgaatctaaa  1320
aaggaccctg aaggttgtga caaagtgat gacaaaaaca ctgtaaacct ctttgggaaa  1380
gttattgaaa ccacagagca agatcaggaa cccagccagg ccaccgttgg gaatggtgag  1440
gtcactctaa cgtatgcaac aggaacaaaa gaagagagtg ctggagttca ggataacctc  1500
tttctagaga aggctatgca gcttgcaaag aggcatgcca atgccctttt cgactacgcg  1560
gtgacaggag acgtgaagat gctgctggcc gtccagcgcc atctcactgc tgtgcaggat  1620
gagaatgggg acagtgtctt acacttagca atcatccacc ttcattctca acttgtgagg  1680
gatctactag aagtcacatc tggtttgatt tctgatgaca ttatcaacat gagaaatgat  1740
ctgtaccaga cgcccttgca cttggcagtg atcactaagc aggaagatgt ggtgaggat  1800
ttgctgaggg ctggggccga cctgagcctt ctggaccgct gggtaactc tgttttgcac  1860
ctagctgcca aagaaggaca tgataaagtt ctcagtatct tactcaagca caaaaaggca  1920
gcactacttc ttgaccaccc caacggggac ggtctgaatg ccattcatct agccatgatg  1980
agcaatagcc tgccatgttt gctgctgctg gtggccgctg gggctgacgt caatgctcag  2040
gagcagaagt ccgggcgcac agcactgcac ctggctgtgg agcacgacaa catctcattg  2100
gcaggctgcc tgctcctgga gggtgatgcc catgtgacac gtactaccta cgatggaacc  2160
acaccctgc atatagcagc tgggagaggg tccaccaggc tggcagctct tctcaaagca  2220
gcaggagcag atccctggt ggagaacttt gagcctctct atgacctgga tgactcttgg  2280
gaaaatgcag gagaggatga aggagttgtg cctggaacca cgcctctaga tatggccacc  2340
agctggcagg tatttgacat attaaatggg aaaccatatg agccagagtt tacatctgat  2400
gatttactag cacaaggaga catgaaacag ctggctgaag atgtgaagct gcagctgtat  2460
aagttactag aaattcctga tccagacaaa aactgggcta ctctggcgca gaaattaggt  2520
ctggggatac ttaataatgc cttccggctg agtcctgctc cttccaaaac acttatggac  2580
aactatgagg tctctggggg tacagtcaga gagctgtgtg aggccctgag acaaatgggc  2640
tacaccgaag caattgaagt gatccaggca gcctccaagc cagtgaagac caccctctcag  2700
gcccactcgc tgcctctctc gcctgcctcc acaaggcagc aaatagacga gctccgagac  2760
agtgacagtg tctgcgacag cggcgtggag acatccttcc gcaaactcag cttttaccgag  2820
tctctgacca gtggtgcctc actgctaact ctcaacaaaa tgcccccatga ttatgggcag  2880
gaaggacctc tagaaggcaa aatttag                                        2907

SEQ ID NO: 28         moltype = DNA   length = 2844
FEATURE               Location/Qualifiers
source                1..2844
                      mol_type = unassigned DNA
                      organism = Homo sapiens
SEQUENCE: 28
atggcagtga tggaaatggc ctgcccaggt gcccctggct cagcagtggg gcagcagaag    60
gaactcccca agccaaggga aagacgccg ccactgggga agaaacagag ctccgtctac   120
aagcttgagg ccgtggagaa gagccctgtg ttctgcggaa agtgggagat cctgaatgac   180
gtgattacca agggcacagc caaggaaggc tccgaggcag ggccagctgc catctctatc   240
atcgccagg ctgagtgtga gaatagccaa gagttcagcc ccaccttttc agaacgcatt   300
ttcatcgctg ggtccaaaca gtacagccag tccgagagtc ttgatcagat ccccaacaat   360
gtggcccatg ctacagaggg caaaatggcc cgtgtgtgtt ggaagggaaa gcgtcgcagc   420
aaagcccgga gaaacgcgaa gagaagagc tcaaagtccc tggctcatgc aggagtggcc   480
ttggccaaac ccctccccag gacccctgag caggagagct gcaccatccc agtgcaggag   540
gatgagtctc cactcggcgc cccatatgtt agaaaccgtc ggagttgtac caagcctctg   600
aaggaaccag gccttgggca actctgtttt aagcagcttg gcgagggcct acggccggct   660
ctgcctcgat cagaactcca caaactgatc agccccttgc aatgtctgaa ccacgtgtgg   720
aaactgcacc accccagga cggaggcccc ctgcccctgc ccacgcaccc cttccctat    780
agcagactgc ctcatccctt cccattccac cctctccagc cctggaaacc tcaccctctg   840
gagtccttcc tgggcaaact ggcctgtgt agacagtcca agcccccagc aaccctgcc tgacccacac   900
ctgagcaaac tggcctgtgt agacagtcca agcccccagc ctggcccaca cctggagccc   960
agctgcctgt ctcgtggtgc ccatgagaag ttttctgtgg aggaatacct agtgcatgct  1020
ctgcaaggca gcgtgagctc aggccaggcc cacagcctga ccagcctggc caagacctgg  1080
gcagcaaggg gctccagatc ccgggagccc agccccaaaa ctgaggacaa cgagggtgtc  1140
ctgctcactg agaaactcaa gccagtggat tatgagtacc agaagaagt ccactgggtc  1200
acgcaccagc tccgcctggg cagaggctcc ttcggagagg tgcacaggat ggaggacaag  1260
cagactggct tccagtgcgc tgtcaaaaag gtgcggctgg aagtatttcg gcagaggag  1320
ctgatggcat gtgcaggatt gacctcaccc agaattgtcc ctttgtatgg agctgtgaga  1380
gaagggcctt gggtcaacat cttcatggag ctgctggaag tggctccct gggccagctg  1440
gtcaaggagc agggctgtct cccagaggac cgggccctgt actacctggg ccaggccctg  1500
```

```
gagggtctgg aatacctcca ctcacgaagg attctgcatg gggacgtcaa agctgacaac  1560
gtgctcctgt ccagcgatgg gagccacgca gccctctgtg actttggcca tgctgtgtgt  1620
cttcaacctg atggcctggg aaagtccttg ctcacagggg actacatccc tggcacagag  1680
acccacatgg ctccggaggt ggtgctgggc aggagctgcg acgccaaggt ggatgtctgg  1740
agcagctgct gtatgatgct gcacatgctc aacggctgcc acccctggac tcagttcttc  1800
cgagggccgc tctgcctcaa gattgccagc gagcctccgc ctgtgaggga gatcccaccc  1860
tcctgcgccc ctctcacagc ccaggccatc caagaggggg tgaggaaaga gcccatccac  1920
cgcgtgtctg cagcggagct gggagggaag gtgaaccggg cactacagca agtgggaggt  1980
ctgaagagcc cttggagggg agaatataaa gaaccaagac atccaccgcc aaatcaagcc  2040
aattaccacc agaccctcca tgcccagccg agagagcttt cgccaagggc cccagggccc  2100
cggccagctg aggagacaac aggcagagcc cctaagctcc agcctcctct cccaccagag  2160
cccccagagc caaacaagtc tcctcccttg actttgagca aggaggagtc tgggatgtgg  2220
gaaccettac ctctgtcctc cctggagcca gccctgcca gaaacccag ctcaccagag  2280
cggaaagcaa ccgtcccgga gcaggaactg cagcagctgg aaatagaatt attcctcaac  2340
agcctgtccc agccatttc tctgaggag caggagcaaa ttctctcgtg cctcagcatc  2400
gacagcctct ccctgtcgga tgacagtgag aagaacccat caaggcctc tcaaagctcg  2460
cgggacaccc tgagctcagg cgtacactcc tggagcagcc aggccgaggc tcgaagctcc  2520
agctggaaca tggtgctggc ccgggggcgg cccaccgaca ccccaagcta tttcaatggt  2580
gtgaaagtcc aaatacagtc tcttaatggt gaacacctgc atccgggaa gttccaccgg  2640
gtcaaagtgg gagacatcgc cactggcatc agcagccaga tcccagctgc agcctcagc  2700
ttggtcacca agacgggca gcctgttcgc tacgacatga ggtgccaga ctcgggcatc  2760
gacctgcagt gcacactggc ccctgatggc agcttcgcct ggagctggag ggtcaagcat  2820
ggccagctgg agaacaggcc ctaa  2844

SEQ ID NO: 29                moltype = DNA  length = 1083
FEATURE                      Location/Qualifiers
source                       1..1083
                             mol_type = unassigned DNA
                             organism = Homo sapiens
SEQUENCE: 29
atgtctcagg agaggcccac gttctaccgg caggagctga acaagacaat ctggaggtg  60
cccgagcgtt accagaacct gtctccagtg ggctctggcg cctatggctc tgtgtgtgct  120
gcttttgaca caaaacggg gttacgtgtg cagtgaaga agctctccag accatttcag  180
tccatcattc atgcgaaaag aacctacaga gaactgcggt tacttaaaca tatgaaacat  240
gaaaatgtga ttggtctgtt ggacgttttt acacctgcaa ggtctctgga ggaattcaat  300
gatgtgtatc tggtgaccca tctcatgggg gcagatctga caacattgt gaaatgtcag  360
aagcttacag atgaccatgt tcagttcctt atctaccaaa ttctccgagg tctaaagtat  420
atacattcag ctgacataat tcacagggac ctaaaaccta gtaatctagc tgtgaatgaa  480
gactgtgagc tgaagattct ggattttgga ctggctcggc acacagatga tgaaatgaca  540
ggctacgtgg ccactaggtg gtacagggct cctgagatca tgctgaactg gatgcattac  600
aaccagacag ttgatatttg gtcagtggga tgcataatgg ccgagctgtt gactggaaga  660
acattgttc ctggtacaga ccatattaac cagcttcagc agattatgcg tctgacagga  720
acacccccg cttatctcat taacaggatg ccaagccatg aggcaagaaa ctatattctgg  780
tctttgactc agatgccgaa gatgaacttt gcgaatgtat ttattggtgc aatcccctg  840
gctgtcgact tgctggagaa gatgcttgta ttggactcag ataagagaat tacagcggcc  900
caagcccttg cacatgccta ctttgctcag taccacgatc ctgatgatga accagtggcc  960
gatccttatg atcagtcctt tgaaagcagg gacctcctta tagatgagtg gaaaagcctg  1020
acctatgatg aagtcatcag ctttgtgcca ccaccccttg accaagaaga gatggagtcc  1080
tga                                                                 1083

SEQ ID NO: 30                moltype = DNA  length = 1656
FEATURE                      Location/Qualifiers
source                       1..1656
                             mol_type = unassigned DNA
                             organism = Homo sapiens
SEQUENCE: 30
atggctggtg atctttcagc aggtttcttc atggaggaac ttaatacata ccgtcagaag  60
cagggagtag tacttaaata tcaagaactg cctaattcag gacctccaca tgataggagg  120
tttacatttc aagttataat agatggaaga gaatttccaa aaggtgaagg tagatcaaag  180
aaggaagcaa aaaatgccgc agccaaatta gctgttgaga tacttaataa ggaaaagaag  240
gcagttagtc cttatattat tgacaacaac gaattcttcag aaggattatc catggggaat  300
tacataggcc ttatcaatag aattgcccag aagaaaagac taactgtaaa ttatgaacag  360
tgtgcatcgg gggtgcatgg gccagaagga tttcattata aatgcaaaat gggacagaaa  420
gaatatagta ttggtacagg ttctactaaa caggaagcaa caaattggc cgctaaactt  480
gcatatcttc agatattatc agaagaaacc tcagtgaaat ctgactacct gtcctctggt  540
tctttttgcta ctacgtgtga gtcccaaagc aactctttag tgaccagcac actgcttct  600
gaatcatcat ctgaaggtga cttctcagca gatacatcag agataaattc taacagtgac  660
agtttaaaca gttcttcgtt gcttatgaat ggtctcagaa ataatcaaag gaaggcaaaa  720
agatctttgg cacccagatt tgaccttcct gacatgaaaa aacaaagta tactgtggac  780
aagaggtttg gcatggattt taaagaaata gaattaattg gctcaggtgg atttggccaa  840
gttttcaaag caaaacacag aattgacgga aagacttacg ttattaaacg tgttaaatat  900
aataacgaga aggcggagcg tgaagtaaaa gcattggcaa acttgatca gtaaatatt  960
gttcactaca tggctgttg gatggatttt gattatgatc ctgagaccag tgatgattct  1020
cttgagagtg gtattatga tcctgagaac agcaaaaata gttcaaggtc cgctaaactt  1080
tgccttttca tccaaatgga attctgtgat aaagggacct ggaacaatg gattgaaaaa  1140
agaagagggg agaaactaga caagttttg gctttggaac tctttgaaca aataacaaaa  1200
ggggtggatt atatacattc aaaaaaatta attcatagag atcttaagcc aagtaatata  1260
ttcttagtag atacaaaaca agtaaagatt ggagactttg gacttgtaac atctctgaaa  1320
aatgatggaa agcgaacaag gagtaaggga actttgcgat acatgagccc agaacagatt  1380
```

-continued

```
tcttcgcaag actatggaaa ggaagtggac ctctacgctt tggggctaat tcttgctgaa   1440
cttcttcatg tatgtgacac tgcttttgaa acatcaaagt ttttcacaga cctacgggat   1500
ggcatcatct cagatatatt tgataaaaaa gaaaaaactc ttctacagaa attactctca   1560
aagaaacctg aggatcgacc taacacatct gaaatactaa ggaccttgac tgtgtggaag   1620
aaaagcccag agaaaaatga acgacacaca tgttag                             1656

SEQ ID NO: 31         moltype = DNA  length = 1443
FEATURE               Location/Qualifiers
source                1..1443
                      mol_type = unassigned DNA
                      organism = Homo sapiens
SEQUENCE: 31
atgagcgacg tggctattgt gaaggagggt tggctgcaca acgagggga gtacatcaag     60
acctggcggc cacgctactt cctcctcaag aatgatggca ccttcattgg ctacaaggag   120
cggccgcagg atgtggacca acgtgaggct ccctcaaca acttctctgt ggcgcagtgc   180
cagctgatga gacgcgagcg gccccggccc aacaccttca tcatccgctg cctgcagtgg   240
accactgtca tcgaacgcac cttccatgtg gagactcctg aggagcggga ggagtggaca   300
accgccatcc agactgtggc tgacggcctc aagaagcagg aggaggagga gatggacttc   360
cggtcgggct cacccagtga caactcaggg gctgaagaga tggaggtgtc cctggccaag   420
cccaagcacc gcgtgaccat gaacgagttt gagtacctga agctgctggg caagggcact   480
ttcggcaagt tgatcctggt gaaggagaag gccacaggcc gctactacgc catgaagatc   540
ctcaagaaga aagtcatcgt ggccaaggac gaggtggcca acacactcac cgagaaccgc   600
gtcctgcaga actccaggca ccccttcctc acagccctga agtactcttt ccagacccac   660
gaccgcctct gctttgtcat ggagtacgcc aacgggggcg agctgttctt ccacctgtcc   720
cgggagcgtg tgttctccga ggaccgggcc cgcttctatg cgctgagat tgtgtcagcc   780
ctggactacc tgcactcgga gaagaacgtg tgtaccggga acctcaagct ggagaacctc   840
atgctggaca aggacgggca cattaagatc acagacttcg ggctgtgcaa ggagggatc    900
aaggacggtg ccaccatgaa gacctttgc ggcacacctg agtactggcc ccccgaggtg    960
ctggaggaca atgactacgg ccgtgcagtg gactggtggg gctgggcgt ggtcatgtac    1020
gagatgatgt gcggtcgcct gccctttac aaccaggaca tgagaagctt ttttgagctc    1080
atcctcatgg aggagatccg cttcccgcgc acgcttggtc ccgaggccaa gtccttgctt   1140
tcagggctgc tcaagaagga ccccaagcag aggcttggcg ggggctccga ggacgccaag   1200
gagatcatgc agcatcgctt ctttgccggt atcgtgtggc agcacgtgta cgagaagaag   1260
ctcagcccac ccttcaagcc ccaggtcacg tcggagactg acaccaggta ttttgatgag   1320
gagttcacgg cccagatgat caccatcaca ccacctgacc aagatgacag catggagtgt   1380
gtggacagcg agcgcaggcc ccacttcccc cagttctcct actcggccag cggcacggcc   1440
tga                                                                  1443

SEQ ID NO: 32         moltype = DNA  length = 2514
FEATURE               Location/Qualifiers
source                1..2514
                      mol_type = unassigned DNA
                      organism = Homo sapiens
SEQUENCE: 32
atggctagca aacgaaaatc tacaactcca tgcatggttc ggacatcaca agtagtagaa     60
caagatgtgc ccgaggaagt agacagggcc aaagagaaag gaatcggcac accacagcct   120
gacgtgacga aggacagttg ggcagcagaa ctttgaaaact cttccaaaga aaacgaaagtg   180
atagaggtga aatctatggg ggaaagccag tccaaaaaac tccaaggtgg ttatgagtgc   240
aaatactgcc cctactccac gcaaaaacctg aacgagttca cggagcatgt cgacatgcag   300
catcccaacg tgattctcaa cccccctctac gtgtgtgcag aatgtaactt cacaaccaaa   360
aagtacgact ccctatccga ccacaactcc aagttccatc ccggggaggc caacttcaag   420
ctgaagttaa ttaaacgcaa taatcaaact gtcttggaac agtccatcga accaccaac    480
catgtcgtgt ccatcaccac cagtggcccc ggaactggtg acagtgattc tgggatctcg   540
gtgagtaaaa cccccatcat gaagcctgga aaaccaaaag cggatgccaa gaaggtgccc   600
aagaagcccg aggagatcac ccccgagaac cacgtggaca ggaccgcccg cctggtgaca   660
gacacagctg agatcctctc gagactcggc ggggtggagc tcctccaaga cacattagga   720
cacgtcatgc cttctgtaca gctgccacca aatatcaacc ttgtgcccaa ggtccctgtc   780
ccactaaata ctaccaaata caactctgcc ctggatacaa atgccacgat gatcaactct   840
ttcaacaagt ttccttaccc gacccaggct gagttgtcct ggctgacagc tgcctccaaa   900
cacccagagg agcacatcag aatctggttt gccacccagc gcttaaagca tggcatcagc   960
tggtccccag aagaggtgga ggaggccggg aagaagatgt tcaacggcac catccagtca   1020
gtaccccga ccatcactgt gctgcccgcc cagttggccc cacaaaaggt gacgcagccc   1080
atcctccaga cggctctacc gtgccagatc ctcggccaga ctagcctggt gctgactcag   1140
gtgaccagcg ggtcaacaac cgtctcttgc tcccccatca cacttgccgt ggcaggagtc   1200
accaaccatg gccagaagag acccttggtg actccccaag ctgcccccga acccaagcgt   1260
ccacacatcg ctcaggtgcc agagccccca cccaaggtgg ccaaccccc gctcacacca    1320
gccagtgacc gcaagaagac aaaggagcag atagcacatc tcaaggccag ctttctccag   1380
agccagttcc ctgacgatgc cgaggtttac cggctcatcg aggtgactgg ccttgccagg   1440
agcgagatca gaagtggtt cagtgaccac cgatatccgt gtcaaaggg catcgtccac   1500
atcaccagcg aatcccttgc caaagaccag ttggccatcg cggcctcccg acacggtcgc   1560
acgtatcatg cgtacccaga cttttgcccc cagaagttca agagaaaac acagggtcag   1620
gttaaaatct tggaagacag cttttttgaaa agttcttttc ctacccaagc agaactggat   1680
cggctaaggg tggagaccaa gctgagcagg agagagatgg actcctggtt ctcggagagg   1740
cggaagcttc gagacagcat ggaacaagct gtcttggatt ccatggggtc tgcaaaaaa    1800
ggccaagatg tgggagcccc caatggtgct ctgtctcgac tcgaccagct ctccggtgcc   1860
cagttaacaa gttctctgcc cagccttccg ccagcaattg caaaaagtca agaacaggtt   1920
catctcctga ggagcacgtt tgcaagaacc cagtggccta ctcccaagga gtacgaccag   1980
ttagcggcca agactggcct ggtccgaact gagattgtgc gttggttcaa ggagaacaga   2040
tgcttgctga aaacgggaac cgtgaagtgg atggagcagt accagcacca gcccatggca   2100
```

```
gatgatcacg gctacgatgc cgtagcaagg aaagcaacaa aacccatggc cgagagccca   2160
aagaacgggg gtgatgtggt tccacaatat tacaaggacc ccaaaaagct ctgcgaagag   2220
gacttggaga agttggtgac cagggtaaaa gtaggcagcg agccagcaaa agactgtttg   2280
ccagcaaagc cctcagaggc cacctcagac cggtcagagg gcagcagccg ggacggccag   2340
ggtagcgacg agaacgagga gtcgagcgtt gtggattacg tgaggtgacg ggtcggggag   2400
gaggatgcga tctcagatag atcagatagc tggagtcagg ctgcggcaga aggtgtgtcg   2460
gaactggctg aatcagactc cgactgcgtc cctgcagagg ctggccaggc ctag         2514

SEQ ID NO: 33         moltype = DNA   length = 567
FEATURE               Location/Qualifiers
source                1..567
                      mol_type = unassigned DNA
                      organism = Homo sapiens
SEQUENCE: 33
atgactgaat ataaacttgt ggtagttgga gctggtggcg taggcaagag tgccttgacg    60
atacagctaa ttcagaatca tttttgtggac gaatatgatc caacaataga ggattcctac   120
aggaagcaag tagtaattga tggagaaacc tgtctcttgg atattctcga cacagcaggt   180
caaggagagt acagtgcaat gagggaccag tacatgagga ctgggggagg cttttctttgt   240
gtatttgcca taaataatac taaatcattt gaagatattc accattatag agaacaaatt   300
aaaagagtta aggactctga agatgtacct atggtcctag taggaaataa atgtgatttg   360
ccttctagaa cagtagacac aaaacaggct caggacttag caagaagtta tggaattcct   420
tttattgaaa catcagcaaa gacaagacag ggtgttgatg atgccttcta tacattagtt   480
cgagaaattc gaaaacataa agaaaagatg agcaaagatg gtaaaagaa gaaaaagaag   540
tcaaagacaa agtgtgtaat tatgtaa                                       567

SEQ ID NO: 34         moltype = DNA   length = 570
FEATURE               Location/Qualifiers
source                1..570
                      mol_type = unassigned DNA
                      organism = Homo sapiens
SEQUENCE: 34
atgactgagt acaaactggt ggtggttgga gcaggtggtg ttgggaaaag cgcactgaca    60
atccagctaa tccagaacca cttttgtagat gaatatgatc ccaccataga ggattcttac   120
agaaaacaag tggtttataga tggtgaaacc tgtttgttgg acatactgga tacagctgga   180
caagaagagt acagtgccat gagagaccaa tacatgagga caggcgaagg cttcctctgt   240
gtatttgcca tcaataatag caagtcattt gcggatatta acctacagg ggagcagatt   300
aagcgagtaa aagactcgga tgatgtacct atggtgctag tgggaaacaa gtgtgatttg   360
ccaacaagga cagttgatac aaaacaagcc cacgaactgg ccaagagtta cgggattcca   420
ttcattgaaa cctcagccaa gaccagacag ggtgttgaag atgcttttta cacactggta   480
agagaaaatc gccagtaccg aatgaaaaaa ctcaacagca gtgatgatgg gactcagggt   540
tgtatgggat tgccatgtgt ggtgatgtaa                                    570

SEQ ID NO: 35         moltype = DNA   length = 2016
FEATURE               Location/Qualifiers
source                1..2016
                      mol_type = unassigned DNA
                      organism = Homo sapiens
SEQUENCE: 35
atgcaaccag acatgtcctt gaatgtcatt aagatgaaat ccagtgactt cctggagagt    60
gcagaactgc acagcggagg ctttgggaag gtgtctctgt gtttccacag aacccaggga   120
ctcatgatca tgaaaacagt gtacaagggg cccaactgca ttgagcacaa cgaggcctc    180
ttggaggagg cgaagatgat gaacagactg agacacagcc gggtggtgaa gctcctgggc   240
gtcatcatag aggaagggaa gtactccctg tgatggagt acatggagaa gggcaacctg   300
atgcacgtgc tgaagccgga gatgagtact ccgctttctg taaaaggaag gataattttg   360
gaaatcattg aaggaatgtg ctactacat ggaaaagcg tgatacacaa ggacctgaag   420
cctgaaaata tccttgttga taatgacttc cacattaaga tcgcagacct cggccttgcc   480
tcctttaaga tgtggagcaa actgaataat gaagagcaca atgagctgag ggaagtggac   540
ggcaccgcta agaagaatgg cggcacccctc tactacatgg cgcccgagca cctgaatgac   600
gtcaacgcaa agcccacaga gaagtcggat gtgtacagct ttgctgtagt actctgggcg   660
atatttgcaa ataaggagcc atatgaaaat gctatctgtg agcagcagtt gataatgtgc   720
ataaaatctg ggaacaggcc agatgtggat gacatcactg agtactgccc aagagaaatt   780
atcagtctca tgaagctctg ctgggaagcg aatccggaag ctcggccgac atttcctggc   840
attgaagaaa aatttaggcc tttttattta agtcaattag aagaaagtgt agaagaggac   900
gtgaagagtt taaagaaaga gtattcaaac gaaaatgcag ttgttaagag aatgcagtct   960
cttcaacttg attgtgtggc agtaccttca agcggtcaa attcagccac agaacagcct  1020
ggttcactgc acagttccca gggacttggg atgggtcctg tggaggagtc ctggtttgct  1080
ccttccctgg agcaccccaca agaagagaat gagcccagcc tgcagagtaa actccaagac  1140
gaagccaact accatcttta tggcagccgc atggacaggc agacaaaca gcagcccaga  1200
cagaatgtgg cttacaacag agaggaggaa aggagacga gggtctccca tgaccctttt  1260
gcacagcaaa gaccttacga gaattttcag aatacagagg gaaaaggcac tgcttattcc  1320
agtgcagcca gtcatggtaa tgcagtgcac cagccctcag ggctcaccag ccaacctcaa  1380
gtactgtatc agaacaatgg attatatagc tcacatggct ttgaacaag accactggat  1440
ccaggaacag caggtcccag agtttggtac aggccaattc caagtcatat gcctagtctg  1500
cataatatcc cagtgcctga gaccaactat caggaaata cacccaccat gccattcagc  1560
tccttgccac caacagatga atctataaaa tataccatat acaatagtac tggcattcag  1620
attggagcct acaattatat ggagattggt gggacgagtt catcactact agacagcaca  1680
aatacgaact tcaagaagag gccagctgct aagtaccaag ctatctttga taataccact  1740
agtctgacgg ataaacaccct ggacccaatc agggaaaatc tgggaaagca ctggaaaaac  1800
tgtgcccgta aactggggctt cacacagtct cagattgatg aaattgacca tgactatgag  1860
```

```
cgagatggac tgaaagaaaa ggtttaccag atgctccaaa agtgggtgat gagggaaggc  1920
ataaagggag ccacggtggg gaagctggcc caggcgctcc accagtgttc caggatcgac  1980
cttctgagca gcttgattta cgtcagcag  aactaa                             2016

SEQ ID NO: 36          moltype = DNA   length = 1569
FEATURE                Location/Qualifiers
source                 1..1569
                       mol_type = unassigned DNA
                       organism = Homo sapiens
SEQUENCE: 36
atgagtctgc taaactgtga aaacagctgt ggatccagcc agtctgaaag tgactgctgt  60
gtggccatgg ccagctcctg tagcgctgta acaaaagatg atagtgtggg tggaactgcc  120
agcacgggga acctccag   ctcatttatg gaggagatcc agggatatga tgtagagttt  180
gacccacccc tggaaagcaa gtatgaatgc cccatctgct tgatggcatt acgagaagca  240
gtgcaaacgc catgcggcca taggttctgc aaagcctgca tcataaaatc aataagggat  300
gcaggtcaca aatgtccagt tgacaatgaa atactgctgg aaaatcaact atttccagac  360
aattttgcaa aacgtgagat tctttctctg atggtgaaat gtccaaatga aggttgtttg  420
cacaagatgg aactgagaca tcttgaggat catcaagcac attgtgagtt tgctcttatg  480
gattgtcccc aatgccagcg tcccttccaa aaattcccata ttaatattca cattctgaag  540
gattgtccaa ggacacaggt tcttgtgac  aactgtgctg catcaatggc atttgaagat  600
aaagagatcc atgaccagaa ctgtcctttg gcaaatgtca tctgtgaata ctgcaatact  660
atactcatca gagaacagat gcctaatcat tatgatctag actgccctac agccccaatt  720
ccatgcacat tcagtacttt tggttgccat gaaaagatgc agaggaatca cttggcacgc  780
cacctacaag agaacaccca gtcacacatg agaatgttgg cccaggctgt tcatagtttg  840
agcgttatac ccgactctgg gtatatctca gaggtccgga tttccagga  aactattcac  900
cagttagagg gtcgccttgt aagacaagac catcaaatcc gggagctgac tgctaaaatg  960
gaaactcaga gtatgtatgt aagtgagctc aaacgaacca ttcgaaccct tgaggacaaa  1020
gttgctgaaa tcgaagcaca gcagtgcaat ggaatttata tttggaagat tggcaacttt  1080
ggaatgcatt tgaaatgtca agaagaggag aaacctgttg tgattcatag ccctggattc  1140
tacactggca aacccgggta caaactgtgc atgcgcttgc accttcagtt accgactgct  1200
cagcgctgtg caaactatat atcccttttt gtccacacaa tgcaaggaga atatgacagc  1260
cacctccctt ggccccttca gggtacaata cgccttacaa ttcttgatca gtctgaagca  1320
cctgtaaggc aaaaccacga agagataatg gatgccaaac cagagctgct tgctttccag  1380
cgacccacaa tcccacggaa cccaaaaggt tttggctatg taactttat  gcatctggaa  1440
gccctaagac aaagaacttt cattaaggat gacacattat tagtgcgctg tgaggtctcc  1500
acccgctttg acatgggtag ccttcggagg gagggttttc agccacgaag tactgatgca  1560
ggggtatag                                                          1569

SEQ ID NO: 37          moltype = DNA   length = 999
FEATURE                Location/Qualifiers
source                 1..999
                       mol_type = unassigned DNA
                       organism = Homo sapiens
SEQUENCE: 37
atggccaacc gttacaccat ggatctgact gccatctacg agagcctcct gtcgctgagc  60
cctgacgtgc ccgtgccatc cgaccatgga gggactgagt ccagcccagg ctggggctcc  120
tcggaccct  ggagcctgag cccctccgac tccagcccgt ctggggtcac ctcccgcctg  180
cctgccgct  ccaccagcct agtggagggc cgcagctgtg ctgggtgcc cccacccct  240
ggcttcgcac cgctggctcc ccgctggcc  cctgagctgt caccctcacc cacttcgccc  300
actgcaacct ccaccacccc ctcgcgctac aagactgagc tatgtcggac cttctcagag  360
agtgggcgct gccgctacgg ggccaagtgc cagtttgccc atggcctggg cgagctgcgc  420
caggccaatc gccacccaa  atacaagacg gaactctgtc acaagttcta cctccagggc  480
cgctgccctc acggctctcg ctgccacttc atccacaacc ctagcgaaga cctggcggcc  540
ccgggccacc ctcctgtgct cgccagagc  atcagcttct ccggcctgcc ctctggccgc  600
cggacctcac caccaccacc aggcctggcc ggcccttccc tgtcctccag ctccttctcg  660
ccctccagct cccaccacc  acctgggac  cttccactgt caccctctgc cttctctgct  720
gcccctggca cccccctggc tcgaagagac cccaccccag tctgttgccc ctcctgccga  780
agggccactc ctatcagcgt ctgggggccc ttggtggcc  tggttcggac cccctctgta  840
cagtccctgg gatccgaccc tgatgaatat gccagcagcg gcagcagcct gggggctctt  900
gactctcccg tcttcgaggc gggagttttt gcaccacccc agcccgtggc agcccccgg  960
cgactcccca tcttcaatcg catctctgtt tctgagtga                         999
```